United States Patent
Yeung et al.

(10) Patent No.: US 10,745,382 B2
(45) Date of Patent: Aug. 18, 2020

(54) COMPOUNDS USEFUL AS IMMUNOMODULATORS

(71) Applicant: BRISTOL-MYERS SQUIBB COMPANY, Princeton, NJ (US)

(72) Inventors: Kap-Sun Yeung, Madison, CT (US); Timothy P. Connolly, Kenosha, WI (US); David B. Frennesson, Naugatuck, CT (US); Katharine A. Grant-Young, Madison, CT (US); Piyasena Hewawasam, Middletown, CT (US); David R. Langley, Meriden, CT (US); Zhaoxing Meng, Middletown, CT (US); Eric Mull, Guilford, CT (US); Kyle E. Parcella, Wallingford, CT (US); Mark George Saulnier, Higganum, CT (US); Li-Qiang Sun, Glastonbury, CT (US); Alan Xiangdong Wang, Wallingford, CT (US); Ningning Xu, Wallingford, CT (US); Juliang Zhu, North Haven, CT (US); Paul Michael Scola, Glastonbury, CT (US)

(73) Assignee: bristol-myers squibb company, princeton, NJ (US)

( * ) Notice: Subject to any disclaimer, the term of this patent is extended or adjusted under 35 U.S.C. 154(b) by 0 days.

(21) Appl. No.: 15/290,167

(22) Filed: Oct. 11, 2016

(65) Prior Publication Data
US 2017/0107202 A1  Apr. 20, 2017

Related U.S. Application Data

(60) Provisional application No. 62/242,072, filed on Oct. 15, 2015.

(51) Int. Cl.
| | |
|---|---|
| *C07D 401/14* | (2006.01) |
| *C07D 213/71* | (2006.01) |
| *C07D 455/02* | (2006.01) |
| *A61K 31/135* | (2006.01) |
| *A61K 31/138* | (2006.01) |
| *A61K 31/166* | (2006.01) |
| *A61K 31/397* | (2006.01) |
| *A61K 31/40* | (2006.01) |
| *A61K 31/4025* | (2006.01) |
| *A61K 31/44* | (2006.01) |
| *A61K 31/4427* | (2006.01) |
| *A61K 31/4439* | (2006.01) |

(Continued)

(52) U.S. Cl.
CPC .......... *C07D 401/14* (2013.01); *A61K 31/135* (2013.01); *A61K 31/138* (2013.01); *A61K 31/166* (2013.01); *A61K 31/397* (2013.01); *A61K 31/40* (2013.01); *A61K 31/4025* (2013.01); *A61K 31/44* (2013.01); *A61K 31/4427* (2013.01); *A61K 31/4439* (2013.01); *A61K 31/4453* (2013.01); *A61K 31/454* (2013.01); *A61K 31/4545* (2013.01); *A61K 31/496* (2013.01); *A61K 31/5375* (2013.01); *A61K 31/5377* (2013.01); *A61K 31/541* (2013.01); *A61K 45/06* (2013.01); *C07C 215/20* (2013.01); *C07C 235/46* (2013.01); *C07D 205/04* (2013.01); *C07D 207/12* (2013.01); *C07D 207/14* (2013.01); *C07D 207/16* (2013.01); *C07D 211/22* (2013.01); *C07D 213/71* (2013.01); *C07D 213/80* (2013.01); *C07D 213/82* (2013.01); *C07D 213/85* (2013.01); *C07D 265/30* (2013.01); *C07D 401/12* (2013.01); *C07D 403/12* (2013.01); *C07D 405/12* (2013.01); *C07D 405/14* (2013.01); *C07D 413/14* (2013.01); *C07D 417/12* (2013.01); *C07D 417/14* (2013.01); *C07D 455/02* (2013.01); *C07D 471/04* (2013.01); *C07D 471/08* (2013.01); *C07D 491/08* (2013.01); *Y02A 50/463* (2018.01)

(58) Field of Classification Search
None
See application file for complete search history.

(56) References Cited

U.S. PATENT DOCUMENTS

| | | | |
|---|---|---|---|
| 5,977,117 A | 11/1999 | Chan et al. | |
| 7,456,218 B2 * | 11/2008 | Yasuma | C07C 59/68 514/568 |

(Continued)

FOREIGN PATENT DOCUMENTS

| | | |
|---|---|---|
| JP | 2005-179281 A | 7/2005 |
| WO | WO 97/25321 A2 | 7/1997 |

(Continued)

OTHER PUBLICATIONS

SciFinder abstract, database CAPLUS Acc. No. 2004:412803, Fukatsu et al., WO 2004/041266 A1 (May 21, 2004).*

(Continued)

*Primary Examiner* — Brian J Davis
(74) *Attorney, Agent, or Firm* — Sterne, Kessler, Goldstein & Fox P.L.L.C.

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

25 Claims, No Drawings
Specification includes a Sequence Listing.

(51) Int. Cl.

| | |
|---|---|
| *A61K 31/4453* | (2006.01) |
| *A61K 31/454* | (2006.01) |
| *A61K 31/4545* | (2006.01) |
| *A61K 31/496* | (2006.01) |
| *A61K 31/5375* | (2006.01) |
| *A61K 31/5377* | (2006.01) |
| *A61K 31/541* | (2006.01) |
| *A61K 45/06* | (2006.01) |
| *C07C 215/20* | (2006.01) |
| *C07C 235/46* | (2006.01) |
| *C07D 205/04* | (2006.01) |
| *C07D 207/12* | (2006.01) |
| *C07D 207/14* | (2006.01) |
| *C07D 207/16* | (2006.01) |
| *C07D 211/22* | (2006.01) |
| *C07D 213/80* | (2006.01) |
| *C07D 213/82* | (2006.01) |
| *C07D 213/85* | (2006.01) |
| *C07D 265/30* | (2006.01) |
| *C07D 401/12* | (2006.01) |
| *C07D 403/12* | (2006.01) |
| *C07D 405/12* | (2006.01) |
| *C07D 405/14* | (2006.01) |
| *C07D 413/14* | (2006.01) |
| *C07D 417/12* | (2006.01) |
| *C07D 417/14* | (2006.01) |
| *C07D 471/04* | (2006.01) |
| *C07D 471/08* | (2006.01) |
| *C07D 491/08* | (2006.01) |

(56) References Cited

U.S. PATENT DOCUMENTS

| | | |
|---|---|---|
| 7,960,369 B2 | 6/2011 | Fukatsu et al. |
| 7,968,552 B2 | 6/2011 | Negoro et al. |
| 9,850,225 B2 | 12/2017 | Chupak et al. |
| 9,872,852 B2 | 1/2018 | Chupak et al. |

FOREIGN PATENT DOCUMENTS

| | | | | |
|---|---|---|---|---|
| WO | WO 2004/007439 A1 | 1/2004 | | |
| WO | WO 2004/041266 A1 * | 5/2004 | ........... | A61K 31/192 |
| WO | WO 2004/080377 A2 | 9/2004 | | |
| WO | WO 2005/080367 A1 | 9/2005 | | |
| WO | WO 2007/017687 A2 | 2/2007 | | |
| WO | WO 2008/130514 A1 | 10/2008 | | |
| WO | WO 2018/009505 A1 | 1/2018 | | |
| WO | WO 2018/044963 A1 | 3/2018 | | |

OTHER PUBLICATIONS

Guzik, K. et al., "Small-Molecule Inhibitors of the Programmed Cell Death-1/Programmed Death-Ligand 1 (PD-1/PD-1) Interaction via Transiently Induced Protein States and Dimerization of PD-L1," Journal of Medicinal Chemistry, 60, pp. 5857-5867 (2017).

Liu, Kefang, et al., "Structural basis of anti-PD-L1 monoclonal antibody avelumab for tumor therapy," Cell Research, 27, pp. 151-153 (2017).

Ohaegbulam, K.C., et al., "Human cancer immunotherapy with antibodies to the PD-1 and PD-L1 pathway," Trends in Molecular Medicine, vol. 21, No. 1, pp. 24-33 (Jan. 2015).

Zak, K.M., et al., "Structural basis for small molecule targeting of the programmed death ligand 1 (PD-L1)," Oncotarget, vol. 7, No. 21, pp. 30323-30335 (2016).

* cited by examiner

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110
```

Ser Leu Arg Ala Glu Leu Arg Val Thr Glu Arg Arg Ala Glu Val Pro
115                 120                 125

Thr Ala His Pro Ser Pro Ser Pro Arg Pro Ala Gly Gln Phe Gln Gly
130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
                180                 185                 190

Thr Pro Glu Val Thr Cys Val Val Val Asp Val Ser His Glu Asp Pro
                195                 200                 205

Glu Val Lys Phe Asn Trp Tyr Val Asp Gly Val Glu Val His Asn Ala
210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
                260                 265                 270

Ile Ser Lys Ala Lys Gly Gln Pro Arg Glu Pro Gln Val Tyr Thr Leu
275                 280                 285

Pro Pro Ser Arg Asp Glu Leu Thr Lys Asn Gln Val Ser Leu Thr Cys
                290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
                355                 360                 365

Leu His Asn His Tyr Thr Gln Lys Ser Leu Ser Leu Ser Pro Gly Lys
370                 375                 380

<210> SEQ ID NO 2
<211> LENGTH: 238
<212> TYPE: PRT
<213> ORGANISM: Homo sapiens

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
                20                  25                  30

Leu Ala Ala Leu Ile Val Tyr Trp Glu Met Glu Asp Lys Asn Ile Ile
                35                  40                  45

Gln Phe Val His Gly Glu Glu Asp Leu Lys Val Gln His Ser Ser Tyr
50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
                100                 105                 110

| | | | | | | | | | | | | |
|---|---|---|---|---|---|---|---|---|---|---|---|---|
| Val | Asn | Ala | Pro | Tyr | Asn | Lys | Ile | Asn | Gln | Arg | Ile | Leu | Val | Val | Asp |
| | | 115 | | | | 120 | | | | | 125 | | | | |
| Pro | Val | Thr | Ser | Glu | His | Glu | Leu | Thr | Cys | Gln | Ala | Glu | Gly | Tyr | Pro |
| 130 | | | | | 135 | | | | | 140 | | | | | |
| Lys | Ala | Glu | Val | Ile | Trp | Thr | Ser | Ser | Asp | His | Gln | Val | Leu | Ser | Gly |
| 145 | | | | | 150 | | | | | 155 | | | | | 160 |
| Lys | Thr | Thr | Thr | Asn | Ser | Lys | Arg | Glu | Glu | Lys | Leu | Phe | Asn | Val | |
| | | | 165 | | | | 170 | | | | | 175 | | | |
| Thr | Ser | Thr | Leu | Arg | Ile | Asn | Thr | Thr | Thr | Asn | Glu | Ile | Phe | Tyr | Cys |
| | | | 180 | | | | 185 | | | | | 190 | | | |
| Thr | Phe | Arg | Arg | Leu | Asp | Pro | Glu | Glu | Asn | His | Thr | Ala | Glu | Leu | Val |
| | | 195 | | | | 200 | | | | | 205 | | | | |
| Ile | Pro | Glu | Leu | Pro | Leu | Ala | His | Pro | Pro | Asn | Glu | Arg | Thr | Gly | Ser |
| | 210 | | | | 215 | | | | | 220 | | | | | |
| Ser | Glu | Thr | Val | Arg | Phe | Gln | Gly | His | His | His | His | His | His | | |
| 225 | | | | | 230 | | | | 235 | | | | | | |

COMPOUNDS USEFUL AS IMMUNOMODULATORS

CROSS-REFERENCE TO RELATED APPLICATIONS

This application claims the benefit of U.S. Provisional Patent Application Ser. No. 62/242,072, filed on Oct. 15, 2015, hereby incorporated by reference in its entirety.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., *Nat. Imm.* 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. *Annu. Rev. Immunol.* 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al., *Immunity* 27:111-122 (2007)). The interaction of PD-L1/CD80 on expressing immune cells has been shown to be an inhibitory one. Blockade of this interaction has been shown to abrogate this inhibitory interaction (Paterson A M, et al., *J Immunol.*, 187:1097-1105 (2011); Yang J et al. *J Immunol.* August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., *New Engl J Med* 2012). Preclinical animal models of tumors have shown that blockade of the PD-1/PD-L1 pathway by monoclonal antibodies can enhance the immune response and result in the immune response to a number of histologically distinct tumors (Dong H, Chen L. *J Mol Med.* 2003; 81(5):281-287; Dong H, Strome S E, Salamoa D R, et al. *Nat Med.* 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. *Nature* 2006; 439(7077):682-687). Humanized mice infected with HIV-1 show enhanced protection against viremia and reduced viral depletion of CD4+ T cells (Palmer et al., *J. Immunol* 2013). Blockade of PD-1/PD-L1 through monoclonal antibodies to PD-L1 can restore in vitro antigen-specific functionality to T cells from HIV patients (Day, *Nature* 2006; Petrovas, *J. Exp. Med.* 2006; Trautman, *Nature Med.* 2006; D'Souza, *J. Immunol.* 2007; Zhang, *Blood* 2007; Kaufmann, *Nature Imm.* 2007; Kasu, *J. Immunol.* 2010; Porichis, *Blood* 2011), HCV patients [Golden-Mason, *J. Virol.* 2007; Jeung, J. Leuk. *Biol.* 2007; Urbani, *J. Hepatol.* 2008; Nakamoto, *PLoS Path.* 2009; Nakamoto, *Gastroenterology* 2008] or HBV patients (Boni, J. *Virol.* 2007; Fisicaro, *Gastro.* 2010; Fisicaro et al., *Gastroenterology*, 2012; Boni et al., *Gastro.*, 2012; Penna et al., *J Hep,* 2012; Raziorrough, *Hepatology* 2009; Liang, *World J Gastro.* 2010; Zhang, *Gastro.* 2008).

Blockade of the PD-L1/CD80 interaction has also been shown to stimulate immunity (Yang J., et al., *J Immunol.* August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., *Nat Rev Immunol* (2013)). These include increased levels of PD-1 and PD-L1 and T cell apoptosis (Guignant, et al, *Crit. Care* (2011)). Antibodies directed to PD-L1 can reduce the level of Immune cell apoptosis (Zhang et al, *Crit. Care* (2011)). Furthermore, mice lacking PD-1 expression are more resistant to septic shock symptoms than wildtype mice (Yang J., et al. *J Immunol.* August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., *The Journal of Experimental Medicine*, vol. 205, no. 3, pp. 543-555, 2008; A. C. Finnefrock, A. Tang, F. Li et al., *The Journal of Immunology*, vol. 182, no. 2, pp. 980-987, 2009; M.-Y. Song, S.-H. Park, H. J. Nam, D.-H. Choi, and Y.-C. Sung, *The Journal of Immunotherapy*, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

In a first aspect the present disclosure provides a compound of formula (I)

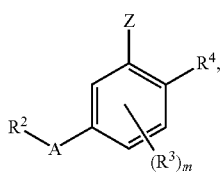

(I)

or a pharmaceutically acceptable salt thereof, wherein:

m is 0, 1, or 2;

Z is hydrogen, —CH$_3$, or —OR$^1$; wherein
  R$^1$ is selected from hydrogen, C$_3$-C$_6$alkenyl, haloC$_1$-C$_4$alkyl, hydroxyC$_1$-C$_4$alkyl, —(CH$_2$)$_n$X, and —(CH$_2$)$_n$Ar;

n is 1, 2, 3, or 4;

X is selected from hydrogen, —CH$_3$, —CF$_3$, C$_1$-C$_4$alkoxy, —N(CH$_3$)$_2$, C$_3$-C$_6$cycloalkyl optionally substituted with one or two halo groups, —CN, —CO$_2$R, —C(O)NH$_2$, —C(O)N(CH$_3$)$_2$,

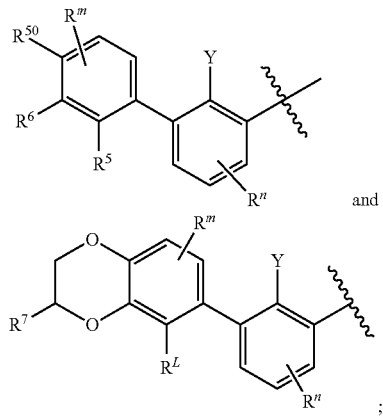

morpholinyl, tetrahydropyranyl, pyrrolidonyl optionally substituted with a hydroxy group, and piperidinyl optionally substituted with one or two groups independently selected from C$_1$-C$_4$alkyl, carboxy, hydroxy, and C$_1$-C$_4$alkoxycarbonyl;

R$^g$ is selected from hydrogen and C$_1$-C$_4$alkyl; and

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from C$_1$-C$_4$alkoxy, C$_1$-C$_4$alkoxycarbonyl, C$_1$-C$_4$alkoxycarbonylamino, C$_1$-C$_4$alkyl, C$_1$-C$_4$alkylcarbonyl, C$_1$-C$_4$alkylsulfonyl, amido, amidoC$_1$-C$_4$alkyl, —(CH$_2$)$_q$CO$_2$C$_1$-C$_4$alkyl, —(CH$_2$)$_q$OH, carboxy, cyano, formyl, halo, haloC$_1$-C$_4$alkyl, haloC$_1$-C$_4$alkoxy, nitro, phenyl optionally substituted with one cyano group, phenyloxy optionally substituted with one halo group, phenylcarbonyl, pyrrole, tetrahydropyran, and

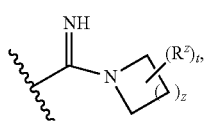

wherein q is 0, 1, 2, 3, or 4 and wherein t, z, and R$^z$ are defined below;

A is selected from —CH$_2$O—, —OCH$_2$—, —(CH$_2$)$_2$—, —CH═CH—, —C(O)NH—, and —NHC(O)—, wherein each group is drawn with its left side attached to R$^2$ and its right side attached to the phenyl ring;

R$^2$ is selected from

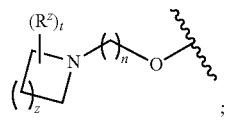

and

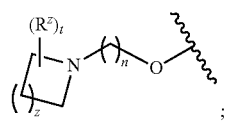

;

wherein

R$^m$ is selected from hydrogen, C$_1$-C$_3$alkyl, —C≡C-Ph, halo, haloC$_1$-C$_3$alkyl, and

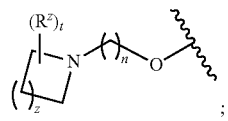

;

R$^n$ is selected from hydrogen, C$_1$-C$_3$alkyl, halo, haloC$_1$-C$_3$alkyl, and

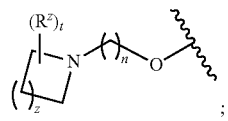

;

Y is selected from hydrogen, C$_1$-C$_3$alkoxy, C$_1$-C$_3$alkyl, cyano, and halo;

R$^5$ is selected from hydrogen, C$_1$-C$_3$alkyl, cyano, halo, haloC$_1$-C$_3$alkyl, and

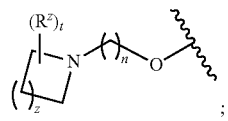

;

R$^L$ is selected from hydrogen, C$_1$-C$_3$alkyl, cyano, halo, and haloC$_1$-C$_3$alkyl;

R$^6$ and R$^{50}$ are selected from hydrogen, —(CH$_2$)NR$^c$R$^d$, —C(O)NR$^c$R$^d$, —NHC(O)(CH$_2$)$_n$NR$^c$R$^d$, —O—(CH$_2$)$_n$C(O)NR$^c$R$^d$, —O—(CH$_2$)$_n$NR$^c$R$^d$, hydroxyC$_1$-C$_6$alkoxy wherein the C$_1$-C$_6$alkoxy is optionally substituted with one or two additional hydroxy groups

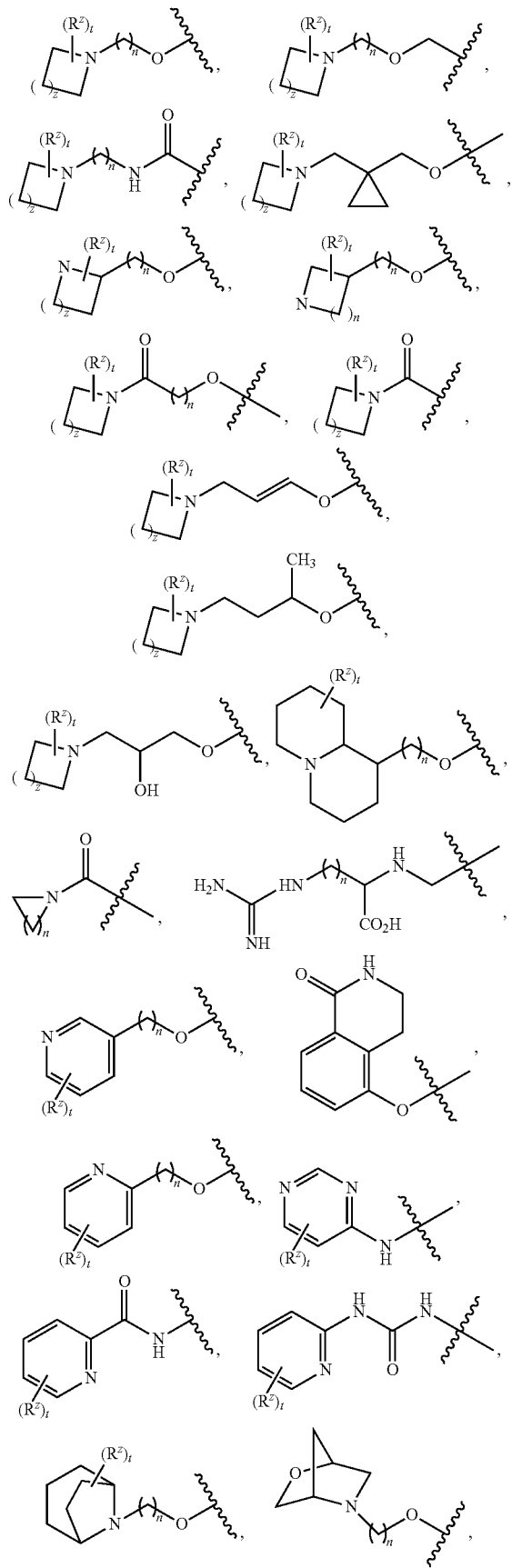
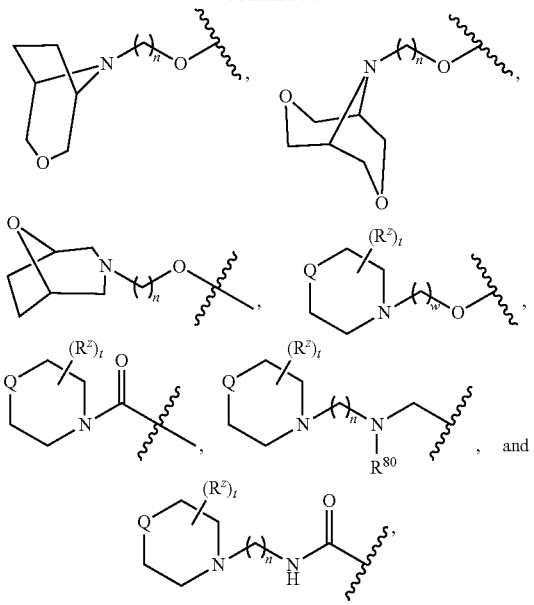

n is 1, 2, 3, or 4;
t is 0, 1, 2, 3, or 4;
w is 1, 2, 3, or 4, provided that when Z is H, —CH$_3$, or —OCH$_3$, w is 3 or 4;
z is 1, 2, or 3;
R$^{80}$ is hydrogen or C$_1$-C$_3$alkyl;
each R$^z$ is independently selected from C$_1$-C$_4$alkoxy, C$_1$-C$_4$alkoxycarbonyl, C$_1$-C$_4$alkoxycarbonylC$_1$-C$_4$alkyl, C$_1$-C$_4$alkyl, C$_1$-C$_4$alkylamido, C$_1$-C$_4$alkylamino, C$_1$-C$_4$alkylcarbonyl, amido, carboxy, carboxyC$_1$-C$_4$alkyl, di(C$_1$-C$_4$alkyl)amido, di(C$_1$-C$_4$alkyl)amino, halo, haloC$_1$-C$_4$alkoxy, haloC$_1$-C$_4$alkyl, hydroxy, hydroxyC$_1$-C$_4$alkyl, morpholinyl, —NR$^c$R$^d$, (NR$^c$R$^d$)C$_1$-C$_4$alkyl, —NR$^e$R$^f$, (NR$^e$R$^f$)C$_1$-C$_4$alkyl, oxo, phenyl, and phenylC$_1$-C$_4$alkyl, wherein the phenyl and the phenyl part of the phenylC$_1$-C$_4$alkyl are optionally substituted with one, two, or three groups independently selected from C$_1$-C$_3$alkyl and halo;
R$^c$ and R$^d$ are independently selected from hydrogen, C$_2$-C$_4$alkenylcarbonyl, C$_1$-C$_4$alkoxycarbonyl, C$_1$-C$_6$alkyl, C$_1$-C$_4$alkylcarbonyl, amidoC$_1$-C$_4$alkyl, aminoC$_1$-C$_4$alkyl, arylC$_1$-C$_4$alkyl, C$_3$-C$_{10}$cycloalkyl, (C$_3$-C$_{10}$cycloalkyl)C$_1$-C$_4$alkyl, haloC$_1$-C$_4$alkylcarbonyl, heterocyclylC$_1$-C$_4$alkyl, heterocyclylC$_1$-C$_4$alkylcarbonyl, hydroxyC$_1$-C$_6$alkyl, and hydroxyC$_1$-C$_4$alkylcarbonyl, wherein the alkyl part of the amidoC$_1$-C$_4$alkyl, the aminoC$_1$-C$_4$alkyl, the arylC$_1$-C$_4$alkyl, the (C$_3$-C$_{10}$cycloalkyl)C$_1$-C$_4$alkyl, the heterocyclylC$_1$-C$_4$alkyl and the heterocyclylC$_1$-C$_4$alkylcarbonyl is optionally substituted with one or two groups independently selected from carboxy and hydroxy; wherein the alkyl part of the hydroxyC$_1$-C$_4$alkyl and the hydroxyC$_1$-C$_4$alkylcarbonyl is optionally substituted with one or two groups independently selected from carboxy and hydroxy; and wherein the aryl part of the arylC$_1$-C$_4$alkyl, the C$_3$-C$_{10}$cycloalkyl, the cycloalkyl part of the (C$_3$-C$_{10}$cycloalkyl)C$_1$-C$_4$alkyl and the heterocyclyl part of the heterocyclylC$_1$-C$_4$alkyl and the heterocyclylC$_1$-C$_4$alkylcarbonyl are each optionally substituted with one, two, or three groups independently selected from $C_1$-$C_4$alkoxycarbonyl, $C_1$-$C_4$alkyl, and halo;

$R^e$ and $R^f$, together with the atom to which they are attached, form a ring selected from morpholine and

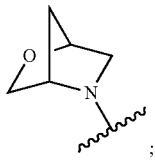
;

Q is selected from S, S(O)$_2$, O, and NR$^p$; wherein R$^p$ is selected from hydrogen, $C_1$-$C_4$alkyl, $C_1$-$C_4$alkylamidoC$_1$-$C_4$alkyl, $C_1$-$C_4$alkylaminoC$_1$-$C_4$alkyl, amidoC$_1$-$C_4$alkyl, aminoC$_1$-$C_4$alkyl, di($C_1$-$C_4$alkyl)amidoC$_1$-$C_4$alkyl, di($C_1$-$C_4$alkyl)aminoC$_1$-$C_3$alkyl, hydroxyC$_1$-$C_4$alkyl, pyridinyl, and phenyl optionally substituted with methoxy;

provided that one of $R^5$, $R^6$, $R^{6'}$, and $R^{50}$ is other than hydrogen; and $R^7$ is hydrogen or

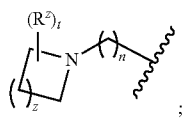
;

wherein n, z, t, and $R^z$ are as defined above in $R^6$; provided that one of $R^L$ and $R^7$ is other than hydrogen;

each $R^3$ is independently selected from $C_2$-$C_4$alkenyl, $C_1$-$C_4$alkoxy, $C_1$-$C_4$alkyl, cyano, halo, and haloC$_1$-$C_4$alkyl; and $R^4$ is selected from —(CH$_2$)$_p$CHO, —(CH$_2$)$_p$CO$_2$H, —(CH$_2$)$_n$OH, —C(O)NR$^{100}$R$^{101}$, —CH(CH$_3$)NR$^q$R$^8$, and —(CH$_2$)$_n$NR$^q$R$^8$; wherein
  $R^{100}$ and $R^{101}$ are selected from hydrogen, $C_1$-$C_6$alkyl, and hydroxy($C_1$-$C_6$alkyl) optionally substituted with an additional hydroxy group; or, $R^{100}$ and $R^{101}$, together with the nitrogen atom to which they are attached, form a six-membered ring optionally substituted with a carboxy group;
  p is 0, 1, 2, or 3;
  n is 1, 2, 3, or 4;
  $R^q$ is selected from hydrogen, $C_1$-$C_4$alkyl, benzyl, ($C_3$-$C_6$cycloalkyl)$C_1$-$C_3$alkyl, haloC$_1$-$C_4$alkyl, hydroxyC$_1$-$C_6$alkyl optionally substituted with a second hydroxy group, and pyridinyl($C_1$-$C_3$alkyl) optionally substituted with a cyano group; and
  $R^8$ is selected from hydrogen, $C_1$-$C_4$alkyl, —(CH$_2$)$_n$N(CH$_3$)$_2$, carboxyC$_2$-$C_6$alkenyl, carboxyC$_1$-$C_6$alkyl, and hydroxyC$_1$-$C_6$alkyl, wherein the alkyl part of the carboxyC$_1$-$C_6$alkyl and the hydroxyC$_1$-$C_6$alkyl is optionally substituted with one hydroxy or phenyl group wherein the phenyl group is further optionally substituted with a hydroxy group;

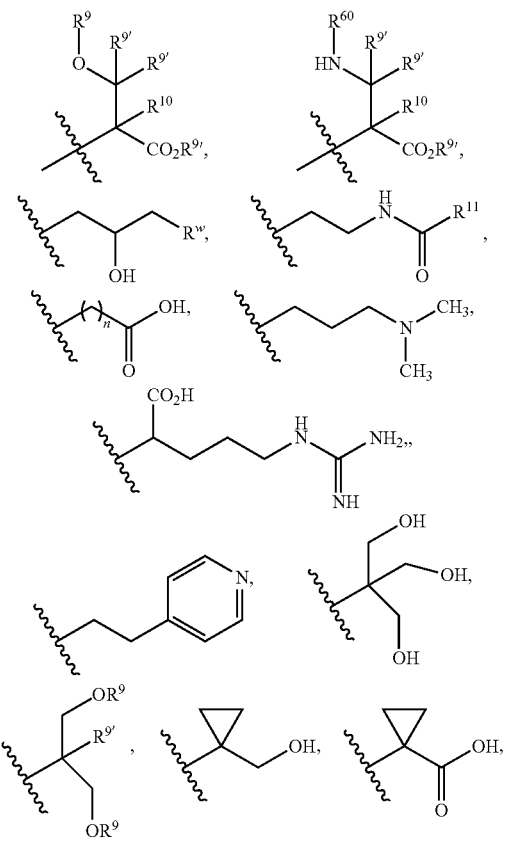

and
$R^w$ is —CONH$_2$,
$R^9$ is selected from hydrogen, benzyl, and methyl;
each $R^{9'}$ is independently selected from hydrogen and $C_1$-$C_3$alkyl;
$R^{10}$ is selected from hydrogen, $C_1$-$C_3$alkyl, and benzyl;
$R^{11}$ is selected from $C_2$-$C_4$alkenyl and $C_1$-$C_4$alkyl; and
$R^{60}$ is selected from hydrogen, $C_1$-$C_6$alkyl, and $C_1$-$C_6$alkoxycarbonyl,
or
$R^8$ and $R^q$, together with the nitrogen atom to which they are attached, form a ring selected from

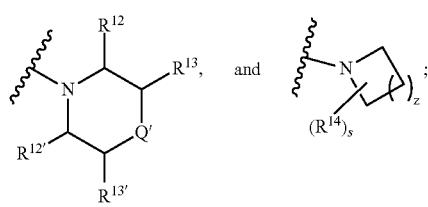

wherein
s is 0, 1, or 2;
z is 1, 2, or 3;
Q' is selected from CHR$^{13''}$, S, O, NH, NC(O)OC$_1$-$C_6$alkyl, N(CH$_2$)$_2$OH, and NCH$_3$;
$R^{12}$ and $R^{12'}$ are independently selected from hydrogen, —CO$_2$H, hydroxyC$_1$-$C_4$alkyl, oxo, and —C(O)NHSO$_2$R$^{16}$;
$R^{13}$ and $R^{13'}$ are independently selected from hydrogen, hydroxyC$_1$-$C_4$alkyl, oxo, and —CO$_2$H;

$R^{13''}$ is selected from hydroxy$C_1$-$C_3$alkyl, and —$CO_2H$;

each $R^{14}$ is independently selected from $C_1$-$C_4$alkoxycarbonyl, $C_1$-$C_6$alkyl, carboxy, halo, hydroxy, hydroxy$C_1$-$C_4$alkyl, —$NR^{c'}R^{d'}$, and phenyloxycarbonyl wherein the phenyl is optionally substituted with a nitro group, wherein $R^{c'}$ and $R^{d'}$ are independently selected from hydrogen, $C_1$-$C_4$alkoxycarbonyl, and $C_1$-$C_4$alkylcarbonyl; and $R^{16}$ is selected from trifluoromethyl, cyclopropyl, $C_1$-$C_4$alkyl, dimethylamino, and imidazolyl substituted with a methyl group.

In a first embodiment the present disclosure provides a compound of formula (I), or a pharmaceutically acceptable salt thereof, wherein Z is —$OR^1$; wherein $R^1$ is selected from hydrogen, $C_3$-$C_6$alkenyl; halo$C_1$-$C_4$alkyl, hydroxy$C_1$-$C_4$alkyl, —$(CH_2)_nX$, and —$(CH_2)_nAr$;

n is 1, 2, 3, or 4;

X is selected from —$CH_3$, —$CF_3$, $C_1$-$C_4$alkoxy, —$N(CH_3)_2$, $C_3$-$C_6$cycloalkyl optionally substituted with one or two halo groups, CN, —$CO_2R^g$, —$C(O)NH_2$, —$C(O)N(CH_3)_2$,

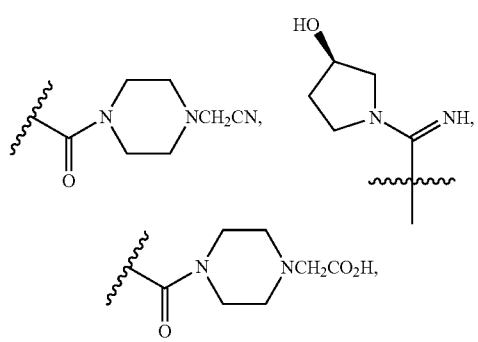

morpholinyl, tetrahydropyranyl, pyrrolidonyl optionally substituted with a hydroxy group, and piperidinyl optionally substituted with one or two groups independently selected from $C_1$-$C_4$alkyl, carboxy, hydroxy, and $C_1$-$C_4$alkoxycarbonyl from hydrogen, methoxy, and —$(CH_2)$pyridinyl substituted with one group selected from methylsulfonyl, amido, and cyano, $R^g$ is selected from hydrogen and $C_1$-$C_4$alkyl; and Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, $C_1$-$C_4$alkylcarbonyl, $C_1$-$C_4$alkylsulfonyl, amido, amido$C_1$-$C_4$alkyl, —$(CH_2)_qCO_2C_1$-$C_4$alkyl, —$(CH_2)_qOH$, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4.

In a second embodiment m is 1 and $R^3$ is halo. In a third embodiment A is —$CH_2O$—. In a fourth embodiment $R^2$ is

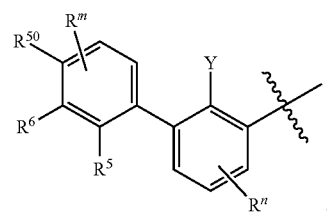

In a fifth embodiment $R^1$ is —$(CH_2)_nAr$, wherein n is 1 and Ar is pyridinyl optionally substituted with one or two groups independently selected from $C_1$-$C_4$alkyl, $C_1$-$C_4$alkylsulfonyl, amido, cyano, and halo. In a sixth embodiment Y and $R^5$ are independently selected from —$CH_3$ and halo. In a seventh embodiment one of $R^6$ and $R^{50}$ is hydrogen and the other is selected from —$O$—$(CH_2)_n$ $NR^cR^d$ and

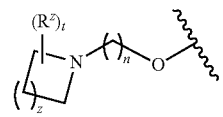

In an eight embodiment the present disclosure provides a compound of formula (I), or a pharmaceutically acceptable salt thereof, wherein Z is —OR; wherein $R^1$ is selected from hydrogen, $C_3$-$C_6$alkenyl; halo$C_1$-$C_4$alkyl, hydroxy$C_1$-$C_4$alkyl, —$(CH_2)_nX$, and —$(CH_2)_nAr$;

n is 1, 2, 3, or 4;

X is selected from —$CH_3$, —$CF_3$, $C_1$-$C_4$alkoxy, —$N(CH_3)_2$, $C_3$-$C_6$cycloalkyl optionally substituted with one or two halo groups, CN, —$CO_2R^9$, —$C(O)NH_2$, —$C(O)N(CH_3)_2$,

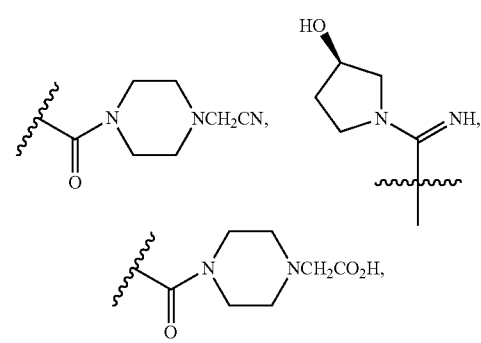

morpholinyl, tetrahydropyranyl, pyrrolidonyl optionally substituted with a hydroxy group, and piperidinyl optionally substituted with one or two groups independently selected from $C_1$-$C_4$alkyl, carboxy, hydroxy, and $C_1$-$C_4$alkoxycarbonyl from hydrogen, methoxy, and —$(CH_2)$pyridinyl substituted with one group selected from methylsulfonyl, amido, and cyano, $R^g$ is selected from hydrogen and $C_1$-$C_4$alkyl; and Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from C$_1$-C$_4$alkoxy, C$_1$-C$_4$alkoxycarbonyl, C$_1$-C$_4$alkoxycarbonylamino, C$_1$-C$_4$alkyl, C$_1$-C$_4$alkylcarbonyl, C$_1$-C$_4$alkylsulfonyl, amido, amidoC$_1$-C$_4$alkyl, —(CH$_2$)$_q$CO$_2$C$_1$-C$_4$alkyl, —(CH$_2$)$_q$OH, carboxy, cyano, formyl, halo, haloC$_1$-C$_4$alkyl, haloC$_1$-C$_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4;

m is 1;
R$^3$ is halo;
A is —CH$_2$O—;
and R$^2$ is

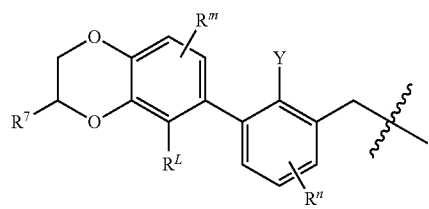

In a second aspect the present disclosure provides a compound of formula (II)

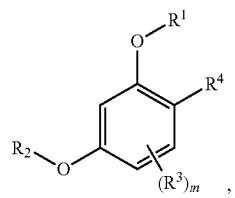

(II)

or a pharmaceutically acceptable salt thereof, wherein:
m is 0, 1, or 2;
R$^1$ is selected from hydrogen, haloC$_1$-C$_4$alkyl, hydroxyC$_1$-C$_4$alkyl, —(CH$_2$)$_n$X, and —(CH$_2$)$_n$Ar; wherein
n is 1, 2, 3, or 4;
X is selected from hydrogen, —CH$_3$, —CF$_3$, C$_1$-C$_4$alkoxy, —N(CH$_3$)$_2$, C$_3$-C$_6$cycloalkyl, CN, —CO$_2$R$^9$, —C(O)NH$_2$,

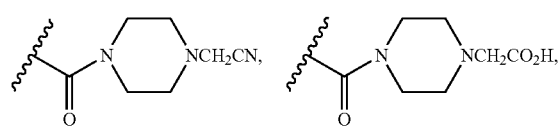

morpholinyl, tetrahydropyranyl, pyrrolidonyl optionally substituted with a hydroxy group, and piperidinyl optionally substituted with one or two groups independently selected from C$_1$-C$_4$alkyl, carboxy, hydroxy, and C$_1$-C$_4$alkoxycarbonyl,
R$^g$ is selected from hydrogen and C$_1$-C$_4$alkyl;
Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from C$_1$-C$_4$alkoxy, C$_1$-C$_4$alkoxycarbonyl, C$_1$-C$_4$alkoxycarbonylamino, C$_1$-C$_4$alkyl, C$_1$-C$_4$alkylcarbonyl, C$_1$-C$_4$alkylsulfonyl, amido, amidoC$_1$-C$_4$alkyl, —(CH$_2$)$_q$CO$_2$C$_1$-C$_4$alkyl, —(CH$_2$)$_q$OH, carboxy, cyano, formyl, halo, haloC$_1$-C$_4$alkyl, haloC$_1$-C$_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4;

R$^2$ is selected from

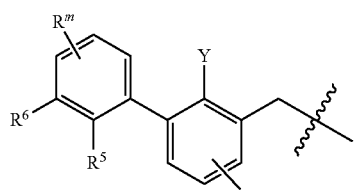

and

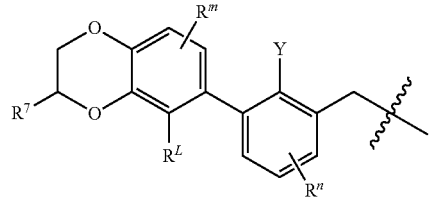

;

wherein
R$^m$ and R$^n$ are selected from hydrogen, C$_1$-C$_3$alkyl, halo, and haloC$_1$-C$_3$alkyl;
Y is selected from hydrogen, C$_1$-C$_3$alkoxy, C$_1$-C$_3$alkyl, cyano, and halo;
R$^5$ and R$^L$ are selected from hydrogen, C$_1$-C$_3$alkyl, cyano, halo, and haloC$_1$-C$_3$alkyl;
R$^6$ is selected from hydrogen, —O—(CH$_2$)$_n$NR$^c$R$^d$,

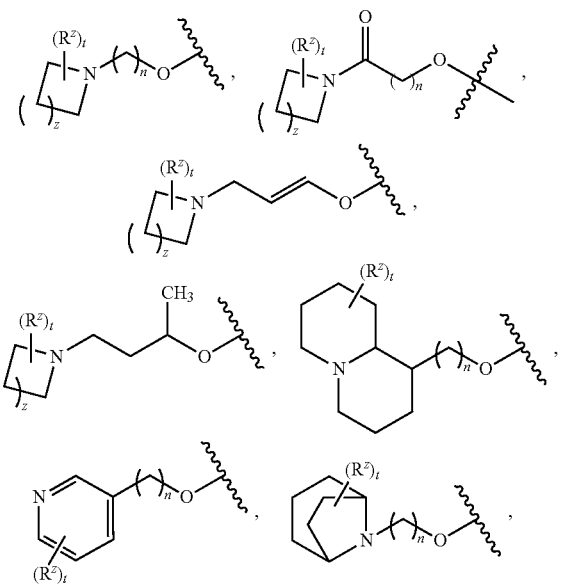

-continued

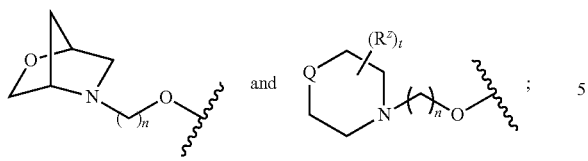

wherein n is 1, 2, 3, or 4;

t is 0, 1, 2, or 3;

z is 1, 2, or 3;

each $R^z$ is independently selected from $C_1$-$C_4$alkoxy, $C_1$-$C_4$alkoxycarbonyl, $C_1$-$C_4$alkoxycarbonyl$C_1$-$C_4$alkyl, $C_1$-$C_4$alkyl, $C_1$-$C_4$alkylamido, $C_1$-$C_4$alkylamino, $C_1$-$C_4$alkylcarbonyl, amido, carboxy, carboxy$C_1$-$C_4$alkyl, di($C_1$-$C_4$alkyl)amido, di($C_1$-$C_4$alkyl)amino, halo, halo$C_1$-$C_4$alkoxy, halo$C_1$-$C_4$alkyl, hydroxy, hydroxy$C_1$-$C_4$alkyl, —$NR^cR^d$, ($NR^cR^d$)$C_1$-$C_4$alkyl, —$NR^eR^f$, ($NR^eR^f$)$C_1$-$C_4$alkyl, phenyl, and phenyl$C_1$-$C_4$alkyl;

$R^c$ and $R^d$ are independently selected from hydrogen, $C_2$-$C_4$alkenylcarbonyl, $C_1$-$C_4$alkoxycarbonyl, $C_1$-$C_6$alkyl, $C_1$-$C_4$alkylcarbonyl, amido$C_1$-$C_4$alkyl, amino$C_1$-$C_4$alkyl, aryl$C_1$-$C_4$alkyl, $C_3$-$C_{10}$cycloalkyl, ($C_3$-$C_{10}$cycloalkyl)$C_1$-$C_4$alkyl, halo$C_1$-$C_4$alkylcarbonyl, heteroaryl$C_1$-$C_4$alkyl, and hydroxy$C_1$-$C_4$alkyl; wherein the alkyl part of the amido$C_1$-$C_4$alkyl, the amino$C_1$-$C_4$alkyl, the aryl$C_1$-$C_4$alkyl, the ($C_3$-$C_{10}$cycloalkyl)$C_1$-$C_4$alkyl, and the heteroaryl$C_1$-$C_4$alkyl is optionally substituted with one or two groups independently selected from carboxy and hydroxy; wherein the alkyl part of the hydroxy$C_1$-$C_4$alkyl is optionally substituted with one or two groups independently selected from carboxy and hydroxy; and wherein the aryl part of the aryl$C_1$-$C_4$alkyl, the $C_3$-$C_{10}$cycloalkyl, the cycloalkyl part of the ($C_3$-$C_{10}$cycloalkyl)$C_1$-$C_4$alkyl and the heteroaryl part of the heteroaryl$C_1$-$C_4$alkyl are each optionally substituted with one, two, or three groups independently selected from $C_1$-$C_4$alkoxycarbonyl, $C_1$-$C_4$alkyl, and halo;

$R^e$ and $R^f$, together with the atom to which they are attached, form a ring selected from morpholine and

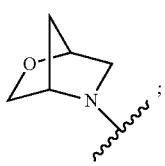

Q is selected from S, O, and $NR^p$; wherein $R^p$ is selected from hydrogen, $C_1$-$C_4$alkyl, $C_1$-$C_4$alkylamido$C_1$-$C_4$alkyl, $C_1$-$C_4$alkylamino$C_1$-$C_4$alkyl, amido$C_1$-$C_4$alkyl, amino$C_1$-$C_4$alkyl, di($C_1$-$C_4$alkyl)amido$C_1$-$C_4$alkyl, di($C_1$-$C_4$alkyl)amino$C_1$-$C_3$alkyl, hydroxy$C_1$-$C_4$alkyl, pyridinyl, and phenyl optionally substituted with methoxy;

provided that one of $R^5$ and $R^6$ is other than hydrogen; and $R^7$ is hydrogen or

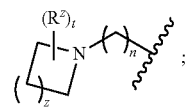

wherein n, z, t, and $R^z$ are as defined above in $R^6$; provided that one of $R^L$ and $R^7$ is other than hydrogen;

each $R^3$ is independently selected from $C_2$-$C_4$alkenyl, $C_1$-$C_4$alkoxy, $C_1$-$C_4$alkyl, cyano, halo, and halo$C_1$-$C_4$alkyl; and $R^4$ is selected from —$(CH_2)_pCHO$, —$(CH_2)_nOH$, and —$(CH_2)_nNR^qR^8$, wherein p is 0, 1, 2, or 3;

n is 1, 2, 3, or 4;

$R^q$ is selected from hydrogen, $C_1$-$C_4$alkyl, and benzyl; and $R^8$ is selected from

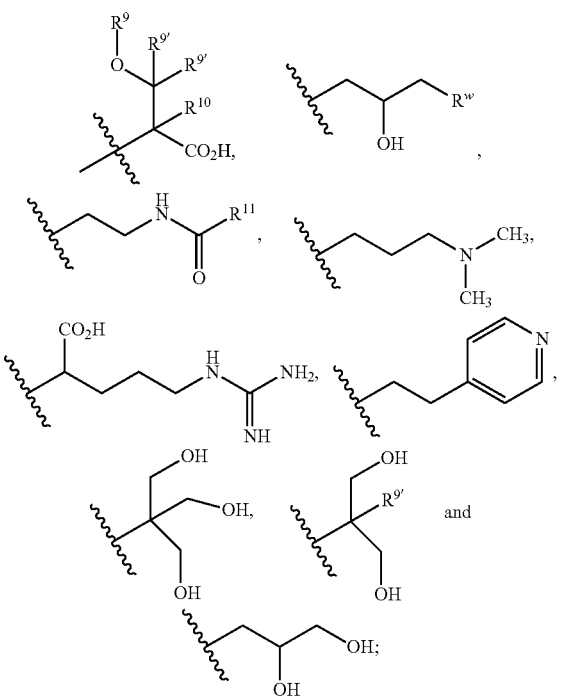

wherein $R^w$ is —$CO_2H$ or —$CONH_2$, $R^9$ is selected from hydrogen, benzyl, and methyl;

each $R^{9'}$ is independently selected from hydrogen and methyl;

$R^{10}$ is selected from hydrogen, $C_1$-$C_3$alkyl, and benzyl; and $R^{11}$ is selected from $C_2$-$C_4$alkenyl and $C_1$-$C_4$alkyl;

or $R^8$ and $R^q$, together with the nitrogen atom to which they are attached, form a ring selected from

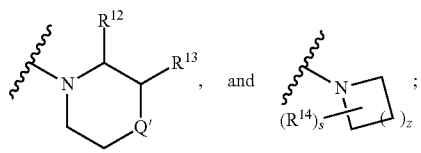

wherein
s is 0, 1, or 2;
z is 1, 2, or 3;
Q' is selected from CHR$^{13'}$, S, O, —N(CH$_2$)$_2$OH, and NCH$_3$;
R$^{12}$ is selected from hydrogen, —CO$_2$H, hydroxyC$_1$-C$_4$alkyl, and —C(O)NHSO$_2$R$^{16}$;
R$^{13}$ is selected from hydrogen, hydroxyC$_1$-C$_4$alkyl, and —CO$_2$H;
R$^{13'}$ is selected from hydroxyC$_1$-C$_3$alkyl, and —CO$_2$H;
R$^{14}$ is selected from C$_1$-C$_4$alkoxycarbonyl, carboxy, halo, hydroxy, hydroxyC$_1$-C$_4$alkyl, and —NR$^{c'}$R$^{d'}$; wherein R$^{c'}$ and R$^{d'}$ are independently selected from hydrogen, C$_1$-C$_4$alkoxycarbonyl, and C$_1$-C$_4$alkylcarbonyl; and
R$^{16}$ is selected from trifluoromethyl, cyclopropyl, C$_1$-C$_4$alkyl, dimethylamino, and imidazolyl substituted with a methyl group.

In a first embodiment of the first second the present disclosure provides a compound of formula (I), or a pharmaceutically acceptable salt thereof, wherein R$^1$ is selected from hydrogen, methoxy, and —(CH$_2$)pyridinyl substituted with one group selected from methylsulfonyl, amido, and cyano.

In a second embodiment of the second aspect the present disclosure provides a compound of formula (I), or a pharmaceutically acceptable salt thereof, wherein R$^1$ is selected from hydrogen, methoxy, and —(CH$_2$)pyridinyl substituted with one group selected from methylsulfonyl, amido, and cyano and R$^2$ is

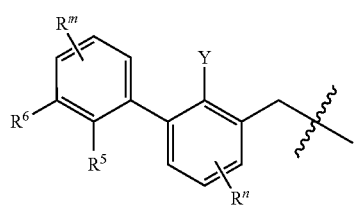

In a third embodiment of the second aspect the present disclosure provides a compound of formula (I), or a pharmaceutically acceptable salt thereof, wherein R$^1$ is selected from hydrogen, methoxy, and —(CH$_2$)pyridinyl substituted with one group selected from methylsulfonyl, amido, and cyano; R$^2$ is

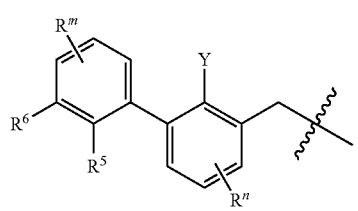

and R$^5$ is hydrogen.

In a fourth embodiment of the second aspect the present disclosure provides a compound of formula (I), or a pharmaceutically acceptable salt thereof, wherein R$^1$ is selected from hydrogen, methoxy, and —(CH$_2$)pyridinyl substituted with one group selected from methylsulfonyl, amido, and cyano; R$^2$ is

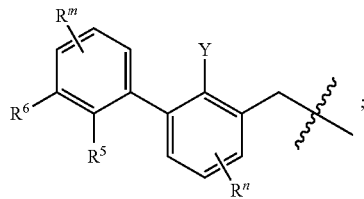

and R$^6$ is hydrogen.

In a fifth embodiment of the second aspect the present disclosure provides a compound of formula I), or a pharmaceutically acceptable salt thereof, wherein R$^2$ is

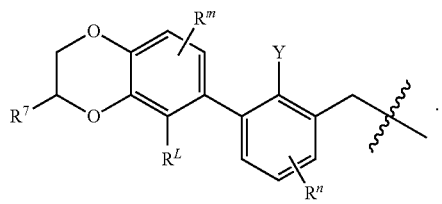

In a sixth embodiment of the second aspect the present disclosure provides a compound of formula (I), or a pharmaceutically acceptable salt thereof, wherein R$^2$ is

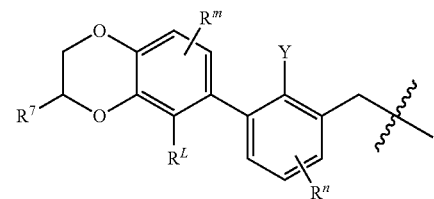

and R$^L$ is hydrogen.

In a seventh embodiment of the second aspect the present disclosure provides a compound of formula (I), or a pharmaceutically acceptable salt thereof, wherein R$^2$ is

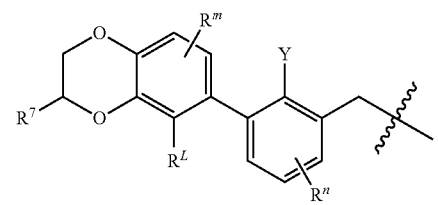

and R$^7$ is hydrogen.

In a third aspect the present disclosure provides a pharmaceutical composition comprising a compound of formula (I), or a pharmaceutically acceptable salt thereof, and a pharmaceutically acceptable carrier.

In a fourth aspect the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the fourth aspect the method further comprises administering an additional agent prior to, after, or simultaneously with the compound of formula (I), or the pharmaceutically acceptable salt thereof. In a second embodiment the additional agent is an antimicrobial agent, an antiviral agent, a cytotoxic agent, a gene expression modulatory agent, and/or an immune response modifier.

In a fifth aspect the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a sixth aspect the present disclosure provides a method of treating an infectious disease in a subject in need thereof, the method comprising administering to the subject a therapeutically effective amount of a compound of formula (I), or a pharmaceutically acceptable salt thereof. In a first embodiment of the sixth aspect the infectious disease is caused by a virus. In a second embodiment the virus is selected from HIV, Hepatitis A, Hepatitis B, Hepatitis C, hepatitis D, herpes viruses, papillomaviruses, and influenza.

In a seventh aspect the present disclosure provides a method of treating septic shock in a subject in need thereof, the method comprising administering to the subject a therapeutically effective amount of a compound of formula (I), or a pharmaceutically acceptable salt thereof.

In an eighth aspect the present disclosure provides a compound of formula (I) or (II) or a pharmaceutically acceptable salt thereof for use as a medicament.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_2$-$C_4$alkenyl," as used herein, refers to a hydrocarbon of two to four carbon atoms that contains one or two double bonds.

The term "$C_2$-$C_6$alkenyl," as used herein, refers to a hydrocarbon of two to six carbon atoms that contains one or two double bonds.

The term "$C_2$-$C_4$alkenylcarbonyl," as used herein, refers to a $C_2$-$C_4$alkenyl group attached to the parent molecular moiety through a carbonyl group.

The term "$C_1$-$C_3$alkoxy," as used herein, refers to a $C_1$-$C_3$alkyl group attached to the parent molecular moiety through an oxygen atom.

The term "$C_1$-$C_4$alkoxy," as used herein, refers to a $C_1$-$C_4$alkyl group attached to the parent molecular moiety through an oxygen atom.

The term "$C_1$-$C_4$alkoxycarbonyl," as used herein, refers to a $C_1$-$C_4$alkoxy group attached to the parent molecular moiety through a carbonyl group.

The term "$C_1$-$C_6$alkoxycarbonyl," as used herein, refers to a $C_1$-$C_6$alkoxy group attached to the parent molecular moiety through a carbonyl group.

The term "$C_1$-$C_4$alkoxycarbonyl$C_1$-$C_4$alkyl," as used herein, refers to a $C_1$-$C_4$alkoxycarbonyl group attached to the parent molecular moiety through a $C_1$-$C_4$alkyl group.

The term "$C_1$-$C_4$alkoxycarbonylamino," as used herein, refers to a $C_1$-$C_4$alkoxycarbonyl group attached to the parent molecular moiety through an —NH group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_4$alkylamido," as used herein, refers to a —C(O)NHR, wherein R is a $C_1$-$C_4$alkyl group.

The term "$C_1$-$C_4$alkylamido$C_1$-$C_4$alkyl," as used herein, refers to a $C_1$-$C_4$alkylamido group attached to the parent molecular moiety through a $C_1$-$C_4$alkyl group.

The term "$C_1$-$C_4$alkylamino," as used herein, refers —NHR, wherein R is a $C_1$-$C_4$alkyl group.

The term "$C_1$-$C_4$alkylamino$C_1$-$C_4$alkyl," as used herein, refers to a $C_1$-$C_4$alkylamino group attached to the parent molecular moiety through a $C_1$-$C_4$alkyl group.

The term "$C_1$-$C_4$alkylcarbonyl," as used herein, refers to a $C_1$-$C_4$alkyl group attached to the parent molecular moiety through a carbonyl group.

The term "$C_1$-$C_4$alkylsulfonyl," as used herein, refers to a $C_1$-$C_4$alkyl group attached to the parent molecular moiety through a sulfonyl group.

The term "amido," as used herein, refers to —C(O)NH$_2$.

The term "amido$C_1$-$C_4$alkyl," as used herein, refers to an amido group attached to the parent molecular moiety through a $C_1$-$C_4$alkyl group.

The term "amino$C_1$-$C_4$alkyl," as used herein, refers to an amino group attached to the parent molecular moiety through a $C_1$-$C_4$alkyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl.

The term "aryl$C_1$-$C_4$alkyl, as used herein, refers to an aryl group attached to the parent molecular moiety through a $C_1$-$C_4$alkyl group.

The term "carbonyl," as used herein, refers to —C(O)—.

The term "carboxy," as used herein, refers to —$CO_2$H.

The term "carboxy$C_2$-$C_6$alkenyl," as used herein, refers to a carboxy group attached to the parent molecular moiety through a $C_2$-$C_6$alkenyl group.

The term "carboxy$C_1$-$C_4$alkyl," as used herein, refers to a carboxy group attached to the parent molecular moiety through a $C_1$-$C_4$alkyl group.

The term "carboxy$C_1$-$C_6$alkyl," as used herein, refers to a carboxy group attached to the parent molecular moiety through a $C_1$-$C_6$alkyl group.

The term "cyano," as used herein, refers to —CN.

The term "$C_3$-$C_6$cycloalkyl," as used herein, refers to a saturated monocyclic hydrocarbon ring system having three to six carbon atoms and zero heteroatoms. Representative examples of cycloalkyl groups include, but are not limited to, cyclopropyl, cyclobutyl, cyclopentyl, and cyclohexyl.

The term "$C_3$-$C_{10}$cycloalkyl," as used herein, refers to a saturated monocyclic, hydrocarbon ring system having three to ten carbon atoms and zero heteroatoms. Representative examples of cycloalkyl groups include, but are not limited to, cyclopropyl, cyclobutyl, cyclopentyl, and cyclohexyl. The cycloalkyl groups containing between seven and ten atoms may be monocyclic or fused, spirocyclic, or bridged bicyclic structures.

The term "($C_3$-$C_6$cycloalkyl)$C_1$-$C_3$alkyl," as used herein, refers to a $C_1$-$C_3$alkyl group substituted with a $C_3$-$C_6$cycloalkyl group.

The term ($C_3$-$C_{10}$cycloalkyl)$C_1$-$C_4$alkyl," as used herein refers to a $C_3$-$C_{10}$cycloalkyl group attached to the parent molecular moiety through a $C_1$-$C_4$alkyl group.

The term "di($C_1$-$C_4$alkyl)amido," as used herein, refers to —C(O)$NR_2$, wherein each R is a $C_1$-$C_4$alkyl group. The R groups may be the same or different.

The term "di($C_1$-$C_4$alkyl)amido$C_1$-$C_4$alkyl," as used herein, refers to a di($C_1$-$C_4$alkyl)amido group attached to the parent molecular moiety through a $C_1$-$C_4$alkyl group.

The term "di($C_1$-$C_4$alkyl)amino," as used herein, refers to —$NR_2$, wherein each R is a $C_1$-$C_4$alkyl group. The R groups may be the same or different.

The term "di($C_1$-$C_4$alkyl)amino$C_1$-$C_4$alkyl," as used herein, refers to a di($C_1$-$C_4$alkyl)amino group attached to the parent molecular moiety through a $C_1$-$C_4$alkyl group.

The term "formyl," as used herein, refers to —C(O)H.

The terms "halo" and "halogen," as used herein, refer to F, $C_1$, Br, or I.

The term "halo$C_1$-$C_4$alkoxy," as used herein, refers to a halo$C_1$-$C_4$alkyl group attached to the parent molecular moiety through an oxygen atom.

The term "halo$C_1$-$C_3$alkyl," as used herein, refers to a $C_1$-$C_3$alkyl group substituted with one, two, or three halogen atoms.

The term "halo$C_1$-$C_4$alkyl," as used herein, refers to a $C_1$-$C_4$alkyl group substituted with one, two, or three halogen atoms.

The term "halo$C_1$-$C_4$alkylcarbonyl," as used herein, refers to a halo$C_1$-$C_4$alkyl group attached to the parent molecular moiety through a carbonyl group.

The term "heteroaryl," as used herein, refers to a five- or six-membered ring aromatic containing one, two, or three heteroatoms independently selected from nitrogen, oxygen, and sulfur. The five-membered ring has two double bonds and the six-membered ring has three double bonds. Examples of heteroaryl groups include, but are not limited to, furyl, imidazolyl, pyrazolyl, pyridinyl, pyrrolyl, thiazolyl, and thienyl.

The term "heteroaryl$C_1$-$C_4$alkyl," as used herein, refers to a heteroaryl group attached to the parent molecular moiety through a $C_1$-$C_4$alkyl group.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oct-2-yl, 2,5-diazabicyclo[2.2.1]heptan-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, oxetanyl, piperazinyl, piperidinyl, pyrazolyl, pyridinyl, pyrrolidinyl, pyrrolopyridinyl, pyrrolyl, quinolinyl, tetrahydrofuranyl, tetrahydropyranyl, thiazolyl, thienyl, and thiomorpholinyl.

The term "heterocyclyl$C_1$-$C_4$alkyl," as used herein, refers to a $C_1$-$C_4$alkyl group substituted with one heterocyclyl group.

The term "heterocyclyl$C_1$-$C_4$alkylcarbonyl, as used herein, refers to a heterocyclyl$C_1$-$C_4$alkyl group attached to the parent molecular moiety through a carbonyl group. The heterocyclyl$C_1$-$C_4$alkyl group is attached to the carbonyl group through the $C_1$-$C_4$alkyl group.

The term "hydroxy," as used herein, refers to —OH.

The term "hydroxy$C_1$-$C_6$alkoxy," as used herein, refers to a $C_1$-$C_6$alkoxy group substituted with a hydroxy group.

The term "hydroxy$C_1$-$C_4$alkyl," as used herein, refers to a hydroxy group attached to the parent molecular moiety through a $C_1$-$C_4$alkyl group.

The term "hydroxy$C_1$-$C_6$alkyl," as used herein, refers to a hydroxy group attached to the parent molecular moiety through a $C_1$-$C_6$alkyl group.

The term "hydroxy$C_1$-$C_4$alkylcarbonyl," as used herein, refers to a hydroxy$C_1$-$C_4$alkyl group attached to the parent molecular moiety through a carbonyl group. The hydroxy$C_1$-$C_4$alkyl group is attached to the carbonyl group through the $C_1$-$C_4$alkyl group.

The term "(NR$^c$R$^d$)$C_1$-$C_4$alkyl," as used herein, refers to an NR$^c$R$^d$ group attached to the parent molecular moiety through a $C_1$-$C_4$alkyl group.

The term "(NR$^e$R$^f$)$C_1$-$C_4$alkyl," as used herein, refers to an NR$^e$R$^f$ group attached to the parent molecular moiety through a $C_1$-$C_4$alkyl group.

The term "nitro," as used herein, refers to —$NO_2$.

The term "oxo," as used herein, refers to =O.

The term "phenyl$C_1$-$C_4$alkyl," as used herein, refers to a phenyl group attached to the parent molecular moiety through a $C_1$-$C_4$alkyl group.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The term "pyridinyl($C_1$-$C_3$)alkyl," as used herein, refers to a pyridinyl group attached to the parent molecular moiety through a $C_1$-$C_3$alkyl group.

The term "sulfonyl," as used herein, refers to —$SO_2O$—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as septic shock, HIV or Hepatitis B, Hepatitis C, and Hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005)*Int. Immunol.* 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) Nature 393: 474-478) and can be used in conjunction with PD-L1 blockade (Ito, N. et al. (2000) Immunobiology 201 (5) 527-40). Activating compounds to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, Giardia, Malaria, Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the disclosure include Candida (albicans, krusei, glabrata, tropicalis, etc.), Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis and Histoplasma capsulatum.

Some examples of pathogenic parasites causing infections treatable by methods of the disclosure include Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, and Nippostrongylus brasiliensis.

In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) Proc. Natl. Acad. Sci. U.S.A. 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) J. Immunother Emphasis Tumor Immunol 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta.peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of formula (I) inhibit the PD-1/PD-L1 interaction with $IC_{50}$ values of 20 μM or less, for example, from 0.48 to 20 μM, as measured by the PD-1/PD-L1 Homogenous Time-Resolved Fluorescence (HTRF) binding assay.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

As used in the present specification, the following terms have the meanings indicated: THF for tetrahydrofuran, min for minutes, rt or RT or Rt for room temperature or retention time (context will dictate), h or hr for hours, EtOAc for ethyl acetate, DCM for dichloromethane, Me for methyl, MeOH for methanol, DMF for N,N-dimethylformamide, DMSO for dimethylsulfoxide, TFA for trifluoroacetic acid, DIPEA for diisopropylethyl amine, TBTU for O-benzotriazole-1-yl-1,1,3,3-tetramethyluronium tetrafluoroborate, hex for hexanes, Dibal-H or DIBAL-H for diisobutylaluminum hydride, Tf$_2$O for trifluoromethanesulfonic anhydride, p-TsOH for para-tolysulfonic acid, DAST for (diethylamino)sulfur trifluoride, EtOH for ethanol, dppf for 1,1'-bis(diphenylphosphino)ferrocene, Ph for phenyl, DIAD for diethyl azodicarboxylate, TBS for tri-butylsilyl, ACN or MeCN for acetonitrile, TEA for triethylamine, OAc for acetate, AcOH for acetic acid, sat'ed or sat'd for saturated, and DCE for dichlorethane.

Examples 1001 to 1087 were prepared as described below.

LC-MS Methods
Condition N-1:
Column=Phenomenex, 2.0×50 mm, 3 μm
Start % B=0; Final % B=100
Gradient time=4 min; Stop time=5 min
Flow Rate=0.8 mL/min; Wavelength=220 nm
Solvent A=0.1% TFA in 10% methanol/90% water
Solvent B=0.1% TFA in 90% methanol/10% water
Oven temp.=40° C.

Intermediate: (2-methyl-3'-(2-morpholinoethoxy)-[1,1'-biphenyl]-3-yl)methanol

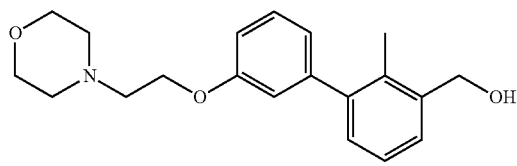 [SMILES: Cc1c(CO)cccc1-c1cccc(OCCN2CCOCC2)c1]

A mixture of 4-(2-(3-bromophenoxy)ethyl)morpholine (0.404 g, 1.411 mmol) and (2-methyl-3-(4,4,5,5-tetramethyl-1,3,2-dioxaborolan-2-yl)phenyl)methanol (0.35 g, 1.411 mmol) in THF (7 ml) and 0.5 M aq potassium phosphate, tribasic (7.08 ml, 3.54 mmol) was stirred under N$_2$ sparging for 15 min, then added with 2nd gen. XPhos precatalyst (0.033 g, 0.042 mmol), sparging was continued for 10 min. The reaction mixture was stirred at rt under N$_2$ for 16 h. The reaction was diluted with EtOAc, washed with brine, dried over anhydrous Na$_2$SO$_4$, filtered and concentrated to yield a dark oil, which was purified on silica gel column (0-20% DCM/MeOH) to yield (2-methyl-3'-(2-morpholinoethoxy)-[1,1'-biphenyl]-3-yl)methanol (0.4 g, 1.222 mmol, 87% yield). LC/MS (Cond. N-1): [M+H]$^+$ 328.3, RT (Retention Time)=2.67 min. $^1$H NMR (400 MHz, CHLOROFORM-d) δ ppm 7.43-7.37 (m, 1H), 7.32 (t, J=7.9 Hz, 1H), 7.28-7.23 (m, 1H), 7.22-7.17 (m, 1H), 6.94-6.87 (m, 2H), 6.85 (dd, J=2.3, 1.8 Hz, 1H), 4.78 (s, 2H), 4.15 (t, J=5.8 Hz, 2H), 3.79-3.69 (m, 4H), 2.83 (t, J=5.6 Hz, 2H), 2.64-2.55 (m, 4H), 2.25 (s, 3H).

Intermediate: 5-chloro-2-hydroxy-4-((2-methyl-3'-(2-morpholinoethoxy)-[1,1'-biphenyl]-3-yl)methoxy)benzaldehyde

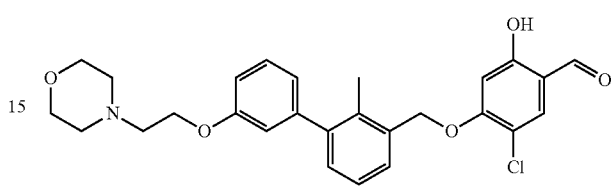

To a solution of (2-methyl-3'-(2-morpholinoethoxy)-[1,1'-biphenyl]-3-yl)methanol (0.2 g, 0.611 mmol), 5-chloro-2,4-dihydroxybenzaldehyde (0.116 g, 0.672 mmol), and triphenylphosphine (0.192 g, 0.733 mmol) in THF (5 ml) was added diisopropyl azodicarboxylate (0.144 ml, 0.733 mmol) in THF (2 mL) at 0° C. The resulting mixture was stirred at room temperature for 16 h. The solvent was diluted with EtOAc and sat. NaHCO$_3$, the organic phase was washed with sat. NaCl, dried over anhydrous Na$_2$SO$_4$, filtered and concentrated. The residue was purified by silica chromatography (0-10% DCM/MeOH) to yield 5-chloro-2-hydroxy-4-((2-methyl-3'-(2-morpholinoethoxy)-[1,1'-biphenyl]-3-yl)methoxy)benzaldehyde (0.15 g, 0.311 mmol, 51.0% yield). LC/MS (Cond. N-1): [M+H]$^+$ 482.3, RT=3.629 min.

Intermediate: 5-((4-chloro-2-formyl-5-((2-methyl-3'-(2-morpholinoethoxy)-[1,1'-biphenyl]-3-yl)methoxy)phenoxy)methyl)nicotinonitrile

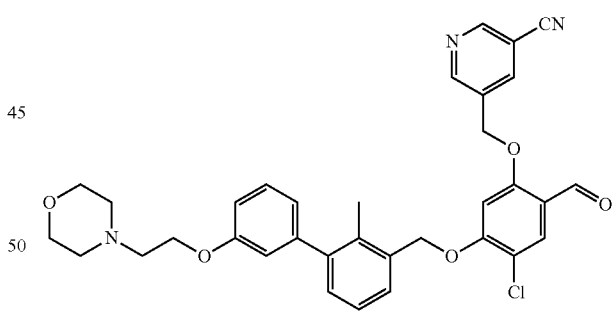

To a stirred mixture of 5-chloro-2-hydroxy-4-((2-methyl-3'-(2-morpholinoethoxy)-[1,1'-biphenyl]-3-yl)methoxy)benzaldehyde (0.15 g, 0.311 mmol) and 5-(chloromethyl)nicotinonitrile, HCl (0.118 g, 0.622 mmol) in DMF (5 mL) was added Cs$_2$CO$_3$ (0.223 g, 0.685 mmol), NaI (4.67 mg, 0.031 mmol). The reaction mixture was heated at 75° C. for 3 h, then allowed to cool to rt. The reaction was diluted with EtOAc and water, the organic phase was washed with sat. NaCl and dried over anhydrous Na$_2$SO$_4$, filtered and concentrated. The residue was purified by silica chromatography (0-50% EtOAC in hexane) to yield 5-((4-chloro-2-formyl-5-((2-methyl-3'-(2-morpholinoethoxy)-[1,1'-biphenyl]-3-yl)methoxy)phenoxy)methyl)nicotinonitrile (0.08 g, 0.134 mmol, 43.0% yield) as a white solid. LC/MS (Cond. N-1): m/z 597.2, RT=3.713 min.

Example 1001: (R)-2-((5-chloro-2-((5-cyanopyridin-3-yl)methoxy)-4-((2-methyl-3'-(2-morpholinoethoxy)-[1,1'-biphenyl]-3-yl)methoxy)benzyl)amino)-3-hydroxypropanoic Acid

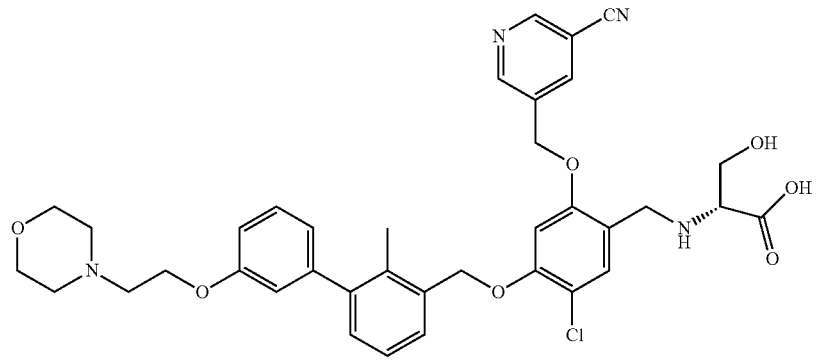 [SMILES: Cc1c(COc2cc(OCc3cncc(C#N)c3)c(CN[C@H](CO)C(=O)O)cc2Cl)cccc1-c1cccc(OCCN2CCOCC2)c1]

To a reaction mixture of (R)-2-amino-3-hydroxypropanoic acid (0.042 g, 0.401 mmol), 5-((4-chloro-2-formyl-5-((2-methyl-3'-(2-morpholinoethoxy)-[1,1'-biphenyl]-3-yl)methoxy)phenoxy)methyl)nicotinonitrile (0.08 g, 0.134 mmol) in DMF (1 mL) was added sodium triacetoxyhydroborate (0.085 g, 0.401 mmol) and acetic acid (0.01 mL). Then the reaction mixture was stirred at rt for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation.

The yield of the product was 10.5 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 687.25, RT=1.59 min. Proton NMR was acquired in deuterated DMSO. $^1$H NMR (500 MHz, DMSO-d$_6$) δ ppm 9.01 (s, 1H), 9.03 (s, 1H), 8.52 (s, 1H), 7.95 (s, 1H), 7.52 (s, 1H), 7.48 (d, J=7.7 Hz, 1H), 7.36 (t, J=7.9 Hz, 1H), 7.28 (t, J=7.5 Hz, 1H), 7.22 (d, J=7.3 Hz, 1H), 7.14 (s, 1H), 6.96 (d, J=8.1 Hz, 1H), 6.89-6.83 (m, 2H), 5.41-5.31 (m, 2H), 5.28 (s, 2H), 4.13 (t, J=5.5 Hz, 2H), 4.01 (q, J=13.2 Hz, 2H), 3.74-3.67 (m, 1H), 3.62 (dd, J=11.2, 6.4 Hz, 1H), 3.57 (t, J=4.2 Hz, 4H), 3.15 (br. s., 1H), 2.92-2.83 (m, 1H), 2.73 (s, 1H), 2.70 (t, J=5.7 Hz, 2H), 2.47 (br. s., 4H), 2.24 (s, 3H).

Example 1002: (S)-2-((5-chloro-2-((5-cyanopyridin-3-yl)methoxy)-4-((2-methyl-3'-(2-morpholinoethoxy)-[1,1'-biphenyl]-3-yl)methoxy)benzyl)amino)-3-hydroxy-2-methylpropanoic Acid

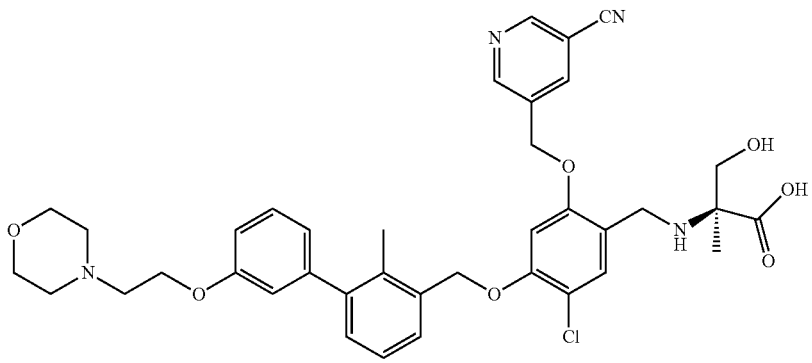 [SMILES: Cc1c(COc2cc(OCc3cncc(C#N)c3)c(CN[C@@](C)(CO)C(=O)O)cc2Cl)cccc1-c1cccc(OCCN2CCOCC2)c1]

Example 1002 was prepared from (S)-2-amino-3-hydroxy-2-methylpropanoic acid, 5-((4-chloro-2-formyl-5-((2-methyl-3'-(2-morpholinoethoxy)-[1,1'-biphenyl]-3-yl)methoxy)phenoxy)methyl)nicotinonitrile, according to the reductive amination conditions as described for Example 1001. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 701.26, RT=1.60 min. Proton NMR was acquired in deuterated DMSO. $^1$H NMR (500 MHz, DMSO-d$_6$) δ ppm 9.02 (d, J=8.1 Hz, 2H), 8.51 (s, 1H), 7.95 (s, 1H), 7.54 (s, 1H), 7.48 (d, J=7.7 Hz, 1H), 7.36 (t, J=7.9 Hz, 1H), 7.28 (t, J=7.5 Hz, 1H), 7.23 (d, J=7.3 Hz, 1H), 7.13 (s, 1H), 6.97 (d, J=7.3 Hz, 1H), 6.90-6.83 (m, 2H), 5.36 (s, 2H), 5.29 (s, 2H), 4.13 (t, J=5.5 Hz, 2H), 3.91 (s, 2H), 3.60-3.53 (m, 5H), 3.53-3.48 (m, 1H), 2.90 (s, 1H), 2.74 (s, 1H), 2.71 (t, J=5.5 Hz, 2H), 2.25 (s, 3H), 1.23-1.18 (m, 3H).

Intermediate: Tert-butyl 2-((3'-((2-chloro-5-((5-cyanopyridin-3-yl)methoxy)-4-formylphenoxy)methyl)-2'-methyl-[1,1'-biphenyl]-3-yl)oxy)acetate

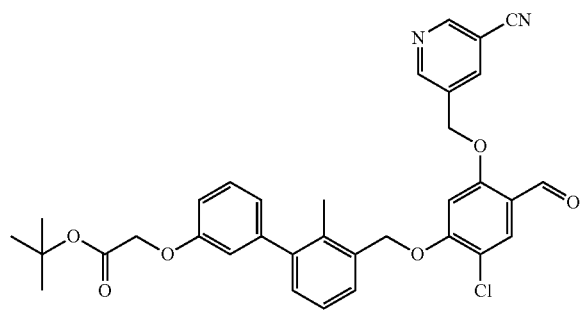 [SMILES: Cc1c(COc2cc(OCc3cncc(C#N)c3)c(C=O)cc2Cl)cccc1-c1cccc(OCC(=O)OC(C)(C)C)c1]

Tert-butyl 2-((3'-((2-chloro-5-((5-cyanopyridin-3-yl)methoxy)-4-formylphenoxy)methyl)-2'-methyl-[1,1'-biphenyl]-3-yl)oxy)acetate was prepared from tert-butyl 2-(3-bromophenoxy)acetate following the procedure described for 5-((4-chloro-2-formyl-5-((2-methyl-3'-(2-morpholinoethoxy)-[1,1'-biphenyl]-3-yl)methoxy)phenoxy)methyl)nicotinonitrile. $^1$H NMR (400 MHz, CHLOROFORM-d) δ ppm 10.28 (s, 1H), 8.91 (t, J=1.9 Hz, 2H), 8.11 (t, J=2.1 Hz, 1H), 7.92 (s, 1H), 7.44 (dd, J=6.1, 2.9 Hz, 1H), 7.35 (t, J=7.9 Hz, 1H), 7.31-7.27 (m, 2H), 6.97-6.84 (m, 3H), 6.67 (s, 1H), 5.25 (d, J=3.0 Hz, 4H), 4.56 (s, 2H), 2.27 (s, 3H), 1.52-1.44 (m, 9H).

Intermediate: 2-((3'-((2-chloro-5-((5-cyanopyridin-3-yl)methoxy)-4-formylphenoxy)methyl)-2'-methyl-[1,1'-biphenyl]-3-yl)oxy)acetic Acid

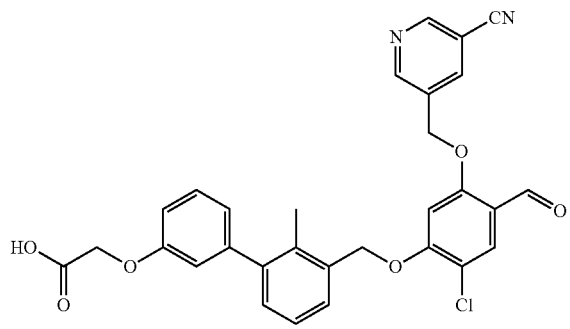 [SMILES: Cc1c(COc2cc(OCc3cncc(C#N)c3)c(C=O)cc2Cl)cccc1-c1cccc(OCC(=O)O)c1]

A mixture of tert-butyl 2-((3'-((2-chloro-5-((5-cyanopyridin-3-yl)methoxy)-4-formylphenoxy)methyl)-2'-methyl-[1,1'-biphenyl]-3-yl)oxy)acetate (0.27 g, 0.451 mmol) and TFA (0.694 mL, 9.01 mmol) in DCM (5 mL) was stirred at rt for 3 h. The reaction mixture was concentrated to dryness to yield 2-((3'-((2-chloro-5-((5-cyanopyridin-3-yl)methoxy)-4-formylphenoxy)methyl)-2'-methyl-[1,1'-biphenyl]-3-yl)oxy)acetic acid (0.3 g, 0.457 mmol, 100% yield). LC/MS (Cond. N-1): [M+H]$^+$ 542.2, RT=4.13 min.

Intermediate: (S)-5-((4-chloro-2-formyl-5-((3'-(2-(3-hydroxypyrrolidin-1-yl)-2-oxoethoxy)-2-methyl-[1,1'-biphenyl]-3-yl)methoxy)phenoxy)methyl)nicotinonitrile

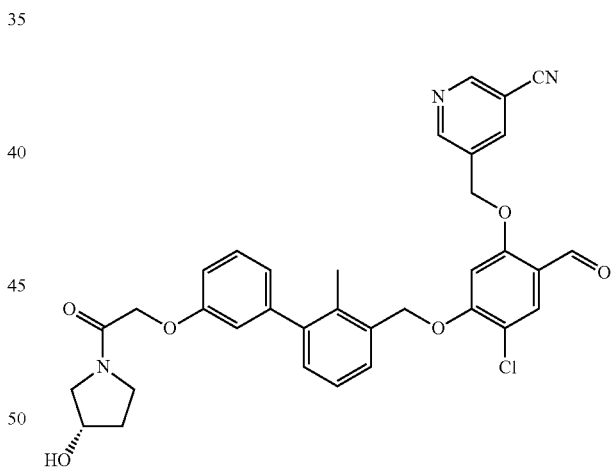

To a mixture of 2-((3'-((2-chloro-5-((5-cyanopyridin-3-yl)methoxy)-4-formylphenoxy)methyl)-2'-methyl-[1,1'-biphenyl]-3-yl)oxy)acetic acid (0.1 g, 0.184 mmol) and (S)-pyrrolidin-3-ol, HCl (0.030 g, 0.239 mmol) in DCM (1 mL) was added DIPEA (0.129 mL, 0.737 mmol) and TBTU (0.077 g, 0.239 mmol) at rt. The reaction mixture was stirred at rt for 3 h. The reaction was diluted with EtOAc, sat. NaHCO$_3$, the organic phase was washed with sat. NaCl, dried over anhydrous Na$_2$SO$_4$, filtered and concentrated. The residue was purified by silica gel chromatography (0-15% MeOH/DCM) to afford (S)-5-((4-chloro-2-formyl-5-((3'-(2-(3-hydroxypyrrolidin-1-yl)-2-oxoethoxy)-2-methyl-[1,1'-biphenyl]-3-yl)methoxy)phenoxy)methyl)nicotinonitrile (0.094 g, 0.154 mmol, 83% yield) as a white solid. LC/MS (Cond. N-1): [M+H]+ 612.3, RT=4.0 min. $^1$H NMR (400 MHz, CHLOROFORM-d) δ ppm 10.29 (s, 1H), 8.91 (d, J=2.0 Hz, 2H), 8.14-8.08 (m, 1H), 7.93 (s, 1H), 7.46-7.40 (m, 1H), 7.36 (t, J=7.9 Hz, 1H), 7.30-7.28 (m, 2H), 6.98-6.93 (m, 2H), 6.93-6.88 (m, 1H), 6.65 (s, 1H), 5.25 (d, J=3.5 Hz, 4H), 4.68 (d, J=11.3 Hz, 2H), 3.81-3.52 (m, 5H), 2.32-2.22 (m, 3H), 2.09 (td, J=5.8, 3.1 Hz, 1H), 1.98 (tt, J=8.7, 4.5 Hz, 1H).

Example 1003: (R)-2-((5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)amino)-3-hydroxypropanoic Acid

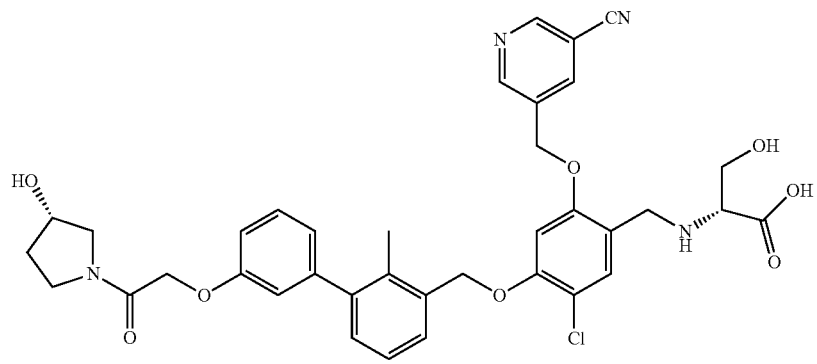 [SMILES: Cc1c(COc2cc(OCc3cncc(C#N)c3)c(CN[C@H](CO)C(=O)O)cc2Cl)cccc1-c1cccc(OCC(=O)N2CC[C@H](O)C2)c1]

To a reaction mixture of (R)-2-amino-3-hydroxypropanoic acid (0.019 g, 0.177 mmol), (S)-5-((4-chloro-2-formyl-5-((3'-(2-(3-hydroxypyrrolidin-1-yl)-2-oxoethoxy)-2-methyl-[1,1'-biphenyl]-3-yl)methoxy)phenoxy)methyl)nicotinonitrile (0.031 g, 0.051 mmol) in DMF (1 mL) was added acetic acid (0.014 mL, 0.253 mmol). The reaction mixture was stirred at rt for 1 h. Then sodium cyanoborohydride (0.011 g, 0.177 mmol) was added. The reaction mixture was stirred at rt for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]+ 701.23, RT=1.34 min. Proton NMR was acquired in deuterated DMSO. $^1$H NMR (500 MHz, DMSO-d$_6$) δ ppm 9.01 (s, 1H), 9.03 (s, 1H), 8.52 (s, 1H), 7.95 (s, 1H), 7.52-7.45 (m, 2H), 7.36 (t, J=7.9 Hz, 1H), 7.28 (t, J=7.7 Hz, 1H), 7.22 (d, J=7.3 Hz, 1H), 7.13 (s, 1H), 6.93 (d, J=8.8 Hz, 1H), 6.89 (d, J=7.3 Hz, 1H), 6.85 (s, 1H), 5.40-5.32 (m, 2H), 5.28 (s, 2H), 4.78 (s, 1H), 4.73 (s, 1H), 4.01-3.89 (m, 2H), 3.68-3.08 (m, 8H), 2.24 (s, 3H), 1.97-1.77 (m, 2H).

Example 1004: (S)-2-((5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)amino)-3-hydroxy-2-methylpropanoic Acid

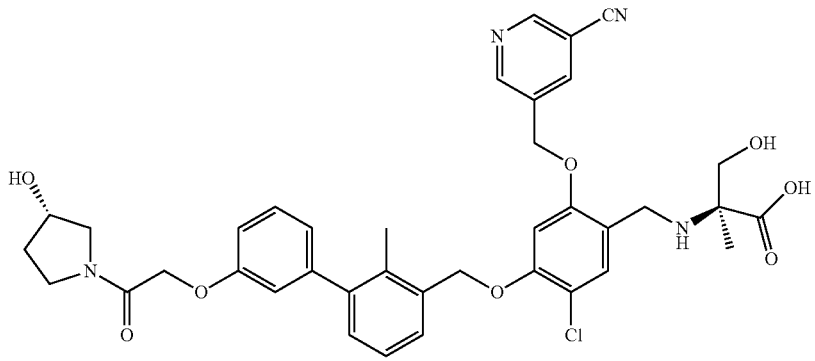 [SMILES: Cc1c(COc2cc(OCc3cncc(C#N)c3)c(CN[C@@](C)(CO)C(=O)O)cc2Cl)cccc1-c1cccc(OCC(=O)N2CC[C@H](O)C2)c1]

Example 1004 was prepared from (S)-2-amino-3-hydroxy-2-methylpropanoic acid, (S)-5-((4-chloro-2-formyl-5-((3'-(2-(3-hydroxypyrrolidin-1-yl)-2-oxoethoxy)-2- methyl-[1,1'-biphenyl]-3-yl)methoxy)phenoxy)methyl) nicotinonitrile according to the reductive amination conditions as described for Example 1003. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The yield of the product was 16.3 mg, and its estimated purity by LCMS analysis was 97%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 715.25, RT=1.37 min. Proton NMR was acquired in deuterated DMSO. $^1$H NMR (500 MHz, DMSO-d$_6$) δ ppm 9.03 (s, 1H), 8.98 (s, 1H), 8.50 (s, 1H), 7.55 (s, 1H), 7.46 (d, J=7.3 Hz, 1H), 7.38-7.33 (m, 1H), 7.27 (t, J=7.5 Hz, 1H), 7.21 (d, J=7.7 Hz, 1H), 7.12 (s, 1H), 6.93 (d, J=8.1 Hz, 1H), 6.88 (d, J=7.3 Hz, 1H), 6.85 (br. s., 1H), 5.36 (s, 2H), 5.28 (s, 2H), 4.78 (s, 1H), 4.73 (s, 1H), 3.90 (s, 2H), 3.65 (d, J=11.4 Hz, 1H), 3.61-3.51 (m, 3H), 3.46-3.27 (m, 3H), 2.23 (s, 3H), 1.93-1.75 (m, 2H), 1.25 (s, 3H).

Example 1005: (S)-1-(5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)piperidine-2-carboxylic Acid Example 1005 was prepared from (S)-piperidine-2-carboxylic acid, (S)-5-((4-chloro-2-formyl-5-((3'-(2-(3-hydroxypyrrolidin-1-yl)-2-oxoethoxy)-2-methyl-[1,1'-biphenyl]-3-yl)methoxy)phenoxy)methyl)nicotinonitrile according to the reductive amination conditions as described for Example 1003. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 96%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 725.3, RT=1.41 min. Proton NMR was acquired in deuterated DMSO. $^1$H NMR (500 MHz, DMSO-d$_6$) δ ppm 9.02-8.96 (m, 2H), 8.46 (s, 1H), 7.51-7.46 (m, 2H), 7.39-7.32 (m, 1H), 7.30-7.25 (m, 1H), 7.24-7.19 (m, 1H), 7.13 (s, 1H), 6.93 (d, J=8.1 Hz, 1H), 6.89 (d, J=7.7 Hz, 1H), 6.85 (br. s., 1H), 5.38-5.32 (m, 2H), 5.27 (s, 2H), 4.77 (s, 1H), 4.73 (s, 1H), 3.93 (d, J=13.6 Hz, 1H), 3.79-3.74 (m, 1H), 3.61-3.53 (m, 2H), 3.47-3.28 (m, 4H), 2.96 (d, J=11.4 Hz, 1H), 2.43-2.36 (m, 1H), 2.28-2.21 (m, 3H), 1.94-1-1.63 (m, 8H).

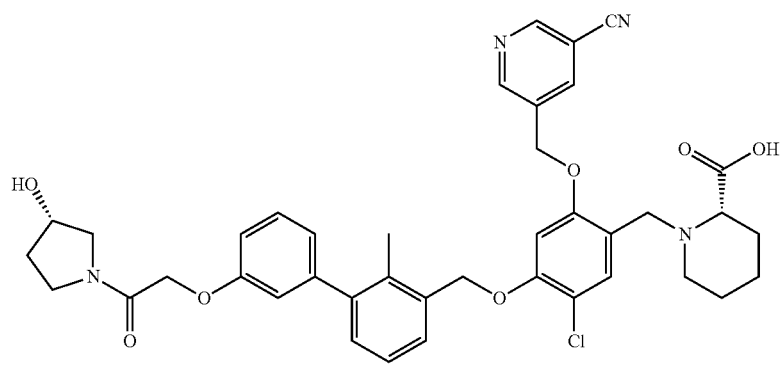 [SMILES: Cc1c(COc2cc(OCc3cncc(C#N)c3)c(CN3CCCC[C@H]3C(=O)O)cc2Cl)cccc1-c1cccc(OCC(=O)N2CC[C@H](O)C2)c1]

Example 1006: (R)-2-((5-chloro-2-((5-cyanopyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)amino)-3-hydroxypropanoic Acid

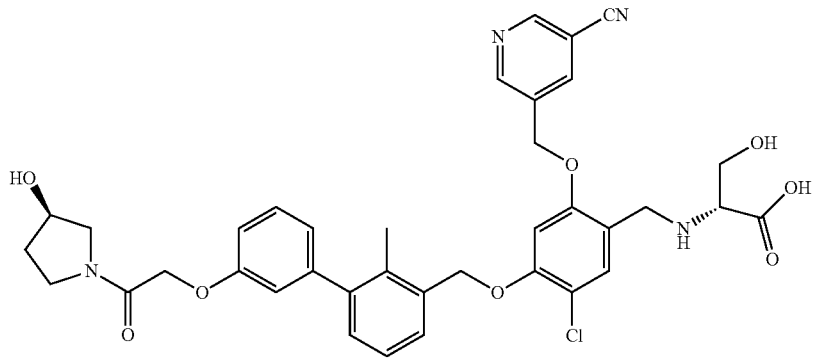 [SMILES: Cc1c(COc2cc(OCc3cncc(C#N)c3)c(CN[C@H](CO)C(=O)O)cc2Cl)cccc1-c1cccc(OCC(=O)N2CC[C@@H](O)C2)c1]

Example 1006 was prepared according to the procedure as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.8 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 701.23, RT=1.31 min. Proton NMR was acquired in deuterated DMSO. $^1$H NMR (500 MHz, DMSO-d$_6$) δ ppm 9.03 (d, J=9.5 Hz, 2H), 8.53 (s, 1H), 7.96 (s, 1H), 7.52 (s, 1H), 7.49 (d, J=7.3 Hz, 1H), 7.36 (t, J=7.9 Hz, 1H), 7.29 (t, J=7.5 Hz, 1H), 7.22 (d, J=7.7 Hz, 1H), 7.15 (s, 1H), 6.93 (d, J=8.1 Hz, 1H), 6.89 (d, J=7.3 Hz, 1H), 6.86 (s, 1H), 5.37 (d, J=8.1 Hz, 2H), 5.29 (s, 2H), 4.78 (s, 1H), 4.73 (s, 1H), 4.34-4.26 (m, 1H), 4.04-3.93 (m, 2H), 3.73-3.67 (m, 1H), 3.64-3.27 (m, 5H), 3.15 (t, J=5.5 Hz, 1H), 2.24 (s, 3H), 1.98-1.69 (m, 2H).

Example 1007: (S)-1-(5-chloro-2-((5-cyanopyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)piperidine-2-carboxylic Acid

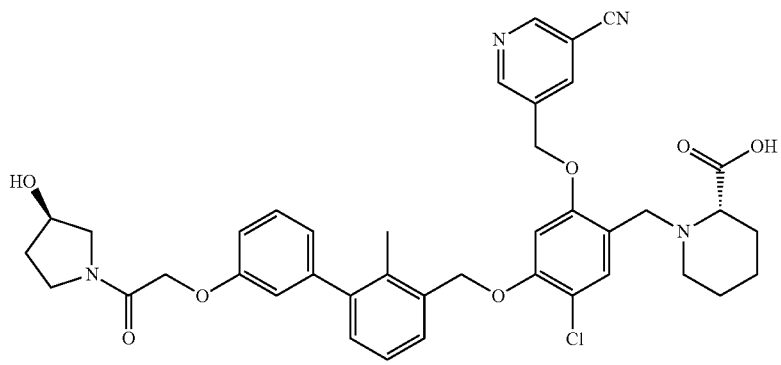 [SMILES: Cc1c(COc2cc(OCc3cncc(C#N)c3)c(CN3CCCC[C@H]3C(=O)O)cc2Cl)cccc1-c1cccc(OCC(=O)N2CC[C@@H](O)C2)c1]

Example 1007 was prepared according to the procedure as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow:

1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 725.27, RT=1.38 min.

Example 1008: (2S,4S)-1-(5-chloro-2-((5-cyano-pyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)-4-hydroxypyrrolidine-2-carboxylic Acid

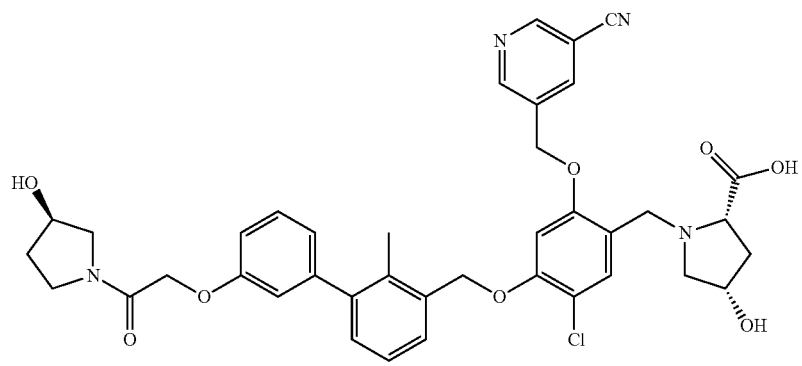 [SMILES: Cc1c(COc2cc(OCc3cncc(C#N)c3)c(CN3C[C@@H](O)C[C@H]3C(=O)O)cc2Cl)cccc1-c1cccc(OCC(=O)N2CC[C@@H](O)C2)c1]

Example 1008 was prepared according to the procedure as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]$^+$ 727.25, RT=1.44 min. Proton NMR was acquired in deuterated DMSO. $^1$H NMR (500 MHz, DMSO-d$_6$) δ ppm 9.02 (br. s., 2H), 8.49 (s, 1H), 7.53-7.47 (m, 2H), 7.36 (t, J=7.9 Hz, 1H), 7.29 (t, J=7.7 Hz, 1H), 7.22 (d, J=7.3 Hz, 1H), 7.15 (s, 1H), 6.94 (d, J=8.4 Hz, 1H), 6.90 (d, J=7.3 Hz, 1H), 6.86 (s, 1H), 5.41-5.31 (m, 2H), 5.28 (s, 2H), 4.79 (s, 1H), 4.74 (s, 1H), 3.99 (d, J=13.6 Hz, 1H), 3.83 (d, J=13.2 Hz, 1H), 3.61-3.53 (m, 1H), 3.47-3.27 (m, 4H), 2.94 (d, J=10.6 Hz, 1H), 2.78-2.71 (m, 1H), 2.37-2.28 (m, 1H), 2.25 (s, 3H), 1.93 (d, J=3.7 Hz, 1H), 1.84 (dd, J=13.0, 3.9 Hz, 2H).

Intermediate: (R)-5-((4-chloro-2-formyl-5-((3'-(3-(3-hydroxypyrrolidin-1-yl)-3-oxopropoxy)-2-meth-[1,1'-biphenyl]-3-yl)methoxy)methyl)nicotinonitrile

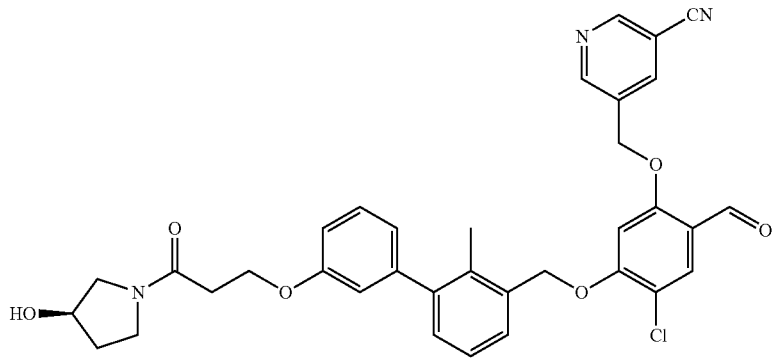 [SMILES: Cc1c(COc2cc(OCc3cncc(C#N)c3)c(C=O)cc2Cl)cccc1-c1cccc(OCCC(=O)N2CC[C@@H](O)C2)c1]

Intermediate: (R)-5-((4-chloro-2-formyl-5-((3'-(3-(3-hydroxypyrrolidin-1-yl)-3-oxopropoxy)-2-methyl-[1,1'-biphenyl]-3-1)methoxy)phenoxy)methyl)nicotinonitrile was prepared from tert-butyl 3-(3-bromophenoxy)propanoate following the procedure described for (S)-5-((4-chloro-2- formyl-5-((3'-(2-(3-hydroxypyrrolidin-1-yl)-2-oxoethoxy)-2-methyl-[1,1'-biphenyl]-3-yl)methoxy)phenoxy)methyl)nicotinonitrile. LC/MS (Cond. N-1): [M+Na]+ 365.30, RT=4.207 min. $^1$H NMR (400 MHz, CHLOROFORM-d) δ ppm 10.29 (s, 1H), 8.95-8.87 (m, 2H), 8.11 (s, 1H), 7.94 (s, 1H), 7.46-7.39 (m, 1H), 7.37-7.29 (m, 2H), 6.96-6.83 (m, 3H), 6.68-6.61 (m, 1H), 5.25 (d, J=11.0 Hz, 4H), 4.42-4.32 (m, 2H), 3.78-3.51 (m, 5H), 3.50 (s, 1H), 2.85-2.77 (m, 2H), 2.30-2.23 (m, 3H), 2.12-1.95 (m, 2H).

Example 1009: (R)-2-((5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)amino)-3-hydroxypropanoic Acid

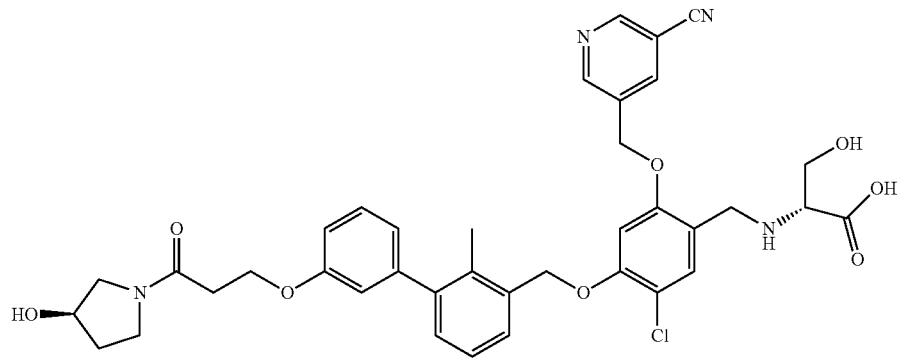 [SMILES: Cc1c(COc2cc(OCc3cncc(C#N)c3)c(CN[C@H](CO)C(=O)O)cc2Cl)cccc1-c1cccc(OCCC(=O)N2CC[C@@H](O)C2)c1]

Example 1009 was prepared according to the reductive amination conditions as described for Example 1003. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]+ 715.25, RT=1.37 min. Proton NMR was acquired in deuterated DMSO. $^1$H NMR (500 MHz, DMSO-d$_6$) δ ppm 9.01 (s, 1H), 9.03 (s, 1H), 8.52 (s, 1H), 7.54 (s, 1H), 7.48 (d, J=7.0 Hz, 1H), 7.37 (t, J=7.7 Hz, 1H), 7.28 (t, J=7.3 Hz, 1H), 7.22 (d, J=7.3 Hz, 1H), 7.14 (s, 1H), 6.95 (d, J=7.7 Hz, 1H), 6.87 (d, J=7.3 Hz, 1H), 6.82 (br. s., 1H), 5.42-5.32 (m, 2H), 5.29 (s, 2H), 4.24 (br. s., 2H), 4.10-3.98 (m, 2H), 3.77-3.70 (m, 1H), 3.63 (dd, J=11.2, 6.8 Hz, 1H), 3.59-3.43 (m, 3H), 3.36-3.25 (m, 2H), 3.18 (d, J=5.5 Hz, 1H), 2.79-2.67 (m, 2H), 2.27-2.20 (m, 3H), 1.98-1.77 (m, 2H).

Example 1010: (S)-2-((5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)amino)-3-hydroxy-2-methylpropanoic Acid

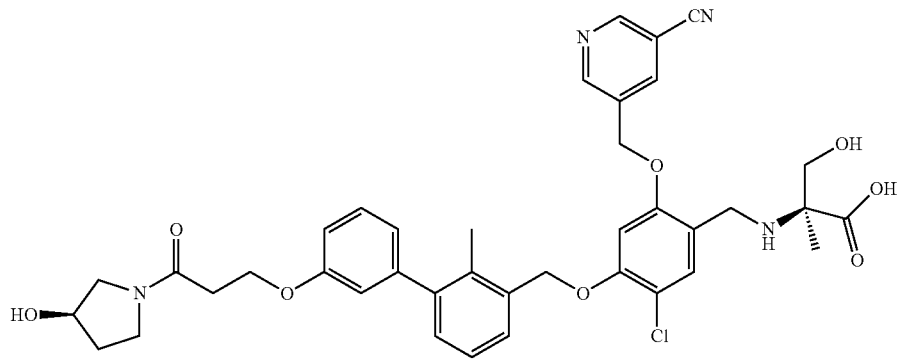 [SMILES: Cc1c(COc2cc(OCc3cncc(C#N)c3)c(CN[C@@](C)(CO)C(=O)O)cc2Cl)cccc1-c1cccc(OCCC(=O)N2CC[C@@H](O)C2)c1]

Example 1010 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with trifluoroacetic acid; Mobile Phase B: 95:5 acetonitrile:water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm. LC/MS (Injection 1 conditions): [M+H]$^+$ 729.3, RT=1.41 min. Proton NMR was acquired in deuterated DMSO. $^1$H NMR (500 MHz, DMSO-d$_6$) δ ppm 8.99 (s, 1H), 9.03 (s, 1H), 8.50 (s, 1H), 7.57 (s, 1H), 7.46 (d, J=7.0 Hz, 1H), 7.37 (t, J=7.9 Hz, 1H), 7.27 (t, J=7.3 Hz, 1H), 7.21 (d, J=7.3 Hz, 1H), 7.12 (s, 1H), 6.95 (d, J=8.1 Hz, 1H), 6.86 (d, J=7.3 Hz, 1H), 6.81 (br. s., 1H), 5.36 (s, 2H), 5.29 (s, 2H), 4.23 (br. s., 2H), 4.01 (br. s., 2H), 3.68-3.57 (m, 5H), 3.36-3.26 (m, 2H), 2.78-2.67 (m, 2H), 2.23 (s, 3H), 1.84 (br. s., 1H), 1.77 (s, 1H), 1.25 (s, 3H).

Example 1011: (S)-1-(5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)piperidine-2-carboxylic Acid

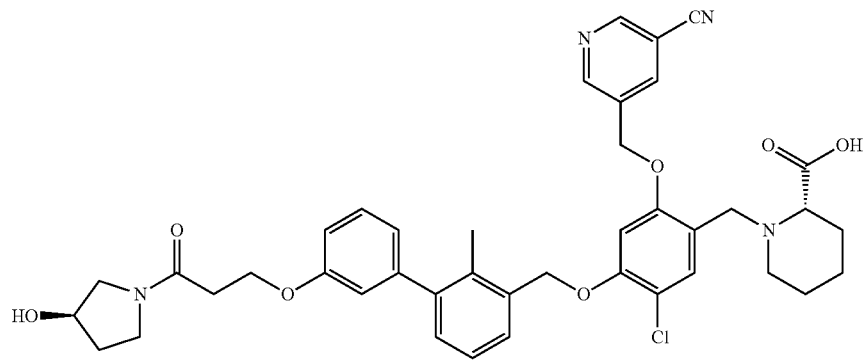 [SMILES: Cc1c(COc2cc(OCc3cncc(C#N)c3)c(CN3CCCC[C@H]3C(=O)O)cc2Cl)cccc1-c1cccc(OCCC(=O)N2CC[C@@H](O)C2)c1]

Example 1011 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 8.1 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 739.282, RT=1.47 min.

Example 1012: (S)-1-(5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)azetidine-2-carboxylic Acid (400 MHz, CHLOROFORM-d) δ ppm 7.19-7.15 (m, 1H), 7.13-7.09 (m, 2H), 6.87 (ddd, J=8.1, 2.4, 1.3 Hz, 1H), 4.14-4.11 (m, 2H), 3.76 (t, J=6.3 Hz, 2H), 2.26 (quin, J=6.1 Hz, 2H).

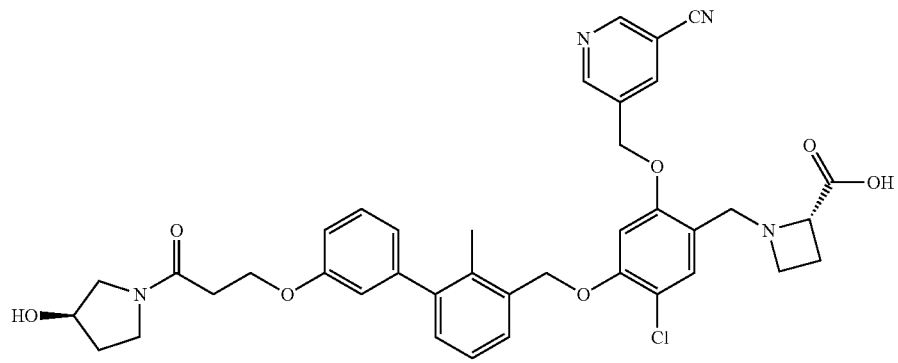 [SMILES: Cc1c(COc2cc(OCc3cncc(C#N)c3)c(CN3CC[C@H]3C(=O)O)cc2Cl)cccc1-c1cccc(OCCC(=O)N2CC[C@@H](O)C2)c1]

Example 1012 was prepared according to the reductive amination conditions as described for Example 1003. Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 99%. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0% B, 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with trifluoroacetic acid; Mobile Phase B: 95:5 acetonitrile:water with trifluoroacetic acid; Temperature: 70° C.; Gradient: 0% B, 0-100% B over 3 minutes, then a 2.0-minute hold at 100% B; Flow: 0.75 mL/min; Detection: UV at 220 nm. LC/MS (Injection 1 conditions): [M+H]⁺ 711.25, RT=1.44 min.

Intermediate: 1-bromo-3-(3-chloropropoxy)benzene

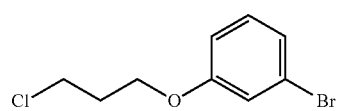 [SMILES: ClCCCOc1cccc(Br)c1]

To a solution of 3-bromophenol (0.625 mL, 5.78 mmol) in DMF (15 mL) was added 1-bromo-3-chloropropane (0.569 mL, 5.78 mmol) and $K_2CO_3$ (0.959 g, 6.94 mmol). The reaction mixture was stirred at 50° C. for 16 h. The reaction was cooled to rt, diluted with EtOAc, the organic phase was washed with sat. $NaHCO_3$, water, sat. NaCl, dried over anhydrous $Na_2SO_4$, filtered and concentrated. The residue was purified by silica chromatography (0-15% EtOAc/hexane) to yield 1-bromo-3-(3-chloropropoxy)benzene (1.2 g, 4.81 mmol, 83% yield) as a clear oil. ¹H NMR Intermediate: (3'-(3-chloropropoxy)-2-methyl-[1,1'-biphenyl]-3-yl)methanol

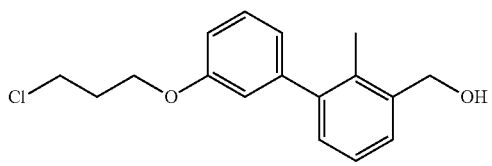 [SMILES: Cc1c(CO)cccc1-c1cccc(OCCCCl)c1]

A mixture of 1-bromo-3-(3-chloropropoxy)benzene (0.6 g, 2.405 mmol) and (2-methyl-3-(4,4,5,5-tetramethyl-1,3,2-dioxaborolan-2-yl)phenyl)methanol (0.597 g, 2.405 mmol) in THF (12 mL) and 0.5 M aqueous potassium phosphate, tribasic solution (12.02 mL, 6.01 mmol) was stirred under $N_2$ sparging for 15 min, then added with 2nd gen. XPhos precatalyst (0.057 g, 0.072 mmol), sparging was continued for 10 min. The reaction mixture was stirred at rt under $N_2$ for 16 h. The reaction was diluted with EtOAc, washed with brine, dried over anhydrous $Na_2SO_4$, filtered and concentrated. The residue was purified on silica gel (0-50% EtOAc/hex) to yield (3'-(3-chloropropoxy)-2-methyl-[1,1'-biphenyl]-3-yl)methanol (0.58 g, 1.995 mmol, 83% yield). LC/MS (Cond. N-1): [M–OH]⁺273.15, RT=4.073 min. ¹H NMR (400 MHz, CHLOROFORM-d) δ ppm 7.45-7.39 (m, 1H), 7.35 (t, J=7.9 Hz, 1H), 7.31-7.26 (m, 1H), 7.25-7.20 (m, 1H), 6.95-6.90 (m, 2H), 6.88-6.85 (m, 1H), 4.80 (d, J=5.5 Hz, 2H), 4.20-4.14 (m, 2H), 3.79 (t, J=6.4 Hz, 2H), 2.31-2.26 (m, 5H).

Intermediate: 5-chloro-4-((3'-(3-chloropropoxy)-2-methyl-[1,1'-biphenyl]-3-yl)methoxy)-2-hydroxybenzaldehyde

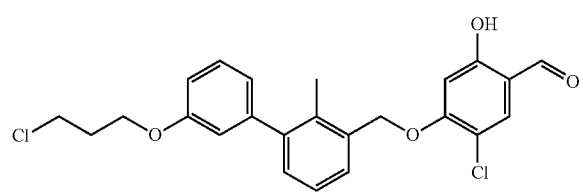 [SMILES: Cc1c(COc2cc(O)c(C=O)cc2Cl)cccc1-c1cccc(OCCCCl)c1]

To a solution of 5-chloro-2,4-dihydroxybenzaldehyde (0.379 g, 2.194 mmol), 5-chloro-2,4-dihydroxybenzaldehyde (0.379 g, 2.194 mmol) and triphenylphosphine (0.523 g, 1.995 mmol) in THF (10 mL) was added diisopropyl azodicarboxylate (0.393 ml, 1.995 mmol) in THF (1 mL) at 0° C. The resulting mixture was stirred at rt for 16 h. The reaction mixture was concentrated. The residue was dissolved in DCM and purified on silica chromatography (0-40% EtOAc/hex) to yield 5-chloro-4-((3'-(3-chloropropoxy)-2-methyl-[1,1'-biphenyl]-3-yl)methoxy)-2-hydroxybenzaldehyde (0.46 g, 1.033 mmol, 51.8% yield). $^1$H NMR (400 MHz, CHLOROFORM-d) δ ppm 11.47 (s, 1H), 9.73 (s, 1H), 7.58 (s, 1H), 7.50 (dd, J=6.5, 2.3 Hz, 1H), 7.39-7.28 (m, 3H), 7.00-6.84 (m, 3H), 6.66 (s, 1H), 5.30-5.21 (m, 2H), 4.21-4.11 (m, 2H), 3.79 (t, J=6.4 Hz, 2H), 2.42-2.25 (m, 5H).

Intermediate: 5-((4-chloro-5-((3'-(3-chloropropoxy)-2-methyl-[1,1'-biphenyl]-3-yl)methoxy)-2-formylphenoxy)methyl)nicotinonitrile

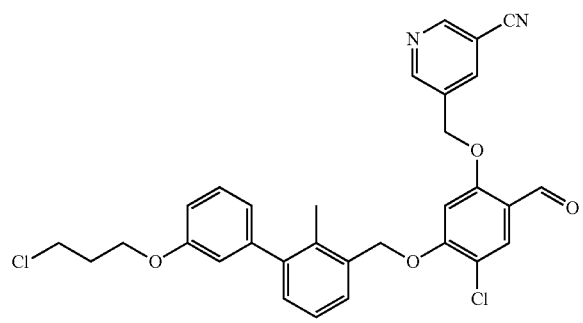 [SMILES: Cc1c(COc2cc(OCc3cncc(C#N)c3)c(C=O)cc2Cl)cccc1-c1cccc(OCCCCl)c1]

A stirred mixture of 5-chloro-4-((3'-(3-chloropropoxy)-2-methyl-[1,1'-biphenyl]-3-yl)methoxy)-2-hydroxybenzaldehyde (0.3 g, 0.674 mmol), 5-(chloromethyl)nicotinonitrile (0.154 g, 1.010 mmol) and Cs$_2$CO$_3$ (0.263 g, 0.808 mmol) in DMF (5 mL) was heated at 70° C. for 3 h. The reaction mixture was added with EtOAc and water, then the organic phase was dried (Na$_2$SO$_4$). The crude product was purified by silica gel (0-50%) to yield the desired product 5-((4-chloro-5-((3'-(3-chloropropoxy)-2-methyl-[1,1'-biphenyl]-3-yl)methoxy)-2-formylphenoxy)methyl)nicotinonitrile (0.3 g, 0.534 mmol, 79% yield) as a white solid. $^1$H NMR (400 MHz, CHLOROFORM-d) δ ppm 10.29 (s, 1H), 8.92 (dd, J=4.3, 2.0 Hz, 2H), 8.12 (t, J=2.0 Hz, 1H), 7.94-7.86 (m, 1H), 7.46 (t, J=4.5 Hz, 1H), 7.36 (t, J=7.9 Hz, 1H), 7.32-7.25 (m, 2H), 6.96-6.90 (m, 2H), 6.89-6.84 (m, 1H), 6.69 (s, 1H), 5.31-5.21 (m, 4H), 4.21-4.14 (m, 2H), 3.84-3.71 (m, 2H), 2.33-2.23 (m, 5H).

Intermediate: (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile

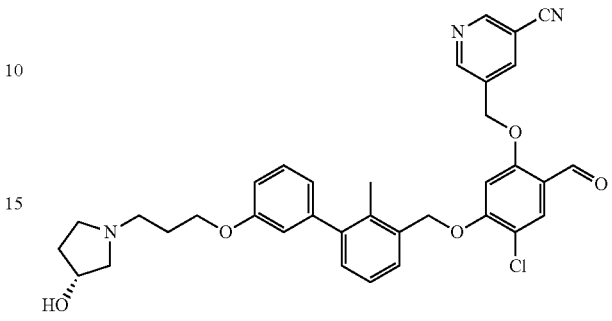

A stirred mixture of 5-((4-chloro-5-((3'-(3-chloropropoxy)-2-methyl-[1,1'-biphenyl]-3-yl)methoxy)-2-formylphenoxy)methyl)nicotinonitrile (0.2 g, 0.356 mmol), (R)-pyrrolidin-3-ol (0.037 g, 0.427 mmol) and K$_2$CO$_3$ (0.059 g, 0.427 mmol), NaI (0.053 g, 0.356 mmol) in DMF (2 mL) was heated at 80° C. for 16 h. The reaction mixture was added with EtOAc and water, then the organic phase was dried (Na$_2$SO$_4$). The crude product was purified by silica gel (0-20% MeOH/DCM) to yield the desired product (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile (0.13 g, 0.212 mmol, 59.6% yield) as a pale yellow solid. LC/MS (Cond. N-1): [M+H]$^+$ 612.3, RT=3.711 min. $^1$H NMR (400 MHz, CHLOROFORM-d) δ ppm 10.28 (s, 1H), 8.92 (dd, J=3.4, 2.1 Hz, 2H), 8.11 (t, J=1.9 Hz, 1H), 7.91 (s, 1H), 7.48-7.42 (m, 1H), 7.34 (t, J=7.9 Hz, 1H), 7.30-7.26 (m, 2H), 6.95-6.84 (m, 3H), 6.68 (s, 1H), 5.25 (s, 4H), 4.36 (ddt, J=7.2, 4.9, 2.4 Hz, 1H), 4.07 (t, J=6.3 Hz, 2H), 2.95 (td, J=8.6, 5.1 Hz, 1H), 2.76 (d, J=10.0 Hz, 1H), 2.68 (t, J=7.4 Hz, 2H), 2.56 (dd, J=10.0, 5.3 Hz, 1H), 2.37-2.31 (m, 1H), 2.30-2.27 (m, 3H), 2.26-2.15 (m, 1H), 2.08-1.98 (m, 2H), 1.82-1.72 (m, 1H).

Example 1013: (S)-1-(5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)piperidine-2-carboxylic Acid

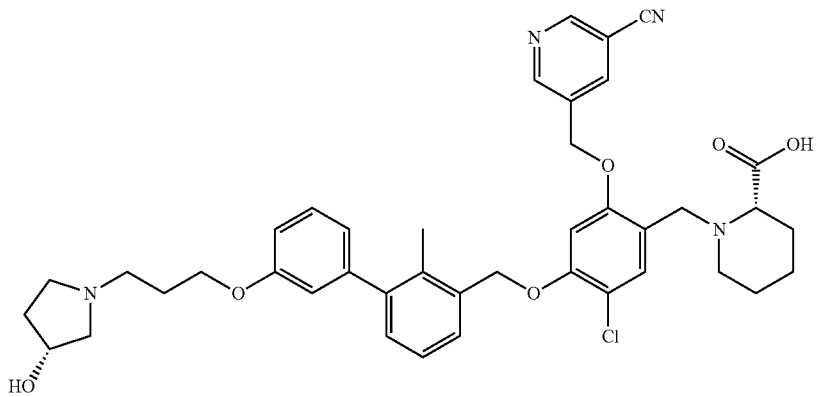 [SMILES: Cc1c(COc2cc(OCc3cncc(C#N)c3)c(CN3CCCC[C@H]3C(=O)O)cc2Cl)cccc1-c1cccc(OCCCN2CC[C@@H](O)C2)c1]

Example 1013 was prepared according to the reductive amination conditions as described for Example 1003. The crude material was purified via preparative LC/MS with the following conditions: Column: XBridge C18, 19×mm, 5-μm particles; Mobile Phase A: 5:95 acetonitrile:water with 10 mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 725.303, RT=1.36 min. Proton NMR was acquired in deuterated DMSO. $^1$H NMR (500 MHz, DMSO-d$_6$) δ ppm 9.01 (d, J=5.9 Hz, 2H), 8.46 (s, 1H), 7.49 (d, J=7.3 Hz, 1H), 7.44 (s, 1H), 7.36 (t, J=7.9 Hz, 1H), 7.28 (t, J=7.5 Hz, 1H), 7.22 (d, J=7.3 Hz, 1H), 7.12 (s, 1H), 6.94 (d, J=8.4 Hz, 1H), 6.87 (d, J=7.7 Hz, 1H), 6.83 (s, 1H), 5.34 (br. s., 2H), 5.26 (s, 2H), 4.18 (br. s., 1H), 4.05 (t, J=6.4 Hz, 2H), 3.81 (d, J=13.9 Hz, 1H), 3.64 (d, J=13.9 Hz, 1H), 3.46 (br. s., 1H), 3.16-3.11 (m, 1H), 2.90 (br. s., 1H), 2.73 (dd, J=9.5, 6.2 Hz, 1H), 2.64-2.54 (m, 4H), 2.48-2.42 (m, 2H), 2.39-2.28 (m, 2H), 2.26-2.20 (m, 3H), 1.97 (dd, J=13.0, 7.2 Hz, 1H), 1.89-1.85 (m, 2H), 1.82-1.66 (m, 2H), 1.54 (br. s., 1H), 1.49 (br. s., 3H), 1.37 (br. s., 1H).

Example 1014: (S)-4-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxybutanoic Acid Example 1014 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.4 mg, and its estimated purity by LCMS analysis was 93%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$715.288, RT=1.27 min. Proton NMR was acquired in deuterated DMSO. $^1$H NMR (500 MHz, DMSO-d$_6$) δ ppm 9.00 (s, 1H), 9.02 (s, 1H), 8.45 (s, 1H), 7.49 (d, J=7.3 Hz, 1H), 7.41 (s, 1H), 7.36 (t, J=7.9 Hz, 1H), 7.28 (t, J=7.5 Hz, 1H), 7.25-7.20 (m, 1H), 7.12 (s, 1H), 6.94 (d, J=8.1 Hz, 1H), 6.87 (d, J=7.3 Hz, 1H), 6.83 (s, 1H), 5.34 (s, 2H), 5.29-5.24 (m, 2H), 4.17 (d, J=6.6 Hz, 1H), 4.05 (t, J=6.2 Hz, 2H), 3.92-3.86 (m, 1H), 3.73 (d, J=5.1 Hz, 2H), 3.46 (br. s., 1H), 2.71 (dd, J=9.4, 6.4 Hz, 1H), 2.59-2.41 (m, 6H), 2.39-2.30 (m, 2H), 2.25 (s, 3H), 2.22-2.20 (m, 1H), 2.01-1.95 (m, 1H), 1.90-1.85 (m, 2H), 1.59-1.48 (m, 1H).

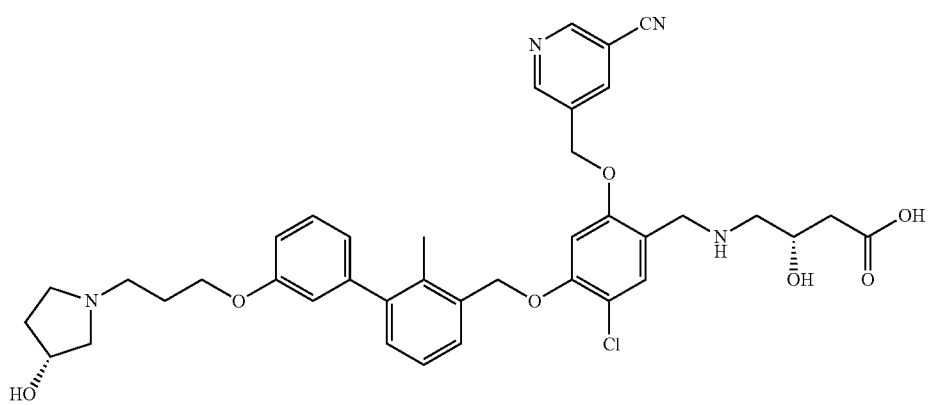 [SMILES: Cc1c(COc2cc(OCc3cncc(C#N)c3)c(CNC[C@@H](O)CC(=O)O)cc2Cl)cccc1-c1cccc(OCCCN2CC[C@@H](O)C2)c1]

Example 1015: (R)—N-(2-((5-chloro-2-((5-cyano-pyridin-3-yl)methoxy)-4-((3'-(3-(3-hydroxypyrroli-din-1-yl)propoxy)-2-methyl-[1,1'-biphenyl]-3-yl)methoxy)benzyl)amino)ethyl)acetamide

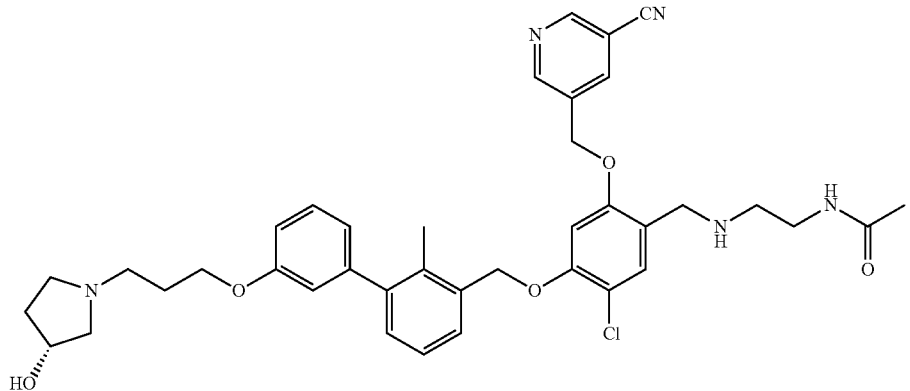 [SMILES: CC(=O)NCCNCc1cc(Cl)c(OCc2cccc(-c3cccc(OCCCN4CC[C@@H](O)C4)c3)c2C)cc1OCc1cncc(C#N)c1]

Example 1015 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 20.4 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]+ 698.31, RT=1.397 min. Proton NMR was acquired in deuterated DMSO. $^1$H NMR (500 MHz, DMSO-$d_6$) δ ppm 8.99 (s, 1H), 9.02 (s, 1H), 8.44 (s, 1H), 7.79 (br. s., 1H), 7.49 (d, J=7.3 Hz, 1H), 7.41-7.33 (m, 2H), 7.28 (t, J=7.5 Hz, 1H), 7.24-7.20 (m, 1H), 7.10 (s, 1H), 6.94 (d, J=8.1 Hz, 1H), 6.86 (d, J=7.7 Hz, 1H), 6.83 (s, 1H), 5.33 (s, 2H), 5.25 (s, 2H), 4.17 (br. s., 1H), 4.05 (t, J=6.2 Hz, 2H), 3.65 (s, 2H), 3.12 (q, J=6.4 Hz, 2H), 2.70 (dd, J=9.5, 6.2 Hz, 1H), 2.60-2.53 (m, 5H), 2.45-2.40 (m, 1H), 2.31 (dd, J=9.5, 3.7 Hz, 1H), 2.26-2.21 (m, 3H), 2.01-1.93 (m, 1H), 1.89-1.85 (m, 2H), 1.78 (s, 3H), 1.53 (d, J=4.4 Hz, 1H).

Example 1016: (R)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxypropanoic Acid

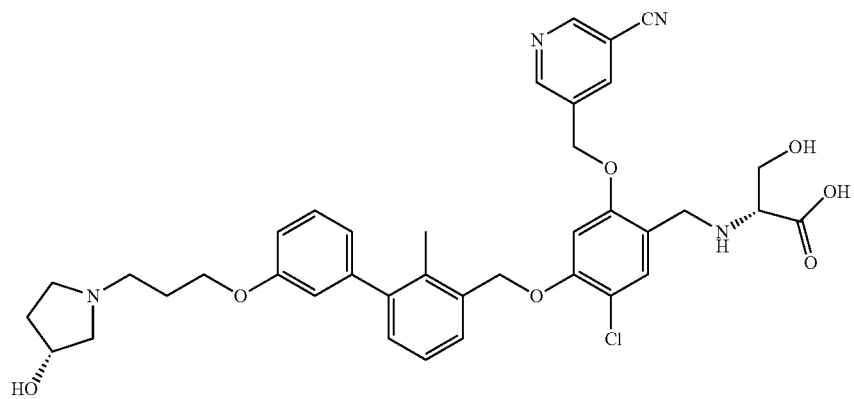 [SMILES: Cc1c(COc2cc(OCc3cncc(C#N)c3)c(CN[C@H](CO)C(=O)O)cc2Cl)cccc1-c1cccc(OCCCN2CC[C@@H](O)C2)c1]

Example 1016 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The yield of the product was 9.2 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): $[M+H]^+$ 701.27, RT=1.338 min. Proton NMR was acquired in deuterated DMSO. $^1$H NMR (500 MHz, DMSO-$d_6$) δ 9.00 (s, 1H), 9.02 (s, 1H), 8.51 (br. s., 1H), 7.52 (s, 1H), 7.47 (d, J=7.0 Hz, 1H), 7.36 (t, J=7.9 Hz, 1H), 7.27 (t, J=7.7 Hz, 1H), 7.21 (d, J=7.3 Hz, 1H), 7.13 (s, 1H), 6.94 (d, J=8.1 Hz, 1H), 6.86 (d, J=7.7 Hz, 1H), 6.81 (s, 1H), 5.41-5.32 (m, 2H), 5.28 (s, 2H), 4.19 (br. s., 1H), 4.09-3.94 (m, 4H), 3.71 (d, J=6.6 Hz, 1H), 3.61 (d, J=10.3 Hz, 1H), 3.15 (br. s., 1H), 2.80-2.71 (m, 1H), 2.68-2.55 (m, 3H), 2.39 (d, J=9.5 Hz, 1H), 2.23 (s, 3H), 2.02-1.94 (m, 1H), 1.93-1.83 (m, 2H), 1.55 (br. s., 1H).

Example 1017: (S)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxy-2-methylpropanoic Acid Example 1017 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): $[M+H]^+$715.282, RT=1.29 min. Proton NMR was acquired in deuterated DMSO. $^1$H NMR (500 MHz, DMSO-$d_6$) δ 9.00 (s, 1H), 9.03 (s, 1H), 8.50 (br. s., 1H), 7.55 (s, 1H), 7.47 (d, J=7.3 Hz, 1H), 7.36 (t, J=8.1 Hz, 1H), 7.27 (t, J=7.5 Hz, 1H), 7.21 (d, J=7.3 Hz, 1H), 7.12 (s, 1H), 6.94 (d, J=8.1 Hz, 1H), 6.85 (d, J=7.3 Hz, 1H), 6.81 (br. s., 1H), 5.36 (s, 2H), 5.29 (s, 2H), 4.18 (br. s., 1H), 4.04 (t, J=6.2 Hz, 2H), 3.96 (br. s., 2H), 3.61 (d, J=11.4 Hz, 1H), 3.54 (br. s., 1H), 2.75-2.68 (m, 1H), 2.61-2.53 (m, 3H), 2.48-2.42 (m, 1H), 2.33 (d, J=9.5 Hz, 1H), 2.23 (s, 3H), 1.97 (dd, J=13.2, 7.3 Hz, 1H), 1.88 (dd, J=12.7, 5.7 Hz, 2H), 1.54 (br. s., 1H), 1.23 (s, 3H).

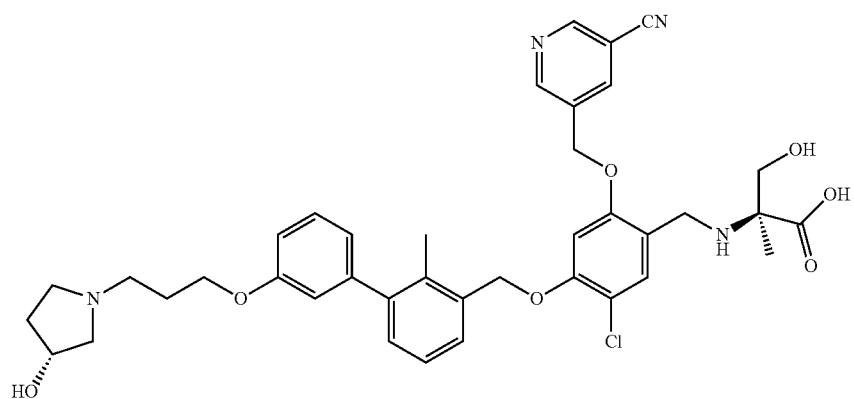 [SMILES: Cc1c(COc2cc(OCc3cncc(C#N)c3)c(CN[C@@](C)(CO)C(=O)O)cc2Cl)cccc1-c1cccc(OCCCN2CC[C@@H](O)C2)c1]

Intermediate: (R)-5-((4-chloro-2-formyl-5-((3'-(3-(3-hydroxypiperidin-1-yl)propoxy)-2-methyl-[1,1'-biphenyl]-3-yl)methoxy)phenoxy)methyl)nicotinonitrile

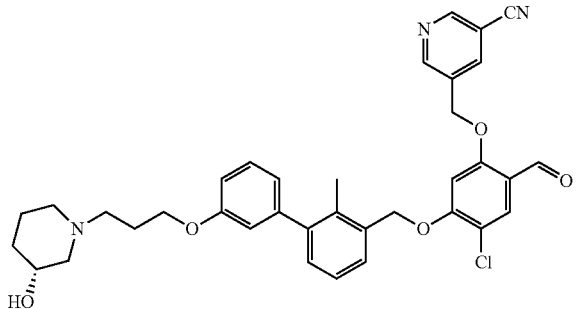 [SMILES: Cc1c(COc2cc(OCc3cncc(C#N)c3)c(C=O)cc2Cl)cccc1-c1cccc(OCCCN2CCC[C@@H](O)C2)c1]

A stirred mixture of 5-((4-chloro-5-((3'-(3-chloropropoxy)-2-methyl-[1,1'-biphenyl]-3-yl)methoxy)-2-formylphenoxy)methyl)nicotinonitrile (0.075 g, 0.134 mmol), (R)-piperidin-3-ol, HCl (0.022 g, 0.160 mmol) and $K_2CO_3$ (0.022 g, 0.160 mmol) and NaI (0.020 g, 0.134 mmol) in DMF (2 mL) was heated at 70° C. for 16 h. The reaction mixture was added with EtOAc and water, then the organic phase was dried over anhydrous $Na_2SO$). The crude was purified by silica gel column (0-20% MeOH/DCM) to yield (R)-5-((4-chloro-2-formyl-5-((3'-(3-(3-hydroxypiperidin-1-yl)propoxy)-2-methyl-[1,1'-biphenyl]-3-yl)methoxy)phenoxy)methyl)nicotinonitrile (0.025 g, 0.040 mmol, 29.9% yield) as a white solid. LC/MS (Cond. N-1): [M+H]$^+$626.3, RT=2.949 min. $^1$H NMR (400 MHz, CHLOROFORM-d) δ ppm 10.29 (s, 1H), 8.92 (t, J=2.3 Hz, 2H), 8.11 (t, J=2.1 Hz, 1H), 7.96-7.92 (m, 1H), 7.48-7.41 (m, 1H), 7.37-7.29 (m, 3H), 6.94-6.83 (m, 3H), 6.66 (s, 1H), 5.28-5.21 (m, 4H), 4.06 (t, J=6.3 Hz, 2H), 3.84 (br. s., 1H), 2.60-2.52 (m, 3H), 2.35-2.25 (m, 4H), 2.06-1.96 (m, 2H), 1.88-1.23 (m, 6H).

Example 1018: (S)-1-(5-chloro-2-((5-cyanopyridin-3-yl)methoxy)-4-((3'-(3-((R)-3-hydroxypiperidin-1-yl)propoxy)-2-methyl-[1,1'-biphenyl]-3-yl)methoxy)benzyl)piperidine-2-carboxylic Acid

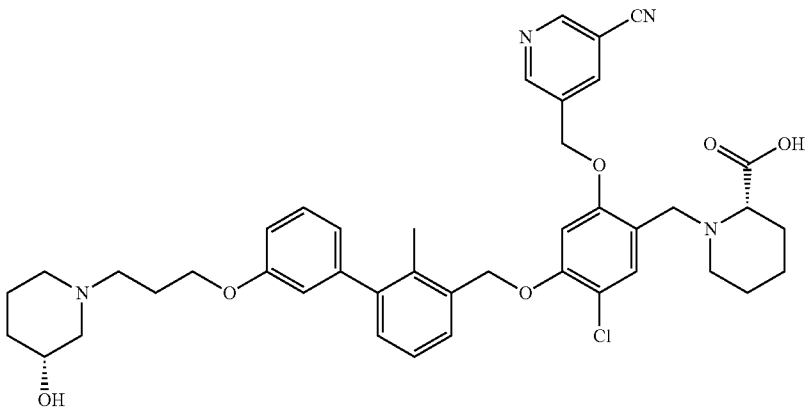 [SMILES: Cc1c(COc2cc(OCc3cncc(C#N)c3)c(CN3CCCC[C@H]3C(=O)O)cc2Cl)cccc1-c1cccc(OCCCN2CCC[C@@H](O)C2)c1]

Example 1018 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$739.318, RT=1.46 min.

Example 1019: (S)-1-(5-chloro-2-((5-cyanopyridin-3-yl)methoxy)-4-((3'-(3-((S)-3-hydroxypiperidin-1-yl)propoxy)-2-methyl-[1,1'-biphenyl]-3-yl)methoxy)benzyl)piperidine-2-carboxylic Acid

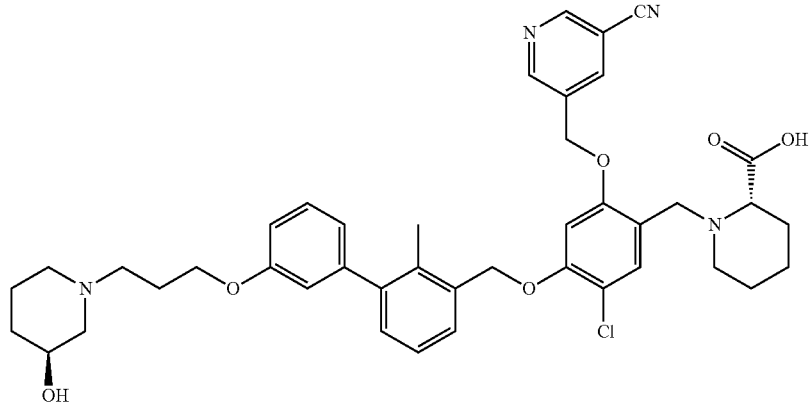 [SMILES: Cc1c(COc2cc(OCc3cncc(C#N)c3)c(CN3CCCC[C@H]3C(=O)O)cc2Cl)cccc1-c1cccc(OCCCN2CCC[C@H](O)C2)c1]

Example 1019 was prepared according to the conditions as described for Example 1018. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 23.7 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 739.318, RT=1.47 min.

Intermediate: (3'-((tert-butyldimethylsilyl)oxy)-2-methyl-[1,1'-biphenyl]-3-yl)methanol

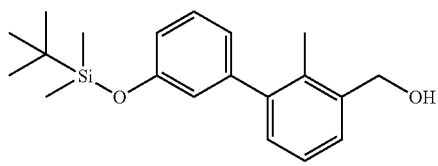 [SMILES: Cc1c(CO)cccc1-c1cccc(O[Si](C)(C)C(C)(C)C)c1]

A mixture of (3-bromophenoxy)(tert-butyl)dimethylsilane (1.2 g, 4.18 mmol) and (2-methyl-3-(4,4,5,5-tetramethyl-1,3,2-dioxaborolan-2-yl)phenyl)methanol (1.036 g, 4.18 mmol) in THF (25 ml) and 0.5 M aq potassium phosphate, tribasic (25.06 ml, 12.53 mmol) was stirred under $N_2$ sparging for 15 min, then added with 2nd gen. XPhos precatalyst (0.099 g, 0.125 mmol), sparging was continued for 10 min. The reaction mixture was stirred at rt under $N_2$ for 16 h. The reaction was diluted with EtOAc, washed with brine, dried over anhydrous $Na_2SO_4$, filtered and concentrated to yield a dark oil, which was purified on silica gel (0-70% EtOAc/hex) to yield (3'-((tert-butyldimethylsilyl)oxy)-2-methyl-[1,1'-biphenyl]-3-yl)methanol (1.33 g, 97% yield). LC/MS (Cond. N-1): [M-OH]$^+$311.3, RT=4.74 min.

Intermediate: 4-((3'-((tert-butyldimethylsilyl)oxy)-2-methyl-[1,1'-biphenyl]-3-yl)methoxy)-5-chloro-2-hydroxybenzaldehyde

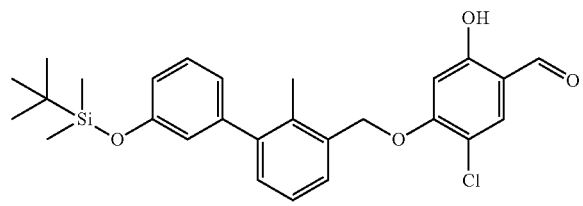 [SMILES: Cc1c(COc2cc(O)c(C=O)cc2Cl)cccc1-c1cccc(O[Si](C)(C)C(C)(C)C)c1]

To a solution of 5-chloro-2,4-dihydroxybenzaldehyde (0.699 g, 4.05 mmol), (3'-((tert-butyldimethylsilyl)oxy)-2-methyl-[1,1'-biphenyl]-3-yl)methanol (1.33 g, 4.05 mmol), and and triphenylphosphine (1.168 g, 4.45 mmol) in THF (10 mL) was added diisopropyl azodicarboxylate (0.877 mL, 4.45 mmol) in THF (1 mL) at 0° C. The resulting mixture was stirred at rt for 16 h. The reaction mixture was concentrated. The residue was dissolved in DCM and purified on silica chromatography (0-30% EtOAc/hex) to yield 4-((3'-((tert-butyldimethylsilyl)oxy)-2-methyl-[1,1'-biphenyl]-3-yl)methoxy)-5-chloro-2-hydroxybenzaldehyde (1.03 g, 2.132 mmol, 52.7% yield). $^1$H NMR (400 MHz, CHLOROFORM-d) δ ppm 11.52-11.38 (m, 1H), 9.77-9.50 (m, 1H), 7.58-7.54 (m, 1H), 7.48 (dd, J=6.9, 2.1 Hz, 1H), 7.32-7.25 (m, 3H), 6.91 (dt, J=7.8, 1.1 Hz, 1H), 6.86 (ddd, J=8.2, 2.4, 0.8 Hz, 1H), 6.83-6.79 (m, 1H), 6.65 (s, 1H), 5.24-5.18 (m, 2H), 2.29-2.22 (m, 3H), 1.02-1.00 (m, 9H), 0.25-0.22 (m, 6H).

Intermediate: 5-((4-chloro-2-formyl-5-((3'-hydroxy-2-methyl-[1,1'-biphenyl]-3-yl)methoxy)phenoxy)methyl)nicotinonitrile

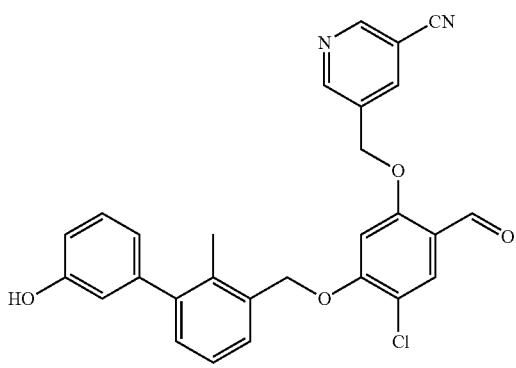 [SMILES: Cc1c(COc2cc(OCc3cncc(C#N)c3)c(C=O)cc2Cl)cccc1-c1cccc(O)c1]

A stirred mixture of 4-((3'-((tert-butyldimethylsilyl)oxy)-2-methyl-[1,1'-biphenyl]-3-yl)methoxy)-5-chloro-2-hydroxybenzaldehyde (1.02 g, 2.111 mmol), 5-(chloromethyl)nicotinonitrile (0.322 g, 2.111 mmol) and Cs$_2$CO$_3$ (0.826 g, 2.53 mmol) in DMF (10 mL) was heated at 75° C. for 2 h. Then the reaction was cool to rt. The reaction mixture was added with EtOAc and water, then the organic phase was dried (Na$_2$SO$_4$). The crude isolate was purified by silica gel chromatography (0-100% EtOAc in hexane) to yield 5-((4-chloro-2-formyl-5-((3'-hydroxy-2-methyl-[1,1'-biphenyl]-3-yl)methoxy)phenoxy)methyl)nicotinonitrile (0.5 g, 1.031 mmol, 48.8% yield) as a yellow solid. LC/MS (Cond. N-1): [M+H]$^+$ 485.14, RT=3.933 min. $^1$H NMR (400 MHz, DMSO-d$_6$) δ ppm 10.23 (s, 1H), 9.53 (s, 1H), 9.04 (t, J=1.9 Hz, 2H), 8.56 (t, J=2.0 Hz, 1H), 7.73 (s, 1H), 7.50 (d, J=6.5 Hz, 1H), 7.33-7.16 (m, 4H), 6.80-6.61 (m, 3H), 5.49 (s, 2H), 5.41 (s, 2H), 2.23 (s, 3H).

Intermediate: Tert-butyl (3-((3'-((2-chloro-5-((5-cyanopyridin-3-yl)methoxy)-4-formylphenoxy)methyl)-2'-methyl-[1,1'-biphenyl]-3-yl)oxy)propyl)carbamate

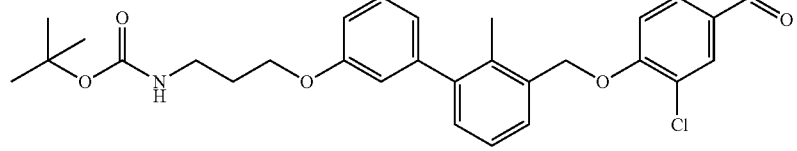

To a solution of 5-((4-chloro-2-formyl-5-((3'-hydroxy-2-methyl-[1,1'-biphenyl]-3-yl)methoxy)phenoxy)methyl)nicotinonitrile (0.2 g, 0.412 mmol) in DMF (5 mL) was added tert-butyl (3-bromopropyl)carbamate (0.108 g, 0.454 mmol) and K$_2$CO$_3$ (0.074 g, 0.536 mmol). The reaction mixture was stirred at rt for 16 h, then heated to 80° C. for 2 h. The reaction was cooled to rt, diluted with EtOAc, the organic phase was washed with sat. NaHCO$_3$, water, sat. NaCl, dried over anhydrous Na$_2$SO$_4$, filtered and concentrated. The residue was purified by silica gel chromatography (0-100% EtOAc/hexane) to yield tert-butyl (3-((3'-((2-chloro-5-((5-cyanopyridin-3-yl)methoxy)-4-formylphenoxy)methyl)-2'-methyl-[1,1'-biphenyl]-3-yl)oxy)propyl)carbamate (0.2 g, 0.311 mmol, 76% yield) as a white solid. $^1$H NMR (400 MHz, CHLOROFORM-d) δ ppm 10.29 (s, 1H), 8.99-8.82 (m, 2H), 8.11 (t, J=2.0 Hz, 1H), 7.94 (s, 1H), 7.47-7.41 (m, 1H), 7.37-7.32 (m, 1H), 7.31-7.28 (m, 2H), 6.95-6.88 (m, 2H), 6.87-6.83 (m, 1H), 6.68-6.63 (m, 1H), 5.25 (d, J=5.8 Hz, 4H), 4.11-4.03 (m, 2H), 3.35 (q, J=6.3 Hz, 2H), 2.34-2.25 (m, 3H), 2.01 (t, J=6.3 Hz, 2H), 1.50-1.38 (m, 9H).

Intermediate: 5-((5-((3'-(3-aminopropoxy)-2-methyl-[1,1'-biphenyl]-3-yl)methoxy)-4-chloro-2-formylphenoxy)methyl)nicotinonitrile

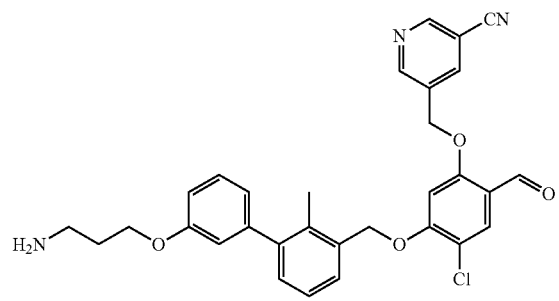 [SMILES: Cc1c(COc2cc(OCc3cncc(C#N)c3)c(C=O)cc2Cl)cccc1-c1cccc(OCCCN)c1]

To a solution of tert-butyl (3-((3'-((2-chloro-5-((5-cyanopyridin-3-yl)methoxy)-4-formylphenoxy)methyl)-2'-methyl-[1,1'-biphenyl]-3-yl)oxy)propyl)carbamate (0.08 g, 0.125 mmol) in DCM (1 mL) was added TFA (0.5 mL, 6.49 mmol). The reaction mixture was stirred at rt for 16 h. The reaction was diluted with EtOAc and sat. NaHCO$_3$, the organic phase was washed with sat. NaCl, dried over anhydrous Na$_2$SO$_4$, filtered and concentrated to yield 5-((5-((3'-(3-aminopropoxy)-2-methyl-[1,1'-biphenyl]-3-yl)methoxy)-4-chloro-2-formylphenoxy)methyl)nicotinonitrile (0.053 g) as a pale yellow solid. LC/MS (Cond. N-1): [M+H]$^+$ 542.3, RT=3.673 min.

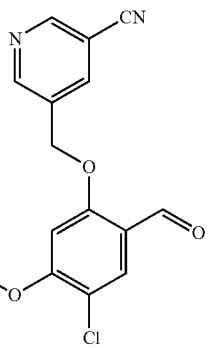

Intermediate: N-(3-((3'-((2-chloro-5-((5-cyanopyridin-3-yl)methoxy)-4-formylphenoxy)methyl)-2'-methyl-[1,1'-biphenyl]-3-yl)oxy)propyl)acrylamide

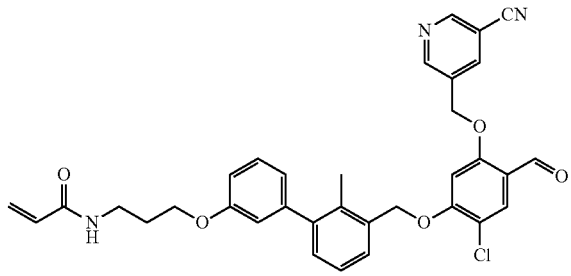 [SMILES: C=CC(=O)NCCCOc1cccc(-c2cccc(COc3cc(OCc4cncc(C#N)c4)c(C=O)cc3Cl)c2C)c1]

To a mixture of 5-((5-((3'-(3-aminopropoxy)-2-methyl-[1,1'-biphenyl]-3-yl)methoxy)-4-chloro-2-formylphenoxy)methyl)nicotinonitrile (0.06 g, 0.111 mmol) and acrylic acid (9.87 μl, 0.144 mmol) in DCM (1 mL) was added DIPEA (0.058 mL, 0.332 mmol) and TBTU (0.046 g, 0.144 mmol) at rt. The reaction mixture was stirred at rt for 16 h. The reaction was diluted with EtOAc, sat. NaHCO₃, the organic phase was washed with sat. NaCl, dried over anhydrous Na₂SO₄, filtered and concentrated to yield N-(3-((3'-((2-chloro-5-((5-cyanopyridin-3-yl)methoxy)-4-formylphenoxy)methyl)-2'-methyl-[1,1'-biphenyl]-3-yl)oxy)propyl)acrylamide (0.066 g, 0.111 mmol, 100% yield) as a white solid. LC/MS (Cond. N-1): [M+H]⁺ 596.24, RT=4.17 min.

Example 1020: (S)-1-(4-((3'-(3-acrylamidopropoxy)-2-methyl-[1,1'-biphenyl]-3-yl)methoxy)-5-chloro-2-((5-cyanopyridin-3-yl)methoxy)benzyl)piperidine-2-carboxylic Acid Example 1020 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 35 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]⁺ 709.28, RT=1.684 min. Proton NMR was acquired in deuterated DMSO. ¹H NMR (500 MHz, DMSO-d₆) δ ppm 9.00 (s, 2H), 8.46 (s, 1H), 8.22 (br. s., 1H), 7.51-7.44 (m, 2H), 7.36 (t, J=7.9 Hz, 1H), 7.28 (t, J=7.5 Hz, 1H), 7.22 (d, J=7.3 Hz, 1H), 7.12 (s, 1H), 6.95 (d, J=8.1 Hz, 1H), 6.87 (d, J=7.3 Hz, 1H), 6.83 (s, 1H), 6.20 (dd, J=17.1, 10.1 Hz, 1H), 6.07 (d, J=17.2 Hz, 1H), 5.57 (d, J=10.3 Hz, 1H), 5.38-5.32 (m, 2H), 5.26 (s, 2H), 4.03 (t, J=5.9 Hz, 2H), 3.94-3.86 (m, 2H), 3.74 (d, J=12.8 Hz, 1H), 3.30 (q, J=6.4 Hz, 2H), 3.17 (br. s., 1H), 2.93 (br. s., 1H), 2.40 (br. s., 1H), 2.24 (s, 3H), 1.90-1.84 (m, 2H), 1.70 (d, J=9.5 Hz, 1H), 1.51 (br. s., 3H), 1.36 (br. s., 1H).

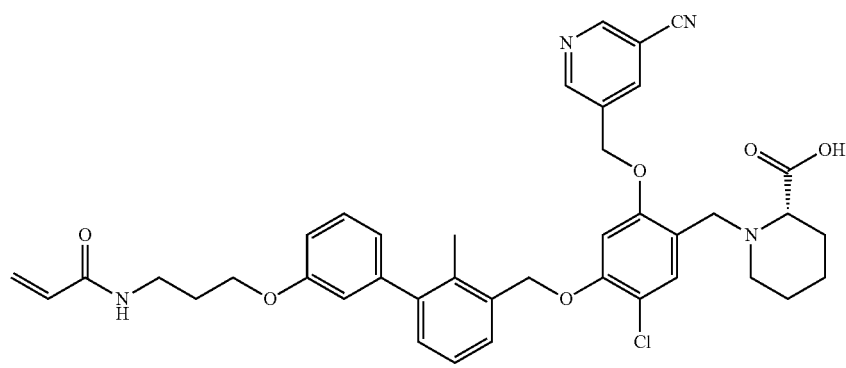 [SMILES: C=CC(=O)NCCCOc1cccc(-c2cccc(COc3cc(OCc4cncc(C#N)c4)c(CN4CCCC[C@H]4C(=O)O)cc3Cl)c2C)c1]

Example 1021: (R)-2-((4-((3'-(3-acrylamidopropoxy)-2-methyl-[1,1'-biphenyl]-3-yl)methoxy)-5-chloro-2-((5-cyanopyridin-3-yl)methoxy)benzyl)amino)-3-hydroxypropanoic Acid

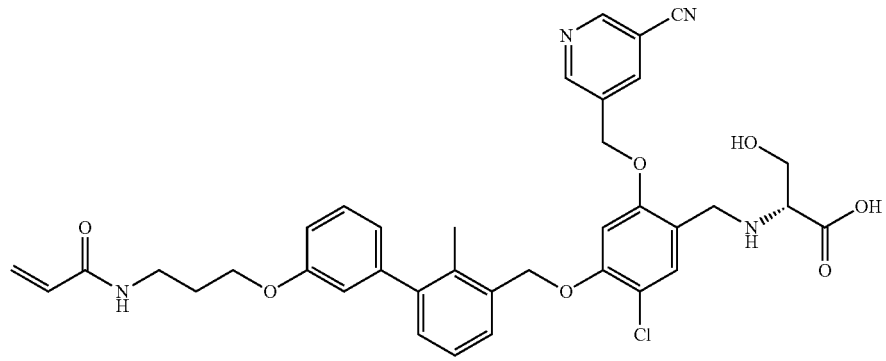 [SMILES: C=CC(=O)NCCCOc1cccc(-c2cccc(COc3cc(OCc4cncc(C#N)c4)c(CN[C@H](CO)C(=O)O)cc3Cl)c2C)c1]

Example 1021 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 94%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]+ 685.24, RT=1.605 min. Proton NMR was acquired in deuterated DMSO. $^1$H NMR (500 MHz, DMSO-$d_6$) δ ppm 9.01 (s, 1H), 9.03 (s, 1H), 8.52 (s, 1H), 8.22 (br. s., 1H), 7.53 (s, 1H), 7.48 (d, J=7.3 Hz, 1H), 7.36 (t, J=7.9 Hz, 1H), 7.31-7.24 (m, 1H), 7.23-7.18 (m, 1H), 7.14 (s, 1H), 6.95 (d, J=8.1 Hz, 1H), 6.87 (d, J=7.7 Hz, 1H), 6.83 (s, 1H), 6.24-6.17 (m, 1H), 6.11-6.04 (m, 1H), 5.57 (dd, J=10.3, 1.8 Hz, 1H), 5.42-5.32 (m, 2H), 5.28 (s, 2H), 4.10-3.97 (m, 4H), 3.90 (s, 1H), 3.73 (dd, J=11.2, 4.6 Hz, 1H), 3.63 (dd, J=11.4, 6.6 Hz, 1H), 3.30 (q, J=6.4 Hz, 2H), 3.17 (t, J=5.3 Hz, 1H), 2.23 (s, 3H), 1.94-1.86 (m, 2H).

Intermediate:
(5-(methylsulfonyl)pyridin-3-yl)methanol

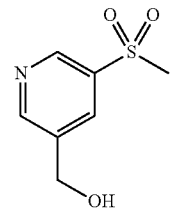

A stirred mixture of (5-bromopyridin-3-yl)methanol (451 mg, 2.399 mmol), sodium methanesulfinate (294 mg, 2.88 mmol), CuI (45.7 mg, 0.240 mmol), L-PROLINE (55.2 mg, 0.480 mmol) and NaOH (0.480 mL, 0.480 mmol) in DMSO (4 mL) was heated at 90° C. under microwave irradiation for 18 h. The cooled mixture was partitioned between ethyl acetate and sat. NaCl. The organic layer was separated, and the aqueous layer was extracted with ethyl acetate. The combined organic layers were washed with brine, dried over NaSO$_4$, and concentrated in vacuo. The residual oil was purified by silica gel FCC (0-15% MeOH/DCM) to afford (5-(methylsulfonyl)pyridin-3-yl)methanol (0.45 g, 2.404 mmol, 100% yield) as a yellow oil. $^1$H NMR (400 MHz, CHLOROFORM-d) δ ppm 9.00 (br. s., 1H), 8.81 (br. s., 1H), 8.25 (s, 1H), 4.76 (br. s., 2H), 4.43 (br. s., 1H), 3.15-3.02 (m, 3H). LC/MS (Cond. N-1): [M+H]+ 188.10, RT=0.54 min.

Intermediate:
3-(chloromethyl)-5-(methylsulfonyl)pyridine

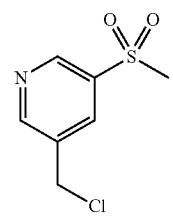

A solution of (5-(methylsulfonyl)pyridin-3-yl)methanol (0.45 g, 2.404 mmol) in DCM (10 mL) was treated with SOCl$_2$ (0.877 mL, 12.02 mmol) and the mixture was stirred at rt for 3 h. The reaction was evaporated to dryness to afford 3-(chloromethyl)-5-(methylsulfonyl)pyridine as a yellow solid. LC/MS (Cond. N-1): [M+H]$^+$ 206.05, RT=1.775 min.

Intermediate: 5-chloro-4-((3'-(3-chloropropoxy)-2-methyl-[1,1'-biphenyl]-3-yl)methoxy)-2-((5-(methylsulfonyl)pyridin-3-yl)methoxy)benzaldehyde

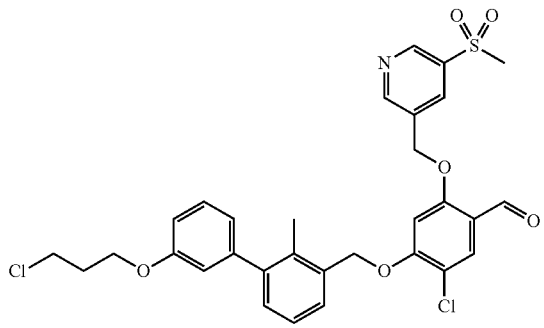 [SMILES: Cc1c(COc2cc(OCc3cncc(S(C)(=O)=O)c3)c(C=O)cc2Cl)cccc1-c1cccc(OCCCCl)c1]

A stirred mixture of 5-chloro-4-((3'-(3-chloropropoxy)-2-methyl-[1,1'-biphenyl]-3-yl)methoxy)-2-hydroxybenzaldehyde (0.166 g, 0.373 mmol), 3-(chloromethyl)-5-(methylsulfonyl)pyridine, HCl (0.117 g, 0.485 mmol) and Cs$_2$CO$_3$ (0.267 g, 0.820 mmol), NaI (5.59 mg, 0.037 mmol) in DMF (5 mL) was heated at 70° C. for 2 h. Then the reaction was cool to rt. The reaction mixture was added with EtOAc and water, then the organic phase was dried (Na$_2$SO$_4$). The crude isolate was purified by silica gel (0-100% EtOAC in hexane) to yield 5-chloro-4-((3'-(3-chloropropoxy)-2-methyl-[1,1'-biphenyl]-3-yl)methoxy)-2-((5-(methylsulfonyl)pyridin-3-yl)methoxy)benzaldehyde (0.18 g, 0.293 mmol, 79% yield) as a yellow solid. LC/MS (Cond. N-1): [M+Na]$^+$=636.19, RT=4.534 min. $^1$H NMR (400 MHz, CHLOROFORM-d) δ ppm 10.28 (s, 1H), 9.19 (d, J=2.0 Hz, 1H), 8.98 (d, J=1.8 Hz, 1H), 8.38 (t, J=2.1 Hz, 1H), 7.93 (s, 1H), 7.46 (t, J=4.5 Hz, 1H), 7.35 (t, J=7.9 Hz, 1H), 7.31-7.28 (m, 2H), 6.95-6.89 (m, 2H), 6.89-6.84 (m, 1H), 6.71 (s, 1H), 5.31-5.23 (m, 4H), 4.20-4.12 (m, 2H), 3.77 (t, J=6.3 Hz, 2H), 3.17 (s, 3H), 2.35-2.21 (m, 5H).

Intermediate: (R)-5-chloro-4-((3'-(3-(3-hydroxypyrrolidin-1-yl)propoxy)-2-methyl-[1,1'-biphenyl]-3-yl)methoxy)-2-((5-(methylsulfonyl)pyridin-3-yl)methoxy)benzaldehyde

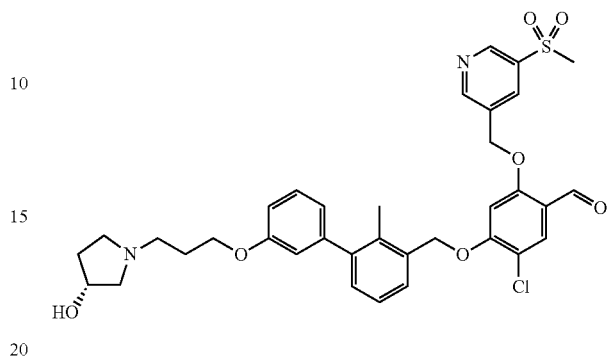

A stirred mixture of 5-chloro-4-((3'-(3-chloropropoxy)-2-methyl-[1,1'-biphenyl]-3-yl)methoxy)-2-((5-(methylsulfonyl)pyridin-3-yl)methoxy)benzaldehyde (0.18 g, 0.293 mmol), (R)-pyrrolidin-3-ol (0.033 g, 0.381 mmol) and K$_2$CO$_3$ (0.053 g, 0.381 mmol) and NaI (0.044 g, 0.293 mmol) in DMF (2 mL) was heated at 70° C. for 16 h. The reaction mixture was added with EtOAc and water, then the organic phase was dried (Na$_2$SO$_4$). The crude isolate was purified by silica gel (0-20% MeOH/DCM) to (R)-5-chloro-4-((3'-(3-(3-hydroxypyrrolidin-1-yl)propoxy)-2-methyl-[1,1'-biphenyl]-3-yl)methoxy)-2-((5-(methylsulfonyl)pyridin-3-yl)methoxy)benzaldehyde (0.11 g, 0.165 mmol, 56.5% yield) as a white solid. LC/MS (Cond. N-1): [M+H]$^+$=665.25, RT=3.586 min. $^1$H NMR (400 MHz, CHLOROFORM-d) δ ppm 10.28 (s, 1H), 9.19 (d, J=2.0 Hz, 1H), 8.99 (d, J=2.0 Hz, 1H), 8.38 (t, J=2.1 Hz, 1H), 7.93 (s, 1H), 7.46 (t, J=4.5 Hz, 1H), 7.36-7.28 (m, 3H), 6.95-6.84 (m, 3H), 6.70 (s, 1H), 5.28 (d, J=3.3 Hz, 4H), 4.35 (td, J=4.8, 2.5 Hz, 1H), 4.11-4.05 (m, 2H), 3.17 (s, 3H), 2.94 (td, J=8.6, 5.1 Hz, 1H), 2.75 (d, J=9.8 Hz, 1H), 2.67 (t, J=7.3 Hz, 2H), 2.54 (dd, J=10.0, 5.3 Hz, 1H), 2.34-2.26 (m, 4H), 2.24-2.14 (m, 1H), 2.04-1.97 (m, 2H), 1.81-1.71 (m, 1H).

Example 1022: (S)-1-(5-chloro-4-((3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)piperidine-2-carboxylic Acid

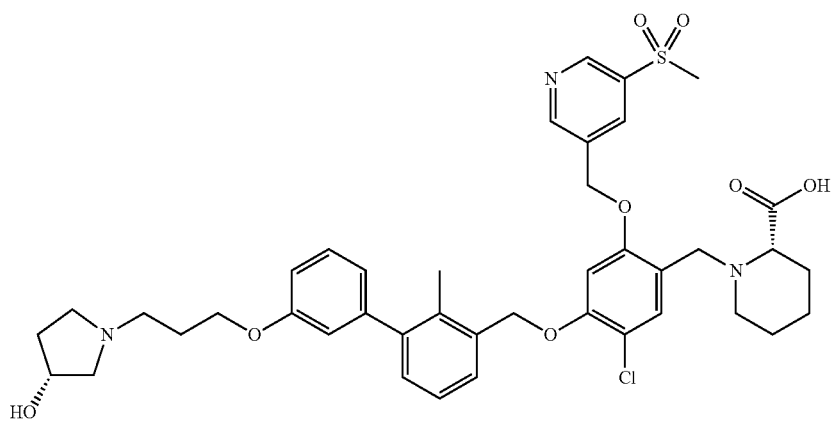 [SMILES: Cc1c(COc2cc(OCc3cncc(S(C)(=O)=O)c3)c(CN3CCCC[C@H]3C(=O)O)cc2Cl)cccc1-c1cccc(OCCCN2CC[C@@H](O)C2)c1]

Example 1022 was prepared according to the reductive amination conditions as described for Example 1003. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 15 minutes, then a 5-minute hold at 100% B; Flow: 20 mL/min. Fractions containing the desired product were combined and dried via centrifugal evaporation. The yield of the product was 18.2 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]$^+$ 778.0, RT=1.400 min.

Example 1023: (R)-2-((5-chloro-4-((3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)amino)-3-hydroxypropanoic Acid Example 1023 was prepared according to the reductive amination conditions as described for Example 1003. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 6.7 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. LC/MS (Injection 1 conditions): [M+H]$^+$ 754.2, RT=1.275 min. Proton NMR was acquired in deuterated DMSO. $^1$H NMR (500 MHz, DMSO-d$_6$) δ ppm 9.07 (d, J=9.9 Hz, 2H), 8.57 (s, 1H), 7.54-7.49 (m, 2H), 7.39-7.33 (m, 1H), 7.32-7.26 (m, 1H), 7.24-7.18 (m, 2H), 6.94 (d, J=8.1 Hz, 1H), 6.87 (d, J=7.7 Hz, 1H), 6.83 (s, 1H), 5.47-5.37 (m, 2H), 5.29 (s, 2H), 4.19 (br. s., 1H), 4.08-3.96 (m, 4H), 3.72-3.66 (m, 1H), 3.60 (dd, J=11.2, 6.4 Hz, 2H), 3.5-3.4 (m, 3H), 3.12 (t, J=5.5 Hz, 1H), 2.76-2.71 (m, 1H), 2.65-2.54 (m, 3H), 2.49-2.45 (m, 1H), 2.40-2.34 (m, 1H), 2.25 (s, 3H), 2.03-1.95 (m, 1H), 1.88 (d, J=6.6 Hz, 2H), 1.55 (br. s., 1H).

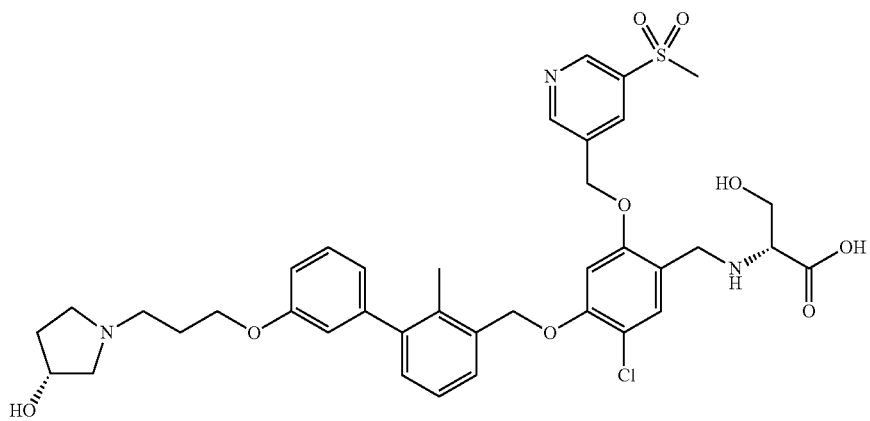 [SMILES: Cc1c(COc2cc(OCc3cncc(S(C)(=O)=O)c3)c(CN[C@H](CO)C(=O)O)cc2Cl)cccc1-c1cccc(OCCCN2CC[C@@H](O)C2)c1]

Example 1024: (S)-2-((5-chloro-4-((3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)amino)-3-hydroxy-2-methylpropanoic Acid

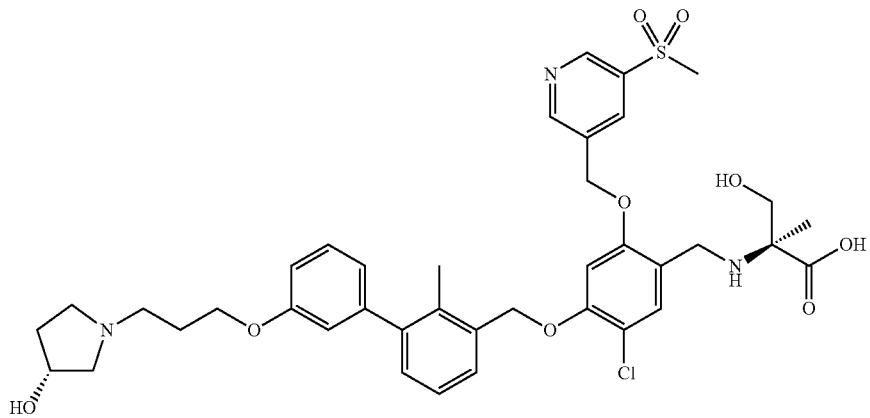

Example 1024 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]+ 768.2, RT=1.323 min. Proton NMR was acquired in deuterated DMSO. $^1$H NMR (500 MHz, DMSO-$d_6$) δ ppm 9.07 (d, J=8.1 Hz, 2H), 8.57 (s, 1H), 7.55 (s, 1H), 7.51 (d, J=7.7 Hz, 1H), 7.36 (t, J=7.7 Hz, 1H), 7.31-7.26 (m, 1H), 7.25-7.19 (m, 2H), 6.94 (d, J=8.4 Hz, 1H), 6.86 (d, J=7.7 Hz, 1H), 6.82 (br. s., 1H), 5.42 (s, 2H), 5.31 (s, 2H), 4.18 (br. s., 1H), 4.05 (t, J=6.2 Hz, 2H), 3.96 (s, 2H), 3.60 (d, J=11.0 Hz, 1H), 3.53-3.51 (m, 1H), 3.40 (s, 3H), 2.75-2.70 (m, 1H), 2.63-2.54 (m, 3H), 2.48-2.42 (m, 1H), 2.35 (dd, J=9.5, 3.3 Hz, 1H), 2.25 (s, 3H), 1.97 (dd, J=13.0, 7.2 Hz, 1H), 1.88 (d, J=6.6 Hz, 2H), 1.53 (d, J=8.4 Hz, 1H), 1.26-1.18 (m, 3H).

Intermediate: 5-chloro-4-((3'-(3-chloropropoxy)-2,2'-dimethyl-[1,1'-biphenyl]-3-yl)methoxy)-2-((5-(methylsulfonyl)pyridin-3-yl)methoxy)benzaldehyde

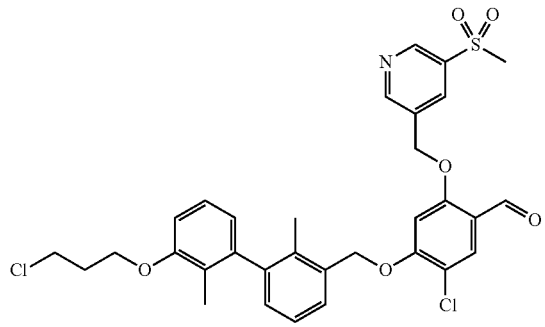

5-Chloro-4-((3'-(3-chloropropoxy)-2,2'-dimethyl-[1,1'-biphenyl]-3-yl)methoxy)-2-((5-(methylsulfonyl)pyridin-3-yl)methoxy)benzaldehyde was prepared from 3-bromo-2-methylphenol, according to the procedures as described for 5-chloro-4-((3'-(3-chloropropoxy)-2-methyl-[1,1'-biphenyl]-3-yl)methoxy)-2-((5-(methylsulfonyl)pyridin-3-yl)methoxy)benzaldehyde. $^1$H NMR (400 MHz, CHLOROFORM-d) δ ppm 10.29-10.26 (m, 1H), 9.19 (br. s., 1H), 8.99 (br. s., 1H), 8.38 (s, 1H), 7.92 (s, 1H), 7.47 (d, J=6.8 Hz, 1H), 7.27 (s, 1H), 7.24-7.14 (m, 2H), 6.89 (d, J=8.0 Hz, 1H), 6.76 (d, J=7.5 Hz, 1H), 6.70 (s, 1H), 5.31-5.25 (m, 4H), 4.22-4.16 (m, 2H), 3.80 (t, J=6.4 Hz, 2H), 3.19-3.13 (m, 3H), 2.31 (quin, J=6.1 Hz, 2H), 2.13-2.09 (m, 3H), 2.07-2.01 (m, 3H).

Intermediate: (R)-5-chloro-4-((3'-(3-(3-hydroxypyr-rolidin-1-yl)propoxy)-2,2'-dimethyl-[1,1'-biphenyl]-3-yl)methoxy)-2-((5-(methylsulfonyl)pyridin-3-yl)methoxy)benzaldehyde

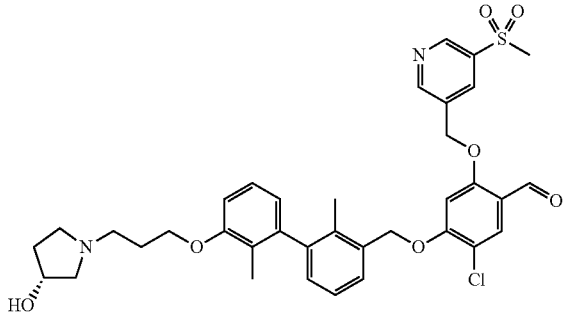 [SMILES: Cc1c(COc2cc(OCc3cncc(S(C)(=O)=O)c3)c(C=O)cc2Cl)cccc1-c1cccc(OCCCN2CC[C@@H](O)C2)c1C]

A stirred mixture of 5-chloro-4-((3'-(3-chloropropoxy)-2,2'-dimethyl-[1,1'-biphenyl]-3-yl)methoxy)-2-((5-(methylsulfonyl)pyridin-3-yl)methoxy)benzaldehyde (0.2 g, 0.318 mmol), (R)-pyrrolidin-3-ol (0.036 g, 0.414 mmol) and K$_2$CO$_3$ (0.057 g, 0.414 mmol) and NaI (0.048 g, 0.318 mmol) in DMF (2 mL) was heated at 70° C. for 16 h. The reaction mixture was added with EtOAc and water, then the organic phase was dried (Na$_2$SO$_4$). The crude isolate was purified by silica gel (0-20% MeOH/DCM) to yield (R)-5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzaldehyde (0.14 g, 0.206 mmol, 64.8% yield) as a pale yellow solid. LC/MS (Cond. N-1): [M+H]$^+$ 679.15, RT=3.586 min. $^1$H NMR (400 MHz, CHLOROFORM-d) δ ppm 10.28 (s, 1H), 9.19 (d, J=2.0 Hz, 1H), 8.99 (d, J=2.0 Hz, 1H), 8.38 (t, J=2.1 Hz, 1H), 7.96-7.91 (m, 1H), 7.46 (d, J=7.5 Hz, 1H), 7.32-7.28 (m, 1H), 7.18 (d, J=8.0 Hz, 2H), 6.87 (d, J=7.8 Hz, 1H), 6.74 (d, J=6.8 Hz, 1H), 6.69 (s, 1H), 5.27 (d, J=8.8 Hz, 4H), 4.37 (td, J=4.8, 2.5 Hz, 1H), 4.12-4.08 (m, 2H), 3.17 (s, 3H), 3.00-2.91 (m, 1H), 2.78-2.67 (m, 2H), 2.58 (dt, J=9.0, 4.7 Hz, 1H), 2.40-2.32 (m, 1H), 2.26-2.17 (m, 1H), 2.13-2.10 (m, 3H), 2.08 (s, 1H), 2.04-2.00 (m, 1H), 1.92 (s, 3H), 1.82-1.72 (m, 2H).

Example 1025: (R)-2-((5-chloro-4-((3'-(3-((R)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic Acid Example 1025 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 768.0, RT=1.472 min. Proton NMR was acquired in deuterated DMSO. $^1$H NMR (500 MHz, DMSO-d$_6$) δ ppm 9.07 (d, J=7.3 Hz, 2H), 8.57 (s, 1H), 7.56-7.48 (m, 2H), 7.28 (t, J=7.7 Hz, 1H), 7.22-7.15 (m, 2H), 7.08 (d, J=7.3 Hz, 1H), 6.96 (d, J=8.1 Hz, 1H), 6.68 (d, J=7.7 Hz, 1H), 5.47-5.35 (m, 2H), 5.34-5.21 (m, 2H), 4.20 (br. s., 1H), 4.09-4.02 (m, 2H), 3.94 (d, J=3.7 Hz, 2H), 3.8-3.68 (br. s., 3H), 3.66-3.62 (m, 1H), 3.58 (d, J=4.8 Hz, 1H), 3.08 (t, J=5.9 Hz, 1H), 2.76-2.72 (m, 1H), 2.65-2.56 (m, 3H), 2.48 (m, 1H), 2.37 (d, J=7.7 Hz, 1H), 2.04 (s, 3H), 2.01-1.91 (m, 3H), 1.83 (s, 3H), 1.56 (m, 1H).

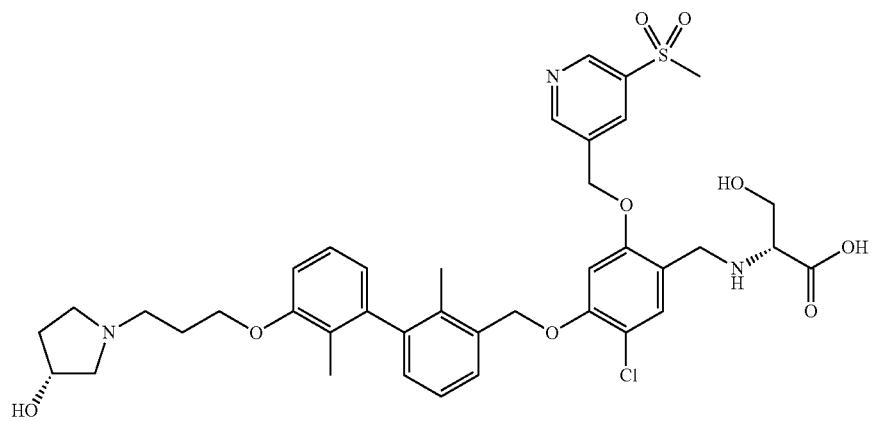 [SMILES: Cc1c(COc2cc(OCc3cncc(S(C)(=O)=O)c3)c(CN[C@H](CO)C(=O)O)cc2Cl)cccc1-c1cccc(OCCCN2CC[C@@H](O)C2)c1C]

Example 1026: (R)-2-((5-chloro-4-((3'-(3-((R)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic Acid

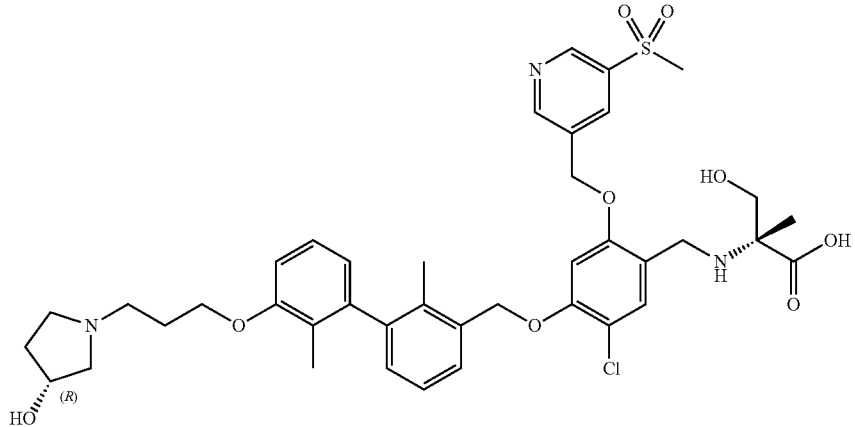

Example 1026 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 16.4 mg, and its estimated purity by LCMS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): $[M+H]^+$ 782.1, RT=1.497 min. Proton NMR was acquired in deuterated DMSO. $^1$H NMR (500 MHz, DMSO-$d_6$) δ ppm 9.07 (d, J=5.1 Hz, 2H), 8.57 (s, 1H), 7.57-7.48 (m, 2H), 7.28 (t, J=7.7 Hz, 1H), 7.23-7.16 (m, 2H), 7.08 (d, J=7.7 Hz, 1H), 6.96 (d, J=8.1 Hz, 1H), 6.68 (d, J=7.3 Hz, 1H), 5.41 (s, 2H), 5.34-5.25 (m, 2H), 4.19 (br. s., 1H), 4.05 (d, J=9.5 Hz, 2H), 3.94 (s, 2H), 3.68 (br. s., 3H), 3.59 (d, J=11.4 Hz, 1H), 3.51 (d, J=11.4 Hz, 1H), 2.77-2.69 (m, 1H), 2.64-2.53 (m, 3H), 2.46 (d, J=8.4 Hz, 1H), 2.38-2.31 (m, 1H), 2.04 (s, 3H), 2.01-1.91 (m, 3H), 1.83 (s, 3H), 1.55 (d, J=4.0 Hz, 1H), 1.22 (s, 3H).

Example 1027: (S)-1-(5-chloro-4-((3'-(3-((R)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic Acid

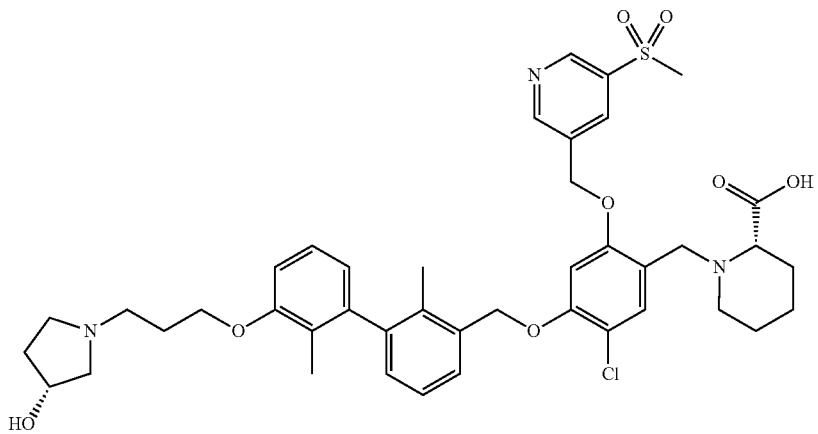 [SMILES: Cc1c(COc2cc(OCc3cncc(S(C)(=O)=O)c3)c(CN3CCCC[C@H]3C(=O)O)cc2Cl)cccc1-c1cccc(OCCCN2CC[C@@H](O)C2)c1C]

Example 1027 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 792.3, RT=1.596 min. Proton NMR was acquired in deuterated DMSO. $^1$H NMR (500 MHz, DMSO-d$_6$) δ ppm 9.05 (s, 1H), 9.08 (s, 1H), 8.47 (s, 1H), 7.53-7.43 (m, 2H), 7.28 (t, J=7.3 Hz, 1H), 7.21 (t, J=7.7 Hz, 1H), 7.15 (s, 1H), 7.08 (d, J=7.3 Hz, 1H), 6.95 (d, J=8.1 Hz, 1H), 6.68 (d, J=7.3 Hz, 1H), 5.40 (s, 2H), 5.32-5.21 (m, 2H), 4.20 (br. s., 1H), 4.05 (d, J=9.5 Hz, 2H), 3.84 (d, J=13.6 Hz, 1H), 3.69 (d, J=13.6 Hz, 1H), 3.37 (s, 3H), 3.14 (d, J=4.4 Hz, 1H), 2.92 (br. s., 1H), 2.81-2.73 (m, 1H), 2.64 (d, J=7.3 Hz, 4H), 2.45-2.38 (m, 1H), 2.34 (br. s., 1H), 2.03 (s, 3H), 2.00 (d, J=5.9 Hz, 1H), 1.94 (d, J=6.6 Hz, 2H), 1.82 (m, 4H), 1.71 (br. s., 1H), 1.56 (br. s., 1H), 1.50 (br. s., 3H), 1.36 (br. s., 1H).

Intermediate: methyl
1-benzyl-4-hydroxypiperidine-4-carboxylate

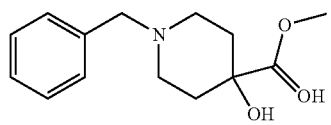 [SMILES: COC(=O)C1(O)CCN(Cc2ccccc2)CC1]

A stirred mixture of 1-benzyl-4-hydroxypiperidine-4-carbonitrile (2 g, 9.25 mmol) in MeOH (12 mL) and conc. HCl (12 mL, 144 mmol) was heated at 85° C. for 18 h. The reaction mixture was cooled to rt, then concentrated and neutralized with 1 N NaOH, extracted with 2×EtOAc, then the combined organic phase was washed with sat. NaCl, dried (Na$_2$SO$_4$). The crude product was purified by silica gel (0-100% EtOAC in hexane) to yield methyl 1-benzyl-4-hydroxypiperidine-4-carboxylate (1.44 g, 5.78 mmol, 62.5% yield). LC/MS (Cond. N-1): [M+H]$^+$ 250.15, RT=1.70 min. $^1$H NMR (400 MHz, CHLOROFORM-d) δ ppm 7.37-7.29 (m, 4H), 7.28-7.22 (m, 1H), 3.82-3.73 (m, 3H), 3.54 (s, 2H), 2.78-2.68 (m, 2H), 2.40 (td, J=11.9, 2.6 Hz, 2H), 2.12 (td, J=12.7, 4.6 Hz, 2H), 1.62 (dq, J=13.8, 2.8 Hz, 2H).

Intermediate: Methyl
4-hydroxypiperidine-4-carboxylate

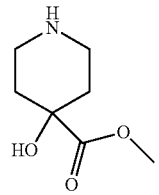

A stirred mixture of methyl 1-benzyl-4-hydroxypiperidine-4-carboxylate (1.24 g, 4.97 mmol) and Pd(OH)$_2$ on carbon (0.140 g, 0.199 mmol) in ethanol (25 mL) was hydrogenated at 45 psi at rt for 18 h. The reaction mixture was filtered through a plug of diatomaceous earth (Celite®), then washed with MeOH, the filtrate was concentrated to yield methyl 4-hydroxypiperidine-4-carboxylate (0.72 g, 4.52 mmol, 91% yield) as a white solid. LC/MS (Cond. N-1): [M+H]$^+$ 160.03, RT=0.48 min. $^1$H NMR (400 MHz, CHLOROFORM-d) δ ppm 3.80-3.76 (m, 3H), 3.02 (td, J=12.0, 3.0 Hz, 2H), 2.91 (dt, J=12.2, 4.0 Hz, 2H), 2.02-1.91 (m, 2H), 1.64-1.53 (m, 2H).

Intermediate: Methyl 1-(3-((3'-((2-chloro-5-((5-cyanopyridin-3-yl)methoxy)-4-formylphenoxy)methyl)-2'-methyl-[1,1'-biphenyl]-3-yl)oxy)propyl)-4-hydroxypiperidine-4-carboxylate

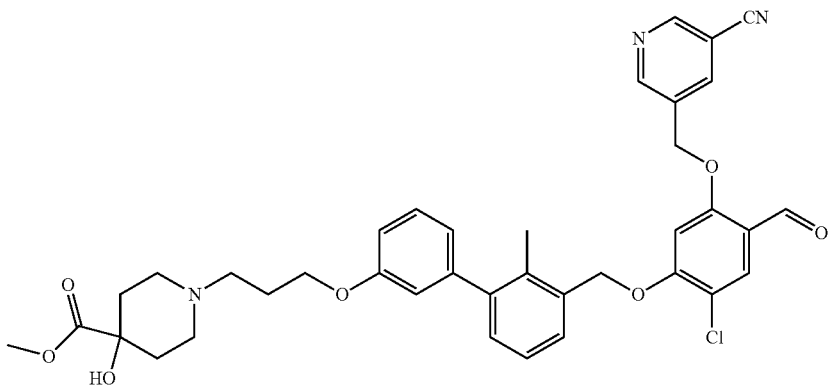 [SMILES: COC(=O)C1(O)CCN(CCCOc2cccc(-c3cccc(COc4cc(OCc5cncc(C#N)c5)c(C=O)cc4Cl)c3C)c2)CC1]

Methyl 1-(3-((3'-((2-chloro-5-((5-cyanopyridin-3-yl)methoxy)-4-formylphenoxy)methyl)-2'-methyl-[1,1'-biphenyl]-3-yl)oxy)propyl)-4-hydroxypiperidine-4-carboxylate was prepared from methyl 4-hydroxypiperidine-4-carboxylate, according to the procedure described in intermediate (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile. LC/MS (Cond. N-1): [M+H]$^+$ 684.3, RT=3.688 min. $^1$H NMR (400 MHz, CHLOROFORM-d) δ ppm 10.29 (s, 1H), 8.91 (t, J=2.3 Hz, 2H), 8.10 (t, J=2.0 Hz, 1H), 8.02 (s, 2H), 7.95-7.91 (m, 1H), 7.43 (dd, J=5.5, 3.5 Hz, 1H), 7.34-7.28 (m, 2H), 6.94-6.84 (m, 2H), 6.67 (s, 1H), 5.28-5.19 (m, 4H), 4.07 (t, J=6.3 Hz, 2H), 3.82-3.77 (s, 3H), 2.81-2.74 (m, 2H), 2.58 (t, J=7.3 Hz, 2H), 2.46-2.36 (m, 2H), 2.32-2.27 (m, 3H), 2.15-1.97 (m, 4H), 1.64 (dd, J=13.8, 2.5 Hz, 2H).

Example 1028: (R)-2-((5-chloro-2-((5-cyanopyridin-3-yl)methoxy)-4-((3'-(3-(4-hydroxy-4-(methoxycarbonyl)piperidin-1-yl)propoxy)-2-methyl-[1,1'-biphenyl]-3-yl)methoxy)benzyl)amino)-3-hydroxypropanoic Acid following conditions: Column: Phenomenex-Luna 30×100 mm S 10; Mobile Phase A: 10:90 MeOH: water with 0.1% TFA; Mobile Phase B: 90:10 MeOH: water with 0.1% TFA; Gradient: 10-90% B over 22 minutes; Flow: 40 mL/min. Fractions containing the desired product were combined and dried via centrifugal evaporation to yield (R)-2-((5-chloro-2-((5-cyanopyridin-3-yl)methoxy)-4-((3'-(3-(4-hydroxy-4-(methoxycarbonyl)piperidin-1-yl)propoxy)-2-methyl-[1,1'-biphenyl]-3-yl)methoxy)benzyl)amino)-3-hydroxypropanoic acid. LC/MS (Cond. N-1): [M+H]$^+$ 773.3, RT=3.263 min.

Example 1029: (R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxypropanoic Acid

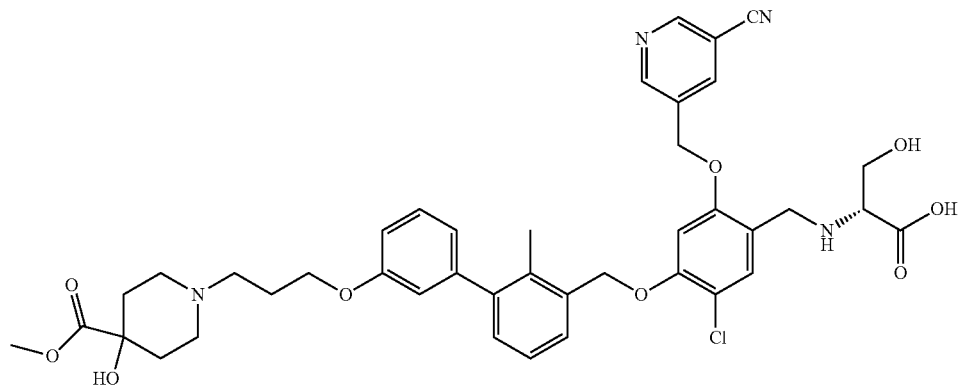 [SMILES: COC(=O)C1(O)CCN(CCCOc2cccc(-c3cccc(COc4cc(OCc5cncc(C#N)c5)c(CN[C@H](CO)C(=O)O)cc4Cl)c3C)c2)CC1]

Example 1028 was prepared according to the reductive amination conditions as described for Example 1003. The crude material was purified via preparative HPLC with the

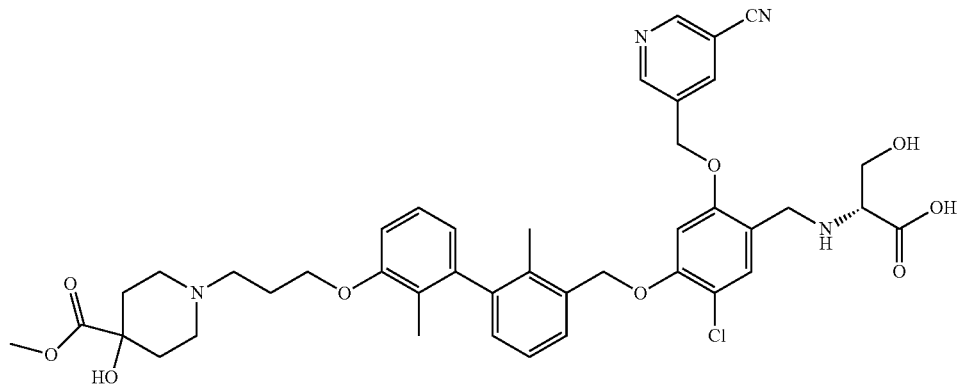 [SMILES: COC(=O)C1(O)CCN(CCCOc2cccc(-c3cccc(COc4cc(OCc5cncc(C#N)c5)c(CN[C@H](CO)C(=O)O)cc4Cl)c3C)c2C)CC1]

Example 1029 was was prepared according to the procedures as described for Example 1028. The crude material was purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 22 minutes; Flow: 40 mL/min. Fractions containing the desired product were combined and dried via centrifugal evaporation to yield (R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxypropanoic acid as a white solid. LC/MS (Cond. N-1): [M+H]+ 787.3, RT=3.24 min. 1H NMR (400 MHz, METHANOL-d) 6 ppm 8.97 (d, J=2.0 Hz, 1H), 8.92 (d, J=2.0 Hz, 1H), 8.42-8.37 (m, 1H), 7.53 (s, 1H), 7.46 (d, J=7.5 Hz, 1H), 7.21 (t, J=7.9 Hz, 1H), 7.25 (t, J=7.7 Hz, 1H), 7.10-7.05 (m, 2H), 6.96 (d, J=8.0 Hz, 1H), 6.73 (d, J=7.3 Hz, 1H), 5.40-5.35 (m, 2H), 5.31 (s, 2H), 4.39-4.27 (m, 2H), 4.17 (t, J=5.0 Hz, 2H), 4.04-3.98 (m, 2H), 3.78 (s, 3H), 3.59 (d, J=12.0 Hz, 2H), 3.45-3.38 (m, 2H), 3.38-3.32 (m, 3H), 2.36-2.20 (m, 4H), 2.08 (s, 3H), 2.06-1.99 (m, 2H), 1.91 (s, 3H).

Example 1030: (R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxy-2-methylpropanoic Acid

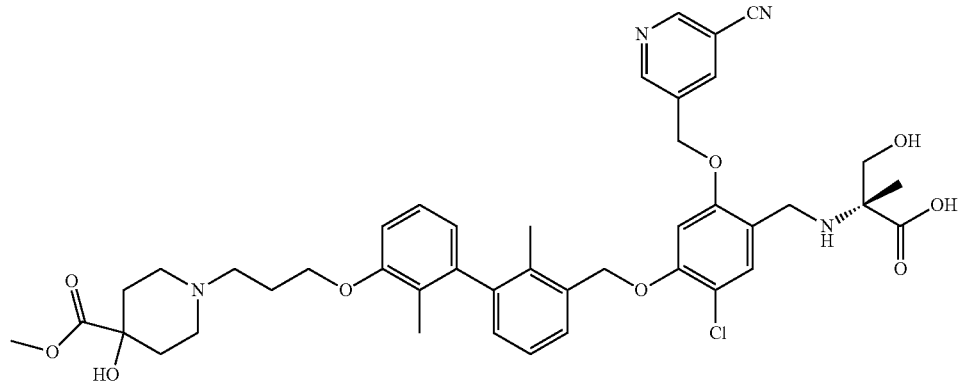

Example 1030 was prepared according to the procedures as described for Example 1028. The crude material was purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 22 minutes; Flow: 40 mL/min. Fractions containing the desired product were combined and dried via centrifugal evaporation to yield (R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxy-2-methylpropanoic acid as a white solid. LC/MS (Cond. N-1): [M+H]+ 801.25, RT=3.256 min. 1H NMR (400 MHz, METHANOL-d) 6 ppm 8.99 (d, J=2.0 Hz, 1H), 8.91 (d, J=2.0 Hz, 1H), 8.42 (t, J=2.0 Hz, 1H), 7.56 (s, 1H), 7.46 (d, J=7.0 Hz, 1H), 7.21 (t, J=7.9 Hz, 1H), 7.24 (t, J=7.7 Hz, 1H), 7.11-7.05 (m, 2H), 6.95 (d, J=8.0 Hz, 1H), 6.73 (d, J=7.0 Hz, 1H), 5.37 (s, 2H), 5.32 (s, 2H), 4.30 (s, 2H), 4.17 (t, J=5.0 Hz, 2H), 4.02 (d, J=12.3 Hz, 1H), 3.82 (d, J=12.0 Hz, 1H), 3.78 (s, 3H), 3.59 (d, J=12.0 Hz, 2H), 3.45-3.39 (m, 2H), 3.37-3.32 (m, 2H), 2.35-2.22 (m, 4H), 2.09 (s, 3H), 2.02 (d, J=14.3 Hz, 2H), 1.91 (s, 3H), 1.55 (s, 3H).

Intermediate: Tert-butyl (2-acrylamidoethyl)carbamate

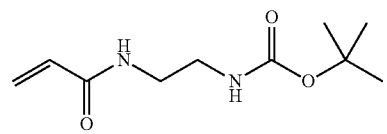

To a mixture of tert-butyl (2-aminoethyl)carbamate, HCl (1.24 g, 6.30 mmol) and acrylic acid (0.476 mL, 6.94 mmol) in DCM (1 mL) was added DIPEA (4.40 mL, 25.2 mmol) and TBTU (2.227 g, 6.94 mmol) at rt. The reaction mixture was stirred at rt for 16 h. The reaction was diluted with EtOAc, sat. NaHCO3, the organic phase was washed with sat. NaCl, dried over anhydrous Na2SO4, filtered and concentrated to yield a yellow solid, which was purified by silica gel (0-100% EtOAc/hex) to afford tert-butyl (2-acrylamidoethyl)carbamate (0.9 g, 4.20 mmol, 66.6% yield) as a white solid. LC/MS (Cond. N-1): [M+Na]+ 237.15, RT=2.556 min. 1H NMR (400 MHz, CHLOROFORM-d) δ ppm 6.48 (br. s., 1H), 6.26 (dd, J=17.1, 1.3 Hz, 1H), 6.10 (dd, J=17.1, 10.3 Hz, 1H), 5.63 (dd, J=10.2, 1.4 Hz, 1H), 5.00 (br. s., 1H), 3.50-3.39 (m, 2H), 3.31 (q, J=5.7 Hz, 2H), 1.50-1.37 (m, 9H).

Intermediate: N-(2-aminoethyl)acrylamide

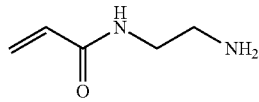

To a mixture of tert-butyl (2-acrylamidoethyl)carbamate (0.36 g, 1.680 mmol) in DCM (10 mL) was added HCl (4 M in ether, 2.100 mL, 8.40 mmol) at rt. The reaction mixture was stirred at rt for 2 h. The reaction was concentrated to yield N-(2-aminoethyl)acrylamide, HCl (0.2 g) as a white solid. 1H NMR (400 MHz, METHANOL-d4) δ ppm 6.28 (d, J=1.5 Hz, 1H), 6.27 (s, 1H), 5.73 (dd, J=6.5, 5.3 Hz, 1H), 3.54 (t, J=5.9 Hz, 2H), 3.10 (t, J=5.9 Hz, 2H).

Example 1031: (R)—N-(2-((5-chloro-2-((5-cyano-pyridin-3-yl)methoxy)-4-((3'-(3-(3-hydroxypyrroli-din-1-yl)propoxy)-2,2'-dimethyl-[1,1'-biphenyl]-3-yl)methoxy)benzyl)amino)ethyl)acrylamide

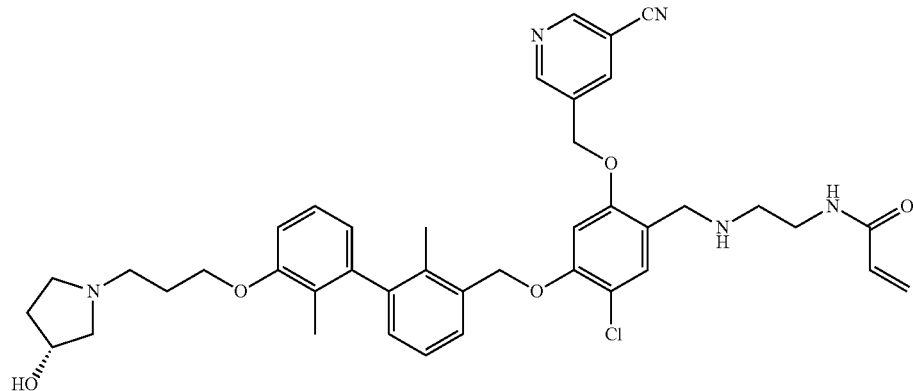 [SMILES: C=CC(=O)NCCNCc1cc(Cl)c(OCc2cccc(-c3cccc(OCCCN4CC[C@@H](O)C4)c3C)c2C)cc1OCc1cncc(C#N)c1]

Example 1031 was prepared from N-(2-aminoethyl)acrylamide, according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 724.1, RT=1.782 min. Proton NMR was acquired in deuterated DMSO. $^1$H NMR (500 MHz, DMSO-d$_6$) δ ppm 9.05-8.96 (m, 2H), 8.46-8.41 (m, 1H), 8.07 (br. s., 1H), 7.48 (d, J=7.3 Hz, 1H), 7.39 (s, 1H), 7.29-7.24 (m, 1H), 7.23-7.19 (m, 1H), 7.12-7.04 (m, 2H), 6.96 (d, J=8.1 Hz, 1H), 6.68 (d, J=7.0 Hz, 1H), 6.20 (dd, J=17.2, 10.3 Hz, 1H), 6.05 (d, J=17.2 Hz, 1H), 5.55 (d, J=9.9 Hz, 1H), 5.34-5.27 (m, 2H), 5.25 (br. s., 2H), 4.19 (br. s., 1H), 4.05 (d, J=9.2 Hz, 2H), 3.63-3.53 (br. s., 2H), 3.23 (q, J=6.0 Hz, 2H), 2.75-2.67 (m, 2H), 2.56 (d, J=6.2 Hz, 4H), 2.47-2.40 (m, 1H), 2.33 (d, J=9.5 Hz, 1H), 2.04 (s, 3H), 2.01-1.91 (m, 3H), 1.83 (s, 3H), 1.54 (br. s., 1H).

Example 1032: (R)-1-(3-((3'-((5-((5-carbamoylpyridin-3-yl)methoxy)-4-(((1-carboxy-2-hydroxyethyl)amino)methyl)-2-chlorophenoxy)methyl)-2'-methyl-[1,1'-biphenyl]-3-yl)oxy)propyl)-4-hydroxypiperidine-4-carboxylic Acid

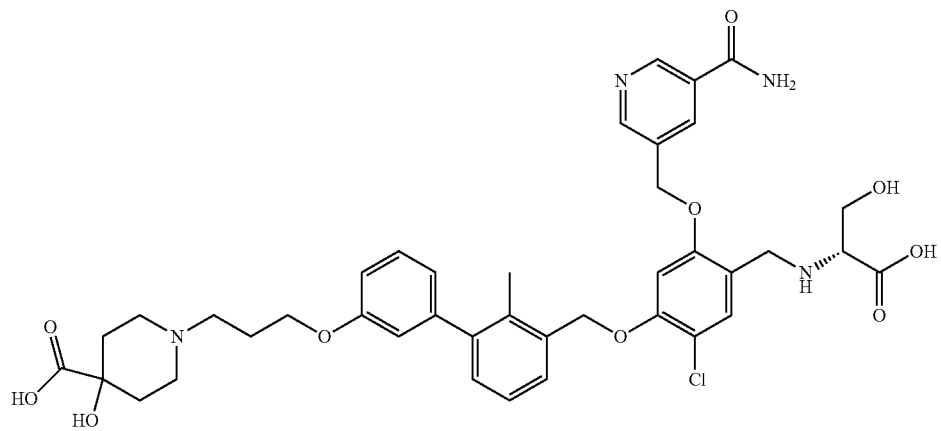 [SMILES: Cc1c(COc2cc(OCc3cncc(C(N)=O)c3)c(CN[C@H](CO)C(=O)O)cc2Cl)cccc1-c1cccc(OCCCN2CCC(O)(C(=O)O)CC2)c1]

Example 1033: (R)-1-(3-((3'-((4-(((1-carboxy-2-hydroxyethyl)amino)methyl)-2-chloro-5-((5-cyanopyridin-3-yl)methoxy)phenoxy)methyl)-2'-methyl-[1,1'-biphenyl]-3-yl)oxy)propyl)-4-hydroxypiperidine-4-carboxylic Acid

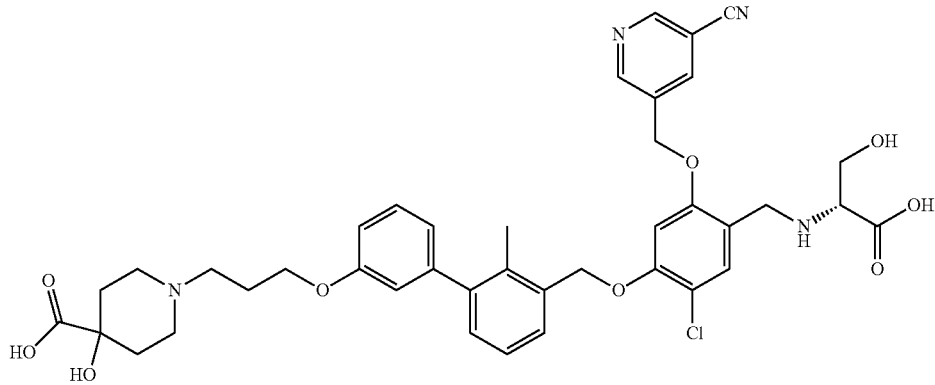 [SMILES: Cc1c(COc2cc(OCc3cncc(C#N)c3)c(CN[C@H](CO)C(=O)O)cc2Cl)cccc1-c1cccc(OCCCN2CCC(O)(C(=O)O)CC2)c1]

Example 1032 and Example 1033 were prepared according to the following procedure: to a mixture of (R)-2-((5-chloro-2-((5-cyanopyridin-3-yl)methoxy)-4-((3'-(3-(4-hydroxy-4-(methoxycarbonyl)piperidin-1-yl)propoxy)-2-methyl-[1,1'-biphenyl]-3-yl)methoxy)benzyl)amino)-3-hydroxypropanoic acid (0.017 g, 0.015 mmol) in THF (1 mL) and MeOH (0.2 mL) was added 1N lithium hydroxide (0.038 mL, 0.038 mmol) at rt. The reaction mixture was stirred at rt for 16 h. The reaction was concentrated, then added a few drops of TFA and MeOH, filtered and purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 20 minutes; Flow: 40 mL/min. Fractions containing the desired products were combined and dried via centrifugal evaporation to yield (R)-1-(3-((3'-((5-((5-carbamoylpyridin-3-yl)methoxy)-4-(((1-carboxy-2-hydroxyethyl)amino)methyl)-2-chlorophenoxy)methyl)-2'-methyl-[1,1'-biphenyl]-3-yl)oxy)propyl)-4-hydroxypiperidine-4-carboxylic acid and (R)-1-(3-((3'-((4-(((1-carboxy-2-hydroxyethyl)amino)methyl)-2-chloro-5-((5-cyanopyridin-3-yl)methoxy)phenoxy)methyl)-2'-methyl-[1,1'-biphenyl]-3-yl)oxy)propyl)-4-hydroxypiperidine-4-carboxylic acid.

Example 1032: LC/MS (Cond. N-1): [M+H]$^+$ 777.25, RT=3.178 min. $^1$H NMR (400 MHz, METHANOL-d$_4$) δ ppm 9.05 (d, J=2.0 Hz, 1H), 8.88 (d, J=2.0 Hz, 1H), 8.50 (t, J=2.0 Hz, 1H), 7.54 (s, 1H), 7.46 (dd, J=7.4, 1.4 Hz, 1H), 7.37 (t, J=7.9 Hz, 1H), 7.28-7.17 (m, 2H), 7.09 (s, 1H), 6.97 (dd, J=7.9, 2.1 Hz, 1H), 6.93-6.86 (m, 2H), 5.46-5.37 (m, 2H), 5.34-5.25 (m, 2H), 4.41-4.28 (m, 2H), 4.17 (t, J=5.6 Hz, 2H), 4.00 (d, J=8.0 Hz, 2H), 3.60 (d, J=12.3 Hz, 2H), 3.43-3.33 (m, 3H), 2.36-2.19 (m, 9H), 2.02 (d, J=13.6 Hz, 2H).

Example 1033: LC/MS (Cond. N-1): [M+H]$^+$ 759.25, RT=3.191 min. $^1$H NMR (400 MHz, METHANOL-d$_4$) δ ppm 9.01-8.88 (m, 2H), 8.39 (d, J=2.0 Hz, 1H), 7.59-7.52 (m, 1H), 7.45 (d, J=6.8 Hz, 1H), 7.40-7.35 (m, 1H), 7.28-7.18 (m, 2H), 7.06 (s, 1H), 6.97 (d, J=8.3 Hz, 1H), 6.93-6.86 (m, 2H), 5.38 (s, 2H), 5.34-5.29 (m, 2H), 4.40-4.29 (m, 2H), 4.17 (t, J=5.6 Hz, 2H), 4.00-3.98 (m, 2H), 3.59 (d, J=11.8 Hz, 2H), 3.44-3.36 (m, 4H), 3.14 (dt, J=3.3, 1.6 Hz, 1H), 2.37-2.21 (m, 7H), 2.07-1.99 (m, 2H).

Example 1034: (R)—N-(2-((5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)ethyl) acrylamide

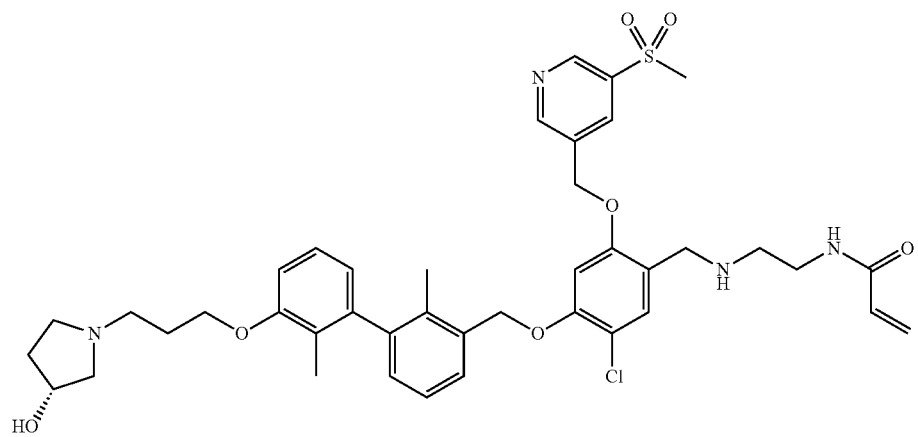 [SMILES: C=CC(=O)NCCNCc1cc(Cl)c(OCc2cccc(-c3cccc(OCCCN4CC[C@@H](O)C4)c3C)c2C)cc1OCc1cncc(S(C)(=O)=O)c1]

Example 1034 was prepared from (R)-5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzaldehyde and N-(2-aminoethyl)acrylamide, according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.7 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): $[M+H]^+$ 777.1, RT=1.456 min. Proton NMR was acquired in deuterated DMSO. $^1$H NMR (500 MHz, DMSO-$d_6$) δ ppm 9.08 (br. s., 1H), 9.03 (br. s., 1H), 8.45 (br. s., 1H), 8.07 (br. s., 1H), 7.49 (d, J=7.3 Hz, 1H), 7.42-7.36 (m, 1H), 7.27 (d, J=7.3 Hz, 1H), 7.20 (d, J=7.7 Hz, 1H), 7.14 (br. s., 1H), 7.08 (d, J=7.7 Hz, 1H), 6.96 (d, J=8.1 Hz, 1H), 6.68 (d, J=7.0 Hz, 1H), 6.25-6.16 (m, 1H), 6.05 (d, J=16.9 Hz, 1H), 5.55 (d, J=9.9 Hz, 1H), 5.42-5.34 (m, 2H), 5.26 (br. s., 2H), 4.18 (br. s., 1H), 4.04 (m, 2H), 3.64-3.54 (m, 2H), 3.3 (s, 3H), 3.23 (d, J=5.5 Hz, 1H), 3.18 (s, 1H), 2.71 (br. s., 1H), 2.57 (d, J=5.5 Hz, 4H), 2.45 (br. s., 1H), 2.33 (d, J=9.2 Hz, 1H), 2.04 (br. s., 3H), 1.97 (d, J=13.6 Hz, 3H), 1.83 (br. s., 3H), 1.53 (br. s., 1H).

Example 1035: (R)-1-(3-((3'-((5-((5-carbamoylpyridin-3-yl)methoxy)-4-(((1-carboxy-2-hydroxyethyl)amino)methyl)-2-chlorophenoxy)methyl)-2,2'-dimethyl-[1,1'-biphenyl]-3-yl)oxy)propyl)-4-hydroxypiperidine-4-carboxylic Acid

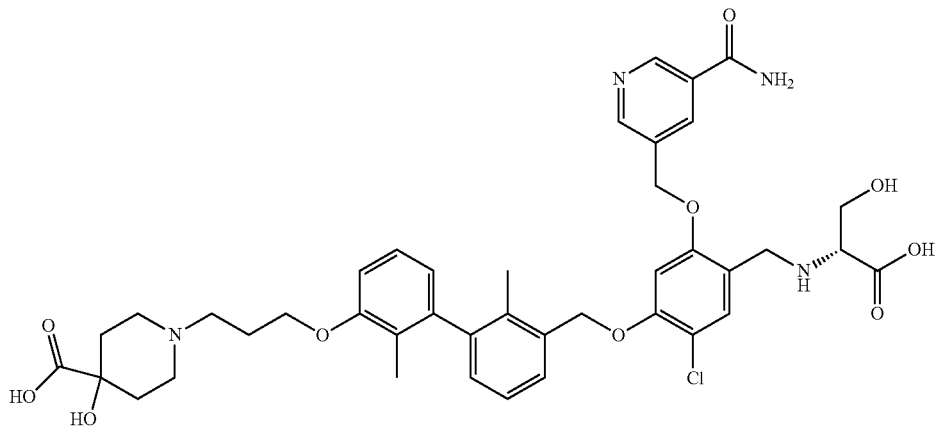 [SMILES: Cc1c(COc2cc(OCc3cncc(C(N)=O)c3)c(CN[C@H](CO)C(=O)O)cc2Cl)cccc1-c1cccc(OCCCN2CCC(O)(C(=O)O)CC2)c1C]

Example 1036: (R)-1-(3-((3'-((4-(((1-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-hydroxypiperidine-4-carboxylic Acid

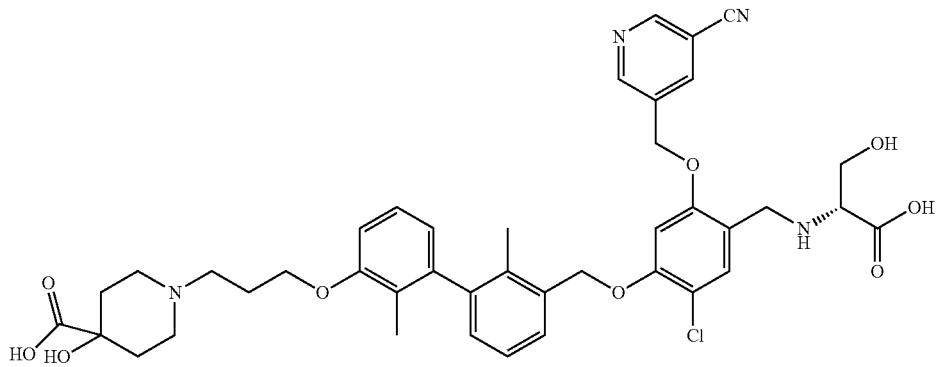 [SMILES: Cc1c(COc2cc(OCc3cncc(C#N)c3)c(CN[C@H](CO)C(=O)O)cc2Cl)cccc1-c1cccc(OCCCN2CCC(O)(C(=O)O)CC2)c1C]

Example 1035 and Example 1036 were prepared according to the procedure described for Example 1032 and Example 1033.

Example 1035: LC/MS (Cond. N-1): [M+H]+ 791.25, RT=3.114 min. $^1$H NMR (400 MHz, METHANOL-$d_4$) δ ppm 9.05 (d, J=2.3 Hz, 1H), 8.88 (d, J=2.0 Hz, 1H), 8.49 (t, J=2.0 Hz, 1H), 7.56-7.51 (m, 1H), 7.46 (d, J=7.3 Hz, 1H), 7.22 (t, J=7.9 Hz, 1H), 7.25 (t, J=7.5 Hz, 1H), 7.12-7.05 (m, 2H), 6.96 (d, J=8.0 Hz, 1H), 6.73 (d, J=7.0 Hz, 1H), 5.40 (s, 2H), 5.31 (s, 2H), 4.41-4.27 (m, 2H), 4.18 (t, J=5.0 Hz, 2H), 4.02-3.99 (m, 3H), 3.60 (d, J=11.5 Hz, 2H), 3.46-3.40 (m, 2H), 3.39-3.34 (m, 2H), 2.37-2.23 (m, 4H), 2.09 (s, 3H), 2.06-1.98 (m, 2H), 1.92 (s, 3H).

Example 1036: LC/MS (Cond. N-1): [M+H]+ 773.3, RT=3.20 min. $^1$H NMR (400 MHz, METHANOL-$d_4$) δ ppm 8.97 (d, J=2.0 Hz, 1H), 8.93 (d, J=2.0 Hz, 1H), 8.40 (s, 1H), 7.53 (s, 1H), 7.46 (d, J=7.8 Hz, 1H), 7.29-7.20 (m, 2H), 7.11-7.05 (m, 2H), 6.97 (d, J=8.3 Hz, 1H), 6.74 (d, J=7.3 Hz, 1H), 5.37 (s, 2H), 5.31 (s, 2H), 4.33 (q, J=13.1 Hz, 2H), 4.18 (t, J=4.8 Hz, 2H), 4.03-3.97 (m, 2H), 3.96-3.93 (m, 1H), 3.60 (d, J=11.5 Hz, 2H), 3.51-3.36 (m, 4H), 2.38-2.26 (m, 4H), 2.09 (s, 3H), 2.02 (d, J=13.6 Hz, 2H), 1.92 (s, 3H).

Example 1037: (R)-1-(3-((3'-((4-(((2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-hydroxypiperidine-4-carboxylic Acid

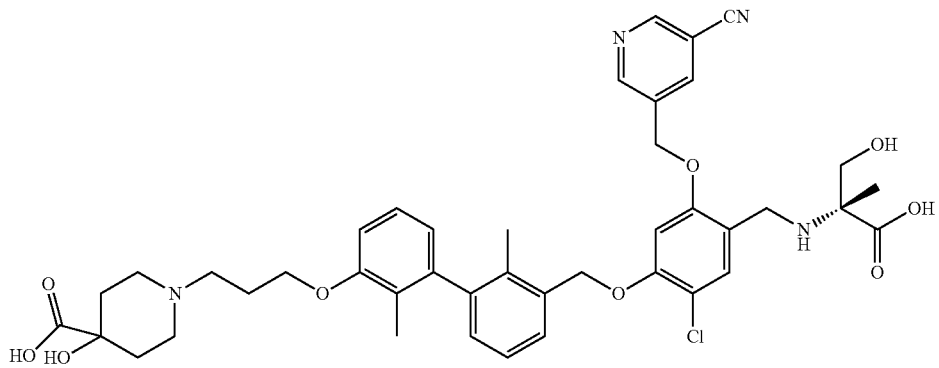

Example 1037 was prepared according to the procedure described for Example 1032 and Example 1033. LC/MS (Cond. N-1): [M+H]+ 787.3, RT=3.273 min. $^1$H NMR (400 MHz, METHANOL-$d_4$) δ ppm 8.99 (d, J=2.0 Hz, 1H), 8.92 (d, J=2.0 Hz, 1H), 8.43 (t, J=2.0 Hz, 1H), 7.56 (s, 1H), 7.47 (d, J=6.8 Hz, 1H), 7.22 (t, J=7.9 Hz, 1H), 7.25 (t, J=7.5 Hz, 1H), 7.10-7.06 (m, 2H), 6.96 (d, J=8.3 Hz, 1H), 6.73 (d, J=7.0 Hz, 1H), 5.38 (s, 2H), 5.32 (s, 2H), 4.30 (s, 2H), 4.18 (t, J=5.1 Hz, 2H), 4.00 (d, J=9.8 Hz, 1H), 3.82 (d, J=12.3 Hz, 1H), 3.60 (d, J=12.0 Hz, 2H), 3.46-3.39 (m, 2H), 3.38-3.33 (m, 2H), 2.37-2.23 (m, 4H), 2.11-2.07 (m, 3H), 2.05-1.97 (m, 2H), 1.92 (s, 3H), 1.55 (s, 3H).

Example 1038: (R)-2-((5-chloro-4-((3'-(3-(4-hydroxy-4-(methoxycarbonyl)piperidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic Acid

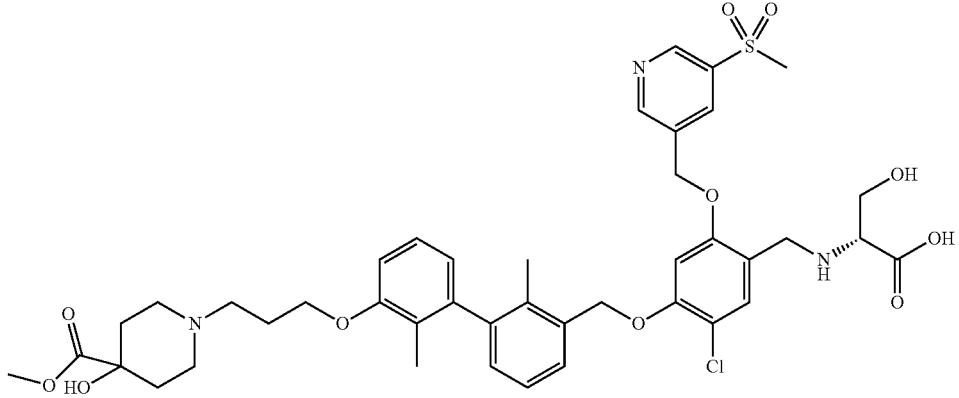 [SMILES: COC(=O)C1(O)CCN(CCCOc2cccc(-c3cccc(COc4cc(OCc5cncc(S(C)(=O)=O)c5)c(CN[C@H](CO)C(=O)O)cc4Cl)c3C)c2C)CC1]

Example 1038 was prepared according to the reductive amination conditions as described for Example 1003. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 95%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 840.3, RT=1.443 min.

Example 1039: (S)-2-((5-chloro-4-((3'-(3-(4-hydroxy-4-(methoxycarbonyl)piperidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic Acid Example 1039 was prepared according to the reductive amination conditions as described for Example 1003. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 854.3, RT=1.466 min. Proton NMR was acquired in deuterated DMSO. $^1$H NMR (500 MHz, DMSO-d$_6$) δ ppm 9.07 (d, J=6.2 Hz, 2H), 8.57 (br. s., 1H), 7.55 (s, 1H), 7.51 (d, J=7.7 Hz, 1H), 7.28 (t, J=7.3 Hz, 1H), 7.24-7.16 (m, 2H), 7.08 (d, J=7.7 Hz, 1H), 6.96 (d, J=7.7 Hz, 1H), 6.68 (d, J=7.3 Hz, 1H), 5.41 (br. s., 2H), 5.37-5.24 (m, 2H), 4.04 (d, J=7.7 Hz, 2H), 3.96 (br. s., 2H), 3.60 (d, J=11.7 Hz, 2H), 3.59 (s., 3H), 3.52 (d, J=11.0 Hz, 2H), 3.40 (s., 3H), 2.55 (br. s., 2H), 2.48-2.42 (m, 2H), 2.31 (t, J=10.6 Hz, 2H), 2.07-2.00 (m, 3H), 1.89-1.78 (m, 5H), 1.59 (d, J=12.5 Hz, 2H), 1.27-1.17 (m, 3H).

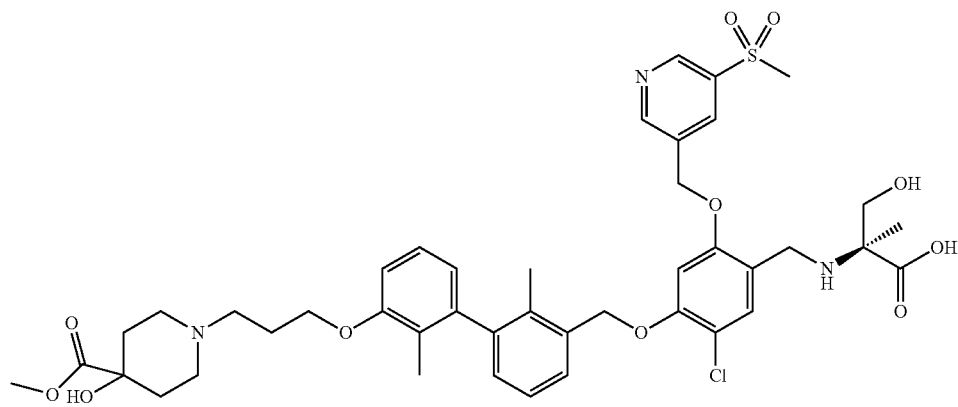

Example 1040: (R)-1-(3-((3'-((4-(((1-carboxy-2-hydroxyethyl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypiperidine-4-carboxylic Acid


Example 1040 was prepared according to the procedure described for Example 1032 and Example 1033. LC/MS (Cond. N-1): [M+H]+ 826.25, RT=3.158 min. 1H NMR (400 MHz, METHANOL-d4) δ ppm 9.12 (d, J=2.3 Hz, 1H), 9.05 (d, J=1.8 Hz, 1H), 8.55 (t, J=2.0 Hz, 1H), 7.54 (s, 1H), 7.48 (d, J=6.8 Hz, 1H), 7.29-7.19 (m, 2H), 7.11 (s, 1H), 7.08 (dd, J=7.5, 1.0 Hz, 1H), 6.96 (d, J=8.0 Hz, 1H), 6.77-6.71 (m, 1H), 5.43 (s, 2H), 5.33 (s, 2H), 4.40-4.29 (m, 2H), 4.18 (t, J=5.1 Hz, 2H), 4.05-3.99 (m, 3H), 3.61 (d, J=12.0 Hz, 2H), 3.46-3.39 (m, 2H), 3.38-3.33 (m, 2H), 3.27 (s, 3H), 2.33 (dd, J=10.2, 4.9 Hz, 4H), 2.09 (s, 3H), 2.02 (d, J=14.8 Hz, 2H), 1.92 (s, 3H).

Example 1041: (S)-1-(3-((3'-((4-(((2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypiperidine-4-carboxylic Acid

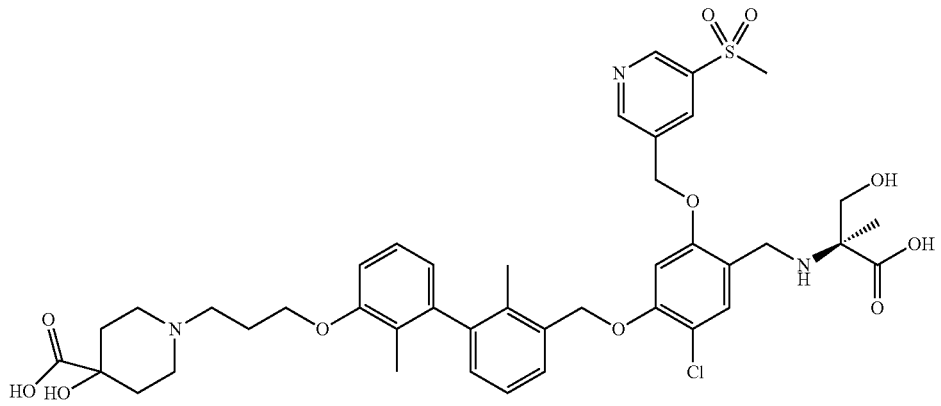

Example 1041 was prepared according to the procedure described for Example 1032 and Example 1033. LC/MS (Cond. N-1): [M+H]+ 840.25, RT=3.168 min. 1H NMR (400 MHz, METHANOL-d4) δ ppm 9.12 (d, J=2.0 Hz, 1H), 9.08 (d, J=2.0 Hz, 1H), 8.58 (t, J=1.9 Hz, 1H), 7.58 (s, 1H), 7.49 (d, J=7.5 Hz, 1H), 7.23 (t, J=7.0 Hz, 1H), 7.27 (t, J=6.8 Hz, 1H), 7.13-7.07 (m, 2H), 6.97 (d, J=8.3 Hz, 1H), 6.75 (d, J=7.5 Hz, 1H), 5.44 (s, 2H), 5.35 (s, 2H), 4.30 (s, 2H), 4.19 (t, J=4.8 Hz, 2H), 4.04-3.98 (m, 1H), 3.81 (d, J=12.0 Hz, 1H), 3.62 (d, J=11.5 Hz, 2H), 3.47-3.41 (m, 2H), 3.39-3.35 (m, 2H), 3.28 (s, 3H), 2.37-2.26 (m, 4H), 2.11 (s, 3H), 2.08-1.99 (m, 2H), 1.93 (s, 3H), 1.53 (s, 3H).

Example 1042: (R)-2-((5-chloro-2-((5-cyanopyridin-3-yl)methoxy)-4-((2,2'-dimethyl-3'-(((1R,9aR)-octahydro-1H-quinolizin-1-yl)methoxy)-[1,1'-biphenyl]-3-yl)methoxy)benzyl)amino)-3-hydroxypropanoic Acid

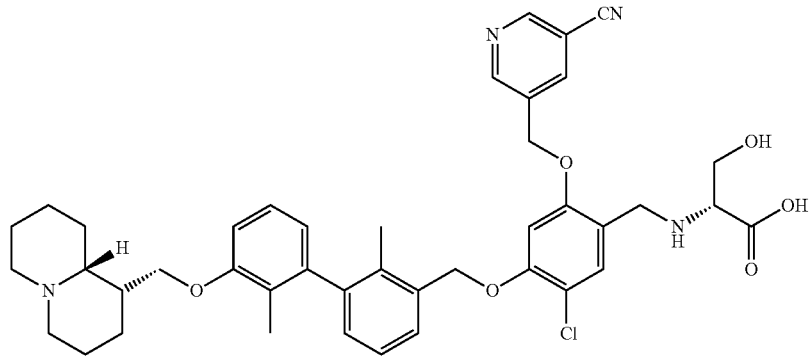

Example 1042 was prepared according to the reductive amination conditions as described for Example 1003. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 15-55% B over 15 minutes, then a 7-minute hold at 100% B; Flow: 20 mL/min. Fractions containing the desired product were combined and dried via centrifugal evaporation. The yield of the product was 7.2 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 739.3, RT=1.625 min.

Example 1043: (S)-1-(5-chloro-2-((5-cyanopyridin-3-yl)methoxy)-4-((2,2'-dimethyl-3'-(((1R,9aR)-octahydro-1H-quinolizin-1-yl)methoxy)-[1,1'-biphenyl]-3-yl)methoxy)benzyl)piperidine-2-carboxylic Acid

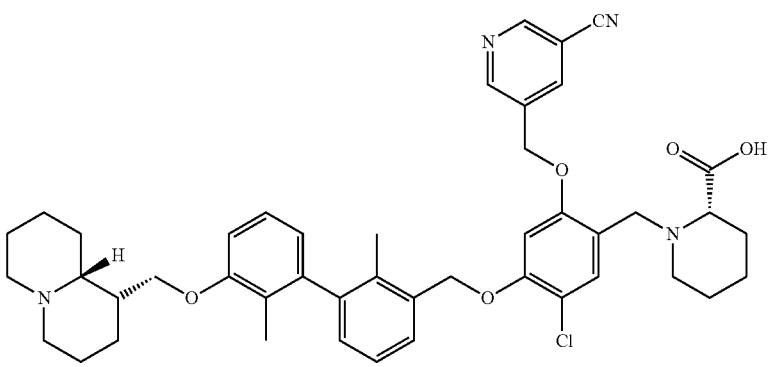

Example 1043 was prepared according to the reductive amination conditions as described for Example 1003. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 35 minutes, then a 5-minute hold at 100% B; Flow: 20 mL/min. Fractions containing the desired product were combined and dried via centrifugal evaporation. The yield of the product was 20.0 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile: water with 10 mM ammonium acetate; Mobile Phase B: 95:5 acetonitrile:water with 10 mM ammonium acetate;

Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]⁺ 763.4, RT=1.700 min.

Intermediate: 1-tert-butyl 3-ethyl 3-((benzyloxy)methyl)pyrrolidine-1,3-dicarboxylate

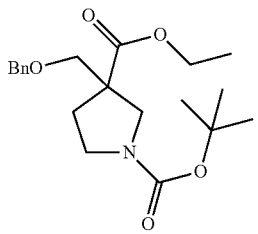 [SMILES: CCOC(=O)C1(COCc2ccccc2)CCN(C(=O)OC(C)(C)C)C1]

To a solution of 1-tert-butyl 3-ethyl pyrrolidine-1,3-dicarboxylate (1.5 g, 6.17 mmol) in THF (10 mL) was added lithium diisopropylamide (2.0 M in THF) (3.70 mL, 7.40 mmol) dropwise at −78° C. The reaction mixture was stirred at −78° C. for 1.5 h. The solution of ((chloromethoxy)methyl)benzene (1.255 g, 8.01 mmol) was added dropwise at −78° C. Then the solution was allowed to warm to room temperature and stirred at rt for 1 h. The reaction was quenched with aq NH₄C₁, then diluted with EtOAc. Then organic phase was washed with water, sat. NaCl, dried over anhydrous Na₂SO₄, and concentrated to yield an oil. The crude product was purified by silica chromatography (0-60% EtOAc/Hex) to yield 1-tert-butyl 3-ethyl 3-((benzyloxy)methyl)pyrrolidine-1,3-dicarboxylate (1.9 g, 5.23 mmol, 85% yield) as a clear oil. LC/MS (Cond. N-1): [M+H]⁺ 386.20, RT=3.993 min. ¹H NMR (400 MHz, CHLOROFORM-d) δ ppm 7.41-7.23 (m, 5H), 4.58-4.46 (m, 2H), 4.22-4.14 (m, 2H), 3.66-3.53 (m, 2H), 3.44-3.35 (m, 2H), 2.37-2.18 (m, 1H), 2.02-1.89 (m, 1H), 1.49-1.41 (m, 9H), 1.29-1.24 (m, 3H).

Intermediate: 1-tert-butyl 3-ethyl 3-(hydroxymethyl)pyrrolidine-1,3-dicarboxylate

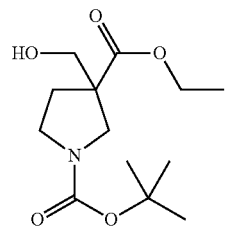 [SMILES: CCOC(=O)C1(CO)CCN(C(=O)OC(C)(C)C)C1]

A stirred mixture of 1-tert-butyl 3-ethyl 3-((benzyloxy)methyl)pyrrolidine-1,3-dicarboxylate (1.8 g, 4.95 mmol) and Palladium hydroxide on carbon (0.209 g, 0.297 mmol) in MeOH was hydrogenated at 50 psi at rt for 18 h. The reaction mixture was filtered through a plug of diatomaceous earth (Celite®) then washed with MeOH, the filtrate was concentrated to yield 1-tert-butyl 3-ethyl 3-(hydroxymethyl)pyrrolidine-1,3-dicarboxylate (1.25 g, 4.57 mmol, 92% yield). LC/MS (Cond. N-1): [M+Na]⁺ 386.20, RT=3.177 min. ¹H NMR (400 MHz, CHLOROFORM-d) δ ppm 4.21-4.11 (m, 2H), 3.75-3.60 (m, 3H), 3.49-3.31 (m, 3H), 2.26-2.16 (m, 1H), 2.03-1.88 (m, 1H), 1.45-1.37 (m, 9H), 1.28-1.18 (m, 3H).

Intermediate: Ethyl 3-(hydroxymethyl)pyrrolidine-3-carboxylate

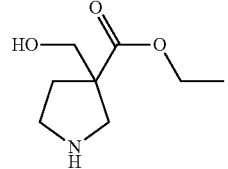

To a mixture of 1-tert-butyl 3-ethyl 3-(hydroxymethyl)pyrrolidine-1,3-dicarboxylate (1.25 g, 4.57 mmol) in DCM (10 mL) was added HCl (2.0 M in ether) (4.57 mL, 9.15 mmol) at rt. The reaction mixture was stirred at rt for 16 h. The reaction was concentrated to dryness to afford ethyl 3-(hydroxymethyl)pyrrolidine-3-carboxylate, HCl (0.7 g, 4.04 mmol, 88% yield). LC/MS (Cond. N-1): [M+H]⁺=174.15, RT=2.01 min.

Intermediate: Ethyl 1-(3-((3'-((2-chloro-4-formyl-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylate

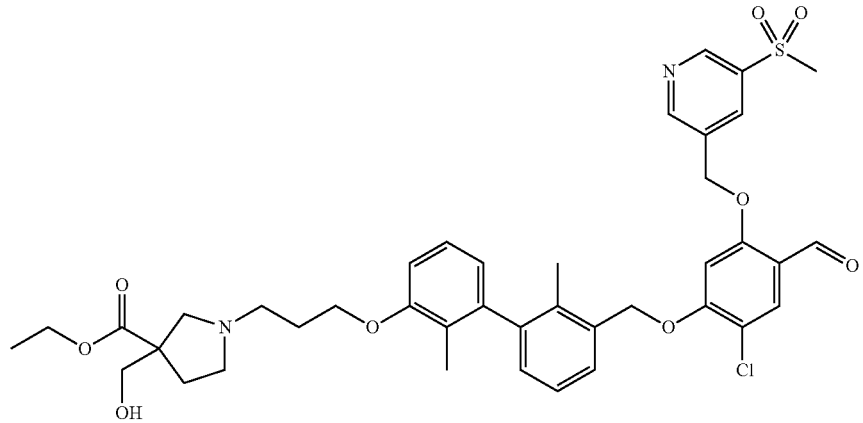 [SMILES: CCOC(=O)C1(CO)CCN(CCCOc2cccc(-c3cccc(COc4cc(OCc5cncc(S(C)(=O)=O)c5)c(C=O)cc4Cl)c3C)c2C)C1]

A stirred mixture of 5-chloro-4-((3'-(3-chloropropoxy)-2,2'-dimethyl-[1,1'-biphenyl]-3-yl)methoxy)-2-((5-(methylsulfonyl)pyridin-3-yl)methoxy)benzaldehyde (0.1 g, 0.159 mmol), ethyl 3-(hydroxymethyl)pyrrolidine-3-carboxylate, HCl (0.050 g, 0.239 mmol), NaI (0.024 g, 0.159 mmol) and $K_2CO_6$ (0.066 g, 0.477 mmol) in DMF (2 mL) was heated at 70° C. for 16 h. The reaction mixture was cooled to rt, added with EtOAc and water, then the organic phase was washed with sat. NaCl, dried ($Na_2SO_4$). The crude material was purified by silica gel (0-100% EtOAc/hex, then 0-10% MeOH/DCM) to yield ethyl 1-(3-((3'-((2-chloro-4-formyl-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylate (0.07 g, 0.091 mmol, 57.5% yield) as a pale yellow solid. LC/MS (Cond. N-1): [M+H]$^+$=765.25, RT=3.599 min. $^1$H NMR (400 MHz, CHLOROFORM-d) δ ppm 10.28 (s, 1H), 9.20 (d, J=2.3 Hz, 1H), 9.01 (d, J=1.8 Hz, 1H), 8.40 (t, J=2.0 Hz, 1H), 7.94 (s, 1H), 7.48 (d, J=7.5 Hz, 1H), 7.34-7.29 (m, 1H), 7.22-7.17 (m, 2H), 6.87 (d, J=8.0 Hz, 1H), 6.79-6.73 (m, 1H), 6.71 (s, 1H), 5.33-5.25 (m, 4H), 4.26-4.17 (m, 2H), 4.13-4.05 (m, 2H), 3.84 (d, J=10.3 Hz, 1H), 3.70 (d, J=10.5 Hz, 1H), 3.22-3.16 (m, 3H), 3.05-2.98 (m, 2H), 2.79-2.66 (m, 2H), 2.54-2.42 (m, 1H), 2.31-2.14 (m, 3H), 2.12 (s, 3H), 2.06-2.02 (m, 1H), 1.98 (dd, J=7.8, 6.0 Hz, 1H), 1.95-1.90 (m, 3H), 1.29 (d, J=6.5 Hz, 3H).

Example 1044: (2R)-2-((5-chloro-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic Acid

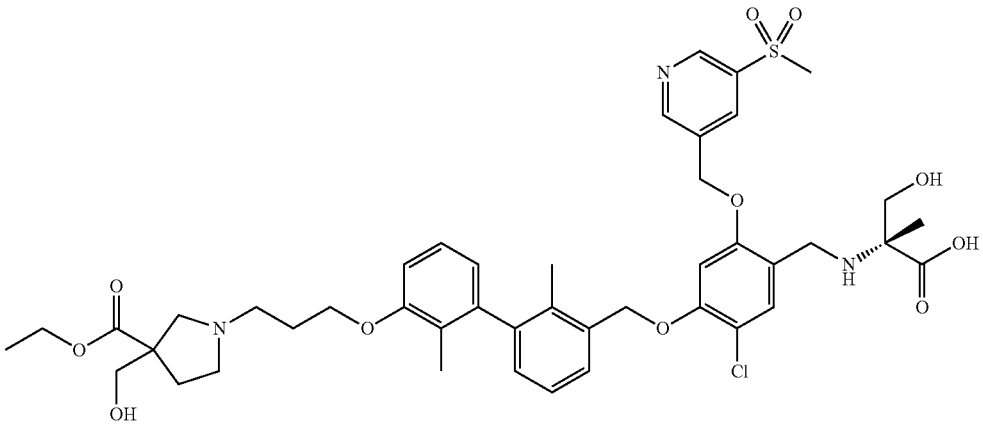

Example 1044 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 12.7 mg, and its estimated purity by LCMS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 868.3, RT=2.168 min. Proton NMR was acquired in deuterated DMSO. $^1$H NMR (500 MHz, DMSO-$d_6$) δ ppm 9.07 (d, J=7.0 Hz, 2H), 8.57 (s, 1H), 7.96 (s, 1H), 7.55 (s, 1H), 7.51 (d, J=7.3 Hz, 1H), 7.28 (t, J=7.5 Hz, 1H), 7.23-7.18 (m, 2H), 7.08 (d, J=7.3 Hz, 1H), 6.95 (d, J=8.1 Hz, 1H), 6.68 (d, J=7.0 Hz, 1H), 5.41 (br. s., 2H), 5.36-5.23 (m, 2H), 4.06 (q, J=7.0 Hz, 4H), 3.97 (m, 2H), 3.61 (d, J=11.0 Hz, 2H), 3.54-3.49 (m, 2H), 3.40 (s, 3H), 2.76 (d, J=9.2 Hz, 2H), 2.54-2.41 (m, 6H), 2.12-2.01 (m, 4H), 1.83 (s, 3H), 1.70-1.63 (m, 1H), 1.23 (s, 3H), 1.17 (t, J=7.0 Hz, 3H).

Example 1045: (2R)-2-((5-chloro-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic Acid

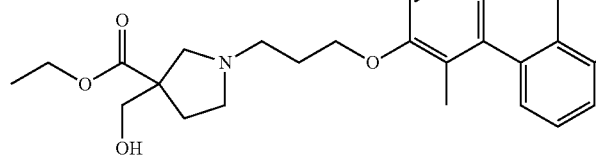

Example 1045 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 5.4 mg, and its estimated purity by LCMS analysis was 93%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]+ 854.3, RT=2.116 min. Proton NMR was acquired in deuterated DMSO. $^1$H NMR (500 MHz, DMSO-d$_6$) δ ppm 9.07 (d, J=9.2 Hz, 2H), 8.57 (s, 1H), 7.95 (s, 1H), 7.55-7.47 (m, 2H), 7.28 (t, J=7.7 Hz, 1H), 7.24-7.18 (m, 2H), 7.08 (d, J=8.1 Hz, 1H), 6.95 (d, J=8.1 Hz, 1H), 6.68 (d, J=7.3 Hz, 1H), 5.49-5.35 (m, 2H), 5.33-5.22 (m, 2H), 4.09-3.98 (m, 6H), 3.74-3.68 (m, 1H), 3.64-3.58 (m, 1H), 3.53 (d, J=6.2 Hz, 2H), 3.40 (s, 3H), 3.16 (t, J=5.5 Hz, 1H), 2.76 (d, J=10.3 Hz, 2H), 2.54-2.41 (m, 6H), 2.12-1.99 (m, 4H), 1.83 (s, 3H), 1.71-1.62 (m, 1H), 1.16 (t, J=7.0 Hz, 3H).

Intermediate: Tert-butyl 3-cyano-3-((trimethylsilyl)oxy)pyrrolidine-1-carboxylate

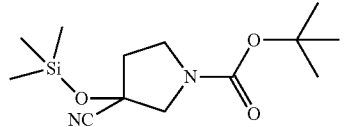 [SMILES: CC(C)(C)OC(=O)N1CCC(C#N)(O[Si](C)(C)C)C1]

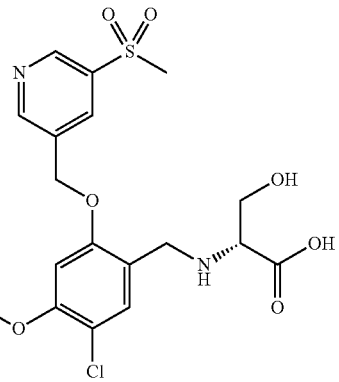

Intermediate: Tert-butyl 3-cyano-3-hydroxypyrrolidine-1-carboxylate

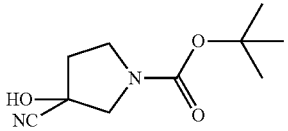

To a solution of tert-butyl 3-oxopyrrolidine-1-carboxylate (1 g, 5.40 mmol) in DCM (10 mL) was added trimethylsilyl cyanide (0.724 mL, 5.40 mmol), KCN (0.035 g, 0.540 mmol) and 18-CROWN-6 (0.143 g, 0.540 mmol) at 0° C. The reaction mixture was warmed to rt and stirred at rt for 16 h. The reaction mixture was cooled to 0° C., and quenched with sat. NaHCO$_3$, then diluted with EtOAc. The organic phase was separated, washed with sat. NaCl, dried over anhydrous Na$_2$SO$_4$, filtered and concentrated. The residue was purified on silica gel chromatography (0-100% EtOAc/hex) to yield tert-butyl 3-cyano-3-((trimethylsilyl)oxy)pyrrolidine-1-carboxylate (0.5 g, 1.758 mmol, 32.6% yield) and tert-butyl 3-cyano-3-hydroxypyrrolidine-1-carboxylate (0.306 g, 1.442 mmol, 26.7% yield).

tert-butyl 3-cyano-3-((trimethylsilyl)oxy)pyrrolidine-1-carboxylate: LC/MS (Cond. N-1): [M+H]+ 213.2, RT=4.359 min. $^1$H NMR (400 MHz, CHLOROFORM-d) δ ppm 3.83-3.72 (m, 1H), 3.72-3.43 (m, 3H), 2.33 (q, J=6.8 Hz, 2H), 1.52-1.42 (m, 9H), 0.19-0.10 (m, 9H).

tert-butyl 3-cyano-3-hydroxypyrrolidine-1-carboxylate: LC/MS (Cond. N-1): [M+H]+ 235.15, RT=2.834 min. $^1$H NMR (400 MHz, CHLOROFORM-d) δ ppm 4.80-4.63 (br. m., 1H), 3.84-3.68 (m, 2H), 3.68-3.47 (m, 2H), 2.39-2.29 (m, 2H), 1.52-1.43 (m, 9H).

Intermediate: Methyl 3-hydroxypyrrolidine-3-carboxylate

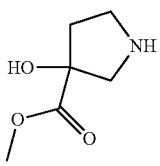

To a solution of tert-butyl 3-cyano-3-((trimethylsilyl)oxy)pyrrolidine-1-carboxylate (0.5 g, 1.758 mmol) and tert-butyl 3-cyano-3-hydroxypyrrolidine-1-carboxylate (0.373 g, 1.758 mmol) in MeOH (10 mL) was added HCl (4 N in dioxane) (5 mL, 20.00 mmol), the reaction mixture was heated in a sealed tube at 70° C. for 16 h. The reaction mixture was cooled to rt then concentrated to dryness to yield methyl 3-hydroxypyrrolidine-3-carboxylate, HCl (0.6 g). $^1$H NMR (400 MHz, METHANOL-d$_4$) δ ppm 3.84 (s, 3H), 3.71-3.50 (m, 3H), 3.47-3.39 (m, 1H), 2.57-2.37 (m, 1H), 2.31-2.19 (m, 1H).

Intermediate: Methyl 1-(3-((3'-((2-chloro-5-((5-cyanopyridin-3-yl)methoxy)-4-formylphenoxy)methyl)-2,2'-dimethyl-[1,1'-biphenyl]-3-yl)oxy)propyl)-3-hydroxypyrrolidine-3-carboxylate

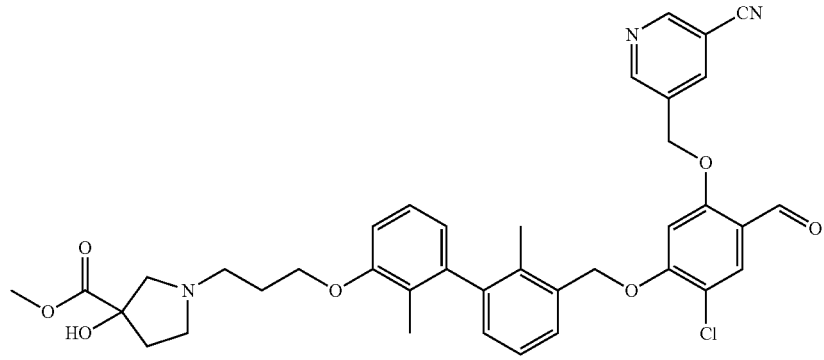 [SMILES: COC(=O)C1(O)CCN(CCCOc2cccc(-c3cccc(COc4cc(OCc5cncc(C#N)c5)c(C=O)cc4Cl)c3C)c2C)C1]

A stirred mixture of 5-((4-chloro-5-((3'-(3-chloropropoxy)-2,2'-dimethyl-[1,1'-biphenyl]-3-yl)methoxy)-2-formylphenoxy)methyl)nicotinonitrile (0.12 g, 0.209 mmol), methyl 3-hydroxypyrrolidine-3-carboxylate, HCl (0.057 g, 0.313 mmol), NaI (0.031 g, 0.209 mmol) and K$_2$CO$_3$ (0.086 g, 0.626 mmol) in DMF (2 mL) was heated at 70° C. for 16 h. The reaction mixture was cooled to rt, added with EtOAc and water, then the organic phase was washed with sat. NaCl, dried (Na$_2$SO$_4$). The crude material was purified by silica gel chromatography (0-100% EtOAc/hex, then 0-10% MeOH/DCM) to methyl 1-(3-((3'-((2-chloro-5-((5-cyanopyridin-3-yl)methoxy)-4-formylphenoxy)methyl)-2,2'-dimethyl-[1,1'-biphenyl]-3-yl)oxy)propyl)-3-hydroxypyrrolidine-3-carboxylate (0.035 g, 0.051 mmol, 24.53% yield). LC/MS (Cond. N-1): [M+H]$^+$=684.25, RT=3.646 min.

Example 1046: (2R)-2-((5-chloro-2-((5-cyanopyridin-3-yl)methoxy)-4-((3'-(3-(3-hydroxy-3-(methoxycarbonyl)pyrrolidin-1-yl)propoxy)-2,2'-dimethyl-[1,1'-biphenyl]-3-yl)methoxy)benzyl)amino)-3-hydroxy-2-methylpropanoic Acid

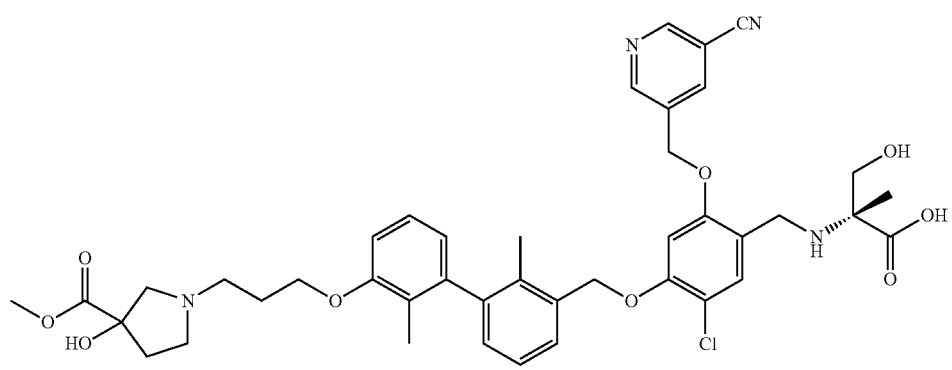

Example 1046 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 30 minutes, then a 5-minute hold at 100% B; Flow: 20 mL/min. Fractions containing the desired product were combined and dried via centrifugal evaporation. The yield of the product was 1.7 μmg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 787.3, RT=2.127 min. Proton NMR was acquired in deuterated DMSO. $^1$H NMR (500 MHz, DMSO-d$_6$) δ ppm 9.03 (d, J=8.4 Hz, 2H), 8.52 (s, 1H), 7.96 (s, 1H), 7.55 (s, 1H), 7.48 (d, J=7.7 Hz, 1H), 7.27 (t, J=7.7 Hz, 1H), 7.21 (t, J=7.7 Hz, 1H), 7.14 (s, 1H), 7.08 (d, J=7.3 Hz, 1H), 6.96 (d, J=8.1 Hz, 1H), 6.68 (d, J=7.3 Hz, 1H), 5.39-5.25 (m, 4H), 4.05 (d, J=8.8 Hz, 2H), 3.96 (s, 2H), 3.72-3.57 (m, 4H), 3.53 (d, J=11.4 Hz, 1H), 2.92 (d, J=9.9 Hz, 1H), 2.73 (m, 1H), 2.63-2.55 (m, 4H), 2.26-2.14 (m, 2H), 2.06-2.01 (m, 3H), 1.86-1.75 (m, 5H), 1.23 (s, 3H).

Example 1047: (2R)-2-((5-chloro-2-((5-cyanopyridin-3-yl)methoxy)-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)benzyl)amino)-3-hydroxypropanoic Acid

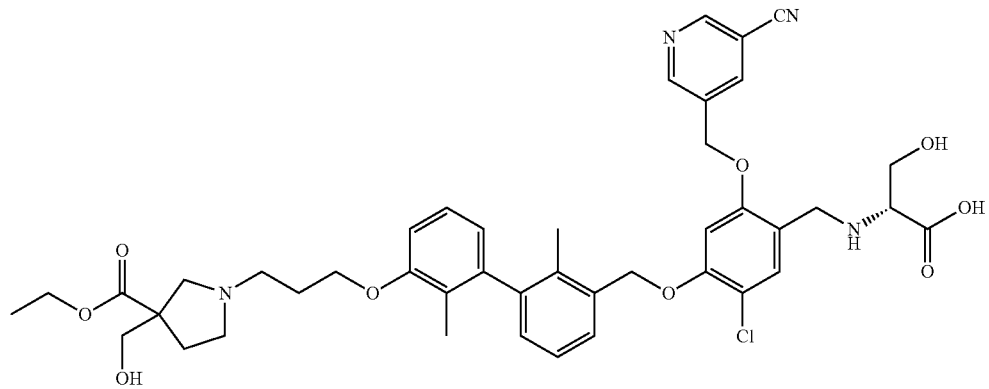 [SMILES: CCOC(=O)C1(CO)CCN(CCCOc2cccc(-c3cccc(COc4cc(OCc5cncc(C#N)c5)c(CN[C@H](CO)C(=O)O)cc4Cl)c3C)c2C)C1]

Example 1047 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]⁺ 801.1, RT=2.13 min.

Example 1048:1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic Acid

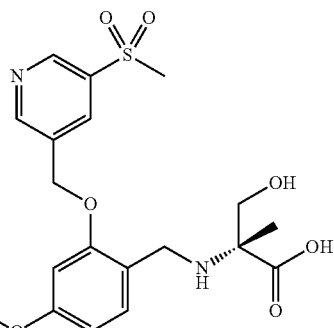

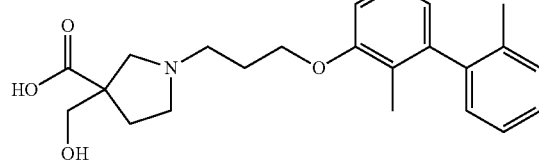

Example 1048 was prepared according to the procedure described for Example 1032 and Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]⁺ 840.1, RT=1.779 min. ¹H NMR (500 MHz, DMSO-d₆) δ ppm 9.03 (d, J=9.2 Hz, 2H), 8.52 (s, 1H), 7.96 (s, 1H), 7.54 (s, 1H), 7.48 (d, J=7.7 Hz, 1H), 7.26 (t, J=7.5 Hz, 1H), 7.21 (t, J=7.9 Hz, 1H), 7.14 (s, 1H), 7.08 (d, J=7.7 Hz, 1H), 6.95 (d, J=8.1 Hz, 1H), 6.68 (d, J=7.3 Hz, 1H), 5.35-5.22 (m, 4H), 4.05 (d, J=8.1 Hz, 4H), 3.94 (br. s., 2H), 3.60 (d, J=11.7 Hz, 1H), 3.52 (d, J=11.7 Hz, 1H), 3.47 (s, 3H), 2.78 (d, J=8.8 Hz, 1H), 2.65-2.56 (m, 5H), 2.11-2.00 (m, 4H), 1.93 (d, J=6.2 Hz, 2H), 1.82 (s, 3H), 1.65-1.57 (m, 1H), 1.23 (s, 3H).

Example 1049: (2R)-2-((5-chloro-2-((5-cyanopyridin-3-yl)methoxy)-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)benzyl)amino)-3-hydroxy-2-methylpropanoic Acid

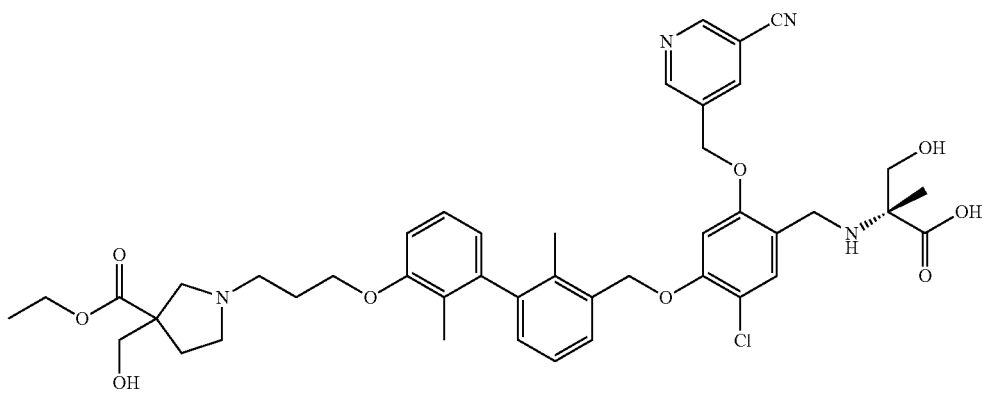

Example 1049 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 17.4 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 815.3, RT=1.743 min. Proton NMR was acquired in deuterated DMSO. $^1$H NMR (500 MHz, DMSO-d$_6$) δ ppm 9.03 (d, J=7.3 Hz, 2H), 8.52 (s, 1H), 7.96 (s, 1H), 7.54 (s, 1H), 7.48 (d, J=7.3 Hz, 1H), 7.27 (t, J=7.3 Hz, 1H), 7.21 (t, J=7.9 Hz, 1H), 7.14 (s, 1H), 7.08 (d, J=7.3 Hz, 1H), 6.95 (d, J=8.1 Hz, 1H), 6.68 (d, J=7.3 Hz, 1H), 5.39-5.27 (m, 4H), 4.10-4.02 (m, 4H), 3.96-3.89 (m, 2H), 3.64-3.44 (m, 4H), 2.79-2.73 (m, 2H), 2.57-2.53 (m, 3H), 2.47-2.41 (m, 1H), 2.12-2.00 (m, 5H), 1.83 (m, 4H), 1.70-1.62 (m, 1H), 1.23 (s, 3H), 1.17 (t, J=7.0 Hz, 3H).

Example 1050: 1-(3-((3'-((4-((((R)-1-carboxy-2-hydroxyethyl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic Acid

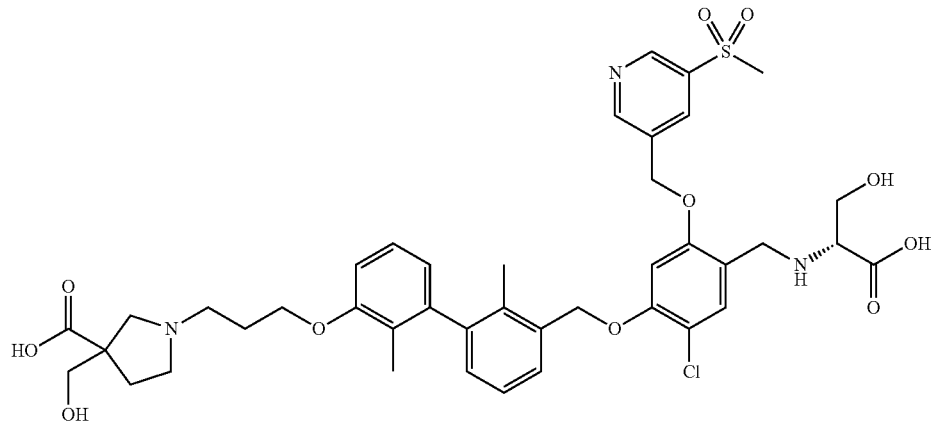 [SMILES: Cc1c(COc2cc(OCc3cncc(S(C)(=O)=O)c3)c(CN[C@H](CO)C(=O)O)cc2Cl)cccc1-c1cccc(OCCCN2CCC(CO)(C(=O)O)C2)c1C]

Example 1050 was prepared according to the procedure described in Example 1032 and Example 1033. Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 826.3, RT=1.619 min.

Example 1051: 1-(3-((3'-((4-((((R)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic Acid

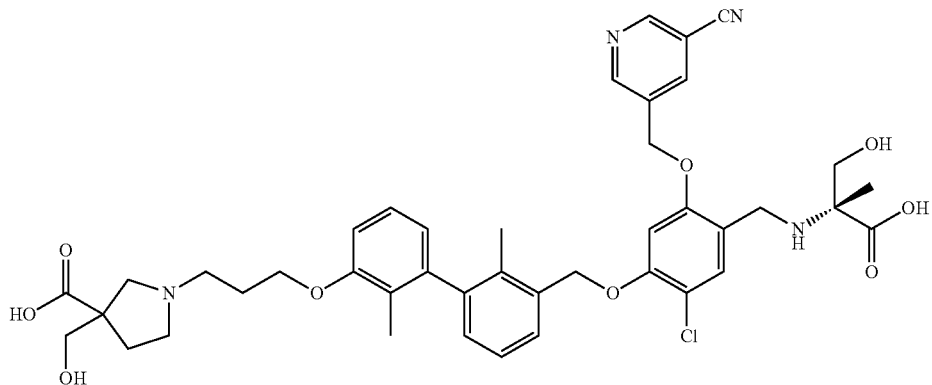

Example 1051 was prepared according to the procedure described in Example 1032 and Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 787.3, RT=1.443 min. Proton NMR was acquired in deuterated DMSO. $^1$H NMR (500 MHz, DMSO-d$_6$) δ ppm 9.08 (d, J=6.6 Hz, 2H), 8.57 (s, 1H), 7.55 (s, 1H), 7.51 (d, J=8.1 Hz, 1H), 7.28 (t, J=7.5 Hz, 1H), 7.24-7.18 (m, 2H), 7.09 (d, J=7.7 Hz, 1H), 6.96 (d, J=8.4 Hz, 1H), 6.68 (d, J=7.7 Hz, 1H), 5.42 (s, 2H), 5.37-5.27 (m, 2H), 4.05 (d, J=8.1 Hz, 2H), 3.97 (s, 2H), 3.61 (d, J=11.4 Hz, 1H), 3.52 (d, J=11.0 Hz, 1H), 3.50 (s, 2H), 2.82 (d, J=9.2 Hz, 1H), 2.66-2.54 (m, 5H), 2.11-2.00 (m, 4H), 1.96-1.91 (m, 2H), 1.83 (s, 3H), 1.69-1.61 (m, 1H), 1.23 (s, 3H).

Example 1052: 1-(3-((3'-((4-((((R)-1-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic Acid

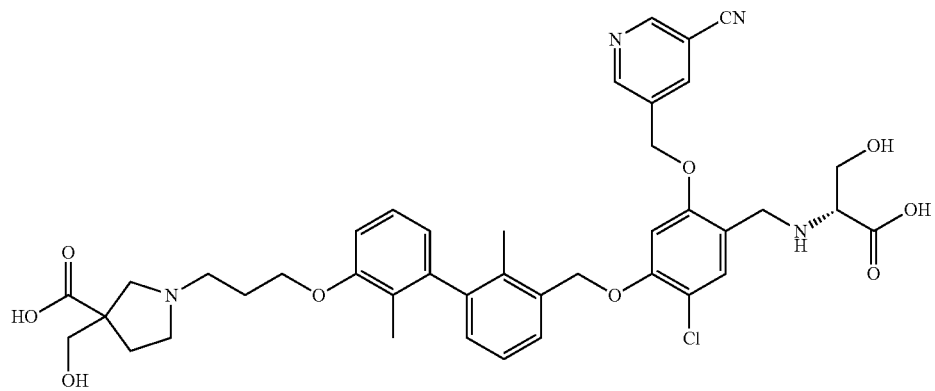 [SMILES: Cc1c(COc2cc(OCc3cncc(C#N)c3)c(CN[C@H](CO)C(=O)O)cc2Cl)cccc1-c1cccc(OCCCN2CCC(CO)(C(=O)O)C2)c1C]

Example 1053: 1-(3-((3'-((5-((5-carbamoylpyridin-3-yl)methoxy)-4-((((R)-1-carboxy-2-hydroxyethyl)amino)methyl)-2-chlorophenoxy)methyl)-2,2'-dimethyl-[1,1'-biphenyl]-3-yl)oxy)propyl)-3-(hydroxymethyl)pyrrolidine-3-carboxylic Acid

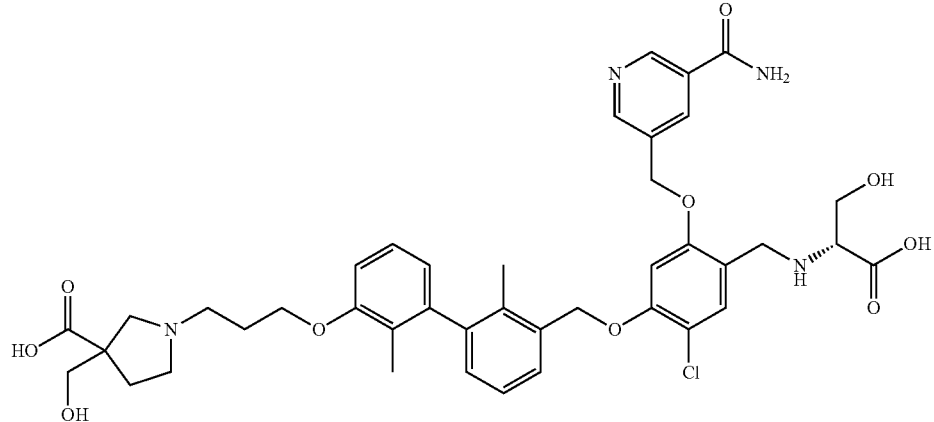 [SMILES: Cc1c(COc2cc(OCc3cncc(C(N)=O)c3)c(CN[C@H](CO)C(=O)O)cc2Cl)cccc1-c1cccc(OCCCN2CCC(CO)(C(=O)O)C2)c1C]

Example 1052 and Example 1053 were prepared according to the procedure described for Example 1032 and Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 1052: LC/MS (Injection 1 conditions): [M+H]$^+$ 773.3, RT=1.424 min. $^1$H NMR (500 MHz, DMSO-$d_6$) δ ppm 9.03 (d, J=5.1 Hz, 2H), 8.53 (s, 1H), 7.96 (s, 1H), 7.52-7.45 (m, 2H), 7.27 (t, J=7.5 Hz, 1H), 7.23-7.18 (m, 1H), 7.14 (s, 1H), 7.08 (d, J=7.7 Hz, 1H), 6.95 (d, J=8.4 Hz, 1H), 6.68 (d, J=7.7 Hz, 1H), 5.40-5.25 (m, 4H), 4.05 (d, J=8.4 Hz, 2H), 3.97-3.88 (m, 2H), 3.68-3.54 (m, 4H), 3.09 (t, J=5.3 Hz, 1H), 2.67-2.55 (m, 5H), 2.11-2.00 (m, 4H), 1.96-1.91 (m, 2H), 1.82 (s, 3H), 1.66-1.57 (m, 1H)

Example 1053: LC/MS (Cond. N-1): [M+H]$^+$ 791.36, RT=3.199 min. $^1$H NMR (400 MHz, METHANOL-$d_4$) δ 9.04 (d, J=2.0 Hz, 1H), 8.82 (d, J=2.0 Hz, 1H), 8.65 (s, 1H), 7.52 (s, 1H), 7.46 (d, J=7.5 Hz, 1H), 7.21 (t, J=7.9 Hz, 1H), 7.24 (t, J=7.7 Hz, 1H), 7.10-7.05 (m, 2H), 6.96 (d, J=8.0 Hz, 1H), 6.73 (d, J=7.5 Hz, 1H), 5.42-5.28 (m, 4H), 4.32 (q, J=13.3 Hz, 2H), 4.17 (t, J=5.4 Hz, 2H), 3.99 (dd, J=11.9, 3.9 Hz, 1H), 3.89-3.81 (m, 2H), 3.77 (d, J=10.5 Hz, 1H), 3.69 (d, J=10.8 Hz, 1H), 3.55 (dd, J=6.9, 3.9 Hz, 1H), 3.48-3.40 (m, 3H), 3.38-3.34 (m, 2H), 2.40-2.25 (m, 3H), 2.21-2.11 (m, 1H), 2.10-2.04 (m, 3H), 1.90 (s, 3H).

Example 1054: 1-(3-((3'-((4-((((R)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-hydroxypyrrolidine-3-carboxylic Acid

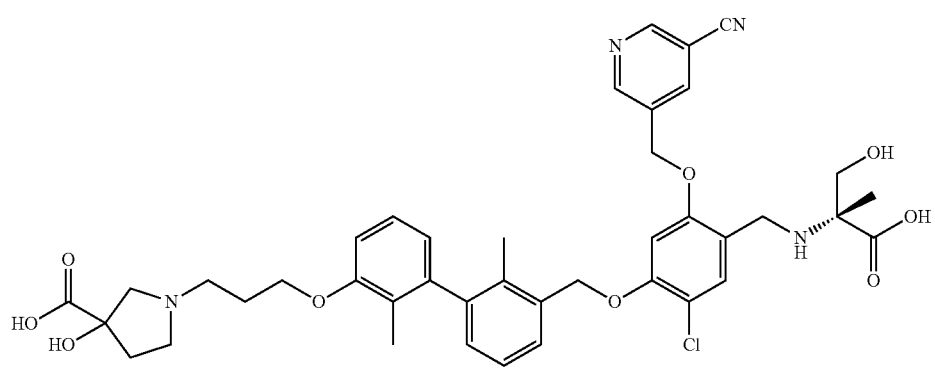

Example 1057: 1-(3-((3'-((5-((5-carbamoylpyridin-3-yl)methoxy)-4-((((R)-2-carboxy-1-hydroxypropan-2-yl)amino)methyl)-2-chlorophenoxy)methyl)-2,2'-dimethyl-[1,1'-biphenyl]-3-yl)oxy)propyl)-3-hydroxypyrrolidine-3-carboxylic Acid

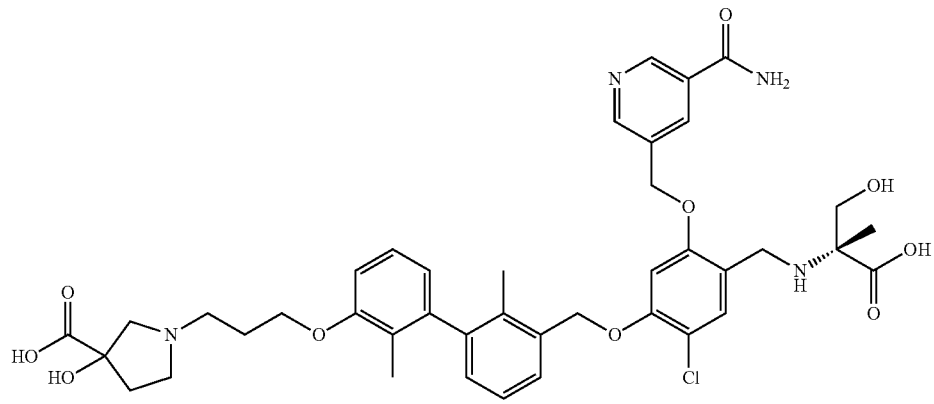

Example 1054 and Example 1057 were prepared according to the procedure described in Example 1032 and Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Example 1054: LC/MS (Injection 1 conditions): [M+H]⁺ 773.3, RT=1.454 min. Example 1057: LC/MS (Cond. N-1): [M+H]⁺ 791.36, RT=3.308 min.

Example 1055: (2R)-2-((5-chloro-4-((3'-(3-(3-hydroxy-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic Acid

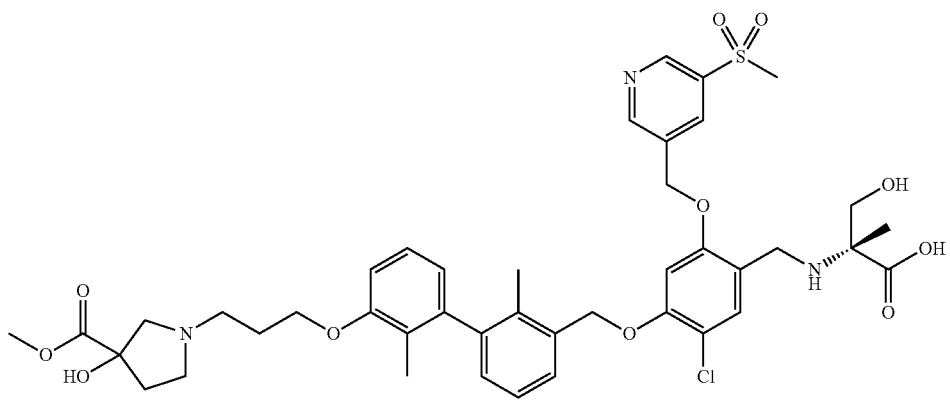

Example 1055 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 84%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]+ 840.3, RT=1.667 min.

Example 1056: (2R)-2-((5-chloro-4-((3'-(3-(3-hydroxy-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic Acid material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-40% B over 30 minutes, then a 7-minute hold at 100% B; Flow: 20 mL/min. Fractions containing the desired product were combined and dried via centrifugal evaporation. The yield of the product was 2.0 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with

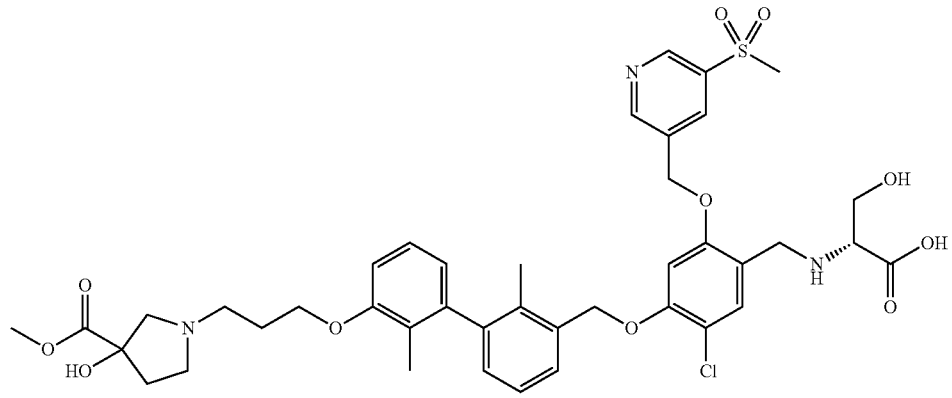 [SMILES: COC(=O)C1(O)CCN(CCCOc2cccc(-c3cccc(COc4cc(OCc5cncc(S(C)(=O)=O)c5)c(CN[C@H](CO)C(=O)O)cc4Cl)c3C)c2C)C1]

Example 1056 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]+ 826.3, RT=1.646 min.

Example 1058: (S)-1-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)piperidine-2-carboxylic Acid

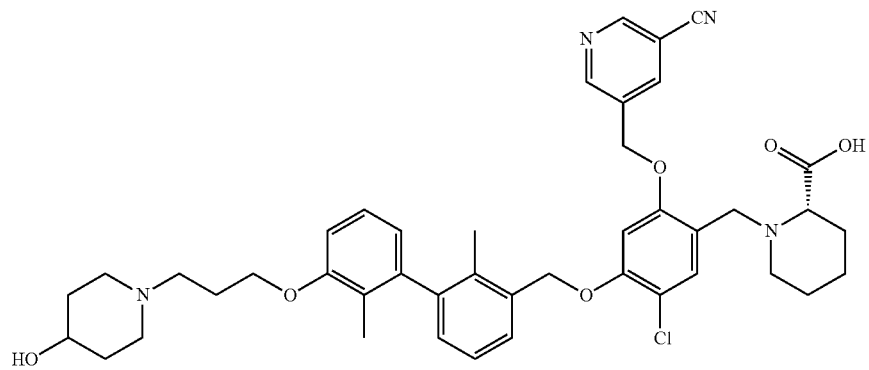 [SMILES: Cc1c(COc2cc(OCc3cncc(C#N)c3)c(CN3CCCC[C@H]3C(=O)O)cc2Cl)cccc1-c1cccc(OCCCN2CCC(O)CC2)c1C]

Example 1058 was prepared according to the reductive amination conditions as described for Example 1003. The crude material was purified via preparative LC/MS with the following conditions: Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation. The yield of the product was 14.5 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 753.3, RT=1.586 min.

Example 1059: (R)-2-((5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)amino)-3-hydroxy-2-methylpropanoic Acid

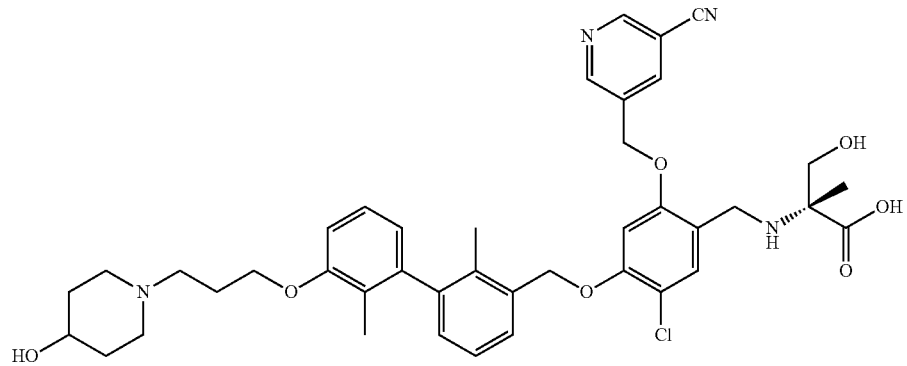

Example 1059 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.8 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 743.1, RT=1.629 min.

Example 1060: (R)-2-((5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)amino)-3-hydroxypropanoic Acid

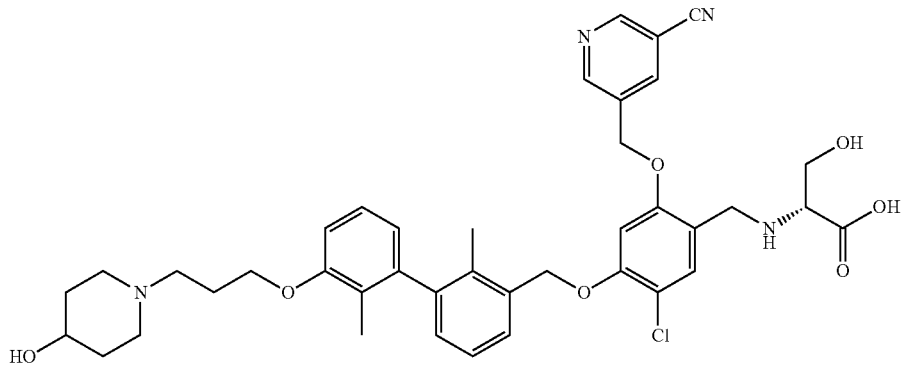 [SMILES: Cc1c(COc2cc(OCc3cncc(C#N)c3)c(CN[C@H](CO)C(=O)O)cc2Cl)cccc1-c1cccc(OCCCN2CCC(O)CC2)c1C]

Example 1060 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 15 minutes, then a 5-minute hold at 100% B; Flow: 20 mL/min. Fractions containing the desired product were combined and dried via centrifugal evaporation. The yield of the product was 16.4 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$ 729.3, RT=1.615 min.

Example 1061: (S)-1-(4-((3'-(3-(4-carboxy-4-hydroxypiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

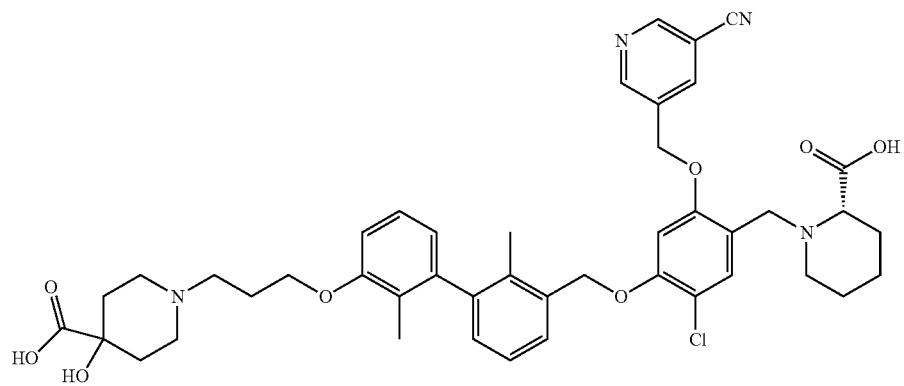 [SMILES: Cc1c(COc2cc(OCc3cncc(C#N)c3)c(CN3CCCC[C@H]3C(=O)O)cc2Cl)cccc1-c1cccc(OCCCN2CCC(O)(C(=O)O)CC2)c1C]

Example 1061 was prepared according to the procedure described in Example 1033. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): $[M+H]^+$ =797.3, RT=1.516 min. $^1$H NMR (400 MHz, METHANOL-$d_4$) δ ppm 9.00-8.91 (m, 2H), 8.40 (d, J=2.0 Hz, 1H), 7.66 (d, J=1.5 Hz, 1H), 7.47 (d, J=7.6 Hz, 1H), 7.23 (t, J=7.8 Hz, 1H), 7.26 (t, J=7.7 Hz, 1H), 7.12-7.02 (m, 2H), 6.97 (d, J=8.3 Hz, 1H), 6.75 (d, J=7.6 Hz, 1H), 5.38 (s, 2H), 5.32 (s, 2H), 4.45 (d, J=13.2 Hz, 1H), 4.31 (d, J=13.0 Hz, 1H), 4.19 (t, J=5.0 Hz, 2H), 3.59-3.48 (m, 3H), 3.40-3.35 (m, 3H), 3.31-3.22 (m, 2H), 2.90 (d, J=18.3 Hz, 1H), 2.37-2.17 (m, 6H), 2.12-2.05 (m, 3H), 1.91 (d, J=4.9 Hz, 3H), 1.87-1.78 (m, 6H).

Intermediate: 1-benzyl 3-ethyl
3-(hydroxymethyl)pyrrolidine-1,3-dicarboxylate
(Enantiomer 1, Eluted 1st on Chiral HPLC)

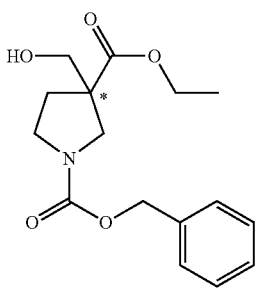

Intermediate: 1-benzyl 3-ethyl
3-(hydroxymethyl)pyrrolidine-1,3-dicarboxylate
(Enantiomer 2, Eluted 2nd on Chiral HPLC)

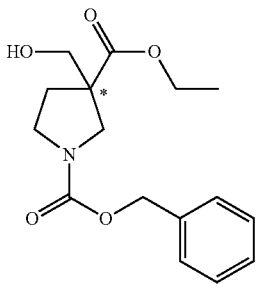 [SMILES: CCOC(=O)C1(CO)CCN(C(=O)OCc2ccccc2)C1]

A stirred mixture of ethyl 3-(hydroxymethyl)pyrrolidine-3-carboxylate, HCl (0.48 g, 2.289 mmol) and $Na_2CO_3$ (0.631 g, 5.95 mmol) in ether (2 mL) and Water (1 mL) was cooled to 0° C., then benzyl carbonochloridate (0.523 mL, 3.66 mmol) was added. The reaction mixture was stirred at 0° C. for 10 min, then allowed to warm to rt and stirred at rt for 16 h. The reaction mixture was added with EtOAc and water, and then the organic phase was washed with sat. NaCl, dried ($Na_2SO_4$). The crude isolated was purified by silica gel (0-100% EtOAc/hex) to yield 1-benzyl 3-ethyl 3-(hydroxymethyl)pyrrolidine-1,3-dicarboxylate. LC/MS (Cond. N-1): $[M+Na]^+$=330.1, RT=3.28 min. $^1$H NMR (400 MHz, CHLOROFORM-d) δ ppm 7.43-7.30 (m, 5H), 5.19-5.09 (m, 2H), 4.22 (q, J=7.2 Hz, 2H), 3.84-3.73 (m, 2H), 3.73-3.65 (m, 1H), 3.65-3.46 (m, 2H), 2.46 (dt, J=16.8, 6.7 Hz, 1H), 2.35-2.19 (m, 1H), 2.13-1.91 (m, 1H), 1.32-1.23 (m, 3H). The racemate was resolved according to the following condition: ChiralPak AD-H, 30×250 mm, 5 μm; Mobile Phase: 30% EtOH/70% $CO_2$; Pressure: 150 bar; Temperature: 40° C.; Flow Rate: 80 mL/min; UV: 205 nm. Enantiomer 1 (1-benzyl 3-ethyl 3-(hydroxymethyl)pyrrolidine-1,3-dicarboxylate) was eluted at 3.15-5.00 min. Enantiomer 2 (1-benzyl 3-ethyl 3-(hydroxymethyl)pyrrolidine-1,3-dicarboxylate) was eluted at 5.75-8.50 min.

Intermediate: Ethyl
3-(hydroxymethyl)pyrrolidine-3-carboxylate
(Enantiomer 1)


A stirred mixture of Enantiomer 1 (1-benzyl 3-ethyl 3-(hydroxymethyl)pyrrolidine-1,3-dicarboxylate) (0.18 g, 0.586 mmol) and Pd—C (0.062 g, 0.059 mmol) in methanol (2 mL) was stirred at rt under H2 for 16 h. The reaction mixture was filtered through a plug of diatomaceous earth (Celite®), washed with MeOH, the filtrate was concentrated to yield enantiomer 1, ethyl 3-(hydroxymethyl)pyrrolidine-3-carboxylate (0.1 g, 0.577 mmol, 99% yield). LC/MS (Cond. N-1): $[M+H]^+$=174.15, RT=0.413 min.

Intermediate: Ethyl
3-(hydroxymethyl)pyrrolidine-3-carboxylate
(Enantiomer 2)

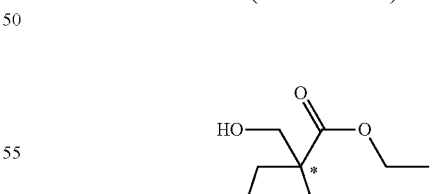

A stirred mixture of Enantiomer 2 (1-benzyl 3-ethyl 3-(hydroxymethyl)pyrrolidine-1,3-dicarboxylate) (0.17 g, 0.553 mmol) and Pd—C (0.059 g, 0.055 mmol) in methanol (2 mL) was stirred at rt under H2 for 16 h. The reaction mixture was filtered through a plug of diatomaceous earth (Celite®), washed with MeOH, the filtrate was concentrated to yield the desired product ethyl 3-(hydroxymethyl)pyrrolidine-3-carboxylate (0.077 g, 0.445 mmol, 80% yield). LC/MS (Cond. N-1): [M+H]⁺=174.15, RT=0.413 min.

Example 1062: (2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic Acid (Diastereomer 1)

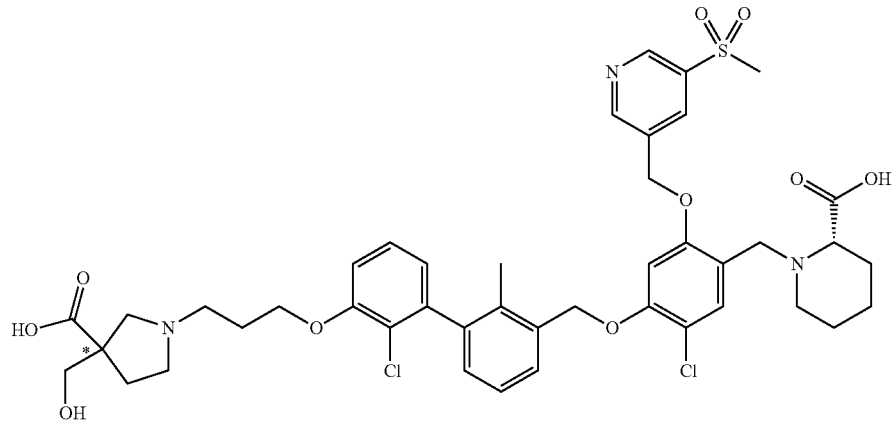 [SMILES: Cc1c(COc2cc(OCc3cncc(S(C)(=O)=O)c3)c(CN3CCCC[C@H]3C(=O)O)cc2Cl)cccc1-c1cccc(OCCCN2CCC(CO)(C(=O)O)C2)c1Cl]

Example 1062 was prepared from 1-benzyl 3-ethyl 3-(hydroxymethyl)pyrrolidine-1,3-dicarboxylate (enantiomer 1, eluted 1st on Chiral HPLC), according to the procedure described in Example 1033. LC/MS (Cond. N-1): [M+H]⁺=870.25, RT=3.368 min.

Example 1063: 1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2-chloro-2'-methyl-[1,1'-biphenyl]-3-yl)oxy)propyl)-3-(hydroxymethyl)pyrrolidine-3-carboxylic Acid (Diastereomer 1)

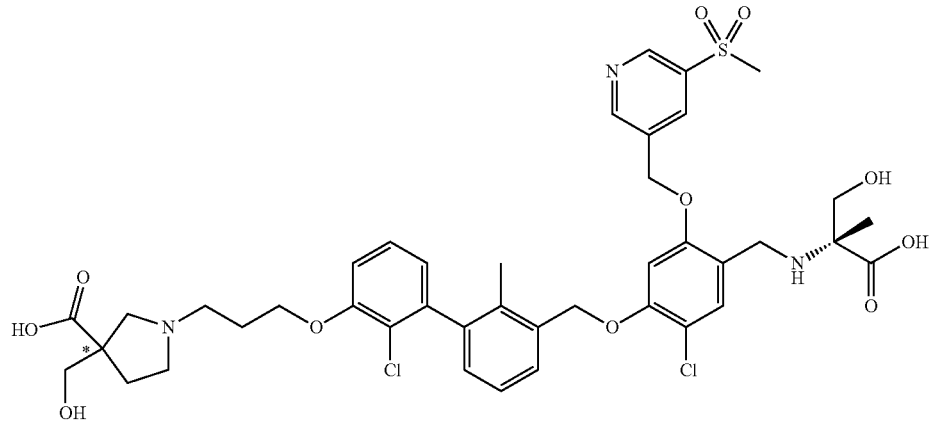

Example 1063 was prepared from 1-benzyl 3-ethyl 3-(hydroxymethyl)pyrrolidine-1,3-dicarboxylate (enantiomer 1, eluted 1st on Chiral HPLC), according to the procedure described in Example 1033. LC/MS (Cond. N-1): [M+H]⁺=860.25, RT=3.318 min.

Example 1064: 1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2-chloro-2'-methyl-[1,1'-biphenyl]-3-yl)oxy)propyl)-3-(hydroxymethyl)pyrrolidine-3-carboxylic Acid (Diastereomer 2)

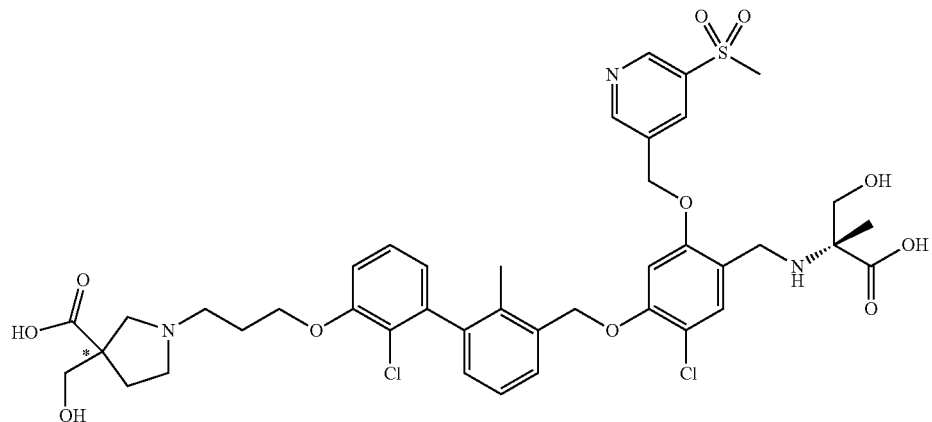

Example 1064 was prepared from 1-benzyl 3-ethyl 3-(hydroxymethyl)pyrrolidine-1,3-dicarboxylate (enantiomer 2, eluted 2nd on Chiral HPLC), according to the procedure described in Example 1033. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=860.2, RT=1.34 min.

Example 1065: (2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic Acid (Diastereomer 2)

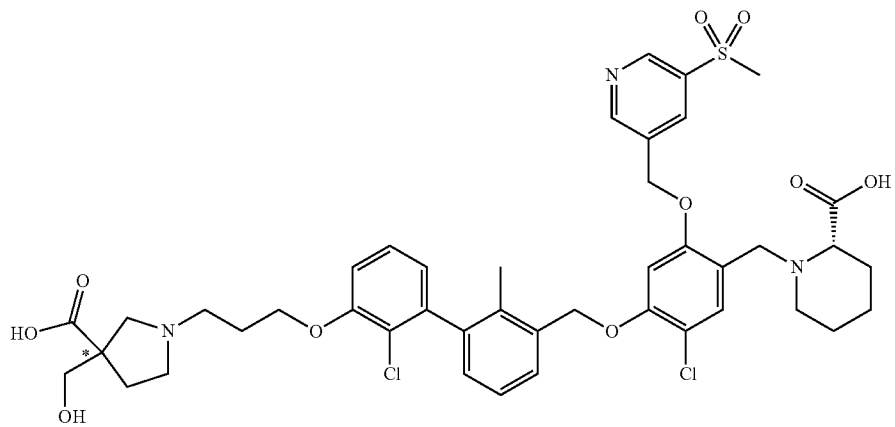 [SMILES: Cc1c(COc2cc(OCc3cncc(S(C)(=O)=O)c3)c(CN3CCCC[C@H]3C(=O)O)cc2Cl)cccc1-c1cccc(OCCCN2CCC(CO)(C(=O)O)C2)c1Cl]

Example 1065 was prepared from 1-benzyl 3-ethyl 3-(hydroxymethyl)pyrrolidine-1,3-dicarboxylate (enantiomer 2, eluted 2nd on Chiral HPLC), according to the procedure described in Example 1033. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 20 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=870.3, RT=1.327 min.

Example 1066: (2S)-1-(4-((3'-(3-(3-carboxy-3-(hydroxymethyl)pyrrolidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid (Diastereomer 1)

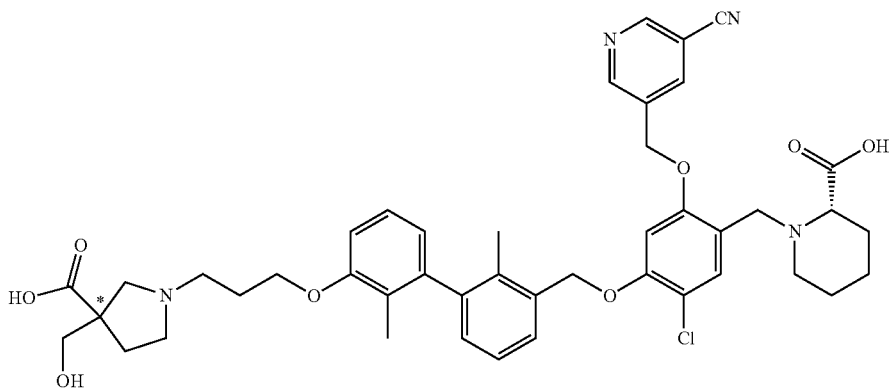 [SMILES: Cc1c(COc2cc(OCc3cncc(C#N)c3)c(CN3CCCC[C@H]3C(=O)O)cc2Cl)cccc1-c1cccc(OCCCN2CCC(CO)(C(=O)O)C2)c1C]

Example 1066 was prepared from 1-benzyl 3-ethyl 3-(hydroxymethyl)pyrrolidine-1,3-dicarboxylate (enantiomer 1, eluted 1st on Chiral HPLC), according to the procedure described in Example 1033. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=797.3, RT=1.474 min.

Example 1067: (2S)-1-(4-((3'-(3-(3-carboxy-3-(hydroxymethyl)pyrrolidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid (Diastereomer 1)

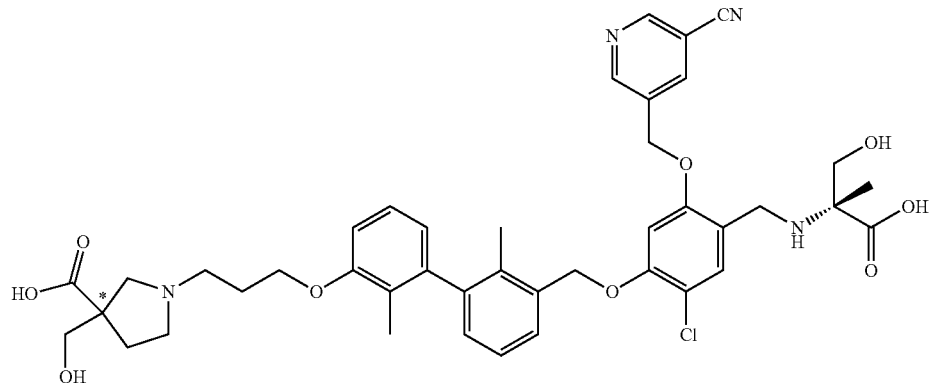

Example 1067 was prepared from 1-benzyl 3-ethyl 3-(hydroxymethyl)pyrrolidine-1,3-dicarboxylate (enantiomer 1, eluted 1st on Chiral HPLC), according to the procedure described in Example 1033. The crude material was purified via preparative LC/MS with the following conditions: Column: waters xbridge c-18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=787.2, RT=1.332 min.

Example 1068: (R)-2-((5-chloro-4-((2'-chloro-3'-(3-((2S,4R)-4-hydroxy-2-(methoxycarbonyl)pyrrolidin-1-yl)propoxy)-2-methyl-[1,1'-biphenyl]-3-yl)methoxy)-2-((5-(methylsulfonyl)pyridin-3-yl)methoxy)benzyl)amino)-3-hydroxy-2-methylpropanoic Acid

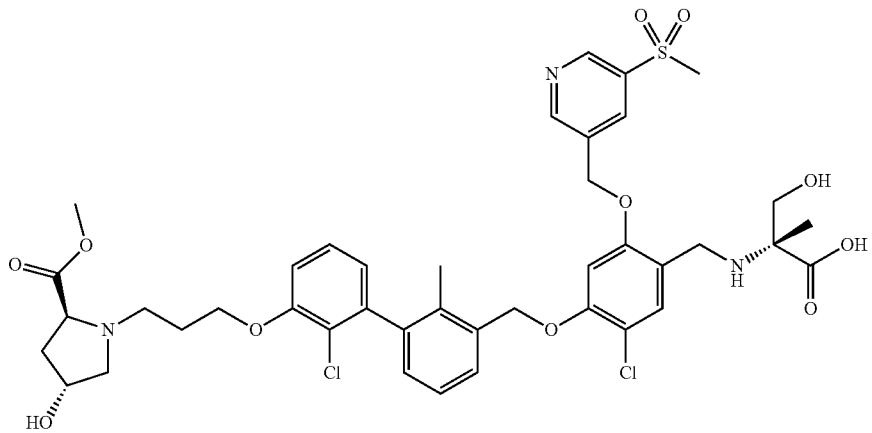

Example 1068 was prepared according to the reductive amination conditions as described for Example 1003. LC/MS (Cond. N-1): [M+H]$^+$=860.25, RT=3.038 min.

Example 1069: (S)-1-(5-chloro-4-((2'-chloro-3'-(3-((2S,4R)-4-hydroxy-2-(methoxycarbonyl)pyrrolidin-1-yl)propoxy)-2-methyl-[1,1'-biphenyl]-3-yl)methoxy)-2-((5-(methylsulfonyl)pyridin-3-yl)methoxy)benzyl)piperidine-2-carboxylic Acid

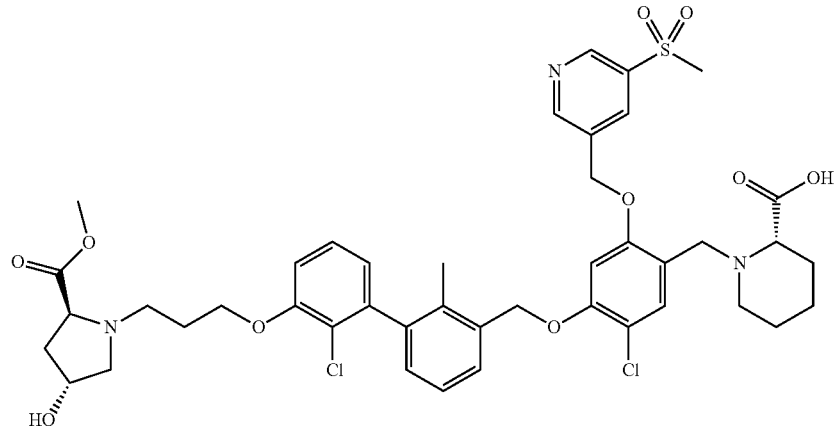 [SMILES: COC(=O)[C@@H]1C[C@@H](O)CN1CCCOc1cccc(-c2cccc(COc3cc(OCc4cncc(S(C)(=O)=O)c4)c(CN4CCCC[C@H]4C(=O)O)cc3Cl)c2C)c1Cl]

Example 1069 was prepared according to the reductive amination conditions as described for Example 1003. LC/MS (Cond. N-1): [M+Na]⁺=892.25, RT=3.043 min.

Example 1070: (R)-2-((5-chloro-2-((5-cyanopyridin-3-yl)methoxy)-4-((4'-(3-((R)-3-hydroxypyrrolidin-1-yl)propoxy)-2,2'-dimethyl-[1,1'-biphenyl]-3-yl)methoxy)benzyl)amino)-3-hydroxypropanoic Acid

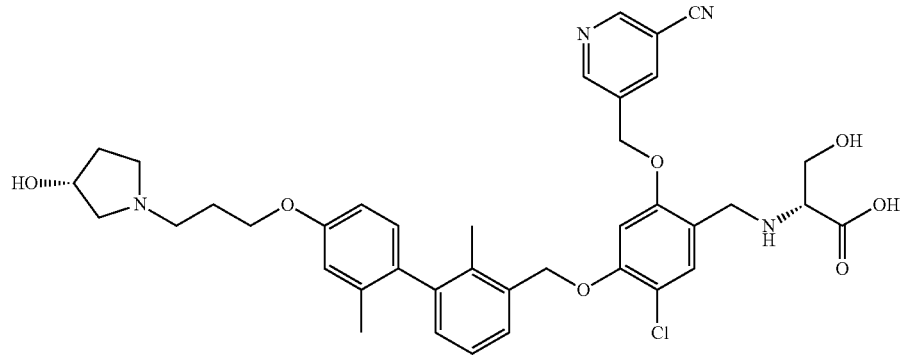 [SMILES: Cc1cc(OCCCN2CC[C@@H](O)C2)ccc1-c1cccc(COc2cc(OCc3cncc(C#N)c3)c(CN[C@H](CO)C(=O)O)cc2Cl)c1C]

Example 1070 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 9.9 mg, and its estimated purity by LCMS analysis was 91%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]⁺=715.3, RT=1.356 min. Proton NMR was acquired in deuterated DMSO. ¹H NMR (500 MHz, DMSO-d₆) δ ppm 9.02 (d, J=5.9 Hz, 2H), 8.52 (s, 1H), 7.52 (s, 1H), 7.46 (d, J=7.3 Hz, 1H), 7.25 (t, J=7.7 Hz, 1H), 7.14 (s, 1H), 7.07 (d, J=7.3 Hz, 1H), 6.97 (d, J=8.4 Hz, 1H), 6.87 (s, 1H), 6.81 (d, J=8.8 Hz, 1H), 5.41-5.22 (m, 4H), 4.21 (br. s., 1H), 4.07-3.97 (m, 4H), 3.71 (dd, J=11.0, 4.4 Hz, 1H), 3.62 (dd, J=11.2, 6.8 Hz, 1H), 3.19-3.13 (m, 1H), 2.77 (dd, J=9.5, 6.2 Hz, 1H), 2.70-2.57 (m, 4H), 2.42 (d, J=11.0 Hz, 1H), 2.06-1.97 (m, 3H), 1.95 (m, 3H), 1.93-1.86 (m, 3H), 1.58 (br. s., 1H).

Example 1071: (S)-1-(5-chloro-2-((5-cyanopyridin-3-yl)methoxy)-4-((4'-(3-((R)-3-hydroxypyrrolidin-1-yl)propoxy)-2,2'-dimethyl-[1,1'-biphenyl]-3-yl)methoxy)benzyl)piperidine-2-carboxylic Acid

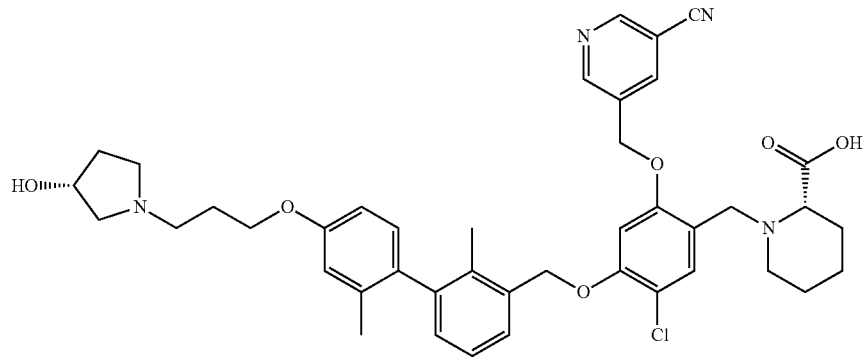 [SMILES: Cc1cc(OCCCN2CC[C@@H](O)C2)ccc1-c1cccc(COc2cc(OCc3cncc(C#N)c3)c(CN3CCCC[C@H]3C(=O)O)cc2Cl)c1C]

Example 1071 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=739.3, RT=1.447 min.

Example 1072: (2S)-1-(5-chloro-4-((3'-(3-(3-hydroxy-4-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic Acid

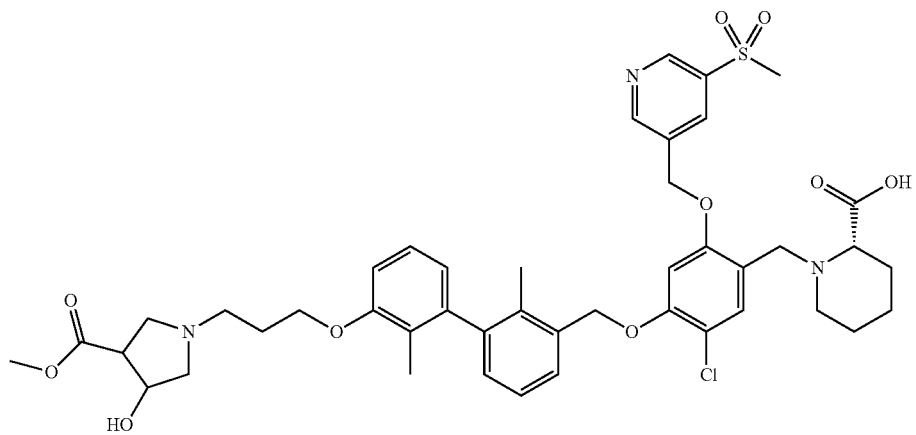 [SMILES: COC(=O)C1CN(CCCOc2cccc(-c3cccc(COc4cc(OCc5cncc(S(C)(=O)=O)c5)c(CN5CCCC[C@H]5C(=O)O)cc4Cl)c3C)c2C)CC1O]

Example 1072 was prepared according to the reductive amination conditions as described for Example 1003. The crude material was purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 20 minutes; Flow: 40 mL/min. Fractions containing the desired products were combined and dried via centrifugal evaporation to yield (2S)-1-(5-chloro-4-((3'-(3-(3-hydroxy-4-(methoxycarbonyl)pyrrolidin-1-yl)propoxy)-2,2'-dimethyl-[1,1'-biphenyl]-3- yl)methoxy)-2-((5-(methylsulfonyl)pyridin-3-yl)methoxy) benzyl)piperidine-2-carboxylic acid. LC/MS (Cond. N-1): [M+H]$^+$=850.35, RT=3.369 min.

Example 1073: (2R)-2-((5-chloro-4-((3'-(3-(3-hydroxy-4-(methoxycarbonyl)pyrrolidin-1-yl) propoxy)-2,2'-dimethyl-[1,1'-biphenyl]-3-yl) methoxy)-2-((5-(methylsulfonyl)pyridin-3-yl) methoxy)benzyl)amino)-3-hydroxy-2-methylpropanoic Acid

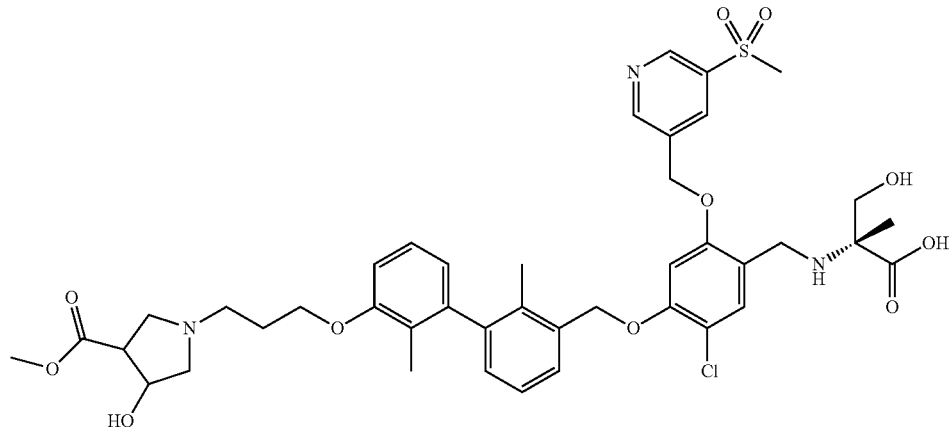

Example 1073 was prepared according to the reductive amination conditions as described for Example 1003. The crude material was purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 20 minutes; Flow: 40 mL/min. Fractions containing the desired products were combined and dried via centrifugal evaporation to yield (2R)-2-((5-chloro-4-((3'-(3-(3-hydroxy-4-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl) methoxy)benzyl)amino)-3-hydroxy-2-methylpropanoic acid. LC/MS (Cond. N-1): [M+H]$^+$=840.35, RT=3.4 min.

Example 1074: (2S)-1-(4-((3'-(3-(3-carboxy-4-hydroxypyrrolidin-1-yl)propoxy)-2,2'-dimethyl-[1,1'-biphenyl]-3-yl)methoxy)-5-chloro-2-((5-(methylsulfonyl)pyridin-3-yl)methoxy)benzyl)piperidine-2-carboxylic Acid Example 1074 was prepared according to the procedures as described for Example 1033. The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 45-85% B over 15 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=836.2, RT=1.336 min. Proton NMR was acquired in deuterated DMSO. $^1$H NMR (500 MHz, DMSO-d$_6$) δ ppm 9.10-9.02 (m, 2H), 8.47 (s, 1H), 7.50 (d, J=7.3 Hz, 1H), 7.46

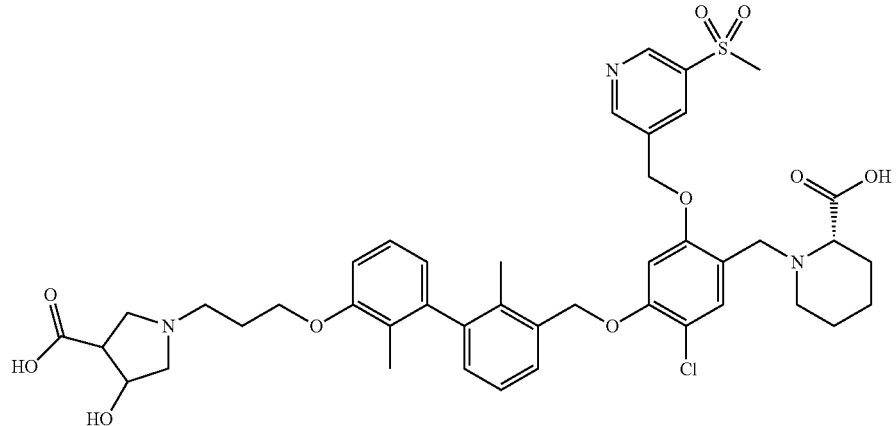 [SMILES: Cc1c(COc2cc(OCc3cncc(S(C)(=O)=O)c3)c(CN3CCCC[C@H]3C(=O)O)cc2Cl)cccc1-c1cccc(OCCCN2CC(O)C(C(=O)O)C2)c1C]

(s, 1H), 7.28 (t, J=7.5 Hz, 1H), 7.24-7.18 (m, 1H), 7.16 (s, 1H), 7.08 (d, J=7.7 Hz, 1H), 6.95 (d, J=8.1 Hz, 1H), 6.68 (d, J=7.7 Hz, 1H), 5.40 (s, 2H), 5.31-5.20 (m, 2H), 4.37-4.32 (m, 1H), 4.05 (d, J=5.9 Hz, 2H), 3.83 (d, J=14.3 Hz, 1H), 3.68 (d, J=13.9 Hz, 1H), 3.37 (s, 3H), 3.17-3.09 (m, 1H), 2.97-2.85 (m, 2H), 2.73-2.65 (m, 2H), 2.63-2.58 (m, 2H), 2.52-2.45 (m, 2H), 2.33 (br. s., 1H), 2.06-1.99 (m, 3H), 1.95-1.90 (m, 2H), 1.82 (m, 4H), 1.71 (br. s., 1H), 1.50 (br. s., 3H), 1.35 (br. s., 1H).

Example 1075: 1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypyrrolidine-3-carboxylic Acid nium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=826.2, RT=1.351 min. Proton NMR was acquired in deuterated DMSO. $^1$H NMR (500 MHz, DMSO-d$_6$) δ ppm 9.10-9.05 (m, 2H), 8.57 (s, 1H), 7.55 (s, 1H), 7.51 (d, J=7.3

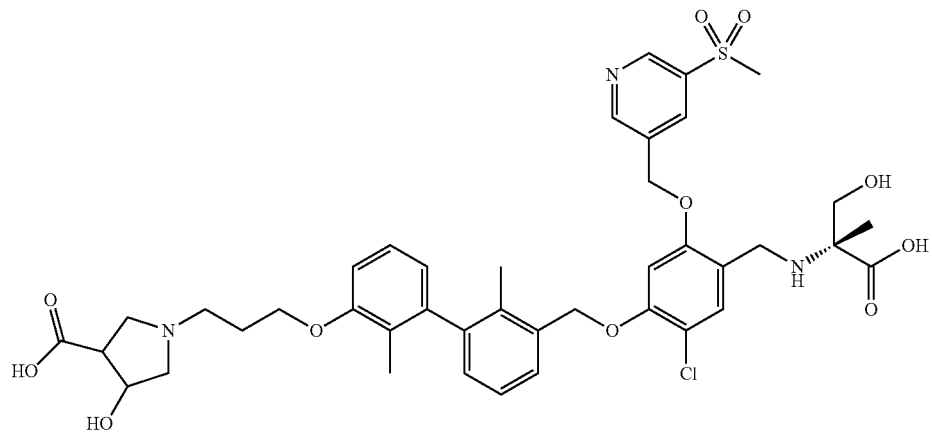

Example 1075 was prepared according to the procedures as described for Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-45% B over 20 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammo- Hz, 1H), 7.28 (t, J=7.5 Hz, 1H), 7.23-7.18 (m, 2H), 7.08 (d, J=7.7 Hz, 1H), 6.96 (d, J=8.4 Hz, 1H), 6.68 (d, J=7.3 Hz, 1H), 5.41 (s, 2H), 5.36-5.25 (m, 2H), 4.34 (br. s., 1H), 4.10-4.01 (m, 2H), 3.97 (s, 2H), 3.62 (br. s., 1H), 3.53 (br. s., 1H), 2.92-2.87 (m, 1H), 2.73-2.66 (m, 2H), 2.61 (d, J=8.4 Hz, 2H), 2.50-2.44 (m, 2H), 2.04 (s, 3H), 1.94-1.91 (m, 2H), 1.83 (s, 3H), 1.23 (s, 3H).

Example 1076: (R)-2-((5-chloro-4-((2'-chloro-2-methyl-3'-(3-(4-(methylcarbamoyl)piperidin-1-yl)propoxy)-[1,1'-biphenyl]-3-yl)methoxy)-2-((5-cyanopyridin-3-yl)methoxy)benzyl)amino)-3-hydroxy-2-methylpropanoic Acid

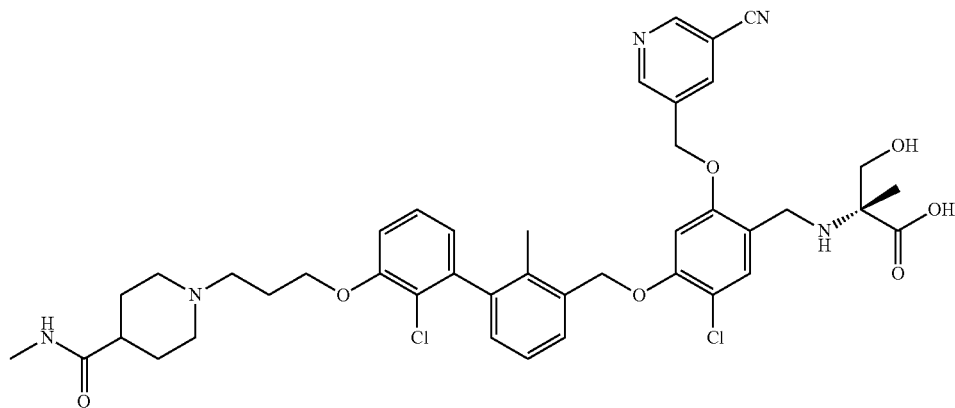

Example 1076 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=804.2, RT=1.423 min.

Example 1077: (S)-1-(5-chloro-4-((2'-chloro-2-methyl-3'-(3-(4-(methylcarbamoyl)piperidin-1-yl)propoxy)-[1,1'-biphenyl]-3-yl)methoxy)-2-((5-cyanopyridin-3-yl)methoxy)benzyl)piperidine-2-carboxylic Acid Example 1077 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 15 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=814.2, RT=1.469 min.

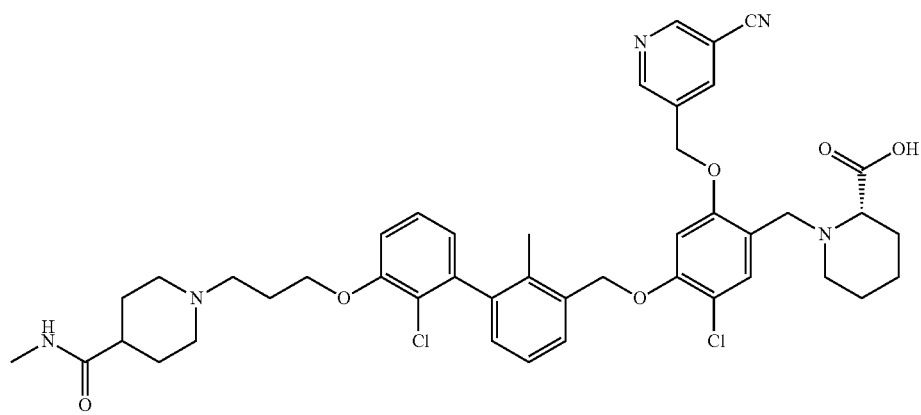 [SMILES: CNC(=O)C1CCN(CCCOc2cccc(-c3cccc(COc4cc(OCc5cncc(C#N)c5)c(CN5CCCC[C@H]5C(=O)O)cc4Cl)c3C)c2Cl)CC1]

Example 1078: (S)-1-(4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic Acid

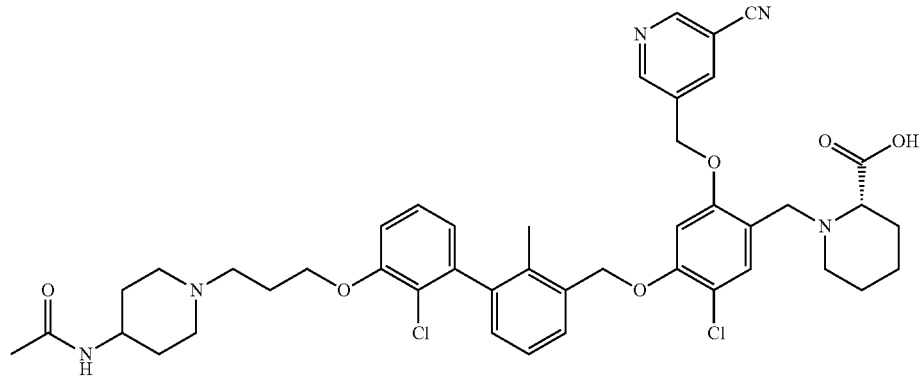 [SMILES: CC(=O)NC1CCN(CCCOc2cccc(-c3cccc(COc4cc(OCc5cncc(C#N)c5)c(CN5CCCC[C@H]5C(=O)O)cc4Cl)c3C)c2Cl)CC1]

Example 1078 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 8.7 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): $[M+H]^+$=814.2, RT=1.488 min.

Example 1079: (R)-2-((4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid

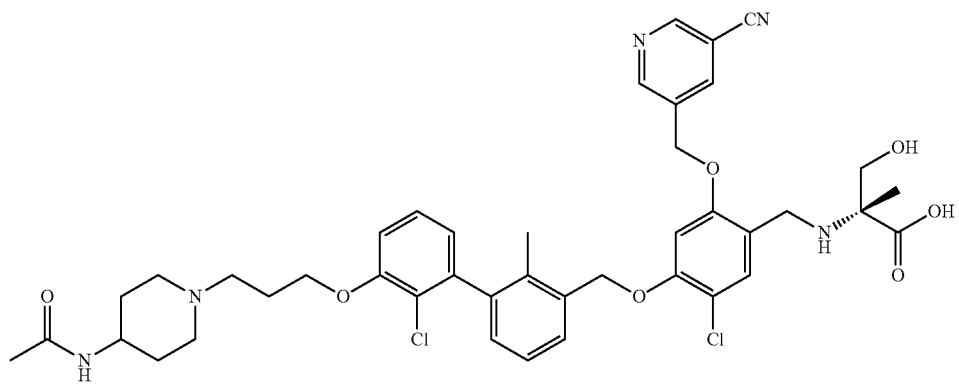

Example 1079 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=804.2, RT=1.448 min. Proton NMR was acquired in deuterated DMSO. $^1$H NMR (500 MHz, DMSO-d$_6$) δ ppm 9.06-8.99 (m, 2H), 8.52 (s, 1H), 7.75 (d, J=7.7 Hz, 1H), 7.54-7.49 (m, 2H), 7.40-7.35 (m, 1H), 7.29 (t, J=7.7 Hz, 1H), 7.18 (d, J=8.4 Hz, 1H), 7.15-7.10 (m, 2H), 6.85 (d, J=7.7 Hz, 1H), 5.39-5.26 (m, 4H), 4.19-4.09 (m, 2H), 3.92-3.86 (m, 2H), 3.56-3.51 (m, 3H), 2.80 (d, J=9.5 Hz, 2H), 2.48-2.41 (m, 2H), 2.07 (s, 3H), 2.00-1.92 (m, 4H), 1.80-1.75 (m, 3H), 1.70 (d, J=12.1 Hz, 2H), 1.41-1.31 (m, 2H), 1.20 (s, 3H).

Example 1080: (R)-2-((5-chloro-2-((5-cyanopyridin-3-yl)methoxy)-4-((3'-(3-(3-hydroxyazetidin-1-yl)propoxy)-2,2'-dimethyl-[1,1'-biphenyl]-3-yl)methoxy)benzyl)amino)-3-hydroxypropanoic Acid

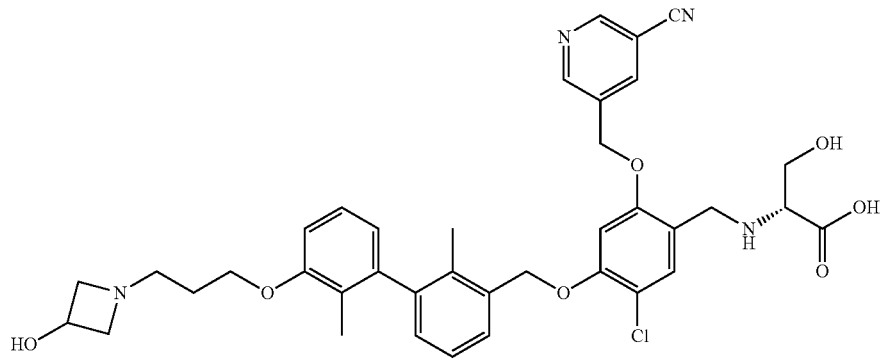 [SMILES: Cc1c(COc2cc(OCc3cncc(C#N)c3)c(CN[C@H](CO)C(=O)O)cc2Cl)cccc1-c1cccc(OCCCN2CC(O)C2)c1C]

Example 1080 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]±=701.2, RT=1.384 min.

Example 1081: (S)-1-(4-((3'-(3-((2S,4R)-2-carboxy-4-hydroxypyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic Acid

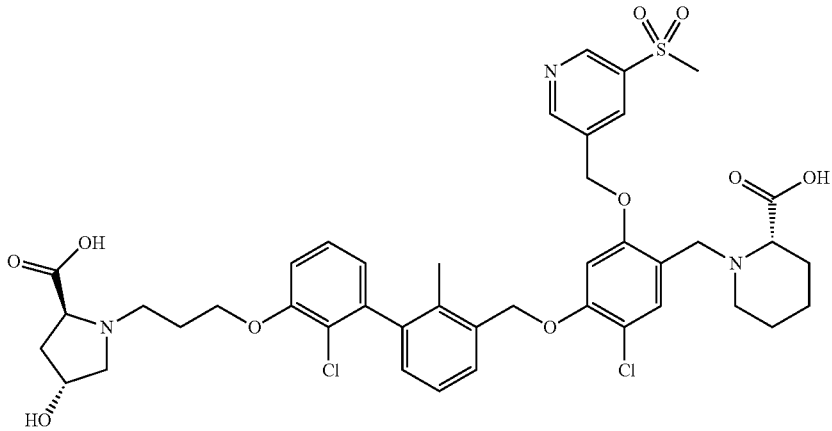 [SMILES: Cc1c(COc2cc(OCc3cncc(S(C)(=O)=O)c3)c(CN3CCCC[C@H]3C(=O)O)cc2Cl)cccc1-c1cccc(OCCCN2C[C@H](O)C[C@H]2C(=O)O)c1Cl]

Example 1081 was prepared according to the procedure as described for Example 1033. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-50% B over 20 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 97%. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. LC/MS (Injection 1 conditions): [M+H]$^+$=856.23, RT=1.271 min.

Example 1082: (R)-2-((5-chloro-4-((3'-(3-((R)-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic Acid

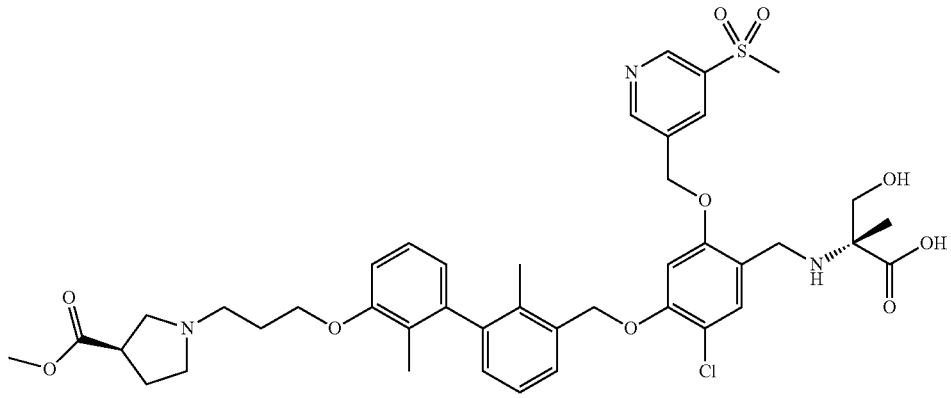

Example 1082 was prepared according to the reductive amination conditions as described for Example 1003 The crude material was purified via preparative HPLC with the following conditions: Column: Phenomenex-LUNA, 30×100 mm S10; Mobile Phase A: 10:90 MeOH: water with 0.1% TFA; Mobile Phase B: 90:10 MeOH: water with 0.1% TFA; Gradient: 10-80% B over 20 minutes; Flow: 40 mL/min. Fractions containing the desired products were combined and dried via centrifugal evaporation to yield (R)-2-((5-chloro-4-((3'-(3-((R)-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid. LC/MS (Cond. N-1): [M+H]$^+$=824.35, RT=3.188 min.

Example 1083: (R)-1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)pyrrolidine-3-carboxylic Acid

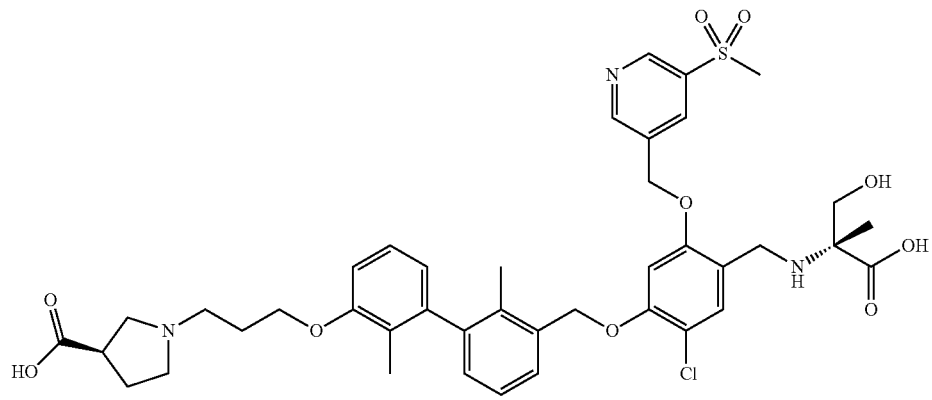

Example 1083 was prepared according to the procedure as described for Example 1033. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=810.2, RT=1.708 min. Proton NMR was acquired in deuterated DMSO. $^1$H NMR (500 MHz, DMSO-d$_6$) δ 9.07 (dd, J=3.9, 2.0 Hz, 2H), 8.57 (s, 1H), 7.55 (s, 1H), 7.51 (d, J=7.3 Hz, 1H), 7.28 (t, J=7.5 Hz, 1H), 7.24-7.18 (m, 2H), 7.09 (d, J=7.7 Hz, 1H), 6.96 (d, J=8.4 Hz, 1H), 6.68 (d, J=7.3 Hz, 1H), 5.46-5.39 (m, 2H), 5.35-5.28 (m, 2H), 4.06 (d, J=6.6 Hz, 2H), 3.99-3.93 (m, 2H), 3.91 (s, 3H), 3.60 (d, J=11.4 Hz, 1H), 3.52 (d, J=11.4 Hz, 1H), 2.93 (t, J=7.5 Hz, 1H), 2.79 (d, J=8.8 Hz, 1H), 2.70-2.57 (m, 5H), 2.05 (s, 3H), 2.00-1.92 (m, 4H), 1.83 (s, 3H), 1.23 (s, 3H).

Example 1084: (S)-1-(4-((3'-(3-((R)-3-carboxypyrrolidin-1-yl)propoxy)-2,2'-dimethyl-[1,1'-biphenyl]-3-yl)methoxy)-5-chloro-2-((5-(methylsulfonyl)pyridin-3-yl)methoxy)benzyl)piperidine-2-carboxylic Acid

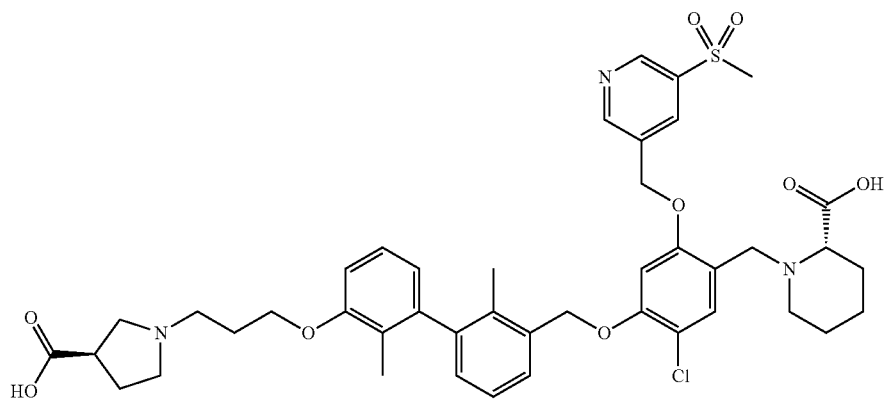 [SMILES: Cc1c(COc2cc(OCc3cncc(S(C)(=O)=O)c3)c(CN3CCCC[C@H]3C(=O)O)cc2Cl)cccc1-c1cccc(OCCCN2CC[C@@H](C(=O)O)C2)c1C]

Example 1084 was prepared according to the procedure as described for Example 1033. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 1.5 mg, and its estimated purity by LCMS analysis was 100%. Two LCMS were used to determine purity. Injection1: Column: Waters BEH C18, 2.0×50 mm, 1.7 μm; Mobile Phase A: 5:95 ACN:H$_2$O with 10 mM NH$_4$OAc; Mobile Phase B: 95:5 ACN:H$_2$O with 10 mM NH$_4$OAc; Temperature: 50° C.; Gradient: 0-100% B over 3 min, then a 0.75 min hold at 100% B; Flow: 1 mL/min. Injection 2: Column: Waters BEH C18, 2.0×50 mm, 1.7-μm; Mobile Phase A: 5:95 MeOH:H$_2$O with 10 mM NH$_4$OAc; Mobile Phase B: 95:5 MeOH:H$_2$O with 10 mM NH$_4$OAc; Temperature: 50° C.; Gradient: 0-100% B over 3.5 min, then a 0.5-min hold at 100% B; Flow: 0.5 mL/min. LC/MS (Cond. Injection 1 conditions): [M+H]$^+$=820.2, RT=1.739 min.

Example 1085: (S)-1-(4-((3'-(3-((2S,4R)-2-carbamoyl-4-hydroxypyrrolidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic Acid

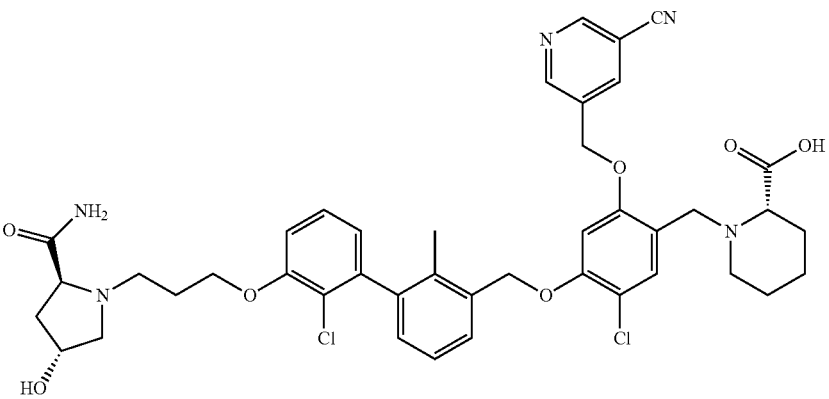 [SMILES: Cc1c(COc2cc(OCc3cncc(C#N)c3)c(CN3CCCC[C@H]3C(=O)O)cc2Cl)cccc1-c1cccc(OCCCN2C[C@H](O)C[C@H]2C(N)=O)c1Cl]

Example 1085 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 15 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=802.2, RT=1.918 min.

Example 1086: (R)-2-((4-((3'-(3-((2S,4R)-2-carbamoyl-4-hydroxypyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC/MS (Injection 1 conditions): [M+H]$^+$=792.2, RT=1.875 min. Proton NMR was acquired in deuterated DMSO. $^1$H NMR (500 MHz, DMSO-d$_6$) δ ppm 9.03 (dd, J=9.5, 1.8 Hz, 2H), 8.51 (s, 1H), 7.96 (s, 1H), 7.55 (s, 1H), 7.51 (d, J=7.7 Hz, 1H), 7.36 (t, J=7.9 Hz, 1H), 7.29 (t, J=7.7 Hz, 1H), 7.19 (d, J=8.4 Hz, 2H), 7.16-7.09 (m, 2H), 6.98 (br. s., 1H), 6.85 (d, J=7.7 Hz, 1H), 5.39-5.24 (m, 4H), 4.22-4.12 (m, 3H), 3.96 (s, 2H), 3.62-3.52 (m, 2H), 3.06 (t, J=8.1 Hz, 1H), 2.78 (d, J=11.7 Hz, 1H), 2.61-2.54 (m, 1H), 2.28-2.22 (m, 1H), 2.10-2.04 (m, 3H), 1.93-1.87 (m, 4H), 1.85-1.76 (m, 1H), 1.24 (s, 3H).

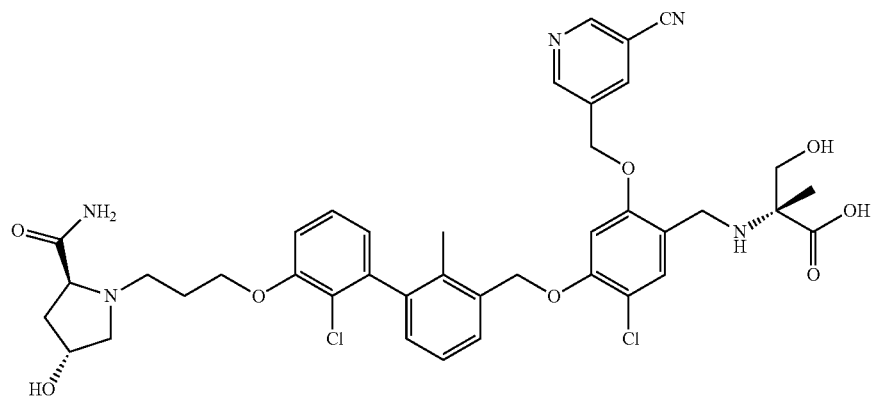

Example 1086 was prepared according to the reductive amination conditions as described for Example 1003. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water Intermediate: (E)-5-((4-chloro-5-((3'-((4-chlorobut-2-en-1-yl)oxy)-2-methyl-[1,1'-biphenyl]-3-yl)methoxy)-2-formylphenoxy)methyl)nicotinonitrile

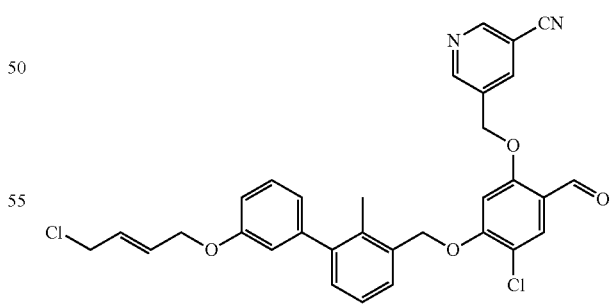

To a solution of 5-((4-chloro-2-formyl-5-((3'-hydroxy-2-methyl-[1,1'-biphenyl]-3-yl)methoxy)phenoxy)methyl)nicotinonitrile (0.1 g, 0.206 mmol) in acetone (6 mL) was added (E)-1,4-dichlorobut-2-ene (0.130 mL, 1.237 mmol) and K$_2$CO$_3$ (0.034 g, 0.247 mmol). The reaction mixture was stirred at 55° C. for 16 h. The reaction was cooled to rt, diluted with EtOAc, the organic phase was washed with sat.

NaHCO₃, water, sat. NaCl, dried over anhydrous Na₂SO₄, filtered and concentrated. The residue was purified by silica chromatography (0-100% EtOAc/hexane) to yield (E)-5-((4-chloro-5-((3'-((4-chlorobut-2-en-1-yl)oxy)-2-methyl-[1,1'-biphenyl]-3-yl)methoxy)-2-formylphenoxy)methyl)nicotinonitrile (0.03 g, 0.052 mmol, 25.4% yield) as a pale yellow solid. LC/MS (Cond. N-1): [M+H]⁺573.25, RT=4.56 min. ¹H NMR (400 MHz, CHLOROFORM-d) δ ppm 10.31 (s, 1H), 9.01-8.88 (m, 2H), 8.12 (t, J=2.0 Hz, 1H), 7.96 (s, 1H), 7.46 (t, J=4.5 Hz, 1H), 7.37 (t, J=7.9 Hz, 1H), 7.31 (d, J=4.3 Hz, 2H), 6.99-6.81 (m, 3H), 6.67 (s, 1H), 6.11-6.00 (m, 2H), 5.27 (d, J=3.8 Hz, 4H), 4.62 (d, J=3.0 Hz, 2H), 4.21-4.02 (m, 2H), 2.36-2.22 (m, 3H).

Intermediate: (R,E)-5-((4-chloro-2-formyl-5-((3'-((4-(3-hydroxypyrrolidin-1-yl)but-2-en-1-yl)oxy)-2-methyl-[1,1'-biphenyl]-3-yl)methoxy)phenoxy)methyl)nicotinonitrile in DMF (2 mL) was heated at 76° C. for 2 h. The reaction mixture was added with EtOAc and water, then the organic phase was washed with water, sat. NaCl, dried (Na₂SO₄) to yield (R,E)-5-((4-chloro-2-formyl-5-((3'-((4-(3-hydroxypyrrolidin-1-yl)but-2-en-1-yl)oxy)-2-methyl-[1,1'-biphenyl]-3-yl)methoxy)phenoxy)methyl)nicotinonitrile (0.033 g, 0.053 mmol, 101% yield) as a yellow solid. ¹H NMR (400 MHz, CHLOROFORM-d) δ ppm 10.33-10.27 (m, 1H), 8.96-8.87 (m, 2H), 8.10 (t, J=2.0 Hz, 1H), 7.95-7.89 (m, 1H), 7.47-7.40 (m, 1H), 7.37-7.30 (m, 1H), 7.28 (d, J=4.3 Hz, 2H), 6.94-6.88 (m, 2H), 6.87-6.82 (m, 1H), 6.69-6.65 (m, 1H), 5.95 (d, J=3.5 Hz, 2H), 5.28-5.13 (m, 4H), 4.58 (d, J=3.8 Hz, 2H), 4.38 (ddt, J=7.1, 4.8, 2.3 Hz, 1H), 3.25 (d, J=5.0 Hz, 2H), 3.02-2.94 (m, 1H), 2.79 (d, J=10.3 Hz, 1H), 2.64 (dd, J=10.4, 5.1 Hz, 1H), 2.50-2.38 (m, 1H), 2.31-2.26 (m, 3H), 2.24-2.12 (m, 1H), 1.84-1.75 (m, 1H). LC/MS (Cond. N-1): [M+H]⁺=626.25, RT=3.719 min.

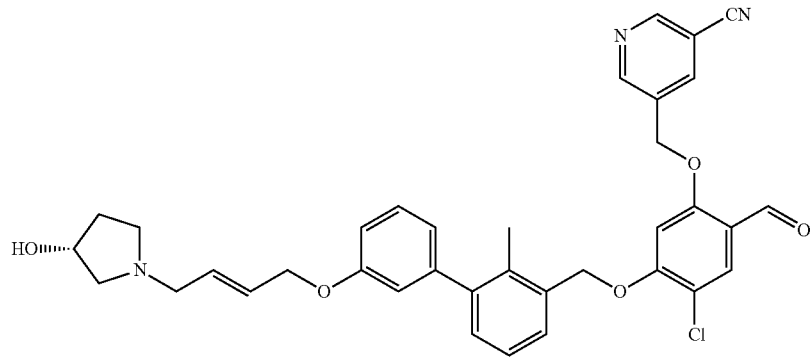 [SMILES: Cc1c(COc2cc(OCc3cncc(C#N)c3)c(C=O)cc2Cl)cccc1-c1cccc(OC/C=C/CN2CC[C@@H](O)C2)c1]

A stirred mixture of (E)-5-((4-chloro-5-((3'-((4-chlorobut-2-en-1-yl)oxy)-2-methyl-[1,1'-biphenyl]-3-yl)methoxy)-2-formylphenoxy)methyl)nicotinonitrile (0.03 g, 0.052 mmol), (R)-pyrrolidin-3-ol (5.47 mg, 0.063 mmol) and K₂CO₃ (8.68 mg, 0.063 mmol), NaI (7.84 mg, 0.052 mmol)

Example 1087: (S)-1-(5-chloro-2-((5-cyanopyridin-3-yl)methoxy)-4-((3'-(((E)-4-((R)-3-hydroxypyrrolidin-1-yl)but-2-en-1-yl)oxy)-2-methyl-[1,1'-biphenyl]-3-yl)methoxy)benzyl)piperidine-2-carboxylic Acid

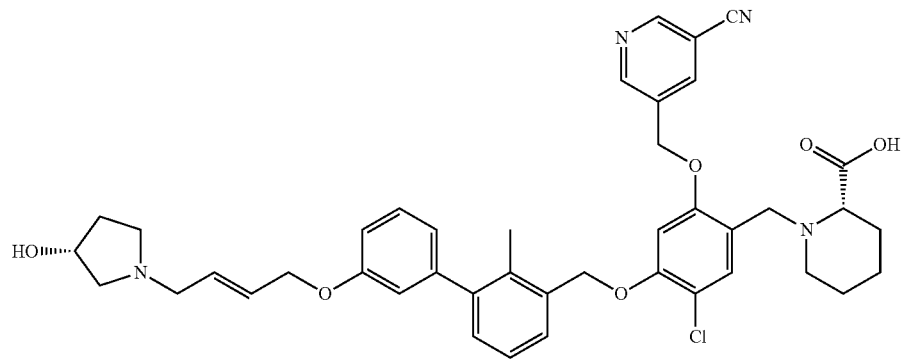 [SMILES: Cc1c(COc2cc(OCc3cncc(C#N)c3)c(CN3CCCC[C@H]3C(=O)O)cc2Cl)cccc1-c1cccc(OC/C=C/CN2CC[C@@H](O)C2)c1]

Example 1087 was prepared according to the reductive amination conditions as described for Example 1003. Mobile Phase A: 5:95 acetonitrile:water with 10-mM ammonium acetate; Mobile Phase B: 95:5 acetonitrile:water with 10-mM ammonium acetate; Gradient: 15-55% B over 40 minutes, then a 5-minute hold at 100% B; Flow: 20 mL/min. Fractions containing the desired product were combined and dried via centrifugal evaporation. The yield of the product was 13.0 mg, and its estimated purity by LCMS analysis was 92%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm. LC/MS (Injection 1 conditions): [M+H]$^+$ 737.31, RT=1.498 min.

The following LC-MS methods were employed for Example 1088 to Example 1119.
Condition N-1:
Column=Phenomenex, 2.0×50 mm, 3 μm
Start % B=0; Final % B=100
Gradient time=4 min; Stop time=5 min
Flow Rate=0.8 mL/min; Wavelength=220 nm
Solvent A=0.1% TFA in 10% methanol/90% water
Solvent B=0.1% TFA in 90% methanol/10% water
Oven temp.=40° C.
Injection 1 Conditions:
Column: Waters Acquity UPLC BEH C18, 2.1×50 mm, 1.7-μm particles;
Mobile Phase A: 5:95 acetonitrile:water with 10 mM ammonium acetate;
Mobile Phase B: 95:5 acetonitrile:water with 10 mM ammonium acetate;
Temperature: 50° C.; Gradient: 0-100% B over 3 min;
Flow: 1.0 mL/min;
Detection: UV at 220 nm.

Example 1088: (S)-1-(5-chloro-4-((2'-chloro-3'-(3-((3R,4R)-4-(4-chlorophenyl)-3,4-dihydroxy-3-methylpiperidin-1-yl)propoxy)-2-methyl-[1,1'-biphenyl]-3-yl)methoxy)-2-((5-cyanopyridin-3-yl)methoxy)benzyl)piperidine-2-carboxylic Acid

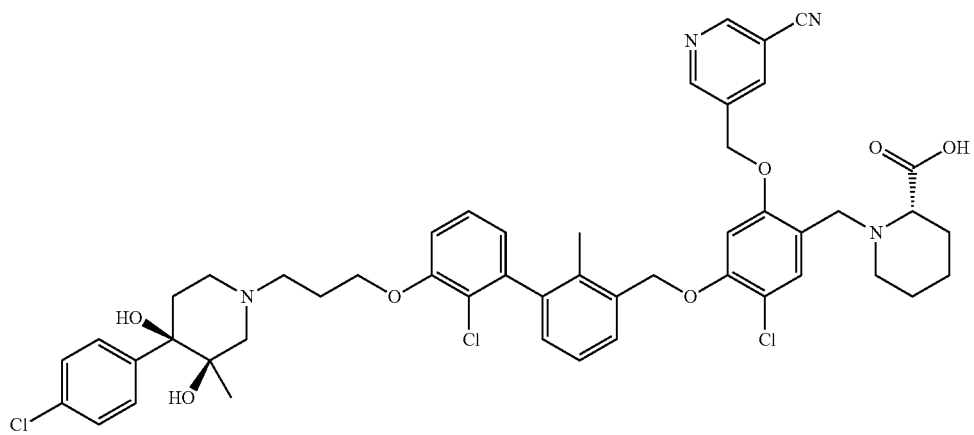 [SMILES: Cc1c(COc2cc(OCc3cncc(C#N)c3)c(CN3CCCC[C@H]3C(=O)O)cc2Cl)cccc1-c1cccc(OCCCN2CC[C@@](O)(c3ccc(Cl)cc3)[C@](C)(O)C2)c1Cl]

Example 1088 was prepared according to the procedure described for Example 1003. LC/MS (Injection 1 conditions): [M+H]$^+$ 913.1, RT=2.3 min.

Example 1089: (5-chloro-4-((2'-chloro-3'-(3-((3R,4R)-4-(4-chlorophenyl)-3,4-dihydroxy-3-methylpiperidin-1-yl)propoxy)-2-methyl-[1,1'-biphenyl]-3-yl)methoxy)-2-((5-cyanopyridin-3-yl)methoxy)benzyl)-D-serine

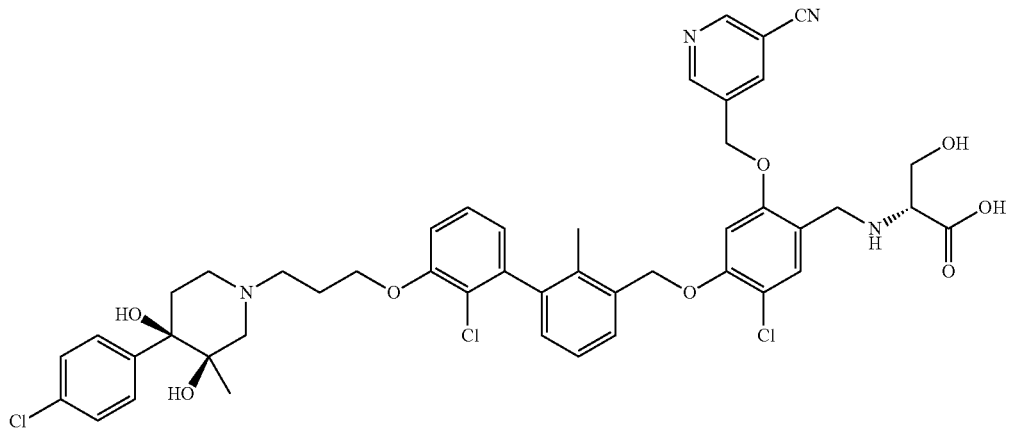 [SMILES: Cc1c(COc2cc(OCc3cncc(C#N)c3)c(CN[C@H](CO)C(=O)O)cc2Cl)cccc1-c1cccc(OCCCN2CC[C@@](O)(c3ccc(Cl)cc3)[C@](C)(O)C2)c1Cl]

Example 1089 was prepared according to the procedure described for Example 1003. LC/MS (Injection 1 conditions): [M+H]$^+$ 889.1, RT=1.944 min.

Example 1090: (S)-1-(5-chloro-4-((3'-(3-((S)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic Acid

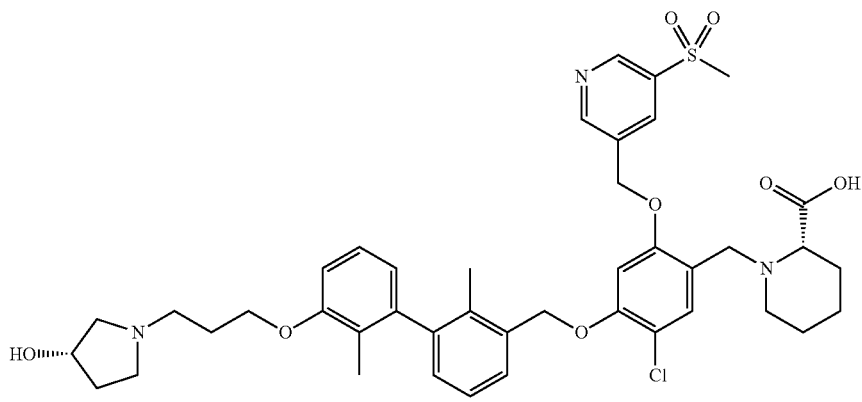 [SMILES: Cc1c(COc2cc(OCc3cncc(S(C)(=O)=O)c3)c(CN3CCCC[C@H]3C(=O)O)cc2Cl)cccc1-c1cccc(OCCCN2CC[C@H](O)C2)c1C]

Example 1090 was prepared according to the procedure described for Example 1003. LC/MS (Injection 1 conditions): [M+H]$^+$ 792.1, RT=1.78 min.

Example 1091: methyl 1-(5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)-4-hydroxypiperidine-4-carboxylate

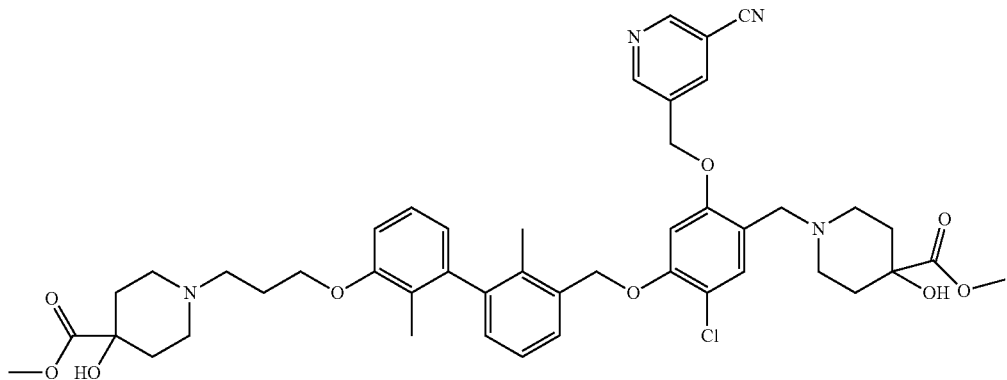

Example 1091 was prepared according to the procedure described for Example 1003. LC/MS (Injection 1 conditions): [M+H]⁺ 841.2, RT=1.92 min.

Example 1092: (5-chloro-2-((5-cyanopyridin-3-yl)methoxy)-4-((4'-(4-((R)-3-hydroxypyrrolidin-1-yl)butoxy)-2,2'-dimethyl-[1,1'-biphenyl]-3-yl)methoxy)benzyl)-D-serine

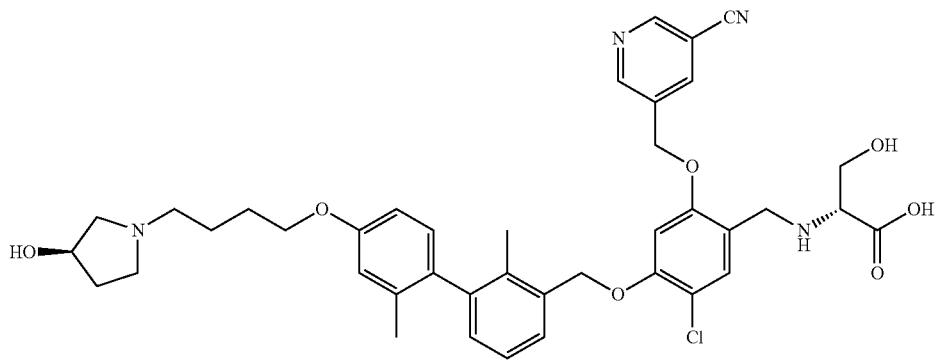 [SMILES: Cc1cc(OCCCCN2CC[C@@H](O)C2)ccc1-c1cccc(COc2cc(OCc3cncc(C#N)c3)c(CN[C@H](CO)C(=O)O)cc2Cl)c1C]

Example 1092 was prepared according to the procedure described for Example 1003. LC/MS (Injection 1 conditions): [M+H]⁺ 792.2, RT=1.395 min.

Example 1093: (S)-1-(5-chloro-2-((5-cyanopyridin-3-yl)methoxy)-4-((4'-(4-((R)-3-hydroxypyrrolidin-1-yl)butoxy)-2,2'-dimethyl-[1,1'-biphenyl]-3-yl)methoxy)benzyl)piperidine-2-carboxylic Acid

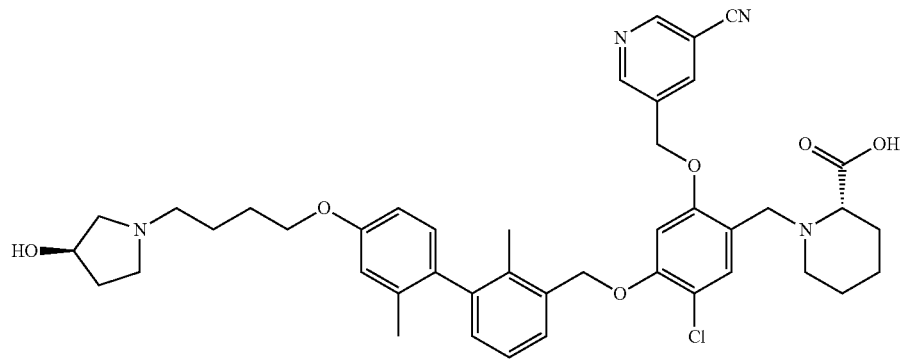 [SMILES: Cc1cc(OCCCCN2CC[C@@H](O)C2)ccc1-c1cccc(COc2cc(OCc3cncc(C#N)c3)c(CN3CCCC[C@H]3C(=O)O)cc2Cl)c1C]

Example 1093 was prepared according to the procedure described for Example 1003. LC/MS (Injection 1 conditions): [M+H]$^+$ 753.2, RT=1.45 min.

Example 1094: (R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2,2'-dimethyl-[1,1'-biphenyl]-3-yl)oxy)propyl)-4-hydroxypiperidine-4-carboxylic Acid

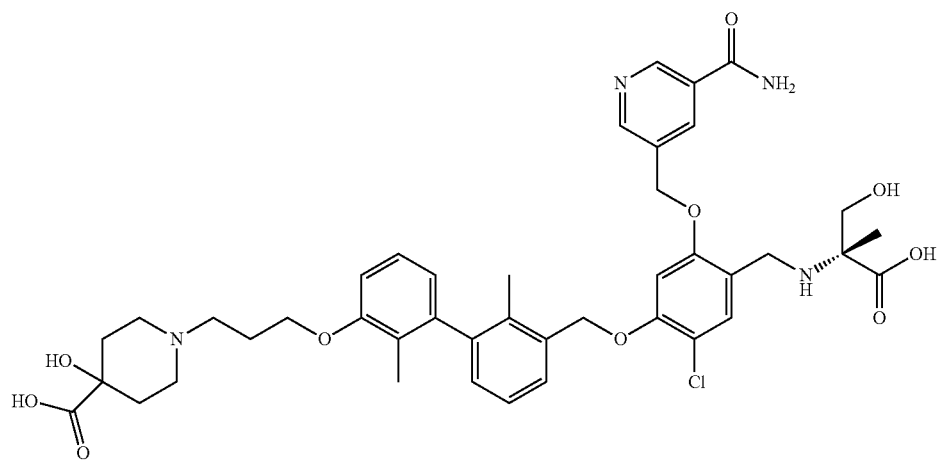

Example 1094 was prepared according to the procedure described for Example 1057. LC/MS (Injection 1 conditions): [M+H]$^+$ 805.2, RT=1.4 min.

Example 1095: (5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)-L-serine

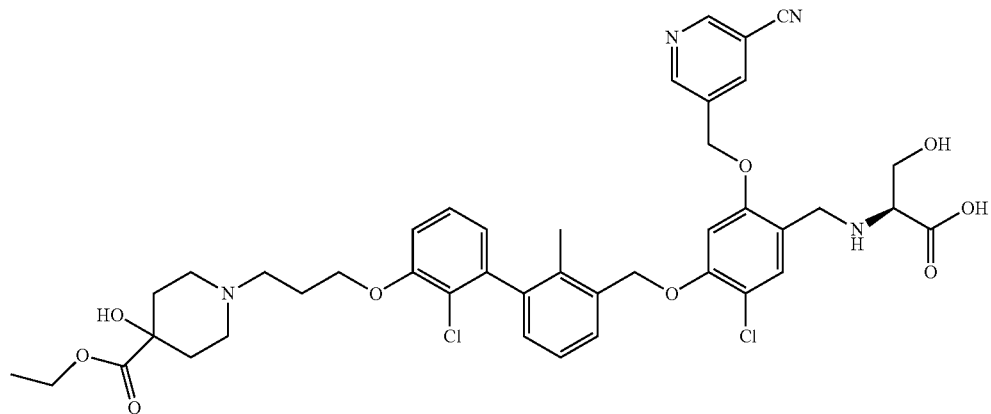 [SMILES: CCOC(=O)C1(O)CCN(CCCOc2cccc(-c3cccc(COc4cc(OCc5cncc(C#N)c5)c(CN[C@@H](CO)C(=O)O)cc4Cl)c3C)c2Cl)CC1]

Example 1095 was prepared according to the procedure described for Example 1003. LC/MS (Injection 1 conditions): [M+H]$^+$ 822.1, RT=1.495 min.

Example 1097: (S)-1-(4-((3'-(3-(4-carboxy-4-hydroxypiperidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic Acid

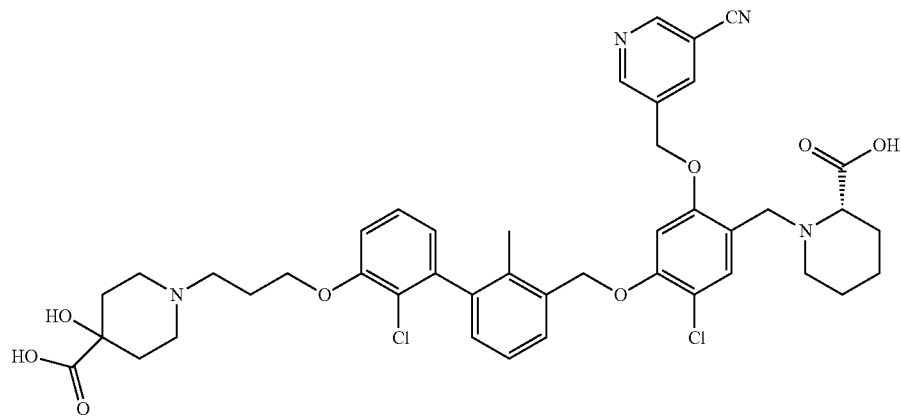 [SMILES: Cc1c(COc2cc(OCc3cncc(C#N)c3)c(CN3CCCC[C@H]3C(=O)O)cc2Cl)cccc1-c1cccc(OCCCN2CCC(O)(C(=O)O)CC2)c1Cl]

Example 1097 was prepared according to the procedure described for Example 1057. LC/MS (Injection 1 conditions): [M+H]$^+$ 817.4, RT=1.38 min.

Example 1098: (R)-2-((5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

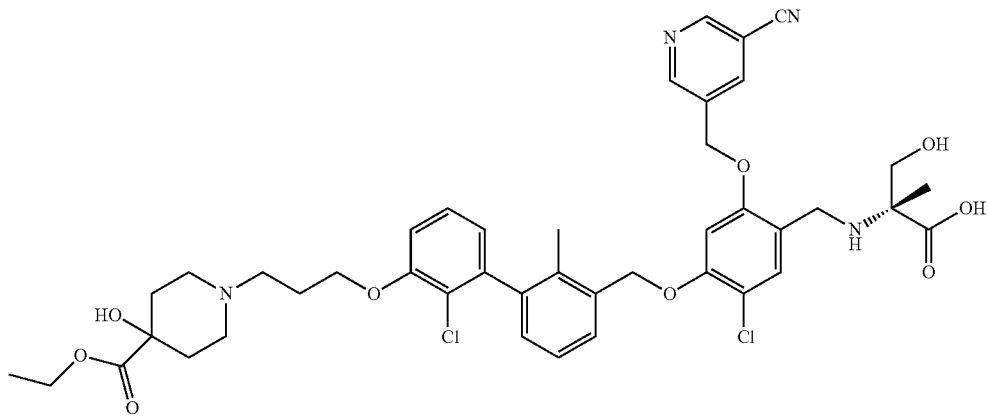

Example 1098 was prepared according to the procedure described for Example 1003. LC/MS (Cond. N-1): [M+H]$^+$ 835.4, RT=3.046 min. LC/MS (Injection 1 conditions): [M+H]$^+$ 835.2, RT=1.52 min. $^1$H NMR (400 MHz, METHANOL-d$_4$) □ 9.00 (d, J=2.0 Hz, 1H), 8.93 (d, J=2.0 Hz, 1H), 8.44 (t, J=2.0 Hz, 1H), 7.59-7.55 (m, 1H), 7.50 (d, J=7.3 Hz, 1H), 7.37 (t, J=8.0 Hz, 1H), 7.27 (t, J=7.5 Hz, 1H), 7.17-7.05 (m, 3H), 6.90 (dd, J=7.5, 1.3 Hz, 1H), 5.35 (d, J=13.1 Hz, 4H), 4.33-4.19 (m, 6H), 4.03 (d, J=12.3 Hz, 1H), 3.83 (d, J=12.3 Hz, 1H), 3.64 (d, J=12.3 Hz, 2H), 3.51-3.41 (m, 2H), 3.39-3.34 (m, 1H), 2.41-2.21 (m, 4H), 2.17-2.09 (m, 3H), 2.02 (d, J=14.6 Hz, 2H), 1.55 (s, 3H), 1.32-1.22 (m, 3H).

Example 1099: (R)-1-(3-((3'-((4-(((2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)-4-hydroxypiperidine-4-carboxylic Acid

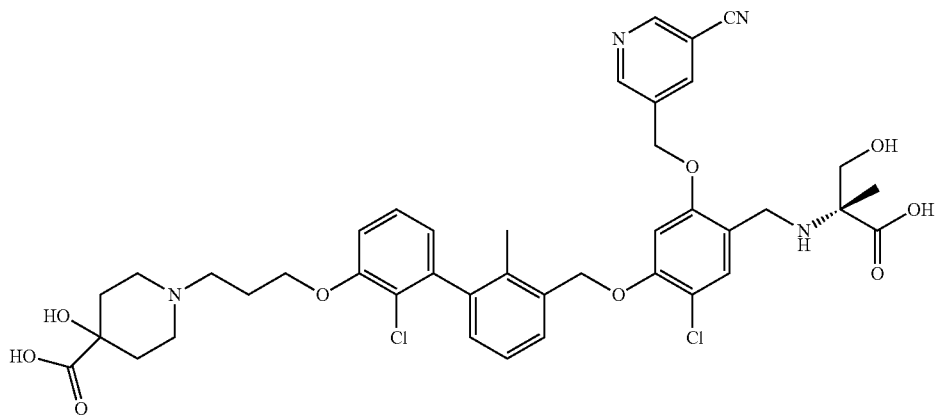

Example 1099 was prepared according to the procedure described for Example 1057. LC/MS (Injection 1 conditions): [M+H]$^+$ 807.3, RT=1.24 min.

Example 1100: (S)-1-(5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)piperidine-2-carboxylic Acid

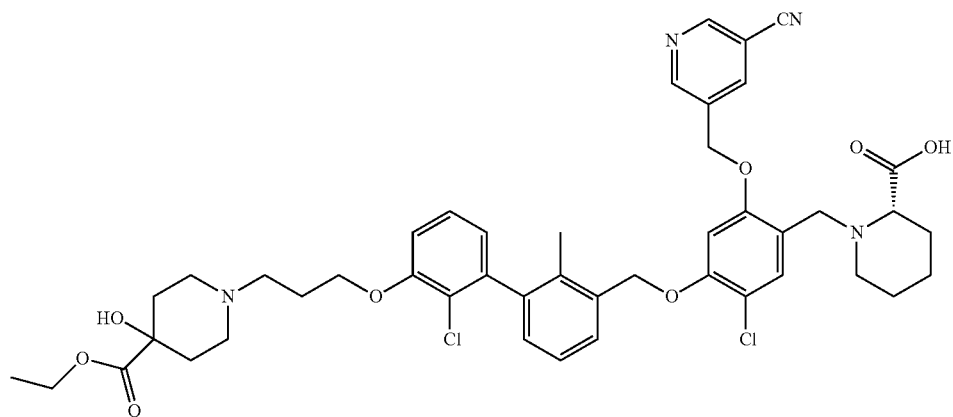 [SMILES: CCOC(=O)C1(O)CCN(CCCOc2cccc(-c3cccc(COc4cc(OCc5cncc(C#N)c5)c(CN5CCCC[C@H]5C(=O)O)cc4Cl)c3C)c2Cl)CC1]

Example 1100 was prepared according to the procedure described for Example 1003. LC/MS (Cond. N-1): [M+H]+ 845.4, RT=3.286 min.

Example 1101: (2S)-1-(5-chloro-4-((2'-chloro-3'-(3-(3-(ethoxycarbonyl)-3-(hydroxymethyl)pyrrolidin-1-yl)propoxy)-2-methyl-[1,1'-biphenyl]-3-yl)methoxy)-2-((5-cyanopyridin-3-yl)methoxy)benzyl)piperidine-2-carboxylic Acid

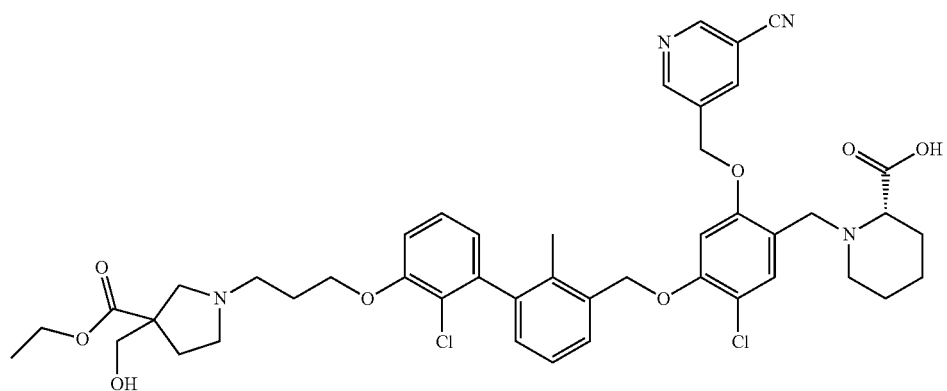 [SMILES: CCOC(=O)C1(CO)CCN(CCCOc2cccc(-c3cccc(COc4cc(OCc5cncc(C#N)c5)c(CN5CCCC[C@H]5C(=O)O)cc4Cl)c3C)c2Cl)C1]

Example 1101 was prepared according to the procedure described for Example 1003. LC/MS (Injection 1 conditions): [M+H]+ 845.2, RT=1.596 min.

Example 1102: ethyl 1-(3-((2-chloro-3'-((2-chloro-5-((5-cyanopyridin-3-yl)methoxy)-4-((3-(ethoxycarbonyl)-3-(hydroxymethyl)pyrrolidin-1-yl)methyl)phenoxy)methyl)-2'-methyl-[1,1'-biphenyl]-3-yl)oxy)propyl)-3-(hydroxymethyl)pyrrolidine-3-carboxylate

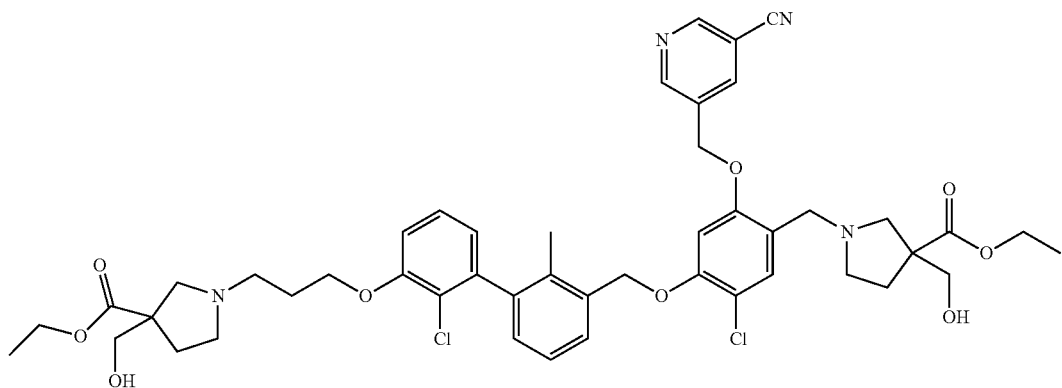 [SMILES: CCOC(=O)C1(CO)CCN(CCCOc2cccc(-c3cccc(COc4cc(OCc5cncc(C#N)c5)c(CN5CCC(CO)(C(=O)OCC)C5)cc4Cl)c3C)c2Cl)C1]

Example 1102 was prepared according to the procedure described for Example 1003. LC/MS (Injection 1 conditions): [M+H]+ 889.2, RT=1.967 min.

Example 1103: (2R)-2-((5-chloro-4-((2'-chloro-3'-(3-(3-(ethoxycarbonyl)-3-(hydroxymethyl)pyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

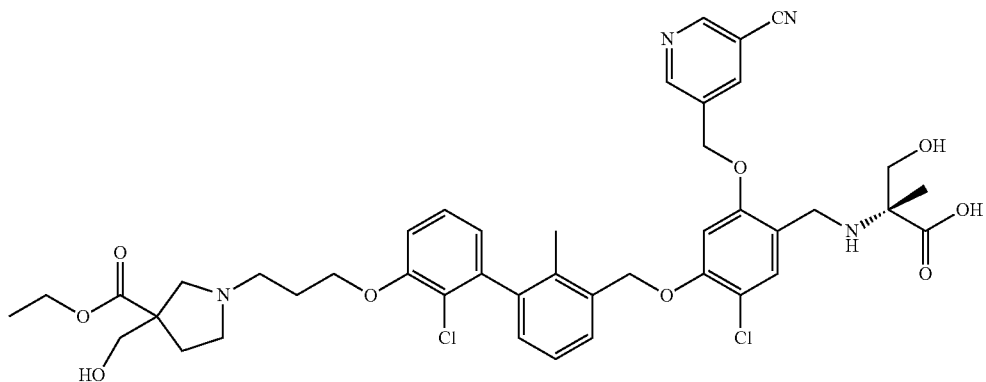

Example 1103 was prepared according to the procedure described for Example 1003. LC/MS (Injection 1 conditions): [M+H]+ 835.0, RT=1.67 min.

Example 1104: ethyl 1-(3-((2-chloro-3'-((2-chloro-5-((5-cyanopyridin-3-yl)methoxy)-4-((3-(ethoxycarbonyl)-3-(hydroxymethyl)pyrrolidin-1-yl)methyl)phenoxy)methyl)-2'-methyl-[1,1'-biphenyl]-3-yl)oxy)propyl)-3-(hydroxymethyl)pyrrolidine-3-carboxylate

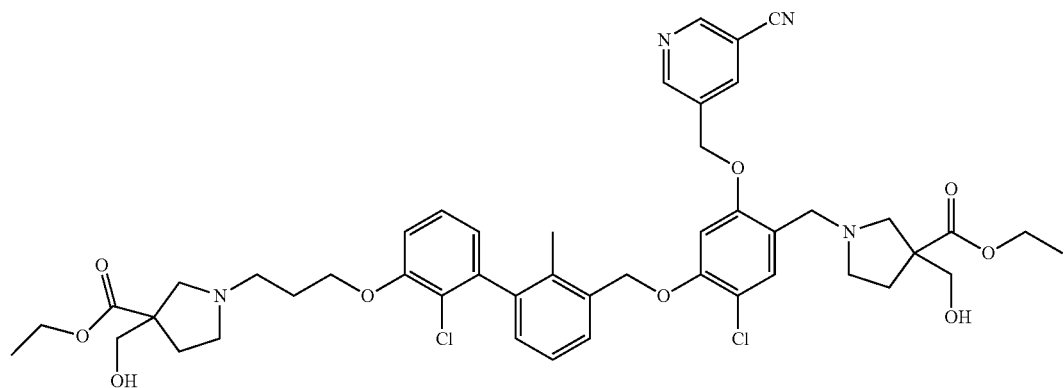 [SMILES: CCOC(=O)C1(CO)CCN(CCCOc2cccc(-c3cccc(COc4cc(OCc5cncc(C#N)c5)c(CN5CCC(CO)(C(=O)OCC)C5)cc4Cl)c3C)c2Cl)C1]

Example 1104 was prepared according to the procedure described for Example 1003. LC/MS (Injection 1 conditions): [M+H]+ 889.0, RT=2.27 min.

Example 1105: (S)-1-(4-((3'-(3-(4-acetamidopiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

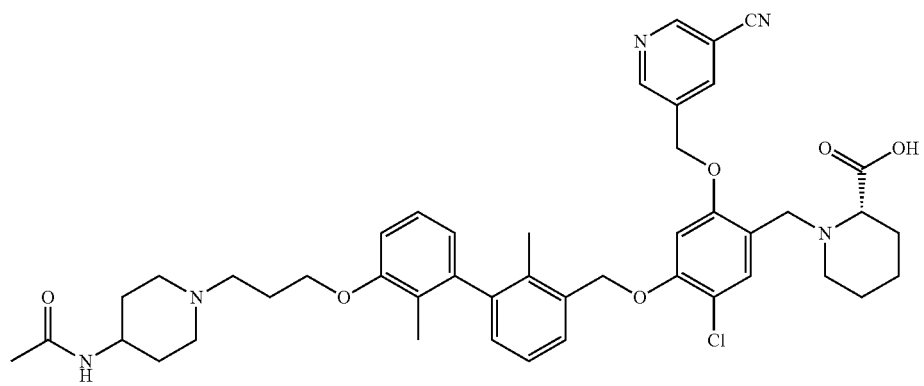 [SMILES: CC(=O)NC1CCN(CCCOc2cccc(-c3cccc(COc4cc(OCc5cncc(C#N)c5)c(CN5CCCC[C@H]5C(=O)O)cc4Cl)c3C)c2C)CC1]

Example 1105 was prepared according to the procedure described for Example 1003. LC/MS (Injection 1 conditions): [M+H]+ 794.1, RT=1.56 min.

Example 1106: (2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic Acid

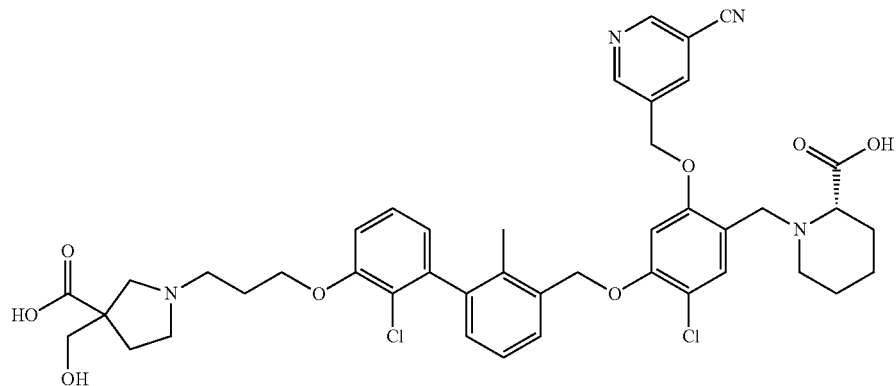 [SMILES: Cc1c(COc2cc(OCc3cncc(C#N)c3)c(CN3CCCC[C@H]3C(=O)O)cc2Cl)cccc1-c1cccc(OCCCN2CCC(CO)(C(=O)O)C2)c1Cl]

Example 1106 was prepared according to the procedure described for Example 1057. LC/MS (Injection 1 conditions): [M+H]$^+$ 817.0, RT=1.36 min.

Example 1107: (2S)-1-(2-((5-carbamoylpyridin-3-yl)methoxy)-4-((3'-(3-(3-carboxy-3-(hydroxymethyl)pyrrolidin-1-yl)propoxy)-2'-chloro-2-methyl-[1,1'-biphenyl]-3-yl)methoxy)-5-chlorobenzyl)piperidine-2-carboxylic Acid

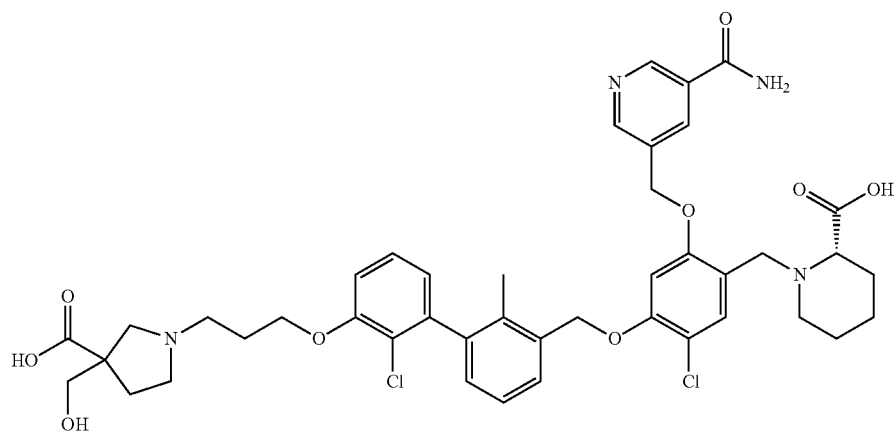 [SMILES: Cc1c(COc2cc(OCc3cncc(C(N)=O)c3)c(CN3CCCC[C@H]3C(=O)O)cc2Cl)cccc1-c1cccc(OCCCN2CCC(CO)(C(=O)O)C2)c1Cl]

Example 1107 was prepared according to the procedure described for Example 1057. LC/MS (Injection 1 conditions): [M+H]$^+$ 835.0, RT=1.2 min.

Example 1108: 1-(3-((3'-((4-((((R)-2-carboxy-1-
hydroxypropan-2-yl)amino)methyl)-2-chloro-5-((5-
cyanopyridin-3-yl)methoxy)phenoxy)methyl)-2-
chloro-2'-methyl-[1,1'-biphenyl]-3-yl)oxy)propyl)-3-
(hydroxymethyl)pyrrolidine-3-carboxylic Acid

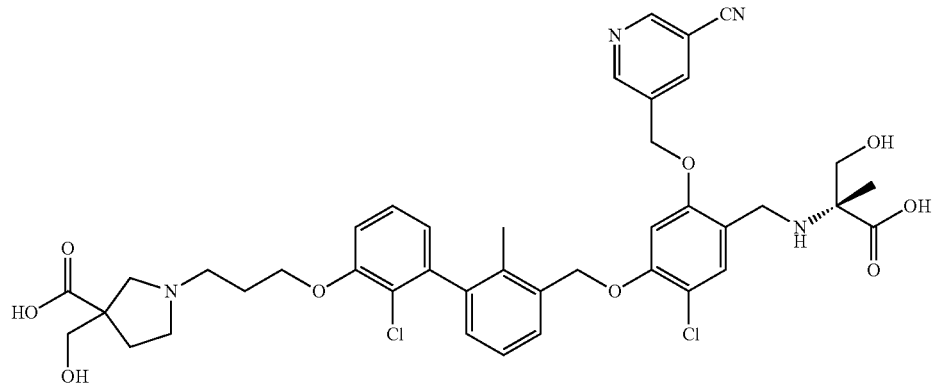

Example 1108 was prepared according to the procedure described for Example 1057. LC/MS (Injection 1 conditions): [M+H]$^+$ 807.0, RT=1.3 min.

Example 1109: 1-(3-((3'-((5-((5-carbamoylpyridin-
3-yl)methoxy)-4-((((R)-2-carboxy-1-hydroxypropan-
2-yl)amino)methyl)-2-chlorophenoxy)methyl)-2-
chloro-2'-methyl-[1,1'-biphenyl]-3-yl)oxy)propyl)-3-
(hydroxymethyl)pyrrolidine-3-carboxylic Acid

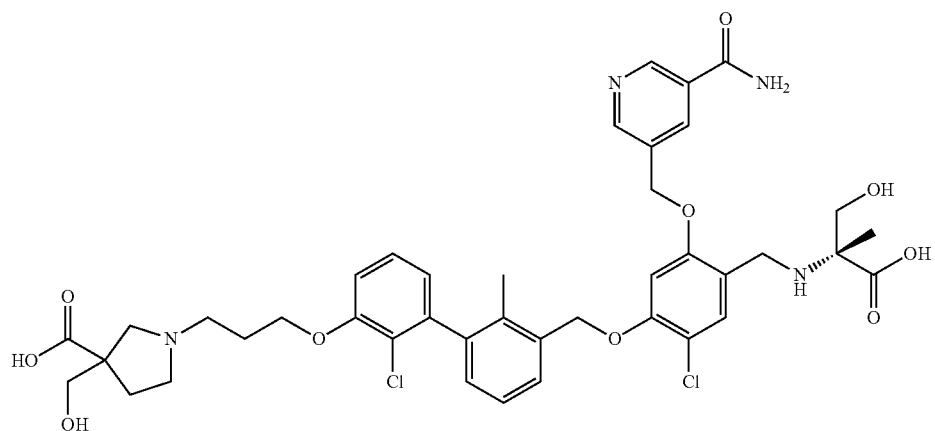

Example 1109 was prepared according to the procedure described for Example 1057. LC/MS (Injection 1 conditions): [M+H]$^+$ 825.0, RT=1.24 min.

Example 1110: (S)-1-(4-((3'-(3-(4-carboxy-4-(hydroxymethyl)piperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

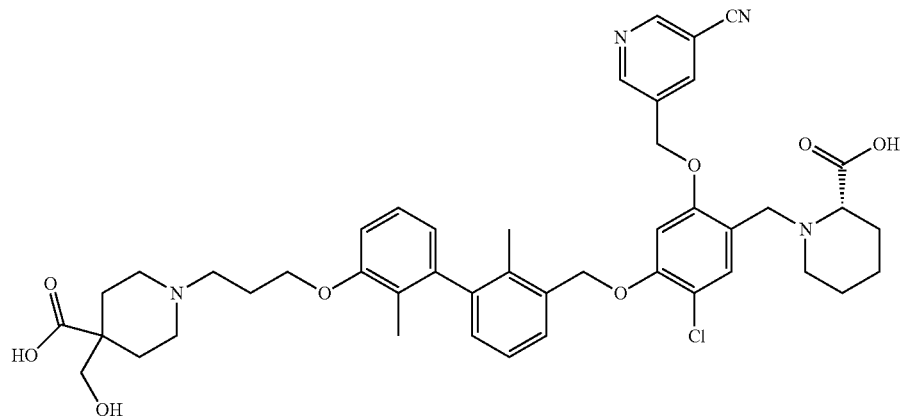 [SMILES: Cc1c(COc2cc(OCc3cncc(C#N)c3)c(CN3CCCC[C@H]3C(=O)O)cc2Cl)cccc1-c1cccc(OCCCN2CCC(CO)(C(=O)O)CC2)c1C]

Example 1110 was prepared according to the procedure described for Example 1057. LC/MS (Injection 1 conditions): [M+H]$^+$ 811.3, RT=1.35 min.

Example 1111: (S)-1-(2-((5-carbamoylpyridin-3-yl)methoxy)-4-((3'-(3-(4-carboxy-4-(hydroxymethyl)piperidin-1-yl)propoxy)-2,2'-dimethyl-[1,1'-biphenyl]-3-yl)methoxy)-5-chlorobenzyl)piperidine-2-carboxylic Acid

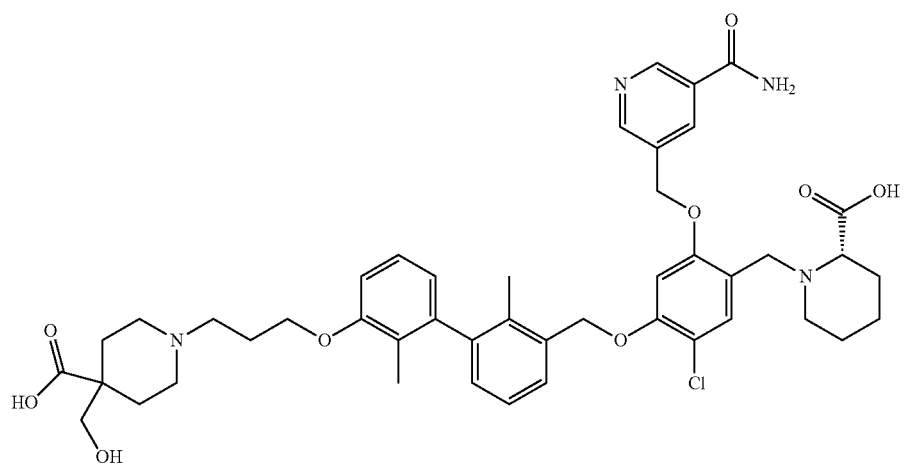 [SMILES: Cc1c(COc2cc(OCc3cncc(C(N)=O)c3)c(CN3CCCC[C@H]3C(=O)O)cc2Cl)cccc1-c1cccc(OCCCN2CCC(CO)(C(=O)O)CC2)c1C]

Example 1111 was prepared according to the procedure described for Example 1057. LC/MS (Injection 1 conditions): [M+H]$^+$ 829.2, RT=1.26 min.

Example 1112: (R)-1-(3-((3'-((4-(((2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-(hydroxymethyl)piperidine-4-carboxylic Acid

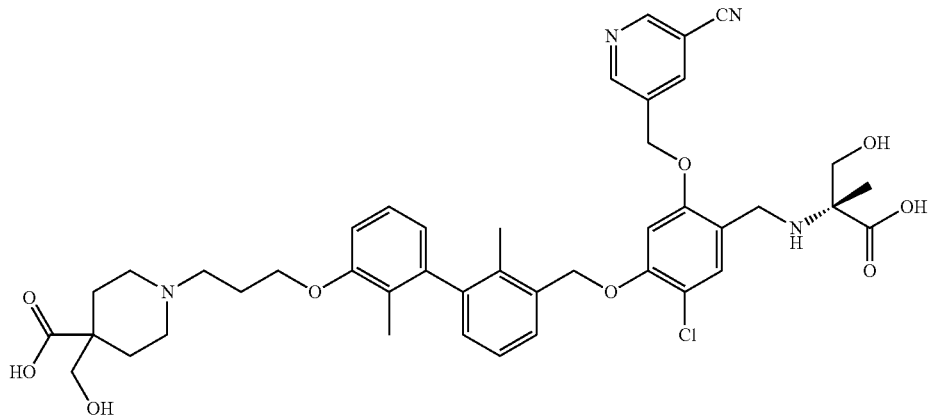

Example 1112 was prepared according to the procedure described for Example 1057. LC/MS (Injection 1 conditions): [M+H]+ 801.3, RT=1.3 min.

Example 1113: (R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2,2'-dimethyl-[1,1'-biphenyl]-3-yl)oxy)propyl)-4-(hydroxymethyl)piperidine-4-carboxylic Acid

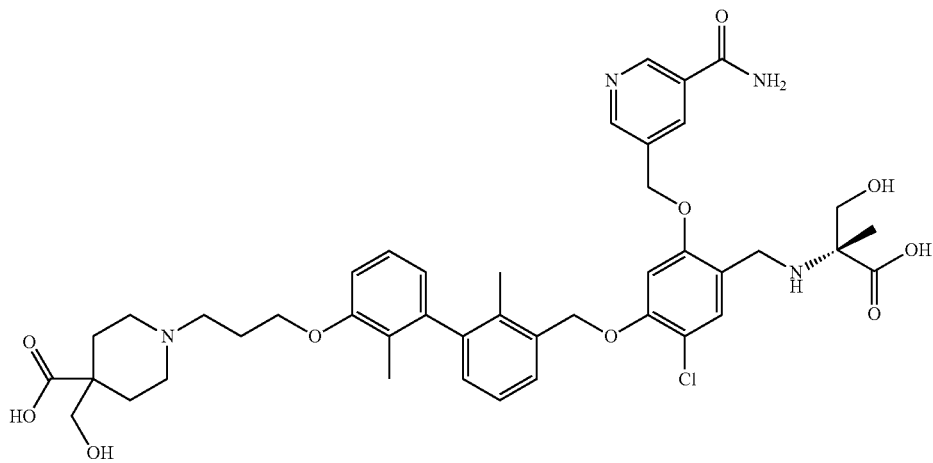

Example 1113 was prepared according to the procedure described for Example 1057. LC/MS (Injection 1 conditions): [M+H]+ 819.2, RT=1.2 min.

Example 1114: (S)-1-(2-((5-carbamoylpyridin-3-yl)methoxy)-4-((3'-(3-(4-carboxy-4-(hydroxymethyl)piperidin-1-yl)propoxy)-2'-chloro-2-methyl-[1,1'-biphenyl]-3-yl)methoxy)-5-chlorobenzyl)piperidine-2-carboxylic Acid

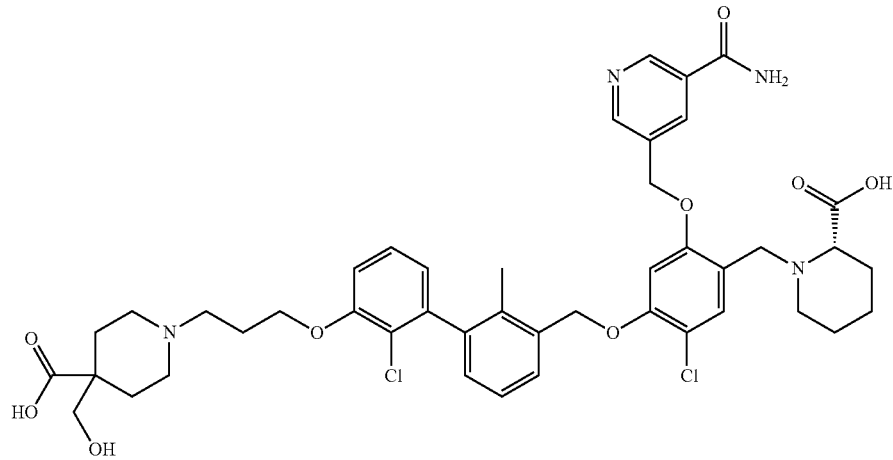 [SMILES: Cc1c(COc2cc(OCc3cncc(C(N)=O)c3)c(CN3CCCC[C@H]3C(=O)O)cc2Cl)cccc1-c1cccc(OCCCN2CCC(CO)(C(=O)O)CC2)c1Cl]

Example 1114 was prepared according to the procedure described for Example 1057. LC/MS (Injection 1 conditions): [M+H]$^+$ 849.3, RT=1.2 min.

Example 1115: (R)-1-(3-((3'-((4-(((2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)-4-(hydroxymethyl)piperidine-4-carboxylic Acid

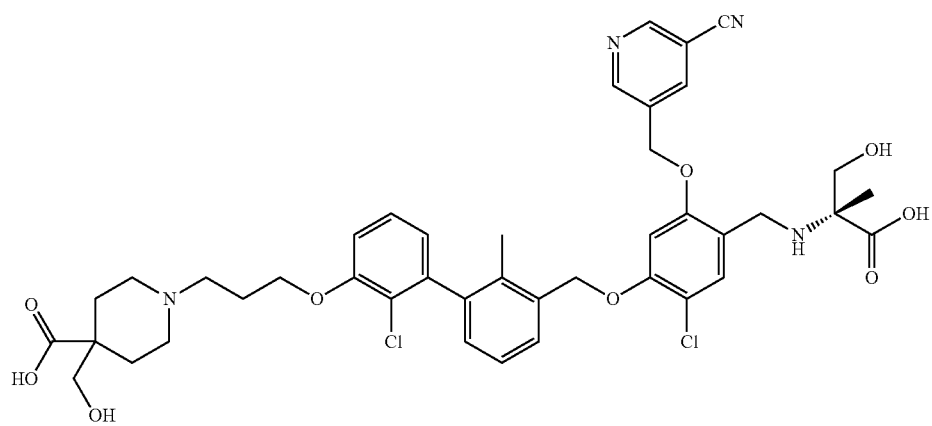

Example 1115 was prepared according to the procedure described for Example 1057. LC/MS (Injection 1 conditions): [M+H]$^+$ 821.1, RT=1.28 min.

Example 1116: (R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2-chloro-2'-methyl-[1,1'-biphenyl]-3-yl)oxy)propyl)-4-(hydroxymethyl)piperidine-4-carboxylic Acid

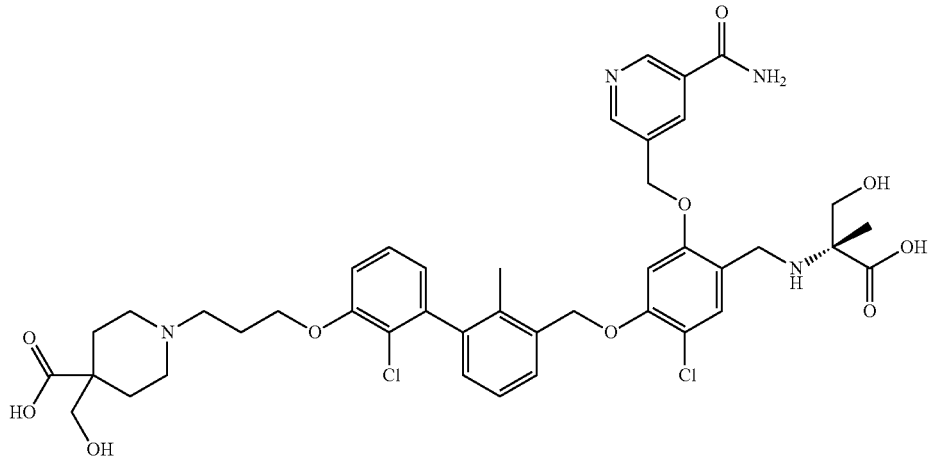

Example 1116 was prepared according to the procedure described for Example 1057. LC/MS (Injection 1 conditions): [M+H]$^+$ 839.1, RT=1.17 min.

Example 1117: ethyl 1-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-3-(hydroxymethyl)pyrrolidine-3-carboxylate

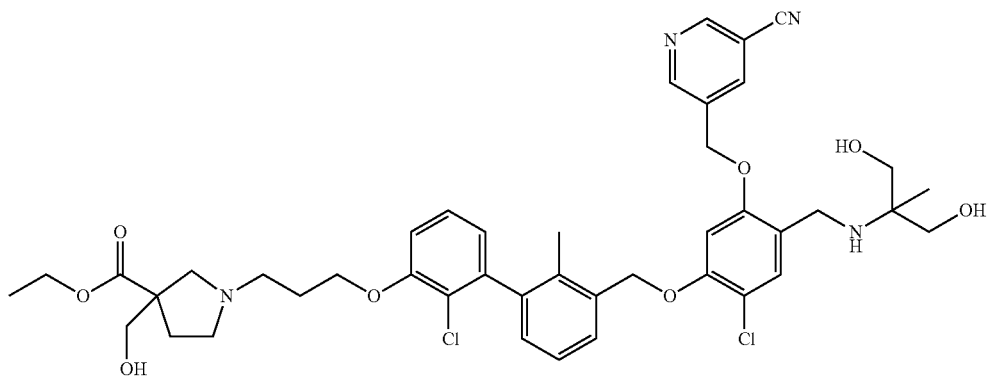 [SMILES: CCOC(=O)C1(CO)CCN(CCCOc2cccc(-c3cccc(COc4cc(OCc5cncc(C#N)c5)c(CNC(C)(CO)CO)cc4Cl)c3C)c2Cl)C1]

Example 1117 was prepared according to the procedure described for Example 1003. LC/MS (Cond. N-1): m/z 821.2, RT=3.0 min.

Example 1118: 1-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-3-(hydroxymethyl)pyrrolidine-3-carboxylic Acid

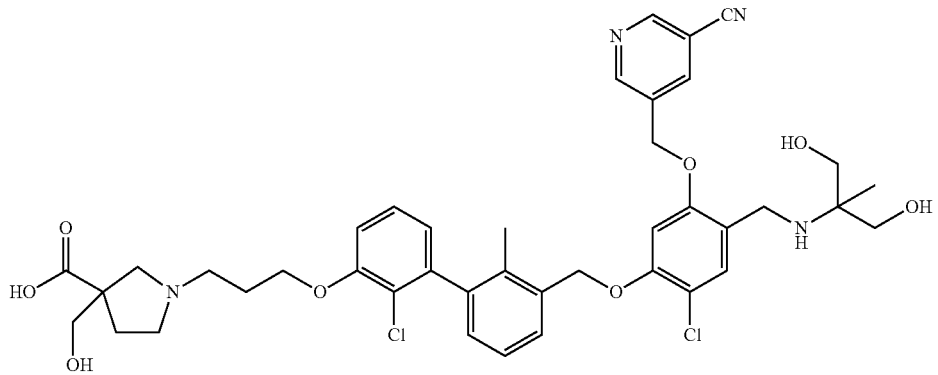 [SMILES: Cc1c(COc2cc(OCc3cncc(C#N)c3)c(CNC(C)(CO)CO)cc2Cl)cccc1-c1cccc(OCCCN2CCC(CO)(C(=O)O)C2)c1Cl]

Example 1118 was prepared according to the procedure described for Example 1057. LC/MS (Injection 1 conditions): [M+H]+ 793.0, RT=1.37 min.

Example 1119: (R)-2-((4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid

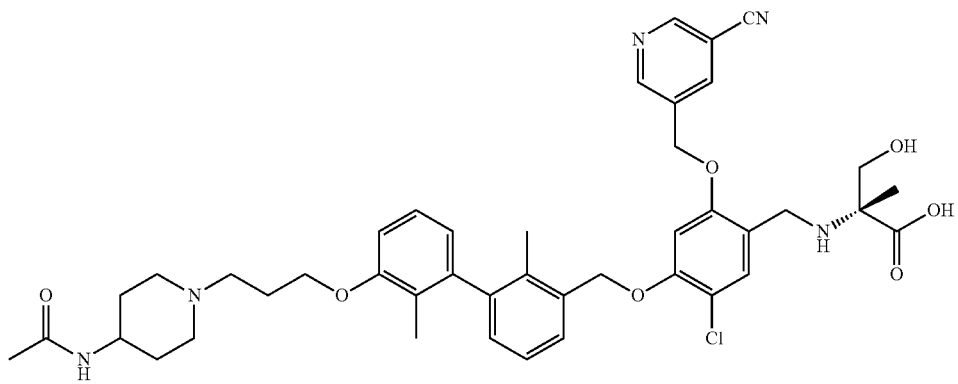

Example 1119 was prepared in a similar manner to Example 1105. LC/MS (Injection 1 conditions): [M+H]+ 784.1, RT=1.50 min.

Intermediate:
1-Bromo-2-chloro-3-(3-chloropropoxy)benzene

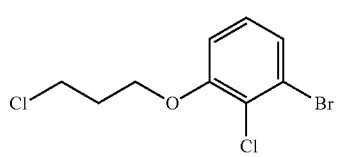 [SMILES: ClCCCOc1cccc(Br)c1Cl]

A stirred solution of 3-bromo-2-chlorophenol (3.730 g, 17.98 mmol) and 1-bromo-3-chloropropane (2.123 ml, 21.58 mmol) in dry DMF (36.0 ml) was treated with anhydrous potassium carbonate (2.98 g, 21.58 mmol) and the slurry was stirred with heating (40° C. oil bath) for 16 hours. The reaction mixture was cooled, and diluted with ether and water. The organic phase was washed with water and brine, then dried over sodium sulfate, filtered, and concentrated under reduced pressure, affording the product (4.71 g, 16.59 mmol, 92% yield) as a clear mobile oil. ¹H NMR (400 MHz, CDCl₃) δ: 7.25 (dd, J=8.2, 1.4 Hz, 1H), 7.09 (t, J=8.2 Hz, 1H), 6.90 (dd, J=8.3, 1.3 Hz, 1H), 4.19 (t, J=5.8 Hz, 2H), 3.82 (t, J=6.1 Hz, 2H), 2.30 (quin, J=6.0 Hz, 2H). (The material contained approximately 10% of the bromopropoxy by-product.)

Intermediate: (2'-Chloro-3'-(3-chloropropoxy)-2-methyl-[1,1'-biphenyl]-3-yl)methanol

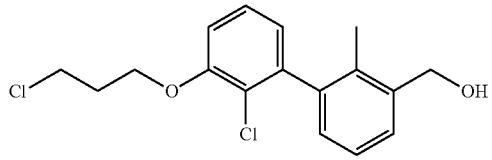 [SMILES: Cc1c(CO)cccc1-c1cccc(OCCCCl)c1Cl]

A mixture of 1-bromo-2-chloro-3-(3-chloropropoxy)benzene (4.71 g, 16.59 mmol) and (2-methyl-3-(4,4,5,5-tetramethyl-1,3,2-dioxaborolan-2-yl)phenyl)methanol (4.20 g, 16.92 mmol) in tetrahydrofuran (75 mL) and 0.5 M aq. potassium phosphate, tribasic (83 mL, 41.5 mmol) was stirred with nitrogen sparging for 15 min, then treated with 2nd generation XPhos precatalyst (0.290 g, 0.369 mmol). The mixture was sparged for 10 min, then stirred under nitrogen for 16 hours. The reaction was diluted with EtOAc, washed with brine, dried over anhydrous $Na_2SO_4$, filtered and concentrated to yield a green oil. The residue was purified by Biotage column chromatography (Premium 220 g $SiO_2$, 10-60% (20 CV) ethyl acetate in hexanes). Product fractions were pooled and concentrated under reduced pressure, affording the product (5.29 g, 16.27 mmol, 98% yield) as a pale green viscous oil which crystallized upon standing. $^1$H NMR (400 MHz, $CDCl_3$) δ: 7.44 (d, J=7.3 Hz, 1H), 7.31-7.22 (m, 2H), 7.11 (d, J=7.6 Hz, 1H), 6.98 (d, J=8.3 Hz, 1H), 6.85 (d, J=7.6 Hz, 1H), 4.79 (d, J=5.1 Hz, 2H), 4.25 (t, J=4.8 Hz, 2H), 3.84 (t, J=6.2 Hz, 2H), 2.33 (quin, J=6.0 Hz, 2H), 2.11 (s, 3H). (The product contained some bromopropoxy by-product.)

Intermediate: (R)-1-(3-((2-Chloro-3'-(hydroxymethyl)-2'-methyl-[1,1'-biphenyl]-3-yl)oxy)propyl)pyrrolidin-3-ol

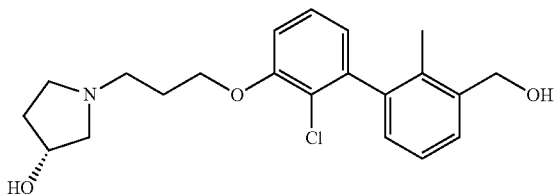 [SMILES: Cc1c(CO)cccc1-c1cccc(OCCCN2CC[C@@H](O)C2)c1Cl]

A solution of (2'-chloro-3'-(3-chloropropoxy)-2-methyl-[1,1'-biphenyl]-3-yl)methanol (0.061 g, 0.188 mmol) and (R)-pyrrolidin-3-ol (0.028 g, 0.321 mmol) in dry N,N-dimethylformamide (2.0 mL) was treated with potassium carbonate (0.031 g, 0.225 mmol) and sodium iodide (0.028 g, 0.188 mmol), and the mixture was then heated (70° C. oil bath) for 16 hours. The reaction was cooled, filtered (0.45 μm syringe tip filter) and the crude material was purified via preparative LCMS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation, affording the product (0.0664 g, 0.177 mmol, 94% yield). The estimated purity was 100% (Condition ACN-AA, ES+) M+H=376.0, 1.27 minutes, calculated exact mass=375.15. $^1$H NMR (500 MHz, DMSO-$d_6$) □ 7.41 (d, J=7.6 Hz, 1H), 7.35-7.28 (m, 1H), 7.22 (t, J=7.6 Hz, 1H), 7.14 (d, J=8.5 Hz, 1H), 6.97 (d, J=7.6 Hz, 1H), 6.79 (d, J=7.6 Hz, 1H), 4.53 (s, 2H), 4.17 (d, J=6.4 Hz, 1H), 4.14-4.08 (m, 2H), 2.70 (d, J=6.1 Hz, 1H), 2.62-2.52 (m, 3H), 2.43 (d, J=6.7 Hz, 1H), 2.33 (dd, J=9.5, 3.1 Hz, 1H), 2.01-1.94 (m, 1H), 1.93-1.87 (m, 7H), 1.58-1.48 (m, 1H).

Condition ACN-AA: Column Waters Acquity UPLC BEH C18, 2.1×50 mm, 1.7-μm particles; Mobile Phase A: 5:95 acetonitrile:water with 10 mM ammonium acetate;

Mobile Phase B: 95:5 acetonitrile:water with 10 mM ammonium acetate;

Temperature: 50° C.; Gradient: 0-100% B over 3 minutes, then a 0.75-minute hold at 100% B; Flow: 1.0 mL/min; Detection: UV at 220 nm. These conditions were also employed for Example 1120 and Example 1121.

Intermediate: 1-Bromo-2-(3-chloropropoxy)benzene

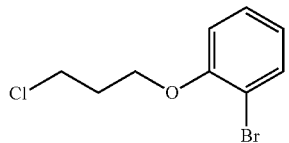 [SMILES: ClCCCOc1ccccc1Br]

A solution of 2-bromophenol (0.303 g, 1.751 mmol) in dry N,N-dimethylformamide (15 mL) was treated with potassium carbonate (0.359 g, 2.60 mmol) followed by 1-bromo-3-chloropropane (0.190 mL, 1.912 mmol). The reaction was stirred at room temperature for 16 hours. The reaction was diluted with EtOAc (50 mL) and washed with water (2×30 mL) and brine, then dried over sodium sulfate, filtered, and concentrated under reduced pressure. The residue was purified by Biotage column chromatography (RediSep 12 g $SiO_2$, 0% (3 CV), 0-60% (30 CV), 25% (2 CV) of ethyl acetate in hexanes). Product fractions were pooled and concentrated under reduced pressure, affording the product (0.420 g, 1.683 mmol, 96% yield) as a clear oil. $^1$H NMR (400 MHz, $CDCl_3$) δ: 7.55 (dd, J=7.8, 1.5 Hz, 1H), 7.27 (ddd, J=8.4, 7.2, 1.5 Hz, 1H), 6.93 (dd, J=8.3, 1.5 Hz, 1H), 6.85 (td, J=7.6, 1.4 Hz, 1H), 4.19 (t, J=5.8 Hz, 2H), 3.84 (t, J=6.3 Hz, 2H), 2.33-2.26 (m, 2H). (The material contained bromopropoxy by-product, and was used without further purification in the following step.)

Intermediate: 5-((4-Chloro-5-((2'-(3-chloropropoxy)-2-methyl-[1,1'-biphenyl]-3-yl)methoxy)-2-formylphenoxy)methyl)nicotinonitrile

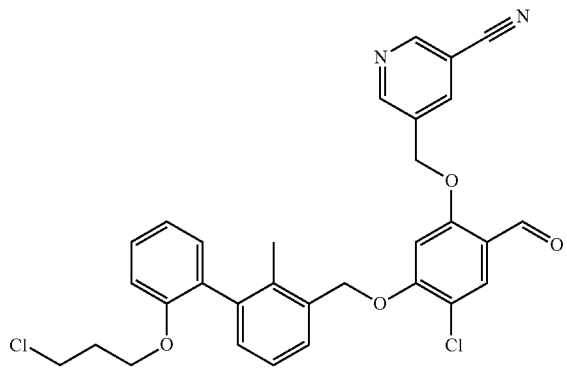 [SMILES: Cc1c(COc2cc(OCc3cncc(C#N)c3)c(C=O)cc2Cl)cccc1-c1ccccc1OCCCCl]

A solution of 1-bromo-2-(3-chloropropoxy)benzene (0.200 g, 0.802 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (0.297 g, 0.573 mmol) in THF (8.18 ml) was treated with potassium phosphate tribasic, 0.5 M aq. solution (2.86 ml, 1.431 mmol) and the mixture was nitrogen sparged for 15 minutes. The mixture was then treated with 2nd generation Xphos precatalyst (0.023 g, 0.029 mmol) and further sparged for 5 minutes, then capped and stirred for 16 hours. The reaction was diluted with ethyl acetate and washed with water then brine. The organic layer was dried over sodium sulfate, filtered, and concentrated under reduced pressure. The residue was purified by Biotage (RediSep 12 g SiO$_2$, 0% (3 CV), 0-100% (15 CV), 100% (2 CV) of ethyl acetate in hexanes). Product fractions were pooled and concentrated under reduced pressure, affording the product (0.270 g, 0.481 mmol, 84% yield). LCMS (ES+) M+Na=583.2. $^1$H NMR (400 MHz, CDCl$_3$) δ:10.29 (s, 1H), 8.93 (d, J=2.0 Hz, 2H), 8.11 (t, J=2.0 Hz, 1H), 7.93 (s, 1H), 7.44 (dd, J=7.4, 1.4 Hz, 1H), 7.37 (ddd, J=8.2, 7.5, 1.9 Hz, 1H), 7.32-7.27 (m, 1H), 7.26-7.22 (m, 1H), 7.18 (dd, J=7.5, 1.8 Hz, 1H), 7.09-7.03 (m, 1H), 7.01 (d, J=8.3 Hz, 1H), 6.69 (s, 1H), 5.33-5.18 (m, 4H), 4.18-3.99 (m, 2H), 3.38 (t, J=6.3 Hz, 2H), 2.17 (s, 3H), 2.02 (quin, J=6.0 Hz, 2H).

Intermediate: (R)-5-((4-Chloro-2-formyl-5-((2'-(3-(3-hydroxypyrrolidin-1-yl)propoxy)-2-methyl-[1,1'-biphenyl]-3-yl)methoxy)phenoxy)methyl)nicotinonitrile

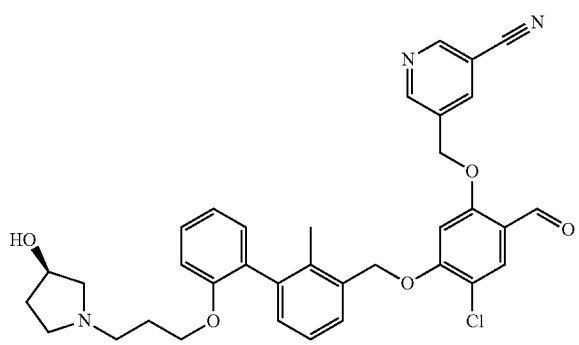 [SMILES: Cc1c(COc2cc(OCc3cncc(C#N)c3)c(C=O)cc2Cl)cccc1-c1ccccc1OCCCN1CC[C@@H](O)C1]

A solution of 5-((4-chloro-5-((2'-(3-chloropropoxy)-2-methyl-[1,1'-biphenyl]-3-yl)methoxy)-2-formylphenoxy)methyl)nicotinonitrile (0.270 g, 0.481 mmol) and (R)-pyrrolidin-3-ol (0.071 g, 0.818 mmol) in dry N,N-dimethylformamide (5.0 mL) was treated with potassium carbonate (0.080 g, 0.577 mmol) and sodium iodide (7.21 mg, 0.048 mmol), and the mixture was heated (70° C. oil bath) for 16 hours. The reaction was cooled, diluted with ethyl acetate (25 mL) and washed successively with water (2×25 mL) and brine. The organic layer was dried over sodium sulfate, filtered, and concentrated under reduced pressure. The residue was triturated with diethyl ether, then dried under vacuum pump. The material was pure enough to proceed to following step. A small sample was purified by Biotage (24 g SiO$_2$, Commodity column, 0-30% (20 CV) methanol in dichloromethane), affording 36 mg of product. Total isolated product (0.180 g, 0.294 mmol, 61.1% yield). LCMS (ES+) M+H=612.0.

Example 1120: (S)-1-(5-Chloro-2-((5-cyanopyridin-3-yl)methoxy)-4-((2'-(3-((R)-3-hydroxypyrrolidin-1-yl)propoxy)-2-methyl-[1,1'-biphenyl]-3-yl)methoxy)benzyl)piperidine-2-carboxylic Acid

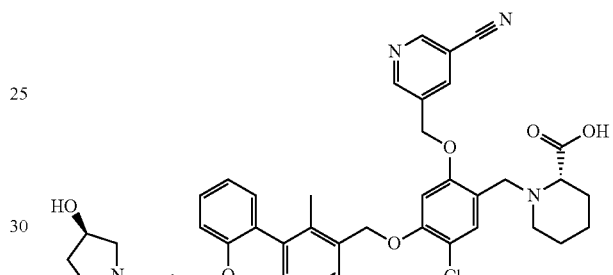

A solution of (R)-5-((4-chloro-2-formyl-5-((2'-(3-(3-hydroxypyrrolidin-1-yl)propoxy)-2-methyl-[1,1'-biphenyl]-3-yl)methoxy)phenoxy)methyl)nicotinonitrile (0.050 g, 0.082 mmol) and (S)-piperidine-2-carboxylic acid (0.026 g, 0.204 mmol) in dry N,N-dimethylformamide (1.5 mL) was treated with acetic acid (0.023 mL, 0.408 mmol), stirred for 1 hour, then treated with sodium cyanoborohydride (0.013 g, 0.204 mmol). The mixture was stirred for 3 days The crude material was purified via preparative LCMS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation, affording the product (0.0036 g, 4.96 μmol, 6.08% yield). The estimated purity was 100% (Condition ACN-AA, ES+) M+H=725.1, 1.57 minutes, calculated exact mass=724.30.

Example 1121: (R)-2-((5-Chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

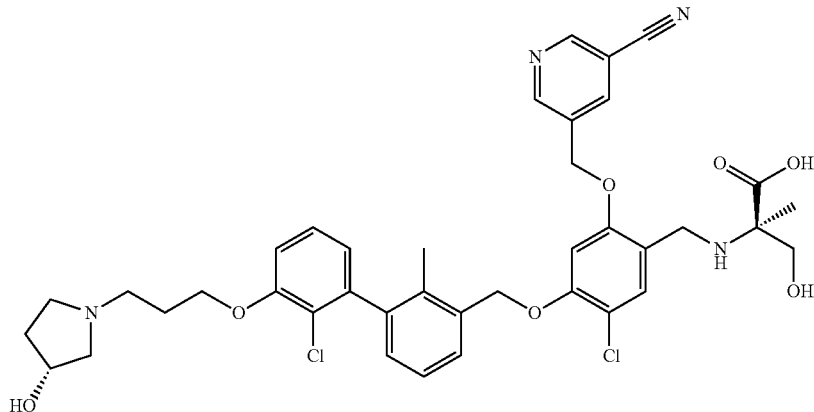 [SMILES: Cc1c(COc2cc(OCc3cncc(C#N)c3)c(CN[C@](C)(CO)C(=O)O)cc2Cl)cccc1-c1cccc(OCCCN2CC[C@@H](O)C2)c1Cl]

A solution of (R)-5-((4-chloro-5-((2'-chloro-3'-(3-(3-hydroxypyrrolidin-1-yl)propoxy)-2-methyl-[1,1'-biphenyl]-3-yl)methoxy)-2-formylphenoxy)methyl)nicotinonitrile (0.102 g, 0.158 mmol) and (R)-2-amino-3-hydroxy-2-methylpropanoic acid (0.056 g, 0.473 mmol) was treated with acetic acid (0.045 mL, 0.789 mmol), stirred for 45 minutes, then treated with sodium cyanoborohydride (0.030 g, 0.473 mmol) and stirred for 16 hours. The reaction was filtered (0.45 µm syringe-tip filter) and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation, affording the product (0.0036 g, 4.71 µm, 3.0% yield). The estimated purity by LCMS analysis was 98%. LCMS (Condition ACN-AA, ES+) M+H=749.1, 1.44 minutes, calculated exact mass=748.24. 
$^1$H NMR (500 MHz, DMSO-$d_6$) δ: 9.03 (s, 1H), 9.01 (d, J=1.8 Hz, 1H), 8.50 (s, 1H), 7.56 (s, 1H), 7.51 (d, J=7.7 Hz, 1H), 7.41-7.35 (m, 1H), 7.29 (t, J=7.5 Hz, 1H), 7.18 (d, J=8.1 Hz, 1H), 7.14 (d, J=4.0 Hz, 1H), 7.10 (d, J=7.7 Hz, 1H), 6.88 (d, J=6.6 Hz, 1H), 5.35 (s, 2H), 5.31 (br. s., 2H), 4.42 (br. s., 1H), 4.24-4.12 (m, 2H), 4.03 (s, 2H), 3.79-3.50 (m, 1H), 2.56-2.52 (m, 6H), 2.17 (d, J=6.6 Hz, 3H), 2.06 (s, 3H), 1.89 (d, J=11.4 Hz, 1H), 1.27 (s, 3H).

Examples 1501 to 1528 were prepared as described below.

LC-MS Conditions:
Method P-1:
Start % B=0, Final % B=100
Gradient Time=2 min, Flow Rate=1 ml/min, Wavelength=254 nm
Solvent Pair=Acetonitrile: Water: Ammonium Actetate
Solvent A=5% Acetonitrile: 95% Water: 10 mM Ammonium Actetate
Solvent B=95% Acetonitrile: 5% Water: 10 mM Ammonium Actetate
Column: Phenomenex LUNA C18, 30×2, 3u, Oven Temp.=40

Preparation of Intermediates:

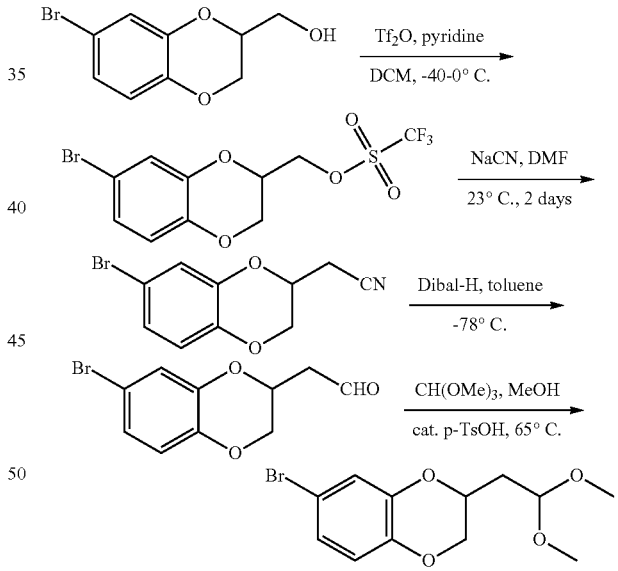

Neat trifluoromethanesulfonic anhydride (2.68 mL, 15.91 mmol) was added to a cold (−40° C.) stirred solution of (7-bromo-2,3-dihydrobenzo[b][1,4]dioxin-2-yl)methanol (3.0 g, 12.24 mmol, prepared as described in the reference: Henning, R., Lattrell, R., Gerhards, H. J., Leven, M. *J. Med. Chem.* 1987, 30, 814-819.) and pyridine (1.287 mL, 15.91 mmol) in DCM (50 mL) and the mixture was allowed to warm to rt (~2 h). Reaction mixture was diluted with DCM (25 mL), washed with cold 1N HCl, water, brine and dried (MgSO$_4$). Evaporation of solvents afforded (7-bromo-2,3-dihydrobenzo[b][1,4]dioxin-2-yl)methyl trifluoromethanesulfonate as a light yellow viscous oil (4.7 g). Crude triflate was dissolved in DMF (10 mL) and added sodium cyanide (0.150 g, 3.06 mmol) and the mixture was stirred at rt for 2 days. Crude product was isolated by aqueous workup and purified by silica gel FCC (0-10% EtOAc in DCM) to afford 2-(7-bromo-2,3-dihydrobenzo[b][1,4]dioxin-2-yl)acetonitrile as a clear oil (2.15 g). $^1$H NMR (400 MHz, CHLOROFORM-d) δ 7.08 (d, J=2.3 Hz, 1H), 6.99 (dd, J=8.5, 2.3 Hz, 1H), 6.79 (d, J=8.8 Hz, 1H), 4.45-4.38 (m, 1H), 4.34 (dd, J=11.5, 2.5 Hz, 1H), 4.18 (dd, J=11.5, 6.0 Hz, 1H), 3.75 (dd, J=11.5, 5.0 Hz, 1H), 3.68 (dd, J=11.5, 7.3 Hz, 1H).

A solution of DIBAL-H in THF (4.72 mL, 4.72 mmol) was added to a stirred cold (−78° C.) solution of 2-(7-bromo-2,3-dihydrobenzo[b][1,4]dioxin-2-yl)acetonitrile (1.0 g, 3.94 mmol) in toluene (12 mL) under nitrogen and the mixture was stirred at −78° C. for 1 h. Then the reaction mixture was quenched with saturated sodium potassium tartarate solution (6 mL) and allowed to warm to rt and then extracted with ethyl acetate and washed with water, brine and dried (Na$_2$SO$_4$), filtered, concentrated and purified by silica gel chromatography to afford 2-(7-bromo-2,3-dihydrobenzo[b][1,4]dioxin-2-yl)acetaldehyde (0.4 g, ~40%).

A stirred solution of trimethyl orthoformate (2 ml, 18.09 mmol), 2-(7-bromo-2,3-dihydrobenzo[b][1,4]dioxin-2-yl)acetaldehyde (1 g, 3.89 mmol) and 4-methylbenzenesulfonic acid (0.033 g, 0.194 mmol) in MeOH (10 ml) was heated at 65° C. for 5 h. Reaction mixture was evaporated to dryness and taken up in EtOAc and washed with satd. NaHCO$_3$, water, brine, dried (MgSO$_4$) and concentrated to afford 7-bromo-2-(2,2-dimethoxyethyl)-2,3-dihydrobenzo[b][1,4]dioxine (1.1 g, 3.63 mmol, 93% yield) as a viscous oil. $^1$H NMR (400 MHz, CHLOROFORM-d) δ 7.09-7.01 (m, 1H), 7.02-6.91 (m, 2H), 6.81-6.71 (m, 2H), 4.68 (dd, J=7.2, 4.0 Hz, 1H), 4.37-4.21 (m, 3H), 3.91 (dd, J=11.4, 7.5 Hz, 2H), 3.40 (d, J=16.6 Hz, 6H), 2.05-1.83 (m, 3H).

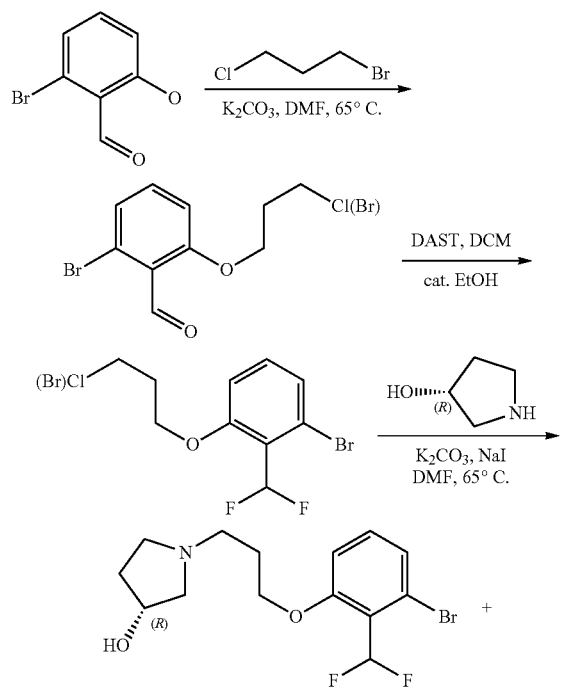

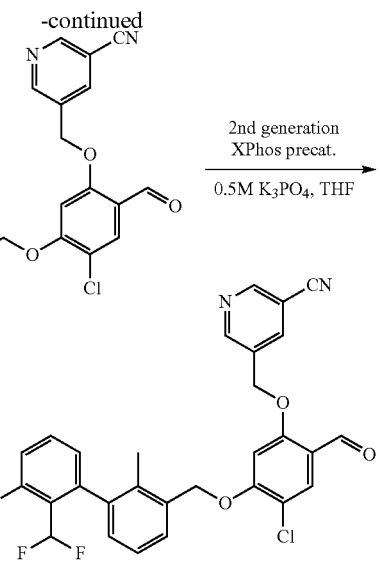

Potassium carbonate (0.722 g, 5.22 mmol) was added to a stirred solution of 2-bromo-6-hydroxybenzaldehyde (0.875 g, 4.35 mmol) and 1-bromo-3-chloropropane (0.857 mL, 8.71 mmol) in DMF (10 mL) and heated at 65° C. overnight. The reaction mixture was cooled to rt and diluted with ether and washed with water, brine, dried (Na$_2$SO$_4$), concentrated and purified by silica gel chromatography (0-10% EtOAc/hexane) to yield a mixture of 2-bromo-6-(3-chloropropoxy)benzaldehyde and 2-bromo-6-(3-bromopropoxy)benzaldehyde in ~7:3 ratio as a clear viscous oil (~1.1 g).

Neat DAST (0.491 mL, 3.72 mmol) was added to a cold (−20° C.) stirred solution of 2-bromo-6-(3-chloropropoxy)benzaldehyde (0.43 g, 1.549 mmol) and EtOH (0.063 µl, 1.085 µmol) in an. DCM (5 mL) and the mixture was allowed to warm to rt and stirred overnight. Reaction mixture was diluted with water and quenched with ice and neutralized with satd. NaHCO$_3$. Organic layer washed with water, brine, dried (MgSO$_4$), concentrated and purified by silica gel flash column chromatography (=FCC) (0-10% EtOAc-hexanes) to afford a mixture of 1-bromo-3-(3-chloropropoxy)-2-(difluoromethyl)benzene and 1-bromo-3-(3-bromopropoxy)-2-(difluoromethyl)benzene in ~7:3 ratio as a clear oil (0.394 g, 1.315 mmol, 85% yield) which was dissolved in DMF (3 mL) and added (R)-pyrrolidin-3-ol (0.174 g, 2.0 mmol), potassium carbonate (0.3 g, 2.2 mmol) and sodium iodide (30 mg, 0.2 mmol) and heated at 65° C. for 12 h. The reaction mixture was diluted with EtOAc and washed with water, brine, dried (Na$_2$SO$_4$), concentrated and purified by silica gel FCC (0-20% MeOH-DCM) to yield (R)-1-(3-(3-bromo-2-(difluoromethyl)phenoxy) propyl)pyrrolidin-3-ol (0.42 g, 91%) as a clear oil.

A mixture of (R)-1-(3-(3-bromo-2-(difluoromethyl)phenoxy)propyl)pyrrolidin-3-ol (0.074 g, 0.210 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (0.11 g, 0.212 mmol) in THF (2 mL) and 0.5 M aq potassium phosphate, tribasic (1.272 mL, 0.636 mmol) was stirred under N$_2$ sparging for 15 min, then added 2nd gen. XPhos precatalyst (5.0 mg, 6.36 µmol), sparging was continued for another 10 min. The reaction mixture was stirred at rt under N$_2$ for 16 h and diluted with EtOAc, washed with, water, brine, dried (Na$_2$SO$_4$), concentrated and purified by silica gel FCC (0-25% EtOAc-DCM) to yield 5-((4-chloro-5-((3'-(3-chloropropoxy)-2'-(difluoromethyl)-

2-methyl-[1,1'-biphenyl]-3-yl)methoxy)-2-formylphenoxy)methyl)nicotinonitrile (0.1 g, 0.164 mmol, 77% yield).

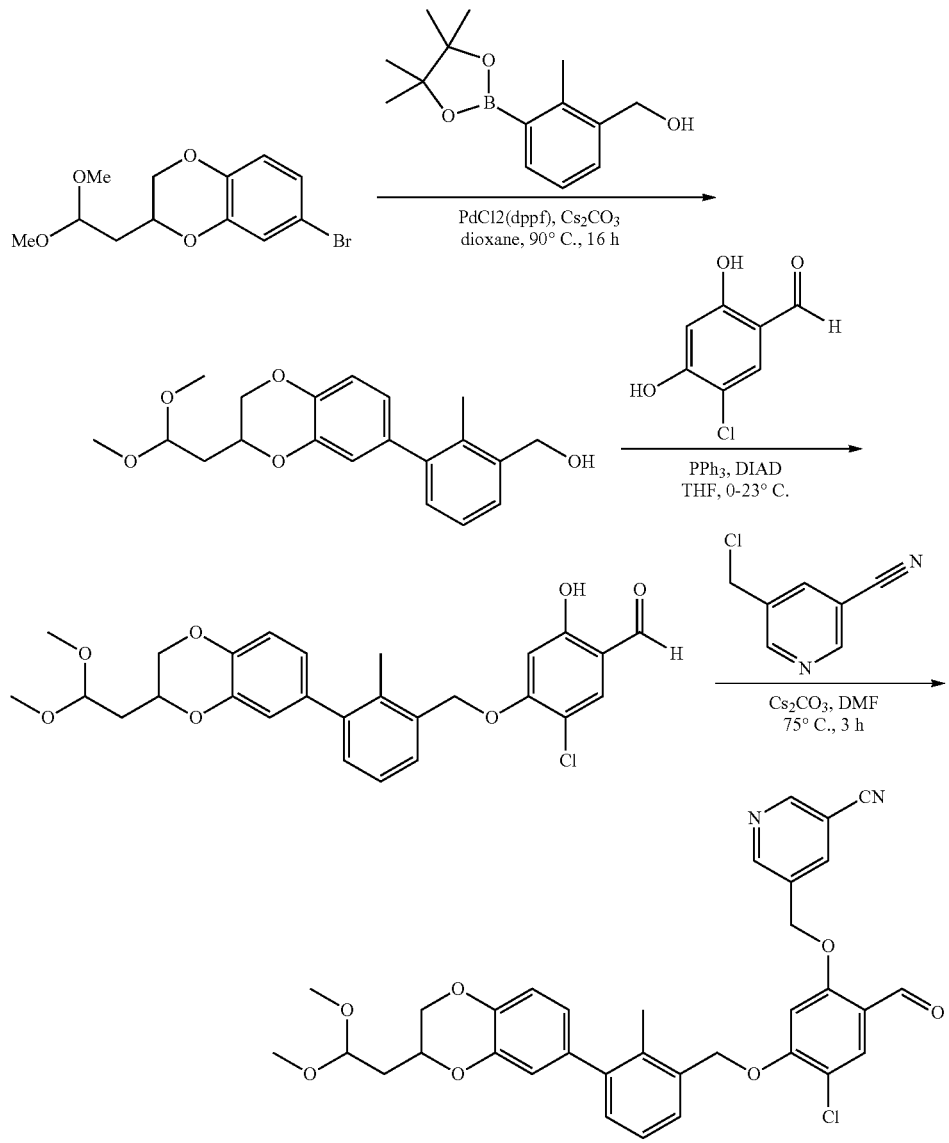

Neat PdCl$_2$(dppf) (0.367 g, 0.501 mmol) was added to a stirred solution of (2-methyl-3-(4,4,5,5-tetramethyl-1,3,2-dioxaborolan-2-yl)phenyl)methanol (2.488 g, 10.03 mmol), 7-bromo-2-(2,2-dimethoxyethyl)-2,3-dihydrobenzo[b][1,4]dioxine (3.2 g, 10.03 mmol) and Cs$_2$CO$_3$ (8.17 g, 25.07 mmol) in dioxane (25 mL) and water (15 mL) sparged with nitrogen for 10-15 min and the mixture was heated at 90° C. for 16 h. The reaction mixture was cooled to rt and diluted with EtOAc, washed with water, brine, dried (MgSO$_4$) and concentrated. The crude isolate was purified by silica gel FCC (10-50% EtOAc/hexanes) to yield (3-(3-(2,2-dimethoxyethyl)-2,3-dihydrobenzo[b][1,4]dioxin-6-yl)-2-methylphenyl)methanol (3.23 g, 9.38 mmol, 94% yield) as a viscous oil. LC-MS (Method P-1): retention time 0.98 min; m/z 327 (M−OH)$^+$. $^1$H NMR (500 MHz, CHLOROFORM-d) δ 7.38 (d, J=7.3 Hz, 1H), 7.24 (t, J=7.6 Hz, 1H), 7.19 (dd, J=7.6, 1.3 Hz, 1H), 6.92 (d, J=8.2 Hz, 1H), 6.83 (d, J=2.0 Hz, 1H), 6.77 (dd, J=8.2, 2.0 Hz, 1H), 4.78 (d, J=4.9 Hz, 2H), 4.72 (dd, J=7.3, 4.0 Hz, 1H), 4.38-4.34 (m, 1H), 4.34-4.30 (m, 1H), 3.98 (dd, J=11.2, 7.6 Hz, 1H), 3.43 (s, 3H), 3.39 (s, 3H), 2.28 (s, 3H), 2.06-2.01 (m, 1H), 1.94 (ddd, J=14.3, 7.3, 4.8 Hz, 1H), 1.70 (t, J=5.4 Hz, 1H).

Neat DIAD (0.373 mL, 1.916 mmol) was added dropwise to a stirred cold (0° C.) solution of (3-(3-(2,2-dimethoxyethyl)-2,3-dihydrobenzo[b][1,4]dioxin-6-yl)-2-methylphenyl)methanol (0.66 g, 1.916 mmol), 5-chloro-2,4-dihydroxybenzaldehyde (0.331 g, 1.916 mmol) and triphenylphosphine (0.503 g, 1.916 mmol) in THF (9 mL). The resulting yellow solution was allowed to warm to r.t. with stirring overnight. Excess solvent was evaporated by rotary evaporator and the residue was purified by silica gel FCC (0-45% ethyl acetate in hexanes) to afford 5-chloro-4-((3-(3-(2,2-dimethoxyethyl)-2,3-dihydrobenzo[b][1,4]dioxin-6-yl)-2-methylbenzyl)oxy)-2-hydroxybenzaldehyde (0.68 g, 71%) as a white solid. $^1$H NMR (400 MHz, CHLOROFORM-d) δ 11.47 (s, 1H), 9.72 (s, 1H), 7.43 (dd, J=6.1, 2.9 Hz, 1H), 7.30 (s, 1H), 7.28-7.26 (m, 2H), 6.94 (d, J=8.3 Hz, 1H), 6.86 (d, J=2.0 Hz, 1H), 6.80 (dd, J=8.2, 2.1

Hz, 1H), 6.56 (s, 1H), 5.15 (s, 2H), 4.73 (dd, J=7.2, 4.0 Hz, 1H), 4.41-4.30 (m, 2H), 3.99 (dd, J=11.4, 7.5 Hz, 1H), 3.43 (s, 3H), 3.39 (s, 3H), 2.28 (s, 3H), 2.24 (s, 3H), 2.06-1.91 (m, 2H).

Neat cesium carbonate (0.435 g, 1.335 mmol) and sodium iodide (0.017 g, 0.111 mmol) were added to a stirred solution of 5-chloro-4-((3-(3-(2,2-dimethoxyethyl)-2,3-dihydrobenzo[b][1,4]dioxin-6-yl)-2-methylbenzyl)oxy)-2-hydroxybenzaldehyde (0.555 g, 1.112 mmol) and 5-(chloromethyl)nicotinonitrile (0.221 g, 1.446 mmol) in DMF (6 mL) and heated at 75° C. for 3 h. Reaction mixture was cooled and diluted with EtOAc, washed with water, brine, dried (MgSO$_4$) and concentrated. Crude isolate was purified by silica gel FCC (10-20% EtOAc in DCM) to afford 5-((4-chloro-5-((3-(3-(2,2-dimethoxyethyl)-2,3-dihydrobenzo[b][1,4]dioxin-6-yl)-2-methylbenzyl)oxy)-2-formylphenoxy)methyl)nicotinonitrile (0.715 g, 1.116 mmol, 100% yield) as a off-white solid. LC-MS (Method P-1): Rt 1.20 min., (M−OMe)$^+$583.2. $^1$H NMR (500 MHz, CHLOROFORM-d) δ 10.28 (s, 1H), 8.91 (d, J=2.0 Hz, 2H), 8.10 (t, J=2.1 Hz, 1H), 7.91 (s, 1H), 7.41 (dd, J=6.1, 3.1 Hz, 1H), 7.30-7.23 (m, 2H), 6.93 (d, J=8.2 Hz, 1H), 6.84 (d, J=2.0 Hz, 1H), 6.78 (dd, J=8.2, 2.1 Hz, 1H), 6.67 (s, 1H), 5.25 (s, 2H), 5.24 (s, 2H), 4.71 (dd, J=7.2, 4.0 Hz, 1H), 4.39-4.30 (m, 2H), 3.98 (dd, J=11.3, 7.6 Hz, 1H), 3.42 (s, 3H), 3.38 (s, 3H), 2.30 (s, 3H), 2.03 (td, J=7.1, 4.0 Hz, 1H), 1.95 (ddd, J=14.3, 7.2, 5.0 Hz, 1H).

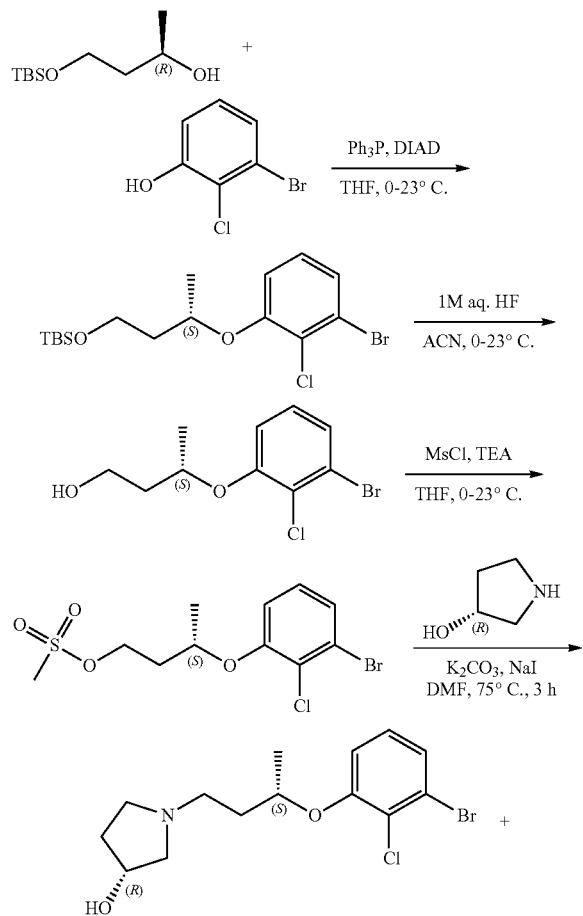

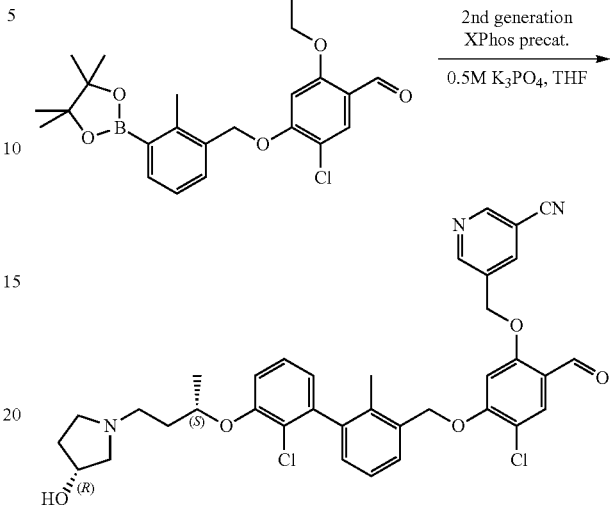

Neat DIAD (0.583 mL, 3.00 mmol) was added dropwise to a stirred cold (0° C.) solution of (R)-4-((tert-butyldimethylsilyl)oxy)butan-2-ol (0.613 g, 3.0 mmol), 3-bromo-2-chlorophenol (0.622 g, 3.00 mmol) and triphenylphosphine (0.787 g, 3.00 mmol) in THF (6 mL). The resulting yellow solution was allowed to warm to r.t. with stirring overnight. Excess solvent was evaporated by rotary evaporator and chromatographed on a 40 g silica gel column and eluted with 0-25% ethyl acetate in hexanes to afford (S)-(3-(3-bromo-2-chlorophenoxy)butoxy)(tert-butyl)dimethylsilane as a clear oil (0.82 g, 69%).

1M aq. HF was added dropwise to a solution of (S)-(3-(3-bromo-2-chlorophenoxy)butoxy)(tert-butyl)dimethylsilane (1.14 g, 2.89 mmol) in acetonitrile (15 mL) and the mixture was stirred at rt for 3 h. Acetonitrile was evaporated and the aq residue was extracted with EtOAc, washed with satd. NaHCO$_3$, water, brine, dried (MgSO$_4$) and concentrated to afford (S)-3-(3-bromo-2-chlorophenoxy)butan-1-ol (0.754 g, 2.70 mmol, 93% yield) as a clear oil. $^1$H NMR (400 MHz, CHLOROFORM-d) δ 7.25 (dd, J=8.0, 1.5 Hz, 1H), 7.09 (t, J=8.2 Hz, 1H), 6.96 (dd, J=8.3, 1.0 Hz, 1H), 4.74-4.63 (m, 1H), 3.96-3.88 (m, 1H), 3.87-3.79 (m, 1H), 2.14-1.92 (m, 3H), 1.39 (d, J=6.0 Hz, 3H).

Neat methanesulfonyl chloride (0.107 mL, 1.374 mmol) was added to a cold (−20° C.) stirred solution of (S)-3-(3-bromo-2-chlorophenoxy)butan-1-ol (0.32 g, 1.145 mmol) and TEA (0.191 mL, 1.374 mmol) in THF (5 mL) and the mixture was allowed to warm to rt overnight. The reaction mixture was diluted with ether, washed consecutively with water, cold 1N HCl, water, brine and dried (MgSO$_4$). Evaporation of solvents afforded (S)-3-(3-bromo-2-chlorophenoxy)butyl trifluoromethanesulfonate as a clear oil (0.42 g, 100%). $^1$H NMR (400 MHz, CHLOROFORM-d) δ 7.29-7.26 (m, 1H), 7.11 (t, J=8.3 Hz, 1H), 6.94 (dd, J=8.4, 0.9 Hz, 1H), 4.67-4.57 (m, 1H), 4.52-4.40 (m, 2H), 2.96 (s, 3H), 2.27-2.11 (m, 2H), 1.40 (d, J=6.3 Hz, 3H).

To a stirred solution of crude mesylate (0.42 g) in DMF (3 mL) was added (R)-pyrrolidin-3-ol (0.120 g, 1.374 mmol), potassium carbonate (0.190 g, 1.374 mmol) and sodium iodide (0.172 g, 1.145 mmol) and then heated at 65° C. for 3 h. Reaction mixture was cooled, diluted with EtOAc, washed with water, brine, dried (MgSO$_4$) and concentrated to afford (R)-1-((S)-3-(3-bromo-2-chlorophenoxy) butyl)pyrrolidin-3-ol (0.36 g, 1.033 mmol, 90% yield) as a clear viscous oil. $^1$H NMR (400 MHz, CHLOROFORM-d) δ 7.22 (dd, J=8.0, 1.3 Hz, 1H), 7.07 (t, J=8.2 Hz, 1H), 6.93 (dd, J=8.3, 1.3 Hz, 1H), 4.58-4.45 (m, 1H), 4.39-4.30 (m, 1H), 2.89-2.85 (m, 1H), 2.72 (d, J=9.0 Hz, 1H), 2.63 (t, J=7.4 Hz, 2H), 2.53 (dd, J=10.0, 5.0 Hz, 1H), 2.41 (br. s., 1H), 2.31 (td, J=8.8, 6.4 Hz, 1H), 2.25-2.13 (m, 1H), 2.08-1.96 (m, 1H), 1.91-1.80 (m, 1H), 1.79-1.69 (m, 1H), 1.37 (d, J=6.0 Hz, 3H).

A mixture of (R)-1-((S)-3-(3-bromo-2-chlorophenoxy)butyl)pyrrolidin-3-ol (0.104 g, 0.298 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (0.103 g, 0.199 mmol) in THF (3 mL) and 0.5 M aq potassium phosphate, tribasic (1.191 mL, 0.596 mmol) was stirred under $N_2$ sparging for 15 min and then added 2nd gen. XPhos precatalyst (4.7 mg, 5.96 μmol) and sparging was continued for another 10 min. The reaction mixture was stirred at rt under $N_2$ for 16 h and diluted with EtOAc, washed with water, brine, dried ($Na_2SO_4$) and concentrated. Crude isolate was purified by silica gel FCC (0-20% MeOH-DCM) to yield 5-((4-chloro-5-((2'-chloro-3'-(((S)-4-((R)-3-hydroxypyrrolidin-1-yl)butan-2-yl)oxy)-2-methyl-[1,1'-biphenyl]-3-yl)methoxy)-2-formylphenoxy)methyl)nicotinonitrile (0.104 g, 0.157 mmol, 79% yield). LC-MS (Method P-1): Rt 0.89 min, m/z 660.1.

HPLC Purification Conditions:
Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation.

LC-MS Conditions 1:
Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

LC-MS Conditions 2:
Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Example 1501 & Example 1502

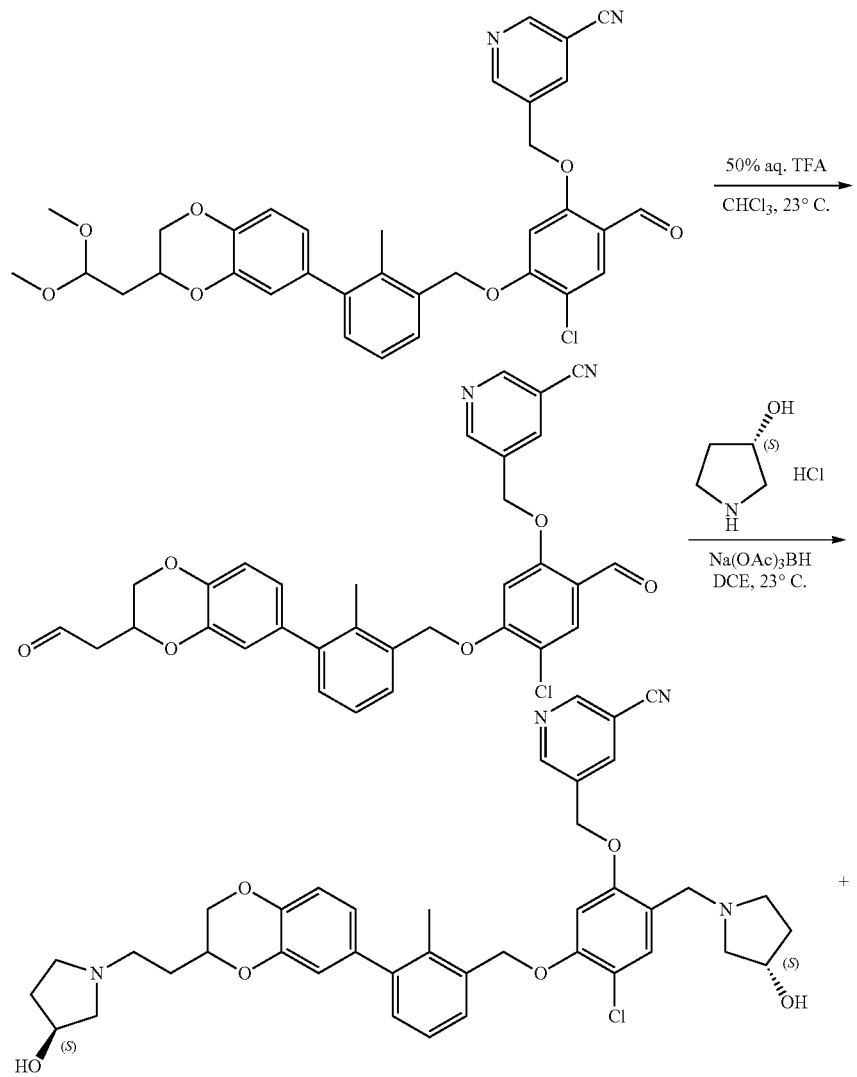

Example#1501

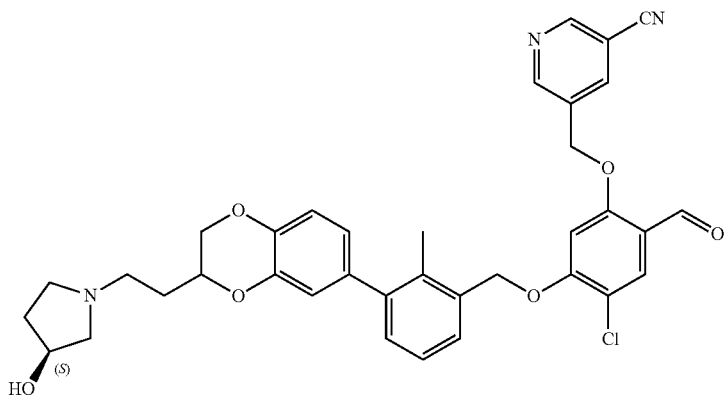

Example #1502

Neat TFA was added dropwise to a biphasic solution of 5-((4-chloro-5-((3-(3-(2,2-dimethoxyethyl)-2,3-dihydrobenzo[b][1,4]dioxin-6-yl)-2-methylbenzyl)oxy)-2-formylphenoxy)methyl)nicotinonitrile (25 mg, 0.041 mmol) in chloroform and water and the mixture was stirred at rt for 90 min. Organic layer was separated and the aq. layer re-extracted with DCM, combined extracts was washed with satd. NaHCO$_3$, water, brine, dried (MgSO$_4$) and concentrated to afford desired aldehyde product 5-((4-chloro-2-formyl-5-((2-methyl-3-(3-(2-oxoethyl)-2,3-dihydrobenzo[b][1,4]dioxin-6-yl)benzyl)oxy)phenoxy)methyl)nicotinonitrile as a viscous oil: $^1$H NMR (500 MHz, CHLOROFORM-d) δ 10.30 (s, 1H), 9.95-9.88 (m, 1H), 8.92 (dd, J=6.3, 1.8 Hz, 2H), 8.15-8.04 (m, 1H), 7.95 (s, 1H), 7.45-7.38 (m, 1H), 7.28-7.27 (m, 2H), 7.00-6.90 (m, 1H), 6.87-6.77 (m, 2H), 6.68-6.60 (m, 1H), 5.26 (s, 2H), 5.24 (s, 2H), 4.84-4.76 (m, 1H), 4.38 (dd, J=11.3, 2.3 Hz, 1H), 4.06 (dd, J=11.4, 7.0 Hz, 1H), 2.97 (ddd, J=17.5, 7.1, 1.8 Hz, 1H), 2.80 (ddd, J=17.5, 5.8, 1.0 Hz, 1H), 2.31 (s, 3H).

Above di-aldehyde intermediate was dissolved in DMF (1 mL) and added (S)-3-hydroxypyrrolidine hydrochloride (20 mg, 0.163 mmol) and sodium acetate (14 mg, 0.163 mmol) followed by sodium triacetoxyborohydride (35 mg, 0.163 mmol) and a drop of AcOH and the mixture stirred at rt overnight. The reaction mixture was diluted with EtOAc (10 mL) and quenched with sat'ed. NaHCO$_3$ (2 mL), organic layer separated, washed with water (2 mL), dried (Na$_2$SO$_4$), concentrated and purified by prep. HPLC to yield 5-((4-chloro-5-((3-(3-(2-((S)-3-hydroxypyrrolidin-1-yl)ethyl)-2,3-dihydrobenzo[b][1,4]dioxin-6-yl)-2-methylbenzyl)oxy)-2-(((S)-3-hydroxypyrrolidin-1-yl)methyl)phenoxy)methyl)nicotinonitrile (Example 1501): LCMS (Condition 2): Rt 2.71 min, m/z 709.6 [M+H]- and 5-((4-chloro-2-formyl-5-((3-(3-(2-((S)-3-hydroxypyrrolidin-1-yl)ethyl)-2,3-dihydrobenzo[b][1,4]dioxin-6-yl)-2-methylbenzyl)oxy)phenoxy)methyl)nicotinonitrile (Example 1502): LCMS (Condition 1): Rt 1.822 min, m/z 640.0 [M+H]$^-$ as mixtures of diastereomers.

Example 1503

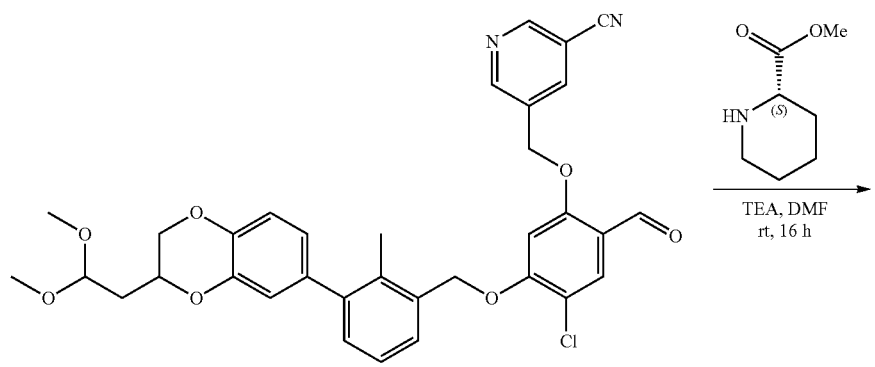

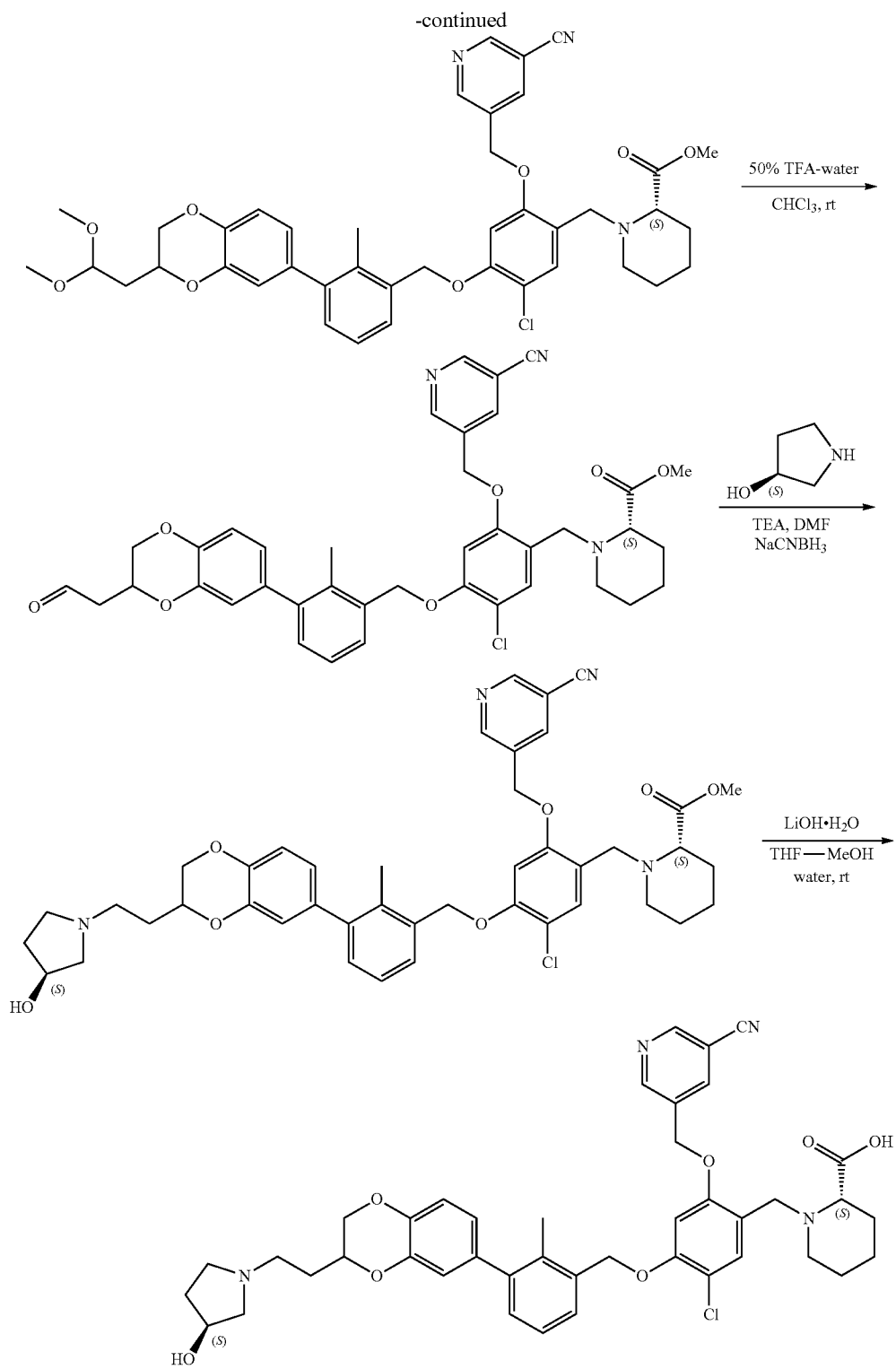

Example#1503

(S)-methyl piperidine-2-carboxylate, HCl (66.6 mg, 0.371 mmol) and TEA (0.052 mL, 0.371 mmol) were added consecutively to a solution of 5-((4-chloro-5-((3-(3-(2,2-dimethoxyethyl)-2,3-dihydrobenzo[b][1,4]dioxin-6-yl)-2-methylbenzyl)oxy)-2-formylphenoxy)methyl)nicotinonitrile (76 mg, 0.124 mmol) in DMF (2 mL) and the mixture stirred at rt overnight. AcOH (0.021 mL, 0.371 mmol) was added and the mixture was stirred at rt for 4 h and then sodium cyanoborohydride (24 mg, 0.371 mmol) was added and the mixture was stirred at rt for 3 days. Reaction was quenched with MeOH (1 mL), diluted with EtOAc, washed with satd. NaHCO$_3$, water, brine, dried (MgSO$_4$), concentrated and purified by silica gel FCC (10-20% EtOAc in DCM) to afford (2S)-methyl 1-(5-chloro-2-((5-cyanopyridin-3-yl)methoxy)-4-((3-(3-(2,2-dimethoxyethyl)-2,3-dihydrobenzo[b][1,4]dioxin-6-yl)-2-methylbenzyl)oxy)benzyl)piperidine-2-carboxylate (56 mg, 58.0% yield) as a viscous oil.

50% TFA in water (4 ml) was added to a solution of (2S)-methyl 1-(5-chloro-2-((5-cyanopyridin-3-yl)methoxy)-4-((3-(3-(2,2-dimethoxyethyl)-2,3-dihydrobenzo[b][1,4]dioxin-6-yl)-2-methylbenzyl)oxy)benzyl)piperidine-2-carboxylate (56 mg, 0.074 mmol) in CHCl₃ (4 ml) and the mixture was stirred at rt overnight. The organic layer was separated and the aq. layer re-extracted with DCM (2×) and the combined extracts were washed with sat'ed. NaHCO₃, brine, dried (MgSO₄) and concentrated to afford desired aldehyde product as a clear film (46 mg). To a solution of the aldehyde in DMF (1 mL) was added (S)-pyrrolidin-3-ol, HCl (27.5 mg, 0.222 mmol) and TEA (0.031 mL, 0.222 mmol). The mixture was stirred for 3 h and added AcOH (0.013 mL, 0.222 mmol). After 2 h sodium cyanoborohydride (14 mg, 0.222 mmol) was added and the mixture stirred at rt overnight. Reaction mixture was quenched with 5% TFA in MeOH and evaporated to dryness to afford (2S)-methyl 1-(5-chloro-2-((5-cyanopyridin-3-yl)methoxy)-4-((3-(3-(2-((S)-3-hydroxypyrrolidin-1-yl)ethyl)-2,3-dihydrobenzo[b][1,4]dioxin-6-yl)-2-methylbenzyl)oxy)benzyl)piperidine-2-carboxylate which was saponified (LiOH.H₂O, THF-MeOH—H₂O) to yield (2S)-1-(5-chloro-2-((5-cyanopyridin-3-yl)methoxy)-4-((3-(3-(2-((S)-3-hydroxypyrrolidin-1-yl)ethyl)-2,3-dihydrobenzo[b][1,4]dioxin-6-yl)-2-methylbenzyl)oxy)benzyl)piperidine-2-carboxylic acid as a mixture of diastereomers. LC-MS (Condition 2): Rt 2.44 min 753.2 (MH⁺).

Example 1504

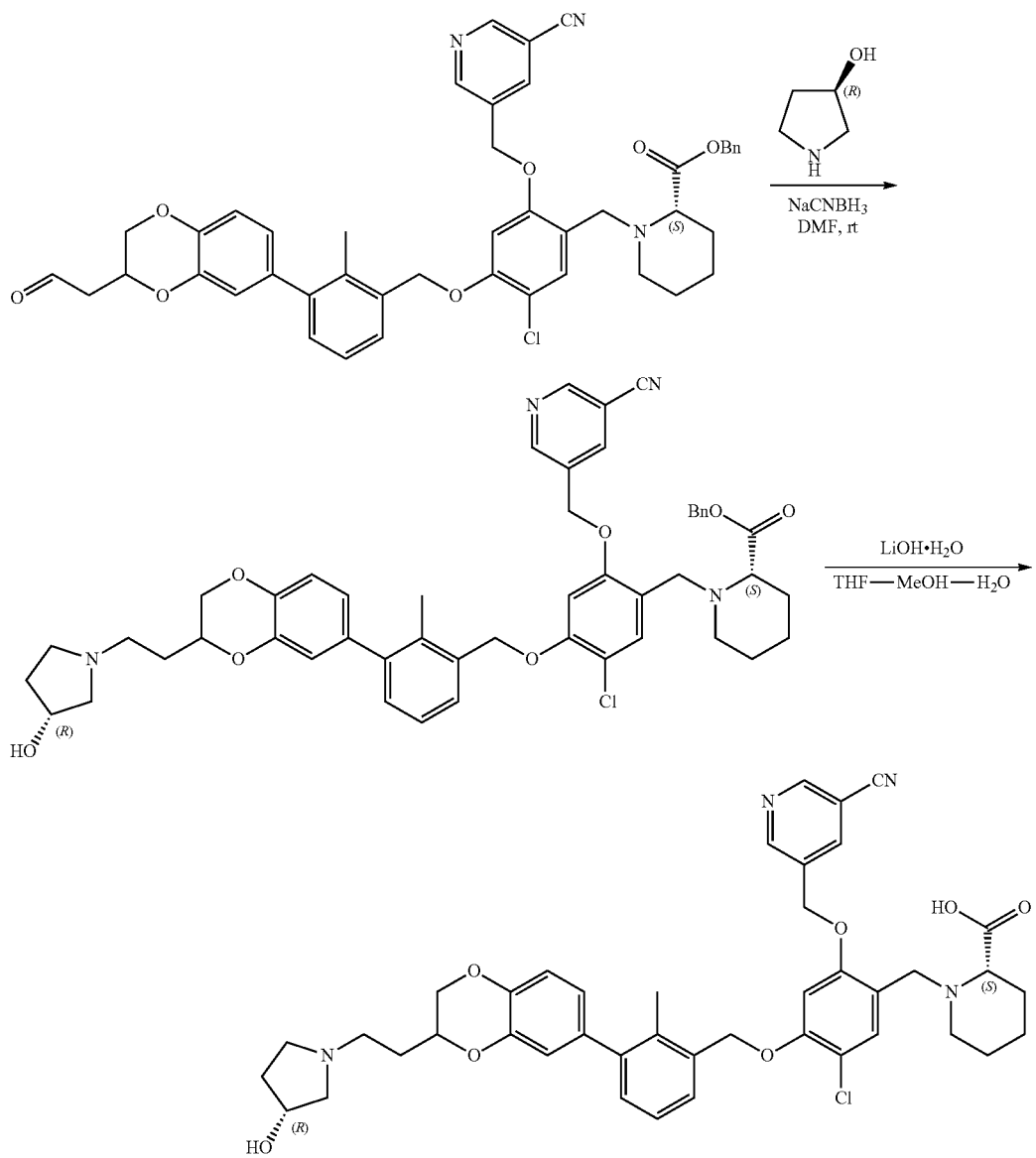

Example#1504

AcOH (10 μl, 0.162 mmol) was added to a stirred mixture of (2S)-benzyl 1-(5-chloro-2-((5-cyanopyridin-3-yl)methoxy)-4-((2-methyl-3-(3-(2-oxoethyl)-2,3-dihydrobenzo[b][1,4]dioxin-6-yl)benzyl)oxy)benzyl)piperidine-2-carboxylate (25 mg, 0.032 mmol) and (R)-pyrrolidin-3-ol (9 mg, 0.097 mmol) in DMF (1 mL). The mixture was stirred at rt for 4 h and then sodium cyanoborohydride (6.10 mg, 0.097 mmol) was added and the mixture was stirred at rt overnight. Reaction mixture was quenched with 5% TFA in MeOH and evaporated to dryness to afford (2S)-benzyl 1-(5-chloro-2-((5-cyanopyridin-3-yl)methoxy)-4-((3-(3-(2-((R)-3-hydroxypyrrolidin-1-yl)ethyl)-2,3-dihydrobenzo[b][1,4]dioxin-6-yl)-2-methylbenzyl)oxy)benzyl)piperidine-2-carboxylate which was saponified (LiOH.H₂O, THF-MeOH—H₂O) to yield (2S)-1-(5-chloro-2-((5-cyanopyridin-3-yl)methoxy)-4-((3-(3-(2-((R)-3-hydroxypyrrolidin-1-yl)ethyl)-2,3-dihydrobenzo[b][1,4]dioxin-6-yl)-2-methylbenzyl)oxy)benzyl)piperidine-2-carboxylic acid as a mixture of diastereomers. LC-MS (Condition 2): Rt 2.46 min 753.3 (MH⁺).

Example 1505 & Example 1506

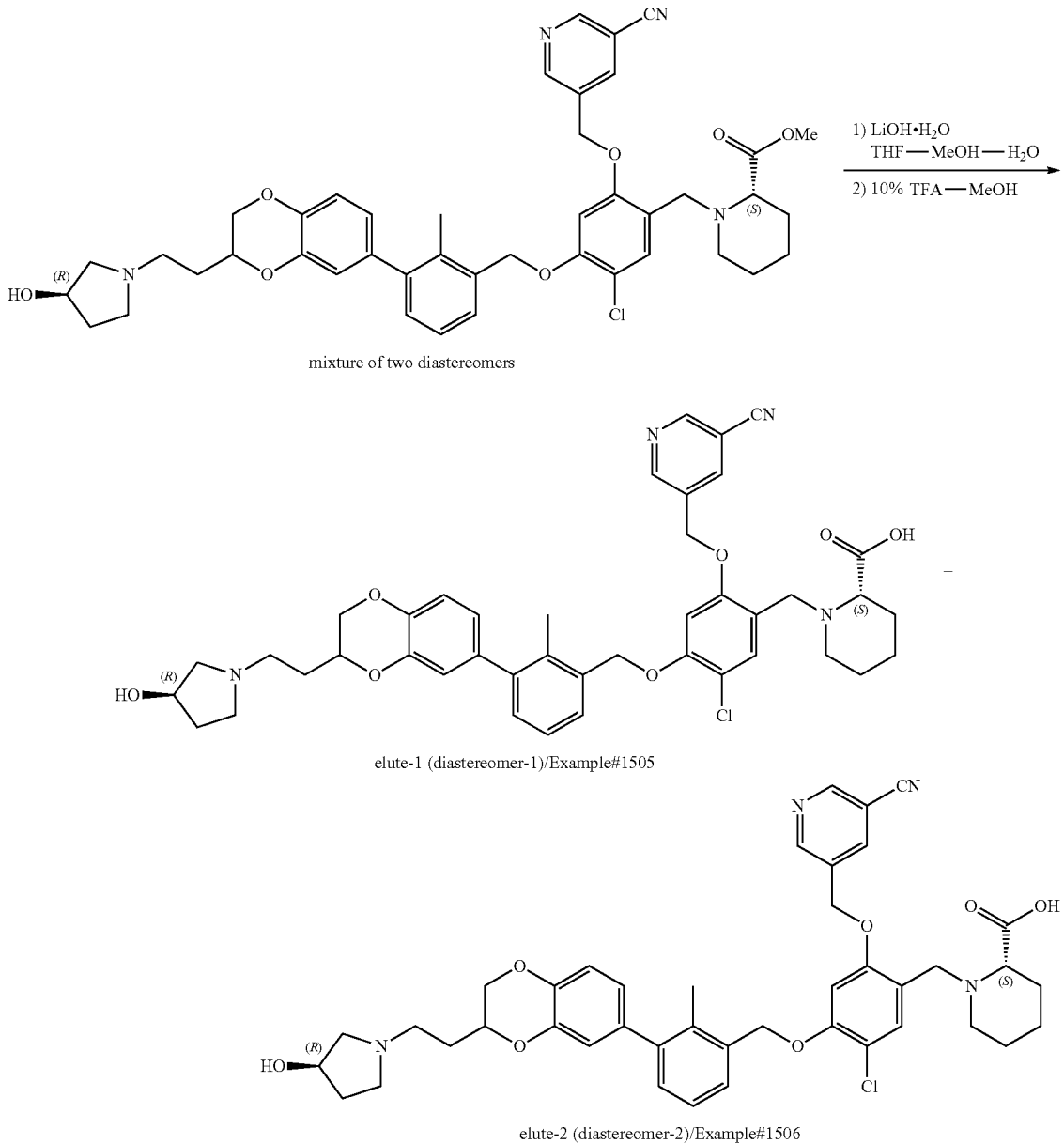

A mixture of (2S)-methyl 1-(5-chloro-2-((5-cyanopyridin-3-yl)methoxy)-4-((3-(3-(2-((R)-3-hydroxypyrrolidin-1-yl)ethyl)-2,3-dihydrobenzo[b][1,4]dioxin-6-yl)-2-methylbenzyl)oxy)benzyl)piperidine-2-carboxylate (69 mg, 0.090 mmol) and lithium hydroxide monohydrate (38 mg, 0.899 mmol) in THF (1 mL), MeOH (1 mL) and water (1 mL) was stirred at rt for 2 days. Reaction mixture was neutralized with TFA and evaporated to dryness. Crude diastereomer mixture was purified and resolved by chiral prep. HPLC to yield diastereomer-1/elute-1: LCMS (Condition 1): Rt 1.310 min, m/z 753.29 [M+H]⁺. and diastereomer-2/elute-2: LCMS (Condition 1): Rt 1.408 min, m/z 753.30 [M+H]⁺.

Example 1507
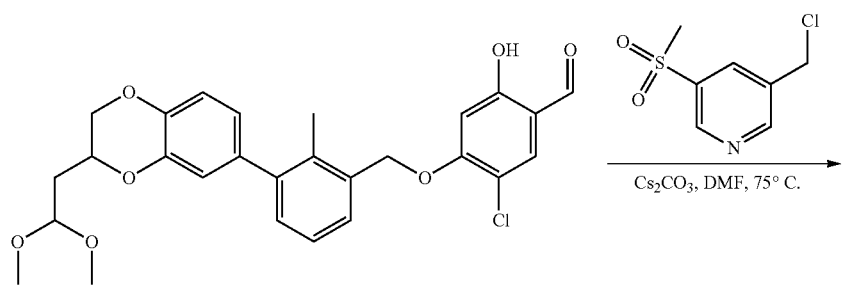
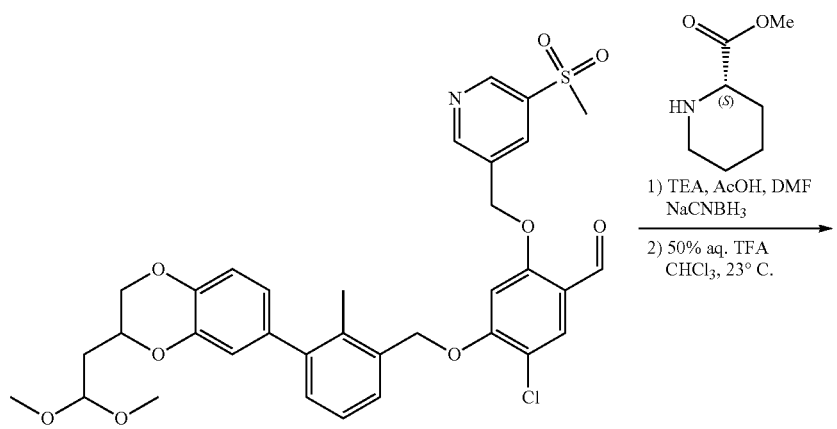
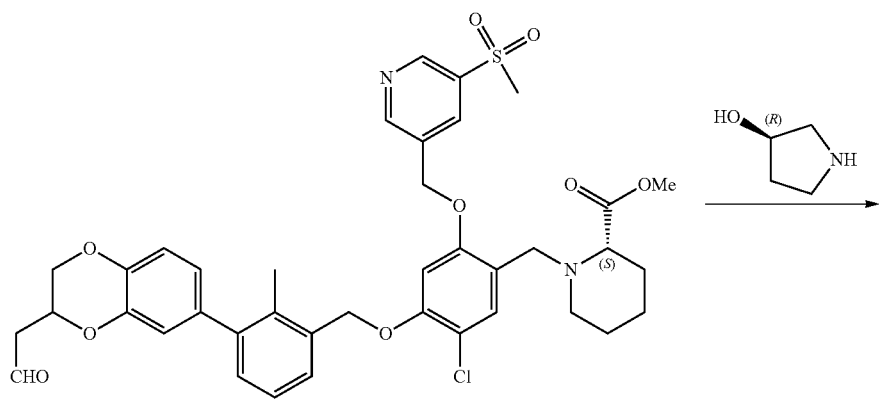
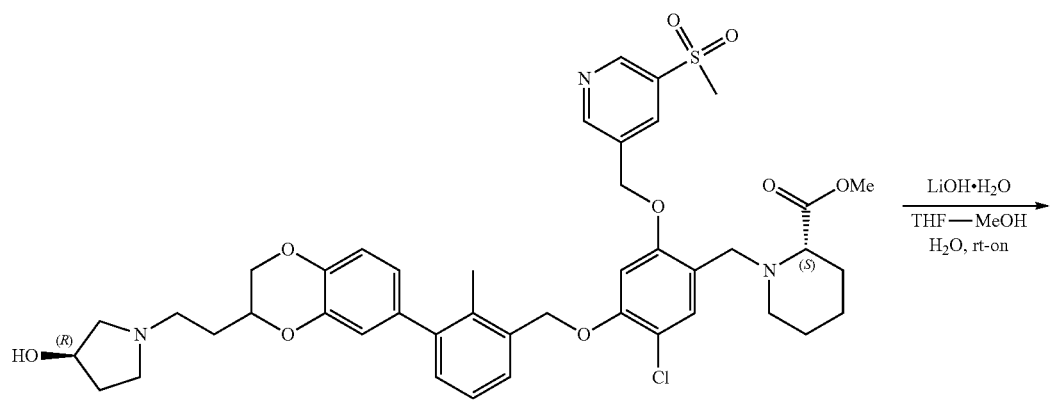

-continued

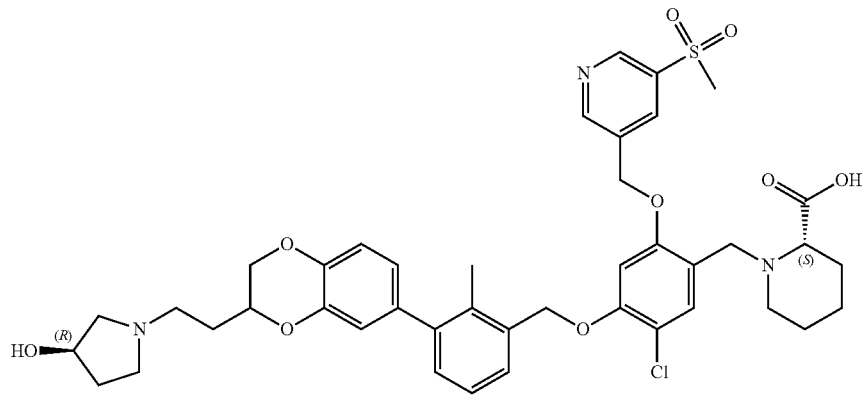

Example#1507

Cesium carbonate (0.307 g, 0.942 mmol) and sodium iodide (7.84 mg, 0.052 mmol) were added to a stirred solution of 5-chloro-4-((3-(3-(2,2-dimethoxyethyl)-2,3-dihydrobenzo[b][1,4]dioxin-6-yl)-2-methylbenzyl)oxy)-2-hydroxybenzaldehyde (0.131 g, 0.262 mmol) and 3-(chloromethyl)-5-(methylsulfonyl)pyridine, HCl (0.114 g, 0.471 mmol) in DMF (4 mL) and heated at 75° C. for 3 h. The reaction was cooled and diluted with EtOAc, washed with water, dried (MgSO$_4$), concentrated and purified by silica gel FCC (30-40% EtOAc in DCM) to afford 5-chloro-4-((3-(3-(2,2-dimethoxyethyl)-2,3-dihydrobenzo[b][1,4]dioxin-6-yl)-2-methylbenzyl)oxy)-2-((5-(methylsulfonyl)pyridin-3-yl)methoxy)benzaldehyde (0.167 g, 96%) as a beige solid. LC-MS (Condition P-1): m/z 636 (M−OMe)$^+$.

Neat (S)-methyl piperidine-2-carboxylate, HCl (0.076 g, 0.425 mmol) and TEA (0.059 mL, 0.425 mmol) were added consecutively to a solution of 5-chloro-4-((3-(3-(2,2-dimethoxyethyl)-2,3-dihydrobenzo[b][1,4]dioxin-6-yl)-2-methylbenzyl)oxy)-2-((5-(methylsulfonyl)pyridin-3-yl)methoxy)benzaldehyde (0.167 g, 0.250 mmol) in DMF (2 mL). After ~1 h AcOH (0.036 mL, 0.625 mmol) was added and the mixture was stirred at rt for 3-4 h and then sodium cyanoborohydride (0.039 g, 0.625 mmol) was added and the mixture was stirred at rt for 2 days. The reaction was quenched with MeOH (1 mL), diluted with EtOAc, washed with satd. NaHCO$_3$, water, brine, dried (MgSO$_4$) and concentrated. Crude isolate was purified by silica gel FCC (5-10% MeOH in DCM) to afford (2S)-methyl 1-(5-chloro-4-((3-(3-(2,2-dimethoxyethyl)-2,3-dihydrobenzo[b][1,4]dioxin-6-yl)-2-methylbenzyl)oxy)-2-((5-(methylsulfonyl)pyridin-3-yl)methoxy)benzyl)piperidine-2-carboxylate (0.166 g, 0.209 mmol, 84% yield) as a viscous oil. LC-MS (Condition P-1): Rt 2.168 min, m/z 795.25 [M+H]$^+$. The above acetal (0.166 g) was dissolved in DCM (12 mL) and stirred with 50% aq. TFA (6 mL) at rt overnight. DCM layer was separated and the aq. layer re-extracted (2×) and the combined DCM extracts were washed with satd. NaHCO$_3$, water, brine, dried (MgSO$_4$) and concentrated to afford (2S)-methyl 1-(5-chloro-4-((2-methyl-3-(3-(2-oxoethyl)-2,3-dihydrobenzo[b][1,4]dioxin-6-yl)benzyl)oxy)-2-((5-(methylsulfonyl)pyridin-3-yl)methoxy)benzyl)piperidine-2-carboxylate (0.145 g, 0.194 mmol, 77% yield) as a clear viscous oil. LC-MS (Condition P-1): Rt 1.89 min, m/z 749.2 [M+H]$^+$.

TEA (0.027 mL, 0.192 mmol) was added to a solution of (2S)-methyl 1-(5-chloro-4-((2-methyl-3-(3-(2-oxoethyl)-2,3-dihydrobenzo[b][1,4]dioxin-6-yl)benzyl)oxy)-2-((5-(methylsulfonyl)pyridin-3-yl)methoxy)benzyl)piperidine-2-carboxylate (48 mg, 0.064 mmol) and (R)-pyrrolidin-3-ol, HCl (24 mg, 0.192 mmol) in DMF (1 mL) and the mixture was stirred at rt overnight. Then acetic acid (0.011 mL, 0.192 mmol) and sodium cyanoborohydride (12.08 mg, 0.192 mmol) were added and the mixture was stirred at rt for 8 h. The reaction mixture was diluted with EtOAc, quenched with sat'ed. NaHCO$_3$, washed with water, brine, dried (MgSO$_4$) and concentrated and purified by silica gel FCC (0-10% MeOH in DCM) to afford (2S)-methyl 1-(5-chloro-4-((3-(3-(2-((R)-3-hydroxypyrrolidin-1-yl)ethyl)-2,3-dihydrobenzo[b][1,4]dioxin-6-yl)-2-methylbenzyl)oxy)-2-((5-(methylsulfonyl)pyridin-3-yl)methoxy)benzyl)piperidine-2-carboxylate as a viscous oil, LC-MS (Condition P-1): Rt 1.924 min, m/z 820.25 [M+H]$^+$, which was saponified (LiOH.H$_2$O, THF-MeOH—H$_2$O, rt-16 h) and purified by prep. HPLC to afford (2S)-1-(5-chloro-4-((3-(3-(2-((R)-3-hydroxypyrrolidin-1-yl)ethyl)-2,3-dihydrobenzo[b][1,4]dioxin-6-yl)-2-methylbenzyl)oxy)-2-((5-(methylsulfonyl)pyridin-3-yl)methoxy)benzyl)piperidine-2-carboxylic acid as a mixture of diastereomers. LCMS (Condition 1): Rt 1.471 min, m/z 806.1 [M+H]$^+$.

Example 1508

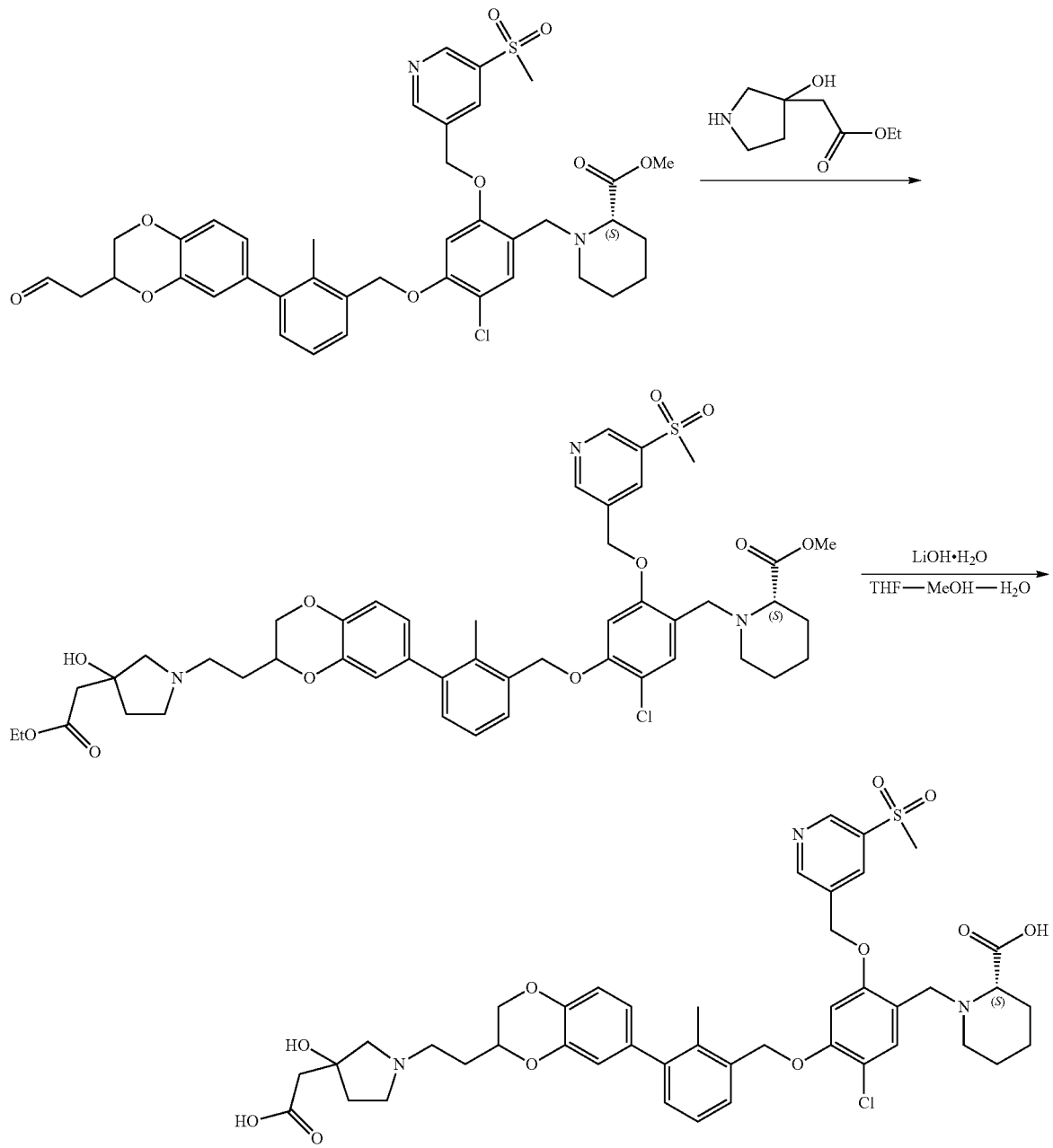

Example#1508

Neat TEA (0.023 mL, 0.166 mmol) was added to a solution of (2S)-methyl 1-(5-chloro-4-((2-methyl-3-(3-(2-oxoethyl)-2,3-dihydrobenzo[b][1,4]dioxin-6-yl)benzyl)oxy)-2-((5-(methylsulfonyl)pyridin-3-yl)methoxy)benzyl)piperidine-2-carboxylate (41.4 mg, 0.055 mmol) and ethyl 2-(3-hydroxypyrrolidin-3-yl)acetate, TFA (48 mg, 0.166 mmol) in DMF (1 mL) and the mixture stirred at rt overnight. Then acetic acid (9.49 µl, 0.166 mmol) and sodium cyanoborohydride (10.42 mg, 0.166 mmol) were added and the mixture was stirred at rt for 8 h. The reaction mixture was diluted with EtOAc and neutralized with sat'ed. NaHCO$_3$, washed with water, brine, dried (MgSO$_4$), concentrated and purified by silica gel FCC (5-10% MeOH in DCM) to afford (2S)-methyl 1-(5-chloro-4-((3-(3-(2-(3-(2-ethoxy-2-oxoethyl)-3-hydroxypyrrolidin-1-yl)ethyl)-2,3-dihydrobenzo[b][1,4]dioxin-6-yl)-2-methylbenzyl)oxy)-2-((5-(methylsulfonyl)pyridin-3-yl)methoxy)benzyl)piperidine-2-carboxylate as a viscous oil which was saponified (LiOH.H$_2$O, THF-MeOH—H$_2$O, rt-16 h) and purified by prep. HPLC to yield (2S)-1-(4-((3-(3-(2-(3-(carboxymethyl)-3-hydroxypyrrolidin-1-yl)ethyl)-2,3-dihydrobenzo[b][1,4]dioxin-6-yl)-2-methylbenzyl)oxy)-5-chloro-2-((5-(methylsulfonyl)pyridin-3-yl)methoxy)benzyl)piperidine-2-carboxylic acid as a mixture of diastereomers. LCMS (Condition 1): Rt 1.265 min, m/z 864.1 [M+H]$^+$.

Example 1509

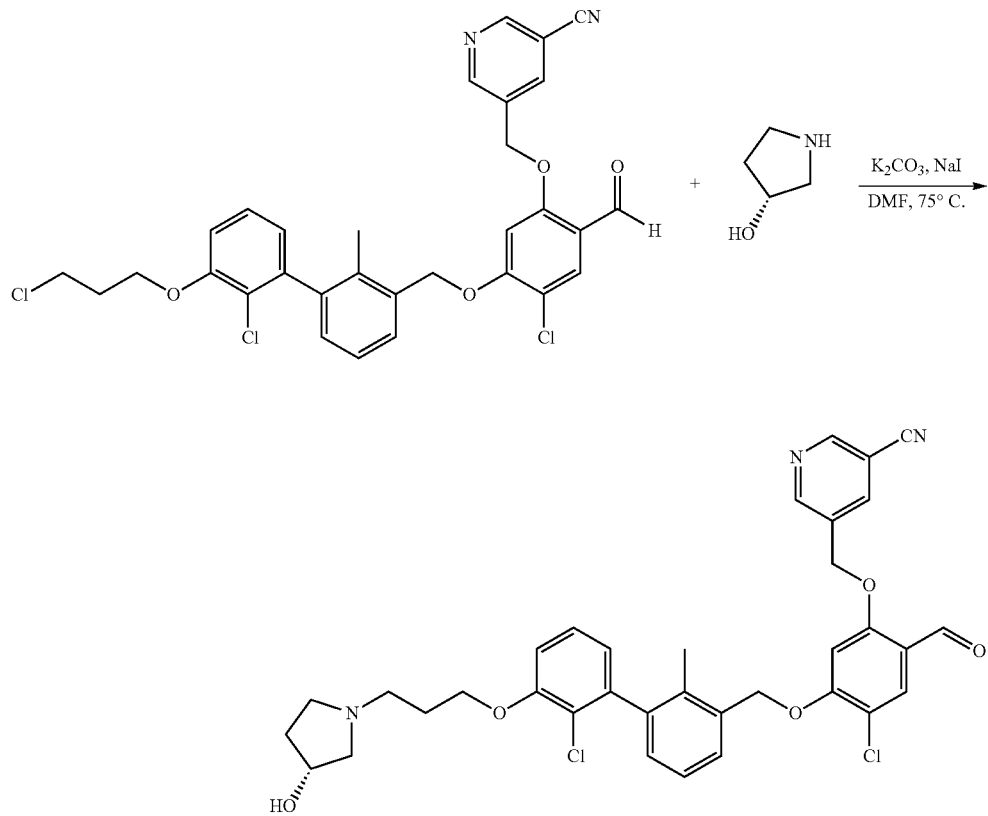

Example#1509

A stirred mixture of 5-((4-chloro-5-((2'-chloro-3'-(3-chloropropoxy)-2-methyl-[1,1'-biphenyl]-3-yl)methoxy)-2-formylphenoxy)methyl)nicotinonitrile (0.163 g, 0.274 mmol), (R)-pyrrolidin-3-ol (0.029 g, 0.328 mmol) and K$_2$CO$_3$ (0.045 g, 0.328 mmol), sodium iodide (0.041 g, 0.274 mmol) in DMF (2 ml) was heated at 75° C. for 16 h. The reaction mixture was diluted with EtOAc and washed with water, brine, dried (Na$_2$SO$_4$), concentrated and purified by silica gel FCC (0-20% MeOH-DCM) to yield (R)-5-((4-chloro-5-((2'-chloro-3'-(3-(3-hydroxypyrrolidin-1-yl)propoxy)-2-methyl-[1,1'-biphenyl]-3-yl)methoxy)-2-formylphenoxy)methyl)nicotinonitrile (0.12 g, 63%) as a beige foamy solid. LCMS (Condition 2): Rt 2.123 min, m/z 646.2 [M+H]$^+$.

Example 1510

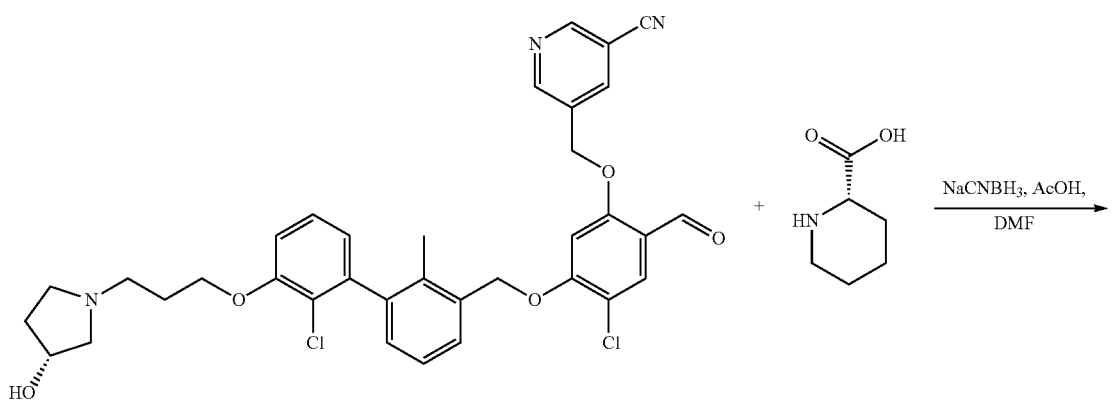

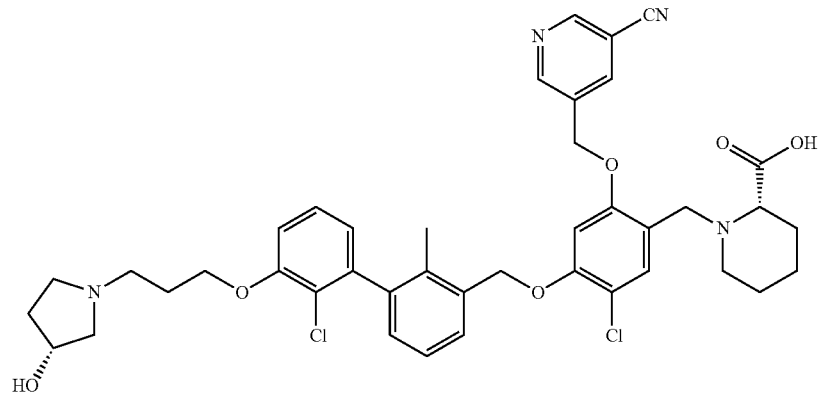

Example#1510

Neat acetic acid (0.014 mL, 0.250 mmol) was added to a stirred solution of (R)-5-((4-chloro-5-((2'-chloro-3'-(3-(3-hydroxypyrrolidin-1-yl)propoxy)-2-methyl-[1,1'-biphenyl]-3-yl)methoxy)-2-formylphenoxy)methyl)nicotinonitrile (32.3 mg, 0.050 mmol) and (S)-piperidine-2-carboxylic acid (22.58 mg, 0.175 mmol) in DMF (1 mL) and the mixture was stirred at rt for 3-4 h and then sodium cyanoborohydride (10.99 mg, 0.175 mmol) was added and the mixture was stirred at rt overnight. The reaction mixture was diluted with 5% TFA in MeOH and purified by prep. HPLC to afford (S)-1-(5-chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)piperidine-2-carboxylic acid. LCMS (Condition 1): Rt 1.425 min, m/z 759.2 [M+H]$^+$.

Example 1511

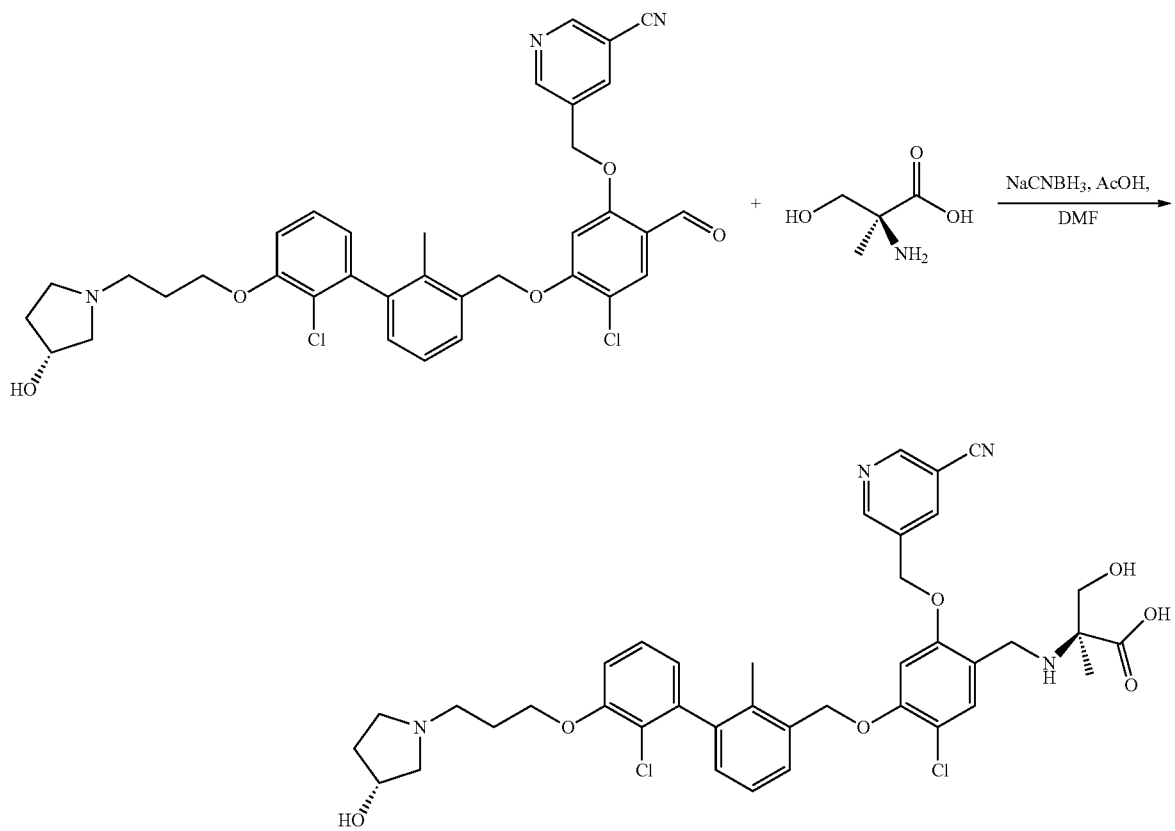

Example#1511

Neat acetic acid (0.017 mL, 0.292 mmol) was added to a stirred solution of (R)-5-((4-chloro-5-((2'-chloro-3'-(3-(3-hydroxypyrrolidin-1-yl)propoxy)-2-methyl-[1,1'-biphenyl]-3-yl)methoxy)-2-formylphenoxy)methyl)nicotinonitrile (37.7 mg, 0.058 mmol) and (S)-2-amino-3-hydroxy-2-methylpropanoic acid (24.31 mg, 0.204 mmol) in DMF (1 mL) and the mixture was stirred at rt for 3 h and then sodium cyanoborohydride (10.99 mg, 0.175 mmol) was added and the mixture was stirred at rt overnight. The reaction mixture was diluted with 5% TFA in MeOH and purified by prep. HPLC to afford (S)-2-((5-chloro-4-((2'-chloro-3'-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid. LCMS (Condition 1): Rt 1.391 min, m/z 749.2 [M+H]+.

Example 1512

Neat acetic acid (0.018 mL, 0.310 mmol) was added to a stirred solution of (R)-5-5-((4-chloro-5-((2'-chloro-3'-(3-(3-hydroxypyrrolidin-1-yl)propoxy)-2-methyl-[1,1'-biphenyl]-3-yl)methoxy)-2-formylphenoxy)methyl)nicotinonitrile (40.1 mg, 0.062 mmol) and D-serine (22.8 mg, 0.217 mmol) in DMF (1 mL) and the mixture was stirred at rt for 2 h, and then sodium cyanoborohydride (11 mg, 0.175 mmol) was added and the mixture stirred at rt overnight. The reaction mixture was diluted with 5% TFA in MeOH and purified by prep. HPLC to afford (R)-2-((5-chloro-4-((2'-chloro-3'-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxypropanoic acid. LCMS (Condition 1): Rt 1.369 min, m/z 735.1 [M+H]+.

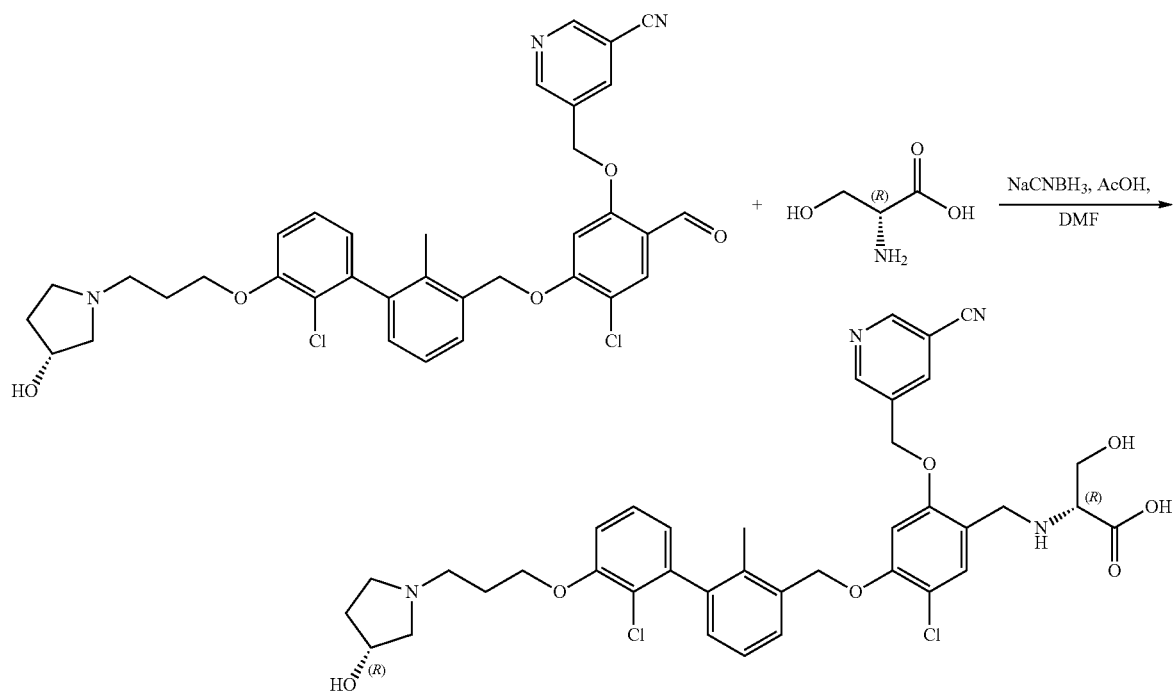

Example#1512

Example 1513

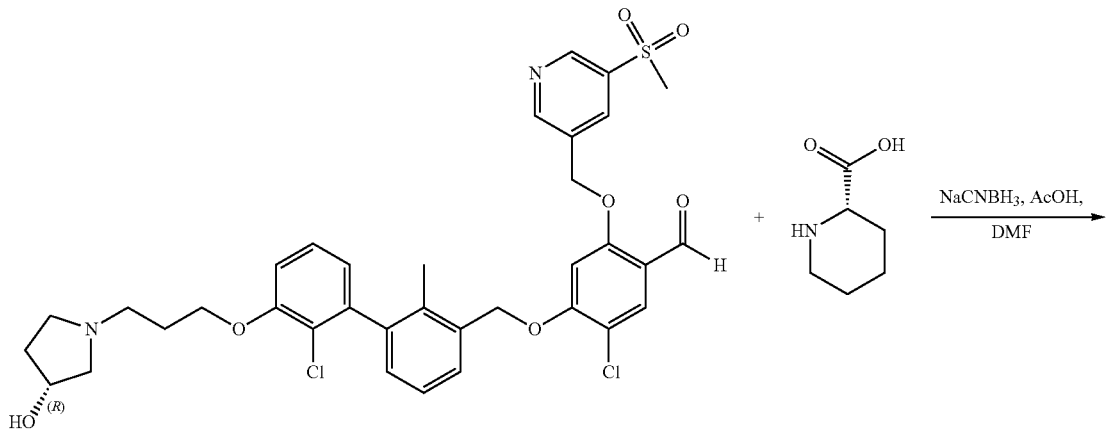

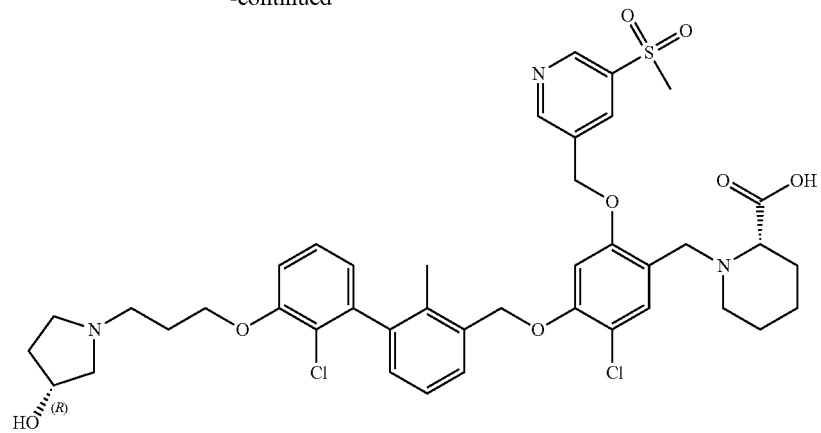

Example#1513

Neat acetic acid (0.015 mL, 0.261 mmol) was added to a stirred solution of (R)-5-chloro-4-((2'-chloro-3'-(3-(3-hydroxypyrrolidin-1-yl)propoxy)-2-methyl-[1,1'-biphenyl]-3-yl)methoxy)-2-((5-(methylsulfonyl)pyridin-3-yl)methoxy)benzaldehyde (36.5 mg, 0.052 mmol) and (S)-piperidine-2-carboxylic acid (23.6 mg, 0.183 mmol) in DMF (1 ml) and the mixture was stirred at rt for 4 h, and then sodium cyanoborohydride (11.5 mg, 0.183 mmol) was added and the mixture was stirred at rt overnight. The reaction mixture was diluted with 5% TFA in MeOH and purified by prep. HPLC to afford (S)-1-(5-chloro-4-((2'-chloro-3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)piperidine-2-carboxylic acid. LCMS (Condition 1): Rt 1.428 min, m/z 811.9 [M+H]$^+$.

Example 1514 & Example 1515

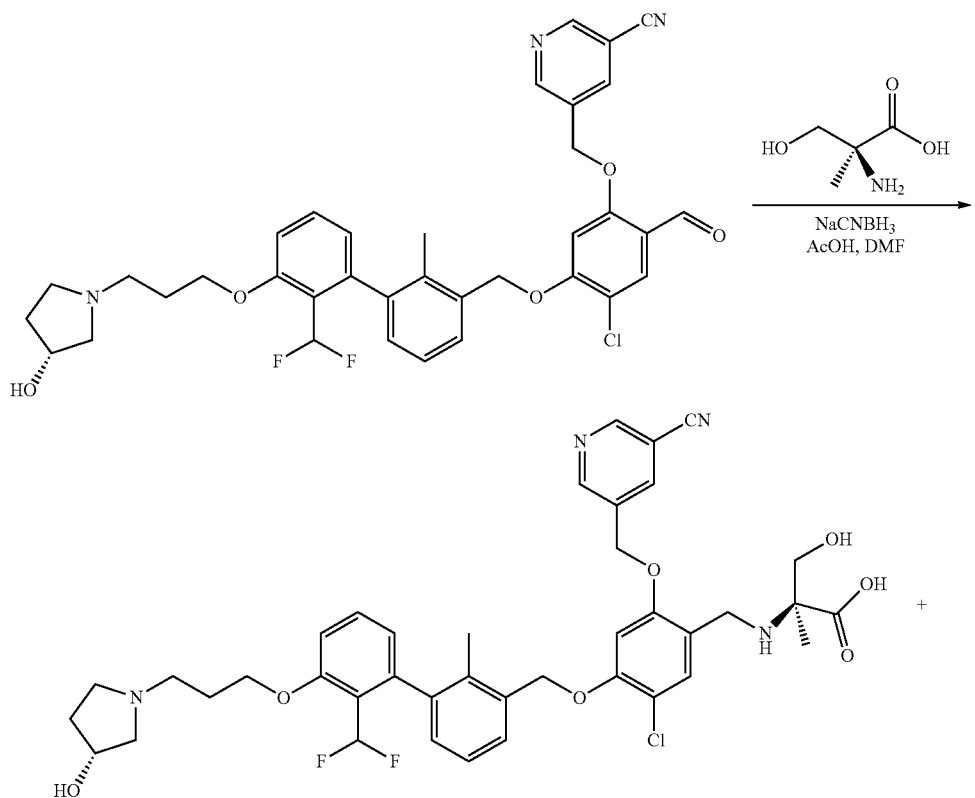

Example#1514

-continued

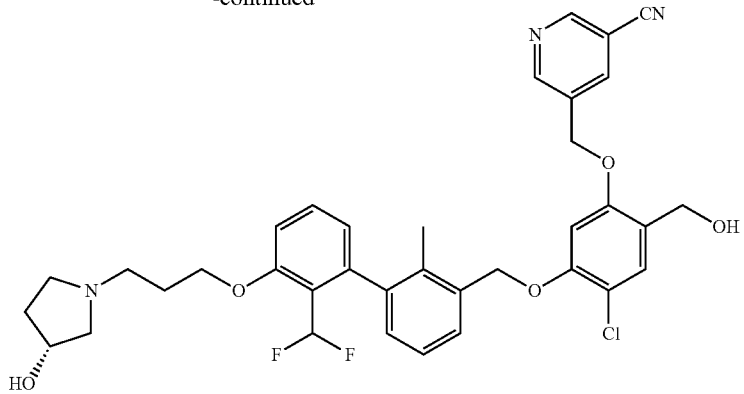

Example#1515

Neat acetic acid (0.024 mL, 0.415 mmol) was added to a stirred solution of (R)-5-((4-chloro-5-((2'-(difluoromethyl)-3'-(3-(3-hydroxypyrrolidin-1-yl)propoxy)-2-methyl-[1,1'-biphenyl]-3-yl)methoxy)-2-formylphenoxy)methyl)nicotinonitrile (55 mg, 0.083 mmol) and (S)-2-amino-3-hydroxy-2-methylpropanoic acid (29.7 mg, 0.249 mmol) in DMF (1 mL) and the mixture was stirred at rt for 3 h, and then sodium cyanoborohydride (10.99 mg, 0.175 mmol) was added and the mixture was stirred at rt overnight. The reaction mixture was diluted with 5% TFA in MeOH and purified by prep. HPLC yield (S)-2-((5-chloro-2-((5-cyanopyridin-3-yl)methoxy)-4-((2'-(difluoromethyl)-3'-(3-((R)-3-hydroxypyrrolidin-1-yl)propoxy)-2-methyl-[1,1'-biphenyl]-3-yl)methoxy)benzyl)amino)-3-hydroxy-2-methylpropanoic acid (Example 1514). LCMS (Condition 1): Rt 1.391 min, m/z 765.1 [M+H]+ and (R)-5-((4-chloro-5-((2'-(difluoromethyl)-3'-(3-(3-hydroxypyrrolidin-1-yl)propoxy)-2-methyl-[1,1'-biphenyl]-3-yl)methoxy)-2-(hydroxymethyl)phenoxy)methyl)nicotinonitrile (Example 1515). LCMS (Condition 1): Rt 1.689 min, m/z 664.1 [M+H]+.

Example 1516

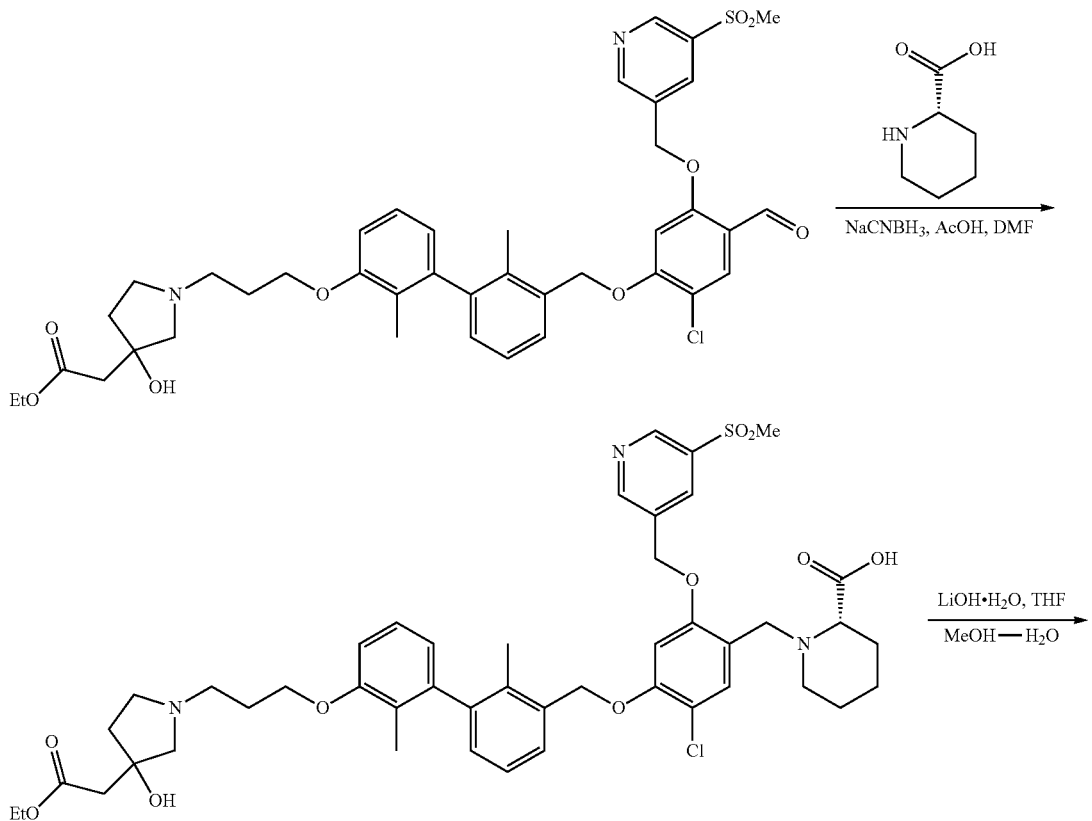

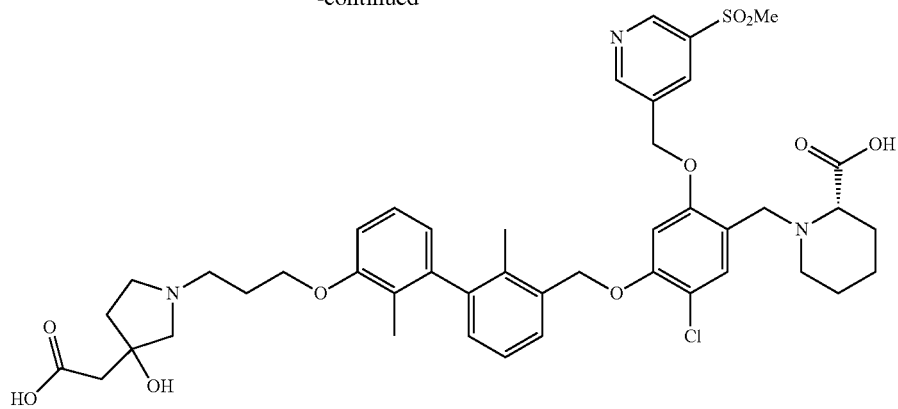

Example#1516

Neat acetic acid (0.021 mL, 0.359 mmol) was added to a stirred solution of ethyl 2-(1-(3-(3'-((2-chloro-4-formyl-5-((5-(methylsulfonyl)pyridin-3-yl)methoxy)phenoxy)methyl)-2,2'-dimethyl-[1,1'-biphenyl]-3-yl)oxy)propyl)-3-hydroxypyrrolidin-3-yl)acetate (55 mg, 0.072 mmol) and (S)-piperidine-2-carboxylic acid (32.5 mg, 0.252 mmol) in DMF (1 mL) and the mixture was stirred at rt for 3-4 h, and then sodium cyanoborohydride (16 mg, 0.252 mmol) was added and the mixture was stirred at rt overnight. The crude reductive amination product was isolated by aqueous workup and saponified (LiOH.H₂O, THF-MeOH—H₂O) and purified by prep. HPLC to afford (2S)-1-(4-((3'-(3-(3-(carboxymethyl)-3-hydroxypyrrolidin-1-yl)propoxy)-2,2'-dimethyl-[1,1'-biphenyl]-3-yl)methoxy)-5-chloro-2-((5-(methylsulfonyl)pyridin-3-yl)methoxy)benzyl)piperidine-2-carboxylic acid as a mixture of diastereomers. LCMS (Condition 1): Rt 1.455 min, m/z 850.0 [M+H]⁺.

Example 1517

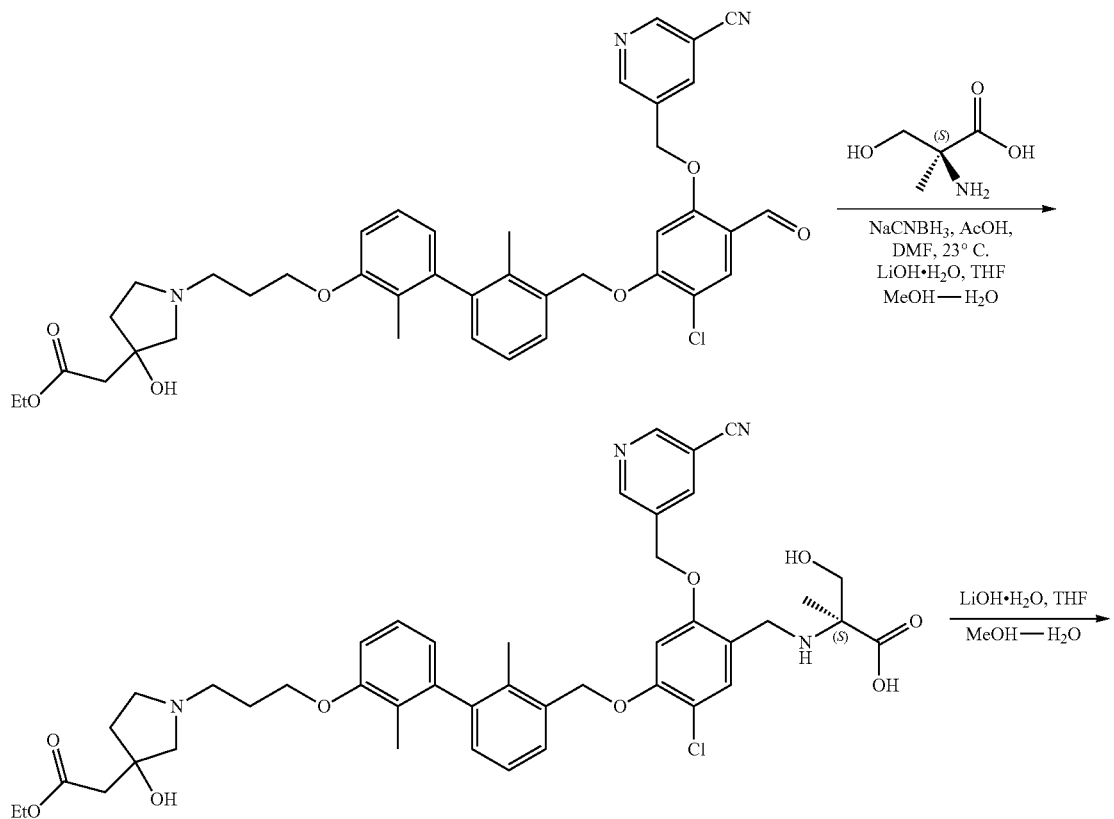

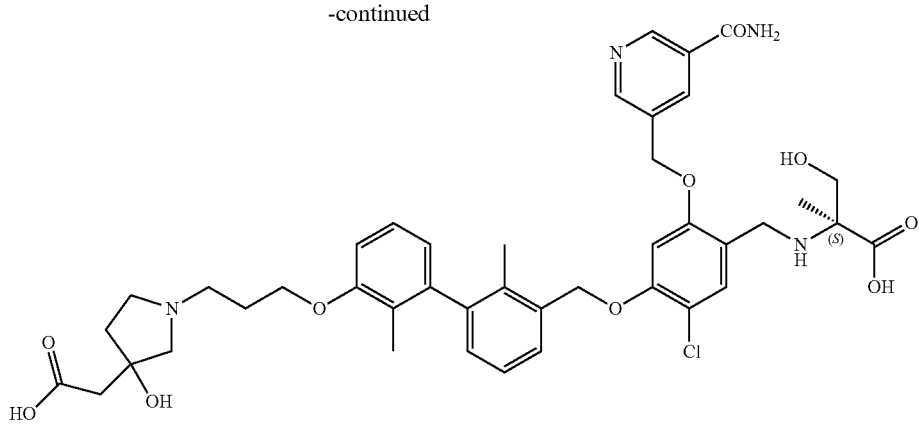

Example #1517

Neat acetic acid (0.014 mL, 0.253 mmol) was added to a stirred solution of ethyl 2-(1-(3-((3'-((2-chloro-5-((5-cyano-pyridin-3-yl)methoxy)-4-formylphenoxy)methyl)-2,2'-dimethyl-[1,1'-biphenyl]-3-yl)oxy)propyl)-3-hydroxypyrrolidin-3-yl)acetate (45 mg, 0.063 mmol) and (S)-2-amino-3-hydroxy-2-methylpropanoic acid (15.05 mg, 0.126 mmol) in DMF (1 mL) and the mixture was stirred at rt for 3-4 h, and then sodium cyanoborohydride (11.91 mg, 0.190 mmol) was added and the mixture was stirred at rt overnight. The crude reductive amination product was isolated by aqueous workup and saponified (LiOH.H$_2$O, THF-MeOH—H$_2$O) and purified by prep. HPLC to afford (2S)-2-((4-((3'-(3-(3-(carboxymethyl)-3-hydroxypyrrolidin-1-yl)propoxy)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid as a mixture of diastereomers. LCMS (Condition 1): Rt 1.437 min, m/z 787.1 [M+H]$^+$.

Example 1518

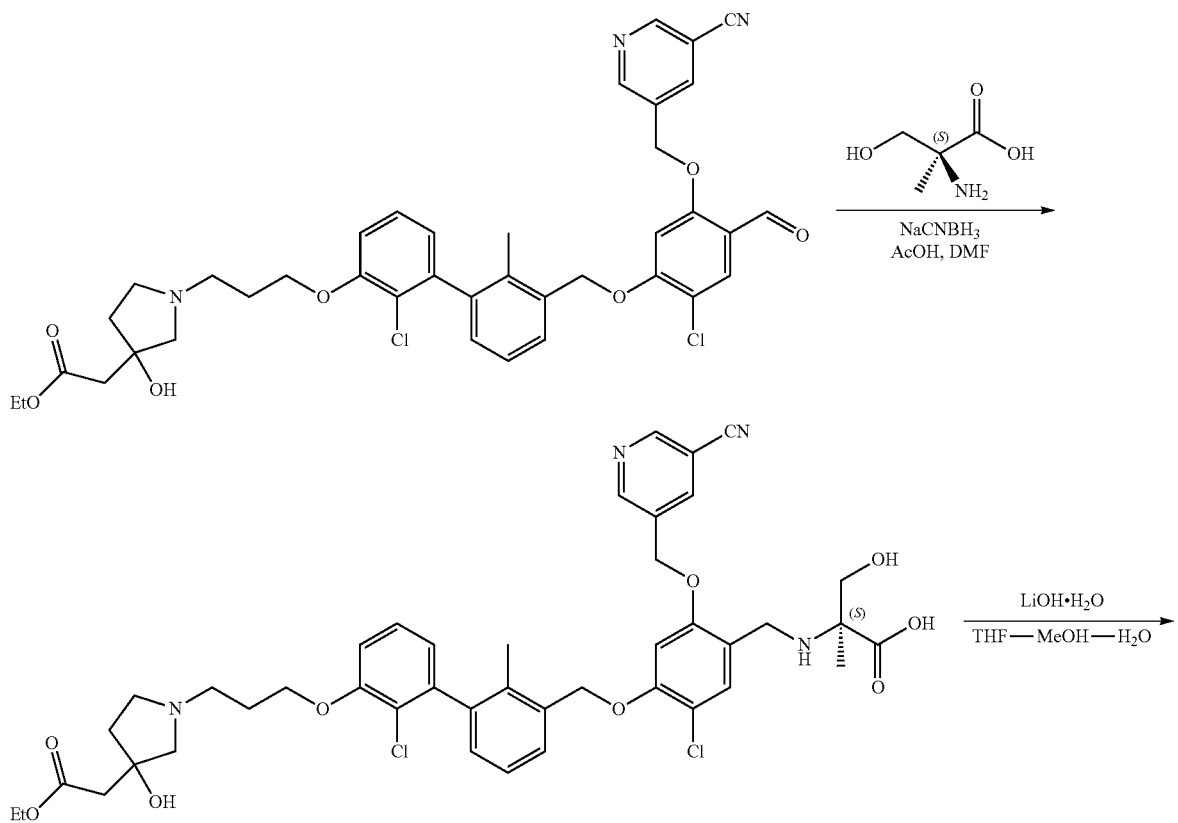

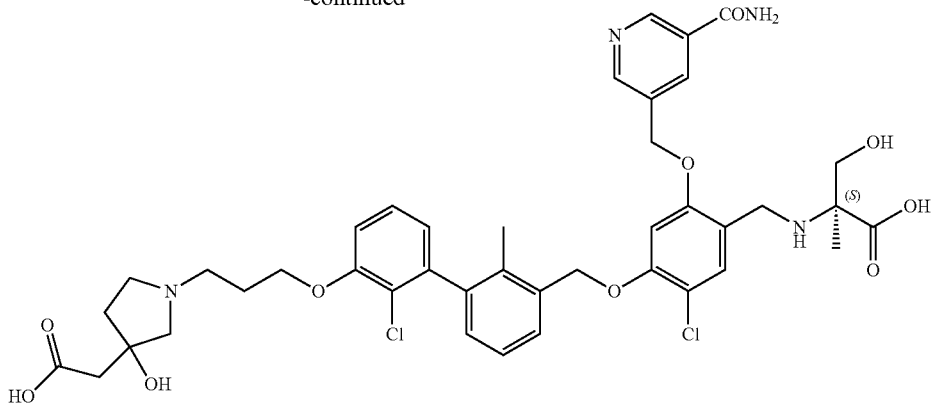

Example #1518

Neat acetic acid (0.021 mL, 0.375 mmol) was added to a stirred solution of ethyl 2-(1-(3-((2-chloro-3'-((2-chloro-5-((5-cyanopyridin-3-yl)methoxy)-4-formylphenoxy)methyl)-2'-methyl-[1,1'-biphenyl]-3-yl)oxy)propyl)-3-hydroxypyrrolidin-3-yl)acetate (55 mg, 0.075 mmol) and (S)-2-amino-3-hydroxy-2-methylpropanoic acid (26.8 mg, 0.225 mmol) in DMF (1 mL) and the mixture was stirred at rt for 3 h, and then sodium cyanoborohydride (10.99 mg, 0.175 mmol) was added and the mixture was stirred at rt for 2 days. The reaction mixture was quenched with MeOH and then evaporated to dryness to afford desired reductive amination product which was saponified (LiOH.H₂O, THF-MeOH—H₂O, rt-16 h). The reaction mixture was acidified with 10% AcOH in MeOH and evaporated to dryness and then purified by prep. HPLC to afford (2S)-2-((2-((5-carbamoylpyridin-3-yl)methoxy)-4-(((3'-(3-(3-(carboxymethyl)-3-hydroxypyrrolidin-1-yl)propoxy)-2'-chloro-2-methyl-[1,1'-biphenyl]-3-yl)methoxy)-5-chlorobenzyl)amino)-3-hydroxy-2-methylpropanoic acid. LCMS (Condition 1): Rt 1.287 min, m/z 825.0 [M+H]⁺.

Example 1519

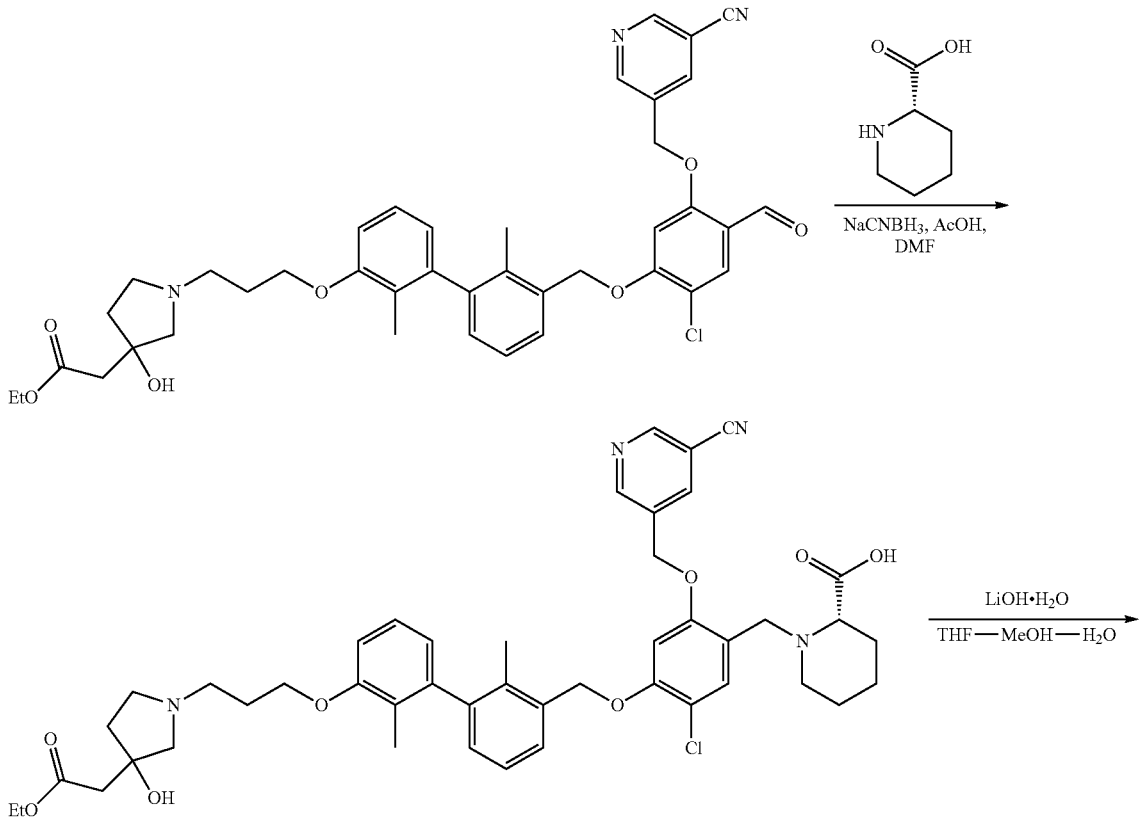

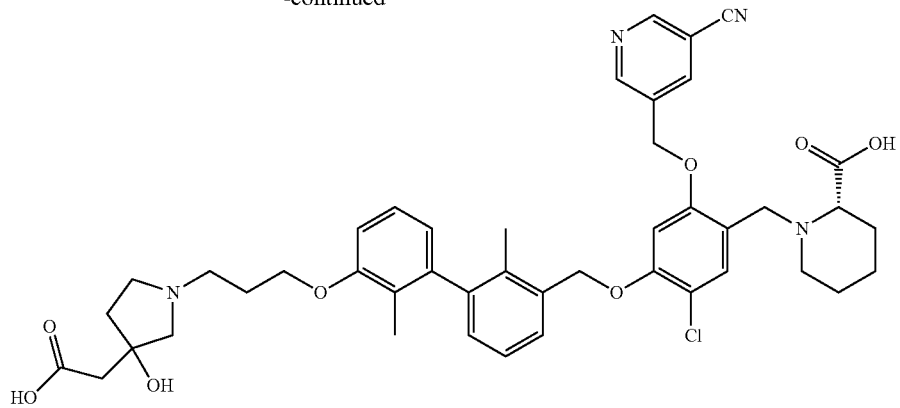

Example#1519

Neat acetic acid (0.017 mL, 0.302 mmol) was added to a stirred solution of ethyl 2-(1-(3-((3'-((2-chloro-5-((5-cyanopyridin-3-yl)methoxy)-4-formylphenoxy)methyl)-2,2'-dimethyl-[1,1'-biphenyl]-3-yl)oxy)propyl)-3-hydroxypyrrolidin-3-yl)acetate (43 mg, 0.060 mmol) and (S)-piperidine-2-carboxylic acid (27.3 mg, 0.211 mmol) in DMF (1 mL) and the mixture was stirred at rt for 3-4 h, and then sodium cyanoborohydride (13.28 mg, 0.211 mmol) was added and the mixture was stirred at rt overnight. The reaction mixture was diluted with EtOAc and quenched with sat'ed. NaHCO₃. The organic layer washed with water, brine, dried (MgSO₄) and concentrated to afford (2S)-1-(5-chloro-2-((5-cyanopyridin-3-yl)methoxy)-4-((3'-(3-(3-(2-ethoxy-2-oxoethyl)-3-hydroxypyrrolidin-1-yl)propoxy)-2,2'-dimethyl-[1,1'-biphenyl]-3-yl)methoxy)benzyl)piperidine-2-carboxylic acid as a mixture of diastereomers which was saponified (LiOH.H₂O, THF-MeOH—H₂O, 23° C.) and purified by prep. HPLC to afford (2S)-1-(4-((3'-(3-(3-(carboxymethyl)-3-hydroxypyrrolidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid as a mixture of diastereomers. LCMS (Condition 1): Rt 1.134 min, m/z 815.2 [M+H]⁺.

Example 1520

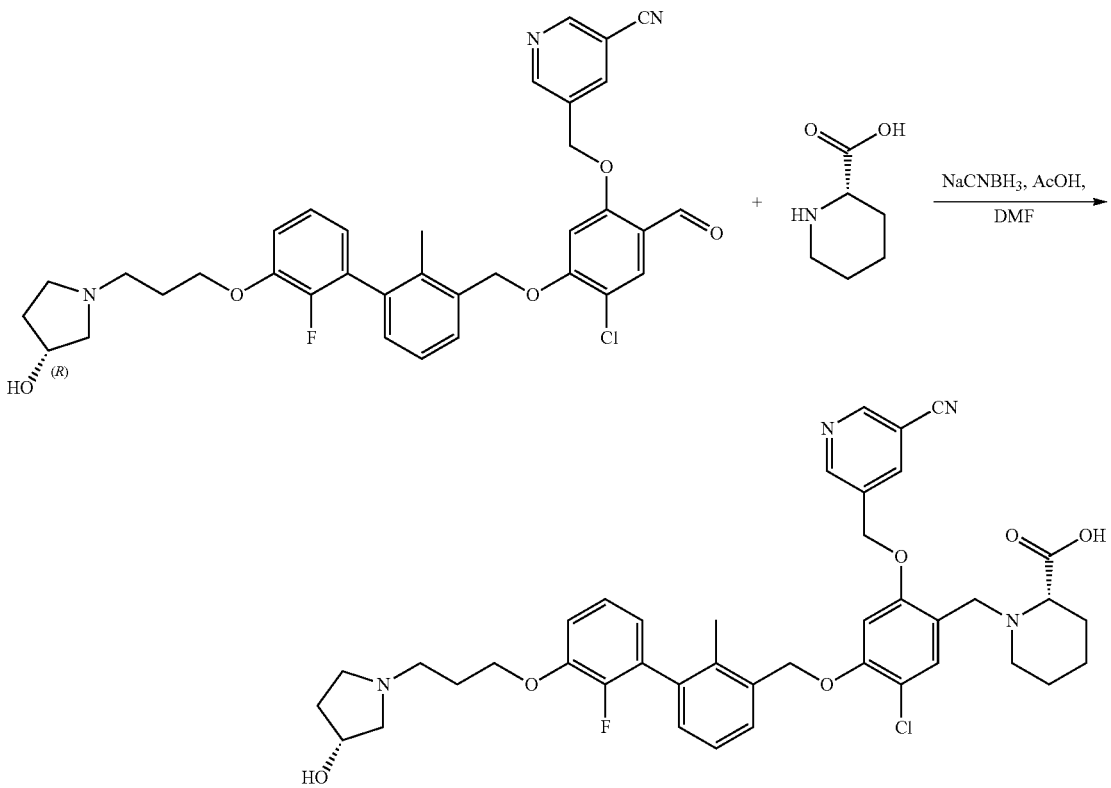

Example#1520

Neat acetic acid (0.025 mL, 0.428 mmol) was added to a stirred solution of (R)-5-((4-chloro-5-((2'-fluoro-3'-(3-(3-hydroxypyrrolidin-1-yl)propoxy)-2-methyl-[1,1'-biphenyl]-3-yl)methoxy)-2-formylphenoxy)methyl)nicotinonitrile (54 mg, 0.086 mmol) and (S)-piperidine-2-carboxylic acid (33.2 mg, 0.257 mmol) in DMF (1 mL) and the mixture was stirred at rt for 3-4 h and then sodium cyanoborohydride (16.2 mg, 0.257 mmol) was added and the mixture was stirred at rt overnight. The reaction mixture was diluted with 5% TFA in MeOH and purified by prep. HPLC to afford (S)-1-(5-chloro-2-((5-cyanopyridin-3-yl)methoxy)-4-((2'-fluoro-3'-(3-((R)-3-hydroxypyrrolidin-1-yl)propoxy)-2-methyl-[1,1'-biphenyl]-3-yl)methoxy)benzyl)piperidine-2-carboxylic acid. LCMS (Condition 1): Rt 1.360 min, m/z 743.1 [M+H]⁺.

Example 1521

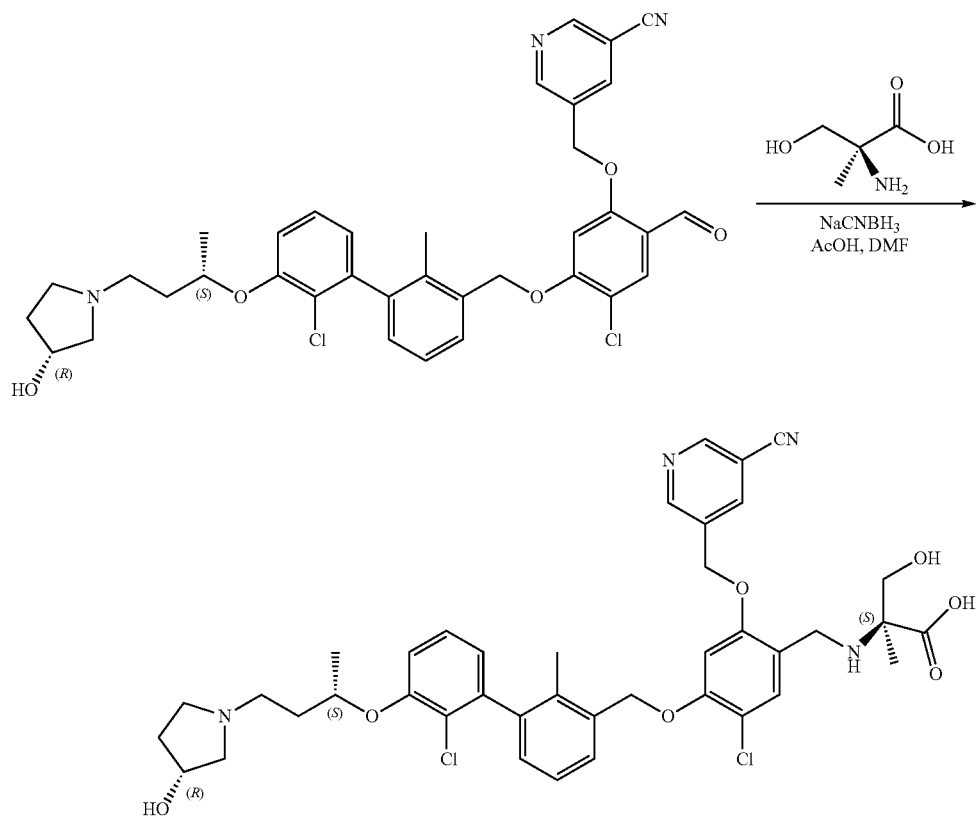

Example#1521

Neat acetic acid (0.018 mL, 0.318 mmol) was added to a stirred solution of 5-((4-chloro-5-((2'-chloro-3'-(((S)-4-((R)-3-hydroxypyrrolidin-1-yl)butan-2-yl)oxy)-2-methyl-[1,1'-biphenyl]-3-yl)methoxy)-2-formylphenoxy)methyl)nicotinonitrile (42 mg, 0.064 mmol) and (S)-2-amino-3-hydroxy-2-methylpropanoic acid (22.72 mg, 0.191 mmol) in DMF (1 mL) and the mixture was stirred at rt for 3 h, and then sodium cyanoborohydride (10.99 mg, 0.175 mmol) was added and the mixture was stirred at rt overnight. The reaction mixture was diluted with 5% TFA in MeOH and purified by prep. HPLC to afford (S)-2-((5-chloro-4-((2'-chloro-3'-(((S)-4-((R)-3-hydroxypyrrolidin-1-yl)butan-2-yl)oxy)-2-methyl-[1,1'-biphenyl]-3-yl)methoxy)-2-((5-cyanopyridin-3-yl)methoxy)benzyl)amino)-3-hydroxy-2-methylpropanoic acid. LCMS (Condition 1): Rt 1.570 min, m/z 763.2 [M+H]⁺.

Example 1522

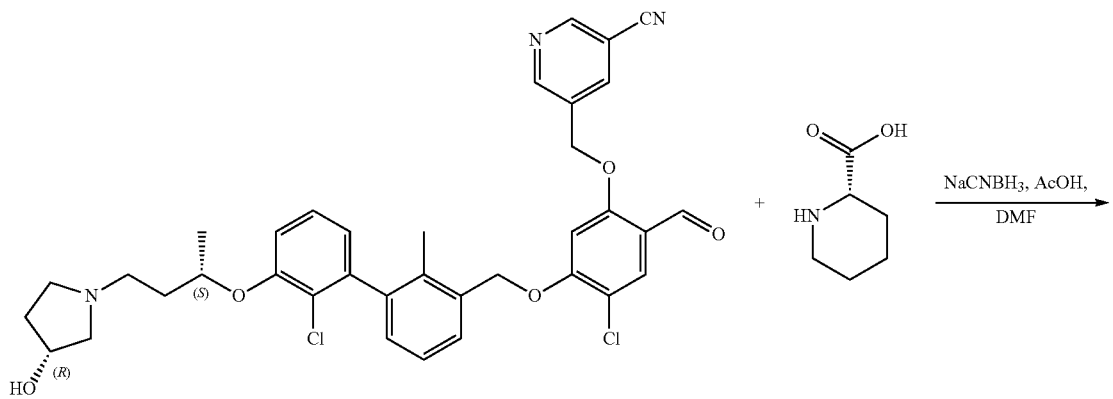

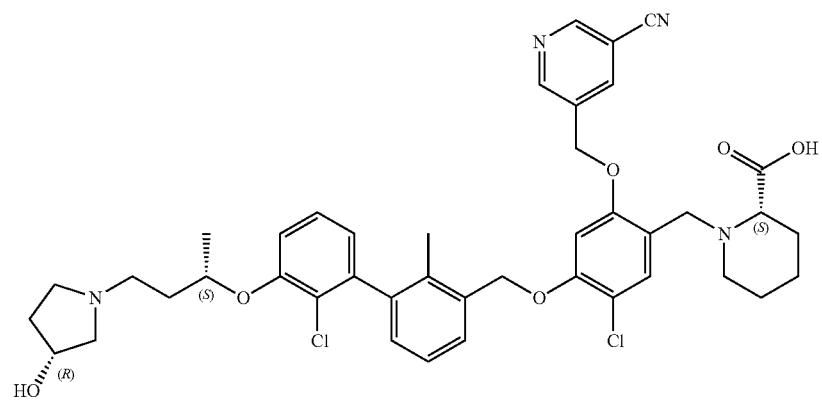

Example#1522

Neat acetic acid (0.014 mL, 0.252 mmol) was added to a stirred solution of 5-((4-chloro-5-((2'-chloro-3'-(((S)-4-((R)-3-hydroxypyrrolidin-1-yl)butan-2-yl)oxy)-2-methyl-[1,1'-biphenyl]-3-yl)methoxy)-2-formylphenoxy)methyl)nicotinonitrile (33.3 mg, 0.050 mmol) and (S)-piperidine-2-carboxylic acid (19.53 mg, 0.151 mmol) in DMF (1 mL) and the mixture was stirred at rt for 3-4 h, and then sodium cyanoborohydride (9.50 mg, 0.151 mmol) was added and the mixture was stirred at rt overnight. The reaction mixture was diluted with 5% TFA in MeOH and purified by prep. HPLC to afford (S)-1-(5-chloro-4-((2'-chloro-3'-(((S)-4-((R)-3-hydroxypyrrolidin-1-yl)butan-2-yl)oxy)-2-methyl-[1,1'-biphenyl]-3-yl)methoxy)-2-((5-cyanopyridin-3-yl)methoxy)benzyl)piperidine-2-carboxylic acid. LCMS (Condition 1): Rt 1.584 min, m/z 773.0 [M+H]+.

Example 1523

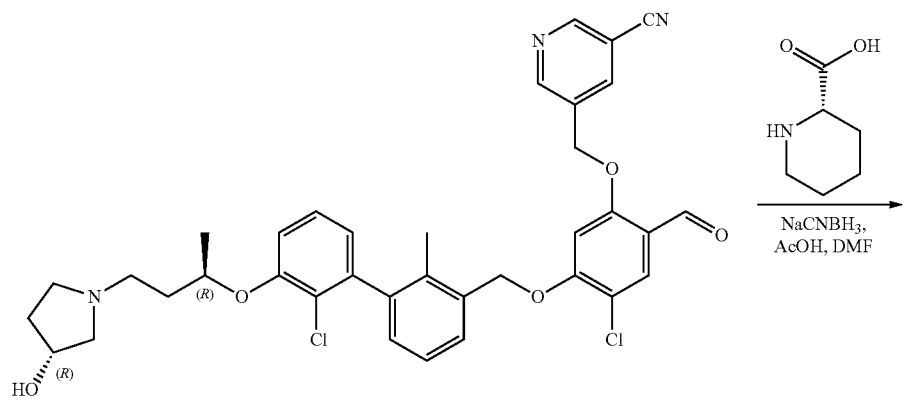

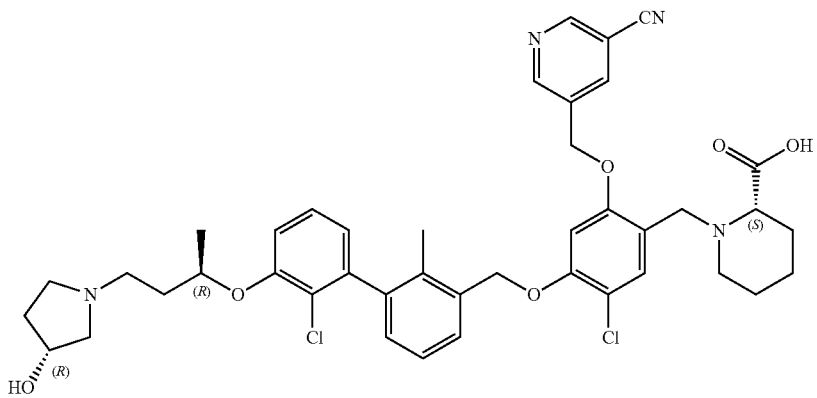

Example#1523

Neat acetic acid (0.018 mL, 0.319 mmol) was added to a stirred solution of 5-((4-chloro-5-((2'-chloro-3'-(((R)-4-((R)-3-hydroxypyrrolidin-1-yl)butan-2-yl)oxy)-2-methyl-[1,1'-biphenyl]-3-yl)methoxy)-2-formylphenoxy)methyl)nicotinonitrile (42.1 mg, 0.064 mmol) and (S)-piperidine-2-carboxylic acid (24.69 mg, 0.191 mmol) in DMF (1 mL) and the mixture was stirred at rt for 3-4 h, and then sodium cyanoborohydride (12.02 mg, 0.191 mmol) was added and the mixture was stirred at rt overnight. The reaction mixture was diluted with 5% TFA in MeOH and then submitted to purification. LCMS (Condition 1): Rt 1.575 min, m/z 773.1 [M+H]$^+$.

Example 1524

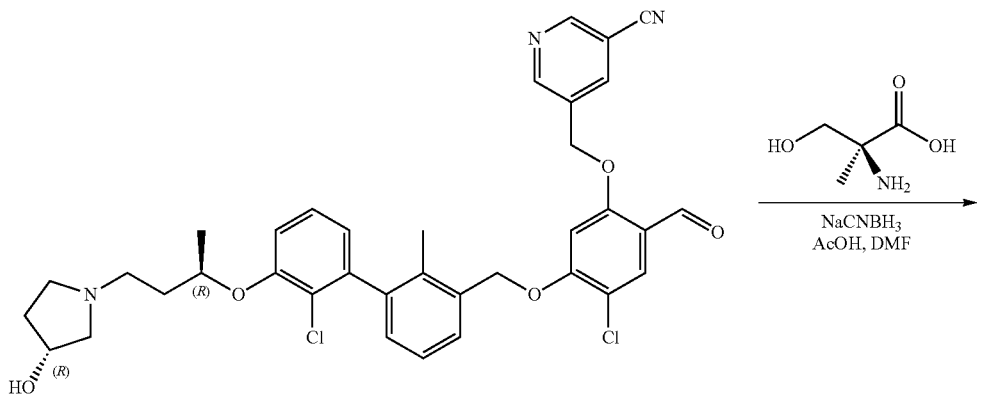

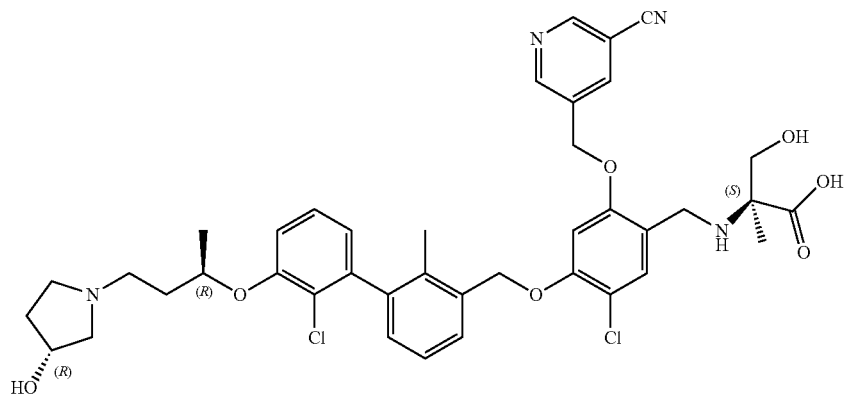

Example#1524

Neat acetic acid (0.018 mL, 0.322 mmol) was added to a stirred solution of 5-((4-chloro-5-((2'-chloro-3'-(((R)-4-((R)-3-hydroxypyrrolidin-1-yl)butan-2-yl)oxy)-2-methyl-[1,1'-biphenyl]-3-yl)methoxy)-2-formylphenoxy)methyl)nicotinonitrile (42.5 mg, 0.064 mmol) and (S)-2-amino-3-hydroxy-2-methylpropanoic acid (22.99 mg, 0.193 mmol) in DMF (1 mL) and the mixture was stirred at rt for 3 h, and then sodium cyanoborohydride (10.99 mg, 0.175 mmol) was added and the mixture was stirred at rt overnight. The reaction mixture was diluted with 5% TFA in MeOH and then submitted to purification. LCMS (Condition 1): Rt 1.547 min, m/z 763.1 [M+H]$^+$.

Example 1525

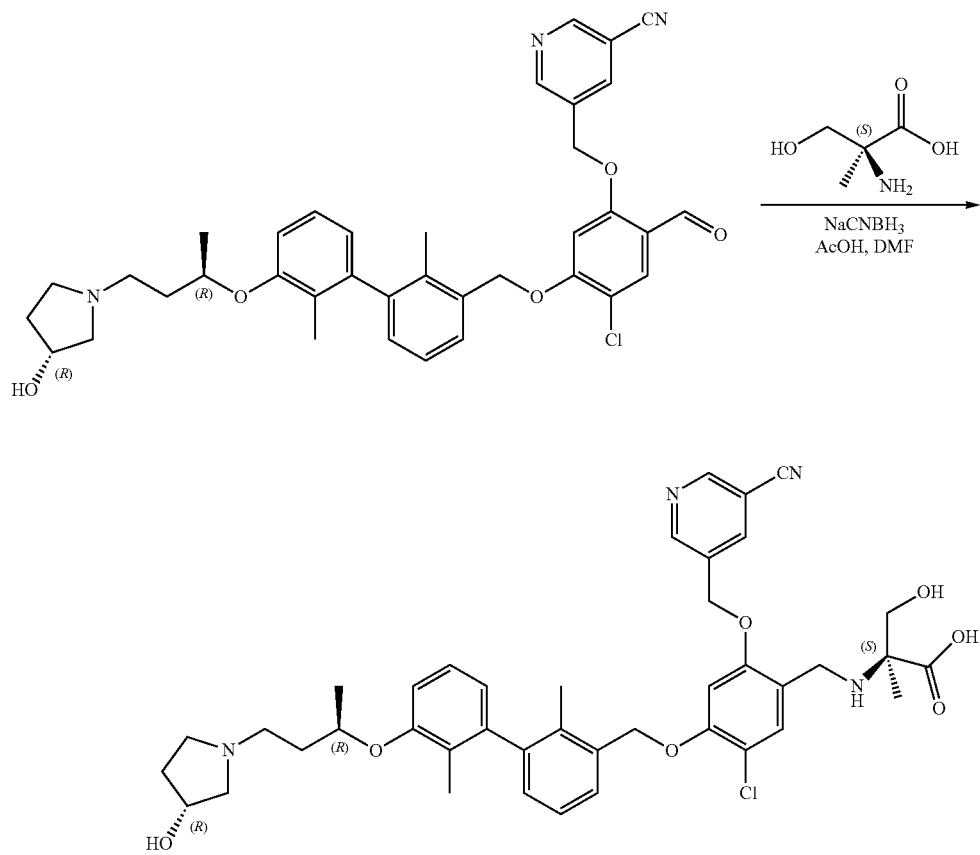

Example#1525

Neat acetic acid (0.023 mL, 0.401 mmol) was added to a stirred solution of 5-((4-chloro-2-formyl-5-((3'-(((R)-4-((R)-3-hydroxypyrrolidin-1-yl)butan-2-yl)oxy)-2,2'-dimethyl-[1,1'-biphenyl]-3-yl)methoxy)phenoxy)methyl)nicotinonitrile (51.3 mg, 0.080 mmol) and (S)-2-amino-3-hydroxy-2-methylpropanoic acid (28.6 mg, 0.240 mmol) in DMF (1 mL) and the mixture was stirred at rt for 3 h, and then sodium cyanoborohydride (11 mg, 0.175 mmol) was added and the mixture was stirred at rt overnight. The reaction mixture was diluted with 5% TFA in MeOH and purified by prep. HPLC to afford (S)-2-((5-chloro-2-((5-cyanopyridin-3-yl)methoxy)-4-((3'-(((R)-4-((R)-3-hydroxypyrrolidin-1-yl)butan-2-yl)oxy)-2,2'-dimethyl-[1,1'-biphenyl]-3-yl)methoxy)benzyl)amino)-3-hydroxy-2-methylpropanoic acid. LCMS (Condition 1): Rt 1.661 min, m/z 743.2 [M+H]$^+$.

Example 1526

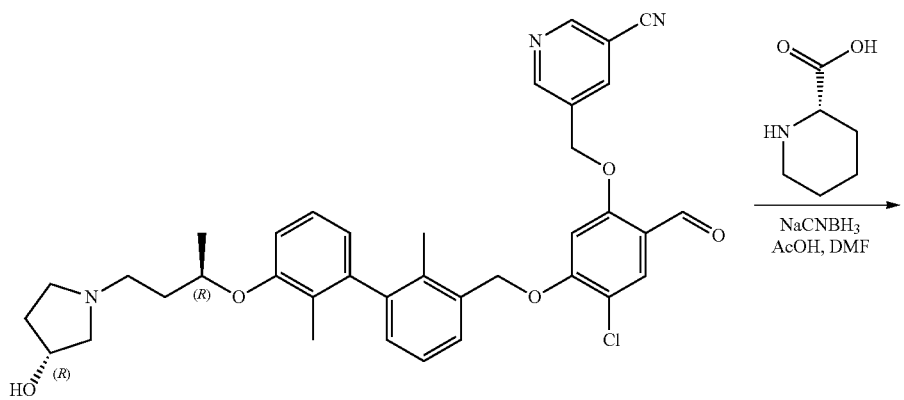

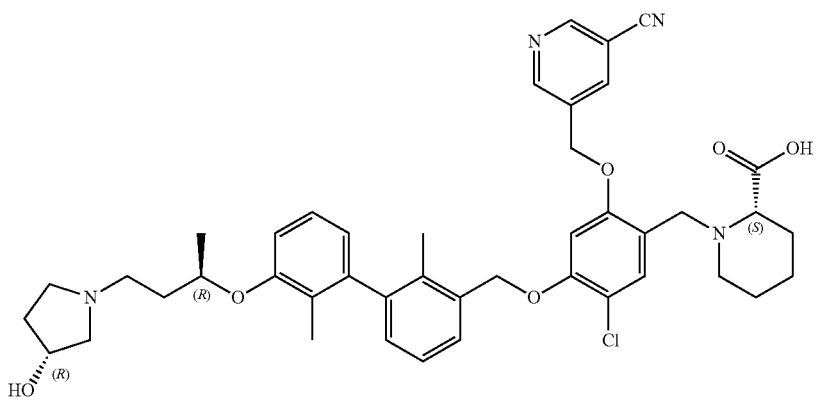

Example#1526

Neat acetic acid (0.032 mL, 0.553 mmol) was added to a stirred solution of 5-((4-chloro-2-formyl-5-((3'-(((R)-4-((R)-3-hydroxypyrrolidin-1-yl)butan-2-yl)oxy)-2,2'-dimethyl-[1,1'-biphenyl]-3-yl)methoxy)phenoxy)methyl)nicotinonitrile (70.8 mg, 0.111 mmol) and (S)-piperidine-2-carboxylic acid (42.9 mg, 0.332 mmol) in DMF (1 mL) and the mixture was stirred at rt for 3-4 h, and then sodium cyanoborohydride (20.85 mg, 0.332 mmol) was added and the mixture was stirred at rt overnight. The reaction mixture was diluted with 5% TFA in MeOH and purified by prep. HPLC to afford (S)-1-(5-chloro-2-((5-cyanopyridin-3-yl)methoxy)-4-((3'-(((R)-4-((R)-3-hydroxypyrrolidin-1-yl)butan-2-yl)oxy)-2,2'-dimethyl-[1,1'-biphenyl]-3-yl)methoxy)benzyl)piperidine-2-carboxylic acid. LCMS (Condition 1): Rt 1.721 min, m/z 753.2 [M+H]$^+$.

Example 1527

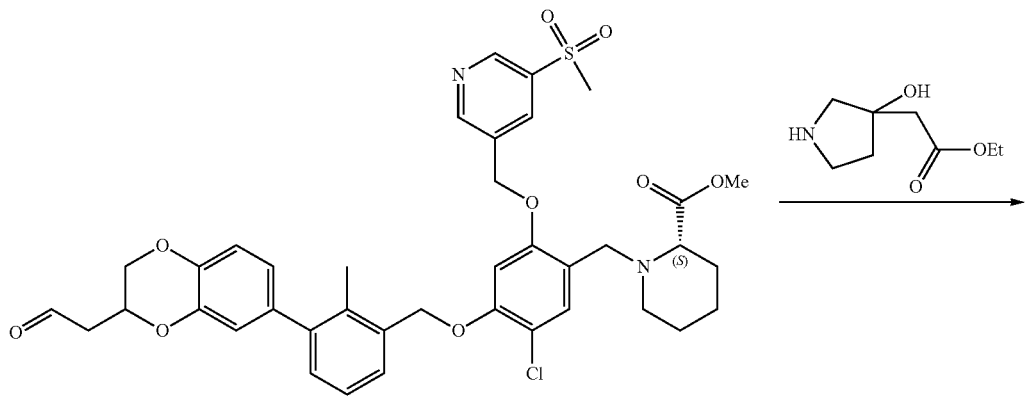

-continued

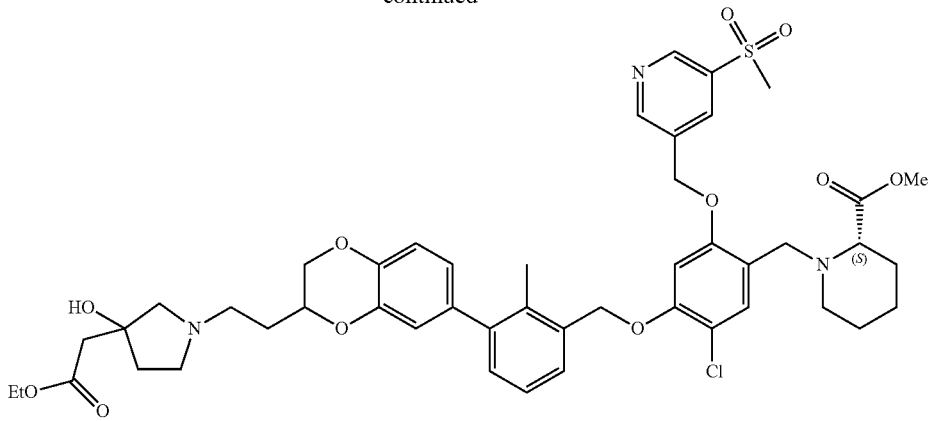

Example#1527

Neat TEA (0.044 mL, 0.316 mmol) was added to a solution of (2S)-methyl 1-(5-chloro-4-((2-methyl-3-(3-(2-oxoethyl)-2,3-dihydrobenzo[b][1,4]dioxin-6-yl)benzyl)oxy)-2-((5-(methylsulfonyl)pyridin-3-yl)methoxy)benzyl)piperidine-2-carboxylate (79 mg, 0.105 mmol) and ethyl 2-(3-hydroxypyrrolidin-3-yl)acetate, HCl (66.3 mg, 0.316 mmol) in DMF (1 mL) and the mixture stirred at rt overnight. Then acetic acid (0.018 mL, 0.316 mmol) and sodium cyanoborohydride (20 mg, 0.316 mmol) were added and the mixture was stirred at rt for 8 h. The reaction mixture was diluted with EtOAc, quenched with sat'ed. NaHCO₃, washed with water, brine, dried (Mg₂SO₄), concentrated and purified by prep. HPLC to afford (2S)-methyl 1-(5-chloro-4-((3-(3-(2-(3-(2-ethoxy-2-oxoethyl)-3-hydroxypyrrolidin-1-yl)ethyl)-2,3-dihydrobenzo[b][1,4]dioxin-6-yl)-2-methyl-benzyl)oxy)-2-((5-(methylsulfonyl)pyridin-3-yl)methoxy)benzyl)piperidine-2-carboxylate as a mixture of diastereomers. LC-MS (Condition 2): Rt 2.428 min; m/z 906.1 [M+H]⁺.

Example 1528

Neat acetic acid (0.028 mL, 0.487 mmol) was added to a stirred solution of (R)-5-((4-chloro-2-formyl-5-((5'-(3-(3-hydroxypyrrolidin-1-yl)propoxy)-2,2'-dimethyl-[1,1'-biphenyl]-3-yl)methoxy)phenoxy)methyl)nicotinonitrile (0.061 g, 0.097 mmol) and (S)-piperidine-2-carboxylic acid (0.044 g, 0.341 mmol) in DMF (1 mL) and the mixture was stirred at rt for 4 h, and then sodium cyanoborohydride (0.021 g, 0.341 mmol) was added and the mixture was stirred at rt overnight. The reaction was quenched with 5% TFA in MeOH and the crude isolate was purified by prep. HPLC to afford (S)-1-(5-chloro-2-((5-cyanopyridin-3-yl)methoxy)-4-((5'-(3-((R)-3-hydroxypyrrolidin-1-yl)propoxy)-2,2'-dimethyl-[1,1'-biphenyl]-3-yl)methoxy)benzyl)piperidine-2-carboxylic acid (26 mg). LCMS (Condition 1): Rt 1.870 min, m/z 739.1 [M+H]⁺

Example 1529 to Example 1535 were prepared in a similar manner as described. LCMS data were obtained with the following conditions.

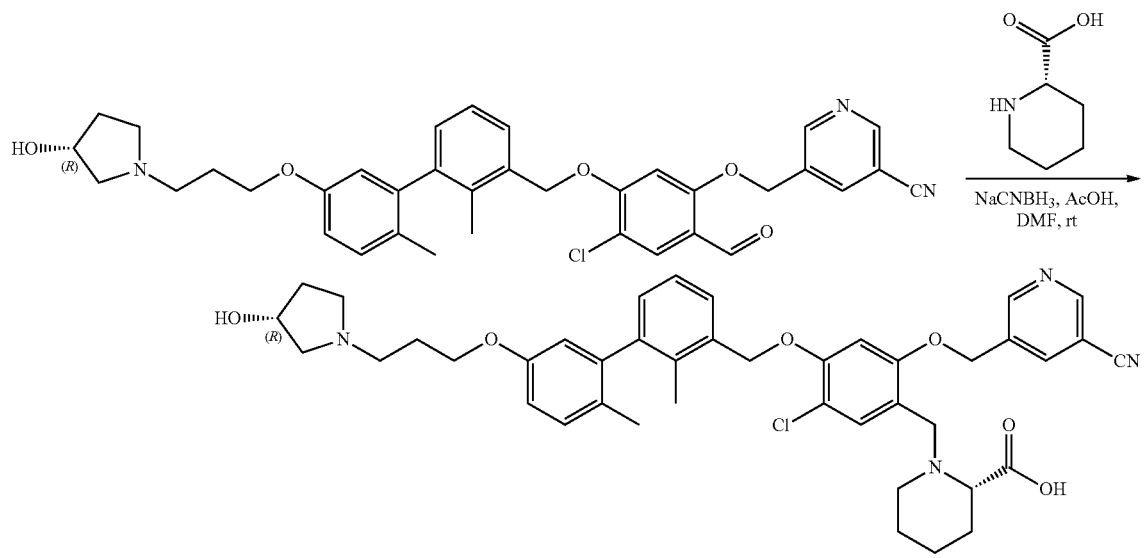

Example#1528

LC-MS Conditions 1:
Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1 mL/min; Detection: UV at 220 nm.

Example 1529: (S)-1-(5-chloro-2-(3-((R)-3-hydroxypyrrolidin-1-yl)propoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

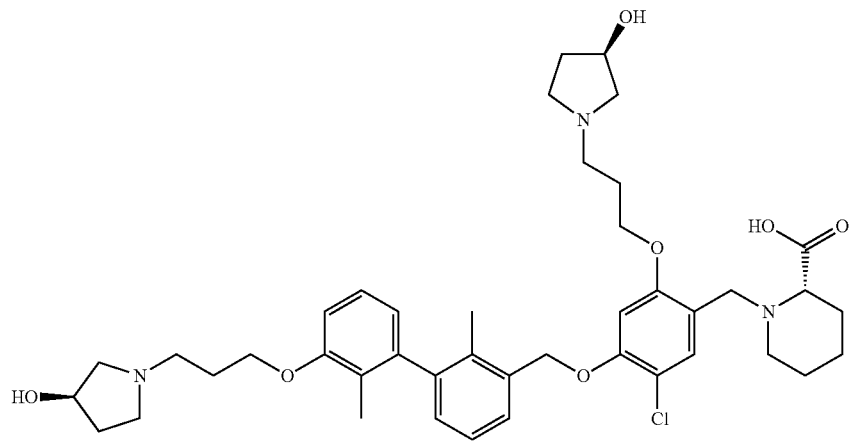 [SMILES: Cc1c(COc2cc(OCCCN3CC[C@@H](O)C3)c(CN3CCCC[C@H]3C(=O)O)cc2Cl)cccc1-c1cccc(OCCCN2CC[C@@H](O)C2)c1C]

LCMS (Condition 1): Rt=1.313 min, m/z=750.2 [M+H]$^+$.

Example 1530: (5-chloro-2-(3-((R)-3-hydroxypyrrolidin-1-yl)propoxy)-4-((3'-(3-((R)-3-hydroxypyrrolidin-1-yl)propoxy)-2,2'-dimethyl-[1,1'-biphenyl]-3-yl)methoxy)benzyl)-L-serine

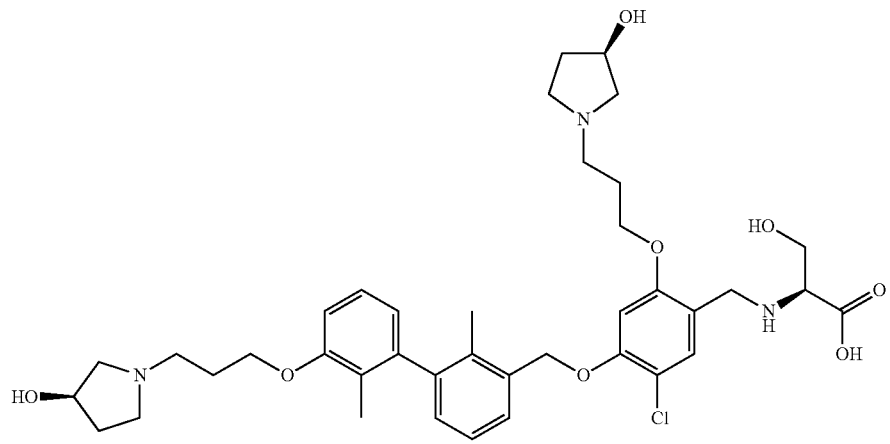 [SMILES: Cc1c(COc2cc(OCCCN3CC[C@@H](O)C3)c(CN[C@@H](CO)C(=O)O)cc2Cl)cccc1-c1cccc(OCCCN2CC[C@@H](O)C2)c1C]

LCMS (Condition 1): Rt=1.223 min, m/z=726.3 [M+H]$^+$.

Example 1531: (R)-2-((5-chloro-2-(3-((R)-3-hydroxypyrrolidin-1-yl)propoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic Acid

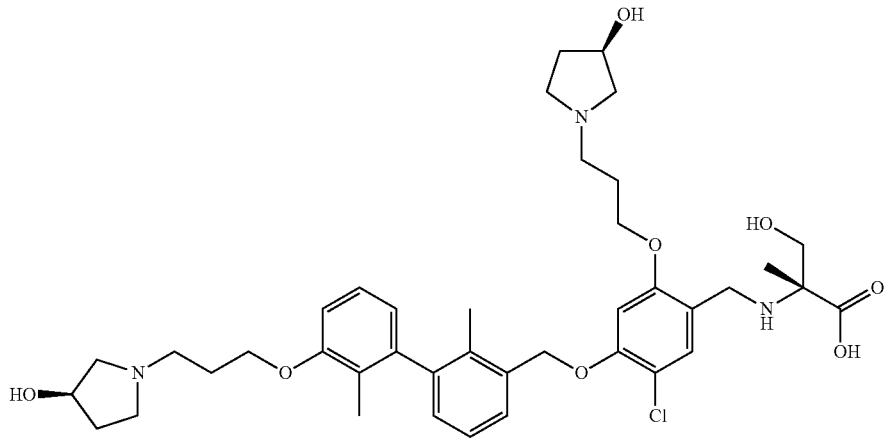 [SMILES: Cc1c(COc2cc(OCCCN3CC[C@@H](O)C3)c(CN[C@](C)(CO)C(=O)O)cc2Cl)cccc1-c1cccc(OCCCN2CC[C@@H](O)C2)c1C]

LCMS (Condition 1): Rt=1.463 min, m/z=740.2 [M+H]⁺.

Example 1532: (R)-2-((5-chloro-4-((2'-chloro-3'-(3-(3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)amino)-2-methylpropane-1,3-diol

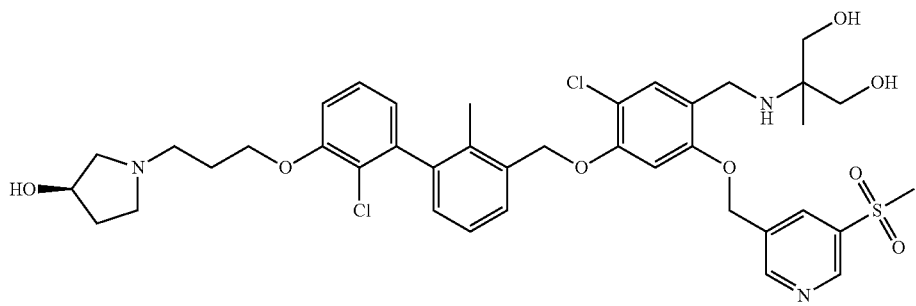 [SMILES: Cc1c(COc2cc(OCc3cncc(S(C)(=O)=O)c3)c(CNC(C)(CO)CO)cc2Cl)cccc1-c1cccc(OCCCN2CC[C@@H](O)C2)c1Cl]

LCMS (Condition 1): Rt=1.588 min, m/z=788.1 [M+H]⁺.

Example 1533: (R)-2-((5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-2-methylpropane-1,3-diol

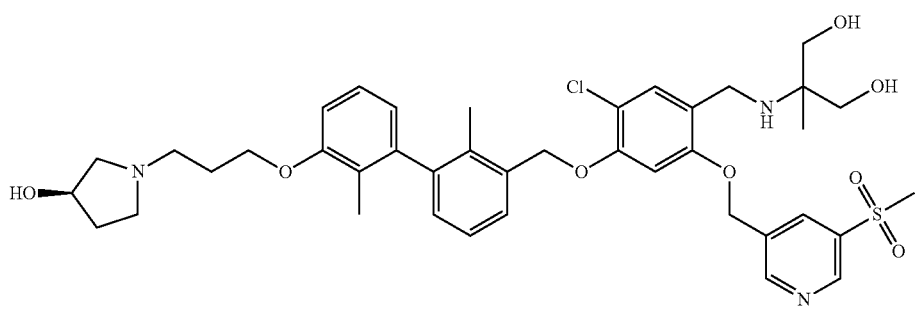 [SMILES: Cc1c(COc2cc(OCc3cncc(S(C)(=O)=O)c3)c(CNC(C)(CO)CO)cc2Cl)cccc1-c1cccc(OCCCN2CC[C@@H](O)C2)c1C]

LCMS (Condition 1): Rt=1.345 min, m/z=768.2[M+H]⁺.

Example 1534: 5-((4-chloro-5-((2'-fluoro-3'-(3-((R)-2-(hydroxymethyl)pyrrolidin-1-yl)propoxy)-2-methyl-[1,1'-biphenyl]-3-yl)methoxy)-2-(((R)-2-(hydroxymethyl)pyrrolidin-1-yl)methyl)phenoxy)methyl)nicotinonitrile

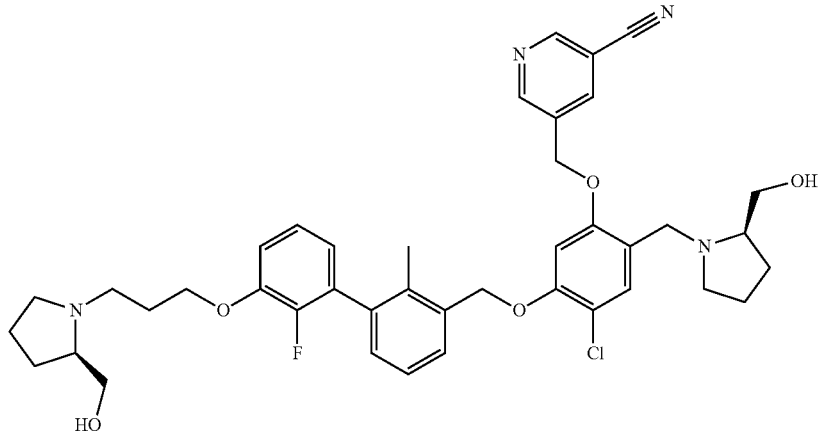 [SMILES: Cc1c(COc2cc(OCc3cncc(C#N)c3)c(CN3CCC[C@@H]3CO)cc2Cl)cccc1-c1cccc(OCCCN2CCC[C@@H]2CO)c1F]

LCMS (Condition 1): Rt=1.524 min, m/z=729.1 [M+H]+.

Example 1535: (S)-1-(5-chloro-4-(((2'-chloro-3'-(3-((R)-3-hydroxypyrrolidin-1-yl)propoxy)-2-methyl-[1,1'-biphenyl]-3-yl)oxy)methyl)-2-((5-cyanopyridin-3-yl)methoxy)benzyl)piperidine-2-carboxylic Acid

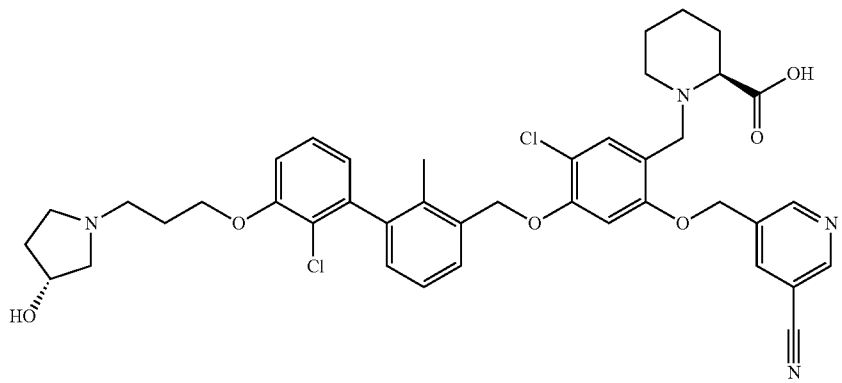 [SMILES: Cc1c(COc2cc(OCc3cncc(C#N)c3)c(CN3CCCC[C@H]3C(=O)O)cc2Cl)cccc1-c1cccc(OCCCN2CC[C@@H](O)C2)c1Cl]

LCMS (Condition 1): Rt=1.482 min, m/z=759.1 [M+H]+.

Examples 2001 to 2034 and Examples 2201 to 2277 were prepared as described below, and the HPLC LC/MS conditions employed for these examples were listed below:

LC/MS Condition A:
Column=Waters Aquity UPLC BEH C18, 2.1×50 mm, 1.7 μm
Start % B=2; Final % B=98
Gradient time=1.5 min; Stop time=2 or 2.5 min
Flow Rate=0.8 mL/min; Wavelength=220 nm or 254 nm
Solvent A=100% water/0.05% TFA
Solvent B=100% ACN/0.05% TFA (ACN=acetonitrile)
Oven temp.=40° C.
LC/MS Condition B:
Column=Phenomenex-Luna C18, 2.0×50 mm, 3 μm
Start % B=0; Final % B=100
Gradient time=4 min; Stop time=5 or 6 min
Flow Rate=0.8 mL/min; Wavelength=220 nm or 254 nm
Solvent A=5% ACN/95% water/10 mM NH4OAc
Solvent B=95% ACN/5% water/10 mM NH4OAc
Oven temp.=40° C.
LC/MS Condition C:
Column=Phenomenex-Luna C18, 2.0×50 mm, 3 am
Start % B=0; Final % B=100
Gradient time=4 min; Stop time=5 or 6 min
Flow Rate=0.8 mL/min; Wavelength=220 nm or 254 nm
Solvent A=10% MeOH/90% H2O/0.1% TFA
Solvent B=90% MeOH/10% H2O/0.1% TFA
Oven temp.=40° C.
LC/MS Condition D:
Column=Waters Aquity UPLC BEH C18, 2.1×50 mm, 1.7 μm
Start % B=2; Final % B=98
Gradient time=1.5 min; Stop time=1.6 min
Flow Rate=0.8 mL/min; Wavelength=220 nm or 254 nm
Solvent A=100% water/0.05% TFA
Solvent B=100% ACN/0.05% TFA
Oven temp.=50° C.
LC/MS Condition E:
Column=Waters Accquity UPLC BEH C18, 2.1×50 mm, 1.7-μm
Start % B=0; Final % B=100
Gradient time=3 min; Stop time=3.75 min
Flow rate=1.0 mL/min; Wavelength=220 nm
Solvent A=5% ACN/95% water/10 mM NH4OAc
Solvent B=95% ACN/5% water/10 mM NH4Oac Oven temp.=50° C.
LC/MS Condition F:
Column=Waters Acquity UPLC BEH C18, 2.1×50 mm, 1.7-µm
Start % B=0; Final % B=100
Gradient time=3 min; Stop time=3.75 min
Flow rate=1.0 mL/min; Wavelength=220 nm
Solvent A=5% ACN/95% water/0.1% TFA
Solvent B=95% ACN/5% water/0.1% TFA
Oven temp.=50° C.

Intermediate:
1-bromo-3-(3-bromopropoxy)-2-methylbenzene

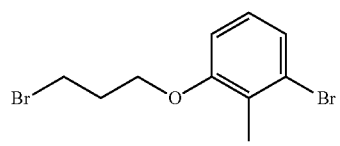

A magnetically stirred solution of 1,3-dibromopropane (61 g, 302 mmol) and 3-bromo-2-methylphenol (5.00 g, 26.7 mmol) in acetone (200 mL) is treated with potassium carbonate (9.8 g, 70.9 mmol). Stirred rt for seven days. The solids were filtered and washed with acetone (800 mL), and the filtrate evap'd in vacuo and then on high vacuum to remove excess 1,3-dibromopropane. The crude liquid was applied to the head of a 330 g Teledyne Isco Silica Flash Column (some hexanes, very little DCM mixed with mostly hexanes used to apply) and purified on Biotage using a gradient from 100% hexanes to 100% CH$_2$Cl$_2$ over 10 col vols (column volumes). The fractions containing the product were evaporated in vacuo then dried on high vacuum to give 13.35 g (92%) of the pure title compound as a colorless liquid.
$^1$H NMR (400 MHz, CHLOROFORM-d) δ 7.18 (dd, J=8.0, 0.8 Hz, 1H), 7.02 (t, J=8.2 Hz, 1H), 6.81 (d, J=8.3 Hz, 1H), 4.11 (t, J=5.8 Hz, 2H), 3.64 (t, J=6.4 Hz, 2H), 2.36 (t, J=5.9 Hz, 2H), 2.33 (s, 3H).

Intermediate: 2-(3-(3-bromopropoxy)-2-methylphenyl)-4,4,5,5-tetramethyl-1,3,2-dioxaborolane

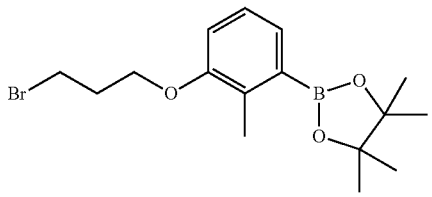 [SMILES: Cc1c(OCCCBr)cccc1B1OC(C)(C)C(C)(C)O1]

An oven dried 150 mL pressure bottle is charged with 2-(3-(3-bromopropoxy)-2-methylphenyl)-4,4,5,5-tetramethyl-1,3,2-dioxaborolane (5.30 g, 17.2 mmol), 4,4,4',4',5,5,5',5'-octamethyl-2,2'-bi(1,3,2-dioxaborolane) (7.3 g, 28.7 mmol), and potassium acetate (5.3 g, 54.0 mmol). Added dioxane (100 mL), bubbled in argon for 10 min, and added [1,1'-bis(diphenylphosphino)ferrocene]dichloropalladium(II) (825 mg, 1.128 mmol). The reaction is sealed and heated in a 80 C oil bath for 21 h. The reaction was treated with water (300 mL) and EtOAc (250 L), and filtered through diatomaceous earth (Celite®) to remove some dark solids. The pad was washed with ethyl acetate (300 mL), and layers partitioned. The organic layer was washed with brine, dried over sodium sulfate, evaporated to a dark oily solid. Applied in CH$_2$Cl$_2$/hex (hexanes) to the head of a 330 g Teledyne Isco Silica Flash Column and purified on Biotage using a gradient from 100% hexanes to 100% CH$_2$Cl$_2$ over 11 col vols. The fractions containing the product were evaporated in vacuo and dried on hi vacuum to give 4.36 g (71%) of the pure title compound as a white solid. $^1$H NMR (500 MHz, CHLOROFORM-d) δ 7.38 (d, J=7.3 Hz, 1H), 7.16 (t, J=7.8 Hz, 1H), 6.94 (d, J=8.1 Hz, 1H), 4.11 (t, J=5.7 Hz, 2H), 3.66 (t, J=6.5 Hz, 2H), 2.44 (s, 3H), 2.36 (quin, J=6.1 Hz, 2H), 1.37 (s, 12H).

Intermediate: 4-((3-bromo-2-methylbenzyl)oxy)-5-chloro-2-hydroxybenzaldehyde

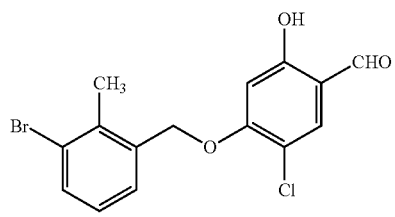 [SMILES: Cc1c(Br)cccc1COc1cc(O)c(C=O)cc1Cl]

(E)-Diisopropyl diazene-1,2-dicarboxylate (3.02 g, 14.92 mmol) was added dropwise to a magnetically stirred solution of (3-bromo-2-methylphenyl)methanol (3.00 g, 14.92 mmol), 5-chloro-2,4-dihydroxybenzaldehyde (2.57 g, 14.92 mmol) and triphenylphosphine (3.91 g, 14.92 mmol) in THF (80 mL) at 0° C. under N2. The resulting yellow solution was allowed to warm to rt and stirred for 2 days under nitrogen. The reaction mixture (just a little bit cloudy) was concentrated and the residue was triturated with cold THF, filtered to collect 2.49 g, 45%) of the pure title compound as white solid: $^1$H NMR (400 MHz, CHLOROFORM-d) δ 11.44 (s, 1H), 9.71 (d, J=0.5 Hz, 1H), 7.60 (dd, J=8.0, 0.8 Hz, 1H), 7.55-7.51 (m, 1H), 7.41 (s, 1H), 7.11 (t, J=7.9 Hz, 1H), 6.59 (s, 1H), 5.17 (s, 2H), 2.46 (s, 3H). LCMS: M-1=353, 355, 357. LC/MS Condition B: ret time 3.68 min; m/e=353, 355 (M−H)$^-$. (ret time=retention time)

Intermediate: 5-((5-((3-bromo-2-methylbenzyl)oxy)-4-chloro-2-formylphenoxy)methyl)nicotinonitrile

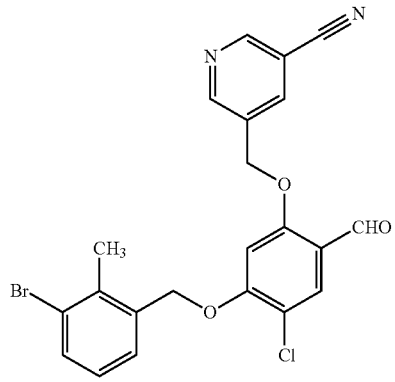 [SMILES: Cc1c(Br)cccc1COc1cc(OCc2cncc(C#N)c2)c(C=O)cc1Cl]

A magnetically stirred mixture of 4-((3-bromo-2-methylbenzyl)oxy)-5-chloro-2-hydroxybenzaldehyde (2.48 g, 6.97 mmol), 5-(chloromethyl)nicotinonitrile (1.277 g, 8.37 mmol) and cesium carbonate (2.73 g, 8.37 mmol), sodium iodide (0.105 g, 0.697 mmol) in dry DMF (25 mL) was heated under $N_2$ at 75° C. for 3 h. The reaction mixture was poured into 150 ml of ice-water and stirred for 20 min. The precipitate was collected by filtration, the cake was washed with minimum amount of cold EtOAc, and dried under vacuum to give 3.17 g, 96%) of the title compound as an off-white solid: $^1$H NMR (400 MHz, DMSO-$d_6$) δ 10.23 (s, 1H), 9.03 (dd, J=5.6, 2.1 Hz, 2H), 8.54 (t, J=2.0 Hz, 1H), 7.73 (s, 1H), 7.66-7.61 (m, 1H), 7.52 (d, J=7.0 Hz, 1H), 7.25 (s, 1H), 7.19 (t, J=7.8 Hz, 1H), 5.48 (s, 2H), 5.42 (s, 2H), 2.42 (s, 3H). LC/MS Condition B: ret time 3.71 min; m/e=471, 473 (M+H)$^+$.

Intermediate: 5-((5-((3'-(3-bromopropoxy)-2,2'-dimethyl-[1,1'-biphenyl]-3-yl)methoxy)-4-chloro-2-formylphenoxy)methyl)nicotinonitrile

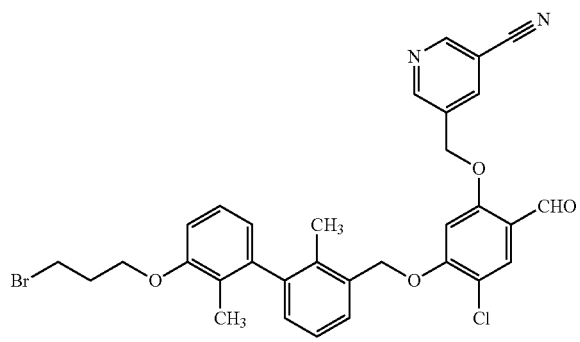 [SMILES: Cc1c(COc2cc(OCc3cncc(C#N)c3)c(C=O)cc2Cl)cccc1-c1cccc(OCCCBr)c1C]

A magnetically stirred solution of 2-(3-(3-bromopropoxy)-2-methylphenyl)-4,4,5,5-tetramethyl-1,3,2-dioxaborolane (0.403 g, 1.134 mmol) in freshly distilled THF (15 mL) was treated with 5-((5-((3-bromo-2-methylbenzyl)oxy)-4-chloro-2-formylphenoxy)methyl)nicotinonitrile (0.5 g, 1.060 mmol), degassed potassium phosphate tribasic 0.5 M (2.12 mL, 1.060 mmol), and 2nd Generation XPhos Precatalyst (0.042 g, 0.053 mmol) at room temperature under $N_2$. The resulting mixture was flushed with N2 for a two min, the reaction flask was sealed, and stirred at rt for 18 h. The reaction mixture was filtered and washed with EtOAc and water. The combined filtrate was partitioned between EtOAc/aqueous sodium bicarbonate. The aqueous layer was extracted with EtOAc. The combined organic layers were twice washed with aqueous sodium bicarbonate and brine, dried over magnesium sulfate, filtered and concentrated in vacuo. The residue was sonicated with 10 ml of MeOH, and the precipitate was collected to give 0.15 g of the title compound as a light-yellow solid. Additional 0.37 g of title compound was obtained by silica gel chromatography (Biotage Horizon System; RediSepRf 80 40 24 12 g column; EtOAc/Hexane, Gradient: 0%-50%) to give a total of 0.52 g (79%): $^1$H NMR (400 MHz, CHLOROFORM-d) δ 10.29 (s, 1H), 8.92 (dd, J=3.6, 2.1 Hz, 2H), 8.11 (t, J=2.0 Hz, 1H), 7.94 (s, 1H), 7.45 (d, J=6.5 Hz, 1H), 7.32-7.28 (m, 1H), 7.23-7.16 (m, 2H), 6.89 (d, J=7.8 Hz, 1H), 6.79-6.73 (m, 1H), 6.66 (s, 1H), 5.25 (d, J=14.8 Hz, 4H), 4.25-4.14 (m, 2H), 3.67 (t, J=6.5 Hz, 2H), 2.43-2.35 (m, 2H), 2.11 (s, 3H), 1.92 (s, 3H), 1.25 (s, 2H) LCMS: M+1=619. LC/MS Condition B: ret time 4.13 min; m/e=619, 621 (M+H)$^+$.

Intermediate: (2S)-1-(4-((3'-(3-bromopropoxy)-2,2'-dimethylbiphenyl-3-yl)methoxy)-5-chloro-2-((5-cyanopyridin-3-yl)methoxy)benzyl)piperidine-2-carboxylic Acid

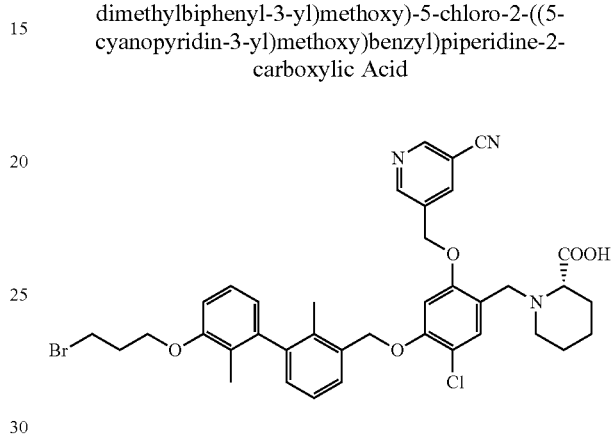

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (0.3 g, 0.484 mmol) and (S)-piperidine-2-carboxylic acid/L-pipecolinic acid (0.125 g, 0.968 mmol) in 1,2-dichloroethane (3 mL) and ethanol (7 mL) was added acetic acid (0.055 mL, 0.968 mmol). The resulting mixture was stirred at rt for 3 h. Sodium cyanoborohydride (0.968 mL, 0.968 mmol, 1.0 M in THF) diluted with THF (3 mL) was added through a syringe over 16 h. LCMS (M+1=732.1) showed desired product with purity of ~38%. The crude reaction mixture was subdivided and was used for the preparation of Example 2202 and other similar derivatives. LC/MS Condition D: ret time 1.03 min; m/e=732.1 (M+H)$^+$.

Intermediate: (2S)-2-(4-((3'-(3-bromopropoxy)-2,2'-dimethylbiphenyl-3-yl)methoxy)-5-chloro-2-((5-cyanopyridin-3-yl)methoxy)benzylamino)-3-hydroxy-2-methylpropanoic Acid

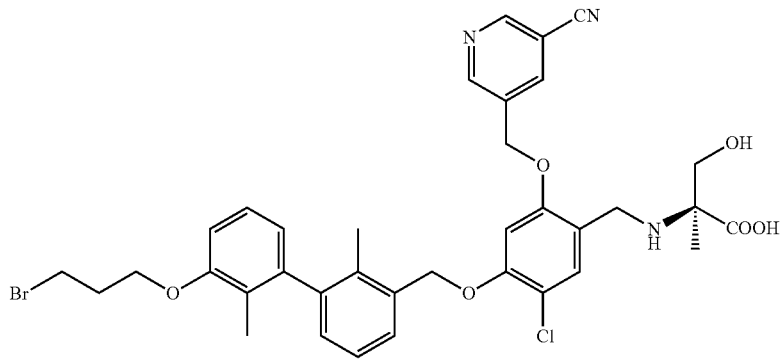 [SMILES: Cc1c(COc2cc(OCc3cncc(C#N)c3)c(CN[C@@](C)(CO)C(=O)O)cc2Cl)cccc1-c1cccc(OCCCBr)c1C]

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (0.3 g, 0.484 mmol) and (S)-2-amino-3-hydroxy-2-methylpropanoic acid/2-methyl-L-serine (0.115 g, 0.968 mmol) in 1,2-dichloroethane (5 mL) and EtOH (10 mL) was added acetic acid (0.055 mL, 0.968 mmol) and ~0.05 g of 4 Å molecule sieves was added and the resulting mixture was stirred at rt for 4 h. Sodium cyanoborohydride (0.581 mL, 0.581 mmol, 1.0 M in THF) diluted with THF (2.5 mL) was added through a syringe over 18 h. LCMS showed a peak of ~18% with M+1=722, consistant with the desired product. The reaction mixture was subdivided and was used for the preparation of Example 2260 and other similar derivatives. LC/MS Condition D: ret time 0.98 min; m/e=722 (M+H)$^+$.

Intermediate: 1-bromo-3-(3-bromopropoxy)-2-chlorobenzene

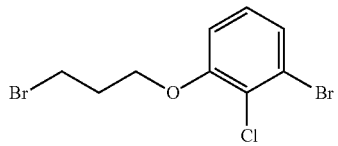

Using the same method described herein for the preparation of 1-bromo-3-(3-bromopropoxy)-2-methylbenzene, 3-bromo-2-chlorophenol (10 g, 48.2 mmol) and 1,3-dibromopropane (166 g, 822 mmol) were used to prepare 13.3 g (84%) of the pure title compound as a colorless liquid: $^1$H NMR (500 MHz, CHLOROFORM-d) δ 7.29-7.25 (m, 1H), 7.11 (t, J=8.2 Hz, 1H), 6.92 (dd, J=8.2, 1.2 Hz, 1H), 4.20 (t, J=5.7 Hz, 2H), 3.69 (t, J=6.3 Hz, 2H), 2.39 (quin, J=6.0 Hz, 2H).

Intermediate: 2-(3-(3-bromopropoxy)-2-chlorophenyl)-4,4,5,5-tetramethyl-1,3,2-dioxaborolane

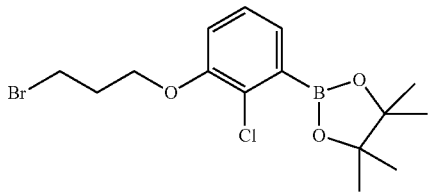 [SMILES: CC1(C)OB(c2cccc(OCCCBr)c2Cl)OC1(C)C]

Using the same method described herein for the preparation of 2-(3-(3-bromopropoxy)-2-methylphenyl)-4,4,5,5-tetramethyl-1,3,2-dioxaborolane, 1-bromo-3-(3-bromopropoxy)-2-chlorobenzene (11.30 g, 34.4 mmol), 4,4,4',4',5,5,5',5'-octamethyl-2,2'-bi(1,3,2-dioxaborolane) (14.9 g, 58.7 mmol), and potassium acetate (10.5 g, 107 mmol) were used to prepare 7.4 g (57%) of the pure title compound as a colorless solid: $^1$H NMR (500 MHz, CHLOROFORM-d) δ 7.30-7.26 (m, 1H), 7.24-7.19 (m, 1H), 7.05-7.01 (m, 1H), 4.18 (t, J=5.6 Hz, 2H), 3.69 (t, J=6.3 Hz, 2H), 2.37 (quin, J=6.0 Hz, 2H), 1.40 (s, 12H).

Intermediate: 5-chloro-2-hydroxy-4-((2-methyl-3-(4,4,5,5-tetramethyl-1,3,2-dioxaborolan-2-yl)benzyl)oxy)benzaldehyde

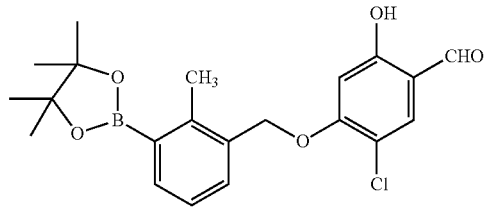 [SMILES: Cc1c(COc2cc(O)c(C=O)cc2Cl)cccc1B1OC(C)(C)C(C)(C)O1]

A magnetically stirred solution of (2-methyl-3-(4,4,5,5-tetramethyl-1,3,2-dioxaborolan-2-yl)phenyl)methanol (8.0 g, 32.2 mmol), 5-chloro-2,4-dihydroxybenzaldehyde (5.56 g, 32.2 mmol), and triphenylphosphine (11.4 g, 43.5 mmol) in freshly distilled anhydrous THF (250 mL) is cooled in an ice/water bath and slowly (over 30 min) treated with DIAD (8.0 mL, 41.1 mmol). The reaction is flushed with Ar, sealed, and allowed to stir overnight while slowly warming to room temp. The reaction is evaporated in vacuo to a thick oil and then applied in CH$_2$Cl$_2$/hex to the head of a 120 g Teledyne Isco Silica Flash Column and purified on Biotage using a gradient from 100% hexanes to 40% EtOAc in hexanes over 12 column volumes. The fractions containing the product were evaporated in vacuo and dried on high vacuum to give 5.5 g (42%) of the pure title compound as a white solid: $^1$H NMR (500 MHz, CHLOROFORM-d) δ 11.43 (s, 1H), 9.71 (s, 1H), 7.80 (d, J=7.5 Hz, 1H), 7.60-7.47 (m, 2H), 7.25 (t, J=7.5 Hz, 1H), 6.61 (s, 1H), 5.19 (s, 2H), 2.59 (s, 3H), 1.39 (s, 12H).

Intermediate: 5-((4-chloro-2-formyl-5-((2-methyl-3-(4,4,5,5-tetramethyl-1,3,2-dioxaborolan-2-yl)benzyl)oxy)phenoxy)methyl)nicotinonitrile

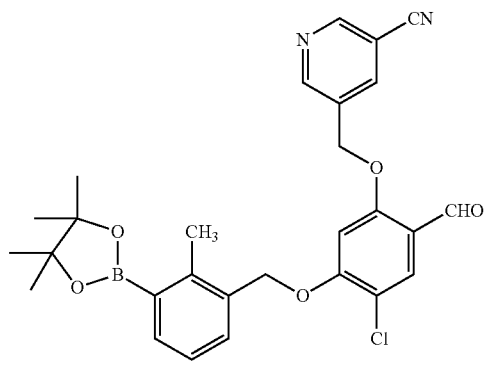 [SMILES: Cc1c(COc2cc(OCc3cncc(C#N)c3)c(C=O)cc2Cl)cccc1B1OC(C)(C)C(C)(C)O1]

To a magnetically stirred solution of 5-chloro-2-hydroxy-4-((2-methyl-3-(4,4,5,5-tetramethyl-1,3,2-dioxaborolan-2-yl)benzyl)oxy)benzaldehyde (2.76 g, 6.85 mmol) in anhydrous DMF (40 mL) is added 5-(chloromethyl)nicotinonitrile (1.26 g, 8.26 mmol), followed by cesium carbonate (3.35 g, 10.28 mmol). The reaction is flushed well with N$_2$, securely capped, and placed into a 75° C. oil bath. After 2.75 h, the reaction is cooled and partitioned with EtOAc (200 mL) and water (150 mL). The aqueous layer is extracted with additional EtOAc (200 mL). The combined the organic layers were washed with brine (2×50 mL), dried over Na$_2$SO$_4$, filtered, and evaporate in vacuo. The residue is dissolved in CH$_2$Cl$_2$ (15 mL) and applied to the head of a 80 g Teledyne Isco Silica Flash Column and purified on Biotage using a gradient from 100% CH$_2$Cl$_2$ to 25% EtOAc/CH$_2$Cl$_2$ over 8 column volumes. The fractions containing the product were evaporated in vacuo then dried on high vacuum to give 1.92 g (54%) of the pure title compound as an off-white solid: $^1$H NMR (500 MHz, CHLOROFORM-d) δ 10.29 (s, 1H), 8.91 (dd, J=11.7, 2.1 Hz, 2H), 8.07 (t, J=2.1 Hz, 1H), 7.93 (s, 1H), 7.81 (dd, J=7.5, 1.2 Hz, 1H), 7.47 (d, J=6.6 Hz, 1H), 7.24 (t, J=7.6 Hz, 1H), 6.57 (s, 1H), 5.24 (s, 2H), 5.19 (s, 2H), 2.60 (s, 3H), 1.39 (s, 12H).

Intermediate: 5-((5-((3'-(3-bromopropoxy)-2'-chloro-2-methyl-[1,1'-biphenyl]-3-yl)methoxy)-4-chloro-2-formylphenoxy)methyl)nicotinonitrile

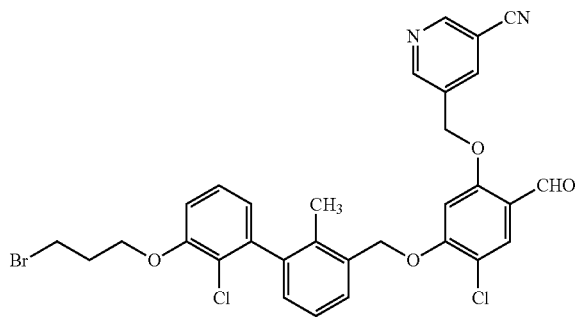

Using the method described herein for the preparation of 5-((5-((3'-(3-bromopropoxy)-2,2'-dimethyl-[1,1'-biphenyl]-3-yl)methoxy)-4-chloro-2-formylphenoxy)methyl)nicotinonitrile, 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (1.92 g, 3.70 mmol) and 1-bromo-3-(3-bromopropoxy)-2-chlorobenzene (1.3 g, 3.96 mmol) were used to prepare 2.0 g (84%) of the pure title compound as a colorless solid: $^1$H NMR (500 MHz, CHLOROFORM-d) δ 10.29 (s, 1H), 8.92 (dd, J=9.6, 2.0 Hz, 2H), 8.09 (t, J=2.1 Hz, 1H), 7.95 (s, 1H), 7.49 (d, J=7.0 Hz, 1H), 7.35-7.30 (m, 2H), 7.23-7.19 (m, 1H), 7.02 (dd, J=8.2, 1.4 Hz, 1H), 6.90 (dd, J=7.6, 1.4 Hz, 1H), 6.62 (s, 1H), 5.36-5.26 (m, 2H), 5.23-5.16 (m, 2H), 4.31-4.22 (m, 2H), 3.71 (t, J=6.3 Hz, 2H), 2.43 (quin, J=6.1 Hz, 2H), 2.17 (s, 3H). LC/MS Condition C: ret time 5.00 min; m/e=639 (M+H)$^+$.

Intermediate: (3'-(3-bromopropoxy)-2,2'-dichloro-[1,1'-biphenyl]-3-yl)methanol

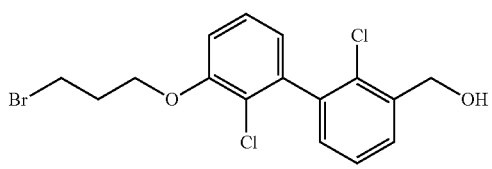

Using the method described herein for the preparation of 5-((5-((3'-(3-bromopropoxy)-2,2'-dimethyl-[1,1'-biphenyl]-3-yl)methoxy)-4-chloro-2-formylphenoxy)methyl)nicotinonitrile, 2-(3-(3-bromopropoxy)-2-chlorophenyl)-4,4,5,5-tetramethyl-1,3,2-dioxaborolane (2.56 g, 6.82 mmol) and (3-bromo-2-chlorophenyl)methanol (1.510 g, 6.82 mmol) were used to prepare 2.44 g (92%) of the pure title compound as a viscous oil: $^1$H NMR (500 MHz, CHLOROFORM-d) δ 7.60-7.55 (m, 1H), 7.38 (t, J=7.6 Hz, 1H), 7.33-7.27 (m, 1H), 7.23 (dd, J=7.6, 1.7 Hz, 1H), 7.03 (dd, J=8.2, 1.4 Hz, 1H), 6.90 (dd, J=7.8, 1.4 Hz, 1H), 4.88 (d, J=6.4 Hz, 2H), 4.25 (td, J=5.8, 2.4 Hz, 2H), 3.71 (td, J=6.4, 1.4 Hz, 2H), 2.52-2.33 (m, 2H), 2.01 (t, J=6.4 Hz, 1H).

Intermediate: 4-((3'-(3-bromopropoxy)-2,2'-dichloro-[1,1'-biphenyl]-3-yl)methoxy)-5-chloro-2-hydroxybenzaldehyde

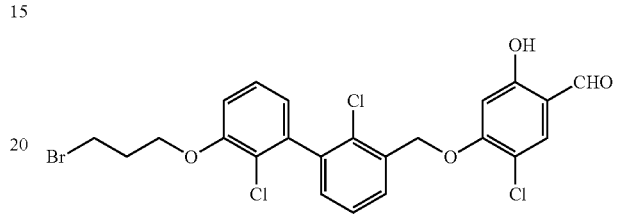

A magnetically stirred solution of (3'-(3-bromopropoxy)-2,2'-dichloro-[1,1'-biphenyl]-3-yl)methanol (1.33 g, 3.41 mmol), 5-chloro-2,4-dihydroxybenzaldehyde (0.588 g, 3.41 mmol) and triphenylphosphine (985 mg, 3.76 mmol) in freshly distilled anhydrous THF (50 mL) under continuos argon flush is cooled in an ice bath. Slowly, over 2 h, DIAD (690 µL, 3.55 mmol) is added. Removed cooling bath and let stir at rt overnight. The solvent is evaporated and the residue dissolved in CH$_2$Cl$_2$ and applied to the head of a 120 g Teledyne Isco Silica Flash Column and purified on Biotage using a gradient from 100% hexanes to 100% CH$_2$Cl$_2$ over 12 col vols. The fractions containing the product were evaporated in vacuo then dried on high vacuum to give 950 mg (51%) of the pure title compound as a white solid: $^1$H NMR (500 MHz, CHLOROFORM-d) δ 11.43 (s, 1H), 9.74 (s, 1H), 7.75-7.70 (m, 1H), 7.60 (s, 1H), 7.43 (t, J=7.6 Hz, 1H), 7.35-7.29 (m, 2H), 7.04 (dd, J=8.3, 1.3 Hz, 1H), 6.93 (dd, J=7.6, 1.4 Hz, 1H), 6.64 (s, 1H), 5.36 (s, 2H), 4.26 (td, J=5.8, 2.6 Hz, 2H), 3.71 (td, J=6.3, 1.5 Hz, 2H), 2.48-2.39 (m, 2H). LC/MS Condition A: ret time 1.59 min; m/e=545 (M+H)$^+$.

Intermediate: 5-((4-chloro-5-((2,2'-dichloro-3'-(3-chloropropoxy)-[1,1'-biphenyl]-3-yl)methoxy)-2-formylphenoxy)methyl)nicotinonitrile

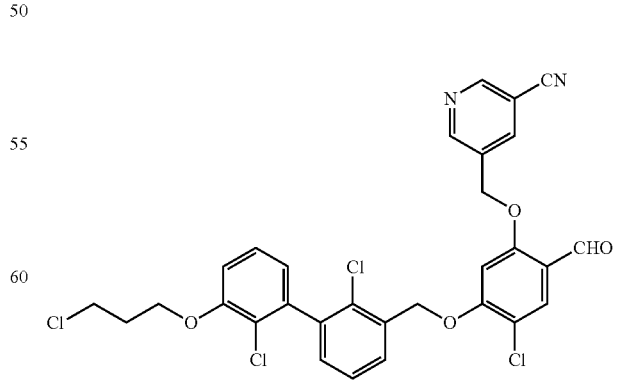

A magnetically stirred mixture of 4-((3'-(3-bromopropoxy)-2,2'-dichloro-[1,1'-biphenyl]-3-yl)methoxy)-5- chloro-2-hydroxybenzaldehyde (580 mg, 1.07 mmol), 5-(chloromethyl)nicotinonitrile (195 mg, 1.28 mmol) and cesium carbonate (520 mg, 1.60 mmol) in dry DMF (mL) was heated under $N_2$ at 75° C. for 3.5 h. The reaction mixture was poured into 100 mL of ice-water and stirred for 20 min. The precipitate was collected by filtration, the cake was washed with minimum amount of cold EtOAc, and dried under vacuum to give 465 mg (96%) of the title compound as a pale yellow solid as a mixture of aliphatic chloro and bromo analogs (predominantly chloro): $^1$H NMR (500 MHz, CHLOROFORM-d) δ 10.29 (s, 1H), 8.91 (dd, J=7.7, 2.1 Hz, 2H), 8.06 (t, J=2.1 Hz, 1H), 7.95 (s, 1H), 7.72-7.68 (m, 1H), 7.44 (t, J=7.7 Hz, 1H), 7.36-7.30 (m, 2H), 7.06 (dd, J=8.2, 1.4 Hz, 1H), 6.91 (dd, J=7.6, 1.2 Hz, 1H), 6.62 (s, 1H), 5.54-5.43 (m, 2H), 5.19 (s, 2H), 4.30-4.23 (m, 2H), 3.84 (t, J=6.3 Hz, 2H), 2.40-2.28 (m, 2H). LC/MS Condition A: ret time 1.54 min; m/e=617 (M+H)$^+$.

Example 2001: 5-((4-chloro-5-((2'-chloro-3'-(3-((R)-3-hydroxypyrrolidin-1-yl)propoxy)-2-methyl-[1,1'-biphenyl]-3-yl)methoxy)-2-(((R)-3-hydroxypyrrolidin-1-yl)methyl)phenoxy)methyl)nicotinonitrile gently stirred at room temp overnight. The solvent was removed under a stream of N2 and the residue was redissolved in MeOH (1.5 mL). The resulting solution was treated with (R)-3-hydroxypyrrolidine HCl (103 mg, 0.833 mmol) and N,N-diisopropylethylamine (225 µL, 1.288 mmol). The reaction was briefly flushed with N2, securely capped, sonicated for 10 sec, and placed in a 65° C. sand bath with shaking for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound: (11.2 mg, 18%). $^1$H NMR (500 MHz, DMSO-d$_6$) δ 9.00 (d, J=13.9 Hz, 2H), 8.43 (s, 1H), 7.53 (d, J=7.3 Hz, 1H), 7.40-7.27 (m, 3H), 7.17 (d, J=8.4 Hz, 1H), 7.14-7.07 (m, 2H), 6.85 (d, J=7.3 Hz, 1H), 5.32 (s, 2H), 5.26 (br d, J=4.4 Hz, 2H), 4.23-4.11 (m, 4H), 2.71-2.64 (m, 2H), 2.57 (br s, 4H), 2.48-2.40 (m, 2H), 2.32

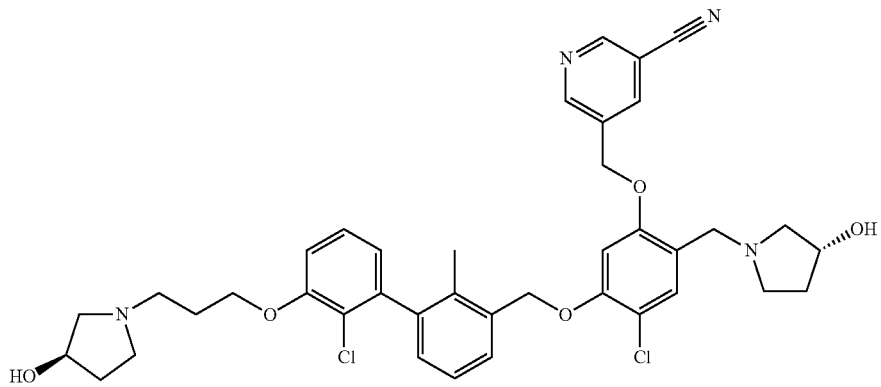 [SMILES: Cc1c(COc2cc(OCc3cncc(C#N)c3)c(CN3CC[C@@H](O)C3)cc2Cl)cccc1-c1cccc(OCCCN2CC[C@@H](O)C2)c1Cl]

To a solution of 5-((5-((3'-(3-bromopropoxy)-2'-chloro-2-methyl-[1,1'-biphenyl]-3-yl)methoxy)-4-chloro-2-formyl-phenoxy)methyl)nicotinonitrile (50 mg, 0.078 mmol), and (R)-3-hydroxypyrrolidine hydrochloride (30 mg, 0.243 mmol) in a mixture of DCE (0.75 mL) and EtOH (1.5 mL) was added acetic acid (9 µL, 0.157 mmol) and 4 A molecular sieves (2 pieces). The resulting solution was stirred at room temp for 45 min, then treated dropwise (over 15 min) with sodium cyanoborohydride, 1.0 M in THF (156 µL, 0.156 mmol). After the addition was complete, the reaction was (td, J=9.2, 3.7 Hz, 2H), 2.03-1.96 (m, 2H), 1.91 (s, 8H), 1.54 (br s, 2H)

LC/MS Condition E: ret time 1.52 min; m/e=717 (M+H)$^+$.
LC/MS Condition F: ret time 1.37 min; m/e=717 (M+H)$^+$.

Example 2002: (R)-5-((4-chloro-5-((2'-chloro-3'-(3-(3-hydroxypyrrolidin-1-yl)propoxy)-2-methyl-[1,1'-biphenyl]-3-yl)methoxy)-2-(hydroxymethyl)phenoxy)methyl)nicotinonitrile

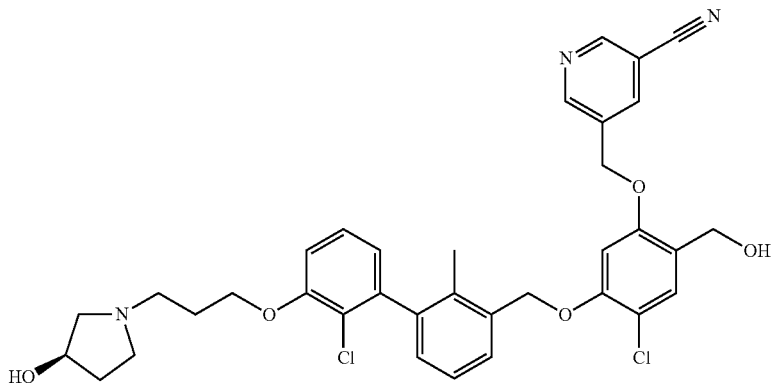 [SMILES: Cc1c(COc2cc(OCc3cncc(C#N)c3)c(CO)cc2Cl)cccc1-c1cccc(OCCCN2CC[C@@H](O)C2)c1Cl]

From Example 2001, the above product was also isolated via preparative LC/MS using the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound: (12.4 mg, 25%). ¹H NMR (500 MHz, DMSO-d₆) δ 9.08-8.92 (m, 2H), 8.43 (s, 1H), 7.52 (d, J=7.3 Hz, 1H), 7.40-7.33 (m, 2H), 7.29 (t, J=7.7 Hz, 1H), 7.17 (d, J=8.1 Hz, 1H), 7.14-7.07 (m, 2H), 6.85 (d, J=7.7 Hz, 1H), 5.32 (s, 2H), 5.26 (d, J=4.4 Hz, 2H), 4.48 (s, 2H), 4.26-4.09 (m, 4H), 2.70 (dd, J=9.9, 6.2 Hz, 1H), 2.62-2.55 (m, 3H), 2.43 (br d, J=8.4 Hz, 1H), 2.32 (dd, J=9.5, 3.3 Hz, 1H), 2.08 (s, 3H), 2.02-1.93 (m, 2H), 1.60-1.47 (m, 1H).

LC/MS Condition E: ret time 1.68 min; m/e=648 (M+H)⁺.
LC/MS Condition F: ret time 1.64 min; m/e=648 (M+H)⁺.

Example 2003: 5-((4-chloro-5-((2'-chloro-3'-(3-(((S)-2,3-dihydroxypropyl)amino)propoxy)-2-methyl-[1,1'-biphenyl]-3-yl)methoxy)-2-((((S)-2,3-dihydroxypropyl)amino)methyl)phenoxy)methyl)nicotinonitrile

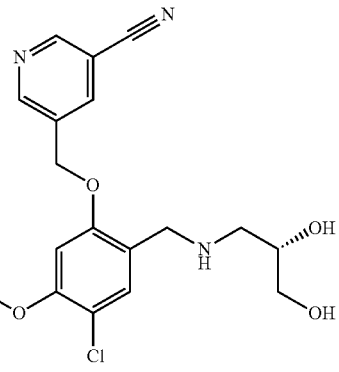
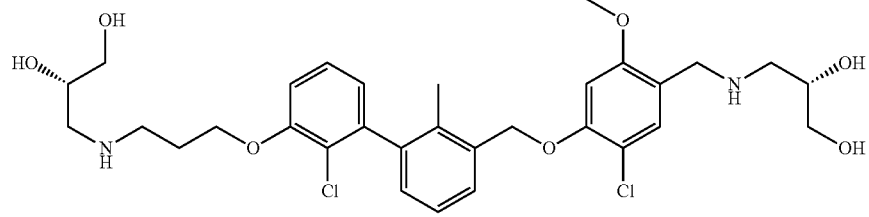

Following the general procedure as described in Example 2001, except using (S)-3-aminopropane-1,2-diol, the above product was isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (35.7 mg, 59%).

LC/MS Condition E: ret time 1.35 min; m/e=725 (M+H)⁺.
LC/MS Condition F: ret time 1.38 min; m/e=725 (M+H)⁺.

Example 2004: (S)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxypropanoic Acid

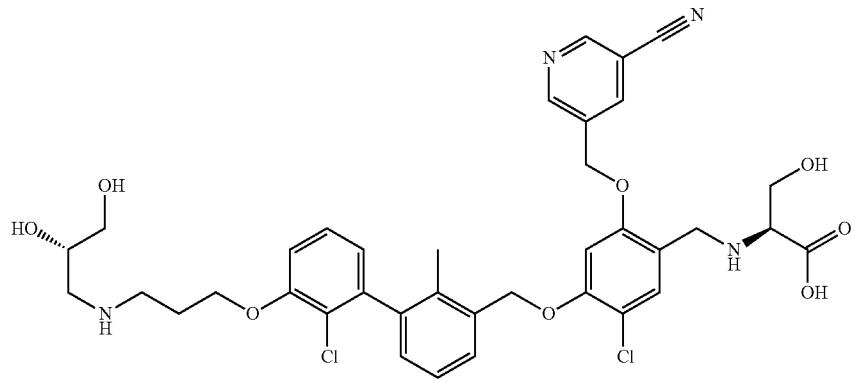 [SMILES: Cc1c(COc2cc(OCc3cncc(C#N)c3)c(CN[C@@H](CO)C(=O)O)cc2Cl)cccc1-c1cccc(OCCCNC[C@H](O)CO)c1Cl]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (50 mg, 0.078 mmol), and L-serine (24 mg, 0.228 mmol) in a mixture of DCE (0.8 mL)

and EtOH (1.6 mL) was added acetic acid (9 μL, 0.157 mmol) and 4 A molecular sieves (2 pieces). The resulting solution was stirred at room temp for 2.5 h, then treated dropwise (over 40 min) with sodium cyanoborohydride, 1.0 M in THF (156 μL, 0.156 mmol). After the addition was complete, the reaction was gently stirred at room temp overnight. The solvent was mostly removed under a stream of $N_2$ and the residue was redissolved in MeOH (1.5 mL). The resulting solution was treated with (S)-3-aminopropane-1,2-diol, (120 mg, 1.32 mmol) and N,N-diisopropylethylamine (250 μL, 1.43 mmol) and placed in a 65° C. oil bath with stirring for 28 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. to give the pure title compound as a TFA salt: (1.3 mg, 1.7%).

From Example 2004, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (3.8 mg, 5.3%) as a TFA salt.

LC/MS Condition E: ret time 1.6 min; m/e=652 (M+H)$^+$.
LC/MS Condition F: ret time 1.59 min; m/e=652 (M+H)$^+$.

Example 2006: (S)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

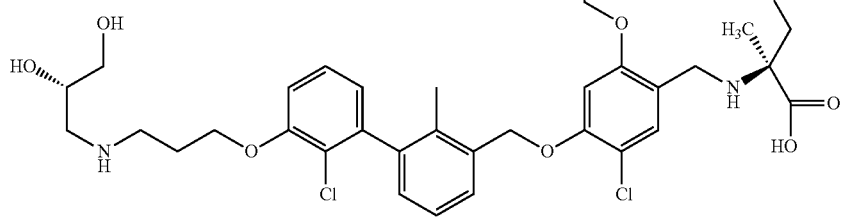

LC/MS Condition E: ret time 1.70 min; m/e=739 (M+H)$^+$.
LC/MS Condition F: ret time 1.88 min; m/e=739 (M+H)$^+$.

Example 2005: (S)-5-((4-chloro-5-((2'-chloro-3'-(3-((2,3-dihydroxypropyl)amino)propoxy)-2-methyl-[1,1'-biphenyl]-3-yl)methoxy)-2-(hydroxymethyl)phenoxy)methyl)nicotinonitrile

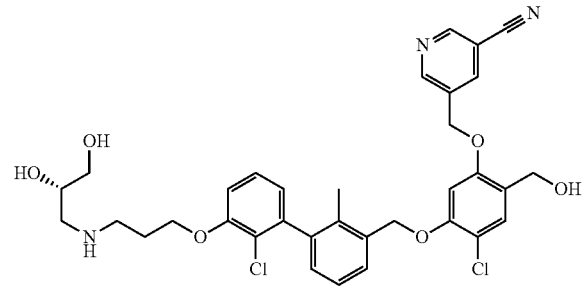 [SMILES: Cc1c(COc2cc(OCc3cncc(C#N)c3)c(CO)cc2Cl)cccc1-c1cccc(OCCCNC[C@H](O)CO)c1Cl]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (50 mg, 0.078 mmol), and 2-methyl-L-serine (27 mg, 0.227 mmol) in a mixture of DCE (0.8 mL) and EtOH (1.6 mL) was added acetic acid (9 μL, 0.157 mmol) and 4 A molecular sieves. The resulting solution was stirred at room temp for 2.5 h, then treated dropwise (over 40 min) with sodium cyanoborohydride, 1.0 M in THF (156 μL, 0.156 mmol). After the addition was complete, the reaction was gently stirred at room temp overnight. The solvent was mostly removed under a stream of N2 and the residue was redissolved in MeOH (1.5 mL). The resulting solution was treated with (S)-3-aminopropane-1,2-diol, (120 mg, 1.32 mmol) and N,N-diisopropylethylamine (250 μL, 1.43 mmol) and placed in a 65° C. oil bath with stirring for 28 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. to give the pure title compound as a TFA salt: (1.9 mg, 2.5%). $^1$H NMR (500 MHz, DMSO-$d_6$) δ 9.03 (dd, J=9.2, 1.8 Hz, 2H), 8.50 (s, 1H), 7.58 (s, 1H), 7.52 (d, J=8.1 Hz, 1H), 7.39 (t, J=8.1 Hz, 1H), 7.30 (t, J=7.7 Hz, 1H), 7.21-7.07 (m, 3H), 6.88 (dd, J=7.7, 1.1 Hz, 1H), 5.38-5.34 (m, 2H), 5.32 (br d, J=3.3 Hz, 2H), 4.32-3.68 (m, 6H), 3.38-2.70 (m, 8H), 2.17 (br s, 2H), 2.08 (s, 3H), 1.32 (s, 3H)

LC/MS Condition E: ret time 1.32 min; m/e=753 (M+H)$^+$.

LC/MS Condition F: ret time 1.32 min; m/e=753 (M+H)$^+$.

Example 2007: (S)-1-(5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)piperidine-2-carboxylic Acid

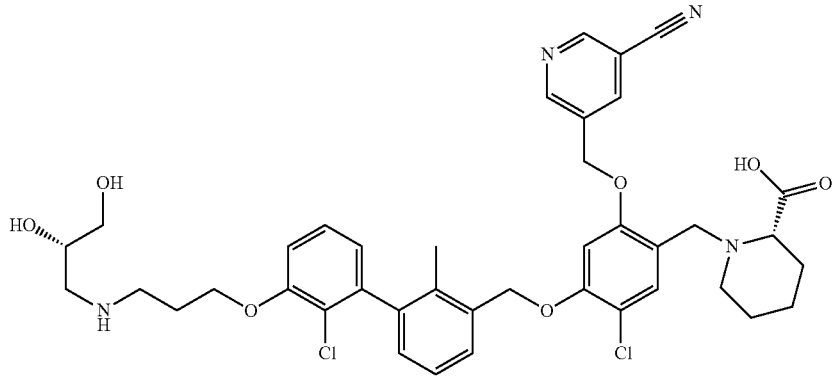 [SMILES: Cc1c(COc2cc(OCc3cncc(C#N)c3)c(CN3CCCC[C@H]3C(=O)O)cc2Cl)cccc1-c1cccc(OCCCNC[C@H](O)CO)c1Cl]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (50 mg, 0.078 mmol), and L-pipecolic acid (30 mg, 0.232 mmol) in a mixture of DCE (0.8 mL) and EtOH (1.6 mL) was added acetic acid (9 μL, 0.157 mmol) and 4 A molecular sieves. The resulting solution was stirred at room temp for 2.5 h, then treated dropwise (over 40 min) with sodium cyanoborohydride, 1.0 M in THF (156 μL, 0.156 mmol). After the addition was complete, the reaction was gently stirred at room temp overnight. The solvent was mostly removed under a stream of $N_2$ and the residue was redissolved in MeOH (1.5 mL). The resulting solution was treated with (S)-3-aminopropane-1,2-diol, (120 mg, 1.32 mmol) and N,N-diisopropylethylamine (250 μL, 1.43 mmol) and placed in a 65° C. oil bath with stirring for 28 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (10.7 mg, 16.5%).

LC/MS Condition E: ret time 1.38 min; m/e=763 (M+H)$^+$.

LC/MS Condition F: ret time 1.46 min; m/e=763 (M+H)$^+$.

Example 2008: (S)-1-(3-((3'-((4-((((R)-2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)piperidine-3-carboxylic Acid

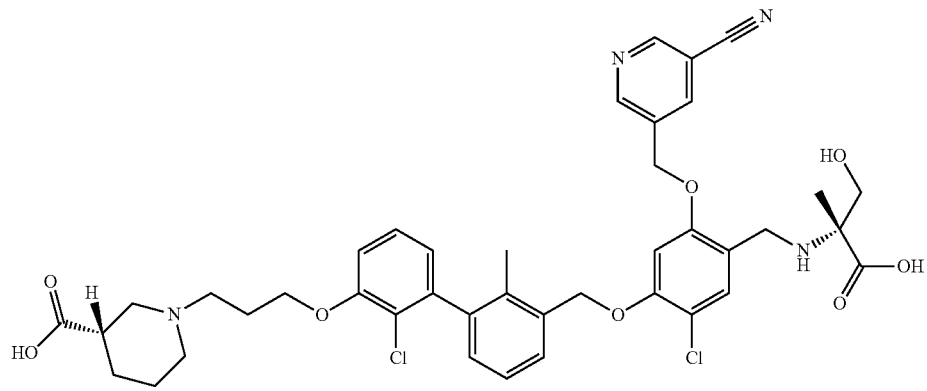 [SMILES: Cc1c(COc2cc(OCc3cncc(C#N)c3)c(CN[C@](C)(CO)C(=O)O)cc2Cl)cccc1-c1cccc(OCCCN2CCC[C@H](C(=O)O)C2)c1Cl]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (50 mg, 0.078 mmol), and 2-methyl-D-serine (30 mg, 0.252 mmol) in a mixture of DCE (0.75 mL) and EtOH (1.5 mL) was added acetic acid (9 µL, 0.157 mmol) and 4 A molecular sieves (2 pieces). The resulting solution was stirred at room temp for 75 min, then treated dropwise (over 4.5 h) with sodium cyanoborohydride, 1.0 M in THF (156 µL, 0.156 mmol). After the addition was complete, the reaction was gently stirred at room temp overnight. The solvent was mostly removed under a stream of $N_2$ and the residue was redissolved in MeOH (1.5 mL). The resulting solution was treated with (S)-(+)-nipecotic acid (90 mg, 0.697 mmol) and N,N-diisopropylethylamine (250 µL, 1.43 mmol) and placed in a 65° C. sand bath with shaking for 28 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (1.7 µmg, 2.5%).

LC/MS Condition E: ret time 1.36 min; m/e=791 (M+H)⁺.
LC/MS Condition F: ret time 1.4 min; m/e=791 (M+H)⁺.

Example 2009: (S)-1-(3-((2-chloro-3'-((2-chloro-5-((5-cyanopyridin-3-yl)methoxy)-4-(hydroxymethyl)phenoxy)methyl)-2'-methyl-[1,1'-biphenyl]-3-yl)oxy)propyl)piperidine-3-carboxylic Acid

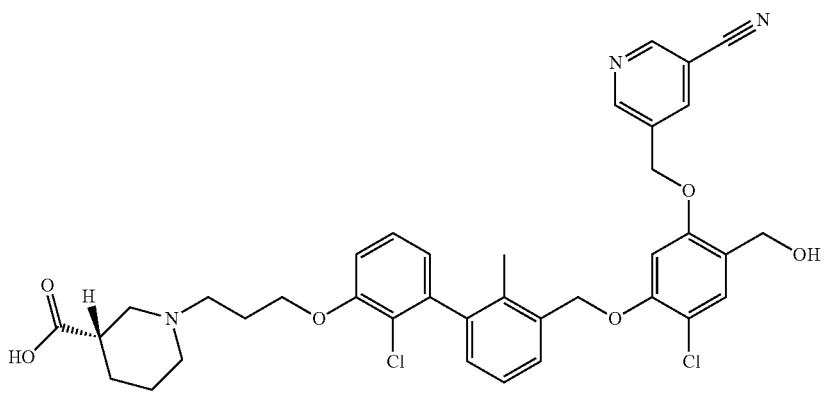 [SMILES: Cc1c(COc2cc(OCc3cncc(C#N)c3)c(CO)cc2Cl)cccc1-c1cccc(OCCCN2CCC[C@H](C(=O)O)C2)c1Cl]

From Example 2008, the above product was also isolated via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (5.4 mg 9.7%).

LC/MS Condition E: ret time 1.62 min; m/e=690 (M+H)+.
LC/MS Condition F: ret time 1.68 min; m/e=690 (M+H)+.

Example 2010: 5-((4-chloro-5-((2'-chloro-2-methyl-3'-(3-((2-(pyridin-4-yl)ethyl)amino)propoxy)-[1,1'-biphenyl]-3-yl)methoxy)-2-(((2-(pyridin-4-yl)ethyl)amino)methyl)phenoxy)methyl)nicotinonitrile 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (21 mg, 33.3%). ¹H NMR (500 MHz, DMSO-$d_6$) δ 9.01 (d, J=2.2 Hz, 1H), 8.96 (d, J=1.8 Hz, 1H), 8.41 (d, J=5.1 Hz, 5H), 7.52 (d, J=7.7 Hz, 1H), 7.39-7.34 (m, 1H), 7.33 (s, 1H), 7.29 (t, J=7.5 Hz, 1H), 7.24 (d, J=5.9 Hz, 2H), 7.20 (d, J=5.9 Hz, 2H), 7.16 (d, J=8.4 Hz, 1H), 7.13-7.08 (m, 2H), 6.87-6.84 (m, 1H), 5.29 (s, 2H), 5.25 (d, J=3.7 Hz, 2H), 4.22-4.10 (m, 2H), 2.86-2.79 (m, 2H), 2.78-2.68 (m, 9H), 1.91 (s, 6H).

LC/MS Condition E: ret time 1.65 min; m/e=787 (M+H)+.
LC/MS Condition F: ret time 1.17 min; m/e=787 (M+H)+.

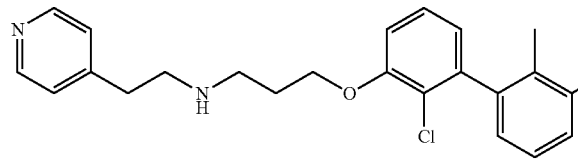
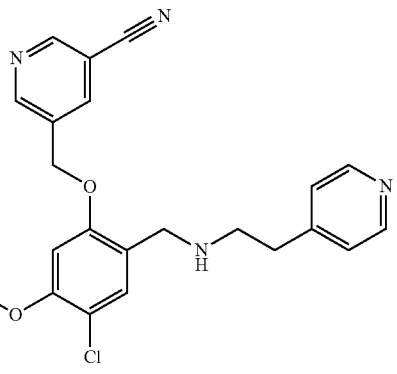

Following the general procedure as described in Example 2001, except using 4-(2-aminoethyl)pyridine, the above product was isolated via preparative LC/MS with the following conditions: Column: XBridge C18, 19×200 mm, 5-μm particles; Mobile Phase A: 5:95 acetonitrile:water with Example 2011: 5-((4-chloro-5-((2'-chloro-3'-(3-(4-(2-hydroxyethyl)piperazin-1-yl)propoxy)-2-methyl-[1,1'-biphenyl]-3-yl)methoxy)-2-((4-(2-hydroxyethyl)piperazin-1-yl)methyl)phenoxy)methyl)nicotinonitrile

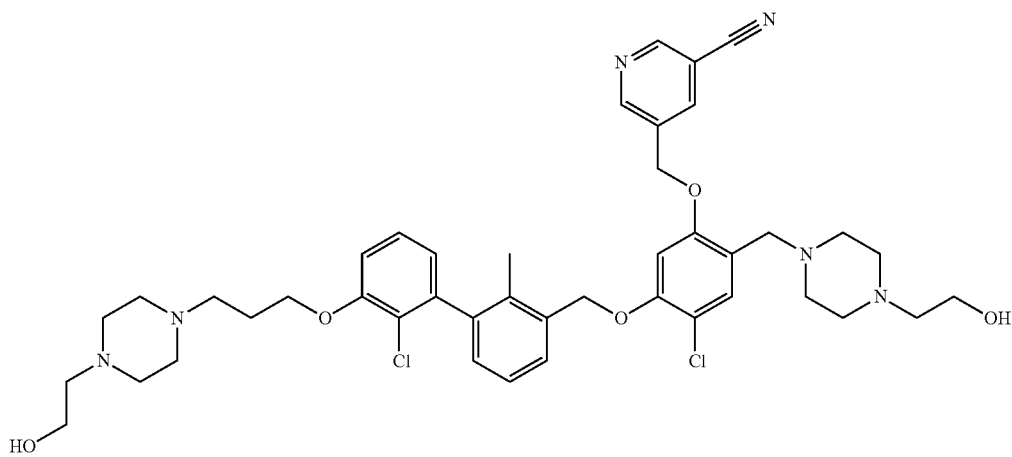 [SMILES: Cc1c(COc2cc(OCc3cncc(C#N)c3)c(CN3CCN(CCO)CC3)cc2Cl)cccc1-c1cccc(OCCCN2CCN(CCO)CC2)c1Cl]

Following the general procedure as described in Example 2001, except using N-(2-hydroxyethyl)piperazine, the above product was isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (33.8 mg, 77%)

LC/MS Condition E: ret time 1.64 min; m/e=803 (M+H)$^+$.
LC/MS Condition F: ret time 1.20 min; m/e=803 (M+H)$^+$.

Intermediate: (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid dropwise (over 5 h) with sodium cyanoborohydride, 1.0 M in THF (1.25 mL, 1.25 mmol). After the addition was complete, the reaction was gently stirred at room temp overnight. The reaction was treated with additional sodium cyanoborohydride, 1.0 M in THF (150 μL, 0.125 mmol) over 1.5 h. After the addition was complete, the reaction was allowed to stir at room temp for 3 h. The solvent was removed under a stream of N$_2$ and the crude product was used directly "as is" without purification in subsequent examples. LC/MS Condition A: ret time 1.21 min; m/e=742, (M+H)$^+$.

Example 2013: (R)-2-((5-chloro-4-((2'-chloro-3'-(3-(3-(dimethylamino)azetidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

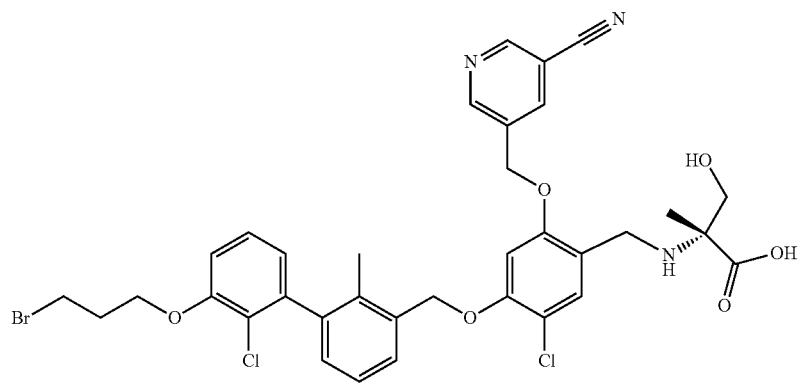 [SMILES: Cc1c(COc2cc(OCc3cncc(C#N)c3)c(CN[C@](C)(CO)C(=O)O)cc2Cl)cccc1-c1cccc(OCCCBr)c1Cl]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (400 mg, 0.625 mmol), and 2-methyl-D-serine (225 mg, 1.89 mmol) in a mixture of DCE (6.4 mL) and EtOH (12.8 mL) was added acetic acid (72 μL, 1.26 mmol) and 4 A molecular sieves. The resulting solution was stirred at room temp for 1 h, then treated

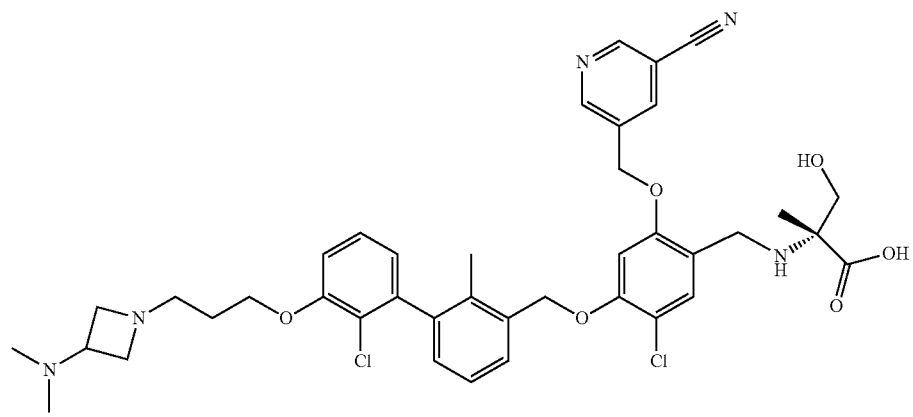 [SMILES: Cc1c(COc2cc(OCc3cncc(C#N)c3)c(CN[C@](C)(CO)C(=O)O)cc2Cl)cccc1-c1cccc(OCCCN2CC(N(C)C)C2)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added N,N-dimethylazetidin-3-amine, 2 HCl (30 mg, 0.173 mmol) and N,N-diisopropylethylamine (80 µL, 0.458 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (7.5 mg).

LC/MS Condition E: ret time 1.83 min; m/e=762 (M+H)$^+$.
LC/MS Condition F: ret time 1.72 min; m/e=762 (M+H)$^+$.

Example 2014: 4-chloro-5-((2'-chloro-3'-(3-(3-(dimethylamino)azetidin-1-yl)propoxy)-2-methyl-[1,1'-biphenyl]-3-yl)methoxy)-2-(hydroxymethyl)phenol

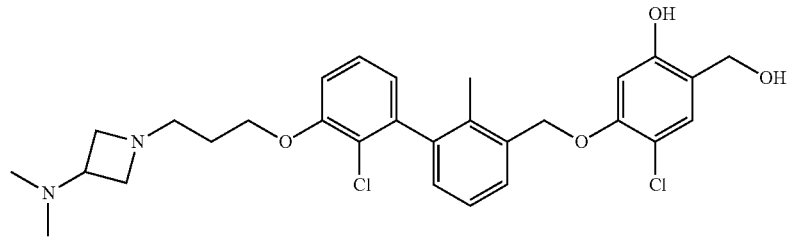 [SMILES: Cc1c(COc2cc(O)c(CO)cc2Cl)cccc1-c1cccc(OCCCN2CC(N(C)C)C2)c1Cl]

From Example 2013, the above product was also isolated via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (7.1 mg). $^1$H NMR (500 MHz, DMSO-d$_6$) δ 7.51 (d, J=7.0 Hz, 1H), 7.36 (t, J=7.9 Hz, 1H), 7.30 (t, J=7.5 Hz, 1H), 7.25 (s, 1H), 7.16 (d, J=7.3 Hz, 1H), 7.10 (d, J=7.7 Hz, 1H), 6.86-6.82 (m, 1H), 6.70 (s, 1H), 5.14 (s, 2H), 4.40 (s, 2H), 4.11 (q, J=6.2 Hz, 2H), 3.90 (s, 1H), 3.18 (s, 1H), 2.78 (br s, 3H), 2.59 (br t, J=7.0 Hz, 2H), 2.05 (s, 3H), 1.91 (s, 6H), 1.78 (br t, J=6.8 Hz, 2H)

LC/MS Condition E: ret time 1.98 min; m/e=545 (M+H)$^+$.
LC/MS Condition F: ret time 1.80 min; m/e=545 (M+H)$^+$.

Example 2015: 5-((4-chloro-5-((2'-chloro-3'-(3-(3-(dimethylamino)azetidin-1-yl)propoxy)-2-methyl-[1,1'-biphenyl]-3-yl)methoxy)-2-(hydroxymethyl)phenoxy)methyl)nicotinonitrile

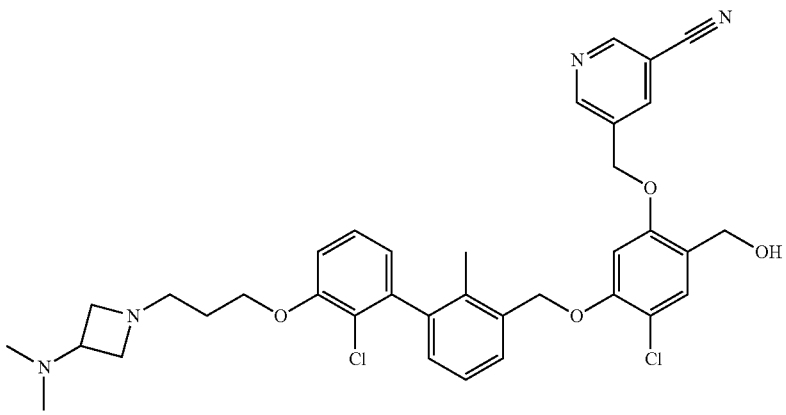 [SMILES: Cc1c(COc2cc(OCc3cncc(C#N)c3)c(CO)cc2Cl)cccc1-c1cccc(OCCCN2CC(N(C)C)C2)c1Cl]

From Example 2013, the above product was also isolated via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (7.1 mg).

LC/MS Condition E: ret time 1.77 min; m/e=661 (M+H)+.
LC/MS Condition F: ret time 1.49 min; m/e=661 (M+H)+.

Example 2016: (R)-2-((5-chloro-4-((2'-chloro-2-methyl-3'-(3-(piperidin-1-yl)propoxy)-[1,1'-biphenyl]-3-yl)methoxy)-2-((5-cyanopyridin-3-yl)methoxy)benzyl)amino)-3-hydroxy-2-methylpropanoic Acid

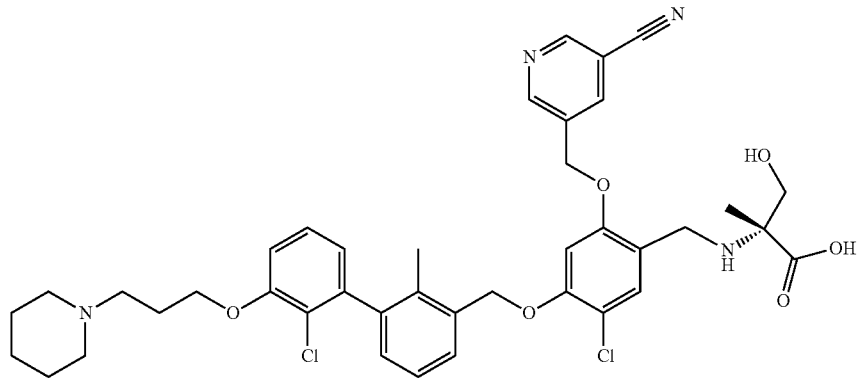 [SMILES: Cc1c(COc2cc(OCc3cncc(C#N)c3)c(CN[C@](C)(CO)C(=O)O)cc2Cl)cccc1-c1cccc(OCCCN2CCCCC2)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added piperidine (18 mg, 0.211 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (5.7 mg). $^1$H NMR (500 MHz, DMSO-d$_6$) δ 9.03 (dd, J=8.8, 1.8 Hz, 2H), 8.51 (s, 1H), 7.57-7.50 (m, 2H), 7.39-7.33 (m, 1H), 7.29 (t, J=7.5 Hz, 1H), 7.18 (d, J=7.3 Hz, 1H), 7.15-7.08 (m, 2H), 6.85 (dd, J=7.5, 1.3 Hz, 1H), 5.35 (s, 2H), 5.30 (d, J=5.5 Hz, 2H), 4.22-4.07 (m, 2H), 3.65-3.50 (m, 1H), 2.90 (s, 2H), 2.74 (s, 2H), 2.55 (s, 2H), 2.45 (t, J=7.2 Hz, 2H), 2.36 (br s, 3H), 2.08 (s, 3H), 1.93 (s, 1H), 1.50 (quin, J=5.5 Hz, 4H), 1.39 (br d, J=4.8 Hz, 2H), 1.23 (s, 3H).

LC/MS Condition E: ret time 1.5 min; m/e=747 (M+H)+.
LC/MS Condition F: ret time 1.44 min; m/e=747 (M+H)+.

Example 2017: 4-chloro-5-((2'-chloro-2-methyl-3'-(3-(piperidin-1-yl)propoxy)-[1,1'-biphenyl]-3-yl)methoxy)-2-(hydroxymethyl)phenol

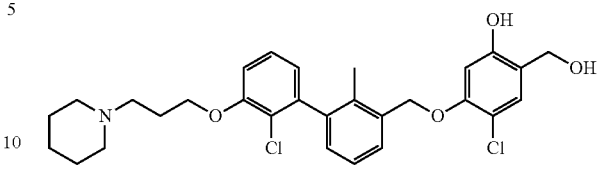

From Example 2016, the above product was also isolated via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (3.2 mg).

LC/MS Condition E: ret time 1.67 min; m/e=530 (M+H)+.
LC/MS Condition F: ret time 1.6 min; m/e=530 (M+H)+.

Example 2018: 5-((4-chloro-5-((2'-chloro-2-methyl-3'-(3-(piperidin-1-yl)propoxy)-[1,1'-biphenyl]-3-yl)methoxy)-2-(hydroxymethyl)phenoxy)methyl)nicotinonitrile

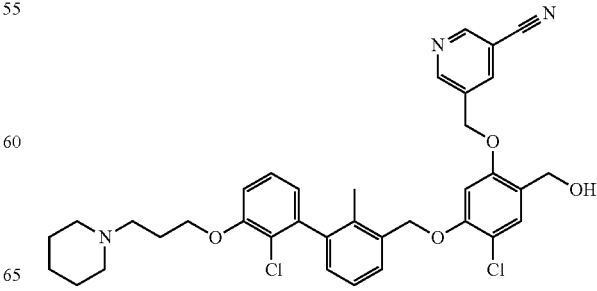

From Example 2016, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound (9.1 mg).

LC/MS Condition E: ret time 1.85 min; m/e=646 (M+H)$^+$.
LC/MS Condition F: ret time 1.75 min; m/e=646 (M+H)$^+$.

Example 2019: (2R)-2-((4-((3'-(3-(3-acetamidopyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid

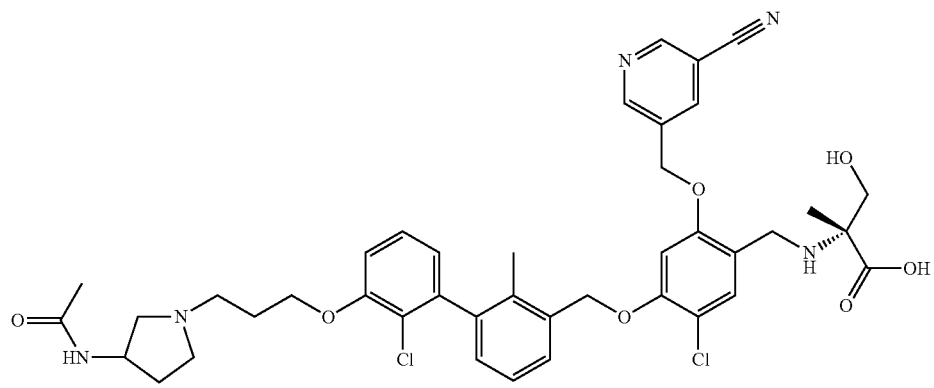 [SMILES: CC(=O)NC1CCN(CCCOc2cccc(-c3cccc(COc4cc(OCc5cncc(C#N)c5)c(CN[C@](C)(CO)C(=O)O)cc4Cl)c3C)c2Cl)C1]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added 3-acetamidopyrrolidine (27 mg, 0.211 mmol) and N,N-diisopropylethylamine (15 □L, 0.086 mmol) and the reaction is heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound (8 mg, 64%).

LC/MS Condition E: ret time 1.42 min; m/e=790 (M+H)$^+$.
LC/MS Condition F: ret time 1.37 min; m/e=790 (M+H)$^+$.

Example 2020: N-(1-(3-((2-chloro-3'-((2-chloro-5-hydroxy-4-(hydroxymethyl)phenoxy)methyl)-2'-methyl-[1,1'-biphenyl]-3-yl)oxy)propyl)pyrrolidin-3-yl)acetamide

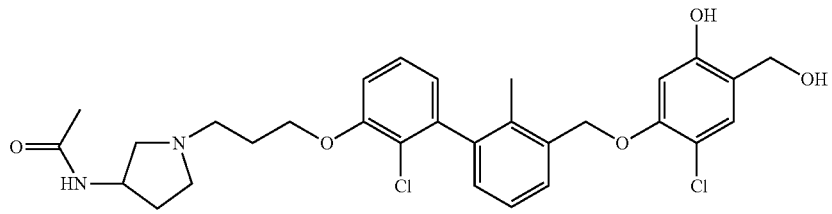 [SMILES: CC(=O)NC1CCN(CCCOc2cccc(-c3cccc(COc4cc(O)c(CO)cc4Cl)c3C)c2Cl)C1]

From Example 2019, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min, to give the pure title compound (7.8 mg).

LC/MS Condition E: ret time 1.58 min; m/e=573 (M+H)+.
LC/MS Condition F: ret time 1.48 min; m/e=573 (M+H)+.

Example 2021: N-(1-(3-((2-chloro-3'-((2-chloro-5-((5-cyanopyridin-3-yl)methoxy)-4-(hydroxymethyl)phenoxy)methyl)-2'-methyl-[1,1'-biphenyl]-3-yl)oxy)propyl)pyrrolidin-3-yl)acetamide From Example 2019, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min, to give the pure title compound (11.8 mg).
LC/MS Condition E: ret time 1.76 min; m/e=689 (M+H)+.
LC/MS Condition F: ret time 1.64 min; m/e=689 (M+H)+.

Example 2022: (R)-2-((4-((3'-(3-((R)-3-acetamidopyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added (3R)-(+)-3-acetamidopyrrolidine (27 mg, 0.211 mmol) and N,N-diisopropylethylamine (15 □L, 0.086 mmol) and the reaction is heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient:

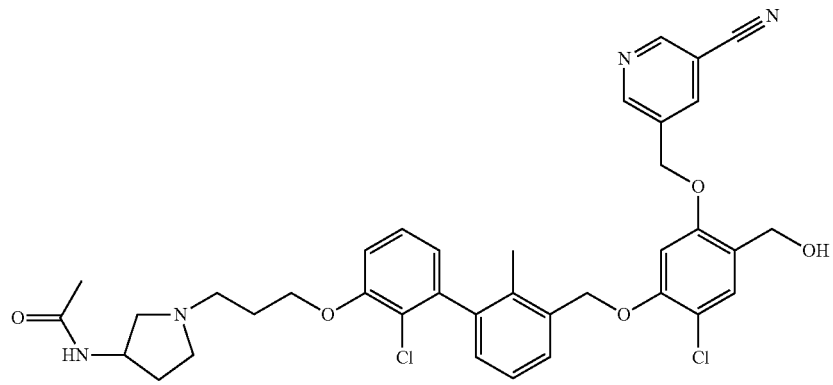 [SMILES: CC(=O)NC1CCN(CCCOc2cccc(-c3cccc(COc4cc(OCc5cncc(C#N)c5)c(CO)cc4Cl)c3C)c2Cl)C1]

20-60% B over 20 minutes, then a 5-minute hold at 100% B; Flow: 20 mL/min to give the title compound (9.9 mg, 79%).

LC/MS Condition E: ret time 1.48 min; m/e=790 (M+H)+.
LC/MS Condition F: ret time 2.83 min; m/e=790 (M+H)+.

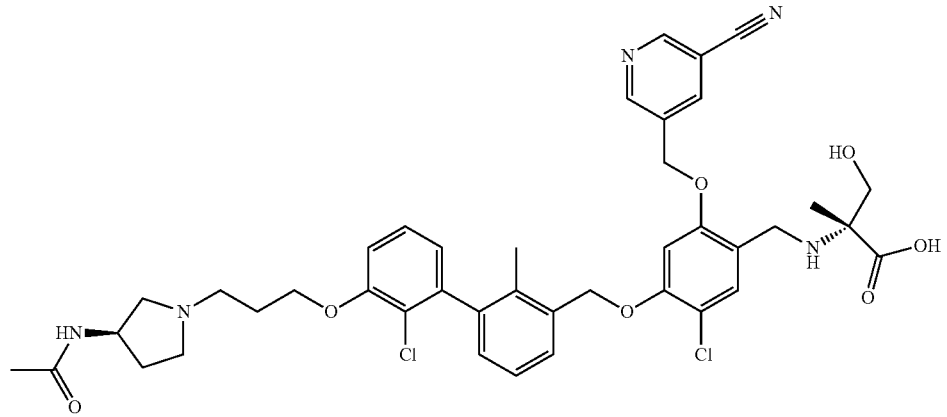 [SMILES: CC(=O)N[C@@H]1CCN(CCCOc2cccc(-c3cccc(COc4cc(OCc5cncc(C#N)c5)c(CN[C@](C)(CO)C(=O)O)cc4Cl)c3C)c2Cl)C1]

Example 2023: (R)-2-((3-((3'-((4-((((R)-2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)amino)-3-hydroxy-2-methylpropanoic Acid

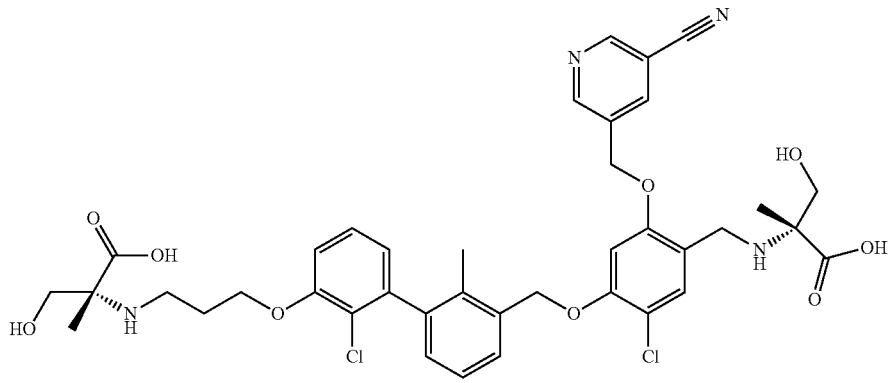 [SMILES: Cc1c(COc2cc(OCc3cncc(C#N)c3)c(CN[C@](C)(CO)C(=O)O)cc2Cl)cccc1-c1cccc(OCCCN[C@](C)(CO)C(=O)O)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added 2-methyl-D-serine (25 mg, 0.210 mmol) and N,N-diisopropylethylamine (15 µL, 0.086 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (1.3 mg, 8.6%).

LC/MS Condition E: ret time 1.67 min; m/e=781 (M+H)$^+$.
LC/MS Condition F: ret time 1.73 min; m/e=781 (M+H)$^+$.

Example 2024: (R)-2-((5-chloro-4-((2'-chloro-3'-(3-(((S)-2,3-dihydroxypropyl)(methyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic Acid To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.2 mL) is added (S)-3-(methylamino)propane-1,2-diol (22 mg, 0.209 mmol) and N,N-diisopropylethylamine (15 µL, 0.086 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (2.4 mg, 19.8%). $^1$H NMR (500 MHz, DMSO-d$_6$) δ 9.03 (dd, J=8.1, 1.8 Hz, 2H), 8.51 (s, 1H), 7.57-7.49 (m, 2H), 7.41-7.34 (m, 1H), 7.29 (t, J=7.7 Hz, 1H), 7.18 (d, J=8.4 Hz, 1H), 7.15-7.09 (m, 2H), 6.85 (dd, J=7.7, 1.5 Hz, 1H), 5.35 (s, 2H), 5.30 (d, J=5.9 Hz, 2H), 4.15 (br d, J=5.5 Hz, 2H), 3.92 (d, J=12.1 Hz, 2H), 3.65-3.48 (m, 2H), 2.41 (dd, J=12.5, 5.5 Hz, 1H), 2.28 (dd, J=12.8, 6.6 Hz, 1H), 2.23 (s, 3H), 2.08 (s, 3H), 1.91 (s, 9H), 1.23 (s, 3H).

LC/MS Condition E: ret time 1.73 min; m/e=767 (M+H)$^+$.
LC/MS Condition F: ret time 1.73 min; m/e=767 (M+H)$^+$.

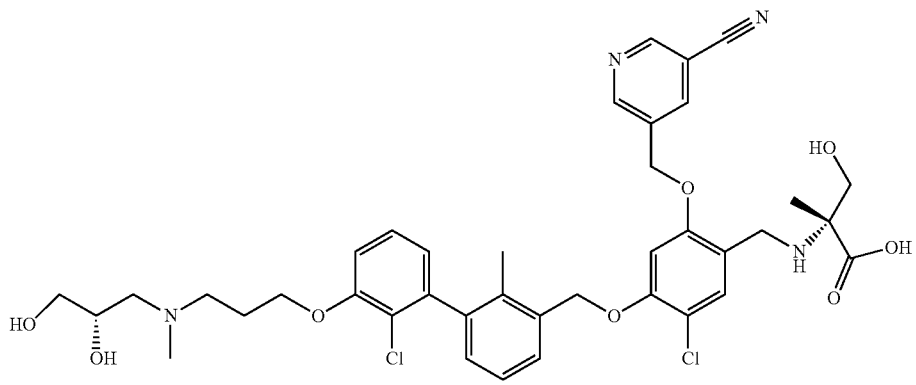 [SMILES: Cc1c(COc2cc(OCc3cncc(C#N)c3)c(CN[C@](C)(CO)C(=O)O)cc2Cl)cccc1-c1cccc(OCCCN(C)C[C@H](O)CO)c1Cl]

Example 2025: (S)-5-((4-chloro-5-((2'-chloro-3'-(3-((2,3-dihydroxypropyl)(methyl)amino)propoxy)-2-methyl-[1,1'-biphenyl]-3-yl)methoxy)-2-(hydroxymethyl)phenoxy)methyl)nicotinonitrile

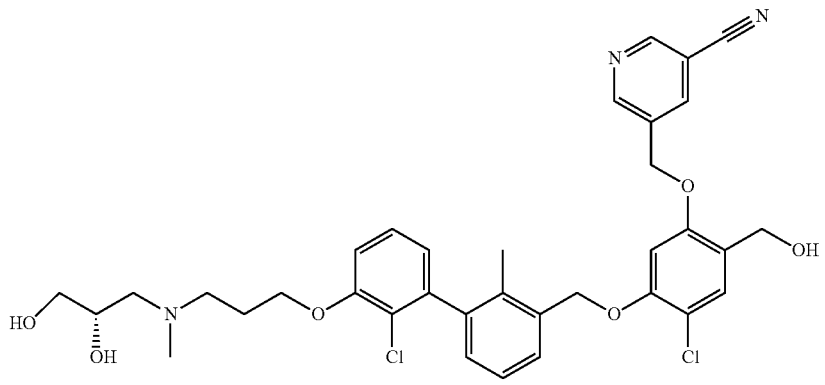 [SMILES: Cc1c(COc2cc(OCc3cncc(C#N)c3)c(CO)cc2Cl)cccc1-c1cccc(OCCCN(C)C[C@H](O)CO)c1Cl]

From Example 2024, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as a TFA salt (9.1 mg).
LC/MS Condition E: ret time 2.00 min; m/e=666 (M+H)$^+$.
LC/MS Condition F: ret time 1.99 min; m/e=666 (M+H)$^+$.

Intermediate: (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (120 mg, 0.187 mmol), and (S)-3-aminopropane-1,2-diol (51 mg, 0.560 mmol) in a mixture of DCE (1.8 mL) and EtOH (3.6 mL) was added acetic acid (21.5 μL, 0.376 mmol) and 4 Å molecular sieves (2 pieces). The resulting solution was stirred at room temp for 75 min, then treated dropwise (over 5 h) with sodium cyanoborohydride, 1.0 M in THF (374 μL, 0.374 mmol). After the addition was complete, the reaction was gently stirred at room temp overnight. The solvent was removed under a stream of N$_2$ and the crude product was used directly "as is" without purification in subsequent examples. LC/MS Condition A: ret time 1.19 min; m/e=714 (M+H)$^+$.


Example 2027: (S)-methyl 1-(3-((2-chloro-3'-((2-chloro-5-((5-cyanopyridin-3-yl)methoxy)-4-(((2,3-dihydroxypropyl)amino)methyl)phenoxy)methyl)-2'-methyl-[1,1'-biphenyl]-3-yl)oxy)propyl)piperidine-4-carboxylate

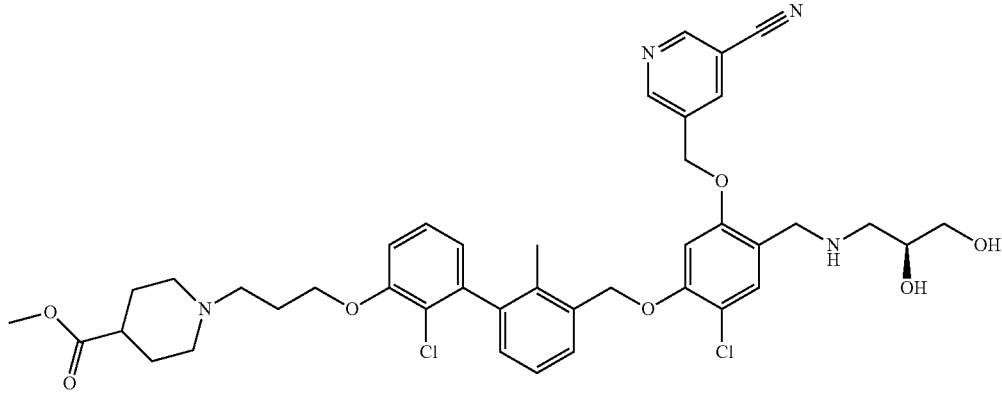 [SMILES: COC(=O)C1CCN(CCCOc2cccc(-c3cccc(COc4cc(OCc5cncc(C#N)c5)c(CNC[C@H](O)CO)cc4Cl)c3C)c2Cl)CC1]

To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl) nicotinonitrile (16.75 mg, 0.023 mmol) in MeOH (1.2 mL) is added methyl 4-piperidinecarboxylate (45.3 μl, 0.335 mmol) and N,N-diisopropylethylamine (20 μl, 0.115 mmol) and the reaction is heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (7.3 mg, 40%).

LC/MS Condition E: ret time 1.69 min; m/e=777 (M+H)$^+$.
LC/MS Condition F: ret time 1.41 min; m/e=777 (M+H)$^+$.

Example 2028: (S)-5-((4-chloro-5-((2'-chloro-3'-(3-(3-(dimethylamino)azetidin-1-yl)propoxy)-2-methyl-[1,1'-biphenyl]-3-yl)methoxy)-2-(((2,3-dihydroxypropyl)amino)methyl)phenoxy)methyl) nicotinonitrile To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl) nicotinonitrile (16.75 mg, 0.023 mmol) in MeOH (1.2 mL) is added 3-(dimethylamino)azetidine dihydrochloride (57 mg, 0.329 mmol) and N,N-diisopropylethylamine (100 μL, 0.573 mmol) and the reaction is heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (9.1 mg, 51%). $^1$H NMR (500 MHz, DMSO-d$_6$) δ 9.01 (dd, J=17.4, 2.0 Hz, 2H), 8.46-8.37 (m, 1H), 7.53 (d, J=7.3 Hz, 1H), 7.41-7.33 (m, 2H), 7.30 (t, J=7.5 Hz, 1H), 7.16 (d, J=8.1 Hz, 1H), 7.13-7.09 (m, 2H), 6.85 (d, J=6.2 Hz, 1H), 5.32 (s, 2H), 5.26 (d, J=4.8 Hz, 2H), 4.17-4.05 (m, 2H), 3.67 (d, J=4.0 Hz, 2H), 3.59-3.50 (m, 1H), 3.38 (s, 1H), 2.78-2.68 (m, 4H), 2.62-2.52 (m, 5H), 2.43 (dd, J=11.7, 7.3 Hz, 1H), 2.08 (s, 3H), 2.00 (s, 6H), 1.77 (quin, J=6.6 Hz, 2H).

LC/MS Condition E: ret time 1.87 min; m/e=734 (M+H)$^+$.
LC/MS Condition F: ret time 1.69 min; m/e=734 (M+H)$^+$.

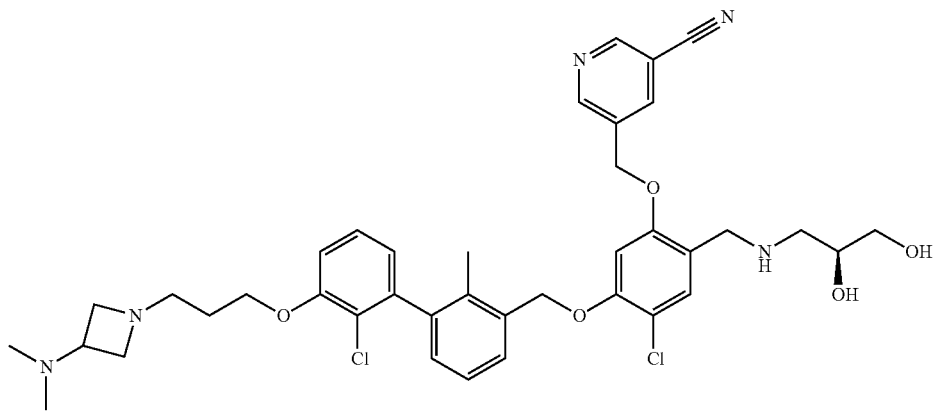 [SMILES: Cc1c(COc2cc(OCc3cncc(C#N)c3)c(CNC[C@H](O)CO)cc2Cl)cccc1-c1cccc(OCCCN2CC(N(C)C)C2)c1Cl]

Example 2029: 5-((4-chloro-5-((2'-chloro-3'-(3-(((S)-2,3-dihydroxypropyl)(methyl)amino)propoxy)-2-methyl-[1,1'-biphenyl]-3-yl)methoxy)-2-((((S)-2,3-dihydroxypropyl)amino)methyl)phenoxy)methyl)nicotinonitrile

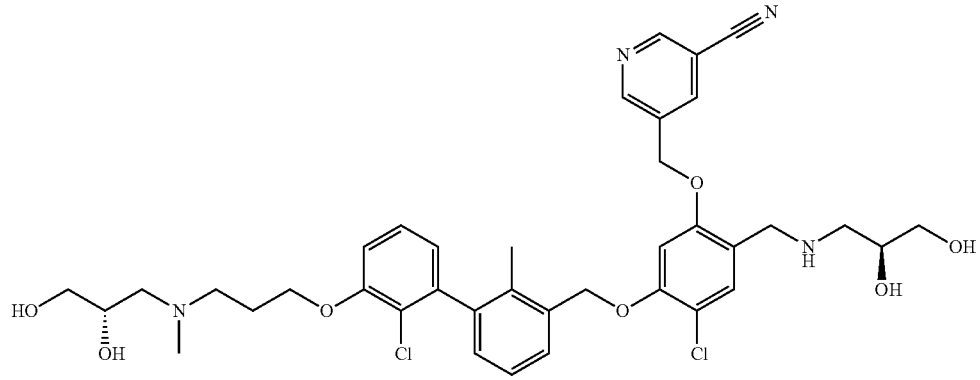 [SMILES: Cc1c(COc2cc(OCc3cncc(C#N)c3)c(CNC[C@H](O)CO)cc2Cl)cccc1-c1cccc(OCCCN(C)C[C@H](O)CO)c1Cl]

To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile (16.75 mg, 0.023 mmol) in MeOH (1.2 mL) was added (S)-3-(methylamino)propane-1,2-diol (33 mg, 0.314 mmol) and N,N-diisopropylethylamine (20 μL, 0.115 mmol) and the reaction was heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (6.1 mg, 35%).

LC/MS Condition E: ret time 1.83 min; m/e=739 (M+H)$^+$.
LC/MS Condition F: ret time 1.75 min; m/e=739 (M+H)$^+$.

To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile (16.75 mg, 0.023 mmol) in MeOH (1.2 mL) is added (3S,4S)-piperidine-3,4-diol, HCl (49 mg, 0.319 mmol) and N,N-diisopropylethylamine (100 μL, 0.573 mmol) and the reaction is heated at 65° C. for 18. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (16.4 mg, 90%).

LC/MS Condition E: ret time 1.87 min; m/e=751 (M+H)$^+$.
LC/MS Condition F: ret time 1.76 min; m/e=751 (M+H)$^+$.

Example 2030: 5-((4-chloro-5-((2'-chloro-3'-(3-((3S,4S)-3,4-dihydroxypiperidin-1-yl)propoxy)-2-methyl-[1,1'-biphenyl]-3-yl)methoxy)-2-((((S)-2,3-dihydroxypropyl)amino)methyl)phenoxy)methyl)nicotinonitrile

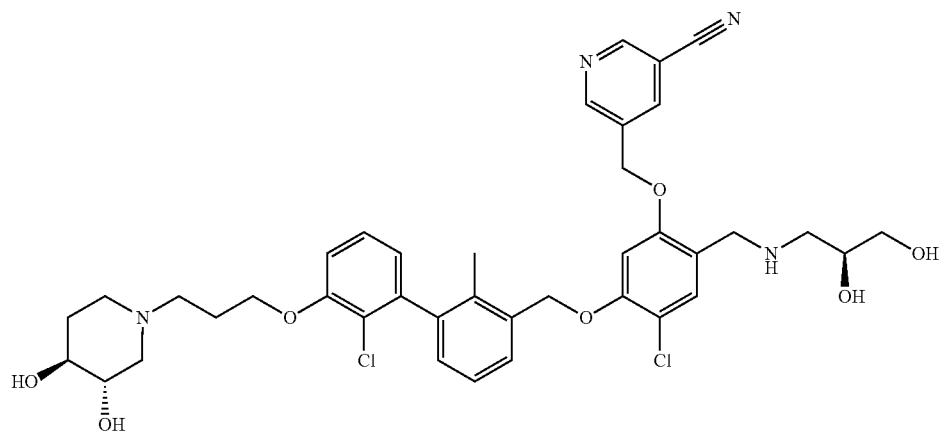 [SMILES: Cc1c(COc2cc(OCc3cncc(C#N)c3)c(CNC[C@H](O)CO)cc2Cl)cccc1-c1cccc(OCCCN2CC[C@H](O)[C@@H](O)C2)c1Cl]

Example 2031: 5-((4-chloro-5-((2'-chloro-3'-(3-((3S,4R)-3-hydroxy-4-(hydroxymethyl)piperidin-1-yl)propoxy)-2-methyl-[1,1'-biphenyl]-3-yl)methoxy)-2-((((S)-2,3-dihydroxypropyl)amino)methyl)phenoxy)methyl)nicotinonitrile

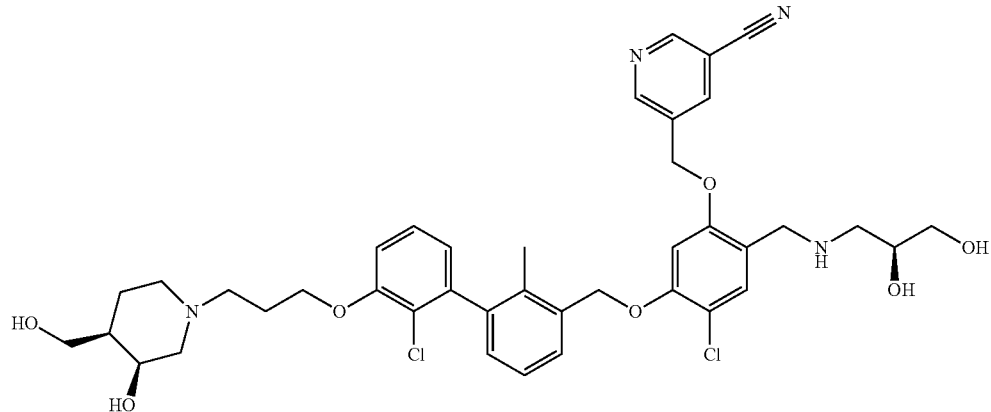 [SMILES: Cc1c(COc2cc(OCc3cncc(C#N)c3)c(CNC[C@H](O)CO)cc2Cl)cccc1-c1cccc(OCCCN2CC[C@H](CO)[C@H](O)C2)c1Cl]

To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile (16.75 mg, 0.023 mmol) in MeOH (1.2 mL) is added (3S,4R)-4-(hydroxymethyl)piperidin-3-ol, HCl (53 mg, 0.316 mmol) and N,N-diisopropylethylamine (100 µL, 0.573 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 40-85% B over 20 minutes, then a 5-minute hold at 100% B; Flow: 20 mL/min, to give the title compound (6.7 mg, 37%).

LC/MS Condition E: ret time 2.00 min; m/e=765 (M+H)$^+$.
LC/MS Condition F: ret time 1.33 min; m/e=765 (M+H)$^+$.

Example 2032: (S)-3-((3-((2-chloro-3'-((2-chloro-5-((5-cyanopyridin-3-yl)methoxy)-4-(((2,3-dihydroxypropyl)amino)methyl)phenoxy)methyl)-2'-methyl-[1,1'-biphenyl]-3-yl)oxy)propyl)(methyl)amino)propanamide

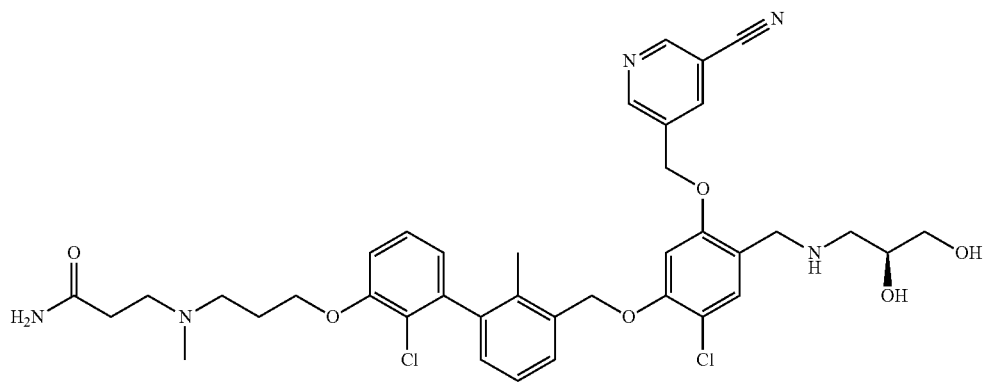 [SMILES: Cc1c(COc2cc(OCc3cncc(C#N)c3)c(CNC[C@H](O)CO)cc2Cl)cccc1-c1cccc(OCCCN(C)CCC(N)=O)c1Cl]

To a solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile (16.75 mg, 0.023 mmol) in MeOH (1.2 mL) is added 3-(methylamino)propanamide (35 mg, 0.343 mmol) and N,N-diisopropylethylamine (22 µL, 0.126 mmol) and the reaction is heated at 65° C. for 18. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (4.4 mg, 25%).

LC/MS Condition E: ret time 1.84 min; m/e=736 (M+H)+.
LC/MS Condition F: ret time 1.79 min; m/e=736 (M+H)+.

Intermediate: (S)-5-((4-chloro-5-((2,2'-dichloro-3'-(3-chloropropoxy)-[1,1'-biphenyl]-3-yl)methoxy)-2-(((2,3-dihydroxypropyl)amino)methyl)phenoxy)methyl)nicotinonitrile

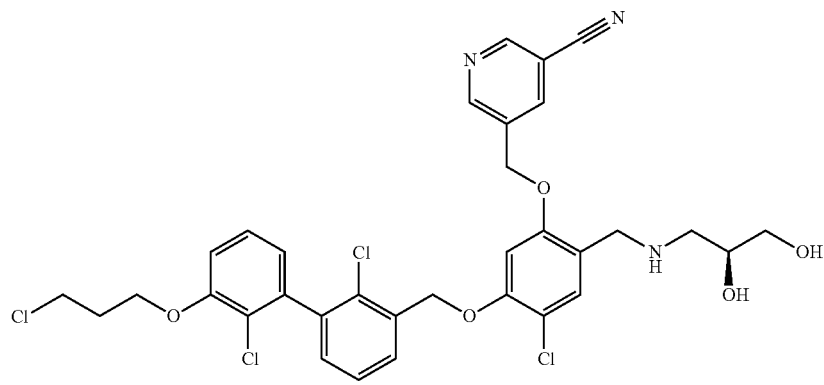 [SMILES: N#Cc1cncc(COc2cc(OCc3cccc(-c4cccc(OCCCCl)c4Cl)c3Cl)c(Cl)cc2CNC[C@H](O)CO)c1]

To a solution of 5-((4-chloro-5-((2,2'-dichloro-3'-(3-chloropropoxy)-[1,1'-biphenyl]-3-yl)methoxy)-2-formylphenoxy)methyl)nicotinonitrile (45 mg, 0.073 mmol), and (S)-3-aminopropane-1,2-diol (23.8 mg, 0.261 mmol) in a mixture of DCE (1.0 mL) and EtOH (0.7 mL) was added acetic acid (14 µL, 0.245 mmol) and three 4 A molecular sieves. The resulting solution was stirred at room temp under N2 for 60 min, then treated dropwise (over 2.75 h) with sodium cyanoborohydride (1.0 M in THF; 0.15 mL, 0.150 mmol). After the addition was complete, the reaction was evaporated under a stream of nitrogen. The crude product was dissolved in methanol (2 mL), and half of this material was used directly "as is" without purification in each of the Examples 2033 and 2034.

LC/MS Condition A: ret time 1.16 min; m/e=690 (M+H)+.

Example 2033: 5-((4-chloro-5-((2,2'-dichloro-3'-(3-(((S)-2,3-dihydroxypropyl)amino)propoxy)-[1,1'-biphenyl]-3-yl)methoxy)-2-((((S)-2,3-dihydroxypropyl)amino)methyl)phenoxy)methyl)nicotinonitrile

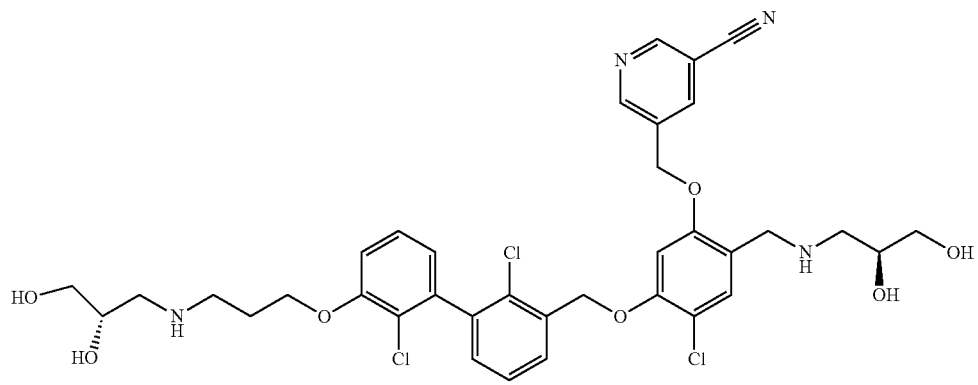 [SMILES: N#Cc1cncc(COc2cc(OCc3cccc(-c4cccc(OCCCNC[C@H](O)CO)c4Cl)c3Cl)c(Cl)cc2CNC[C@H](O)CO)c1]

To a solution of (S)-5-((4-chloro-5-((2,2'-dichloro-3'-(3-chloropropoxy)-[1,1'-biphenyl]-3-yl)methoxy)-2-(((2,3-dihydroxypropyl)amino)methyl)phenoxy)methyl)nicotinonitrile (25 mg, 0.023 mmol) in MeOH (1 mL) is added (S)-3-aminopropane-1,2-diol (55 mg, 0.604 mmol), sodium iodide (12 mg) and N,N-diisopropylethylamine (40 µl, 0.229 mmol) and the reaction is heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (1.7 µmg, 6%).

LC/MS Condition E: ret time 1.59 min; m/e=745 (M+H)⁺.
LC/MS Condition F: ret time 1.50 min; m/e=745 (M+H)⁺.

Example 2034: 5-((4-chloro-5-((2,2'-dichloro-3'-(3-((R)-3-hydroxypyrrolidin-1-yl)propoxy)-[1,1'-biphenyl]-3-yl)methoxy)-2-((((S)-2,3-dihydroxypropyl)amino)methyl)phenoxy)methyl)nicotinonitrile 2H), 2.70 (dd, J=9.6, 6.3 Hz, 1H), 2.61-2.50 (m, 6H), 2.46-2.39 (m, 2H), 2.32 (dd, J=9.5, 3.7 Hz, 1H), 2.02-1.91 (m, 3H), 1.91 (s, 6H), 1.58-1.49 (m, 1H).

LC/MS Condition E: ret time 1.63 min; m/e=741 (M+H)⁺.
LC/MS Condition F: ret time 1.53 min; m/e=741 (M+H)⁺.

Examples 2035 to 2123 and Examples 2278 to 2385 were prepared as described below. The LC/MS Conditions A to F as listed for Examples 2001 to 2034 and Condition G were employed for these Examples.

LC/MS Condition G:
Column=Waters Aquity UPLC BEH C18, 2.1×50 mm, 1.7 am
Start % B=0; Final % B=100
Gradient time=2 min; Stop time=3 min
Flow Rate=0.8 mL/min; Wavelength=220 nm or 254 nm
Solvent A=10% MeOH/90% Water/0.1% TFA
Solvent B=90% MeOH/10% Water/0.1% TFA
Oven temp.=0° C.

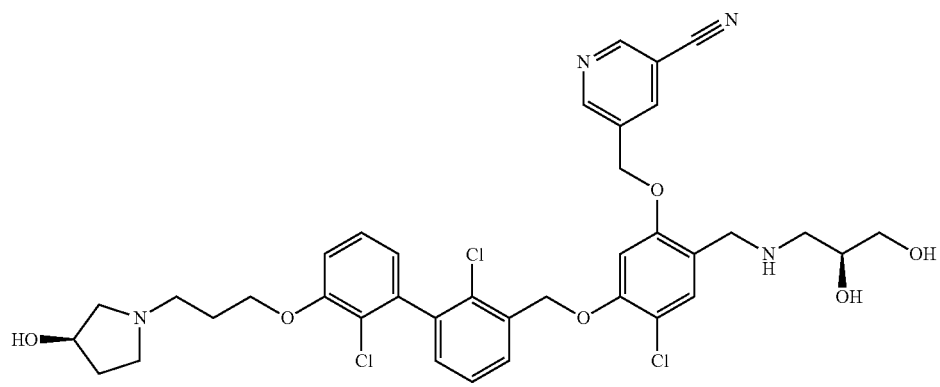 [SMILES: N#Cc1cncc(COc2cc(OCc3cccc(-c4cccc(OCCCN5CC[C@@H](O)C5)c4Cl)c3Cl)c(Cl)cc2CNC[C@H](O)CO)c1]

To a solution of (S)-5-((4-chloro-5-((2,2'-dichloro-3'-(3-chloropropoxy)-[1,1'-biphenyl]-3-yl)methoxy)-2-(((2,3-dihydroxypropyl)amino)methyl)phenoxy)methyl)nicotinonitrile (25 mg, 0.023 mmol) in MeOH (1 mL) is added (R)-pyrrolidin-3-ol, HCl (60 mg, 0.486 mmol), sodium iodide (12 mg) and N,N-diisopropylethylamine (90 µl, 0.515 mmol) and the reaction is heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (5.3 mg, 18%).
¹H NMR (500 MHz, DMSO-d₆) δ 9.01 (d, J=1.8 Hz, 1H), 8.97 (d, J=1.8 Hz, 1H), 8.41 (s, 1H), 7.72 (d, J=7.9 Hz, 1H), 7.50 (t, J=7.6 Hz, 1H), 7.41-7.36 (m, 2H), 7.33 (d, J=6.1 Hz, 1H), 7.21 (d, J=8.5 Hz, 1H), 7.07 (s, 1H), 6.93-6.86 (m, 1H), 5.33 (s, 2H), 5.30 (s, 2H), 4.23-4.07 (m, 4H), 3.69-3.66 (m, Intermediate: 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile

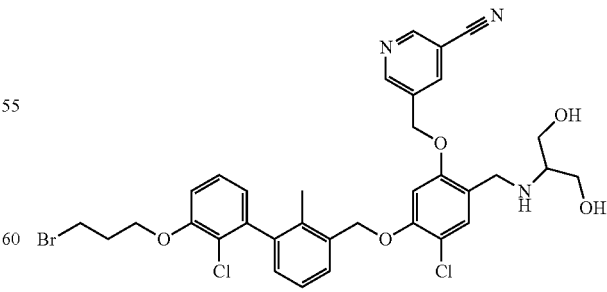

To a dry 25 mL round bottom flask under N₂ was added 5-((5-((3'-(3-bromopropoxy)-2'-chloro-2-methyl-[1,1'-biphenyl]-3-yl)methoxy)-4-chloro-2-formylphenoxy)methyl)nicotinonitrile (80 mg, 0.125 mmol), 2-amino-1,3-propanediol (34 mg, 0.373 mmol), 1,2-dichloroethane (1.2 mL), EtOH (2.4 mL) and 2-3 pieces of 4 A sieves. The reaction was treated with acetic acid (14.3 µL, 0.250 mmol), allowed to stir for 1 h at room temp then treated dropwise (over 2.5 h) with sodium cyanoborohydride, 1.0 M in THF (250 µL, 0.250 mmol). After the addition was complete, the reaction was allowed to stir at room temp for 1.5 h, and the solvent removed under a stream of $N_2$. The crude product was dissolved in methanol (4.0 mL) and used directly "as is" without purification in subsequent reactions.

LC/MS Condition A: ret time 1.19 min; m/e=714 (M+H)⁺.

Example 2035: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxypropan-2-yl)amino)methyl)phenoxy)methyl)nicotinonitrile capped and heated at 65° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the title compound (16.1 mg, 71%).

LC/MS Condition E: ret time 1.45 min; m/e=721 (M+H)⁺.
LC/MS Condition F: ret time 1.64 min; m/e=721 (M+H)⁺.

Example 2036: (S)-5-((4-chloro-5-((2'-chloro-3'-(3-((2,3-dihydroxypropyl)amino)propoxy)-2-methyl-[1,1'-biphenyl]-3-yl)methoxy)-2-(((1,3-dihydroxypropan-2-yl)amino)methyl)phenoxy)methyl)nicotinonitrile

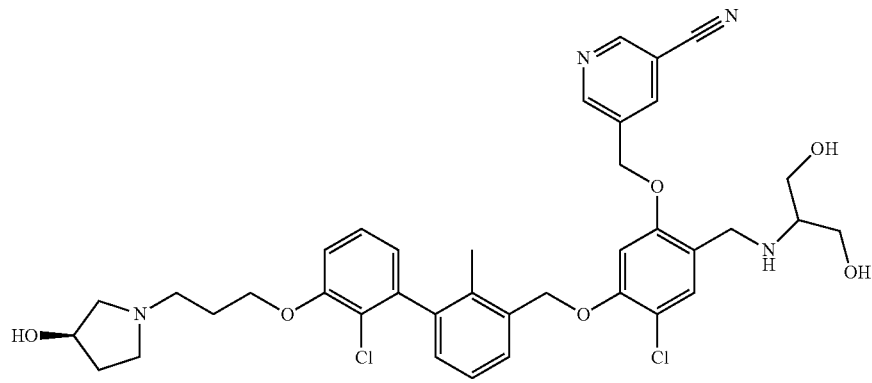 [SMILES: Cc1c(COc2cc(OCc3cncc(C#N)c3)c(CNC(CO)CO)cc2Cl)cccc1-c1cccc(OCCCN2CC[C@@H](O)C2)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.25 mg, 0.031 mmol) in MeOH (1.1 mL) was added (R)-3-hydroxypyrrolidine hydrochloride (55 mg, 0.445 mmol) and N,N-diisopropylethylamine (100 µL, 0.573 mmol). The reaction was flushed briefly with $N_2$,

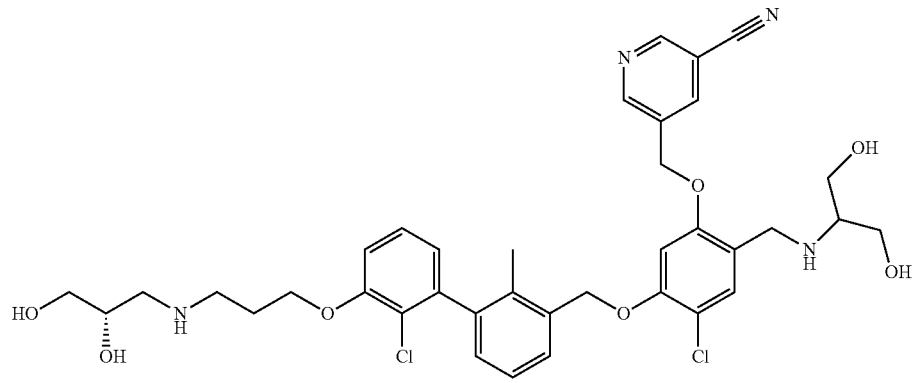 [SMILES: Cc1c(COc2cc(OCc3cncc(C#N)c3)c(CNC(CO)CO)cc2Cl)cccc1-c1cccc(OCCCNC[C@H](O)CO)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.25 mg, 0.031 mmol) in MeOH was added (S)-3-aminopropane-1,2-diol (40 mg, 0.439 mmol) and N,N-diisopropylethylamine (25 µL, 0.143 mmol). The reaction was flushed briefly with $N_2$, capped and heated at 65° C. sand bath for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the title compound (8.9 mg, 39%).

LC/MS Condition E: ret time 1.38 min; m/e=725 (M+H)[+].
LC/MS Condition F: ret time 1.58 min; m/e=725 (M+H)[+].

Example 2037: 5-((4-chloro-5-((2'-chloro-2-methyl-3'-(3-((2-(pyridin-3-yl)ethyl)amino)propoxy)-[1,1'-biphenyl]-3-yl)methoxy)-2-(((1,3-dihydroxypropan-2-yl)amino)methyl)phenoxy)methyl)nicotinonitrile 3-(2-aminoethyl)pyridine (55 µL, 0.468 mmol), and N,N-diisopropylethylamine (25 µL, 0.143 mmol). The reaction was flushed briefly with $N_2$, capped and heated at 65° C. sand bath for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the title compound (16.6 mg, 68%).

LC/MS Condition E: ret time 1.52 min; m/e=756 (M+H)[+].
LC/MS Condition F: ret time 1.50 min; m/e=756 (M+H)[+].

Example 2038: (R)-2-((5-chloro-4-((2'-chloro-3'-(3-((1,3-dihydroxypropan-2-yl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

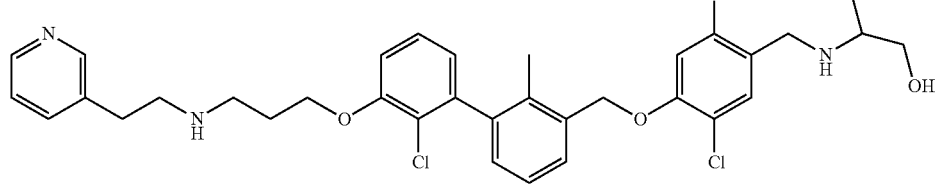

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.25 mg, 0.031 mmol) in MeOH was added

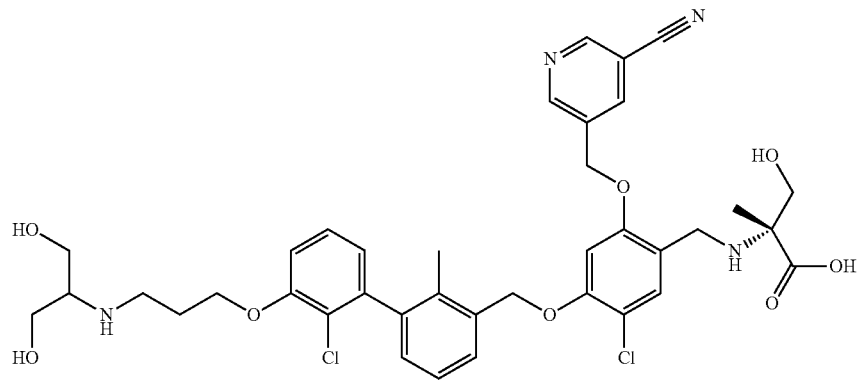 [SMILES: Cc1c(COc2cc(OCc3cncc(C#N)c3)c(CN[C@](C)(CO)C(=O)O)cc2Cl)cccc1-c1cccc(OCCCNC(CO)CO)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.1 mL) was added 2-amino-1,3-propanediol (22 mg, 0.241 mmol) and N,N-diisopropylethylamine (20 µL, 0.115 mmol). The reaction was flushed briefly with N₂, capped and heated at 65° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-75% B over 15 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min to give the title compound as a TFA salt (2.7 mg, 17%).

LC/MS Condition E: ret time 1.33 min; m/e=753 (M+H)⁺.
LC/MS Condition F: ret time 1.57 min; m/e=753 (M+H)⁺.

Example 2039: 5-((4-chloro-5-((2'-chloro-3'-(3-((1,3-dihydroxypropan-2-yl)amino)propoxy)-2-methyl-[1,1'-biphenyl]-3-yl)methoxy)-2-(hydroxymethyl)phenoxy)methyl)nicotinonitrile

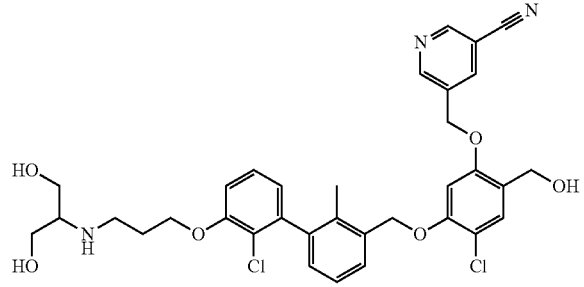 [SMILES: Cc1c(COc2cc(OCc3cncc(C#N)c3)c(CO)cc2Cl)cccc1-c1cccc(OCCCNC(CO)CO)c1Cl]

From Example 2038, the above product was also isolated via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-75% B over 15 minutes, then a 5-minute hold at 100% B; Flow: 20 mL/min to give the title compound (6.1 mg, 58%).

LC/MS Condition E: ret time 1.62 min; m/e=652 (M+H)⁺.
LC/MS Condition F: ret time 1.60 min; m/e=652 (M+H)⁺.

Example 2040: (R)-2-((5-chloro-4-((2'-chloro-3'-(3-((1,3-dihydroxy-2-(hydroxymethyl)propan-2-yl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

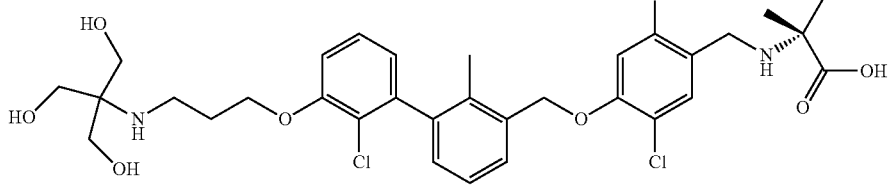

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH was added tris(hydroxymethyl)aminomethane (24 µL, 0.267 mmol) and N,N-diisopropylethylamine (20 µL, 0.115 mmol). The reaction was flushed briefly with N₂, capped and heated at 65° C. for 36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 30 minutes, then a 5-minute hold at 100% B; Flow: 20 mL/min (1.7 µmg, 13%).

LC/MS Condition E: ret time 1.62 min; m/e=652 (M+H)⁺.
LC/MS Condition F: ret time 1.60 min; m/e=652 (M+H)⁺.

Example 2041: 5-((4-chloro-5-((2'-chloro-3'-(3-((1,3-dihydroxy-2-(hydroxymethyl)propan-2-yl)amino)propoxy)-2-methyl-[1,1'-biphenyl]-3-yl)methoxy)-2-(hydroxymethyl)phenoxy)methyl)nicotinonitrile

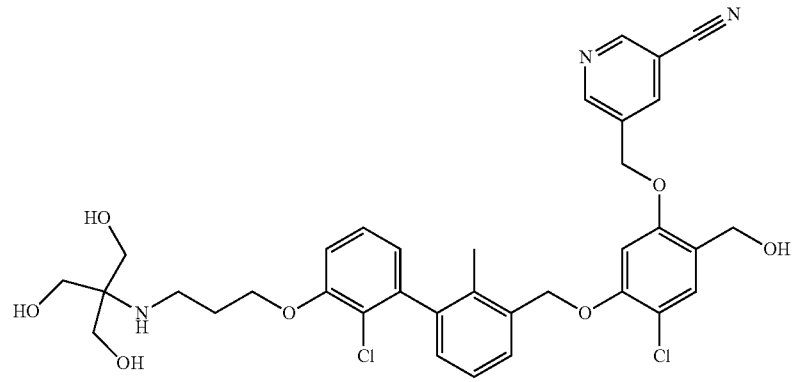 [SMILES: Cc1c(COc2cc(OCc3cncc(C#N)c3)c(CO)cc2Cl)cccc1-c1cccc(OCCCNC(CO)(CO)CO)c1Cl]

From Example 2040, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 30 minutes, then a 5-minute hold at 100% B; Flow: 20 mL/min to give the title compound (8.6 mg, 77%).

LC/MS Condition E: ret time 1.60 min; m/e=682 (M+H)$^+$.
LC/MS Condition F: ret time 1.59 min; m/e=682 (M+H)$^+$.

Example 2042: 5-((4-chloro-5-((2'-chloro-3'-(3-((1,3-dihydroxypropan-2-yl)amino)propoxy)-2-methyl-[1,1'-biphenyl]-3-yl)methoxy)-2-(((1,3-dihydroxypropan-2-yl)amino)methyl)phenoxy)methyl)nicotinonitrile

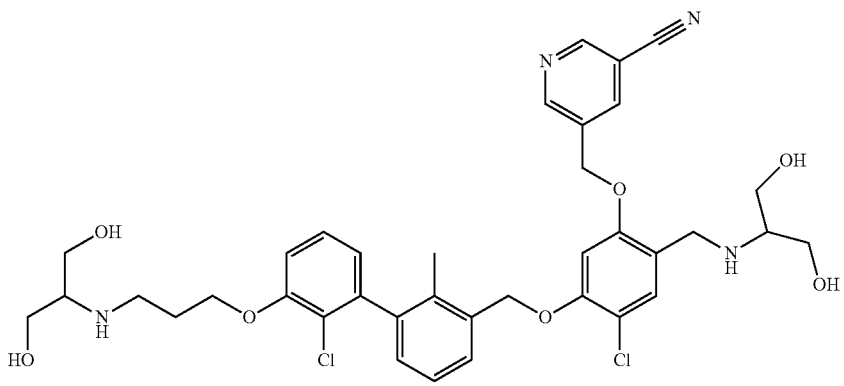 [SMILES: Cc1c(COc2cc(OCc3cncc(C#N)c3)c(CNC(CO)CO)cc2Cl)cccc1-c1cccc(OCCCNC(CO)CO)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.25 mg, 0.031 mmol) in MeOH (1.1 mL) was added 2-amino-1,3-propanediol (40 mg, 0.439 mmol) and N,N-diisopropylethylamine (25 μL, 0.143 mmol). The reaction was flushed briefly with N$_2$, capped and heated at 65° C. for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (8.6 mg, 35%).

LC/MS Condition E: ret time 1.34 min; m/e=725 (M+H)$^+$.
LC/MS Condition F: ret time 1.31 min; m/e=725 (M+H)$^+$.

Example 2043: (2R)-2-((5-chloro-4-((2'-chloro-3'-(3-(3-(hydroxymethyl)piperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

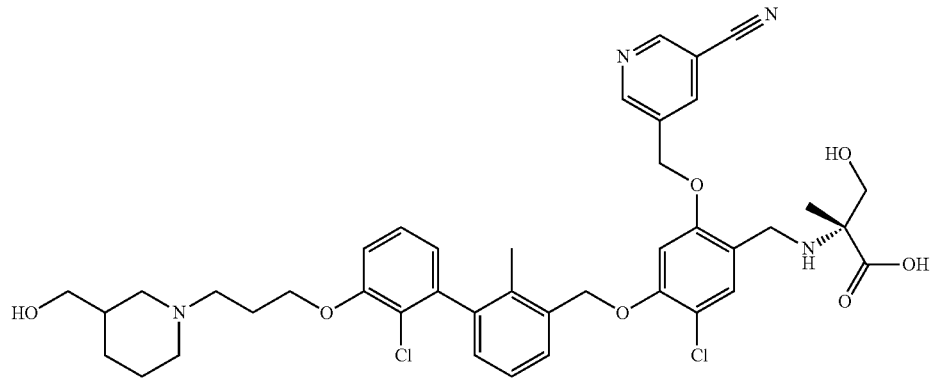 [SMILES: Cc1c(COc2cc(OCc3cncc(C#N)c3)c(CN[C@](C)(CO)C(=O)O)cc2Cl)cccc1-c1cccc(OCCCN2CCCC(CO)C2)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (11.5 mg, 0.015 mmol) in MeOH (1.1 mL) was added 3-piperidinemethanol (25 mg, 0.217 mmol) followed by N,N-diisopropylethylamine (20 μL, 0.115 mmol). The reaction was flushed briefly with $N_2$, capped and heated at 65° C. sand bath for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-80% B over 20 minutes, then a 5-minute hold at 100% B; Flow: 20 mL/min to give the title compound (9.4 mg, 70%).

LC/MS Condition E: ret time 1.41 min; m/e=777 (M+H)$^+$.
LC/MS Condition F: ret time 1.69 min; m/e=777 (M+H)$^+$.

Example 2044: 5-((4-chloro-5-((2'-chloro-3'-(3-(3-(hydroxymethyl)piperidin-1-yl)propoxy)-2-methyl-[1,1'-biphenyl]-3-yl)methoxy)-2-(hydroxymethyl)phenoxy)methyl)nicotinonitrile

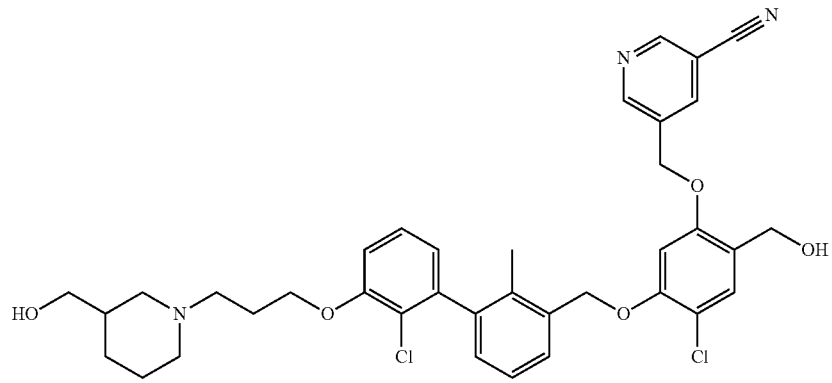 [SMILES: Cc1c(COc2cc(OCc3cncc(C#N)c3)c(CO)cc2Cl)cccc1-c1cccc(OCCCN2CCCC(CO)C2)c1Cl]

From Example 2043, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-80% B over 20 minutes, then a 5-minute hold at 100% B; Flow: 20 mL/min to give the title compound (14.2 mg)

LC/MS Condition E: ret time 1.74 min; m/e=676 (M+H)$^+$.
LC/MS Condition F: ret time 2.00 min; m/e=676 (M+H)$^+$.

311

Intermediate: 5-((4-chloro-5-((2,2'-dichloro-3'-(3-iodopropoxy)-[1,1'-biphenyl]-3-yl)methoxy)-2-formylphenoxy)methyl)nicotinonitrile

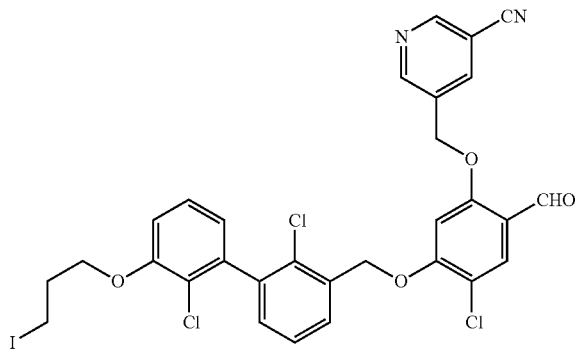 [SMILES: N#Cc1cncc(COc2cc(OCc3cccc(-c4cccc(OCCCI)c4Cl)c3Cl)c(Cl)cc2C=O)c1]

A solution of 5-((4-chloro-5-((2,2'-dichloro-3'-(3-chloropropoxy)-[1,1'-biphenyl]-3-yl)methoxy)-2-formylphenoxy)methyl)nicotinonitrile (115 mg, 0.187 mmol) in Acetone-d6 (2 mL) was treated with sodium iodide (200 mg, 1.334 mmol) and allowed to stir at room temp. for 3 h, then heated to 65 C for 1 h. The reaction was stirred for 18 h at room temp., then additional sodium iodide (235 mg, 1.57 mmol) was added and the reaction heated to 65 C for 3 h. The reaction was removed from the bath and stirred at room temp. for 80 h. The reaction was then heated to 65 C for 7 h, then cooled, filtered and the solvent was removed under a stream of $N_2$. The residue was taken up in dichloromethane (10 mL), stirred for 1 h, filtered and evaporated to dryness to give the title compound (135 mg) that was used "as is" without purification in subsequent reactions.

LC/MS Condition A: ret time 1.6 min; m/e=707 (M+H)$^+$.

312

Intermediate: (S)-1-(5-chloro-2-((5-cyanopyridin-3-yl)methoxy)-4-((2,2'-dichloro-3'-(3-iodopropoxy)-[1,1'-biphenyl]-3-yl)methoxy)benzyl)piperidine-2-carboxylic Acid

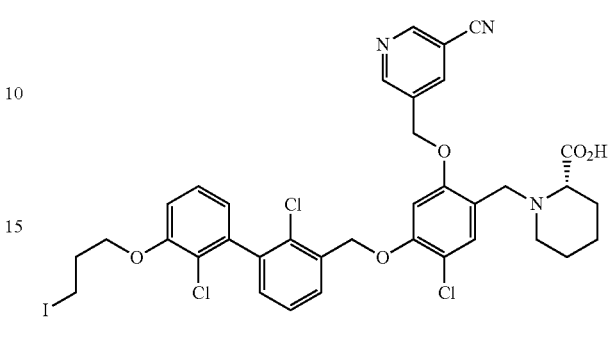

A mixture of 5-((4-chloro-5-((2,2'-dichloro-3'-(3-iodopropoxy)-[1,1'-biphenyl]-3-yl)methoxy)-2-formylphenoxy)methyl)nicotinonitrile (135 mg, 0.191 mmol) and (S)-piperidine-2-carboxylic acid (50 mg, 0.387 mmol) in dichloroethane (2 mL) and ethanol (1.4 mL) was treated with glacial acetic acid (20 µl, 0.349 mmol), 4 A activated molecular sieves and stirred at room temp. for 45 min. The reaction was then treated dropwise (over 3 h) with sodium cyanoborohydride, 1 M in THF (400 µl, 0.400 mmol). The solvent was removed under a gentle stream of $N_2$ and the crude title compound was redissolved in MeOH (4 mL) and used directly "as is" without purification in subsequent reactions.

LC/MS Condition A: ret time 1.26 min; m/e=822 (M+H)$^+$.

Example 2045: (S)-1-(5-chloro-2-((5-cyanopyridin-3-yl)methoxy)-4-((2,2'-dichloro-3'-(3-(piperidin-1-yl)propoxy)-[1,1'-biphenyl]-3-yl)methoxy)benzyl)piperidine-2-carboxylic Acid

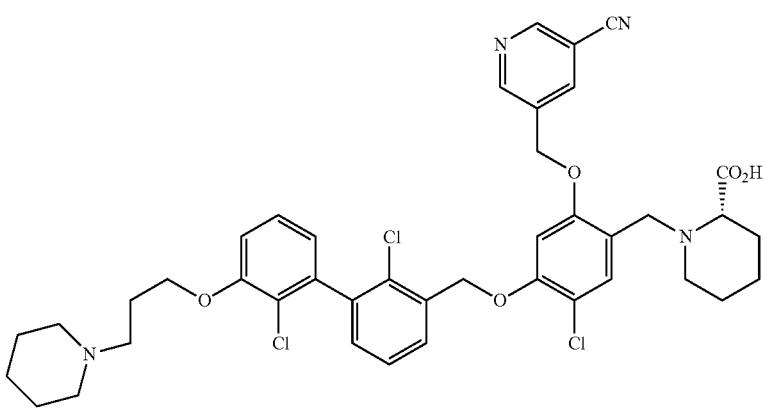 [SMILES: N#Cc1cncc(COc2cc(OCc3cccc(-c4cccc(OCCCN5CCCCC5)c4Cl)c3Cl)c(Cl)cc2CN2CCCC[C@H]2C(=O)O)c1]

To a solution of (S)-1-(5-chloro-2-((5-cyanopyridin-3-yl)methoxy)-4-((2,2'-dichloro-3'-(3-iodopropoxy)-[1,1'-biphenyl]-3-yl)methoxy)benzyl)piperidine-2-carboxylic acid (37 mg, 0.045 mmol) in MeOH (1.0 mL) was added piperidine (75 µL, 0.759 mmol). The reaction was flushed briefly with $N_2$, capped and heated at 65° C. for 75 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 28-78% B over 25 minutes, then a 5-minute hold at 100% B; Flow: 20 mL/min to give the title compound (8.4 mg, 22%)

LC/MS Condition E: ret time 1.49 min; m/e=777 (M+H)+.
LC/MS Condition F: ret time 1.62 min; m/e=777 (M+H)+.

Example 2046: 5-((4-chloro-5-((2,2'-dichloro-3'-(3-(piperidin-1-yl)propoxy)-[1,1'-biphenyl]-3-yl)methoxy)-2-(hydroxymethyl)phenoxy)methyl)nicotinonitrile

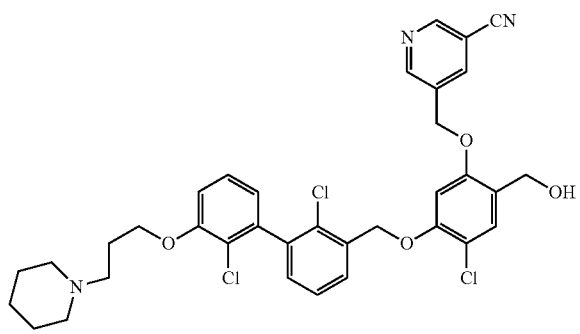 [SMILES: N#Cc1cncc(COc2cc(OCc3cccc(-c4cccc(OCCCN5CCCCC5)c4Cl)c3Cl)c(Cl)cc2CO)c1]

From Example 2045, the above product was also isolated via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-78% B over 25 minutes, then a 5-minute hold at 100% B; Flow: 20 mL/min to give the title compound (5.2 mg, 16%)

LC/MS Condition E: ret time 1.80 min; m/e=666 (M+H)+.

LC/MS Condition F: ret time 1.88 min; m/e=666 (M+H)+.

Example 2047: (2S)-1-(4-((3'-(3-(3-acetamidopyrrolidin-1-yl)propoxy)-2,2'-dichloro-[1,1'-biphenyl]-3-yl)methoxy)-5-chloro-2-((5-cyanopyridin-3-yl)methoxy)benzyl)piperidine-2-carboxylic Acid

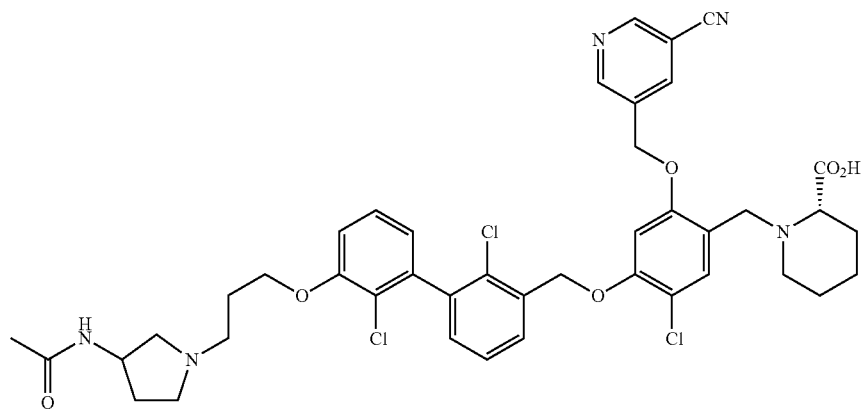 [SMILES: CC(=O)NC1CCN(CCCOc2cccc(-c3cccc(COc4cc(OCc5cncc(C#N)c5)c(CN5CCCC[C@H]5C(=O)O)cc4Cl)c3Cl)c2Cl)C1]

To a solution of (S)-1-(5-chloro-2-((5-cyanopyridin-3-yl)methoxy)-4-((2,2'-dichloro-3'-(3-iodopropoxy)-[1,1'-biphenyl]-3-yl)methoxy)benzyl)piperidine-2-carboxylic acid (37 mg, 0.045 mmol) in MeOH (1.0 mL) was added N-(pyrrolidin-3-yl)acetamide (40 mg, 0.312 mmol) and N,N-diisopropylethylamine (40 μL, 0.229 mmol). The reaction was flushed briefly with $N_2$, capped and heated at 65° C. for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 20 minutes, then a 5-minute hold at 100% B; Flow: 20 mL/min to give the title compound (10.9 mg, 28%).

LC/MS Condition E: ret time 1.43 min; m/e=820 (M+H)+.
LC/MS Condition F: ret time 1.54 min; m/e=820 (M+H)+.

Example 2048: (R)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

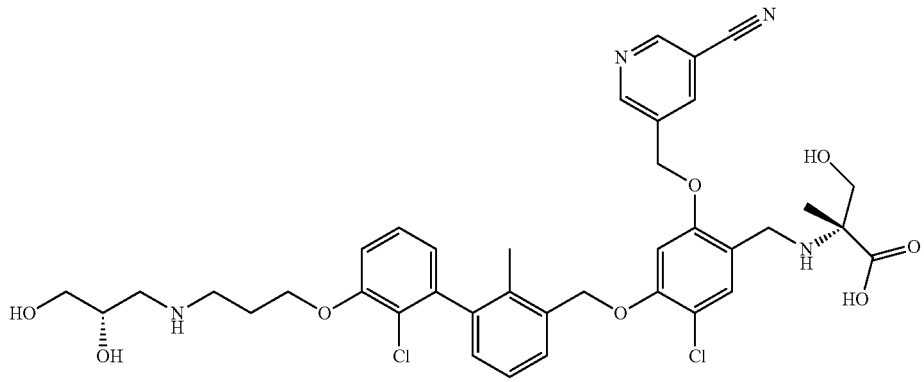 [SMILES: Cc1c(COc2cc(OCc3cncc(C#N)c3)c(CN[C@](C)(CO)C(=O)O)cc2Cl)cccc1-c1cccc(OCCCNC[C@H](O)CO)c1Cl]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (29 mg, 0.039 mmol) in MeOH (1.1 mL) was added (S)-3-amino-1,2-propanediol (65 mg, 0.713 mmol) and N,N-diisopropylethylamine (40 µL, 0.229 mmol). The reaction was flushed briefly with $N_2$, capped, and placed in a 65° C. sand bath for 8.75 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min to give the title compound (7.4 mg, 23%)
LC/MS Condition E: ret time 1.47 min; m/e=753 (M+H)+.
LC/MS Condition F: ret time 1.44 min; m/e=753 (M+H)+.

Example 2049: (S)-1-(5-chloro-2-((5-cyanopyridin-3-yl)methoxy)-4-((2,2'-dichloro-3'-(3-(((S)-2,3-dihydroxypropyl)amino)propoxy)-[1,1'-biphenyl]-3-yl)methoxy)benzyl)piperidine-2-carboxylic Acid

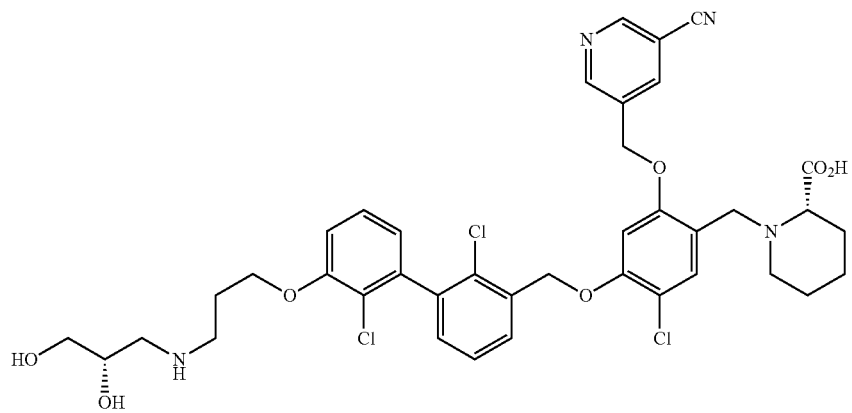 [SMILES: N#Cc1cncc(COc2cc(OCc3cccc(-c4cccc(OCCCNC[C@H](O)CO)c4Cl)c3Cl)c(Cl)cc2CN2CCCC[C@H]2C(=O)O)c1]

A solution of (S)-1-(5-chloro-2-((5-cyanopyridin-3-yl)methoxy)-4-((2,2'-dichloro-3'-(3-iodopropoxy)-[1,1'-biphenyl]-3-yl)methoxy)benzyl)piperidine-2-carboxylic acid (37 mg, 0.045 mmol), (S)-3-aminopropane-1,2-diol (35 mg, 0.384 mmol), and N,N-diisopropylethylamine (40 µl, 0.229 mmol) was heated at 65° C. 3.5 h, then heated at 45° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the title compound (5.6 mg, 15%).

LC/MS Condition E: ret time 1.91 min; m/e=783 (M+H)+.
LC/MS Condition F: ret time 2.12 min; m/e=783 (M+H)+.

Example 2050: (S)-5-((4-chloro-5-((2'-chloro-3'-(3-((2,3-dihydroxypropyl)(methyl)amino)propoxy)-2-methyl-[1,1'-biphenyl]-3-yl)methoxy)-2-(((1,3-dihydroxypropan-2-yl)amino)methyl)phenoxy)methyl)nicotinonitrile

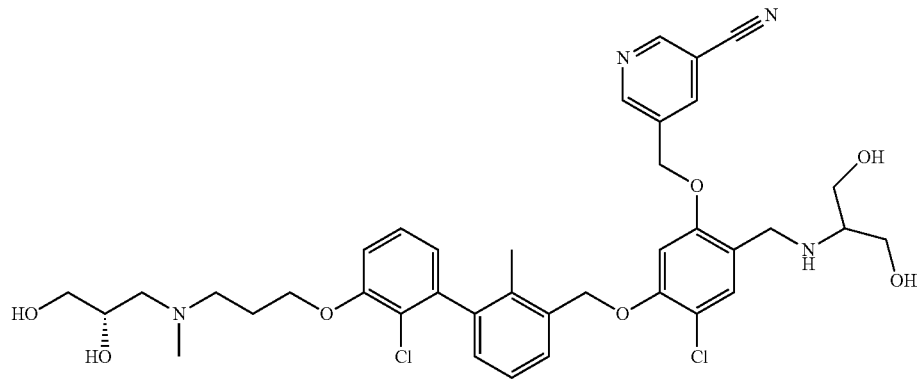 [SMILES: Cc1c(COc2cc(OCc3cncc(C#N)c3)c(CNC(CO)CO)cc2Cl)cccc1-c1cccc(OCCCN(C)C[C@H](O)CO)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added (S)-3-(methylamino)propane-1,2-diol (45 mg, 0.428 mmol) and N,N-diisopropylethylamine (25 µL, 0.143 mmol). The reaction was flushed with N₂, capped and heated at 65° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound (15.6 mg, 67%).
LC/MS Condition E: ret time 1.45 min; m/e=739 (M+H)+.
LC/MS Condition F: ret time 1.43 min; m/e=739 (M+H)+.

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added piperidine (0.081 mL, 0.822 mmol). The reaction was flushed with N₂, capped and heated at 65° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to give the title compound (4.9 mg, 21%).
LC/MS Condition E: ret time 1.59 min; m/e=719 (M+H)+.
LC/MS Condition F: ret time 1.54 min; m/e=719 (M+H)+.

Example 2051: 5-((4-chloro-5-((2'-chloro-2-methyl-3'-(3-(piperidin-1-yl)propoxy)-[1,1'-biphenyl]-3-yl)methoxy)-2-(((1,3-dihydroxypropan-2-yl)amino)methyl)phenoxy)methyl)nicotinonitrile

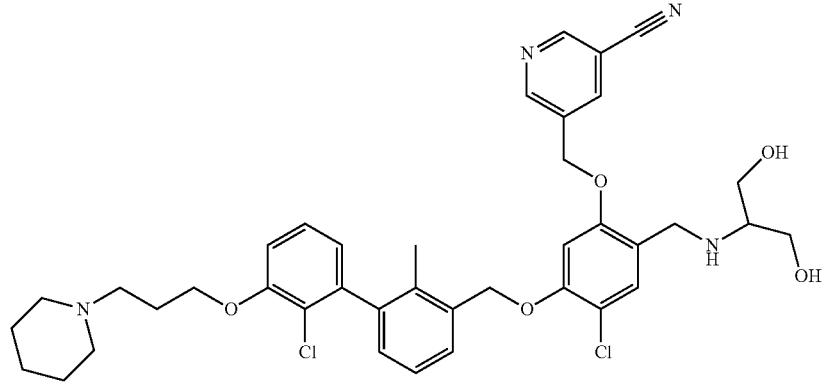 [SMILES: Cc1c(COc2cc(OCc3cncc(C#N)c3)c(CNC(CO)CO)cc2Cl)cccc1-c1cccc(OCCCN2CCCCC2)c1Cl]

Example 2052: N-(1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)pyrrolidin-3-yl)acetamide To a solution of 5-((4-chloro-5-((2,2'-dichloro-3'-(3-iodopropoxy)-[1,1'-biphenyl]-3-yl)methoxy)-2-formylphenoxy)methyl)nicotinonitrile (50 mg, 0.071 mmol) in a mixture of ClCH₂CH₂Cl (550 µL) and EtOH (385 µL) was added 2-amino-2-methylpropane-1,3-diol (24 mg, 0.228 mmol),

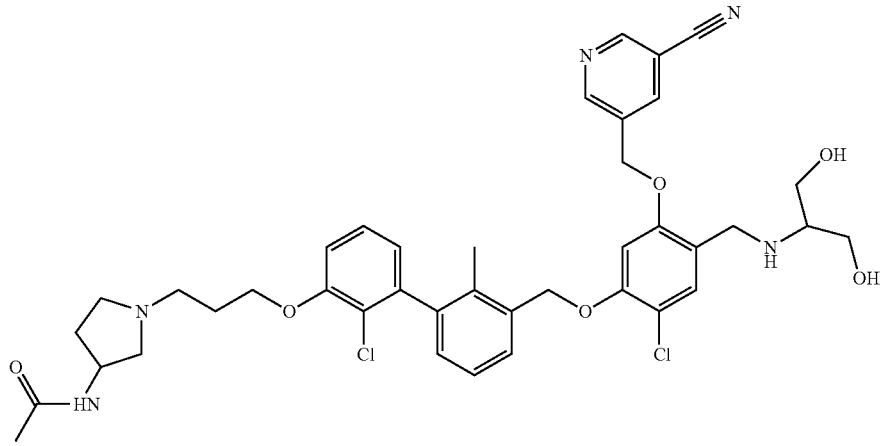 [SMILES: CC(=O)NC1CCN(CCCOc2cccc(-c3cccc(COc4cc(OCc5cncc(C#N)c5)c(CNC(CO)CO)cc4Cl)c3C)c2Cl)C1]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added 3-acetamidopyrrolidine (52 mg, 0.406 mmol) and N,N-diisopropylethylamine (25 µL, 0.143 mmol). The reaction was flushed briefly with N₂, capped and heated at ° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (8.7 mg, 37%).

LC/MS Condition E: ret time 1.53 min; m/e=762 (M+H)⁺.
LC/MS Condition F: ret time 1.45 min; m/e=762 (M+H)⁺.

acetic acid (12 µL, 0.210 mmol) and activated 4 A mol. sieves. The reaction was flushed briefly with N₂, capped, stirred at room temp. for 1 h then treated dropwise (over 4 h) with sodium cyanoborohydride, 1.0M in THF (140 µL, 0.140 mmol). After the addition was complete, the solvent was removed under a gentle stream of N₂ and the crude title compound was redissolved in MeOH (4 mL) and used directly "as is" without purification in subsequent reactions.

LC/MS Condition A: ret time 1.23 min; m/e=796 (M+H)⁺.

Intermediate: 5-((4-chloro-5-((2,2'-dichloro-3'-(3-iodopropoxy)-[1,1'-biphenyl]-3-yl)methoxy)-2-(((1,3-dihydroxy-2-methylpropan-2-yl)amino)methyl)phenoxy)methyl)nicotinonitrile

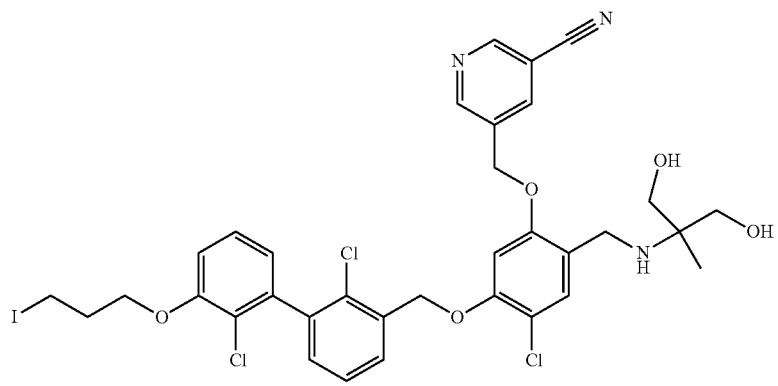 [SMILES: CC(CO)(CO)NCc1cc(Cl)c(OCc2cccc(-c3cccc(OCCCI)c3Cl)c2Cl)cc1OCc1cncc(C#N)c1]

Example 2053 (R)-5-((4-chloro-5-((2,2'-dichloro-3'-(3-(3-hydroxypyrrolidin-1-yl)propoxy)-[1,1'-biphenyl]-3-yl)methoxy)-2-(((1,3-dihydroxy-2-methylpropan-2-yl)amino)methyl)phenoxy)methyl)nicotinonitrile

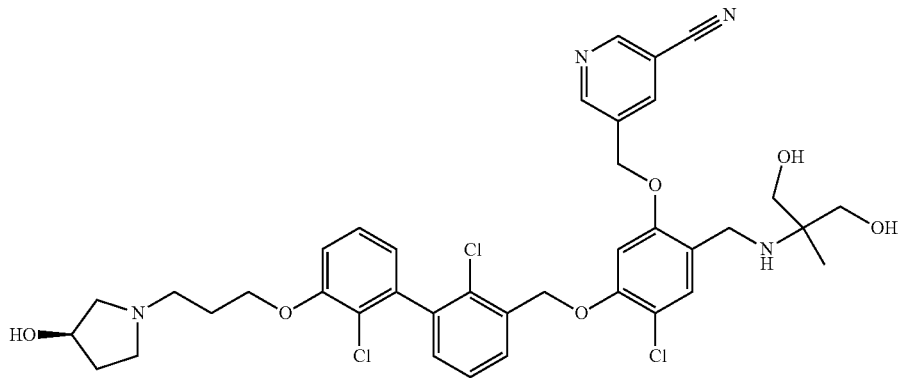 [SMILES: CC(CO)(CO)NCc1cc(Cl)c(OCc2cccc(-c3cccc(OCCCN4CC[C@@H](O)C4)c3Cl)c2Cl)cc1OCc1cncc(C#N)c1]

To a solution of 5-((4-chloro-5-((2,2'-dichloro-3'-(3-iodopropoxy)-[1,1'-biphenyl]-3-yl)methoxy)-2-(((1,3-dihydroxy-2-methylpropan-2-yl)amino)methyl)phenoxy)methyl)nicotinonitrile (28.2 mg, 0.035 mmol) in methanol (1.0 mL) was added (R)-3-hydroxypyrrolidine hydrochloride (65 mg, 0.526 mmol) and N,N-diisopropylethylamine (120 μL, 0.687 mmol). The reaction was flushed with N$_2$, capped, and heated at 65° C. for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (11.7 μmg, 43%).

LC/MS Condition E: ret time 1.46 min; m/e=755 (M+H)$^+$.
LC/MS Condition F: ret time 1.45 min; m/e=755 (M+H)$^+$.

Example 2054: (S)-5-((4-chloro-5-((2,2'-dichloro-3'-(3-((2,3-dihydroxypropyl)amino)propoxy)-[1,1'-biphenyl]-3-yl)methoxy)-2-(((1,3-dihydroxy-2-methylpropan-2-yl)amino)methyl)phenoxy)methyl)nicotinonitrile To a solution of 5-((4-chloro-5-((2,2'-dichloro-3'-(3-iodopropoxy)-[1,1'-biphenyl]-3-yl)methoxy)-2-(((1,3-dihydroxy-2-methylpropan-2-yl)amino)methyl)phenoxy)methyl)nicotinonitrile (28.2 mg, 0.035 mmol) in Methanol (1.0 mL) was added (S)-3-amino-1,2-propanediol (45 mg, 0.494 mmol) and N,N-diisopropylethylamine (30 μL, 0.172 mmol). The reaction was flushed with N$_2$, capped, and heated at 65° C. oil bath for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (9.4 mg, 34%).

LC/MS Condition E: ret time 1.46 min; m/e=755 (M+H)$^+$.
LC/MS Condition F: ret time 1.45 min; m/e=755 (M+H)$^+$.

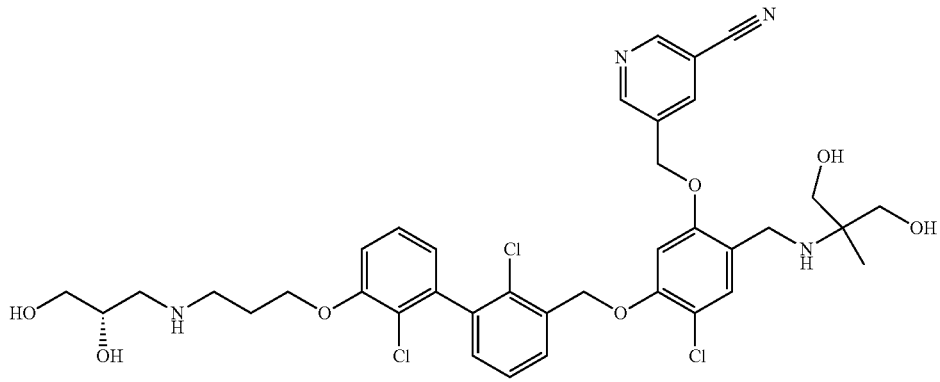 [SMILES: CC(CO)(CO)NCc1cc(Cl)c(OCc2cccc(-c3cccc(OCCCNC[C@H](O)CO)c3Cl)c2Cl)cc1OCc1cncc(C#N)c1]

323

Intermediate: 3-((5-((3'-(3-bromopropoxy)-2,2'-dichloro-[1,1'-biphenyl]-3-yl)methoxy)-4-chloro-2-formylphenoxy)methyl)-4-fluorobenzonitrile

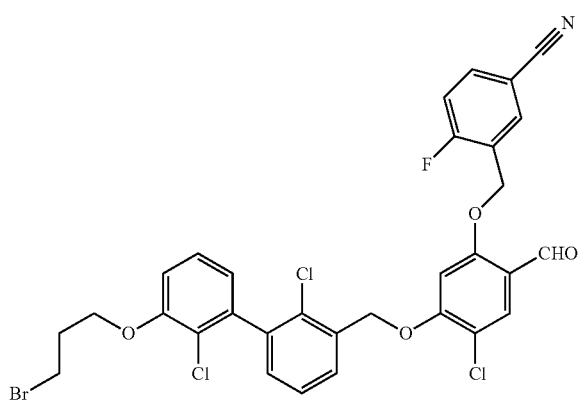 [SMILES: N#Cc1ccc(F)c(COc2cc(OCc3cccc(-c4cccc(OCCCBr)c4Cl)c3Cl)c(Cl)cc2C=O)c1]

To a dry 2-dram reaction vial under N₂ was added 4-((3'-(3-bromopropoxy)-2,2'-dichloro-[1,1'-biphenyl]-3-yl)methoxy)-5-chloro-2-hydroxybenzaldehyde (45 mg, 0.083 mmol), cesium carbonate (54 mg, 0.166 mmol) and DMF (500 μL). The resulting yellow solution was flushed briefly with N₂, capped, stirred at room temp. for 2 min, then treated with 3-(bromomethyl)-4-fluorobenzonitrile (23 mg, 0.107 mmol). The reaction was flushed with N₂, capped and stirred at room temp for 1 h. The solvent was removed under a gentle stream of N₂ and the residue was treated with 1,2-dichloroethane. The insoluble solids were filtered off and the filtrate that contained the title compound was used directly "as is" without purification in subsequent reactions.

LC/MS Condition A: ret time 1.64 min; m/e=676 (M+H)⁺.

324

Intermediate: 3-((5-((3'-(3-bromopropoxy)-2,2'-dichloro-[1,1'-biphenyl]-3-yl)methoxy)-4-chloro-2-(((1,3-dihydroxy-2-methylpropan-2-yl)amino)methyl)phenoxy)methyl)-4-fluorobenzonitrile

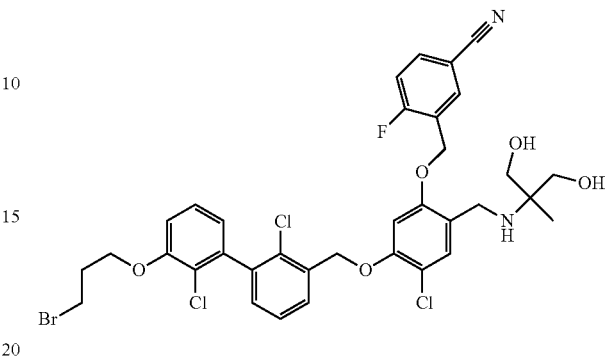

To a solution of 3-((5-((3'-(3-bromopropoxy)-2,2'-dichloro-[1,1'-biphenyl]-3-yl)methoxy)-4-chloro-2-formylphenoxy)methyl)-4-fluorobenzonitrile (56 mg, 0.083 mmol) in 1,2-dichloroethane (1.5 mL) was added 2-amino-2-methyl-1,3-propanediol (26 mg, 0.247 mmol), ethanol (1.0 mL), acetic acid (15 μL, 0.262 mmol) and 4 Å mol sieves. The reaction was flushed with N₂, capped, stirred at room temp for 1 h and then treated dropwise (over 2.75 h) with sodium cyanoborohydride, 1.0M in THF (216 μL, 0.216 mmol). After the addition was complete, the solvent was evaporated under a gentle stream of N₂ to give the title compound, that was used "as is" without purification in subsequent reactions.

LC/MS Condition A: ret time 1.26 min; m/e=765 (M+H)⁺.

Example 2055: (R)-3-((4-chloro-5-((2,2'-dichloro-3'-(3-(3-hydroxypyrrolidin-1-yl)propoxy)-[1,1'-biphenyl]-3-yl)methoxy)-2-(((1,3-dihydroxy-2-methylpropan-2-yl)amino)methyl)phenoxy)methyl)-4-fluorobenzonitrile

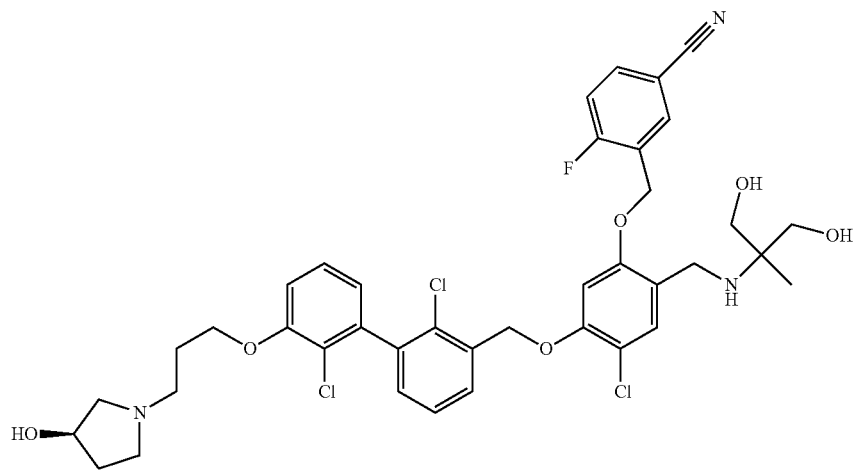 [SMILES: CC(CO)(CO)NCc1cc(Cl)c(OCc2cccc(-c3cccc(OCCCN4CC[C@@H](O)C4)c3Cl)c2Cl)cc1OCc1cc(C#N)ccc1F]

To a solution of 3-((5-((3'-(3-bromopropoxy)-2,2'-dichloro-[1,1'-biphenyl]-3-yl)methoxy)-4-chloro-2-(((1,3-dihydroxy-2-methylpropan-2-yl)amino)methyl)phenoxy)methyl)-4-fluorobenzonitrile in MeOH was added (R)-3-hydroxypyrrolidine hydrochloride (125 mg, 1.011 mmol)

and N,N-diisopropylethylamine (225 µL, 1.288 mmol). The reaction mixture was flushed briefly with N₂, capped, and heated at 65° C. for 2.5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 18 minutes, then a 3-minute hold at 100% B; Flow: 20 mL/min to give the title compound (41.4 mg, 64%).

LC/MS Condition E: ret time 1.57 min; m/e=772 (M+H)⁺.
LC/MS Condition F: ret time 1.51 min; m/e=772 (M+H)⁺.

Example 2056: 1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)-4-hydroxypiperidine-4-carboxylic Acid water (150 µL) and DMF (500 µL) were added, and the reaction was heated at 70° C. for 18 h. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at

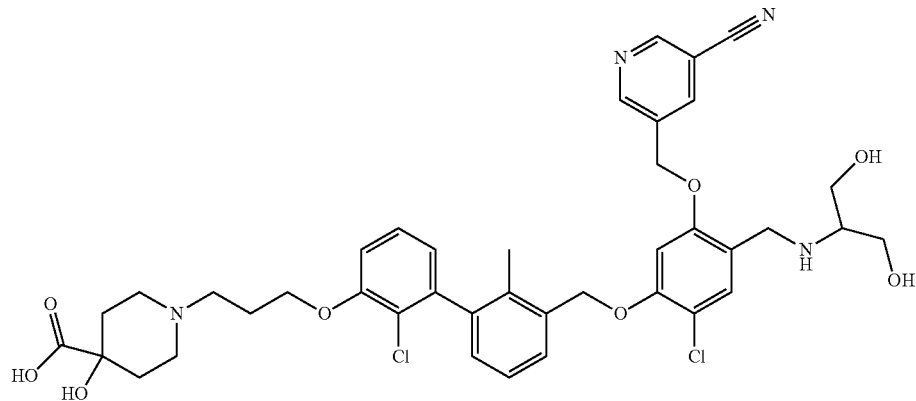 [SMILES: Cc1c(COc2cc(OCc3cncc(C#N)c3)c(CNC(CO)CO)cc2Cl)cccc1-c1cccc(OCCCN2CCC(O)(C(=O)O)CC2)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.2 mL) was added 4-hydroxypiperidine-4-carboxylic acid hydrochloride (70 mg, 0.385 mmol) and N,N-diisopropylethylamine (100 µL, 0.573 mmol). The reaction was flushed with N₂, capped and heated at 65° C. for 3 h. Additional amounts of N,N-diisopropylethylamine (35 µL, 0.197 mmol), HPLC grade 100% B; Flow: 20 mL/min to give the title compound as a TFA salt (3.4 mg, 14%).

LC/MS Condition E: ret time 1.43 min; m/e=779 (M+H)⁺.
LC/MS Condition F: ret time 1.40 min; m/e=779 (M+H)⁺.

Intermediate: 5-((5-((3'-(3-bromopropoxy)-2'-chloro-2-methyl-[1,1'-biphenyl]-3-yl)methoxy)-4-chloro-2-(((1,3-dihydroxypropan-2-yl)(methyl)amino)methyl)phenoxy)methyl)nicotinonitrile

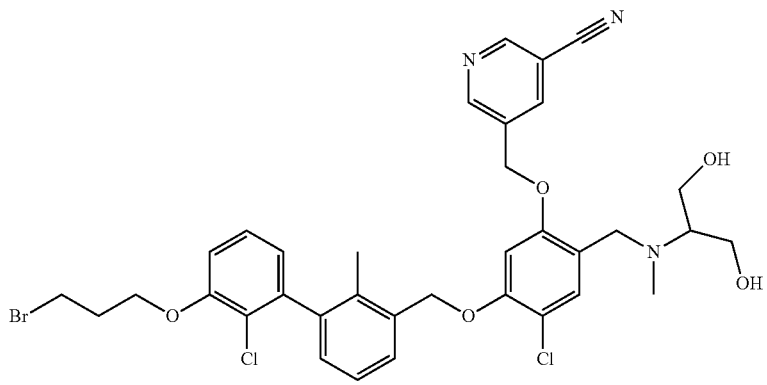 [SMILES: Cc1c(COc2cc(OCc3cncc(C#N)c3)c(CN(C)C(CO)CO)cc2Cl)cccc1-c1cccc(OCCCBr)c1Cl]

327

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added N,N-diisopropylethylamine (22 µL, 0.126 mmol), followed by iodomethane (4 µL, 0.064 mmol). The reaction was flushed with N$_2$, capped and heated at 45° C. for 75 min. Additional amounts of N,N-diisopropylethylamine (11 µL, 0.063 mmol) and iodomethane (12 µL, 0.192 mmol) were added, and the reaction heated at 65° C. for 1 h, and then stirred at room temp for 18 h. The solvent was removed under a gentle stream of N$_2$ and the crude title compound was used "as is" without further purification in subsequent reactions.

LC/MS Condition A: ret time 1.21 min; m/e=728 (M+H)$^+$.

Example 2057 (S)-5-((4-chloro-5-((2'-chloro-3'-(3-((2,3-dihydroxypropyl)amino)propoxy)-2-methyl-[1,1'-biphenyl]-3-yl)methoxy)-2-(((1,3-dihydroxypropan-2-yl)(methyl)amino)methyl)phenoxy)methyl)nicotinonitrile

328

Intermediate: (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic Acid

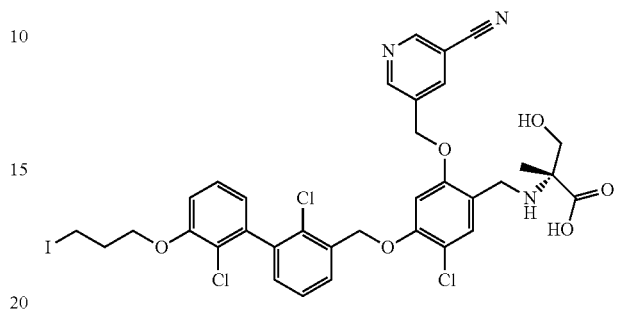

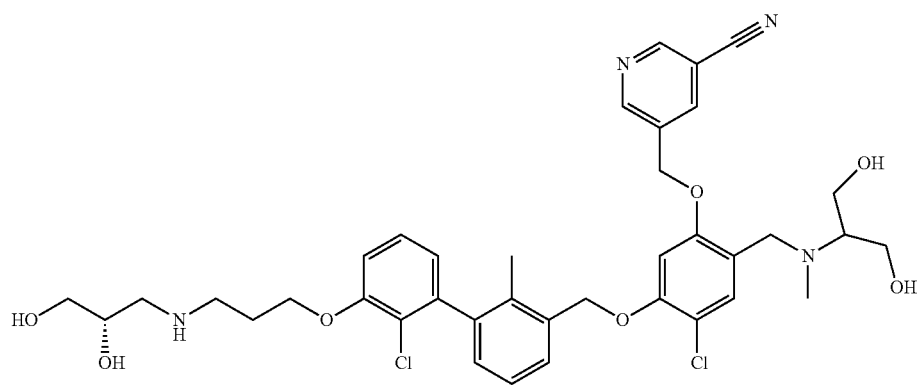 [SMILES: Cc1c(COc2cc(OCc3cncc(C#N)c3)c(CN(C)C(CO)CO)cc2Cl)cccc1-c1cccc(OCCCNC[C@H](O)CO)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)(methyl)amino)methyl)phenoxy)methyl)nicotinonitrile (22.7 mg, 0.031 mmol) in MeOH (1.1 mL) was added (S)-3-amino-1,2-propanediol (35 mg, 0.384 mmol) and N,N-diisopropylethylamine (30 µL, 0.172 mmol). The reaction was flushed briefly with N$_2$, capped, and heated at 65° C. for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (10.6 mg, 46%).

LC/MS Condition E: ret time 1.43 min; m/e=739 (M+H)$^+$.
LC/MS Condition F: ret time 1.37 min; m/e=739 (M+H)$^+$.

To a solution of 5-((4-chloro-5-((2,2'-dichloro-3'-(3-iodopropoxy)-[1,1'-biphenyl]-3-yl)methoxy)-2-formylphenoxy)methyl)nicotinonitrile (182.2 mg, 0.257 mmol) in ClCH$_2$CH$_2$Cl (2.7 mL) and ethanol (5.4 mL) was added 2-methyl-d-serine (92 mg, 0.772 mmol), acetic acid (30 µL, 0.524 mmol) and 4 A mol sieves. The reaction was flushed well with N$_2$, capped, stirred at room temp for 1 h and then treated dropwise (over 6.5 h) with sodium cyanoborohydride, 1.0M in THF (515 µL, 0.515 mmol). During the course of addition, DMF (1.6 mL) was added to the reaction. After the addition was complete, the reaction was stirred at room temp for 18 h. The reaction was then treated dropwise (over 7 h) with additional sodium cyanoborohydride, 1.0 M in THF (260 µL, 0.260 mmol) and stirred at room temp for 18 h. Most of the solvent was removed under a gentle stream of N$_2$ and the crude title compound was then dissolved in MeOH (2 mL) and used "as is" without purification in subsequent reactions.

LC/MS Condition A: ret time 1.23 min; m/e=810 (M+H)$^+$.

Example 2058: (R)-2-((5-chloro-2-((5-cyanopyridin-3-yl)methoxy)-4-((2,2'-dichloro-3'-(3-(piperidin-1-yl)propoxy)-[1,1'-biphenyl]-3-yl)methoxy)benzyl)amino)-3-hydroxy-2-methylpropanoic Acid

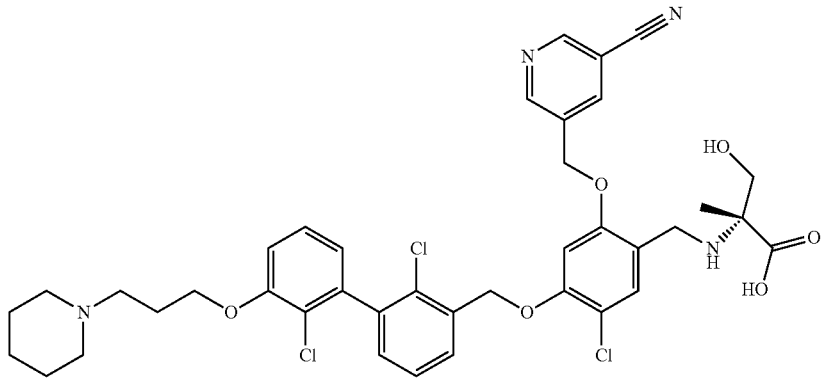 [SMILES: C[C@](CO)(NCc1cc(Cl)c(OCc2cccc(-c3cccc(OCCCN4CCCCC4)c3Cl)c2Cl)cc1OCc1cncc(C#N)c1)C(=O)O]

To a solution of (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic acid (26.1 mg, 0.032 mmol) in MeOH (500 µL) was added piperidine (73.3 µL, 0.740 mmol). The reaction was flushed briefly with $N_2$, capped and heated at 65° C. for 45 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (5.6 mg, 22%).

LC/MS Condition E: ret time 1.52 min; m/e=767 (M+H)$^+$.
LC/MS Condition F: ret time 1.51 min; m/e=767 (M+H)$^+$.

Intermediate: 3-((5-((3'-(3-bromopropoxy)-2,2'-dichloro-[1,1'-biphenyl]-3-yl)methoxy)-4-chloro-2-formylphenoxy)methyl)benzonitrile

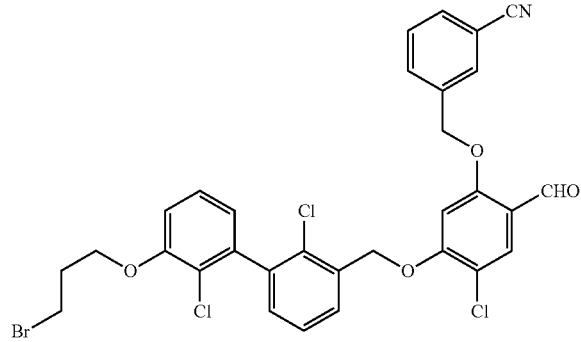 [SMILES: N#Cc1cccc(COc2cc(OCc3cccc(-c4cccc(OCCCBr)c4Cl)c3Cl)c(Cl)cc2C=O)c1]

To a dry 2-dram reaction vial under $N_2$ was added 4-((3'-(3-bromopropoxy)-2,2'-dichloro-[1,1'-biphenyl]-3-yl)methoxy)-5-chloro-2-hydroxybenzaldehyde (45 mg, 0.083 mmol), cesium carbonate (54 mg, 0.166 mmol) and DMF (500 µL). The resulting yellow solution was flushed briefly with $N_2$, capped and stirred at room temp for 2 min. Solid 3-cyanobenzyl bromide (21 mg, 0.107 mmol) was added in a single portion and the reaction was again flushed with $N_2$, capped and allowed to stir at room temp for 90 min. The solvent was removed under a gentle stream of $N_2$ and the crude product was dissolved in 1,2-dichloroethane (2 mL), filtered through a 45 µfrit. The solvent was removed under a gentle stream of $N_2$ to give the title compound that was used "as is" without purification in subsequent reactions.

LC/MS Condition A: ret time 1.65 min; m/e=658 (M+H)$^+$.

Intermediate: 3-((5-((3'-(3-bromopropoxy)-2,2'-dichloro-[1,1'-biphenyl]-3-yl)methoxy)-4-chloro-2-(((1,3-dihydroxy-2-methylpropan-2-yl)amino)methyl)phenoxy)methyl)benzonitrile

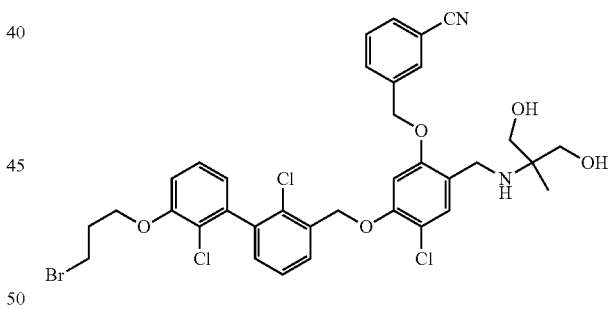

To a mixture of 3-((5-((3'-(3-bromopropoxy)-2,2'-dichloro-[1,1'-biphenyl]-3-yl)methoxy)-4-chloro-2-formylphenoxy)methyl)benzonitrile (54.5 mg, 0.083 mmol) in $CH_2Cl_2$ (1.5 mL) and ethanol (1.0 mL) was added 2-amino-2-methyl-1,3-propanediol (26 mg, 0.247 mmol), acetic acid (15 µL, 0.262 mmol) and 4 A mol sieves. The reaction was flushed briefly with $N_2$, capped, stirred at room temp for 45 min and then treated dropwise (over 3 h) with sodium cyanoborohydride, 1.0 M in THF (216 µL, 0.216 mmol). The solvent was removed under a gentle stream of $N_2$ to give the title compound that was used "as is" without purification in subsequent reactions.

LC/MS Condition A: ret time 1.26 min; m/e=747 (M+H)$^+$.

Example 2059: (R)-3-((4-chloro-5-((2,2'-dichloro-3'-(3-(3-hydroxypyrrolidin-1-yl)propoxy)-[1,1'-biphenyl]-3-yl)methoxy)-2-(((1,3-dihydroxy-2-methylpropan-2-yl)amino)methyl)phenoxy)methyl)benzonitrile

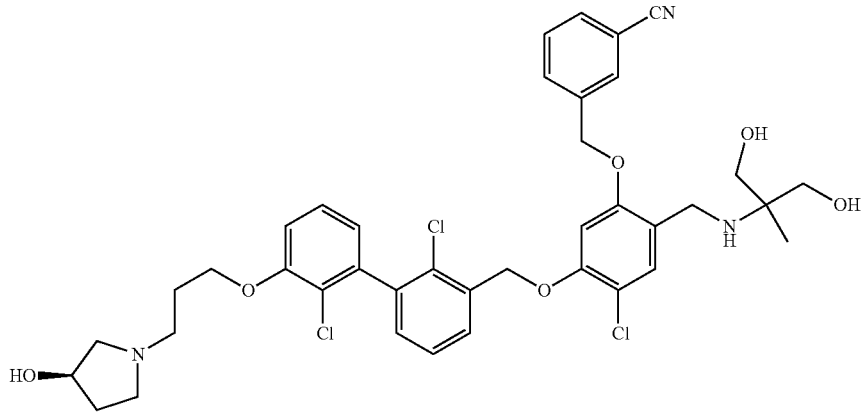 [SMILES: CC(CO)(CO)NCc1cc(Cl)c(OCc2cccc(-c3cccc(OCCCN4CC[C@@H](O)C4)c3Cl)c2Cl)cc1OCc1cccc(C#N)c1]

To a suspension of 3-((5-((3'-(3-bromopropoxy)-2,2'-dichloro-[1,1'-biphenyl]-3-yl)methoxy)-4-chloro-2-(((1,3-dihydroxy-2-methylpropan-2-yl)amino)methyl)phenoxy)methyl)benzonitrile (30.95 mg, 0.041 mmol) in MeOH (1.1 mL) was added (R)-3-hydroxypyrrolidine hydrochloride (65 mg, 0.526 mmol), N,N-diisopropylethylamine (120 μL, 0.687 mmol) and DMF (100 μlit). The reaction was capped and heated at 65° C. for 3.5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to give the title compound (6.6 mg, 21%).

LC/MS Condition E: ret time 1.58 min; m/e=754 (M+H)$^+$.
LC/MS Condition F: ret time 1.52 min; m/e=754 (M+H)$^+$.

Example 2060: (S)-3-((4-chloro-5-((2,2'-dichloro-3'-(3-((2,3-dihydroxypropyl)amino)propoxy)-[1,1'-biphenyl]-3-yl)methoxy)-2-(((1,3-dihydroxy-2-methylpropan-2-yl)amino)methyl)phenoxy)methyl)benzonitrile

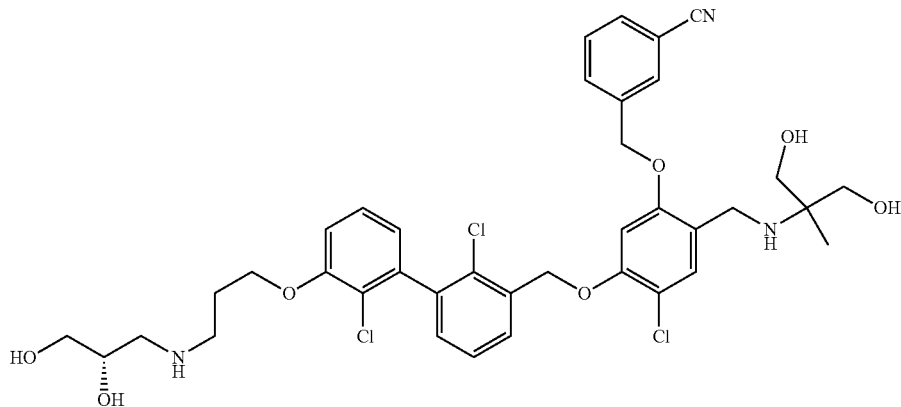 [SMILES: CC(CO)(CO)NCc1cc(Cl)c(OCc2cccc(-c3cccc(OCCCNC[C@H](O)CO)c3Cl)c2Cl)cc1OCc1cccc(C#N)c1]

To a fine suspension of 3-((5-((3'-(3-bromopropoxy)-2,2'-dichloro-[1,1'-biphenyl]-3-yl)methoxy)-4-chloro-2-(((1,3-dihydroxy-2-methylpropan-2-yl)amino)methyl)phenoxy)methyl)benzonitrile (61.9 mg, 0.083 mmol) in MeOH (1.1 mL) was added (S)-3-amino-1,2-propanediol (95 mg, 1.043 mmol), N,N-diisopropylethylamine (60 μL, 0.344 mmol), and DMF (100 μlit). The reaction was capped and heated at 65 C for 3.5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 20 minutes, then a 5-minute hold at 100% B; Flow: 20 mL/min to give the title compound (6.1 mg, 10%).

LC/MS Condition E: ret time 1.50 min; m/e=758 (M+H)+.
LC/MS Condition F: ret time 1.48 min; m/e=758 (M+H)+.

Example 2061: (R)-2-((5-chloro-4-((2'-chloro-3'-(3-(4-hydroxy-4-(hydroxymethyl)piperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

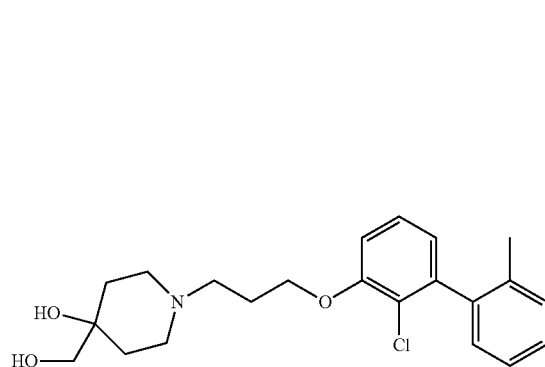

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (29 mg, 0.039 mmol) in MeOH (1.1 mL) was added 4-hydroxy-4-hydroxymethylpiperidine hydrochloride (82 mg, 0.489 mmol) and N,N-diisopropylethylamine (110 µL, 0.630 mmol). The reaction was flushed briefly with N₂, capped, and heated at 65° C. for 3.5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-60% B over 20 minutes, then a 5-minute hold at 100% B; Flow: 20 mL/min to give the title compound (7.6 mg, 24%).

LC/MS Condition E: ret time 1.47 min; m/e=793 (M+H)+.
LC/MS Condition F: ret time 1.40 min; m/e=793 (M+H)+.

Example 2062: N-(1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)piperidin-4-yl)acetamide

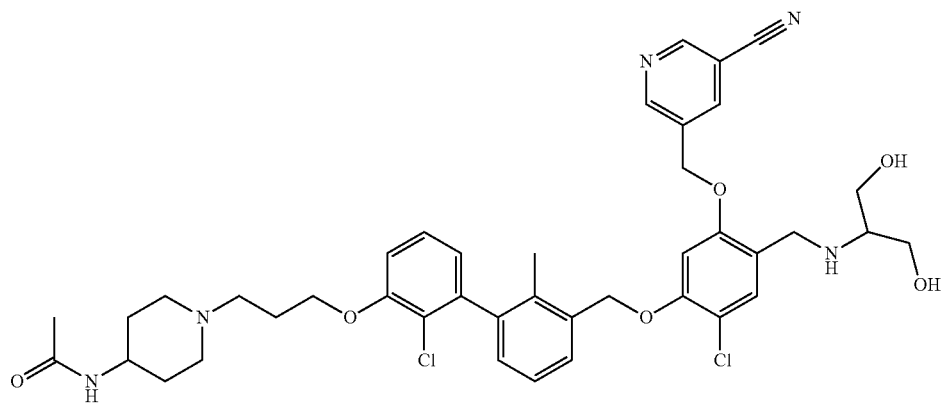 [SMILES: CC(=O)NC1CCN(CCCOc2cccc(-c3cccc(COc4cc(OCc5cncc(C#N)c5)c(CNC(CO)CO)cc4Cl)c3C)c2Cl)CC1]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added 4-acetamidopiperidine (55 mg, 0.387 mmol) and N,N-diisopropylethylamine (30 µL, 0.172 mmol). The reaction was flushed briefly with N₂, capped, and heated at 65° C. for 7.5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to give the title compound (22.8 mg, 94%).

LC/MS Condition E: ret time 1.69 min; m/e=776 (M+H)+.
LC/MS Condition F: ret time 1.38 min; m/e=776 (M+H)+.
$^1$H NMR (500 MHz, METHANOL-$d_4$) δ 8.97 (d, J=2.0 Hz, 1H), 8.94 (d, J=1.8 Hz, 1H), 8.41 (t, J=2.0 Hz, 1H), 7.52-7.47 (m, 2H), 7.34 (t, J=7.9 Hz, 1H), 7.27 (t, J=7.6 Hz, 1H), 7.15-7.09 (m, 2H), 7.02 (s, 1H), 6.87 (dd, J=7.6, 1.3 Hz, 1H), 5.35-5.30 (m, 4H), 4.24-4.17 (m, 2H), 4.14 (s, 2H), 3.80 (s, 1H), 3.74 (dd, J=11.7, 4.8 Hz, 3H), 3.65 (dd, J=11.7, 6.3 Hz, 2H), 3.37 (s, 2H), 3.15 (br d, J=12.1 Hz, 2H), 3.10-3.03 (m, 1H), 2.88-2.82 (m, 2H), 2.43 (br t, J=11.3 Hz, 2H), 2.14 (s, 3H), 1.94 (s, 3H), 1.61 (br d, J=11.1 Hz, 2H).

Example 2063: 5-((4-chloro-5-((2'-chloro-3'-(3-(4-hydroxy-4-(hydroxymethyl)piperidin-1-yl)propoxy)-2-methyl-[1,1'-biphenyl]-3-yl)methoxy)-2-(((1,3-dihydroxypropan-2-yl)amino)methyl)phenoxy)methyl)nicotinonitrile was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min to give the title compound as a TFA salt (34.2 mg, 99%).

LC/MS Condition E: ret time 1.61 min; m/e=765 (M+H)+.
LC/MS Condition F: ret time 1.38 min; m/e=765 (M+H)+.
$^1$H NMR (500 MHz, METHANOL-$d_4$) δ 8.98 (d, J=2.1 Hz, 1H), 8.95 (d, J=1.8 Hz, 1H), 8.43 (t, J=2.1 Hz, 1H), 7.55 (s, 1H), 7.50 (d, J=7.8 Hz, 1H), 7.40-7.35 (m, 1H), 7.28 (t, J=7.6 Hz, 1H), 7.16 (dd, J=8.4, 1.4 Hz, 1H), 7.11 (d, J=7.6 Hz, 1H), 7.08 (s, 1H), 6.93-6.89 (m, 1H), 6.91 (dd, J=7.6, 1.4 Hz, 1H), 5.38 (d, J=2.3 Hz, 2H), 5.33 (d, J=2.0 Hz, 2H), 4.34 (s, 2H), 4.32-4.24 (m, 2H), 3.86-3.79 (m, 2H), 3.73 (dd, J=11.9, 6.4 Hz, 2H), 3.58 (br s, 2H), 3.48-3.41 (m, 4H),

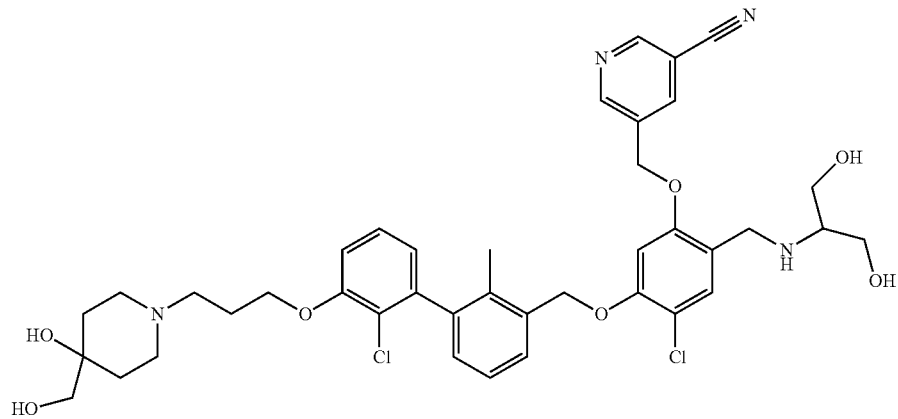 [SMILES: Cc1c(COc2cc(OCc3cncc(C#N)c3)c(CNC(CO)CO)cc2Cl)cccc1-c1cccc(OCCCN2CCC(O)(CO)CC2)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in MeOH (1.1 mL) was added 4-hydroxy-4-hydroxymethylpiperidine hydrochloride (65 mg, 0.388 mmol) and N,N-diisopropylethylamine (85 μL, 0.487 mmol). The reaction was flushed briefly with N$_2$, capped, and heated at 65° C. for 7.5 h. The crude material 3.30-3.25 (m, 2H), 2.35 (br d, J=5.2 Hz, 2H), 2.14 (s, 3H), 2.03-1.91 (m, 2H), 1.81 (br d, J=14.5 Hz, 2H).

Example 2064: (R)-2-((5-chloro-2-((5-cyanopyridin-3-yl)methoxy)-4-((2,2'-dichloro-3'-(3-(((S)-2,3-dihydroxypropyl)(methyl)amino)propoxy)-[1,1'-biphenyl]-3-yl)methoxy)benzyl)amino)-3-hydroxy-2-methylpropanoic Acid

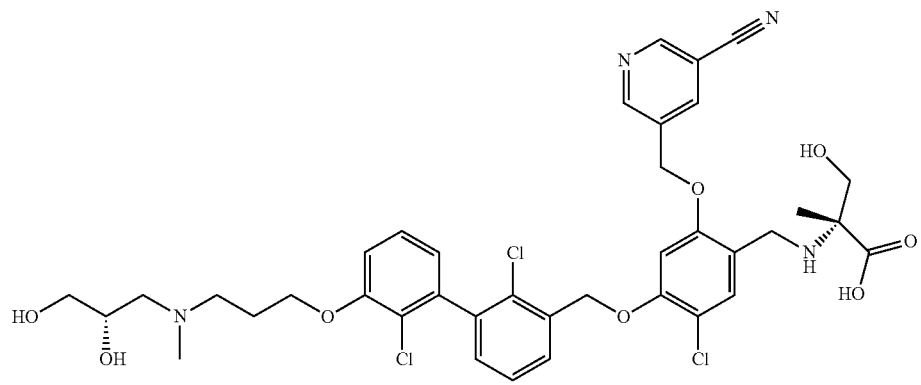 [SMILES: CN(CCCOc1cccc(-c2cccc(COc3cc(OCc4cncc(C#N)c4)c(CN[C@](C)(CO)C(=O)O)cc3Cl)c2Cl)c1Cl)C[C@H](O)CO]

To a solution of (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic acid (25.9 mg, 0.032 mmol) in MeOH (1.4 mL) was added (S)-3-(methylamino)propane-1,2-diol (35 mg, 0.333 mmol) and N,N-diisopropylethylamine (35 µL, 0.200 mmol). The reaction was flushed briefly with N₂, capped, and heated at 65° C. for 65 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the title compound (4.2 mg, 16%).

LC/MS Condition E: ret time 1.52 min; m/e=787 (M+H)⁺.
LC/MS Condition F: ret time 1.41 min; m/e=787 (M+H)⁺.

Example 2065: (R)-2-((5-chloro-2-((5-cyanopyridin-3-yl)methoxy)-4-((2,2'-dichloro-3'-(3-(4-hydroxy-4-(hydroxymethyl)piperidin-1-yl)propoxy)-[1,1'-biphenyl]-3-yl)methoxy)benzyl)amino)-3-hydroxy-2-methylpropanoic Acid trile:water with 10-mM ammonium acetate; Gradient: 20-60% B over 15 minutes, then a 5-minute hold at 100% B; Flow: 20 mL/min to give the title compound (5 mg, 19%).

LC/MS Condition E: ret time 1.50 min; m/e=813 (M+H)⁺.
LC/MS Condition F: ret time 1.42 min; m/e=813 (M+H)⁺.

Intermediate: 4-((3'-(3-bromopropoxy)-2,2'-dichloro-[1,1'-biphenyl]-3-yl)methoxy)-5-chloro-2-((3-chlorobenzyl)oxy)benzaldehyde

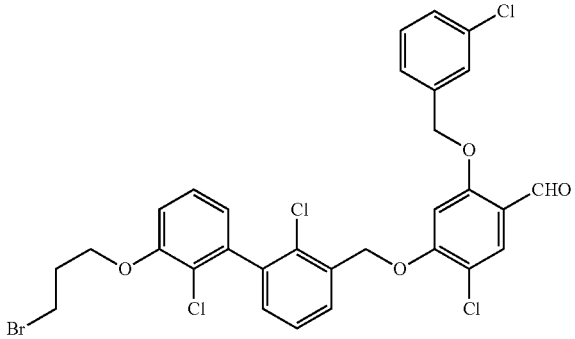

To a dry 2 mL scint vial containing 4-((3'-(3-bromopropoxy)-2,2'-dichloro-[1,1'-biphenyl]-3-yl)methoxy)-5-

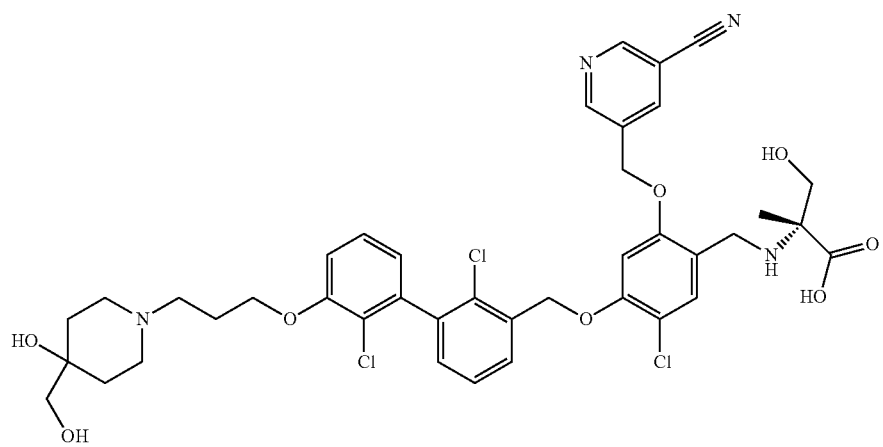 [SMILES: C[C@](CO)(NCc1cc(Cl)c(OCc2cccc(-c3cccc(OCCCN4CCC(O)(CO)CC4)c3Cl)c2Cl)cc1OCc1cncc(C#N)c1)C(=O)O]

To a solution of (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic acid (26.1 mg, 0.032 mmol) in MeOH (1.4 mL) was added 4-hydroxy-4-hydroxymethylpiperidine hydrochloride (55 mg, 0.328 mmol) and N,N-diisopropylethylamine (80 µL, 0.458 mmol). The reaction was flushed briefly with N₂, capped, and heated at 65° C. for 65 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Mobile Phase B: 95:5 acetonichloro-2-hydroxybenzaldehyde (29.6 mg, 0.054 mmol) was added cesium carbonate (36 mg, 0.110 mmol) and 3-chlorobenzyl bromide (9.58 µL, 0.073 mmol), followed immediately by DMF (500 µL). The resulting yellow solution was flushed briefly with Ar, capped and stirred at room temp for 90 min. The solvent was evaporated off under a gentle stream of N₂. The crude residue was dissolved in 1,2-dichloroethane (2.5 mL) and filtered through a 45 µfrit to give the title compound that was used "as is" without further purification in subsequent reactions.

LC/MS Condition A: ret time 1.76 min; m/e=667 (M+H)⁺.

339

Intermediate: 2-((4-((3'-(3-bromopropoxy)-2,2'-dichloro-[1,1'-biphenyl]-3-yl)methoxy)-5-chloro-2-((3-chlorobenzyl)oxy)benzyl)amino)-2-methylpropane-1,3-diol

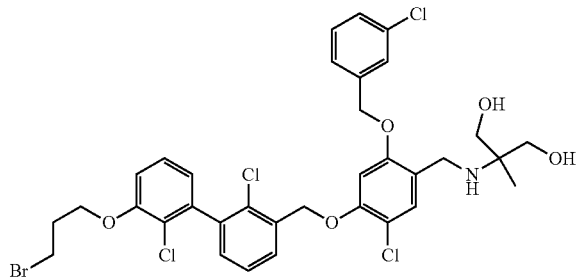

To a solution of 4-((3'-(3-bromopropoxy)-2,2'-dichloro-[1,1'-biphenyl]-3-yl)methoxy)-5-chloro-2-((3-chlorobenzyl)oxy)benzaldehyde (36.1 mg, 0.054 mmol) in a mixture of 1,2-dichloroethane (980 µL) and EtOH (650 µL) was added 2-amino-2-methyl-1,3-propanediol (17 mg, 0.162 mmol), acetic acid (10 µL, 0.175 mmol) and activated 4 A mol. sieves. The resulting solution was flushed briefly with $N_2$, capped, stirred at room temp for 3.5 h, then treated dropwise (over several hours) with sodium cyanoborohydride, 1.0 M in THF (140 µL, 0.140 mmol). After the addition was complete, the reaction was stirred at room temp for 45 min, and then the solvent evaporated under a gentle stream of $N_2$ overnight to give the title compound that was used "as is" without further purification in subsequent reactions.

LC/MS Condition A: ret time 1.33 min; m/e=756 (M+H)$^+$.

Example 2066: (R)-2-((5-chloro-2-((3-chlorobenzyl)oxy)-4-((2,2'-dichloro-3'-(3-(3-hydroxypyrrolidin-1-yl)propoxy)-[1,1'-biphenyl]-3-yl)methoxy)benzyl)amino)-2-methylpropane-1,3-diol

340

To the vial containing crude 2-((4-((3'-(3-bromopropoxy)-2,2'-dichloro-[1,1'-biphenyl]-3-yl)methoxy)-5-chloro-2-((3-chlorobenzyl)oxy)benzyl)amino)-2-methylpropane-1,3-diol (41.0 mg, 0.054 mmol) was added (R)-3-hydroxypyrrolidine hydrochloride (80 mg, 0.647 mmol), MeOH (1.1 mL) and N,N-diisopropylethylamine (150 µL, 0.859 mmol). The reaction was flushed briefly with $N_2$, capped, and heated at 65° C. for 4 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min to give the title compound (34 mg, 79%).

LC/MS Condition E: ret time 1.91 min; m/e=763 (M+H)$^+$.
LC/MS Condition F: ret time 1.63 min; m/e=763 (M+H)$^+$.

Intermediate: 5-((5-((3'-(3-bromopropoxy)-2'-chloro-2-methyl-[1,1'-biphenyl]-3-yl)methoxy)-4-chloro-2-(((1-hydroxy-2-methylpropan-2-yl)amino)methyl)phenoxy)methyl)nicotinonitrile

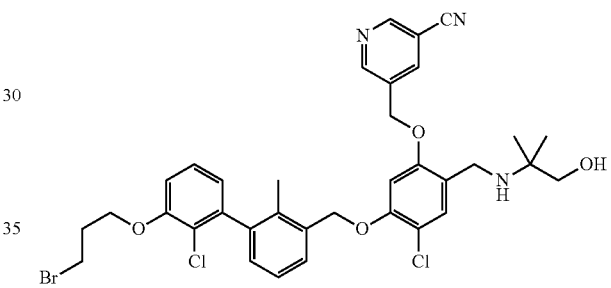

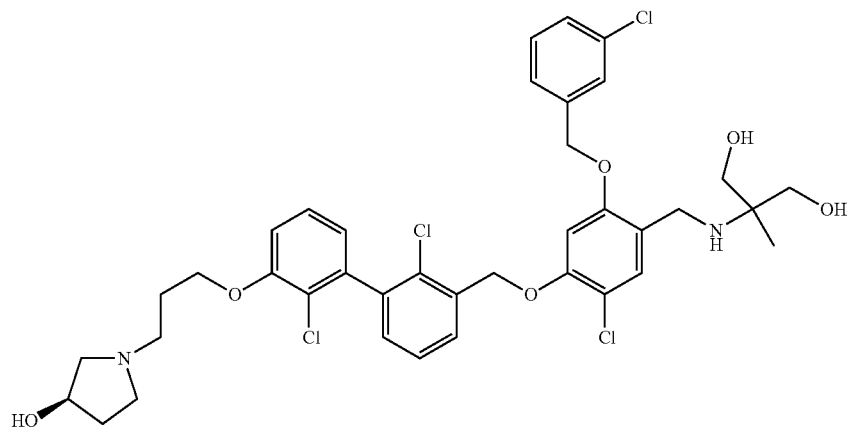 [SMILES: CC(CO)(CO)NCc1cc(Cl)c(OCc2cccc(-c3cccc(OCCCN4CC[C@@H](O)C4)c3Cl)c2Cl)cc1OCc1cccc(Cl)c1]

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (27 mg, 0.042 mmol) in a mixture of 1,2-dichloroethane (0.8 mL) and EtOH (0.5 mL) was added 2-amino-2-methyl-1-propanol (12.5 μL, 0.130 mmol), acetic acid (7 μL, 0.122 mmol) and 4 A mol sieves. The reaction was flushed briefly with N$_2$, capped, stirred at room temp for 1 h, then treated dropwise (over 2 h) with sodium cyanoborohydride, 1.0M in THF (90 μL, 0.090 mmol). After the addition was complete, the reaction was stirred at room temp for 50 min and the solvent was evaporated off under a gentle stream of N$_2$ to give the title compound that is used "as is" without purification in subsequent reactions.

LC/MS Condition A: ret time 1.23 min; m/e=712 (M+H)$^+$.

Example 2067: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1-hydroxy-2-methylpropan-2-yl)amino)methyl)phenoxy)methyl)nicotinonitrile Intermediate: 5-((5-((3'-(3-bromopropoxy)-2'-chloro-2-methyl-[1,1'-biphenyl]-3-yl)methoxy)-4-chloro-2-(((2-hydroxy-2-methylpropyl)(methyl)amino)methyl)phenoxy)methyl)nicotinonitrile

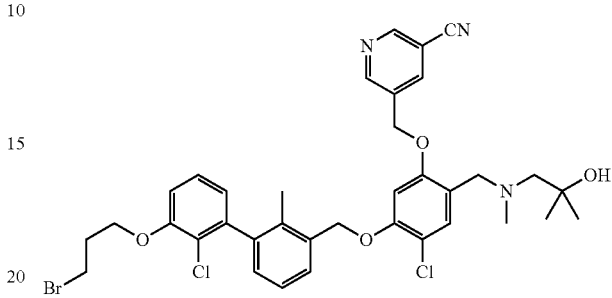

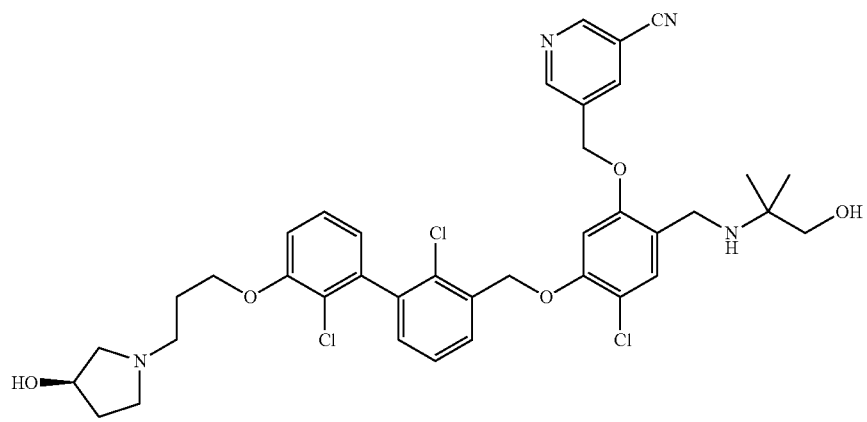 [SMILES: CC(C)(CO)NCc1cc(Cl)c(OCc2cccc(-c3cccc(OCCCN4CC[C@@H](O)C4)c3Cl)c2Cl)cc1OCc1cncc(C#N)c1]

To the vial containing crude 5-((5-((3'-(3-bromopropoxy)-2'-chloro-2-methyl-[1,1'-biphenyl]-3-yl)methoxy)-4-chloro-2-(((1-hydroxy-2-methylpropan-2-yl)amino)methyl)phenoxy)methyl)nicotinonitrile (30.0 mg, 0.042 mmol) was added (R)-3-hydroxypyrrolidine hydrochloride (65 mg, 0.526 mmol), MeOH and N,N-diisopropylethylamine (125 μL, 0.716 mmol). The reaction was flushed briefly with N2, capped, and heated at 65° C. for 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min to give the title compound (18 mg, 53%).

LC/MS Condition E: ret time 1.67 min; m/e=719 (M+H)$^+$.
LC/MS Condition F: ret time 1.48 min; m/e=719 (M+H)$^+$.

To a solution of 5-((5-((3'-(3-bromopropoxy)-2'-chloro-2-methyl-[1,1'-biphenyl]-3-yl)methoxy)-4-chloro-2-formylphenoxy)methyl)nicotinonitrile (27 mg, 0.042 mmol) in a mixture of 1,2-dichloroethane (0.8 mL) and EtOH (0.5 mL) was added 2-methyl-1-(methylamino)propan-2-ol (13 mg, 0.126 mmol), acetic acid (7 μL, 0.122 mmol) and 4 A mol sieves. The reaction was flushed briefly with N$_2$, capped and stirred at room temp for 1 h. The reaction was then treated dropwise (over 3.5 h) with sodium cyanoborohydride, 1.0M in THF (90 μL, 0.090 mmol). After the addition was complete, the reaction was stirred at room temp for 50 min and the solvent was evaporated off under a gentle stream of N$_2$ to give the title compound that was used "as is" without purification in subsequent reactions.

LC/MS Condition A: ret time 1.26 min; m/e=726 (M+H)$^+$.

Example 2068: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((2-hydroxy-2-methyl-propyl)(methyl)amino)methyl)phenoxy)methyl)nicotinonitrile

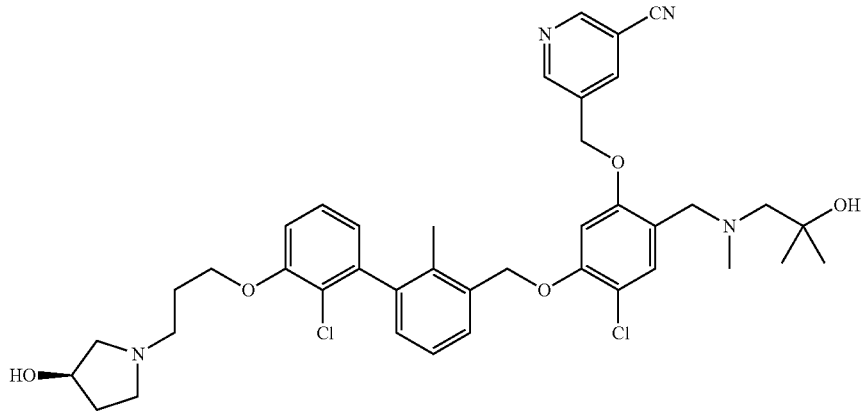 [SMILES: Cc1c(COc2cc(OCc3cncc(C#N)c3)c(CN(C)CC(C)(C)O)cc2Cl)cccc1-c1cccc(OCCCN2CC[C@@H](O)C2)c1Cl]

To the vial containing crude 5-((5-((3'-(3-bromopropoxy)-2'-chloro-2-methyl-[1,1'-biphenyl]-3-yl)methoxy)-4-chloro-2-(((2-hydroxy-2-methylpropyl)(methyl)amino)methyl)phenoxy)methyl)nicotinonitrile (30.6 mg, 0.042 mmol) was added (R)-3-hydroxypyrrolidine hydrochloride (65 mg, 0.526 mmol), MeOH (1.1 mL) and N,N-diisopropylethylamine (120 µL, 0.687 mmol). The reaction was flushed briefly with $N_2$, capped, and heated at 65° C. for 5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 38-78% B over 18 minutes, then a 3-minute hold at 100% B; Flow: 20 mL/min to give the title compound (8.2 mg, 26%).

LC/MS Condition E: ret time 1.76 min; m/e=733 (M+H)$^+$.
LC/MS Condition F: ret time 1.39 min; m/e=733 (M+H)$^+$.

Example 2069: (S)—N-(1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)pyrrolidin-3-yl)acetamide To a solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.25 mg, 0.031 mmol) in MeOH (1.1 mL) in MeOH (1.1 mL) was added (S)—N-(pyrrolidin-3-yl)acetamide, 1.0 HCl (55 mg, 0.334 mmol) and N,N-diisopropylethylamine (90 µL, 0.515 mmol). The reaction was flushed briefly with $N_2$, capped and heated at 65° C. for 4.5 h, then at 45° C. for 18 h. The reaction was then further heated at 65° C. for several more hours. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to give the title compound (14.8 mg, 60%).

LC/MS Condition E: ret time 1.42 min; m/e=762 (M+H)$^+$.
LC/MS Condition F: ret time 1.29 min; m/e=762 (M+H)$^+$.

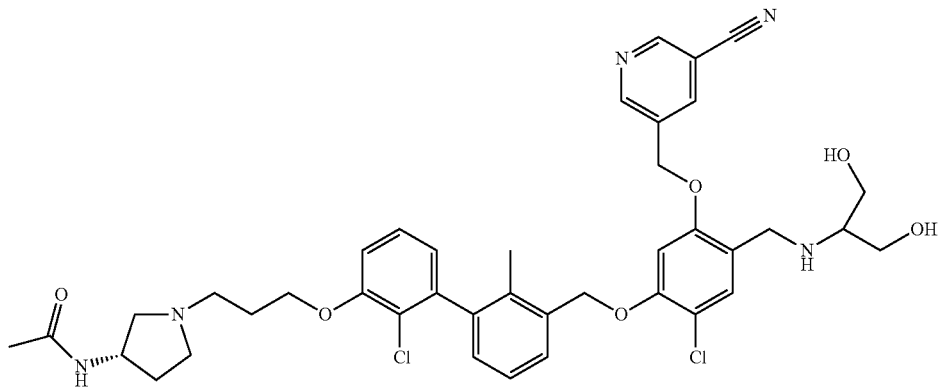 [SMILES: CC(=O)N[C@H]1CCN(CCCOc2cccc(-c3cccc(COc4cc(OCc5cncc(C#N)c5)c(CNC(CO)CO)cc4Cl)c3C)c2Cl)C1]

Example 2070: (R)-2-((4-((3'-(3-((S)-3-acetamidopyrrolidin-1-yl)propoxy)-2,2'-dichloro-[1,1'-biphenyl]-3-yl)methoxy)-5-chloro-2-((5-cyanopyridin-3-yl)methoxy)benzyl)amino)-3-hydroxy-2-methylpropanoic Acid

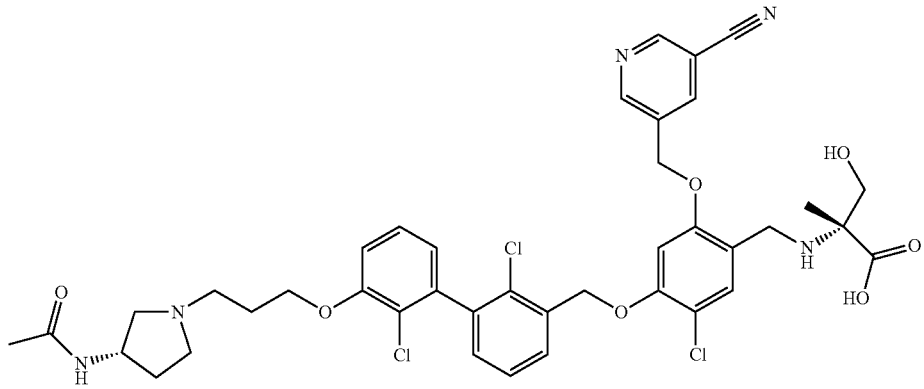 [SMILES: CC(=O)N[C@H]1CCN(CCCOc2cccc(-c3cccc(COc4cc(OCc5cncc(C#N)c5)c(CN[C@](C)(CO)C(=O)O)cc4Cl)c3Cl)c2Cl)C1]

To a solution of (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic acid (25.9 mg, 0.032 mmol) in MeOH (1.1 mL) was added (S)—N-(pyrrolidin-3-yl)acetamide, 1.0 HCl (60 mg, 0.364 mmol) and N,N-diisopropylethylamine (100 µL, 0.573 mmol). The reaction was flushed briefly with $N_2$, capped and heated at 65° C. for 4.5 h, followed by heating at 45° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 18 minutes, then a 5-minute hold at 100% B; Flow: 20 mL/min to give the title compound (4.0 mg, 15%).

LC/MS Condition E: ret time 1.66 min; m/e=790 (M+H)$^+$.
LC/MS Condition F: ret time 1.44 min; m/e=790 (M+H)$^+$.

Example 2071: (R)-2-((4-((3'-(3-((S)-3-acetamidopyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic Acid To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (29 mg, 0.039 mmol) in MeOH (1.1 mL) was added (S)—N-(pyrrolidin-3-yl)acetamide, 1.0 HCl (70 mg, 0.425 mmol) and N,N-diisopropylethylamine (100 µL, 0.573 mmol). The reaction was flushed briefly with $N_2$, capped and heated at 65° C. for 4.5 h, followed by heating at 45° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-58% B over 20 minutes, then a 5-minute hold at 100% B; Flow: 20 mL/min to give the title compound (3.8 mg, 11%).

LC/MS Condition E: ret time 1.66 min; m/e=810 (M+H)$^+$.
LC/MS Condition F: ret time 1.44 min; m/e=810 (M+H)$^+$.

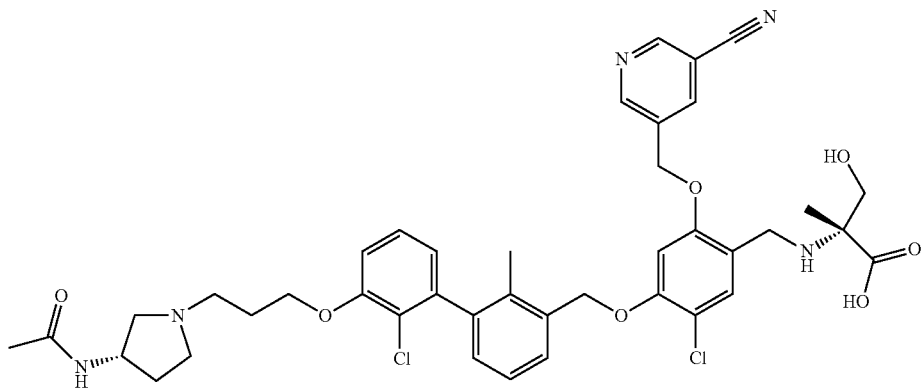 [SMILES: CC(=O)N[C@H]1CCN(CCCOc2cccc(-c3cccc(COc4cc(OCc5cncc(C#N)c5)c(CN[C@](C)(CO)C(=O)O)cc4Cl)c3C)c2Cl)C1]

Intermediate: (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)(ethyl)amino)-3-hydroxy-2-methylpropanoic Acid

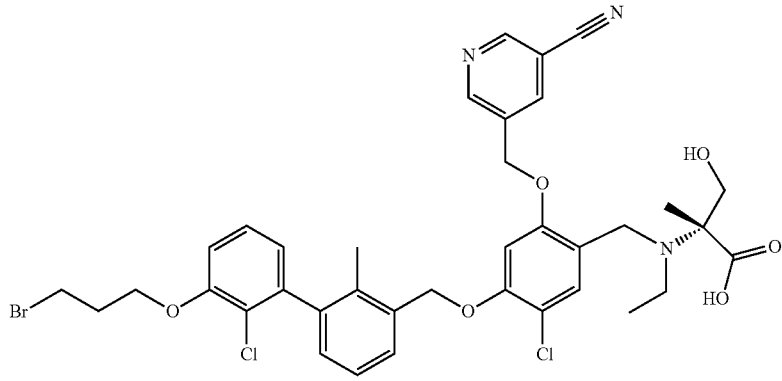 [SMILES: CCN(Cc1cc(Cl)c(OCc2cccc(-c3cccc(OCCCBr)c3Cl)c2C)cc1OCc1cncc(C#N)c1)[C@](C)(CO)C(=O)O]

To the vial containing (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid (29 mg, 0.039 mmol) was added 1,2-dichloroethanol (1.5 mL), EtOH (1.0 mL), acetaldehyde (22 µL, 0.392 mmol) and acetic acid (7 µL, 0.122 mmol). The resulting solution was flushed briefly with $N_2$, capped, stirred at room temp for 30 min, and then treated dropwise (over 40 min) with sodium cyanoborohydride, 1.0M in THF (78 µL, 0.078 mmol). After the addition was complete, the reaction was stirred at room temp for 30 min and the solvent removed under a gentle stream of $N_2$ to give the title compound that was used "as is" without purification in subsequent reactions.

LC/MS Condition A: ret time 1.25 min; m/e=770 (M+H)$^+$.

Example 2072: (R)-2-((5-chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)(ethyl)amino)-3-hydroxy-2-methylpropanoic Acid

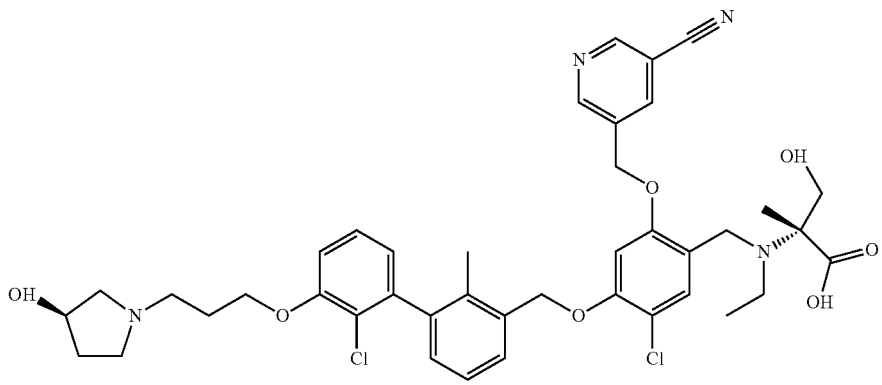 [SMILES: CCN(Cc1cc(Cl)c(OCc2cccc(-c3cccc(OCCCN4CC[C@@H](O)C4)c3Cl)c2C)cc1OCc1cncc(C#N)c1)[C@](C)(CO)C(=O)O]

To a solution of (R)-2-((4-((3'-(3-bromopropoxy)-2'-chloro-2-methyl-[1,1'-biphenyl]-3-yl)methoxy)-5-chloro-2-((5-cyanopyridin-3-yl)methoxy)benzyl)(ethyl)amino)-3-hydroxy-2-methylpropanoic acid (30.1 mg, 0.039 mmol) in MeOH was added (R)-3-hydroxypyrrolidine hydrochloride (60 mg, 0.486 mmol) and N,N-diisopropylethylamine (110 µL, 0.630 mmol). The reaction was flushed briefly with $N_2$, capped and heated at 65° C. for 6 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (7.2 mg, 23%).

LC/MS Condition E: ret time 1.43 min; m/e=777 (M+H)$^+$.
LC/MS Condition F: ret time 1.51 min; m/e=777 (M+H)$^+$.

Example 2073: N-(1-(3-((2-chloro-3'-((2-chloro-5-((5-cyanopyridin-3-yl)methoxy)-4-(((1,3-dihydroxypropan-2-yl)(3,3,3-trifluoropropyl)amino)methyl)phenoxy)methyl)-2'-methyl-[1,1'-biphenyl]-3-yl)oxy)propyl)piperidin-4-yl)acetamide LC/MS Condition E: ret time 1.91 min; m/e=872 (M+H)+.
LC/MS Condition F: ret time 1.55 min; m/e=872 (M+H)+.
$^1$H NMR (500 MHz, METHANOL-d$_4$) δ 8.93 (dd, J=7.5, 1.8 Hz, 2H), 8.34 (t, J=2.1 Hz, 1H), 7.49 (d, J=6.9 Hz, 1H), 7.45 (s, 1H), 7.37-7.30 (m, 1H), 7.26 (t, J=7.6 Hz, 1H), 7.14-7.09 (m, 2H), 6.91 (s, 1H), 6.86 (dd, J=7.6, 1.4 Hz, 1H),

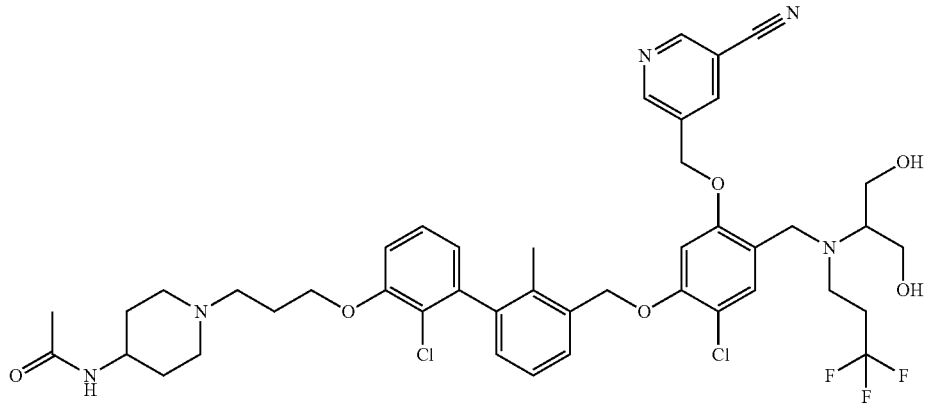 [SMILES: CC(=O)NC1CCN(CCCOc2cccc(-c3cccc(COc4cc(OCc5cncc(C#N)c5)c(CN(CCC(F)(F)F)C(CO)CO)cc4Cl)c3C)c2Cl)CC1]

To a solution of N-(1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)piperidin-4-yl)acetamide (7.9 mg, 10.17 mol) in 1,2-dichloroethane (500 μL) and EtOH (335 μL) was added 3,3,3-trifluoropropanal (9 μL, 0.104 mmol), acetic acid (2 μL, 0.035 mmol) and activated 4 A mol sieves. The reaction was stirred at room temp for 20 min, then treated dropwise (over 30 min) with sodium cyanoborohydride, 1.0M in THF (21 μL, 0.021 mmol). After the addition was complete, the reaction was stirred at room temp for 75 min (during which time additional 3,3,3-trifluoropropanal (5 mg, 0.04 mmol) and sodium cyanoborohydride, 1.0 M in THF (several drops) were added), then the solvent was removed under a gentle stream of N$_2$. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to give the title compound (1.2 mg, 13%).

5.29-5.23 (m, 4H), 4.22-4.16 (m, 2H), 3.81 (s, 2H), 3.75-3.69 (m, 1H), 3.66-3.56 (m, 4H), 3.09-3.02 (m, 2H), 2.93 (br d, J=7.5 Hz, 2H), 2.88 (br t, J=6.5 Hz, 2H), 2.76-2.71 (m, 2H), 2.68 (s, 4H), 2.33-2.18 (m, 4H), 2.15-2.07 (m, 6H), 1.91 (br s, 1H), 1.57 (br d, J=10.1 Hz, 2H).

Example 2074: 5-((4-chloro-5-((2'-chloro-3'-(3-(4-hydroxy-4-(hydroxymethyl)piperidin-1-yl)propoxy)-2-methyl-[1,1'-biphenyl]-3-yl)methoxy)-2-(((1,3-dihydroxypropan-2-yl)(3,3,3-trifluoropropyl)amino)methyl)phenoxy)methyl)nicotinonitrile

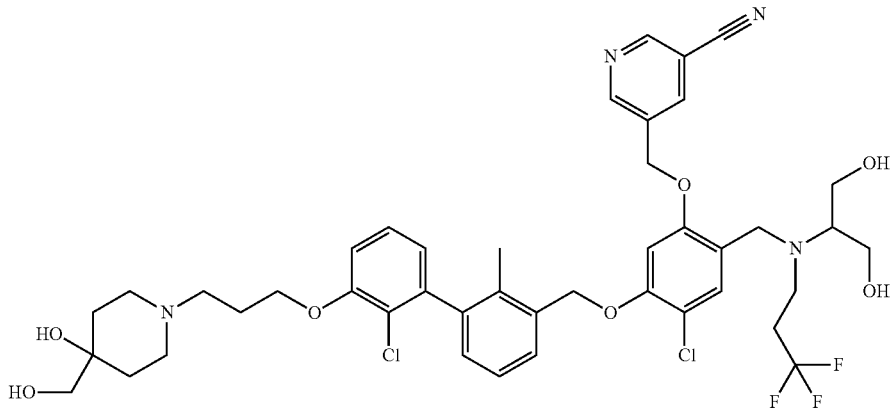 [SMILES: Cc1c(COc2cc(OCc3cncc(C#N)c3)c(CN(CCC(F)(F)F)C(CO)CO)cc2Cl)cccc1-c1cccc(OCCCN2CCC(O)(CO)CC2)c1Cl]

To a solution of 5-((4-chloro-5-((2'-chloro-3'-(3-(4-hydroxy-4-(hydroxymethyl)piperidin-1-yl)propoxy)-2-methyl-[1,1'-biphenyl]-3-yl)methoxy)-2-(((1,3-dihydroxypropan-2-yl)amino)methyl)phenoxy)methyl)nicotinonitrile, 3 TFA (8.0 mg, 7.22 μmol) in 1,2-dichloroethanol (500 μL) and EtOH (330 μL) was added 3,3,3-trifluoropropanal (12 mg, 0.107 mmol), acetic acid (10 μlit), and activated 4 A mol sieves. The reaction was stirred at room temp for 20 min, then treated dropwise (over 30 min) with sodiumcyanoborohydride, 1.0M in THF (20 μlit) over 30 min and stirred at room temp for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 22 minutes, then a 5-minute hold at 100% B; Flow: 20 mL/min to give the title compound (1.7 μmg, 27%).

LC/MS Condition E: ret time 1.76 min; m/e=861 (M+H)$^+$.
LC/MS Condition F: ret time 1.48 min; m/e=861 (M+H)$^+$.

Example 2075: 5-((4-chloro-5-((2'-chloro-3'-(3-(((S)-2,3-dihydroxypropyl)(ethyl)amino)propoxy)-2-methyl-[1,1'-biphenyl]-3-yl)methoxy)-2-((((S)-2,3-dihydroxypropyl)(ethyl)amino)methyl)phenoxy)methyl)nicotinonitrile

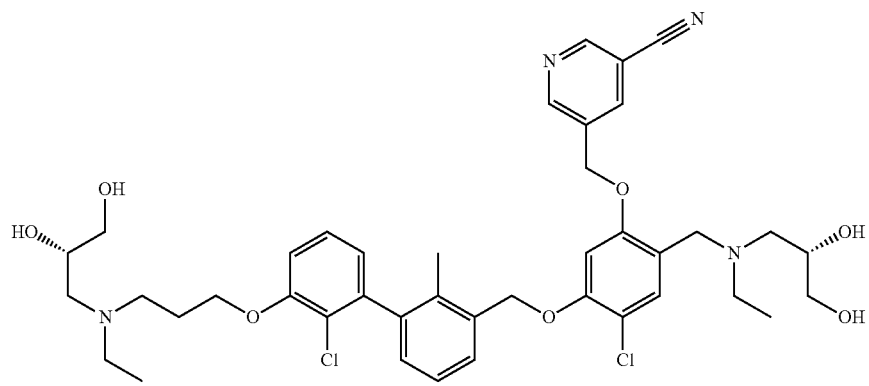 [SMILES: CCN(CCCOc1cccc(-c2cccc(COc3cc(OCc4cncc(C#N)c4)c(CN(CC)C[C@H](O)CO)cc3Cl)c2C)c1Cl)C[C@H](O)CO]

To the vial containing 5-((4-chloro-5-((2'-chloro-3'-(3-(((S)-2,3-dihydroxypropyl)amino)propoxy)-2-methyl-[1,1'-biphenyl]-3-yl)methoxy)-2-((((S)-2,3-dihydroxypropyl)amino)methyl)phenoxy)methyl)nicotinonitrile (15 mg, 0.021 mmol) was added 1,2-dichloroethane (600 μL), EtOH (400 μL), acetaldehyde (12 μL, 0.214 mmol), acetic acid (4 μL, 0.070 mmol) and 4 Å mol sieves. The resulting solution was stirred at room temp for 45 min, then treated dropwise (over 1 h) with sodium cyanoborohydride (41 μL, 0.041 mmol) and stirred at room temp for 45 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 21 minutes, then a 5-minute hold at 100% B; Flow: 20 mL/min to give the tile compound (2 mg, 10%).

LC/MS Condition E: ret time 1.55 min; m/e=781 (M+H)$^+$.
LC/MS Condition F: ret time 1.38 min; m/e=781 (M+H)$^+$.

Intermediate: 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)(methyl)amino)methyl)phenoxy)methyl)nicotinonitrile

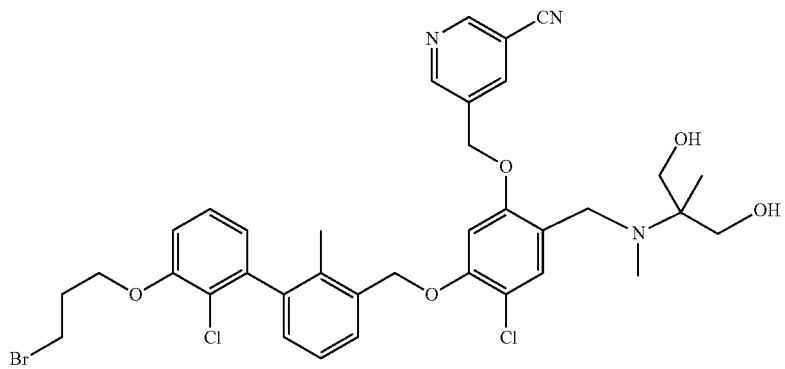 [SMILES: Cc1c(COc2cc(OCc3cncc(C#N)c3)c(CN(C)C(C)(CO)CO)cc2Cl)cccc1-c1cccc(OCCCBr)c1Cl]

353

To a solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)methyl)nicotinonitrile (0.028 g, 0.039 mmol) in MeOH (1.1 mL) was added N,N-diisopropylethylamine (45 μL, 0.258 mmol), followed by iodomethane (15 μL, 0.240 mmol). The reaction was securely capped and heated at 65° C. for 2 h 50 min. The solvent was removed under a gentle stream of N₂ to give the title compound that was used "as is" without purification in subsequent reactions.

LC/MS Condition A: ret time 1.18 min; m/e=742 (M+H)⁺.

Example 2076: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxy-2-methylpropan-2-yl)(methyl)amino)methyl)phenoxy)methyl)nicotinonitrile

354

Intermediate: 5-((5-((3'-(3-bromopropoxy)-2'-chloro-2-methyl-[1,1'-biphenyl]-3-yl)methoxy)-4-chloro-2-(((1-(hydroxymethyl)cyclopropyl)amino)methyl)phenoxy)methyl)nicotinonitrile

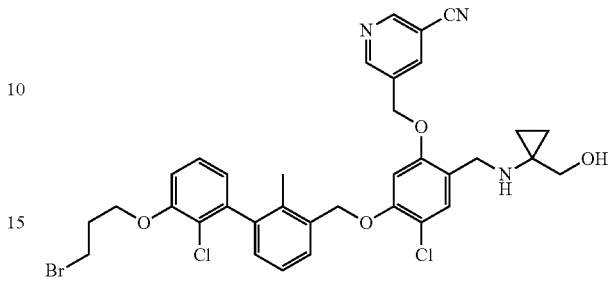

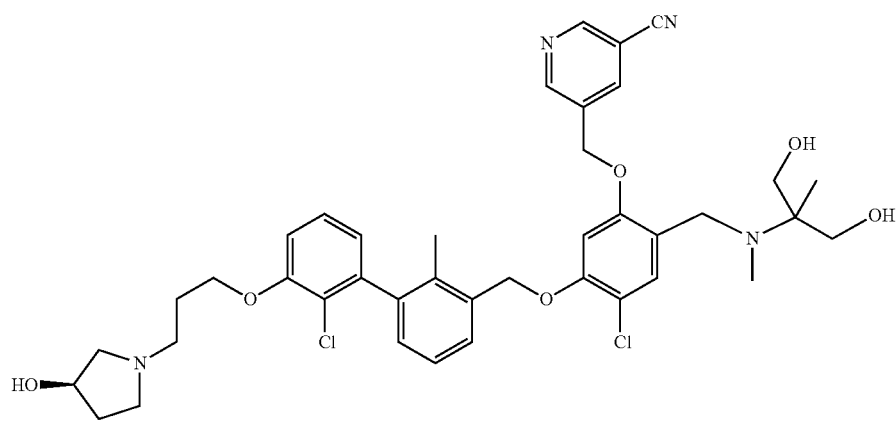 [SMILES: Cc1c(COc2cc(OCc3cncc(C#N)c3)c(CN(C)C(C)(CO)CO)cc2Cl)cccc1-c1cccc(OCCCN2CC[C@@H](O)C2)c1Cl]

To a solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)(methyl)amino)methyl)phenoxy)methyl)nicotinonitrile (29.0 mg, 0.039 mmol) in MeOH (1.1 mL) was added (R)-3-hydroxypyrrolidine hydrochloride (50 mg, 0.405 mmol) and N,N-diisopropylethylamine (100 μL, 0.573 mmol). The reaction was flushed briefly with N₂, capped, heated at 65° C. for 3 h and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min to give the title compound (14.7 mg, 46%).

LC/MS Condition E: ret time 1.56 min; m/e=749 (M+H)⁺.
LC/MS Condition F: ret time 1.47 min; m/e=749 (M+H)⁺.

To a solution of 5-((5-((3'-(3-bromopropoxy)-2'-chloro-2-methyl-[1,1'-biphenyl]-3-yl)methoxy)-4-chloro-2-formyl-phenoxy)methyl)nicotinonitrile (20 mg, 0.031 mmol) in a mixture of 1,2-dichloroethanel (0.8 mL) and EtOH (0.5 mL) was added (1-aminocyclopropyl)methanol, HCl (12 mg, 0.097 mmol), acetic acid (3 μL, 0.052 mmol), and 4 A mol sieves. The reaction was flushed briefly with N₂, capped, stirred at room temp for 90 min, then treated dropwise (over 1 h) with sodium cyanoborohydride, 1.0M in THF (65 μL, 0.065 mmol) and stirred at room temp for 18 h. Additional sodium cyanoborohydride (15 μlit) was added dropwise and the reaction was stirred at room temp for 1 h. N,N-diisopropylethylamine (15 μL) was added and the reaction stirred at room temp for 1.5 h. The solvent was removed under a gentle stream of N₂ to give the title compound that was used "as is" without purification in subsequent reactions.

LC/MS Condition A: ret time 1.18 min; m/e=710 (M+H)⁺.

Example 2077: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1-(hydroxymethyl)cyclopropyl)amino)methyl)phenoxy)methyl)nicotinonitrile

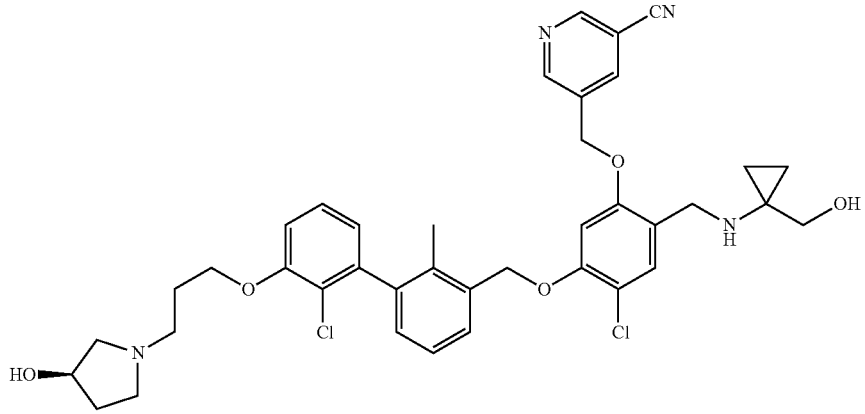 [SMILES: Cc1c(COc2cc(OCc3cncc(C#N)c3)c(CNC3(CO)CC3)cc2Cl)cccc1-c1cccc(OCCCN2CC[C@@H](O)C2)c1Cl]

To a solution of 5-((5-((3'-(3-bromopropoxy)-2'-chloro-2-methyl-[1,1'-biphenyl]-3-yl)methoxy)-4-chloro-2-(((1-(hydroxymethyl)cyclopropyl)amino)methyl)phenoxy)methyl)nicotinonitrile (22.06 mg, 0.031 mmol) in MeOH (1.1 mL) was added (R)-3-hydroxypyrrolidine hydrochloride (40 mg, 0.324 mmol) and N,N-diisopropylethylamine (80 µl, 0.458 mmol). The reaction was flushed briefly with N₂, securely capped and placed in a 65° C. for 3 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min to give the title compound (1.9 mg, 7%).

LC/MS Condition E: ret time 1.76 min; m/e=717 (M+H)⁺.
LC/MS Condition F: ret time 1.48 min; m/e=717 (M+H)⁺.

Example 2078: (R)-2-((5-chloro-2-((5-cyanopyridin-3-yl)methoxy)-4-((2,2'-dichloro-3'-(3-((3R,4R)-3,4-dihydroxypyrrolidin-1-yl)propoxy)-[1,1'-biphenyl]-3-yl)methoxy)benzyl)amino)-3-hydroxy-2-methylpropanoic Acid

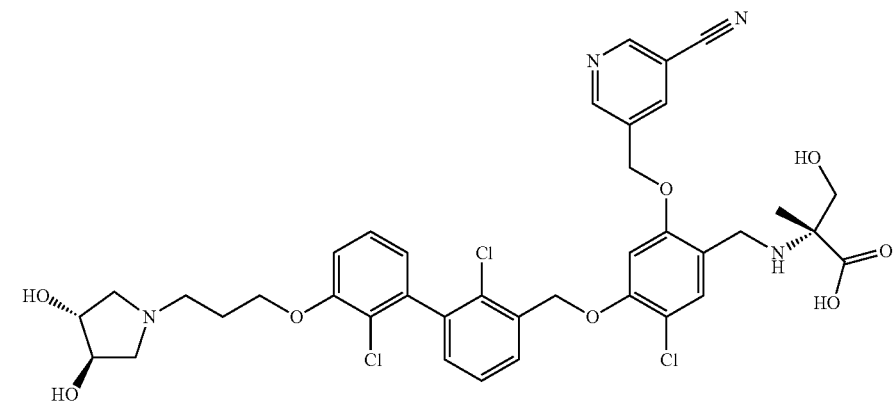 [SMILES: C[C@](CO)(NCc1cc(Cl)c(OCc2cccc(-c3cccc(OCCCN4C[C@@H](O)[C@H](O)C4)c3Cl)c2Cl)cc1OCc1cncc(C#N)c1)C(=O)O]

To a reaction vial under N₂ was added (3R,4R)-pyrrolidine-3,4-diol, 1.0 TFA (80 mg, 0.368 mmol) and (R)-2-((5-chloro-2-((5-cyanopyridin-3-yl)methoxy)-4-((2,2'-dichloro-3'-(3-iodopropoxy)-[1,1'-biphenyl]-3-yl)methoxy)benzyl)amino)-3-hydroxy-2-methylpropanoic acid (26.1 mg, 0.032 mmol) and MeOH (1.3 mL). The reaction was flushed with N₂, treated with N,N-diisopropylethylamine (200 µL, 1.145 mmol), flushed with N₂ again and heated at 70° C. for 1.5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (4.6 mg, 18%).

LC/MS Condition E: ret time 1.38 min; m/e=785 (M+H)$^+$.

LC/MS Condition F: ret time 1.41 min; m/e=785 (M+H)$^+$.

Intermediate: 5-((4-chloro-5-((2'-chloro-3'-hydroxy-2-methyl-[1,1'-biphenyl]-3-yl)methoxy)-2-formylphenoxy)methyl)nicotinonitrile

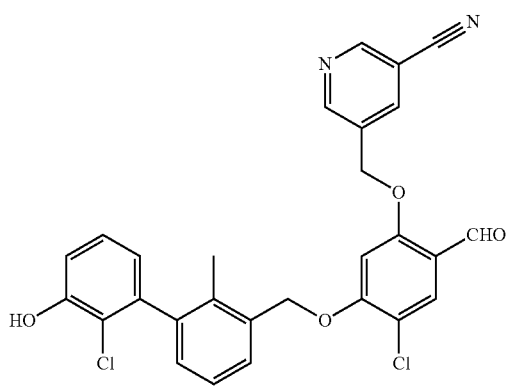 [SMILES: Cc1c(COc2cc(OCc3cncc(C#N)c3)c(C=O)cc2Cl)cccc1-c1cccc(O)c1Cl]

To a dry 100 mL round bottom flask under N$_2$ was added 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (400 mg, 0.771 mmol), 3-bromo-2-chlorophenol (170 mg, 0.819 mmol) and THF (20 mL). The reaction was flushed with argon and then treated with potassium phosphate tribasic, 0.5 M in water (3.85 mL, 1.925 mmol). The reaction was again flushed with argon, treated with 2$^{nd}$ Generation X-Phos precatalyst (39 mg, 0.050 mmol), flushed with argon again, capped and stirred at room temp for 18 h. The reaction was diluted with water (25 mL), 1.0M HCl (5.2 mL) and EtOAc (200 mL). The pH of the water layer was adjusted to pH ~7 with the addition of sat'd NaHCO$_3$. The organic layer was extracted with water (3×25 mL), brine (1×25 mL), dried over Na$_2$SO$_4$, filtered and evaporated to dryness in vacuo. The crude material was dissolved in CH$_2$Cl$_2$ (10 mL), applied to the head of a 80 g Teledyne Isco Silica Flash Column and the column was eluted with a linear gradient from 100% CH$_2$Cl$_2$ to 20% EtOAc/CH$_2$Cl$_2$ over 18 column volumes, a hold at 20% EtOAc/CH$_2$Cl$_2$ for 1 column volume, then 20% EtOAc/CH$_2$Cl$_2$ to 100% EtOAc over 5 column volumes. The fractions that contain the desired product were pooled and evaporated to dryness to give the title compound (123 mg, 31%).

LC/MS Condition A: ret time 1.29 min; m/e=519 (M+H)$^+$.

$^1$H NMR (500 MHz, DMSO-d$_6$) δ 10.24 (s, 2H), 9.04 (t, J=2.0 Hz, 2H), 8.56 (t, J=1.9 Hz, 1H), 7.74 (s, 1H), 7.55 (d, J=7.3 Hz, 1H), 7.34-7.27 (m, 2H), 7.20 (t, J=7.8 Hz, 1H), 7.14 (d, J=6.7 Hz, 1H), 7.01 (dd, J=8.1, 1.4 Hz, 1H), 6.71 (dd, J=7.6, 1.3 Hz, 1H), 5.49 (s, 2H), 5.46-5.39 (m, 2H), 2.09 (s, 3H)

Intermediate: 5-((4-chloro-5-((2'-chloro-3'-(3-hydroxy-2-(hydroxymethyl)propoxy)-2-methyl-[1,1'-biphenyl]-3-yl)methoxy)-2-formylphenoxy)methyl)nicotinonitrile

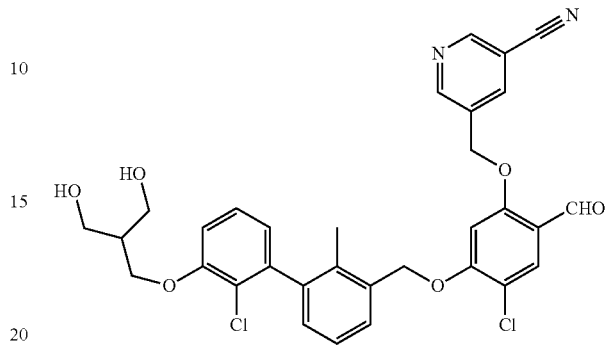

To a suspension of 5-((4-chloro-5-((2'-chloro-3'-hydroxy-2-methyl-[1,1'-biphenyl]-3-yl)methoxy)-2-formylphenoxy)methyl)nicotinonitrile (30 mg, 0.058 mmol), 2-(hydroxymethyl)-1,3-propanediol (20 mg, 0.188 mmol) and triphenylphosphine (31 mg, 0.118 mmol) in THF (1.0 mL) was added over 1-2 min DIAD (17 μL, 0.087 mmol). The reaction was flushed with Ar and stirred at room temp for 90 min. The solvent was removed under a gentle stream of N$_2$ and the residue is redissolved in 1,2-dichloroethane. The solvent was again removed under a gentle stream of N$_2$ to give the title compound that was used "as is" without purification in subsequent reactions.

LC/MS Condition A: ret time 1.22 min; m/e=607 (M+H)$^+$.

Example 2079: 5-((4-chloro-5-((2'-chloro-3'-(3-hydroxy-2-(hydroxymethyl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile

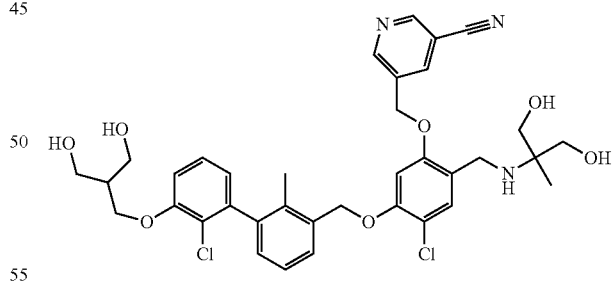

To a vial containing 5-((4-chloro-5-((2'-chloro-3'-(3-hydroxy-2-(hydroxymethyl)propoxy)-2-methyl-[1,1'-biphenyl]-3-yl)methoxy)-2-formylphenoxy)methyl)nicotinonitrile (35.1 mg, 0.058 mmol) was added 1,2-dichloroethane (1.2 mL), EtOH (800 μL), 2-amino-2-methyl-1,3-propanediol (20 mg, 0.190 mmol), acetic acid (10 μL, 0.175 mmol) and 4 A mol sieves. The reaction was flushed well with N$_2$, capped and allowed to stir at room temp for 75 min, then treated slowly (over 1 h 45 min) with sodium cyanoborohydride, 1.0 M in THF (145 μL, 0.145 mmol). The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 minutes, then a 5-minute hold at 100% B; Flow: 20 mL/min to give the title compound (14.8 mg, 35%).

LC/MS Condition E: ret time 1.54 min; m/e=696 (M+H)+.
LC/MS Condition F: ret time 1.55 min; m/e=696 (M+H)+.

Intermediate: 5-((4-chloro-5-((2'-chloro-3'-(3-hydroxy-3-methylbutoxy)-2-methyl-[1,1'-biphenyl]-3-yl)methoxy)-2-formylphenoxy)methyl)nicotinonitrile

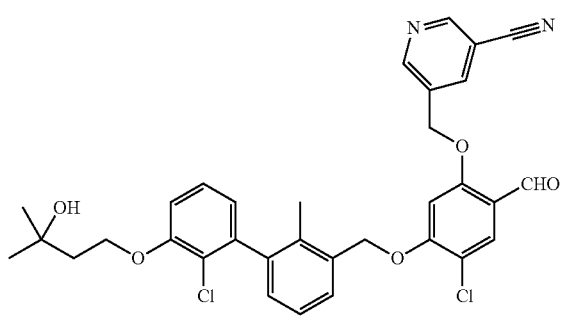 [SMILES: Cc1c(COc2cc(OCc3cncc(C#N)c3)c(C=O)cc2Cl)cccc1-c1cccc(OCCC(C)(C)O)c1Cl]

To a dry reaction vial under N₂ was added 5-((4-chloro-5-((2'-chloro-3'-hydroxy-2-methyl-[1,1'-biphenyl]-3-yl)methoxy)-2-formylphenoxy)methyl)nicotinonitrile (30 mg, 0.058 mmol), 4-bromo-2-methylbutan-2-ol (30 mg, 0.180 mmol) and anhydrous DMF (1.1 mL). The resulting solution was then treated with cesium carbonate (95 mg, 0.292 mmol), flushed briefly with N₂, capped and allowed to stir at room temp for 18 h. The solvent was removed under a gentle stream of N₂. The residue was taken up in 1,2-dichloroethane, filtered through a 45 μfrit and the solvent was evaporated again under a gentle stream of N₂ to give the title compound that was used "as is" without purification in subsequent reactions.

LC/MS Condition A: ret time 1.41 min; m/e=605 (M+H)+.

Example 2080: 5-((4-chloro-5-((2'-chloro-3'-(3-hydroxy-3-methylbutoxy)-2-methyl-[1,1'-biphenyl]-3-yl)methoxy)-2-(((1,3-dihydroxy-2-methylpropan-2-yl)amino)methyl)phenoxy)methyl)nicotinonitrile

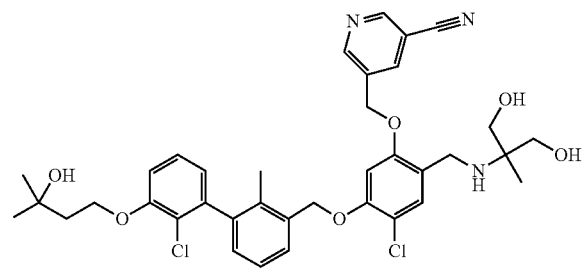 [SMILES: Cc1c(COc2cc(OCc3cncc(C#N)c3)c(CNC(C)(CO)CO)cc2Cl)cccc1-c1cccc(OCCC(C)(C)O)c1Cl]

To a solution of 5-((4-chloro-5-((2'-chloro-3'-(3-hydroxy-3-methylbutoxy)-2-methyl-[1,1'-biphenyl]-3-yl)methoxy)-2-formylphenoxy)methyl)nicotinonitrile (35.1 mg, 0.058 mmol) in 1,2-dichloroethane (1.5 mL) was added 2-amino-2-methyl-1,3-propanediol (20 mg, 0.190 mmol), ethanol (1.0 mL), acetic acid (10 μL, 0.175 mmol) and 4 A sieves. The reaction was flushed with N₂, stirred at room temp for 1 h, and then treated dropwise (over 1 h) with sodium cyanoborohydride, 1.0M in THF (150 μL, 0.150 mmol). The reaction was stirred at room temp for 30 min and the crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 15 minutes, then a 5-minute hold at 100% B; Flow: 20 mL/min to give the title compound (31.4 mg, 59%) as a TFA salt.

LC/MS Condition E: ret time 1.93 min; m/e=694 (M+H)+.
LC/MS Condition F: ret time 1.83 min; m/e=694 (M+H)+.

Intermediate: 5-((4-chloro-5-((2'-chloro-2-methyl-3'-(2-(pyridin-2-yl)ethoxy)-[1,1'-biphenyl]-3-yl)methoxy)-2-formylphenoxy)methyl)nicotinonitrile

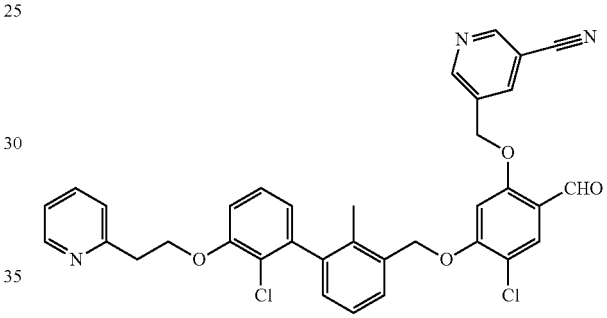

To a suspension of 5-((4-chloro-5-((2'-chloro-3'-hydroxy-2-methyl-[1,1'-biphenyl]-3-yl)methoxy)-2-formylphenoxy)methyl)nicotinonitrile (30 mg, 0.058 mmol), cesium carbonate (42 mg, 0.129 mmol) in acetone (1.0 mL) was added 2-(2-bromoethyl)pyridine, 1.0 hydrobromide (17 mg, 0.064 mmol). The reaction was briefly flushed with N₂ and allowed to stir at room temp for 18 h. Additional 2-(2-bromoethyl)pyridine (50 mg, 0.187 mmol) and Cs₂CO₃ (155 mg, 0.475 mmol) was added and the reaction stirred at room temp for 18 h. The acetone was evaporated under a gentle stream of N₂, and the residue redissolved in anhydrous DMF (1.5 mL). Additional 2-(2-bromoethyl)pyridine (50 mg, 0.187 mmol) and Cs₂CO₃ (155 mg, 0.475 mmol) was added, and the reaction heated at 70° C. for several hours followed by stirring at room temp for 90 h. The reaction was filtered through a 45 t frit and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 20 minutes, then a 5-minute hold at 100% B; Flow: 20 mL/min to give the title compound (13.6 mg, 37%).

LC/MS Condition E: ret time 2.45 min; m/e=624 (M+H)+.
LC/MS Condition F: ret time 1.90 min; m/e=624 (M+H)+.

Example 2081: 5-((4-chloro-5-((2'-chloro-2-methyl-3'-(2-(pyridin-2-yl)ethoxy)-[1,1'-biphenyl]-3-yl)methoxy)-2-(((1,3-dihydroxy-2-methylpropan-2-yl)amino)methyl)phenoxy)methyl)nicotinonitrile

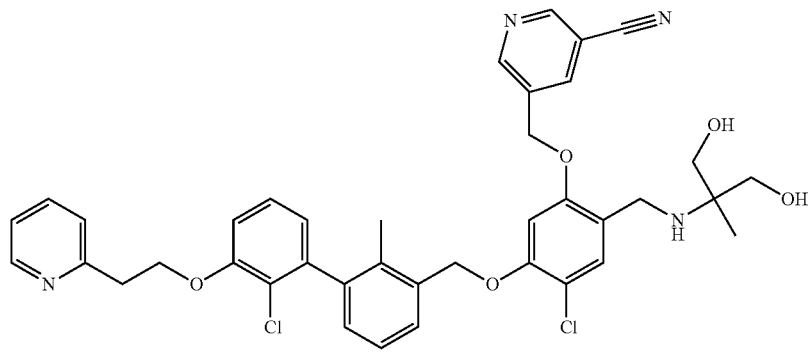 [SMILES: Cc1c(COc2cc(OCc3cncc(C#N)c3)c(CNC(C)(CO)CO)cc2Cl)cccc1-c1cccc(OCCc2ccccn2)c1Cl]

To a solution of 5-((4-chloro-5-((2'-chloro-2-methyl-3'-(2-(pyridin-2-yl)ethoxy)-[1,1'-biphenyl]-3-yl)methoxy)-2-formylphenoxy)methyl)nicotinonitrile (13.6 mg, 0.022 mmol) in a mixture of 1,2-dichloroethane (1 mL) and ethanol (665 L) was added 2-amino-2-methyl-1,3-propanediol (15 mg, 0.143 mmol), acetic acid (5 µL, 0.087 mmol) and 4 A sieves. The reaction was flushed briefly with $N_2$, capped, stirred at room temp for 2 h, treated dropwise (over 45 min) with sodium cyanoborohydride, 1.0 M in THF (55 µL, 0.055 mmol) and then stirred at room temp for 20 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min to give the title compound (15.8 mg, quant).

LC/MS Condition E: ret time 1.96 min; m/e=713 (M+H)⁺.
LC/MS Condition F: ret time 1.43 min; m/e=713 (M+H)⁺.

Intermediate:
3-(3-bromo-2-chlorophenoxy)propane-1,2-diol

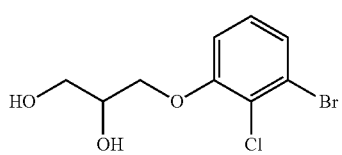 [SMILES: OCC(O)COc1cccc(Br)c1Cl]

To a solution of 3-bromo-2-chlorophenol (500 mg, 2.410 mmol) in anhydrous DMF (8 mL) was added cesium carbonate (4.0 g, 12.28 mmol), followed by 3-bromo-1,2-propanediol (650 µL, 7.42 mmol). The reaction was flushed briefly with $N_2$, and stirred at room temp for 3.5 h. The reaction was heated to 70° C. for 3.5 h, then stirred at room temp for 18 h. Additional 3-bromo-1,2-propanediol (200 µL, 2.284 mmol) was added and reaction heated to 70° C. for several hours. The solvent was evaporated under a gentle stream of $N_2$, and the residue dissolved in a mixture of EtOAc (200 mL) and ice cold aq 1N NaOH (20 mL). The organic layer was extracted with water (2×20 mL), brine (1×20 mL) and dried over $Na_2SO_4$, filtered and evaporated to dryness to give the title compound (530 mg, 78%) that was used "as is" without further purification in subsequent reactions.

¹H NMR (500 MHz, CHLOROFORM-d) δ 7.32-7.29 (m, 1H), 7.12 (t, J=8.2 Hz, 1H), 6.92 (d, J=8.4 Hz, 1H), 4.22-4.07 (m, 3H), 3.96-3.80 (m, 2H), 2.74 (d, J=4.7 Hz, 1H), 2.11 (t, J=6.1 Hz, 1H)

Intermediate: 5-((4-chloro-5-((2'-chloro-3'-(2,3-dihydroxypropoxy)-2-methyl-[1,1'-biphenyl]-3-yl)methoxy)-2-formylphenoxy)methyl)nicotinonitrile

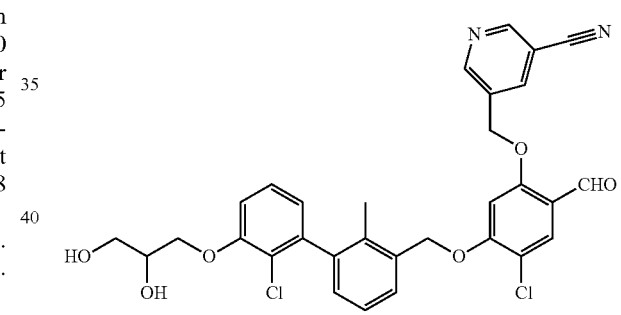

To a dry reaction vial under $N_2$ was added 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (100 mg, 0.193 mmol), 3-(3-bromo-2-chlorophenoxy)propane-1,2-diol (60 mg, 0.213 mmol) and anhydrous THF (5 mL). The reaction was flushed with argon, treated with potassium phosphate tribasic, 0.5 M in water (965 µL, 0.483 mmol), followed by 2$^{nd}$ generation X-phos precatalyst (14 mg, 0.018 mmol). The reaction was again flushed with Ar, capped and stirred at room temp for 18 h. The reaction mixture was diluted with $CH_2Cl_2$ (175 mL) and water (15 mL). The water layer was back extracted with $CH_2Cl_2$ (25 mL). The organic layers were combined and extracted with brine (1×20 mL), dried over $Na_2SO_4$, filtered and evaporated to dryness. The residue was dissolve in $CH_2Cl_2$ (5 mL), applied to the head of a 12 g Teledyne Isco Silica Flash Column and eluted the column with a linear gradient from 100% $CH_2Cl_2$ to 100% EtOAc over 12 column volumes, with a hold at 100% EtAOc for 7 column volumes. The fractions containing the desired product were pooled and evaporated to dryness to give the title compound (60 mg, 53%).

LC/MS Condition A: ret time 1.20 min; m/e=593 (M+H)+.

Example 2082: 5-((4-chloro-5-((2'-chloro-3'-(2,3-dihydroxypropoxy)-2-methyl-[1,1'-biphenyl]-3-yl)methoxy)-2-(((1,3-dihydroxy-2-methylpropan-2-yl)amino)methyl)phenoxy)methyl)nicotinonitrile

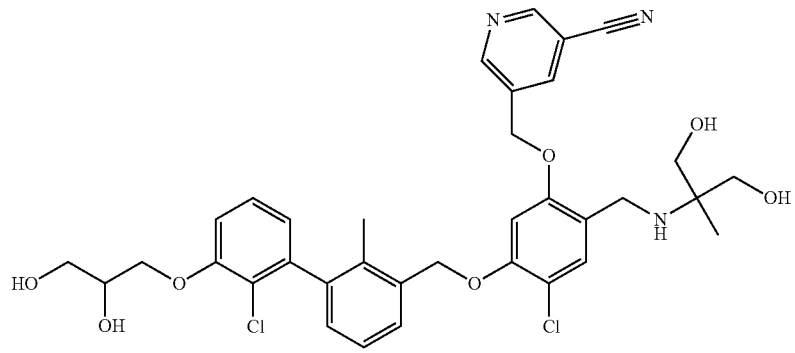 [SMILES: Cc1c(COc2cc(OCc3cncc(C#N)c3)c(CNC(C)(CO)CO)cc2Cl)cccc1-c1cccc(OCC(O)CO)c1Cl]

To a solution of 5-((4-chloro-5-((2'-chloro-3'-(2,3-dihydroxypropoxy)-2-methyl-[1,1'-biphenyl]-3-yl)methoxy)-2-formylphenoxy)methyl)nicotinonitrile (21 mg, 0.035 mmol) and 2-amino-2-methylpropane-1,3-diol (25 mg, 0.238 mmol) in a mixture of 1,2-dichloroethane (700 μL) and EtOH (450 μL) was added acetic acid (9 μL, 0.157 mmol) and 4 A mol sieves. The reaction was flushed with N₂, stirred at room temp for 90 min, treated dropwise (over 1 h) with sodium cyanoborohydride, 1.0M in THF (90 μL, 0.090 mmol), then allowed to stir at room temp for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (17.6 mg, 73%).

LC/MS Condition E: ret time 1.64 min; m/e=682 (M+H)+.
LC/MS Condition F: ret time 1.52 min; m/e=682 (M+H)+.

Example 2083: (2S)-1-(5-chloro-4-((2'-chloro-3'-(2,3-dihydroxypropoxy)-2-methyl-[1,1'-biphenyl]-3-yl)methoxy)-2-((5-cyanopyridin-3-yl)methoxy)benzyl)piperidine-2-carboxylic Acid

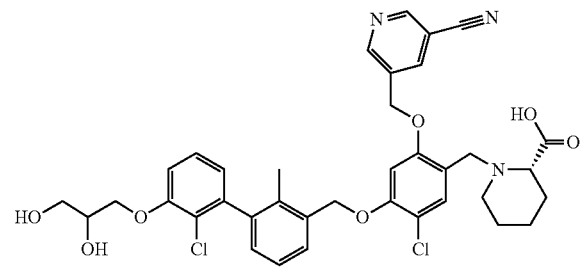 [SMILES: Cc1c(COc2cc(OCc3cncc(C#N)c3)c(CN3CCCC[C@H]3C(=O)O)cc2Cl)cccc1-c1cccc(OCC(O)CO)c1Cl]

To a solution of 5-((4-chloro-5-((2'-chloro-3'-(2,3-dihydroxypropoxy)-2-methyl-[1,1'-biphenyl]-3-yl)methoxy)-2-formylphenoxy)methyl)nicotinonitrile (39 mg, 0.066 mmol) and L-pipecolic acid (57 mg, 0.441 mmol) in a mixture of 1,2-dichloroethane (1.3 mL) and EtOH (870 μL) was added acetic acid (16 μL, 0.279 mmol) and 4 A mol sieves. The reaction was flushed briefly with N₂, stirred at room temp for 90 min, treated dropwise (over 1 h) with sodium cyanoborohydride, 1.0M in THF (90 μL, 0.090 mmol), and then stirred at room temp for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the title compound (18.2 mg, 39%).

LC/MS Condition E: ret time 1.59 min; m/e=706 (M+H)+.
LC/MS Condition F: ret time 1.57 min; m/e=706 (M+H)+.

Intermediate: 2-((3-bromo-2-chlorophenoxy)methyl)(hydroxymethyl)propane-1,3-diol

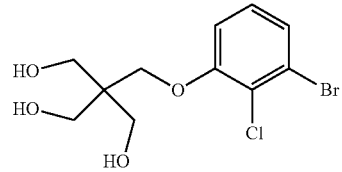 [SMILES: OCC(CO)(CO)COc1cccc(Br)c1Cl]

To a solution of 3-bromo-2-chlorophenol (500 mg, 2.410 mmol), pentaerythritol (1 mL, 7.35 mmol) and triphenylphosphine (1.3 g, 4.96 mmol) in anhydrous THF (8 mL) was added diamide (625 mg, 3.63 mmol). The reaction turned bright yellow. The reaction was flushed with N₂, capped and stirred at room temp for 18 h. The reaction was treated with additional TMAD (155 mg, 0.9 mmol) and triphenylphosphine (250 mg, 0.95 mmol), and stirred at room temp for 18 h. The white solid was filtered off through a disposable frit, washed with THF and the filtrate evaporated to dryness in vacuo. The residue was dissolved in CH₂Cl₂ (35 mL) and apply to the head of a 80 g Teledyne Isco Silica Flash Column. The column was eluted with a linear gradient from 100% CH₂Cl₂ to 100% EtOAc over 12 column volumes. The fractions containing the desired product were pooled and evaporated to dryness to give the title compound (194 mg, 25%).

LC/MS Condition A: ret time 0.920 min; m/e=325 (M+H)+.

¹H NMR (500 MHz, METHANOL-d₄) δ 7.27 (dd, J=8.1, 1.4 Hz, 1H), 7.18 (t, J=8.2 Hz, 1H), 7.09 (dd, J=8.2, 1.4 Hz, 1H), 4.08 (s, 2H), 3.76 (s, 6H)

Intermediate: 5-((4-chloro-5-((2'-chloro-3'-(3-hydroxy-2,2-bis(hydroxymethyl)propoxy)-2-methyl-[1,1'-biphenyl]-3-yl)methoxy)-2-formylphenoxy)methyl)nicotinonitrile

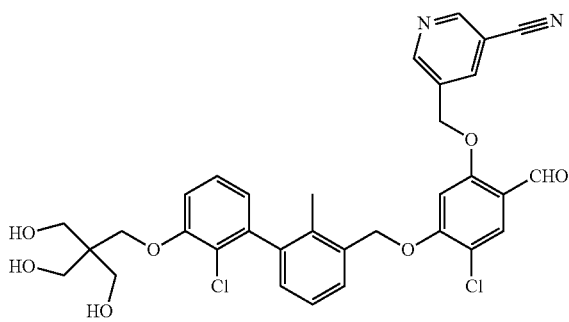 [SMILES: Cc1c(COc2cc(OCc3cncc(C#N)c3)c(C=O)cc2Cl)cccc1-c1cccc(OCC(CO)(CO)CO)c1Cl]

To a dry reaction vial under N₂ was added 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (100 mg, 0.193 mmol), 2-((3-bromo-2-chlorophenoxy)methyl)-2-(hydroxymethyl)propane-1,3-diol (70 mg, 0.215 mmol) and THF (5 mL). The reaction was flushed with argon, treated with potassium phosphate tribasic, 0.5 M in water (965 µL, 0.483 mmol) followed by 2ⁿᵈ Generation X-Phos precatalyst (8 mg, 10.17 µmol). The reaction mixture was flushed with Ar again, capped and allowed to stir at room temp for 42 h. The reaction was diluted with CH₂Cl₂ (200 mL) and water (25 mL), and the water layer was back extracted with additional CH₂Cl₂ (25 mL). The organic layers were combined and washed with brine (25 mL), dried over Na₂SO₄, filtered and evaporated to dryness. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to give the title compound (52.7 mg, 39%).

LC/MS Condition A: ret time 1.22 min; m/e=637 (M+H)⁺.

Example 2084: (S)-1-(5-chloro-4-((2'-chloro-3'-(3-hydroxy-2,2-bis(hydroxymethyl)propoxy)-2-methyl-[1,1'-biphenyl]-3-yl)methoxy)-2-((5-cyanopyridin-3-yl)methoxy)benzyl)piperidine-2-carboxylic Acid To a solution of 5-((4-chloro-5-((2'-chloro-3'-(3-hydroxy-2,2-bis(hydroxymethyl)propoxy)-2-methyl-[1,1'-biphenyl]-3-yl)methoxy)-2-formylphenoxy)methyl)nicotinonitrile (26.4 mg, 0.041 mmol) and L-pipecolic acid (32 mg, 0.248 mmol) in a mixture of 1,2-dichloroethane (800 µL) and EtOH (530 µL) was added acetic acid (10 µL, 0.175 mmol) and activated 4 A mol sieves. The reaction was stirred at room temp for 1 h, treated dropwise (over several hours) with sodium cyanoborohydride, 1.0M in THF (105 µL, 0.105 mmol) and stirred overnight at room temp. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-48% B over 20 minutes, then a 5-minute hold at 100% B; Flow: 20 mL/min to give the title compound (9.2 mg, 30%)

LC/MS Condition E: ret time 1.49 min; m/e=750 (M+H)⁺.
LC/MS Condition F: ret time 1.55 min; m/e=750 (M+H)⁺.

Example 2085: 5-((4-chloro-5-((2'-chloro-3'-(3-hydroxy-2,2-bis(hydroxymethyl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile To a solution of 5-((4-chloro-5-((2'-chloro-3'-(3-hydroxy-2,2-bis(hydroxymethyl)propoxy)-2-methyl-[1,1'-biphenyl]-3-yl)methoxy)-2-formylphenoxy)methyl)nicotinonitrile (26.4 mg, 0.041 mmol) and 2-amino-2-methyl-1,3-propanediol (30 mg, 0.285 mmol) in a mixture of 1,2-dichloroethane (800 μL) and EtOH (530 μL) was added acetic acid (10 μL, 0.175 mmol) and activated 4 A mol sieves. The reaction was stirred at room temp for 1 h, treated dropwise (over several hours) with sodium cyanoborohydride, 1.0M in THF (105 μL, 0.105 mmol) and stirred at room temp for several hours. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (26.2 mg, 84%).

LC/MS Condition E: ret time 1.56 min; m/e=726 (M+H)$^+$.
LC/MS Condition F: ret time 1.49 min; m/e=726 (M+H)$^+$.

Intermediate: (3R)-1-(3-(3-bromo-2-chlorophenoxy)-2-hydroxypropyl)pyrrolidin-3-ol

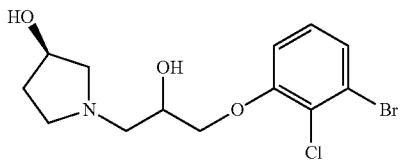 [SMILES: OC(COc1cccc(Br)c1Cl)CN1CC[C@@H](O)C1]

To a mixture of 3-bromo-2-chlorophenol (494 mg, 2.381 mmol) and cesium carbonate (1.9 g, 5.83 mmol) was added dry DMF (4 mL). The reaction was flushed with argon, treated with 1,3-dibromopropan-2-ol (1.16 g, 5.32 mmol), capped and stirred at room temp for 18 h. The reaction was then diluted with DMF (4.5 mL), treated with (R)-pyrrolidin-3-ol, HCl (1.58 g, 12.79 mmol), N,N-diisopropylethylamine (2.4 mL, 13.74 mmol) and heated at 65° C. for 18 h. The reaction was partitioned with ethyl acetate (150 mL) and 1 N aq NaOH (20 mL). The organic layer was extracted with 1 N aq NaOH (10 mL), water (3×20 mL) and brine (50 mL), dried over Na$_2$SO$_4$ filtered and evaporated to dryness. The crude material was purified via preparative LC/MS with the following conditions: Column: XBridge C18, 50×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-60% B over 30 minutes, then a 7-minute hold at 100% B; Flow: 100 mL/min to give the title compound (64 mg, 8%).

LC/MS Condition E: ret time 1.32 min; m/e=350 (M+H)$^+$.
LC/MS Condition F: ret time 1.18 min; m/e=350 (M+H)$^+$.

Intermediate: 5-((4-chloro-5-((2'-chloro-3'-(2-hydroxy-3-((R)-3-hydroxypyrrolidin-1-yl)propoxy)-2-methyl-[1,1'-biphenyl]-3-yl)methoxy)-2-formylphenoxy)methyl)nicotinonitrile

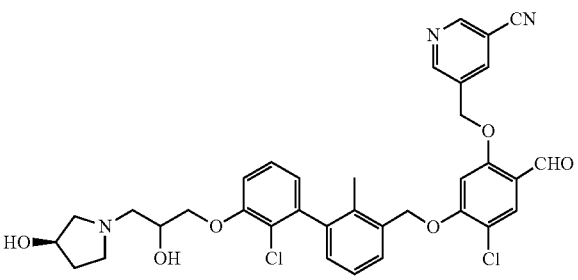 [SMILES: Cc1c(COc2cc(OCc3cncc(C#N)c3)c(C=O)cc2Cl)cccc1-c1cccc(OCC(O)CN2CC[C@@H](O)C2)c1Cl]

To a solution of (3R)-1-(3-(3-bromo-2-chlorophenoxy)-2-hydroxypropyl)pyrrolidin-3-ol (64 mg, 0.183 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (95 mg, 0.183 mmol) in THF (4 mL) under argon was added potassium phosphate tribasic 0.5 M in water (0.95 mL, 0.475 mmol), followed 2$^{nd}$ Generation X-Phos precatalyst (9.8 mg, 0.012 mmol). The reaction was flushed with argon, capped and stirred at room temp for 66 h. The reaction was then treated with additional 2$^{nd}$ Generation X-Phos precatalyst (8 mg, 0.01 mmol), flushed with argon and stirred at room temp for 18 h. The reaction was partitioned with EtOAc (40 mL) and water (20 mL). The organic layer was extracted with brine, dried over sodium sulfate, filtered and evaporated to dryness. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to give the title compound (7.3 mg, 6%).

LC/MS Condition E: ret time 1.80 min; m/e=662 (M+H)$^+$.
LC/MS Condition F: ret time 1.83 min; m/e=662 (M+H)$^+$.

Example 2086: 5-((4-chloro-5-((2'-chloro-3'-(2-hydroxy-3-((R)-3-hydroxypyrrolidin-1-yl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile

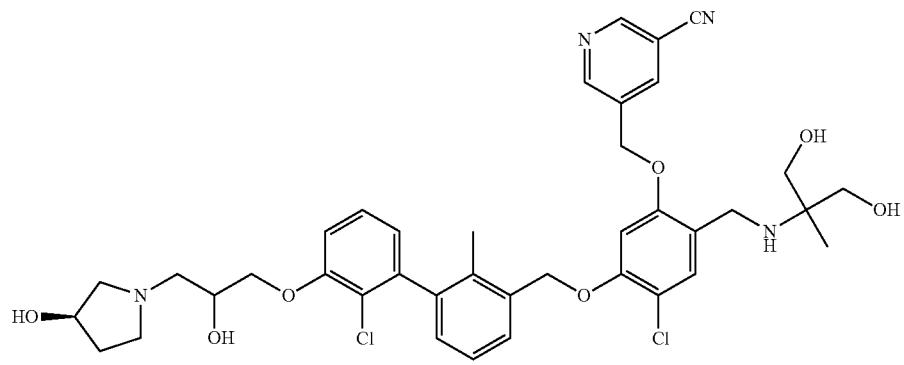 [SMILES: Cc1c(COc2cc(OCc3cncc(C#N)c3)c(CNC(C)(CO)CO)cc2Cl)cccc1-c1cccc(OCC(O)CN2CC[C@@H](O)C2)c1Cl]

To a solution of 5-((4-chloro-5-((2'-chloro-3'-(2-hydroxy-3-((R)-3-hydroxypyrrolidin-1-yl)propoxy)-2-methyl-[1,1'-biphenyl]-3-yl)methoxy)-2-formylphenoxy)methyl)nicotinonitrile (7.3 mg, 0.011 mmol) in a mixture of 1,2-dichloroethane (500 µL) and ethanol (330 µL) was added 2-amino-2-methyl-1,3-propanediol (9.1 mg, 0.087 mmol), acetic acid (2.5 µL, 0.044 mmol) and 4 A mol sieves. The reaction was stirred at room temp for 1 h, treated dropwise (over 30 min) with sodium cyanoborohydride, 1.0M in THF (30 µL, 0.030 mmol) and stirred for 30 min at room temp. Additional 2-amino-2-methyl-1,3-propanediol (6 mg, 0.06 mmol) and sodium cyanoborohydride (10 µlit, 0.010 mmol) were added, and the reaction was stirred at room temp for 18 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 7-47% B over 20 minutes, then a 5-minute hold at 100% B; Flow: 20 mL/min to give the title compound (2.2 mg, 23%).

LC/MS Condition E: ret time 1.58 min; m/e=751 (M+H)$^+$.
LC/MS Condition F: ret time 1.32 min; m/e=751 (M+H)$^+$.

Intermediate: tert-butyl (3-(3-bromo-2-chlorophenoxy)propyl)carbamate

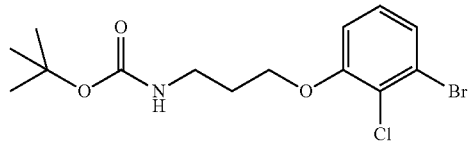 [SMILES: CC(C)(C)OC(=O)NCCCOc1cccc(Br)c1Cl]

To a solution of tert-butyl (3-bromopropyl)carbamate (4.29 g, 18.02 mmol) and 3-bromo-2-chlorophenol (3.74 g, 18.02 mmol) in DMF (25 mL) under argon was added potassium carbonate (5 g, 36.2 mmol) and the reaction was heated at 50-55 C for 19 h. The reaction was diluted with EtOAc (600 mL). The organic layer was washed with water (4×150 mL), brine (100 mL), dried over Na$_2$SO$_4$, filtered and the solvent was removed in vacuo to give the title compound (6.5 g, 94%) that was used "as is" without further purification.
$^1$H NMR (500 MHz, CHLOROFORM-d) □ 7.26 (dd, J=8.1, 1.2 Hz, 1H), 7.10 (t, J=8.2 Hz, 1H), 6.88 (dd, J=8.3, 1.1 Hz, 1H), 5.17 (br.s., 1H), 4.13 (t, J=5.8 Hz, 2H), 3.40 (q, J=5.8 Hz, 2H), 2.10-2.04 (m, 2H), 1.46 (s, 9H).

Intermediate: 3-(3-bromo-2-chlorophenoxy)propan-1-amine

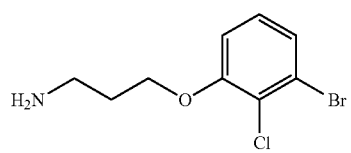 [SMILES: NCCCOc1cccc(Br)c1Cl]

To a solution of tert-butyl (3-(3-bromo-2-chlorophenoxy)propyl)carbamate (750 mg, 2.057 mmol) in anhydrous CH$_2$Cl$_2$ (50 mL) was added TFA (15 mL, 195 mmol) and the reaction was allowed to stand at room temp for 30 min. The solvent was evaporated in vacuo, and the residue dissolved in EtOAc (425 mL). The organic mixture was extracted with aq sat'd NaHCO$_3$ (3×30 mL), water (1×30 mL), brine (1×30 mL), dried over Na$_2$SO$_4$, filtered and evaporated to dryness to give the title compound (530 mg, 97%) that was used "as is" without further purification.

LC/MS Condition A: ret time 0.805 min; m/e=264 (M+H)$^+$.

$^1$H NMR (500 MHz, DMSO-d$_6$) δ 7.35-7.30 (m, 1H), 7.25 (t, J=8.2 Hz, 1H), 7.20-7.15 (m, 1H), 4.15 (t, J=6.2 Hz, 2H), 2.76 (t, J=6.8 Hz, 2H), 1.85 (quin, J=6.5 Hz, 2H)

Intermediate: N-(3-(3-bromo-2-chlorophenoxy)propyl)-2,3-dihydroxypropanamide

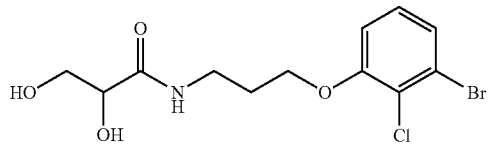 [SMILES: O=C(NCCCOc1cccc(Br)c1Cl)C(O)CO]

To a suspension of 3-(3-bromo-2-chlorophenoxy)propan-1-amine (125 mg, 0.473 mmol) in anhydrous CH$_2$Cl$_2$ (10 mL) was added DL-glyceric acid, 20% in water (~2 mol/L) (2.0 g, 3.77 mmol), and 1-hydroxy-7-azabenzotriazole (110 mg, 0.808 mmol). The resulting 2-phase reaction was flushed briefly with N$_2$, then treated with EDC (360 mg, 1.878 mmol), followed by N,N-diisopropylethylamine (500 µL, 2.86 mmol). The reaction was flushed with N$_2$, capped and stirred at room temp for 18 h. Additional DL-glyceric acid (500 mg, 0.943 mmol), EDC (50 mg, 0.26 mmol) and N,N-diisopropylethylamine (150 µlit, 0.859 mmol) were added and the reaction was stirred at room temp for several hours. The reaction was diluted with EtOAc (450 mL). The organic layer was extracted with aq. 1.0 M HCl (1×20 mL), aq. sat'd NaHCO$_3$ (1×20 mL), water (1×20 mL) and brine (2×15 mL), dried over Na$_2$SO$_4$, and filtered. The solvent was removed in vacuo to give the title compound that was used "as is" without further purification in subsequent reactions.

LC/MS Condition A: ret time 0.905 min; m/e=352 (M+H)$^+$.

Intermediate: N-(3-((2-chloro-3'-((2-chloro-5-((5-cyanopyridin-3-yl)methoxy)-4-formylphenoxy)methyl)-2'-methyl-[1,1'-biphenyl]-3-yl)oxy)propyl)-2,3-dihydroxypropanamide

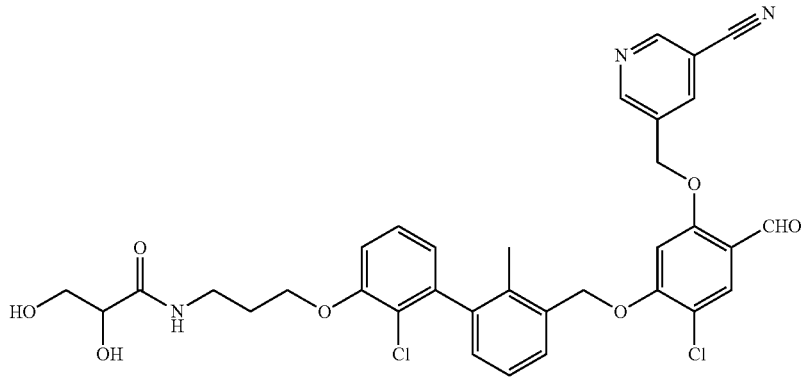 [SMILES: Cc1c(COc2cc(OCc3cncc(C#N)c3)c(C=O)cc2Cl)cccc1-c1cccc(OCCCNC(=O)C(O)CO)c1Cl]

To a solution of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (61 mg, 0.118 mmol) and N-(3-(3-bromo-2-chlorophenoxy)propyl)-2,3-dihydroxypropanamide (41.6 mg, 0.118 mmol) in THF (7 mL) was added potassium phosphate tribasic, 0.5M in water (590 µL, 0.295 mmol). The reaction was purged very well with argon, then treated with $2^{nd}$ generation X-Phos precatalyst (5 mg, 6.35 µmol). The reaction was purged with argon again, capped, and stirred at room temp for 66 h. The reaction was diluted EtOAc (200 mL), and the organic layer was extracted with water (2×20 mL), brine (1×10 mL), dried over $Na_2SO_4$, filtered and evaporated in vacuo. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 30 minutes, then a 5-minute hold at 100% B; Flow: 20 mL/min to give the title compound (13.8 mg, 16%)
LC/MS Condition E: ret time 1.92 min; m/e=664 (M+H)$^+$.
LC/MS Condition F: ret time 2.01 min; m/e=664 (M+H)$^+$.

Example 2088: N-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-2,3-dihydroxypropanamide

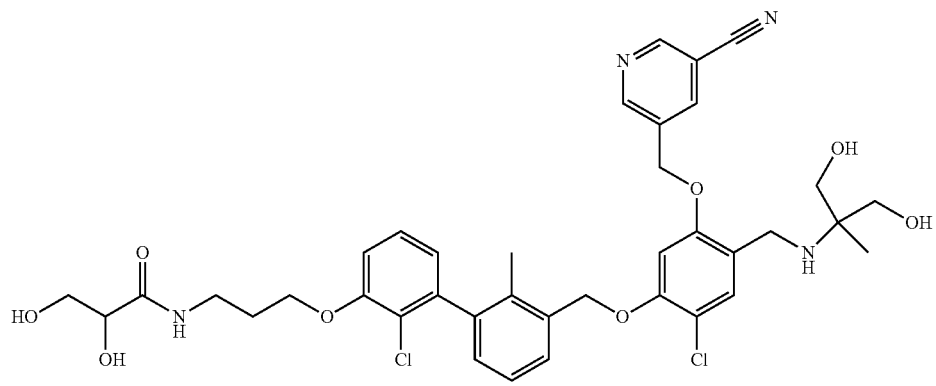 [SMILES: Cc1c(COc2cc(OCc3cncc(C#N)c3)c(CNC(C)(CO)CO)cc2Cl)cccc1-c1cccc(OCCCNC(=O)C(O)CO)c1Cl]

To the vial containing N-(3-((2-chloro-3'-((2-chloro-5-((5-cyanopyridin-3-yl)methoxy)-4-formylphenoxy)methyl)-2'-methyl-[1,1'-biphenyl]-3-yl)oxy)propyl)-2,3-dihydroxypropanamide (13.8 mg, 0.021 mmol) was added 2-amino-2-methyl-1,3-propanediol (16 mg, 0.152 mmol), 1,2-dichloroethane (600 µL), ethanol (400 µL), acetic acid (5 µL, 0.087 mmol) and 4 Å mol sieves. The reaction was flushed briefly with $N_2$, capped, stirred at room temp for 1 h, then treated dropwise (over 1.5 h) with sodium cyanoborohydride, 1.0M in THF (60 µL, 0.060 mmol) and was stirred at room temp for 45 min. The crude material was purified via preparative LC/MS with the following conditions: Column: XBridge C18, 19×200 mm, 5-µm particles; Mobile Phase A:

5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (13 mg, 83%).

LC/MS Condition E: ret time 1.63 min; m/e=753 (M+H)$^+$.
LC/MS Condition F: ret time 1.47 min; m/e=753 (M+H)$^+$.

Intermediate: N-(3-(3-bromo-2-chlorophenoxy)propyl)-2-(pyridin-2-yl)acetamide

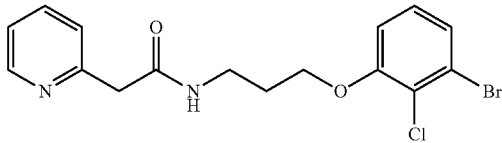 [SMILES: O=C(Cc1ccccn1)NCCCOc1cccc(Br)c1Cl]

To a solution of 3-(3-bromo-2-chlorophenoxy)propan-1-amine (125 mg, 0.473 mmol) and 2-(pyridin-2-yl)acetate, 1.0 lithium salt (300 mg, 2.097 mmol) in anhydrous CH$_2$Cl$_2$ (8 mL) was added 1-hydroxy-7-azabenzotriazole (100 mg, 0.735 mmol), followed by HCl, 1.0 M in water (2.1 mL, 2.100 mmol). The reaction was flushed briefly with N$_2$, then treated with EDC (410 mg, 2.139 mmol), capped and stirred at room temp for 18 h. The reaction was diluted with CH$_2$Cl$_2$ (225 mL) and the organic layer was extracted with aq sat'd NaHCO$_3$ (2×20 mL), brine (1×10 mL), dried over Na$_2$SO$_4$, filtered and evaporated to dryness in vacuo. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 20 minutes, then a 5-minute hold at 100% B; Flow: 20 mL/min to give the title compound (129 mg, 71%).

LC/MS Condition E: ret time 1.83 min; m/e=385 (M+H)$^+$.
LC/MS Condition F: ret time 1.27 min; m/e=385 (M+H)$^+$.
$^1$H NMR (500 MHz, CHLOROFORM-d) δ 8.50-8.44 (m, 1H), 7.65 (td, J=7.7, 1.8 Hz, 1H), 7.46 (br s, 1H), 7.28-7.24 (m, 2H), 7.17 (ddd, J=7.5, 4.9, 1.0 Hz, 1H), 7.09 (t, J=8.2 Hz, 1H), 6.85 (dd, J=8.3, 1.3 Hz, 1H), 4.05 (t, J=6.0 Hz, 2H), 3.75 (s, 2H), 3.54 (q, J=6.4 Hz, 2H), 2.14-2.02 (m, 2H)

Intermediate: N-(3-((2-chloro-3'-((2-chloro-5-((5-cyanopyridin-3-yl)methoxy)-4-formylphenoxy) methyl)-2'-methyl-[1,1'-biphenyl]-3-yl)oxy)propyl)-2-(pyridin-2-yl)acetamide

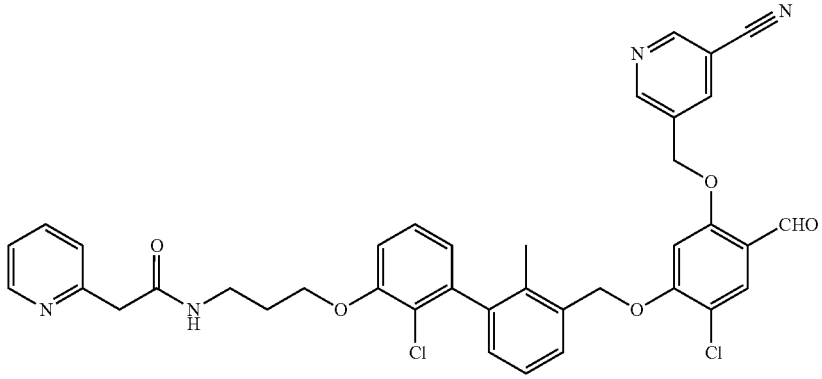 [SMILES: Cc1c(COc2cc(OCc3cncc(C#N)c3)c(C=O)cc2Cl)cccc1-c1cccc(OCCCNC(=O)Cc2ccccn2)c1Cl]

To a solution of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (50 mg, 0.096 mmol) and N-(3-(3-bromo-2-chlorophenoxy)propyl)-2-(pyridin-2-yl) acetamide (40 mg, 0.104 mmol) in THF (5 mL) was added potassium phosphate tribasic, 0.5M in water (485 μL, 0.243 mmol). The reaction was flushed with argon, treated with 2$^{nd}$ generation X-Phos precatalyst (5 mg, 6.35 μmol), flushed with argon again, capped and stirred at room temp for 18 h. Additional X-Phos precatalyst (10 mg, 0.013 mmol) was added, and the reaction mixture flushed with Ar, capped and stirred at room temp for 18 h. The reaction was diluted with EtOAc (125 mL) and the organic layer was extracted with water (1×40 mL). The water layer was back extracted with EtOAc (1×50 mL). The organic layers were combined, extracted with brine (1×40 mL), dried over Na$_2$SO$_4$, filtered and evaporated to dryness. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-80% B over 20 minutes, then a 5-minute hold at 100% B; Flow: 20 mL/min to give the title compound (9.4 mg, 14%).

LC/MS Condition E: ret time 2.19 min; m/e=695 (M+H)$^+$.
LC/MS Condition F: ret time 1.94 min; m/e=695 (M+H)$^+$.

Example 2089: N-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-2-(pyridin-2-yl)acetamide

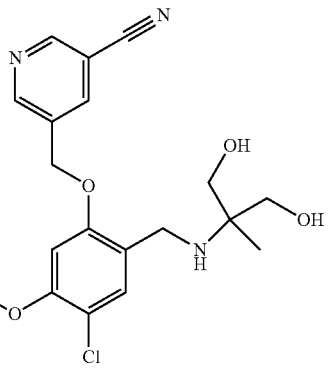

To a solution of N-(3-((2-chloro-3'-((2-chloro-5-((5-cyanopyridin-3-yl)methoxy)-4-formylphenoxy)methyl)-2'-methyl-[1,1'-biphenyl]-3-yl)oxy)propyl)-2-(pyridin-2-yl)acetamide (9.4 mg, 0.014 mmol) and 2-amino-2-methylpropane-1,3-diol (10 mg, 0.095 mmol) in a mixture of 1,2-dichloroethane (600 μL) and EtOH (400 μL) was added acetic acid (4 μL, 0.070 mmol) and 4 A mol sieves. The reaction was stirred at room temp for 1 h, treated dropwise with sodium cyanoborohydride, 1.0 M in THF (35 μL, 0.035 mmol) and stirred at room temp for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (2.3 mg, 14%)

LC/MS Condition E: ret time 1.75 min; m/e=784 (M+H)+.
LC/MS Condition F: ret time 1.40 min; m/e=784 (M+H)+.

Intermediate: N-(3-bromo-2-chlorobenzyl)-2-morpholinoethan-1-amine

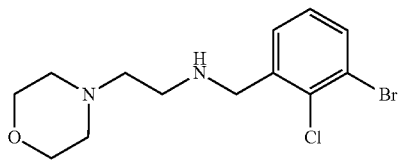 [SMILES: Clc1c(Br)cccc1CNCCN1CCOCC1]

To a dry 100 mL round bottom flask under N₂ was added 3-bromo-2-chlorobenzaldehyde (300 mg, 1.367 mmol), 4-(2-aminoethyl)morpholine (215 mg, 1.651 mmol), 1,2-dichloroethane (20 mL), EtOH (13 mL), acetic acid (200 μL, 3.49 mmol) and 4 A mol sieves. The reaction was stirred at room temp for 30 min, then treated dropwise (over 1 h) with sodium cyanoborohydride, 1.0 M in THF (3.0 mL, 3.00 mmol), stirred at room temp for 40 min and the solvent removed under a gentle stream of N₂. The crude material was purified via reverse phase chromatography with the following conditions: Column: Waters Sunfire Prep C18 OBD 50×300 mm S10; Mobile Phase A: 5:95 acetonitrile:water with 10-mM ammonium acetate; Mobile Phase B: 95:5 acetonitrile:water with 10-mM ammonium acetate; Gradient 10-100% B over 30 min; flow rate=150 mL/min, λ=220 nM. The fractions containing the desired product were pooled, and evaporated to dryness to give the title compound (163 mg, 36%).

LC/MS Condition A: ret time 0.640 min; m/e=333 (M+H)+.

¹H NMR (400 MHz, CHLOROFORM-d) δ 7.57 (dd, J=8.0, 1.5 Hz, 1H), 7.37 (dd, J=7.5, 1.5 Hz, 1H), 7.13 (t, J=7.8 Hz, 1H), 3.97 (s, 2H), 3.73-3.66 (m, 4H), 2.78-2.69 (m, 2H), 2.57-2.49 (m, 2H), 2.43-2.36 (m, 4H)

Intermediate: 5-((4-chloro-5-((2'-chloro-2-methyl-3'-(((2-morpholinoethyl)amino)methyl)-[1,1'-biphenyl]-3-yl)methoxy)-2-formylphenoxy)methyl)nicotinonitrile

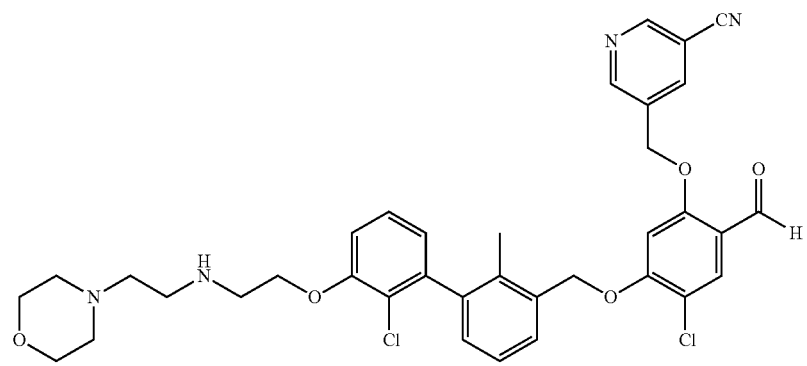 [SMILES: Cc1c(COc2cc(OCc3cncc(C#N)c3)c(C=O)cc2Cl)cccc1-c1cccc(OCCNCCN2CCOCC2)c1Cl]

To a solution of N-(3-bromo-2-chlorobenzyl)-2-morpholinoethanamine (50 mg, 0.150 mmol), and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (82 mg, 0.158 mmol) in THF (6 mL) was added potassium phosphate tribasic, 0.5M in water (750 µL, 0.375 mmol). The reaction was flushed with Ar, treated with 2$^{nd}$ generation X-Phos precatalyst (12 mg, 0.015 mmol), capped and stirred at room temp for 66 h. The reaction was charged with additional catalyst (4.5 mg, 0.006 mmol), flushed with argon, capped and heated at 45° C. for 5 h. The reaction was diluted with EtOAc (100 mL) and water (10 mL), and organic layer was extracted with brine (1×10 mL), dried over Na$_2$SO$_4$, filtered and evaporated to dryness to give the title compound that was used "as is" without purification in subsequent reactions.

LC/MS Condition A: ret time 0.940 min; m/e=645 (M+H)$^+$.

Example 2092: 5-((4-chloro-5-((2'-chloro-2-methyl-3'-(((2-morpholinoethyl)amino)methyl)-[1,1'-biphenyl]-3-yl)methoxy)-2-(((1,3-dihydroxy-2-methylpropan-2-yl)amino)methyl)phenoxy)methyl)nicotinonitrile

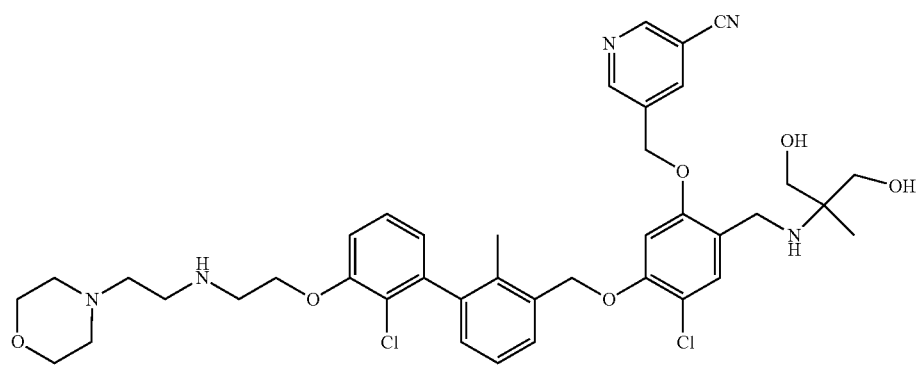 [SMILES: Cc1c(COc2cc(OCc3cncc(C#N)c3)c(CNC(C)(CO)CO)cc2Cl)cccc1-c1cccc(OCCNCCN2CCOCC2)c1Cl]

To a solution of 5-((4-chloro-5-((2'-chloro-2-methyl-3'-(((2-morpholinoethyl)amino)methyl)-[1,1'-biphenyl]-3-yl)methoxy)-2-formylphenoxy)methyl)nicotinonitrile (40 mg, 0.062 mmol) and 2-amino-2-methyl-1,3-propanediol (28 mg, 0.266 mmol) in a mixture of 1,2-dichloroethane (800 µL) and EtOH (500 µL) was added acetic acid (14 µL, 0.245 mmol) and 4 A mol sieves. The reaction was flushed with N2, capped, stirred at room temp for 30 min, then treated dropwise (over 2.5 h) with sodium cyanoborohydride, 1.0 M in THF (217 µL, 0.217 mmol) and allowed to stir at room temp for 1 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min to give the title compound (16.5 mg, 25%) as a TFA salt.

LC/MS Condition E: ret time 1.59 min; m/e=734 (M+H)$^+$.
LC/MS Condition F: ret time 1.28 min; m/e=734 (M+H)$^+$.

Intermediate: (2,4-dichloro-3-iodophenyl)methanol

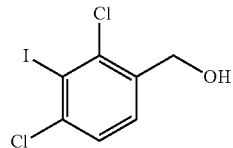

To a dry 500 mL flask under N$_2$ was added (2,4-dichlorophenyl)methanol (7.5 g, 42.4 mmol) and THF (250 mL). The reaction was capped, flushed well with Ar, treated with diisopropylamine (3 mL, 21.05 mmol) and cooled to −78° C. The reaction was then treated slowly (over 20 min) with n-butyllithium, 2.5M in hexanes (34 mL, 85 mmol). After 90 min, the reaction was quenched with a solution of iodine (12.4 g, 48.9 mmol) in THF (15 mL) at −78 C and stirred for 18 h while slowly warming to room temp. The reaction was diluted with aq Na$_2$S$_2$O$_3$ (73 g, 0.462 mmol, and treated with water (150 mL) and EtOAc (800 mL). The organic layer was extracted with water (1×50 mL), brine (1×50 mL), dried over Na$_2$SO$_4$, filtered and evaporated to dryness. The crude material was dissolved in CH$_2$Cl$_2$ (40 mL), applied to the head of a 220 g Teledyne Isco Silica Flash Column, and the column was eluted with a linear gradient from 100% CH$_2$Cl$_2$ to 25% EtOAc/CH$_2$Cl$_2$ over 10 column volumes. The fractions containing the desired product were pooled, evaporated to dryness and reapplied to the head of a 120 g Teledyne Isco Silica Flash Column. The column was eluted with a linear gradient from 100% Hexanes to 35% EtOAc/Hexanes over 15 column volumes. The fractions containing the desired product were pooled and evaporated to dryness to give the title compound (3.11 g, 24%).

$^1$H NMR (500 MHz, DMSO-d$_6$) δ 7.64-7.52 (m, 2H), 5.58 (t, J=5.6 Hz, 1H), 4.54 (d, J=5.8 Hz, 2H).

Intermediate: 5-((4-chloro-5-((2,4-dichloro-3-iodo-benzyl)oxy)-2-formylphenoxy)methyl)nicotinonitrile

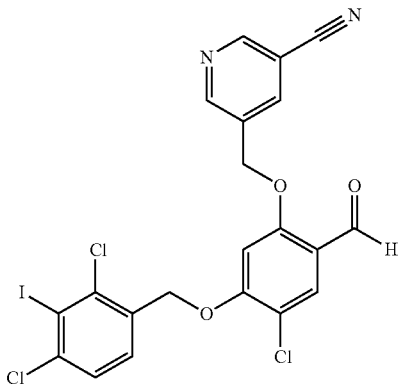 [SMILES: N#Cc1cncc(COc2cc(OCc3ccc(Cl)c(I)c3Cl)c(Cl)cc2C=O)c1]

To a dry vial under N₂ was added (2,4-dichloro-3-iodo-phenyl)methanol (150 mg, 0.495 mmol), 5-chloro-2,4-dihydroxybenzaldehyde (85 mg, 0.495 mmol), triphenylphosphine (136 mg, 0.519 mmol) and THF (2.5 mL). The reaction was flushed with argon, treated with DIAD (100 µL, 0.514 mmol), capped and stirred at room temp for 1 h. The reaction was charged with additional PPh₃ (27 mg, 0.103 mmol) and DIAD (20 µlit, 0.103 mmol), flushed with argon, capped, and stirred at room temp for 18 h. The reaction was then treated with triphenylphosphine (170 mg, 0.648 mmol), 5-(hydroxymethyl)nicotinitrile (83 mg, 0.619 mmol), TMAD (107.3 mg, 0.617 mmol), THF (4.5 mL). The mixture was flushed with N₂, capped and heated at 65° C. in an oil bath for 2 h, followed by room temp for 18 h. The reaction was filtered and the filtrate was evaporated to dryness in vacuo. The residue was applied to the head of a 40 g Teledyne Isco Silica Flash Column, and the column was eluted with a linear gradient from 100% Hexanes to 100% EtOAc over 15 column volumes. The fractions containing the desired product were pooled and evaporated to dryness to give the title compound (91.5 mg, 32%).

¹H NMR (500 MHz, CHLOROFORM-d) δ 10.31 (s, 1H), 8.93 (br d, J=6.4 Hz, 2H), 8.10 (s, 1H), 7.97 (s, 1H), 7.62 (d, J=8.4 Hz, 1H), 7.49 (d, J=8.4 Hz, 1H), 6.55 (s, 1H), 5.31 (s, 2H), 5.25 (s, 2H).

Intermediate: 5-((5-((3'-(3-bromopropoxy)-2,6-dichloro-2'-methyl-[1,1'-biphenyl]-3-yl)methoxy)-4-chloro-2-formylphenoxy)methyl)nicotinonitrile

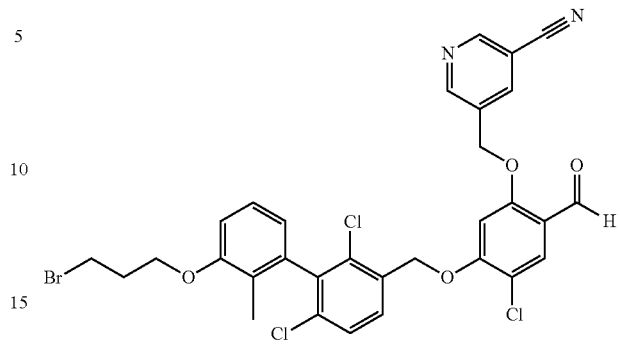

To a suspension of 5-((4-chloro-5-((2,4-dichloro-3-iodo-benzyl)oxy)-2-formylphenoxy)methyl)nicotinonitrile (90 mg, 0.157 mmol) and 2-(3-(3-bromopropoxy)-2-methylphenyl)-4,4,5,5-tetramethyl-1,3,2-dioxaborolane (61.3 mg, 0.173 mmol) in THF (6.3 mL) was added potassium phosphate tribasic, 0.5M in water (785 µL, 0.393 mmol). The reaction was flushed with argon, treated with 2$^{nd}$ Generation X-Phos precatalyst (12 mg, 0.015 mmol), flushed with argon again, capped and heated at 45° C. for 18 h. The reaction was diluted with EtOAc (100 mL) and water (10 mL), and the organic layer was extracted with brine (1×10 mL), dried over Na₂SO₄, filtered and evaporated to dryness. The residue was dissolved in CH₂Cl₂, applied to the head of a 24 g Teledyne Isco Silica Flash Column, and the column was eluted with a linear gradient from 100% hexanes to 100% EtOAc over 15 column volumes. The fractions containing the desired product were pooled and evaporatd to dryness to give the title compound (72.4 mg, 68%).

LC/MS Condition G: ret time 1.65 min; m/e=673 (M+H)⁺.

¹H NMR (500 MHz, CHLOROFORM-d) δ 10.31 (s, 1H), 8.93 (dd, J=7.6, 1.7 Hz, 2H), 8.10 (s, 1H), 7.97 (s, 1H), 7.68 (d, J=8.4 Hz, 1H), 7.53 (d, J=8.4 Hz, 1H), 7.31 (m, 1H), 6.98 (d, J=8.1 Hz, 1H), 6.73 (d, J=7.6 Hz, 1H), 6.65 (s, 1H), 5.36 (s, 2H), 5.23 (s, 2H), 4.20 (t, J=5.7 Hz, 1H), 4.14 (m, 1H), 3.67 (t, J=6.4 Hz, 1H), 3.43 (t, J=6.7 Hz, 1H), 2.40 (dt, J=19.8, 6.2 Hz, 2H), 1.95 (s, 3H).

Intermediate: 5-((5-((3'-(3-bromopropoxy)-2,6-dichloro-2'-methyl-[1,1'-biphenyl]-3-yl)methoxy)-4-chloro-2-(((1,3-dihydroxy-2-methylpropan-2-yl)amino)methyl)phenoxy)methyl)nicotinonitrile

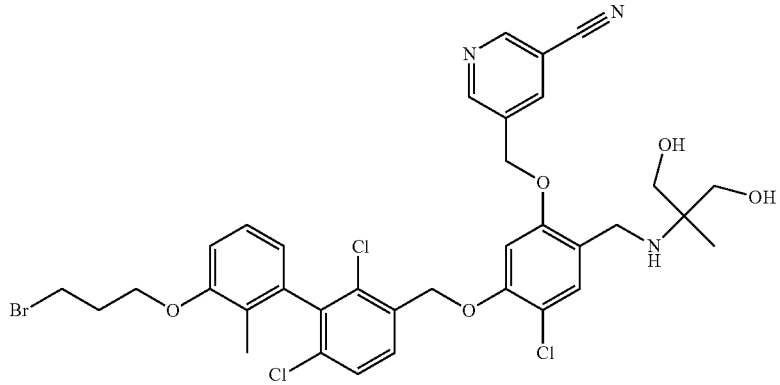 [SMILES: Cc1c(OCCCBr)cccc1-c1c(Cl)ccc(COc2cc(OCc3cncc(C#N)c3)c(CNC(C)(CO)CO)cc2Cl)c1Cl]

To a solution of 5-((5-((3'-(3-bromopropoxy)-2,6-dichloro-2'-methyl-[1,1'-biphenyl]-3-yl)methoxy)-4-chloro-2-formylphenoxy)methyl)nicotinonitrile (36.2 mg, 0.054 mmol) and 2-amino-2-methyl-1,3-propanediol (17 mg, 0.162 mmol) in a mixture of 1,2-dichloroethane (800 µL) and EtOH (500 µL) was added acetic acid (12.5 µL, 0.218 mmol) and 4 Å mol sieves (activated). The reaction was flushed briefly with N₂, capped, stirred at room temp for 35 min, then treated dropwise (over 1.5 h) with sodium cyanoborohydride, 1.0M in THF (185 µL, 0.185 mmol) and then stirred at room temp for 30 min. The solvent was removed under a gentle stream of N₂ to give the title compound that was used "as is" without further purification in subsequent reactions.

LC/MS Condition A: ret time 1.10 min; m/e=762 (M+H)⁺.

Example 2093: 5-((4-chloro-5-((2,6-dichloro-3'-(3-((R)-3-hydroxypyrrolidin-1-yl)propoxy)-2'-methyl-[1,1'-biphenyl]-3-yl)methoxy)-2-(((1,3-dihydroxy-2-methylpropan-2-yl)amino)methyl)phenoxy)methyl)nicotinonitrile µL, 0.687 mmol). The reaction was flushed briefly with N₂, capped, and heated at 65° C. for 5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to give the title compound (7.7 mg, 36%).

LC/MS Condition E: ret time 1.62 min; m/e=769 (M+H)⁺.
LC/MS Condition F: ret time 1.43 min; m/e=769 (M+H)⁺.

Example 2094: N-((3S)-1-(3-((2',6'-dichloro-3'-((2-chloro-5-((5-cyanopyridin-3-yl)methoxy)-4-(((1,3-dihydroxy-2-methylpropan-2-yl)amino)methyl)phenoxy)methyl)-2-methyl-[1,1'-biphenyl]-3-yl)oxy)propyl)pyrrolidin-3-yl)acetamide

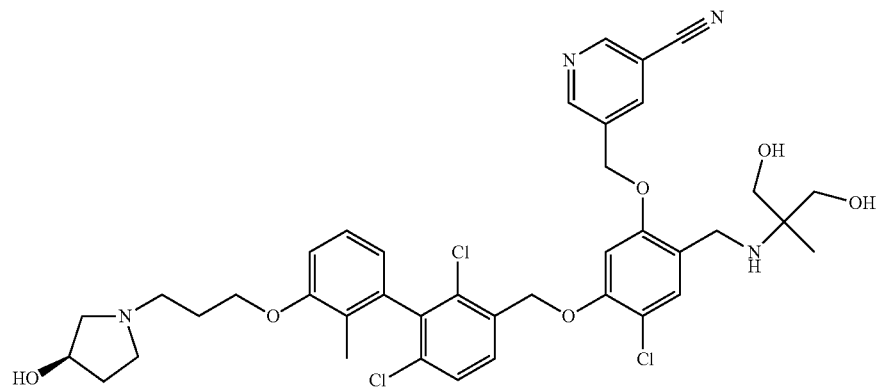 [SMILES: Cc1c(OCCCN2CC[C@@H](O)C2)cccc1-c1c(Cl)ccc(COc2cc(OCc3cncc(C#N)c3)c(CNC(C)(CO)CO)cc2Cl)c1Cl]

To a solution of 5-((5-((3'-(3-bromopropoxy)-2,6-dichloro-2'-methyl-[1,1'-biphenyl]-3-yl)methoxy)-4-chloro-2-(((1,3-dihydroxy-2-methylpropan-2-yl)amino)methyl)phenoxy)methyl)nicotinonitrile (20.63 mg, 0.027 mmol) MeOH (2 mL) was added (R)-3-hydroxypyrrolidine hydrochloride (50 mg, 0.405 mmol) and N,N-diisopropylethylamine (120

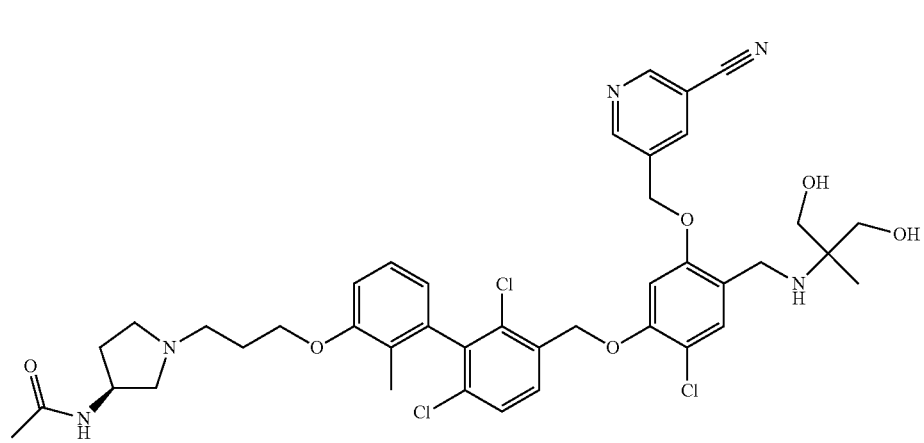 [SMILES: CC(=O)N[C@H]1CCN(CCCOc2cccc(-c3c(Cl)ccc(COc4cc(OCc5cncc(C#N)c5)c(CNC(C)(CO)CO)cc4Cl)c3Cl)c2C)C1]

To a solution of 5-((5-((3'-(3-bromopropoxy)-2,6-dichloro-2'-methyl-[1,1'-biphenyl]-3-yl)methoxy)-4-chloro-2-(((1,3-dihydroxy-2-methylpropan-2-yl)amino)methyl)phenoxy)methyl)nicotinonitrile (20.63 mg, 0.027 mmol) in MeOH (2 mL) was added (S)—N-(pyrrolidin-3-yl)acetamide hydrochloride (67 mg, 0.407 mmol) and N,N-diisopropylethylamine (120 µL, 0.687 mmol). The reaction was flushed briefly with $N_2$, capped, and heated at 65° C. for 5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to give the title compound (15.3 mg, 59%).

LC/MS Condition E: ret time 1.75 min; m/e=810 $(M+H)^+$.
LC/MS Condition F: ret time 1.41 min; m/e=810 $(M+H)^+$.

Intermediate: 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)methyl)nicotinonitrile

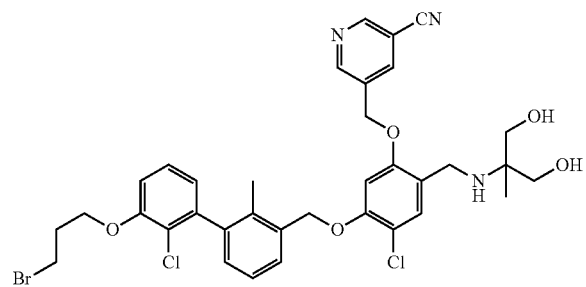 [SMILES: Cc1c(COc2cc(OCc3cncc(C#N)c3)c(CNC(C)(CO)CO)cc2Cl)cccc1-c1cccc(OCCCBr)c1Cl]

A mixture of 5-((5-((3'-(3-bromopropoxy)-2'-chloro-2-methyl-[1,1'-biphenyl]-3-yl)methoxy)-4-chloro-2-formylphenoxy)methyl)nicotinonitrile (82 mg, 0.128 mmol) and 2-amino-2-methylpropane-1,3-diol (47 mg, 0.447 mmol) in $ClCH_2CH_2Cl$ (1 mL) and ethanol (0.7 mL) was treated with acetic acid (22 µl, 0.384 mmol) and stirred under argon for 2 min. The mixture was added 4 A activated molecular sieves and stirred at rt for 50 min, and then added slowly with stirring over 3.5 h, sodium cyanoborohydride 1 M in THF (0.25 mL, 0.250 mmol). After a couple hours, the solvent was evaporated under $N_2$ stream very slowly overnight, the residue dissolved in methanol and the crude mixture was subdivided and used for the preparation of Example 2097 and other similar derivatives.

LC/MS Condition A: ret time 1.20 min; m/e=730 $(M+H)^+$.

Example 2097: (S)-5-((4-chloro-5-((2'-chloro-3'-((2,3-dihydroxypropyl)amino)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile

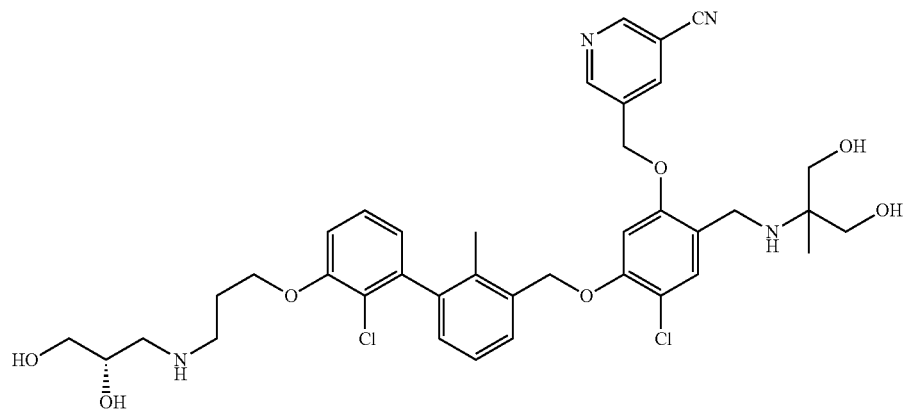 [SMILES: Cc1c(COc2cc(OCc3cncc(C#N)c3)c(CNC(C)(CO)CO)cc2Cl)cccc1-c1cccc(OCCCNC[C@H](O)CO)c1Cl]

A solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)

methyl)nicotinonitrile (23 mg, 0.032 mmol), (S)-3-aminopropane-1,2-diol (62 mg, 0.681 mmol), and Hunig's Base (30 µl, 0.172 mmol) in MeOH (1 mL) was heated at 65° C. in a sand bath shaker overnight. The material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as its TFA salt (10.7 mg, 29%).

LC/MS Condition E: ret time 1.56 min; m/e=739 (M+H)$^+$.
LC/MS Condition F: ret time 1.55 min; m/e=739 (M+H)$^+$.

Example 2098: 5-((4-chloro-5-((2'-chloro-3'-(3-(3-(hydroxymethyl)piperidin-1-yl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile

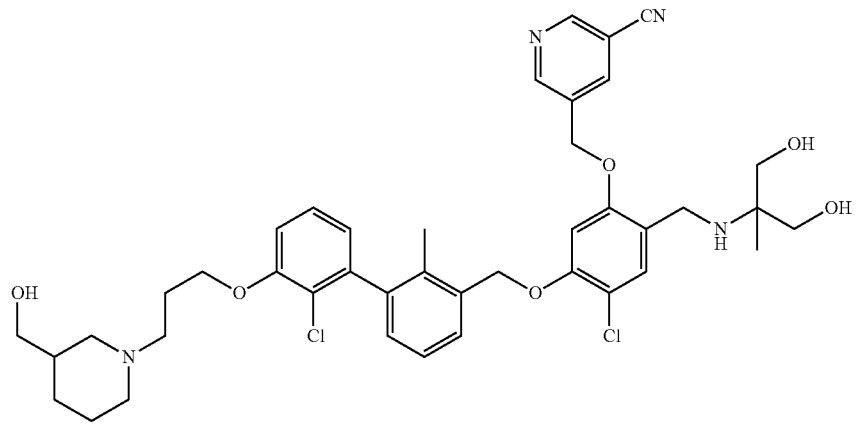 [SMILES: Cc1c(COc2cc(OCc3cncc(C#N)c3)c(CNC(C)(CO)CO)cc2Cl)cccc1-c1cccc(OCCCN2CCCC(CO)C2)c1Cl]

A solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)methyl)nicotinonitrile (23 mg, 0.032 mmol), piperidin-3-ylmethanol (64 mg, 0.556 mmol), and Hunig's Base (50 µl, 0.286 mmol) in MeOH (1 mL) was heated at 65° C. in a sand bath shaker overnight. The material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as its TFA salt (10.8 mg, 31%).

LC/MS Condition E: ret time 1.82 min; m/e=763 (M+H)$^+$.
LC/MS Condition F: ret time 1.57 min; m/e=763 (M+H)$^+$.

Example 2099: 2-((5-chloro-4-((2'-chloro-3'-(3-(3-(hydroxymethyl)piperidin-1-yl)propoxy)-2-methyl-[1,1'-biphenyl]-3-yl)methoxy)-2-((5-((3-(hydroxymethyl)piperidin-1-yl)(imino)methyl)pyridin-3-yl)methoxy)benzyl)amino)-2-methylpropane-1,3-diol

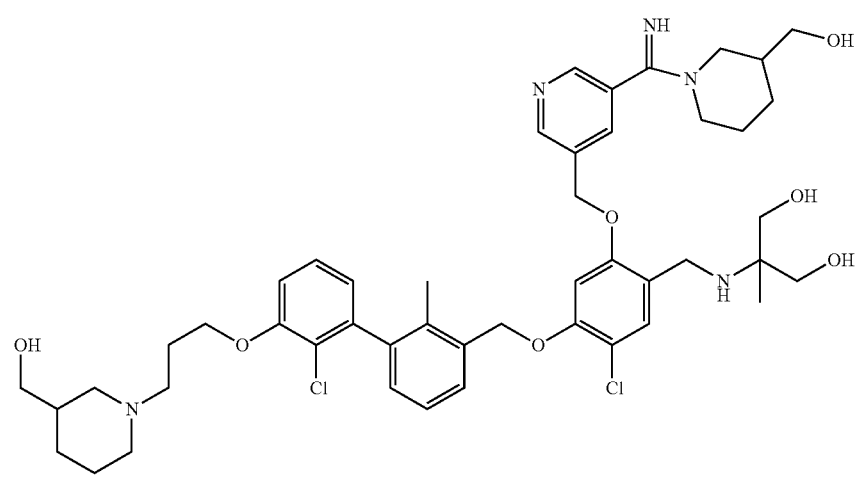 [SMILES: Cc1c(COc2cc(OCc3cncc(C(=N)N4CCCC(CO)C4)c3)c(CNC(C)(CO)CO)cc2Cl)cccc1-c1cccc(OCCCN2CCCC(CO)C2)c1Cl]

During the purification of the material of Example 2098, the pure title compound was also obtained as its TFA salt (13.1 mg, 30%).

LC/MS Condition E: ret time 1.64 min; m/e=878 (M+H)+.
LC/MS Condition F: ret time 1.39 min; m/e=878 (M+H)+.

Example 2100: 5-((4-chloro-5-((2,2'-dichloro-3'-(3-((R)-3-hydroxypyrrolidin-1-yl)propoxy)-[1,1'-biphenyl]-3-yl)methoxy)-2-((((S)-2,3-dihydroxypropyl)amino)methyl)phenoxy)methyl)nicotinonitrile

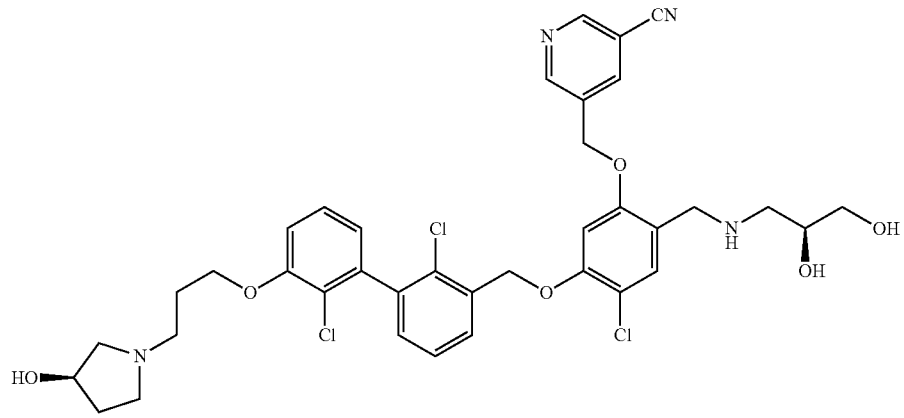 [SMILES: N#Cc1cncc(COc2cc(OCc3cccc(-c4cccc(OCCCN5CC[C@@H](O)C5)c4Cl)c3Cl)c(Cl)cc2CNC[C@H](O)CO)c1]

A solution of (S)-5-((4-chloro-5-((2,2'-dichloro-3'-(3-chloropropoxy)-[1,1'-biphenyl]-3-yl)methoxy)-2-(((2,3-dihydroxypropyl)amino)methyl)phenoxy)methyl)nicotinonitrile (25 mg, 0.036 mmol), (R)-pyrrolidin-3-ol, HCl (60 mg, 0.486 mmol), sodium iodide (2 mg, 0.013 mmol) and Hunig's Base (90 µl, 0.515 mmol) in methanol (1 mL) was heated at 65° C. in a sand bath shaker overnight. More (R)-pyrrolidin-3-ol, HCl (24 mg), Hunig's Base (50 µl), and sodium iodide (10 mg) were added and heating continued at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (5.3 mg, 18%). $^1$H NMR (500 MHz, DMSO-$d_6$) δ 9.01 (d, J=1.8 Hz, 1H), 8.97 (d, J=1.8 Hz, 1H), 8.41 (s, 1H), 7.72 (d, J=7.9 Hz, 1H), 7.50 (t, J=7.6 Hz, 1H), 7.41-7.36 (m, 2H), 7.33 (d, J=6.1 Hz, 1H), 7.21 (d, J=8.5 Hz, 1H), 7.07 (s, 1H), 6.93-6.86 (m, 1H), 5.33 (s, 2H), 5.30 (s, 2H), 4.23-4.07 (m, 4H), 3.69-3.66 (m, 2H), 2.70 (dd, J=9.6, 6.3 Hz, 1H), 2.61-2.50 (m, 6H), 2.46-2.39 (m, 2H), 2.32 (dd, J=9.5, 3.7 Hz, 1H), 2.02-1.91 (m, 3H), 1.91 (s, 6H), 1.58-1.49 (m, 1H).

LC/MS Condition E: ret time 1.63 min; m/e=741 (M+H)+.
LC/MS Condition F: ret time 1.53 min; m/e=741 (M+H)+.

Example 2101: (S)-3-((5-chloro-4-((2,2'-dichloro-3'-(3-((R)-3-hydroxypyrrolidin-1-yl)propoxy)-[1,1'-biphenyl]-3-yl)methoxy)-2-((5-(((R)-3-hydroxypyrrolidin-1-yl)(imino)methyl)pyridin-3-yl)methoxy)benzyl)amino)propane-1,2-diol

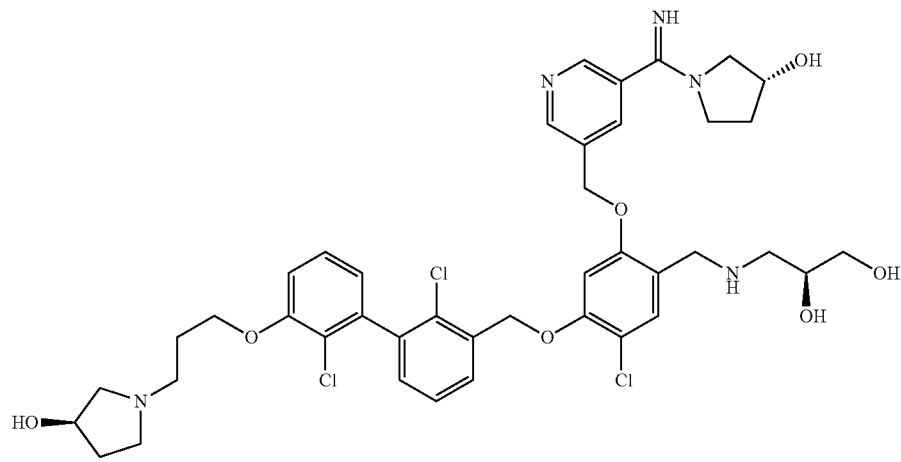 [SMILES: N=C(c1cncc(COc2cc(OCc3cccc(-c4cccc(OCCCN5CC[C@@H](O)C5)c4Cl)c3Cl)c(Cl)cc2CNC[C@H](O)CO)c1)N1CC[C@@H](O)C1]

During the purification of the material of Example 2100, the pure title compound was also obtained (2.4 mg, 7%).
LC/MS Condition E: ret time 1.41 min; m/e=828 (M+H)+.
LC/MS Condition F: ret time 1.34 min; m/e=828 (M+H)+.

Example 2102: 5-((4-chloro-5-((2'-chloro-3'-(3-((1,3-dihydroxy-2-methylpropan-2-yl)amino)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile

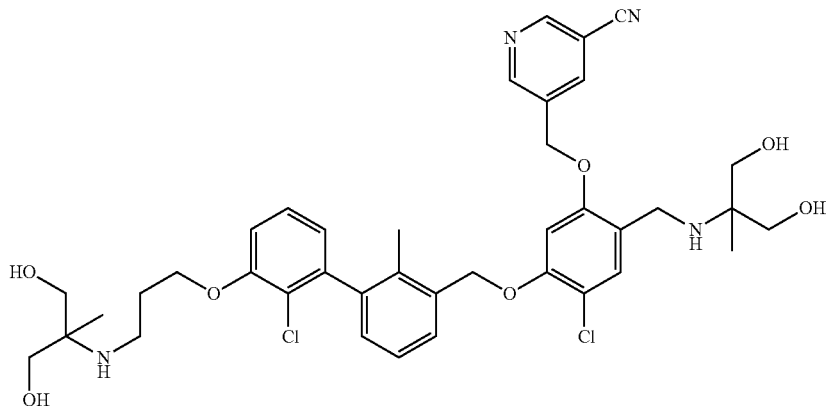 [SMILES: Cc1c(COc2cc(OCc3cncc(C#N)c3)c(CNC(C)(CO)CO)cc2Cl)cccc1-c1cccc(OCCCNC(C)(CO)CO)c1Cl]

A solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)methyl)nicotinonitrile (23 mg, 0.032 mmol), 2-amino-2-methylpropane-1,3-diol (63.6 mg, 0.605 mmol), and Hunig's Base (50 µl, 0.286 mmol) in MeOH (1 mL) was heated at 65° C. in a sand bath shaker for 24 h. The material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as its TFA salt (8.0 mg, 23%).
LC/MS Condition E: ret time 1.63 min; m/e=753 (M+H)+.
LC/MS Condition F: ret time 1.54 min; m/e=753 (M+H)+.

Example 2103: 5-((4-chloro-5-((2,2'-dichloro-3'-(3-(((S)-2,3-dihydroxypropyl)amino)propoxy)-[1,1'-biphenyl]-3-yl)methoxy)-2-((((S)-2,3-dihydroxypropyl)amino)methyl)phenoxy)methyl)nicotinonitrile

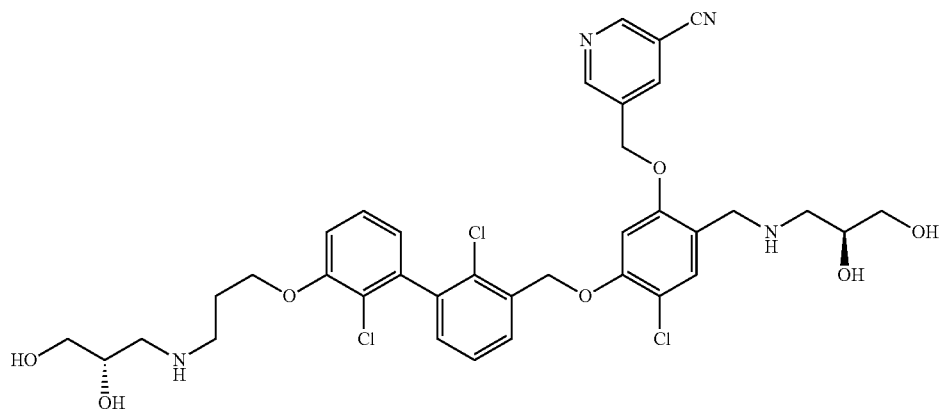 [SMILES: N#Cc1cncc(COc2cc(OCc3cccc(-c4cccc(OCCCNC[C@H](O)CO)c4Cl)c3Cl)c(Cl)cc2CNC[C@H](O)CO)c1]

A solution of (S)-5-((4-chloro-5-((2,2'-dichloro-3'-(3-chloropropoxy)-[1,1'-biphenyl]-3-yl)methoxy)-2-(((2,3-dihydroxypropyl)amino)methyl)phenoxy)methyl)nicotinonitrile (25 mg, 0.036 mmol), (S)-3-aminopropane-1,2-diol (55 mg, 0.604 mmol), sodium iodide (12 mg), and Hunig's Base (40 µl, 0.229 mmol) in MeOH (1 mL) was heated 65° C. in a sand bath shaker for 48 h. The material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as its TFA salt (1.7 µmg, 4%).

LC/MS Condition E: ret time 1.56 min; m/e=745 (M+H)+.
LC/MS Condition F: ret time 1.50 min; m/e=745 (M+H)+.

Example 2104: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min, to give the pure title compound as its TFA salt (15.0 mg, 43%).

LC/MS Condition E: ret time 1.74 min; m/e=735 (M+H)+.

LC/MS Condition F: ret time 1.54 min; m/e=735 (M+H)+

Example 2105: 2-((5-chloro-4-((2'-chloro-3'-(3-((R)-3-hydroxypyrrolidin-1-yl)propoxy)-2-methyl-[1,1'-biphenyl]-3-yl)methoxy)-2-((5-(((R)-3-hydroxypyrrolidin-1-yl)(imino)methyl)pyridin-3-yl)methoxy)benzyl)amino)-2-methylpropane-1,3-diol

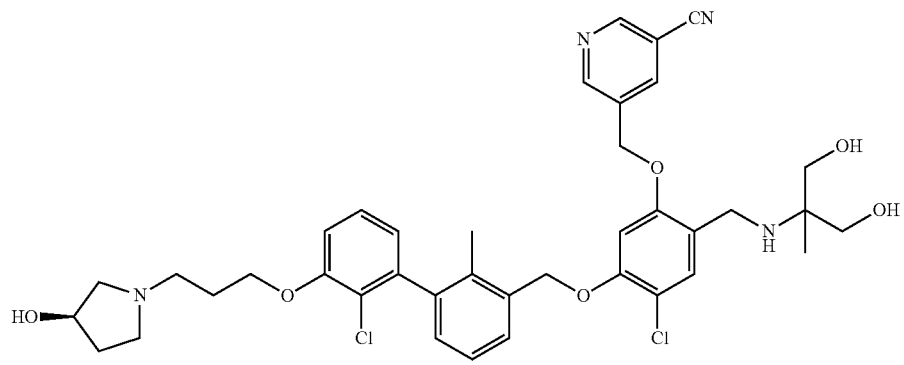 [SMILES: Cc1c(COc2cc(OCc3cncc(C#N)c3)c(CNC(C)(CO)CO)cc2Cl)cccc1-c1cccc(OCCCN2CC[C@@H](O)C2)c1Cl]

A solution of 5-((5-((3'-(3-bromopropoxy)-2'-chloro-2-methyl-[1,1'-biphenyl]-3-yl)methoxy)-4-chloro-2-(((1,3-dihydroxy-2-methylpropan-2-yl)amino)methyl)phenoxy)methyl)nicotinonitrile (23 mg, 0.032 mmol), (R)-pyrrolidin-3-ol (50 mg, 0.574 mmol), and Hunig's Base (90 µl, 0.515 mmol) in MeOH (1 mL) was heated at 65° C. in a sand bath shaker overnight. The material was purified via preparative

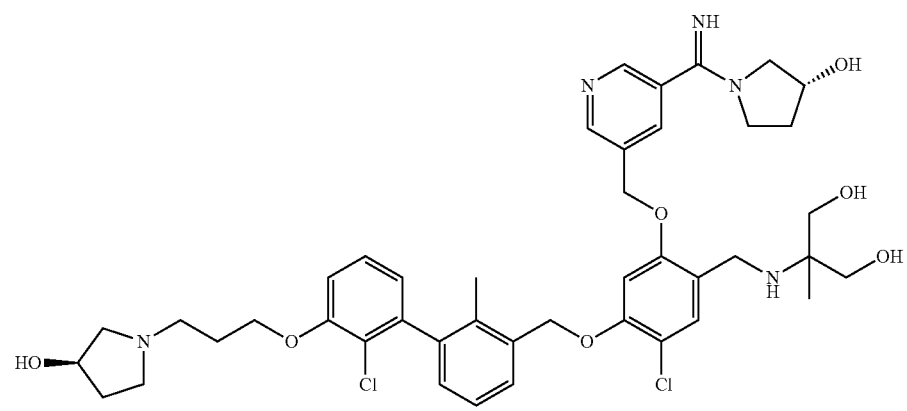 [SMILES: Cc1c(COc2cc(OCc3cncc(C(=N)N4CC[C@@H](O)C4)c3)c(CNC(C)(CO)CO)cc2Cl)cccc1-c1cccc(OCCCN2CC[C@@H](O)C2)c1Cl]

During the purification of the material of Example 2104, the pure title compound was also obtained (6.9 mg, 17%).

LC/MS Condition E: ret time 1.50 min; m/e=822 (M+H)+.
LC/MS Condition F: ret time 1.34 min; m/e=822 (M+H)+.

Example 2106: (S)-1-(5-chloro-2-((5-cyanopyridin-3-yl)methoxy)-4-((2,2'-dichloro-3'-(3-((R)-3-hydroxypyrrolidin-1-yl)propoxy)-[1,1'-biphenyl]-3-yl)methoxy)benzyl)piperidine-2-carboxylic Acid

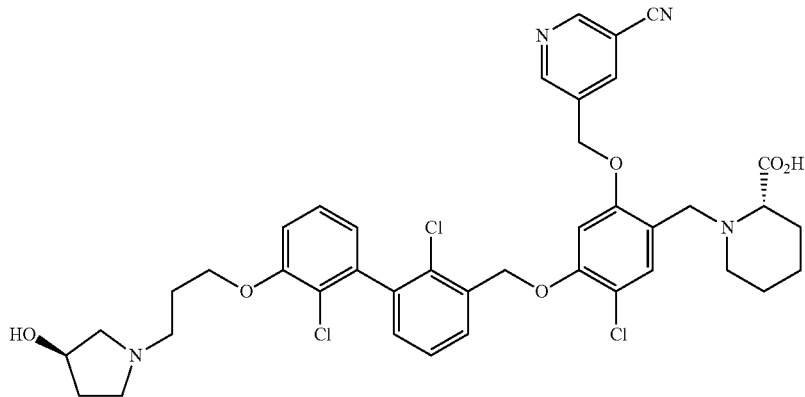 [SMILES: N#Cc1cncc(COc2cc(OCc3cccc(-c4cccc(OCCCN5CC[C@@H](O)C5)c4Cl)c3Cl)c(Cl)cc2CN2CCCC[C@H]2C(=O)O)c1]

A solution of (S)-1-(5-chloro-2-((5-cyanopyridin-3-yl)methoxy)-4-((2,2'-dichloro-3'-(3-iodopropoxy)-[1,1'-biphenyl]-3-yl)methoxy)benzyl)piperidine-2-carboxylic acid (37 mg, 0.045 mmol), (R)-pyrrolidin-3-ol, HCl (58 mg, 0.469 mmol), and Hunig's Base (90 µl, 0.515 mmol) in methanol (1 mL) was heated at 65° C. in a sand bath shaker for 3.5 h and then at 45° C. overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (10.3 mg, 27%).

LC/MS Condition E: ret time 1.97 min; m/e=779 (M+H)+.
LC/MS Condition F: ret time 2.18 min; m/e=779 (M+H)+.

Intermediate: 4-((3'-(3-bromopropoxy)-2,2'-dichloro-[1,1'-biphenyl]-3-yl)methoxy)-5-chloro-2-(3,3,3-trifluoropropoxy)benzaldehyde

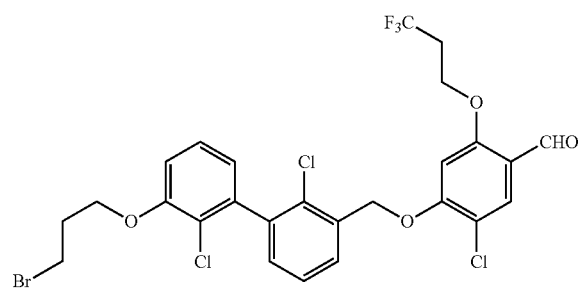 [SMILES: O=Cc1cc(Cl)c(OCc2cccc(-c3cccc(OCCCBr)c3Cl)c2Cl)cc1OCCC(F)(F)F]

A mixture of 4-((3'-(3-bromopropoxy)-2,2'-dichloro-[1,1'-biphenyl]-3-yl)methoxy)-5-chloro-2-hydroxybenzaldehyde (44 mg, 0.081 mmol) and cesium carbonate (102 mg, 0.313 mmol) was treated with dry DMF (0.5 mL) under argon flush. The yellow solution immediately resulted was stirred at rt for 2-3 min and added neat 3,3,3-trifluoropropyl trifluoromethanesulfonate (60 µL, 0.434 mmol). The mixture was stirred at rt for 2.5 h and then evaporated under N₂ overnight. The residue was added 3 mL 1,2-dichloroethane, filtered through a 0.45 uM frit, and the resulting product, 4-((3'-(3-bromopropoxy)-2,2'-dichloro-[1,1'-biphenyl]-3-yl)methoxy)-5-chloro-2-(3,3,3-trifluoropropoxy)benzaldehyde, was used directly in the following reaction.

LC/MS Condition A: ret time 1.64 min; m/e=641 (M+H)+.

Intermediate: 2-((4-((3'-(3-bromopropoxy)-2,2'-dichloro-[1,1'-biphenyl]-3-yl)methoxy)-5-chloro-2-(3,3,3-trifluoropropoxy)benzyl)amino)-2-methylpropane-1,3-diol

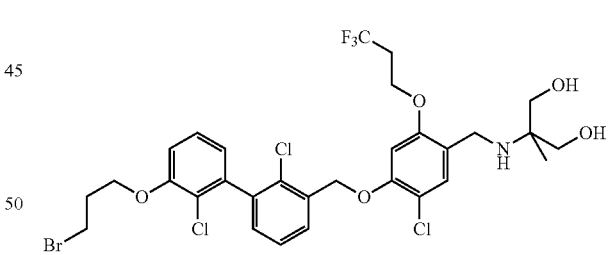

A mixture of 4-((3'-(3-bromopropoxy)-2,2'-dichloro-[1,1'-biphenyl]-3-yl)methoxy)-5-chloro-2-(3,3,3-trifluoropropoxy)benzaldehyde (50 mg, 0.078 mmol) and 2-amino-2-methylpropane-1,3-diol (25 mg, 0.238 mmol) in CH₂Cl₂ (1.5 mL) and ethanol (1 mL) was treated under argon flush with acetic acid (14 µl, 0.245 mmol), added three 4 A mol sieves and stirred in a sealed vial under argon at rt for 30 min. Then slowly with stirring over 2.5 h, the mixture was added sodium cyanotrihydroborate 1M in THF (0.2 mL, 0.200 mmol). The solvent was evaporated under a N₂ stream and the residue used directly in Example 2107.

LC/MS Condition A: ret time 1.26 min; m/e=730 (M+H)+.

Example 2107: (R)-2-((5-chloro-4-((2,2'-dichloro-3'-(3-(3-hydroxypyrrolidin-1-yl)propoxy)-[1,1'-biphenyl]-3-yl)methoxy)-2-(3,3,3-trifluoropropoxy)benzyl)amino)-2-methylpropane-1,3-diol

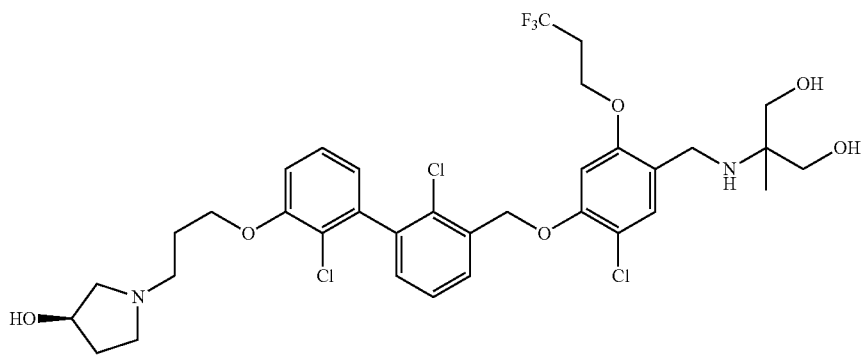 [SMILES: CC(CO)(CO)NCc1cc(Cl)c(OCc2cccc(-c3cccc(OCCCN4CC[C@@H](O)C4)c3Cl)c2Cl)cc1OCCC(F)(F)F]

A solution of 2-((4-((3'-(3-bromopropoxy)-2,2'-dichloro-[1,1'-biphenyl]-3-yl)methoxy)-5-chloro-2-(3,3,3-trifluoropropoxy)benzyl)amino)-2-methylpropane-1,3-diol (57 mg, 0.078 mmol), (R)-pyrrolidin-3-ol, HCl (163 mg, 1.319 mmol), and Hunig's Base (260 µl, 1.489 mmol) in methanol (3 mL) was heated at 65° C. in an oil for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (24.6 mg, 39%).

LC/MS Condition E: ret time 1.55 min; m/e=735 (M+H)⁺.
LC/MS Condition F: ret time 1.56 min; m/e=735 (M+H)⁺.

Example 2108: (R)-2-((5-chloro-4-((2,2'-dichloro-3'-(3-(3-hydroxypyrrolidin-1-yl)propoxy)-[1,1'-biphenyl]-3-yl)methoxy)-2-(2-(dimethylamino)ethoxy)benzyl)amino)-2-methylpropane-1,3-diol 2-((4-((3'-(3-bromopropoxy)-2,2'-dichloro-[1,1'-biphenyl]-3-yl)methoxy)-5-chloro-2-(2-(dimethylamino)ethoxy)benzyl)amino)-2-methylpropane-1,3-diol (50 mg, 0.071 mmol) was made in a similar fashion as described above for transforming 4-((3'-(3-bromopropoxy)-2,2'-dichloro-[1,1'-biphenyl]-3-yl)methoxy)-5-chloro-2-(3,3,3-trifluoropropoxy)benzaldehyde into 2-((4-((3'-(3-bromopropoxy)-2,2'-dichloro-[1,1'-biphenyl]-3-yl)methoxy)-5-chloro-2-(3,3,3-trifluoropropoxy)benzyl)amino)-2-methylpropane-1,3-diol. The 2-(dimethylamino)ethoxy starting material was treated with (R)-pyrrolidin-3-ol, HCl (162 mg, 1.311 mmol) and Hunig's Base (250 µl, 1.431 mmol) in methanol (3 mL), and heated at 65° C. overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (1.3 mg, 2.5%).

LC/MS Condition E: ret time 1.36 min; m/e=710 (M+H)⁺.
LC/MS Condition F: ret time 1.21 min; m/e=710 (M+H)⁺.

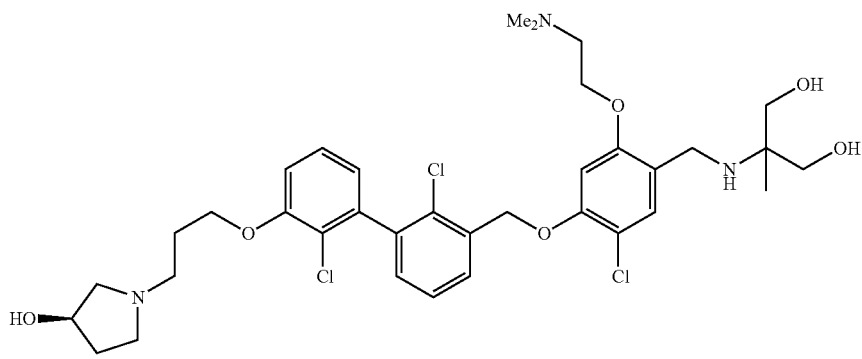 [SMILES: CN(C)CCOc1cc(OCc2cccc(-c3cccc(OCCCN4CC[C@@H](O)C4)c3Cl)c2Cl)c(Cl)cc1CNC(C)(CO)CO]

Example 2109: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dimethoxypropan-2-yl)amino)methyl)phenoxy)methyl)nicotinonitrile

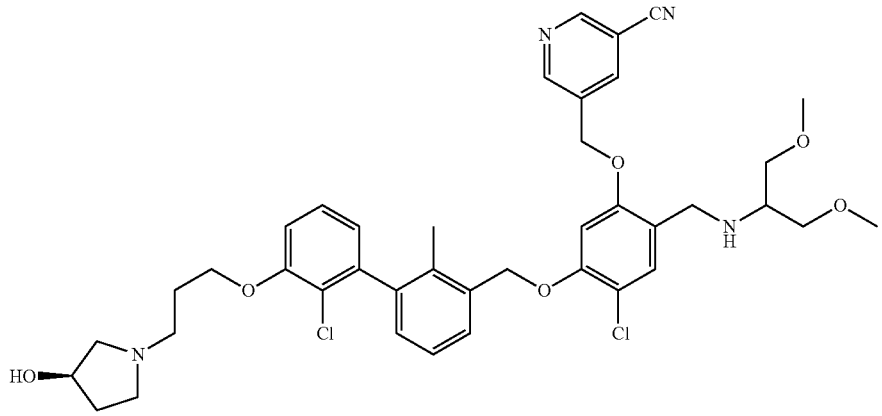 [SMILES: COCC(COC)NCc1cc(Cl)c(OCc2cccc(-c3cccc(OCCCN4CC[C@@H](O)C4)c3Cl)c2C)cc1OCc1cncc(C#N)c1]

5-((5-((3'-(3-bromopropoxy)-2'-chloro-2-methyl-[1,1'-biphenyl]-3-yl)methoxy)-4-chloro-2-(((1,3-dimethoxypropan-2-yl)amino)methyl)phenoxy)methyl)nicotinonitrile (30 mg, 0.040 mmol) was made in a similar fashion as described above for 2-((4-((3'-(3-bromopropoxy)-2,2'-dichloro-[1,1'-biphenyl]-3-yl)methoxy)-5-chloro-2-(3,3,3-trifluoropropoxy)benzyl)amino)-2-methylpropane-1,3-diol and was treated with (R)-pyrrolidin-3-ol, HCl (70 mg, 0.566 mmol) and Hunig's Base (100 μl, 0.573 mmol) in methanol (1 mL) and heated at 65° C. overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound 8.4 mg, 28%).

LC/MS Condition E: ret time 2.00 min; m/e=749 (M+H)$^+$.
LC/MS Condition F: ret time 1.55 min; m/e=749 (M+H)$^+$.

Example 2110: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((3-(hydroxymethyl)oxetan-3-yl)amino)methyl)phenoxy)methyl)nicotinonitrile

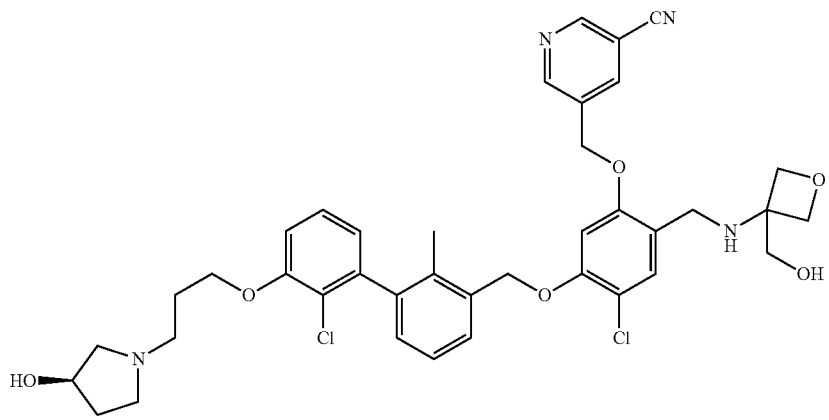 [SMILES: Cc1c(COc2cc(OCc3cncc(C#N)c3)c(CNC3(CO)COC3)cc2Cl)cccc1-c1cccc(OCCCN2CC[C@@H](O)C2)c1Cl]

5-((5-((3'-(3-bromopropoxy)-2'-chloro-2-methyl-[1,1'-biphenyl]-3-yl)methoxy)-4-chloro-2-(((3-(hydroxymethyl)oxetan-3-yl)amino)methyl)phenoxy)methyl)nicotinonitrile (30 mg, 0.041 mmol) was made in a similar fashion using the protocol described above from 5-((5-((3'-(3-bromopropoxy)-2'-chloro-2-methyl-[1,1'-biphenyl]-3-yl)methoxy)-4-chloro-2-formylphenoxy)methyl)nicotinonitrile (27 mg, 0.042 mmol) and was treated with (R)-pyrrolidin-3-ol, HCl (70 mg, 0.566 mmol), and Hunig's Base (100 μl, 0.573 mmol) in methanol (1 mL), and the mixture heated at 65° C. for 6 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound 16.3 mg, 52%).

LC/MS Condition E: ret time 1.75 min; m/e=733 (M+H)$^+$.
LC/MS Condition F: ret time 1.41 min; m/e=733 (M+H)$^+$.

Intermediate: 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile

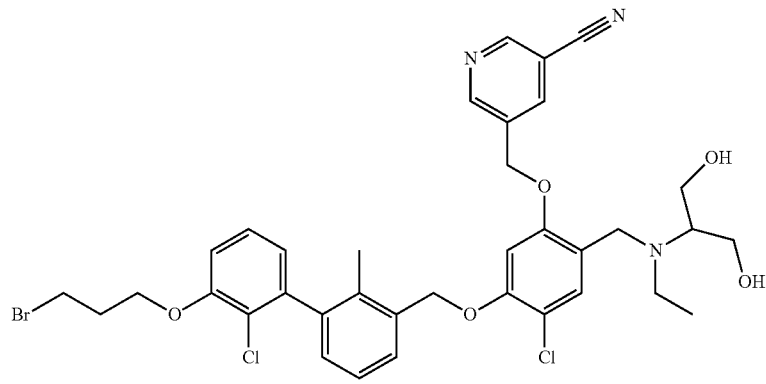 [SMILES: CCN(Cc1cc(Cl)c(OCc2cccc(-c3cccc(OCCCBr)c3Cl)c2C)cc1OCc1cncc(C#N)c1)C(CO)CO]

A solution of 5-((5-((3'-(3-bromopropoxy)-2'-chloro-2-methyl-[1,1'-biphenyl]-3-yl)methoxy)-4-chloro-2-(((1,3-dihydroxypropan-2-yl)amino)methyl)phenoxy)methyl)nicotinonitrile (22.3 mg, 0.031 mmol) in methanol (1 ml) was treated with iodoethane (20 μl, 0.247 mmol) and Hunig's base (30 μl, 0.172 mmol) and heated at 65° C. overnight. More amounts of iodoethane (20 μl) and Hunig's base (40 μl) was added and the reaction was kept at 65 μl for 5 h. The solvent was evaporated and the crude product, 5-((5-((3'-(3-bromopropoxy)-2'-chloro-2-methyl-[1,1'-biphenyl]-3-yl)methoxy)-4-chloro-2-(((1,3-dihydroxypropan-2-yl)(ethyl)amino)methyl)phenoxy)methyl)nicotinonitrile, was used directly as described below in Example 2111.

LC/MS Condition A: ret time 1.22 min; m/e=744 (M+H)$^+$.

Example 2111: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxypropan-2-yl)(ethyl)amino)methyl)phenoxy)methyl)nicotinonitrile

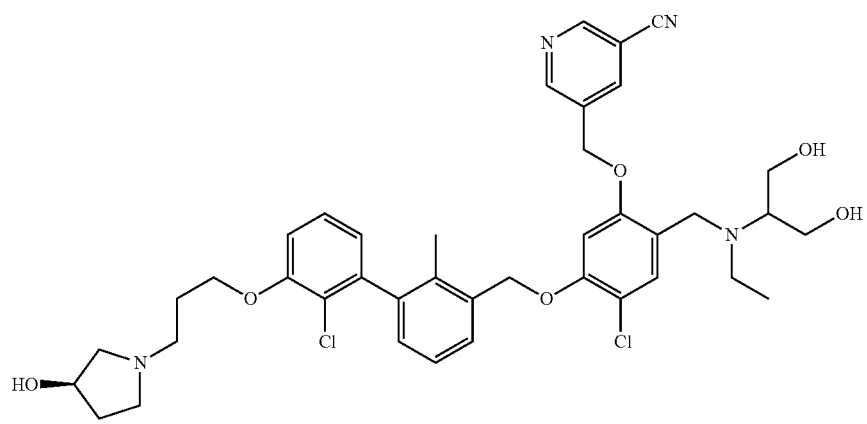 [SMILES: CCN(Cc1cc(Cl)c(OCc2cccc(-c3cccc(OCCCN4CC[C@@H](O)C4)c3Cl)c2C)cc1OCc1cncc(C#N)c1)C(CO)CO]

Using the procedure described in Example 2035, 5-((5-((3'-(3-bromopropoxy)-2'-chloro-2-methyl-[1,1'-biphenyl]-3-yl)methoxy)-4-chloro-2-(((1,3-dihydroxypropan-2-yl)(ethyl)amino)methyl)phenoxy)methyl)nicotinonitrile (22 mg, 0.030 mmol) was transformed into the crude title compound which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound 5.0 mg, 22%).

LC/MS Condition E: ret time 1.78 min; m/e=749 (M+H)$^+$.
LC/MS Condition F: ret time 1.46 min; m/e=749 (M+H)$^+$.

Intermediate: 4-((3'-(3-bromopropoxy)-2,2'-dichloro-[1,1'-biphenyl]-3-yl)methoxy)-5-chloro-2-((2,5-dichlorobenzyl)oxy)benzaldehyde

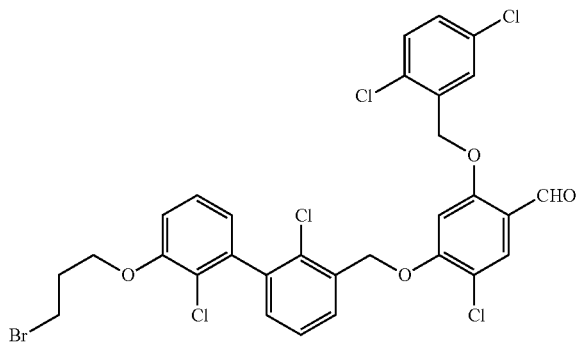 [SMILES: O=Cc1cc(Cl)c(OCc2cccc(-c3cccc(OCCCBr)c3Cl)c2Cl)cc1OCc1cc(Cl)ccc1Cl]

A mixture of 4-((3'-(3-bromopropoxy)-2,2'-dichloro-[1,1'-biphenyl]-3-yl)methoxy)-5-chloro-2-hydroxybenzaldehyde (30.8 mg, 0.057 mmol), 2-(bromomethyl)-1,4-dichlorobenzene (20 mg, 0.083 mmol), and cesium carbonate (84 mg, 0.258 mmol) was treated with dry DMF (0.5 mL) under argon flush. The yellow solution immediately resulted was stirred at rt for 30 min and then evaporated under N$_2$ overnight. Dichloroethane (3 mL) was added to the mixture which was then filtered. The filtrate was evaporated by about ½ volume under a stream N$_2$ and then the crude product was used directly as describe below.

LC/MS Condition A: ret time 1.83 min; m/e=703 (M+H)$^+$.

Intermediate: 2-((4-((3'-(3-bromopropoxy)-2,2'-dichloro-[1,1'-biphenyl]-3-yl)methoxy)-5-chloro-2-((2,5-dichlorobenzyl)oxy)benzyl)amino)-2-methylpropane-1,3-diol

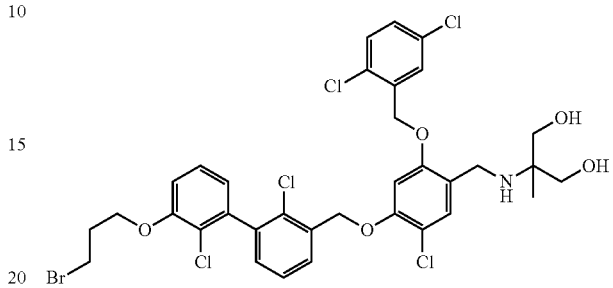

A mixture of 4-((3'-(3-bromopropoxy)-2,2'-dichloro-[1,1'-biphenyl]-3-yl)methoxy)-5-chloro-2-((2,5-dichlorobenzyl)oxy)benzaldehyde (39 mg, 0.055 mmol) and 2-amino-2-methylpropane-1,3-diol (22 mg, 0.209 mmol) in CH$_2$Cl$_2$ (1.5 mL) and ethanol (1 mL) was treated under argon flush with acetic acid (8 μl, 0.140 mmol), added three 4 A mol sieves, and stirred under argon at rt for 55 min. Sodium cyanotrihydroborate 1M in THF (0.12 mL, 0.120 mmol) was added slowly over 1 h via syringe to the mixture under stirring. The mixture was stirred for 1 h and the solvent was evaporated under a stream of N$_2$ overnight. The crude 2-((4-((3'-(3-bromopropoxy)-2,2'-dichloro-[1,1'-biphenyl]-3-yl)methoxy)-5-chloro-2-((2,5-dichlorobenzyl)oxy)benzyl)amino)-2-methylpropane-1,3-diol was used directly in Example 2112

LC/MS Condition A: ret time 1.35 min; m/e=792 (M+H)$^+$.

Example 2112: (R)-2-((5-chloro-4-((2,2'-dichloro-3'-(3-(3-hydroxypyrrolidin-1-yl)propoxy)-[1,1'-biphenyl]-3-yl)methoxy)-2-((2,5-dichlorobenzyl)oxy)benzyl)amino)-2-methylpropane-1,3-diol

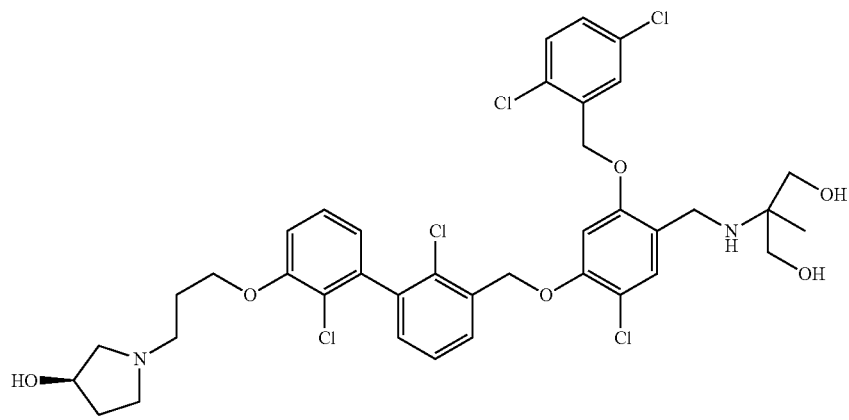 [SMILES: CC(CO)(CO)NCc1cc(Cl)c(OCc2cccc(-c3cccc(OCCCN4CC[C@@H](O)C4)c3Cl)c2Cl)cc1OCc1cc(Cl)ccc1Cl]

Using the procedure described in Example 2035, 2-((4-((3'-(3-bromopropoxy)-2,2'-dichloro-[1,1'-biphenyl]-3-yl)methoxy)-5-chloro-2-((2,5-dichlorobenzyl)oxy)benzyl)amino)-2-methylpropane-1,3-diol (43 mg, 0.054 mmol) was transformed into the crude title compound which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (18.3 mg, 42%).

LC/MS Condition E: ret time 1.97 min; m/e=797 (M+H)$^+$.
LC/MS Condition F: ret time 1.67 min; m/e=797 (M+H)$^+$.

Intermediate: 5-((5-((3'-(3-bromopropoxy)-2'-chloro-2-methyl-[1,1'-biphenyl]-3-yl)methoxy)-4-chloro-2-(((cyclopropylmethyl)(1,3-dihydroxypropan-2-yl)amino)methyl)phenoxy)methyl)nicotinonitrile

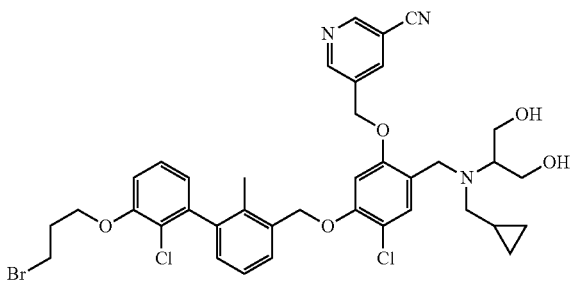 [SMILES: Cc1c(COc2cc(OCc3cncc(C#N)c3)c(CN(CC3CC3)C(CO)CO)cc2Cl)cccc1-c1cccc(OCCCBr)c1Cl]

A mixture of 5-((5-((3'-(3-bromopropoxy)-2'-chloro-2-methyl-[1,1'-biphenyl]-3-yl)methoxy)-4-chloro-2-formylphenoxy)methyl)nicotinonitrile (26.1 mg, 0.041 mmol) and 2-aminopropane-1,3-diol (13.2 mg, 0.145 mmol) in 1,2-dichloroethane (1.5 mL) and ethanol (1 mL) was treated with acetic acid (7 μl, 0.122 mmol) and stirred under argon for 2 min. Three 4 Å activated molecular sieves were added and the mixture stirred at rt for 20 min. Then sodium cyanotrihydroborate 1M in THF (0.09 mL, 0.090 mmol) was added slowly over 30 min via syringe to the mixture under stirring. The mixture was stirred for 1 h and cyclopropanecarbaldehyde (35 μl, 0.468 mmol) was then added. The mixture was stirred for another 5 min, then slowly added more sodium cyanoborohydride 1 M in THF (0.20 mL) over 1 h. The solvent was evaporated under a stream of N$_2$ overnight. The crude 5-((5-((3'-(3-bromopropoxy)-2'-chloro-2-methyl-[1,1'-biphenyl]-3-yl)methoxy)-4-chloro-2-(((cyclopropylmethyl)(1,3-dihydroxypropan-2-yl)amino)methyl)phenoxy)methyl)nicotinonitrile was used directly in Example 2113

LC/MS Condition A: ret time 1.63 min; m/e=770 (M+H)$^+$.

Example 2113: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((cyclopropylmethyl)(1,3-dihydroxypropan-2-yl)amino)methyl)phenoxy)methyl)nicotinonitrile

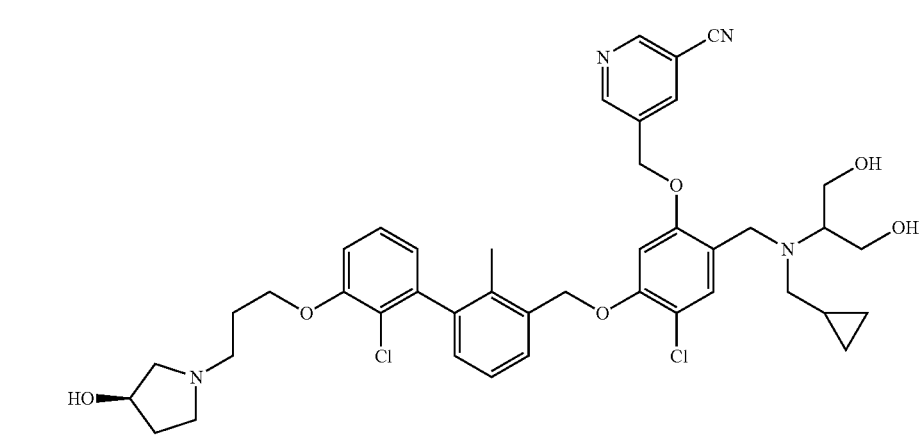 [SMILES: Cc1c(COc2cc(OCc3cncc(C#N)c3)c(CN(CC3CC3)C(CO)CO)cc2Cl)cccc1-c1cccc(OCCCN2CC[C@@H](O)C2)c1Cl]

Using the procedure described in Example 2035, 5-((5-((3'-(3-bromopropoxy)-2'-chloro-2-methyl-[1,1'-biphenyl]-3-yl)methoxy)-4-chloro-2-(((cyclopropylmethyl)(1,3-dihydroxypropan-2-yl)amino)methyl)phenoxy)methyl)nicotinonitrile (30 mg, 0.039 mmol) was transformed into the crude title compound which was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (15.4 mg, 51%).

LC/MS Condition E: ret time 1.73 min; m/e=775 (M+H)$^+$.
LC/MS Condition F: ret time 1.42 min; m/e=775 (M+H)$^+$.

Example 2114: (R)-5-((4-chloro-5-((2'-chloro-3'-(3-(3-hydroxypyrrolidin-1-yl)propoxy)-2-methyl-[1,1'-biphenyl]-3-yl)methoxy)-2-(((cyclopropylmethyl)(1,3-dihydroxy-2-methylpropan-2-yl)amino)methyl)phenoxy)methyl)nicotinonitrile

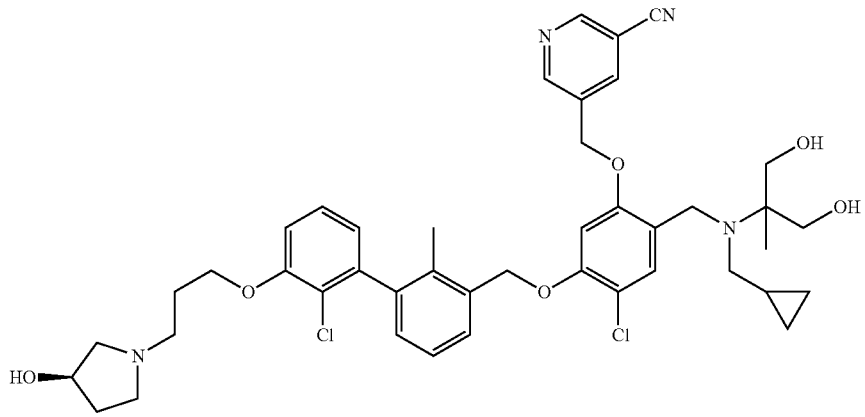 [SMILES: Cc1c(COc2cc(OCc3cncc(C#N)c3)c(CN(CC3CC3)C(C)(CO)CO)cc2Cl)cccc1-c1cccc(OCCCN2CC[C@@H](O)C2)c1Cl]

The same tandem double reductive amination and alkylation method used for the preparation of the compound in Example 2113 was used to convert 5-((5-((3'-(3-bromopropoxy)-2'-chloro-2-methyl-[1,1'-biphenyl]-3-yl)methoxy)-4-chloro-2-formylphenoxy)methyl)nicotinonitrile (26.1 mg, 0.041 mmol) into the desired title compound. Following purification by the same method as used in Example 2113, the pure title compound was obtained (7.0 mg, 22%).

LC/MS Condition E: ret time 1.64 min; m/e=789 (M+H)$^+$.
LC/MS Condition F: ret time 1.50 min; m/e=789 (M+H)$^+$.

Example 2115: 5-((4-chloro-5-((2'-chloro-3'-(3-((R)-3-hydroxypyrrolidin-1-yl)propoxy)-2-methyl-[1,1'-biphenyl]-3-yl)methoxy)-2-(((R)-3-(hydroxymethyl)morpholino)methyl)phenoxy)methyl)nicotinonitrile

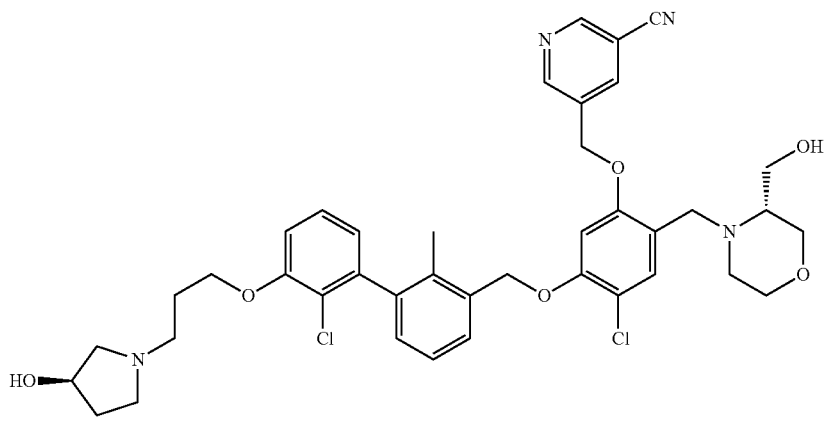 [SMILES: Cc1c(COc2cc(OCc3cncc(C#N)c3)c(CN3CCOC[C@H]3CO)cc2Cl)cccc1-c1cccc(OCCCN2CC[C@@H](O)C2)c1Cl]

The same reductive amination and alkylation method used for the preparation of the compound in Example 2113 was used to convert 5-((5-((3'-(3-bromopropoxy)-2'-chloro-2-methyl-[1,1'-biphenyl]-3-yl)methoxy)-4-chloro-2-formylphenoxy)methyl)nicotinonitrile (27 mg, 0.042 mmol) into the desired title compound. Following purification via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 15 minutes, then a 5-minute hold at 100% B; Flow: 20 mL/min the pure title compound was obtained as a TFA salt (0.9 mg, 2%).

LC/MS Condition E: ret time 1.72 min; m/e=747 (M+H)$^+$.
LC/MS Condition F: ret time 1.44 min; m/e=747 (M+H)$^+$.

Example 2116: (S)-5-((4-chloro-5-((2'-chloro-3'-(3-hydroxypropoxy)-2-methyl-[1,1'-biphenyl]-3-yl)methoxy)-2-(((2,3-dihydroxypropyl)amino)methyl)phenoxy)methyl)nicotinonitrile

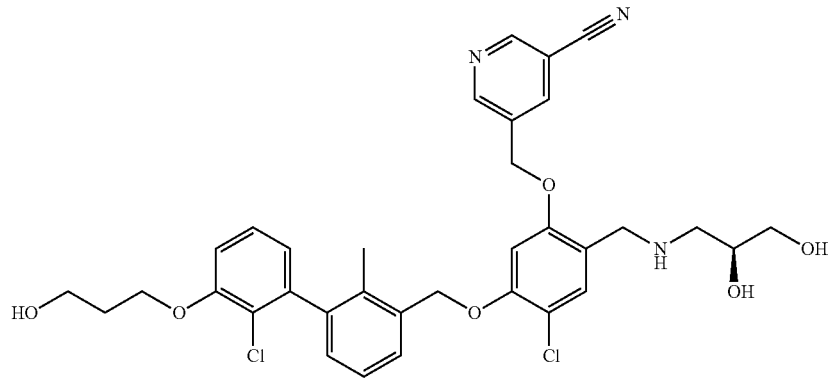

A solution of (S)-5-((5-((3'-(3-bromopropoxy)-2'-chloro-2-methyl-[1,1'-biphenyl]-3-yl)methoxy)-4-chloro-2-(((2,3-dihydroxypropyl)amino)methyl)phenoxy)methyl)nicotinonitrile (16.7 mg, 0.023 mmol) in methanol was evaporated to dryness under $N_2$, then added solid potassium acetate (70 mg, 0.713 mmol) and DMF (1 mL) and heated at 65° C. for 1.5 h. The solvent was evaporated under $N_2$ overnight, and the residue was dissolved in MeOH (1.5 mL) and treated with potassium carbonate (26 mg, 0.188 mmol) and water (180 mg) and heated at 65° C. for 25 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (2.2 mg, 14%).

LC/MS Condition E: ret time 1.66 min; m/e=652 (M+H)$^+$.
LC/MS Condition F: ret time 1.65 min; m/e=652 (M+H)$^+$.

Example 2117: (S)-5-((4-chloro-5-((2'-chloro-3'-(3-hydroxypropoxy)-2-methyl-[1,1'-biphenyl]-3-yl)methoxy)-2-(((2,3-dihydroxypropyl)amino)methyl)phenoxy)methyl)nicotinamide During the purification of the product of Example 2116, there was also obtained the above title compound (5.1 mg, 32%).

LC/MS Condition E: ret time 1.40 min; m/e=670 (M+H)$^+$.
LC/MS Condition F: ret time 1.41 min; m/e=670 (M+H)$^+$.

Intermediate: 3-(3-bromo-2-chlorophenoxy)propanoic Acid

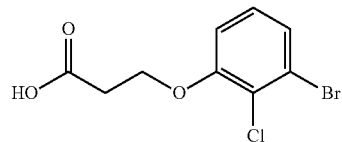

To a stirred suspension of 3-bromopropanoic acid (2.25 g, 14.71 mmol) and 3-bromo-2-chlorophenol (3.00 g, 14.46 mmol) in water (23 mL) was added solid sodium hydroxide (1.21 g, 30.3 mmol) and the reaction was heated at 105° C. for 18 h. The reaction was treated with 1 N HCl (27 mL, 27 mmol) and the resulting solid was collected by filtration to give the title compound (1.22 g, 30%) that was used in subsequent reactions.

$^1$H NMR (500 MHz, CHLOROFORM-d) δ 7.30-7.27 (m, 1H), 7.10 (t, J=8.2 Hz, 1H), 6.93 (dd, J=8.2, 1.2 Hz, 1H), 4.34 (t, J=6.3 Hz, 2H), 2.95 (t, J=6.3 Hz, 2H).

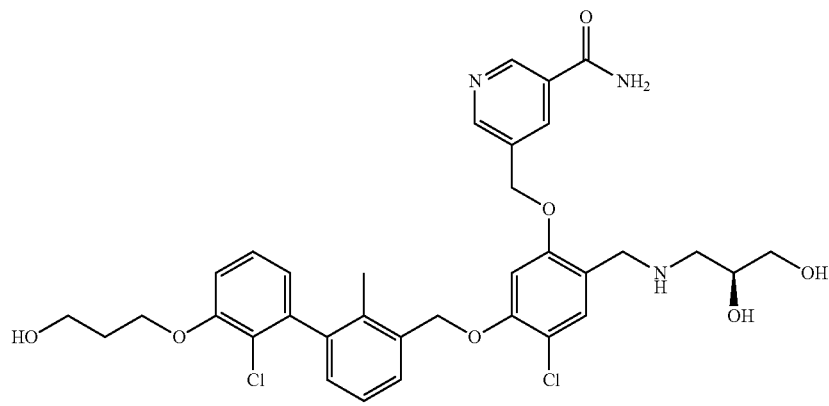 [SMILES: Cc1c(COc2cc(OCc3cncc(C(N)=O)c3)c(CNC[C@H](O)CO)cc2Cl)cccc1-c1cccc(OCCCO)c1Cl]

Intermediate: (S)-3-(3-bromo-2-chlorophenoxy)-N-(2,3-dihydroxypropyl)propanamide

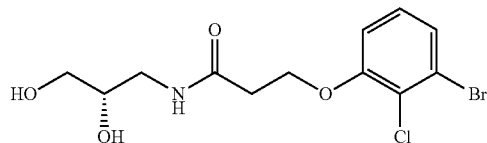 [SMILES: O=C(CCOc1cccc(Br)c1Cl)NC[C@H](O)CO]

To a mixture of 3-(3-bromo-2-chlorophenoxy)propanoic acid (204 mg, 0.730 mmol), (S)-3-aminopropane-1,2-diol (90 mg, 0.988 mmol), and 1-hydroxy-7-azabenzotriazole (33.5 mg, 0.246 mmol) in CH$_2$Cl$_2$ (5 mL) was added EDC (175 mg, 0.913 mmol) followed after 1 min by Hunig's Base (250 μl, 1.431 mmol). The reaction was stirred at room temp for 75 min and the solvent was removed under a gentle stream of N$_2$. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 20 minutes, then a 5-minute hold at 100% B; Flow: 20 mL/min to give the title compound (44.2 mg, 17%) that was used in subsequent reactions.

LC/MS Condition B: ret time 2.24 min; m/e=352 (M−H)$^-$.

Intermediate: (S)-3-((2-chloro-3'-((2-chloro-5-((5-cyanopyridin-3-yl)methoxy)-4-formylphenoxy)methyl)-2'-methyl-[1,1'-biphenyl]-3-yl)oxy)-N-(2,3-dihydroxypropyl)propanamide

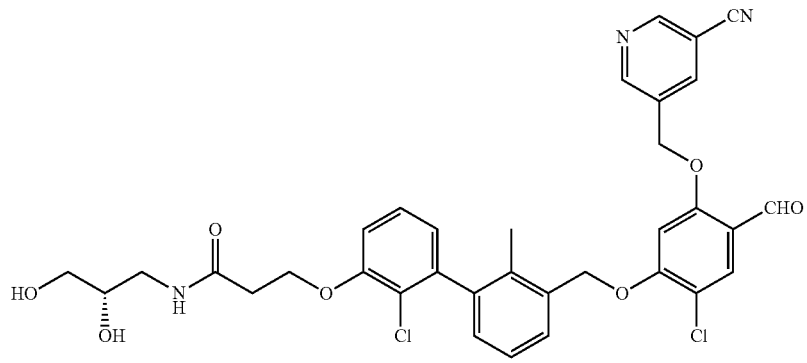 [SMILES: Cc1c(COc2cc(OCc3cncc(C#N)c3)c(C=O)cc2Cl)cccc1-c1cccc(OCCC(=O)NC[C@H](O)CO)c1Cl]

To a solution of (S)-3-(3-bromo-2-chlorophenoxy)-N-(2,3-dihydroxypropyl)propanamide (44.2 mg, 0.125 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (66.4 mg, 0.128 mmol) in THF (6 mL) under argon was added potassium phosphate tribasic 0.5 M in water (640 μl, 0.320 mmol) and added 2$^{nd}$ generation X-phos precatalyst (5 mg, 6.35 μmol). The reaction was flushed with argon, capped and stirred at room temp for 45 h. The reaction was partitioned with EtOAc (40 mL) and water (20 mL) and the organic layer was extracted with brine, dried over sodium sulfate and the solvent was removed in vacuo. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to give the title compound (19.1 mg, 16%) that was used in subsequent reactions.

LC/MS Condition E: ret time 1.97 min; m/e=664 (M+H)$^+$.
LC/MS Condition F: ret time 1.93 min; m/e=664 (M+H)$^+$.

Example 2118: (S)-3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)-N-(2,3-dihydroxypropyl)propanamide (250 mg, 1.45 mmol) and stirred at room temp for 94 h. The reaction was filtered, the filtrate evaporated to dryness in vacuo, and crude product applied to the head of a 80 g Teledyne Isco Silica Flash Column. The column was eluted with a linear gradient 100% hexanes to 100% EtOAc over 12

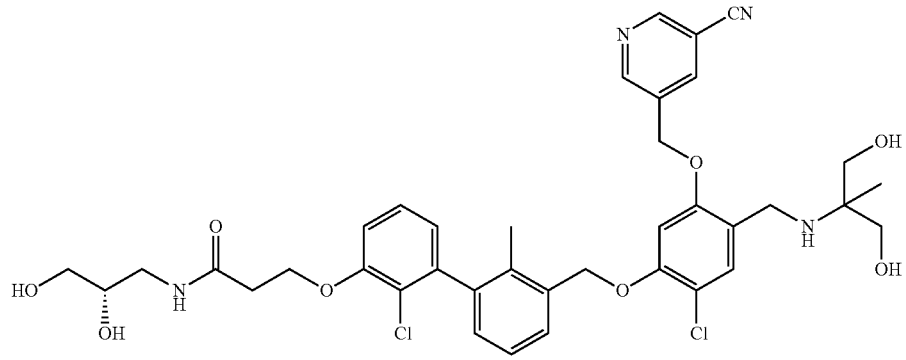 [SMILES: Cc1c(COc2cc(OCc3cncc(C#N)c3)c(CNC(C)(CO)CO)cc2Cl)cccc1-c1cccc(OCCC(=O)NC[C@H](O)CO)c1Cl]

To a solution of (S)-3-((2-chloro-3'-((2-chloro-5-((5-cyanopyridin-3-yl)methoxy)-4-formylphenoxy)methyl)-2'-methyl-[1,1'-biphenyl]-3-yl)oxy)-N-(2,3-dihydroxypropyl)propanamide (19.1 mg, 0.029 mmol) and 2-amino-2-methylpropane-1,3-diol (12 mg, 0.114 mmol) in CH$_2$Cl$_2$ (1 mL) and ethanol (0.7 mL) was added acetic acid (5 μL, 0.087 mmol) and activated 4 A mol. sieves. The reaction was flushed briefly with argon, stirred at room temp for 45 min, then treated dropwise (over 3 h) with sodium cyanotrihydroborate 1 M in THF (0.08 mL, 0.080 mmol) and stirred at room temp for 5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the title compound (12.3 mg, 57%).

LC/MS Condition E: ret time 1.56 min; m/e=753 (M+H)$^+$.

LC/MS Condition F: ret time 1.46 min; m/e=753 (M+H)$^+$.

Intermediate: tert-butyl (S)-3-((3-bromo-2-chlorophenoxy)methyl)pyrrolidine-1-carboxylate

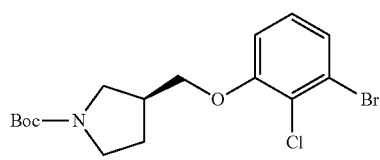 [SMILES: CC(C)(C)OC(=O)N1CC[C@H](COc2cccc(Br)c2Cl)C1]

To a mixture of (R)-3-hydroxymethyl-pyrrolidine-1-carboxylic acid tert-butyl ester (500 mg, 2.48 mmol), 3-bromo-2-chlorophenol (532 mg, 2.56 mmol), and triphenylphosphine (841 mg, 3.21 mmol) in tetrahydrofuran (12 mL) under a gentle stream of argon was added solid TMAD (500 mg, 2.90 mmol). The reaction was capped, stirred at room temp for 2 h, then heated to 45° C. for 2.5 h, then stirred at room temp for 18 h. The reaction was charged with additional triphenylphosphine (420 mg, 1.6 mmol) and TMAD col vols and the fractions containing the desired product were pooled and evaporated to dryness to give the title compound (830 mg, 86%).

$^1$H NMR (500 MHz, CHLOROFORM-d) δ 7.27 (br d, J=8.1 Hz, 1H), 7.09 (t, J=8.2 Hz, 1H), 6.87 (dd, J=8.2, 1.1 Hz, 1H), 3.99 (br dd, J=14.3, 6.5 Hz, 2H), 3.74-3.35 (m, 3H), 3.27 (br d, J=5.3 Hz, 1H), 2.76 (br s, 1H), 2.13 (br d, J=6.1 Hz, 1H), 1.96-1.80 (m, 1H), 1.49 (s, 9H).

Intermediate: (S)-3-((3-bromo-2-chlorophenoxy)methyl)pyrrolidine

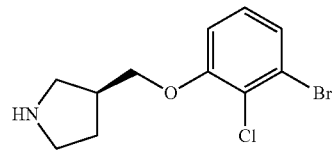

A solution of (S)-tert-butyl 3-((3-bromo-2-chlorophenoxy)methyl)pyrrolidine-1-carboxylate (530 mg, 1.357 mmol) in CH$_2$Cl$_2$ (10 mL) was treated with TFA (10 mL), allowed to stand 2 h at room temp, then slowly evaporated off under a gentle stream of N$_2$ to give the title compound (589 mg, quant) as a TFA salt.

LC/MS Condition A: ret time 0.85 min; m/e=290 (M+H)$^+$.

Intermediate: 3-((S)-3-((3-bromo-2-chlorophenoxy)methyl)pyrrolidin-1-yl)propane-1,2-diol

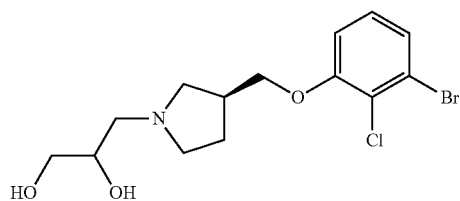 [SMILES: OCC(O)CN1CC[C@H](COc2cccc(Br)c2Cl)C1]

To a mixture of (S)-3-((3-bromo-2-chlorophenoxy)methyl)pyrrolidine, TFA (147.7 mg, 0.365 mmol) and 3-bromopropane-1,2-diol (200 mg, 1.290 mmol) in dry DMF (1.5 mL) under argon was added Hunig's Base and the reaction was stirred at room temp for 17 h, then heated to 40° C. for 48 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 8-48% B over 20 minutes, then a 5-minute hold at 100% B; Flow: 20 mL/min to give the title compound (91.2 mg, 51%) as a TFA salt that was used in subsequent reactions.

LC/MS Condition E: ret time 1.27 min; m/e=364 (M+H)$^+$.
LC/MS Condition F: ret time 1.24 min; m/e=364 (M+H)$^+$.

Intermediate: 5-((4-chloro-5-((2'-chloro-3'-(((3S)-1-(2,3-dihydroxypropyl)pyrrolidin-3-yl)methoxy)-2-methyl-[1,1'-biphenyl]-3-yl)methoxy)-2-formylphenoxy)methyl)nicotinonitrile at room temp for 66 h. The reaction partitioned with EtOAc (40 mL) and water (20 mL), and the organic layer was extracted with brine, dried over sodium sulfate and evaporated in vacuo to dryness. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min to give the title compound (54.8 mg, 33%) that was used in subsequent reactions.

LC/MS Condition E: ret time 2.00 min; m/e=676 (M+H)$^+$.
LC/MS Condition F: ret time 2.53 min; m/e=676 (M+H)$^+$.

Example 2119: 5-((4-chloro-5-((2'-chloro-3'-(((3S)-1-(2,3-dihydroxypropyl)pyrrolidin-3-yl)methoxy)-2-methyl-[1,1'-biphenyl]-3-yl)methoxy)-2-(((1,3-dihydroxy-2-methylpropan-2-yl)amino)methyl)phenoxy)methyl)nicotinonitrile

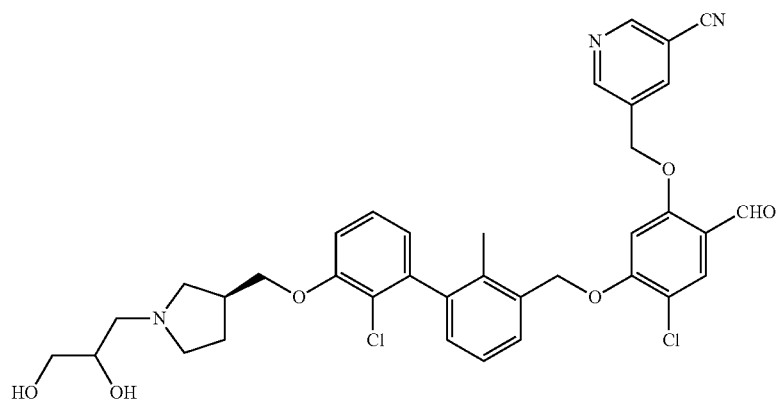 [SMILES: Cc1c(COc2cc(OCc3cncc(C#N)c3)c(C=O)cc2Cl)cccc1-c1cccc(OC[C@H]2CCN(CC(O)CO)C2)c1Cl]

To a solution of 3-((S)-3-((3-bromo-2-chlorophenoxy)methyl)pyrrolidin-1-yl)propane-1,2-diol, TFA (91.2 mg, 0.191 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (100 mg, 0.193 mmol) in THF (6 mL) under argon was added potassium phosphate tribasic 0.5 M in water (950 μl, 0.475 mmol), 2$^{nd}$ generation xphos precatalyst (29 mg, 0.037 mmol) and the reaction was stirred

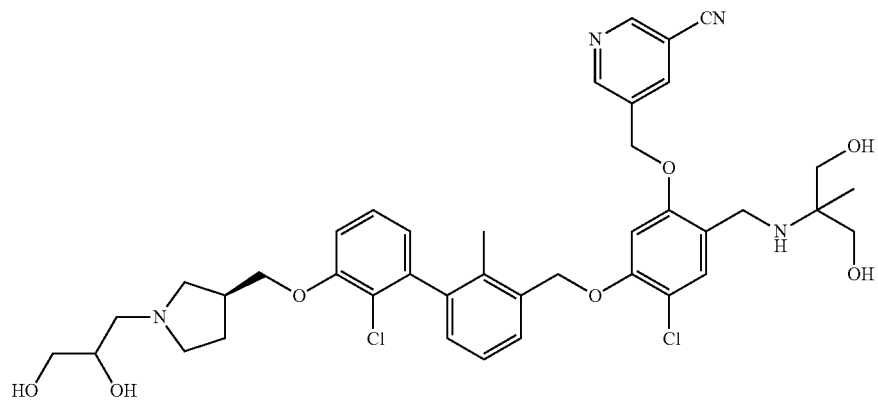 [SMILES: Cc1c(COc2cc(OCc3cncc(C#N)c3)c(CNC(C)(CO)CO)cc2Cl)cccc1-c1cccc(OC[C@H]2CCN(CC(O)CO)C2)c1Cl]

To a solution of 5-((4-chloro-5-((2'-chloro-3'-(((3S)-1-(2,3-dihydroxypropyl)pyrrolidin-3-yl)methoxy)-2-methyl-[1,1'-biphenyl]-3-yl)methoxy)-2-formylphenoxy)methyl)nicotinonitrile (15.1 mg, 0.022 mmol) and 2-amino-2-methylpropane-1,3-diol (11.5 mg, 0.109 mmol) in CH₂Cl₂ (1 mL) and ethanol (0.7 mL) was added acetic acid (5 µL, 0.087 mmol) and activated 4 A mol. sieves. The reaction was flushed briefly with argon, stirred at room temp for 40 min, treated dropwise (over 3 h) with sodium cyanotrihydroborate 1 M in THF (0.07 mL, 0.070 mmol) and stirred at room temp for 4 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (5.5 mg, 32%)

LC/MS Condition E: ret time 1.56 min; m/e=765 (M+H)⁺.
LC/MS Condition F: ret time 1.51 min; m/e=765 (M+H)⁺.

Example 2120: (2S)-1-(5-chloro-4-((2'-chloro-3'-(((3S)-1-(2,3-dihydroxypropyl)pyrrolidin-3-yl)methoxy)-2-methyl-[1,1'-biphenyl]-3-yl)methoxy)-2-((5-cyanopyridin-3-yl)methoxy)benzyl)piperidine-2-carboxylic Acid

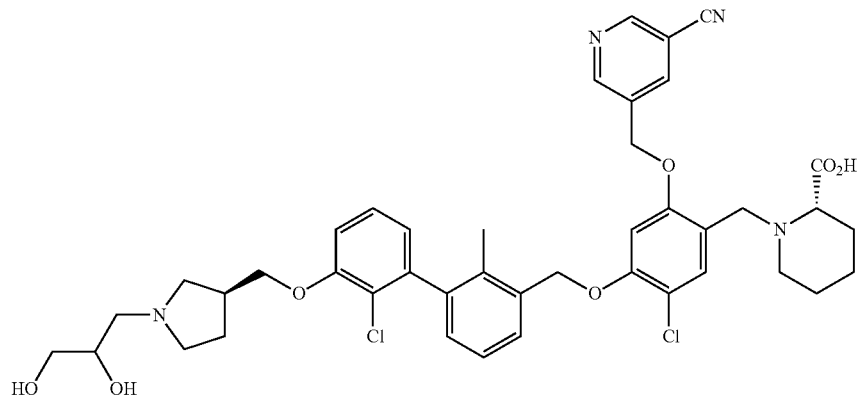 [SMILES: Cc1c(COc2cc(OCc3cncc(C#N)c3)c(CN3CCCC[C@H]3C(=O)O)cc2Cl)cccc1-c1cccc(OC[C@H]2CCN(CC(O)CO)C2)c1Cl]

To a solution of 5-((4-chloro-5-((2'-chloro-3'-(((3S)-1-(2,3-dihydroxypropyl)pyrrolidin-3-yl)methoxy)-2-methyl-[1,1'-biphenyl]-3-yl)methoxy)-2-formylphenoxy)methyl)nicotinonitrile (39.6 mg, 0.059 mmol) and (S)-piperidine-2-carboxylic acid (32.6 mg, 0.252 mmol) in CH₂Cl₂ (1.5 mL) and ethanol (1 mL) was added acetic acid (12 µL, 0.210 mmol) and activated 4 A mol. sieves. The reaction was flushed briefly with argon, stirred at room temp for 70 min, treated dropwise (over 3.5 h) with sodium cyanotrihydroborate 1 M in THF (0.15 mL, 0.150 mmol) and stirred at room temp for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the title compound (3.7 mg, 8%).

LC/MS Condition E: ret time 1.36 min; m/e=789 (M+H)⁺.
LC/MS Condition F: ret time 1.34 min; m/e=789 (M+H)⁺.

Intermediate: 5-((5-((3'-(3-bromopropoxy)-2,2'-dimethyl-[1,1'-biphenyl]-3-yl)methoxy)-4-chloro-2-(((2-morpholinoethyl)amino)methyl)phenoxy)methyl)nicotinonitrile

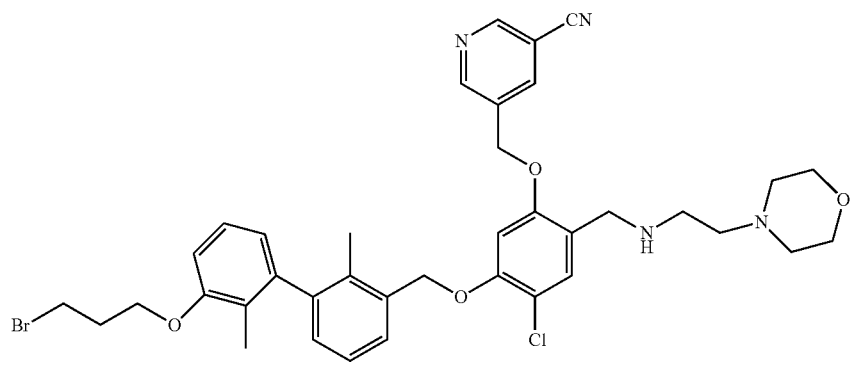 [SMILES: Cc1c(COc2cc(OCc3cncc(C#N)c3)c(CNCCN3CCOCC3)cc2Cl)cccc1-c1cccc(OCCCBr)c1C]

To a solution of 5-((5-((3'-(3-bromopropoxy)-2,2'-dimethyl-[1,1'-biphenyl]-3-yl)methoxy)-4-chloro-2-formylphenoxy)methyl)nicotinonitrile (79 mg, 0.127 mmol) and 2-morpholinoethanamine (48 mg, 0.369 mmol) in DCE (1.5 mL) and ethanol (1 mL) was added acetic acid (23 μl, 0.402 mmol) and activated 4 A mol. sieves. The reaction was flushed briefly with argon, stirred at room temp for 20 min, treated dropwise (over 3 h) with sodium cyanoborohydride 1 M in THF (0.39 mL, 0.390 mmol) and then stirred at room temp for 4 h. The solvent was removed under a gentle stream of $N_2$ and the crude title compound was used "as is" in subsequent reactions without purification.

LC/MS Condition A: ret time 1.00 min; m/e=733 $(M+H)^+$.

Example 2122: (R)-5-((4-chloro-5-((3'-(3-(3-hydroxypyrrolidin-1-yl)propoxy)-2,2'-dimethyl-[1,1'-biphenyl]-3-yl)methoxy)-2-(((2-morpholinoethyl)amino)methyl)phenoxy)methyl)nicotinonitrile

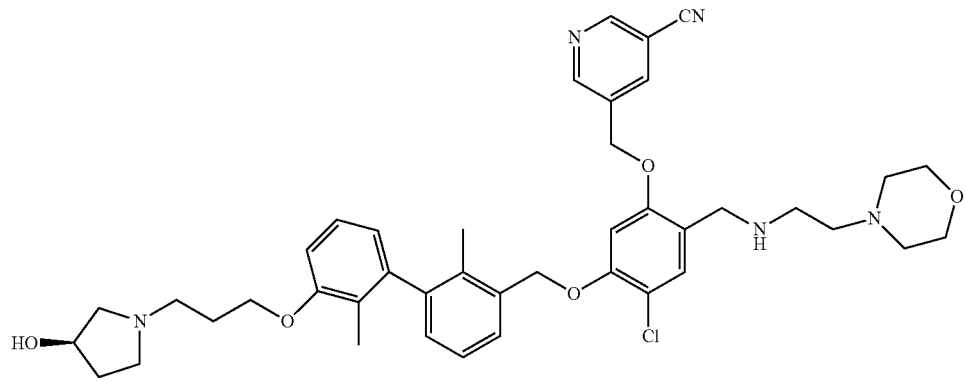 [SMILES: Cc1c(COc2cc(OCc3cncc(C#N)c3)c(CNCCN3CCOCC3)cc2Cl)cccc1-c1cccc(OCCCN2CC[C@@H](O)C2)c1C]

To a mixture of 5-((5-((3'-(3-bromopropoxy)-2,2'-dimethyl-[1,1'-biphenyl]-3-yl)methoxy)-4-chloro-2-(((2-morpholinoethyl)amino)methyl)phenoxy)methyl)nicotinonitrile (94 mg, 0.128 mmol) and (R)-pyrrolidin-3-ol, HCl (170 mg, 1.376 mmol) in MeOH (4 mL) was added Hunig's Base (350 μl, 2.004 mmol) and the reaction was heated to 65° C. for 66 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min to give the title compound (34.8 mg, 34%).

LC/MS Condition E: ret time 1.61 min; m/e=740 $(M+H)^+$.
LC/MS Condition F: ret time 1.27 min; m/e=740 $(M+H)^+$.

Intermediate:
3-((3-bromo-2-methylphenoxy)methyl)-4-chlorophenyl acetate

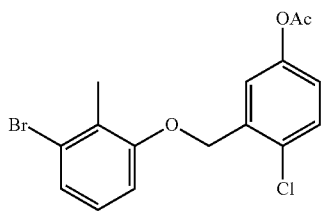 [SMILES: CC(=O)Oc1ccc(Cl)c(COc2cccc(Br)c2C)c1]

To a mixture of 3-(bromomethyl)-4-chlorophenyl acetate (880 mg, 3.34 mmol), 3-bromo-2-methylphenol (631 mg, 3.37 mmol), and cesium carbonate (2.21 g, 6.78 mmol) was added acetone (30 mL), and the reaction was stirred at room temp for 18 h. The crude material was applied to the head of a 80 g Teledyne Isco Silica Flash Column, and the column was eluted with a linear gradient from 100% hexanes to 100% $CH_2Cl_2$ over 9 column volumes. The fractions that contain the desired product were pooled and evaporated to dryness to give the title compound (150 mg, 12%). $^1H$ NMR (400 MHz, CHLOROFORM-d) δ 7.42 (d, J=8.5 Hz, 1H), 7.31 (d, J=2.8 Hz, 1H), 7.21 (d, J=7.3 Hz, 1H), 7.08-6.98 (m, 2H), 6.84 (d, J=8.0 Hz, 1H), 5.14 (s, 2H), 2.42 (s, 3H), 2.32 (s, 3H).

Intermediate:
3-((3-bromo-2-methylphenoxy)methyl)-4-chlorophenol

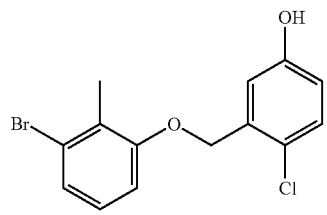 [SMILES: Cc1c(Br)cccc1OCc1cc(O)ccc1Cl]

To a solution of 3-((3-bromo-2-methylphenoxy)methyl)-4-chlorophenyl acetate (137.1 mg, 0.371 mmol) in MeOH (17 mL) was added potassium carbonate (151 mg, 1.09 mmol) and the reaction was stirred at room temp for 1 h. The crude material was applied to the head of a 24 g Teledyne Isco Silica Flash Column, and the column was eluted with a linear gradient from 100% $CH_2Cl_2$ to 100% ethyl acetate over 12 column volumes. The fractions that contain the desired product were pooled and evaporated to dryness to give the title compound (120 mg, 99%). $^1H$ NMR (400 MHz, CHLOROFORM-d) δ 7.27 (s, 1H), 7.21 (d, J=8.0 Hz, 1H), 7.07-6.98 (m, 2H), 6.83 (d, J=8.0 Hz, 1H), 6.76 (dd, J=8.5, 3.0 Hz, 1H), 5.12 (s, 2H), 4.93 (s, 1H), 2.43 (s, 3H).

419

Intermediate: 5-((3-bromo-2-methylphenoxy)methyl)-4-chloro-2-((dimethylamino)methyl)phenol

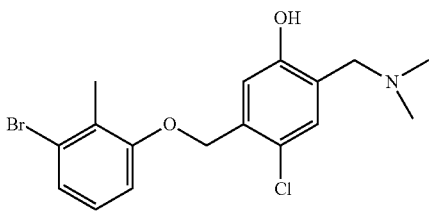 [SMILES: Cc1c(Br)cccc1OCc1cc(O)c(CN(C)C)cc1Cl]

To a pressure vial under N₂ was added 3-((3-bromo-2-methylphenoxy)methyl)-4-chlorophenol (15 mg, 0.046 mmol), dimethylamine, 40% in water (7.8 µL, 0.062 mmol), formaldehyde, 37% in water (4.0 µL, 0.054 mmol), water (400 µL) and MeOH (400 µL). The reaction was stirred at room temp for 2 h, and then treated with additional dimethylamine, 40% in water (78 lit) and formaldehyde (40 lit) and stirred at room temp for 18 h. The reaction was then heated to 80° C. for 2.5 h and the solvent was removed under a gentle stream of N₂ to give the title compound that was used "as is" without purification in subsequent reactions.

LC/MS Condition B: ret time 3.95 min; m/e=384 (M+H)⁺.

Intermediate: 5-(((3'-(3-bromopropoxy)-2,2'-dimethyl-[1,1'-biphenyl]-3-yl)oxy)methyl)-4-chloro-2-((dimethylamino)methyl)phenol

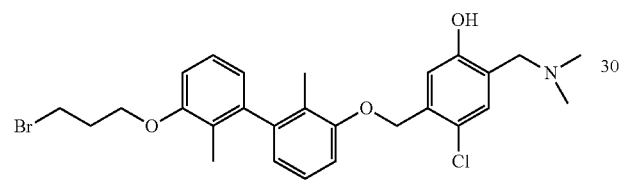

420

To a solution of 5-((3-bromo-2-methylphenoxy)methyl)-4-chloro-2-((dimethylamino)methyl)phenol (17.6 mg, 0.046 mmol) and 2-(3-(3-bromopropoxy)-2-methylphenyl)-4,4,5,5-tetramethyl-1,3,2-dioxaborolane (16.5 mg, 0.046 mmol) in anhydrous THF (600 µL) was added potassium phosphate tribasic, 0.5M in water (241 µL, 0.121 mmol). The reaction was purged well with argon, then treated with $2^{nd}$ generation X-Phos precatalyst (2.5 mg, 3.18 µmol) and stirred at room temp for 18 h. The reaction was treated additional catalyst (4.5 mg, 0.006 mmol) and heated at 40° C. for 3 h, followed by room temp for 18 h. The solvent was removed under a gentle stream of N₂ to give the title compound that was used "as is" without purification in subsequent reactions.

LC/MS Condition B: ret time 4.64 min; m/e=534 (M+H)⁺.

Example 2123: (R)-1-(3-((3'-((2-chloro-4-((dimethylamino)methyl)-5-hydroxybenzyl)oxy)-2,2'-dimethyl-[1,1'-biphenyl]-3-yl)oxy)propyl)pyrrolidin-3-ol

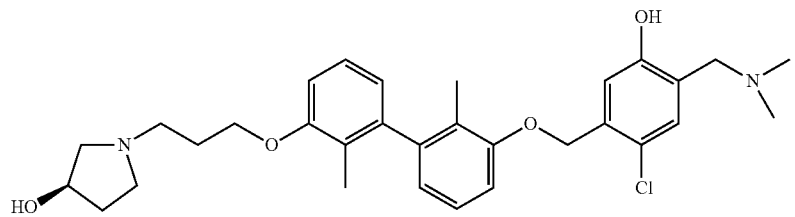 [SMILES: Cc1c(OCCCN2CC[C@@H](O)C2)cccc1-c1cccc(OCc2cc(O)c(CN(C)C)cc2Cl)c1C]

To a solution of 5-(((3'-(3-bromopropoxy)-2,2'-dimethyl-[1,1'-biphenyl]-3-yl)oxy)methyl)-4-chloro-2-((dimethylamino)methyl)phenol (24 mg, 0.045 mmol) in methanol (1.0 mL) was added (R)-3-hydroxypyrrolidine hydrochloride (55 mg, 0.445 mmol), and N,N-diisopropylethylamine (175 µL, 1.002 mmol) and the reaction was heated at 70° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min to give the pure title compound (0.3 mg).

LC/MS Condition A: ret time 0.872 min; m/e=539 (M+H)⁺.

Example 2201: 5-((4-chloro-2-(((R)-3-hydroxypyr-rolidin-1-yl)methyl)-5-((3'-(3-((R)-3-hydroxypyrroli-din-1-yl)propoxy)-2,2'-dimethylbiphenyl-3-yl)methoxy)phenoxy)methyl)nicotinonitrile

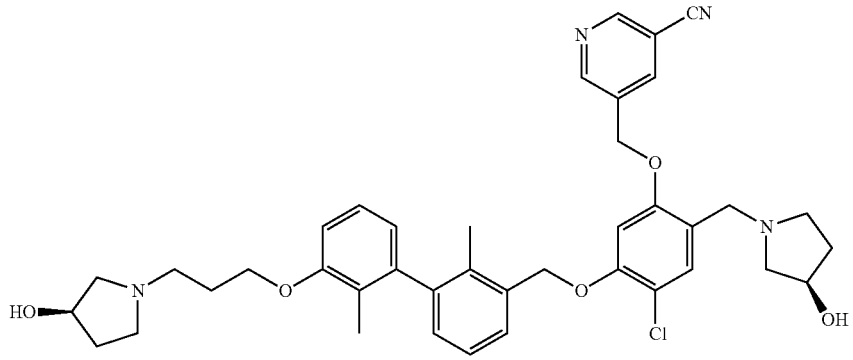 [SMILES: Cc1c(COc2cc(OCc3cncc(C#N)c3)c(CN3CC[C@@H](O)C3)cc2Cl)cccc1-c1cccc(OCCCN2CC[C@@H](O)C2)c1C]

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (40 mg, 0.065 mmol), (R)-pyrrolidin-3-ol, HCl (15.95 mg, 0.129 mmol) in dichloroethane (0.3 mL) and ethanol (0.7 mL) was added acetic acid (7.39 µl, 0.129 mmol). The resulting mixture was stirred at rt for 6 h. sodium cyanoborohydride (0.129 mL, 0.129 mmol) was added through a syringe over 16 h. More (R)-pyrrolidin-3-ol (60 mg, 0.50 mmol) was added followed by DIPEA (0.113 mL, 0.645 mmol). The resulting mixture was stirred at 65° C. for 18 h. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound: (9.4 mg, 20%). $^1$H NMR (500 MHz, DMSO-$d_6$) δ 9.01 (s, 1H), 8.98 (s, 1H), 8.42 (s, 1H), 7.49 (d, J=7.3 Hz, 1H), 7.33 (s, 1H), 7.27 (t, J=7.5 Hz, 1H), 7.21 (t, J=7.9 Hz, 1H), 7.10 (s, 1H), 7.07 (d, J=8.1 Hz, 1H), 6.95 (d, J=8.4 Hz, 1H), 6.68 (d, J=7.7 Hz, 1H), 5.32 (s, 2H), 5.25 (s, 2H), 4.19 (br. s., 2H), 4.10-3.99 (m, 2H), 3.53-3.40 (m, 6H), 2.89 (s, 2H), 2.72-2.63 (m, 2H), 2.62-2.53 (m, 6H), 2.47-2.37 (m, 2H), 2.37-2.27 (m, 2H), 2.03 (s, 3H), 2.01-1.93 (m, 2H), 1.82 (s, 3H), 1.54 (d, J=5.1 Hz, 2H). LC/MS Condition E: RT (Retention Time)=1.48 min; m/e=697.1 (M+H)$^+$.

Example 2202: (2S)-1-(5-chloro-2-((5-cyanopyridin-3-yl)methoxy)-4-((3'-(3-(2-(hydroxymethyl)piperidin-1-yl)propoxy)-2,2'-dimethylbiphenyl-3-yl)methoxy)benzyl)piperidine-2-carboxylic Acid

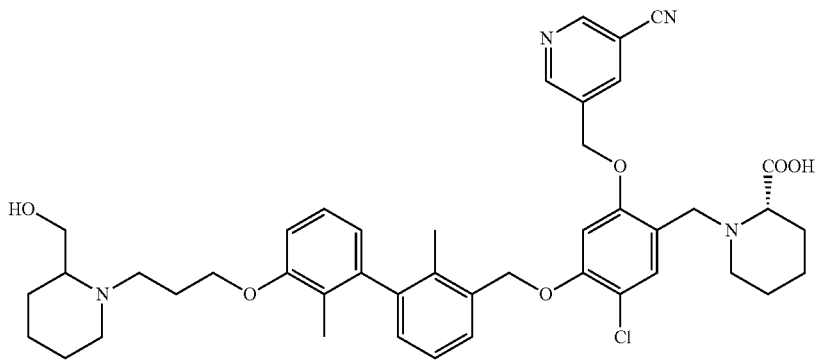 [SMILES: Cc1c(COc2cc(OCc3cncc(C#N)c3)c(CN3CCCC[C@H]3C(=O)O)cc2Cl)cccc1-c1cccc(OCCCN2CCCCC2CO)c1C]

To a solution of (S)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid (20 mg, 0.027 mmol) in DCE (0.2 ml)/EtOH (0.5 ml)/THF (0.2 ml) was added piperidin-2-ylmethanol (31.4 mg, 0.273 mmol) and DIPEA (0.048 mL, 0.273 mmol) and the resulting mixture was stirred at 65° C. for 16 h. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient:

20-60% B over 20 minutes, then a 5-minute hold at 100% B; Flow: 20 mL/min. Fractions containing the desired product were combined and dried via centrifugal evaporation to give the pure title compound: (9.2 mg, 39%). $^1$H NMR (500 MHz, DMSO-$d_6$) δ 9.01 (s, 1H), 9.00 (s, 1H), 8.46 (s, 1H), 7.49 (d, J=7.7 Hz, 1H), 7.44 (s, 1H), 7.27 (t, J=7.5 Hz, 1H), 7.23-7.16 (m, 1H), 7.11 (br. s., 1H), 7.08 (d, J=7.3 Hz, 1H), 6.95 (d, J=8.1 Hz, 1H), 6.68 (d, J=7.0 Hz, 1H), 5.33 (br. s., 2H), 5.26 (br. s., 2H), 4.02 (br. s., 2H), 3.81 (d, J=13.2 Hz, 1H), 3.63 (d, J=13.6 Hz, 1H), 3.50 (d, J=11.7 Hz, 6H), 3.12 (br. s., 1H), 2.97-2.89 (m, 2H), 2.83 (d, J=11.4 Hz, 1H), 2.28 (br. s., 2H), 2.25-2.14 (m, 1H), 2.03 (s, 3H), 1.82 (s, 3H), 1.42-1.21 (m, 6H), 0.87 (br. s., 1H). HNMR of the aliphatic region showed some impurities. LC/MS Condition E: RT=1.56 min; m/e=767.2 (M+H)$^+$.

65° C. for 16 h. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound: (17.2 mg, 60%). LC/MS Condition E: RT=1.41 min; m/e=783.2 (M+H)$^+$.

Example 2203: (2S)-1-(5-chloro-2-((5-cyanopyridin-3-yl)methoxy)-4-((3'-(3-((3 S,4R)-3-hydroxy-4-(hydroxymethyl)piperidin-1-yl)propoxy)-2,2'-dimethylbiphenyl-3-yl)methoxy)benzyl)piperidine-2-carboxylic Acid Example 2204: (2S)-1-(4-((3'-(3-((S)-3-carboxypiperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

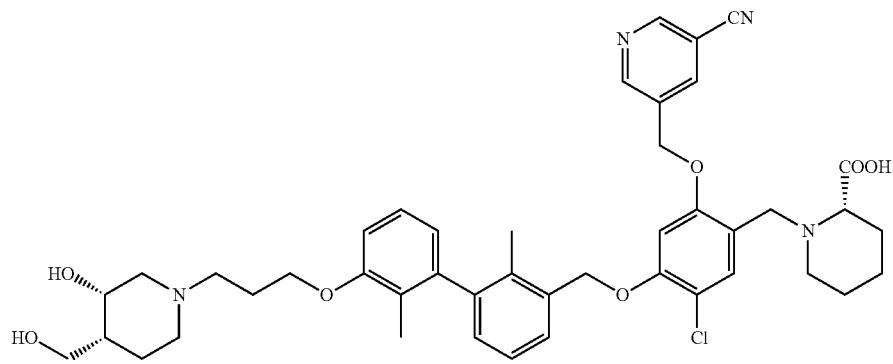 [SMILES: Cc1c(COc2cc(OCc3cncc(C#N)c3)c(CN3CCCC[C@H]3C(=O)O)cc2Cl)cccc1-c1cccc(OCCCN2CC[C@H](CO)[C@H](O)C2)c1C]

To a solution of (S)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid (25 mg, 0.034 mmol) in DCE (0.2 ml)/EtOH (0.5 ml)/THF (0.2 ml) was added (3S,4R)-4-(hydroxymethyl)piperidin-3-ol (44.7 mg, 0.341 mmol) and DIPEA (0.060 mL, 0.341 mmol) and the resulting mixture was stirred at

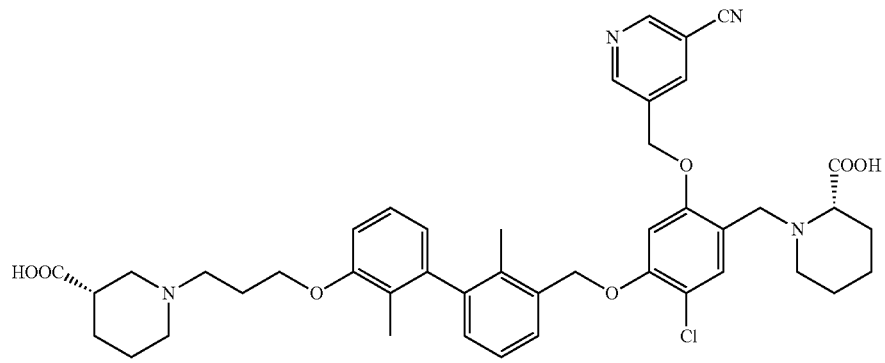 [SMILES: Cc1c(COc2cc(OCc3cncc(C#N)c3)c(CN3CCCC[C@H]3C(=O)O)cc2Cl)cccc1-c1cccc(OCCCN2CCC[C@H](C(=O)O)C2)c1C]

To a solution (S)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid (25 mg, 0.034 mmol) in DCE (0.2 ml)/EtOH (0.5 ml)/THF (0.2 ml) was added (S)-piperidine-3-carboxylic acid (44.0 mg, 0.341 mmol) and DIPEA (0.060 mL, 0.341 mmol) and the resulting mixture was stirred at 65° C. for 16 h. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound: (9.6 mg, 36%). LC/MS Condition E: RT=1.40 min; m/e=781.2 (M+H)$^+$.

Example 2205: (2S)-1-(4-((3'-(3-((R)-3-carboxypiperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound: (10.1 mg, 38%). LC/MS Condition E: RT=1.50 min; m/e=781.2 (M+H)$^+$.

Example 2206: (2S)-1-(5-chloro-2-((5-cyanopyridin-3-yl)methoxy)-4-((3'-(3-(3-(hydroxymethyl)piperidin-1-yl)propoxy)-2,2'-dimethylbiphenyl-3-yl)methoxy)benzyl)piperidine-2-carboxylic Acid

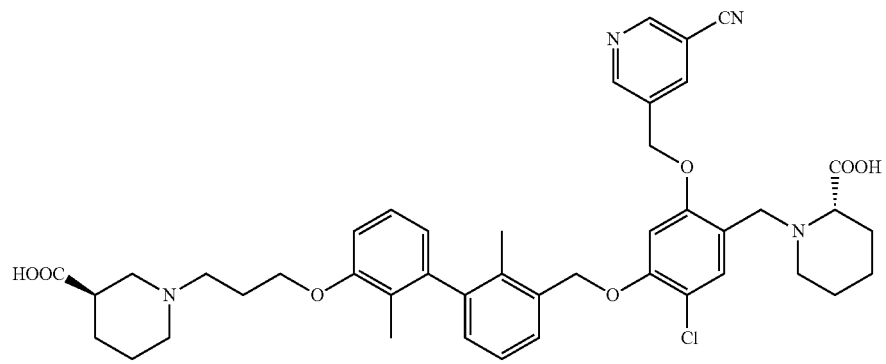 [SMILES: Cc1c(COc2cc(OCc3cncc(C#N)c3)c(CN3CCCC[C@H]3C(=O)O)cc2Cl)cccc1-c1cccc(OCCCN2CCC[C@@H](C(=O)O)C2)c1C]

To a solution (R)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid

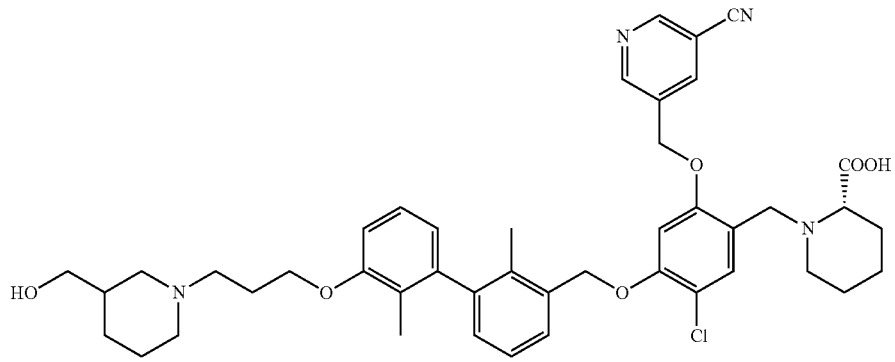 [SMILES: Cc1c(COc2cc(OCc3cncc(C#N)c3)c(CN3CCCC[C@H]3C(=O)O)cc2Cl)cccc1-c1cccc(OCCCN2CCCC(CO)C2)c1C]

(25 mg, 0.034 mmol) in DCE (0.2 ml)/EtOH (0.5 ml)/THF (0.2 ml) was added (S)-piperidine-3-carboxylic acid (44.0 mg, 0.341 mmol) and DIPEA (0.060 mL, 0.341 mmol) and the resulting mixture was stirred at 65° C. for 16 h. The The compound was prepared and purified with the same method as that for Example 2205 to give the pure title compound: (9.1 mg, 34%). LC/MS Condition E: RT=1.54 min; m/e=767.1 (M+H)$^+$.

Example 2207: (2S)-1-(4-((3'-(3-(3-carbamoylpiperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

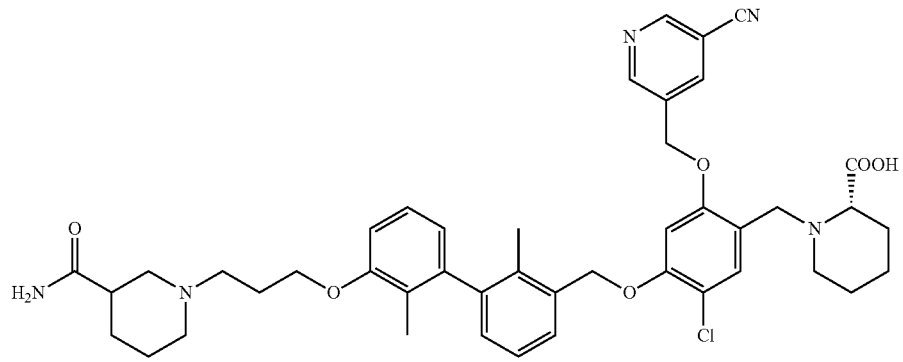 [SMILES: Cc1c(COc2cc(OCc3cncc(C#N)c3)c(CN3CCCC[C@H]3C(=O)O)cc2Cl)cccc1-c1cccc(OCCCN2CCCC(C(N)=O)C2)c1C]

The compound was prepared and purified with the same method as that for Example 2205 to give the pure title compound: (9.8 mg, 36%). LC/MS Condition E: RT=1.47 min; m/e=780.2 (M+H)+.

Example 2208: (2S)-1-(5-chloro-2-((5-cyanopyridin-3-yl)methoxy)-4-((3'-(3-(3-(diethylcarbamoyl)piperidin-1-yl)propoxy)-2,2'-dimethylbiphenyl-3-yl)methoxy)benzyl)piperidine-2-carboxylic Acid

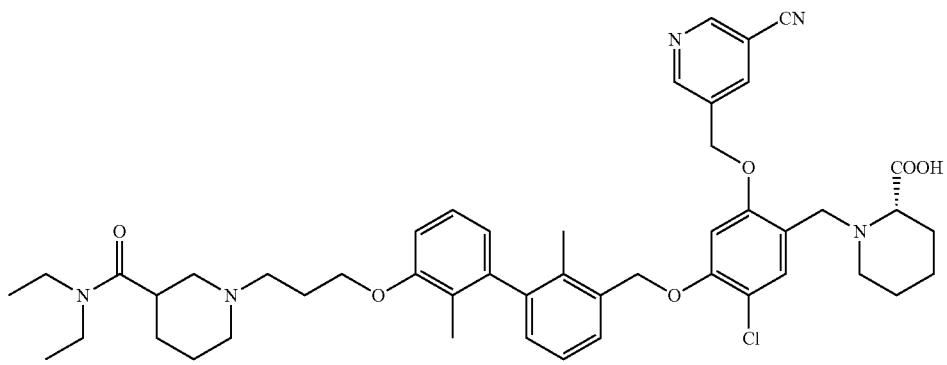 [SMILES: CCN(CC)C(=O)C1CCCN(CCCOc2cccc(-c3cccc(COc4cc(OCc5cncc(C#N)c5)c(CN5CCCC[C@H]5C(=O)O)cc4Cl)c3C)c2C)C1]

The compound was prepared and purified with the same method as that for Example 2205 to give the pure title compound: (19.0 mg, 67%). LC/MS Condition E: RT=1.63 min; m/e=836.3 (M+H)+.

Example 2209: (2S)-1-(4-((3'-(3-((S)-1-carboxy-2-(pyridin-4-yl)ethylamino)propoxy)-2,2'-dimethylbiphenyl-3-yl)methoxy)-5-chloro-2-((5-cyanopyridin-3-yl)methoxy)benzyl)piperidine-2-carboxylic Acid

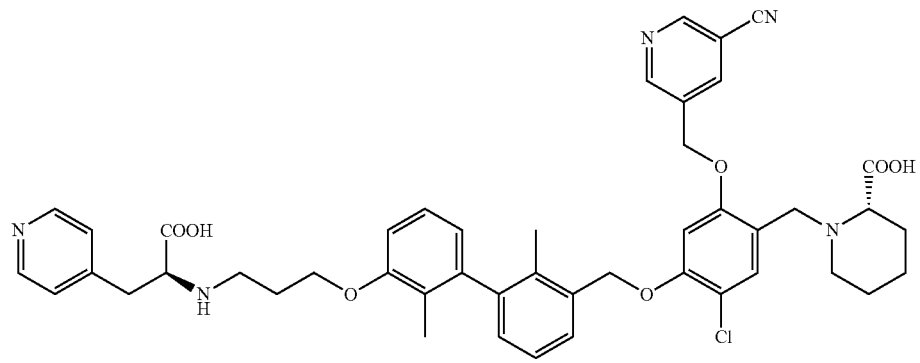 [SMILES: Cc1c(COc2cc(OCc3cncc(C#N)c3)c(CN3CCCC[C@H]3C(=O)O)cc2Cl)cccc1-c1cccc(OCCCN[C@@H](Cc2ccncc2)C(=O)O)c1C]

The compound was prepared and purified with the same method as that for Example 2205 to give the pure title compound: (1.9 mg, 7%). LC/MS Condition E: RT=1.49 min; m/e=818.2 (M+H)⁺.

Example 2210: (2S)-1-(5-chloro-2-((5-cyanopyridin-3-yl)methoxy)-4-((2,2'-dimethyl-3'-(3-(2-(pyridin-4-yl)ethylamino)propoxy)biphenyl-3-yl)methoxy)benzyl)piperidine-2-carboxylic Acid

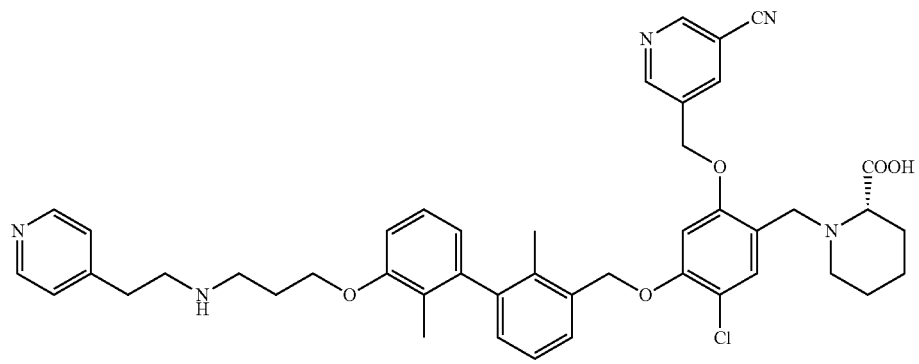 [SMILES: Cc1c(COc2cc(OCc3cncc(C#N)c3)c(CN3CCCC[C@H]3C(=O)O)cc2Cl)cccc1-c1cccc(OCCCNCCc2ccncc2)c1C]

The compound was prepared and purified with the same method as that for Example 2205 to give the pure title compound: (4.4 mg, 17%). LC/MS Condition E: RT=1.47 min; m/e=774.2 (M+H)⁺.

Example 2211: (2S)-1-(5-chloro-2-((5-cyanopyridin-3-yl)methoxy)-4-((3'-(3-(4-(2-hydroxyethyl)piperazin-1-yl)propoxy)-2,2'-dimethylbiphenyl-3-yl)methoxy)benzyl)piperidine-2-carboxylic Acid

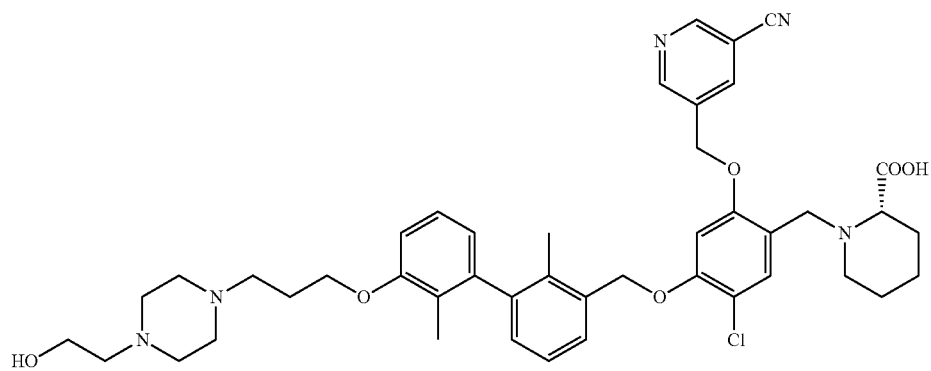 [SMILES: Cc1c(COc2cc(OCc3cncc(C#N)c3)c(CN3CCCC[C@H]3C(=O)O)cc2Cl)cccc1-c1cccc(OCCCN2CCN(CCO)CC2)c1C]

The compound was prepared and purified with the same method as that for Example 2205 to give the pure title compound: (22.0 mg, 66%). LC/MS Condition E: RT=1.52 min; m/e=782.1 (M+H)⁺.

Example 2212: (2S)-1-(5-chloro-2-((5-cyanopyridin-3-yl)methoxy)-4-((2,2'-dimethyl-3'-(3-morpholinopropoxy)biphenyl-3-yl)methoxy)benzyl)piperidine-2-carboxylic Acid

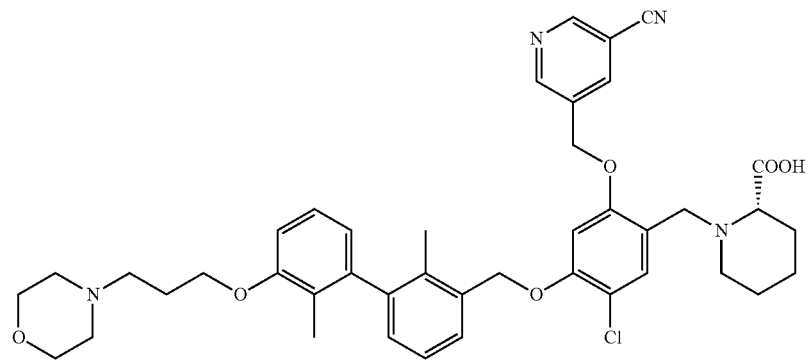 [SMILES: Cc1c(COc2cc(OCc3cncc(C#N)c3)c(CN3CCCC[C@H]3C(=O)O)cc2Cl)cccc1-c1cccc(OCCCN2CCOCC2)c1C]

The compound was prepared and purified with the same method as that for Example 2205 to give the pure title compound: (15.8 mg, 52%). LC/MS Condition E: RT=1.62 min; m/e=739.2 (M+H)$^+$.

Example 2213: (2S)-1-(5-chloro-2-((5-cyanopyridin-3-yl)methoxy)-4-((2,2'-dimethyl-3'-(3-(piperidin-1-yl)propoxy)biphenyl-3-yl)methoxy)benzyl)piperidine-2-carboxylic Acid

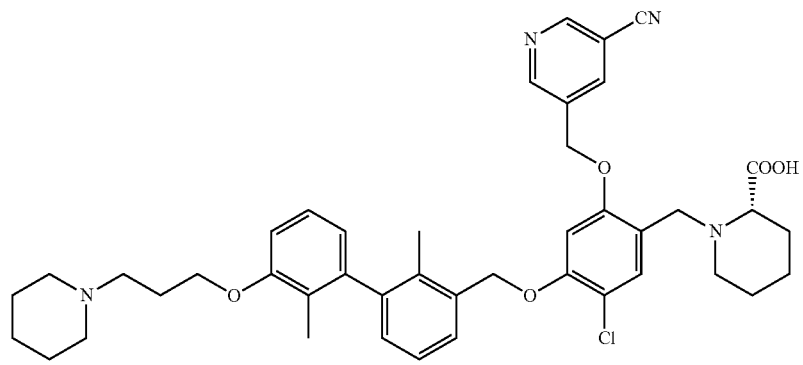 [SMILES: Cc1c(COc2cc(OCc3cncc(C#N)c3)c(CN3CCCC[C@H]3C(=O)O)cc2Cl)cccc1-c1cccc(OCCCN2CCCCC2)c1C]

The compound was prepared and purified with the same method as that for Example 2205 to give the pure title compound: (9.3 mg, 37%). LC/MS Condition E: RT=1.64 min; m/e=737.2 (M+H)$^+$.

Example 2214: (2S)-1-(5-chloro-2-((5-cyanopyridin-3-yl)methoxy)-4-((3'-(3-(4-(hydroxymethyl)piperidin-1-yl)propoxy)-2,2'-dimethylbiphenyl-3-yl)methoxy)benzyl)piperidine-2-carboxylic Acid

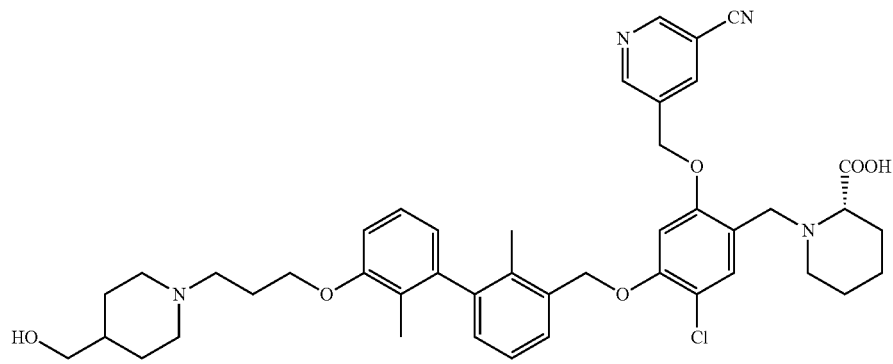 [SMILES: Cc1c(COc2cc(OCc3cncc(C#N)c3)c(CN3CCCC[C@H]3C(=O)O)cc2Cl)cccc1-c1cccc(OCCCN2CCC(CO)CC2)c1C]

The compound was prepared and purified with the same method as that for Example 2205 to give the pure title compound: (7.6 mg, 29%). LC/MS Condition E: RT=1.50 min; m/e=767.2 (M+H)+.

Example 2215: (2S)-1-(4-((3'-(3-(3-acetamidopyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

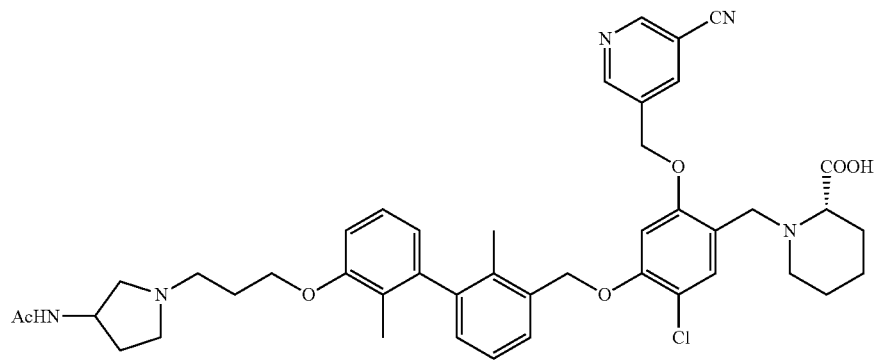 [SMILES: CC(=O)NC1CCN(CCCOc2cccc(-c3cccc(COc4cc(OCc5cncc(C#N)c5)c(CN5CCCC[C@H]5C(=O)O)cc4Cl)c3C)c2C)C1]

The compound was prepared and purified with the same method as that for Example 2205 to give the pure title compound: (12.4 mg, 47%). LC/MS Condition E: RT=1.58 min; m/e=780.2 (M+H)+.

Example 2216: (2S)-1-(5-chloro-2-((5-cyanopyridin-3-yl)methoxy)-4-((2,2'-dimethyl-3'-(3-(4-(pyridin-2-yl)piperazin-1-yl)propoxy)biphenyl-3-yl)methoxy)benzyl)piperidine-2-carboxylic Acid

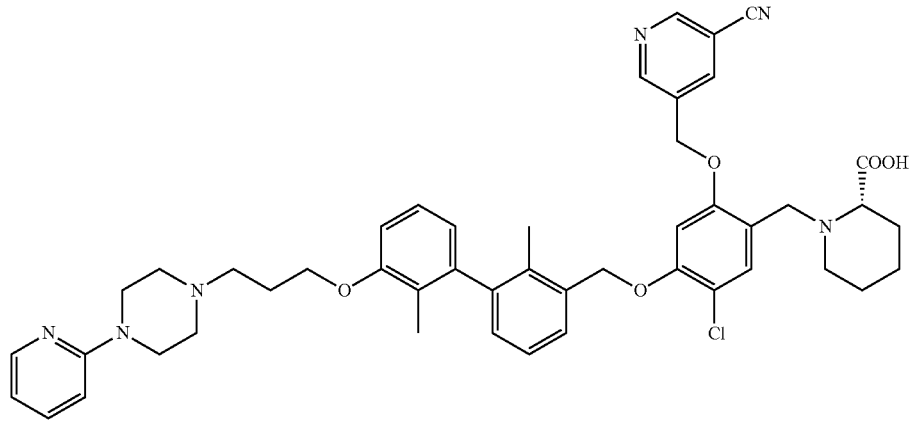 [SMILES: Cc1c(COc2cc(OCc3cncc(C#N)c3)c(CN3CCCC[C@H]3C(=O)O)cc2Cl)cccc1-c1cccc(OCCCN2CCN(c3ccccn3)CC2)c1C]

The compound was prepared and purified with the same method as that for Example 2205 to give the pure title compound: (2.4, 47%). $^1$H NMR (500 MHz, DMSO-d$_6$) δ 9.01 (d, J=8.8 Hz, 2H), 8.46 (s, 1H), 8.10 (d, J=2.9 Hz, 1H), 7.56-7.47 (m, 2H), 7.43 (s, 1H), 7.27 (t, J=7.7 Hz, 1H), 7.24-7.17 (m, 1H), 7.11 (s, 1H), 7.08 (d, J=7.3 Hz, 1H), 6.98 (d, J=8.4 Hz, 1H), 6.81 (d, J=8.4 Hz, 1H), 6.69 (d, J=7.3 Hz, 1H), 6.64-6.59 (m, 1H), 5.35-5.25 (m, 4H), 4.08 (d, J=8.8 Hz, 2H), 3.78 (d, J=13.2 Hz, 1H), 3.60 (d, J=13.9 Hz, 1H), 3.47 (d, J=4.4 Hz, 4H), 3.37 (br. s., 4H), 3.12 (br. s., 1H), 2.89 (br. s., 1H), 2.27 (br. s., 1H), 2.04 (s, 3H), 2.00-1.94 (m, 2H), 1.84 (s, 3H), 1.82-1.66 (m, 2H), 1.48 (br. s., 3H), 1.36 (br. s., 1H). LC/MS Condition E: RT=1.48 min; m/e=815.2 (M+H)$^+$.

Example 2217: (2S)-1-(5-chloro-2-((5-cyanopyridin-3-yl)methoxy)-4-((3'-(3-(4-(2-(isopropylamino)-2-oxoethyl)piperazin-1-yl)propoxy)-2,2'-dimethylbiphenyl-3-yl)methoxy)benzyl)piperidine-2-carboxylic Acid

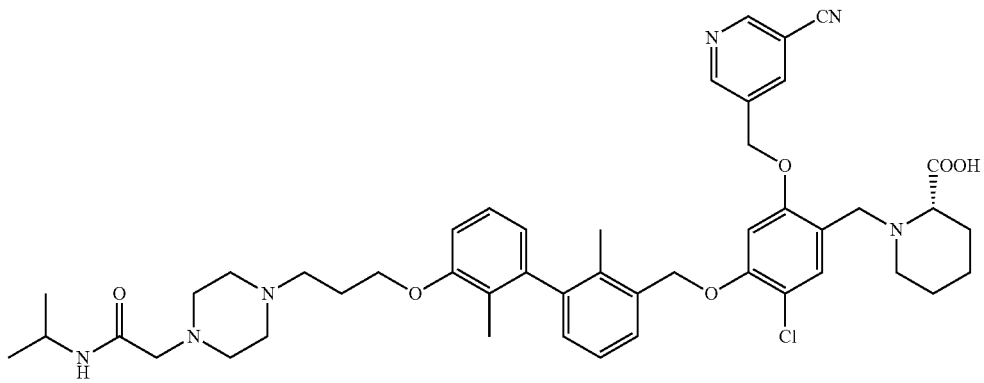 [SMILES: Cc1c(COc2cc(OCc3cncc(C#N)c3)c(CN3CCCC[C@H]3C(=O)O)cc2Cl)cccc1-c1cccc(OCCCN2CCN(CC(=O)NC(C)C)CC2)c1C]

The compound was prepared and purified with the same method as that for Example 2205 to give the pure title compound: (10.9 mg, 38%). LC/MS Condition E: RT=1.59 min; m/e=837.4 (M+H)$^+$.

Example 2218: (2S)-1-(5-chloro-2-((5-cyanopyridin-3-yl)methoxy)-4-((2,2'-dimethyl-3'-(3-(methyl(phenethyl)amino)propoxy)biphenyl-3-yl)methoxy)benzyl)piperidine-2-carboxylic Acid

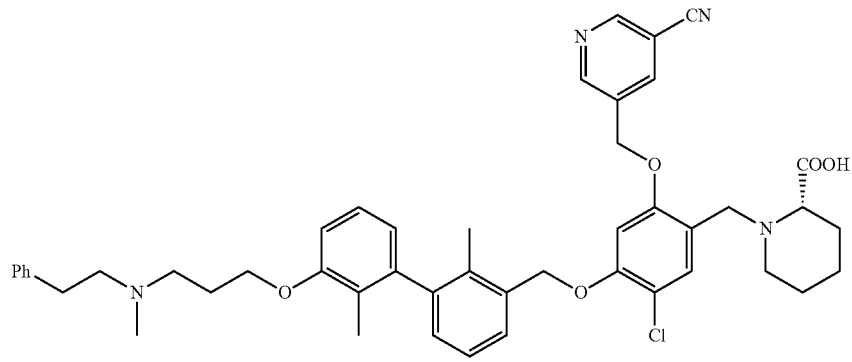 [SMILES: Cc1c(COc2cc(OCc3cncc(C#N)c3)c(CN3CCCC[C@H]3C(=O)O)cc2Cl)cccc1-c1cccc(OCCCN(C)CCc2ccccc2)c1C]

The compound was prepared and purified with the same method as that for Example 2205 to give the pure title compound: (4.2 mg, 16%). LC/MS Condition E: RT=1.78 min; m/e=787.2 (M+H)$^+$.

Example 2219: (2S)-1-(5-chloro-2-((5-cyanopyridin-3-yl)methoxy)-4-((3'-(3-(4-(2-methoxyphenyl)piperazin-1-yl)propoxy)-2,2'-dimethylbiphenyl-3-yl)methoxy)benzyl)piperidine-2-carboxylic Acid

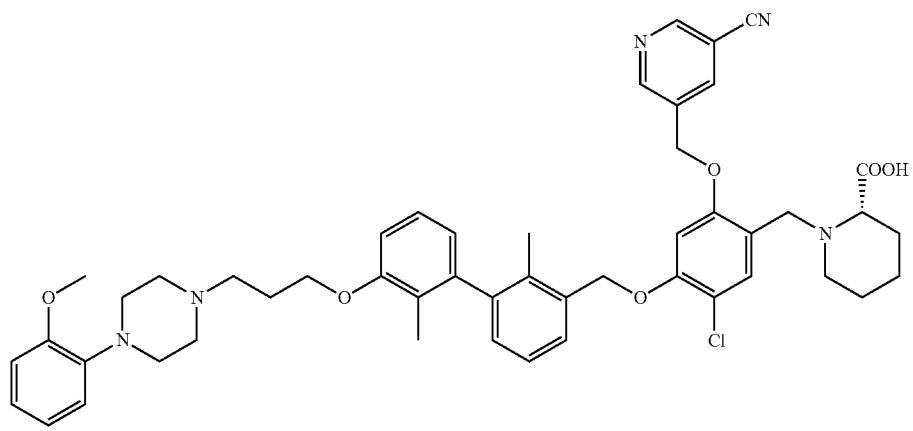 [SMILES: COc1ccccc1N1CCN(CCCOc2cccc(-c3cccc(COc4cc(OCc5cncc(C#N)c5)c(CN5CCCC[C@H]5C(=O)O)cc4Cl)c3C)c2C)CC1]

The compound was prepared and purified with the same method as that for Example 2205 to give the pure title compound: (6.4 mg, 22%). LC/MS Condition E: RT=1.68 min; m/e=844.2 (M+H)$^+$.

Example 2220: (2S)-1-(5-chloro-2-((5-cyanopyridin-3-yl)methoxy)-4-((3'-(3-((R)-2-hydroxy-2-phenylethylamino)propoxy)-2,2'-dimethylbiphenyl-3-yl)methoxy)benzyl)piperidine-2-carboxylic Acid

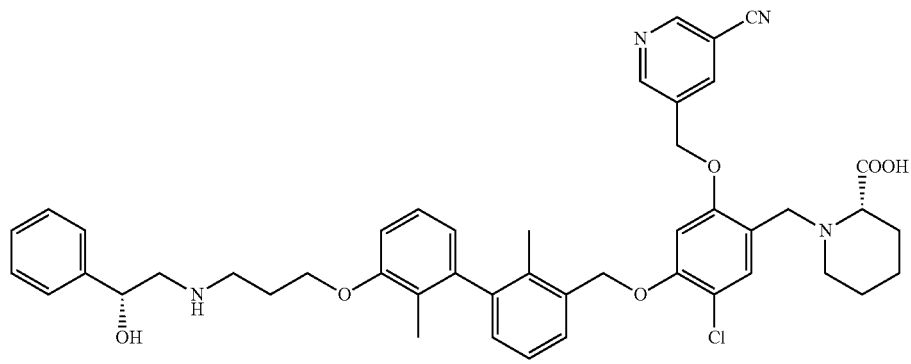 [SMILES: Cc1c(COc2cc(OCc3cncc(C#N)c3)c(CN3CCCC[C@H]3C(=O)O)cc2Cl)cccc1-c1cccc(OCCCNC[C@H](O)c2ccccc2)c1C]

The compound was prepared and purified with the same method as that for Example 2205 to give the pure title compound: (6.6 mg, 25%). LC/MS Condition E: RT=1.65 min; m/e=789.2 (M+H)$^+$.

Example 2221: (2S)-1-(5-chloro-2-((5-cyanopyridin-3-yl)methoxy)-4-((3'-(3-((S)-2-hydroxy-2-phenylethylamino)propoxy)-2,2'-dimethylbiphenyl-3-yl)methoxy)benzyl)piperidine-2-carboxylic Acid

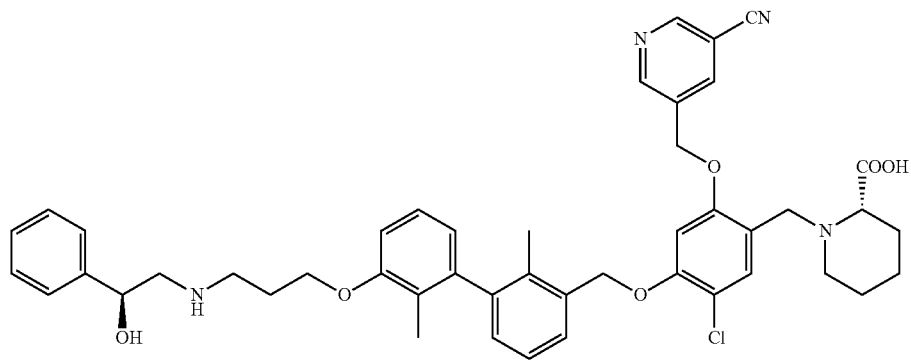 [SMILES: Cc1c(COc2cc(OCc3cncc(C#N)c3)c(CN3CCCC[C@H]3C(=O)O)cc2Cl)cccc1-c1cccc(OCCCNC[C@@H](O)c2ccccc2)c1C]

The compound was prepared and purified with the same method as that for Example 2205 to give the pure title compound: (5.6 mg, 20%). LC/MS Condition E: RT=1.70 min; m/e=789.1 (M+H)$^+$.

Example 2222: (2S)-1-(5-chloro-2-((5-cyanopyridin-3-yl)methoxy)-4-((3'-(3-(2-hydroxy-2-(pyridin-2-yl)ethylamino)propoxy)-2,2'-dimethylbiphenyl-3-yl)methoxy)benzyl)piperidine-2-carboxylic Acid

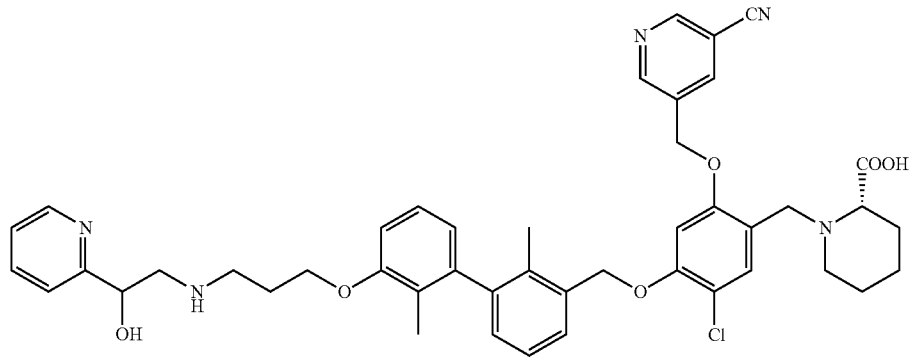 [SMILES: Cc1c(COc2cc(OCc3cncc(C#N)c3)c(CN3CCCC[C@H]3C(=O)O)cc2Cl)cccc1-c1cccc(OCCCNCC(O)c2ccccn2)c1C]

The compound was prepared and purified with the same method as that for Example 2205 to give the pure title compound: (8.6 mg, 30%). LC/MS Condition E: RT=1.60 min; m/e=790.4 (M+H)+.

Example 2223: (2S)-1-(5-chloro-2-((5-cyanopyridin-3-yl)methoxy)-4-((3'-(3-((R)-3-hydroxypiperidin-1-yl)propoxy)-2,2'-dimethylbiphenyl-3-yl)methoxy)benzyl)piperidine-2-carboxylic Acid

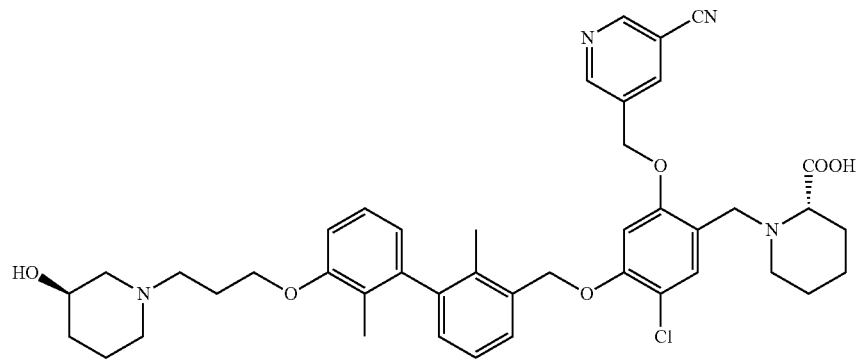 [SMILES: Cc1c(COc2cc(OCc3cncc(C#N)c3)c(CN3CCCC[C@H]3C(=O)O)cc2Cl)cccc1-c1cccc(OCCCN2CCC[C@@H](O)C2)c1C]

The compound was prepared and purified with the same method as that for Example 2205 to give the pure title compound: (10.9 mg, 32%). LC/MS Condition E: RT=1.59 min; m/e=753.2 (M+H)+.

Example 2224: (2S)-1-(5-chloro-2-((5-cyanopyridin-3-yl)methoxy)-4-((3'-(3-((S)-3-hydroxypiperidin-1-yl)propoxy)-2,2'-dimethylbiphenyl-3-yl)methoxy)benzyl)piperidine-2-carboxylic Acid

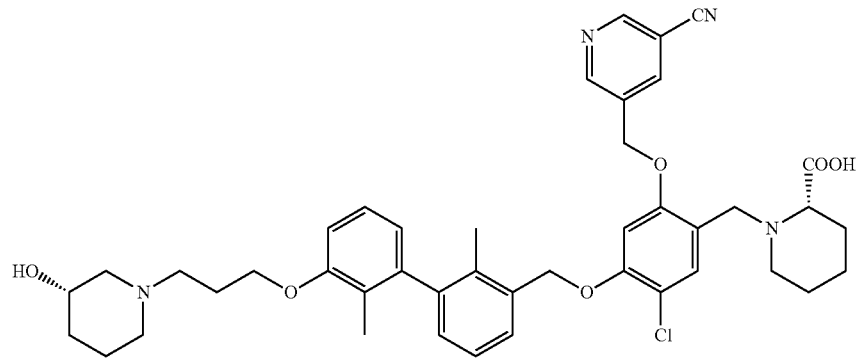 [SMILES: Cc1c(COc2cc(OCc3cncc(C#N)c3)c(CN3CCCC[C@H]3C(=O)O)cc2Cl)cccc1-c1cccc(OCCCN2CCC[C@H](O)C2)c1C]

The compound was prepared and purified with the same method as that for Example 2205 to give the pure title compound: (13.3 mg, 51%). LC/MS Condition E: RT=1.57 min; m/e=753.1 (M+H)⁺.

Example 2225: (2S)-1-(5-chloro-2-((5-cyanopyridin-3-yl)methoxy)-4-((2,2'-dimethyl-3'-(3-(2-(pyridin-2-yl)ethylamino)propoxy)biphenyl-3-yl)methoxy)benzyl)piperidine-2-carboxylic Acid

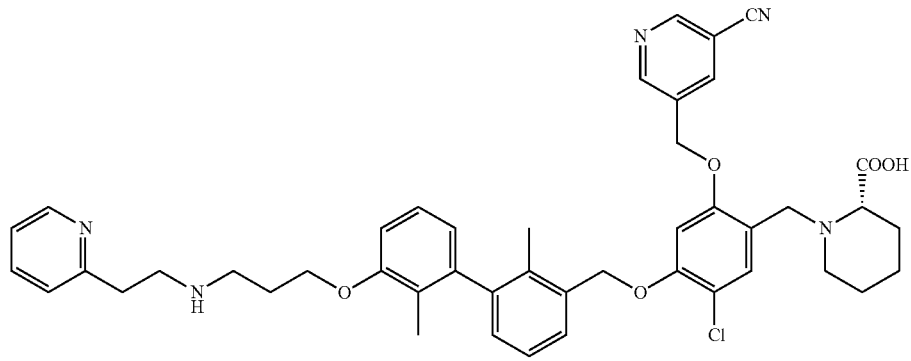 [SMILES: Cc1c(COc2cc(OCc3cncc(C#N)c3)c(CN3CCCC[C@H]3C(=O)O)cc2Cl)cccc1-c1cccc(OCCCNCCc2ccccn2)c1C]

The compound was prepared and purified with the same method as that for Example 2205 to give the pure title compound: (4.3 mg, 16%). $^1$H NMR (500 MHz, DMSO-d$_6$) δ 9.03 (d, J=11.7 Hz, 2H), 8.47 (s, 2H), 7.77 (t, J=7.7 Hz, 1H), 7.54-7.47 (m, 2H), 7.35 (d, J=7.7 Hz, 1H), 7.31-7.22 (m, 3H), 7.21-7.14 (m, 1H), 7.09-7.04 (m, 1H), 6.99 (d, J=8.4 Hz, 1H), 6.72 (d, J=7.7 Hz, 1H), 5.41-5.26 (m, 4H), 4.23-4.05 (m, 4H), 3.22 (br. s., 3H), 3.14-3.08 (m, 2H), 2.94 (br. s., 1H), 2.74 (s, 1H), 2.20-2.11 (m, 2H), 2.04 (s, 3H), 1.84 (d, J=2.9 Hz, 3H), 1.79-1.39 (m, 5H).

LC/MS Condition E: RT=1.61 min; m/e=774.2 (M+H)⁺.

Example 2226: (2S)-1-(5-chloro-2-((5-cyanopyridin-3-yl)methoxy)-4-((2,2'-dimethyl-3'-(3-(methyl(pyridin-3-ylmethyl)amino)propoxy)biphenyl-3-yl)methoxy)benzyl)piperidine-2-carboxylic Acid

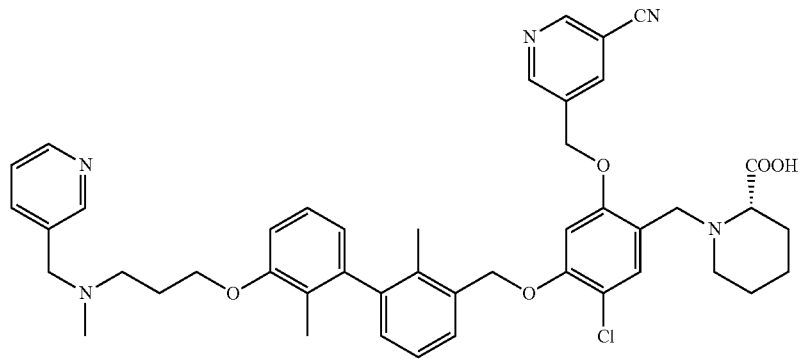 [SMILES: Cc1c(COc2cc(OCc3cncc(C#N)c3)c(CN3CCCC[C@H]3C(=O)O)cc2Cl)cccc1-c1cccc(OCCCN(C)Cc2cccnc2)c1C]

The compound was prepared and purified with the same method as that for Example 2205 to give the pure title compound: (2.2 mg, 8%). $^1$H NMR (500 MHz, DMSO-d$_6$) δ 9.01 (d, J=7.3 Hz, 1H), 8.47 (d, J=7.3 Hz, 1H), 8.42 (d, J=3.7 Hz, 1H), 7.69 (d, J=7.3 Hz, 1H), 7.49 (d, J=7.3 Hz, 1H), 7.43 (s, 1H), 7.30-7.24 (m, 2H), 7.21 (t, J=7.7 Hz, 1H), 7.12 (s, 1H), 7.08 (d, J=7.3 Hz, 1H), 6.94 (d, J=8.4 Hz, 1H), 6.68 (d, J=7.7 Hz, 1H), 5.37-5.21 (m, 4H), 4.11-3.98 (m, 2H), 3.81 (d, J=13.6 Hz, 1H), 3.65 (d, J=13.9 Hz, 1H), 3.55 (br. s., 1H), 3.16 (br. s., 1H), 2.90 (s, 2H), 2.61-2.56 (m, 1H), 2.32 (br. s., 1H), 2.25-2.13 (m, 3H), 2.03 (s, 3H), 1.96 (br. s., 1H), 1.82 (br. s., 1H), 1.76-1.66 (m, 3H), 1.49 (br. s., 2H), 1.37 (br. s., 1H)

LC/MS Condition E: RT=1.43 min; m/e=774.2 (M+H)⁺.

Example 2227: (S)-1-(4-((3'-(3-((3s,5s,7s)-adamantan-1-ylamino)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

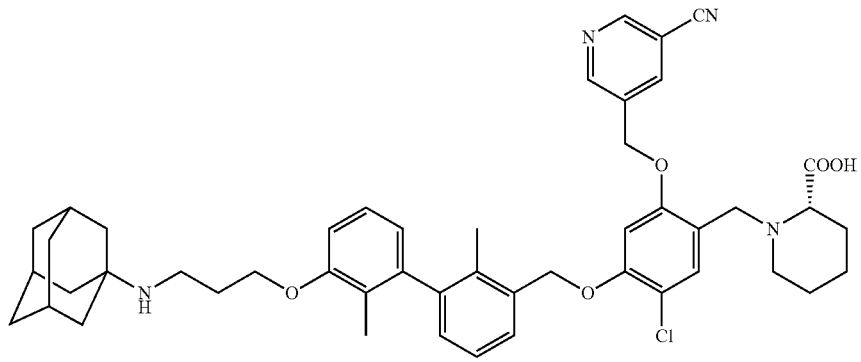 [SMILES: Cc1c(COc2cc(OCc3cncc(C#N)c3)c(CN3CCCC[C@H]3C(=O)O)cc2Cl)cccc1-c1cccc(OCCCNC23CC4CC(CC(C4)C2)C3)c1C]

The compound was prepared and purified with the same method as that for Example 2205 to give the pure title compound: (5.3 mg, 19%). LC/MS Condition E: RT=1.78 min; m/e=803.2 (M+H)$^+$.

Example 2228: (2S)-1-(5-chloro-2-((5-cyanopyridin-3-yl)methoxy)-4-((2,2'-dimethyl-3'-(3-(methyl(pyridin-2-ylmethyl)amino)propoxy)biphenyl-3-yl)methoxy)benzyl)piperidine-2-carboxylic Acid

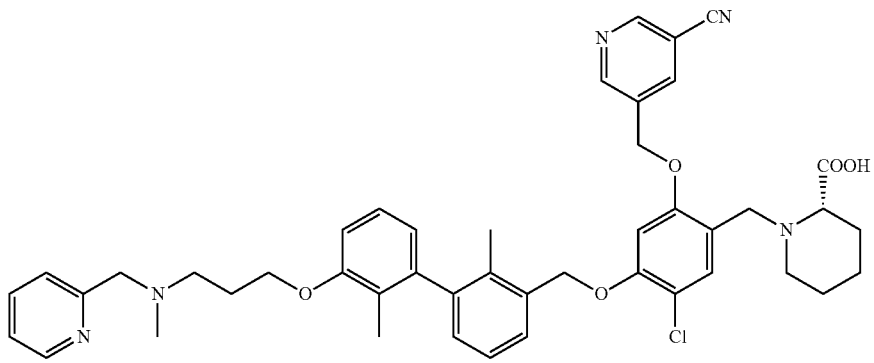 [SMILES: Cc1c(COc2cc(OCc3cncc(C#N)c3)c(CN3CCCC[C@H]3C(=O)O)cc2Cl)cccc1-c1cccc(OCCCN(C)Cc2ccccn2)c1C]

The compound was prepared and purified with the same method as that for Example 2205 to give the pure title compound: (8.6 mg, 31%). $^1$H NMR (500 MHz, DMSO-d$_6$) δ 9.01 (d, J=7.7 Hz, 2H), 8.49-8.41 (m, 2H), 7.66-7.59 (m, 1H), 7.49 (d, J=7.3 Hz, 1H), 7.43 (s, 1H), 7.39 (d, J=7.7 Hz, 1H), 7.28 (t, J=7.5 Hz, 1H), 7.23-7.15 (m, 2H), 7.12 (s, 1H), 7.07 (d, J=7.3 Hz, 1H), 6.95 (d, J=8.4 Hz, 1H), 6.68 (d, J=7.7 Hz, 1H), 5.38-5.21 (m, 4H), 4.11-4.00 (m, 2H), 3.79 (d, J=13.6 Hz, 1H), 3.64 (s, 1H), 3.14 (br. s., 1H), 2.90 (s, 1H), 2.30 (br. s., 1H), 2.23 (s, 3H), 2.03 (s, 3H), 1.95 (t, J=6.4 Hz, 2H), 1.79 (br. s., 1H), 1.68-1.67 (m, 1H), 1.49 (br. s., 3H), 1.36 (br. s., 1H). LC/MS Condition E: RT=1.85 min; m/e=774.2 (M+H)$^+$.

Example 2229: (2S)-1-(5-chloro-2-((5-cyanopyridin-3-yl)methoxy)-4-((3'-(3-((1r,4r)-4-(methoxycarbonyl)cyclohexylamino)propoxy)-2,2'-dimethylbiphenyl-3-yl)methoxy)benzyl)piperidine-2-carboxylic Acid

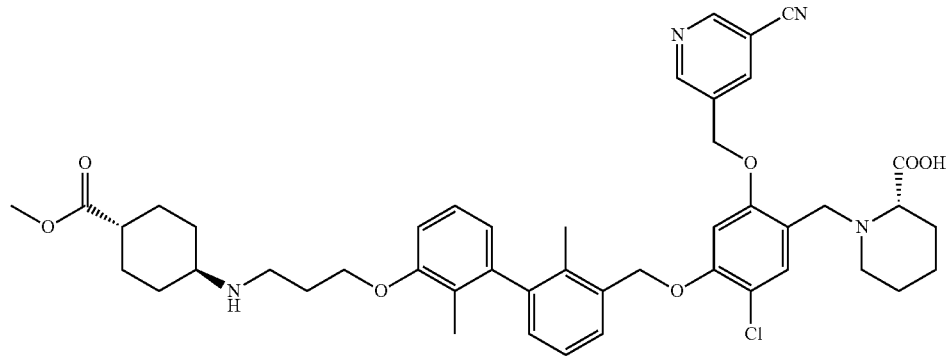 [SMILES: COC(=O)[C@H]1CC[C@H](NCCCOc2cccc(-c3cccc(COc4cc(OCc5cncc(C#N)c5)c(CN5CCCC[C@H]5C(=O)O)cc4Cl)c3C)c2C)CC1]

The compound was prepared and purified with the same method as that for Example 2205 to give the pure title compound: (5.0 mg, 18%). $^1$H NMR (500 MHz, METHANOL-d$_4$) δ 8.96 (d, J=15.0 Hz, 2H), 8.41 (br. s., 1H), 7.64 (s, 1H), 7.47 (d, J=7.3 Hz, 1H), 7.31-7.20 (m, 2H), 7.12-7.05 (m, 2H), 6.98 (d, J=8.4 Hz, 1H), 6.75 (d, J=7.7 Hz, 1H), 5.42-5.28 (m, 4H), 4.86 (br. s., 1H), 4.45 (d, J=14.7 Hz, 1H), 4.33 (d, J=12.5 Hz, 1H), 4.20 (br. s., 2H), 3.69 (s, 3H), 3.61 (br. s., 1H), 3.17 (t, J=11.6 Hz, 1H), 3.02-2.88 (m, 1H), 2.39 (t, J=11.9 Hz, 1H), 2.25 (br. s., 5H), 2.15 (d, J=12.5 Hz, 2H), 2.09 (s, 3H), 1.91 (d, J=7.7 Hz, 3H), 1.81 (br. s., 3H), 1.71 (br. s., 1H), 1.61-1.37 (m, 6H). LC/MS Condition E: RT=1.64 min; m/e=809.2 (M+H)$^+$.

Example 2230: (2S)-1-(5-chloro-2-((5-cyanopyridin-3-yl)methoxy)-4-((3'-(3-((R)-2-hydroxy-1-phenylethylamino)propoxy)-2,2'-dimethylbiphenyl-3-yl)methoxy)benzyl)piperidine-2-carboxylic Acid

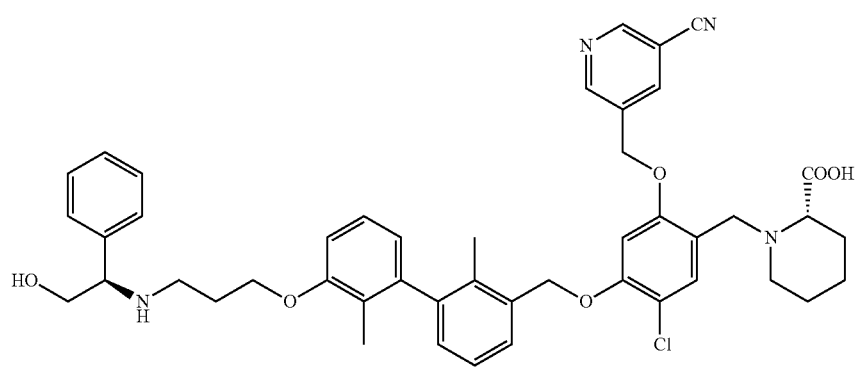 [SMILES: Cc1c(COc2cc(OCc3cncc(C#N)c3)c(CN3CCCC[C@H]3C(=O)O)cc2Cl)cccc1-c1cccc(OCCCN[C@@H](CO)c2ccccc2)c1C]

The compound was prepared and purified with the same method as that for Example 2205 to give the pure title compound: (8.3 mg, 28%). LC/MS Condition E: RT=1.78 min; m/e=789.1 (M+H)$^+$.

Example 2231: (2S)-1-(5-chloro-4-((3'-(3-(2-(5-chloro-1-methyl-1H-imidazol-4-yl)ethylamino)propoxy)-2,2'-dimethylbiphenyl-3-yl)methoxy)-2-((5-cyanopyridin-3-yl)methoxy)benzyl)piperidine-2-carboxylic Acid

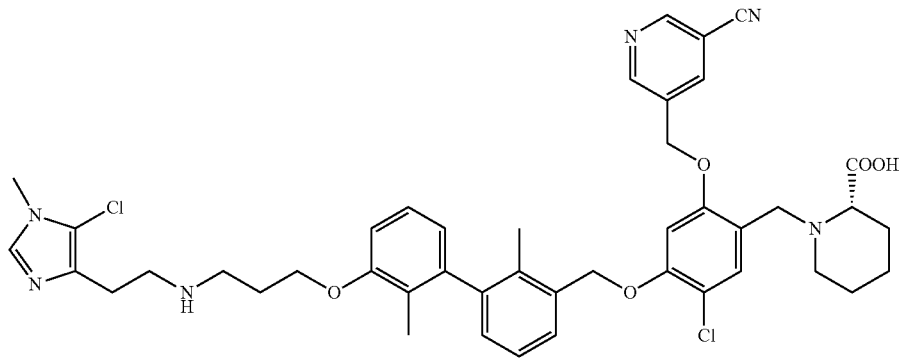 [SMILES: Cc1c(COc2cc(OCc3cncc(C#N)c3)c(CN3CCCC[C@H]3C(=O)O)cc2Cl)cccc1-c1cccc(OCCCNCCc2ncn(C)c2Cl)c1C]

The compound was prepared and purified with the same method as that for Example 2205 to give the pure title compound: (2.4 mg, 8%). $^1$H NMR (500 MHz, DMSO-d$_6$) δ 9.00 (d, J=9.2 Hz, 2H), 8.45 (br. s., 1H), 7.63 (s, 1H), 7.49 (d, J=7.7 Hz, 1H), 7.43 (s, 1H), 7.27 (t, J=7.5 Hz, 1H), 7.21 (t, J=7.9 Hz, 1H), 7.13-7.04 (m, 2H), 6.95 (d, J=8.4 Hz, 1H), 6.68 (d, J=7.7 Hz, 1H), 5.35-5.23 (m, 4H), 4.12-4.00 (m, 2H), 3.79 (d, J=13.9 Hz, 1H), 3.60 (dd, J=12.8, 6.6 Hz, 1H), 3.09 (br. s., 1H), 2.80 (q, J=7.5 Hz, 4H), 2.59 (t, J=7.3 Hz, 2H), 2.25 (br. s., 1H), 2.02 (s, 3H), 1.96-1.86 (m, 5H), 1.79 (d, J=10.3 Hz, 4H), 1.72 (br. s., 1H), 1.49 (br. s., 3H). LC/MS Condition E: RT=1.60 min; m/e=811.1 (M+H)$^+$.

Example 2232: (2S)-1-(5-chloro-2-((5-cyanopyridin-3-yl)methoxy)-4-((3'-(3-(3-(dimethylamino)azetidin-1-yl)propoxy)-2,2'-dimethylbiphenyl-3-yl)methoxy)benzyl)piperidine-2-carboxylic Acid

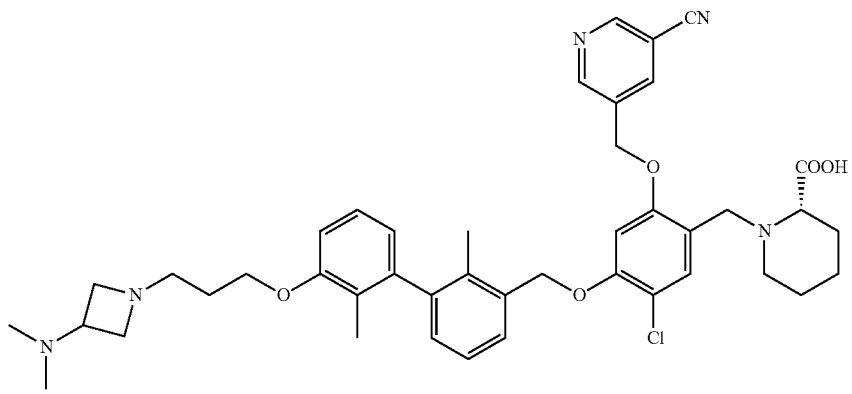 [SMILES: Cc1c(COc2cc(OCc3cncc(C#N)c3)c(CN3CCCC[C@H]3C(=O)O)cc2Cl)cccc1-c1cccc(OCCCN2CC(N(C)C)C2)c1C]

The compound was prepared and purified with the same method as that for Example 2205 to give the pure title compound: (4.4 mg, 16%). $^1$H NMR (500 MHz, DMSO-d$_6$) δ 9.00 (d, J=8.1 Hz, 2H), 8.46 (s, 1H), 7.49 (d, J=7.7 Hz, 1H), 7.44 (s, 1H), 7.27 (t, J=7.5 Hz, 1H), 7.20 (t, J=7.7 Hz, 1H), 7.11 (s, 1H), 7.07 (d, J=8.1 Hz, 1H), 6.94 (d, J=8.1 Hz, 1H), 6.68 (d, J=7.3 Hz, 1H), 5.39-5.22 (m, 4H), 4.07-3.96 (m, 2H), 3.81 (d, J=13.9 Hz, 1H), 3.64 (d, J=12.8 Hz, 1H), 3.39 (br. s., 2H), 3.13 (br. s., 1H), 2.94-2.90 (m, 1H), 2.78-2.74 (m, 1H), 2.30 (br. s., 1H), 1.99 (s, 6H), 1.91 (s, 6H), 1.85-1.68 (m, 7H), 1.49 (br. s., 3H), 1.37 (br. s., 1H). LC/MS Condition E: RT=1.40 min; m/e=752.1 (M+H)$^+$.

Example 2233: (2S)-1-(5-chloro-2-((5-cyanopyridin-3-yl)methoxy)-4-((3'-(3-((2-hydroxyethyl)(methyl)amino)propoxy)-2,2'-dimethylbiphenyl-3-yl)methoxy)benzyl)piperidine-2-carboxylic Acid

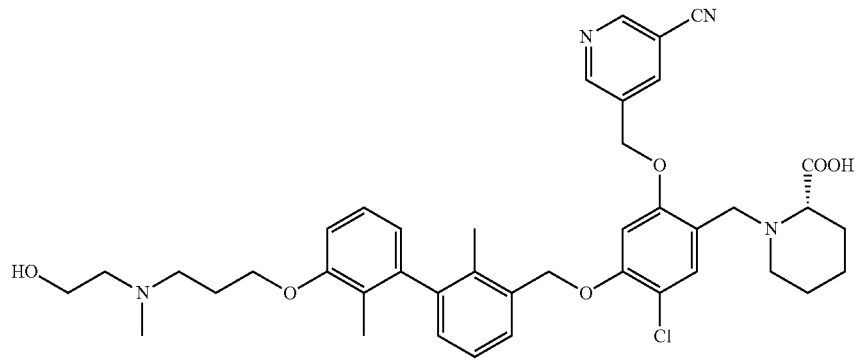 [SMILES: Cc1c(COc2cc(OCc3cncc(C#N)c3)c(CN3CCCC[C@H]3C(=O)O)cc2Cl)cccc1-c1cccc(OCCCN(C)CCO)c1C]

The compound was prepared and purified with the same method as that for Example 2205 to give the pure title compound: (9.5 mg, 38%). $^1$H NMR (500 MHz, DMSO-d$_6$) δ 9.01 (d, J=8.8 Hz, 2H), 8.46 (s, 1H), 7.49 (d, J=7.3 Hz, 1H), 7.45 (s, 1H), 7.29-7.21 (m, 2H), 7.13 (s, 1H), 7.07 (d, J=7.0 Hz, 1H), 6.98 (d, J=8.8 Hz, 1H), 6.72 (d, J=7.7 Hz, 1H), 5.34 (br. s., 2H), 5.28 (s, 2H), 4.13-4.05 (m, 2H), 3.86 (br. s., 1H), 3.74 (br. s., 3H), 3.31-3.11 (m, 4H), 2.94 (br. s., 1H), 2.83 (s, 3H), 2.18 (br. s., 2H), 2.03 (s, 3H), 1.84 (d, J=4.0 Hz, 4H), 1.73 (br. s., 1H), 1.51 (br. s., 3H), 1.38 (br. s., 1H). LC/MS Condition E: RT=1.45 min; m/e=727.2 (M+H)$^+$.

Example 2234: (2S)-1-(5-chloro-2-((5-cyanopyridin-3-yl)methoxy)-4-((3'-(3-(3-hydroxy-2,2-dimethylpropylamino)propoxy)-2,2'-dimethylbiphenyl-3-yl)methoxy)benzyl)piperidine-2-carboxylic Acid

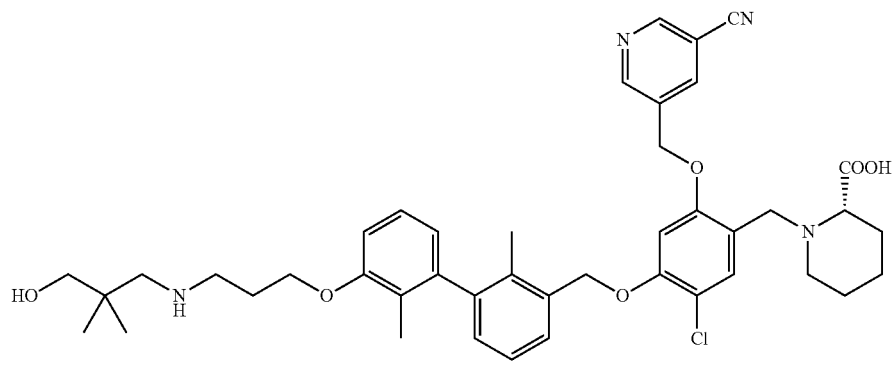 [SMILES: Cc1c(COc2cc(OCc3cncc(C#N)c3)c(CN3CCCC[C@H]3C(=O)O)cc2Cl)cccc1-c1cccc(OCCCNCC(C)(C)CO)c1C]

The compound was prepared and purified with the same method as that for Example 2205 to give the pure title compound: (9.6 mg, 35%). $^1$H NMR (500 MHz, DMSO-d$_6$) δ 9.00 (d, J=7.0 Hz, 2H), 8.45 (br. s., 1H), 7.51-7.43 (m, 2H), 7.27 (t, J=7.3 Hz, 1H), 7.20 (t, J=7.9 Hz, 1H), 7.12-7.02 (m, 2H), 6.95 (d, J=8.1 Hz, 1H), 6.68 (d, J=7.3 Hz, 1H), 5.34-5.23 (m, 4H), 4.06 (d, J=6.2 Hz, 2H), 3.84 (d, J=13.2 Hz, 1H), 3.66 (br. s., 1H), 3.20 (s, 2H), 3.10 (br. s., 1H), 2.96-2.90 (m, 1H), 2.89 (s, 2H), 2.81 (t, J=6.8 Hz, 2H), 2.30 (br. s., 1H), 2.01 (s, 3H), 1.99-1.93 (m, 2H), 1.89 (s, 12H), 1.80 (d, J=7.7 Hz, 4H), 1.71 (br. s., 1H), 1.49 (br. s., 4H), 1.35 (br. s., 1H), 0.83 (s, 6H). LC/MS Condition E: RT=1.53 min; m/e=755.2 (M+H)$^+$.

Example 2235: (2S)-1-(5-chloro-2-((5-cyanopyridin-3-yl)methoxy)-4-((3'-(3-(2,3-dihydroxypropylamino)propoxy)-2,2'-dimethylbiphenyl-3-yl)methoxy)benzyl)piperidine-2-carboxylic Acid

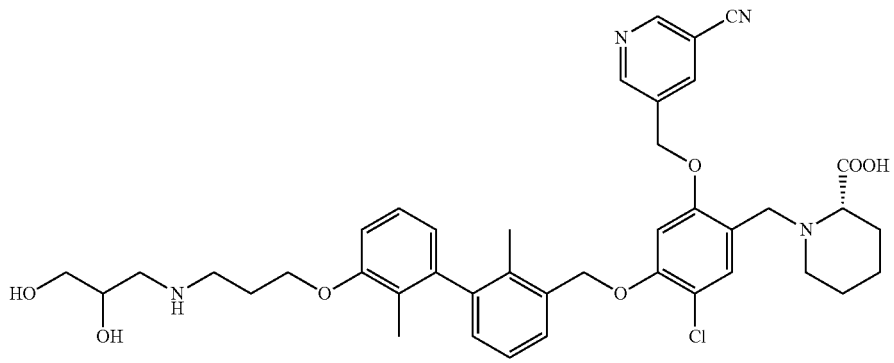 [SMILES: Cc1c(COc2cc(OCc3cncc(C#N)c3)c(CN3CCCC[C@H]3C(=O)O)cc2Cl)cccc1-c1cccc(OCCCNCC(O)CO)c1C]

The compound was prepared and purified with the same method as that for Example 2205 to give the pure title compound: (4.7 mg, 19%). $^1$H NMR (500 MHz, DMSO-d$_6$) δ 9.01 (d, J=7.0 Hz, 2H), 8.46 (s, 1H), 7.49 (d, J=7.7 Hz, 1H), 7.45 (s, 1H), 7.28 (t, J=7.3 Hz, 1H), 7.23 (t, J=7.7 Hz, 1H), 7.13 (d, J=2.6 Hz, 1H), 7.07 (d, J=7.0 Hz, 1H), 6.97 (d, J=8.1 Hz, 1H), 6.71 (d, J=7.3 Hz, 1H), 5.38-5.22 (m, 4H), 4.18-4.02 (m, 2H), 3.85 (d, J=14.3 Hz, 1H), 3.78 (br. s., 1H), 3.70 (d, J=14.3 Hz, 1H), 3.33 (dd, J=10.8, 6.4 Hz, 1H), 3.24-3.12 (m, 4H), 2.89 (s, 3H), 2.37 (br. s., 1H), 2.14 (br. s., 2H), 2.03 (s, 3H), 1.84 (d, J=4.4 Hz, 4H), 1.72 (br. s., 1H), 1.51 (br. s., 3H), 1.37 (br. s., 1H). LC/MS Condition E: RT=1.42 min; m/e=743.1 (M+H)$^+$.

Example 2236: (2S)-1-(4-((3'-(3-(benzyl(2-hydroxyethyl)amino)propoxy)-2,2'-dimethylbiphenyl-3-yl)methoxy)-5-chloro-2-((5-cyanopyridin-3-yl)methoxy)benzyl)piperidine-2-carboxylic Acid

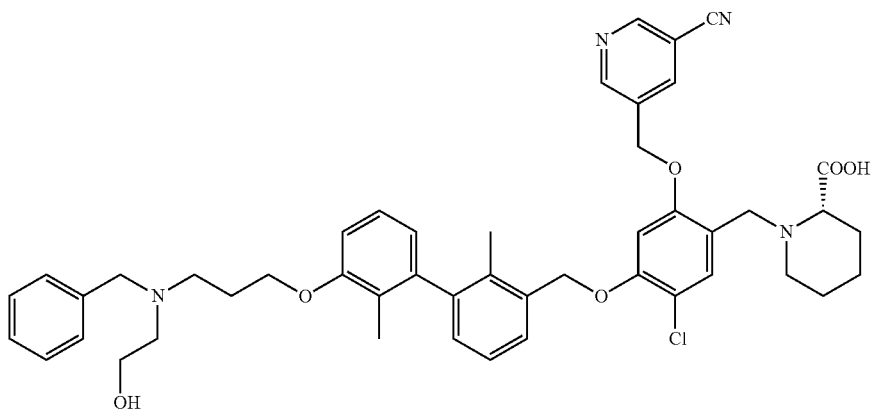 [SMILES: Cc1c(COc2cc(OCc3cncc(C#N)c3)c(CN3CCCC[C@H]3C(=O)O)cc2Cl)cccc1-c1cccc(OCCCN(CCO)Cc2ccccc2)c1C]

The compound was prepared and purified with the same method as that for Example 2205 to give the pure title compound: (5.2 mg, 19%). $^1$H NMR (500 MHz, DMSO-d$_6$) δ 9.03 (d, J=9.2 Hz, 2H), 8.47 (s, 1H), 7.55 (br. s., 2H), 7.50 (s, 2H), 7.44 (d, J=5.1 Hz, 3H), 7.33-7.25 (m, 1H), 7.22 (t, J=7.9 Hz, 1H), 7.18 (s, 1H), 7.07 (d, J=7.7 Hz, 1H), 6.95 (d, J=8.4 Hz, 1H), 6.70 (d, J=7.7 Hz, 1H), 5.39-5.27 (m, 4H), 4.40 (br. s., 2H), 4.08 (dd, J=11.6, 6.1 Hz, 4H), 3.77 (br. s., 2H), 3.34-3.07 (m, 5H), 2.65 (br. s., 1H), 2.24 (br. s., 2H), 2.03 (s, 3H), 2.00-1.95 (m, 1H), 1.74 (d, J=2.2 Hz, 4H), 1.60 (br. s., 3H), 1.45 (br. s., 1H). LC/MS Condition E: RT=2.01 min; m/e=803.2 (M+H)$^+$.

Example 2237: (2S)-1-(5-chloro-2-((5-cyanopyridin-3-yl)methoxy)-4-((3'-(3-((R)-1-hydroxy-3-methylbutan-2-ylamino)propoxy)-2,2'-dimethylbiphenyl-3-yl)methoxy)benzyl)piperidine-2-carboxylic Acid

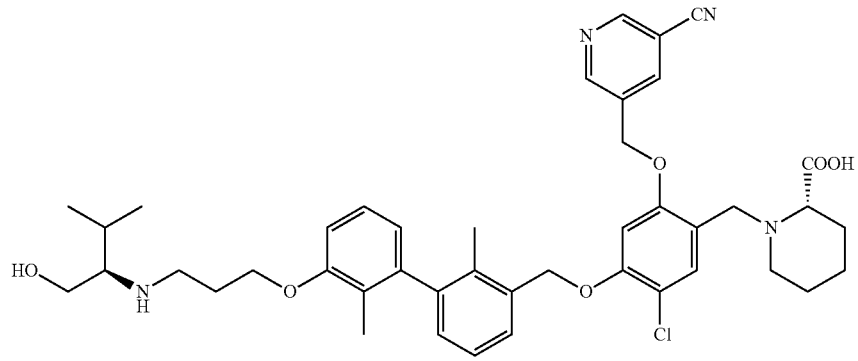 [SMILES: Cc1c(COc2cc(OCc3cncc(C#N)c3)c(CN3CCCC[C@H]3C(=O)O)cc2Cl)cccc1-c1cccc(OCCCN[C@@H](CO)C(C)C)c1C]

The compound was prepared and purified with the same method as that for Example 2205 to give the pure title compound: (4.6 mg, 18%). $^1$H NMR (500 MHz, DMSO-d$_6$) δ 9.03-8.96 (m, 2H), 8.46 (s, 1H), 7.49 (d, J=8.1 Hz, 1H), 7.43 (s, 1H), 7.27 (t, J=7.7 Hz, 1H), 7.21 (t, J=7.7 Hz, 1H), 7.10 (d, J=7.0 Hz, 1H), 7.09-7.03 (m, 1H), 6.96 (d, J=8.1 Hz, 1H), 6.68 (d, J=7.7 Hz, 1H), 5.36-5.23 (m, 4H), 4.14-4.04 (m, 2H), 3.79 (d, J=13.6 Hz, 1H), 3.61 (d, J=10.6 Hz, 1H), 3.34-3.26 (m, 1H), 3.10 (br. s., 1H), 2.90 (s, 2H), 2.85-2.77 (m, 1H), 2.29 (d, J=4.8 Hz, 2H), 2.02 (s, 3H), 1.90 (s, 5H), 1.79-1.64 (m, 3H), 1.49 (br. s., 3H), 1.36 (br. s., 1H), 0.87-0.81 (m, 6H). LC/MS Condition E: RT=1.57 min; m/e=755.2 (M+H)$^+$.

Example 2238: (2S)-1-(5-chloro-2-((5-cyanopyridin-3-yl)methoxy)-4-((3'-(3-((S)-1-hydroxy-3-methylbutan-2-ylamino)propoxy)-2,2'-dimethylbiphenyl-3-yl)methoxy)benzyl)piperidine-2-carboxylic Acid

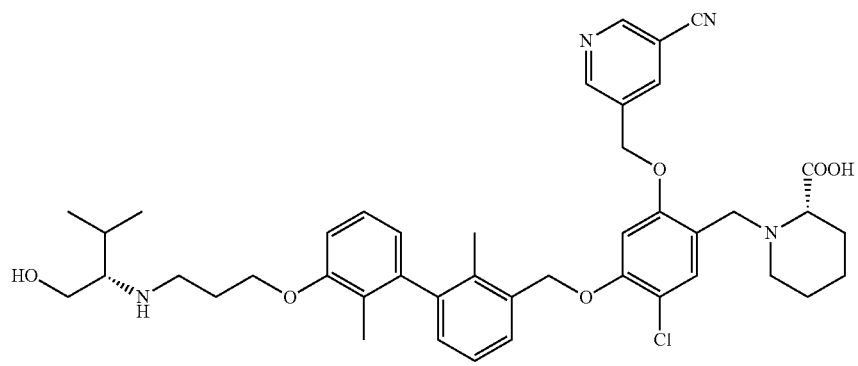 [SMILES: Cc1c(COc2cc(OCc3cncc(C#N)c3)c(CN3CCCC[C@H]3C(=O)O)cc2Cl)cccc1-c1cccc(OCCCN[C@H](CO)C(C)C)c1C]

The compound was prepared and purified with the same method as that for Example 2205 to give the pure title compound: (7.6 mg, 28%). $^1$H NMR (500 MHz, DMSO-d$_6$) δ 9.03-8.96 (m, 2H), 8.46 (s, 1H), 7.49 (d, J=8.1 Hz, 1H), 7.43 (s, 1H), 7.27 (t, J=7.7 Hz, 1H), 7.21 (t, J=7.7 Hz, 1H), 7.10 (d, J=7.0 Hz, 1H), 7.09-7.03 (m, 1H), 6.96 (d, J=8.1 Hz, 1H), 6.68 (d, J=7.7 Hz, 1H), 5.36-5.23 (m, 4H), 4.14-4.04 (m, 2H), 3.79 (d, J=13.6 Hz, 1H), 3.61 (d, J=10.6 Hz, 1H), 3.34-3.26 (m, 1H), 3.10 (br. s., 1H), 2.90 (s, 2H), 2.85-2.77 (m, 1H), 2.29 (d, J=4.8 Hz, 2H), 2.02 (s, 3H), 1.90 (s, 5H), 1.79-1.64 (m, 3H), 1.49 (br. s., 3H), 1.36 (br. s., 1H), 0.87-0.81 (m, 6H). LC/MS Condition E: RT=1.58 min; m/e=755.2 (M+H)$^+$.

Example 2239: (3R)-1-(3-(3'-((4-(((S)-2-carboxy-1-hydroxypropan-2-ylamino)methyl)-2-chloro-5-((5-cyanopyridin-3-yl)methoxy)phenoxy)methyl)-2,2'-dimethylbiphenyl-3-yloxy)propyl)piperidine-3-carboxylic Acid

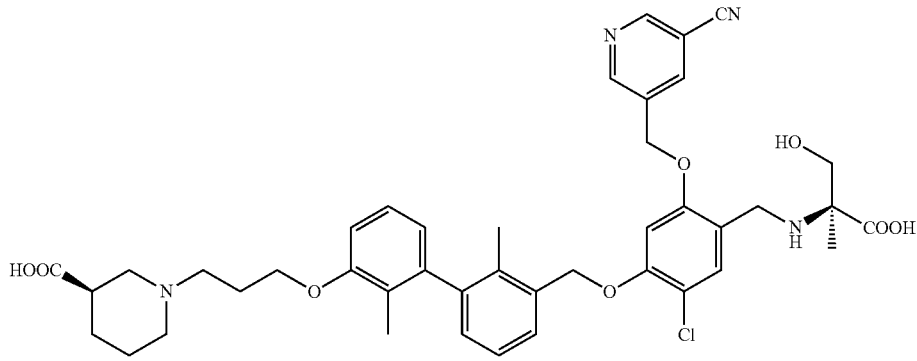 [SMILES: Cc1c(COc2cc(OCc3cncc(C#N)c3)c(CN[C@@](C)(CO)C(=O)O)cc2Cl)cccc1-c1cccc(OCCCN2CCC[C@@H](C(=O)O)C2)c1C]

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (0.06 g, 0.097 mmol) and (S)-2-amino-3-hydroxy-2-methylpropanoic acid (2-methyl-L-serine) (0.023 g, 0.194 mmol) in 1,2-dichloroethane (0.4 mL) and ethanol (0.6 mL) was added acetic acid (0.011 mL, 0.194 mmol) and ~0.03 g of 4 A molecule sieves. Sodium cyanoborohydride (0.194 mL, 0.194 mmol) diluted with THF (0.2 mL) was added through a syringe over 24 h. The reaction mixture was filtered and to the filtrate was added (R)-piperidine-3-carboxylic acid (0.125 g, 0.968 mmol) and DIPEA (0.169 mL, 0.968 mmol). The resulting mixture was stirred at 60° C. for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 minutes, then a 5-minute hold at 100% B; Flow: 20 mL/min. Fractions containing the desired product were combined and dried via centrifugal evaporation to give the title compound (7.7 mg, 10%). $^1$H NMR (500 MHz, DMSO-$d_6$) δ 9.04 (d, J=2.9 Hz, 2H), 8.51 (s, 1H), 7.96 (s, 1H), 7.58 (s, 1H), 7.49 (d, J=7.7 Hz, 1H), 7.28 (t, J=7.5 Hz, 1H), 7.24 (t, J=7.9 Hz, 1H), 7.16 (d, J=4.0 Hz, 1H), 7.07 (d, J=7.7 Hz, 1H), 6.98 (d, J=8.4 Hz, 1H), 6.71 (d, J=7.3 Hz, 1H), 5.38-5.31 (m, 4H), 4.17-4.01 (m, 4H), 3.78 (d, J=12.1 Hz, 1H), 3.69 (d, J=11.4 Hz, 1H), 3.27 (br. s., 2H), 2.82-2.75 (m, 1H), 2.19 (br. s., 2H), 2.04 (s, 3H), 2.01-1.94 (m, 1H), 1.85 (s, 4H), 1.74 (br. s., 1H), 1.53 (br. s., 1H), 1.34 (s, 3H). LC/MS Condition E: RT=1.41 min; m/e=771.2 (M+H)$^+$.

Example 2240: (2S)-1-(4-((3'-(3-((2S,4S)-2-carboxy-4-hydroxypyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

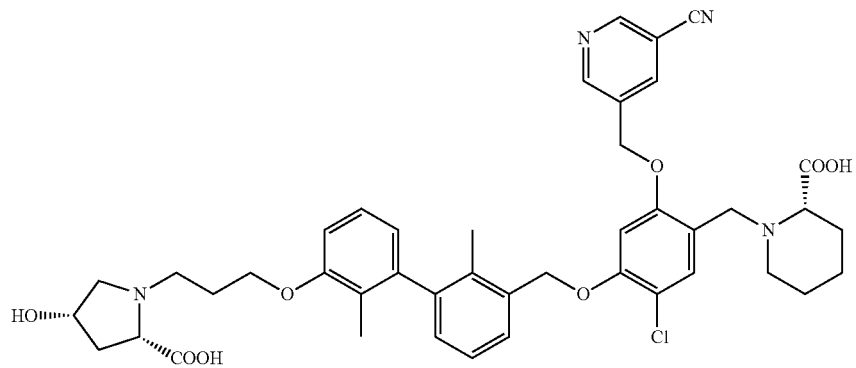 [SMILES: Cc1c(COc2cc(OCc3cncc(C#N)c3)c(CN3CCCC[C@H]3C(=O)O)cc2Cl)cccc1-c1cccc(OCCCN2C[C@@H](O)C[C@H]2C(=O)O)c1C]

The compound was prepared and purified with the same method as that for Example 2205 to give the pure title compound: (9.3 mg, 28%). $^1$H NMR (500 MHz, DMSO-$d_6$) δ 9.02 (d, J=9.5 Hz, 2H), 8.46 (br. s., 1H), 7.95 (s, 1H), 7.53-7.46 (m, 2H), 7.30-7.26 (m, 1H), 7.23 (t, J=7.9 Hz, 1H), 7.16 (d, J=5.9 Hz, 1H), 7.07 (d, J=4.0 Hz, 1H), 6.97 (d, J=8.1 Hz, 1H), 6.70 (d, J=7.7 Hz, 1H), 5.40-5.26 (m, 4H), 4.38 (br. s., 1H), 4.27 (d, J=7.3 Hz, 1H), 4.13-3.98 (m, 4H), 3.59 (br. s., 1H), 3.37 (br. s., 1H), 3.30 (br. s., 1H), 3.20 (br. s., 1H), 3.12 (br. s., 1H), 2.64 (br. s., 1H), 2.57 (d, J=4.4 Hz, 1H), 2.23-2.09 (m, 3H), 2.03 (s, 3H), 1.98 (br. s., 1H), 1.83 (d, J=12.8 Hz, 3H), 1.72 (d, J=9.9 Hz, 3H), 1.59 (br. s., 3H), 1.43 (br. s., 1H). LC/MS Condition E: RT=1.43 min; m/e=783.2 (M+H)$^+$.

Example 2241: (2S)-1-(4-((3'-(3-((2S,4R)-2-carboxy-4-hydroxypyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

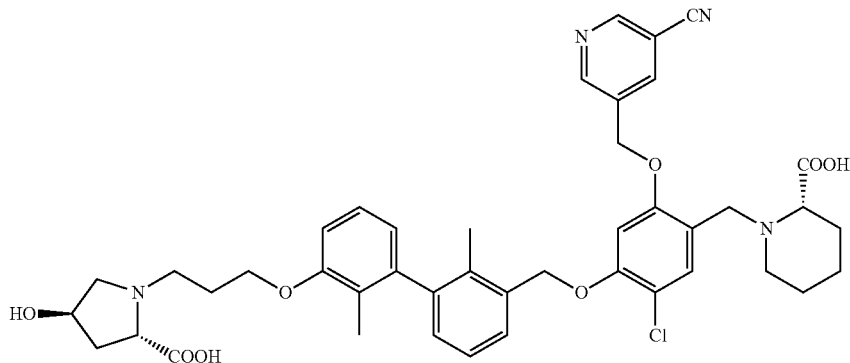 [SMILES: Cc1c(COc2cc(OCc3cncc(C#N)c3)c(CN3CCCC[C@H]3C(=O)O)cc2Cl)cccc1-c1cccc(OCCCN2C[C@H](O)C[C@H]2C(=O)O)c1C]

The compound was prepared and purified with the same method as that for Example 2205 to give the pure title compound: (3.8 mg, 13%). $^1$H NMR (500 MHz, DMSO-$d_6$) δ 9.05-8.99 (m, 2H), 8.46 (br. s., 1H), 7.95 (s, 1H), 7.52-7.44 (m, 2H), 7.30-7.25 (m, 2H), 7.24-7.20 (m, 1H), 7.15 (s, 1H), 7.10-7.03 (m, 2H), 6.96 (d, J=8.4 Hz, 1H), 6.70 (d, J=7.3 Hz, 1H), 5.38-5.28 (m, 4H), 4.36 (br. s., 1H), 4.20-3.99 (m, 5H), 3.71 (dd, J=11.9, 5.0 Hz, 1H), 3.64-3.56 (m, 1H), 3.26 (br. s., 1H), 3.12 (br. s., 1H), 3.01 (d, J=11.4 Hz, 1H), 2.64 (br. s., 1H), 2.27-2.18 (m, 1H), 2.16-2.08 (m, 3H), 2.03 (s, 3H), 1.98 (br. s., 1H), 1.81 (d, J=17.6 Hz, 4H), 1.72 (d, J=11.7 Hz, 1H), 1.59 (br. s., 3H), 1.44 (br. s., 1H). LC/MS Condition E: RT=1.42 min; m/e=783.1 (M+H)$^+$.

Example 2242: (2S)-1-(4-((3'-(3-((S)-2-carboxy-2-hydroxyethylamino)propoxy)-2,2'-dimethylbiphenyl-3-yl)methoxy)-5-chloro-2-((5-cyanopyridin-3-yl)methoxy)benzyl)piperidine-2-carboxylic Acid

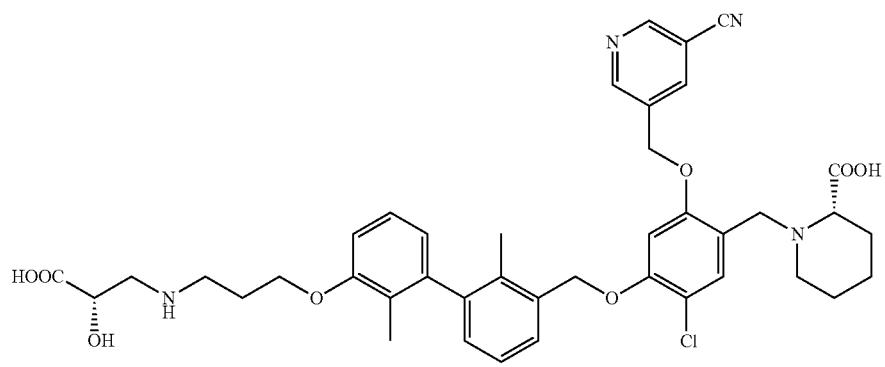 [SMILES: Cc1c(COc2cc(OCc3cncc(C#N)c3)c(CN3CCCC[C@H]3C(=O)O)cc2Cl)cccc1-c1cccc(OCCCNC[C@H](O)C(=O)O)c1C]

The compound was prepared and purified with the same method as that for Example 2205 to give the pure title compound: (2.9 mg, 10%). $^1$H NMR (500 MHz, DMSO-$d_6$) δ 9.02 (d, J=9.9 Hz, 2H), 8.47 (s, 1H), 7.52-7.44 (m, 2H), 7.30-7.21 (m, 2H), 7.16 (br. s., 1H), 7.07 (d, J=8.1 Hz, 1H), 6.97 (d, J=8.4 Hz, 1H), 6.71 (d, J=7.3 Hz, 1H), 5.39-5.27 (m, 4H), 4.33 (d, J=6.6 Hz, 1H), 4.13-4.04 (m, 2H), 3.97 (br. s., 1H), 3.36-3.28 (m, 3H), 3.23-2.97 (m, 5H), 2.15 (br. s., 2H), 2.04 (s, 3H), 1.91 (br. s., 1H), 1.84 (d, J=4.0 Hz, 3H), 1.72 (br. s., 1H), 1.56 (br. s., 3H), 1.43 (br. s., 1H). LC/MS Condition E: RT=1.49 min; m/e=757.2 (M+H)$^+$.

Example 2243: (2S)-1-(5-chloro-2-((5-cyanopyridin-3-yl)methoxy)-4-((3'-(3-((S)-2-(methoxycarbonyl)piperidin-1-yl)propoxy)-2,2'-dimethylbiphenyl-3-yl)methoxy)benzyl)piperidine-2-carboxylic Acid

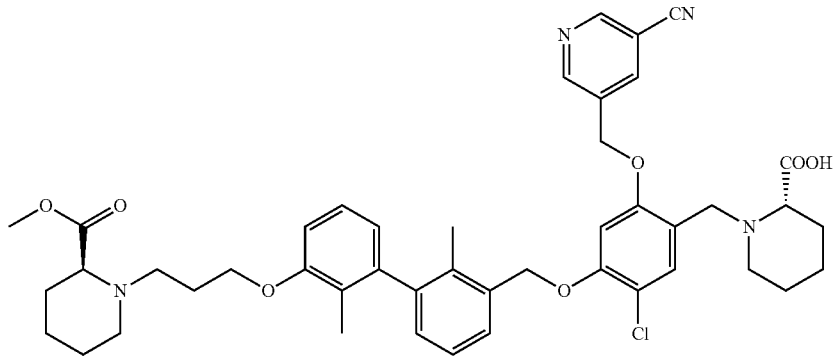 [SMILES: COC(=O)[C@@H]1CCCCN1CCCOc1cccc(-c2cccc(COc3cc(OCc4cncc(C#N)c4)c(CN4CCCC[C@H]4C(=O)O)cc3Cl)c2C)c1C]

The compound was prepared and purified with the same method as that for Example 2205 to give the pure title compound: (1.7 μmg, 8%). $^1$H NMR (500 MHz, DMSO-$d_6$) δ 9.01 (d, J=6.6 Hz, 2H), 8.46 (s, 1H), 7.49 (d, J=7.0 Hz, 1H), 7.43 (s, 1H), 7.27 (t, J=7.7 Hz, 1H), 7.21 (t, J=7.9 Hz, 1H), 7.12 (s, 1H), 7.07 (d, J=7.7 Hz, 1H), 6.95 (d, J=8.1 Hz, 1H), 6.68 (d, J=7.7 Hz, 1H), 5.36-5.24 (m, 4H), 4.09-3.96 (m, 2H), 3.78 (d, J=13.9 Hz, 1H), 3.61 (d, J=13.2 Hz, 1H), 3.56 (s, 3H), 3.18-3.10 (m, 2H), 2.96 (d, J=5.5 Hz, 1H), 2.89-2.85 (m, 1H), 2.71-2.60 (m, 1H), 2.43 (dd, J=12.8, 6.2 Hz, 1H), 2.32-2.18 (m, 2H), 2.03 (s, 3H), 1.88 (t, J=6.6 Hz, 2H), 1.80 (s, 4H), 1.67 (d, J=13.6 Hz, 3H), 1.50 (d, J=7.0 Hz, 6H), 1.36 (br. s., 2H). LC/MS Condition E: RT=2.21 min; m/e=795.2 (M+H)$^+$.

Example 2244: (2S)-1-(4-((3'-(3-(2-carbamoylpiperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

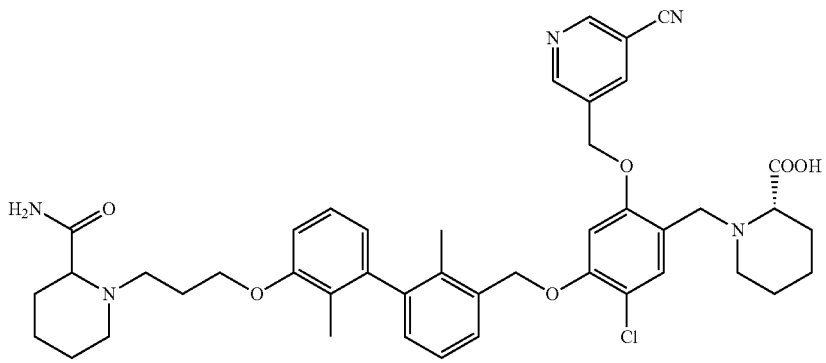 [SMILES: Cc1c(COc2cc(OCc3cncc(C#N)c3)c(CN3CCCC[C@H]3C(=O)O)cc2Cl)cccc1-c1cccc(OCCCN2CCCCC2C(N)=O)c1C]

The compound was prepared and purified with the same method as that for Example 2205 to give the pure title compound: (3.4 mg, 10%). $^1$H NMR (500 MHz, DMSO-$d_6$) δ 9.00 (d, J=4.0 Hz, 2H), 8.46 (s, 1H), 7.49 (d, J=7.7 Hz, 1H), 7.45 (s, 1H), 7.27 (t, J=7.3 Hz, 1H), 7.22-7.17 (m, 1H), 7.13-7.05 (m, 3H), 6.96 (d, J=8.4 Hz, 1H), 6.91 (br. s., 1H), 6.67 (d, J=7.3 Hz, 1H), 5.33 (s, 2H), 5.26 (s, 2H), 4.10-3.96 (m, 2H), 3.81 (d, J=13.2 Hz, 1H), 3.62 (br. s., 1H), 3.06 (d, J=9.9 Hz, 2H), 2.70 (br. s., 1H), 2.59 (d, J=9.5 Hz, 1H), 2.26 (d, J=5.9 Hz, 2H), 2.03 (s, 3H), 1.94 (d, J=6.6 Hz, 3H), 1.81 (s, 3H), 1.79-1.75 (m, 1H), 1.73-1.62 (m, 3H), 1.61-1.39 (m, 7H), 1.34 (br. s., 1H), 1.22 (d, J=13.2 Hz, 1H). LC/MS Condition E: RT=1.52 min; m/e=780.2 (M+H)$^+$.

Example 2245: (2S)-1-(5-chloro-2-((5-cyanopyridin-3-yl)methoxy)-4-((2,2'-dimethyl-3'-(3-(2-methylpiperidin-1-yl)propoxy)biphenyl-3-yl)methoxy)benzyl)piperidine-2-carboxylic Acid

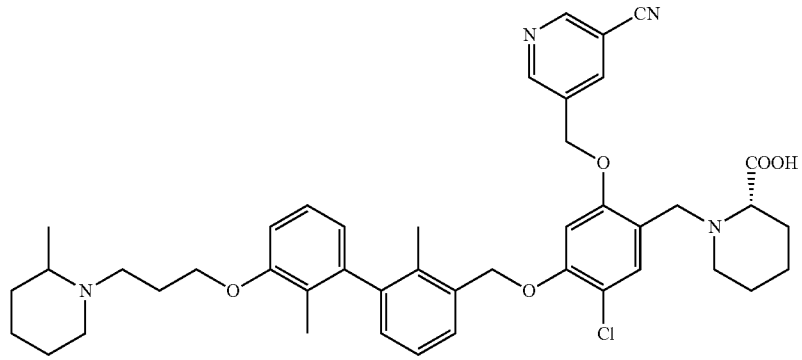 [SMILES: Cc1c(COc2cc(OCc3cncc(C#N)c3)c(CN3CCCC[C@H]3C(=O)O)cc2Cl)cccc1-c1cccc(OCCCN2CCCCC2C)c1C]

The compound was prepared and purified with the same method as that for Example 2205 to give the pure title compound: (13 mg, 32%). $^1$H NMR (500 MHz, DMSO-d$_6$) δ 9.01 (d, J=9.5 Hz, 2H), 8.47 (s, 1H), 7.50 (d, J=7.3 Hz, 1H), 7.44 (s, 1H), 7.31-7.26 (m, 1H), 7.23 (d, J=8.1 Hz, 2H), 7.14 (br. s., 1H), 7.07 (d, J=8.1 Hz, 1H), 6.98 (d, J=8.1 Hz, 1H), 6.72 (d, J=7.3 Hz, 1H), 5.35 (s, 2H), 5.28 (s, 2H), 4.21-4.04 (m, 2H), 3.89-3.80 (m, 1H), 3.73 (br. s., 1H), 3.23 (br. s., 2H), 2.93 (d, J=7.3 Hz, 1H), 2.39 (d, J=19.1 Hz, 1H), 2.16 (br. s., 2H), 2.03 (s, 3H), 1.84 (d, J=3.7 Hz, 6H), 1.71 (br. s., 4H), 1.51 (br. s., 5H), 1.39 (br. s., 1H), 1.28 (br. s., 4H). LC/MS Condition E: RT=1.63 min; m/e=751.2 (M+H)$^+$.

Example 2246: (2S)-1-(4-((3'-(3-(4-(tert-butoxycarbonyl(methyl)amino)piperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

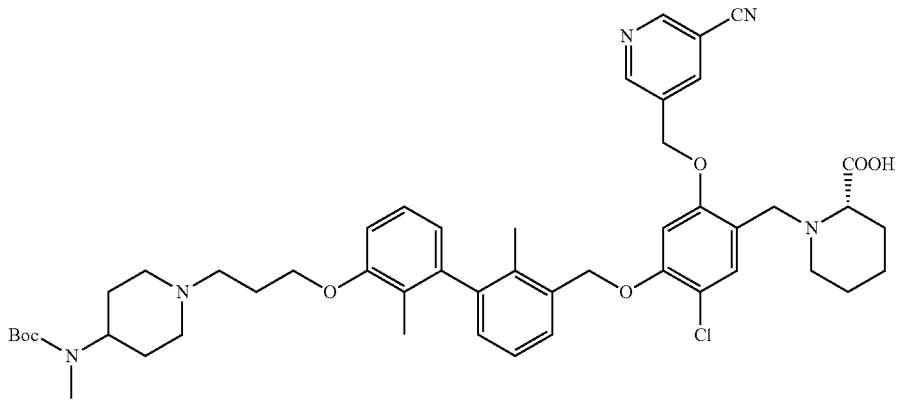 [SMILES: Cc1c(COc2cc(OCc3cncc(C#N)c3)c(CN3CCCC[C@H]3C(=O)O)cc2Cl)cccc1-c1cccc(OCCCN2CCC(N(C)C(=O)OC(C)(C)C)CC2)c1C]

The compound was prepared and purified with the same method as that for Example 2205 to give the pure title compound: (15.3 mg, 42%). $^1$H NMR (500 MHz, DMSO-d$_6$) δ 9.00 (d, J=8.1 Hz, 2H), 8.46 (s, 1H), 7.49 (d, J=7.3 Hz, 1H), 7.44 (s, 1H), 7.27 (t, J=7.3 Hz, 1H), 7.21 (t, J=7.9 Hz, 1H), 7.10 (s, 1H), 7.07 (d, J=7.7 Hz, 1H), 6.96 (d, J=8.1 Hz, 1H), 6.68 (d, J=7.7 Hz, 1H), 5.32 (br. s., 2H), 5.26 (s, 2H), 4.04 (d, J=10.3 Hz, 3H), 3.76 (br. s., 11H), 3.56 (d, J=13.2 Hz, 1H), 3.05 (br. s., 1H), 2.94 (d, J=11.7 Hz, 2H), 2.90 (s, 3H), 2.89-2.83 (m, 1H), 2.47 (t, J=7.2 Hz, 3H), 2.21 (br. s., 1H), 2.03 (s, 3H), 1.97-1.89 (m, 4H), 1.82 (s, 3H), 1.76 (d, J=5.5 Hz, 1H), 1.72-1.60 (m, 4H), 1.48 (br. s., 5H), 1.39 (s, 9H), 1.37-1.31 (m, 1H). LC/MS Condition E: RT=2.08 min; m/e=866.3 (M+H)$^+$.

Example 2247: (2S)-1-(5-chloro-2-((5-cyanopyridin-3-yl)methoxy)-4-((3'-(3-((S)-3-fluoropyrrolidin-1-yl)propoxy)-2,2'-dimethylbiphenyl-3-yl)methoxy)benzyl)piperidine-2-carboxylic Acid

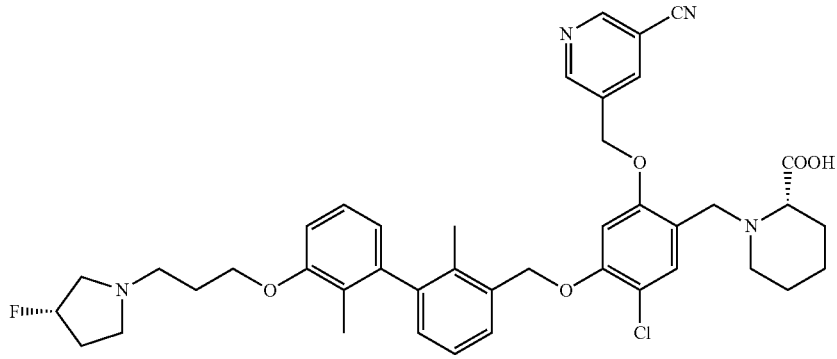 [SMILES: Cc1c(COc2cc(OCc3cncc(C#N)c3)c(CN3CCCC[C@H]3C(=O)O)cc2Cl)cccc1-c1cccc(OCCCN2CC[C@H](F)C2)c1C]

The compound was prepared and purified with the same method as that for Example 2205 to give the pure title compound: (8.0 mg, 26%). $^1$H NMR (500 MHz, DMSO-d$_6$) δ 9.00 (d, J=7.7 Hz, 2H), 8.46 (s, 1H), 7.49 (d, J=7.7 Hz, 1H), 7.44 (s, 1H), 7.27 (t, J=7.7 Hz, 1H), 7.23-7.17 (m, 1H), 7.11 (s, 1H), 7.08 (d, J=7.7 Hz, 1H), 6.96 (d, J=8.4 Hz, 1H), 6.68 (d, J=7.7 Hz, 1H), 5.36-5.25 (m, 4H), 5.25-5.10 (m, 1H), 4.13-3.99 (m, 2H), 3.79 (d, J=13.6 Hz, 1H), 3.60 (d, J=13.9 Hz, 1H), 3.09 (d, J=3.7 Hz, 1H), 2.88-2.76 (m, 3H), 2.66-2.57 (m, 3H), 2.34-2.22 (m, 2H), 2.20-2.07 (m, 1H), 2.03 (s, 3H), 1.98-1.91 (m, 2H), 1.83 (s, 3H), 1.80-1.66 (m, 2H), 1.49 (br. s., 3H), 1.36 (br. s., 1H). LC/MS Condition E: RT=1.56 min; m/e=741.2 (M+H)$^+$.

Example 2248: (2S)-1-(5-chloro-2-((5-cyanopyridin-3-yl)methoxy)-4-((2,2'-dimethyl-3'-(3-(4-morpholinopiperidin-1-yl)propoxy)biphenyl-3-yl)methoxy)benzyl)piperidine-2-carboxylic Acid The compound was prepared and purified with the same method as that for Example 2205 to give the pure title compound: (12.1 mg, 25%). LC/MS Condition E: RT=1.35 min; m/e=822.3 (M+H)$^+$.

Example 2249: (2S)-1-(4-((3'-(3-(2-oxa-5-azabicyclo[2.2.1]heptan-5-yl)propoxy)-2,2'-dimethylbiphenyl-3-yl)methoxy)-5-chloro-2-((5-cyanopyridin-3-yl)methoxy)benzyl)piperidine-2-carboxylic Acid

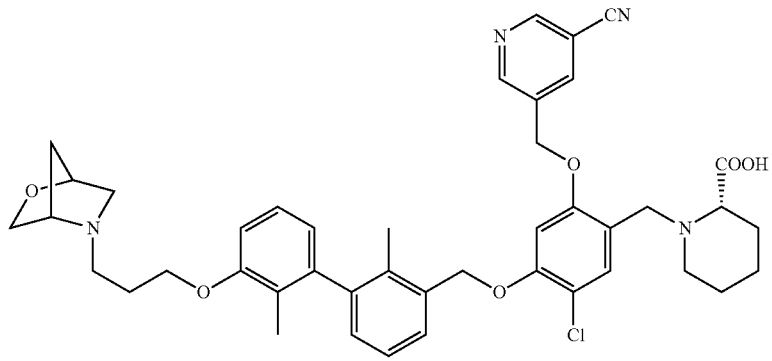 [SMILES: Cc1c(COc2cc(OCc3cncc(C#N)c3)c(CN3CCCC[C@H]3C(=O)O)cc2Cl)cccc1-c1cccc(OCCCN2CC3CC2CO3)c1C]

The compound was prepared and purified with the same method as that for Example 2205 to give the pure title compound: (10.4 mg, 30%). $^1$H NMR (500 MHz, DMSO-$d_6$) δ 9.02-8.98 (m, 2H), 8.46 (s, 1H), 7.49 (d, J=7.7 Hz, 1H), 7.45 (s, 1H), 7.27 (t, J=7.5 Hz, 1H), 7.21 (t, J=7.9 Hz, 1H), 7.11 (s, 1H), 7.07 (d, J=7.7 Hz, 1H), 6.96 (d, J=8.4 Hz, 1H), 6.68 (d, J=7.7 Hz, 1H), 5.33 (s, 2H), 5.26 (s, 2H), 4.32 (s, 1H), 4.13-4.02 (m, 2H), 3.88-3.78 (m, 3H), 3.64 (d, J=12.1 Hz, 1H), 3.10 (br. s., 1H), 2.80 (d, J=9.5 Hz, 1H), 2.72-2.60 (m, 2H), 2.40 (d, J=9.5 Hz, 1H), 2.31 (br. s., 1H), 2.03 (s, 3H), 1.88-1.83 (m, 3H), 1.82 (s, 3H), 1.72 (d, J=9.2 Hz, 3H), 1.56 (d, J=9.2 Hz, 1H), 1.49 (br. s., 4H), 1.35 (br. s., 1H). LC/MS Condition E: RT=1.64 min; m/e=751.2 (M+H)$^+$.

Example 2250: (2S)-1-(4-((3'-(3-((R)-3-acetamidopyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

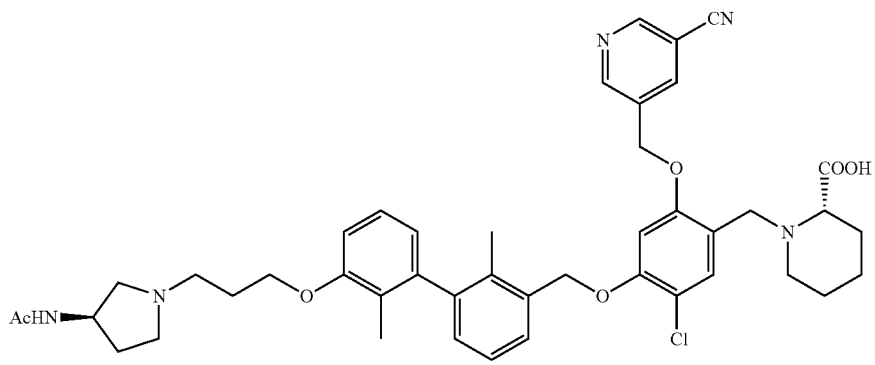 [SMILES: CC(=O)N[C@@H]1CCN(CCCOc2cccc(-c3cccc(COc4cc(OCc5cncc(C#N)c5)c(CN5CCCC[C@H]5C(=O)O)cc4Cl)c3C)c2C)C1]

The compound was prepared and purified with the same method as that for Example 2205 to give the pure title compound: (12.9 mg, 40%). $^1$H NMR (500 MHz, DMSO-$d_6$) δ 9.01 (d, J=8.4 Hz, 2H), 8.46 (s, 1H), 7.99 (d, J=7.0 Hz, 1H), 7.49 (d, J=7.3 Hz, 1H), 7.43 (s, 1H), 7.27 (t, J=7.7 Hz, 1H), 7.21 (t, J=7.9 Hz, 1H), 7.11 (s, 1H), 7.07 (d, J=7.7 Hz, 1H), 6.96 (d, J=8.4 Hz, 1H), 6.68 (d, J=7.3 Hz, 1H), 5.33 (br. s., 2H), 5.26 (s, 2H), 4.17-4.02 (m, 3H), 3.79 (d, J=13.9 Hz, 1H), 3.60 (d, J=12.8 Hz, 1H), 3.10 (br. s., 1H), 2.89-2.83 (m, 1H), 2.68-2.55 (m, 4H), 2.42-2.31 (m, 2H), 2.27 (br. s., 1H), 2.13-2.05 (m, 1H), 2.03 (s, 3H), 1.96-1.91 (m, 2H), 1.82 (s, 3H), 1.78 (s, 3H), 1.72 (br. s., 1H), 1.58-1.43 (m, 5H), 1.36 (br. s., 1H). LC/MS Condition E: RT=1.55 min; m/e=780.2 (M+H)$^+$.

Example 2251: (2S)-1-(4-((3'-(3-(2-(carboxymethyl)piperidin-1-yl)propoxy)-2,2'-dimethylbiphenyl-3-yl)methoxy)-5-chloro-2-((5-cyanopyridin-3-yl)methoxy)benzyl)piperidine-2-carboxylic Acid

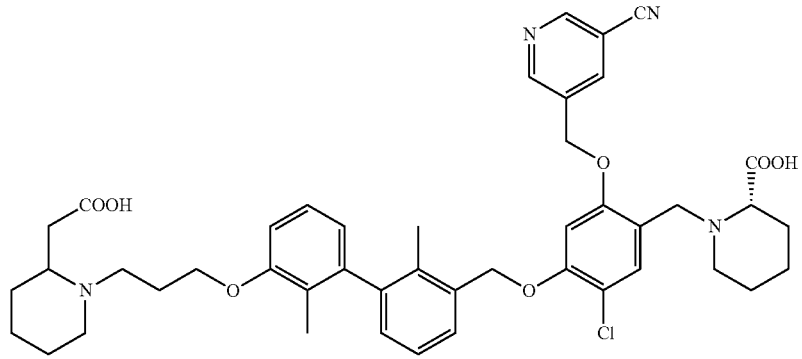 [SMILES: Cc1c(COc2cc(OCc3cncc(C#N)c3)c(CN3CCCC[C@H]3C(=O)O)cc2Cl)cccc1-c1cccc(OCCCN2CCCCC2CC(=O)O)c1C]

The compound was prepared and purified with the same method as that for Example 2205 to give the pure title compound: (2.2 mg, 7%). $^1$H NMR (500 MHz, DMSO-$d_6$) δ 9.03-8.97 (m, 2H), 8.46 (s, 1H), 7.48 (d, J=7.7 Hz, 1H), 7.46 (s, 1H), 7.27 (t, J=7.7 Hz, 1H), 7.21 (t, J=7.9 Hz, 1H), 7.11 (s, 1H), 7.07 (d, J=7.3 Hz, 1H), 6.95 (d, J=8.4 Hz, 1H), 6.68 (d, J=7.7 Hz, 1H), 5.33 (s, 2H), 5.27 (br. s., 2H), 4.10-4.00 (m, 2H), 3.84 (d, J=10.3 Hz, 1H), 3.67 (br. s., 1H), 3.11 (br. s., 1H), 2.98 (br. s., 3H), 2.72-2.64 (m, 1H), 2.49-2.42 (m, 2H), 2.32 (br. s., 1H), 2.22 (dd, J=15.4, 6.6 Hz, 1H), 2.02 (s, 3H), 1.95 (br. s., 2H), 1.81 (d, J=3.3 Hz, 4H), 1.70 (br. s., 2H), 1.61-1.30 (m, 10H). LC/MS Condition E: RT=1.57 min; m/e=795.2 (M+H)$^+$.

Example 2252: (2S)-1-(5-chloro-2-((5-cyanopyridin-3-yl)methoxy)-4-((3'-(3-((R)-3-methoxypyrrolidin-1-yl)propoxy)-2,2'-dimethylbiphenyl-3-yl)methoxy)benzyl)piperidine-2-carboxylic Acid

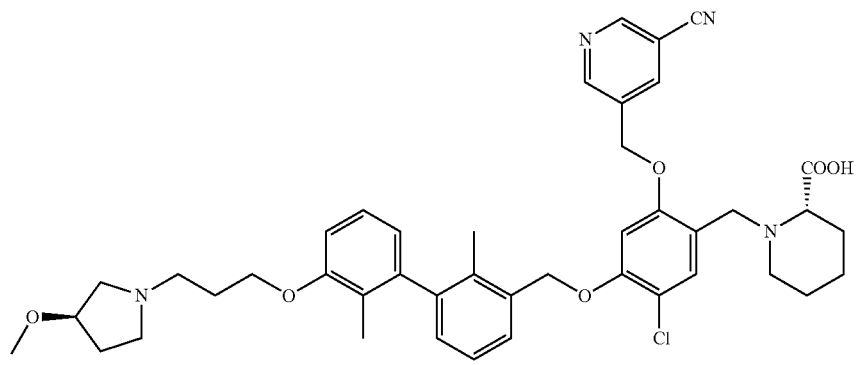 [SMILES: CO[C@@H]1CCN(CCCOc2cccc(-c3cccc(COc4cc(OCc5cncc(C#N)c5)c(CN5CCCC[C@H]5C(=O)O)cc4Cl)c3C)c2C)C1]

The compound was prepared and purified with the same method as that for Example 2205 to give the pure title compound: (4.2 mg, 10%). $^1$H NMR (500 MHz, DMSO-$d_6$) δ 9.03 (d, J=8.1 Hz, 2H), 8.48 (s, 1H), 7.52-7.47 (m, 2H), 7.28 (t, J=7.5 Hz, 1H), 7.25-7.22 (m, 1H), 7.20 (s, 1H), 7.07 (s, 1H), 6.97 (d, J=8.4 Hz, 1H), 6.71 (d, J=7.3 Hz, 1H), 5.38 (d, J=4.4 Hz, 2H), 5.31 (br. s., 2H), 4.19-4.04 (m, 5H), 3.48 (br. s., 6H), 3.35 (br. s., 3H), 3.26 (s, 3H), 3.17 (br. s., 2H), 2.17 (br. s., 2H), 2.04 (s, 5H), 1.85 (d, J=1.8 Hz, 3H), 1.78-1.44 (m, 5H). LC/MS Condition E: RT=1.53 min; m/e=753.2 (M+H)$^+$.

Example 2253: (2S)-1-(5-chloro-2-((5-cyanopyridin-3-yl)methoxy)-4-((3'-(3-(dimethylamino)propoxy)-2,2'-dimethylbiphenyl-3-yl)methoxy)benzyl)piperidine-2-carboxylic Acid

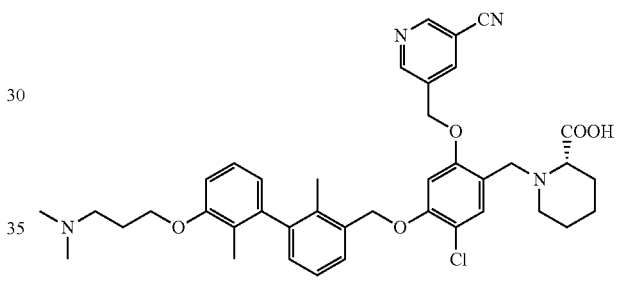

The compound was prepared and purified with the same method as that for Example 2205 to give the pure title compound: (5.9 mg, 15%). $^1$H NMR (500 MHz, DMSO-$d_6$) δ 9.04-9.00 (m, 2H), 8.47 (s, 1H), 7.50 (d, J=7.7 Hz, 1H), 7.47 (s, 1H), 7.28 (t, J=7.7 Hz, 2H), 7.22 (d, J=8.1 Hz, 2H), 7.16 (s, 1H), 7.07 (d, J=7.3 Hz, 1H), 6.97 (d, J=8.1 Hz, 1H), 6.71 (d, J=7.7 Hz, 1H), 5.36 (br. s., 2H), 5.29 (s, 2H), 4.17-4.03 (m, 2H), 3.94 (br. s., 1H), 3.84 (br. s., 1H), 3.30-3.23 (m, 2H), 3.01 (br. s., 1H), 2.83 (s, 6H), 2.20-2.11 (m, 2H), 2.03 (s, 3H), 1.91 (br. s., 1H), 1.85 (d, J=2.6 Hz, 3H), 1.71 (br. s., 1H), 1.54 (br. s., 3H), 1.41 (br. s., 1H). LC/MS Condition E: RT=1.51 min; m/e=697.2 (M+H)+.

Example 2254: 5-((4-chloro-2-(((2,3-dihydroxypropyl)(methyl)amino)methyl)-5-((3-(3-((2,3-dihydroxypropyl) (methyl)amino)propoxy)-2,2'-dimethylbiphenyl-3-yl)methoxy)phenoxy)methyl)nicotinonitrile

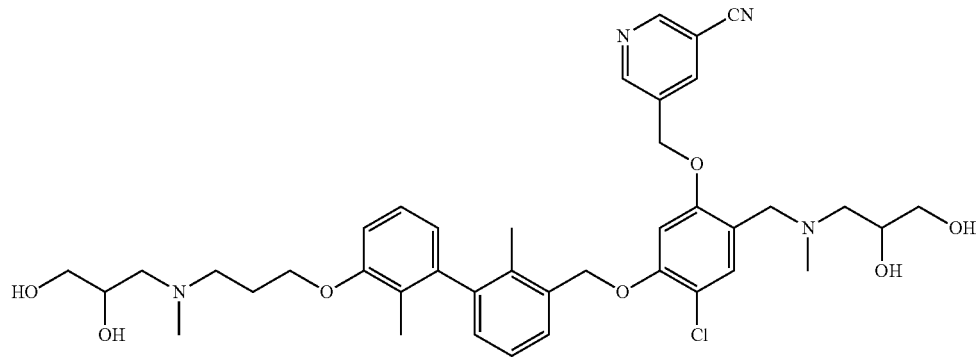 [SMILES: Cc1c(COc2cc(OCc3cncc(C#N)c3)c(CN(C)CC(O)CO)cc2Cl)cccc1-c1cccc(OCCCN(C)CC(O)CO)c1C]

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (0.03 g, 0.048 mmol) and 3-methylamino-1,2-propanediol (10.18 mg, 0.097 mmol) in DCE (0.3 mL) and EtOH (0.7 mL) was added acetic acid (5.54 μl, 0.097 mmol) and ~0.01 g of 4 A molecule sieves and sodium cyanoborohydride (0.073 mL, 0.073 mmol). The resulting mixture was stirred at rt for 16 h. Additional 8 equivalent of 3-methylamino-1,2-propanediol (40 mg, 0.4 mmol) and DIPEA (0.085 mL, 0.484 mmol) were added and the reaction mixture was stirred at 60° C. for 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation to give the pure title compound: (18.6 mg, 52%). 1H NMR (500 MHz, DMSO-d6) δ 9.01 (s, 1H), 8.97 (s, 1H), 8.43 (s, 1H), 7.48 (d, J=7.3 Hz, 1H), 7.38 (s, 1H), 7.27 (t, J=7.5 Hz, 1H), 7.21 (t, J=7.7 Hz, 1H), 7.10 (s, 1H), 7.07 (d, J=7.3 Hz, 1H), 6.96 (d, J=8.1 Hz, 1H), 6.68 (d, J=7.3 Hz, 1H), 5.31 (s, 2H), 5.25 (br. s., 2H), 4.05 (d, J=7.3 Hz, 2H), 3.60 (d, J=5.1 Hz, 2H), 3.35-3.25 (m, 4H), 2.61 (br. s., 2H), 2.44 (dd, J=12.5, 5.1 Hz, 2H), 2.38-2.30 (m, 2H), 2.28 (s, 2H), 2.15 (s, 3H), 2.03 (s, 3H), 1.93 (br. s., 2H), 1.83 (s, 3H). LC/MS Condition E: RT=1.35 min; m/e=733.2 (M+H)+.

Example 2255: 5-((4-chloro-2-((3-(hydroxymethyl)piperidin-1-yl)methyl)-5-((3'-(3-(3-(hydroxymethyl)piperidin-1-yl)propoxy)-2,2'-dimethylbiphenyl-3-yl)methoxy)phenoxy)methyl)nicotinonitrile

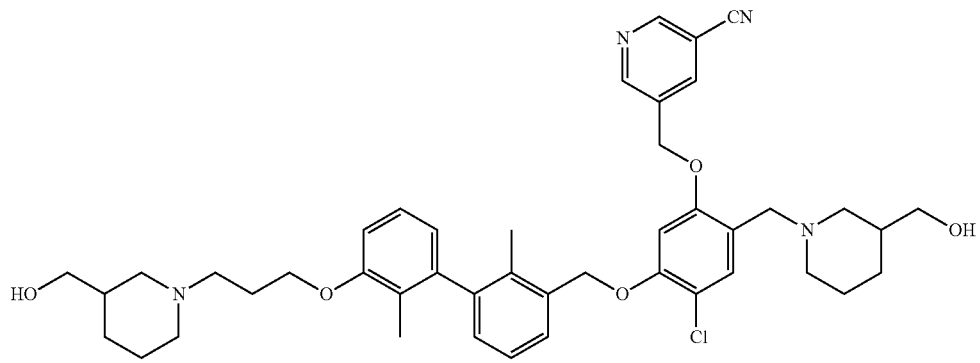 [SMILES: Cc1c(COc2cc(OCc3cncc(C#N)c3)c(CN3CCCC(CO)C3)cc2Cl)cccc1-c1cccc(OCCCN2CCCC(CO)C2)c1C]

The compound was prepared with the same method as that for Example 2254. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 5-minute hold at 100% B; Flow: 20 mL/min. Fractions containing the desired product were combined and dried via centrifugal evaporation to give the pure title compound as TFA salt: (18.5 mg, 34%). $^1$H NMR (500 MHz, DMSO-d$_6$) δ 9.06 (d, J=7.7 Hz, 2H), 8.50 (s, 1H), 7.63 (s, 1H), 7.52 (d, J=8.1 Hz, 1H), 7.30 (t, J=7.7 Hz, 1H), 7.26-7.20 (m, 3H), 7.16 (br. s., 1H), 7.09 (d, J=7.3 Hz, 1H), 7.06 (br. s., 1H), 6.99 (d, J=8.4 Hz, 1H), 6.72 (d, J=7.3 Hz, 1H), 5.39 (s, 2H), 5.36-5.30 (m, 2H), 4.23 (br. s., 2H), 4.16-4.03 (m, 2H), 3.53 (d, J=11.0 Hz, 2H), 3.36 (d, J=6.6 Hz, 3H), 3.28 (br. s., 3H), 3.21 (br. s., 1H), 2.84 (br. s., 2H), 2.67 (d, J=10.6 Hz, 2H), 2.19 (br. s., 2H), 2.05 (s, 3H), 1.94-1.77 (m, 8H), 1.75-1.57 (m, 5H), 1.22-1.06 (m, 2H). LC/MS Condition E: RT=1.72 min; m/e=753.3 (M+H)$^+$.

Example 2256: 5-((4-chloro-2-((2-(hydroxymethyl)piperidin-1-yl)methyl)-5-((3'-(3-(2-(hydroxymethyl)piperidin-1-yl)propoxy)-2,2'-dimethylbiphenyl-3-yl)methoxy)phenoxy)methyl)nicotinonitrile

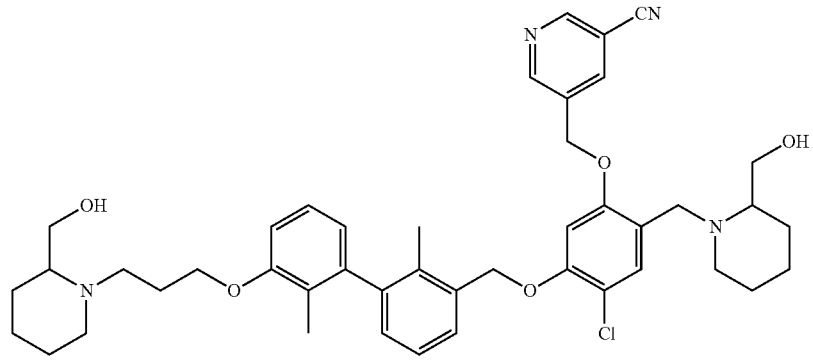 [SMILES: Cc1c(COc2cc(OCc3cncc(C#N)c3)c(CN3CCCCC3CO)cc2Cl)cccc1-c1cccc(OCCCN2CCCCC2CO)c1C]

The compound was prepared and purified with the same method as that for Example 2254 to give the pure title compound: (8.3 mg, 23%). $^1$H NMR (500 MHz, DMSO-d$_6$) δ 9.01 (d, J=2.6 Hz, 2H), 8.43 (s, 1H), 7.49 (d, J=7.7 Hz, 1H), 7.36 (s, 1H), 7.31-7.25 (m, 1H), 7.21 (t, J=8.1 Hz, 1H), 7.11-7.05 (m, 2H), 6.96 (d, J=8.4 Hz, 1H), 6.68 (d, J=7.3 Hz, 1H), 5.33 (d, J=4.4 Hz, 2H), 5.25 (br. s., 2H), 4.07-3.97 (m, 3H), 3.61-3.53 (m, 3H), 3.35 (br. s., 2H), 3.21 (d, J=14.3 Hz, 1H), 2.90 (s, 3H), 2.81 (d, J=10.6 Hz, 1H), 2.64 (d, J=12.1 Hz, 1H), 2.26 (br. s., 2H), 2.19 (t, J=10.8 Hz, 1H), 2.03 (s, 3H), 2.02-1.95 (m, 1H), 1.88 (br. s., 2H), 1.83 (s, 3H), 1.64 (br. s., 5H), 1.54-1.16 (m, 9H). LC/MS Condition E: RT=1.74 min; m/e=753.3 (M+H)$^+$.

Example 2257: 5-((4-chloro-2-(((3S,4R)-3-hydroxy-4-(hydroxymethyl)piperidin-1-yl)methyl)-5-((3'-(3-((3S,4R)-3-hydroxy-4-(hydroxymethyl)piperidin-1-yl)propoxy)-2,2'-dimethylbiphenyl-3-yl)methoxy)phenoxy)methyl)nicotinonitrile

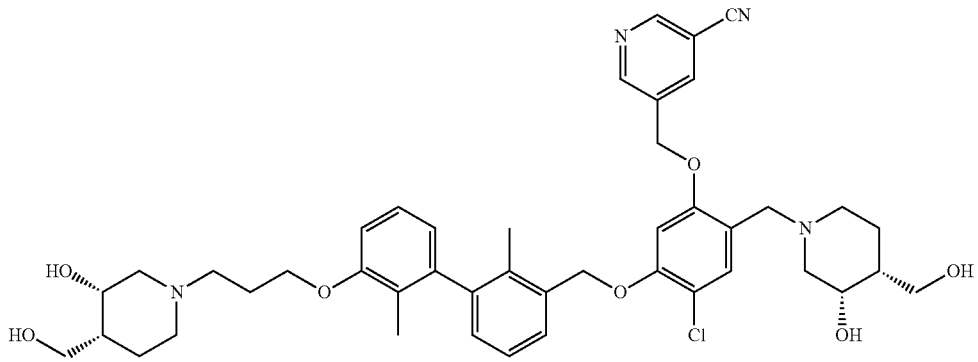 [SMILES: Cc1c(COc2cc(OCc3cncc(C#N)c3)c(CN3CC[C@H](CO)[C@H](O)C3)cc2Cl)cccc1-c1cccc(OCCCN2CC[C@H](CO)[C@H](O)C2)c1C]

The compound was prepared with the same method as that for Example 2254. The crude material was purified via preparative LC/MS with the following conditions: Column: XBridge C18, 19×200 mm, 5-μm particles; Mobile Phase A: 5:95 acetonitrile:water with 10-mM ammonium acetate;

Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evaporation
to give the pure title compound as TFA salt: (5.8 mg, 10%). $^1$H NMR (500 MHz, DMSO-$d_6$) δ 9.05 (d, J=7.0 Hz, 2H), 8.51 (s, 1H), 7.67 (s, 1H), 7.51 (d, J=7.3 Hz, 1H), 7.33-7.21 (m, 6H), 7.17 (s, 3H), 7.12-7.05 (m, 4H), 6.98 (d, J=8.4 Hz, 1H), 6.71 (d, J=7.7 Hz, 1H), 5.40 (s, 2H), 5.33 (br. s., 2H), 4.29-4.03 (m, 5H), 3.99 (br. s., 1H), 3.48-3.19 (m, 9H), 3.15-3.07 (m, 2H), 3.00 (d, J=11.0 Hz, 3H), 2.30-2.08 (m, 2H), 2.05 (s, 3H), 1.86 (s, 3H), 1.64 (br. s., 6H). LC/MS Condition E: RT=1.58 min; m/e=785.2 (M+H)$^+$.

Example 2258: 5-((4-chloro-2-((4-(2-hydroxyethyl)piperazin-1-yl)methyl)-5-((3'-(3-(4-(2-hydroxyethyl)piperazin-1-yl)propoxy)-2,2'-dimethylbiphenyl-3-yl)methoxy)phenoxy)methyl)nicotinonitrile

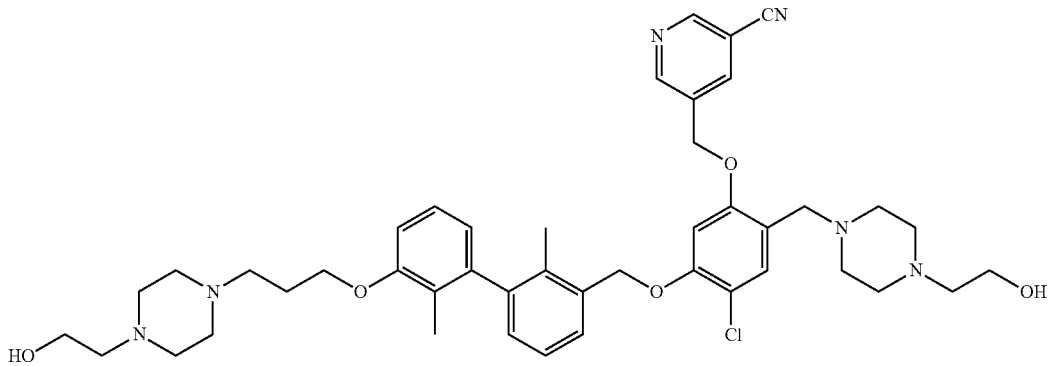 [SMILES: Cc1c(COc2cc(OCc3cncc(C#N)c3)c(CN3CCN(CCO)CC3)cc2Cl)cccc1-c1cccc(OCCCN2CCN(CCO)CC2)c1C]

The compound was prepared and purified with the same method as that for Example 2254 to give the pure title compound: (19.4 mg, 50%). $^1$H NMR (500 MHz, DMSO-$d_6$) δ 9.01 (s, 2H), 8.41 (s, 1H), 7.49 (d, J=7.3 Hz, 1H), 7.29 (s, 1H), 7.27 (t, J=7.5 Hz, 1H), 7.20 (t, J=7.9 Hz, 1H), 7.11 (s, 1H), 7.07 (d, J=7.3 Hz, 1H), 6.95 (d, J=8.1 Hz, 1H), 6.68 (d, J=7.0 Hz, 1H), 5.33 (s, 2H), 5.26 (br. s., 2H), 4.10-3.98 (m, 2H), 3.48 (br. s., 2H), 3.41 (s, 2H), 2.48-2.27 (m, 22H), 2.03 (s, 3H), 1.91-1.86 (m, 4H), 1.82 (s, 3H). LC/MS Condition E: RT=1.25 min; m/e=783.3 (M+H)$^+$.

Example 2259: (3S)-1-(3-(3'-((4-(((S)-3-carboxypiperidin-1-yl)methyl)-2-chloro-5-((5-cyanopyridin-3-yl)methoxy)phenoxy)methyl)-2,2'-dimethylbiphenyl-3-yloxy)propyl)piperidine-3-carboxylic Acid

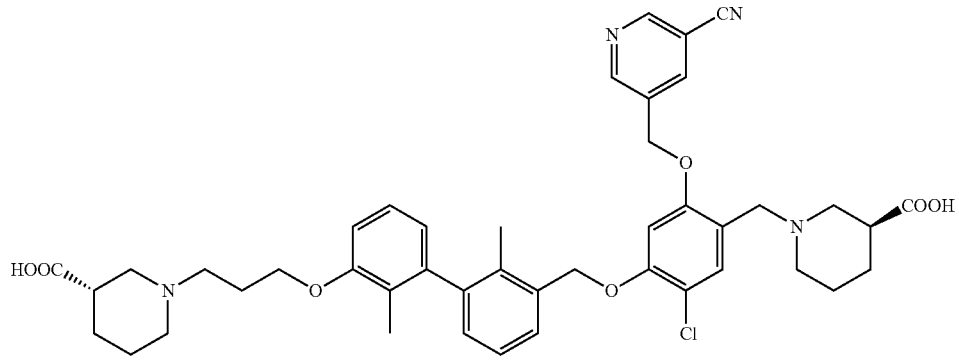 [SMILES: Cc1c(COc2cc(OCc3cncc(C#N)c3)c(CN3CCC[C@H](C(=O)O)C3)cc2Cl)cccc1-c1cccc(OCCCN2CCC[C@H](C(=O)O)C2)c1C]

The compound was prepared and purified with the same method as that for Example 2254 to give the pure title compound: (9.3 mg, 23%). $^1$H NMR (500 MHz, DMSO-$d_6$) δ 9.00 (s, 2H), 8.40 (s, 1H), 7.49 (d, J=7.6 Hz, 1H), 7.32 (s, 1H), 7.27 (t, J=7.5 Hz, 1H), 7.20 (t, J=7.8 Hz, 1H), 7.11 (s, 1H), 7.07 (d, J=7.6 Hz, 1H), 6.95 (d, J=8.5 Hz, 1H), 6.68 (d, J=7.3 Hz, 1H), 5.32 (s, 2H), 5.26 (s, 2H), 4.08-4.00 (m, 2H), 3.45 (d, J=3.7 Hz, 2H), 2.85 (d, J=11.0 Hz, 1H), 2.79 (d, J=9.5 Hz, 1H), 2.67 (br. s., 1H), 2.61 (br. s., 1H), 2.45-2.33 (m, 3H), 2.16 (d, J=11.3 Hz, 2H), 2.06 (br. s., 2H), 2.03 (s, 3H), 1.93 (d, J=6.7 Hz, 2H), 1.81 (s, 3H), 1.80-1.73 (m, 2H), 1.63 (br. s., 2H), 1.51-1.28 (m, 5H). LC/MS Condition E: RT=1.47 min; m/e=781.2 (M+H)$^+$.

Example 2260: (2S)-2-(5-chloro-2-((5-cyanopyridin-3-yl)methoxy)-4-((3'-(3-(3-(hydroxymethyl) piperidin-1-yl)propoxy)-2,2'-dimethylbiphenyl-3-yl) methoxy)benzylamino)-3-hydroxy-2-methylpropanoic Acid

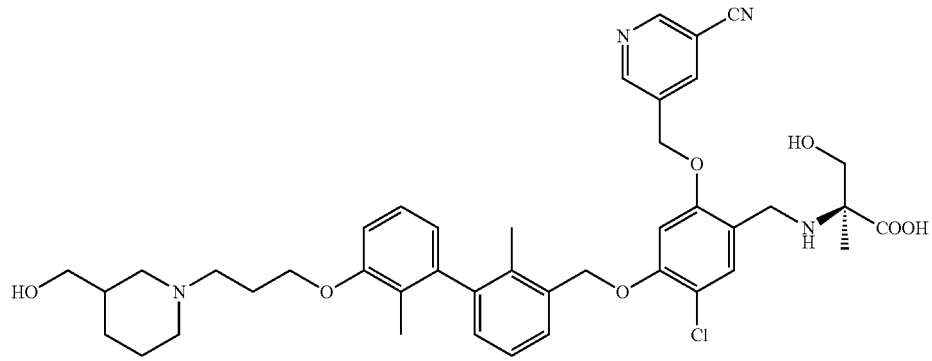 [SMILES: Cc1c(COc2cc(OCc3cncc(C#N)c3)c(CN[C@@](C)(CO)C(=O)O)cc2Cl)cccc1-c1cccc(OCCCN2CCCC(CO)C2)c1C]

To a solution of (S)-2-((4-((3'-(3-bromopropoxy)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid (30 mg, 0.041 mmol) in DCE (0.3 mL), EtOH (0.8 mL) and THF (0.3 mL) was added piperidin-3-ylmethanol (47.8 mg, 0.415 mmol), sodium iodide (18.66 mg, 0.124 mmol) in 0.1 ml of water and DIPEA (0.072 mL, 0.415 mmol). The resulting mixture was stirred at 70° C. under nitrogen for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound: (8.0 mg, 25%). $^1$H NMR (500 MHz, DMSO-$d_6$) δ 9.02 (d, J=9.2 Hz, 2H), 8.52 (s, 1H), 7.54 (s, 1H), 7.47 (d, J=7.3 Hz, 1H), 7.26 (t, J=7.7 Hz, 1H), 7.21 (t, J=7.9 Hz, 1H), 7.13 (s, 1H), 7.08 (d, J=7.3 Hz, 1H), 6.96 (d, J=8.4 Hz, 1H), 6.67 (d, J=7.3 Hz, 1H), 5.35 (s, 2H), 5.30 (d, J=2.6 Hz, 2H), 4.08-4.01 (m, 2H), 3.94 (s, 2H), 3.59 (br. s., 1H), 3.52 (d, J=11.4 Hz, 1H), 3.29 (dd, J=10.3, 4.8 Hz, 1H), 3.24-3.19 (m, 1H), 2.93-2.90 (m, 1H), 2.77 (d, J=9.9 Hz, 1H), 2.46 (t, J=7.3 Hz, 2H), 2.03 (s, 3H), 1.90-1.86 (m, 2H), 1.82 (s, 3H), 1.69-1.54 (m, 5H), 1.44 (d, J=12.8 Hz, 1H), 1.23 (s, 3H), 0.88 (d, J=9.9 Hz, 1H). LC/MS Condition E: RT=1.43 min; m/e=757.2 (M+H)$^+$.

Example 2261: (2S)-2-(5-chloro-2-((5-cyanopyridin-3-yl)methoxy)-4-((3'-(3-((3 S,4R)-3-hydroxy-4-(hydroxymethyl)piperidin-1-yl)propoxy)-2,2'-dimethylbiphenyl-3-yl)methoxy)benzylamino)-3-hydroxy-2-methylpropanoic Acid

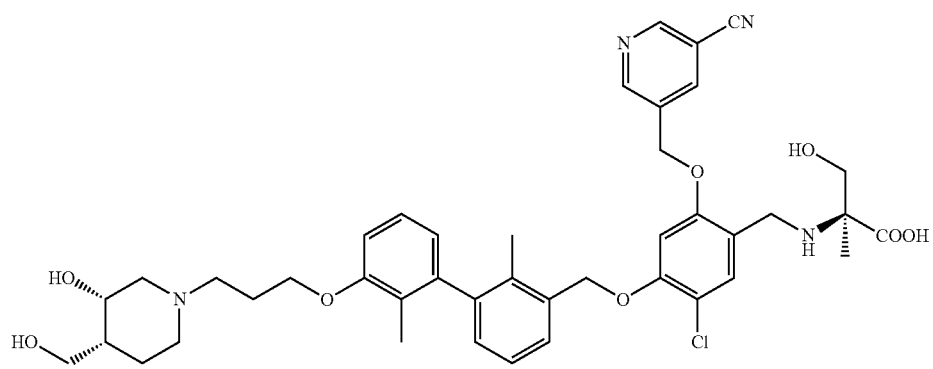 [SMILES: Cc1c(COc2cc(OCc3cncc(C#N)c3)c(CN[C@@](C)(CO)C(=O)O)cc2Cl)cccc1-c1cccc(OCCCN2CC[C@H](CO)[C@H](O)C2)c1C]

The compound was prepared and purified with the same method as that for Example 2260 to give the pure title compound: (8.0 mg, 23%). $^1$H NMR (500 MHz, DMSO-d$_6$) δ 9.03 (dd, J=8.6, 1.7 Hz, 2H), 8.52 (s, 1H), 7.54 (s, 1H), 7.47 (d, J=7.3 Hz, 1H), 7.26 (t, J=7.5 Hz, 1H), 7.21 (t, J=7.9 Hz, 1H), 7.13 (s, 1H), 7.08 (d, J=8.1 Hz, 1H), 6.97 (d, J=8.1 Hz, 1H), 6.67 (d, J=7.7 Hz, 1H), 5.35 (s, 2H), 5.30 (d, J=2.9 Hz, 2H), 4.06 (d, J=7.0 Hz, 2H), 3.94 (s, 2H), 3.74 (br. s., 1H), 3.60 (d, J=11.0 Hz, 1H), 3.52 (d, J=11.4 Hz, 1H), 3.47-3.44 (m, 1H), 3.26 (dd, J=10.3, 6.6 Hz, 1H), 2.80 (br. s., 2H), 2.49-2.40 (m, 2H), 2.07 (d, J=11.4 Hz, 1H), 2.03 (s, 3H), 2.01-1.92 (m, 2H), 1.82 (s, 3H), 1.55-1.34 (m, 4H), 1.22 (s, 3H). LC/MS Condition E: RT=1.42 min; m/e=773.2 (M+H)$^+$.

Example 2262: (2S)-2-(5-chloro-2-((5-cyanopyridin-3-yl)methoxy)-4-((3'-(3-((S)-3-hydroxypiperidin-1-yl)propoxy)-2,2'-dimethylbiphenyl-3-yl)methoxy)benzylamino)-3-hydroxy-2-methylpropanoic Acid

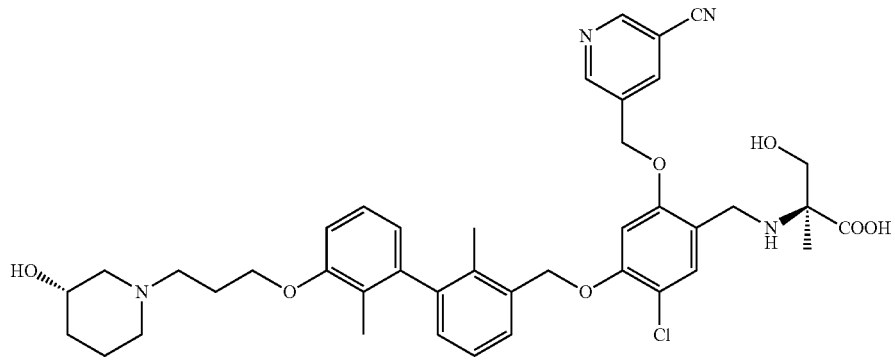 [SMILES: Cc1c(COc2cc(OCc3cncc(C#N)c3)c(CN[C@@](C)(CO)C(=O)O)cc2Cl)cccc1-c1cccc(OCCCN2CCC[C@H](O)C2)c1C]

The compound was prepared and purified with the same method as that for Example 2260 to give the pure title compound: (9.6 mg, 31%). $^1$H NMR (500 MHz, DMSO-d$_6$) δ 9.03 (d, J=8.4 Hz, 2H), 8.52 (s, 1H), 7.55 (s, 1H), 7.47 (d, J=7.7 Hz, 1H), 7.26 (t, J=7.5 Hz, 1H), 7.21 (t, J=7.9 Hz, 1H), 7.13 (s, 1H), 7.08 (d, J=7.0 Hz, 1H), 6.96 (d, J=8.1 Hz, 1H), 6.67 (d, J=7.7 Hz, 1H), 5.35 (s, 2H), 5.30 (br. s., 2H), 4.04 (m, 3H), 3.95 (s, 2H), 3.63-3.59 (m, 1H), 3.52 (d, J=11.7 Hz, 1H), 2.84 (d, J=10.6 Hz, 1H), 2.68 (d, J=8.1 Hz, 1H), 2.48-2.41 (m, 2H), 2.03 (s, 3H), 1.86-1.83 (m, 1H), 1.82 (s, 3H), 1.80-1.68 (m, 3H), 1.61 (d, J=12.5 Hz, 1H), 1.40 (d, J=13.2 Hz, 1H), 1.23 (s, 3H), 1.07 (d, J=13.2 Hz, 1H). LC/MS Condition E: RT=1.51 min; m/e=743.2 (M+H)$^+$.

Example 2263: (2S)-2-(5-chloro-2-((5-cyanopyridin-3-yl)methoxy)-4-((3'-(3-(4-(2-hydroxyethyl)piperazin-1-yl)propoxy)-2,2'-dimethylbiphenyl-3-yl)methoxy)benzylamino)-3-hydroxy-2-methylpropanoic Acid

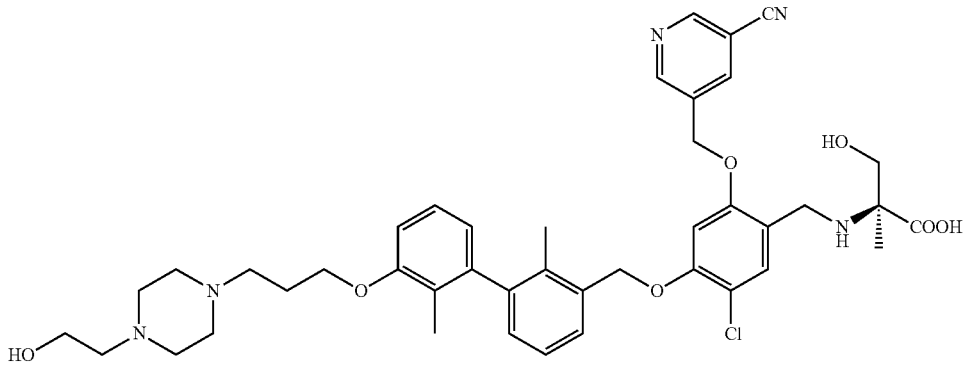 [SMILES: Cc1c(COc2cc(OCc3cncc(C#N)c3)c(CN[C@@](C)(CO)C(=O)O)cc2Cl)cccc1-c1cccc(OCCCN2CCN(CCO)CC2)c1C]

The compound was prepared and purified with the same method as that for Example 2260 to give the pure title compound: (9.3 mg, 28%). $^1$H NMR (500 MHz, DMSO-$d_6$) δ 9.02 (dd, J=9.0, 1.7 Hz, 2H), 8.52 (s, 1H), 7.54 (s, 1H), 7.47 (d, J=7.3 Hz, 1H), 7.26 (t, J=7.7 Hz, 1H), 7.21 (t, J=8.1 Hz, 1H), 7.13 (s, 1H), 7.07 (d, J=7.7 Hz, 1H), 6.96 (d, J=8.4 Hz, 1H), 6.67 (d, J=7.7 Hz, 1H), 5.35 (s, 2H), 5.29 (d, J=3.3 Hz, 2H), 4.09-3.99 (m, 2H), 3.94 (s, 2H), 3.60 (d, J=11.4 Hz, 1H), 3.52 (d, J=11.4 Hz, 1H), 3.49-3.46 (m, 2H), 2.48-2.29 (m, 12H), 2.03 (s, 3H), 1.92 (br. s., 2H), 1.82 (s, 3H), 1.22 (s, 3H). LCMS: LC/MS Condition E: RT=1.51 min; m/e=772.2 (M+H)$^+$.

Example 2264: (3S)-1-(3-(3'-((4-(((S)-2-carboxy-1-hydroxypropan-2-ylamino)methyl)-2-chloro-5-((5-cyanopyridin-3-yl)methoxy)phenoxy)methyl)-2,2'-dimethylbiphenyl-3-yloxy)propyl)piperidine-3-carboxylic Acid

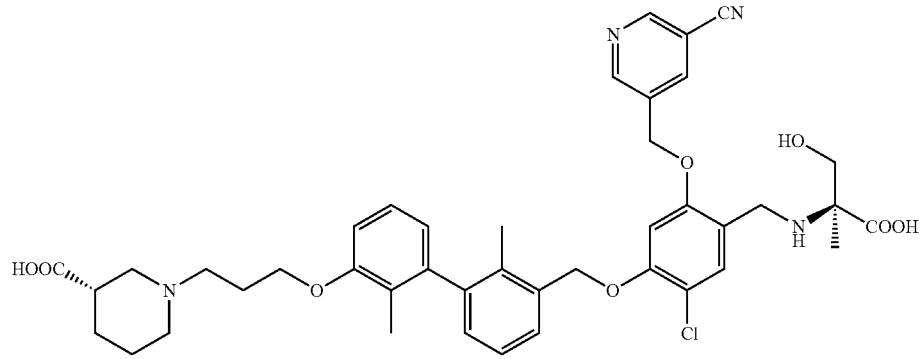 [SMILES: Cc1c(COc2cc(OCc3cncc(C#N)c3)c(CN[C@@](C)(CO)C(=O)O)cc2Cl)cccc1-c1cccc(OCCCN2CCC[C@H](C(=O)O)C2)c1C]

The compound was prepared and purified with the same method as that for Example 2260 to give the pure title compound: (5.0 mg, 16%). $^1$H NMR (500 MHz, DMSO-$d_6$) δ 9.02 (d, J=10.6 Hz, 2H), 8.52 (s, 1H), 7.53 (s, 1H), 7.47 (d, J=7.3 Hz, 1H), 7.29-7.25 (m, 1H), 7.20 (t, J=7.9 Hz, 1H), 7.13 (s, 1H), 7.07 (d, J=7.3 Hz, 1H), 6.95 (d, J=8.4 Hz, 1H), 6.67 (d, J=7.3 Hz, 1H), 5.35 (s, 2H), 5.29 (d, J=2.9 Hz, 2H), 4.11-4.02 (m, 2H), 3.93 (s, 2H), 3.60 (d, J=11.4 Hz, 1H), 3.51 (d, J=11.4 Hz, 1H), 2.84 (br. s., 1H), 2.66 (br. s., 1H), 2.50-2.44 (m, 2H), 2.38 (d, J=9.5 Hz, 1H), 2.17 (br. s., 1H), 2.03 (s, 4H), 1.92 (d, J=6.6 Hz, 2H), 1.82 (s, 3H), 1.79-1.74 (m, 1H), 1.63 (d, J=12.8 Hz, 1H), 1.51-1.34 (m, 2H), 1.22 (s, 3H). LCMS: LC/MS Condition E: RT=1.37 min; m/e=771.2 (M+H)$^+$.

Example 2265: 5-((4-chloro-2-(((S)-2,3-dihydroxypropylamino)methyl)-5-((3'-(3-((S)-2,3-dihydroxypropylamino)propoxy)-2,2'-dimethylbiphenyl-3-yl)methoxy)phenoxy)methyl)nicotinonitrile

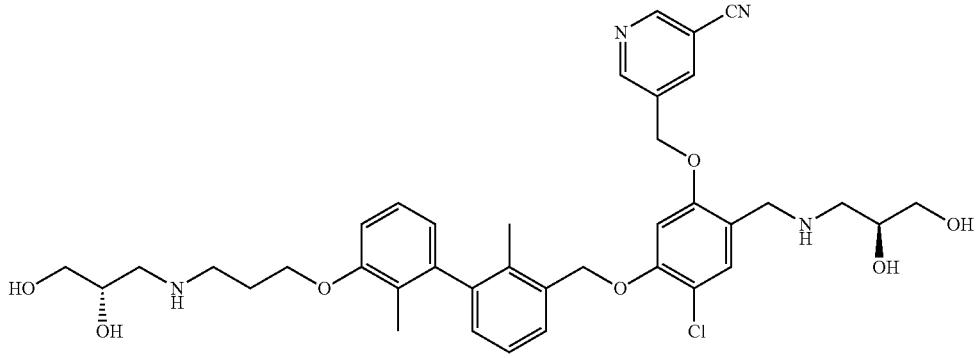 [SMILES: Cc1c(COc2cc(OCc3cncc(C#N)c3)c(CNC[C@H](O)CO)cc2Cl)cccc1-c1cccc(OCCCNC[C@H](O)CO)c1C]

The compound was prepared and purified with the same method as that for Example 2254 to give the pure title compound: (9.1 mg, 26%). $^1$H NMR (500 MHz, DMSO-$d_6$) δ 9.02 (s, 1H), 8.99 (s, 1H), 8.44 (s, 1H), 7.48 (d, J=7.7 Hz, 1H), 7.41 (s, 1H), 7.27 (t, J=7.5 Hz, 1H), 7.21 (t, J=7.9 Hz, 1H), 7.11 (s, 1H), 7.07 (d, J=7.7 Hz, 1H), 6.97 (d, J=8.1 Hz, 1H), 6.68 (d, J=7.7 Hz, 1H), 5.32 (s, 2H), 5.25 (br. s., 2H), 4.08 (q, J=6.6 Hz, 2H), 3.71 (s, 2H), 3.44-3.29 (m, 8H), 2.81 (t, J=7.0 Hz, 2H), 2.58 (t, J=5.5 Hz, 1H), 2.53 (d, J=5.9 Hz, 1H), 2.04 (s, 3H), 1.95-1.91 (m, 2H), 1.83 (s, 3H). LC/MS Condition E: RT=1.45 min; m/e=705.2 (M+H)+.

Example 2266: 3-((3-(3'-((4-(((3-amino-3-oxopropyl)(methyl)amino)methyl)-2-chloro-5-((5-cyanopyridin-3-yl)methoxy)phenoxy)methyl)-2,2'-dimethylbiphenyl-3-yloxy)propyl)(methyl)amino)propanamide

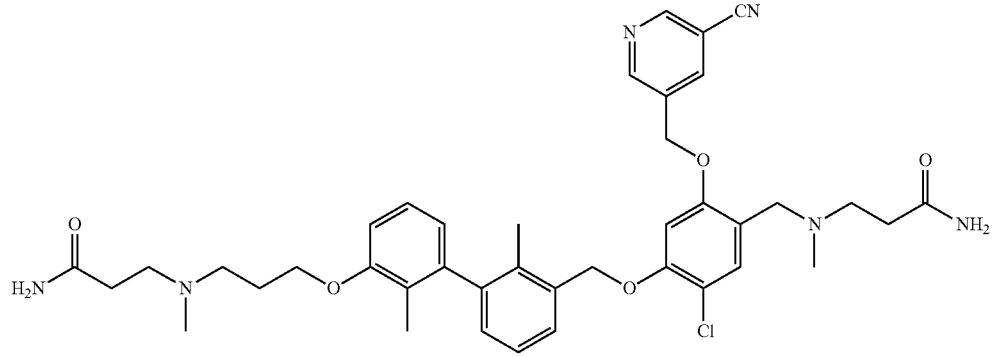 [SMILES: Cc1c(COc2cc(OCc3cncc(C#N)c3)c(CN(C)CCC(N)=O)cc2Cl)cccc1-c1cccc(OCCCN(C)CCC(N)=O)c1C]

The compound was prepared and purified with the same method as that for Example 2254 to give the pure title compound: (7.5 mg, 19%). 1H NMR (500 MHz, DMSO-d6) δ 9.01 (d, J=1.5 Hz, 1H), 8.98 (s, 1H), 8.44 (s, 1H), 7.49 (d, J=7.3 Hz, 1H), 7.36 (br. s., 2H), 7.33 (s, 1H), 7.27 (t, J=7.3 Hz, 1H), 7.21 (t, J=7.9 Hz, 1H), 7.11 (s, 1H), 7.08 (d, J=7.3 Hz, 1H), 6.95 (d, J=8.1 Hz, 1H), 6.74 (br. s., 2H), 6.68 (d, J=7.3 Hz, 1H), 5.32 (s, 2H), 5.25 (br. s., 2H), 4.10-3.96 (m, 2H), 2.60-2.54 (m, 5H), 2.50 (br. s., 2H), 2.25-2.18 (m, 4H), 2.17 (s, 3H), 2.11 (s, 3H), 2.04 (s, 3H), 1.90-1.85 (m, 3H), 1.83 (s, 3H). LC/MS Condition E: RT=1.63 min; m/e=727.2 (M+H)+.

Example 2267: N-((3R)-1-(3-(3'-((4-(((R)-3-acetamidopyrrolidin-1-yl)methyl)-2-chloro-5-((5-cyanopyridin-3-yl)methoxy)phenoxy)methyl)-2,2'-dimethylbiphenyl-3-yloxy)propyl)pyrrolidin-3-yl)acetamide

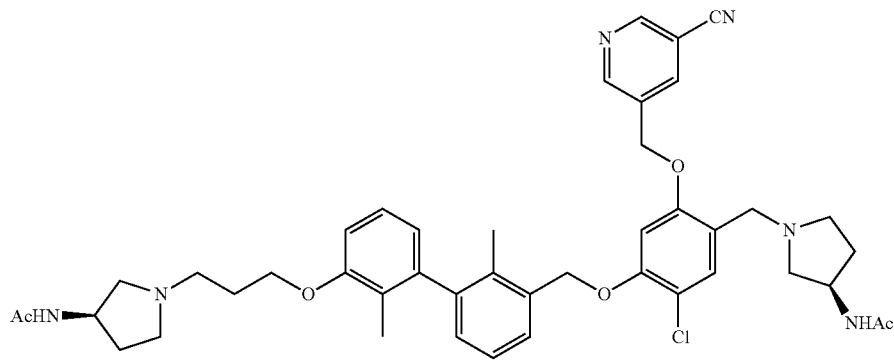 [SMILES: CC(=O)N[C@@H]1CCN(CCCOc2cccc(-c3cccc(COc4cc(OCc5cncc(C#N)c5)c(CN5CC[C@@H](NC(C)=O)C5)cc4Cl)c3C)c2C)C1]

The compound was prepared and purified with the same method as that for Example 2254 to give the pure title compound: (14.9 mg, 39%). 1H NMR (500 MHz, DMSO-d6) δ 9.01 (s, 1H), 8.99 (s, 1H), 8.41 (s, 1H), 7.99 (t, J=6.2 Hz, 2H), 7.49 (d, J=7.3 Hz, 1H), 7.34 (s, 1H), 7.27 (t, J=7.7 Hz, 1H), 7.21 (t, J=8.1 Hz, 1H), 7.11 (s, 1H), 7.07 (d, J=7.7 Hz, 1H), 6.96 (d, J=8.4 Hz, 1H), 6.68 (d, J=7.3 Hz, 1H), 5.32 (s, 2H), 5.25 (br. s., 2H), 4.16-4.02 (m, 4H), 3.54 (s, 2H), 2.69-2.55 (m, 6H), 2.40 (d, J=7.0 Hz, 2H), 2.33 (dd, J=9.0, 4.6 Hz, 1H), 2.29-2.23 (m, 1H), 2.07 (d, J=6.2 Hz, 2H), 2.03 (s, 3H), 1.93 (br. s., 2H), 1.82 (s, 3H), 1.77 (d, J=4.4 Hz, 6H), 1.53 (br. s., 2H). LC/MS Condition E: RT=1.74 min; m/e=779.2 (M+H)+.

Example 2268: (2S)-1-(3-(3'-((4-(((S)-2-carboxypiperidin-1-yl)methyl)-2-chloro-5-((5-cyanopyridin-3-yl)methoxy)phenoxy)methyl)-2,2'-dimethylbiphenyl-3-yloxy)propyl)piperidine-2-carboxylic Acid

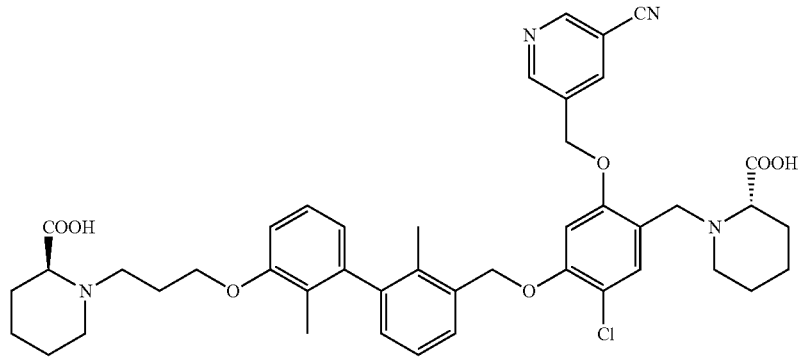 [SMILES: Cc1c(COc2cc(OCc3cncc(C#N)c3)c(CN3CCCC[C@H]3C(=O)O)cc2Cl)cccc1-c1cccc(OCCCN2CCCC[C@H]2C(=O)O)c1C]

The compound was prepared and purified with the same method as that for Example 2254 to give the pure title compound: (10.8 mg, 33%). $^1$H NMR (500 MHz, DMSO-$d_6$) δ 9.01 (d, J=7.7 Hz, 2H), 8.46 (s, 1H), 7.96 (s, 1H), 7.49 (d, J=7.7 Hz, 1H), 7.43 (s, 1H), 7.31-7.25 (m, 1H), 7.21 (t, J=7.9 Hz, 1H), 7.11 (d, J=5.1 Hz, 1H), 7.07 (d, J=7.7 Hz, 1H), 6.95 (d, J=8.4 Hz, 1H), 6.69 (d, J=7.7 Hz, 1H), 5.33 (br. s., 2H), 5.27 (br. s., 2H), 4.10-3.99 (m, 2H), 3.78 (d, J=16.9 Hz, 1H), 3.24 (d, J=10.3 Hz, 1H), 3.17-3.02 (m, 3H), 2.89-2.76 (m, 2H), 2.57 (br. s., 1H), 2.24 (br. s., 1H), 2.03 (s, 5H), 1.88-1.74 (m, 5H), 1.74-1.54 (m, 5H), 1.48 (br. s., 3H), 1.36 (br. s., 2H). LC/MS Condition E: RT=1.41 min; m/e=781.2 (M+H)$^+$.

Example 2269: (2S)-1-(5-chloro-2-((5-cyanopyridin-3-yl)methoxy)-4-((2,2'-dimethyl-3'-(3-(4-(methylamino)piperidin-1-yl)propoxy)biphenyl-3-yl)methoxy)benzyl)piperidine-2-carboxylic Acid A solution of (example 2246) (S)-1-(4-((3'-(3-(4-((tert-butoxycarbonyl)(methyl)amino)piperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid (8 mg, 9.23 μmol) in CH$_2$Cl$_2$ (0.3 mL) and TFA (0.021 mL, 0.277 mmol) was stirred at rt under nitrogen for 5 h. The reaction mixture was concentrated and the residue was dissolved in 1 ml of MeOH and was then purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation to give the pure title compound: (1.8 mg, 25%). $^1$H NMR (500 MHz, DMSO-$d_6$) δ 9.01 (dd, J=7.3, 1.8 Hz, 2H), 8.46 (s, 1H), 7.49 (d, J=7.3 Hz, 1H), 7.44 (s, 1H), 7.30-7.26 (m, 1H), 7.23-7.17 (m, 1H), 7.12 (s, 1H), 7.06 (s, 1H), 6.96 (d, J=8.4 Hz, 1H), 6.69 (d, J=7.3 Hz, 1H), 5.34 (s, 2H), 5.28 (s, 2H), 4.05 (d, J=8.8 Hz, 2H), 3.83 (d, J=13.9 Hz, 1H), 3.67 (d, J=14.3 Hz, 1H), 3.10-2.90 (m, 3H), 2.56 (s, 3H), 2.35 (br. s., 1H), 2.03 (s, 3H), 2.00-1.87 (m, 8H), 1.82 (d, J=2.9 Hz, 4H), 1.73 (br. s., 1H), 1.50 (br. s., 5H), 1.37 (br. s., 1H). LC/MS Condition E: RT=1.44 min; m/e=766.2 (M+H)$^+$.

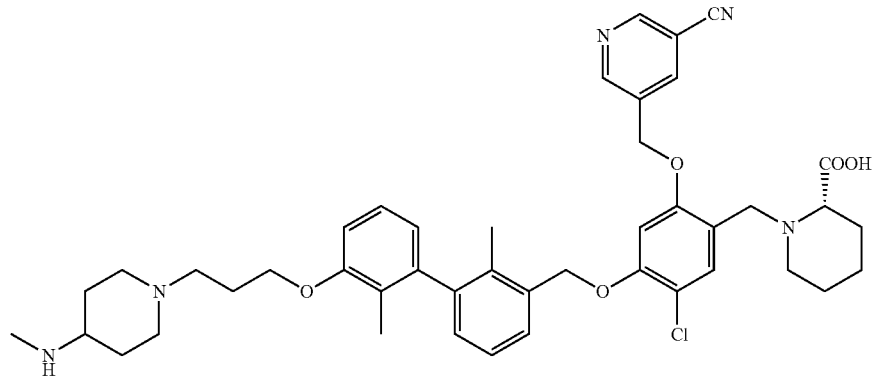 [SMILES: CNC1CCN(CCCOc2cccc(-c3cccc(COc4cc(OCc5cncc(C#N)c5)c(CN5CCCC[C@H]5C(=O)O)cc4Cl)c3C)c2C)CC1]

Example 2270: (2S)-2-(4-((3'-(3-((R)-3-acetamidopyrrolidin-1-yl)propoxy)-2,2'-dimethylbiphenyl-3-yl)methoxy)-5-chloro-2-((5-cyanopyridin-3-yl)methoxy)benzylamino)-3-hydroxy-2-methylpropanoic Acid

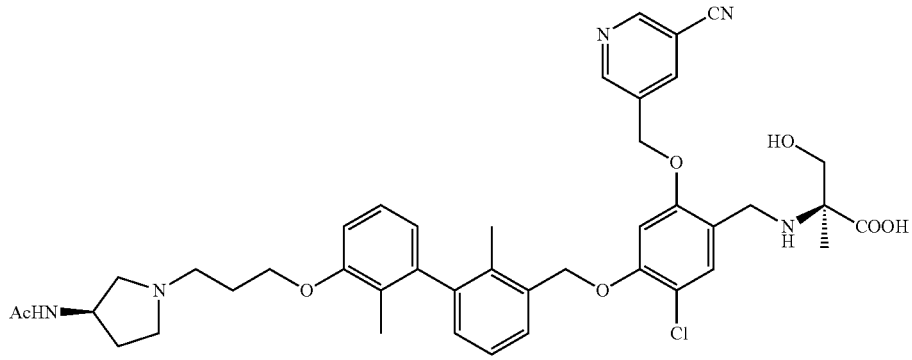 [SMILES: CC(=O)N[C@@H]1CCN(CCCOc2cccc(-c3cccc(COc4cc(OCc5cncc(C#N)c5)c(CN[C@@](C)(CO)C(=O)O)cc4Cl)c3C)c2C)C1]

The compound was prepared and purified with the same method as that for Example 2260 to give the pure title compound: (9.8 mg, 30%). $^1$H NMR (500 MHz, DMSO-$d_6$) δ 9.02 (dd, J=9.4, 2.0 Hz, 2H), 8.51 (s, 1H), 7.98 (d, J=7.3 Hz, 1H), 7.54 (s, 1H), 7.47 (d, J=7.7 Hz, 1H), 7.27 (t, J=7.7 Hz, 1H), 7.21 (t, J=7.9 Hz, 1H), 7.13 (s, 1H), 7.07 (d, J=6.6 Hz, 1H), 6.96 (d, J=8.4 Hz, 1H), 6.68 (d, J=7.3 Hz, 1H), 5.35 (s, 2H), 5.29 (d, J=2.9 Hz, 2H), 4.21-4.01 (m, 3H), 3.94 (s, 2H), 2.70-2.55 (m, 4H), 2.43-2.29 (m, 2H), 2.12-2.05 (m, 1H), 2.04 (s, 3H), 1.93 (s, 4H), 1.82 (s, 3H), 1.78 (s, 3H), 1.60-1.46 (m, 1H), 1.23 (s, 3H). LC/MS Condition E: RT=1.48 min; m/e=770.2 (M+H)$^+$.

Example 2271: 5-((4-chloro-2-((((S)-2,3-dihydroxypropyl)(methyl)amino)methyl)-5-((3'-(3-(((S)-2,3-dihydroxypropyl)(methyl)amino)propoxy)-2,2'-dimethylbiphenyl-3-yl)methoxy)phenoxy)methyl)nicotinonitrile

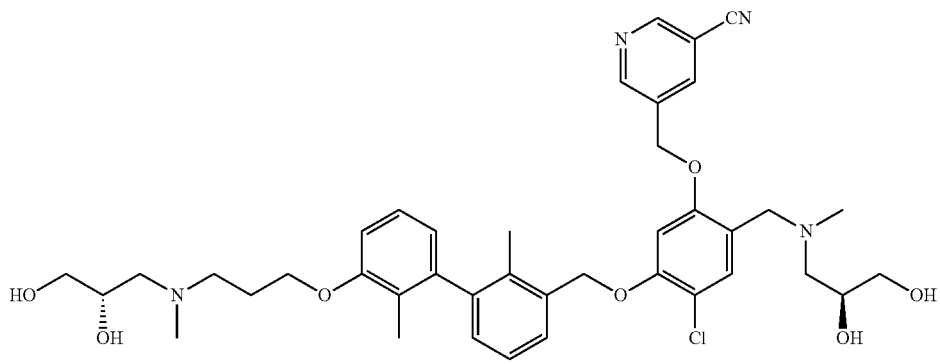 [SMILES: Cc1c(COc2cc(OCc3cncc(C#N)c3)c(CN(C)C[C@H](O)CO)cc2Cl)cccc1-c1cccc(OCCCN(C)C[C@H](O)CO)c1C]

The compound was prepared and purified with the same method as that for Example 2254 to give the pure title compound: (9.1 mg, 17%). $^1$H NMR (400 MHz, Methanol-$d_4$) δ 8.93 (d, J=2.0 Hz, 1H), 8.89 (d, J=1.8 Hz, 1H), 8.33 (s, 1H), 7.69 (s, 1H), 7.51 (s, 1H), 7.45 (d, J=7.5 Hz, 1H), 7.27-7.15 (m, 2H), 7.08 (d, J=7.5 Hz, 1H), 6.99 (s, 1H), 6.91 (d, J=8.3 Hz, 1H), 6.74 (d, J=7.5 Hz, 1H), 5.34 (s, 2H), 5.27 (s, 2H), 4.19-4.13 (m, 2H), 4.07-3.94 (m, 2H), 3.63-3.45 (m, 6H), 3.18 (br. s., 1H), 2.97 (s, 3H), 2.82 (br. s., 3H), 2.64 (s, 5H), 2.31 (d, J=6.0 Hz, 2H), 2.07 (s, 3H), 1.90 (s, 3H). LC/MS Condition E: RT=1.53 min; m/e=733.3 (M+H)$^+$.

Example 2272: (S)-2-((5-chloro-2-((5-cyanopyridin-3-yl)methoxy)-4-((2,2'-dimethyl-3'-(3-(piperidin-1-yl)propoxy)-[1,1'-biphenyl]-3-yl)methoxy)benzyl)amino)-3-hydroxy-2-methylpropanoic Acid

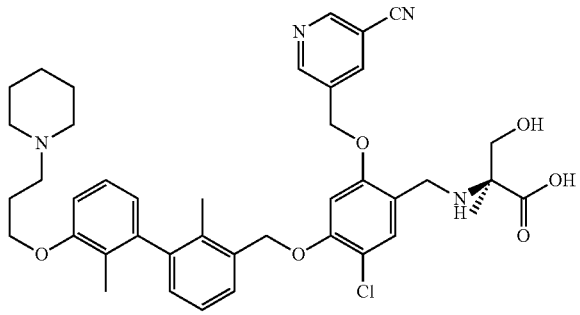 [SMILES: Cc1c(COc2cc(OCc3cncc(C#N)c3)c(CN[C@@](C)(CO)C(=O)O)cc2Cl)cccc1-c1cccc(OCCCN2CCOCC2)c1C]

The compound was prepared and purified with the same method as that for Example 2260 to give the pure title compound: (9.4 mg, 22%) $^1$H NMR (500 MHz, DMSO-d$_6$) δ 9.04 (s, 1H), 9.02 (d, J=1.8 Hz, 1H), 8.50 (s, 1H), 7.56 (s, 1H), 7.48 (d, J=7.3 Hz, 1H), 7.27 (t, J=7.5 Hz, 1H), 7.23 (t, J=7.9 Hz, 1H), 7.13 (d, J=6.2 Hz, 1H), 7.06 (d, J=7.7 Hz, 1H), 6.97 (d, J=8.1 Hz, 1H), 6.70 (d, J=7.7 Hz, 1H), 5.35 (d, J=3.3 Hz, 2H), 5.31 (s, 2H), 4.16-4.05 (m, 2H), 4.03 (s, 2H), 3.68 (d, J=12.5 Hz, 1H), 3.59 (d, J=11.4 Hz, 1H), 3.20 (d, J=6.6 Hz, 1H), 2.22-2.13 (m, 2H), 2.02 (s, 3H), 1.83 (d, J=2.6 Hz, 3H), 1.74 (br. s., 5H), 1.54 (br. s., 2H), 1.28 (s, 3H). LC/MS Condition E: RT=2.00 min; m/e=727.2 (M+H)$^+$.

Example 2273: (S)-2-((5-chloro-2-((5-cyanopyridin-3-yl)methoxy)-4-((2,2'-dimethyl-3'-(3-morpholinopropoxy)-[1,1'-biphenyl]-3-yl)methoxy)benzyl)amino)-3-hydroxy-2-methylpropanoic Acid

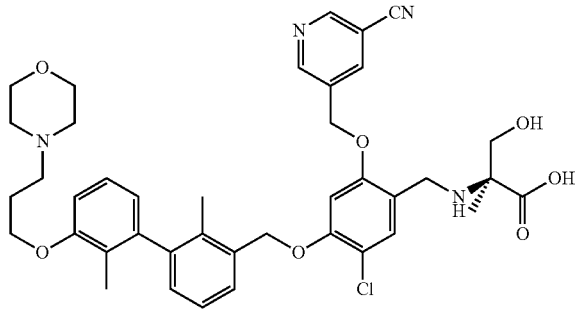

The compound was prepared and purified with the same method as that for Example 2260 to give the pure title compound: (13.7 mg, 31%). $^1$H NMR (500 MHz, DMSO-d$_6$) δ 9.02 (d, J=2.2 Hz, 1H), 8.50 (br. s., 1H), 7.54 (s, 1H), 7.48 (d, J=7.3 Hz, 1H), 7.27 (t, J=7.5 Hz, 1H), 7.21 (t, J=7.9 Hz, 1H), 7.13 (s, 1H), 7.08 (d, J=7.7 Hz, 1H), 6.97 (d, J=8.1 Hz, 1H), 6.68 (d, J=7.7 Hz, 1H), 5.34 (br. s., 2H), 5.29 (d, J=2.9 Hz, 2H), 4.12-3.99 (m, 2H), 3.58 (t, J=4.6 Hz, 3H), 2.47 (t, J=7.2 Hz, 2H), 2.38 (br. s., 4H), 2.04 (s, 3H), 1.97-1.88 (m, 3H), 1.83 (s, 3H), 1.21 (br. s., 3H). LC/MS Condition E: RT=1.91 min; m/e=729.2 (M+H)$^+$.

Example 2274: (2S)-2-((5-chloro-2-((5-cyanopyridin-3-yl)methoxy)-4-((2,2'-dimethyl-3'-(3-(3-(2,2,2-trifluoroacetamido)pyrrolidin-1-yl)propoxy)-[1,1'-biphenyl]-3-yl)methoxy)benzyl)amino)-3-hydroxy-2-methylpropanoic Acid

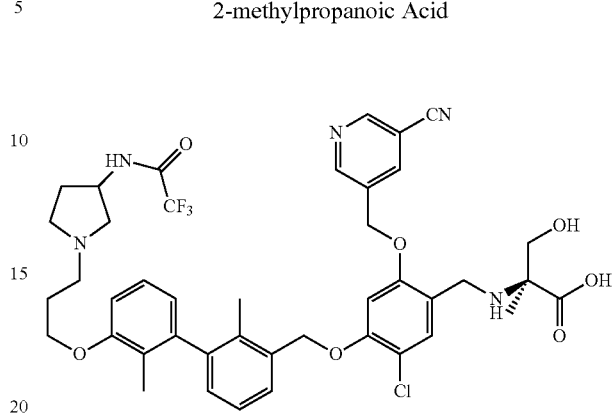

The compound was prepared and purified with the same method as that for Example 2260 to give the pure title compound: (7.2 mg, 16%). $^1$H NMR (500 MHz, DMSO-d$_6$) δ 9.02 (dd, J=9.5, 1.8 Hz, 2H), 8.51 (s, 1H), 7.54 (s, 1H), 7.47 (d, J=7.7 Hz, 1H), 7.27 (t, J=7.7 Hz, 1H), 7.21 (t, J=7.9 Hz, 1H), 7.13 (s, 1H), 7.07 (d, J=7.3 Hz, 1H), 6.96 (d, J=8.4 Hz, 1H), 6.68 (d, J=7.7 Hz, 1H), 5.35 (s, 2H), 5.29 (d, J=2.6 Hz, 2H), 4.24 (br. s., 1H), 4.06 (td, J=9.4, 6.2 Hz, 2H), 3.93 (s, 2H), 3.59 (d, J=11.4 Hz, 1H), 3.54-3.48 (d, 1H), 2.79-2.74 (m, 1H), 2.70-2.56 (m, 3H), 2.48 (dd, J=9.4, 5.3 Hz, 2H), 2.18-2.10 (m, 1H), 2.04 (s, 3H), 1.96-1.91 (m, 2H), 1.83 (s, 3H), 1.80-1.71 (m, 1H), 1.22 (s, 3H). LC/MS Condition E: RT=1.92 min; m/e=824.1 (M+H)$^+$.

Example 2275: (S)-2-((5-chloro-2-((5-cyanopyridin-3-yl)methoxy)-4-((3'-(3-(4-(hydroxymethyl)piperidin-1-yl)propoxy)-2,2'-dimethyl-[1,1'-biphenyl]-3-yl)methoxy)benzyl)amino)-3-hydroxy-2-methylpropanoic Acid

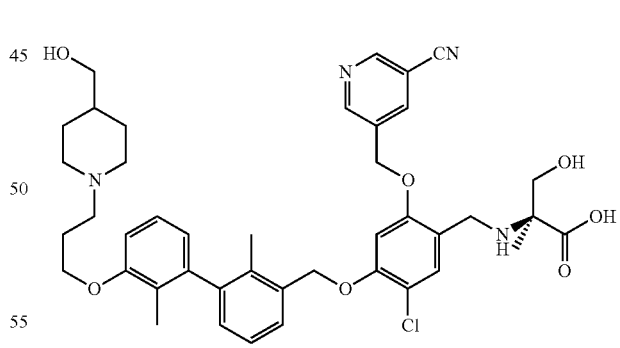

The compound was prepared and purified with the same method as that for Example 2260 to give the pure title compound: (17.1 mg, 40%). $^1$H NMR (500 MHz, DMSO-d$_6$) δ 9.03 (d, J=2.2 Hz, 1H), 9.01 (d, J=1.8 Hz, 1H), 8.51 (s, 1H), 7.54 (s, 1H), 7.47 (d, J=7.3 Hz, 1H), 7.26 (t, J=7.5 Hz, 1H), 7.23-7.18 (m, 1H), 7.13 (s, 1H), 7.07 (d, J=7.0 Hz, 1H), 6.96 (d, J=8.1 Hz, 1H), 6.67 (d, J=7.3 Hz, 1H), 4.09-3.99 (m, 3H), 3.93 (s, 2H), 3.60 (d, J=11.4 Hz, 2H), 3.52 (d, J=11.0 Hz, 2H), 3.24 (d, J=6.6 Hz, 2H), 2.88 (br. s., 1H), 2.47 (t, J=7.2 Hz, 2H), 2.04 (s, 3H), 1.82 (s, 3H), 1.63 (d, J=12.5 Hz, 2H), 1.34 (br. s., 1H), 1.23 (s, 3H), 1.18-1.07 (m, 2H). LC/MS Condition E: RT=1.41 min; m/e=757.2 (M+H)+.

Example 2276: N-((3R)-1-(3-(3'-((2-chloro-5-((5-cyanopyridin-3-yl)methoxy)-4-(hydroxymethyl)phenoxy)methyl)-2,2'-dimethylbiphenyl-3-yloxy)propyl)pyrrolidin-3-yl)acetamide

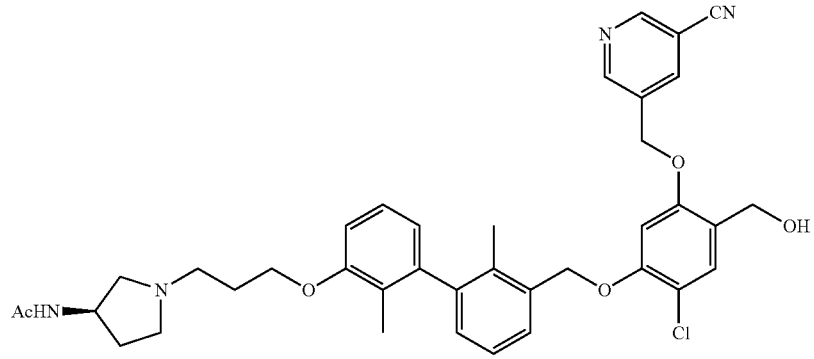 [SMILES: CC(=O)N[C@@H]1CCN(CCCOc2cccc(-c3cccc(COc4cc(OCc5cncc(C#N)c5)c(CO)cc4Cl)c3C)c2C)C1]

To a solution of (S)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid (30 mg, 0.041 mmol) containing ~30% of 5-((5-((3'-(3-bromopropoxy)-2,2'-dimethylbiphenyl-3-yl)methoxy)-4-chloro-2-(hydroxymethyl)phenoxy)methyl)nicotinonitrile in DCE (0.3 mL), EtOH (0.8 mL) and THF (0.3 mL) (see Example 2250) was added (3R)-(+)-3-acetamideopyrroline (52.5 mg, 0.409 mmol), sodium iodide (18.40 mg, 0.123 mmol) in 0.1 ml of water and DIPEA (0.071 mL, 0.409 mmol). The resulting mixture was stirred at 70° C. under nitrogen for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation. Example 2250 and the title compound Example 2276 (12.9 mg, 5.5 mg, 19%) were obtained in the same reaction. $^1$H NMR (500 MHz, DMSO-$d_6$) δ 9.02 (d, J=1.5 Hz, 1H), 8.97 (s, 1H), 8.43 (s, 1H), 7.98 (d, J=7.0 Hz, 1H), 7.48 (d, J=7.3 Hz, 1H), 7.36 (s, 1H), 7.26 (t, J=7.5 Hz, 1H), 7.21 (t, J=7.9 Hz, 1H), 7.10 (s, 1H), 7.07 (d, J=7.3 Hz, 1H), 6.96 (d, J=8.4 Hz, 1H), 6.68 (d, J=7.7 Hz, 1H), 5.32 (s, 2H), 5.26 (br. s., 2H), 4.48 (s, 2H), 4.16-4.03 (m, 3H), 2.68-2.56 (m, 3H), 2.43-2.28 (m, 2H), 2.13-2.04 (m, 3H), 2.05-2.01 (m, 4H), 1.93 (s, 3H), 1.83 (s, 3H), 1.78 (s, 3H), 1.57-1.44 (m, 1H). LC/MS Condition E: RT=1.75 min; m/e=669.1 (M+H)+.

Example 2277: 5-((4-chloro-2-(hydroxymethyl)-5-((3'-(3-((R)-3-methoxypyrrolidin-1-yl)propoxy)-2,2'-dimethylbiphenyl-3-yl)methoxy)phenoxy)methyl)nicotinonitrile

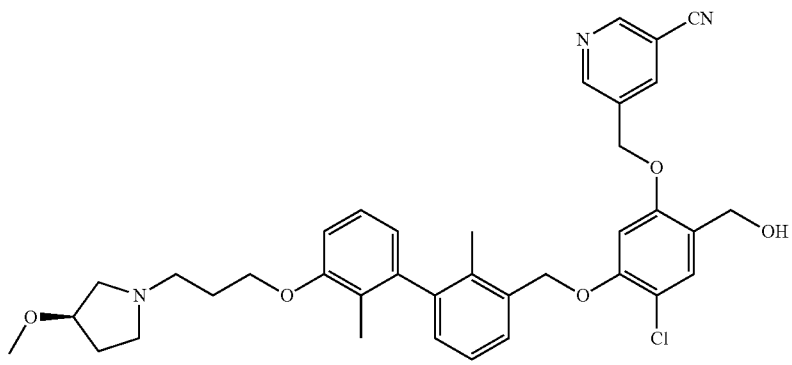 [SMILES: CO[C@@H]1CCN(CCCOc2cccc(-c3cccc(COc4cc(OCc5cncc(C#N)c5)c(CO)cc4Cl)c3C)c2C)C1]

The compound was prepared and purified with the same method as that for Example 2276 to give the pure title compound: (3.3 mg, 12%). $^1$H NMR (500 MHz, DMSO-$d_6$) δ 9.01 (s, 1H), 8.97 (s, 1H), 7.46 (d, J=7.3 Hz, 1H), 7.35 (s, 1H), 7.26 (t, J=7.7 Hz, 1H), 7.21 (t, J=7.9 Hz, 1H), 7.11-7.04 (m, 2H), 6.96 (d, J=8.4 Hz, 1H), 6.68 (d, J=7.3 Hz, 1H), 5.31 (s, 2H), 5.25 (s, 2H), 4.47 (s, 2H), 4.11-3.99 (m, 2H), 3.91 (d, J=9.5 Hz, 1H), 3.18 (s, 3H), 2.82 (br. s., 1H), 2.73 (s, 4H), 2.61 (br. s., 1H), 2.03 (s, 3H), 2.02-1.92 (m, 3H), 1.82 (s, 3H), 1.72 (br. s., 1H). LC/MS Condition E: RT=1.84 min; m/e=642.1 (M+H)+.

Example 2278: 5-((4-chloro-2-(((1-hydroxy-2-(hydroxymethyl)butan-2-yl)amino)methyl)-5-((3'-(3-((1-hydroxy-2-(hydroxymethyl)butan-2-yl)amino)propoxy)-2,2'-dimethyl-[1,1'-biphenyl]-3-yl)methoxy)phenoxy)methyl)nicotinonitrile

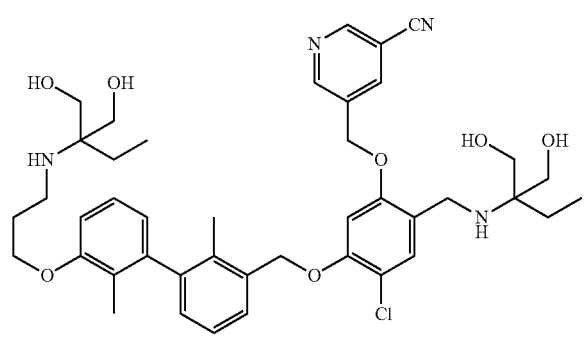 [SMILES: CCC(CO)(CO)NCCCOc1cccc(-c2cccc(COc3cc(OCc4cncc(C#N)c4)c(CNC(CC)(CO)CO)cc3Cl)c2C)c1C]

To a mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (0.15 g, 0.242 mmol) and 2-amino-2-ethyl-1,3-propanediol (0.058 g, 0.484 mmol) was added acetic acid (0.028 mL, 0.484 mmol). The resulting mixture was stirred at rt for 1 h. Sodium cyanoborohydride (1.0 M in THF) (0.363 mL, 0.363 mmol) was added. The resulting mixture was stirred at rt for 5 h. The crude reaction mixture was subdivided into 4 portions (about 44 mg each). To one portion of the crude reaction mixture of 5-((5-((3'-(3-bromopropoxy)-2,2'-dimethyl-[1,1'-biphenyl]-3-yl)methoxy)-4-chloro-2-(((1-hydroxy-2-(hydroxymethyl)butan-2-yl)amino)methyl)phenoxy)methyl)nicotinonitrile (44 mg, 0.037 mmol) in DCM (0.5 mL) and MeOH (0.5 mL) was added 2-amino-2-ethylpropane-1,3-diol (43.5 mg, 0.365 mmol) and DIPEA (0.064 mL, 0.365 mmol). The resulting mixture was stirred at 60° C. for 16 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 30 minutes, then a 5-minute hold at 100% B; Flow: 20 mL/min. Fractions containing the desired product were combined and dried via centrifugal evaporation (8.6 mg, 30%). $^1$H NMR (500 MHz, DMSO-$d_6$) δ 9.01 (d, J=1.8 Hz, 1H), 8.99 (d, J=1.8 Hz, 1H), 8.44 (s, 1H), 7.48 (d, J=7.0 Hz, 1H), 7.40 (s, 1H), 7.26 (t, J=7.7 Hz, 1H), 7.20 (t, J=7.9 Hz, 1H), 7.10 (s, 1H), 7.07 (d, J=7.3 Hz, 1H), 6.96 (d, J=8.1 Hz, 1H), 6.67 (d, J=7.3 Hz, 1H), 5.32 (s, 2H), 5.25 (s, 2H), 4.09 (d, J=9.2 Hz, 2H), 3.22 (d, J=2.2 Hz, 2H), 2.63 (t, J=6.2 Hz, 2H), 2.04 (s, 3H), 1.83 (s, 3H), 1.36-1.21 (m, 4H), 0.74 (t, J=7.0 Hz, 6H). LC/MS Condition E: RT=1.44 min; m/e=761.2 (M+H)+.

Example 2279: (S)-5-((4-chloro-5-((3'-(3-((2,3-dihydroxypropyl)amino)propoxy)-2,2'-dimethyl-[1,1'-biphenyl]-3-yl)methoxy)-2-(((1-hydroxy-2-(hydroxymethyl)butan-2-yl)amino)methyl)phenoxy)methyl)nicotinonitrile

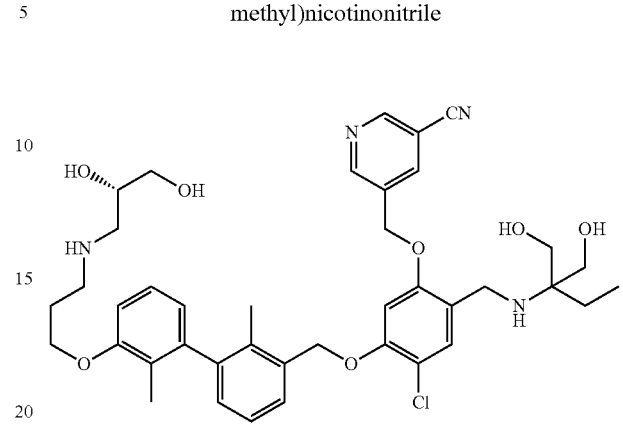

The compound was prepared and purified with the same method as that for Example 2278 to give the pure title compound: (8.5 mg, 32%). $^1$H NMR (500 MHz, DMSO-$d_6$) δ 9.01 (d, J=1.8 Hz, 1H), 8.99 (d, J=1.8 Hz, 1H), 8.44 (s, 1H), 7.47 (d, J=7.0 Hz, 1H), 7.40 (s, 1H), 7.26 (t, J=7.7 Hz, 1H), 7.21 (t, J=7.9 Hz, 1H), 7.12-7.03 (m, 2H), 6.96 (d, J=8.4 Hz, 1H), 6.68 (d, J=7.7 Hz, 1H), 5.32 (s, 2H), 5.26 (br. s., 2H), 4.15-4.02 (m, 2H), 3.56 (s, 2H), 2.80 (t, J=7.2 Hz, 2H), 2.72 (dd, J=11.9, 4.2 Hz, 1H), 2.04 (s, 3H), 1.99-1.93 (m, 2H), 1.83 (s, 3H), 1.32 (q, J=7.3 Hz, 2H), 0.74 (t, J=7.5 Hz, 3H). LC/MS Condition E: RT=1.40 min; m/e=733.2 (M+H)+.

Example 2280: (R)-5-((4-chloro-2-(((1-hydroxy-2-(hydroxymethyl)butan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

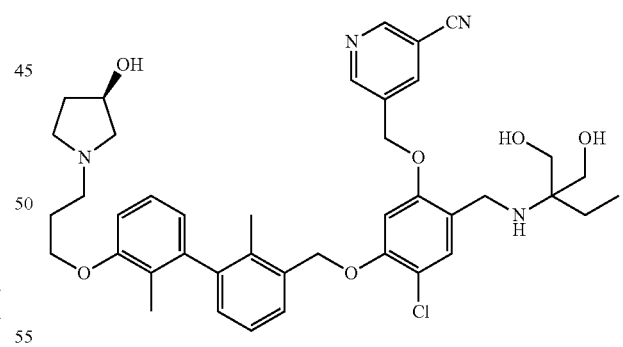

The compound was prepared and purified with the same method as that for Example 2278 to give the pure title compound: (14.0 mg, 36%). $^1$H NMR (500 MHz, DMSO-$d_6$) δ 9.04 (t, J=2.2 Hz, 2H), 8.53 (s, 1H), 7.56 (s, 1H), 7.49 (d, J=7.3 Hz, 1H), 7.28 (t, J=7.5 Hz, 1H), 7.23 (t, J=7.9 Hz, 2H), 7.19 (s, 2H), 7.08 (d, J=7.3 Hz, 1H), 6.98 (d, J=8.4 Hz, 1H), 6.70 (d, J=7.3 Hz, 1H), 5.37-5.31 (m, 4H), 4.44 (br. s., 1H), 4.19-4.03 (m, 4H), 3.62-3.47 (m, 2H), 2.17 (d, J=5.5 Hz, 3H), 2.04 (s, 4H), 1.94-1.87 (m, 4H), 1.86 (s, 4H), 1.62 (q, J=7.1 Hz, 2H), 0.79 (t, J=7.5 Hz, 3H). LC/MS Condition E: RT=1.43 min; m/e=729.2 (M+H)+.

Example 2281: 5-((4-chloro-2-(((1,3-dihydroxy-2-(hydroxymethyl)propan-2-yl)amino)methyl)-5-((3'-(3-((1,3-dihydroxy-2-(hydroxymethyl)propan-2-yl)amino)propoxy)-2,2'-dimethyl-[1,1'-biphenyl]-3-yl)methoxy)phenoxy)methyl)nicotinonitrile Example 2283: 5-((4-chloro-2-(((1-hydroxy-2-(hydroxymethyl)butan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile

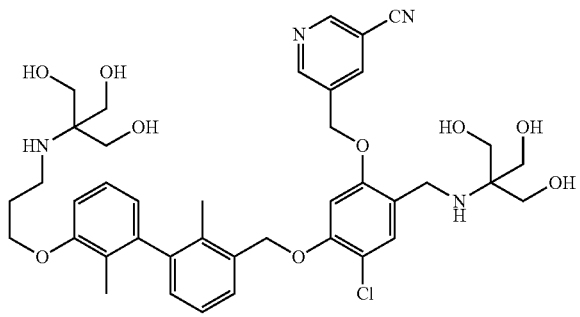 [SMILES: Cc1c(COc2cc(OCc3cncc(C#N)c3)c(CNC(CO)(CO)CO)cc2Cl)cccc1-c1cccc(OCCCNC(CO)(CO)CO)c1C]

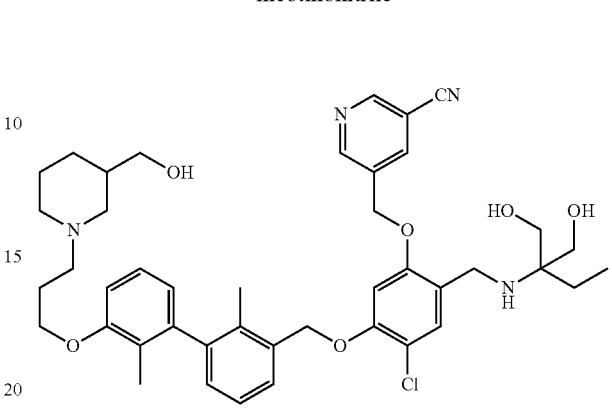

The compound was prepared and purified with the same method as that for Example 2278 to give the pure title compound: (4.1 mg, 9%). $^1$H NMR (500 MHz, DMSO-$d_6$) δ 9.00 (d, J=8.4 Hz, 2H), 8.44 (s, 1H), 7.48 (d, J=7.7 Hz, 1H), 7.43 (s, 1H), 7.27 (t, J=7.3 Hz, 1H), 7.21 (t, J=7.9 Hz, 1H), 7.13-7.04 (m, 2H), 6.97 (d, J=8.1 Hz, 1H), 6.69 (d, J=7.3 Hz, 1H), 5.33 (s, 2H), 5.25 (br. s., 2H), 4.09 (d, J=9.2 Hz, 2H), 3.72 (s, 2H), 2.89 (d, J=2.6 Hz, 2H), 2.04 (s, 3H), 1.98-1.92 (m, 2H), 1.84 (s, 3H). LC/MS Condition E: RT=1.34 min; m/e=765.2 (M+H)$^+$.

The compound was prepared and purified with the same method as that for Example 2278 to give the pure title compound: (13.3 mg, 33%). $^1$H NMR (500 MHz, DMSO-$d_6$) δ 9.04 (t, J=2.4 Hz, 2H), 8.53 (s, 1H), 8.15 (br. s., 1H), 7.56 (s, 1H), 7.50 (d, J=7.3 Hz, 1H), 7.28 (t, J=7.7 Hz, 1H), 7.24 (t, J=8.1 Hz, 1H), 7.19 (s, 1H), 7.08 (d, J=7.3 Hz, 1H), 6.98 (d, J=8.4 Hz, 1H), 6.70 (d, J=7.3 Hz, 1H), 5.41-5.28 (m, 4H), 4.19-4.06 (m, 4H), 3.62-3.45 (m, 3H), 3.41-3.21 (m, 1H), 2.84 (br. s., 1H), 2.71-2.61 (m, 1H), 2.19 (d, J=5.1 Hz, 2H), 2.04 (s, 3H), 1.91 (d, J=9.5 Hz, 2H), 1.74-1.55 (m, 4H), 0.79 (t, J=7.5 Hz, 3H). LC/MS Condition E: RT=1.56 min; m/e=757.3 (M+H)$^+$.

Example 2282: (S)-5-((4-chloro-2-(((1,3-dihydroxy-2-(hydroxymethyl)propan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile Example 2284: 5-((4-chloro-2-(((1,3-dihydroxy-2-(hydroxymethyl)propan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile

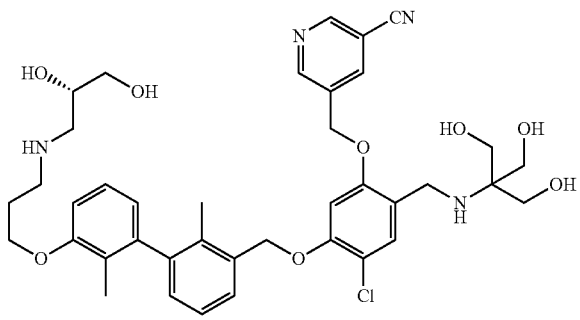 [SMILES: Cc1c(COc2cc(OCc3cncc(C#N)c3)c(CNC(CO)(CO)CO)cc2Cl)cccc1-c1cccc(OCCCNC[C@H](O)CO)c1C]

The compound was prepared and purified with the same method as that for Example 2278 to give the pure title compound: (23.2 mg, 51%). $^1$H NMR (500 MHz, DMSO-$d_6$) δ 9.00 (dd, J=8.1, 1.8 Hz, 2H), 8.44 (s, 1H), 7.48 (d, J=7.3 Hz, 1H), 7.42 (s, 1H), 7.26 (t, J=7.7 Hz, 1H), 7.21 (t, J=7.9 Hz, 1H), 7.12-7.04 (m, 2H), 6.97 (d, J=8.1 Hz, 1H), 6.68 (d, J=7.7 Hz, 1H), 5.33 (s, 2H), 5.25 (d, J=1.8 Hz, 2H), 4.15-3.99 (m, 2H), 3.37-3.27 (m, 2H), 2.81 (t, J=7.2 Hz, 2H), 2.74-2.69 (m, 1H), 2.04 (s, 2H), 1.96 (t, J=6.6 Hz, 1H), 1.84 (s, 1H). LC/MS Condition E: RT=1.34 min; m/e=735.2 (M+H).

The compound was prepared and purified with the same method as that for Example 2278 to give the pure title compound: (4.1 mg, 9%). $^1$H NMR (500 MHz, DMSO-$d_6$) δ 9.00 (d, J=8.4 Hz, 2H), 8.44 (s, 1H), 7.48 (d, J=7.7 Hz, 1H), 7.43 (s, 1H), 7.27 (t, J=7.3 Hz, 1H), 7.21 (t, J=7.9 Hz, 1H), 7.13-7.04 (m, 2H), 6.97 (d, J=8.1 Hz, 1H), 6.69 (d, J=7.3 Hz, 1H), 5.33 (s, 2H), 5.25 (br. s., 2H), 4.09 (d, J=9.2 Hz, 2H), 3.72 (s, 2H), 2.89 (d, J=2.6 Hz, 2H), 2.04 (s, 3H), 1.98-1.92 (m, 2H), 1.84 (s, 3H). LC/MS Condition E: RT=1.34 min; m/e=765.2 (M+H)$^+$.

Example 2285: (R)-5-((4-chloro-2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

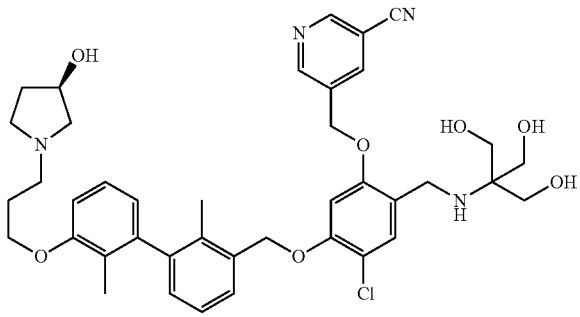 [SMILES: Cc1c(COc2cc(OCc3cncc(C#N)c3)c(CNC(CO)(CO)CO)cc2Cl)cccc1-c1cccc(OCCCN2CC[C@@H](O)C2)c1C]

The compound was prepared and purified with the same method as that for Example 2278 to give the pure title compound: (33.9 mg, 72%). $^1$H NMR (500 MHz, DMSO-$d_6$) δ 9.01 (dd, J=6.4, 2.0 Hz, 2H), 8.46 (s, 1H), 7.50-7.43 (m, 2H), 7.27 (t, J=7.5 Hz, 1H), 7.21 (t, J=8.1 Hz, 1H), 7.11 (s, 1H), 7.07 (d, J=8.4 Hz, 1H), 6.96 (d, J=8.4 Hz, 1H), 6.68 (d, J=7.7 Hz, 1H), 5.36-5.25 (m, 4H), 4.23 (br. s., 1H), 4.06 (d, J=9.2 Hz, 2H), 3.51-3.34 (m, 1H), 2.85-2.63 (m, 3H), 2.04 (s, 4H), 1.95 (br. s., 2H), 1.83 (s, 3H), 1.60 (br. s., 1H). LC/MS Condition E: RT=1.57 min; m/e=731.2 (M+H)$^+$.

Example 2286: (S)-2-((5-chloro-2-((5-cyanopyridin-3-yl)methoxy)-4-((3'-(3-(((S)-2,3-dihydroxypropyl)amino)propoxy)-2,2'-dimethyl-[1,1'-biphenyl]-3-yl)methoxy)benzyl)amino)-3-hydroxy-2-methylpropanoic Acid

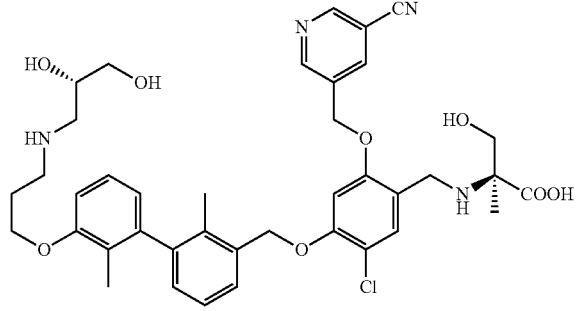 [SMILES: Cc1c(COc2cc(OCc3cncc(C#N)c3)c(CN[C@@](C)(CO)C(=O)O)cc2Cl)cccc1-c1cccc(OCCCNC[C@H](O)CO)c1C]

The compound was prepared and purified with the same method as that for Example 2278 to give the pure title compound: (8.3 mg, 19%). $^1$H NMR (500 MHz, DMSO-$d_6$) δ 9.02 (dd, J=5.5, 1.8 Hz, 2H), 8.50 (s, 1H), 7.51 (s, 1H), 7.48 (d, J=7.7 Hz, 1H), 7.26 (t, J=7.5 Hz, 1H), 7.21 (t, J=7.9 Hz, 1H), 7.10 (s, 1H), 7.07 (d, J=7.0 Hz, 1H), 6.96 (d, J=8.4 Hz, 1H), 6.68 (d, J=7.3 Hz, 1H), 5.33 (s, 2H), 5.29 (s, 2H), 4.14-4.02 (m, 2H), 3.87 (s, 2H), 3.42-3.27 (m, 1H), 2.81 (t, J=7.0 Hz, 2H), 2.75-2.70 (m, 2H), 2.60-2.56 (m, 1H), 2.02 (s, 3H), 1.96 (t, J=6.8 Hz, 2H), 1.80 (s, 3H), 1.20 (s, 3H). LC/MS Condition E: RT=1.38 min; m/e=733.2 (M+H)$^+$.

Example 2287: 5-((4-chloro-2-(((1,3-dihydroxy-2-methylpropan-2-yl)amino)methyl)-5-((2,2'-dimethyl-3'-(3-(piperidin-1-yl)propoxy)-[1,1'-biphenyl]-3-yl)methoxy)phenoxy)methyl)nicotinonitrile

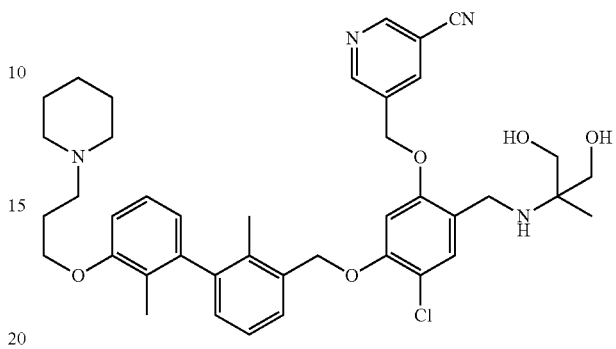

The compound was prepared and purified with the same method as that for Example 2278 to give the pure title compound: (5.6 mg, 24%). $^1$H NMR (500 MHz, DMSO-$d_6$) δ 9.01 (dd, J=6.4, 2.0 Hz, 1H), 8.45 (s, 1H), 7.47 (d, J=7.3 Hz, 1H), 7.43 (s, 1H), 7.26 (t, J=7.5 Hz, 1H), 7.21 (t, J=7.9 Hz, 1H), 7.10 (s, 1H), 7.07 (d, J=8.1 Hz, 1H), 6.96 (d, J=8.1 Hz, 1H), 6.67 (d, J=7.3 Hz, 1H), 5.33 (s, 2H), 5.27 (d, J=2.2 Hz, 2H), 4.10-3.95 (m, 2H), 2.46 (t, J=7.2 Hz, 2H), 2.37 (br. s., 3H), 2.04 (s, 3H), 1.94-1.87 (m, 4H), 1.82 (s, 3H), 1.50 (quin, J=5.6 Hz, 4H), 1.39 (d, J=4.8 Hz, 2H), 0.94 (s, 3H). LC/MS Condition E: RT=1.58 min; m/e=713.2 (M+H)$^+$.

Example 2288: 5-((4-chloro-2-(((1,3-dihydroxy-2-methylpropan-2-yl)amino)methyl)-5-((3'-(3-(4-(hydroxymethyl)piperidin-1-yl)propoxy)-2,2'-dimethyl-[1,1'-biphenyl]-3-yl)methoxy)phenoxy)methyl)nicotinonitrile

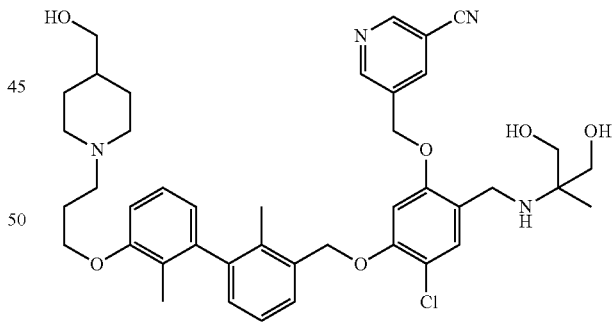

The compound was prepared and purified with the same method as that for Example 2278 to give the pure title compound: (7.7 mg, 31%). $^1$H NMR (500 MHz, DMSO-$d_6$) δ 9.01 (dd, J=7.9, 2.0 Hz, 1H), 8.44 (s, 1H), 7.48 (d, J=7.3 Hz, 1H), 7.41 (s, 1H), 7.26 (t, J=7.7 Hz, 1H), 7.21 (t, J=8.1 Hz, 1H), 7.11-7.04 (m, 2H), 6.96 (d, J=8.4 Hz, 1H), 6.68 (d, J=7.7 Hz, 1H), 5.32 (s, 2H), 5.25 (s, 2H), 4.10-4.01 (m, 2H), 3.24 (d, J=6.2 Hz, 1H), 2.93-2.81 (m, 2H), 2.45 (t, J=7.2 Hz, 2H), 2.04 (s, 3H), 1.87 (br. s., 1H), 1.82-1.80 (m, 1H), 1.63 (d, J=12.8 Hz, 2H), 1.33 (br. s., 1H), 1.19-1.05 (m, 2H), 0.91 (s, 3H). LC/MS Condition E: RT=1.51 min; m/e=743.2 (M+H)$^+$.

Example 2289: (R)-5-((4-chloro-2-(((1,3-dihydroxy-2-methylpropan-2-yl)amino)methyl)-5-((3'-(3-(hydroxymethyl)piperidin-1-yl)propoxy)-2,2'-dimethyl-[1,1'-biphenyl]-3-yl)methoxy)phenoxy)methyl)nicotinonitrile

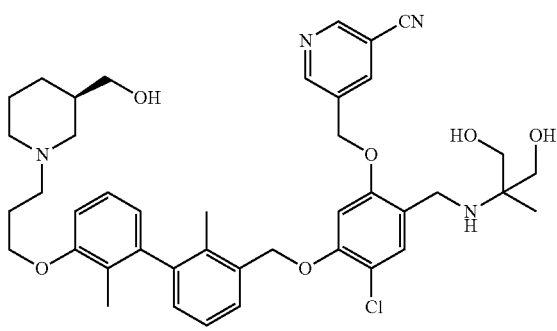 [SMILES: Cc1c(COc2cc(OCc3cncc(C#N)c3)c(CNC(C)(CO)CO)cc2Cl)cccc1-c1cccc(OCCCN2CCC[C@@H](CO)C2)c1C]

The compound was prepared and purified with the same method as that for Example 2278 to give the pure title compound: (5.0 mg, 19%). ¹H NMR (500 MHz, DMSO-d₆) δ 9.01 (dd, J=8.1, 2.2 Hz, 2H), 8.44 (s, 1H), 7.48 (d, J=7.3 Hz, 1H), 7.41 (s, 1H), 7.26 (t, J=7.5 Hz, 1H), 7.21 (t, J=7.9 Hz, 1H), 7.12-7.04 (m, 2H), 6.96 (d, J=8.1 Hz, 1H), 6.68 (d, J=7.3 Hz, 1H), 5.33 (s, 2H), 5.26 (d, J=2.6 Hz, 2H), 4.05 (d, J=6.6 Hz, 2H), 2.93-2.67 (m, 2H), 2.44 (t, J=7.2 Hz, 2H), 2.04 (s, 3H), 1.83 (s, 3H), 1.70-1.56 (m, 4H), 1.44 (d, J=11.7 Hz, 1H), 0.91 (s, 3H). LC/MS Condition E: RT=1.52 min; m/e=743.2 (M+H)⁺.

Example 2290: (R)—N-(1-(3-((3'-((2-chloro-5-((5-cyanopyridin-3-yl)methoxy)-4-(((1,3-dihydroxy-2-methylpropan-2-yl)amino)methyl)phenoxy)methyl)-2,2'-dimethyl-[1,1'-biphenyl]-3-yl)oxy)propyl)pyrrolidin-3-yl)acetamide

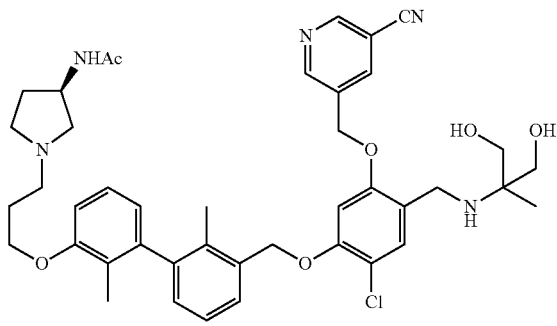 [SMILES: CC(=O)N[C@@H]1CCN(CCCOc2cccc(-c3cccc(COc4cc(OCc5cncc(C#N)c5)c(CNC(C)(CO)CO)cc4Cl)c3C)c2C)C1]

The compound was prepared and purified with the same method as that for Example 2278 to give the pure title compound: (7.2 mg, 28%). ¹H NMR (500 MHz, DMSO-d₆) δ 8.99 (d, J=4.4 Hz, 1H), 8.43 (s, 1H), 8.00 (br. s., 1H), 7.46 (d, J=7.3 Hz, 1H), 7.40 (s, 1H), 7.26 (t, J=7.7 Hz, 1H), 7.20 (t, J=8.1 Hz, 1H), 7.10-7.03 (m, 2H), 6.95 (d, J=8.4 Hz, 1H), 6.66 (d, J=7.3 Hz, 1H), 5.31 (s, 2H), 5.24 (s, 2H), 4.19-3.96 (m, 3H), 2.69-2.54 (m, 5H), 2.40 (d, J=8.8 Hz, 1H), 2.32 (dd, J=9.5, 4.8 Hz, 1H), 2.12-2.03 (m, 1H), 2.02 (s, 3H), 1.95-1.90 (m, 2H), 1.81 (s, 3H), 1.78 (s, 3H), 1.52 (d, J=6.2 Hz, 1H), 0.92 (s, 3H). All of the aromatic Hs were shown. LC/MS Condition E: RT=1.58 min; m/e=756.2 (M+H)⁺.

Example 2291: 5-((4-chloro-2-(((1,3-dihydroxypropan-2-yl)amino)methyl)-5-((2,2'-dimethyl-3'-(3-(piperidin-1-yl)propoxy)-[1,1'-biphenyl]-3-yl)methoxy)phenoxy)methyl)nicotinonitrile

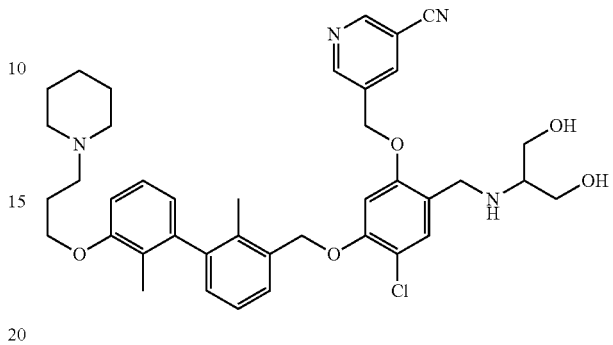

The compound was prepared and purified with the same method as that for Example 2278 to give the pure title compound: (11.5 mg, 49%). ¹H NMR (500 MHz, DMSO-d₆) δ 9.02 (d, J=1.8 Hz, 1H), 8.99 (d, J=1.8 Hz, 1H), 8.44 (s, 1H), 7.48 (d, J=7.3 Hz, 1H), 7.41 (s, 1H), 7.27 (t, J=7.3 Hz, 1H), 7.21 (t, J=7.9 Hz, 1H), 7.10 (s, 1H), 7.08 (d, J=6.6 Hz, 1H), 6.96 (d, J=8.4 Hz, 1H), 6.68 (d, J=7.7 Hz, 1H), 5.32 (s, 2H), 5.26 (d, J=2.2 Hz, 2H), 4.13-3.95 (m, 2H), 2.58-2.52 (m, 2H), 2.44-2.39 (m, 2H), 2.34 (br. s., 3H), 2.04 (s, 3H), 1.83 (s, 3H), 1.54-1.45 (m, 4H), 1.39 (d, J=5.1 Hz, 2H). LC/MS Condition E: RT=1.56 min; m/e=699.2 (M+H)⁺.

Example 2292: (R)-5-((4-chloro-2-(((1,3-dihydroxypropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile

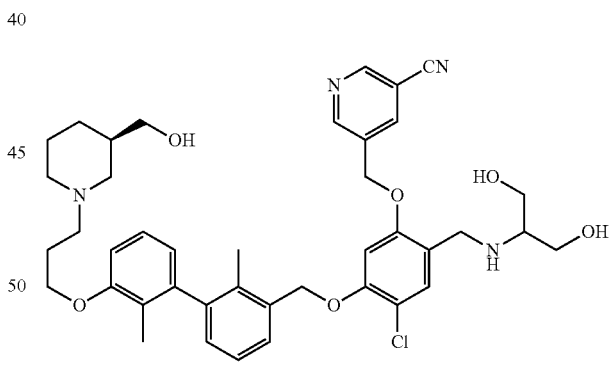

The compound was prepared and purified with the same method as that for Example 2278 to give the pure title compound: (8.1 mg, 33%). ¹H NMR (500 MHz, DMSO-d₆) δ 9.02 (d, J=1.8 Hz, 1H), 8.99 (d, J=1.8 Hz, 1H), 8.44 (s, 1H), 7.48 (d, J=7.0 Hz, 1H), 7.41 (s, 1H), 7.27 (t, J=7.5 Hz, 1H), 7.21 (t, J=8.1 Hz, 1H), 7.10 (s, 1H), 7.08 (d, J=7.3 Hz, 1H), 6.96 (d, J=8.1 Hz, 1H), 6.68 (d, J=7.3 Hz, 1H), 5.32 (s, 2H), 5.26 (d, J=2.6 Hz, 2H), 4.05 (d, J=6.6 Hz, 2H), 3.30-3.15 (m, 1H), 2.89 (d, J=11.4 Hz, 1H), 2.79-2.68 (m, 1H), 2.59-2.53 (m, 1H), 2.44 (t, J=7.2 Hz, 2H), 2.04 (s, 3H), 1.83 (s, 3H), 1.68-1.55 (m, 4H), 1.44 (d, J=12.5 Hz, 1H), 0.89 (d, J=11.0 Hz, 1H). LC/MS Condition E: RT=1.50 min; m/e=729.2 (M+H)⁺.

Example 2293: (S)-5-((4-chloro-2-(((1,3-dihydroxy-propan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile

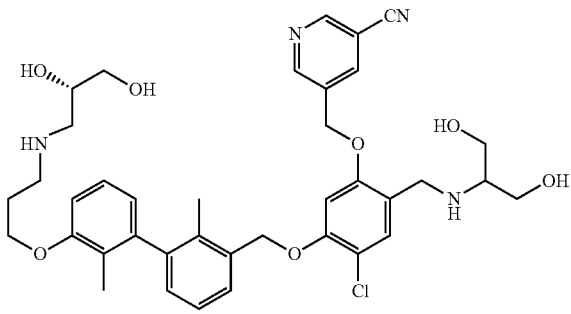 [SMILES: Cc1c(COc2cc(OCc3cncc(C#N)c3)c(CNC(CO)CO)cc2Cl)cccc1-c1cccc(OCCCNC[C@H](O)CO)c1C]

The compound was prepared and purified with the same method as that for Example 2278 to give the pure title compound: (5.9 mg, 25%). $^1$H NMR (500 MHz, DMSO-$d_6$) δ 9.02 (d, J=1.8 Hz, 1H), 9.00 (d, J=1.8 Hz, 1H), 8.44 (s, 1H), 7.49 (d, J=7.7 Hz, 1H), 7.41 (s, 1H), 7.27 (t, J=7.5 Hz, 1H), 7.21 (t, J=7.9 Hz, 1H), 7.11 (s, 1H), 7.07 (d, J=7.3 Hz, 1H), 6.97 (d, J=8.1 Hz, 1H), 6.69 (d, J=7.3 Hz, 1H), 5.32 (s, 2H), 5.26 (d, J=2.2 Hz, 2H), 4.14-4.01 (m, 2H), 3.57 (d, J=5.9 Hz, 1H), 3.43-3.33 (m, 1H), 2.79 (t, J=7.0 Hz, 2H), 2.74-2.66 (m, 1H), 2.59-2.53 (m, 3H), 2.04 (s, 3H), 1.98-1.92 (m, 2H), 1.84 (s, 3H).
LC/MS Condition E: RT=1.43 min; m/e=705.1 (M+H)$^+$.

Example 2294: 5-((4-chloro-2-(((1,3-dihydroxypropan-2-yl)amino)methyl)-5-((3'-(3-(4-(hydroxymethyl)piperidin-1-yl)propoxy)-2,2'-dimethyl-[1,1'-biphenyl]-3-yl)methoxy)phenoxy)methyl)nicotinonitrile

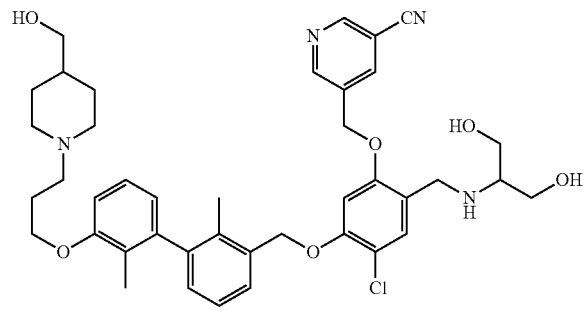 [SMILES: Cc1c(COc2cc(OCc3cncc(C#N)c3)c(CNC(CO)CO)cc2Cl)cccc1-c1cccc(OCCCN2CCC(CO)CC2)c1C]

The compound was prepared and purified with the same method as that for Example 2278 to give the pure title compound: (7.3 mg, 29%). $^1$H NMR (500 MHz, DMSO-$d_6$) δ 9.02 (d, J=1.8 Hz, 1H), 8.99 (d, J=2.2 Hz, 1H), 8.44 (s, 1H), 7.48 (d, J=7.3 Hz, 1H), 7.41 (s, 1H), 7.27 (t, J=7.5 Hz, 1H), 7.21 (t, J=7.9 Hz, 1H), 7.10 (s, 1H), 7.07 (d, J=7.3 Hz, 1H), 6.96 (d, J=8.1 Hz, 1H), 6.68 (d, J=7.3 Hz, 1H), 5.32 (s, 2H), 5.26 (d, J=2.2 Hz, 2H), 4.11-3.98 (m, 2H), 3.38-3.30 (m, 1H), 3.24 (d, J=6.2 Hz, 2H), 2.91-2.81 (m, 2H), 2.45 (t, J=7.2 Hz, 2H), 2.04 (s, 3H), 1.87 (br. s., 2H), 1.83 (s, 3H), 1.63 (d, J=11.7 Hz, 2H), 1.33 (br. s., 1H), 1.20-1.04 (m, 2H).
LC/MS Condition E: RT=1.49 min; m/e=729.2 (M+H)$^+$.

Example 2295: (S)-5-((4-chloro-2-(((1,3-dihydroxy-2-methylpropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile

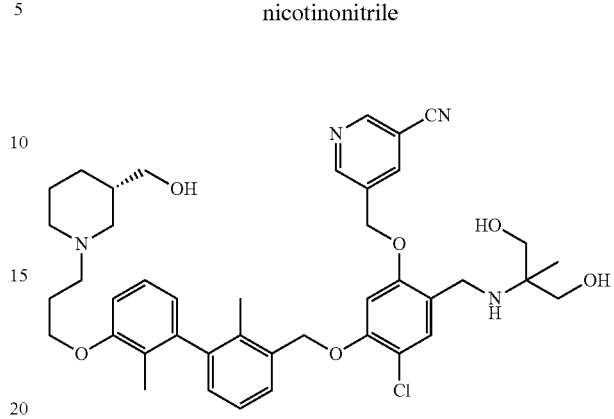

The compound was prepared and purified with the same method as that for Example 2278 to give the pure title compound: (10.8 mg, 45%). $^1$H NMR (500 MHz, DMSO-$d_6$) δ 9.01 (dd, J=8.1, 1.8 Hz, 2H), 8.44 (s, 1H), 7.48 (d, J=7.7 Hz, 1H), 7.42 (s, 1H), 7.26 (t, J=7.5 Hz, 1H), 7.21 (t, J=7.9 Hz, 1H), 7.12-7.03 (m, 2H), 6.96 (d, J=8.1 Hz, 1H), 6.68 (d, J=7.3 Hz, 1H), 5.32 (s, 2H), 5.26 (d, J=2.2 Hz, 2H), 4.05 (d, J=6.2 Hz, 2H), 3.24-3.15 (m, 1H), 2.92-2.69 (m, 2H), 2.45 (t, J=7.2 Hz, 2H), 2.04 (s, 3H), 1.83 (s, 3H), 1.68-1.52 (m, 4H), 1.44 (d, J=11.7 Hz, 1H), 0.92 (s, 3H).
LC/MS Condition E: RT=1.49 min; m/e=743.3 (M+H)$^+$.

Example 2296: (S)-5-((4-chloro-2-(((1,3-dihydroxy-propan-2-yl)amino)methyl)-5-((3'-(3-(3-(hydroxymethyl)piperidin-1-yl)propoxy)-2,2'-dimethyl-[1,12'-biphenyl]-3-yl)methoxy)phenoxy)methyl)nicotinonitrile

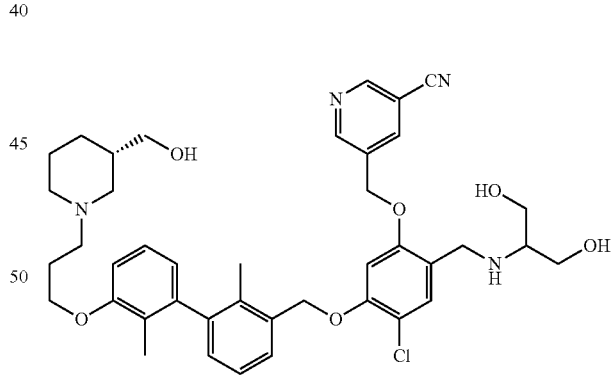

The compound was prepared and purified with the same method as that for Example 2278 to give the pure title compound: (8.2 mg, 33%). $^1$H NMR (500 MHz, DMSO-$d_6$) δ 9.02 (d, J=2.2 Hz, 1H), 8.99 (d, J=2.2 Hz, 1H), 8.44 (s, 1H), 7.48 (d, J=7.3 Hz, 1H), 7.41 (s, 1H), 7.27 (t, J=7.5 Hz, 1H), 7.21 (t, J=8.1 Hz, 1H), 7.10 (s, 1H), 7.08 (d, J=7.7 Hz, 1H), 6.96 (d, J=8.1 Hz, 1H), 6.68 (d, J=7.3 Hz, 1H), 5.32 (s, 2H), 5.26 (d, J=2.6 Hz, 2H), 4.05 (d, J=6.2 Hz, 2H), 3.38-3.18 (m, 2H), 2.90-2.84 (m, 1H), 2.45-2.40 (m, 2H), 2.04 (s, 3H), 1.83 (s, 3H), 1.61 (s, 3H), 1.61 (d, J=9.9 Hz, 4H), 1.44 (d, J=11.7 Hz, 1H). LC/MS Condition E: RT=1.50 min; m/e=729.2 (M+H)$^+$.

Example 2297: (S)-5-((4-chloro-2-(((1,3-dihydroxy-2-methylpropan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile

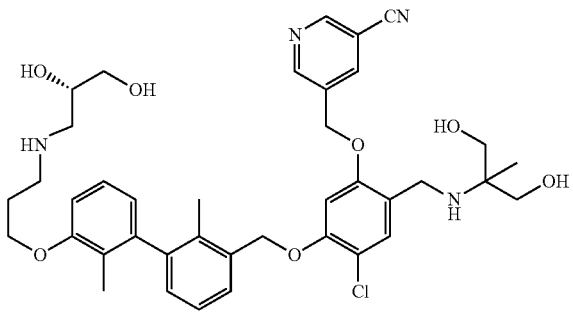 [SMILES: Cc1c(COc2cc(OCc3cncc(C#N)c3)c(CNC(C)(CO)CO)cc2Cl)cccc1-c1cccc(OCCCNC[C@H](O)CO)c1C]

The compound was prepared and purified with the same method as that for Example 2278 to give the pure title compound: (3.0 mg, 9%). $^1$H NMR (500 MHz, DMSO-d$_6$) δ 9.04 (s, 2H), 8.52 (s, 1H), 7.55 (s, 1H), 7.50 (d, J=7.7 Hz, 1H), 7.28 (t, J=7.7 Hz, 1H), 7.24 (t, J=8.1 Hz, 1H), 7.19 (s, 1H), 7.08 (d, J=7.3 Hz, 1H), 6.98 (d, J=8.1 Hz, 1H), 6.70 (d, J=7.7 Hz, 1H), 5.44-5.28 (m, 5H), 4.19-4.03 (m, 4H), 3.79 (br. s., 1H), 3.58-3.46 (m, 2H), 3.42-3.36 (m, 4H), 3.19-3.10 (m, 2H), 2.92-2.82 (m, 1H), 2.15 (d, J=7.3 Hz, 2H), 2.04 (s, 3H), 1.85 (s, 3H), 1.12 (s, 3H). LC/MS Condition E: RT=1.42 min; m/e=719.2 (M+H)$^+$.

Example 2298: 5-((4-chloro-5-((2-chloro-3'-(3-((3S,4R)-3-hydroxy-4-(hydroxymethyl)piperidin-1-yl)propoxy)-2'-methyl-[1,1'-biphenyl]-3-yl)methoxy)-2-(((1,3-dihydroxypropan-2-yl)amino)methyl)phenoxy)methyl)nicotinonitrile

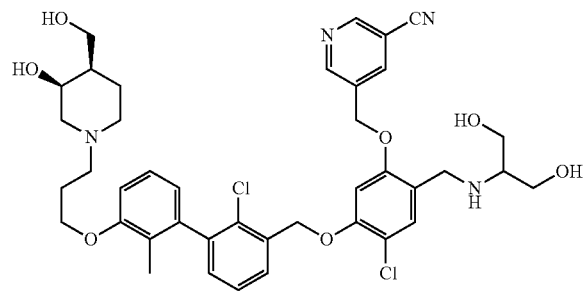 [SMILES: Cc1c(OCCCN2CC[C@H](CO)[C@H](O)C2)cccc1-c1cccc(COc2cc(OCc3cncc(C#N)c3)c(CNC(CO)CO)cc2Cl)c1Cl]

The compound was prepared and purified with the same method as that for Example 2278 to give the pure title compound: (18.2 mg, 67%). $^1$H NMR (500 MHz, DMSO-d$_6$) δ 9.01 (d, J=1.8 Hz, 1H), 8.98 (d, J=1.8 Hz, 1H), 8.43 (s, 1H), 7.68 (d, J=6.2 Hz, 1H), 7.47 (t, J=7.7 Hz, 1H), 7.44 (s, 1H), 7.28 (d, J=6.2 Hz, 1H), 7.23 (t, J=7.9 Hz, 1H), 7.07 (s, 1H), 7.01 (d, J=8.4 Hz, 1H), 6.73 (d, J=7.3 Hz, 1H), 5.32 (d, J=9.5 Hz, 4H), 4.07 (d, J=6.2 Hz, 2H), 3.72 (s, 3H), 3.50-3.19 (m, 1H), 2.82-2.70 (m, 2H), 2.58-2.52 (m, 3H), 2.46 (d, J=12.8 Hz, 2H), 2.04 (d, J=10.6 Hz, 1H), 1.91 (s, 7H), 1.88 (s, 3H). LC/MS Condition E: RT=1.41 min; m/e=765.1 (M+H)$^+$.

Example 2299: (S)-5-((4-chloro-5-((2-chloro-3'-(3-((2,3-dihydroxypropyl)amino)propoxy)-2'-methyl-[1,1'-biphenyl]-3-yl)methoxy)-2-(((1,3-dihydroxypropan-2-yl)amino)methyl)phenoxy)methyl)nicotinonitrile

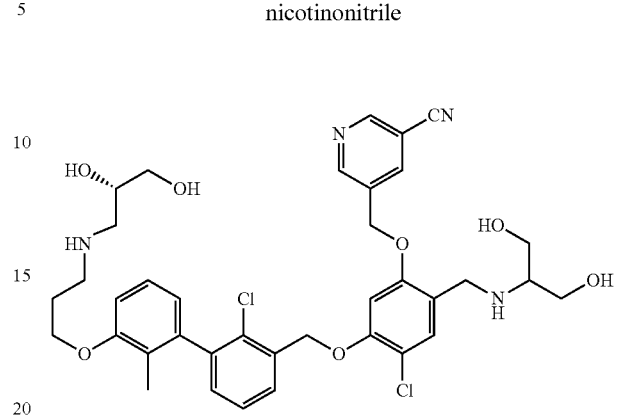

The compound was prepared and purified with the same method as that for Example 2278 to give the pure title compound: (3.1 mg, 12%). $^1$H NMR (500 MHz, DMSO-d$_6$) δ 9.01 (d, J=1.8 Hz, 1H), 8.98 (d, J=2.2 Hz, 1H), 8.45-8.41 (m, 1H), 7.68 (d, J=7.7 Hz, 1H), 7.47 (t, J=7.5 Hz, 1H), 7.44 (s, 1H), 7.31-7.26 (m, 1H), 7.23 (t, J=7.9 Hz, 1H), 7.07 (s, 1H), 7.00 (d, J=8.1 Hz, 1H), 6.73 (d, J=7.3 Hz, 1H), 5.32 (d, J=7.3 Hz, 4H), 4.14-4.01 (m, 2H), 3.72 (s, 2H), 3.60-3.52 (m, 1H), 3.37-3.27 (m, 1H), 2.75 (t, J=7.0 Hz, 2H), 2.70-2.61 (m, 1H), 1.98-1.90 (m, 2H), 1.89 (br. s., 3H). LC/MS Condition E: RT=1.40 min; m/e=725.2 (M+H)$^+$.

Example 2300: (R)-5-((4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)methyl)nicotinonitrile

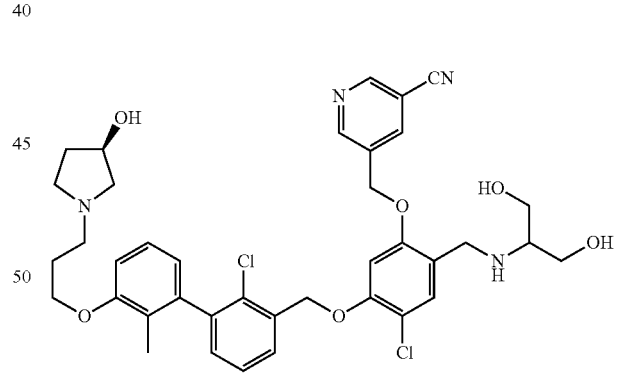

The compound was prepared and purified with the same method as that for Example 2278 to give the pure title compound: (6.0 mg, 15%). $^1$H NMR (500 MHz, DMSO-d$_6$) δ 9.01 (d, J=1.8 Hz, 1H), 8.98 (d, J=2.2 Hz, 1H), 8.43 (s, 1H), 7.68 (d, J=6.2 Hz, 1H), 7.51-7.45 (m, 1H), 7.44 (s, 1H), 7.30-7.27 (m, 1H), 7.23 (t, J=7.9 Hz, 1H), 7.07 (s, 1H), 7.00 (d, J=8.1 Hz, 1H), 6.73 (d, J=7.7 Hz, 1H), 5.32 (d, J=9.2 Hz, 4H), 4.24-4.12 (m, 1H), 4.09-4.00 (m, 2H), 2.70 (dd, J=9.5, 6.2 Hz, 1H), 2.60-2.55 (m, 7H), 2.46-2.39 (m, 1H), 2.33-2.27 (m, 1H), 2.03-1.89 (m, 4H), 1.88 (br. s., 3H), 1.61-1.46 (m, 1H). LC/MS Condition E: RT=1.45 min; m/e=721.1 (M+H)$^+$.

Example 2301: 5-((4-chloro-5-((2-chloro-2'-methyl-3'-(3-(piperidin-1-yl)propoxy)-[1,1'-biphenyl]-3-yl)methoxy)-2-(((1,3-dihydroxypropan-2-yl)amino)methyl)phenoxy)methyl)nicotinonitrile

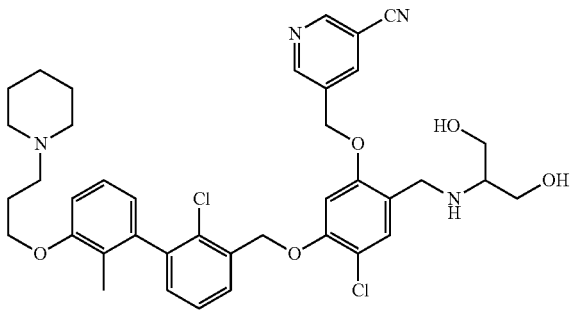 [SMILES: Cc1c(OCCCN2CCCCC2)cccc1-c1cccc(COc2cc(OCc3cncc(C#N)c3)c(CNC(CO)CO)cc2Cl)c1Cl]

The compound was prepared and purified with the same method as that for Example 2278 to give the pure title compound: (12.2 mg, 48%). $^1$H NMR (500 MHz, DMSO-$d_6$) δ 9.01 (d, J=2.2 Hz, 1H), 8.98 (d, J=2.2 Hz, 1H), 8.44-8.41 (m, 1H), 7.68 (d, J=7.7 Hz, 1H), 7.47 (t, J=7.5 Hz, 1H), 7.44 (s, 1H), 7.28 (dd, J=7.5, 1.7 Hz, 1H), 7.23 (t, J=7.9 Hz, 1H), 7.07 (s, 1H), 7.00 (d, J=8.4 Hz, 1H), 6.73 (d, J=7.3 Hz, 1H), 5.32 (s, 2H), 5.31 (s, 2H), 4.12-3.99 (m, 2H), 2.45 (t, J=7.2 Hz, 2H), 2.37 (br. s., 3H), 1.97-1.90 (m, 4H), 1.88 (s, 3H), 1.50 (quin, J=5.5 Hz, 4H), 1.39 (d, J=6.2 Hz, 2H). LC/MS Condition E: RT=1.52 min; m/e=719.1 (M+H)$^+$.

Example 2302: (S)-1-(5-chloro-4-((2-chloro-3'-(3-((R)-3-hydroxypyrrolidin-1-yl)propoxy)-2'-methyl-[1,1'-biphenyl]-3-yl)methoxy)-2-((5-cyanopyridin-3-yl)methoxy)benzyl)piperidine-2-carboxylic Acid

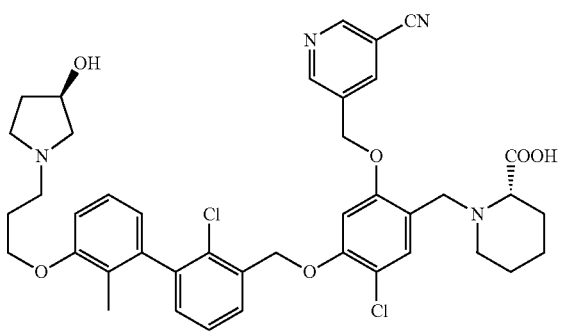 [SMILES: Cc1c(OCCCN2CC[C@@H](O)C2)cccc1-c1cccc(COc2cc(OCc3cncc(C#N)c3)c(CN3CCCC[C@H]3C(=O)O)cc2Cl)c1Cl]

The compound was prepared and purified with the same method as that for Example 2278 to give the pure title compound: (8.7 mg, 30%). $^1$H NMR (500 MHz, DMSO-$d_6$) δ 9.00 (d, J=1.8 Hz, 1H), 8.98 (d, J=1.8 Hz, 1H), 8.44 (s, 1H), 7.69 (d, J=7.3 Hz, 1H), 7.50-7.43 (m, 2H), 7.28 (d, J=7.3 Hz, 1H), 7.22 (t, J=7.9 Hz, 1H), 7.07 (d, J=2.2 Hz, 1H), 6.99 (d, J=8.1 Hz, 1H), 6.73 (d, J=7.7 Hz, 1H), 5.32 (d, J=8.4 Hz, 4H), 4.18 (d, J=2.9 Hz, 1H), 4.11-4.01 (m, 2H), 3.78 (d, J=13.9 Hz, 1H), 3.58 (d, J=13.9 Hz, 1H), 3.07 (br. s., 1H), 2.87 (br. s., 1H), 2.71 (dd, J=9.5, 6.2 Hz, 1H), 2.62-2.55 (m, 3H), 2.48-2.38 (m, 1H), 2.33 (dd, J=9.5, 3.7 Hz, 1H), 2.24 (br. s., 1H), 2.05-1.90 (m, 3H), 1.87 (s, 3H), 1.83-1.65 (m, 2H), 1.58-1.43 (m, 4H), 1.35 (br. s., 1H). LC/MS Condition E: RT=1.52 min; m/e=759.1 (M+H)$^+$.

Example 2303: (S)-1-(5-chloro-4-((2-chloro-3'-(3-(((S)-2,3-dihydroxypropyl)amino)propoxy)-2'-methyl-[1,1'-biphenyl]-3-yl)methoxy)-2-((5-cyanopyridin-3-yl)methoxy)benzyl)piperidine-2-carboxylic Acid

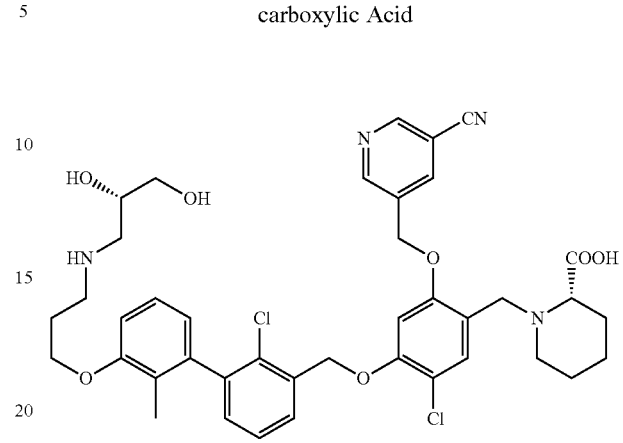

The compound was prepared and purified with the same method as that for Example 2278 to give the pure title compound: (6.8 mg, 68%). $^1$H NMR (500 MHz, DMSO-$d_6$) δ 9.02 (d, J=1.8 Hz, 1H), 8.99 (s, 1H), 8.45 (s, 1H), 7.70 (d, J=8.1 Hz, 1H), 7.51-7.45 (m, 2H), 7.26 (dd, J=16.3, 7.9 Hz, 2H), 7.13 (d, J=2.6 Hz, 1H), 7.01 (d, J=8.1 Hz, 1H), 6.76 (d, J=7.7 Hz, 1H), 5.35 (s, 4H), 4.12 (dd, J=10.8, 5.3 Hz, 2H), 3.78 (br. s., 2H), 3.21-3.10 (m, 3H), 3.06-2.83 (m, 2H), 2.16 (br. s., 2H), 1.90 (s, 3H), 1.74 (br. s., 1H), 1.55 (br. s., 3H), 1.42 (br. s., 1H), 1.26 (d, J=7.7 Hz, 1H). LC/MS Condition E: RT=1.49 min; m/e=763.1 (M+H)$^+$.

Example 2304: (S)-1-(5-chloro-4-((2-chloro-3'-((S)-3-hydroxypyrrolidin-1-yl)propoxy)-2'-methyl-[1,1'-biphenyl]-3-yl)methoxy)-2-((5-cyanopyridin-3-yl)methoxy)benzyl)piperidine-2-carboxylic Acid

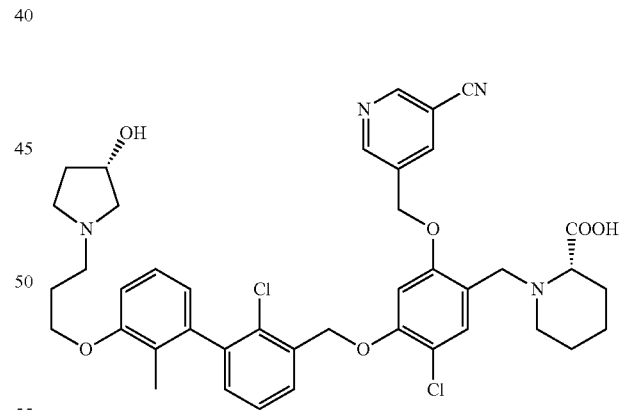

The compound was prepared and purified with the same method as that for Example 2278 to give the pure title compound: (3.8 mg, 22%). $^1$H NMR (500 MHz, DMSO-$d_6$) δ 9.02 (d, J=1.8 Hz, 1H), 8.99 (s, 1H), 8.45 (s, 1H), 8.27 (br. s., 1H), 7.70 (d, J=7.7 Hz, 1H), 7.53-7.41 (m, 2H), 7.33-7.21 (m, 2H), 7.12 (d, J=4.4 Hz, 1H), 7.01 (d, J=8.1 Hz, 1H), 6.76 (d, J=7.7 Hz, 1H), 5.35 (s, 4H), 4.32 (br. s., 1H), 4.18-4.01 (m, 2H), 3.99-3.69 (m, 1H), 3.07-2.87 (m, 1H), 2.41 (s, 1H), 2.20-2.07 (m, 2H), 1.90 (s, 5H), 1.83 (s, 3H), 1.75 (br. s., 1H), 1.54 (br. s., 3H), 1.42 (br. s., 1H). LC/MS Condition E: RT=1.53 min; m/e=800.2 (M+H)$^+$.

Example 2305: (R)-5-((4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxy-2-methylpropan-2-yl)amino)methyl)phenoxy)methyl)nicotinonitrile

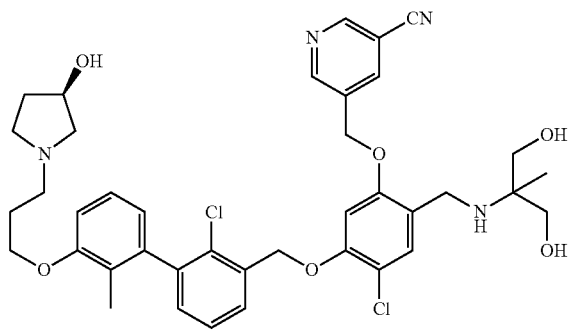 [SMILES: Cc1c(OCCCN2CC[C@@H](O)C2)cccc1-c1cccc(COc2cc(OCc3cncc(C#N)c3)c(CNC(C)(CO)CO)cc2Cl)c1Cl]

The compound was prepared and purified with the same method as that for Example 2278 to give the pure title compound: (12.3 mg, 65%). $^1$H NMR (500 MHz, DMSO-$d_6$) δ 9.01 (d, J=1.8 Hz, 1H), 8.99 (d, J=1.8 Hz, 1H), 8.43 (s, 1H), 7.67 (d, J=6.6 Hz, 1H), 7.50-7.42 (m, 2H), 7.28 (d, J=6.2 Hz, 1H), 7.22 (t, J=8.1 Hz, 1H), 7.06 (s, 1H), 6.99 (d, J=8.1 Hz, 1H), 6.72 (d, J=7.7 Hz, 1H), 5.32 (d, J=7.7 Hz, 4H), 4.19 (br. s., 1H), 4.10-3.97 (m, 2H), 3.66 (s, 1H), 3.29 (s, 1H), 2.72 (dd, J=9.5, 6.6 Hz, 1H), 2.65-2.55 (m, 3H), 2.48-2.30 (m, 2H), 2.03-1.94 (m, 1H), 1.91 (s, 4H), 1.59-1.46 (m, 1H), 0.92 (s, 3H). LC/MS Condition E: RT=1.38 min; m/e=735.1 (M+H)$^+$.

Example 2306: (S)-1-(5-chloro-4-((2-chloro-2'-methyl-3'-(3-(piperidin-1-yl)propoxy)-[1,1'-biphenyl]-3-yl)methoxy)-2-((5-cyanopyridin-3-yl)methoxy)benzyl)piperidine-2-carboxylic Acid

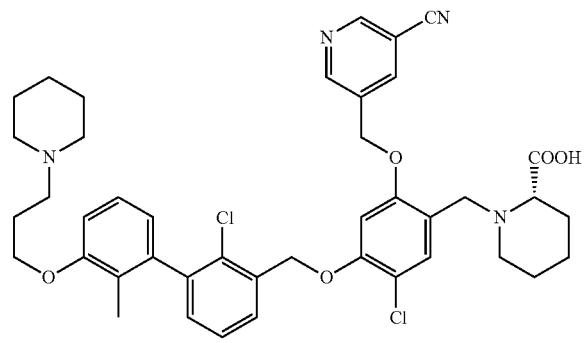 [SMILES: Cc1c(OCCCN2CCCCC2)cccc1-c1cccc(COc2cc(OCc3cncc(C#N)c3)c(CN3CCCC[C@H]3C(=O)O)cc2Cl)c1Cl]

The compound was prepared and purified with the same method as that for Example 2278 to give the pure title compound: (8.9 mg, 74%). $^1$H NMR (500 MHz, DMSO-$d_6$) δ 9.01 (d, J=1.8 Hz, 1H), 8.98 (s, 1H), 8.44 (s, 1H), 7.69 (d, J=7.3 Hz, 1H), 7.47 (t, J=7.5 Hz, 1H), 7.44 (s, 1H), 7.26-7.26 (m, 1H), 7.28 (d, J=6.6 Hz, 1H), 7.24-7.19 (m, 1H), 7.08 (d, J=3.3 Hz, 1H), 7.00 (d, J=8.1 Hz, 1H), 6.73 (d, J=7.3 Hz, 1H), 5.33 (d, J=9.2 Hz, 4H), 4.10-3.98 (m, 2H), 3.77 (d, J=13.9 Hz, 1H), 3.60 (d, J=13.2 Hz, 1H), 3.13 (d, J=4.8 Hz, 1H), 2.87 (br. s., 1H), 2.47-2.23 (m, 7H), 1.99-1.88 (m, 3H), 1.84-1.64 (m, 2H), 1.56-1.42 (m, 7H), 1.38 (br. s., 3H).

LC/MS Condition E: RT=1.52 min; m/e=757.2 (M+H)$^+$.

Example 2307: (S)-5-((4-chloro-5-((2-chloro-3'-(3-((2,3-dihydroxypropyl)amino)propoxy)-2'-methyl-[1,1'-biphenyl]-3-yl)methoxy)-2-(((1,3-dihydroxy-2-methylpropan-2-yl)amino)methyl)phenoxy)methyl)nicotinonitrile

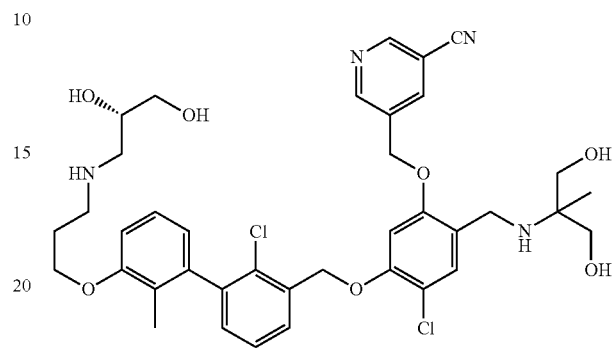

The compound was prepared and purified with the same method as that for Example 2278 to give the pure title compound: (9.4 mg, 52%). $^1$H NMR (500 MHz, DMSO-$d_6$) δ 9.01 (d, J=1.8 Hz, 1H), 8.99 (d, J=1.8 Hz, 1H), 8.43 (s, 1H), 7.67 (d, J=7.0 Hz, 1H), 7.52-7.42 (m, 2H), 7.28 (d, J=6.2 Hz, 1H), 7.25-7.19 (m, 1H), 7.06 (s, 1H), 7.00 (d, J=8.4 Hz, 1H), 6.73 (d, J=7.7 Hz, 1H), 5.32 (d, J=4.0 Hz, 4H), 4.14-3.99 (m, 2H), 3.57 (d, J=4.8 Hz, 1H), 2.79 (t, J=6.8 Hz, 2H), 2.72-2.66 (m, 1H), 1.95 (t, J=6.4 Hz, 2H), 1.91 (s, 3H), 0.91 (s, 3H). LC/MS Condition E: RT=1.34 min; m/e=739.1 (M+H)$^+$.

Example 2308: 5-((4-chloro-5-((2-chloro-2'-methyl-3'-(3-(piperidin-1-yl)propoxy)-[1,1'-biphenyl]-3-yl)methoxy)-2-(((1,3-dihydroxy-2-methylpropan-2-yl)amino)methyl)phenoxy)methyl)nicotinonitrile

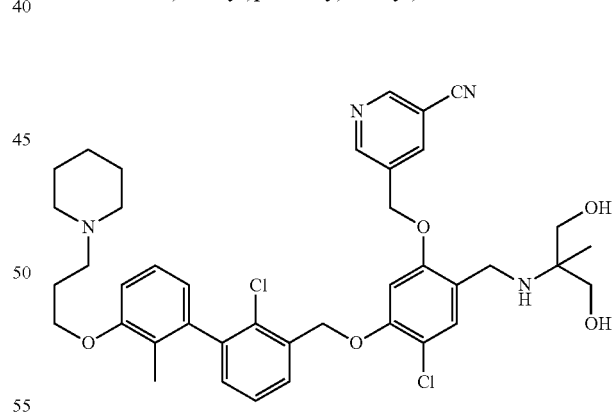

The compound was prepared and purified with the same method as that for Example 2278 to give the pure title compound: (14.7 mg, 79%). $^1$H NMR (500 MHz, DMSO-$d_6$) δ 9.00 (d, J=2.2 Hz, 1H), 8.98 (d, J=2.2 Hz, 1H), 8.43 (s, 1H), 7.67 (d, J=6.2 Hz, 1H), 7.50-7.40 (m, 2H), 7.27 (dd, J=7.5, 1.7 Hz, 1H), 7.22 (t, J=7.9 Hz, 1H), 7.06 (s, 1H), 6.99 (d, J=8.1 Hz, 1H), 6.72 (d, J=7.3 Hz, 1H), 5.32 (d, J=7.7 Hz, 4H), 4.11-3.96 (m, 2H), 2.43 (t, J=7.2 Hz, 2H), 2.35 (br. s., 4H), 1.94-1.89 (m, 4H), 1.50 (quin, J=5.6 Hz, 4H), 1.38 (d, J=5.1 Hz, 2H), 0.92 (s, 3H). LC/MS Condition E: RT=2.01 min; m/e=733.2 (M+H)$^+$.

Example 2309: (S)-1-(5-chloro-4-((2-chloro-2'-methyl-3'-(3-morpholinopropoxy)-[1,1'-biphenyl]-3-yl)methoxy)-2-((5-cyanopyridin-3-yl)methoxy)benzyl)piperidine-2-carboxylic Acid

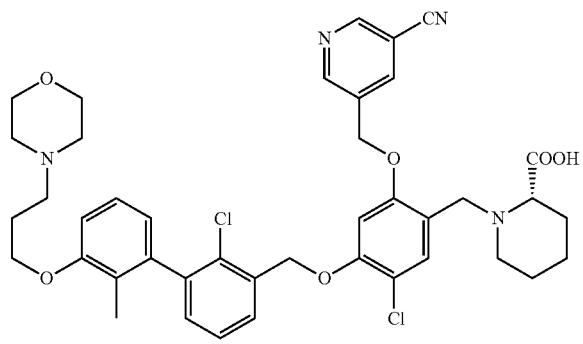 [SMILES: Cc1c(OCCCN2CCOCC2)cccc1-c1cccc(COc2cc(OCc3cncc(C#N)c3)c(CN3CCCC[C@H]3C(=O)O)cc2Cl)c1Cl]

The compound was prepared and purified with the same method as that for Example 2278 to give the pure title compound: (8.8 mg, 57%). $^1$H NMR (500 MHz, DMSO-$d_6$) δ 9.01 (d, J=1.8 Hz, 1H), 9.00 (s, 1H), 8.46 (s, 1H), 7.69 (d, J=7.7 Hz, 1H), 7.55-7.44 (m, 2H), 7.29-7.22 (m, 2H), 7.14 (d, J=4.0 Hz, 1H), 7.01 (d, J=8.1 Hz, 1H), 6.76 (d, J=7.7 Hz, 1H), 5.36 (s, 4H), 4.19-3.95 (m, 3H), 3.81 (br. s., 1H), 3.33-3.01 (m, 2H), 2.15 (d, J=6.2 Hz, 2H), 1.94 (br. s., 1H), 1.90 (s, 3H), 1.74 (d, J=12.5 Hz, 1H), 1.58 (br. s., 3H), 1.43 (br. s., 1H), 1.31-1.19 (m, 1H). LC/MS Condition E: RT=1.55 min; m/e=759.1 (M+H)$^+$.

Example 2310: (S)-1-(5-chloro-4-((2-chloro-3'-(3-(1,1-dioxidothiomorpholino)propoxy)-2'-methyl-[1,1'-biphenyl]-3-yl)methoxy)-2-((5-cyanopyridin-3-yl)methoxy)benzyl)piperidine-2-carboxylic Acid

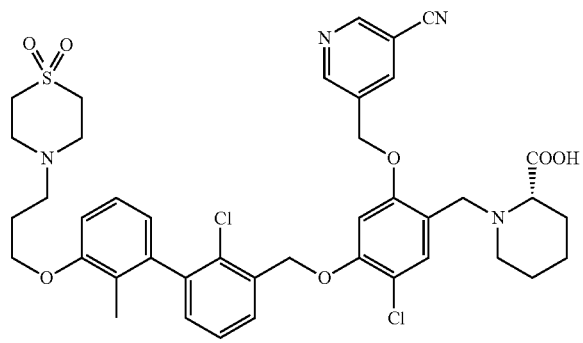 [SMILES: Cc1c(OCCCN2CCS(=O)(=O)CC2)cccc1-c1cccc(COc2cc(OCc3cncc(C#N)c3)c(CN3CCCC[C@H]3C(=O)O)cc2Cl)c1Cl]

The compound was prepared and purified with the same method as that for Example 2278 to give the pure title compound: (3.0 mg, 23%). $^1$H NMR (500 MHz, DMSO-$d_6$) δ 9.00 (d, J=1.5 Hz, 1H), 8.98 (d, J=1.5 Hz, 1H), 8.44 (s, 1H), 7.68 (d, J=7.0 Hz, 1H), 7.53-7.39 (m, 2H), 7.33-7.20 (m, 2H), 7.08 (s, 1H), 7.01 (d, J=8.4 Hz, 1H), 6.73 (d, J=7.7 Hz, 1H), 5.33 (d, J=4.4 Hz, 4H), 4.15-3.99 (m, 2H), 3.83-3.57 (m, 1H), 3.18-3.13 (m, 1H), 3.08 (d, J=5.1 Hz, 3H), 2.96-2.83 (m, 5H), 2.67 (t, J=7.2 Hz, 2H), 2.30 (br. s., 1H), 1.97-1.89 (m, 3H), 1.88 (s, 3H), 1.84-1.66 (m, 2H), 1.59-1.32 (m, 4H). LC/MS Condition E: RT=1.57 min; m/e=807.1 (M+H)$^+$.

Example 2311: (S)—N-(1-(3-((2'-chloro-3'-((2-chloro-5-((5-cyanopyridin-3-yl)methoxy)-4-(((1,3-dihydroxypropan-2-yl)amino)methyl)phenoxy)methyl)-2-methyl-[1,1'-biphenyl]-3-yl)oxy)propyl)pyrrolidin-3-yl)acetamide

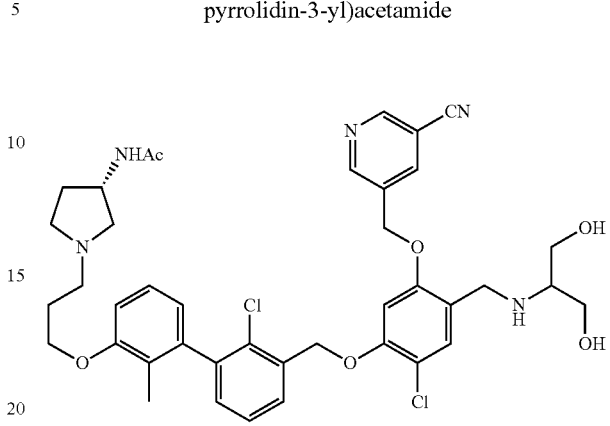

The compound was prepared and purified with the same method as that for Example 2278 to give the pure title compound: (6.9 mg, 33%). $^1$H NMR (500 MHz, DMSO-$d_6$) δ 9.01 (d, J=1.8 Hz, 1H), 8.98 (d, J=1.8 Hz, 1H), 8.43 (s, 1H), 7.97 (d, J=7.0 Hz, 1H), 7.68 (d, J=7.7 Hz, 1H), 7.52-7.42 (m, 2H), 7.28 (d, J=6.2 Hz, 1H), 7.25-7.17 (m, 1H), 7.07 (s, 1H), 7.00 (d, J=8.4 Hz, 1H), 6.73 (d, J=7.7 Hz, 1H), 5.32 (d, J=9.2 Hz, 4H), 4.20-3.98 (m, 3H), 3.75 (s, 2H), 2.73-2.56 (m, 4H), 2.45-2.28 (m, 2H), 2.12-2.03 (m, 1H), 1.91 (s, 4H), 1.78 (s, 3H), 1.59-1.45 (m, 1H).
LC/MS Condition E: RT=1.31 min; m/e=762.2 (M+H)$^+$.

Example 2312: (R)-5-(2-((5-chloro-4-((2-chloro-3'-(3-(3-hydroxypyrrolidin-1-yl)propoxy)-2'-methyl-[1,1'-biphenyl]-3-yl)methoxy)-2-((5-cyanopyridin-3-yl)methoxy)benzyl)(1,3-dihydroxypropan-2-yl)amino)ethyl)nicotinonitrile

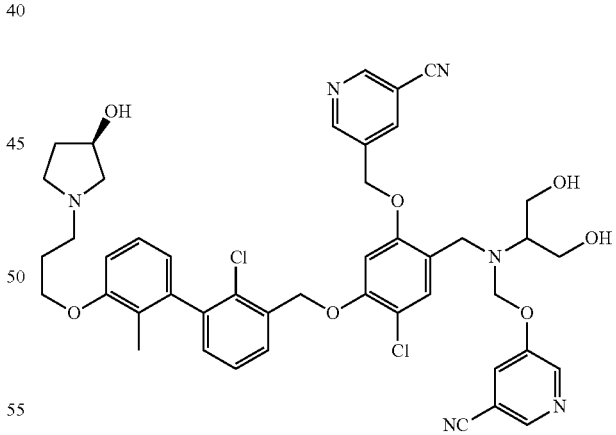

A mixture of (R)-5-((4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)methyl)nicotinonitrile (20 mg, 0.016 mmol)/Example 2300, 5-(2-iodoethyl)nicotinonitrile (20.38 mg, 0.079 mmol) and potassium carbonate (4.37 mg, 0.032 mmol) in MeCN (1 mL) was stirred at 80° C. under nitrogen for 22 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to give the pure title compound: (2.4 mg, 12%). $^1$H NMR (500 MHz, DMSO-$d_6$) δ 8.99 (d, J=1.8 Hz, 1H), 8.96 (d, J=1.8 Hz, 1H), 8.78 (d, J=1.8 Hz, 1H), 8.57 (d, J=2.2 Hz, 1H), 8.40 (s, 1H), 8.01 (s, 1H), 7.69 (d, J=6.6 Hz, 1H), 7.63 (dd, J=11.4, 7.3 Hz, 3H), 7.57-7.53 (m, 1H), 7.47 (t, J=7.7 Hz, 1H), 7.28 (d, J=6.2 Hz, 1H), 7.22 (t, J=8.1 Hz, 1H), 7.15 (s, 1H), 7.01-6.93 (m, 2H), 6.73 (d, J=7.7 Hz, 1H), 5.38-5.24 (m, 4H), 4.25-4.16 (m, 1H), 4.10-3.98 (m, 2H), 2.87 (t, J=6.2 Hz, 2H), 2.81-2.64 (m, 4H), 2.46-2.26 (m, 3H), 2.04-1.90 (m, 3H), 1.88 (s, 3H), 1.54 (d, J=4.0 Hz, 1H). LC/MS Condition E: RT=1.53 min; m/e=851.6 (M+H)$^+$.

Example 2313: (R)-2-((2-(allyloxy)-5-chloro-4-((2-chloro-3'-(3-(3-hydroxypyrrolidin-1-yl)propoxy)-2'-methyl-[1,1'-biphenyl]-3-yl)methoxy)benzyl)amino)propane-1,3-diol

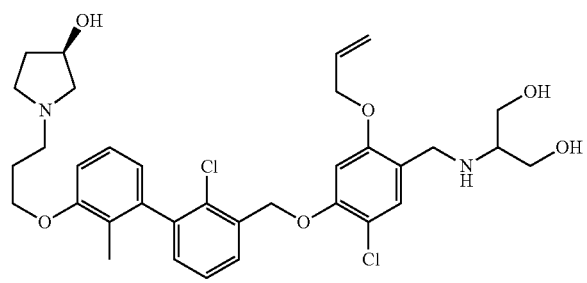 [SMILES: C=CCOc1cc(OCc2cccc(-c3cccc(OCCCN4CC[C@@H](O)C4)c3C)c2Cl)c(Cl)cc1CNC(CO)CO]

A mixture of 4-((3'-(3-bromopropoxy)-2-chloro-2'-methyl-[1,1'-biphenyl]-3-yl)methoxy)-5-chloro-2-hydroxybenzaldehyde (50 mg, 0.095 mmol), 3-bromoprop-1-ene (23.08 mg, 0.191 mmol), cesium carbonate (37.3 mg, 0.114 mmol) and sodium iodide (1.430 mg, 9.54 µmol) in DMF (2 mL) was stirred at rt for 7 h. The reaction mixture was filtered, concentrated and was pumped overnight to get crude 2-(allyloxy)-4-((3'-(3-bromopropoxy)-2-chloro-2'-methyl-[1,1'-biphenyl]-3-yl)methoxy)-5-chlorobenzaldehyde (0.48 g). The crude was dissolved in DCE (1 mL) and EtOH (1 mL), 2-aminopropane-1,3-diol (17.38 mg, 0.191 mmol) and acetic acid (10.92 µl, 0.191 mmol) were added. The resulting mixture was stirred at rt for 1 h. Sodium cyanoborohydride (0.134 ml, 0.134 mmol) was added and the resulting mixture was stirred at rt for 1 h. The reaction mixture was concentrated and the residue was pumped for 30 min. The residue was dissolved in 1.5 ml DMF, (R)-pyrrolidin-3-ol, HCl (94 mg, 0.763 mmol) and DIPEA (0.200 ml, 1.145 mmol) and sodium iodide (1.430 mg, 9.54 µmol) were added and the resulting mixture was stirred at 60° C. for 16 h. The reaction mixture was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to give the pure title compound (15.4, 24%). $^1$H NMR (500 MHz, DMSO-$d_6$) δ 7.67 (s, 1H), 7.66 (s, 1H), 7.47 (t, J=7.5 Hz, 1H), 7.42 (s, 1H), 7.27 (dd, J=7.7, 1.5 Hz, 1H), 7.23 (t, J=7.9 Hz, 1H), 6.99 (d, J=8.1 Hz, 1H), 6.90 (s, 1H), 6.72 (d, J=7.3 Hz, 1H), 6.10-6.00 (m, 1H), 5.41 (dd, J=17.4, 1.7 Hz, 1H), 5.33 (s, 2H), 5.26 (dd, J=10.6, 1.5 Hz, 1H), 4.62 (d, J=5.1 Hz, 2H), 4.25-4.18 (m, 1H), 4.11-4.01 (m, 2H), 2.80-2.72 (m, 1H), 2.71-2.55 (m, 4H), 2.40 (d, J=7.3 Hz, 1H), 2.07-1.92 (m, 3H), 1.88 (s, 3H), 1.57 (dd, J=8.3, 4.6 Hz, 1H). LC/MS Condition E: RT=1.50 min; m/e=645.2 (M+H)$^+$.

Example 2314: (R)-2-(4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)acetonitrile

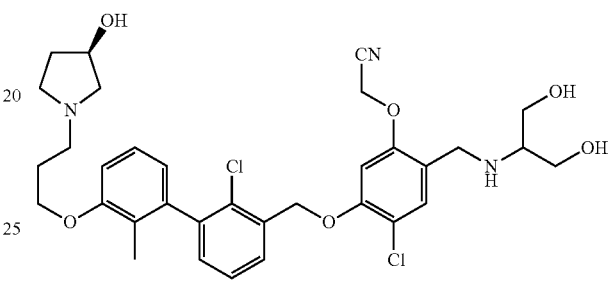

The compound was prepared and purified with the same method as that for Example 2313 to give the pure title compound: (8.1 mg, 13%). $^1$H NMR (500 MHz, DMSO-$d_6$) δ 7.71 (d, J=7.7 Hz, 1H), 7.50 (s, 1H), 7.48 (t, J=7.5 Hz, 1H), 7.30-7.27 (m, 1H), 7.22 (t, J=8.1 Hz, 1H), 7.14 (s, 1H), 6.99 (d, J=8.4 Hz, 1H), 6.73 (d, J=7.3 Hz, 1H), 5.26 (s, 2H), 4.21-4.14 (m, 1H), 4.10-3.99 (m, 2H), 2.72-2.67 (m, 1H), 2.64-2.55 (m, 5H), 2.43 (d, J=8.4 Hz, 1H), 2.32 (dd, J=9.5, 3.7 Hz, 1H), 2.03-1.90 (m, 3H), 1.89 (s, 4H), 1.58-1.48 (m, 1H). LC/MS Condition E: RT=1.40 min; m/e=644.2 (M+H)$^+$.

Example 2315: 2-((5-chloro-4-((2-chloro-3'-(3-((R)-3-hydroxypyrrolidin-1-yl)propoxy)-2'-methyl-[1,1'-biphenyl]-3-yl)methoxy)-2-(2-((R)-3-hydroxypyrrolidin-1-yl)-2-iminoethoxy)benzyl)amino)propane-1,3-diol

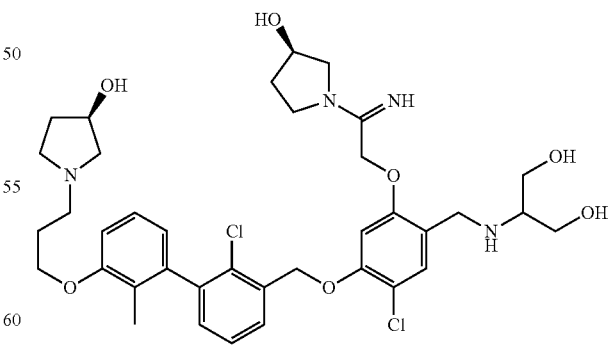

The compound was isolated and purified from the reaction mixture for Example 2314 to give the pure title compound: (9.1 mg, 9%). $^1$H NMR (500 MHz, DMSO-$d_6$) δ 7.73 (d, J=7.3 Hz, 1H), 7.65-7.62 (m, 1H), 7.51 (t, J=7.7 Hz, 1H), 7.30 (d, J=7.7 Hz, 1H), 7.26 (t, J=7.9 Hz, 1H), 7.23-7.20 (m, 1H), 7.01 (d, J=8.1 Hz, 1H), 6.76 (d, J=7.3 Hz, 1H), 5.43-5.33 (m, 2H), 5.29-5.23 (m, 1H), 4.55-4.38 (m, 2H), 4.28 (br. s., 2H), 4.15-4.01 (m, 2H), 3.71 (br. s., 4H), 2.17 (d, J=3.7 Hz, 2H), 2.10-1.93 (m, 2H), 1.91 (s, 3H). LCMS: LC/MS Condition E: RT=1.23 min; m/e=731.1 (M+H)$^+$.

Example 2316: (R)-2-(4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)acetamide

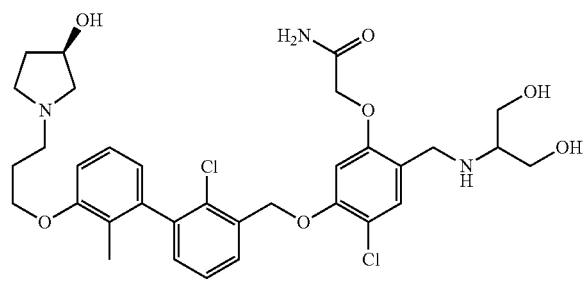 [SMILES: Cc1c(OCCCN2CC[C@@H](O)C2)cccc1-c1cccc(COc2cc(OCC(N)=O)c(CNC(CO)CO)cc2Cl)c1Cl]

The compound was prepared and purified with the same method as that for Example 2314 to give the pure title compound: (36.3 mg, 56%). $^1$H NMR (500 MHz, DMSO-d$_6$) δ 7.84 (br. s., 1H), 7.69 (d, J=6.6 Hz, 1H), 7.47 (t, J=7.7 Hz, 1H), 7.39 (s, 2H), 7.27 (dd, J=7.7, 1.5 Hz, 1H), 7.22 (t, J=8.1 Hz, 1H), 7.01-6.95 (m, 2H), 6.72 (d, J=7.3 Hz, 1H), 5.31 (s, 2H), 4.58 (s, 2H), 4.25-4.15 (m, 1H), 4.10-3.99 (m, 2H), 3.74 (s, 2H), 2.72 (dd, J=9.5, 6.2 Hz, 1H), 2.64-2.56 (m, 4H), 2.48-2.28 (m, 2H), 2.04-1.92 (m, 2H), 1.91 (s, 3H), 1.58-1.49 (m, 1H). LC/MS Condition E: RT=1.34 min; m/e=622.1 (M+H)$^+$.

Example 2317: (R)-2-(4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)-N,N-dimethylacetamide

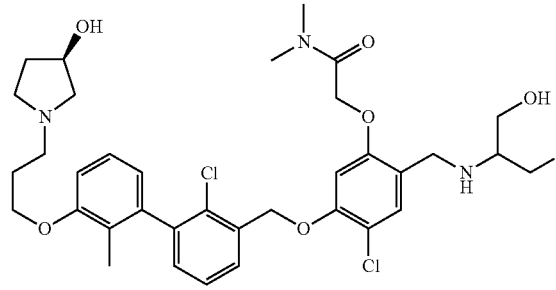

The compound was prepared and purified with the same method as that for Example 2314 to give the pure title compound: (48.9 mg, 73%). $^1$H NMR (500 MHz, DMSO-d$_6$) δ 7.67 (d, J=7.7 Hz, 1H), 7.47 (t, J=7.7 Hz, 1H), 7.30-7.26 (m, 1H), 7.25-7.19 (m, 1H), 6.99 (d, J=8.1 Hz, 1H), 6.90 (s, 1H), 6.72 (d, J=7.7 Hz, 1H), 5.29 (s, 2H), 4.90 (s, 2H), 4.24-4.16 (m, 1H), 4.10-3.98 (m, 2H), 3.00 (s, 3H), 2.84 (s, 3H), 2.71 (dd, J=9.5, 6.2 Hz, 1H), 2.64-2.55 (m, 9H), 2.47-2.28 (m, 2H), 1.98 (dd, J=12.8, 7.0 Hz, 1H), 1.91 (s, 3H), 1.54 (d, J=3.7 Hz, 1H). LC/MS Condition E: RT=1.35 min; m/e=690.2 (M+H)$^+$.

Example 2318: (R)-2-((5-chloro-4-((2-chloro-3'-(3-(3-hydroxypyrrolidin-1-yl)propoxy)-2'-methyl-[1,1'-biphenyl]-3-yl)methoxy)-2-(2,2-difluoroethoxy)benzyl)amino)propane-1,3-diol

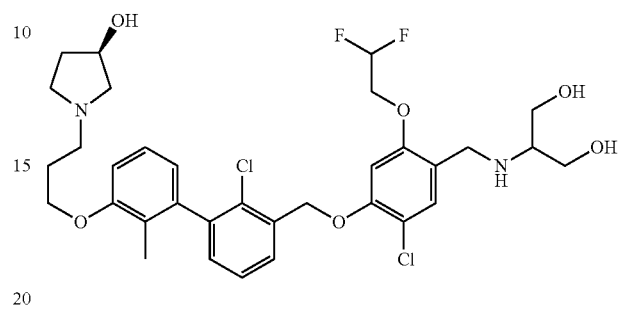

The compound was prepared and purified with the same method as that for Example 2314 to give the pure title compound: (42.6 mg, 65%). $^1$H NMR (500 MHz, DMSO-d$_6$) δ 7.70 (d, J=6.6 Hz, 1H), 7.51-7.43 (m, 2H), 7.30-7.27 (m, 1H), 7.23 (t, J=7.9 Hz, 1H), 7.04 (s, 1H), 7.00 (d, J=8.4 Hz, 1H), 6.73 (d, J=7.7 Hz, 1H), 6.54-6.25 (m, 1H), 5.35 (s, 2H), 4.48-4.35 (m, 2H), 4.23 (br. s., 1H), 4.13-3.97 (m, 2H), 3.74 (s, 1H), 2.87-2.55 (m, 5H), 2.06-1.93 (m, 3H), 1.89 (s, 3H), 1.59 (br. s., 1H).

LC/MS Condition E: RT=1.35 min; m/e=669.3 (M+H)$^+$.

Example 2319: (R)-2-((5-chloro-4-((2-chloro-3'-(3-(3-hydroxypyrrolidin-1-yl)propoxy)-2'-methyl-[1,1'-biphenyl]-3-yl)methoxy)-2-(cyclopropylmethoxy)benzyl)amino)propane-1,3-diol

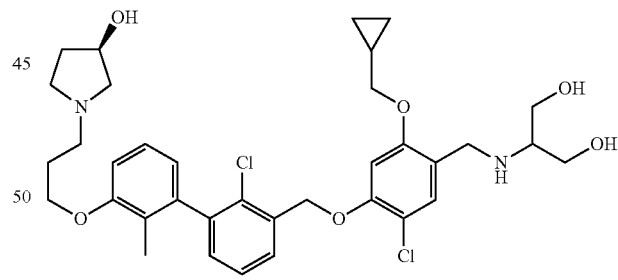

The compound was prepared and purified with the same method as that for Example 2314 to give the pure title compound: (33.4 mg, 53%). $^1$H NMR (500 MHz, DMSO-d$_6$) δ 7.66 (d, J=6.6 Hz, 1H), 7.47 (t, J=7.7 Hz, 1H), 7.38 (s, 1H), 7.27 (d, J=5.9 Hz, 1H), 7.23 (t, J=7.9 Hz, 1H), 7.00 (d, J=8.4 Hz, 1H), 6.84 (s, 1H), 6.71 (d, J=7.3 Hz, 1H), 5.32 (s, 2H), 4.19 (br. s., 1H), 4.11-3.98 (m, 2H), 3.87 (d, J=6.6 Hz, 2H), 3.69 (s, 2H), 2.71 (dd, J=9.5, 6.2 Hz, 1H), 2.64-2.53 (m, 8H), 2.47-2.29 (m, 2H), 2.08-1.92 (m, 2H), 1.88 (s, 3H), 1.54 (dd, J=8.4, 4.8 Hz, 1H), 1.22 (br. s., 1H), 0.63-0.50 (m, 2H), 0.33 (d, J=5.9 Hz, 2H). LC/MS Condition E: RT=1.43 min; m/e=659.1 (M+H)$^+$.

Example 2320: 2-((5-chloro-4-((2-chloro-3'-(3-((R)-3-hydroxypyrrolidin-1-yl)propoxy)-2'-methyl-[1,1'-biphenyl]-3-yl)methoxy)-2-((2,2-difluorocyclopropyl)methoxy)benzyl)amino)propane-1,3-diol

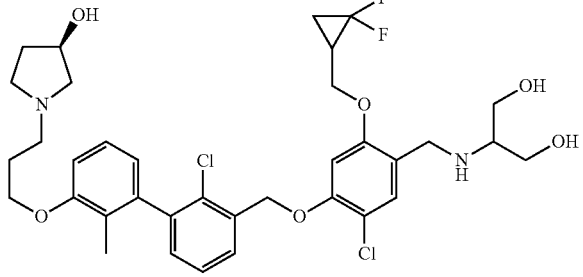

The compound was prepared and purified with the same method as that for Example 2314 to give the pure title compound: (21.7 μmg, 32%). $^1$H NMR (500 MHz, DMSO-d$_6$) δ 7.68 (d, J=8.1 Hz, 1H), 7.47 (t, J=7.5 Hz, 1H), 7.41 (s, 1H), 7.27 (d, J=5.9 Hz, 1H), 7.25-7.19 (m, 1H), 6.99 (d, J=8.4 Hz, 1H), 6.94 (s, 1H), 6.72 (d, J=7.7 Hz, 1H), 5.34 (s, 2H), 4.25-4.16 (m, 2H), 4.14-3.96 (m, 3H), 3.70 (d, J=3.7 Hz, 2H), 2.72 (dd, J=9.5, 6.2 Hz, 1H), 2.67-2.54 (m, 8H), 2.48-2.31 (m, 2H), 2.24 (d, J=6.6 Hz, 1H), 2.05-1.92 (m, 3H), 1.88 (s, 3H), 1.78-1.66 (m, 1H), 1.59-1.39 (m, 2H). LC/MS Condition E: RT=1.51 min; m/e=695.2 (M+H)$^+$.

Example 2321: (R)-2-((5-chloro-4-((2-chloro-3'-(3-(3-hydroxypyrrolidin-1-yl)propoxy)-2'-methyl-[1,1'-biphenyl]-3-yl)methoxy)-2-((3-methylbut-2-en-1-yl)oxy)benzyl)amino)propane-1,3-diol

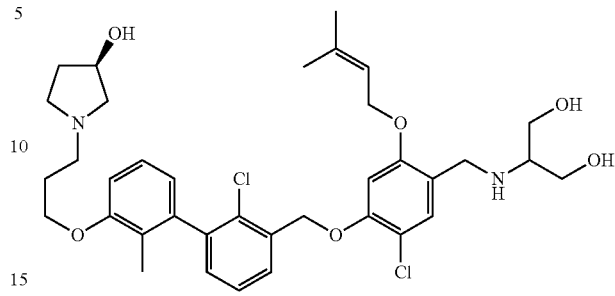

The compound was prepared and purified with the same method as that for Example 2314 to give the pure title compound: (43 mg, 67%). $^1$H NMR (500 MHz, DMSO-d$_6$) δ 7.66 (d, J=8.1 Hz, 1H), 7.48 (t, J=7.5 Hz, 1H), 7.39 (s, 1H), 7.30-7.25 (m, 1H), 7.23 (t, J=7.9 Hz, 1H), 7.00 (d, J=8.1 Hz, 1H), 6.88 (s, 1H), 6.72 (d, J=7.7 Hz, 1H), 5.41 (br. s., 1H), 5.34 (s, 2H), 4.58 (d, J=6.6 Hz, 2H), 4.20 (d, J=7.7 Hz, 1H), 4.12-4.01 (m, 2H), 3.67 (s, 2H), 2.76-2.56 (m, 4H), 2.54-2.52 (m, 1H), 2.46 (d, J=8.1 Hz, 1H), 2.36 (dd, J=9.9, 3.7 Hz, 1H), 2.12-1.93 (m, 2H), 1.88 (s, 3H), 1.74 (s, 3H), 1.71 (s, 3H), 1.63-1.48 (m, 1H). LC/MS Condition E: RT=1.76 min; m/e=673.1 (M+H)$^+$.

Example 2322: tert-butyl (S)-3-(((3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)oxy)methyl)pyrrolidine-1-carboxylate

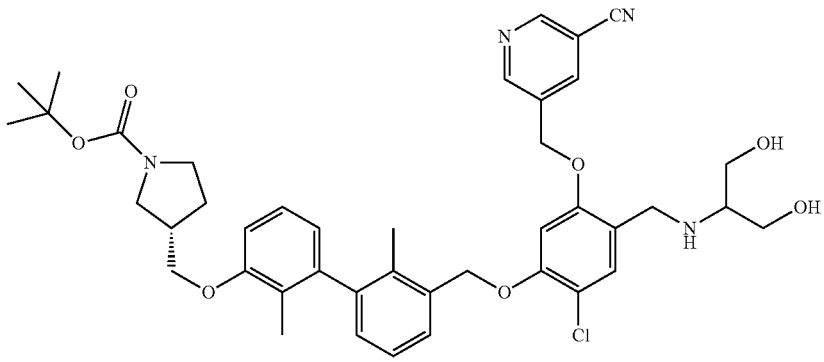 [SMILES: Cc1c(COc2cc(OCc3cncc(C#N)c3)c(CNC(CO)CO)cc2Cl)cccc1-c1cccc(OC[C@H]2CCN(C(=O)OC(C)(C)C)C2)c1C]

A mixture of (S)-tert-butyl 3-(((2-chloro-3'-((2-chloro-5-((5-cyanopyridin-3-yl)methoxy)-4-formylphenoxy)methyl)-2'-methyl-[1,1'-biphenyl]-3-yl)oxy)methyl)pyrrolidine-1-carboxylate (141 mg, 0.201 mmol), 2-aminopropane-1,3-diol (36.6 mg, 0.401 mmol) and acetic acid (0.023 mL, 0.401 mmol) in DCE (1 mL) was stirred at rt for 30 min. Sodium cyanoborohydride (0.221 mL, 0.221 mmol) was added and stirring continued for 1 h. The reaction mixture was concentrated and the residue was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 5-minute hold at 100% B; Flow: 20 mL/min. Fractions containing the desired product were combined and dried via centrifugal evaporation to give the pure title compound: (5.4 mg, 4%). ¹H NMR (500 MHz, DMSO-d₆) δ 9.02 (d, J=2.2 Hz, 1H), 9.00 (d, J=1.8 Hz, 1H), 8.44 (s, 1H), 7.53 (d, J=7.3 Hz, 1H), 7.41 (s, 1H), 7.40-7.34 (m, 1H), 7.30 (t, J=7.5 Hz, 1H), 7.19 (d, J=7.3 Hz, 1H), 7.15-7.07 (m, 2H), 6.87 (d, J=6.6 Hz, 1H), 5.32 (s, 2H), 5.26 (d, J=4.8 Hz, 2H), 4.19-3.98 (m, 2H), 3.71 (s, 2H), 3.54-3.43 (m, 1H), 3.32-3.09 (m, 2H), 2.68 (d, J=4.8 Hz, 1H), 2.54-2.43 (m, 6H), 2.08 (s, 3H), 2.04 (br. s., 1H), 1.78 (br. s., 1H), 1.40 (s, 9H). LC/MS Condition E: RT=2.10 min; m/e=777.1 (M+H)⁺.

Example 2323: (S)-5-((4-chloro-2-(((1,3-dihydroxy-propan-2-yl)amino)methyl)-5-((2,2'-dimethyl-3'-(pyrrolidin-3-ylmethoxy)-[1,1'-biphenyl]-3-yl)methoxy)phenoxy)methyl)nicotinonitrile

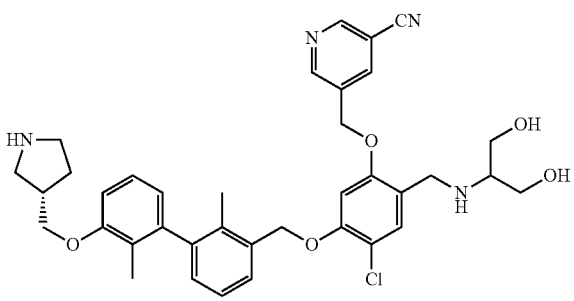 [SMILES: Cc1c(COc2cc(OCc3cncc(C#N)c3)c(CNC(CO)CO)cc2Cl)cccc1-c1cccc(OC[C@H]2CCNC2)c1C]

To a suspension of (S)-tert-butyl 3-(((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)methyl)pyrrolidine-1-carboxylate (40 mg, 0.051 mmol) in DCM (1 mL) was added TFA (0.198 mL, 2.57 mmol) to generate a clear solution that was stirred at rt for 2 h. The reaction mixture was concentrated under vacuum. The residue was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation to give the pure title compound: (2.7 mg, 8%). ¹H NMR (500 MHz, DMSO-d₆) δ 9.01 (s, 1H), 8.99 (s, 1H), 8.43 (s, 1H), 7.52 (d, J=7.7 Hz, 1H), 7.41 (s, 1H), 7.39-7.33 (m, 1H), 7.29 (t, J=7.5 Hz, 1H), 7.18 (d, J=7.7 Hz, 1H), 7.14-7.07 (m, 3H), 6.86 (d, J=6.6 Hz, 1H), 5.31 (s, 2H), 5.25 (d, J=4.0 Hz, 2H), 4.14-3.94 (m, 2H), 3.71 (s, 2H), 3.44-3.27 (m, 2H), 3.07-2.70 (m, 3H), 2.08 (s, 3H), 1.93 (br. s., 1H), 1.57 (br. s., 1H). LC/MS Condition E: RT=1.44 min.; m/e=677.1 (M+H)⁺.

Example 2324: (R)-5-((4-chloro-2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

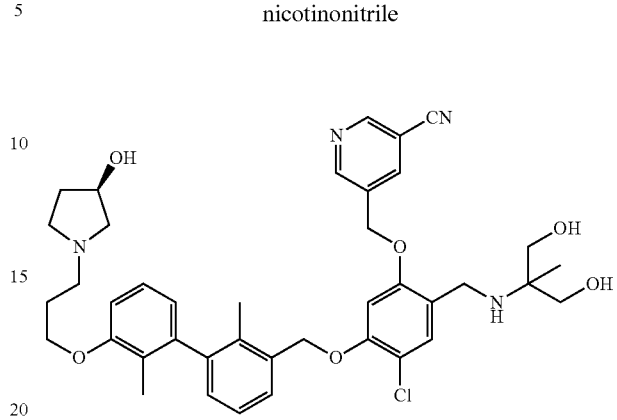

The compound was prepared and purified with the same method as that for Example 2278 to give the pure title compound: (26 mg, 53%). ¹H NMR (500 MHz, DMSO-d₆) δ 9.05 (dd, J=3.7, 2.2 Hz, 2H), 8.56-8.49 (m, 1H), 7.56 (s, 1H), 7.50 (d, J=7.3 Hz, 1H), 7.28 (t, J=7.7 Hz, 1H), 7.23 (t, J=7.9 Hz, 1H), 7.20 (s, 1H), 7.08 (d, J=7.3 Hz, 1H), 6.98 (d, J=8.4 Hz, 1H), 6.71 (d, J=7.7 Hz, 1H), 5.42-5.30 (m, 4H), 4.46 (br. s., 1H), 4.26-4.00 (m, 4H), 3.53 (q, J=11.4 Hz, 2H), 2.18 (d, J=3.7 Hz, 3H), 2.05 (s, 3H), 1.86 (s, 3H), 1.12 (s, 3H). LC/MS Condition E: RT=1.46 min.; m/e=715.1 (M+H)⁺.

Example 2325: (R)-5-((4-chloro-2-(((1,3-dihydroxy-propan-2-yl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

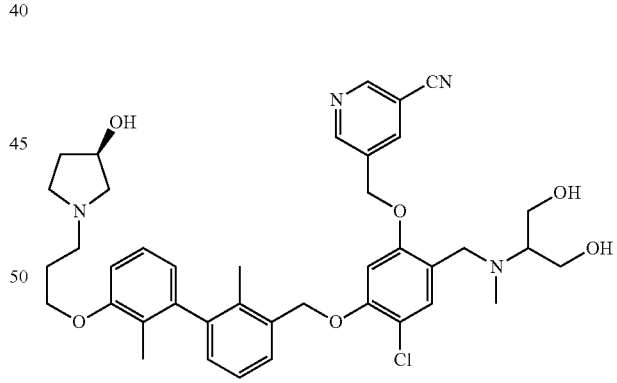

A mixture of 5-((5-((3'-(3-bromopropoxy)-2,2'-dimethyl-[1,1'-biphenyl]-3-yl)methoxy)-4-chloro-2-(((1,3-dihydroxypropan-2-yl)amino)methyl)phenoxy)methyl)nicotinonitrile (30 mg, 0.043 mmol), iodomethane (12.25 mg, 0.086 mmol) and potassium carbonate (11.93 mg, 0.086 mmol) in DMF (1 mL) was stirred at rt under nitrogen for 17 h. (R)-pyrrolidin-3-ol, HCl (53.3 mg, 0.432 mmol) and DIPEA (0.090 mL, 0.518 mmol) were added. The resulting reaction mixture was stirred at 60° C. for 3 h. The reaction mixture was filtered and the filtrate was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation ti give the title compound: (18.2 mg, 55%). $^1$H NMR (500 MHz, DMSO-$d_6$) δ 9.01 (d, J=1.8 Hz, 1H), 8.98 (d, J=2.2 Hz, 1H), 8.44 (s, 1H), 7.49 (d, J=7.7 Hz, 1H), 7.41 (s, 1H), 7.27 (t, J=7.5 Hz, 1H), 7.21 (t, J=7.9 Hz, 1H), 7.11-7.05 (m, 2H), 6.96 (d, J=8.4 Hz, 1H), 6.68 (d, J=7.3 Hz, 1H), 5.32 (s, 2H), 5.25 (d, J=1.8 Hz, 2H), 4.19 (br. s., 1H), 4.10-3.99 (m, 2H), 3.69 (s, 2H), 3.59-3.42 (m, 2H), 2.78-2.56 (m, 5H), 2.48-2.31 (m, 2H), 2.04 (s, 3H), 2.02-1.92 (m, 2H), 1.92 (s, 3H), 1.90 (br. s., 1H), 1.83 (s, 3H), 1.59-1.48 (m, 1H). LC/MS condition E: RT=1.46 min.; m/e=715.1 (M+H)$^+$.

Example 2326: (R)-5-((2-((tert-butylamino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile

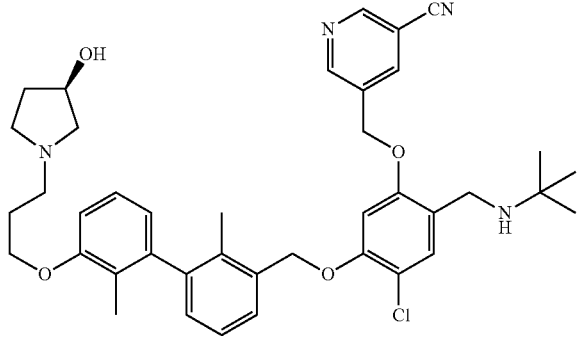 [SMILES: Cc1c(COc2cc(OCc3cncc(C#N)c3)c(CNC(C)(C)C)cc2Cl)cccc1-c1cccc(OCCCN2CC[C@@H](O)C2)c1C]

A mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (40 mg, 0.065 mmol), 2-methylpropan-2-amine (9.44 mg, 0.129 mmol), acetic acid (7.39 µl, 0.129 mmol) and ~10 mg of 4 A molecule sieves in DCE (0.5 mL) and EtOH (1 mL) was stirred at rt under nitrogen for 1 h. Sodium cyanoborohydride (0.129 mL, 0.129 mmol) was added and stirring continued for 17 h. LCMS showed a peak of ~21% with M+1=676/5-((5-((3'-(3-bromopropoxy)-2,2'-dimethyl-[1,1'-biphenyl]-3-yl)methoxy)-2-((tert-butylamino)methyl)-4-chlorophenoxy)methyl)nicotinonitrile. The reaction mixture was blown dry with N$_2$, and the residue was dissolved in DMF (1 mL). (R)-pyrrolidin-3-ol, HCl (63.8 mg, 0.516 mmol) and DIPEA (0.113 mL, 0.645 mmol) were then added to the mixture. The resulting mixture was stirred at 65° C. for 5 h. The reaction mixture was cooled to rt, filtered and the filtrate was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation to give the title compound as TFA salt (7.7 mg, 11%). LC/MS condition E: RT=1.44 min.; m/e=638.2 (M+H)$^+$.

Example 2327: (S)-2-((5-chloro-2-((5-cyanopyridin-3-yl)methoxy)-4-((3'-(3-(3,5-dioxopiperazin-1-yl)propoxy)-2,2'-dimethyl-[1,1'-biphenyl]-3-yl)methoxy)benzyl)amino)-3-hydroxy-2-methylpropanoic Acid

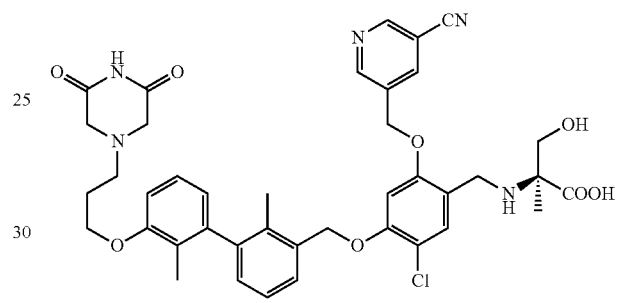

The compound was prepared and purified with the same method as that for Example 2260 to give the pure title compound: (2.1 mg, 6%). LC/MS Condition E: RT=1.75 min.; m/e=756.0 (M+H)$^+$.

Example 2328: (S)-2-((5-chloro-2-((5-cyanopyridin-3-yl)methoxy)-4-((2,2'-dimethyl-3'-(3-(4-methyl-3-oxopiperazin-1-yl)propoxy)-[1,1'-biphenyl]-3-yl)methoxy)benzyl)amino)-3-hydroxy-2-methylpropanoic Acid

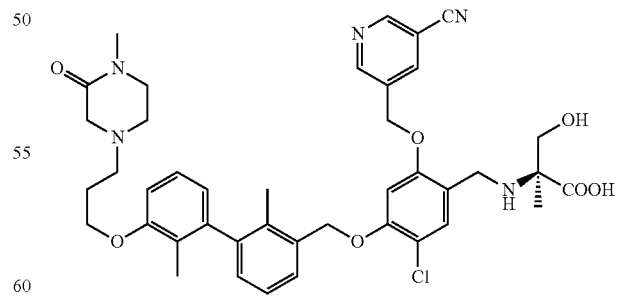

The compound was prepared and purified with the same method as that for Example 2260 to give the pure title compound: (2.0 mg, 6%). LC/MS Condition E: RT=1.73 min.; m/e=756.1 (M+H)$^+$.

Example 2329: (R)-5-((4-chloro-2-((3,5-dioxopiperazin-1-yl)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile Example 2331: (R)-5-((4-chloro-5-((3'-(3-(3-hydroxypyrrolidin-1-yl)propoxy)-2,2'-dimethyl-[1,1'-biphenyl]-3-yl)methoxy)-2-((3-oxopiperazin-1-yl)methyl)phenoxy)methyl)nicotinonitrile

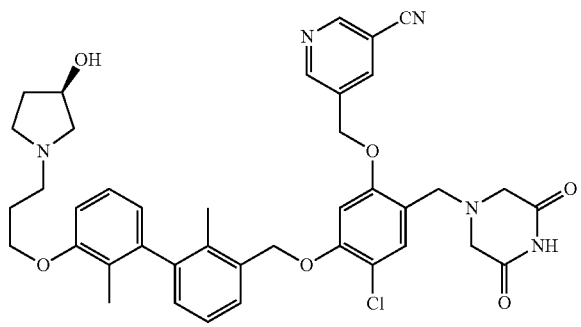 [SMILES: Cc1c(COc2cc(OCc3cncc(C#N)c3)c(CN3CC(=O)NC(=O)C3)cc2Cl)cccc1-c1cccc(OCCCN2CC[C@@H](O)C2)c1C]

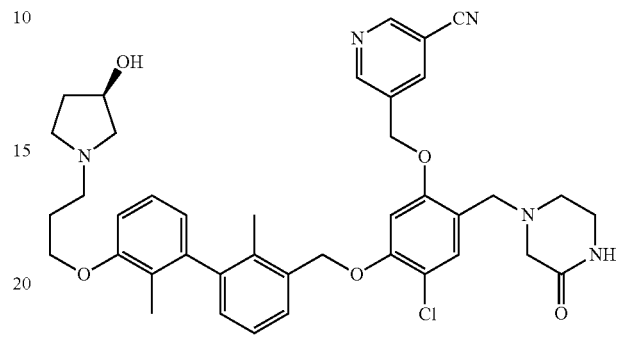

The compound was prepared and purified with the same method as that for Example 2326 to give the pure title compound: (6.7 mg, 28%). LC/MS Condition E: RT=1.80 min.; m/e=724.1 (M+H)⁺.

The compound was prepared and purified with the same method as that for Example 2326 to give the pure title compound: (24.2 mg, 68%). LC/MS Condition E: RT=1.82 min.; m/e=724.1 (M+H)⁺.

Example 2330: (R)-5-((4-chloro-5-((3'-(3-(3-hydroxypyrrolidin-1-yl)propoxy)-2,2'-dimethyl-[1,1'-biphenyl]-3-yl)methoxy)-2-((4-methyl-3-oxopiperazin-1-yl)methyl)phenoxy)methyl)nicotinonitrile Example 2332: (S)-1-(5-chloro-2-((5-cyanopyridin-3-yl)methoxy)-4-((3'-(3-(((S)-2,3-dihydroxypropyl)(methyl)amino)propoxy)-2,2'-dimethyl-[1,1'-biphenyl]-3-yl)methoxy)benzyl)piperidine-2-carboxylic Acid

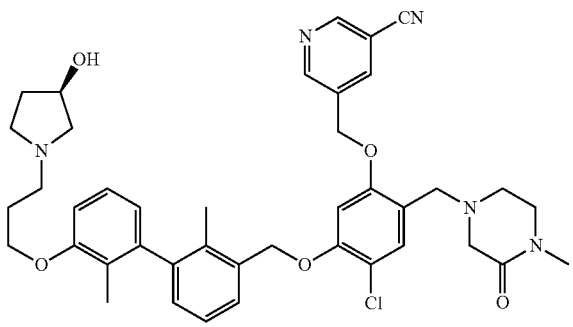 [SMILES: Cc1c(COc2cc(OCc3cncc(C#N)c3)c(CN3CCN(C)C(=O)C3)cc2Cl)cccc1-c1cccc(OCCCN2CC[C@@H](O)C2)c1C]

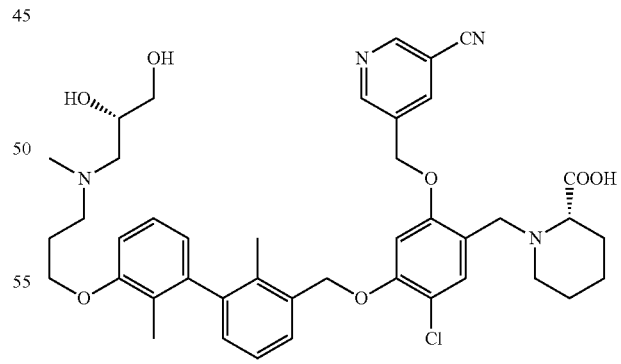

The compound was prepared and purified with the same method as that for Example 2326 to give the pure title compound: (2.9 mg, 12%). LC/MS Condition E: RT=1.82 min.; m/e=724.1 (M+H)⁺.

The compound was prepared and purified with the same method as that for Example 2205 to give the pure title compound: (11 mg, 42%). LC/MS Condition E: RT=1.34 min; m/e=757.3 (M+H)⁺.

Example 2333; (S)-1-(5-chloro-2-((5-cyanopyridin-3-yl)methoxy)-4-((3'-(3-(((S)-2,3-dihydroxypropyl)amino)propoxy)-2,2'-dimethyl-[1,1'-biphenyl]-3-yl)methoxy)benzyl)piperidine-2-carboxylic Acid

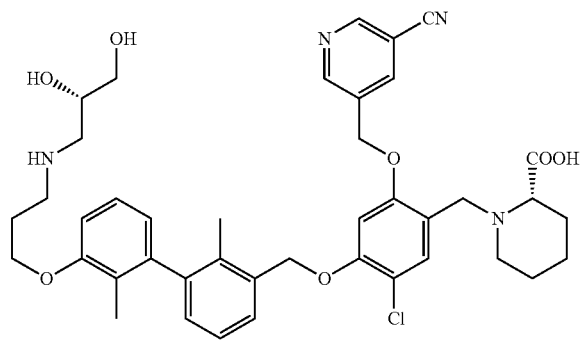 [SMILES: Cc1c(COc2cc(OCc3cncc(C#N)c3)c(CN3CCCC[C@H]3C(=O)O)cc2Cl)cccc1-c1cccc(OCCCNC[C@H](O)CO)c1C]

The compound was prepared and purified with the same method as that for Example 2205 to give the pure title compound: (14 mg, 49%). LC/MS Condition E: RT=1.33 min; m/e=743.2 (M+H)+.

Example 2334: 5-((4-chloro-2-((2-(hydroxymethyl)piperidin-1-yl)methyl)-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile

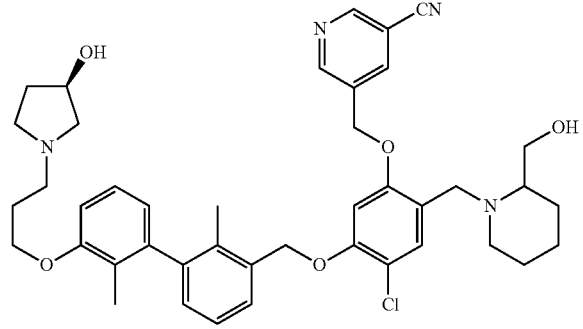 [SMILES: Cc1c(COc2cc(OCc3cncc(C#N)c3)c(CN3CCCCC3CO)cc2Cl)cccc1-c1cccc(OCCCN2CC[C@@H](O)C2)c1C]

The compound was prepared and purified with the same method as that for Example 2205 to give the pure title compound: (2.8 mg, 44%). LC/MS Condition E: RT=1.41 min; m/e=725.2 (M+H)+.

Example 2335: (2S)-1-(5-chloro-2-((5-cyanopyridin-3-yl)methoxy)-4-((3'-(((3R)-1-(2,3-dihydroxypropyl)piperidin-3-yl)methoxy)-2,2'-dimethyl-[1,1'-biphenyl]-3-yl)methoxy)benzyl)piperidine-2-carboxylic Acid The compound was prepared and purified with the same method as that for Example 2205 to give the pure title compound: (1.4 mg, 30%). LC/MS Condition E: RT=1.46 min; m/e=783.1 (M+H)+.

Intermediate: (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic Acid

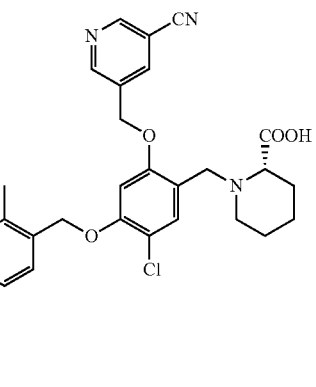

$^1$H NMR (400 MHz, METHANOL-$d_4$) δ 8.95 (s, 1H), 8.88 (d, J=1.5 Hz, 1H), 8.38 (t, J=2.0 Hz, 1H), 7.69 (dd, J=7.5, 1.3 Hz, 1H), 7.55 (s, 1H), 7.50-7.44 (m, 1H), 7.16 (t, J=7.5 Hz, 1H), 6.93 (s, 1H), 5.35 (s, 2H), 5.26 (s, 2H), 4.22 (s, 2H), 3.92 (d, J=12.0 Hz, 1H), 3.72 (d, J=11.8 Hz, 1H), 2.57 (s, 3H), 1.44 (s, 3H), 1.38 (s, 12H). There was ~6 equivalents of AcONH$_4$ based on H NMR.

Example 2336: (R)-4-(3-((3'-((4-(((2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-methylmorpholin-4-ium

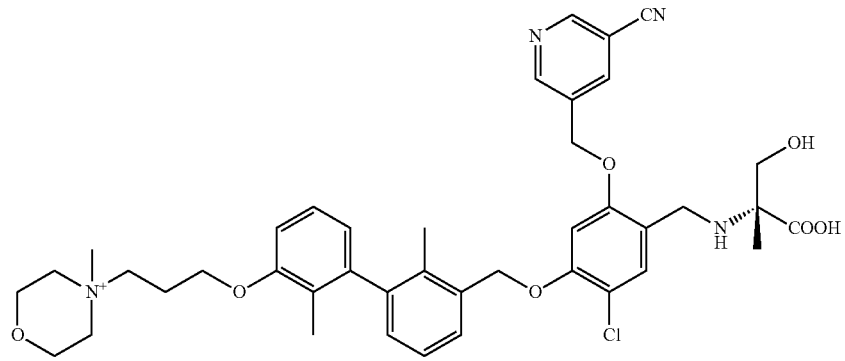 [SMILES: Cc1c(COc2cc(OCc3cncc(C#N)c3)c(CN[C@](C)(CO)C(=O)O)cc2Cl)cccc1-c1cccc(OCCC[N+]2(C)CCOCC2)c1C]

To a suspension of (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic acid, (0.115 g, 0.118 mmol, based on 6 equivalents of acetate), 4-(3-(3-bromo-2-methylphenoxy)propyl)-4-methylmorpholin-4-ium (0.047 g, 0.141 mmol) in THF (10 mL) (freshly distilled before use) was added potassium phosphate tribasic (1.178 mL, 0.589 mmol) (blown with $N_2$ for 1 h before use). The resulting mixture was blown with a stream of $N_2$ for a 10 min. and 2nd generation XPhos precatalyst (0.026 g, 0.035 mmol) was added to the mixture. The vial was sealed and stirred at rt for 18 h. 1.5 mL more of the 0.5 M phosphate solution and another 25 mg more of the Pd catalyst were added. The mixture was flushed well with argon and was stirred at 40° C. overnight. LCMS showed expected product. The reaction mixture was partitioned between EtOAc/aqueous sodium bicarbonate. The aqueous layer was extracted with EtOAc (3×5 ml). The combined organic layers were washed with aqueous sodium bicarbonate (5 ml) and brine (5 ml), dried over magnesium sulfate, filtered and concentrated under vacuum. The residue was dissolved in MeOH and was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 22 minutes, then a 5-minute hold at 100% B; Flow: 20 mL/min. Fractions containing the desired product were combined and dried via centrifugal evaporation to give the pure title compound: (2.4 mg, 3%).

LC/MS Condition E: RT=1.41 min; m/e=743.1 $(M+H)^+$.

Example 2340: N-(3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)-3-(hydroxymethyl)picolinamide

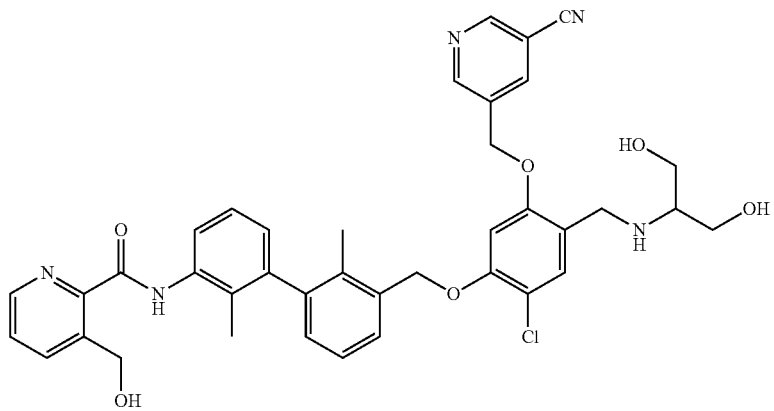 [SMILES: Cc1c(COc2cc(OCc3cncc(C#N)c3)c(CNC(CO)CO)cc2Cl)cccc1-c1cccc(NC(=O)c2ncccc2CO)c1C]

A mixture of N-(3'-((2-chloro-5-((5-cyanopyridin-3-yl)methoxy)-4-formylphenoxy)methyl)-2,2'-dimethyl-[1,1'-biphenyl]-3-yl)-4-(hydroxymethyl)nicotinamide (0.1 g, 0.032 mmol), 2-aminopropane-1,3-diol (8.63 mg, 0.095 mmol), acetic acid (3.62 μl, 0.063 mmol) and a few 4 A MS in DCE/EtOH was stirred at rt under nitrogen for 2 h. Sodium cyanoborohydride (0.063 ml, 0.063 mmol) was added and the reaction mixture was stirred at rt under nitrogen for 4 h. The reaction mixture was concentrated under vacuum. The residue was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation evaporation to give the pure title compound: (6.7 mg, 30%). LC/MS Condition E: RT=1.45 min; m/e=708.0 (M+H)$^+$.

Intermediate: 1-((3-bromo-2-methylphenoxy)methyl)cyclopropane-1-carbaldehyde

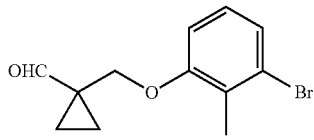

To a solution of (1-((3-bromo-2-methylphenoxy)methyl)cyclopropyl)methanol (0.5 g, 1.844 mmol), 4-methylmorpholine n-oxide (0.259 g, 2.213 mmol) and 100 mg of 4 A MS in CH$_2$Cl$_2$ (5 mL) was added tetrapropylammonium perruthenate (0.032 g, 0.092 mmol) at 0° C. The resulting mixture was stirred at rt for 16 h. The reaction mixture was loaded directly to a 80 g of silica gel chromatography (Biotage Horizon System, EtOAc/Hexane, Gradient: 0%~40%) to get the product as a white solid. $^1$H NMR (400 MHz, CHLOROFORM-d) ☐ 9.04 (s, 1H), 7.18 (dd, J=8.0, 0.8 Hz, 1H), 7.01 (t, J=8.2 Hz, 1H), 6.81 (d, J=8.0 Hz, 1H), 4.22 (s, 2H), 2.29 (s, 3H), 1.40-1.34 (m, 2H), 1.33-1.27 (m, 2H).

Intermediate: (R)-1-((1-((3-bromo-2-methylphenoxy)methyl)cyclopropyl)methyl)pyrrolidin-3-ol

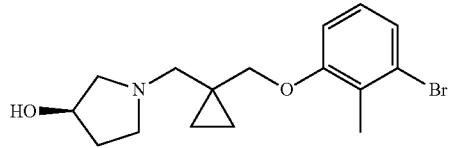 [SMILES: Cc1c(Br)cccc1OCC1(CN2CC[C@@H](O)C2)CC1]

A mixture of 1-((3-bromo-2-methylphenoxy)methyl)cyclopropanecarbaldehyde (0.287 g, 1.066 mmol), (R)-pyrrolidin-3-ol, HCl (0.264 g, 2.133 mmol), acetic acid (0.122 ml, 2.133 mmol) and ~100 mg of 4 A MS in 8 ml of EtOH was stirred at rt for 2 h. Sodium cyanoborohydride (2.133 ml, 2.133 mmol) was added. Stirring was continued for 16 h. The reaction mixture was partitioned between EtOAc/aqueous sodium bicarbonate. The aqueous layer was extracted with EtOAc (3×10 ml). The combined organic layers were washed with aqueous sodium bicarbonate (2×10 ml) and brine (10 ml), dried over magnesium sulfate, filtered and concentrated under vacuum to give ~300 mg of a colorless oil. The crude material was purified by silica gel chromatography (Biotage Horizon System; RediSepRf 12 g column; 2.0 M NH$_3$ in methanol/EtOAc, Gradient: 0%~10%) to get (R)-1-((1-((3-bromo-2-methylphenoxy)methyl)cyclopropyl)methyl)pyrrolidin-3-ol (120 mg, 0.335 mmol, 31.4% yield) as colorless oil. $^1$H NMR (400 MHz, METHANOL-d$_4$) ☐ 7.11 (dd, J=8.2, 0.9 Hz, 1H), 7.01 (t, J=8.2 Hz, 1H), 6.88 (d, J=8.0 Hz, 1H), 4.38-4.28 (m, 1H), 4.00-3.84 (m, 2H), 2.83 (dd, J=10.3, 6.0 Hz, 1H), 2.80-2.69 (m, 1H), 2.66-2.46 (m, 4H), 2.32 (s, 3H), 2.19-2.07 (m, 1H), 1.68 (dddd, J=13.5, 8.1, 5.3, 3.0 Hz, 1H), 0.69-0.63 (m, 2H), 0.54-0.48 (m, 2H). LC/MS Condition C: RT=1.71 min; m/e=340.2 (M+H)$^+$.

Example 2341: (R)-2-((5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)amino)-3-hydroxy-2-methylpropanoic Acid

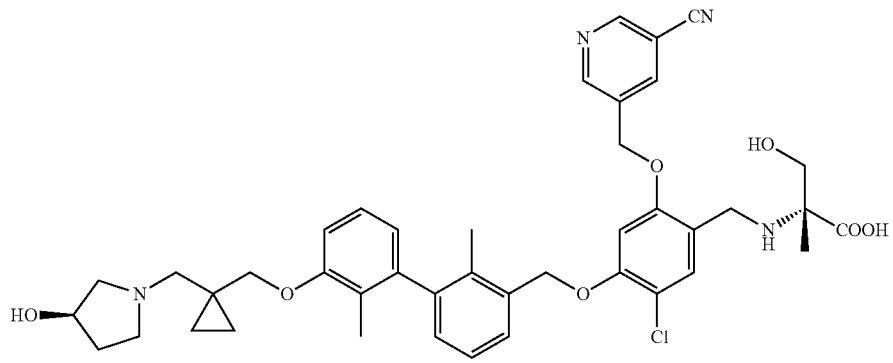 [SMILES: Cc1c(COc2cc(OCc3cncc(C#N)c3)c(CN[C@](C)(CO)C(=O)O)cc2Cl)cccc1-c1cccc(OCC2(CN3CC[C@@H](O)C3)CC2)c1C]

To a suspension of (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2- methylpropanoic acid (0.03 g, 0.048 mmol) and (R)-1-((1-((3-bromo-2-methylphenoxy)methyl)cyclopropyl)methyl) pyrrolidin-3-ol (0.020 g, 0.058 mmol) in THF (3 mL) (blown with $N_2$ before use) was added potassium phosphate tribasic (0.241 mL, 0.121 mmol) (blown with $N_2$ for 1 h before use). The resulting mixture was blown with $N_2$ for a 10 min. and 2nd generation XPhos precatalyst (1.796 mg, 2.412 μmol) was added. The vial was sealed and stirred at rt for 2 h. It was then stirred at 45° C. for 16 h. The reaction was concentrated and the residue was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation to give the pure title compound: (12 mg, 24%).

LC/MS Condition E: RT=1.60 min; m/e=755.1 $(M+H)^+$.

Intermediate: (R)-5-((4-chloro-2-formyl-5-((3'-((1-((3-hydroxypyrrolidin-1-yl)methyl)cyclopropyl) methoxy)-2,2'-dimethyl-[1,1'-biphenyl]-3-yl) methoxy)phenoxy)methyl)nicotinonitrile

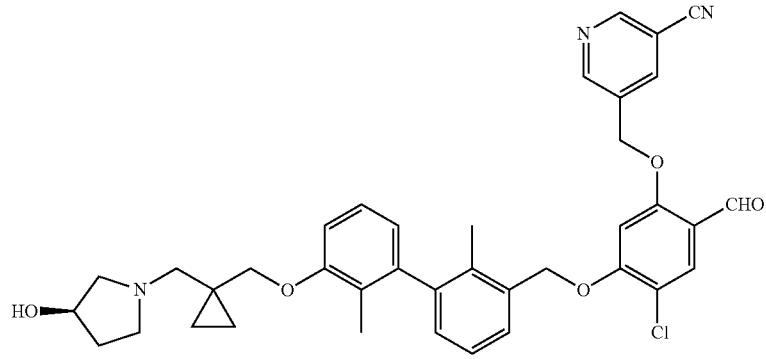 [SMILES: Cc1c(COc2cc(OCc3cncc(C#N)c3)c(C=O)cc2Cl)cccc1-c1cccc(OCC2(CN3CC[C@@H](O)C3)CC2)c1C]

To a suspension of 5-((4-chloro-2-formyl-5-((2-methyl-3-(4,4,5,5-tetramethyl-1,3,2-dioxaborolan-2-yl)benzyl)oxy) phenoxy)methyl)nicotinonitrile (0.168 g, 0.323 mmol), (R)-1-((1-((3-bromo-2-methylphenoxy)methyl)cyclopropyl) methyl)pyrrolidin-3-ol (0.1 g, 0.294 mmol) in THF (3 mL) (blown with $N_2$ before use) was added potassium phosphate tribasic (1.469 mL, 0.735 mmol) (blown with $N_2$ for 1 h before use). The resulting mixture was blown with $N_2$ for a 10 min. 2nd generation XPhos precatalyst (10.94 mg, 0.015 mmol) was added. The vial was sealed and stirred at rt for 16 h. The reaction mixture was partitioned between EtOAc/aqueous sodium bicarbonate. The aqueous layer was extracted with EtOAc (3×20 ml). The combined organic layers were washed with aqueous sodium bicarbonate (2×20 ml) and brine (20 ml), dried over magnesium sulfate, filtered and concentrated under vacuum. The residue was purified by silica gel chromatography (Biotage Horizon System; RediSepRf 24 g column; 2.0 M $NH_3$ in methanol/EtOAc, Gradient: 0%~20%) to get (R)-5-((4-chloro-2-formyl-5-((3'-((1-((3-hydroxypyrrolidin-1-yl)methyl)cyclopropyl)methoxy)-2,2'-dimethyl-[1,1'-biphenyl]-3-yl)methoxy)phenoxy) methyl)nicotinonitrile (124 mg, 0.133 mmol, 45.3% yield) as white solid. LC/MS Condition E: RT=2.07 min; m/e=652.3 $(M+H)^+$.

Example 2342: (R)-5-((4-chloro-2-(((1,3-dihydroxy-propan-2-yl)amino)methyl)-5-((3'-((1-((3-hydroxy-pyrrolidin-1-yl)methyl)cyclopropyl)methoxy)-2,2'-dimethyl-[1,1'-biphenyl]-3-yl)methoxy)phenoxy)methyl)nicotinonitrile

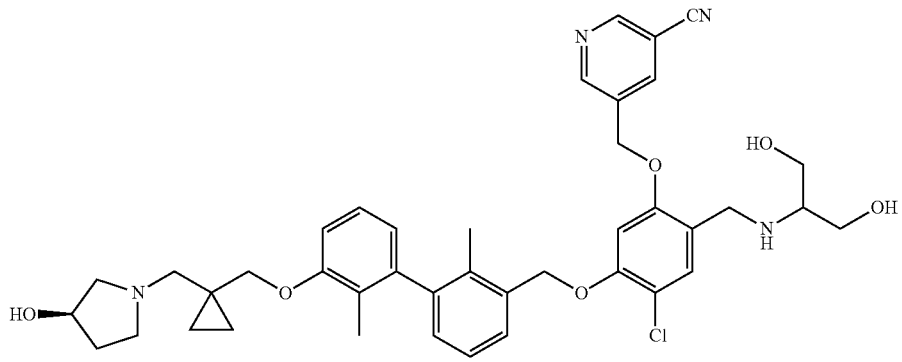 [SMILES: Cc1c(COc2cc(OCc3cncc(C#N)c3)c(CNC(CO)CO)cc2Cl)cccc1-c1cccc(OCC2(CN3CC[C@@H](O)C3)CC2)c1C]

The compound was prepared and purified with the same method as that for Example 2340 to give the pure title compound: (25 mg, 90%). LC/MS Condition E: RT=1.44 min; m/e=727.0 (M+H)+.

Example 2343: 1-(3'-((2-chloro-5-((5-cyanopyridin-3-yl)methoxy)-4-formylphenoxy)methyl)-2,2'-dimethyl-[1,1'-biphenyl]-3-yl)-3-(cyclopropylmethyl)urea

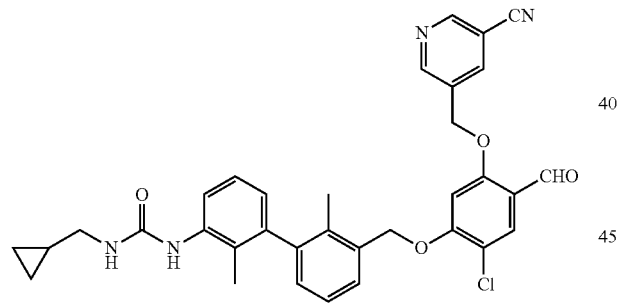

The compound was prepared and purified with the method using potassium phosphate tribasic, 2nd generation XPhos precatalyst in THF at rt to give the pure title compound: (11 mg, 9%). LC/MS Condition E: RT=1.84 min; m/e=595.0 (M+H)+.

Example 2346: (S)-1-(5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)piperidine-2-carboxylic Acid

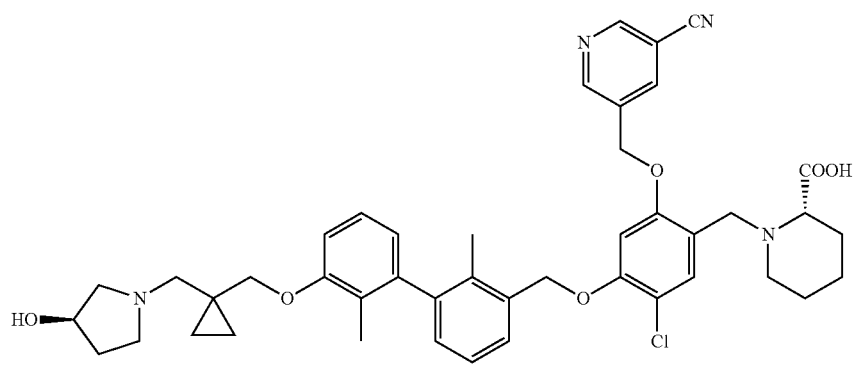 [SMILES: Cc1c(COc2cc(OCc3cncc(C#N)c3)c(CN3CCCC[C@H]3C(=O)O)cc2Cl)cccc1-c1cccc(OCC2(CN3CC[C@@H](O)C3)CC2)c1C]

The compound was prepared and purified with the same method as that for Example 2340 to give the pure title compound: (9 mg, 34%). LC/MS Condition E: RT=1.66 min; m/e=765.1 (M+H)+.

Example 2347: N-(3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)-2-(cyclopropylamino)acetamide

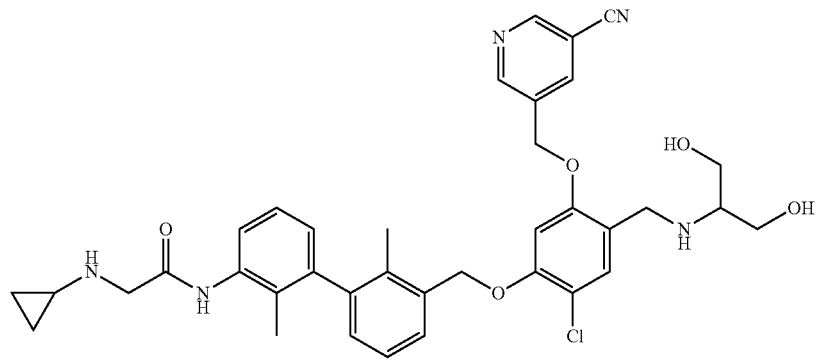 [SMILES: Cc1c(COc2cc(OCc3cncc(C#N)c3)c(CNC(CO)CO)cc2Cl)cccc1-c1cccc(NC(=O)CNC2CC2)c1C]

The compound was prepared and purified with the same method as that for Example 2340 to give the pure title compound: (5 mg, 45%). LC/MS Condition E: RT=1.70 min; m/e=670.0 (M+H)+.

Example 2348: (S)-2-((5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)amino)-3-hydroxy-2-methylpropanoic Acid

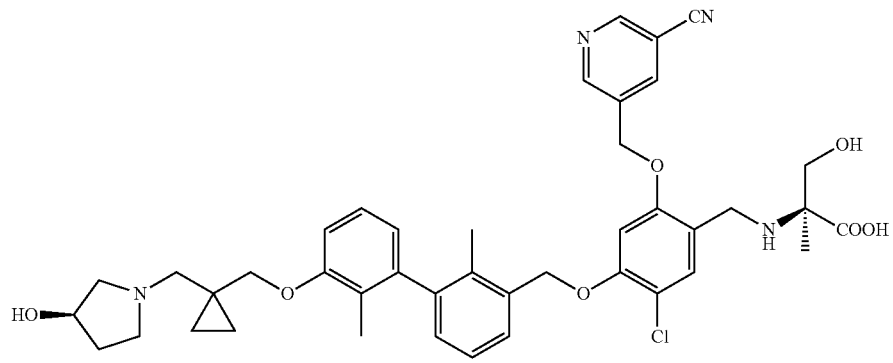 [SMILES: Cc1c(COc2cc(OCc3cncc(C#N)c3)c(CN[C@@](C)(CO)C(=O)O)cc2Cl)cccc1-c1cccc(OCC2(CN3CC[C@@H](O)C3)CC2)c1C]

The compound was prepared and purified with the same method as that for Example 2340 to give the pure title compound: (12 mg, 25%). LC/MS Condition E: RT=1.60 min; m/e=755.1 (M+H)+.

Example 2349: 5-((4-chloro-2-(((1,3-dihydroxypropan-2-yl)amino)methyl)-5-((2,2'-dimethyl-4'-(morpholine-4-carbonyl)-[1,1'-biphenyl]-3-yl)methoxy)phenoxy)methyl)nicotinonitrile

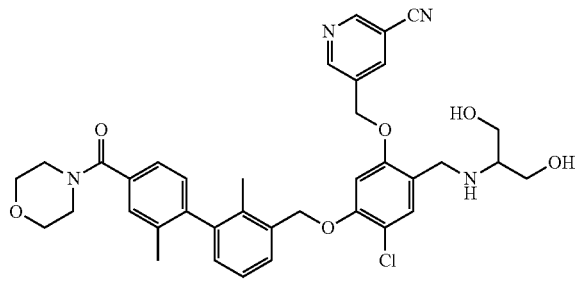 [SMILES: Cc1cc(C(=O)N2CCOCC2)ccc1-c1cccc(COc2cc(OCc3cncc(C#N)c3)c(CNC(CO)CO)cc2Cl)c1C]

The compound was prepared and purified with the same method as that for Example 2340 to give the pure title compound: (25 mg, 85%). LC/MS Condition E: RT=1.64 min; m/e=671.0 (M+H)+.

Example 2350: 5-((4-chloro-2-(((1,3-dihydroxypropan-2-yl)amino)methyl)-5-((2,2'-dimethyl-3'-((6-morpholinopyrimidin-4-yl)amino)-[1,1'-biphenyl]-3-yl)methoxy)phenoxy)methyl)nicotinonitrile

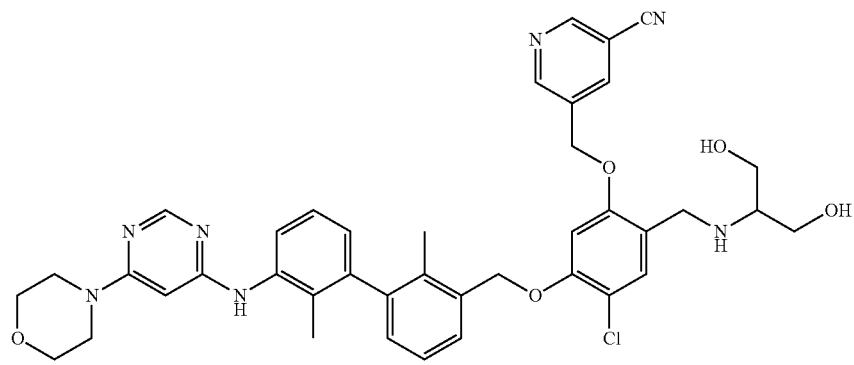 [SMILES: Cc1c(COc2cc(OCc3cncc(C#N)c3)c(CNC(CO)CO)cc2Cl)cccc1-c1cccc(Nc2cc(N3CCOCC3)ncn2)c1C]

The compound was prepared and purified with the same method as that for Example 2340 to give the pure title compound: (16 mg, 52%). LC/MS Condition E: RT=1.46 min; m/e=736.2 (M+H)+.

Example 2351: 1-(3'-((2-chloro-5-((5-cyanopyridin-3-yl)methoxy)-4-formylphenoxy)methyl)-2,2'-dimethyl-[1,1'-biphenyl]-3-yl)-3-(pyridin-2-yl)urea

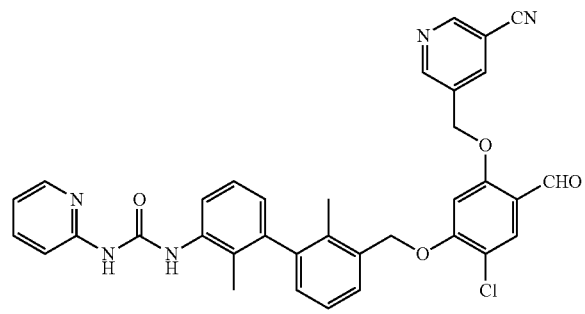 [SMILES: Cc1c(COc2cc(OCc3cncc(C#N)c3)c(C=O)cc2Cl)cccc1-c1cccc(NC(=O)Nc2ccccn2)c1C]

The compound was prepared and purified with the same method as that for Example 2341 to give the pure title compound: (7 mg, 5%). LC/MS Condition E: RT=1.94 min; m/e=618.0 (M+H)+.

Example 2352: 5-((4-chloro-5-((2,2'-dimethyl-3'-((1-oxo-1,2,3,4-tetrahydroisoquinolin-5-yl)oxy)-[1,1'-biphenyl]-3-yl)methoxy)-2-formylphenoxy)methyl)nicotinonitrile

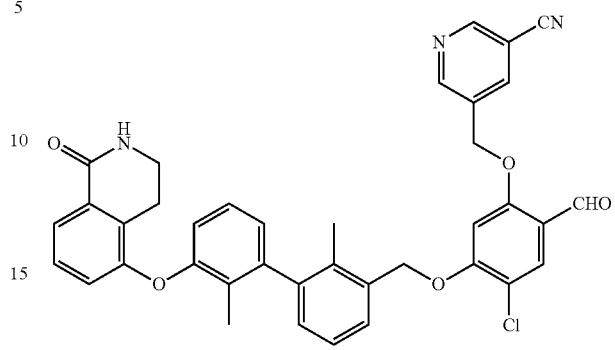

The compound was prepared and purified with the same method as that for Example 2341 to give the pure title compound: (11 mg, 9%). LC/MS Condition E: RT=1.94 min; m/e=618.0 (M+H)+.

Example 2354: 5-((4-chloro-2-(((1,3-dihydroxypropan-2-yl)amino)methyl)-5-((2,2'-dimethyl-3'-((1-oxo-1,2,3,4-tetrahydroisoquinolin-5-yl)oxy)-[1,1'-biphenyl]-3-yl)methoxy)phenoxy)methyl)nicotinonitrile

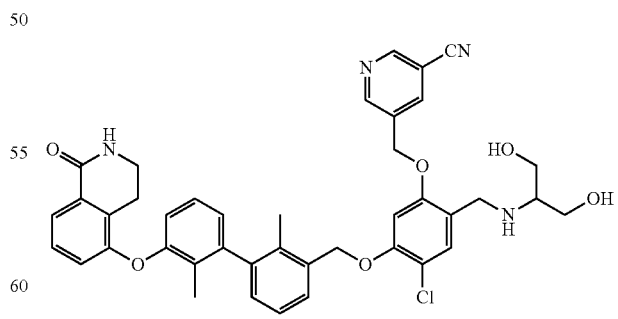

The compound was prepared and purified with the same method as that for Example 2340 to give the pure title compound: (24 mg, 90%). LC/MS Condition E: RT=1.93 min; m/e=719.0 (M+H)+.

Example 2364: (S)-1-(4-((3'-(3-(4-carboxypiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

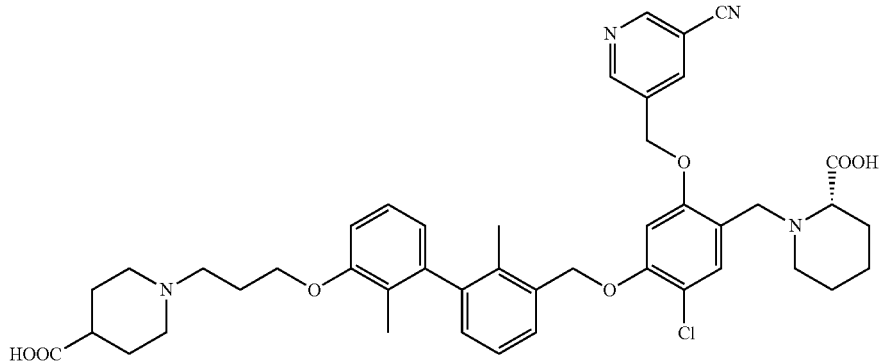 [SMILES: Cc1c(COc2cc(OCc3cncc(C#N)c3)c(CN3CCCC[C@H]3C(=O)O)cc2Cl)cccc1-c1cccc(OCCCN2CCC(C(=O)O)CC2)c1C]

A mixture of (S)-1-(4-((3'-(3-bromopropoxy)-2,2'-dimethyl-[1,1'-biphenyl]-3-yl)methoxy)-5-chloro-2-((5-cyanopyridin-3-yl)methoxy)benzyl)piperidine-2-carboxylic acid (20 mg, 0.016 mmol), piperidine-4-carboxylic acid (8.46 mg, 0.065 mmol) and potassium carbonate (11.31 mg, 0.082 mmol), in MeOH (1 mL) and Water (0.5 mL) was stirred at 80° C. for 8 h. The reaction mixture was concentrated and the residue was dissolved in DMF and was filtered. The filtrate was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation to give the pure title compound: (2 mg, 11%). $^1$H NMR (500 MHz, DMSO-$d_6$) δ 8.98 (s, 2H), 8.41 (s, 1H), 7.48 (d, J=7.3 Hz, 1H), 7.41 (s, 1H), 7.27 (t, J=7.3 Hz, 1H), 7.23-7.17 (m, 1H), 7.10-7.05 (m, 2H), 6.96 (d, J=8.4 Hz, 1H), 6.68 (d, J=8.4 Hz, 1H), 5.32 (br. s., 2H), 5.26 (s, 2H), 4.06 (d, J=7.0 Hz, 2H), 3.90 (d, J=5.1 Hz, 1H), 3.84-3.71 (m, 1H), 3.66-3.55 (m, 1H), 3.28 (s, 1H), 2.88 (s, 1H), 2.81 (br. s., 2H), 2.37 (s, 1H), 2.32-2.15 (m, 2H), 2.04 (s, 4H), 1.92 (s, 4H), 1.65-1.44 (m, 6H). LC/MS Condition E: RT=1.62 min; m/e=781.0 (M+H)$^+$.

Example 2370: 4-nitrophenyl (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylate

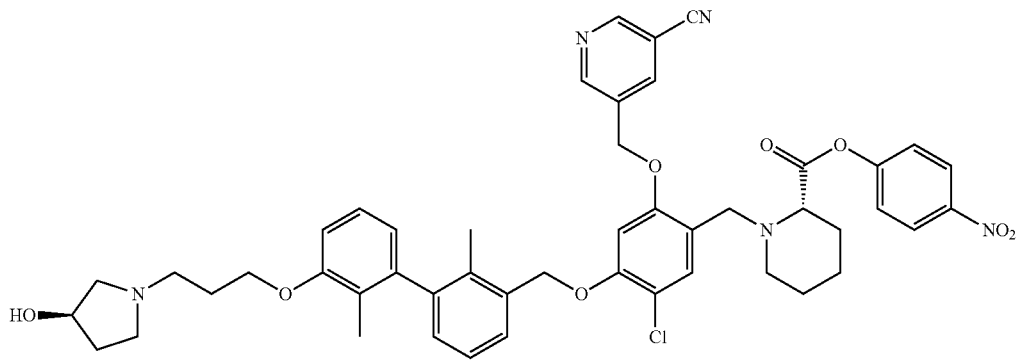 [SMILES: Cc1c(COc2cc(OCc3cncc(C#N)c3)c(CN3CCCC[C@H]3C(=O)Oc3ccc([N+](=O)[O-])cc3)cc2Cl)cccc1-c1cccc(OCCCN2CC[C@@H](O)C2)c1C]

A mixture of 4-nitrophenol (2.258 mg, 0.016 mmol), (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid (10 mg, 0.014 mmol), DCC (4.19 mg, 0.020 mmol), a trace amount of DMAP and a few pieces of 4 A MS in CH$_2$Cl$_2$ (1 mL) and THF (1 mL) (the acid was not soluble in DCM) was stirred at rt for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 55-95% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic
acid; Gradient: 35-75% B over 15 minutes, then a 5-minute hold at 100% B; Flow: 20 mL/min. Fractions containing the desired product were combined and dried via centrifugal evaporation to give the pure title compound: (4 mg 26%). LC/MS Condition E: RT=2.49 min; m/e=860.1 (M+H)$^+$. $^1$H NMR (500 MHz, DMSO-d$_6$) δ 8.97 (d, J=9.9 Hz, 2H), 8.38 (s, 1H), 8.29 (d, J=8.8 Hz, 2H), 7.50 (d, J=7.7 Hz, 2H), 7.44 (d, J=6.6 Hz, 3H), 7.32-7.21 (m, 3H), 7.15 (s, 1H), 7.07 (d, J=7.3 Hz, 1H), 6.98 (d, J=8.4 Hz, 1H), 6.72 (d, J=7.7 Hz, 1H), 5.35 (br. s., 2H), 5.29 (s, 2H), 4.54-4.37 (m, 1H), 4.12 (d, J=7.7 Hz, 3H), 4.02-3.83 (m, 2H), 3.71 (s, 1H), 3.04 (br. s., 1H), 2.19 (br. s., 3H), 2.06 (s, 3H), 2.02 (br. s., 2H), 1.87 (s, 4H), 1.61 (br. s., 6H).

Intermediate: (R)-5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzoic Acid mL/min, Wavelength=220, Solvent A=0.1% TFA in 90:10 water/MeOH, Solvent B=0.1% TFA in 10:90 water/MeOH, Column 1=Phenomenex-Luna 30×100 mm S10 Axia). The collected fractions were combined and concentrated to give (R)-5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzoic acid (98 mg, 0.113 mmol, 71.8% yield) as a white solid. $^1$H NMR (400 MHz, METHANOL-d$_4$) δ 8.96 (s, 1H), 8.83 (s, 1H), 8.39 (s, 1H), 7.97 (s, 1H), 7.47 (d, J=7.0 Hz, 1H), 7.25 (t, J=7.5 Hz, 1H), 7.19 (t, J=7.9 Hz, 1H), 7.09 (d, J=6.8 Hz, 1H), 6.91-6.84 (m, 2H), 6.75 (d, J=7.5 Hz, 1H), 5.29 (d, J=4.8 Hz, 4H), 4.60-4.54 (m, 1H), 4.22-4.06 (m, 2H), 3.79 (d, J=6.3 Hz, 2H), 3.56-3.40 (m, 3H), 3.20-3.03 (m, 1H), 2.28 (dd, J=8.8, 4.5 Hz, 2H), 2.16-2.09 (m, 2H), 2.07 (s, 3H), 1.89 (s, 3H). LCMS: M+1=642.10 min; RT=0.98 min.). LC/MS Condition E: RT=0.98 min; m/e=642.1 (M+H)$^+$.

Example 2378: (R)-5-chloro-2-((5-cyanopyridin-3-yl)methoxy)-N-(1,3-dihydroxy-2-methylpropan-2-yl)-4-((3'-(3-(3-hydroxypyrrolidin-1-yl)propoxy)-2,2'-dimethyl-[1,1'-biphenyl]-3-yl)methoxy)benzamide

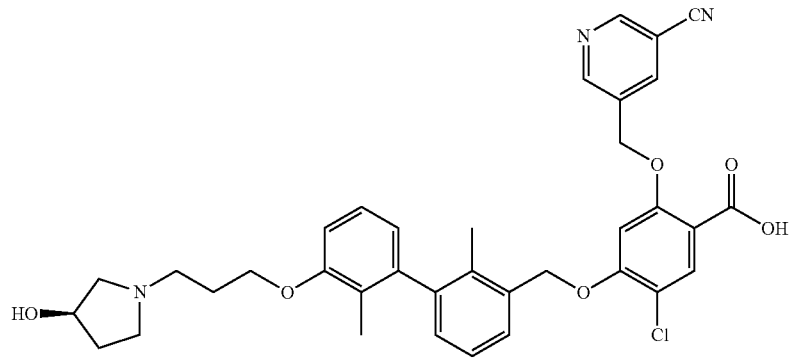 [SMILES: Cc1c(COc2cc(OCc3cncc(C#N)c3)c(C(=O)O)cc2Cl)cccc1-c1cccc(OCCCN2CC[C@@H](O)C2)c1C]

A mixture of 4-((3'-(3-bromopropoxy)-2,2'-dimethyl-[1,1'-biphenyl]-3-yl)methoxy)-5-chloro-2-((5-cyanopyridin-3-yl)methoxy)benzoic acid (100 mg, 0.157 mmol), (R)-pyrrolidin-3-ol, HCl (97 mg, 0.786 mmol) and DIPEA (0.165 mL, 0.943 mmol) in DMF (3 mL) was stirred at 60° C. for 16 h. The reaction mixture was purified by Prep. HPLC (Start % B=0, Final % B=100, Gradient time=12 min, Flow rate=40

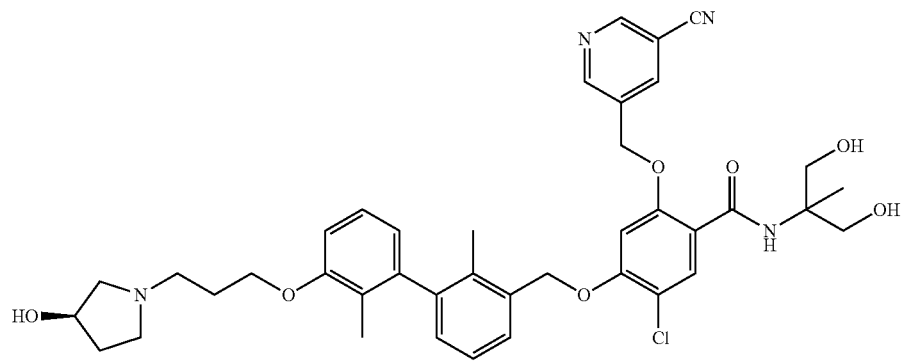 [SMILES: Cc1c(COc2cc(OCc3cncc(C#N)c3)c(C(=O)NC(C)(CO)CO)cc2Cl)cccc1-c1cccc(OCCCN2CC[C@@H](O)C2)c1C]

DIPEA (5.94 µl, 0.034 mmol) was added to a stirring solution of 3-((dimethylamino)(dimethyliminio)methyl)-3H-[1,2,3]triazolo[4,5-b]pyridine 1-oxide hexafluorophosphate(V) (HATU, 3.88 mg, 10.20 µmol), (R)-5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzoic acid, 2 TFA (10 mg, 8.50 µmol), 2-amino-2-methylpropane-1,3-diol (1.788 mg, 0.017 mmol) in DMF (1 mL) at rt. The resulting mixture was stirred at rt for 2 h. The crude reaction mixture was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 23-63% B over 20 minutes, then a 5-minute hold at 100% B; Flow: 20 mL/min. Fractions containing the desired product were combined and dried via centrifugal evaporation to get the titled compound: (5.1 mg, 75%) $^1$H NMR (500 MHz, DMSO-$d_6$) δ 9.01 (d, J=1.8 Hz, 2H), 8.46 (s, 1H), 7.88-7.81 (m, 2H), 7.51 (d, J=7.0 Hz, 1H), 7.29 (t, J=7.5 Hz, 1H), 7.24-7.16 (m, 2H), 7.09 (d, J=7.3 Hz, 1H), 6.97 (d, J=8.1 Hz, 1H), 6.68 (d, J=7.3 Hz, 1H), 5.44 (s, 2H), 5.38 (s, 2H), 4.23-4.16 (m, 1H), 4.08 (q, J=6.6 Hz, 2H), 3.51 (d, J=10.6 Hz, 2H), 3.44-3.36 (m, 1H), 2.72 (dd, J=9.5, 6.2 Hz, 1H), 2.63-2.56 (m, 3H), 2.48-2.41 (m, 1H), 2.35 (dd, J=9.5, 3.7 Hz, 1H), 2.06 (s, 3H), 2.02-1.89 (m, 3H), 1.84 (s, 3H), 1.64-1.44 (m, 1H), 1.18 (s, 3H). LC/MS Condition E: RT=1.76 min; m/e=729.1 (M+H)$^+$.

Example 2379: (R)-5-chloro-2-((5-cyanopyridin-3-yl)methoxy)-N-(2-hydroxyethyl)-4-((3'-(3-(3-hydroxypyrrolidin-1-yl)propoxy)-2,2'-dimethyl-[1,1'-biphenyl]-3-yl)methoxy)benzamide

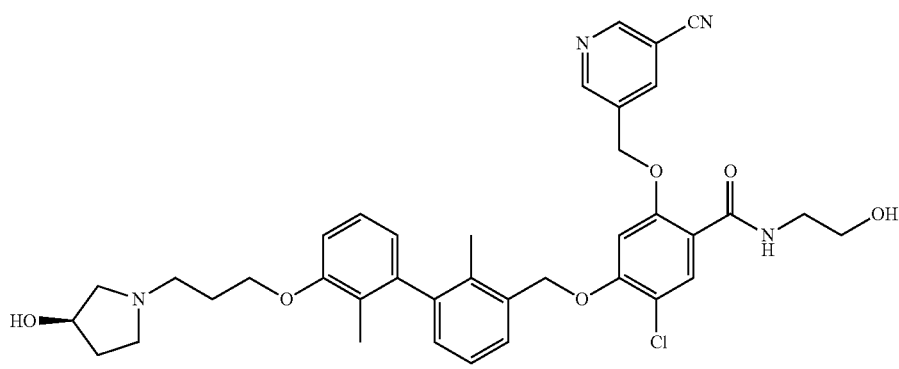 [SMILES: Cc1c(COc2cc(OCc3cncc(C#N)c3)c(C(=O)NCCO)cc2Cl)cccc1-c1cccc(OCCCN2CC[C@@H](O)C2)c1C]

The compound was prepared and purified with the same method as that for Example 2378 to give the pure title compound: salt: (3 mg, 14%). LC/MS Condition E: RT=1.58 min; m/e=685.0 (M+H)$^+$.

Example 2380: (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzoyl)piperidine-2-carboxylic Acid

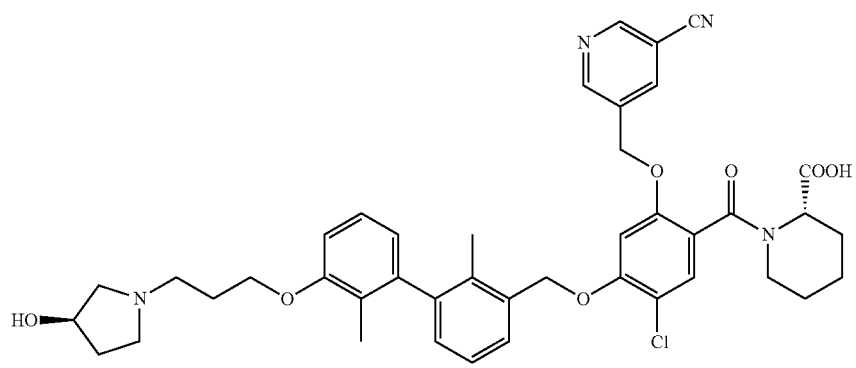 [SMILES: Cc1c(COc2cc(OCc3cncc(C#N)c3)c(C(=O)N3CCCC[C@H]3C(=O)O)cc2Cl)cccc1-c1cccc(OCCCN2CC[C@@H](O)C2)c1C]

The compound was prepared and purified with the same method as that for Example 2378 to give the pure title compound: salt: (2.6 mg, 11%). LC/MS Condition E: RT=1.73 min; m/e=753.1 (M+H)$^+$.

Example 2385: 1-(3-((3'-((2-chloro-5-((5-cyanopyridin-3-yl)methoxy)-4-formylphenoxy)methyl)-2,2'-dimethyl-[1,1'-biphenyl]-3-yl)oxy)propyl)-4-hydroxypiperidine-4-carboxylic Acid

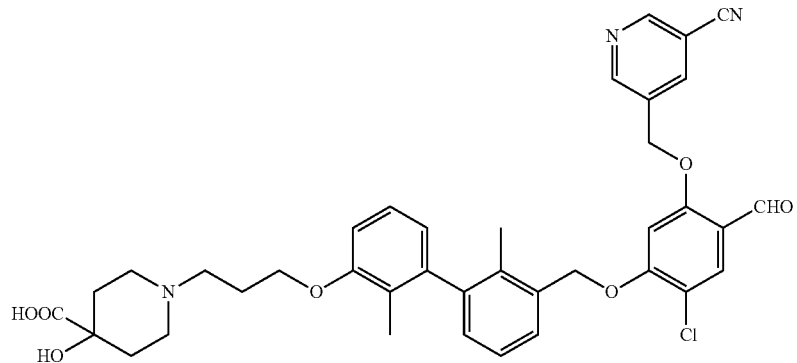 [SMILES: Cc1c(COc2cc(OCc3cncc(C#N)c3)c(C=O)cc2Cl)cccc1-c1cccc(OCCCN2CCC(O)(C(=O)O)CC2)c1C]

A mixture of 5-((5-((3'-(3-bromopropoxy)-2,2'-dimethyl-[1,1'-biphenyl]-3-yl)methoxy)-4-chloro-2-formylphenoxy)methyl)nicotinonitrile (60 mg, 0.097 mmol), methyl 4-hydroxypiperidine-4-carboxylate (30.8 mg, 0.194 mmol) (the reagent was a HCl salt and was passed a short column washed with a ~1/1 mixture of 2.0M of $NH_3$ in MeOH and DCM), sodium iodide (43.5 mg, 0.290 mmol) and DIPEA (0.051 mL, 0.290 mmol) in MeOH (5 mL) and THF (3 mL) was stirred at 60° C. for 16 h. The reaction was stirred at 80° C. for 7 h. The reaction was cooled to rt and lithium hydroxide (0.182 mL, 0.484 mmol) was added and the resulting mixture was stirred at rt for 18 h. The reaction mixture was concentrated and the residue was dissolved in DMF and was filtered. The filtrate was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 14.3 mg (22%). $^1$H NMR (500 MHz, DMSO-$d_6$) δ 10.24 (s, 1H), 9.07-8.98 (m, 2H), 8.51 (s, 1H), 7.74 (s, 1H), 7.53 (d, J=7.3 Hz, 1H), 7.33-7.26 (m, 2H), 7.24-7.17 (m, 1H), 7.11 (d, J=7.0 Hz, 1H), 6.98 (d, J=8.1 Hz, 1H), 6.70 (d, J=7.7 Hz, 1H), 5.49 (s, 2H), 5.43 (s, 2H), 4.08 (q, J=6.5 Hz, 2H), 2.72 (d, J=10.3 Hz, 2H), 2.61 (t, J=7.2 Hz, 2H), 2.48-2.39 (m, 2H), 2.06 (s, 3H), 2.01-1.89 (m, 5H), 1.85 (s, 3H), 1.53 (d, J=13.2 Hz, 2H). LC/MS Condition E: RT=1.87 min; m/e=648.0 (M+H)$^+$.

Example 2386: (S)-2-((5-chloro-2-((5-cyanopyridin-3-yl)methoxy)-4-((2,2'-dimethyl-3'-(3-(piperidin-1-yl)propoxy)-[1,1'-biphenyl]-3-yl)methoxy)benzyl)amino)-3-hydroxy-2-methylpropanoic Acid

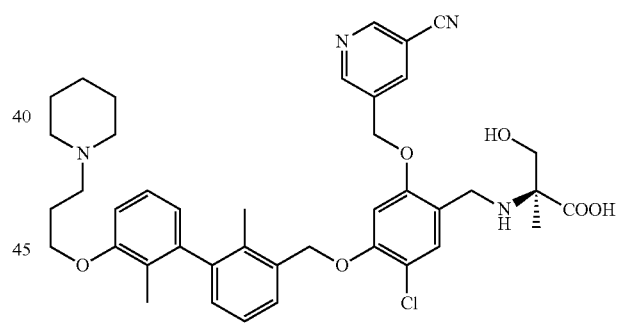

To a solution of (S)-2-((4-((3'-(3-bromopropoxy)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid (40 mg, 0.055 mmol) in DCM (0.3 mL) and MeOH (0.8 mL) was added piperidine (47.1 mg, 0.553 mmol), sodium iodide (24.88 mg, 0.166 mmol) in 0.1 ml of water and DIPEA (0.097 mL, 0.553 mmol). The resulting mixture was stirred at 60° C. under nitrogen for 16 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation to get 5.2 mg (12% yield) of the title compound. $^1$H NMR (500 MHz, DMSO-$d_6$) δ 9.07-8.99 (m, 2H), 8.51 (s, 1H), 7.58 (s, 1H), 7.49 (d, J=7.0 Hz, 1H), 7.28 (t, J=7.7 Hz, 1H), 7.23 (t, J=7.9 Hz, 1H), 7.15 (d, J=4.4 Hz, 1H), 7.07 (d, J=7.7 Hz, 1H), 6.98 (d, J=8.4 Hz, 1H), 6.71 (d, J=7.3 Hz, 1H), 5.36 (br. s., 2H), 5.32 (s, 2H), 4.16-4.02 (m, 4H), 3.73 (d, J=11.7 Hz, 1H), 3.64 (d, J=11.4 Hz, 1H), 3.28-3.19 (m, 1H), 2.24-2.14 (m, 2H), 2.03 (s, 3H), 1.84 (d, J=1.5 Hz, 3H), 1.76 (br. s., 6H), 1.31 (s, 3H). LC/MS Condition E: RT=2.00 min; m/e=727.2 (M+H)+.

Examples 3001 to 3044 were prepared as described below:

Intermediate: 1-bromo-3-(3-chloropropoxy)benzene and 1-bromo-3-(3-bromopropoxy)benzene

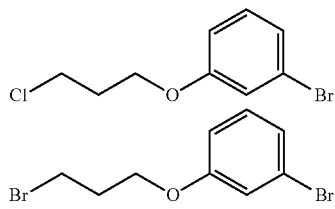

To a solution of 3-bromophenol (2 g, 1.250 mL, 11.56 mmol) in DMF (30 mL) was added 1-bromo-3-chloropropane (1.82 g, 1.138 mL, 11.56 mmol) and K₂CO₃ (1.917 g, 13.87 mmol). The reaction mixture was stirred at 50° C. for for 19 hr. The reaction mixture was cooled to room temperature, and diluted with EtOAc. The organic phase was washed with sat. NaHCO₃, water, brine, dried over anhydrous Na₂SO₄, filtered and concentrated. The residue was purified by silica gel chromatography (120 g, 0-15% EtOAc/hexane, the product was eluted at ~10-15% EtOAc/hexane) to yield 2.58 g of a mixture of 1-bromo-3-(3-chloropropoxy)benzene (80%) and 1-bromo-3-(3-bromopropoxy)benzene (20%). ¹H NMR for 1-bromo-3-(3-chloropropoxy)benzene (400 MHz, CHLOROFORM-d) δ ppm 7.19-7.15 (m, 1H), 7.13-7.09 (m, 2H), 6.87 (ddd, J=8.1, 2.4, 1.3 Hz, 1H), 4.14-4.11 (m, 2H), 3.76 (t, J=6.3 Hz, 2H), 2.26 (quin, J=6.1 Hz, 2H).

Intermediate: 5-((4-chloro-5-((3'-(3-chloropropoxy)-2-methyl-[1,1'-biphenyl]-3-yl)methoxy)-2-formylphenoxy)methyl)nicotinonitrile

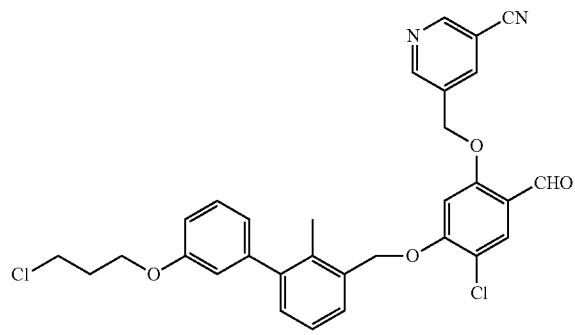 [SMILES: Cc1c(COc2cc(OCc3cncc(C#N)c3)c(C=O)cc2Cl)cccc1-c1cccc(OCCCCl)c1]

A mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (150 mg, 0.289 mmol), 1-bromo-3-(3-chloropropoxy)benzene (87 mg, 0.347 mmol, the 4:1 mixture prepared above and assumed 0.347 mmol), 2nd generation XPhos precatalyst (11.37 mg, 0.014 mmol), and potassium phosphate tribasic (1.446 mL, 0.723 mmol) in THF (4.5 mL) was degassed, and then sealed. The mixture was stirred at room temperature over a weekend. The solvent was removed. The residue was partitioned between dichloromethane and water. The aqueous phase was extracted once with dichloromethane. The organic extract was washed with brine then dried over sodium sulfate. The drying agent was removed, and the residue was purified by silica gel column chromatography (Biotage 25s, 0-35% EtOAc/hexane) to give 5-((4-chloro-5-((3'-(3-chloropropoxy)-2-methyl-[1,1'-biphenyl]-3-yl)methoxy)-2-formylphenoxy)methyl)nicotinonitrile (125 mg, 77%) as a white solid (only the chloro product was observed and isolated). ¹H NMR (400 MHz, CHLOROFORM-d) δ ppm 10.31 (s, 1H), 8.93 (dd, J=3.8, 2.0 Hz, 2H), 8.12 (d, J=2.0 Hz, 1H), 7.96 (s, 1H), 7.49-7.44 (m, 1H), 7.40-7.34 (m, 1H), 7.33-7.30 (m, 2H), 6.98-6.91 (m, 2H), 6.88 (d, J=1.8 Hz, 1H), 6.68 (s, 1H), 5.27 (d, J=5.3 Hz, 4H), 4.18 (t, J=5.9 Hz, 2H), 3.79 (t, J=6.3 Hz, 2H), 2.41-2.24 (m, 2H), 2.31 (s, 3H).

Intermediate: (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile

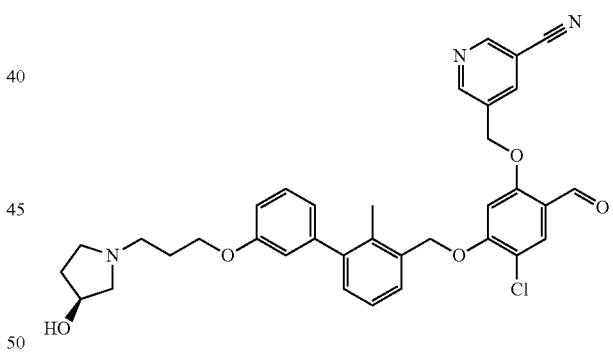

A stirred mixture of 5-((4-chloro-5-((3'-(3-chloropropoxy)-2-methyl-[1,1'-biphenyl]-3-yl)methoxy)-2-formylphenoxy)methyl)nicotinonitrile (125 mg, 0.223 mmol), (R)-pyrrolidin-3-ol, HCl salt (41.3 mg, 0.334 mmol), K₂CO₃ (46.2 mg, 0.334 mmol), and sodium iodide (33.4 mg, 0.223 mmol) in DMF (4 mL) was heated at 80° C. for 16 hrs. The solvent was removed. The residue was purified by silica gel chromatography using a short column (0-20% MeOH/DCM) (DCM=dichloromethane) to give 82 mg of the crude target compound, which was directly used for the next reaction without further purification. MS: ESI(+) m/z 612 (M+H).

Example 3001: (R)-5-((4-chloro-2-(((3-(dimethyl-amino)propyl)amino)methyl)-5-((3'-(3-(3-hydroxy-pyrrolidin-1-yl)propoxy)-2-methyl-[1,1'-biphenyl]-3-yl)methoxy)phenoxy)methyl)nicotinonitrile

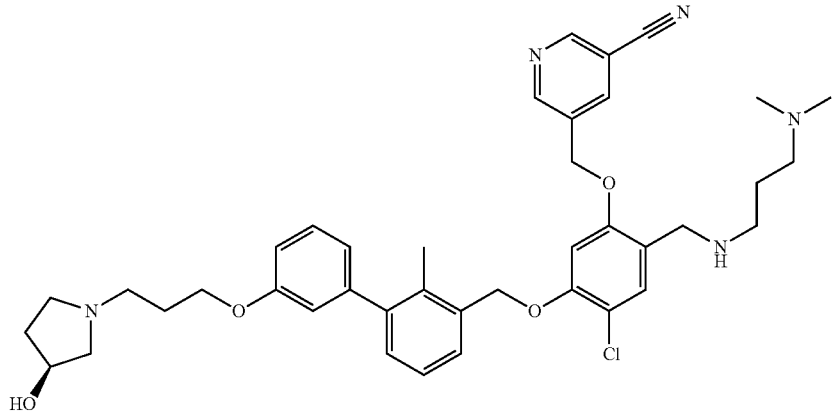 [SMILES: Cc1c(COc2cc(OCc3cncc(C#N)c3)c(CNCCCN(C)C)cc2Cl)cccc1-c1cccc(OCCCN2CC[C@H](O)C2)c1]

To a suspension of (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile (41 mg, 0.067 mmol) in MeOH (1 mL), and acetic acid (0.1 mL) was added N,N-dimethyl-1,3-propanediamine (8.21 mg, 0.080 mmol) followed by borane-2-picoline complex (8.60 mg, 0.080 mmol). The mixture was stirred at room temperature overnight. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 55-95% B over 20 minutes, then a 5-minute hold at 100% B; Flow: 20 mL/min. Fractions containing the desired product were combined and dried via centrifugal evaporation (17.5 mg, yield 37%, purity 99%). $^1$H NMR (500 MHz, DMSO-$d_6$) δ ppm 9.00 (d, J=8.4 Hz, 2H), 8.44 (s, 1H), 7.48 (d, J=7.3 Hz, 1H), 7.44 (s, 1H), 7.35 (t, J=7.9 Hz, 1H), 7.27 (t, J=7.70 Hz, 1H), 7.21 (d, J=7.3 Hz, 1H), 7.12 (s, 1H), 6.94 (d, J=8.1 Hz, 1H), 6.86 (d, J=7.7 Hz, 1H), 6.82 (s, 1H), 5.34 (s, 2H), 5.27 (s, 2H), 4.20 (br. s., 1H), 4.11 (br. s., 1H), 4.04 (t, J=6.1 Hz, 2H), 3.77 (s, 2H), 2.78 (dd, J=9.7, 6.1 Hz, 1H), 2.70-2.57 (m, 5H), 2.56-2.49 (m, 1H), 2.42 (dd, J=9.9, 2.6 Hz, 1H), 2.32 (t, J=7.0 Hz, 2H), 2.24 (s, 3H), 2.14 (s, 6H), 2.03-1.88 (m, 3H), 1.65-1.52 (m, 2H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.49 min, ESI m/z 698 (M+H)

LCMS (Injection 2 conditions) Rt=2.66 min, ESI m/z 698 (M+H)

Example 3002: (S)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-5-guanidinopentanoic Acid

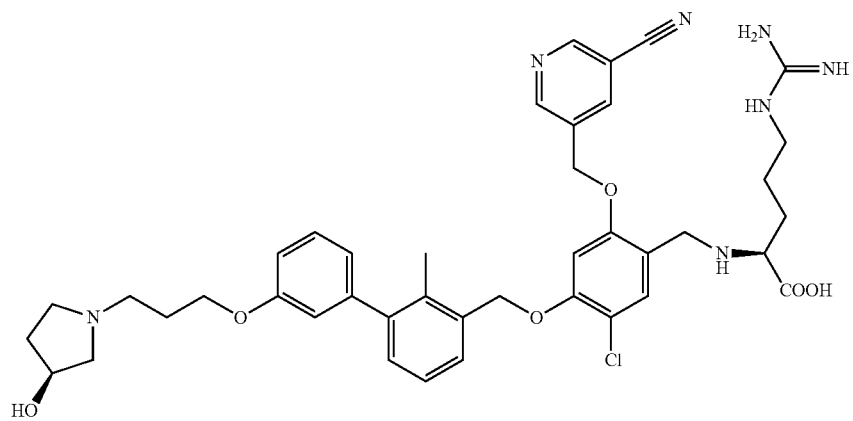 [SMILES: Cc1c(COc2cc(OCc3cncc(C#N)c3)c(CN[C@@H](CCCNC(=N)N)C(=O)O)cc2Cl)cccc1-c1cccc(OCCCN2CC[C@H](O)C2)c1]

(S)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-5-guanidinopentanoic acid (29.9 mg, 55.6%) was obtained from (R)-5-

((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile and (S)-2-amino-5-guanidinopentanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 55-95% B over 20 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.01 (s, 1H), 8.97 (S, 1H), 8.44 (s, 1H), 7.47 (d, J=7.3 Hz, 1H), 7.44 (s, 1H), 7.34 (t, J=7.9 Hz, 1H), 7.25 (t, J=7.70 Hz, 1H), 7.20 (d, J=7.3 Hz, 1H), 7.08 (s, 1H), 6.93 (d, J=8.1 Hz, 1H), 6.85 (d, J=7.7 Hz, 1H), 6.81 (s, 1H), 5.37-5.29 (m, 2H), 5.24 (s, 2H), 4.21-4.10 (m, 3H), 4.03 (t, J=6.1 Hz, 2H), 3.82 (d, J=13.6 Hz, 1H), 3.74 (d, J=13.6 Hz, 1H), 303 (br, s 2H), 2.75 (dd, J=9.7, 6.1 Hz, 1H), 2.69-2.55 (m, 3H), 2.56-2.49 (m, 1H), 2.39 (dd, J=9.9, 2.6 Hz, 1H), 2.23 (s, 3H), 2.03-1.85 (m, 3H), 1.65-1.52 (m, 4H). Two analytical LC/MS injections were used to determine the final purity.
Injection 1 conditions: Column: Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.22 min, ESI m/z 770 (M+H), 768 (M−H)

LCMS (Injection 2 conditions) Rt=2.43 min, ESI m/z 698 (M+H), 768 (M−H).

Intermediate: 1-bromo-3-(3-chloropropoxy)-2-methylbenzene and 1-bromo-3-(3-bromopropoxy)-2-methylbenzene The mixture (1.058 g, 75%) of 1-bromo-3-(3-chloropropoxy)-2-methylbenzene (75%) and 1-bromo-3-(3-bromopropoxy)-2-methylbenzene (25%) was obtained from 3-bromo-2-methylphenol and 1-bromo-3-chloropropane using the procedure described for 1-bromo-3-(3-chloropropoxy)benzene. $^1$H NMR for 1-bromo-3-(3-chloropropoxy)-2-methylbenzene (400 MHz, CHLOROFORM-d) δ 7.23-7.16 (m, 1H), 7.03 (t, J=8.0 Hz, 1H), 6.82 (d, J=8.3 Hz, 1H), 4.17-4.12 (m, 2H), 3.79 (t, J=6.3 Hz, 2H), 2.34 (s, 3H), 2.33-2.25 (m, 2H).

Intermediate: 5-((4-chloro-5-((3'-(3-chloropropoxy)-2,2'-dimethyl-[1,1'-biphenyl]-3-yl)methoxy)-2-formylphenoxy)methyl)nicotinonitrile

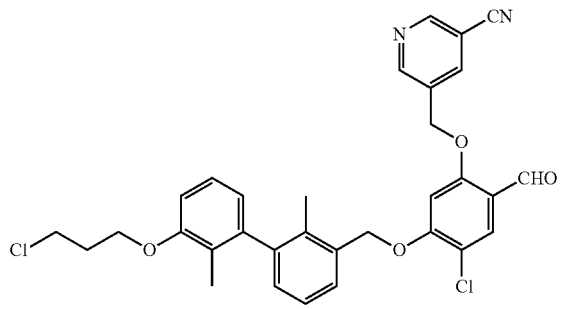 [SMILES: Cc1c(COc2cc(OCc3cncc(C#N)c3)c(C=O)cc2Cl)cccc1-c1cccc(OCCCCl)c1C]

(5-((4-chloro-5-((3'-(3-chloropropoxy)-2,2'-dimethyl-[1,1'-biphenyl]-3-yl)methoxy)-2-formylphenoxy)methyl)nicotinonitrile (89 mg, 54%) was obtained from 5-((4-chloro-2-formyl-5-((2-methyl-3-(4,4,5,5-tetramethyl-1,3,2-dioxaborolan-2-yl)benzyl)oxy)phenoxy)methyl)nicotinonitrile and 1-bromo-3-(3-chloropropoxy)-2-methylbenzene (the 3:1 mixture prepared above) using the procedure described for 5-((4-chloro-5-((3'-(3-chloropropoxy)-2-methyl-[1,1'-biphenyl]-3-yl)methoxy)-2-formylphenoxy)methyl)nicotinonitrile. (Only the chloro product was observed and isolated). $^1$H NMR (500 MHz, DMSO-d$_6$) δ 10.23 (s, 1H), 9.03 (s, 2H), 8.54 (s, 1H), 7.73 (s, 1H), 7.52 (d, J=7.7 Hz, 1H), 7.32-7.26 (m, 2H), 7.23 (t, J=7.9 Hz, 1H), 7.11 (d, J=7.7 Hz, 1H), 6.99 (d, J=8.1 Hz, 1H), 6.71 (d, J=7.3 Hz, 1H), 5.49 (s, 2H), 5.42 (br. s., 2H), 4.19-4.09 (m, 2H), 3.84 (t, J=6.4 Hz, 2H), 2.22 (t, J=6.1 Hz, 2H), 2.04 (s, 3H), 1.84 (s, 3H).

Intermediate: (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile

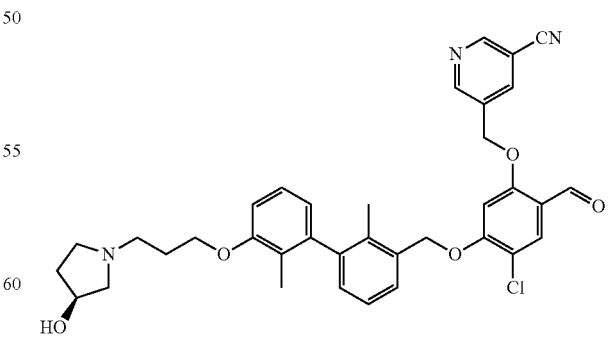

(R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile (96 mg, 59%) was obtained from 5-((4-chloro-5-((3'-(3-chloropropoxy)-2,2'- dimethyl-[1,1'-biphenyl]-3-yl)methoxy)-2-formylphenoxy)methyl)nicotinonitrile (9) and (R)-pyrrolidin-3-ol HCl salt using the procedure described for (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl) nicotinonitrile. ¹H NMR (400 MHz, CHLOROFORM-d) δ 10.29 (s, 1H), 8.93 (d, J=1.3 Hz, 2H), 8.13 (s, 1H), 7.93 (s, 1H), 7.46 (d, J=7.5 Hz, 1H), 7.33-7.26 (m, 1H), 7.24-7.15 (m, 2H), 6.87 (d, J=8.0 Hz, 1H), 6.77 (d, J=7.5 Hz, 1H), 6.68 (s, 1H), 5.29 (s, 2H), 5.25 (s, 2H), 4.52 (br, s, 1H), 4.19-4.07 (m, 2H), 3.37-3.27 (m, 1H), 3.13 (d, J=11.0 Hz, 1H), 3.05 (t, J=7.3 Hz, 2H), 2.98 (br, s, 1H), 2.82 (br, s, 1H), 2.38-2.21 (m, 3H), 2.11 (s, 3H), 2.02 (br, s, 1H), 1.91 (s, 3H).

Example 3003: (S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic Acid

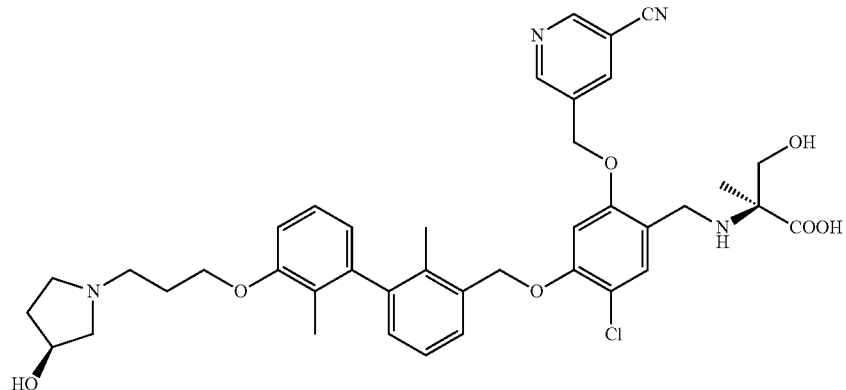 [SMILES: Cc1c(COc2cc(OCc3cncc(C#N)c3)c(CN[C@@](C)(CO)C(=O)O)cc2Cl)cccc1-c1cccc(OCCCN2CC[C@H](O)C2)c1C]

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid (13.7 mg, 36.8%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and (S)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. ¹H NMR (500 MHz, DMSO-d₆) δ 9.03 (dd, J=4.9, 2.0 Hz, 2H), 8.52 (t, J=2.0 Hz, 1H), 7.54 (s, 1H), 7.48 (d, J=6.8 Hz, 1H), 7.27 (t, J=7.6 Hz, 1H), 7.21 (t, J=7.8 Hz, 1H), 7.14 (s, 1H), 7.08 (dd, J=7.6, 1.0 Hz, 1H), 6.96 (d, J=8.0 Hz, 1H), 6.68 (d, J=7.1 Hz, 1H), 5.39-5.32 (m, 2H), 5.32-5.26 (m, 2H), 4.19 (tt, J=6.9, 3.5 Hz, 1H), 4.11-4.00 (m, 2H), 3.91 (s, 2H), 3.58 (d, J=11.0 Hz, 1H), 3.51 (d, J=11.2 Hz, 1H), 2.75-2.68 (m, 1H), 2.63-2.54 (m, 3H), 2.48-2.40 (m, 1H), 2.34 (dd, J=9.5, 3.7 Hz, 1H), 2.04 (s, 3H), 2.02-1.96 (m, 1H), 1.96-1.87 (m, 2H), 1.83 (s, 3H), 1.58-1.50 (m, 1H), 1.22 (s, 3H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.409 min, ESI m/z 729 (M+H), 727 (M−H)

LCMS (Injection 2 conditions) Rt=2.939 min, ESI m/z 729 (M+H), 727 (M−H)

Example 3004: (S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoic Acid

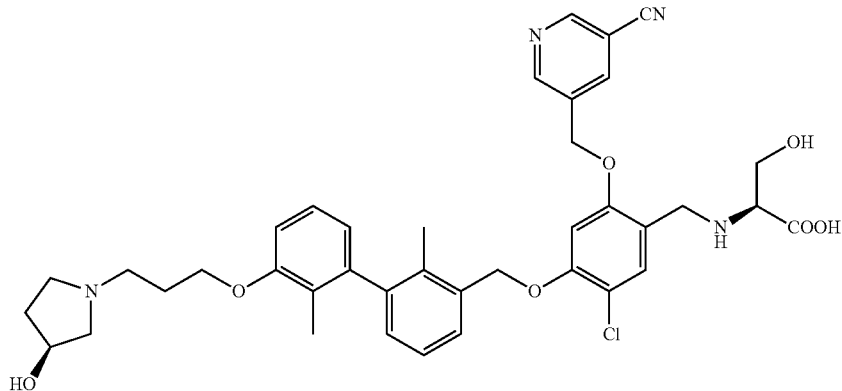 [SMILES: Cc1c(COc2cc(OCc3cncc(C#N)c3)c(CN[C@@H](CO)C(=O)O)cc2Cl)cccc1-c1cccc(OCCCN2CC[C@H](O)C2)c1C]

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoic acid (25.6 mg, 70%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and (S)-2-amino-3-hydroxypropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-100% B over 20 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (d, J=1.7 Hz, 2H), 8.52 (s, 1H), 7.52-7.47 (m, 2H), 7.27 (t, J=7.6 Hz, 1H), 7.20 (t, J=8.0 Hz, 1H), 7.13 (s, 1H), 7.07 (d, J=6.6 Hz, 1H), 6.96 (d, J=8.0 Hz, 1H), 6.69 (d, J=7.6 Hz, 1H), 5.39-5.31 (m, 2H), 5.31-5.25 (m, 2H), 4.23-4.16 (m, 1H), 4.11-3.89 (m, 4H), 3.68-3.64 (m, 1H), 3.64-3.56 (m, 1H), 3.11 (t, J=5.6 Hz, 1H), 2.76-2.70 (m, 1H), 2.66-2.54 (m, 3H), 2.49-2.42 (m, 1H), 2.39-2.33 (m, 1H), 2.03 (S, 3H), 2.02-1.95 (m, 1H), 1.95-1.88 (m, 2H), 1.82 (s, 3H), 1.59-1.51 (m, 1H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.393 min, ESI m/z 715 (M+H), 713 (M−H)

LCMS (Injection 2 conditions) Rt=2.928 min, ESI m/z 715 (M+H), 713 (M−H)

Example 3005: (R)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic Acid

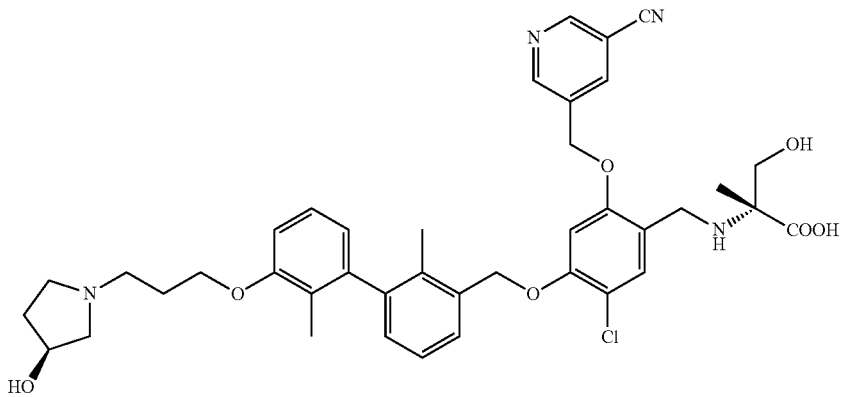 [SMILES: Cc1c(COc2cc(OCc3cncc(C#N)c3)c(CN[C@](C)(CO)C(=O)O)cc2Cl)cccc1-c1cccc(OCCCN2CC[C@H](O)C2)c1C]

(R)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid (7 mg, 20%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and (R)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 55-100% B over 30 minutes, then a 10-minute hold at 100% B; Flow: 20 mL/min. Fractions containing the desired product were combined and dried via centrifugal evaporation. $^1$H NMR (500 MHz, DMSO-$d_6$) δ 9.03 (d, J=7.3 Hz, 2H), 8.52 (s, 1H), 7.54 (s, 1H), 7.48 (d, J=7.7 Hz, 1H), 7.27 (t, J=7.5 Hz, 1H), 7.21 (t, J=8.1 Hz, 1H), 7.13 (s, 1H), 7.08 (d, J=7.3 Hz, 1H), 6.96 (d, J=8.4 Hz, 1H), 6.68 (d, J=7.3 Hz, 1H), 5.35 (s, 2H), 5.32-5.24 (m, 2H), 4.19 (br. s., 1H), 4.11-3.98 (m, 2H), 3.93 (s, 2H), 3.59 (d, J=13.6 Hz, 1H), 3.52 (d, J=11.3 Hz, 1H), 2.75-2.69 (m, 1H), 2.66-2.54 (m, 3H), 2.53-2.42 (m, 1H), 2.36-2.31 (m, 1H), 2.03 (s, 3H), 2.02-1.95 (m, 1H), 1.95-1.88 (m, 2H), 1.82 (s, 3H), 1.54 (br, s, 1H), 1.22 (s, 3H).

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.419 min, ESI m/z 729 (M+H), 727 (M−H)

LCMS (Injection 2 conditions) Rt=2.937 min, ESI m/z 729 (M+H), 727 (M−H)

Example 3006: (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

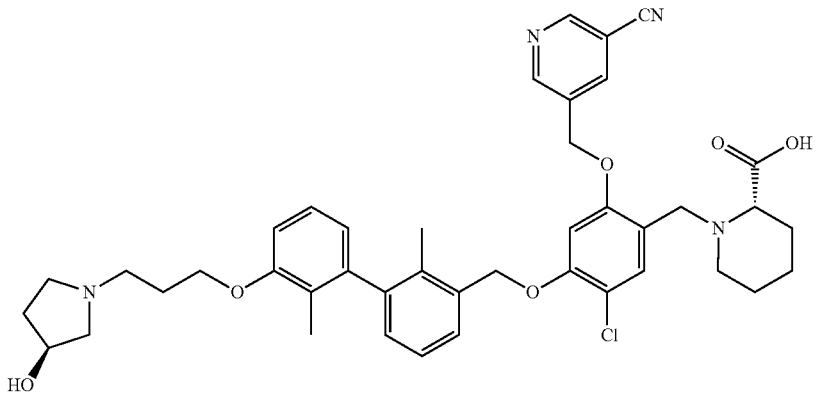 [SMILES: Cc1c(COc2cc(OCc3cncc(C#N)c3)c(CN3CCCC[C@H]3C(=O)O)cc2Cl)cccc1-c1cccc(OCCCN2CC[C@H](O)C2)c1C]

(S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid (10.6 mg, 28.1%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and (S)-piperidine-2-carboxylic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.00 (d, J=5.9 Hz, 2H), 8.46 (s, 1H), 7.49 (d, J=7.7 Hz, 1H), 7.45 (s, 1H), 7.27 (t, J=7.5 Hz, 1H), 7.20 (t, J=7.9 Hz, 1H), 7.11 (s, 1H), 7.07 (d, J=7.7 Hz, 1H), 6.95 (d, J=8.4 Hz, 1H), 6.67 (d, J=7.7 Hz, 1H), 5.33 (s, 2H), 5.28-5.24 (m, 2H), 4.19 (br. s., 1H), 4.11-3.98 (m, 2H), 3.84 (d, J=14.7 Hz, 1H), 3.66 (d, J=13.6 Hz, 1H), 3.12 (m, 1H), 2.89 (br, s, 1H), 2.77-2.70 (m, 1H), 2.66-2.54 (m, 3H), 2.53-2.42 (m, 1H), 2.41-2.27 (m, 2H), 2.06-1.95 (m, 1H), 2.03 (s, 3H), 1.95-1.88 (m, 2H), 1.81 (s, 4H), 1.71 (d, J=9.2 Hz, 1H), 1.60-1.44 (m, 4H), 1.36 (br. s., 1H).

Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 50° C.; Gradient: 0-100% B over 3 minutes, then a 2.0-minute hold at 100% B; Flow: 0.75 mL/min; Detection: UV at 220 nm.

LCMS (Injection 1 conditions) Rt=1.455 min, ESI m/z 739 (M+H), 737 (M−H)

LCMS (Injection 2 conditions) Rt=1.235 min, ESI m/z 739 (M+H)

Example 3007: (R)-5-((4-chloro-2-(((3-(dimethylamino)propyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile

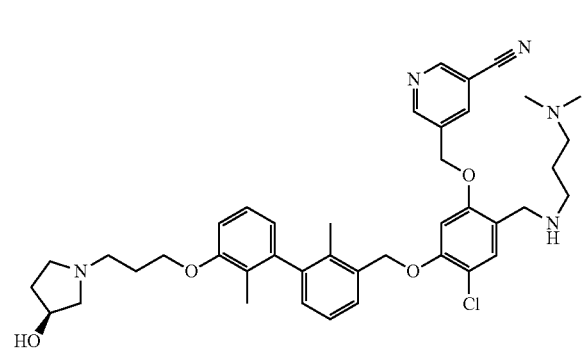 [SMILES: Cc1c(COc2cc(OCc3cncc(C#N)c3)c(CNCCCN(C)C)cc2Cl)cccc1-c1cccc(OCCCN2CC[C@H](O)C2)c1C]

(R)-5-((4-chloro-2-(((3-(dimethylamino)propyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile (15.2 mg, 33%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and N,N-dimethyl-1,3-propanediamine using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 50-90% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (s, 1H), 8.99 (s, 1H), 8.44 (s, 1H), 7.49 (d, J=7.7 Hz, 1H), 7.39 (s, 1H), 7.27 (t, J=7.3 Hz, 1H), 7.21 (t, J=7.9 Hz, 1H), 7.11 (s, 1H), 7.07 (d, J=7.3 Hz, 1H), 6.96 (d, J=8.4 Hz, 1H), 6.68 (d, J=7.7 Hz, 1H), 5.32 (s, 2H), 5.30-5.22 (m, 2H), 4.19 (br. s., 1H), 4.05 (br, s, 2H), 3.66 (br, s, 2H), 2.73-2.67 (m, 1H), 2.62-2.54 (m, 3H), 2.54-2.47 (m, 1H), 2.44 (d, J=8.4 Hz, 2H), 2.33 (dd, J=9.5, 3.3 Hz, 1H), 2.23 (t, J=7.0 Hz, 2H), 2.09 (s, 6H), 2.04 (s, 3H), 1.98 (dd, J=13.0, 7.2 Hz, 1H), 1.94-1.87 (m, 2H), 1.83 (s, 3H), 1.59-1.50 (m, 3H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-µm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.428 min, ESI m/z 712 (M+H)

LCMS (Injection 2 conditions) Rt=2.43 min, ESI m/z 712 (M+H)

Intermediate:
2-bromo-6-(3-chloropropoxy)benzonitrile

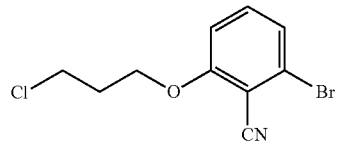

2-Bromo-6-(3-chloropropoxy)benzonitrile (1.293 g, 93%) was obtained from 2-bromo-6-hydroxybenzonitrile and 1-bromo-3-chloropropane using the procedure described for 1-bromo-3-(3-chloropropoxy)benzene. $^1$H NMR (400 MHz, CHLOROFORM-d) δ 7.40 (t, J=8.28 Hz, 1H), 7.32-7.26 (m, 1H), 6.97 (d, J=8.5 Hz, 1H), 4.28 (t, 5.77 Hz, 2H), 3.83 (t, J=6.0 Hz, 2H), 2.33 (quin, J=5.9 Hz, 2H).

Intermediate: 5-((4-chloro-5-((3'-(3-chloropropoxy)-2'-cyano-2-methyl-[1,1'-biphenyl]-3-yl)methoxy)-2-formylphenoxy)methyl)nicotinonitrile

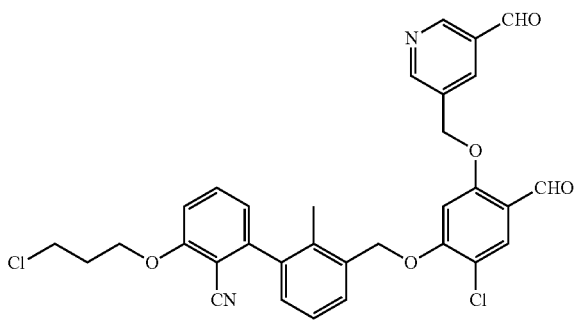 [SMILES: Cc1c(COc2cc(OCc3cncc(C=O)c3)c(C=O)cc2Cl)cccc1-c1cccc(OCCCCl)c1C#N]

5-((4-chloro-5-((3'-(3-chloropropoxy)-2'-cyano-2-methyl-[1,1'-biphenyl]-3-yl)methoxy)-2-formylphenoxy) methyl)nicotinonitrile (175 mg, 100%) was obtained from 5-((4-chloro-2-formyl-5-((2-methyl-3-(4,4,5,5-tetramethyl-1,3,2-dioxaborolan-2-yl)benzyl)oxy)phenoxy)methyl)nicotinonitrile and 2-bromo-6-(3-chloropropoxy)benzonitrile using the procedure described for 5-((4-chloro-5-((3'-(3-chloropropoxy)-2-methyl-[1,1'-biphenyl]-3-yl)methoxy)-2-formylphenoxy)methyl)nicotinonitrile. $^1$H NMR (400 MHz, CHLOROFORM-d) δ 10.30 (s, 1H), 8.90 (dd, J=6.9, 2.1 Hz, 2H), 8.07 (t, J=2.0 Hz, 1H), 7.95 (s, 1H), 7.67-7.59 (m, 1H), 7.42 (d, J=7.5 Hz, 1H), 7.32 (t, J=7.7 Hz, 1H), 7.27-7.22 (m, 1H), 7.06 (d, J=8.0 Hz, 1H), 7.01 (d, J=7.5 Hz, 1H), 6.47 (s, 1H), 5.47-5.30 (m, 2H), 5.17-5.04 (m, 2H), 4.34 (td, J=5.8, 3.6 Hz, 2H), 3.86 (t, J=6.0 Hz, 2H), 2.37 (quin, J=5.9 Hz, 2H), 2.26 (s, 3H).

(R)-5-((4-chloro-5-((2'-cyano-3'-(3-(3-hydroxypyrrolidin-1-yl)propoxy)-2-methyl-[1,1'-biphenyl]-3-yl)methoxy)-2-formylphenoxy)methyl)nicotinonitrile

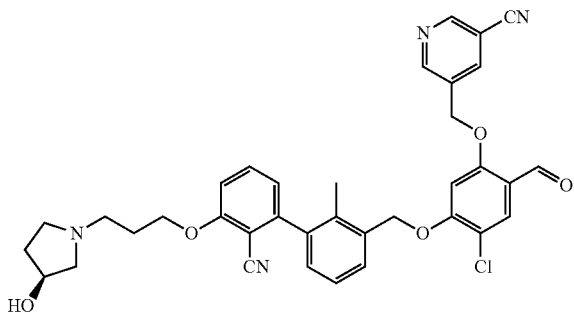

(R)-5-((4-chloro-5-((2'-cyano-3'-(3-(3-hydroxypyrrolidin-1-yl)propoxy)-2-methyl-[1,1'-biphenyl]-3-yl)methoxy)-2-formylphenoxy)methyl)nicotinonitrile (96 mg, 51.4%) was obtained from 5-((4-chloro-5-((3'-(3-chloropropoxy)-2'-cyano-2-methyl-[1,1'-biphenyl]-3-yl)methoxy)-2-formylphenoxy)methyl)nicotinonitrile and (R)-pyrrolidin-3-ol HCl salt using the procedure described for (R)-5-((4-chloro-2-formyl-5-((3'-(3-(3-hydroxypyrrolidin-1-yl)propoxy)-2-methyl-[1,1'-biphenyl]-3-yl)methoxy)phenoxy)methyl)nicotinonitrile. $^1$H NMR (400 MHz, CHLOROFORM-d) δ 10.29 (s, 1H), 8.90 (d, J=2.0 Hz, 1H), 8.87 (d, J=1.8 Hz, 1H), 8.08 (t, J=2.0 Hz, 1H), 7.94 (s, 1H), 7.63-7.57 (m, 1H), 7.40 (d, J=7.3 Hz, 1H), 7.34-7.29 (m, 1H), 7.25-7.20 (m, 1H), 7.03 (d, J=8.5 Hz, 1H), 6.97 (d, J=7.3 Hz, 1H), 6.45 (s, 1H), 5.47-5.40 (m, 1H), 5.37-5.29 (m, 1H), 5.17-5.10 (m, 1H), 5.08-5.02 (m, 1H), 4.38 (td, J=4.8, 2.5 Hz, 1H), 4.31-4.18 (m, 2H), 2.95 (td, J=8.6, 5.4 Hz, 1H), 2.75 (t, J=6.9 Hz, 3H), 2.68-2.60 (m, 1H), 2.44-2.35 (m, 1H), 2.25 (s, 3H), 2.23-2.17 (m, 1H), 2.12 (quin, J=6.7 Hz, 2H), 1.85-1.73 (m, 1H).

Example 3008: (S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid was obtained from (R)-5-((4-chloro-5-((2'-cyano-3'-(3-(3-hydroxypyrrolidin-1-yl)propoxy)-2-methyl-[1,1'-biphenyl]-3-yl)methoxy)-2-formylphenoxy)methyl)nicotinonitrile and (S)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (s, 1H), 9.00 (s, 1H), 8.50 (s, 1H), 7.70 (t, J=8.1 Hz, 1H), 7.59-7.54 (m, 2H), 7.34 (t, J=7.5 Hz, 1H), 7.27 (d, J=8.8 Hz, 1H), 7.22 (d, J=7.7 Hz, 1H), 7.12 (s, 1H), 6.97 (d, J=7.7 Hz, 1H), 5.38-5.28 (m, 4H), 4.23 (d, J=5.5 Hz, 3H), 3.98 (br. s., 2H), 3.66-3.50 (m, 2H), 2.77-2.69 (m, 1H), 2.66-2.55 (m, 3H), 2.50-2.43 (m, 1H), 2.39-2.33 (m, 1H), 2.17-2.09 (m, 3H), 2.03-1.91 (m, 3H), 1.55 (br, s, 1H), 1.24 (s, 3H).

Two analytical LC/MS injections were used to determine the final purity.

Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm

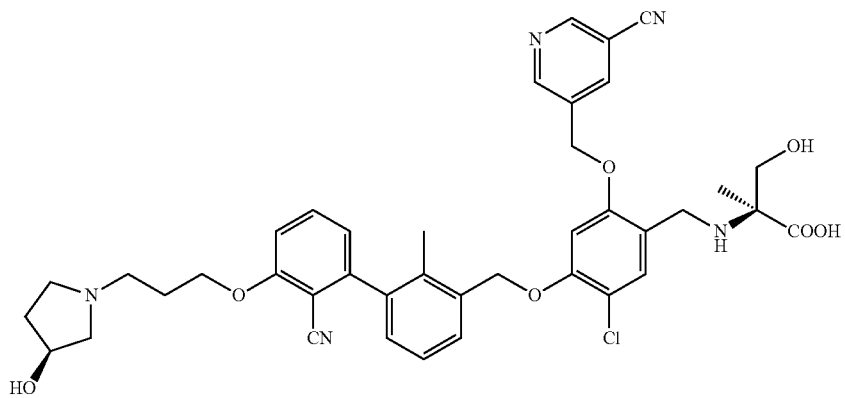

(S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid (16.1 mg, 64%)

LCMS (Injection 1 conditions) Rt=1.557 min, ESI m/z 740 (M+H), 738 (M−H)

LCMS (Injection 2 conditions) Rt=1.344 min, ESI m/z 740 (M+H), 738 (M−H)

Example 3009: (S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxypropanoic Acid

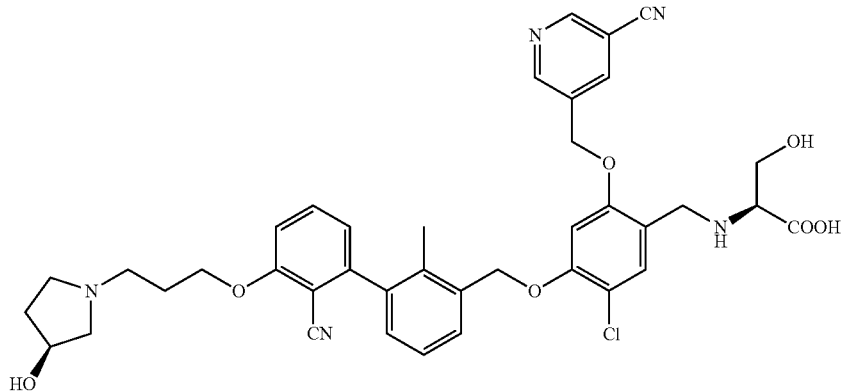 [SMILES: Cc1c(COc2cc(OCc3cncc(C#N)c3)c(CN[C@@H](CO)C(=O)O)cc2Cl)cccc1-c1cccc(OCCCN2CC[C@H](O)C2)c1C#N]

(S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxypropanoic acid (4.7 mg, 27%) was obtained from (R)-5-((4-chloro-5-((2'-cyano-3'-(3-(3-hydroxypyrrolidin-1-yl)propoxy)-2-methyl-[1,1'-biphenyl]-3-yl)methoxy)-2-formylphenoxy)methyl)nicotinonitrile and (S)-2-amino-3-hydroxypropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (d, J=4.8 Hz, 2H), 8.52 (s, 1H), 7.70 (t, J=7.9 Hz, 1H), 7.58 (d, J=7.3 Hz, 1H), 7.51 (s, 1H), 7.34 (t, J=7.5 Hz, 1H), 7.28 (d, J=8.8 Hz, 1H), 7.23 (d, J=7.3 Hz, 1H), 7.14 (s, 1H), 6.99 (d, J=7.7 Hz, 1H), 5.39-5.26 (m, 4H), 4.28-4.16 (m, 3H), 4.01-3.92 (m, 2H), 3.66 (dd, J=10.8, 5.0 Hz, 1H), 3.60 (dd, J=10.8, 5.7 Hz, 1H), 3.11 (t, J=5.5 Hz, 1H), 2.76-2.69 (m, 1H), 2.64-2.55 (m, 3H), 2.46 (d, J=7.0 Hz, 1H), 2.35 (d, J=6.6 Hz, 1H), 2.16 (s, 3H), 2.01-1.91 (m, 3H), 1.55 (d, J=4.0 Hz, 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.599 min, ESI m/z 726 (M+H), 724 (M−H)

LCMS (Injection 2 conditions) Rt=1.296 min, ESI m/z 726 (M+H), 724 (M−H)

Example 3010: (R)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic Acid

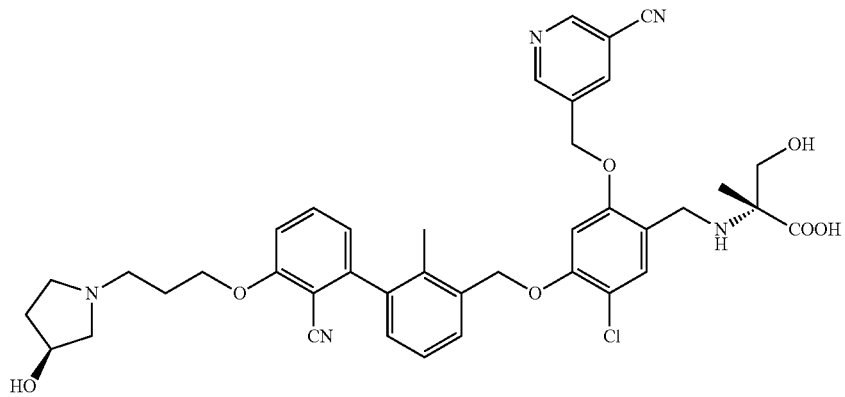 [SMILES: Cc1c(COc2cc(OCc3cncc(C#N)c3)c(CN[C@](C)(CO)C(=O)O)cc2Cl)cccc1-c1cccc(OCCCN2CC[C@H](O)C2)c1C#N]

(R)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid (3.4 mg 20%) was obtained from (R)-5-((4-chloro-5-((2'-cyano-3'-(3-(3-hydroxypyrrolidin-1-yl)propoxy)-2-methyl-[1,1'-biphenyl]-3-yl)methoxy)-2-formylphenoxy)methyl)nicotinonitrile and (R)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.02 (d, J=11.4 Hz, 2H), 8.50 (br. s., 1H), 7.76-7.70 (m, 1H), 7.61-7.54 (m, 2H), 7.34 (t, J=7.3 Hz, 1H), 7.28 (d, J=8.4 Hz, 1H), 7.21 (d, J=7.3 Hz, 1H), 7.13 (d, J=9.2 Hz, 1H), 7.01 (d, J=7.3 Hz, 1H), 5.39-5.28 (m, 4H), 4.43 (br. s., 1H), 4.27 (d, J=6.2 Hz, 2H), 4.08 (br. s., 2H), 3.72 (d, J=11.7 Hz, 1H), 3.63 (d, J=11.7 Hz, 2H), 3.39-3.07 (m, 5H), 2.27-2.00 (m, 3H), 2.15 (s, 3H), 1.88 (br. s., 1H), 1.30 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.677 min, ESI m/z 740 (M+H), 738 (M−H)

LCMS (Injection 2 conditions) Rt=1.344 min, ESI m/z 740 (M+H), 738 (M−H)

Intermediate: 1-bromo-3-(3-chloropropoxy)-2-(trifluoromethyl)benzene

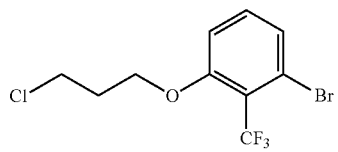 [SMILES: FC(F)(F)c1c(Br)cccc1OCCCCl]

1-Bromo-3-(3-chloropropoxy)-2-(trifluoromethyl)benzene (560 mg, 85%) was obtained from 3-bromo-2-(trifluoromethyl)phenol and 1-bromo-3-chloropropane using the procedure described for 1-bromo-3-(3-chloropropoxy)benzene. $^1$H NMR (400 MHz, CHLOROFORM-d) □ 7.37-7.26 (m, 2H), 7.00 (d, J=8.0 Hz, 1H), 4.21 (t, J=5.52 Hz, 2H), 3.79 (t, J=6.3 Hz, 2H), 2.29 (quin, J=5.9 Hz, 2H).

Intermediate: (R)-1-(3-(3-bromo-2-(trifluoromethyl)phenoxy)propyl)pyrrolidin-3-ol

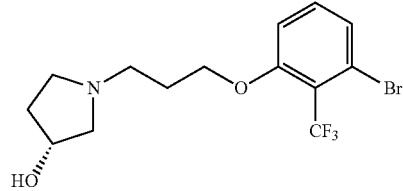 [SMILES: O[C@@H]1CCN(CCCOc2cccc(Br)c2C(F)(F)F)C1]

A stirred mixture of 1-bromo-3-(3-chloropropoxy)-2-(trifluoromethyl)benzene (560 mg, 1.764 mmol), (R)-pyrrolidin-3-ol, HCl salt (327 mg, 2.65 mmol) and $K_2CO_3$ (366 mg, 2.65 mmol), and sodium iodide (264 mg, 1.764 mmol) in DMF (10 mL) was heated at 80° C. for 16 hr. The solvent was removed. The residue was partitioned between EtOAc and water. The aqueous phase was extracted once with ethyl acetate. The organic extracts were combined and washed with brine and then dried over sodium sulfate. The drying agent was removed by filtration and the solvent removed in vacuo. The resulting crude product (640 mg, 99%) was used for the next step without further purification. $^1$H NMR (400 MHz, METHANOL-$d_4$) δ 7.49-7.32 (m, 2H), 7.27-7.16 (m, 1H), 4.39 (br. s., 1H), 4.25-4.11 (m, 2H), 3.41-3.30 (m, 2H), 2.96-2.48 (m, 4H), 2.25-2.11 (m, 1H), 2.04 (br. s., 2H), 1.76 (br. s., 1H).

(R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile

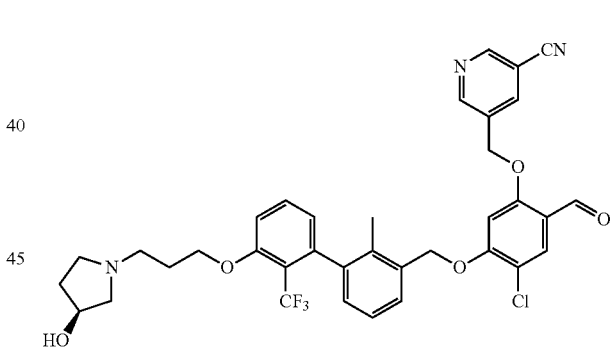

(R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile (170 mg, 65%) was obtained from 5-((4-chloro-2-formyl-5-((2-methyl-3-(4,4,5,5-tetramethyl-1,3,2-dioxaborolan-2-yl)benzyl)oxy)phenoxy)methyl)nicotinonitrile and (R)-1-(3-(3-bromo-2-(trifluoromethyl)phenoxy)propyl)pyrrolidin-3-ol using the procedure described for for 5-((4-chloro-5-((3'-(3-chloropropoxy)-2-methyl-[1,1'-biphenyl]-3-yl)methoxy)-2-formylphenoxy)methyl)nicotinonitrile. $^1$H NMR (400 MHz, CHLOROFORM-d) δ 10.29 (s, 1H), 8.92 (d, J=2.0 Hz, 1H), 8.90 (d, J=2.0 Hz, 1H), 8.08 (s, 1H), 7.95 (s, 1H), 7.50 (t, J=7.8 Hz, 1H), 7.40 (d, J=7.8 Hz, 1H), 7.27-7.23 (m, 1H), 7.15 (d, J=7.3 Hz, 1H), 7.08 (d, J=8.3 Hz, 1H), 6.98 (d, J=7.5 Hz, 1H), 6.52 (s, 1H), 5.40-5.26 (m, 2H), 5.18-5.05 (m, 2H), 4.44-4.35 (m, 1H), 4.27-4.17 (m, 1H), 4.16-4.08 (m, 1H), 3.06-2.94 (m, 1H), 2.86-2.74 (m, 2H), 2.71 (t, J=7.2 Hz, 1H), 2.17-1.98 (m, 2H), 2.12 (s, 3H), 1.91-1.67 (m, 4H).

Example 3011: (S)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic Acid

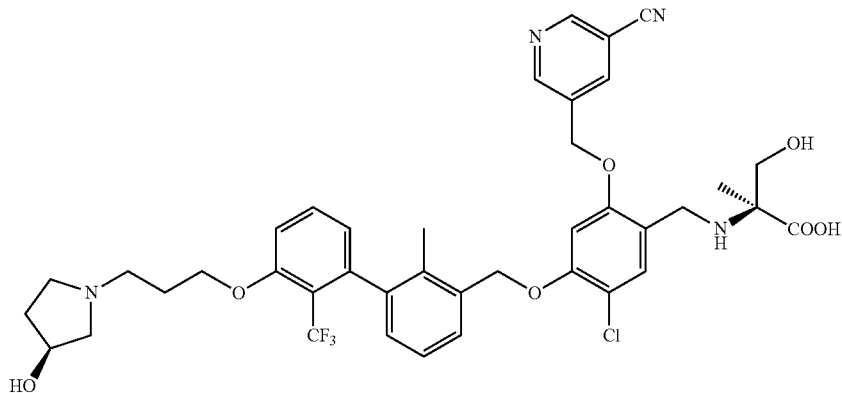 [SMILES: Cc1c(COc2cc(OCc3cncc(C#N)c3)c(CN[C@@](C)(CO)C(=O)O)cc2Cl)cccc1-c1cccc(OCCCN2CC[C@H](O)C2)c1C(F)(F)F]

(S)-2-((5-Chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic acid (9 mg, 20%) was obtained from (R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile and (S)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (d, J=2.9 Hz, 2H), 8.50 (s, 1H), 7.65 (t, J=7.9 Hz, 1H), 7.59 (s, 1H), 7.49 (d, J=7.7 Hz, 1H), 7.33-7.23 (m, 2H), 7.15 (s, 1H), 7.07 (d, J=7.3 Hz, 1H), 6.79 (d, J=7.7 Hz, 1H), 5.40-5.27 (m, 4H), 4.45 (br. s., 1H), 4.23 (br. s., 2H), 4.19-4.08 (m, 2H), 3.83-3.76 (m, 1H), 3.71-3.62 (m, 2H), 3.29 (br. s., 4H), 3.15 (br, s, 1H), 2.17 (br. s., 2H), 2.06-1.81 (m, 2H), 2.04 (s, 3H), 1.35 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.440 min, ESI m/z 783 (M+H), 781 (M−H)

LCMS (Injection 2 conditions) Rt=1.448 min, ESI m/z 783 (M+H), 781 (M−H)

Example 3012: (S)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxypropanoic Acid

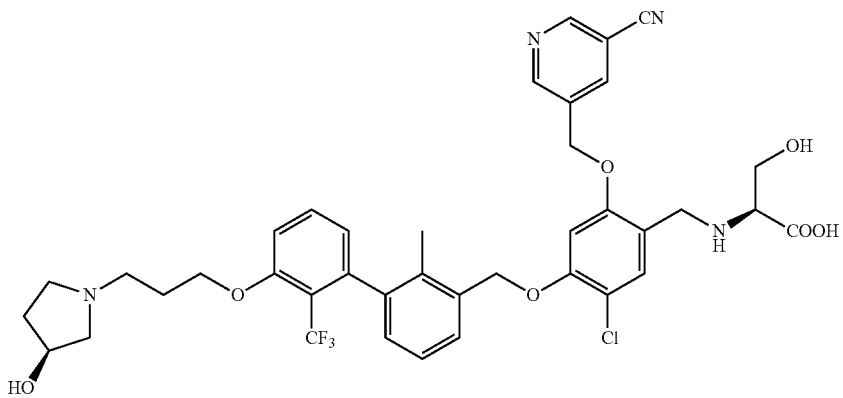

(S)-2-((5-Chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxypropanoic acid (2.9 mg, 6%) was obtained from (R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile and (S)-2-amino-3-hydroxypropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (br. s., 2H), 8.53 (s, 1H), 7.61 (t, J=8.3 Hz, 1H), 7.53-7.47 (m, 2H), 7.32-7.21 (m, 2H), 7.14 (s, 1H), 7.08 (d, J=7.7 Hz, 1H), 6.76 (d, J=7.7 Hz, 1H), 5.39-5.22 (m, 4H), 4.18 (d, J=5.5 Hz, 3H), 4.01-3.91 (m, 2H), 3.72-3.53 (m, 3H), 3.14-3.08 (m, 1H), 2.73-2.68 (m, 1H), 2.58 (dt, J=12.9, 6.6 Hz, 3H), 2.44 (d, J=7.3 Hz, 1H), 2.34 (d, J=9.5 Hz, 1H), 2.04 (s, 3H), 1.98 (dd, J=13.0, 7.2 Hz, 1H), 1.93-1.84 (m, 1H), 1.55 (br, s, 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.787 min, ESI m/z 769 (M+H), 767 (M−H)

LCMS (Injection 2 conditions) Rt=1.398 min, ESI m/z 769 (M+H)

Example 3013: (R)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic Acid

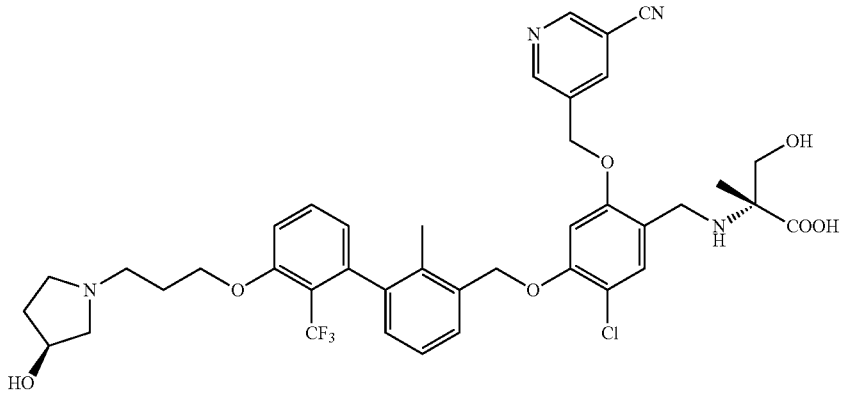

(R)-2-((5-Chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic acid (6.6 mg, 14%) was obtained from (R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile and (R)-2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.02 (d, J=6.6 Hz, 2H), 8.52 (s, 1H), 7.61 (t, J=7.9 Hz, 1H), 7.54 (s, 1H), 7.48 (d, J=7.3 Hz, 1H), 7.32-7.22 (m, 2H), 7.12 (s, 1H), 7.08 (d, J=7.3 Hz, 1H), 6.75 (d, J=7.7 Hz, 1H), 5.38-5.23 (m, 4H), 4.23-4.12 (m, 4H), 3.95-3.90 (m, 2H), 3.63-3.47 (m, 2H), 2.70 (dd, J=9.4, 6.4 Hz, 1H), 2.63-2.55 (m, 3H), 2.43 (d, J=7.0 Hz, 1H), 2.33 (d, J=6.6 Hz, 1H), 2.04 (s, 3H), 1.98 (dd, J=13.2, 6.6 Hz, 1H), 1.92-1.83 (m, 1H), 1.54 (br, s, 1H), 1.22 (s, 3H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.404 min, ESI m/z 783 (M+H), 781 (M−H)

LCMS (Injection 2 conditions) Rt=1.422 min, ESI m/z 783 (M+H)

Example 3014: (S)-1-(5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)piperidine-2-carboxylic Acid

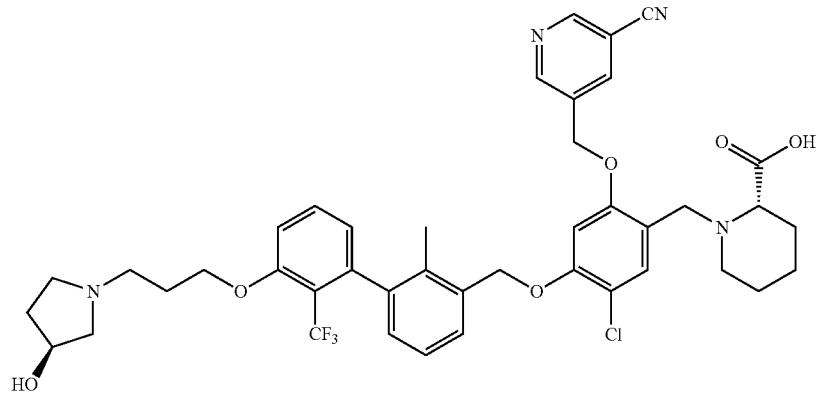 [SMILES: Cc1c(COc2cc(OCc3cncc(C#N)c3)c(CN3CCCC[C@H]3C(=O)O)cc2Cl)cccc1-c1cccc(OCCCN2CC[C@H](O)C2)c1C(F)(F)F]

(S)-1-(5-Chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)piperidine-2-carboxylic acid (17.3 mg, 35%) was obtained from (R)-5-((4-chloro-2-formyl-5-((3'-(3-(3-hydroxypyrrolidin-1-yl)propoxy)-2-methyl-2'-(trifluoromethyl)-[1,1'-biphenyl]-3-yl)methoxy)phenoxy)methyl)nicotinonitrile and (S)-piperidine-2-carboxylic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.01 (d, J=8.8 Hz, 2H), 8.46 (br. s., 1H), 7.65-7.57 (m, 1H), 7.49 (d, J=7.7 Hz, 1H), 7.43 (br. s., 1H), 7.32-7.22 (m, 2H), 7.14-7.05 (m, 2H), 6.75 (d, J=8.1 Hz, 1H), 5.32 (br. s., 2H), 5.29-5.20 (m, 2H), 4.23-4.11 (m, 4H), 3.80 (d, J=12.5 Hz, 1H), 3.62 (d, J=14.7 Hz, 1H), 3.12 (br. s., 1H), 2.89 (br. s., 1H), 2.70 (br. s., 1H), 2.56 (br. s., 3H), 2.42 (br. s., 1H), 2.39-2.24 (m, 3H), 2.13 (s, 1H), 2.03 (br. s., 3H), 1.99 (d, J=13.9 Hz, 1H), 1.84-1.65 (m, 2H), 1.49 (br. s., 3H), 1.36 (br. s., 1H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.743 min, ESI m/z 793 (M+H), 791 (M−H)

LCMS (Injection 2 conditions) Rt=1.494 min, ESI m/z 793 (M+H), 791 (M−H)

Intermediate: (R)-1-(3-(3-bromo-2-methylphenoxy)propyl)pyrrolidin-3-ol

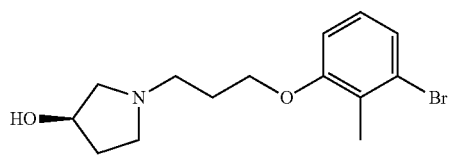 [SMILES: Cc1c(Br)cccc1OCCCN1CC[C@@H](O)C1]

To a solution of 3-bromo-2-methylphenol (2 g, 10.69 mmol, 1 eq) in DMF (30 mL) was added 1-bromo-3-chloropropane (1.052 mL, 10.69 mmol, 1 eq) and K$_2$CO$_3$ (1.773 g, 12.83 mmol, 1.2 eq.). The reaction mixture was stirred at 50° C. for 16 hr. The reaction mixture was cooled to room temperature and diluted with EtOAc. The organics were washed with sat. NaHCO₃, water, brine, and dried over anhydrous Na₂SO₄, filtered and then concentrated. The crude product was purified by chromatography on silica gel (220 g Isco cartridge) employing 20 column volumes of 0-20% EtOAc/hexane to give 2.16 g (40%) of a mixture 1-bromo-3-(3-chloropropoxy)-2-methylbenzene and 1-bromo-3-(3-bromopropoxy)-2-methylbenzene as a colorless oil. ¹H NMR (400 MHz, CDCl₃) δ 7.20-7.15 (m, 1H), 7.01 (m, 1H), 6.80 (m, 1H), 4.12 (m, 2H), 3.77 (t, J=6.2 Hz, 1.70H), 3.63 (t, J=6.2 Hz, 0.30H), 2.36-2.23 (m, 5H).

To a sealed tube was added (R)-3-hydroxypyrrolidine HCl salt (1.153 g, 9.33 mmol, 1.5 eq), DMF (20 mL), the mixture 1-bromo-3-(3-chloropropoxy)-2-methylbenzene/1-bromo-3-(3-bromopropoxy)-2-methylbenzene (2.05 g, 6.22 mmol) prepared above, sodium iodide (1.399 g, 9.33 mmol, 1.5 eq), and K₂CO₃ (2.150 g, 15.56 mmol, 2.5 eq). The vessel was sealed and the mixture stirred overnight at 50° C. The mixture was cooled to room temperature and evaporated to give a paste. The mixture was taken up in 30 mL of DCM, washed with 10 mL water thrice, and then brine. The organic layer was dried over anhydrous Na₂SO₄, filtered and concentrated. The resulting residue was diluted with 10 mL of methanol and then pushed through a Waters 5 g MCX cartridge. The cartridge was flushed with 20 mL of methanol and the product eluted with 20 mL of 2M ammonia in methanol. Evaporation of the 2M ammonia solution gave 1.15 g (59%) of (R)-1-(3-(3-bromo-2-methylphenoxy)propyl)pyrrolidin-3-ol as a light yellow powder. ¹H NMR (500 MHz, DMSO-d₆) δ 7.22-7.17 (m, 1H), 7.12 (t, J=8.1 Hz, 1H), 6.99 (d, J=8.1 Hz, 1H), 5.51 (d, J=3.8 Hz, 1H), 4.46-4.37 (m, 1H), 4.08 (t, J=6.0 Hz, 2H), 3.32-3.24 (m, 5H), 3.17 (d, J=4.4 Hz, 1H), 2.26 (s, 3H), 2.22-2.13 (m, 3H), 1.90 (m, 1H). LCMS Rt=1.328 min., m/z 316.2 (M+H). The LC/MS data was obtained on a Shimadzu analytical LC/Micromass Platform LC (ESI+) at 220 nm using the following set of conditions: Phenomenex Luna 3 □m C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Intermediate: (R)-5-((4-chloro-2-formyl-5-((3'-(3-(3-hydroxypyrrolidin-1-yl)propoxy)-2'-methyl-[1,1'-biphenyl]-3-yl)methoxy)phenoxy)methyl)nicotinonitrile To a sealed tube was added tetrahydrofuran (5 mL), water (1 mL), potassium phosphate tribasic (83 mg, 0.391 mmol, 3 eq), 5-((4-chloro-2-formyl-5-((3-(4,4,5,5-tetramethyl-1,3,2-dioxaborolan-2-yl)benzyl)oxy)phenoxy)methyl)nicotinonitrile (82.2 mg, 0.130 mmol), (R)-1-(3-(3-bromo-2-methylphenoxy)propyl)pyrrolidin-3-ol (57.3 mg, 0.182 mmol, 1.4 eq), and 2nd generation XPhos precatalyst (3.08 mg, 3.91 μmol, 0.03 eq). The vessel was sealed, the mixture de-gassed/flushed with nitrogen for 5 minutes and then stirred at 80° C. for 16 hours. The reaction mixture was cooled, the resulting crude product diluted with EtOAC and water. The organic layer was washed with brine, dried over anhydrous magnesium sulfate, filtered through diatomaceous earth (Celite®), and evaporated to give a yellow oil. The resulting residue was taken up in 15 mL of methanol and pushed through a Waters MCX cartridge (5 g, 35 cc). The cartridge was flushed with 50 mL of methanol and then the product eluted with 50 mL of 2M ammonia in methanol to give 80.8 mg (73% yield) of (R)-5-((4-chloro-2-formyl-5-((3'-(3-(3-hydroxypyrrolidin-1-yl)propoxy)-2'-methyl-[1,1'-biphenyl]-3-yl)methoxy)phenoxy)methyl) nicotinonitrile as a yellow solid. ¹H NMR (400 MHz, THF-d₈) δ 10.28 (s, 1H), 8.93-8.89 (m, 2H), 8.29 (s, 1H), 7.81 (s, 1H), 7.49-7.40 (m, 1H), 7.33-7.22 (m, 1H), 7.18-7.11 (m, 1H), 7.08 (s, 1H), 7.02-6.95 (m, 2H), 6.88 (m, 1H), 6.79 (d, J=7.5 Hz, 1H), 5.36 (s, 2H), 5.32 (s, 2H), 4.27-4.16 (m, 1H), 4.13-4.00 (m, 2H), 2.74-2.57 (m, 2H), 2.48-2.36 (m, 2H), 2.19 (m, 2H), 2.10 (s, 3H), 2.08-1.88 (m, 3H), 1.61 (m, 1H). LCMS Rt=2.147 min, m/z 612.4 (M+H), 615.4 (M+H). The LC/MS data was obtained on a Shimadzu analytical LC/Micromass Platform LC (ESI+) at 220 nm using the following set of conditions: Phenomenex Luna 3 □m C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

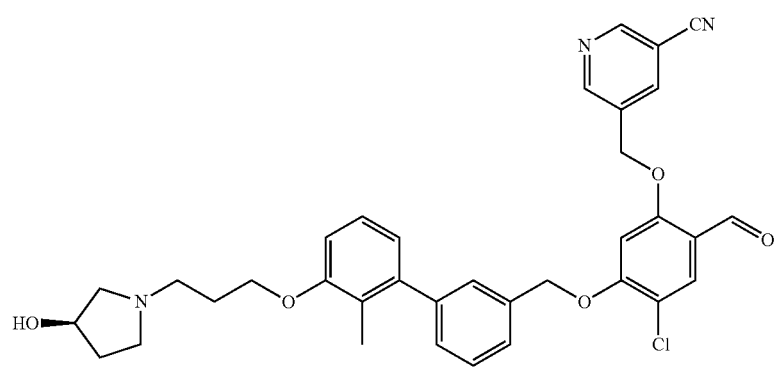 [SMILES: Cc1c(OCCCN2CC[C@@H](O)C2)cccc1-c1cccc(COc2cc(OCc3cncc(C#N)c3)c(C=O)cc2Cl)c1]

Example 3015: (R)-2-((5-chloro-2-((5-cyanopyridin-3-yl)methoxy)-4-((3'-(3-((R)-3-hydroxypyrrolidin-1-yl)propoxy)-2'-methyl-[1,1'-biphenyl]-3-yl)methoxy)benzyl)amino)-3-hydroxypropanoic Acid

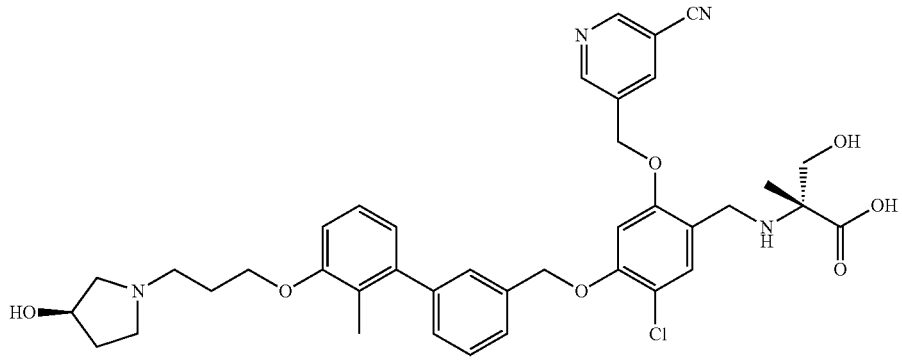 [SMILES: Cc1c(OCCCN2CC[C@@H](O)C2)cccc1-c1cccc(COc2cc(OCc3cncc(C#N)c3)c(CN[C@](C)(CO)C(=O)O)cc2Cl)c1]

To a small vial was added (R)-5-((4-chloro-2-formyl-5-((3'-(3-(3-hydroxypyrrolidin-1-yl)propoxy)-2'-methyl-[1,1'-biphenyl]-3-yl)methoxy)phenoxy)methyl)nicotinonitrile (49.4 mg, 0.058 mmol), DMF (1.4 mL), acetic acid (0.140 mL), 2-methyl-D-serine (17.30 mg, 0.145 mmol, 2.5 eq), and borane-2-picoline complex (7.46 mg, 0.070 mmol, 1.2 eq). The vial was sealed and the mixture shaken overnight at room temperature. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-60% B over 30 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 acetonitrile:water with 0.1% trifluoroacetic acid and mobile phase B was 95:5 acetonitrile:water with 0.1% trifluoroacetic acid at a gradient of 20-60% B over 15 minutes with a 5-minute hold at 100% B at a flow rate of 20 mL/minute. Fractions containing the desired product were combined and dried via centrifugal evaporation. The yield of the product was 6.0 mg (13%), and its estimated purity by LCMS analysis was 100%. $^1$H NMR (500 MHz, DMSO-$d_6$) δ 8.98 (br. s., 2H), 8.44 (s, 1H), 7.58 (s, 1H), 7.51-7.40 (m, 2H), 7.29 (s, 1H), 7.26-7.16 (m, 2H), 7.08 (s, 1H), 6.95 (d, J=8.1 Hz, 1H), 6.81 (d, J=7.3 Hz, 1H), 5.40 (s, 2H), 5.28 (s, 2H), 4.43 (m., 1H), 4.05 (m, 4H), 3.76 (m, 1H), 3.70 (m, 1H), 3.60 (m, 1H), 3.39 (m, 1H), 3.13 (m, 1H), 2.93 (m, 3H), 2.15 (m, 3H), 1.90 (s, 3H), 1.34-1.21 (m, 4H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.416 min; ESI-MS (+) m/z=716.0 (M+H)

Analysis condition 2: Retention time=1.392 min; ESI-MS (+) m/z=716.0 (M+H)

Example 3016: (R)-2-((5-chloro-2-((5-cyanopyridin-3-yl)methoxy)-4-((3'-(3-((R)-3-hydroxypyrrolidin-1-yl)propoxy)-2'-methyl-[1,1'-biphenyl]-3-yl)methoxy)benzyl)amino)-3-hydroxypropanoic Acid

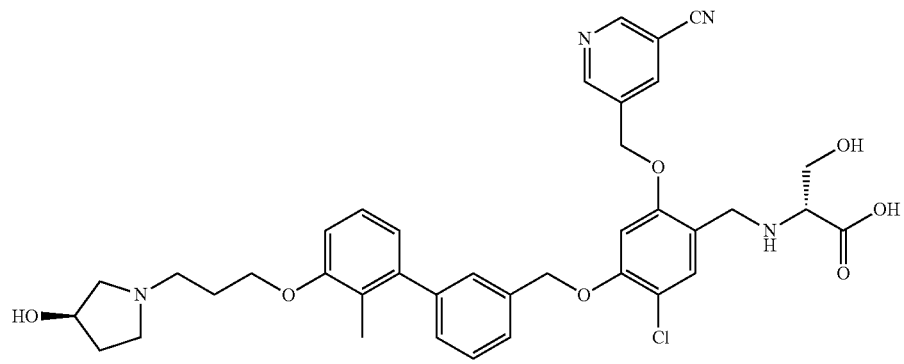 [SMILES: Cc1c(OCCCN2CC[C@@H](O)C2)cccc1-c1cccc(COc2cc(OCc3cncc(C#N)c3)c(CN[C@H](CO)C(=O)O)cc2Cl)c1]

(R)-2-((5-Chloro-2-((5-cyanopyridin-3-yl)methoxy)-4-((3'-(3-((R)-3-hydroxypyrrolidin-1-yl)propoxy)-2'-methyl-[1,1'-biphenyl]-3-yl)methoxy)benzyl)amino)-3-hydroxypropanoic acid, was synthesized in an analogous fashion as Example 3015. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-60% B over 30 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 acetonitrile:water with 0.1% trifluoroacetic acid and mobile phase B was 95:5 acetonitrile:water with 0.1% trifluoroacetic acid at a gradient of 10-50% B over 25 minutes with a 5-minute hold at 100% B at a flow rate of 20 mL/minute. Fractions containing the desired product were combined and dried via centrifugal evaporation. The yield of the product was 7.1 mg (15.0%), and its estimated purity by LCMS analysis was 100%. $^1$H NMR (500 MHz, DMSO-d$_6$) δ 9.00 (s, 1H), 8.97 (s, 1H), 8.43 (s, 1H), 7.58 (s, 1H), 7.51-7.41 (m, 2H), 7.36 (s, 1H), 7.30-7.19 (m, 2H), 7.09 (s, 1H), 6.97 (d, J=8.4 Hz, 1H), 6.82 (d, J=7.7 Hz, 1H), 5.36 (s, 2H), 5.30 (m, 2H), 4.44 (m, 1H), 4.15 (m, 2H), 4.08 (t, J=5.7 Hz, 2H), 3.87-3.74 (m, 2H), 3.62 (m, 1H), 3.34 (m, 3H), 3.29-3.21 (m, 1H), 2.83 (s, 2H), 2.16 (m, 3H), 1.99 (s, 3H), 1.91 (m, 1H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.393 min; ESI-MS (+) m/z=702.0 (M+H)

Analysis condition 2: Retention time=1.398 min; ESI-MS (+) m/z=702.0 (M+H)

Intermediate: 5-chloro-4-((2-chloro-3-(4,4,5,5-tetramethyl-1,3,2-dioxaborolan-2-yl)benzyl)oxy)-2-hydroxybenzaldehyde

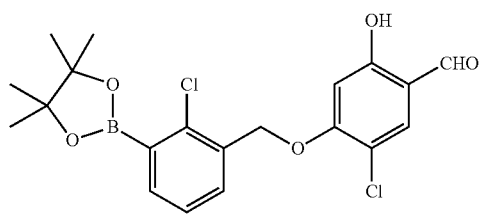 [SMILES: CC1(C)OB(c2cccc(COc3cc(O)c(C=O)cc3Cl)c2Cl)OC1(C)C]

A solution of diisopropyl azodicarboxylate (219 mg, 1.084 mmol, 1.2 eq) in tetrahydrofuran (2 mL) was added dropwise to a solution of (2-chloro-3-(4,4,5,5-tetramethyl-1,3,2-dioxaborolan-2-yl)phenyl) methanol (242 mg, 0.903 mmol, 1 eq), 5-chloro-2,4-dihydroxybenzaldehyde (187 mg, 1.084 mmol, 1.2 eq), and triphenylphosphine (284 mg, 1.084 mmol, 1.2 eq) in tetrahydrofuran (6 mL) at 0° C. The resulting yellow solution was allowed to warm to room temperature and stirred overnight under nitrogen. The solvent was removed, and the residue was purified by silica gel column chromatography (Isco 80 g cartridge) using 20 column volumes of 0 to 25% EtOAc/Hexane to give 140 mg (33%) of 5-chloro-4-((2-chloro-3-(4,4,5,5-tetramethyl-1,3,2-dioxaborolan-2-yl)benzyl)oxy)-2-hydroxybenzaldehyde as a white solid. LCMS Rt=2.187 min., m/z 423.2 (M+H), 426.2 (M+H). The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Intermediate: 5-((4-chloro-5-((2-chloro-3-(4,4,5,5-tetramethyl-1,3,2-dioxaborolan-2-yl)benzyl)oxy)-2-formylphenoxy)methyl)nicotinonitrile

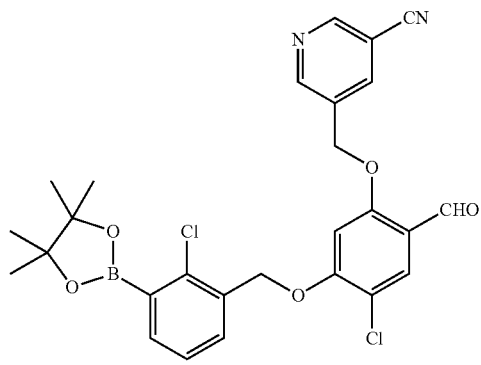 [SMILES: CC1(C)OB(c2cccc(COc3cc(OCc4cncc(C#N)c4)c(C=O)cc3Cl)c2Cl)OC1(C)C]

To 5-chloro-4-((2-chloro-3-(4,4,5,5-tetramethyl-1,3,2-dioxaborolan-2-yl)benzyl)oxy)-2-hydroxybenzaldehyde (140 mg, 0.331 mmol), in DMF (5 mL), was added cesium carbonate (156 mg, 0.480 mmol, 1.45 eq), and 5-(chloromethyl)nicotinonitrile (65.6 mg, 0.430 mmol, 1.3 eq). The flask was sealed and the mixture stirred overnight at room temperature. The solvent was removed, the residue diluted with dichloromethane and water. The organic extract was washed with brine, dried over anhydrous Na$_2$SO$_4$, filtered and concentrated. The resulting residue was purified by silica gel chromatography (Isco 40 g cartridge) using 20 column volumes of 0 to 60% EtOAc/Hexanes to give 53.2 mg (30%) of 5-((4-chloro-5-((2-chloro-3-(4,4,5,5-tetramethyl-1,3,2-dioxaborolan-2-yl)benzyl)oxy)-2-formylphenoxy)methyl)nicotinonitrile as a white solid. $^1$H NMR (400 MHz, THF-d$_8$) δ 10.29 (s, 1H), 8.94 (d, J=2.0 Hz, 1H), 8.89 (d, J=2.0 Hz, 1H), 8.30 (t, J=2.0 Hz, 1H), 7.82 (s, 1H), 7.72 (m, 2H), 7.33 (t, J=7.5 Hz, 1H), 6.96 (s, 1H), 5.41 (s, 2H), 5.36 (s, 2H), 1.42-1.30 (m, 12H). LCMS Rt=2.212 min, m/z 539.3 (M+H), 542.2 (M+H). The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/

0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Intermediate: (R)-5-((4-chloro-5-((2-chloro-3'-(3-(3-hydroxypyrrolidin-1-yl)propoxy)-2'-methyl-[1,1'-biphenyl]-3-yl)methoxy)-2-formylphenoxy)methyl) nicotinonitrile

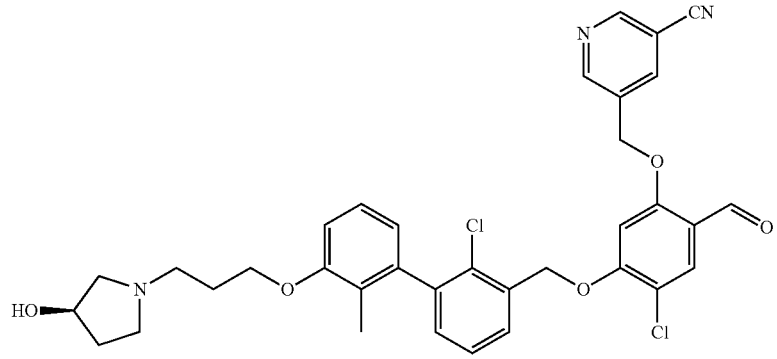 [SMILES: Cc1c(OCCCN2CC[C@@H](O)C2)cccc1-c1cccc(COc2cc(OCc3cncc(C#N)c3)c(C=O)cc2Cl)c1Cl]

To a sealed tube was added tetrahydrofuran (3 mL), water (600 µL), potassium phosphate tribasic (62.8 mg, 0.296 mmol, 3 eq), 5-((4-chloro-5-((2-chloro-3-(4,4,5,5-tetramethyl-1,3,2-dioxaborolan-2-yl)benzyl)oxy)-2-formylphenoxy)methyl)nicotinonitrile (53.2 mg, 0.099 mmol, 1 eq), (R)-1-(3-(3-bromo-2-methylphenoxy)propyl)pyrrolidin-3-ol (43.4 mg, 0.138 mmol, 1.4 eq), and 2nd generation XPhos precatalyst (2.33 mg, 2.96 µmol, 0.03 eq). The vessel was sealed, the mixture de-gassed/flushed with nitrogen for 5 minutes and then stirred at 80° C. for 16 hours. The reaction mixture was cooled, the resulting crude product diluted with EtOAC and water, and extracted. The organic extract was washed with brine, dried over anhydrous magnesium sulfate, filtered through diatomaceous earth (Celite®), and evaporated to give a yellow oil. The resulting residue was taken up in 15 mL of methanol and pushed through a Waters MCX cartridge (5 g, 35 cc). The cartridge was flushed with 50 mL of methanol and then the product eluted with 50 mL of 2M ammonia in methanol to give 46.9 mg (74% yield) of (R)-5-((4-chloro-5-((2-chloro-3'-(3-(3-hydroxypyrrolidin-1-yl)propoxy)-2'-methyl-[1,1'-biphenyl]-3-yl)methoxy)-2-formylphenoxy)methyl)nicotinonitrile as a yellow solid. $^1$H NMR (400 MHz, THF-$d_8$) δ 10.30 (s, 1H), 8.93-8.88 (m, 2H), 8.27 (s, 1H), 7.76 (m, 1H), 7.33-7.22 (m, 1H), 7.18-7.11 (m, 1H), 7.08 (s, 1H), 7.02-6.95 (m, 2H), 6.88 (m, 1H), 6.70 (d, J=7.5 Hz, 1H), 5.37 (s, 2H), 5.28 (s, 2H), 4.20 (m, 1H), 4.05 (m, 2H), 2.74-2.57 (m, 2H), 2.40 (m, 2H), 2.28 (s, 3H), 2.19 (m, 2H), 2.02-1.90 (m, 3H), 1.60 (m, 1H). LCMS Rt=1.648 min, m/z 646.4 (M+H), 649.3 (M+H). The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Example 3017: (R)-2-((5-chloro-4-((2-chloro-3'-(3-((R)-3-hydroxypyrrolidin-1-yl)propoxy)-2'-methyl-[1,1'-biphenyl]-3-yl)methoxy)-2-((5-cyanopyridin-3-yl)methoxy)benzyl)amino)-3-hydroxy-2-methylpropanoic Acid

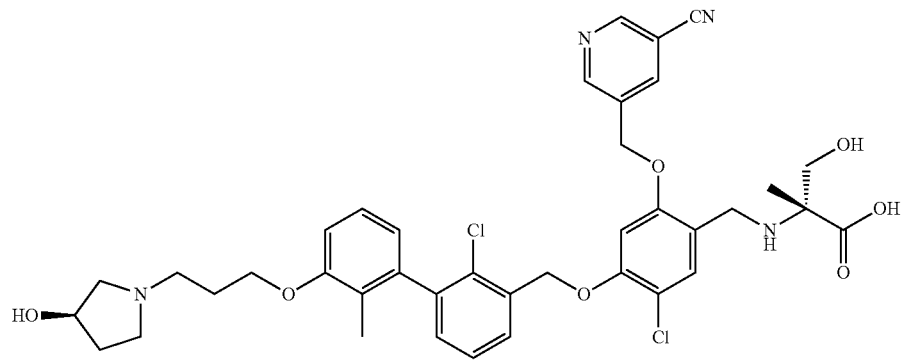 [SMILES: Cc1c(OCCCN2CC[C@@H](O)C2)cccc1-c1cccc(COc2cc(OCc3cncc(C#N)c3)c(CN[C@](C)(CO)C(=O)O)cc2Cl)c1Cl]

To a small vial was added (R)-5-((4-chloro-5-((2-chloro-3'-(3-(3-hydroxypyrrolidin-1-yl)propoxy)-2'-methyl-[1,1'-biphenyl]-3-yl)methoxy)-2-formylphenoxy)methyl)nicotinonitrile (46.9 mg, 0.044 mmol, 1 eq), DMF (1.4 mL), acetic acid (0.140 mL), 2-methyl-D-serine (12.96 mg, 0.109 mmol, 2.5 eq), and borane-2-picoline complex (5.59 mg, 0.052 mmol, 1.2 eq). The vial was sealed and the mixture shaken overnight at room temperature. The crude material was purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 50-90% B over 20 minutes with a 5-minute hold at 100% B at a flow rate of 20 mL/minute. Fractions containing the desired product were combined and dried via centrifugal evaporation. The yield of the product was 3 mg (8%), and its estimated purity by LCMS analysis was 89%. $^1$H NMR (500 MHz, DMSO-$d_6$) δ 9.00 (m, 2H), 8.49 (s, 1H), 7.67 (m, 1H), 7.54 (s, 1H), 7.46 (m, 1H), 7.28 (m, 1H), 7.22 (m, 1H), 7.09 (s, 1H), 6.99 (m, 1H), 6.72 (m, 1H), 5.35 (m, 4H), 4.18 (m, 1H), 4.05 (m, 2H), 3.90 (m, 3H), 3.56 (m, 2H), 2.71 (m, 1H), 2.57 (m, 2H), 2.44 (m, 1H), 2.34 (m, 1H), 1.95 (m, 3H), 1.86 (s, 3H), 1.53 (m, 1H), 1.20 (s, 3H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.660 min; ESI-MS (+) m/z=750.0 (M+H)

Analysis condition 2: Retention time=1.421 min; ESI-MS (+) m/z=750.1 (M+H)

Example 3018: 2-((5-chloro-2-((5-cyanopyridin-3-yl)methoxy)-4-((3'-((5-cyanopyridin-3-yl)methoxy)-2-methyl-[1,1'-biphenyl]-3-yl)methoxy)benzyl)amino)-3-hydroxy-2-methylpropanoic Acid

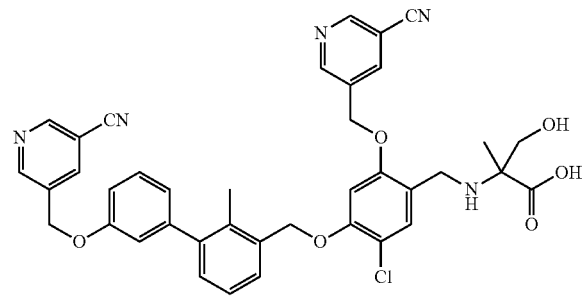 [SMILES: Cc1c(COc2cc(OCc3cncc(C#N)c3)c(CNC(C)(CO)C(=O)O)cc2Cl)cccc1-c1cccc(OCc2cncc(C#N)c2)c1]

To a vial was added DMF (1.0 mL), racemic 2-amino-3-hydroxy-2-methylpropanoic acid (19.82 mg, 0.166 mmol), 5-((4-chloro-5-((3'-((5-cyanopyridin-3-yl)methoxy)-2-methyl-[1,1'-biphenyl]-3-yl)methoxy)-2-formylphenoxy)methyl)nicotinonitrile (40 mg, 0.067 mmol), and borane-2-picoline complex (8.54 mg, 0.080 mmol). The vial was sealed and the mixture shaken overnight at room temperature. The crude material was purified via preparative LC/MS with the following conditions: Waters XBridge 5 μm C18, 19×200 mm where mobile phase A was 5:95 acetonitrile: water with 10 mM ammonium acetate and mobile phase B was 95:5 acetonitrile:water with 10 mM ammonium acetate at a gradient of 35-75% B over 15 minutes with a 5-minute hold at 100% B at a flow rate of 20 mL/minute. Fractions containing the desired product were combined and dried via centrifugal evaporation giving 10.3 mgs (21% yield, 95% UV purity) of racemic 2-((5-chloro-2-((5-cyanopyridin-3-yl)methoxy)-4-((3'-((5-cyanopyridin-3-yl)methoxy)-2-methyl-[1,1'-biphenyl]-3-yl)methoxy)benzyl)amino)-3-hydroxy-2-methylpropanoic acid. $^1$H NMR (500 MHz, DMSO-$d_6$) δ 8.99 (m, 4H), 8.49 (s, 1H), 8.41 (s, 1H), 7.55 (s, 1H), 7.46 (d, J=7.7 Hz, 1H), 7.40 (t, J=7.9 Hz, 1H), 7.31-7.24 (m, 1H), 7.20 (d, J=7.3 Hz, 1H), 7.11 (s, 1H), 7.09-7.03 (m, 1H), 6.96 (br. s., 1H), 6.91 (d, J=7.3 Hz, 1H), 5.35 (s, 2H), 5.27 (m, 4H), 3.97 (s, 2H), 3.63 (d, J=11.4 Hz, 1H), 3.54 (m, 1H), 2.20 (s, 3H), 1.23 (s, 3H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.76 min; ESI-MS (+) m/z=704.1 (M+H), 705.4 (M+H).

Analysis condition 2: Retention time=2.72 min; ESI-MS (+) m/z=704.3 (M+H), 705.4 (M+H).

Intermediate: (1R,3R,5S)-8-(3-(3-bromophenoxy)propyl)-8-azabicyclo[3.2.1]octan-3-ol

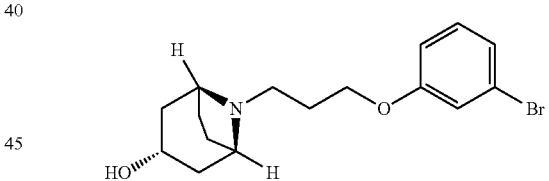

To a solution of 3-bromophenol (1 g, 5.78 mmol) in DMF (15 mL) was added 1-bromo-3-chloropropane (0.569 mL, 5.78 mmol) and $K_2CO_3$ (0.959 g, 6.94 mmol, 1.2 eq). The reaction mixture was stirred at 50° C. for 19 hrs. The reaction mixture was cooled to room temperature and diluted with EtOAc. The organic solution was washed with sat. $NaHCO_3$, water, brine, dried over anhydrous $Na_2SO_4$, filtered and concentrated. The crude product was purified on silica gel (220 g Isco cartridge) employing 20 column volumes of 0-20% EtOAc/hexane to give 1.24 g (86%) of a mixture of 1-bromo-3-(3-chloropropoxy) benzene and 1-bromo-3-(3-bromopropoxy) benzene as a colorless oil. $^1$H NMR (400 MHz, CDCl$_3$) δ 7.19-7.05 (m, 3H), 6.89-6.82 (m, 1H), 4.14-4.08 (m, 2H), 3.74 (t, J=6.4 Hz, 1.60H), 3.60 (t, J=6.4 Hz, 0.40H), 2.32 (m, 0.40H), 2.24 (m, 1.60H).

To a sealed tube was added nortropine (0.632 g, 4.97 mmol), DMF (49.7 ml), 1-bromo-3-(3-chloropropoxy)benzene (1.24 g, 4.97 mmol, using the mixture obtained above and assuming the chloropropoxy was the major compound), sodium iodide (1.117 g, 7.45 mmol, 1.5 eq.), and potassium carbonate (1.717 g, 12.42 mmol, 2.5 eq.). The vessel was sealed and the mixture stirred overnight at 50° C. The mixture was cooled to room temperature and evaporated to a paste. The mixture was taken up in 30 mL of EtOAc, washed with 10 mL water thrice, brine, dried over anhydrous $Na_2SO_4$, filtered and concentrated. The resulting residue was diluted with 10 mL of methanol and then pushed through a Waters 5 g MCX cartridge. The cartridge was flushed with 20 mL of methanol and the product eluted with 20 mL of 2M ammonia in methanol. Evaporation of the 2M ammonia solution gave 0.835 g (42%) of (1R,3R,5S)-8-(3-(3-bromophenoxy)propyl)-8-azabicyclo[3.2.1]octan-3-ol as a tan oil. $^1$H NMR (500 MHz, DMSO-$d_6$) δ 7.27-7.20 (m, 1H), 7.15-7.12 (m, 1H), 7.12-7.08 (m, 1H), 6.94 (m, 1H), 4.25 (d, J=1.6 Hz, 1H), 4.05 (t, J=6.4 Hz, 2H), 3.80 (t, J=4.6 Hz, 1H), 3.18 (m, 1H), 3.06 (m, 2H), 2.38 (t, J=6.9 Hz, 2H), 2.05-1.99 (m, 2H), 1.86 (dt, J=13.9, 4.2 Hz, 2H), 1.83-1.73 (m, 2H), 1.54 (m, 2H). The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.285 min., m/z 341.2 (M+H).

Example 3019: (R)-2-((5-chloro-2-((5-cyanopyridin-3-yl)methoxy)-4-((3'-(3-((1R,3R,5S)-3-hydroxy-8-azabicyclo[3.2.1]octan-8-yl)propoxy)-2-methyl-[1,1'-biphenyl]-3-yl)methoxy)benzyl)amino)-3-hydroxy-2-methylpropanoic Acid 2H), 3.80 (m, 1H), 3.59 (d, J=11.0 Hz, 1H), 3.51 (d, J=11.0 Hz, 1H), 3.21 (m, 2H), 2.54 (m, 2H), 2.23 (s, 3H), 2.07 (d, J=7.0 Hz, 2H), 1.93 (m, 2H), 1.88-1.77 (m, 4H), 1.58 (d, J=13.6 Hz, 2H), 1.22 (s, 3H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.686 min; ESI-MS (+) m/z=756.1 (M+H)

Analysis condition 2: Retention time=1.429 min; ESI-MS (+) m/z=756.1 (M+H)

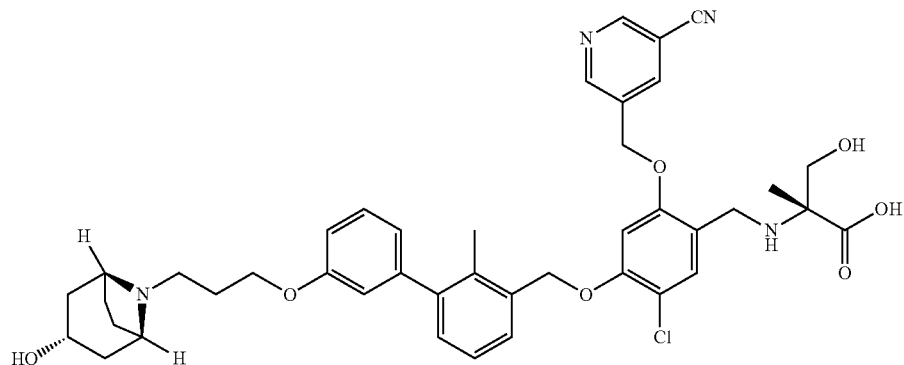 [SMILES: Cc1c(COc2cc(OCc3cncc(C#N)c3)c(CN[C@](C)(CO)C(=O)O)cc2Cl)cccc1-c1cccc(OCCCN2[C@@H]3CC[C@H]2C[C@@H](O)C3)c1]

(R)-2-((5-Chloro-2-((5-cyanopyridin-3-yl)methoxy)-4-((3'-(3-((R,3R,5S)-3-hydroxy-8-azabicyclo[3.2.1]octan-8-yl)propoxy)-2-methyl-[1,1'-biphenyl]-3-yl)methoxy)benzyl)amino)-3-hydroxy-2-methylpropanoic acid was synthesized in an analogous fashion as Example 3015. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 20-60% B over 15 minutes with a 5-minute hold at 100% B at a flow rate of 20 mL/minute. Fractions containing the desired product were combined and dried via centrifugal evaporation. The yield of the product was 15.8 mg, and its estimated purity by LCMS analysis was 99%. $^1$H NMR (500 MHz, DMSO-$d_6$) δ 9.02 (m, 2H), 8.51 (s, 1H), 7.53 (s, 1H), 7.47 (d, J=7.3 Hz, 1H), 7.35 (t, J=7.9 Hz, 1H), 7.26 (d, J=7.3 Hz, 1H), 7.21 (d, J=7.7 Hz, 1H), 7.11 (s, 1H), 6.94 (d, J=8.1 Hz, 1H), 6.85 (d, J=7.7 Hz, 1H), 6.82 (s, 1H), 5.35 (s, 2H), 5.28 (s, 2H), 4.07 (t, J=6.2 Hz, 2H), 3.92 (s, Intermediate: 5-((4-chloro-5-((2,2'-dimethyl-[1,1'-biphenyl]-3-yl)methoxy)-2-formylphenoxy)methyl)nicotinonitrile

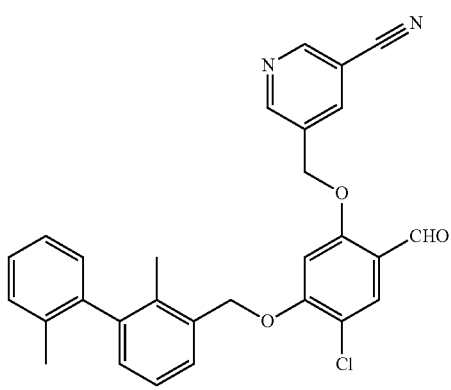 [SMILES: Cc1ccccc1-c1cccc(COc2cc(OCc3cncc(C#N)c3)c(C=O)cc2Cl)c1C]

5-((4-Chloro-5-((2,2'-dimethyl-[1,1'-biphenyl]-3-yl)methoxy)-2-formylphenoxy)methyl)nicotinonitrile (98.8 mg, 70%) was obtained from 5-((4-chloro-2-formyl-5-((2-methyl-3-(4,4,5,5-tetramethyl-1,3,2-dioxaborolan-2-yl)benzyl)oxy)phenoxy)methyl)nicotinonitrile and 1-bromo-2-methylbenzene using the procedure described for 5-((4-chloro-5-((3'-(3-chloropropoxy)-2-methyl-[1,1'-biphenyl]-3-yl)methoxy)-2-formylphenoxy)methyl)nicotinonitrile. $^1$H NMR (400 MHz, CHLOROFORM-d) δ 10.30 (s, 1H), 8.93 (t, J=1.5 Hz, 2H), 8.12 (t, J=2.0 Hz, 1H), 7.94 (s, 1H), 7.47 (d, J=6.8 Hz, 1H), 7.36-7.23 (m, 4H), 7.20 (dd, J=7.5, 1.0 Hz, 1H), 7.13 (d, J=7.3 Hz, 1H), 6.69 (s, 1H), 5.28 (s, 2H), 5.25 (s, 2H), 2.12 (s, 3H), 2.07 (s, 3H).

Example 3020: (S)-2-((5-chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic Acid

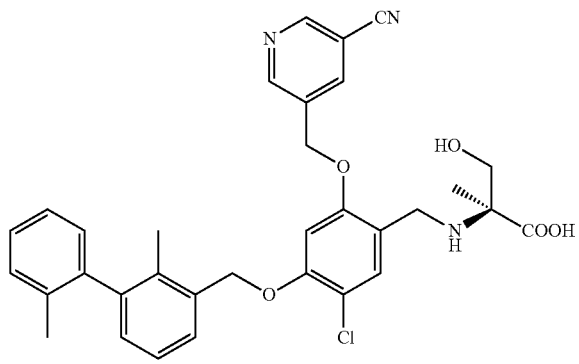 [SMILES: Cc1ccccc1-c1cccc(COc2cc(OCc3cncc(C#N)c3)c(CN[C@@](C)(CO)C(=O)O)cc2Cl)c1C]

(S)-2-((5-Chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic acid (6.4 mg, 21%) was obtained from 5-((4-chloro-5-((2,2'-dimethyl-[1,1'-biphenyl]-3-yl)methoxy)-2-formylphenoxy)methyl)nicotinonitrile and 2-amino-3-hydroxy-2-methylpropanoic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (d, J=6.6 Hz, 2H), 8.52 (s, 1H), 7.53 (s, 1H), 7.49 (d, J=7.3 Hz, 1H), 7.35-7.23 (m, 4H), 7.14 (s, 1H), 7.09 (t, J=6.8 Hz, 2H), 5.35 (s, 2H), 5.25 (s, 2H), 3.91 (s, 2H), 3.58 (d, J=11.0 Hz, 1H), 3.51 (d, J=11.0 Hz, 1H), 2.04 (s, 3H), 1.99 (s, 3H), 1.22 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.463 min, ESI m/z 586 (M+1), 584 (M−1)

LCMS (Injection 2 conditions) Rt=2.040 min, ESI m/z 586 (M+1), 584 (M−1)

Example 3021: (S)-2-((5-chloro-2-((5-cyanopyridin-3-yl)methoxy)-4-((2,2'-dimethyl-[1,1'-biphenyl]-3-yl)methoxy)benzyl)amino)-3-hydroxypropanoic Acid

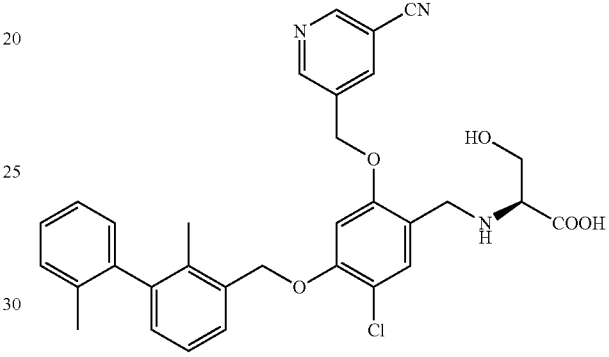

(S)-2-((5-Chloro-2-((5-cyanopyridin-3-yl)methoxy)-4-((2,2'-dimethyl-[1,1'-biphenyl]-3-yl)methoxy)benzyl) amino)-3-hydroxypropanoic acid (4.6 mg, 15%) was obtained from 5-((4-chloro-5-((2,2'-dimethyl-[1,1'-biphenyl]-3-yl)methoxy)-2-formylphenoxy)methyl)nicotinonitrile and (S)-2-amino-3-hydroxypropanoic acid acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl) methoxy)phenoxy)methyl)nicotinonitrile (Example 3001). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 7-minute hold at 100% B; Flow: 20 mL/min. Fractions containing the desired product were combined and dried via centrifugal evaporation. $^1$H NMR (500 MHz, DMSO-d$_6$) δ 9.03 (br. s., 2H), 8.53 (s, 1H), 7.52-7.48 (m, 2H), 7.34-7.24 (m, 4H), 7.15 (s, 1H), 47.12-7.07 (m, 2H), 5.28-5.27 (m, 4H), 3.98-3.90 (m, 2H), 3.65-3.62 (m, 1H), 3.62-3.57 (m, 1H), 3.12-3.07 (m, 1H), 2.04 (s, 3H), 1.91 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.151 min, ESI m/z 572 (M+1), 570 (M−1)

LCMS (Injection 2 conditions) Rt=1.998 min, ESI m/z 572 (M+1), 570 (M−1)

Example 3022: (R)-2-((5-chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic Acid

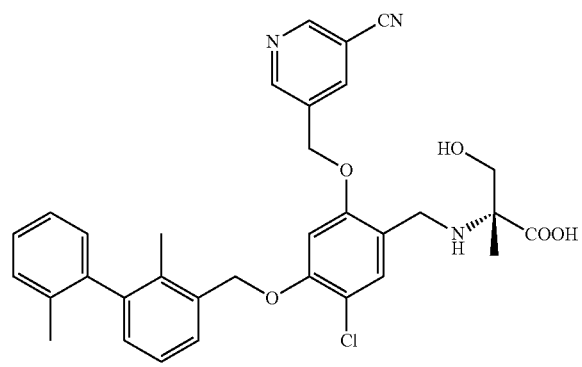 [SMILES: Cc1ccccc1-c1cccc(COc2cc(OCc3cncc(C#N)c3)c(CN[C@](C)(CO)C(=O)O)cc2Cl)c1C]

(R)-2-((5-Chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic acid (7.5 mg, 25%) was obtained from 5-((4-chloro-5-((2,2'-dimethyl-[1,1'-biphenyl]-3-yl)methoxy)-2-formylphenoxy)methyl)nicotinonitrile and (R)-2-amino-3-hydroxy-2-methylpropanoic acid acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (d, J=6.6 Hz, 2H), 8.52 (s, 1H), 7.54 (s, 1H), 7.49 (d, J=7.7 Hz, 1H), 7.35-7.24 (m, 4H), 7.14 (s, 1H), 7.09 (t, J=6.8 Hz, 2H), 5.36 (s, 2H), 5.30 (br. s., 2H), 3.92 (s, 2H), 3.59 (d, J=11.4 Hz, 1H), 3.51 (d, J=11.4 Hz, 1H), 2.04 (s, 3H), 1.99 (s, 3H), 1.22 (s, 3H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.211 min, ESI m/z 586 (M+1), 584 (M−1)

LCMS (Injection 2 conditions) Rt=2.025 min, ESI m/z 586 (M+1), 584 (M−1)

Example 3023: (S)-1-(5-chloro-2-((5-cyanopyridin-3-yl)methoxy)-4-((2,2'-dimethyl-[1,1'-biphenyl]-3-yl)methoxy)benzyl)piperidine-2-carboxylic Acid

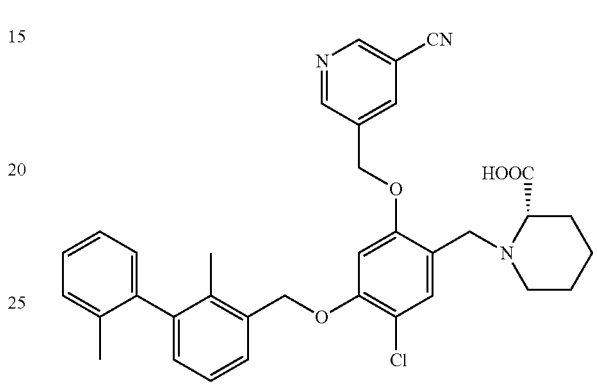

(S)-1-(5-chloro-2-((5-cyanopyridin-3-yl)methoxy)-4-((2,2'-dimethyl-[1,1'-biphenyl]-3-yl)methoxy)benzyl)piperidine-2-carboxylic acid (7.7 mg, 25%) was obtained from 5-((4-chloro-5-((2,2'-dimethyl-[1,1'-biphenyl]-3-yl)methoxy)-2-formylphenoxy)methyl)nicotinonitrile and (S)-piperidine-2-carboxylic acid using the procedure described for (R)-5-((4-chloro-2-(((3-(dimethylamino)propyl)amino)methyl)-5-((3'-(3-(3-hydroxypyrrolidin-1-yl)propoxy)-2-methyl-[1,1'-biphenyl]-3-yl)methoxy)phenoxy)methyl)nicotinonitrile (Example 3001). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (d, J=8.4 Hz, 2H), 8.47 (s, 1H), 7.50 (d, J=7.3 Hz, 1H), 7.42 (s, 1H), 7.35-7.22 (m, 4H), 7.15-7.05 (m, 3H), 5.39-5.22 (m, 4H), 3.81-3.73 (m, 1H), 3.60 (br. s., 1H), 3.14 (br. s., 1H), 2.90 (br, s, 1H), 2.28 (br. s., 1H), 2.04 (s, 3H), 1.99 (s, 3H), 1.85-1.66 (m, 2H), 1.49 (br. s., 3H), 1.37 (br. s., 1H).

Two analytical LC/MS injections were used to determine the final purity. Injection 1 conditions: Column: Waters Acquity UPLC BEH C18, 2.1×50 mm, 1.7-10 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm LCMS (Injection 1 conditions) Rt=2.217 min, ESI m/z 596 (M+1), 594 (M−1)

LCMS (Injection 2 conditions) Rt=2.094 min, ESI m/z 596 (M+1), 594 (M−1).

Intermediate: 2-methyl-3-(4,4,5,5-tetramethyl-1,3,2-dioxaborolan-2-yl)phenol

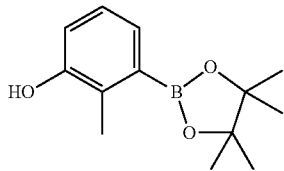 [SMILES: Cc1c(O)cccc1B1OC(C)(C)C(C)(C)O1]

To a sealed tube was added 3-bromo-2-methylphenol (501 mg, 2.68 mmol) in dioxane (15.0 ml) along with potassium acetate (789 mg, 8.04 mmol), bis(pinacolato)diboron (1089 mg, 4.29 mmol) and [1,1'-bis(diphenylphosphino)ferrocene]dichloropalladium(II) (255 mg, 0.348 mmol). The vessel was sealed, the contents evacuated/flushed with nitrogen ×3 and then heated for 24 hours at 90° C. The volatiles were removed under a stream of nitrogen. The resulting residue was diluted with 30 mL of ethyl acetate and pushed through diatomaceous earth (Celite®), the bed then washed with 2×10 mL of ethyl acetate. The combined filtrates were washed with 10 mL of water, brine, dried over sodium sulfate, then evaporated to a dark oily solid. Purification was performed by using column chromatography that was run using a 40 g Thomson silica gel cartridge, 20 column volumes of 0-9% MeOH/DCM to give a 96% yield of 2-methyl-3-(4,4,5,5-tetramethyl-1,3,2-dioxaborolan-2-yl)phenol as a light tan solid. $^1$H NMR (500 MHz, DMSO-$d_6$) □ 9.19 (s, 1H), 7.06 (d, J=7.3 Hz, 1H), 6.97 (t, J=7.3 Hz, 1H), 6.87 (d, J=7.3 Hz, 1H), 2.29 (s, 3H), 1.33-1.25 (m, 12H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.650 min., m/z 235.2 (M+H).

Intermediate: 2-(3-(3-chloropropoxy)-2-methylphenyl)-4,4,5,5-tetramethyl-1,3,2-dioxaborolane and 2-(3-(3-bromopropoxy)-2-methylphenyl)-4,4,5,5-tetramethyl-1,3,2-dioxaborolane

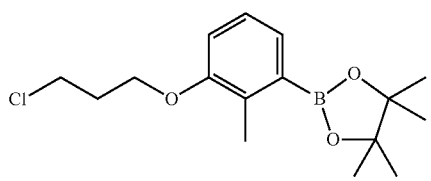

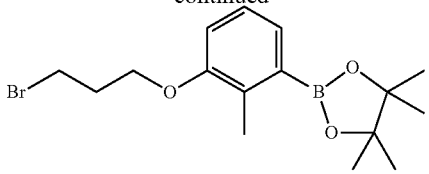

To a mixture of 2-methyl-3-(4,4,5,5-tetramethyl-1,3,2-dioxaborolan-2-yl)phenol (707 mg, 2.57 mmol) in DMF (8 mL) was added potassium carbonate (426 mg, 3.08 mmol) and 1-bromo-3-chloropropane (0.253 mL, 2.57 mmol). The mixture was stirred overnight at room temperature. To the reaction mixture was added 1 eq. of 1-bromo-3-chloropropane (0.253 mL, 2.57 mmol), 0.5 eq. (178 mgs, 1.29 mmol) of potassium carbonate, and stirring was continued at room temperature for four days. The resulting product was taken up in 50 mL of DCM, washed with 5 mL of water, 20 mL of brine, dried over sodium sulfate, filtered, and evaporated under a stream of nitrogen. The crude dark oily product was purified on a 40 g Isco silica gel cartridge with 20 column volumes of 0 to 20% ethyl acetate/hexane to give a mixture of 2-(3-(3-chloropropoxy)-2-methylphenyl)-4,4,5,5-tetramethyl-1,3,2-dioxaborolane and 2-(3-(3-bromopropoxy)-2-methylphenyl)-4,4,5,5-tetramethyl-1,3,2-dioxaborolane as a clear colorless oil (55% yield). $^1$H NMR (500 MHz, CDCl$_3$) δ 7.37 (m, 1H), 7.15 (t, J=8.0 Hz, 1H), 6.94 (dd, J=7.5, 1.0 Hz, 1H), 4.11 (m, 2H), 3.79 (t, J=6.5 Hz, 1.8H), 3.65 (t, J=6.5 Hz, 0.2H), 2.43 (s, 3H), 2.27 (quin, J=6.1 Hz, 2H), 1.36 (s, 12H).

Intermediate: (R)-1-(3-(2-methyl-3-(4,4,5,5-tetramethyl-1,3,2-dioxaborolan-2-yl)phenoxy)propyl)pyrrolidin-3-ol

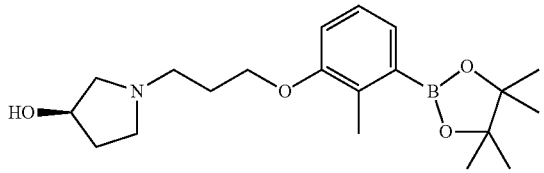 [SMILES: Cc1c(OCCCN2CC[C@@H](O)C2)cccc1B1OC(C)(C)C(C)(C)O1]

To a sealed flask was added (R)-3-hydroxypyrrolidine hydrochloride (223 mg, 1.804 mmol, 1.3 eq), 2-(3-(3-chloropropoxy)-2-methylphenyl)-4,4,5,5-tetramethyl-1,3,2-dioxaborolane (574.7 mg, 1.388 mmol, using the mixture obtained above and assuming the chloropropoxy was the major compound), DMF (8 mL), sodium iodide (312 mg, 2.081 mmol, 1.5 eq), and potassium carbonate (479 mg, 3.47 mmol, 2.5 eq). The flask was sealed and the mixture stirred overnight at 50° C. The reaction mixture was cooled to room temperature, and (R)-3-hydroxypyrrolidine hydrochloride (223 mg, 1.804 mmol, 1.3 eq) was added along with potassium carbonate (479 mg, 3.47 mmol, 2.5 eq), and sodium iodide (312 mg, 2.081 mmol, 1.5 eq). The mixture was heated overnight at 50° C. The crude product was diluted with 70 mL of DCM, washed with 10 mL of water, brine, dried over sodium sulfate, and evaporated under a stream of nitrogen overnight. The crude oil was taken up in 10 mL of methanol and pushed through 5 g of SCX (strong cation exchange) resin. The resin was washed with 50 mL of methanol. The desired product was then eluted with 50 mL of 2M NH$_3$ in methanol. Evaporation of the volatiles gave 320 mgs (60% yield) of (R)-1-(3-(2-methyl-3-(4,4,5,5-tetramethyl-1,3,2-dioxaborolan-2-yl)phenoxy)propyl)pyrrolidin-3-ol as a light yellow thick viscous oil. $^1$H NMR (500 MHz, CDCl$_3$) δ 7.34 (dd, J=7.5, 1.0 Hz, 1H), 7.17-7.11 (t, J=7.5 Hz, 1H), 6.91 (dd, J=7.5, 1.0 Hz, 1H), 4.38-4.29 (m, 1H), 4.05-3.97 (m, 2H), 2.91 (m, 1H), 2.75-2.63 (m, 2H), 2.58-2.45 (m, 2H), 2.43 (s, 3H), 2.35-2.28 (m, 1H), 2.24-2.15 (m, 1H), 2.08-1.95 (m, 2H), 1.81-1.69 (m, 1H), 1.35 (s, 12H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.338 min., m/z 362.3 (M+H).

Intermediate: 4-((3-bromo-2-methoxybenzyl)oxy)-5-chloro-2-hydroxybenzaldehyde

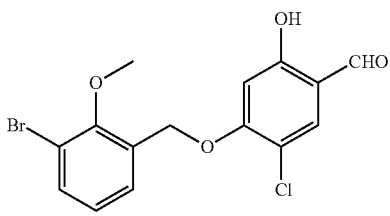 [SMILES: COc1c(Br)cccc1COc1cc(O)c(C=O)cc1Cl]

A solution of (E)-diisopropyl diazene-1,2-dicarboxylate (335 mg, 1.659 mmol) in THF (5 mL) was added dropwise to the solution of (3-bromo-2-methoxyphenyl)methanol (300 mg, 1.382 mmol), 5-chloro-2,4-dihydroxybenzaldehyde (286 mg, 1.659 mmol) and triphenylphosphine (435 mg, 1.659 mmol) in THF (7 mL) at 0° C. The resulting yellow solution was allowed to warm to room temperature and stirred overnight under nitrogen. The solvent was removed and the resulting residue was taken up in ethyl acetate and purified on a 90 g Thomson silica gel cartridge using 20 column volumes of 0 to 40% ethyl acetate/hexane to give a 60% yield of 4-((3-bromo-2-methoxybenzyl)oxy)-5-chloro-2-hydroxybenzaldehyde as a white solid. $^1$H NMR (500 MHz, DMSO-$d_6$) δ 10.05 (s, 1H), 7.71 (s, 1H), 7.69 (dd, J=7.8, 1.6 Hz, 1H), 7.54 (dd, J=7.8, 1.6 Hz, 1H), 7.18 (t, J=7.8 Hz, 1H), 6.83 (s, 1H), 5.30 (s, 2H), 3.85 (s, 3H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.000 min., m/z 373.0 (M+H).

Intermediate: 5-((5-((3-bromo-2-methoxybenzyl)oxy)-4-chloro-2-formylphenoxy)methyl)nicotinonitrile

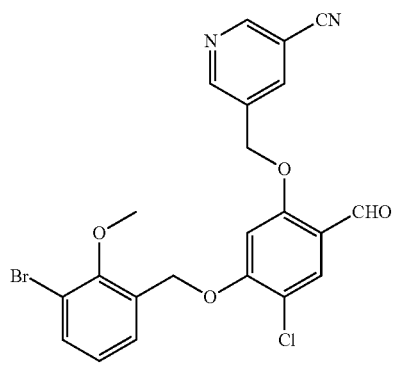 [SMILES: COc1c(Br)cccc1COc1cc(OCc2cncc(C#N)c2)c(C=O)cc1Cl]

To 4-((3-bromo-2-methoxybenzyl)oxy)-5-chloro-2-hydroxybenzaldehyde (316 mg, 0.850 mmol) in DMF (8 mL) was added 5-(chloromethyl)nicotinonitrile (169 mg, 1.105 mmol) and cesium carbonate (402 mg, 1.233 mmol). The flask was sealed and the mixture stirred overnight at room temperature. The crude product was further diluted with 70 mL of DCM, washed with 10 mL of water, brine, dried over sodium sulfate, filtered, and evaporated under a stream of nitrogen. The resulting solid was triturated with 15 mL of water to give 390 mgs of 5-((5-((3-bromo-2-methoxybenzyl)oxy)-4-chloro-2-formylphenoxy)methyl)nicotinonitrile as a light yellow solid (89% yield). $^1$H NMR (500 MHz, DMSO-$d_6$) δ 10.24 (s, 1H), 9.04 (m, 2H), 8.55 (s, 1H), 7.74 (s, 1H), 7.71 (dd, J=7.8, 1.3 Hz, 1H), 7.60-7.56 (m, 1H), 7.26 (s, 1H), 7.19 (t, J=7.8 Hz, 1H), 5.50 (s, 2H), 5.38 (s, 2H), 3.87 (s, 3H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.978 min., m/z 488.0 (M+H).

Example 3024: (R)-5-((4-chloro-2-formyl-5-((3'-(3-(3-hydroxypyrrolidin-1-yl)propoxy)-2-methoxy-2'-methyl-[1,1'-biphenyl]-3-yl)methoxy)phenoxy)methyl)nicotinonitrile

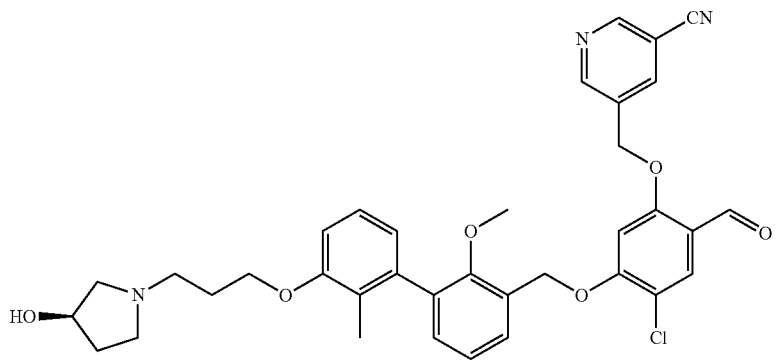 [SMILES: COc1c(COc2cc(OCc3cncc(C#N)c3)c(C=O)cc2Cl)cccc1-c1cccc(OCCCN2CC[C@@H](O)C2)c1C]

To a sealed tube was added (R)-1-(3-(2-methyl-3-(4,4,5,5-tetramethyl-1,3,2-dioxaborolan-2-yl)phenoxy)propyl)pyrrolidin-3-ol (76 mg, 0.200 mmol), 5-((5-((3-bromo-2-methoxybenzyl)oxy)-4-chloro-2-formylphenoxy)methyl)nicotinonitrile (103 mg, 0.20 mmol), THF (7 mL), water (2.3 mL), potassium phosphate, tribasic (85 mg, 0.400 mmol), and second generation X-Phos precatalyst (7.87 mg, 10.00 μmol). The flask was sealed, the mixture de-gassed/flushed with nitrogen then heated overnight at 80° C. The reaction mixture was cooled, concentrated to an oil, diluted with 50 mL of DCM, extracted, washed with 5 mL of water, brine, dried over sodium sulfate, filtered, and evaporated to give a yellow oil. The resulting crude product was taken up in 10 mL of methanol and pushed through 2 g of SCX resin. The product was eluted with 15 mL of 2M $NH_3$ in methanol. The volatiles were removed and the impure product was further purified using a Shimadzu preparative HPLC employing acetonitrile/water/TFA where solvent A was 10% acetonitrile/90% water/0.1% trifluoroacetic acid and solvent B was 10% water/90% acetonitrile/0.1% trifluoroacetic acid with a XTERRA 5 μm C18 30×100 mm column at a gradient of 30-100% B and a flow rate of 40 mL/min. over 15 minutes with a 10 minute hold to give 55 mgs (30% yield) of (R)-5-((4-chloro-2-formyl-5-((3'-(3-(3-hydroxypyrrolidin-1-yl)propoxy)-2-methoxy-2'-methyl-[1,1'-biphenyl]-3-yl)methoxy)phenoxy)methyl)nicotinonitrile, as a yellow solid. $^1$H NMR (500 MHz, DMSO-$d_6$) δ 10.25 (s, 1H), 9.04 (m, 2H), 8.56 (s, 1H), 7.74 (s, 1H), 7.58 (d, J=7.7 Hz, 1H), 7.31-7.18 (m, 4H), 6.98 (d, J=8.1 Hz, 1H), 6.85 (d, J=7.7 Hz, 1H), 5.50 (s., 2H), 5.43 (d, J=10.6 Hz, 1H), 5.36 (d, J=10.6 Hz, 1H), 4.18 (br. s., 1H), 4.10-3.99 (m, 2H), 2.74-2.65 (m, 1H), 2.57-2.48 (m, 6H), 2.41 (m, 1H), 2.36-2.27 (m, 1H), 2.01-1.87 (m, 6H), 1.53 (m, 1H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS Rt=1.575 min., m/z 643.3 (M+H).

Example 3025: (R)-2-((5-chloro-2-((5-cyanopyridin-3-yl)methoxy)-4-((3'-(3-((R)-3-hydroxypyrrolidin-1-yl)propoxy)-2-methoxy-2'-methyl-[1,1'-biphenyl]-3-yl)methoxy)benzyl)amino)-3-hydroxy-2-methylpropanoic Acid

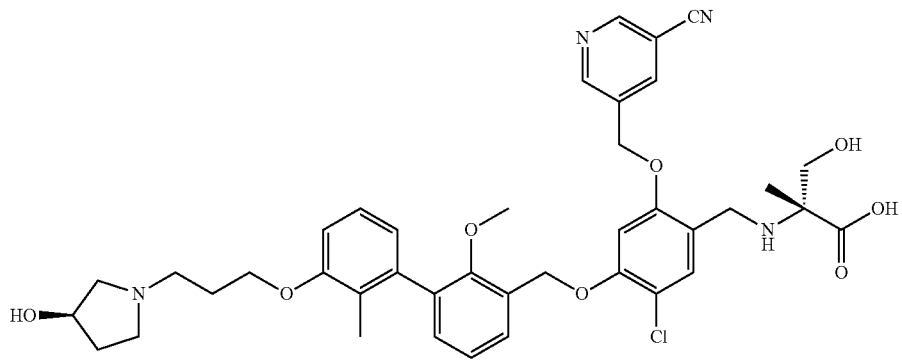 [SMILES: COc1c(COc2cc(OCc3cncc(C#N)c3)c(CN[C@](C)(CO)C(=O)O)cc2Cl)cccc1-c1cccc(OCCCN2CC[C@@H](O)C2)c1C]

To a screw capped vial was added DMF (1 ml), acetic acid (0.10 ml), (R)-5-((4-chloro-2-formyl-5-((3'-(3-(3-hydroxypyrrolidin-1-yl)propoxy)-2-methoxy-2'-methyl-[1,1'-biphenyl]-3-yl)methoxy)phenoxy)methyl)nicotinonitrile (20 mg, 0.031 mmol), (R)-2-amino-3-hydroxy-2-methylpropanoic acid (9.28 mg, 0.078 mmol), and borane-2-picoline complex (4.0 mg, 0.037 mmol). The vial was sealed and the mixture shaken overnight at room temperature. The crude material was purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 50-90% B over 20 minutes with a 5-minute hold at a flow rate of 20 mL/minute. Fractions containing the desired product were combined and dried via centrifugal evaporation. The yield of the product was 5.2 mg (22%), and its estimated purity by LCMS analysis was 95%. $^1$H NMR (500 MHz, DMSO-$d_6$) δ 9.02 (s, 2H), 8.51 (s, 1H), 7.57-7.48 (m, 2H), 7.29-7.14 (m, 3H), 7.12 (s, 1H), 6.97 (d, J=8.1 Hz, 1H), 6.83 (d, J=7.3 Hz, 1H), 5.34 (s, 2H), 5.32-5.20 (m, 2H), 4.19 (m, 1H), 4.11-3.97 (m, 2H), 3.87 (s, 3H), 3.61-3.42 (m, 2H), 2.74-2.69 (m, 1H), 2.60-2.49 (m, 2H), 2.49 (s, 3H), 2.46 (m, 1H), 2.44 (m, 1H), 2.34 (m, 6H), 1.54 (m, 1H), 1.19 (s, 3H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.574 min; ESI-MS (+) m/z=746.0 (M+H)

Analysis condition 2: Retention time=1.439 min; ESI-MS (+) m/z=746.0 (M+H)

Intermediate: 4-((3-bromo-2,5-dimethylbenzyl)oxy)-5-chloro-2-hydroxybenzaldehyde

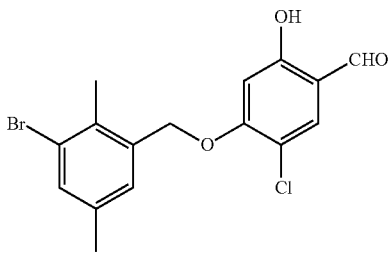 [SMILES: Cc1cc(Br)c(C)c(COc2cc(O)c(C=O)cc2Cl)c1]

A solution of (E)-diisopropyl diazene-1,2-dicarboxylate (207 mg, 1.025 mmol) in THF (3 mL) was added dropwise to a solution of (3-bromo-2,5-dimethylphenyl)methanol (183.7 mg, 0.854 mmol), 5-chloro-2,4-dihydroxybenzaldehyde (177 mg, 1.025 mmol), and triphenylphosphine (269 mg, 1.025 mmol) in THF (7 mL) at 0° C. The resulting yellow reaction mixture was allowed to warm to room temperature and stirred overnight under nitrogen. The volatiles were removed and the crude residue was taken up in ethyl acetate and purified on a 40 g Thompson silica gel cartridge using 20 column volumes of 0 to 30% ethyl acetate/hexane to give 190 mg of 4-((3-bromo-2,5-dimethylbenzyl)oxy)-5-chloro-2-hydroxybenzaldehyde as a white solid (54% yield). $^1$H NMR (500 MHz, THF-d$_8$) δ 9.74 (s, 1H), 7.71 (s, 1H), 7.43 (s, 1H), 7.31 (s, 1H), 6.80 (s, 1H), 5.23 (s, 2H), 2.41 (s, 3H), 2.30 (s, 3H).

(3-bromo-2,5-dimethylphenyl)methanol was synthesized from 2,5-dimethylbenzoic acid via bromination using NBS and then borane reduction.)

Intermediate: 5-((5-((3-bromo-2,5-dimethylbenzyl)oxy)-4-chloro-2-formylphenoxy)methyl)nicotinonitrile

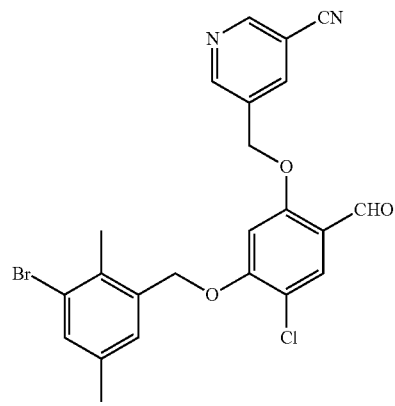 [SMILES: Cc1cc(Br)c(C)c(COc2cc(OCc3cncc(C#N)c3)c(C=O)cc2Cl)c1]

To a small round-bottomed flask was added 4-((3-bromo-2,5-dimethylbenzyl)oxy)-5-chloro-2-hydroxybenzaldehyde (190 mg, 0.514 mmol), DMF (4.2 mL), 5-(chloromethyl)nicotinonitrile (102 mg, 0.668 mmol), and cesium carbonate (243 mg, 0.745 mmol). The flask was sealed and the mixture stirred overnight at room temperature. The reaction mixture was further diluted with 50 mL of DCM, washed with 10 mL of water, brine, dried over sodium sulfate, filtered, and concentrated under a stream of nitrogen overnight. The resulting crude oily solid was triturated with 10 mL of water, then 1:1 ether/hexane followed by further drying to give (68% yield, 212 mgs) of 5-((5-((3-bromo-2,5-dimethylbenzyl)oxy)-4-chloro-2-formylphenoxy)methyl)nicotinonitrile as a light tan solid. $^1$H NMR (500 MHz, DMSO-d$_6$) δ 10.24 (s, 1H), 9.04 (m, 2H), 8.55 (br. s., 1H), 7.74 (s, 1H), 7.50 (s, 1H), 7.36 (s, 1H), 7.25 (s, 1H), 5.48 (s, 2H), 5.37 (s, 2H), 2.37 (s, 3H), 2.30 (s, 3H).

Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.590 min; ESI-MS (+) m/z=486.8 (M+H)

Analysis condition 2: Retention time=2.514 min; ESI-MS (+) m/z=486.8 (M+H)

Intermediate: (R)-5-((4-chloro-2-formyl-5-((3'-(3-(3-hydroxypyrrolidin-1-yl)propoxy)-2,2',5-trimethyl-[1,1'-biphenyl]-3-yl)methoxy)phenoxy)methyl) Nicotinonitrile, TFA

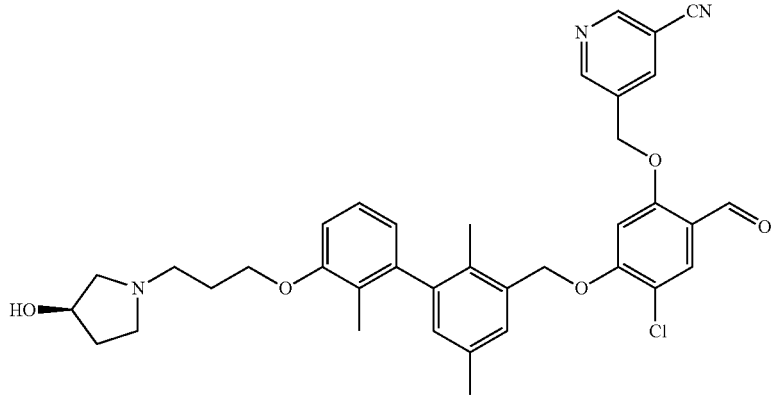 [SMILES: Cc1cc(COc2cc(OCc3cncc(C#N)c3)c(C=O)cc2Cl)c(C)c(-c2cccc(OCCCN3CC[C@@H](O)C3)c2C)c1]

To a sealed tube was added (R)-1-(3-(2-methyl-3-(4,4,5,5-tetramethyl-1,3,2-dioxaborolan-2-yl)phenoxy)propyl)pyrrolidin-3-ol (94.0 mg, 0.247 mmol), 5-((5-((3-bromo-2,5-dimethylbenzyl)oxy)-4-chloro-2-formylphenoxy)methyl) nicotinonitrile (120 mg, 0.247 mmol), THF (7 mL), water (2.3 mL), potassium phosphate, tribasic (105 mg, 0.494 mmol), and second generation X-Phos precatalyst (9.72 mg, 12.0 mol). The flask was sealed, the mixture de-gassed/flushed with nitrogen then heated overnight at 80° C. The reaction mixture was concentrated, diluted and extracted with 30 mL DCM (×2), washed with water, brine, dried over sodium sulfate, filtered, and evaporated to give a yellow oil. The oil was taken up in 10 mL of methanol and pushed through 2.5 g of SCX resin. The product was eluted with 20 mL of 2M NH$_3$ in methanol. The impure product was further purified using a Shimadzu preparative HPLC employing acetonitrile/water/TFA where solvent A was 10% acetonitrile/90% water/0.1% trifluoroacetic acid and solvent B was 10% water/90% acetonitrile/0.1% trifluoroacetic acid with a XTERRA 5 μm C18 30×100 mm column at a gradient of 30-100% B and a flow rate of 40 mL/min. over 15 minutes with a 10 minute hold to give 62 mgs of (R)-5-((4-chloro-2-formyl-5-((3'-(3-(3-hydroxypyrrolidin-1-yl)propoxy)-2,2',5-trimethyl-[1,1'-biphenyl]-3-yl)methoxy)phenoxy) methyl) nicotinonitrile, TFA salt (30% yield) as a yellow solid. $^1$H NMR (500 MHz, THF-d$_8$) δ 10.29 (s, 1H), 8.95 (s, 1H), 8.91 (s, 1H), 8.34 (s, 1H), 7.81 (s, 1H), 7.34 (s, 1H), 7.15 (t, J=7.8 Hz, 1H), 7.05 (s, 1H), 6.92 (m, 2H), 6.70 (d, J=7.4 Hz, 1H), 5.38 (s, 2H), 5.30 (s, 2H), 4.49 (m, 1H), 4.13 (m, 2H), 3.40 (m, 2H), 3.31-3.23 (m, 1H), 2.83 (m, 1H), 2.42-2.27 (m, 6H), 2.09-1.98 (m, 4H), 1.97-1.87 (m, 4H), 1.84 (m, 1H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.625 min., m/z 640.3 (M+H).

Example 3026: (R)-2-((5-chloro-2-((5-cyanopyridin-3-yl)methoxy)-4-((3'-(3-((R)-3-hydroxypyrrolidin-1-yl)propoxy)-2,2',5-trimethyl-[1,1'-biphenyl]-3-yl) methoxy)benzyl)amino)-3-hydroxy-2-methylpropanoic Acid, 2TFA

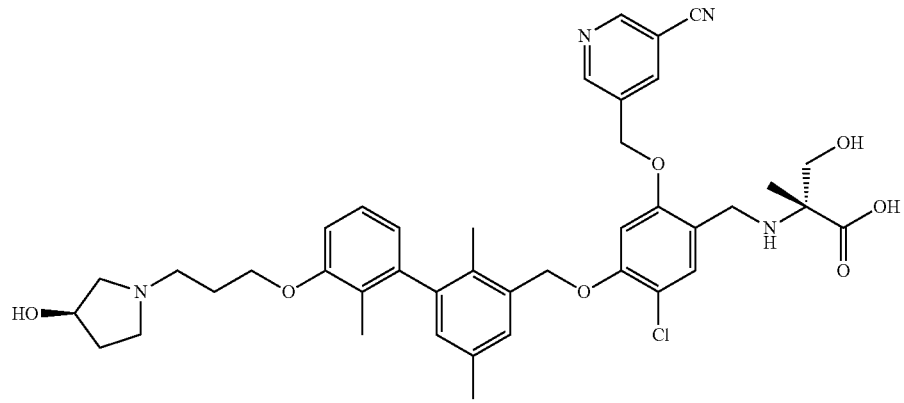 [SMILES: Cc1cc(COc2cc(OCc3cncc(C#N)c3)c(CN[C@](C)(CO)C(=O)O)cc2Cl)c(C)c(-c2cccc(OCCCN3CC[C@@H](O)C3)c2C)c1]

To a screw capped vial was added (R)-5-((4-chloro-2-formyl-5-((3'-(3-(3-hydroxypyrrolidin-1-yl)propoxy)-2,2',5-trimethyl-[1,1'-biphenyl]-3-yl)methoxy)phenoxy)methyl)

nicotinonitrile (20 mg, 0.031 mmol), DMF (1 mL), acetic acid (0.1 mL), (R)-2-amino-3-hydroxy-2-methylpropanoic acid (9.30 mg, 0.078 mmol), and borane-2-picoline complex (4.01 mg, 0.037 mmol). The vial was sealed and the mixture shaken overnight at room temperature. The crude material was purified via preparative LC/MS using the following conditions: Waters XBridge 5 µm C18, 19×200 mm where mobile phase A was 5:95 methanol: water with 10 mM ammonium acetate and mobile phase B was 95:5 methanol: water with 10 mM ammonium acetate at a gradient of 30-70% B over 20 minutes with a 5-minute hold at a flow rate of 20 mL/minute. Fractions containing the desired product were combined and dried via centrifugal evaporation. The compound was then re-purified using the following conditions: Waters XBridge 5 µm C18, 19×200 mm where mobile phase A was 5:95 acetonitrile:water with 0.1% TFA and mobile phase B was 95:5 acetonitrile:water with 0.1% TFA at a gradient of 15-55% B over 15 minutes with a 5-minute hold at a flow rate of 20 mL/minute. Fractions containing the desired product were combined and dried via centrifugal evaporation. The yield of the product, (R)-2-((5-chloro-2-((5-cyanopyridin-3-yl)methoxy)-4-((3'-(3-((R)-3-hydroxypyrrolidin-1-yl)propoxy)-2,2',5-trimethyl-[1,1'-biphenyl]-3-yl)methoxy)benzyl)amino)-3-hydroxy-2-methylpropanoic acid, 2TFA, was 3.0 mg (10%), and its estimated purity by LCMS analysis was 100%. $^1$H NMR (500 MHz, DMSO-$d_6$) δ 9.02 (s, 2H), 8.51 (s, 1H), 7.57-7.48 (m, 2H), 7.29-7.14 (m, 3H), 7.12 (s, 1H), 6.97 (d, J=8.1 Hz, 1H), 6.83 (d, J=7.3 Hz, 1H), 5.34 (s, 2H), 5.32-5.20 (m, 2H), 4.19 (m, 1H), 4.11-3.97 (m, 2H), 3.87 (s, 3H), 3.61-3.42 (m, 2H), 2.74-2.69 (m, 1H), 2.60-2.49 (m, 2H), 2.49 (s, 3H), 2.46 (m, 1H), 2.44 (m, 1H), 2.34 (m, 6H), 1.54 (m, 1H), 1.19 (s, 3H).

Two analytical LC/MS injections were used to determine the final purity. Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 µm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.571 min; ESI-MS (+) m/z=744.1 (M+H)

Analysis condition 2: Retention time=1.540 min; ESI-MS (+) m/z=744.1 (M+H)

Intermediate: 3-bromo-2,4-dimethylphenol

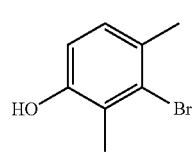

To a stirred suspension of 3-bromo-2,4-dimethylaniline (500 mg, 2.499 mmol) in 10% $H_2SO_4$ (5 mL) at 0° C. in an ice bath was added dropwise a solution of sodium nitrite (179 mg, 2.60 mmol) in water (1 mL). The reaction mixture was stirred for 1 hr. A solution of 50% $H_2SO_4$ (5 mL) was added and the mixture was heated to 100° C. and stirred for 1 hr. The reaction mixture was poured into ice water (50 mL), stirred for 30 min. The water was removed, and the residue was purified by silica gel column chromatography (Biotage 25s, EtOAc/Hexane 0-20%) to give the target compound (231 mg). This crude compound was directly used for the next step reaction without further purification.

Intermediate: 2-bromo-4-(3-chloropropoxy)-1,3-dimethylbenzene and 2-bromo-4-(3-bromopropoxy)-1,3-dimethylbenzene

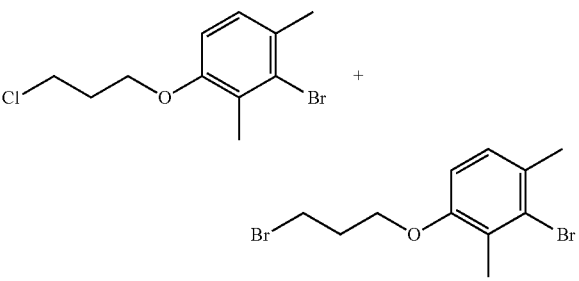

To a solution of 3-bromo-2,4-dimethylphenol (231 mg, 1.149 mmol) in DMF (7 mL) was added 1-bromo-3-chloropropane (0.113 mL, 1.149 mmol) and $K_2CO_3$ (191 mg, 1.379 mmol). The reaction mixture was stirred at 60° C. for for 19 hr. The reaction was cooled to room temperature, and diluted with EtOAc. The organic phase was washed with sat. $NaHCO_3$, water, saturated NaCl, dried over anhydrous $Na_2SO_4$, filtered and concentrated. The residue was purified by silica gel chromatography (Biotage 25m, 0-15% EtOAc/hexane) to yield 184 mg of the target compound as a clear oil which contained a mixture of 2-bromo-4-(3-chloropropoxy)-1,3-dimethylbenzene (72%) and 2-bromo-4-(3-bromopropoxy)-1,3-dimethylbenzene (28%). $^1$H NMR (400 MHz, CHLOROFORM-d) □ 7.06 (d, J=8.3 Hz, 1H), 6.76 (d, J=8.3 Hz, 1H), 4.14-4.09 (m, 2H), 3.79 (t, J=6.3 Hz, 1.43H), 3.65 (t, J=6.5 Hz, 0.57H), 2.39 (s, 3H), 2.38-2.35 (m, 3H), 2.40-2.34 (m, 0.34), 2.28 (quin, J=6.1 Hz, 1.46H).

Intermediate: (R)-1-(3-(3-bromo-2,4-dimethylphenoxy)propyl)pyrrolidin-3-ol

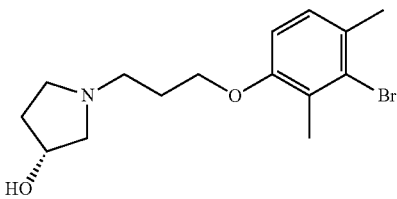 [SMILES: Cc1ccc(OCCCN2CC[C@@H](O)C2)c(C)c1Br]

A stirred mixture of 2-bromo-4-(3-chloropropoxy)-1,3-dimethylbenzene (184 mg, 0.663 mmol, the 72:28 mixture obtained above was used), (R)-pyrrolidin-3-ol, HCl (123 mg, 0.994 mmol) and K$_2$CO$_3$ (137 mg, 0.994 mmol), sodium iodide (99 mg, 0.663 mmol) in DMF (3 mL) was heated at 80° C. for 16 hrs. The solvent was removed. The residue was partitioned between EtOAc and water. The aqueous phase was extracted once with ethyl acetate. The organic extracts were combined and washed with brine then dried over sodium sulfate. The drying agent was removed by filtration and solvent removed in vacuo. The resulting crude product (262 mg) was used directly in the next step without further purification.

Example 3027: 5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile

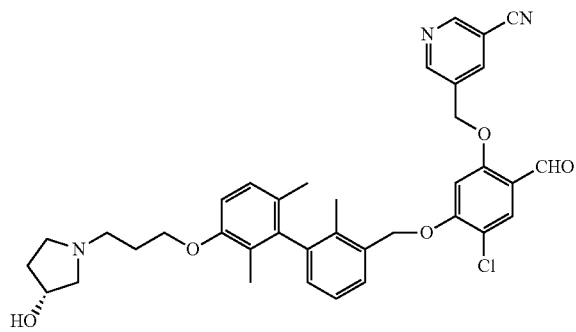 [SMILES: Cc1ccc(OCCCN2CC[C@@H](O)C2)c(C)c1-c1cccc(COc2cc(OCc3cncc(C#N)c3)c(C=O)cc2Cl)c1C]

A mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (262 mg, 0.505 mmol), (R)-1-(3-(3-bromo-2,4-dimethylphenoxy)propyl)pyrrolidin-3-ol (199 mg, 0.606 mmol), 2$^{nd}$ generation XPhos precatalyst (19.87 mg, 0.025 mmol), and 0.5M potassium phosphate tribasic (2.53 mL, 1.263 mmol) in THF (7.5 mL) was degassed, and then sealed. The mixture was stirred at rt (rt=room temperature) for 19 hrs. The solvent was removed. The residue was partitioned between dichloromethane and water. The aqueous phase was extracted once with dichloromethane. The organic extracts were combined and washed with brine then dried over Na$_2$SO$_4$. The drying agent was removed, and the filtrate was evaporated and purified by column (Biotage 25s, 0-20% MeOH/DCM) to give 240 mg (74%) of target compound. $^1$H NMR (500 MHz, DMSO-d$_6$) δ 10.23 (s, 1H), 9.04 (d, J=4.0 Hz, 2H), 8.56 (s, 1H), 7.73 (s, 1H), 7.52 (d, J=7.3 Hz, 1H), 7.33 (t, J=7.3 Hz, 1H), 7.28 (s, 1H), 7.08 (d, J=8.1 Hz, 1H), 7.00 (d, J=7.7 Hz, 1H), 6.86 (d, J=8.4 Hz, 1H), 5.49 (s, 2H), 5.44 (s, 2H), 4.18 (br. s., 1H), 4.06-3.96 (m, 2H), 2.73-2.67 (m, 1H), 2.62-2.53 (m, 3H), 2.48-2.40 (m, 1H), 2.33 (dd, J=9.0, 3.1 Hz, 1H), 2.02-1.95 (m, 1H) 1.96 (s, 3H), 1.92-1.85 (m, 2H), 1.80 (s, 3H), 1.74 (s, 3H), 1.53 (br, s, 1H).

Example 3028: (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic Acid

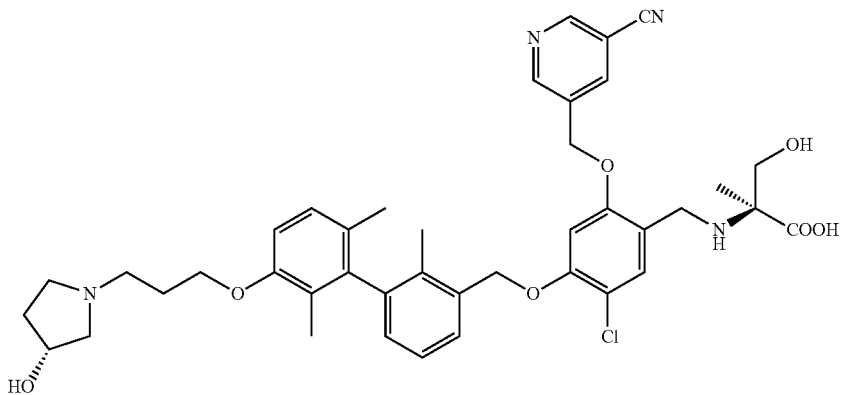 [SMILES: Cc1ccc(OCCCN2CC[C@@H](O)C2)c(C)c1-c1cccc(COc2cc(OCc3cncc(C#N)c3)c(CN[C@@](C)(CO)C(=O)O)cc2Cl)c1C]

To a suspension of 5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile (Example 3027, 40 mg, 0.062 mmol) and acetic acid (0.1 mL) in DMF (1 mL) was added 2-amino-3-hydroxy-2-methylpropanoic acid (8.93 mg, 0.075 mmol) followed by borane 2-picoline complex (17.1 mg, 0.144 mol). The mixture was stirred at rt 2 hrs. Another amount of borane 2-picoline (8.55 mg, 0.072 mol) complex was added. The mixture was stirred at rt over two days. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 22.8 mg. $^1$H NMR (500 MHz, DMSO-$d_6$) δ 9.03 (d, J=8.9 Hz, 2H), 8.52 (s, 1H), 7.54 (s, 1H), 7.47 (d, J=7.6 Hz, 1H), 7.29 (t, J=7.5 Hz, 1H), 7.13 (s, 1H), 7.08 (d, J=8.2 Hz, 1H), 6.97 (d, J=7.6 Hz, 1H), 6.86 (d, J=8.2 Hz, 1H), 5.34 (s, 2H), 5.31 (s, 2H), 4.20 (br. s., 1H), 4.01 (d, J=6.4 Hz, 3H), 3.95 (br. s., 2H), 3.64-3.58 (m, 1H), 3.53 (d, J=11.3 Hz, 1H), 2.80-2.75 (m, 1H), 2.67-2.56 (m, 4H), 2.55-2.45 (m, 1H), 2.38 (d, J=10.1 Hz, 1H), 2.03-1.92 (m, 1H), 1.95 (s, 3H), 1.79 (s, 3H), 1.73 (s, 3H), 1.55 (br. s., 1H), 1.23 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.635 min, ESI m/z 743 (M+1), 741 (M−1).

LCMS (Injection 2 conditions) Rt=1.524 min, ESI m/z 743 (M+1), 741 (M−1).

Example 3029: (2R)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic Acid (2R)-2-((5-Chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (25.6 mg, 55%) was obtained from 5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile (Example 3027) and (R)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028).

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (d, J=6.6 Hz, 2H), 8.52 (s, 1H), 7.53 (s, 1H), 7.47 (d, J=7.3 Hz, 1H), 7.30 (t, J=7.3 Hz, 1H), 7.14 (s, 1H), 7.08 (d, J=8.4 Hz, 1H), 6.97 (d, J=7.7 Hz, 1H), 6.86 (d, J=8.4 Hz, 1H), 5.33 (s, 2H), 5.31 (s, 2H), 4.19 (br. s., 1H), 4.01 (d, J=7.0 Hz, 3H), 3.95-3.90 (m, 2H), 3.60 (d, J=11.4 Hz, 1H), 3.52 (d, J=11.0 Hz, 1H), 2.76-2.69 (m, 1H), 2.66-2.54 (m, 4H), 2.47 (d, J=8.1 Hz, 1H), 2.36 (d, J=6.2 Hz, 1H), 2.04-1.93 (m, 1H), 1.95 (s, 3H), 1.80 (s, 3H), 1.73 (s, 3H), 1.54 (br. s., 1H), 1.22 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

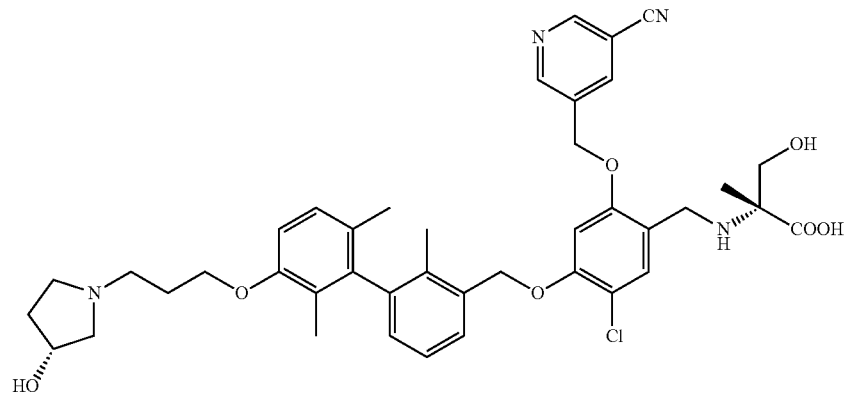 [SMILES: Cc1ccc(OCCCN2CC[C@@H](O)C2)c(C)c1-c1cccc(COc2cc(OCc3cncc(C#N)c3)c(CN[C@](C)(CO)C(=O)O)cc2Cl)c1C]

LCMS (Injection 1 conditions) Rt=1.617 min, ESI m/z 743 (M+1), 741 (M−1).

LCMS (Injection 2 conditions) Rt=1.512 min, ESI m/z 743 (M+1), 741 (M−1).

Example 3030: (2S)-1-(5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)piperidine-2-carboxylic Acid

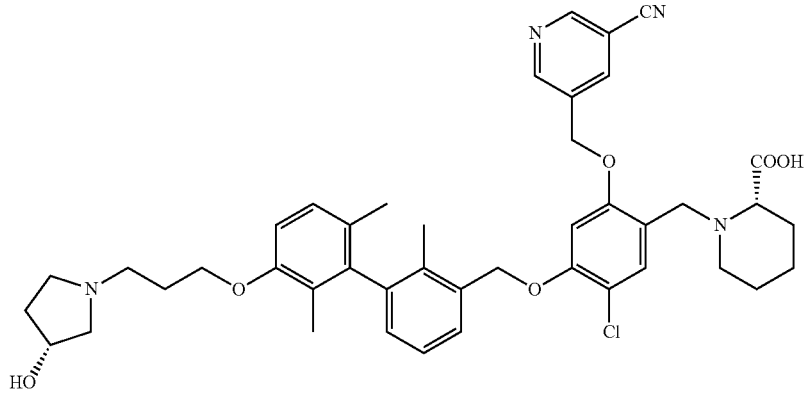 [SMILES: Cc1ccc(OCCCN2CC[C@@H](O)C2)c(C)c1-c1cccc(COc2cc(OCc3cncc(C#N)c3)c(CN3CCCC[C@H]3C(=O)O)cc2Cl)c1C]

(2S)-1-(5-Chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)piperidine-2-carboxylic acid (11.7 μmg, 23%) was obtained from 5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile (Example 3027) and (S)-piperidine-2-carboxylic acid using the procedure described for (S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.02 (s, 1H), 9.00 (s, 1H), 8.46 (s, 1H), 7.48 (d, J=7.6 Hz, 1H), 7.43 (s, 1H), 7.29 (t, J=7.8 Hz, 1H), 7.16-7.05 (m, 2H), 6.97 (d, J=7.3 Hz, 1H), 6.86-6.83 (m, 1H), 5.30 (d, J=17.4 Hz, 4H), 4.19 (br. s., 1H), 4.05-3.95 (m, 3H), 3.80 (d, J=14.0 Hz, 2H), 3.12 (br. s., 1H), 2.90 (br, s, 1H), 2.76-2.69 (m, 1H), 2.65-2.53 (m, 4H), 2.47 (d, J=7.0 Hz, 1H), 2.41-2.32 (m, 1H), 2.03-1.92 (m, 1H), 1.94 (s, 3H), 1.92-1.85 (m, 1H), 1.85-1.76 (m, 1H), 1.79 (s, 3H), 1.76-1.66 (m, 1H), 1.72 (s, 3H), 1.60-1.42 (m, 4H), 1.35 (br. s., 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.737 min, ESI m/z 753 (M+1), 751 (M−1).

LCMS (Injection 2 conditions) Rt=1.560 min, ESI m/z 753 (M+1), 751 (M−1).

Example 3031: (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxypropanoic Acid

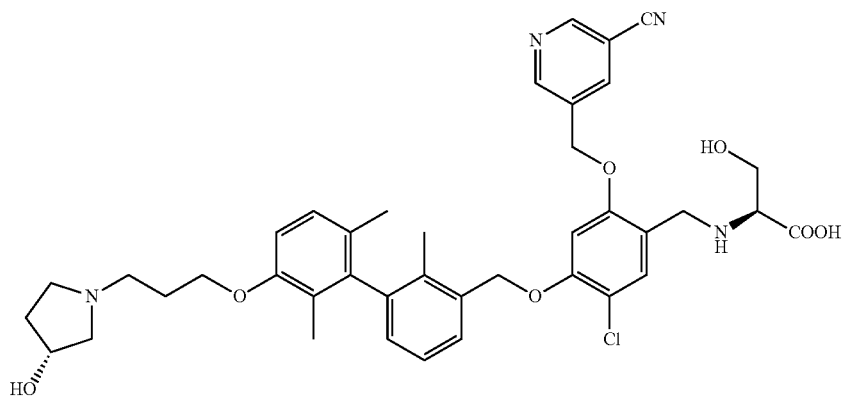 [SMILES: Cc1ccc(OCCCN2CC[C@@H](O)C2)c(C)c1-c1cccc(COc2cc(OCc3cncc(C#N)c3)c(CN[C@@H](CO)C(=O)O)cc2Cl)c1C]

(2S)-2-((5-Chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxypropanoic acid (8.7 mg, 19%) was obtained from 5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile (Example 3027) and (S)-2-amino-3-hydroxypropanoic acid using the procedure described for (S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 30 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (s, 2H), 8.53 (br. s., 1H), 7.52-7.44 (m, 2H), 7.30 (t, J=7.5 Hz, 1H), 7.17-7.11 (m, 1H), 7.08 (d, J=8.1 Hz, 1H), 6.97 (d, J=7.3 Hz, 1H), 6.88-6.83 (m, 1H), 5.38-5.30 (m, 4H), 4.19 (br. s., 1H), 4.00 (br. s., 2H), 3.90 (br. s., 2H), 3.59 (t, J=5.9 Hz, 2H), 3.08-3.00 (m, 1H), 2.76-2.66 (m, 1H), 2.64-2.53 (m, 4H), 2.55-2.38 (m, 2H), 2.34 (m, 1H), 2.05-1.90 (m, 1H), 1.95 (s, 3H), 1.80 (s, 3H), 1.73 (s, 3H), 1.54 (br. s., 1H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.546 min, ESI m/z 729 (M+1), 727 (M−1).

LCMS (Injection 2 conditions) Rt=1.488 min, ESI m/z 729 (M+1), 727 (M−1).

Intermediate: 5-chloro-2-methoxy-4-((2-methyl-3-(4,4,5,5-tetramethyl-1,3,2-dioxaborolan-2-yl)benzyl)oxy)benzaldehyde

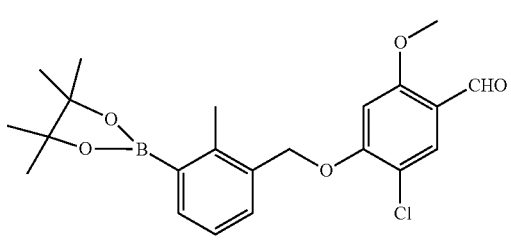 [SMILES: COc1cc(OCc2cccc(B3OC(C)(C)C(C)(C)O3)c2C)c(Cl)cc1C=O]

A suspension of 5-chloro-2-hydroxy-4-((2-methyl-3-(4,4,5,5-tetramethyl-1,3,2-dioxaborolan-2-yl)benzyl)oxy)benzaldehyde (300 mg, 0.745 mmol), iodomethane (211 mg, 1.490 mmol) and potassium carbonate (237 mg, 1.714 mmol) in DMF (3 mL) was stirred at rt overnight. The solvent was removed, and the residue (315 mg, crude) was directly used in the next reaction without further purification.

Intermediate: 5-chloro-4-((3'-(3-chloropropoxy)-2,2'-dimethyl-[1,1'-biphenyl]-3-yl)methoxy)-2-methoxybenzaldehyde and 4-((3'-(3-bromopropoxy)-2,2'-dimethyl-[1,1'-biphenyl]-3-yl)methoxy)-5-chloro-2-methoxybenzaldehyde

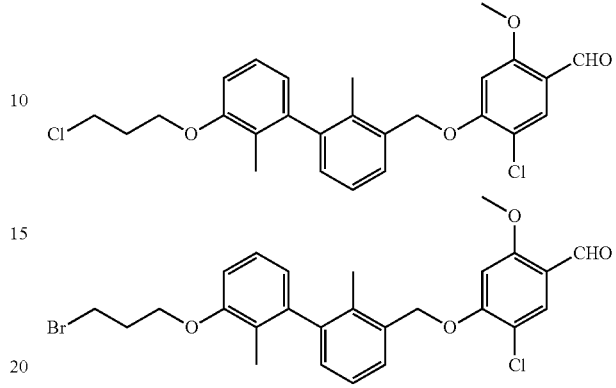

A mixture of 5-chloro-2-methoxy-4-((2-methyl-3-(4,4,5,5-tetramethyl-1,3,2-dioxaborolan-2-yl)benzyl)oxy)benzaldehyde (310 mg, 0.744 mmol, crude), 1-bromo-3-(3-chloropropoxy)-2-methylbenzene (235 mg, 0.893 mmol, the 3:1 mixture prepared above and assumed 0.893 mmol), 2$^{nd}$ generation XPhos precatalyst (29.3 mg, 0.037 mmol), and 0.5M potassium phosphate tribasic (3.72 mL, 1.860 mmol) in THF (11 mL) was degassed, and then sealed. The mixture was stirred at rt over night. The mixture was then stirred at 60° C. for 6 hrs. The solvent was removed. The residue was partitioned between dichloromethane and water. The aqueous phase was extracted once with dichloromethane. The organic extracts were combined and washed with brine and then dried over sodium sulfate. The drying agent was removed, and the residue was purified by silica gel column chromatography (Biotage 25s, EtOAc/Hexane=0 to 35%) to give 180 mg of a mixture of 5-chloro-4-((3'-(3-chloropropoxy)-2,2'-dimethyl-[1,1'-biphenyl]-3-yl)methoxy)-2-methoxybenzaldehyde and 4-((3'-(3-bromopropoxy)-2,2'-dimethyl-[1,1'-biphenyl]-3-yl)methoxy)-5-chloro-2-methoxybenzaldehyde in 75:25 ratio. $^1$H NMR (500 MHz, CHLOROFORM-d) δ 10.31-10.29 (m, 1H), 7.91-7.89 (m, 1H), 7.50 (d, J=7.4 Hz, 1H), 7.33-7.28 (m, 1H), 7.22 (t, J=7.9 Hz, 1H), 7.20-7.15 (m, 1H), 6.93-6.88 (m, 1H), 6.78 (d, J=7.6 Hz, 1H), 6.63-6.60 (m, 1H), 5.31-5.28 (m, 2H), 4.27-4.16 (m, 2H), 3.95 (s, 3H), 3.82 (t, J=6.4 Hz, 1.5H), 3.45 (t, J=6.7 Hz, 0.5H), 2.40-2.29 (m, 2H), 2.12 (s, 3H), 1.93 (s, 3H).

Example 3032: (R)-5-chloro-4-((3'-(3-(3-hydroxypyrrolidin-1-yl)propoxy)-2,2'-dimethyl-[1,1'-biphenyl]-3-yl)methoxy)-2-methoxybenzaldehyde

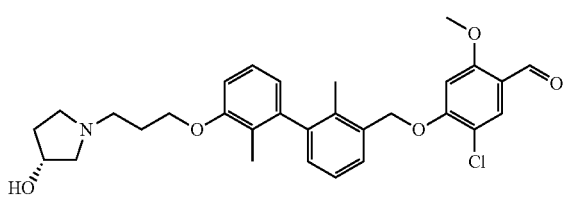 [SMILES: COc1cc(OCc2cccc(-c3cccc(OCCCN4CC[C@@H](O)C4)c3C)c2C)c(Cl)cc1C=O]

A stirred mixture of 5-chloro-4-((3'-(3-chloropropoxy)-2,2'-dimethyl-[1,1'-biphenyl]-3-yl)methoxy)-2-methoxybenzaldehyde (180 mg, 0.380 mmol, the 75:25 mixture obtained above was used), (R)-pyrrolidin-3-ol, HCl (70.5 mg, 0.570 mmol) and potassium carbonate (79 mg, 0.570 mmol), sodium iodide (57.0 mg, 0.380 mmol) in DMF (4 mL) was heated at 80° C. for 16 hrs. The solvent was removed. The residue was partitioned between EtOAc and water. The aqueous phase was extracted once with ethyl acetate. The organic extracts were combined and washed with brine then dried over sodium sulfate. The drying agent was removed by filtration and solvent removed in vacuo. The resulting residue was purified by silica gel column (Biotage 25s, 0-20% MeOH/DCM) to 179 mg (90%) of the target compound. $^1$H NMR (500 MHz, DMSO-$d_6$) δ 10.17 (s, 1H), 7.69 (s, 1H), 7.55 (d, J=7.3 Hz, 1H), 7.31 (t, J=7.5 Hz, 1H), 7.24-7.18 (m, 1H), 7.14-7.09 (m, 2H), 6.96 (d, J=8.2 Hz, 1H), 6.68 (d, J=7.0 Hz, 1H), 5.48-5.41 (m, 2H), 4.18 (br. s., 1H), 4.05 (m, 2H), 4.01 (s, 3H), 2.73-2.67 (m, 1H), 2.56-2.52 (m, 3H), 2.46-2.38 (m, 1H), 2.35-2.29 (d, J=8.9 Hz, 1H), 2.04 (s, 3H), 1.98 (dd, J=13.4, 6.7 Hz, 1H), 1.95-1.87 (s, 2H), 1.83 (s, 3H), 1.54 (br. s., 1H).

Example 3033: (2S)-2-((5-chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxy-2-methylpropanoic Acid

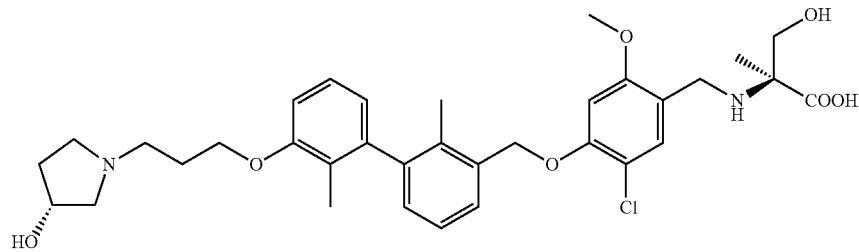 [SMILES: COc1cc(OCc2cccc(-c3cccc(OCCCN4CC[C@@H](O)C4)c3C)c2C)c(Cl)cc1CN[C@@](C)(CO)C(=O)O]

(2S)-2-((5-Chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxy-2-methylpropanoic acid (9.1 mg, 18%) was obtained from (R)-5-chloro-4-((3'-(3-(3-hydroxypyrrolidin-1-yl)propoxy)-2,2'-dimethyl-[1,1'-biphenyl]-3-yl)methoxy)-2-methoxybenzaldehyde (Example 3032) and (S)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.52 (d, J=7.3 Hz, 1H), 7.48 (s, 1H), 7.28 (t, J=7.5 Hz, 1H), 7.24-7.17 (m, 1H), 7.08 (d, J=7.7 Hz, 1H), 7.01-6.92 (m, 2H), 6.67 (d, J=7.3 Hz, 1H), 5.31 (s, 2H), 4.19 (br. s., 1H), 4.05 (d, J=9.2 Hz, 3H), 3.84 (br, s, 1H) 3.87 (s, 3H), 3.59 (d, J=11.0 Hz, 2H), 3.52 (d, J=11.0 Hz, 2H), 2.75-2.67 (m, 1H), 2.63-2.50 (m, 3H), 2.50-2.40 (m, 1H), 2.37-2.30 (m, 1H), 2.04 (s, 3H), 1.98 (dd, J=13.2, 7.0 Hz, 1H), 1.82 (s, 3H), 1.54 (br. s., 1H), 1.24 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.491 min, ESI m/z 627 (M+1), 625 (M−1).

LCMS (Injection 2 conditions) Rt=1.464 min, ESI m/z 627 (M+1).

Example 3034: (2R)-2-((5-chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxy-2-methylpropanoic Acid

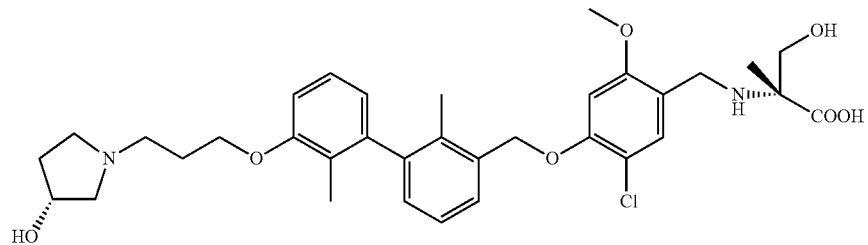 [SMILES: COc1cc(OCc2cccc(-c3cccc(OCCCN4CC[C@@H](O)C4)c3C)c2C)c(Cl)cc1CN[C@](C)(CO)C(=O)O]

(2R)-2-((5-Chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxy-2-methylpropanoic acid (2.2 mg, 4.6%) was obtained from (R)-5-chloro-4-((3'-(3-

(3-hydroxypyrrolidin-1-yl)propoxy)-2,2'-dimethyl-[1,1'-biphenyl]-3-yl)methoxy)-2-methoxybenzaldehyde (Example 3032) and (R)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.52 (d, J=8.1 Hz, 1H), 7.49 (s, 1H), 7.29 (t, J=7.2 Hz, 1H), 7.21 (t, J=7.5 Hz, 1H), 7.08 (d, J=7.0 Hz, 1H), 7.00-6.93 (m, 2H), 6.72-6.65 (m, 1H), 5.32 (s, 2H), 4.19 (br. s., 1H), 4.06 (br. s., 3H), 3.87 (s, 3H), 3.84 (d, J=14.7 Hz, 1H), 3.65-3.58 (m, 2H), 3.56-3.50 (m, 2H), 2.76-2.68 (m, 1H), 2.65-2.53 (m, 3H), 2.49-2.41 (m, 1H), 2.35 (d, J=12.1 Hz, 1H), 2.04 (s, 3H), 2.01-1.95 (m, 1H), 1.82 (s, 3H) 1.55 (d, J=4.8 Hz, 1H), 1.26 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.458 min, ESI m/z 627 (M+1), 625 (M−1).

LCMS (Injection 2 conditions) Rt=1.410 min, ESI m/z 627 (M+1).

Example 3035: (2S)-2-((5-chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxypropanoic Acid (2S)-2-((5-Chloro-4-((3'-(3-((R)-3-hydroxypyrrolidin-1-yl)propoxy)-2,2'-dimethyl-[1,1'-biphenyl]-3-yl)methoxy)-2-methoxybenzyl)amino)-3-hydroxypropanoic acid (2.4 mg, 5.0%) was obtained from (R)-5-chloro-4-((3'-(3-(3-hydroxypyrrolidin-1-yl)propoxy)-2,2'-dimethyl-[1,1'-biphenyl]-3-yl)methoxy)-2-methoxybenzaldehyde (Example 3032) and (S)-2-amino-3-hydroxypropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.52 (d, J=7.3 Hz, 1H), 7.44 (s, 1H), 7.28 (t, J=7.3 Hz, 1H), 7.20 (t, J=7.8 Hz, 1H), 7.07 (d, J=7.3 Hz, 1H), 7.01-6.93 (m, 2H), 6.68 (d, J=7.6 Hz, 1H), 5.34-5.27 (m, 2H), 4.20 (br. s., 1H), 4.05 (d, J=9.2 Hz, 2H), 3.92-3.84 (m, 1H), 3.87 (s, 3H), 2.68-2.56 (m, 2H), 3.09 (br. s., 1H), 2.74 (br. s., 1H), 2.59 (d, J=6.4 Hz, 3H), 2.47 (d, J=5.8 Hz, 1H), 2.37 (d, J=7.9 Hz, 1H), 2.03 (s, 3H), 1.98 (dd, J=13.7, 7.3 Hz, 1H), 1.95-1.88 (m, 2H), 1.82 (s, 3H), 1.56 (br. s., 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

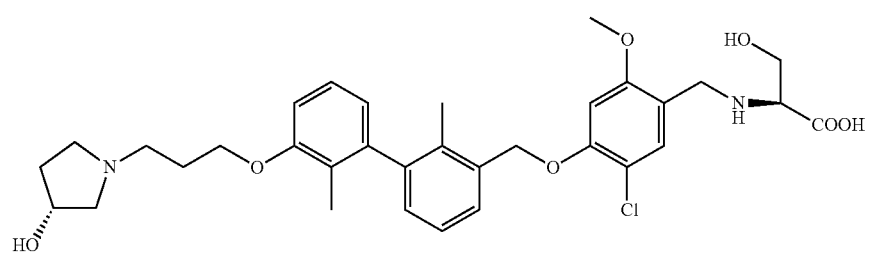 [SMILES: COc1cc(OCc2cccc(-c3cccc(OCCCN4CC[C@@H](O)C4)c3C)c2C)c(Cl)cc1CN[C@@H](CO)C(=O)O]

LCMS (Injection 1 conditions) Rt=1.428 min, ESI m/z 613 (M+1), 611 (M−1).
LCMS (Injection 2 conditions) Rt=1.380 min, ESI m/z 613 (M+1).

Example 3036: (2S)-1-(5-chloro-4-((3'-(3-((R)-3-hydroxypyrrolidin-1-yl)propoxy)-2,2'-dimethyl-[1,1'-biphenyl]-3-yl)methoxy)-2-methoxybenzyl)piperidine-2-carboxylic Acid

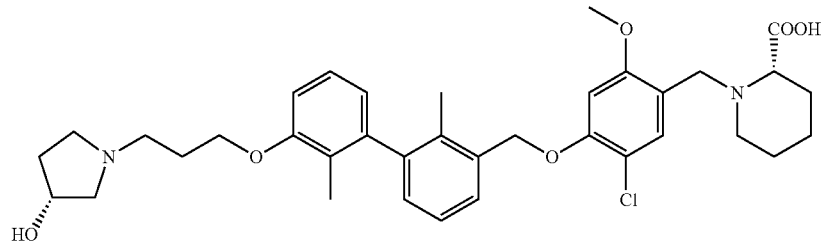 [SMILES: COc1cc(OCc2cccc(-c3cccc(OCCCN4CC[C@@H](O)C4)c3C)c2C)c(Cl)cc1CN1CCCC[C@H]1C(=O)O]

(2S)-1-(5-Chloro-4-((3'-(3-((R)-3-hydroxypyrrolidin-1-yl)propoxy)-2,2'-dimethyl-[1,1'-biphenyl]-3-yl)methoxy)-2-methoxybenzyl)piperidine-2-carboxylic acid (9.3 mg, 19%) was obtained from (R)-5-chloro-4-((3'-(3-(3-hydroxypyrrolidin-1-yl)propoxy)-2,2'-dimethyl-[1,1'-biphenyl]-3-yl)methoxy)-2-methoxybenzaldehyde (Example 3032) and (S)-piperidine-2-carboxylic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 7.52 (d, J=7.0 Hz, 1H), 7.42 (s, 1H), 7.29 (t, J=7.5 Hz, 1H), 7.21 (t, J=7.9 Hz, 1H), 7.08 (d, J=7.6 Hz, 1H), 6.99-6.90 (m, 2H), 6.68 (d, J=7.6 Hz, 1H), 5.29 (s, 2H), 4.19 (br. s., 1H), 4.05 (d, J=9.2 Hz, 2H), 3.82 (s, 3H), 3.74 (d, J=14.6 Hz, 1H), 3.61 (d, J=15.0 Hz, 1H), 3.07 (br. s., 1H), 2.95-2.86 (m, 1H), 2.75-2.69 (m, 1H), 2.63-2.54 (m, 3H), 2.45 (d, J=7.0 Hz, 1H), 2.37-2.31 (m, 1H), 2.26 (br. s., 1H), 2.04 (s, 3H), 2.01-1.94 (m, 1H), 1.94-1.86 (m, 2H), 1.85-1.78 (m, 1H), 1.82 (s, 3H), 1.70 (d, J=9.2 Hz, 1H), 1.51 (br. s., 4H), 1.35 (br. s., 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.548 min, ESI m/z 637 (M+1), 635 (M−1).
LCMS (Injection 2 conditions) RT=1.524 min, ESI m/z 637 (M+1).

Intermediate: 5-((4-chloro-2-formyl-5-((3'-(3-(3-hydroxy-3-phenylpyrrolidin-1-yl)propoxy)-2,2'-dimethyl-[1,1'-biphenyl]-3-yl)methoxy)phenoxy)methyl)nicotinonitrile

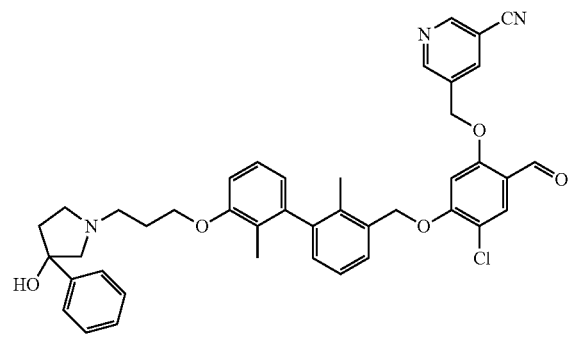 [SMILES: Cc1c(COc2cc(OCc3cncc(C#N)c3)c(C=O)cc2Cl)cccc1-c1cccc(OCCCN2CCC(O)(c3ccccc3)C2)c1C]

A stirred mixture of 5-((4-chloro-5-((3'-(3-chloropropoxy)-2,2'-dimethyl-[1,1'-biphenyl]-3-yl)methoxy)-2-formylphenoxy)methyl)nicotinonitrile (15, 125 mg, 0.217 mmol), 3-phenylpyrrolidin-3-ol (35.5 mg, 0.217 mg), K$_2$CO$_3$ (45.0 mg, 0.326 mmol), and sodium iodide (32.6 mg, 0.217 mmol) in DMF (2 mL) was heated at 80° C. for 16 hr. The solvent was removed. The residue was partitioned between EtOAc and water. The aqueous phase was extracted once with ethyl acetate. The organic extracts were combined and washed with brine and then dried over sodium sulfate. The drying agent was removed by filtration and solvent removed in vacuo. The resulting residue was purified by silica gel column chromatography (Biotage 25s, 0-20% MeOH/DCM) to give 66.4 mg (43.5%) of the target compound. $^1$H NMR (400 MHz, CHLOROFORM-d) δ 10.30 (s, 1H), 8.91 (s, 2H), 8.11 (s, 1H), 7.95 (s, 1H), 7.56-7.48 (m, 2H), 7.47-7.34 (m, 4H), 7.34-7.27 (m, 1H), 7.25-7.17 (m, 2H), 6.90 (d, J=8.3 Hz, 1H), 6.77 (d, J=7.3 Hz, 1H), 6.66 (s, 1H), 5.29 (s, 2H), 5.22 (s, 2H), 3.95-3.84 (m, 1H), 3.83-3.74 (m, 2H), 3.29 (br. s., 1H), 3.15-3.05 (m, 1H), 2.95-2.81 (m, 2H), 2.51-2.38 (m, 1H), 2.37-2.21 (m, 2H), 2.19-2.05 (m, 2H), 2.12 (s, 3H), 1.94 (s, 3H).

Example 3037: (2S)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic Acid

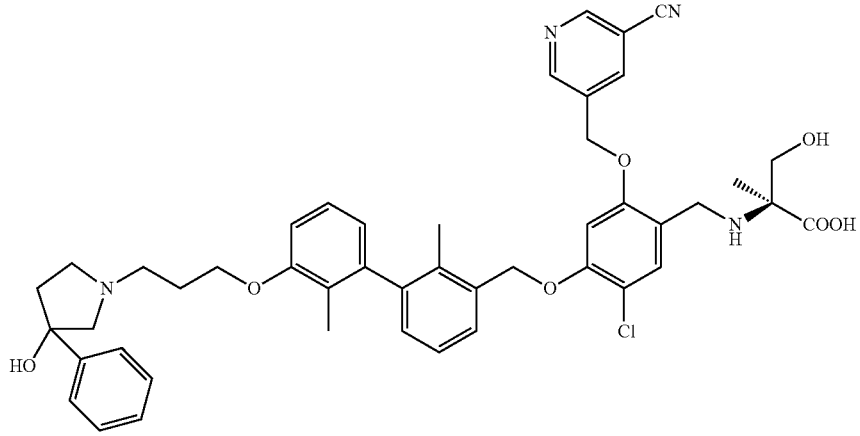 [SMILES: Cc1c(COc2cc(OCc3cncc(C#N)c3)c(CN[C@@](C)(CO)C(=O)O)cc2Cl)cccc1-c1cccc(OCCCN2CCC(O)(c3ccccc3)C2)c1C]

(2S)-2-((5-Chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic acid (5.3 mg, 6.3%) was obtained from 5-((4-chloro-2-formyl-5-((3'-(3-(3-hydroxy-3-phenylpyrrolidin-1-yl)propoxy)-2,2'-dimethyl-[1,1'-biphenyl]-3-yl)methoxy)phenoxy)methyl)nicotinonitrile and (S)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.02 (d, J=9.2 Hz, 2H), 8.51 (s, 1H), 7.55-7.44 (m, 4H), 7.32-7.16 (m, 5H), 7.13 (s, 1H), 7.07 (d, J=7.7 Hz, 1H), 6.98 (d, J=8.1 Hz, 1H), 6.68 (d, J=7.3 Hz, 1H), 5.34 (s, 2H), 5.32-5.24 (m, 2H), 4.10 (m, 2H), 3.91 (s, 2H), 3.61-3.54 (m, 1H), 3.50 (d, J=11.0 Hz, 1H), 2.90 (d, J=9.9 Hz, 1H), 2.82 (t, J=6.4 Hz, 2H), 2.76-2.62 (m, 3H), 2.16-2.06 (m, 1H), 2.06-1.99 (m, 1H), 2.03 (s, 3H), 1.95 (t, J=6.2 Hz, 2H), 1.83 (s, 3H), 1.21 (s, 3H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.794 min, ESI m/z 805 (M+1), 803 (M−1).

LCMS (Injection 2 conditions) Rt=1.608 min, ESI m/z 805 (M+1).

Example 3038: (2R)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic Acid

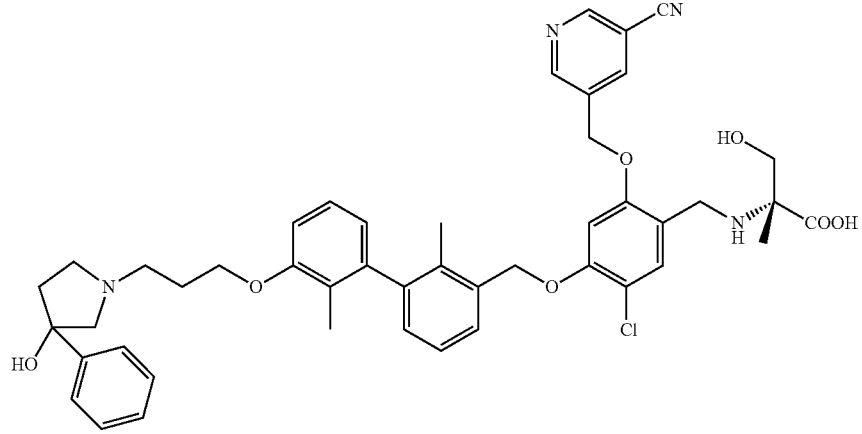 [SMILES: Cc1c(COc2cc(OCc3cncc(C#N)c3)c(CN[C@](C)(CO)C(=O)O)cc2Cl)cccc1-c1cccc(OCCCN2CCC(O)(c3ccccc3)C2)c1C]

(2R)-2-((5-Chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic acid (5.2 mg, 26%) was obtained from 5-((4-chloro-2-formyl-5-((3'-(3-(3-hydroxy-3-phenylpyrrolidin-1-yl)propoxy)-2,2'-dimethyl-[1,1'-biphenyl]-3-yl)methoxy)phenoxy)methyl)nicotinonitrile and (R)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.02 (d, J=8.4 Hz, 2H), 8.52 (s, 1H), 7.53 (s, 1H), 7.51-7.45 (m, 3H), 7.32-7.24 (m, 3H), 7.20 (dt, J=14.7, 7.3 Hz, 2H), 7.13 (s, 1H), 7.08 (d, J=7.3 Hz, 1H), 6.98 (d, J=8.4 Hz, 1H), 6.68 (d, J=7.3 Hz, 1H), 5.34 (s, 2H), 5.33-5.25 (m, 2H), 4.10 (d, J=8.1 Hz, 2H), 3.92 (s, 2H), 3.61-3.55 (m, 1H), 3.51 (d, J=11.4 Hz, 1H), 2.90 (d, J=9.5 Hz, 1H), 2.82 (t, J=6.8 Hz, 2H), 2.76-2.62 (m, 3H), 2.16-2.08 (m, 1H), 2.05-1.98 (m, 1H), 2.03 (s, 3H), 1.98-1.92 (m, 2H), 1.83 (s, 3H), 1.21 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm LCMS (Injection 1 conditions) Rt=1.788 min, ESI m/z 805 (M+1), 803 (M−1).
LCMS (Injection 2 conditions) Rt=1.614 min, ESI m/z 805 (M+1).

Example 3039: (2S)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxypropanoic Acid

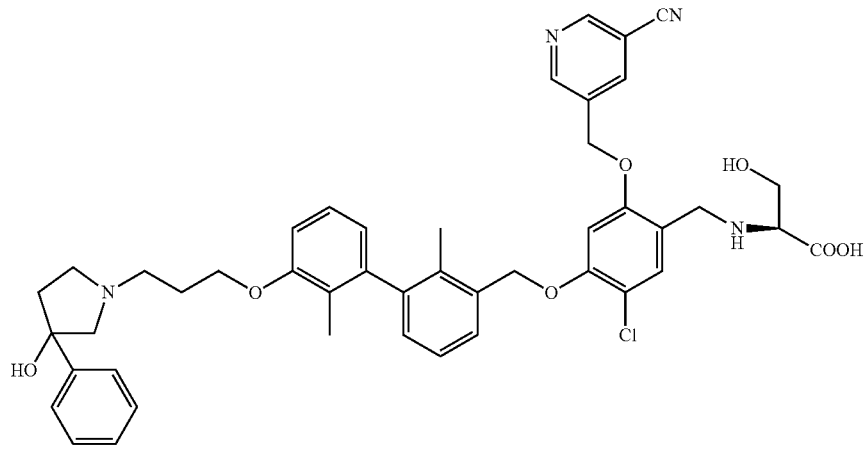 [SMILES: Cc1c(COc2cc(OCc3cncc(C#N)c3)c(CN[C@@H](CO)C(=O)O)cc2Cl)cccc1-c1cccc(OCCCN2CCC(O)(c3ccccc3)C2)c1C]

(2S)-2-((5-Chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxypropanoic acid (5 mg, 24%) was obtained from 5-((4-chloro-2-formyl-5-((3'-(3-(3-hydroxy-3-phenylpyrrolidin-1-yl)propoxy)-2,2'-dimethyl-[1,1'-biphenyl]-3-yl)methoxy)phenoxy)methyl)nicotinonitrile and (S)-2-amino-3-hydroxypropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (br. s., 2H), 8.53 (s, 1H), 7.50 (d, J=7.0 Hz, 4H), 7.33-7.25 (m, 3H), 7.24-7.17 (m, 2H), 7.14 (s, 1H), 7.08 (d, J=7.3 Hz, 1H), 6.98 (d, J=7.7 Hz, 1H), 6.69 (d, J=7.7 Hz, 1H), 5.39-5.24 (m, 4H), 4.10 (d, J=9.2 Hz, 2H), 3.96 (br. s., 2H), 3.70-3.64 (m, 1H), 3.63-3.57 (m, 1H), 3.12 (br. s., 1H), 2.93 (d, J=7.0 Hz, 1H), 2.85 (t, J=6.6 Hz, 2H), 2.80-2.66 (m, 3H), 2.18-2.10 (m, 1H), 2.06-2.00 (m, 1H), 2.03 (s, 3H), 1.96 (t, J=6.2 Hz, 2H), 1.83 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100%

B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.758 min, ESI m/z 791 (M+1).

LCMS (Injection 2 conditions) Rt=1.584 min, ESI m/z 791 (M+1).

Example 3040: (2S)-1-(5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)piperidine-2-carboxylic Acid 3H), 2.24 (br. s., 1H), 2.16-2.09 (m, 1H), 2.06-1.99 (m, 1H), 2.03 (s, 3H), 1.99-1.92 (m, 2H), 1.86-1.66 (m, 2H), 1.83 (s, 3H), 1.48 (d, J=1.5 Hz, 3H), 1.35 (d, J=1.1 Hz, 1H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

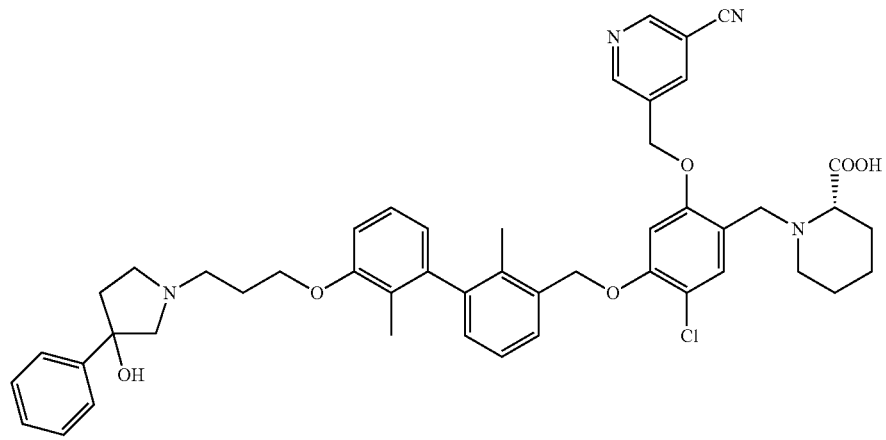 [SMILES: Cc1c(COc2cc(OCc3cncc(C#N)c3)c(CN3CCCC[C@H]3C(=O)O)cc2Cl)cccc1-c1cccc(OCCCN2CCC(O)(c3ccccc3)C2)c1C]

(2S)-1-(5-Chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)piperidine-2-carboxylic acid (5.5 mg, 28.%) was obtained from 5-((4-chloro-2-formyl-5-((3'-(3-(3-hydroxy-3-phenylpyrrolidin-1-yl)propoxy)-2,2'-dimethyl-[1,1'-biphenyl]-3-yl)methoxy)phenoxy)methyl)nicotinonitrile and (S)-piperidine-2-carboxylic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. ¹H NMR (500 MHz, DMSO-d₆) δ 9.00 (d, J=7.0 Hz, 2H), 8.46 (s, 1H), 7.49 (d, J=7.3 Hz, 3H), 7.43 (s, 1H), 7.28 (q, J=7.2 Hz, 3H), 7.24-7.14 (m, 2H), 7.11 (s, 1H), 7.08 (d, J=7.3 Hz, 1H), 6.98 (d, J=8.1 Hz, 1H), 6.69 (d, J=7.3 Hz, 1H), 5.35 (s, 2H), 5.29 (br. s., 2H), 4.10 (dd, J=7.2, 0.9 Hz, 2H), 3.77 (d, J=13.2 Hz, 1H), 3.58 (d, J=13.6 Hz, 1H), 3.10 (d, J=1.8 Hz, 1H), 2.95-2.85 (m, 2H), 2.82 (t, J=6.4 Hz, 2H), 2.77-2.62 (m, LCMS (Injection 1 conditions) Rt=1.824 min, ESI m/z 815 (M+1), 813 (M−1).

LCMS (Injection 2 conditions) Rt=1.650 min, ESI m/z 815 (M+1).

Intermediate: 5-methyl-2,3-dihydrobenzo[b][1,4]dioxine

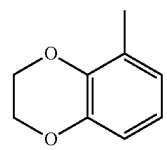

A mixture of 3-methylbenzene-1,2-diol (4 g, 32.2 mmol), 1,2-dibromoethane (24.21 g, 129 mmol), potassium carbonate (8.91 g, 64.4 mmol) in ethylene glycol (160 mL) was heated to 130° C. under N₂ for 48 hrs. The reaction mixture was cooled to rt, and poured into brine (320 mL). The mixture was extracted with EtOAc. The organic layer was washed with brine, dried over Mg₂SO₄, and the solvent was removed. The residue was purified by silica gel column chromatography (Biotage 40m, EtOAc/Hexane=0 to 40%) to give 1.02 g (21.8%) of the target compound. ¹H NMR (500 MHz, CHLOROFORM-d) δ 6.79-6.71 (m, 3H), 4.34-4.30 (m, 2H), 4.29-4.25 (m, 2H), 2.23 (s, 3H).

Intermediate: 6-bromo-5-methyl-2,3-dihydrobenzo[b][1,4]dioxine

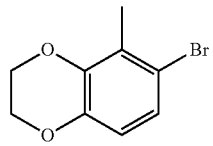

5-Methyl-2,3-dihydrobenzo[b][1,4]dioxine (500 mg, 3.33 mmol) was dissolved in acetonitrile (6.5 mL), and N-brompsuccinimide (711 mg, 4.00 mmol) was added. The mixture was stirred at rt for 4 days. The reaction mixture was poured into sat. $Na_2CO_3$. The mixture was extracted with EtOAc. The organic layer was evaporated, and the residue was purified by silica gel column chromatography (Biotage 25s, EtOAc/Hexane=0 to 30%) to give (525 mg, 69%) of the target compound. $^1$H NMR (400 MHz, CHLOROFORM-d) δ 7.03 (d, J=8.8 Hz, 1H), 6.64 (dd, J=8.8, 0.5 Hz, 1H), 4.32-4.28 (m, 2H), 4.27-4.22 (m, 2H), 2.29 (s, 3H).

Intermediate: 5-((4-chloro-2-formyl-5-((2-methyl-3-(5-methyl-2,3-dihydrobenzo[b][1,4]dioxin-6-yl)benzyl)oxy)phenoxy)methyl)nicotinonitrile

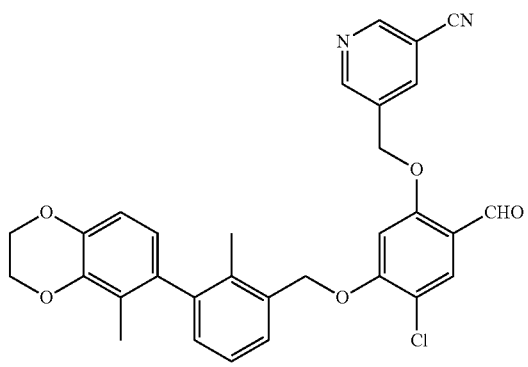 [SMILES: Cc1c(COc2cc(OCc3cncc(C#N)c3)c(C=O)cc2Cl)cccc1-c1ccc2c(c1C)OCCO2]

A mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (200 mg, 0.386 mmol), 6-bromo-5-methyl-2,3-dihydrobenzo[b][1,4]dioxine (106 mg, 0.463 mmol), 2nd generation XPhos precatalyst (15.17 mg, 0.019 mmol), and 0.5M potassium phosphate tribasic (1.928 mL, 0.964 mmol) in THF (6 mL) was degassed, and then sealed. The mixture was stirred at room temperature over two days. The solvent was removed. The residue was partitioned between dichloromethane and water. The aqueous phase was extracted once with dichloromethane. The organic extracts were combined and washed with brine then dried over sodium sulfate. The drying agent was removed, and the residue was purified by silica gel column chromatography (Biotage 25s, methanol/$CH_2Cl_2$=0 to 20%) to give the target compound (210 mg). $^1$H NMR (500 MHz, DMSO-d$_6$) δ 10.24 (s, 1H), 9.04 (d, J=2.9 Hz, 2H), 8.56 (s, 1H), 7.74 (s, 1H), 7.51 (d, J=7.3 Hz, 1H), 7.36-7.21 (m, 2H), 7.10 (d, J=7.7 Hz, 1H), 6.77 (d, J=8.4 Hz, 1H), 6.57 (d, J=8.4 Hz, 1H), 5.49 (s, 2H), 5.42 (d, J=2.9 Hz, 2H), 4.41-4.22 (m, 4H), 2.05 (s, 3H), 1.81 (s, 3H).

Example 3041: (2S)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic Acid

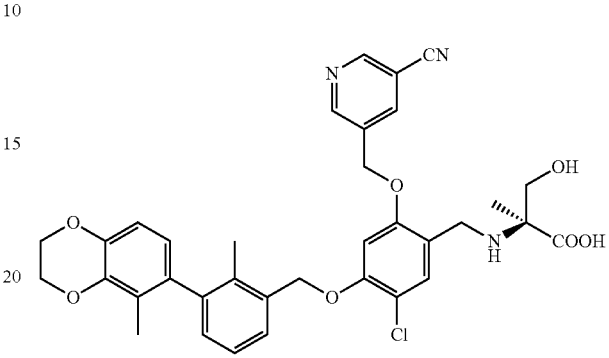

(S)-2-((5-Chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic acid (6.3 mg, 14%) was obtained from 5-((4-chloro-2-formyl-5-((2-methyl-3-(5-methyl-2,3-dihydrobenzo[b][1,4]dioxin-6-yl)benzyl)oxy)phenoxy)methyl)nicotinonitrile and (S)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.03 (d, J=7.7 Hz, 2H), 8.52 (s, 1H), 7.54 (s, 1H), 7.46 (d, J=7.3 Hz, 1H), 7.24 (t, J=7.7 Hz, 1H), 7.13 (s, 1H), 7.07 (d, J=7.3 Hz, 1H), 6.77 (d, J=8.4 Hz, 1H), 6.56 (d, J=8.4 Hz, 1H), 5.35 (s, 2H), 5.32-5.25 (m, 2H), 4.37-4.24 (m, 4H), 3.94 (s, 2H), 3.62-3.57 (m, 1H), 3.52 (d, J=11.0 Hz, 1H), 2.05 (s, 3H), 1.81 (s, 3H), 1.22 (s, 3H).

Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.983 min, ESI m/z 644 (M+1), 642 (M−1).

LCMS (Injection 2 conditions) Rt=1.650 min, ESI m/z 642 (M+1).

Example 3042: (2R)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic Acid

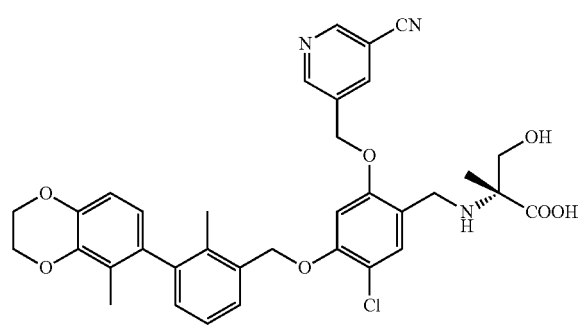 [SMILES: Cc1c(COc2cc(OCc3cncc(C#N)c3)c(CN[C@](C)(CO)C(=O)O)cc2Cl)cccc1-c1ccc2c(c1C)OCCO2]

(2R)-2-((5-Chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic acid (6.3 mg, 14%) was obtained from 5-((4-chloro-2-formyl-5-((2-methyl-3-(5-methyl-2,3-dihydrobenzo[b][1,4]dioxin-6-yl)benzyl)oxy)phenoxy)methyl)nicotinonitrile and (R)-2-amino-3-hydroxy-2-methylpropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.02 (d, J=8.1 Hz, 2H), 8.52 (s, 1H), 7.54 (s, 1H), 7.46 (d, J=7.3 Hz, 1H), 7.24 (t, J=7.7 Hz, 1H), 7.13 (s, 1H), 7.06 (d, J=7.3 Hz, 1H), 6.77 (d, J=8.4 Hz, 1H), 6.56 (d, J=8.4 Hz, 1H), 5.35 (s, 2H), 5.28 (br. s., 2H), 4.37-4.30 (m, 2H), 4.29-4.23 (m, 2H), 3.93 (s, 2H), 3.62-3.56 (m, 1H), 3.52 (d, J=11.4 Hz, 1H), 2.05 (s, 3H), 1.80 (s, 3H), 1.22 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.977 min, ESI m/z 644 (M+1), 642 (M−1).

LCMS (Injection 2 conditions) Rt=1.896 min, ESI m/z 644 (M+1), 642 (M−1).

Example 3043: (2S)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxypropanoic Acid

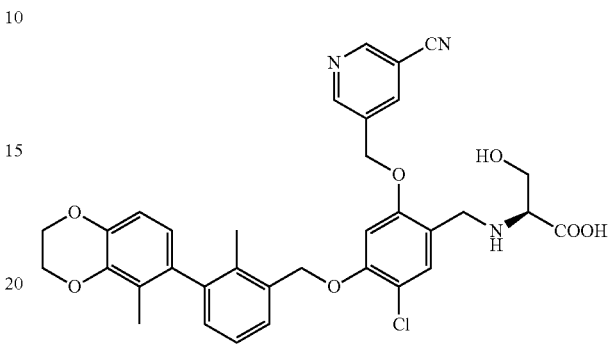

(2S)-2-((5-Chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxypropanoic acid (2 mg, 4.5%) was obtained from 5-((4-chloro-2-formyl-5-((2-methyl-3-(5-methyl-2,3-dihydrobenzo[b][1,4]dioxin-6-yl)benzyl)oxy)phenoxy)methyl)nicotinonitrile and (S)-2-amino-3-hydroxypropanoic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters CSH c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (d, J=5.9 Hz, 2H), 8.49 (s, 1H), 7.56 (s, 1H), 7.47 (d, J=7.7 Hz, 1H), 7.25 (t, J=7.5 Hz, 1H), 7.16 (s, 1H), 7.08 (d, J=7.7 Hz, 1H), 6.77 (d, J=8.1 Hz, 1H), 6.56 (d, J=8.4 Hz, 1H), 5.40-5.26 (m, 4H), 4.38-4.23 (m, 4H), 4.19-4.09 (m, 2H), 3.86-3.74 (m, 2H), 3.67 (br. s., 1H), 2.05 (s, 3H), 1.81 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×

50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.851 min, ESI m/z 630 (M+1).

LCMS (Injection 2 conditions) Rt=1.872 min, ESI m/z 630 (M+1).

Example 3044: (2S)-1-(5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)piperidine-2-carboxylic Acid

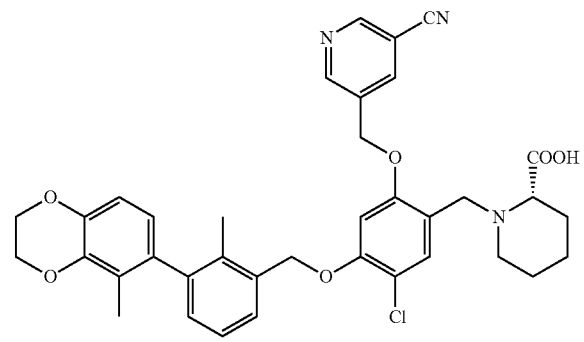

(2S)-1-(5-Chloro-2-((5-cyanopyridin-3-yl)methoxy)-4-((2-methyl-3-(5-methyl-2,3-dihydrobenzo[b][1,4]dioxin-6-yl)benzyl)oxy)benzyl)piperidine-2-carboxylic acid (1.4 mg, 2.9%) was obtained from 5-((4-chloro-2-formyl-5-((2-methyl-3-(5-methyl-2,3-dihydrobenzo[b][1,4]dioxin-6-yl)benzyl)oxy)phenoxy)methyl)nicotinonitrile and (S)-piperidine-2-carboxylic acid using the procedure described for (2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid (Example 3028). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.01 (d, J=8.8 Hz, 2H), 8.46 (s, 1H), 7.47 (d, J=7.3 Hz, 1H), 7.43 (s, 1H), 7.25 (t, J=7.5 Hz, 1H), 7.11 (s, 1H), 7.07 (d, J=7.7 Hz, 1H), 6.77 (d, J=8.4 Hz, 1H), 6.57 (d, J=8.4 Hz, 1H), 5.37-5.29 (m, 2H), 5.29-5.22 (m, 2H), 4.37-4.23 (m, 4H), 3.79 (d, J=13.9 Hz, 1H), 3.61 (d, J=13.9 Hz, 1H), 3.11 (br. s., 1H), 2.88 (br. s., 1H), 2.28 (br. s., 1H), 2.05 (s, 3H), 1.83-1.76 (m, 1H), 1.81 (s, 3H), 1.72 (br. s., 1H), 1.49 (br. s., 3H), 1.36 (br. s., 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.031 min, ESI m/z 654 (M+1), 652 (M−1).

LCMS (Injection 2 conditions) Rt=1.962 min, ESI m/z 654 (M+1).

Example 3045 to Example 3072 were prepared as described below.

Intermediate: 1,3-dibromo-5-(3-chloropropoxy)benzene and 1,3-dibromo-5-(3-bromopropoxy)benzene

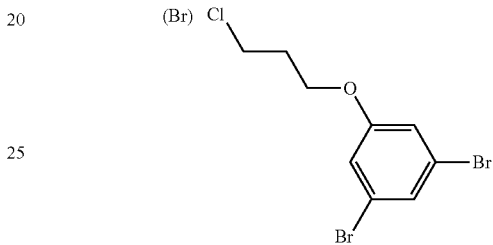

To 3,5-dibromophenol (2 g, 7.94 mmol) in DMF (27 ml) was added 1-bromo-3-chloropropane (0.781 ml, 7.94 mmol) and potassium carbonate (1.097 g, 7.94 mmol). The flask was sealed and the mixture stirred overnight at room temperature. The reaction mixture was further diluted with 60 mL of DCM, washed with 6 mL of water, brine, dried over sodium sulfate, filtered, and evaporated under a stream of nitrogen to give an oil. The crude product was purified via Biotage (0 to 10% DCM/hexane, 20 CVs; 80 g Isco silica gel cartridge) to give 1.98 g (63% yield) of a 5.6:1 mixture of 1,3-dibromo-5-(3-chloropropoxy)benzene and 1,3-dibromo-5-(3-bromopropoxy)benzene. $^1$H NMR (500 MHz, CDCl$_3$) δ 7.27 (m, 1H), 7.02 (m, 2H), 4.13-4.08 (m, 2H), 3.73 (t, J=6.15 Hz, 1.7H), 3.59 (t, J=6.15 Hz, 0.3H), 2.34-2.29 (m, 0.3H), 2.26-2.21 (m, 1.7H). (CV=column volume)

Intermediate: 1-bromo-3-(3-chloropropoxy)-5-(phenylethynyl)benzene and 1-bromo-3-(3-bromopropoxy)-5-(phenylethynyl)benzene

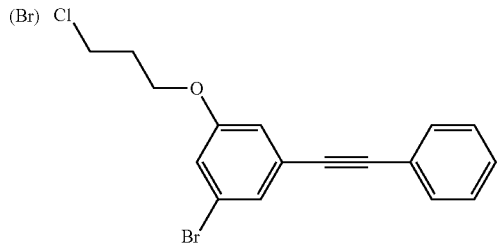

To a sealed tube was added THF (4.0 mL), the above mixture of 1,3-dibromo-5-(3-chloropropoxy) benzene and 1,3-dibromo-5-(3-bromopropoxy)benzene (300 mg, 0.913 mmol (the number of mmols was based on the major product, the chloride), ethynylbenzene (70.2 μl, 0.639 mmol), copper(I) iodide (3.48 mg, 0.018 mmol), palladium tetrakis(triphenylphosphine) (21.1 mg, 0.018 mmol), and triethylamine (1.4 mL, 9.96 mmol). The mixture was degassed/flushed with nitrogen then heated overnight at 80° C. The reaction mixture was cooled, concentrated to an oil, then taken up in 6 mL of acetonitrile, and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a XTERRA 5 □m C18 30×100 mm column at a gradient of 30-100% B and a flow rate of 40 mL/min. over 15 minutes with a 10 minute hold to give 143 mgs (34% yield) of a mixture of 1-bromo-3-(3-chloropropoxy)-5-(phenylethynyl)benzene and 1-bromo-3-(3-bromopropoxy)-5-(phenylethynyl)benzene as a clear colorless oil. $^1$H NMR (500 MHz, CDCl$_3$) δ 7.53 (m, 2H), 7.36 (m, 3H), 7.30 (t, J=1.5 Hz, 1H), 7.06 (t, J=2.0 Hz, 1H), 7.01 (m, 1H), 4.14 (m, 2H), 3.75 (m, 1.7H), 3.61 (m, 0.3H), 2.33 (m, 0.3H), 2.25 (m, 1.7H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.410 min., m/z 351.0 (M+H), m/z 701.1 (2M+H).

Intermediate: (R)-1-(3-(3-bromo-5-(phenylethynyl)phenoxy)propyl) pyrrolidin-3-ol

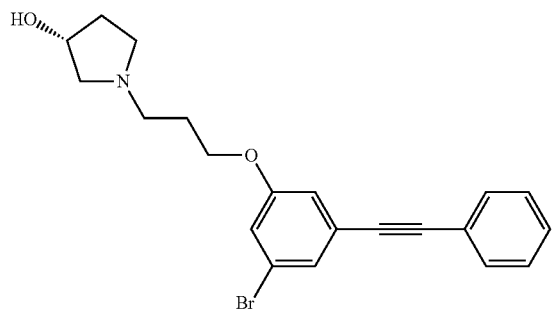 [SMILES: O[C@@H]1CCN(CCCOc2cc(Br)cc(C#Cc3ccccc3)c2)C1]

To a small sealed tube was added the above product mixture, 1-bromo-3-(3-chloropropoxy)-5-(phenylethynyl)benzene and 1-bromo-3-(3-bromopropoxy)-5-(phenylethynyl)benzene (143 mg, 0.409 mmol, based on the chloride compound), DMF (8 mL), (R)-pyrrolidin-3-ol hydrochloride (197.1 mg, 1.60 mmol), sodium iodide (92 mg, 0.613 mmol), and potassium carbonate (141 mg, 1.022 mmol). The tube was sealed and the mixture heated at 50° C. for four days. The mixture was cooled, concentrated to an yellow oily residue, taken up in 50 mL of 1:1 EtOAc/DCM, washed with water, brine, dried over sodium sulfate, filtered, and evaporated to give 196 mgs (96% yield) of (R)-1-(3-(3-bromo-5-(phenylethynyl)phenoxy)propyl) pyrrolidin-3-ol as a yellow solid. $^1$H NMR (500 MHz, CDCl$_3$) δ 7.52 (m, 2H), 7.36 (m, 3H), 7.28-7.24 (m, 1H), 7.06 (m, 1H), 7.03 (m, 1H), 4.37 (m, 1H), 4.04 (m, 2H), 2.92 (m, 1H), 2.72 (d, J=9.8 Hz, 1H), 2.64 (t, J=7.3 Hz, 1H), 2.56 (m, 1H), 2.45 (t, J=7.2 Hz, 1H), 2.37-2.29 (m, 1H), 2.26-2.16 (m, 1H), 2.08-1.92 (m, 2H), 1.82-1.72 (m, 1H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.522 min., m/z 402.2 (M+H).

Intermediate; (R)-5-((4-chloro-2-formyl-5-((3'-(3-(3-hydroxypyrrolidin-1-yl)propoxy)-2-methyl-5'-(phenylethynyl)-[1,1'-biphenyl]-3-yl)methoxy)phenoxy) methyl)nicotinonitrile

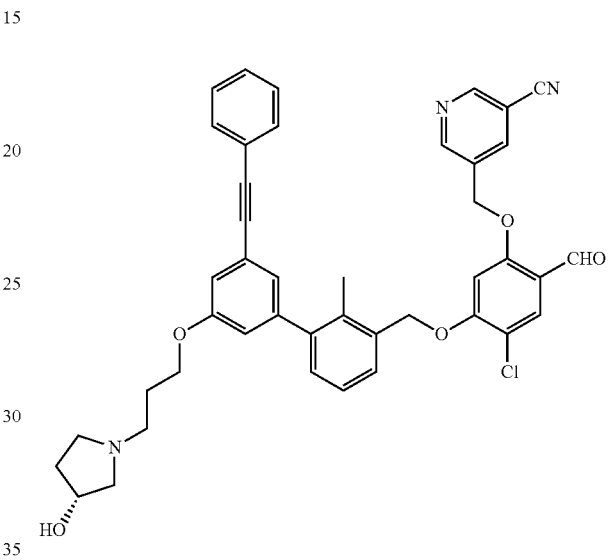

To a sealed tube was added (R)-1-(3-(3-bromo-5-(phenylethynyl)phenoxy)propyl)pyrrolidin-3-ol (100 mg, 0.250 mmol), 5-((4-chloro-2-formyl-5-((2-methyl-3-(4,4,5,5-tetramethyl-1,3,2-dioxaborolan-2-yl)benzyl)oxy)phenoxy) methyl)nicotinonitrile (130 mg, 0.250 mmol), THF (9.0 mL), water (3.0 mL), potassium phosphate tribasic (106 mg, 0.500 mmol), and second generation X-Phos precatalyst (9.83 mg, 0.012 mmol). The tube was sealed, the reaction mixture de-gassed/flushed with nitrogen then heated overnight at 80° C. The reaction mixture was diluted with 40 mL of DCM, washed with water, brine, dried over sodium sulfate, filtered, and evaporated to a yellow oil. The crude product was taken up in 6 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a XTERRA 5 um C18 30×100 mm column at a gradient of 40-100% B and a flow rate of 40 mL/min. over 15 minutes with a 10 minute hold to give 103.1 mgs (48%) of (R)-5-((4-chloro-2-formyl-5-((3'-(3-(3-hydroxypyrrolidin-1-yl)propoxy)-2-methyl-5'-(phenylethynyl)-[1,1'-biphenyl]-3-yl) methoxy)phenoxy) methyl)nicotinonitrile, TFA, as a white solid. $^1$H NMR (500 MHz, DMSO-d$_6$) δ 10.25 (s, 1H), 9.05 (m, 2H), 8.56 (t, J=2.0 Hz, 1H), 7.75 (s, 1H), 7.57 (m, 3H), 7.45 (m, 3H), 7.40-7.27 (m, 3H), 7.17 (m, 1H), 7.09 (m, 1H), 6.94 (m, 1H), 5.51 (s, 2H), 5.44 (s, 2H), 4.51-4.38 (m, 1H), 4.16 (t, J=5.9 Hz, 2H), 3.44-3.06 (m, 5H), 2.84 (m, 2H), 2.27 (s, 3H), 2.14 (m, 2H), 2.05-1.85 (m, 1H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.803 min., m/z 712.3 (M+H).

Example 3045: (R)-2-((5-chloro-2-((5-cyanopyridin-3-yl)methoxy)-4-((3'-(3-((R)-3-hydroxypyrrolidin-1-yl)propoxy)-2-methyl-5'-(phenylethynyl)-[1,1'-biphenyl]-3-yl)methoxy)benzyl)amino)-3-hydroxy-2-methylpropanoic Acid trile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

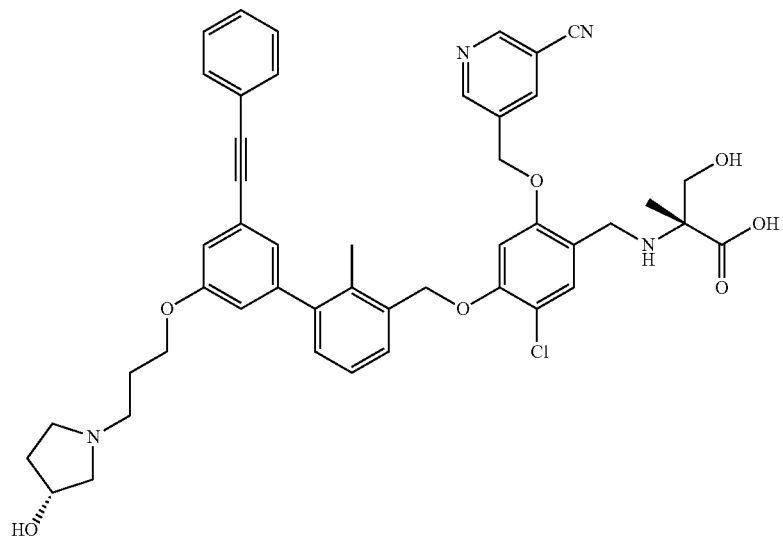 [SMILES: Cc1c(COc2cc(OCc3cncc(C#N)c3)c(CN[C@](C)(CO)C(=O)O)cc2Cl)cccc1-c1cc(C#Cc2ccccc2)cc(OCCCN2CC[C@@H](O)C2)c1]

To a screw capped vial was added DMF (1.0 mL), acetic acid (50 μL), (R)-5-((4-chloro-2-formyl-5-((3'-(3-(3-hydroxypyrrolidin-1-yl)propoxy)-2-methyl-5'-(phenylethynyl)-[1,1'-biphenyl]-3-yl)methoxy)phenoxy)methyl)nicotinonitrile, TFA (25.0 mg, 0.030 mmol), (R)-2-amino-3-hydroxy-2-methylpropanoic acid (9.01 mg, 0.076 mmol), and borane-2-picoline complex (3.88 mg, 0.036 mmol). The vial was capped and the mixture shaken overnight at room temperature. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 35-75% B over 15 minutes with a 5-minute hold at a flow rate of 20 mL/minute. Fractions containing the desired product were combined and dried via centrifugal evaporation. The yield of the product was 4.6 mg (17% yield), and its estimated purity by LCMS analysis was 92%. $^1$H NMR (500 MHz, DMSO-$d_6$) δ 9.09-8.93 (m, 2H), 8.51 (s, 1H), 7.63-7.40 (m, 7H), 7.37-7.20 (m, 2H), 7.13 (d, J=5.1 Hz, 2H), 7.03 (s, 1H), 6.89 (s, 1H), 5.36 (s, 2H), 5.29 (s, 2H), 4.18 (m, 1H), 4.11 (t, J=6.2 Hz, 2H), 3.95-3.82 (m, 3H), 3.54-3.44 (m, 1H), 2.70 (m, 1H), 2.61-2.53 (m, 1H), 2.49-2.40 (m, 2H), 2.32 (d, J=8.8 Hz, 1H), 2.26 (s, 3H), 2.16 (m, 1H), 1.96 (m, 1H), 1.87 (m, 2H), 1.54 (m, 1H), 1.20 (s, 3H).
Two analytical LC/MS injections were used to determine the final purity.
Injection 1 conditions: Waters Acquity UPLC BEH 1.7 μm C18, 2.1×50 mm where mobile phase A was 5:95 acetoni- Analysis condition 1: Retention time=1.850 min; ESI-MS (+) m/z=815.1 (M+H)

Analysis condition 2: Retention time=1.784 min; ESI-MS (+) m/z=815.1 (M+H)

Intermediate: (1R,5S)-3-(3-(3-bromo-2-methylphenoxy)propyl)-8-oxa-3-azabicyclo[3.2.1]octane

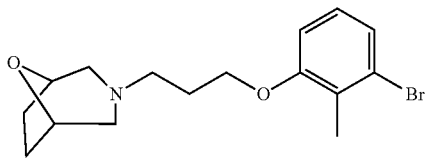 [SMILES: Cc1c(Br)cccc1OCCCN1CC2CCC(C1)O2]

To a small sealed tube was added 8-oxa-3-azabicyclo [3.2.1]octane hydrochloride (77 mg, 0.512 mmol), DMF (5.0 mL), the mixture of 1-bromo-3-(3-chloropropoxy)-2-methylbenzene and 1-bromo-3-(3-bromopropoxy)-2-methylbenzene (90 mg, 0.341 mmol, based on mol. weight of the chloride), sodium iodide (77 mg, 0.512 mmol), and potassium carbonate (118 mg, 0.854 mmol). The vessel was sealed and the mixture stirred overnight at 80° C. The reaction mixture was further diluted with 10 mL of water and pushed through a Waters 1 g HLB extraction cartridge. The cartridge was flushed with 30 mL of water, the product eluted with 30 mL of methanol. The methanol mixture was pushed through a 1 g Waters MCX cartridge. The cartridge was flushed with 30 mL of methanol, the product eluted with 30 mL of 2M ammonia in methanol. The volatiles were removed under a stream of nitrogen to give 80 mg (62% yield) of (1R,5S)-3-(3-(3-bromo-2-methylphenoxy)propyl)-8-oxa-3-azabicyclo[3.2.1]octane as a tan solid. $^1$H NMR (500 MHz, CDCl$_3$) δ 7.15 (d, J=8.1 Hz, 1H), 7.00 (t, J=8.1 Hz, 1H), 6.79 (d, J=8.1 Hz, 1H), 4.29 (m, 2H), 4.02 (t, J=6.3 Hz, 2H), 2.59 (d, J=10.9 Hz, 2H), 2.48 (t, J=7.0 Hz, 2H), 2.36-2.29 (m, 5H), 2.00-1.79 (m, 6H). The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 1 minute hold at a rate of 0.8 mL/minute. LCMS rt=1.154 min., m/z 340.00 & 341.85 (M+H).

Intermediate: 5-((5-((3'-(3-((1R,5S)-8-oxa-3-azabicyclo[3.2.1]octan-3-yl) propoxy)-2,2'-dimethyl-[1,1'-biphenyl]-3-yl)methoxy)-4-chloro-2-formylphenoxy)methyl) nicotinonitrile.TFA

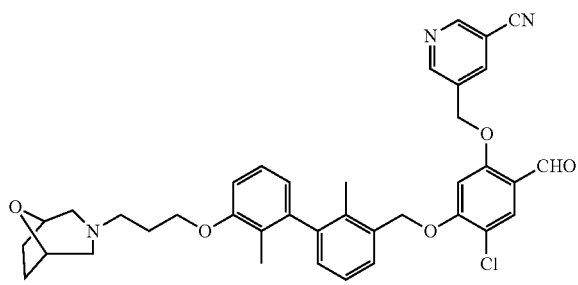 [SMILES: Cc1c(COc2cc(OCc3cncc(C#N)c3)c(C=O)cc2Cl)cccc1-c1cccc(OCCCN2CC3CCC(C2)O3)c1C]

To a sealed tube was added (1R,5S)-3-(3-(3-bromo-2-methylphenoxy)propyl)-8-oxa-3-azabicyclo[3.2.1]octane (36.1 mg, 0.106 mmol), THF (6.0 mL), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (50 mg, 0.096 mmol), potassium phosphate tribasic (51.1 mg, 0.241 mmol), water (2.0 mL), and second generation X-Phos precatalyst (3.79 mg, 4.82 μmol). The vessel was sealed, the mixture de-gassed/flushed with nitrogen, then heated overnight at 80° C. The crude mixture was cooled to room temperature then concentrated under a stream of nitrogen. The crude product was diluted with 25 mL of ethyl acetate, extracted, washed with water, brine, dried over magnesium sulfate, filtered through diatomaceous earth (Celite®) and evaporated to a yellow oil. The crude reaction mixture was taken up in 3.8 mL of acetonitrile and 200 uL DMF and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 um C18 19×50 mm column at a gradient of 30-100% B and a flow rate of 25 mL/min. over 10 minutes with a 5 minute hold to give 35.0 mgs (40% yield) of 5-((5-((3'-(3-((1R,5S)-8-oxa-3-azabicyclo[3.2.1]octan-3-yl) propoxy)-2,2'-dimethyl-[1,1'-biphenyl]-3-yl)methoxy)-4-chloro-2-formylphenoxy)methyl) nicotinonitrile TFA salt as a tan solid. $^1$H NMR (500 MHz, CDCl$_3$) δ 10.28 (s, 1H), 8.94 (br. s., 2H), 8.16 (s, 1H), 7.94 (s, 1H), 7.45 (d, J=7.4 Hz, 1H), 7.32-7.28 (m, 1H), 7.17 (m, 2H), 6.79 (m, 2H), 6.65 (s, 1H), 5.28 (s, 2H), 5.24 (s, 2H), 4.55 (s, 2H), 4.08 (m, 2H), 3.69 (dd, J=11.8, 3.8 Hz, 2H), 3.34 (m, 2H), 3.05 (m, 2H), 2.37-2.20 (m, 4H), 2.20-2.10 (m, 2H), 2.08 (s, 3H), 1.87 (s, 3H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS rt=1.557 min., m/z 653.35 (M+H).

Example 3046: (S)-1-(4-((3'-(3-((1R,5S)-8-oxa-3-azabicyclo[3.2.1]octan-3-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

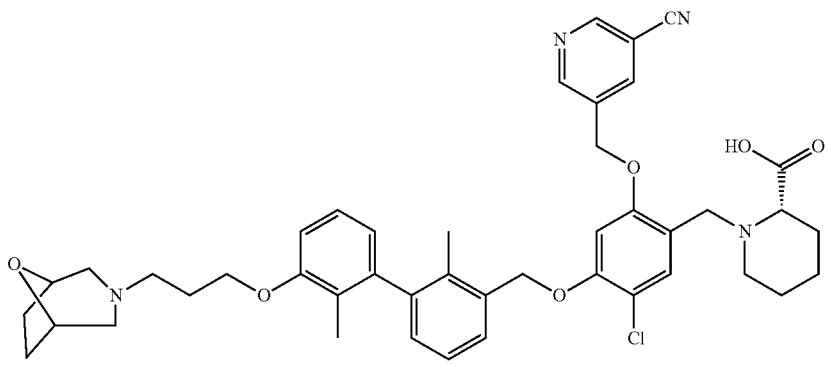 [SMILES: Cc1c(COc2cc(OCc3cncc(C#N)c3)c(CN3CCCC[C@H]3C(=O)O)cc2Cl)cccc1-c1cccc(OCCCN2CC3CCC(C2)O3)c1C]

To a small RBF was added 5-((5-((3'-(3-((1R,5S)-8-oxa-3-azabicyclo[3.2.1]octan-3-yl) propoxy)-2,2'-dimethyl-[1,1'-biphenyl]-3-yl)methoxy)-4-chloro-2-formylphenoxy)methyl) nicotinonitrile TFA salt (35 mgs, 0.046 mmol), DMF (90 uL), acetic acid (100 uL), L-pipecolic acid (8.85 mg, 0.069 mmol), and borane-2-picoline complex (9.77 mg, 0.091 mmol). The flask was sealed and the mixture stirred overnight at room temperature. To the mixture was again added 1-pipecolic acid (8.85 mg, 0.069 mmol) followed by borane-2-picoline complex (9.77 mg, 0.091 mmol). The mixture stirred at room temperature for four days. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 45-85% B over 20 minutes with a 3 minute hold at a flow rate of 20 mL/minute. Fractions containing the desired product were combined and dried via centrifugal evaporation. The yield of the product was 10.8 mg (29%), and its estimated purity by LCMS analysis was 95%. $^1$H NMR (500 MHz, DMSO-$d_6$) δ 9.00 (m, 2H), 8.45 (s, 1H), 7.49 (d, J=7.3 Hz, 1H), 7.44 (s, 1H), 7.27 (t, J=7.5 Hz, 1H), 7.21 (t, J=7.9 Hz, 1H), 7.14-7.05 (m, 2H), 6.97 (d, J=8.2 Hz, 1H), 6.68 (d, J=7.6 Hz, 1H), 5.33 (br. s., 2H), 5.27 (s, 2H), 4.20 (br. s., 2H), 4.06 (q, J=6.1 Hz, 2H), 3.79 (m, 1H), 3.61 (m, 1H), 3.40 (m, 3H), 3.14-3.09 (m, 1H), 2.90 (m, 1H), 2.61-2.53 (m, 2H), 2.43 (m, 1H), 2.33-2.23 (m, 1H), 2.15 (m, 2H), 2.03 (s, 3H), 1.93-1.84 (m, 2H), 1.84-1.75 (m, 5H), 1.69 (m, 3H), 1.49 (m, 2H), 1.40-1.31 (m, 1H). Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.996 min; ESI-MS (+) m/z=766.1 (M+H)

Analysis condition 2: Retention time=1.850 min; ESI-MS (+) m/z=766.1 (M+H)

Example 3047 to Example 3052 were synthesized in a similar fashion as Example 3046.

Intermediate: (R)-(4-(3-(3-bromo-2-methylphenoxy)propyl)morpholin-2-yl)methanol

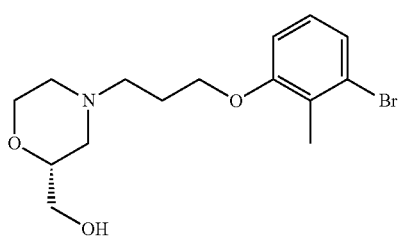 [SMILES: Cc1c(Br)cccc1OCCCN1CCO[C@@H](CO)C1]

(R)-(4-(3-(3-bromo-2-methylphenoxy)propyl)morpholin-2-yl)methanol was obtained (90.8 mgs, 63% yield) as a white solid. $^1$H NMR (500 MHz, CDCl$_3$) δ 7.15 (d, J=8.1 Hz, 1H), 6.99 (t, J=8.1 Hz, 1H), 6.77 (d, J=8.1 Hz, 1H), 4.01 (t, J=6.2 Hz, 2H), 3.96-3.90 (m, 1H), 3.75-3.63 (m, 3H), 3.62-3.56 (m, 1H), 2.81-2.70 (m, 2H), 2.60-2.51 (m, 2H), 2.31 (s, 3H), 2.18 (td, J=11.3, 3.3 Hz, 2H), 2.05-1.96 (m, 2H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.195 min., m/z 343.95 & 346.00 (M+H).

Intermediate: (R)-5-((4-chloro-2-formyl-5-((3'-(3-(2-(hydroxymethyl)morpholino)propoxy)-2,2'-dimethyl-[1,1'-biphenyl]-3-yl)methoxy)phenoxy)methyl)nicotinonitrile TFA

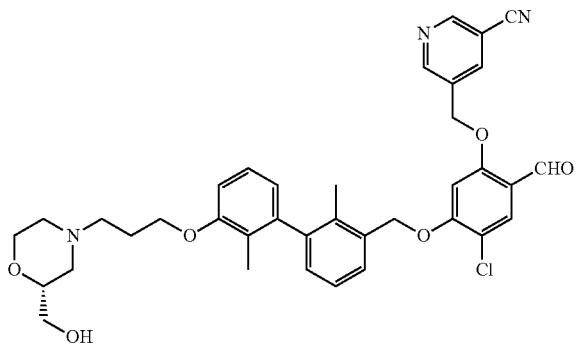 [SMILES: Cc1c(COc2cc(OCc3cncc(C#N)c3)c(C=O)cc2Cl)cccc1-c1cccc(OCCCN2CCO[C@@H](CO)C2)c1C]

(R)-5-((4-chloro-2-formyl-5-((3'-(3-(2-(hydroxymethyl)morpholino)propoxy)-2,2'-dimethyl-[1,1'-biphenyl]-3-yl)methoxy)phenoxy)methyl)nicotinonitrile TFA salt was obtained (39.4 mgs, 32% yield) as a tan solid. $^1$H NMR (500 MHz, CDCl$_3$) δ 10.27 (s, 1H), 8.93 (m, 2H), 8.18 (s, 1H), 7.93 (s, 1H), 7.44 (m, 1H), 7.29 (m, 1H), 7.21 (m, 1H), 7.15 (d, J=7.4 Hz, 1H), 6.86-6.76 (m, 2H), 6.65 (br. s., 1H), 5.32-5.19 (m, 4H), 4.12 (m, 2H), 4.02 (m, 2H), 3.87 (m, 2H), 3.69 (m, 1H), 3.39 (m, 1H), 3.27 (m, 1H), 3.12 (m, 1H), 2.96 (m, 1H), 2.34 (m, 2H), 2.12-2.08 (m, 4H), 1.89 (m, 4H). The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 1 minute hold at a rate of 0.8 mL/minute. LCMS rt=1.489 min., m/z 657.35 (M+H).

Example 3047 (S)-1-(5-chloro-2-((5-cyanopyridin-3-yl)methoxy)-4-((3'-(3-((R)-2-(hydroxymethyl)morpholino) propoxy)-2,2'-dimethyl-[1,1'-biphenyl]-3-yl)methoxy)benzyl)piperidine-2-carboxylic Acid

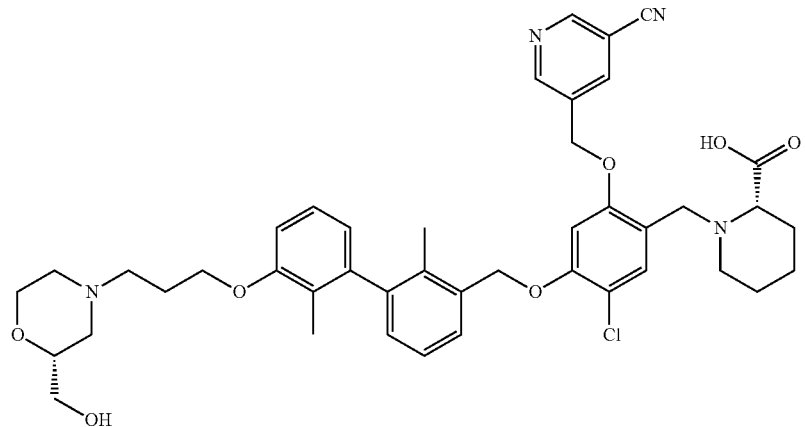 [SMILES: Cc1c(COc2cc(OCc3cncc(C#N)c3)c(CN3CCCC[C@H]3C(=O)O)cc2Cl)cccc1-c1cccc(OCCCN2CCO[C@@H](CO)C2)c1C]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 28-68% B over 17 minutes with a 3 minute hold at a flow rate of 20 mL/minute. Fractions containing the desired product were combined and dried via centrifugal evaporation. The yield of the product was 8.7 mg (22%), and its estimated purity by LCMS analysis was 98%. $^1$H NMR (500 MHz, DMSO-$d_6$) δ 9.00 (m, 2H), 8.46 (s, 1H), 7.49 (d, J=7.3 Hz, 1H), 7.43 (s, 1H), 7.27 (t, J=7.5 Hz, 1H), 7.21 (t, J=7.9 Hz, 1H), 7.14-7.06 (m, 2H), 6.96 (d, J=7.9 Hz, 1H), 6.68 (d, J=7.6 Hz, 1H), 5.33 (s, 2H), 5.26 (s, 2H), 4.07 (m, 2H), 3.77 (m, 2H), 3.62 (m, 2H), 3.51 (m, 1H), 3.31 (m, 2H), 3.11 (m, 1H), 2.93-2.80 (m, 2H), 2.70 (m, 1H), 2.49-2.43 (m, 3H), 2.27 (m, 1H), 2.09-1.96 (m, 4H), 1.96-1.87 (m, 1H), 1.87-1.66 (m, 5H), 1.49 (m, 3H), 1.36 (m, 1H).

Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.
Analysis condition 1: Retention time=1.621 min; ESI-MS (+) m/z=770.2 (M+H)

Analysis condition 2: Retention time=1.425 min; ESI-MS (+) m/z=770.4 (M+H)

Intermediate: (1R,5S)-8-(3-(3-bromo-2-methylphenoxy)propyl)-8-azabicyclo[3.2.1]octan-3-ol

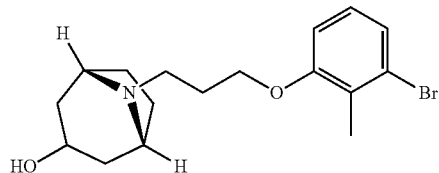 [SMILES: Cc1c(Br)cccc1OCCCN1[C@@H]2CC[C@H]1CC(O)C2]

(1R,5S)-8-(3-(3-bromo-2-methylphenoxy)propyl)-8-azabicyclo[3.2.1]octan-3-ol was obtained (104.8 mgs, 78% yield) as a white solid. $^1$H NMR (500 MHz, CDCl$_3$) δ 7.14 (dd, J=8.2, 0.8 Hz, 1H), 7.02-6.96 (m, 1H), 6.78 (d, J=8.2 Hz, 1H), 4.07-4.00 (m, 3H), 3.23-3.15 (m, 2H), 2.56-2.50 (m, 2H), 2.31 (s, 3H), 2.13-2.05 (m, 4H), 2.00-1.91 (m, 4H), 1.70-1.63 (m, 2H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS rt=1.232 min., m/z 354.05 & 356.00 (M+H).

Intermediate: 5-((4-chloro-2-formyl-5-((3'-(3-((1R,5S)-3-hydroxy-8-azabicyclo[3.2.1]octan-8-yl)propoxy)-2,2'-dimethyl-[1,1'-biphenyl]-3-yl)methoxy)phenoxy)methyl)nicotinonitrile TFA

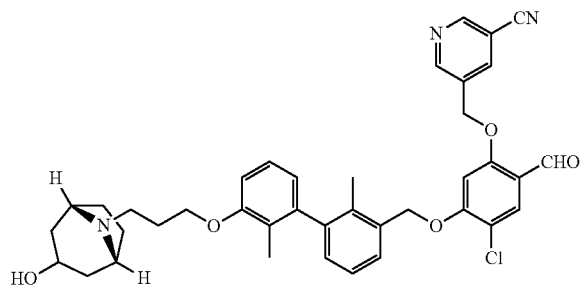 [SMILES: Cc1c(COc2cc(OCc3cncc(C#N)c3)c(C=O)cc2Cl)cccc1-c1cccc(OCCCN2[C@@H]3CC[C@H]2CC(O)C3)c1C]

5-((4-chloro-2-formyl-5-((3'-(3-((1R,5S)-3-hydroxy-8-azabicyclo[3.2.1]octan-8-yl)propoxy)-2,2'-dimethyl-[1,1'-biphenyl]-3-yl)methoxy)phenoxy)methyl)nicotinonitrile TFA salt was obtained (49.7 mgs, 40% yield) as a tan solid. $^1$H NMR (500 MHz, CDCl$_3$) δ 10.27 (s, 1H), 8.94 (m, 2H), 8.17 (s, 1H), 7.93 (s, 1H), 7.45 (d, J=7.6 Hz, 1H), 7.29 (m, 1H), 7.21 (t, J=7.7 Hz, 1H), 7.15 (d, J=7.6 Hz, 1H), 6.86-6.75 (m, 2H), 6.67 (s, 1H), 5.30-5.23 (m, 4H), 4.26-3.89 (m, 3H), 3.22 (m, 2H), 2.68-2.54 (m, 4H), 2.31 (m, 2H), 2.16 (m, 2H), 2.12-1.99 (m, 5H), 1.87 (s, 3H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.550 min., m/z 667.35 (M+H).

Example 3048: (2S)-1-(5-chloro-2-((5-cyanopyridin-3-yl)methoxy)-4-((3'-(3-((1R,5S)-3-hydroxy-8-azabicyclo[3.2.1]octan-8-yl)propoxy)-2,2'-dimethyl-[1,1'-biphenyl]-3-yl)methoxy)benzyl)piperidine-2-carboxylic Acid The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 20-60% B over 17 minutes with a 3 minute hold at a flow rate of 20 mL/minute. Fractions containing the desired product were combined and dried via centrifugal evaporation. The yield of the product was 9.8 mg (20%), and its estimated purity by LCMS analysis was 99%. $^1$H NMR (500 MHz, DMSO-d$_6$) δ 9.07-8.94 (m, 2H), 8.45 (s, 1H), 7.49 (d, J=7.3 Hz, 1H), 7.43 (s, 1H), 7.27 (t, J=7.6 Hz, 1H), 7.20 (t, J=7.9 Hz, 1H), 7.08 (m, 2H), 6.96 (d, J=8.2 Hz, 1H), 6.68 (d, J=7.3 Hz, 1H), 5.32 (s, 2H), 5.27 (s, 2H), 4.08 (m, 3H), 3.84-3.74 (m, 3H), 3.59 (m, 2H), 3.18-3.06 (m, 2H), 2.93-2.85 (m, 1H), 2.30-2.21 (m, 1H), 2.08-1.99 (m, 4H), 1.96-1.84 (m, 6H), 1.84-1.75 (m, 6H), 1.75-1.67 (m, 1H), 1.64-1.29 (m, 5H), 1.35 (m, 1H).
Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Analysis condition 1: Retention time=1.455 min; ESI-MS (+) m/z=780.2 (M+H)
Analysis condition 2: Retention time=2.783 min; ESI-MS (+) m/z=780.2 (M+H)

Intermediate: (2R,6S)-4-(3-(3-bromo-2-methylphenoxy)propyl)-2,6-dimethylmorpholine was obtained (91.8 mgs, 66% yield) as a Tan Solid

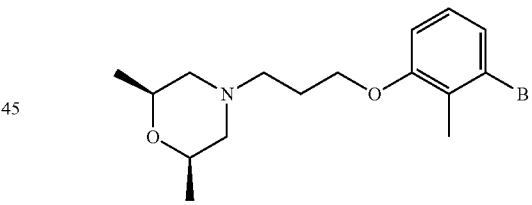

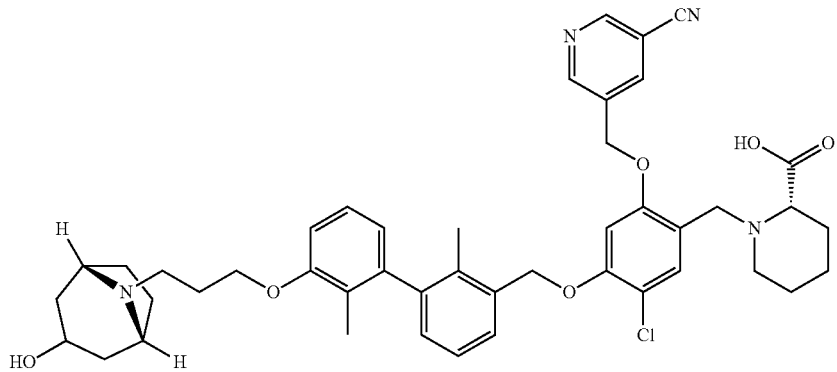 [SMILES: Cc1c(COc2cc(OCc3cncc(C#N)c3)c(CN3CCCC[C@H]3C(=O)O)cc2Cl)cccc1-c1cccc(OCCCN2[C@@H]3CC[C@H]2CC(O)C3)c1C]

(2R,6S)-4-(3-(3-bromo-2-methylphenoxy)propyl)-2,6-dimethylmorpholine was obtained (91.8 mgs, 66% yield) as a tan solid. $^1$H NMR (500 MHz, CDCl$_3$) δ 7.15 (m, 1H), 7.00 (m, 1H), 6.78 (m, 1H), 4.01 (m, 2H), 3.69 (m, 2H), 2.77 (m, 2H), 2.52 (m, 2H), 2.32 (s, 3H), 2.00 (m, 2H), 1.87-1.50 (m, 2H), 1.18 (m, 6H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.915 min., m/z 342.00 & 344.00 (M+H).

Intermediate: 5-((4-chloro-5-((3'-(3-((2R,6S)-2,6-dimethylmorpholino)propoxy)-2,2'-dimethyl-[1,1'-biphenyl]-3-yl)methoxy)-2-formylphenoxy)methyl)nicotinonitrile TFA

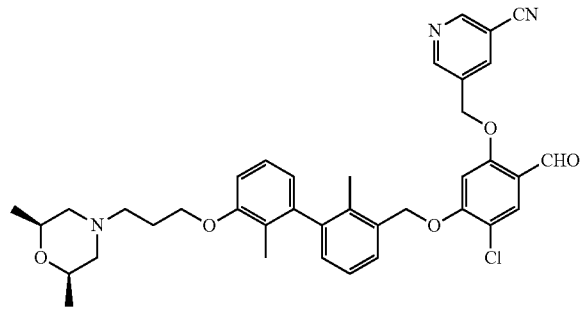 [SMILES: Cc1c(COc2cc(OCc3cncc(C#N)c3)c(C=O)cc2Cl)cccc1-c1cccc(OCCCN2C[C@@H](C)O[C@@H](C)C2)c1C]

5-((4-Chloro-5-((3'-(3-((2R,6S)-2,6-dimethylmorpholino)propoxy)-2,2'-dimethyl-[1,1'-biphenyl]-3-yl)methoxy)-2-formylphenoxy)methyl)nicotinonitrile TFA salt was obtained (38.2 mgs, 46% yield) as a tan solid. $^1$H NMR (CDCl$_3$) δ 10.28 (s, 1H), 8.94 (br. s., 2H), 8.15 (s, 1H), 7.93 (s, 1H), 7.45 (d, J=7.4 Hz, 1H), 7.34-7.26 (m, 1H), 7.21 (t, J=7.9 Hz, 1H), 7.16 (d, J=7.1 Hz, 1H), 6.80 (m, 2H), 6.65 (s, 1H), 5.27 (s, 2H), 5.24 (s, 2H), 4.12 (m, 2H), 4.03 (m, 2H), 3.62 (d, J=11.3 Hz, 2H), 3.33 (m, 2H), 2.45 (t, J=10.4 Hz, 2H), 2.34 (m, 2H), 2.09 (s, 3H), 1.88 (s, 3H), 1.27 (d, J=6.3 Hz, 6H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.512 min., m/z 654.35 & 655.35 (M+H).

Example 3049: (S)-1-(5-chloro-2-((5-cyanopyridin-3-yl)methoxy)-4-((3'-(3-((2S,6R)-2,6-dimethylmorpholino)propoxy)-2,2'-dimethyl-[1,1'-biphenyl]-3-yl)methoxy)benzyl)piperidine-2-carboxylic Acid

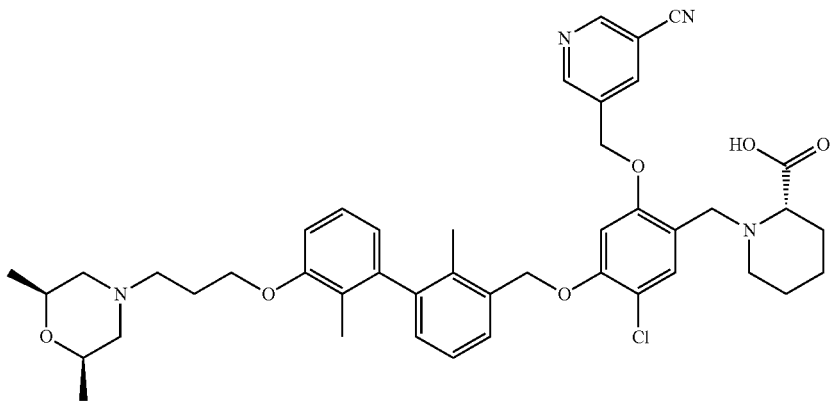 [SMILES: Cc1c(COc2cc(OCc3cncc(C#N)c3)c(CN3CCCC[C@H]3C(=O)O)cc2Cl)cccc1-c1cccc(OCCCN2C[C@@H](C)O[C@@H](C)C2)c1C]

The crude oil was taken up in methanol and was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 40-80% B over 18 minutes with a 3-minute hold at a flow rate of 20 mL/minute. Fractions containing the desired product were combined and dried via centrifugal evaporation. The yield of the product was 4.4 mg (5%) as the bis-TFA salt, and its estimated purity by LCMS analysis was 97%. $^1$H NMR (500 MHz, DMSO-d$_6$) δ 9.00 (m, 2H), 8.45 (s, 1H), 7.49 (d, J=7.3 Hz, 1H), 7.44 (s, 1H), 7.27 (t, J=7.6 Hz, 1H), 7.21 (t, J=7.9 Hz, 1H), 7.12-7.04 (m, 2H), 6.96 (d, J=8.2 Hz, 1H), 6.68 (d, J=7.6 Hz, 1H), 5.32 (s, 2H), 5.25 (s, 2H), 4.11-3.97 (m, 2H), 3.76 (d, J=14.0 Hz, 2H), 3.54 (m, 2H), 2.99 (m, 1H), 2.87 (m, 1H), 2.76 (d, J=10.7 Hz, 2H), 2.44 (t, J=7.0 Hz, 2H), 2.16 (m, 1H), 2.03 (s, 3H), 1.96-1.89 (m, 2H), 1.87 (m, 1H), 1.82 (s, 3H), 1.72 (m, 1H), 1.63-1.55 (m, 2H), 1.45 (m, 2H), 1.36-1.26 (m, 2H), 1.04 (d, J=6.4 Hz, 6H).
Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.146 min; ESI-MS (+) m/z=768.1 (M+H)

Analysis condition 2: Retention time=1.642 min; ESI-MS (+) m/z=768.1 (M+H)

Intermediate: (4-(3-(3-bromo-2-methylphenoxy) propyl)morpholin-3-yl)methanol was Obtained

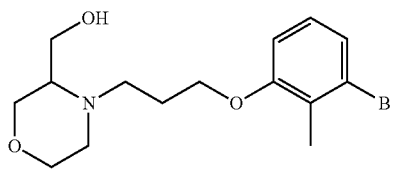

(4-(3-(3-bromo-2-methylphenoxy)propyl)morpholin-3-yl)methanol was obtained (60.0 mgs, 46% yield) as a tan solid. $^1$H NMR (500 MHz, CDCl$_3$) δ 7.16 (d, J=7.4 Hz, 1H), 7.03-6.97 (m, 1H), 6.80-6.76 (m, 1H), 4.08-3.98 (m, 2H), 3.90-3.79 (m, 3H), 3.67-3.57 (m, 2H), 3.45 (dd, J=11.4, 2.3 Hz, 1H), 3.10 (m, 1H), 2.92 (dt, J=11.8, 2.8 Hz, 1H), 2.53-2.41 (m, 3H), 2.35-2.30 (s, 3H), 2.02 (m, 2H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.112 min., m/z 343.95 & 345.90 (M+H).

Intermediate: 5-((4-chloro-2-formyl-5-((3'-(3-(3-(hydroxymethyl)morpholino)propoxy)-2,2'-dimethyl-[1,1'-biphenyl]-3-yl)methoxy)phenoxy)methyl) nicotinonitrile TFA Salt

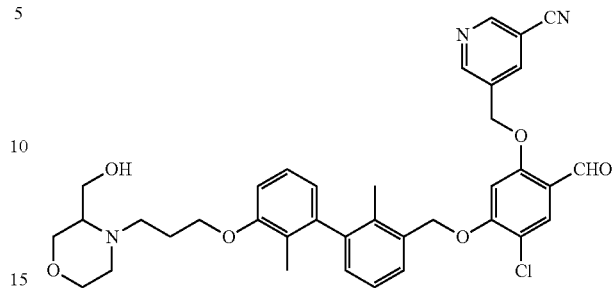

5-((4-chloro-2-formyl-5-((3'-(3-(3-(hydroxymethyl)morpholino)propoxy)-2,2'-dimethyl-[1,1'-biphenyl]-3-yl)methoxy)phenoxy)methyl)nicotinonitrile TFA salt was obtained (39.6 mgs, 48% yield) as a tan solid. $^1$H NMR (500 MHz, CDCl$_3$) δ 10.27 (s, 1H), 8.93 (m, 2H), 8.18 (s, 1H), 7.93 (s, 1H), 7.44 (m, 1H), 7.29 (m, 1H), 7.21 (m, 1H), 7.15 (d, J=7.4 Hz, 1H), 6.86-6.76 (m, 2H), 6.65 (br. s., 1H), 5.32-5.19 (m, 4H), 4.12 (m, 2H), 4.02 (m, 2H), 3.87 (m, 2H), 3.69 (m, 1H), 3.39 (m, 1H), 3.27 (m, 1H), 3.12 (m, 1H), 2.96 (m, 1H), 2.34 (m, 2H), 2.12-2.08 (m, 4H), 1.89 (m, 4H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.526 min., m/z 656.35 & 657.35 (M+H).

Example 3050: (2S)-1-(5-chloro-2-((5-cyanopyridin-3-yl)methoxy)-4-((3'-(3-(3-(hydroxymethyl) morpholino)propoxy)-2,2'-dimethyl-[1,1'-biphenyl]-3-yl)methoxy)benzyl)piperidine-2-carboxylic Acid

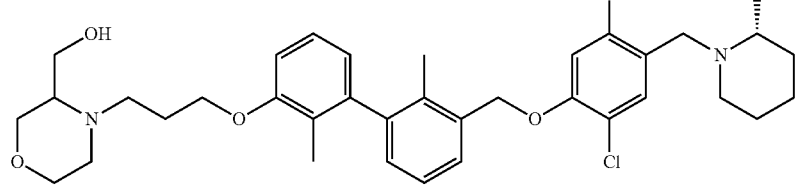

The crude oil was taken up in methanol and was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 18-58% B over 20 minutes with a 5-minute hold at a flow rate of 20 mL/minute. Fractions containing the desired product were combined and dried via centrifugal evaporation. The yield of the product was 12.9 mg (20%) as the bis-TFA salt, and its estimated purity by LCMS analysis was 94%. $^1$H NMR (500 MHz, DMSO-d$_6$) δ 9.01 (m, 2H), 8.46 (s, 1H), 7.49 (d, J=7.3

Hz, 1H), 7.42 (s, 1H), 7.28 (t, J=7.5 Hz, 1H), 7.24-7.18 (m, 1H), 7.12 (s, 1H), 7.08 (d, J=7.3 Hz, 1H), 6.97 (d, J=8.2 Hz, 1H), 6.69 (d, J=7.3 Hz, 1H), 5.33 (s, 2H), 5.27 (s, 2H), 4.05 (m, 2H), 3.83-3.70 (m, 2H), 3.70-3.57 (m, 5H), 3.16 (m, 3H), 3.03-2.85 (m, 2H), 2.81-2.68 (m, 1H), 2.44-2.26 (m, 3H), 2.04 (s, 3H), 1.92 (m, 2H), 1.87-1.70 (m, 5H), 1.49 (m, 3H), 1.38 (m, 1H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.812 min; ESI-MS (+) m/z=770.1 (M+H)

Analysis condition 2: Retention time=1.554 min; ESI-MS (+) m/z=770.0 (M+H)

Intermediate: (1R,5S)-8-(3-(3-bromo-2-methylphenoxy)propyl)-3-oxa-8-azabicyclo[3.2.1]octane was obtained (80.7 mgs, 62% yield) as a Colorless Oil

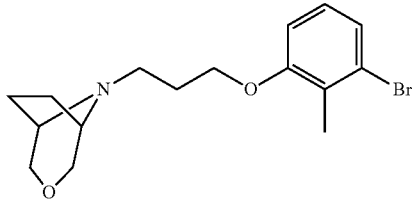 [SMILES: Cc1c(Br)cccc1OCCCN1C2CCC1COC2]

(1R,5S)-8-(3-(3-bromo-2-methylphenoxy)propyl)-3-oxa-8-azabicyclo[3.2.1]octane was obtained (80.7 mgs, 62% yield) as a colorless oil. $^1$H NMR (500 MHz, CDCl$_3$) δ 7.15 (dd, J=8.0, 0.6 Hz, 1H), 7.00 (t, J=8.1 Hz, 1H), 6.80 (d, J=8.2 Hz, 1H), 4.07 (t, J=6.1 Hz, 2H), 3.71 (d, J=10.2 Hz, 2H), 3.52 (dd, J=10.2, 1.8 Hz, 2H), 3.06 (m, 2H), 2.47 (t, J=7.2 Hz, 2H), 2.32 (s, 3H), 2.01-1.84 (m, 6H). The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.335 min., m/z 340.00 & 341.95 (M+H).

Intermediate: 5-((5-((3'-(3-((1R,5S)-3-oxa-8-azabicyclo[3.2.1]octan-8-yl)propoxy)-2,2'-dimethyl-[1,1'-biphenyl]-3-yl)methoxy)-4-chloro-2-formylphenoxy)methyl)nicotinonitrile TFA Salt

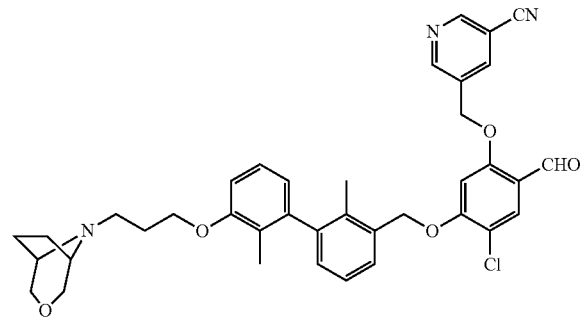 [SMILES: Cc1c(COc2cc(OCc3cncc(C#N)c3)c(C=O)cc2Cl)cccc1-c1cccc(OCCCN2C3CCC2COC3)c1C]

5-((5-((3'-(3-((1R,5S)-3-oxa-8-azabicyclo[3.2.1]octan-8-yl)propoxy)-2,2'-dimethyl-[1,1'-biphenyl]-3-yl)methoxy)-4-chloro-2-formylphenoxy)methyl)nicotinonitrile TFA salt was obtained (38.2 mgs, 40% yield) as a yellow solid. $^1$H NMR (500 MHz, CDCl$_3$) δ 10.27 (s, 1H), 9.00-8.87 (m, 2H), 8.19 (t, J=1.9 Hz, 1H), 7.93 (s, 1H), 7.49-7.39 (m, 1H), 7.32-7.28 (m, 1H), 7.21 (m, 1H), 7.15 (dd, J=7.6, 1.1 Hz, 1H), 6.87-6.75 (m, 2H), 6.66 (s, 1H), 5.26 (m, 4H), 4.17 (d, J=12.8 Hz, 2H), 4.15-4.08 (m, 2H), 3.99 (m, 2H), 3.76 (d, J=12.3 Hz, 2H), 3.26 (m, 2H), 2.37-2.28 (m, 4H), 2.24-2.17 (m, 2H), 2.08 (s, 3H), 1.90-1.85 (m, 3H). The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.672 min., m/z 653.55 (M+H).

Example 3051: (S)-1-(4-((3'-(3-((1R,5S)-3-oxa-8-azabicyclo[3.2.1]octan-8-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

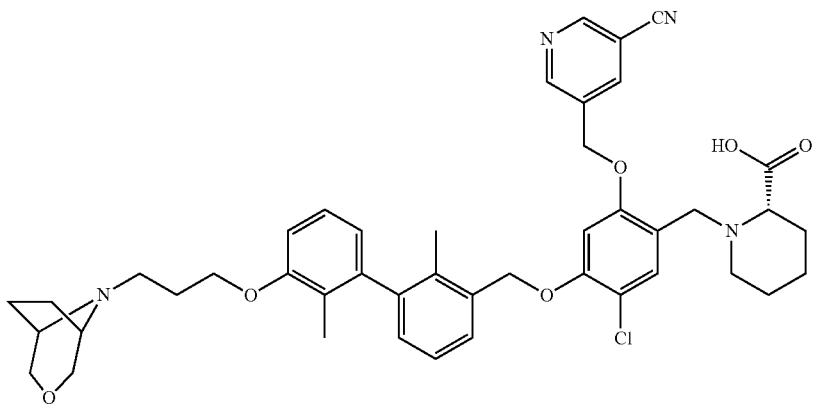 [SMILES: Cc1c(COc2cc(OCc3cncc(C#N)c3)c(CN3CCCC[C@H]3C(=O)O)cc2Cl)cccc1-c1cccc(OCCCN2C3CCC2COC3)c1C]

The crude oil was taken up in methanol and was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 28-68% B over 20 minutes with a 3-minute hold at a flow rate of 20 mL/minute. Fractions containing the desired product were combined and dried via centrifugal evaporation. The yield of the product was 13.8 mg (33%) as the bis-TFA salt, and its estimated purity by LCMS analysis was 98%. $^1$H NMR (500 MHz, DMSO-$d_6$) δ 9.01 (m, 2H), 8.46 (s, 1H), 7.49 (d, J=7.3 Hz, 1H), 7.43 (s, 1H), 7.27 (t, J=7.5 Hz, 1H), 7.21 (t, J=7.9 Hz, 1H), 7.11 (s, 1H), 7.08 (d, J=7.6 Hz, 1H), 6.98 (d, J=8.2 Hz, 1H), 6.68 (d, J=7.3 Hz, 1H), 5.33 (s, 2H), 5.27 (s, 2H), 4.11 (m, 2H), 3.78 (d, J=13.4 Hz, 1H), 3.61 (d, J=13.7 Hz, 1H), 3.52 (m, 4H), 3.13 (m, 1H), 3.05 (m, 2H), 2.89 (m, 1H), 2.41 (t, J=7.0 Hz, 2H), 2.28 (m, 1H), 2.03 (s, 3H), 1.93-1.86 (m, 4H), 1.82 (s, 3H), 1.76-1.66 (m, 2H), 1.49 (m, 3H), 1.37 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.872 min; ESI-MS (+) m/z=766.1 (M+H)

Analysis condition 2: Retention time=1.583 min; ESI-MS (+) m/z=766.1 (M+H)

Intermediate: (1s,5s)-9-(3-(3-bromo-2-methylphenoxy)propyl)-3,7-dioxa-9-azabicyclo[3.3.1]nonane

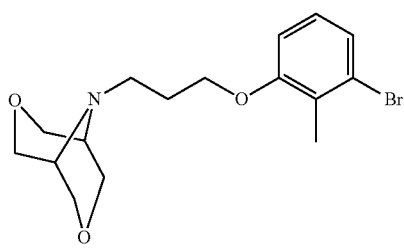 [SMILES: Cc1c(Br)cccc1OCCCN1C2COCC1COC2]

(1s,5s)-9-(3-(3-bromo-2-methylphenoxy)propyl)-3,7-dioxa-9-azabicyclo[3.3.1]nonane (33.0 mgs, 20% yield) was obtained as a tan oil. $^1$H NMR (500 MHz, CDCl$_3$) δ 7.16 (d, J=8.1 Hz, 1H), 7.01 (t, J=8.1 Hz, 1H), 6.80 (d, J=8.1 Hz, 1H), 4.17-4.03 (m, 6H), 3.88 (d, J=11.0 Hz, 4H), 3.05 (t, J=6.8 Hz, 2H), 2.47 (br. s., 2H), 2.31 (s, 3H), 1.94 (quin, J=6.4 Hz, 2H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.210 min., m/z 356.00 & 358.00 (M+H).

Intermediate: 5-((5-((3'-(3-((1 s,5s)-3,7-dioxa-9-azabicyclo[3.3.1]nonan-9-yl)propoxy)-2,2'-dimethyl-[1,1'-biphenyl]-3-yl)methoxy)-4-chloro-2-formylphenoxy)methyl)nicotinonitrile TFA Salt

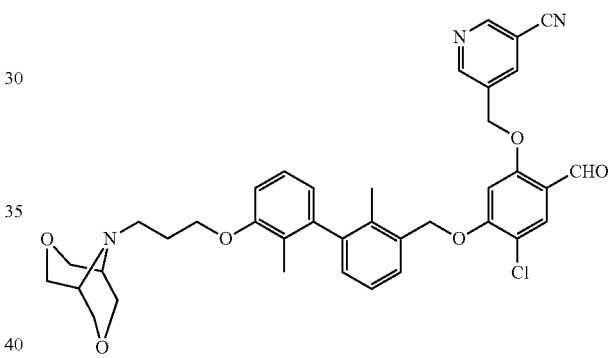

5-((5-((3'-(3-((1 s,5s)-3,7-Dioxa-9-azabicyclo[3.3.1]nonan-9-yl)propoxy)-2,2'-dimethyl-[1,1'-biphenyl]-3-yl)methoxy)-4-chloro-2-formylphenoxy)methyl)nicotinonitrile TFA salt was obtained (27.1 mgs, 39%) as a yellow solid. $^1$H NMR (500 MHz, CDCl$_3$) δ 10.27 (s, 1H), 8.94 (m, 2H), 8.19 (t, J=1.9 Hz, 1H), 7.93 (s, 1H), 7.45 (d, J=6.8 Hz, 1H), 7.29 (m, 1H), 7.22 (t, J=7.9 Hz, 1H), 7.15 (dd, J=7.6, 1.0 Hz, 1H), 6.81 (m, 2H), 6.66 (s, 1H), 5.26 (m, 4H), 4.38 (m, 4H), 4.26-4.09 (m, 6H), 3.85-3.72 (m, 2H), 3.53 (br. s., 2H), 2.32 (m, 2H), 2.09 (s, 3H), 1.89 (s, 3H). The LC/MS data was obtained on a Shimadzu analytical LC/Micromass Platform LC (ESI+) at 220 nm using the following set of conditions: Phenomenex Luna 3 mm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.574 min., m/z 669.30 (M+H).

Example 3052: (S)-1-(4-((3'-(3-((1s,5s)-3,7-dioxa-9-azabicyclo[3.3.1]nonan-9-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic Acid

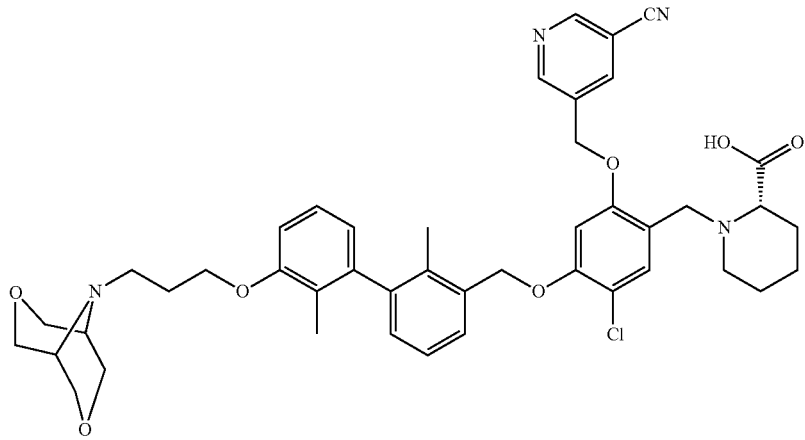 [SMILES: Cc1c(COc2cc(OCc3cncc(C#N)c3)c(CN3CCCC[C@H]3C(=O)O)cc2Cl)cccc1-c1cccc(OCCCN2C3COCC2COC3)c1C]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 40-90% B over 25 minutes with a 5-minute hold at a flow rate of 20 mL/minute. Fractions containing the desired product were combined and dried via centrifugal evaporation. The yield of the product was 11.1 mg (41%), and its estimated purity by LCMS analysis was 100%. $^1$H NMR (500 MHz, DMSO-$d_6$) δ 9.00 (m, 2H), 8.45 (s, 1H), 7.49 (d, J=7.3 Hz, 1H), 7.43 (s, 1H), 7.31-7.25 (m, 1H), 7.24-7.17 (m, 1H), 7.11 (s, 1H), 7.07 (d, J=7.3 Hz, 1H), 6.98 (d, J=8.2 Hz, 1H), 6.68 (d, J=7.6 Hz, 1H), 5.33 (s, 2H), 5.26 (s, 2H), 4.10 (m, 2H), 3.97-3.88 (m, 4H), 3.79 (d, J=13.7 Hz, 1H), 3.69 (d, J=10.7 Hz, 4H), 3.62 (d, J=13.7 Hz, 1H), 3.12 (m, 1H), 2.98 (t, J=6.6 Hz, 2H), 2.94-2.85 (m, 1H), 2.46 (br. s., 2H), 2.33-2.25 (m, 1H), 2.03 (s, 3H), 1.87 (t, J=6.6 Hz, 2H), 1.82 (m, 5H), 1.49 (m, 3H), 1.41-1.31 (m, 1H).
Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.
Analysis condition 1: Retention time=1.835 min; ESI-MS (+) m/z=782.1 (M+H).
Analysis condition 2: Retention time=1.492 min; ESI-MS (+) m/z=782.1 (M+H).

Intermediate:
4-(3-(3-bromo-2-methylphenoxy)propyl)morpholine

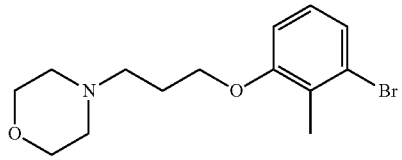 [SMILES: Cc1c(Br)cccc1OCCCN1CCOCC1]

To a small sealed tube was added morpholine (0.123 mL, 1.423 mmol), 1-bromo-3-(3-chloropropoxy)-2-methylbenzene (250 mg, 0.949 mmol), DMF (5.0 mL), sodium iodide (213 mg, 1.423 mmol), and potassium carbonate (328 mg, 2.371 mmol). The vessel was sealed and the mixture stirred overnight at 65° C. The mixture was cooled, further diluted with 10 mL of water and pushed through a Waters 1 g HLB extraction cartridge. The cartridge flushed with 30 mL of water, the crude product eluted with 30 mL of methanol. The methanol mixture was pushed through a 5 g Biotage SCX-2 cartridge. The SCX-2 cartridge flushed with 30 mL of methanol, the product eluted with 30 mL of 2M ammonia in methanol to give 228.2 mgs of 4-(3-(3-bromo-2-methylphenoxy)propyl)morpholine as a clear colorless oil (77% yield). $^1$H NMR (500 MHz, CDCl$_3$) δ 7.15 (dd, J=8.0, 0.6 Hz, 1H), 7.00 (t, J=8.1 Hz, 1H), 6.78 (d, J=8.0 Hz, 1H), 4.02 (t, J=6.1 Hz, 2H), 3.79-3.69 (m, 4H), 2.58-2.52 (m, 2H), 2.48 (m, 4H), 2.32 (s, 3H), 2.04-1.93 (m, 2H). The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.235 min., m/z 314.00 & 315.90 (M+H).

Intermediate: 3-((4-chloro-2-formyl-5-((2-methyl-3-(4,4,5,5-tetramethyl-1,3,2-dioxaborolan-2-yl)benzyl)oxy)phenoxy)methyl)benzonitrile

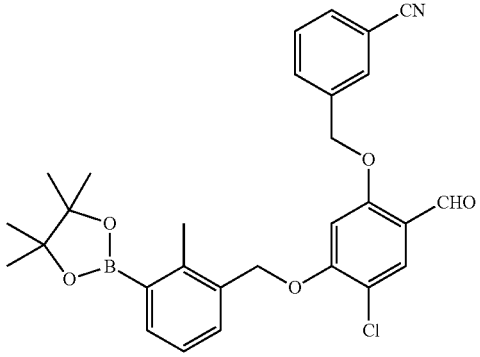 [SMILES: Cc1c(COc2cc(OCc3cccc(C#N)c3)c(C=O)cc2Cl)cccc1B1OC(C)(C)C(C)(C)O1]

To a RBF containing 5-chloro-2-hydroxy-4-((2-methyl-3-(4,4,5,5-tetramethyl-1,3,2-dioxaborolan-2-yl)benzyl)oxy)benzaldehyde (500 mg, 1.242 mmol) in DMF (5.0 ml), was added cesium carbonate (587 mg, 1.800 mmol), and 3-cyanobenzyl bromide (316 mg, 1.614 mmol). The mixture was stirred at room temperature overnight. The reaction mixture was diluted with 10 mL of water and pushed through a 1 g Waters HLB extraction cartridge. The cartridge was flushed with 20 mL of additional water, then 30 mL of methanol, the product eluted with 50 mL of THF to give 650 mgs (91% yield) of 3-((4-chloro-2-formyl-5-((2-methyl-3-(4,4,5,5-tetramethyl-1,3,2-dioxaborolan-2-yl)benzyl)oxy)phenoxy)methyl)benzonitrile. $^1$H NMR (500 MHz, DMSO-$d_6$) δ 10.23 (s, 1H), 8.04 (s, 1H), 7.91-7.82 (m, 2H), 7.72 (s, 1H), 7.69-7.62 (m, 2H), 7.56 (dd, J=7.5, 1.2 Hz, 1H), 7.25-7.20 (m, 2H), 5.44 (s, 2H), 5.36 (s, 2H), 2.53 (s, 3H), 1.35-1.30 (m, 12H). The LC/MS data was obtained on a Shimadzu analytical LC 15/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=2.310 min., m/z 518.30 (M+H).

Intermediate: 3-((4-chloro-5-((2,2'-dimethyl-3'-(3-morpholinopropoxy)-[1,1'-biphenyl]-3-yl)methoxy)-2-formylphenoxy)methyl) Benzonitrile

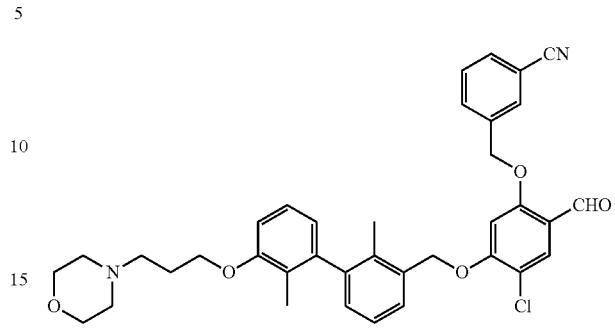

To a sealed tube was added 3-((4-chloro-2-formyl-5-((2-methyl-3-(4,4,5,5-tetramethyl-1,3,2-dioxaborolan-2-yl)benzyl)oxy)phenoxy)methyl)benzonitrile (407 mg, 0.786 mmol), THF (9.0 mL), 4-(3-(3-bromo-2-methylphenoxy)propyl)morpholine (224.4 mg, 0.714 mmol), potassium phosphate, tribasic (379 mg, 1.785 mmol), water (3.0 mL), and second generation X-Phos precatalyst (28.1 mg, 0.036 mmol). The mixture was de-gassed/flushed with nitrogen then heated overnight at 80° C. Volatiles were removed under a stream of nitrogen to give a black oily mixture which was purified on silica gel using 20 CV of 0-10% methanol/DCM to give 260 mgs (58% yield) of 3-((4-chloro-5-((2,2'-dimethyl-3'-(3-morpholinopropoxy)-[1,1'-biphenyl]-3-yl)methoxy)-2-formylphenoxy)methyl) benzonitrile as a yellow solid. $^1$H NMR (400 MHz, CDCl$_3$) δ 10.33 (s, 1H), 7.92 (s, 1H), 7.77-7.62 (m, 3H), 7.61-7.48 (m, 2H), 7.43 (d, J=7.6 Hz, 1H), 7.24-7.10 (m, 2H), 6.87 (dd, J=8.3, 2.7 Hz, 1H), 6.74 (d, J=7.6 Hz, 1H), 6.62 (s, 1H), 5.22 (s, 2H), 5.19 (s, 2H), 4.09 (m, 2H), 3.77-3.69 (m, 4H), 2.58 (m, 2H), 2.48 (m, 4H), 2.08 (s, 3H), 2.01 (m, 2H), 1.92 (s, 3H). The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS rt=1.735 min., m/z 626.30 (M+H).

Example 3053: (S)-methyl 1-(5-chloro-2-((3-cyanobenzyl)oxy)-4-((2,2'-dimethyl-3'-(3-morpholinopropoxy)-[1,1'-biphenyl]-3-yl)methoxy)benzyl)piperidine-2-carboxylate, 2 TFA

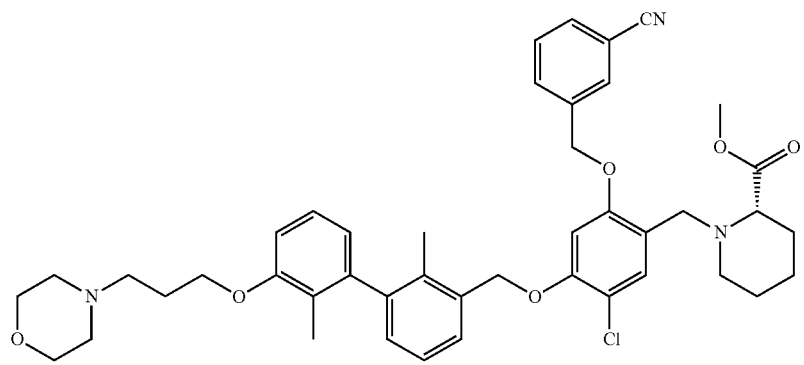 [SMILES: COC(=O)[C@@H]1CCCCN1Cc1cc(Cl)c(OCc2cccc(-c3cccc(OCCCN4CCOCC4)c3C)c2C)cc1OCc1cccc(C#N)c1]

To a vial was added 3-((4-chloro-5-((2,2'-dimethyl-3'-(3-morpholinopropoxy)-[1,1'-biphenyl]-3-yl)methoxy)-2-formylphenoxy)methyl)benzonitrile (30 mg, 0.048 mmol), (S)-methyl piperidine-2-carboxylate, HCl (12.93 mg, 0.072 mmol), DMF (1.0 mL), AcOH (111 μL), and borane-2-picoline complex (10.27 mg, 0.096 mmol). The vial was capped and the mixture shaken overnight at room temperature. The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 15-100% B over 25 minutes with a 7-minute hold at a flow rate of 20 mL/minute. Fractions containing the desired product were combined and dried via centrifugal evaporation. The yield of the product was 3.9 mg (10.5%), and its estimated purity by LCMS analysis was 97.6%. $^1$H NMR (500 MHz, DMSO-$d_6$) δ 7.90-7.75 (m, 2H), 7.69-7.59 (m, 1H), 7.46 (m, 1H), 7.25 (m, 2H), 7.15 (m, 2H), 7.08-7.00 (m, 2H), 6.99 (m, 1H), 6.71 (m, 1H), 5.40-5.22 (m, 4H), 4.20-4.04 (m, 3H), 3.94-3.85 (m, 2H), 3.78-3.61 (m, 7H), 3.38-3.26 (m, 4H), 3.26-2.98 (m, 2H), 2.26-2.12 (m, 2H), 2.03 (s, 3H), 1.85 (s, 3H), 1.78-1.67 (m, 1H), 1.67-1.52 (m, 3H), 1.52-1.33 (m, 1H). Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.952 min; ESI-MS (+) m/z=753.1 (M+H)

Analysis condition 2: Retention time=1.691 min; ESI-MS (+) m/z=753.1 (M+H)

Example 3054: (S)-1-(5-chloro-2-((3-cyanobenzyl)oxy)-4-((2,2'-dimethyl-3'-(3-morpholinopropoxy)-[1,1'-biphenyl]-3-yl)methoxy)benzyl)piperidine-2-carboxylic Acid Example 3054 was synthesized in a similar fashion as Example 3053: The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 35-100% B over 25 minutes with a 5-minute hold at a flow rate of 20 mL/minute. Fractions containing the desired product were combined and dried via centrifugal evaporation. The yield of the product was 4.2 mg (12%), and its estimated purity by LCMS analysis was 93.3%. $^1$H NMR (500 MHz, DMSO-$d_6$) δ 7.95 (s, 1H), 7.82 (m 2H), 7.67-7.59 (m, 1H), 7.49-7.42 (m, 2H), 7.27 (t, J=7.6 Hz, 1H), 7.21 (t, J=7.9 Hz, 1H), 7.09-7.04 (m, 2H), 6.96 (d, J=8.2 Hz, 1H), 6.67 (d, J=7.3 Hz, 1H), 5.26 (m, 4H), 4.11-3.99 (m, 2H), 3.82 (d, J=14.0 Hz, 1H), 3.64 (d, J=14.0 Hz, 1H), 3.61-3.55 (m, 4H), 3.10 (m, 1H), 2.91 (m, 1H), 2.46 (t, J=7.2 Hz, 2H), 2.37 (m, 4H), 2.29 (m, 1H), 2.03 (s, 3H), 1.98-1.89 (m, 2H), 1.82 (m, 4H), 1.71 (m, 1H), 1.49 (m, 3H), 1.35 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.963 min; ESI-MS (+) m/z=739.1 (M+H)

Analysis condition 2: Retention time=1.602 min; ESI-MS (+) m/z=739.2 (M+H)

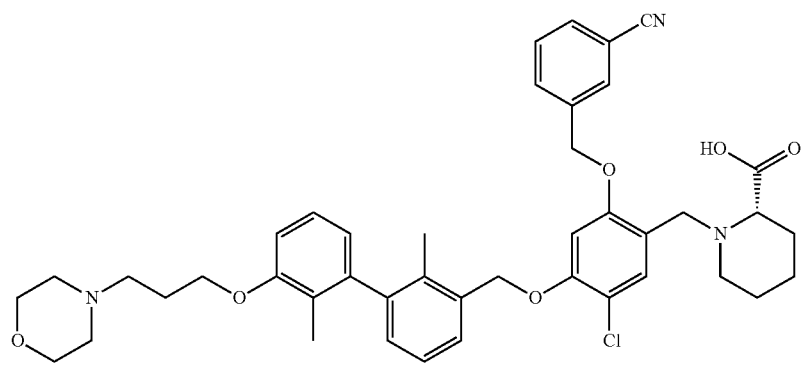 [SMILES: Cc1c(COc2cc(OCc3cccc(C#N)c3)c(CN3CCCC[C@H]3C(=O)O)cc2Cl)cccc1-c1cccc(OCCCN2CCOCC2)c1C]

Intermediate: 3-((5-((3'-(3-((1R,5S)-3-oxa-8-azabicyclo[3.2.1]octan-8-yl)propoxy)-2,2'-dimethyl-[1,1'-biphenyl]-3-yl)methoxy)-4-chloro-2-formylphenoxy)methyl)benzonitrile

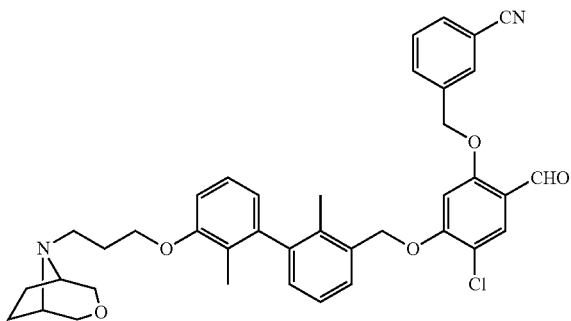 [SMILES: Cc1c(COc2cc(OCc3cccc(C#N)c3)c(C=O)cc2Cl)cccc1-c1cccc(OCCCN2C3CCC2COC3)c1C]

To a sealed tube was added 3-((4-chloro-2-formyl-5-((2-methyl-3-(4,4,5,5-tetramethyl-1,3,2-dioxaborolan-2-yl)benzyl)oxy)phenoxy)methyl)benzonitrile (76 mg, 0.147 mmol), (1R,5S)-8-(3-(3-bromo-2-methylphenoxy)propyl)-3-oxa-8-azabicyclo[3.2.1]octane (50 mg, 0.147 mmol), THF (6.0 mL), water (2.0 mL), tribasic potassium phosphate (78 mg, 0.367 mmol), and Second Generation X-Phos precatalyst (5.78 mg, 7.35 μmol). The vessel was sealed, the mixture de-gassed/flushed with nitrogen, then heated overnight at 80° C. The reaction mixture was diluted with 10 mL of water and pushed through a 1 g Waters HLB extraction cartridge. The cartridge was flushed with 20 mL of additional water, then 30 mL of methanol; the product eluted with 50 mL of THF to give 117 mgs (85% yield) of 3-((5-((3'-(3-((1R,5S)-3-oxa-8-azabicyclo[3.2.1]octan-8-yl)propoxy)-2,2'-dimethyl-[1,1'-biphenyl]-3-yl)methoxy)-4-chloro-2-formylphenoxy)methyl)benzonitrile as a yellow solid. $^1$H NMR (500 MHz, CDCl$_3$) δ 10.33 (s, 1H), 7.92 (s, 1H), 7.73 (s, 1H), 7.72-7.65 (m, 2H), 7.59-7.53 (m, 1H), 7.43 (m, 1H), 7.27 (m, 1H), 7.23-7.12 (m, 2H), 6.89 (d, J=8.4 Hz, 1H), 6.73 (d, J=6.9 Hz, 1H), 6.62 (s, 1H), 5.22 (s, 2H), 5.19 (s, 2H), 4.13-4.04 (m, 2H), 3.74-3.68 (m, 2H), 3.56-3.49 (m, 2H), 3.12-3.00 (m, 2H), 2.56-2.44 (m, 2H), 2.09 (s, 3H), 2.05-1.84 (m, 9H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS rt=1.734 min., m/z 652.30 (M+H).

Example 3055: (S)-1-(4-((3'-(3-((1R,5S)-3-oxa-8-azabicyclo[3.2.1]octan-8-yl)propoxy)-2,2'-dimethyl-[1,1'-biphenyl]-3-yl)methoxy)-5-chloro-2-((3-cyanobenzyl)oxy)benzyl)piperidine-2-carboxylic Acid

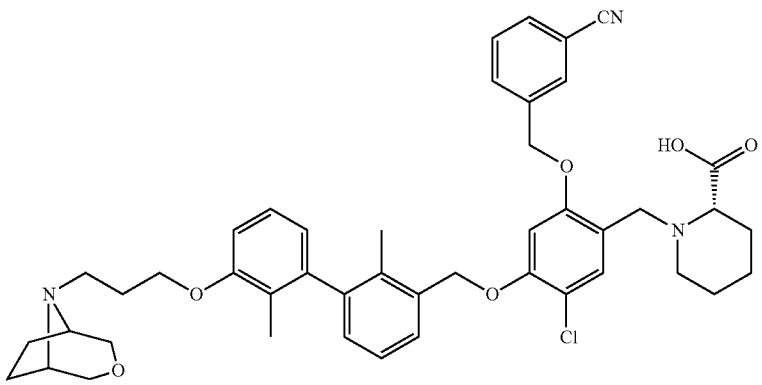 [SMILES: Cc1c(COc2cc(OCc3cccc(C#N)c3)c(CN3CCCC[C@H]3C(=O)O)cc2Cl)cccc1-c1cccc(OCCCN2C3CCC2COC3)c1C]

To a vial was added 3-((5-((3'-(3-((1R,5S)-3-oxa-8-azabicyclo[3.2.1]octan-8-yl)propoxy)-2,2'-dimethyl-[1,1'-biphenyl]-3-yl)methoxy)-4-chloro-2-formylphenoxy)methyl)benzonitrile (35 mg, 0.054 mmol), (S)-piperidine-2-carboxylic acid (10.41 mg, 0.081 mmol), DMF (1.0 mL), AcOH (111 μL), and borane-2-picoline complex (11.50 mg, 0.107 mmol). The vial was capped and the mixture shaken overnight at room temperature. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 45-85% B over 25 minutes with a 5-minute hold at a flow rate of 20 mL/minute. Fractions containing the desired product were combined and dried via centrifugal evaporation. The material was further purified via preparative LC/MS with the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 10-75% B over 25 minutes with a 5-minute hold at a flow rate of 20 mL/minute. Fractions containing the desired product were combined and dried via centrifugal evaporation. The yield of the product was 3.2 mg (7.4%), and its estimated purity by LCMS analysis was 95.1%. $^1$H NMR (500 MHz, DMSO-$d_6$) δ 7.95 (s, 1H), 7.82 (t, J=7.9 Hz, 2H), 7.66-7.59 (m, 1H), 7.51-7.43 (m, 2H), 7.27 (t, J=7.6 Hz, 1H), 7.21 (t, J=7.8 Hz, 1H), 7.12-7.03 (m, 2H), 6.97 (d, J=8.5 Hz, 1H), 6.68 (d, J=7.6 Hz, 1H), 5.25 (m, 4H), 4.10 (m, 2H), 3.75 (d, J=14.0 Hz, 2H), 3.56 (m, 7H), 3.04 (m, 3H), 2.88 (m, 1H), 2.41 (t, J=7.0 Hz, 2H), 2.27-2.12 (m, 1H), 2.03 (s, 3H), 1.95-1.80 (m, 6H), 1.75 (m, 1H), 1.70 (d, J=7.0 Hz, 2H), 1.47 (m, 2H), 1.33 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.838 min; ESI-MS (+) m/z=765.1 (M+H)

Analysis condition 2: Retention time=1.656 min; ESI-MS (+) m/z=765.1 (M+H)

Example 3056: (2S)-1-(5-chloro-2-((5-cyanopyridin-3-yl)methoxy)-4-((2,2'-dimethyl-3'-(3-(2-phenylmorpholino) propoxy)-[1,1'-biphenyl]-3-yl) methoxy)benzyl)piperidine-2-carboxylic Acid

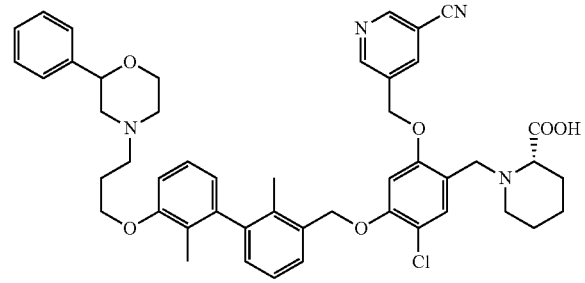 [SMILES: Cc1c(COc2cc(OCc3cncc(C#N)c3)c(CN3CCCC[C@H]3C(=O)O)cc2Cl)cccc1-c1cccc(OCCCN2CCOC(c3ccccc3)C2)c1C]

To a small sealed tube was added DMF (2.0 mL), sodium iodide (4.35 mg, 0.030 mmol), potassium carbonate (20.1 mg, 0.146 mmol), 2-phenylmorpholine (47.4 mg, 0.290 mmol), and a 1:4 mixture of (S)-1-(5-chloro-4-((3'-(3-bromopropoxy)-2,2'-dimethyl-[1,1'-biphenyl]-3-yl)methoxy)-2-((5-cyanopyridin-3-yl)methoxy)benzyl)piperidine-2-carboxylic acid and (S)-1-(5-chloro-4-((3'-(3-chloropropoxy)-2,2'-dimethyl-[1,1'-biphenyl]-3-yl)methoxy)-2-((5-cyanopyridin-3-yl)methoxy)benzyl)piperidine-2-carboxylic acid (10 mg, 0.015 mmol) (prepared in a similar manner as described above). The vial was sealed and the mixture stirred at 80° C. overnight. The reaction mixture was cooled, further diluted with methanol and was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 42-82% B over 20 minutes with a 5-minute hold at a flow rate of 20 mL/minute. Fractions containing the desired product were combined and dried via centrifugal evaporation. The yield of the product was 8.9 mg (72%) and its estimated purity by LCMS analysis was 96%. $^1$H NMR (500 MHz, DMSO-$d_6$) δ 9.01 (dd, J=7.2, 2.0 Hz, 2H), 8.46 (s, 1H), 7.49 (d, J=7.6 Hz, 1H), 7.42 (s, 1H), 7.39-7.30 (m, 4H), 7.30-7.24 (m, 2H), 7.22 (t, J=7.9 Hz, 1H), 7.11 (s, 1H), 7.07 (d, J=7.6 Hz, 1H), 6.98 (d, J=8.2 Hz, 1H), 6.69 (d, J=7.6 Hz, 1H), 5.33 (br.s., 2H), 5.26 (br.s., 2H), 4.49 (d, J=8.2 Hz, 1H), 4.14-4.02 (m, 2H), 3.95 (d, J=9.2 Hz, 1H), 3.77 (d, J=14.6 Hz, 1H), 3.68 (dd, J=11.4, 9.3 Hz, 1H), 3.60 (d, J=13.7 Hz, 1H), 3.14 (dd, J=7.2, 4.1 Hz, 2H), 2.97-2.79 (m, 4H), 2.32-2.23 (m, 1H), 2.13 (m, 1H), 2.03 (s, 3H), 2.01-1.92 (m, 3H), 1.87-1.67 (m, 5H), 1.49 (m, 4H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.342 min; ESI-MS (+) m/z=816.1 (M+H)

Analysis condition 2: Retention time=1.704 min; ESI-MS (+) m/z=816.1 (M+H)

Example 3057: (S)-1-(5-chloro-2-((5-cyanopyridin-3-yl)methoxy)-4-((3'-(3-((R)-3-fluoropyrrolidin-1-yl) propoxy)-2,2'-dimethyl-[1,1'-biphenyl]-3-yl) methoxy)benzyl)piperidine-2-carboxylic Acid

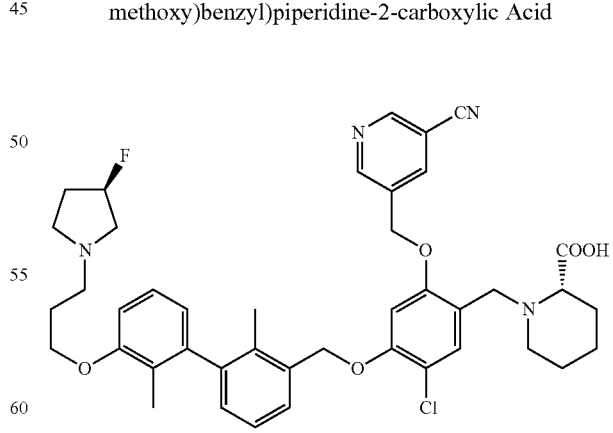

Example 3057 was prepared in a similar manner as Example 3056. The crude oil was taken up in methanol and was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 35-75% B over 20 minutes with a 5-minute hold at a flow rate of 20 mL/minute. Fractions containing the desired product were combined and dried via centrifugal evaporation. The yield of the product was 12.4 mg (56%) and its estimated purity by LCMS analysis was 97%. $^1$H NMR (500 MHz, DMSO-$d_6$) δ 9.01 (dd, J=8.4, 2.0 Hz, 2H), 8.46 (s, 1H), 7.49 (d, J=7.6 Hz, 1H), 7.42 (s, 1H), 7.27 (t, J=7.6 Hz, 1H), 7.21 (t, J=7.6 Hz, 1H), 7.11 (s, 1H), 7.08 (d, J=7.3 Hz, 1H), 6.96 (d, J=8.5 Hz, 1H), 6.69 (d, J=7.3 Hz, 1H), 5.40-5.10 (m, 5H), 4.08 (m, 2H), 3.76 (m, 2H), 3.60 (m, 2H), 3.18-3.10 (m, 2H), 2.93-2.76 (m, 2H), 2.70-2.58 (m, 2H), 2.36-2.23 (m, 2H), 2.21-2.07 (m, 1H), 2.04 (s, 3H), 1.98-1.87 (m, 2H), 1.87-1.67 (m, 5H), 1.57-1.29 (m, 4H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water With 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.934 min; ESI-MS (+) m/z=742.1 (M+H)

Analysis condition 2: Retention time=1.550 min; ESI-MS (+) m/z=742.1 (M+H)

Example 3058: (2S)-1-(5-chloro-2-((5-cyanopyridin-3-yl)methoxy)-4-((2,2'-dimethyl-3'-(3-(2-(trifluoromethyl)morpholino)propoxy)-[1,1'-biphenyl]-3-yl)methoxy)benzyl)piperidine-2-carboxylic Acid

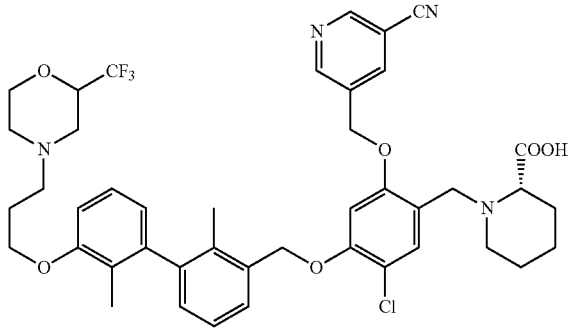 [SMILES: Cc1c(COc2cc(OCc3cncc(C#N)c3)c(CN3CCCC[C@H]3C(=O)O)cc2Cl)cccc1-c1cccc(OCCCN2CCOC(C(F)(F)F)C2)c1C]

Example 3058 was prepared in a similar manner as Example 3056. The crude material was purified via preparative LC/MS using the following conditions: Waters XBridge 5 μm C18, 19×200 mm where mobile phase A was 5:95 methanol: water with 10 mM ammonium acetate and mobile phase B was 95:5 methanol: water 10 mM ammonium acetate at a gradient of 45-85% B over 20 minutes with a 5-minute hold at a flow rate of 20 mL/minute. Fractions containing the desired product were combined and dried via centrifugal evaporation. The yield of the product was 3.6 mg (15%), and its estimated purity by LCMS analysis was 100%. $^1$H NMR (500 MHz, DMSO-$d_6$) δ 9.01 (dd, J=7.3, 1.8 Hz, 2H), 8.46 (s, 1H), 7.49 (d, J=7.3 Hz, 1H), 7.42 (s, 1H), 7.27 (t, J=7.5 Hz, 1H), 7.21 (t, J=7.9 Hz, 1H), 7.11 (s, 1H), 7.07 (d, J=7.6 Hz, 1H), 6.97 (d, J=8.2 Hz, 1H), 6.69 (d, J=7.3 Hz, 1H), 5.33 (br. s., 2H), 5.26 (br. s., 2H), 4.19-4.00 (m, 4H), 3.98-3.89 (m, 1H), 3.78 (m, 1H), 3.68-3.57 (m, 4H), 3.16-3.09 (m, 1H), 2.95 (m, 1H), 2.87 (m, 1H), 2.77 (m, 1H), 2.62-2.54 (m, 2H), 2.27 (m, 1H), 2.18-2.05 (m, 1H), 2.04 (s, 3H), 2.00-1.90 (m, 1H), 1.83 (s, 3H), 1.80-1.69 (m, 1H), 1.49 (m, 3H), 1.37 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.232 min; ESI-MS (+) m/z=808.1 (M+H)

Analysis condition 2: Retention time=1.662 min; ESI-MS (+) m/z=808.1 (M+H)

Intermediate: 3'-((2-chloro-5-((5-cyanopyridin-3-yl)methoxy)-4-formylphenoxy)methyl)-2,2'-dimethyl-[1,1'-biphenyl]-3-carboxylic Acid

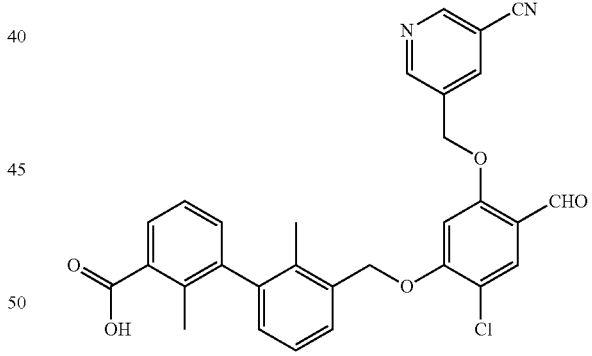

To a sealed tube was added 3-bromo-2-methylbenzoic acid (45.6 mg, 0.212 mmol), 5-((4-chloro-2-formyl-5-((2-methyl-3-(4,4,5,5-tetramethyl-1,3,2-dioxaborolan-2-yl)benzyl)oxy)phenoxy)methyl) nicotinonitrile (100 mg, 0.193 mmol), THF (15.0 mL), tribasic potassium phosphate (82 mg, 0.386 mmol), water (3 mL), and 2nd Generation XPhos precatalyst (7.58 mg, 9.64 μmol). The vessel was sealed, the mixture de-gassed/flushed with nitrogen, then heated overnight at 80° C. The reaction mixture was cooled, diluted with 50 mL of DCM, washed with water, brine, dried over sodium sulfate, filtered through diatomaceous earth (Celite®), and evaporated to give 144 mgs (71% yield) of 3'-((2-chloro-5-((5-cyanopyridin-3-yl)methoxy)-4-formylphenoxy)methyl)-2,2'-dimethyl-[1,1'-biphenyl]-3-carboxylic acid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=95% HPLC grade acetonitrile/10Mm ammonium acetate/5% HPLC grade water), (A=95% HPLC grade water/10Mm ammonium acetate/5% HPLC grade acetonitrile), in 2 minutes with a 1 minute hold at a rate of 1 mL/minute. LCMS Rt=1.395 min., m/z 527.1 (M+H).

Intermediate: 5-((4-chloro-5-((2,2'-dimethyl-3'-(4-methylpiperazine-1-carbonyl)-[1,1'-biphenyl]-3-yl)methoxy)-2-formylphenoxy)methyl)nicotinonitrile

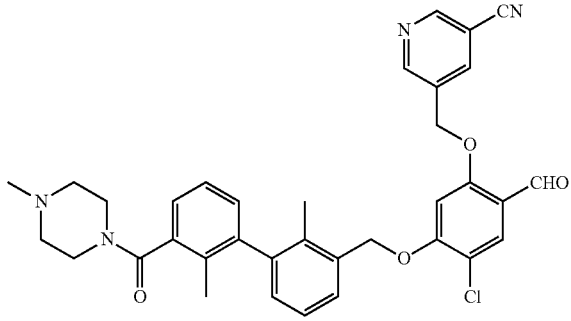 [SMILES: Cc1c(COc2cc(OCc3cncc(C#N)c3)c(C=O)cc2Cl)cccc1-c1cccc(C(=O)N2CCN(C)CC2)c1C]

To the crude mixture 3'-((2-chloro-5-((5-cyanopyridin-3-yl)methoxy)-4-formylphenoxy)methyl)-2,2'-dimethyl-[1,1'-biphenyl]-3-carboxylic acid (144 mg, 0.273 mmol) in DMF (5.0 mL) was added, 1-methylpiperazine (36 μL, 0.328 mmol), N-ethyl-N-isopropylpropan-2-amine (95 μL, 0.547 mmol), and 2-(3H-[1,2,3]triazolo[4,5-b]pyridin-3-yl)-1,1,3,3-tetramethylisouronium hexafluorophosphate(V) (HATU) (208 mg, 0.547 mmol). The reaction mixture was shaken at room temperature overnight. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a XTERRA 5 μm C18 30×100 mm column at a gradient of 30-100% B and a flow rate of 40 mL/min. over 15 minutes with a 10 minute hold to give 17 mgs (10% yield) of 5-((4-chloro-5-((2,2'-dimethyl-3'-(4-methylpiperazine-1-carbonyl)-[1,1'-biphenyl]-3-yl)methoxy)-2-formylphenoxy)methyl)nicotinonitrile TFA salt as a white solid. $^1$H NMR (500 MHz, CDCl$_3$) δ10.27 (s, 1H), 8.96 (m, 2H), 8.22 (s, 1H), 7.94 (s, 1H), 7.52 (d, J=7.3 Hz, 1H), 7.40-7.29 (m, 2H), 7.25 (m, 1H), 7.21 (d, J=7.6 Hz, 1H), 7.16 (d, J=7.4 Hz, 1H), 6.68 (s, 1H), 5.37-5.20 (m, 4H), 3.72 (m, 4H), 3.07-2.87 (m, 4H), 2.19-1.87 (m, 6H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.475 min., m/z 610.30 (M+H).

Example 3059: (S)-1-(5-chloro-2-((5-cyanopyridin-3-yl)methoxy)-4-((2,2'-dimethyl-3'-(4-methylpiperazine-1-carbonyl)-[1,1'-biphenyl]-3-yl)methoxy)benzyl)piperidine-2-carboxylic Acid

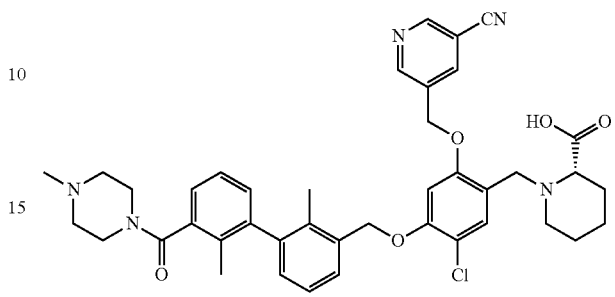

To a vial was added (S)-piperidine-2-carboxylic acid (4.55 mg, 0.035 mmol), 5-((4-chloro-5-((2,2'-dimethyl-3'-(4-methylpiperazine-1-carbonyl)-[1,1'-biphenyl]-3-yl)methoxy)-2-formylphenoxy) methyl)nicotinonitrile, TFA (17 mg, 0.024 mmol), DMF (1.0 mL), AcOH (111 μL), and borane-2-picoline complex (5.03 mg, 0.047 mmol). The vial was capped and the mixture shaken overnight at room temperature. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water 10 mM ammonium acetate at a gradient of 15-55% B over 20 minutes with a 5-minute hold at a flow rate of 20 mL/minute. Fractions containing the desired product were combined and dried via centrifugal evaporation. The yield of the product was 7.2 mg (42%), and its estimated purity by LCMS analysis was 98%. $^1$H NMR (500 MHz, DMSO-d$_6$) δ 9.05-8.96 (m, 2H), 8.45 (s, 1H), 7.52 (d, J=7.6 Hz, 1H), 7.42 (s, 1H), 7.32 (dd, J=18.2, 6.0 Hz, 2H), 7.23-7.07 (m, 4H), 5.33 (br. s., 2H), 5.28 (br. s., 2H), 3.78 (d, J=13.4 Hz, 1H), 3.74-3.58 (m, 3H), 3.22-3.10 (m, 4H), 2.94-2.84 (m, 1H), 2.44-2.23 (m, 4H), 2.19 (s, 3H), 2.04 (d, J=5.8 Hz, 3H), 1.86 (s, 3H), 1.83-1.67 (m, 2H), 1.49 (m, 3H), 1.42-1.32 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.596 min; ESI-MS (+) m/z=723.1 (M+H)

Analysis condition 2: Retention time=1.390 min; ESI-MS (+) m/z=723.1 (M+H)

Intermediate: 3-bromo-N-(2-chloroethyl)-2-methylbenzamide

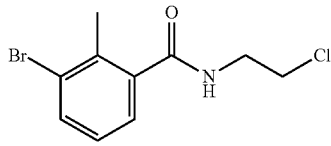

To a large vial was added N-ethyl-N-isopropylpropan-2-amine (1.6 mL, 9.30 mmol), 3-bromo-2-methylbenzoic acid (1.00 g, 4.65 mmol), DMF (40 mL), and 2-chloroethylamine hydrochloride (539 mg, 4.65 mmol). The vial was sealed and the contents shaken rapidly for 10 minutes at room temperature. To the mixture was then added HATU (5.30 g, 14.0 mmol) and the vial was re-capped and the mixture shaken at room temperature for 30 minutes. The reaction mixture was diluted with 30 mL of water and pushed through a 5 g Waters extraction HLB resin cartridge. The cartridge was flushed with 30 mL of water, and product eluted with 30 mL of methanol. Volatiles were evaporated to give 1.42 g (40% yield) of 3-bromo-N-(2-chloroethyl)-2-methylbenzamide as a pink solid. $^1$H NMR (500 MHz, CDCl$_3$) δ 7.62 (dd, J=8.0, 0.9 Hz, 1H), 7.30 (dd, J=7.6, 0.9 Hz, 1H), 7.12-7.05 (m, 1H), 6.20 (br. s., 1H), 3.83-3.72 (m, 4H), 2.48 (s, 3H). The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.625 min., m/z 275.85 & 277.85 (M+H).

Intermediate: (R)-3-bromo-N-(2-(3-hydroxy pyrrolidin-1-yl)ethyl)-2-methylbenzamide

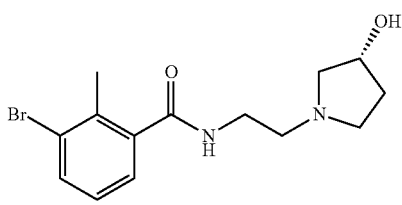 [SMILES: Cc1c(Br)cccc1C(=O)NCCN1CC[C@@H](O)C1]

To a RBF was added (R)-pyrrolidin-3-ol hydrochloride (2.22 g, 17.9 mmol), DMF (20 ml), 3-bromo-N-(2-chloroethyl)-2-methylbenzamide (496 mg, 1.79 mmol), sodium iodide (672 mg, 4.49 mmol), and potassium carbonate (992 mg, 7.18 mmol). The mixture was stirred overnight at 50° C. The mixture was cooled and volatiles removed overnight under a stream of nitrogen. The crude product was taken up in methanol, filtered, and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a XTERRA 5 μm C18 30×100 mm column at a gradient of 0-75% B and a flow rate of 40 mL/min. over 15 minutes with a 10 minute hold to give 302.8 mgs (32% yield) of (R)-3-bromo-N-(2-(3-hydroxy pyrrolidin-1-yl)ethyl)-2-methylbenzamide TFA salt as a light yellow oily solid. $^1$H NMR (500 MHz, CDCl$_3$) δ 7.64 (d, J=8.0 Hz, 1H), 7.33-7.28 (m, 1H), 7.11-7.01 (m, 1H), 4.76-4.61 (m, 1H), 4.09-3.78 (m, 3H), 3.66-3.50 (m, 1H), 3.50-3.27 (m, 2H), 3.20 (d, J=12.5 Hz, 1H), 3.13-2.99 (m, 1H), 2.51-2.38 (m, 4H), 2.29-2.11 (m, 1H). The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.935 min., m/z 326.90 & 328.95 (M+H).

Intermediate: (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic Acid

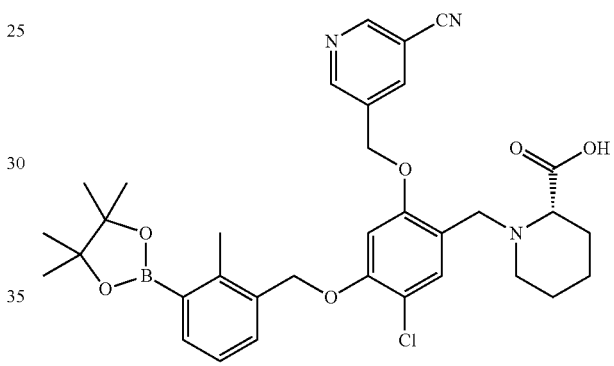

To a vial was added acetic acid (55 μL, 0.964 mmol), DCE (2.0 mL), ethanol (6.0 mL), THF (2.0 mL), 20 mgs of oven dried, ground, 4 A molecular sieves, (S)-piperidine-2-carboxylic acid (124 mg, 0.964 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (250 mg, 0.482 mmol), and sodium cyanoborohydride (60.6 mgs, 0.964 mmol). The vial was capped and the mixture shaken overnight at room temperature. Volatiles were removed, and the resulting mixture diluted with 60 mL of DCM, washed with water, brine, dried over sodium sulfate, filtered and evaporated to give 301.0 mgs of crude (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (31% yield based on UV analysis/purity) as a yellow solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS Rt=1.632 min., m/z 632.30 (M+H).

Example 3060: (S)-1-(5-chloro-2-((5-cyanopyridin-3-yl)methoxy)-4-((3'-((2-((R)-3-hydroxypyrrolidin-1-yl)ethyl)carbamoyl)-2,2'-dimethyl-[1,1'-biphenyl]-3-yl)methoxy)benzyl)piperidine-2-carboxylic Acid

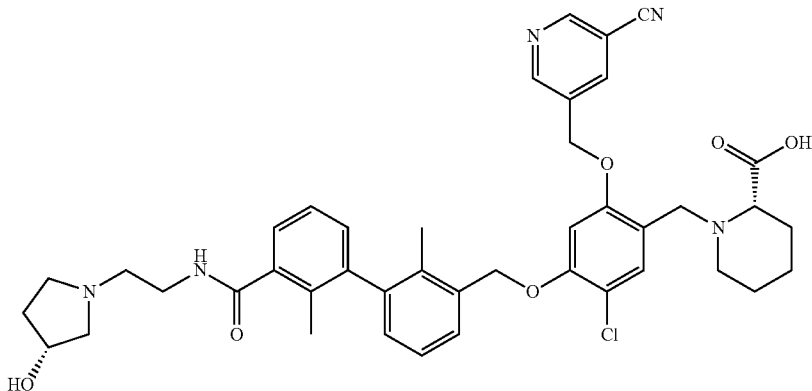 [SMILES: Cc1c(COc2cc(OCc3cncc(C#N)c3)c(CN3CCCC[C@H]3C(=O)O)cc2Cl)cccc1-c1cccc(C(=O)NCCN2CC[C@@H](O)C2)c1C]

To a sealed tube was added THF (6.0 mL), water (2.0 mL), (R)-3-bromo-N-(2-(3-hydroxypyrrolidin-1-yl)ethyl)-2-methylbenzamide, TFA (34.9 mg, 0.079 mmol), (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (50 mg, 0.079 mmol), tribasic potassium phosphate (42.0 mg, 0.198 mmol), and 2nd Generation X-Phos precatalyst (3.11 mg, 3.96 μmol). The mixture was de-gassed/flushed with nitrogen then heated overnight at 70° C. The reaction mixture was cooled, evaporated to near dryness, taken up in 2 mL of methanol, filtered and purified using preparative LC/MS with the following conditions: Waters XBridge 5 μm C18, 19×200 mm where mobile phase A was 5:95 acetonitrile:water with 10 mM ammonium acetate and mobile phase B was 95:5 acetonitrile:water 10 mM ammonium acetate at a gradient of 7-47% B over 27 minutes with a 5-minute hold at a flow rate of 20 mL/minute. Fractions containing the desired product were combined and dried via centrifugal evaporation. The yield of the product was 3.3 mg (5%), and its estimated purity by LCMS analysis was 90%. $^1$H NMR (500 MHz, DMSO-$d_6$) δ 8.99 (dd, J=8.7, 1.7 Hz, 2H), 8.44 (s, 1H), 7.52 (m, 1H), 7.44 (s, 1H), 7.29 (m, 1H), 7.14 (m, 1H), 7.04 (s, 1H), 6.99 (m, 1H), 6.90 (d, J=7.3 Hz, 1H), 6.83 (d, J=7.6 Hz, 1H), 5.31 (s, 2H), 5.13 (s, 2H), 3.91 (br.s., 1H), 3.77 (d, J=14.0 Hz, 2H), 3.18 (m, 3H), 2.98 (m, 3H), 2.86 (m, 2H), 2.15 (m, 4H), 2.05 (m, 2H), 1.97 (m, 2H), 1.86 (s, 3H), 1.80-1.63 (m, 2H), 1.56-1.42 (m, 3H), 1.37-1.23 (m, 1H). Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.205 min; ESI-MS (+) m/z=752.2 (M+H)
Analysis condition 2: Retention time=1.252 min; ESI-MS (+) m/z=752.2 (M+H)

Intermediate: 5-((4-chloro-2-formyl-5-((3'-formyl-2-methyl[1,1'-biphenyl]-3-yl)methoxy)phenoxy)methyl)nicotinonitrile

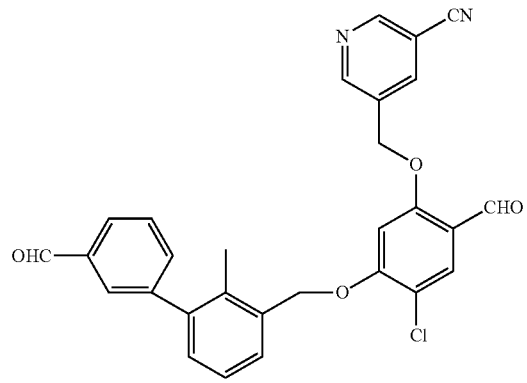 [SMILES: Cc1c(COc2cc(OCc3cncc(C#N)c3)c(C=O)cc2Cl)cccc1-c1cccc(C=O)c1]

A mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (150 mg, 0.289 mmol), 3-bromobenzaldehyde (64.2 mg, 0.347 mmol), 2nd generation XPhos precatalyst (11.37 mg, 0.014 mmol), and potassium phosphate tribasic (1.445 mL, 0.723 mmol) in THF (4.5 mL) was degassed, and then sealed. The mixture was stirred at room temperature for 22 hrs. The solvent was removed. The crude product was used directly for the next step without further purification. $^1$H NMR (500 MHz, DMSO-$d_6$) δ 10.24 (s, 1H), 10.09 (s, 1H), 9.03 (s, 2H), 8.54 (s, 1H), 7.94 (d, J=6.2 Hz, 1H), 7.86 (s, 1H), 7.76-7.66 (m, 3H), 7.57 (d, J=7.3 Hz, 1H), 7.40-7.33 (m, 1H), 7.33-7.24 (m, 2H), 5.50 (s, 2H), 5.44 (s, 2H), 2.25 (s, 3H).

Example 3061: (S)-2-(((3'-((4-((((S)-1-carboxy-4-guanidinobutyl)amino)methyl)-2-chloro-5-((5-cyanopyridin-3-yl)methoxy)phenoxy)methyl)-2'-methyl-[1,1'-biphenyl]-3-yl)methyl)amino)-5-guanidinopentanoic Acid

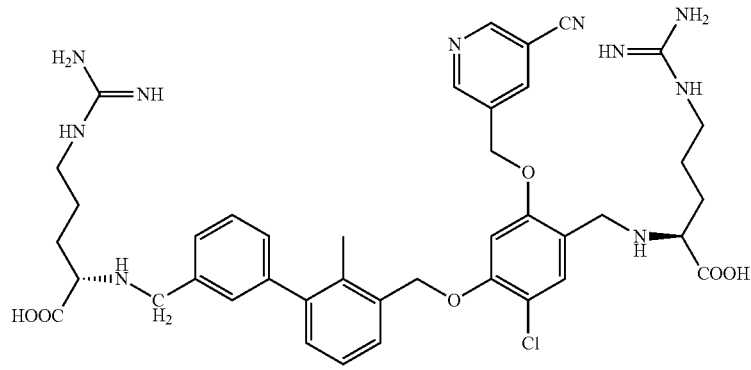 [SMILES: Cc1c(COc2cc(OCc3cncc(C#N)c3)c(CN[C@@H](CCCNC(=N)N)C(=O)O)cc2Cl)cccc1-c1cccc(CN[C@@H](CCCNC(=N)N)C(=O)O)c1]

To a suspension of (S)-2-amino-5-guanidinopentanoic acid (20.31 mg, 0.117 mmol) in MeOH (1 mL) and acetic acid (0. mL) was added 5-((4-chloro-2-formyl-5-((3'-formyl-2-methyl-[1,1'-biphenyl]-3-yl)methoxy)phenoxy)methyl)nicotinonitrile (26.3 mg, 0.053 mmol, crude) followed by borane-2-picoline complex (12.47 mg, 0.117 mmol). The mixture was stirred at rt overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 12.6 mg (28%). $^1$H NMR (500 MHz, DMSO-$d_6$) δ 8.98 (d, J=8.2 Hz, 2H), 8.44 (br. s., 1H), 7.45 (d, J=7.9 Hz, 1H), 7.42-7.37 (m, 2H), 7.33 (d, J=7.0 Hz, 1H), 7.30-7.21 (m, 2H), 7.19 (br. s., 2H), 7.05 (s, 1H), 5.36-5.21 (m, 4H), 3.86 (m, 2H), 3.05-2.91 (m, 8H), 2.21 (s, 3H), 1.64-1.39 (m, 8H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 conditions) Rt=1.052 min, ESI m/z 813 (M+1), 811 (M−1).

LCMS (Injection 2 conditions) Rt=2.443 min, ESI m/z 813 (M+1), 811 (M−1).

Example 3062: 5-((4-chloro-2-(((3-(dimethylamino)propyl)amino)methyl)-5-((3'-(((3-(dimethylamino)propyl)amino)methyl)-2-methyl-[1,1'-biphenyl]-3-yl)methoxy)phenoxy)methyl)nicotinonitrile

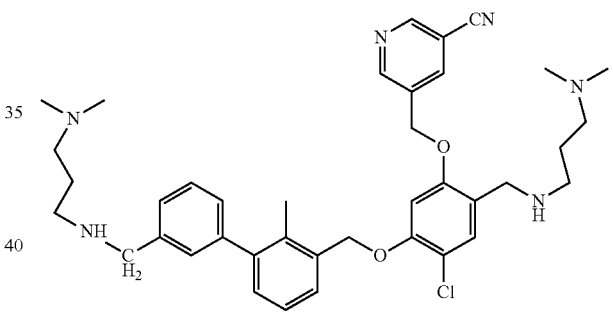

5-((4-Chloro-2-(((3-(dimethylamino)propyl)amino)methyl)-5-((3'-(((3-(dimethylamino)propyl)amino)methyl)-2-methyl-[1,1'-biphenyl]-3-yl)methoxy)phenoxy)methyl)nicotinonitrile (18.9 mg, 52%) was obtained from 5-((4-chloro-2-formyl-5-((3'-formyl-2-methyl-[1,1'-biphenyl]-3-yl)methoxy)phenoxy)methyl)nicotinonitrile and N,N-dimethyl-1,3-propanediamine using the procedure described for (S)-2-(((3'-((4-((((S)-1-carboxy-4-guanidinobutyl)amino)methyl)-2-chloro-5-((5-cyanopyridin-3-yl)methoxy)phenoxy)methyl)-2'-methyl-[1,1'-biphenyl]-3-yl)methyl)amino)-5-guanidinopentanoic acid, Example 3061. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:

water with 10-mM ammonium acetate; Gradient: 30-70% B over 30 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.02 (s, 1H), 8.99 (s, 1H), 8.43 (s, 1H), 7.49 (d, J=7.3 Hz, 1H), 7.43-7.38 (m, 2H), 7.34 (d, J=7.3 Hz, 1H), 7.31-7.26 (m, 2H), 7.20 (dd, J=13.0, 7.5 Hz, 2H), 7.12 (s, 1H), 5.34 (s, 2H), 5.27 (s, 2H), 3.79 (s, 2H), 3.70-3.50 (m, 2H), 2.57 (t, J=7.0 Hz, 2H), 2.55-2.47 (m, 2H), 2.29-2.20 (m, 7H), 2.10 (d, J=5.1 Hz, 12H), 1.62-1.51 (m, 4H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 minutes, then a 0.5-minute hold at 100% B; Flow: 0.5 mL/min; Detection: UV at 220 nm.

LCMS (Injection 1 conditions) Rt=1.383 min, ESI m/z 669 (M+1).

LCMS (Injection 2 conditions) Rt=2.762 min, ESI m/z 669 (M+1).

Intermediate: (3R,3'R)-1,1'-(((5-bromo-1,3-phenylene)bis(oxy))bis(propane-3,1-diyl))bis(pyrrolidin-3-ol)

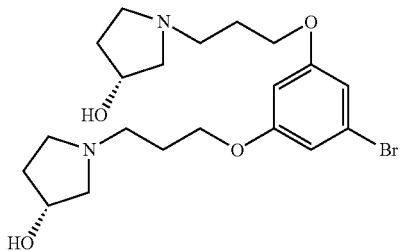 [SMILES: O[C@@H]1CCN(CCCOc2cc(Br)cc(OCCCN3CC[C@@H](O)C3)c2)C1]

To a solution of 5-bromobenzene-1,3-diol (1 g, 5.29 mmol) in DMF (15 mL) was added 1-bromo-3-chloropropane (1.145 mL, 11.64 mmol) and K$_2$CO$_3$ (2.194 g, 15.87 mmol). The reaction mixture was stirred at 50° C. for 19 hrs. The solvent was removed to give the crude compound, 1-bromo-3,5-bis(3-chloropropoxy)benzene, as an oil (1.83 g). The compound was used directly for the next step without further purification. $^1$H NMR (500 MHz, CHLOROFORM-d) δ 6.71 (d, J=2.2 Hz, 2H), 6.45-6.40 (m, 1H), 4.15-4.07 (m, 4H), 3.75 (t, J=6.3 Hz, 4H), 2.24 (quin, J=6.1 Hz, 4H).

A stirred mixture of 1-bromo-3,5-bis(3-chloropropoxy) benzene (330 mg, 0.965 mmol), (R)-pyrrolidin-3-ol, HCl (298 mg, 2.412 mmol) and K$_2$CO$_3$ (333 mg, 2.412 mmol), sodium iodide (289 mg, 1.930 mmol) in DMF (2 mL) was heated at 80° C. for 15 h. The solvent was removed. The residue was partitioned between EtOAc and water. The aqueous phase was extracted once with ethyl acetate. The organic extracts were combined and washed with brine then dried over sodium sulfate. The drying agent was removed by filtration and solvent removed in vacuo. The resulting residue was purified by preparative HPLC to give the target compound (352 mg). $^1$H NMR (400 MHz, METHANOL-d4) δ 6.78 (d, J=2.3 Hz, 2H), 6.54 (s, 1H), 4.61 (br. s., 2H), 4.10 (t, J=5.6 Hz, 4H), 3.92-3.75 (m, 3H), 3.64 (d, J=11.8 Hz, 1H), 3.55-3.30 (m, 5H), 3.30-3.12 (m, 3H), 2.48-2.34 (m, 1H), 2.29-2.01 (m, 7H).

Intermediate: 5-((5-((3',5'-bis(3-((R)-3-hydroxypyrrolidin-1-yl)propoxy)-2-methyl-[1,1'-biphenyl]-3-yl) methoxy)-4-chloro-2-formylphenoxy)methyl)nicotinonitrile

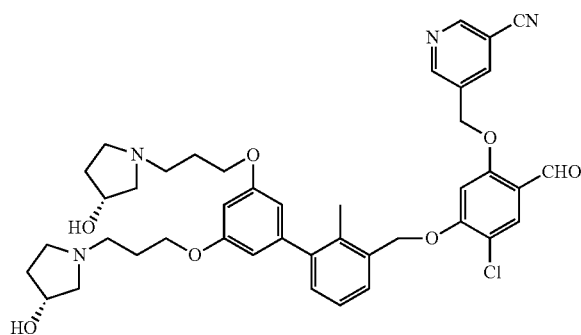 [SMILES: Cc1c(COc2cc(OCc3cncc(C#N)c3)c(C=O)cc2Cl)cccc1-c1cc(OCCCN2CC[C@@H](O)C2)cc(OCCCN2CC[C@@H](O)C2)c1]

5-((5-((3',5'-bis(3-((R)-3-Hydroxypyrrolidin-1-yl) propoxy)-2-methyl-[1,1'-biphenyl]-3-yl)methoxy)-4-chloro-2-formylphenoxy)methyl)nicotinonitrile (201 mg, 92%) was obtained from 5-((4-chloro-2-formyl-5-((2-methyl-3-(4,4,5,5-tetramethyl-1,3,2-dioxaborolan-2-yl)benzyl)oxy)phenoxy)methyl)nicotinonitrile and (3R,3'R)-1,1'-(((5-bromo-1,3-phenylene)bis(oxy))bis(propane-3,1-diyl)) bis(pyrrolidin-3-ol) using the procedure described for 5-((4-chloro-2-formyl-5-((3'-formyl-2-methyl[1,1'-biphenyl]-3-yl)methoxy)phenoxy)methyl)nicotinonitrile. $^1$H NMR (500 MHz, METHANOL-d$_4$) δ 10.25 (s, 1H), 8.98 (d, J=1.9 Hz, 1H), 8.92 (d, J=1.7 Hz, 1H), 8.37 (s, 1H), 7.81 (s, 1H), 7.49 (d, J=6.8 Hz, 1H), 7.29-7.20 (m, 2H), 7.08 (s, 1H), 6.76 (d, J=2.2 Hz, 1H), 6.61-6.57 (m, 1H), 6.55-6.48 (m, 1H), 5.44 (s, 2H), 5.38 (s, 2H), 4.58 (dq, J=5.1, 2.6 Hz, 3H), 4.22-4.05 (m, 5H), 3.70-3.53 (m, 2H), 3.48-3.35 (m, 9H), 2.39-2.14 (m, 5H), 2.28 (s, 3H), 2.11-1.98 (m, 2H), Example 3063: 5-((5-((3',5'-bis(3-((R)-3-hydroxypyrrolidin-1-yl)propoxy)-2-methyl-[1,1'-biphenyl]-3-yl)methoxy)-4-chloro-2-(hydroxymethyl)phenoxy) methyl)nicotinonitrile

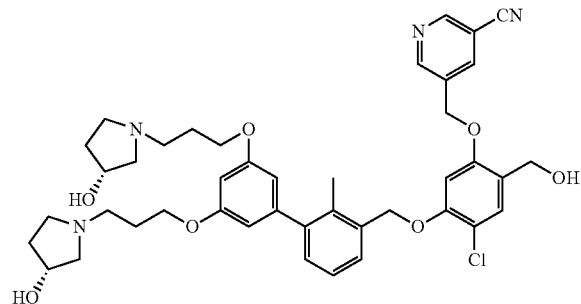 [SMILES: Cc1c(COc2cc(OCc3cncc(C#N)c3)c(CO)cc2Cl)cccc1-c1cc(OCCCN2CC[C@@H](O)C2)cc(OCCCN2CC[C@@H](O)C2)c1]

5-((5-((3',5'-bis(3-((R)-3-Hydroxypyrrolidin-1-yl)propoxy)-2-methyl-[1,1'-biphenyl]-3-yl)methoxy)-4-chloro-2-(hydroxymethyl)phenoxy)methyl)nicotinonitrile (10.1 mg, 19%) was obtained from 5-((5-((3',5'-bis(3-((R)-3-hydroxypyrrolidin-1-yl)propoxy)-2-methyl-[1,1'-biphenyl]-3-yl)methoxy)-4-chloro-2-formylphenoxy)methyl)nicotinonitrile under the conditions using borane-2-picoline complex in MeOH and acetic acid at room temperature. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (s, 1H), 8.97 (s, 1H), 8.41 (s, 1H), 7.47 (d, J=7.7 Hz, 1H), 7.36 (s, 1H), 7.26 (t, J=7.7 Hz, 1H), 7.22-7.17 (m, 1H), 7.09 (s, 1H), 6.52 (br. s., 1H), 6.44 (s, 2H), 5.37-5.31 (m, 2H), 5.25 (s, 2H), 4.55-4.43 (m, 2H), 4.38 (br. s., 2H), 4.06 (t, J=5.7 Hz, 4H), 3.32-2.96 (m, 13H), 2.24 (s, 3H), 2.17-1.98 (m, 6H), 1.80 (br. s., 2H).

Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.548 min, ESI m/z 757 (M+1).

LCMS (Injection 2 conditions) Rt=2.958 min, ESI m/z 757 (M+1).

Example 3064: (S)-2-((4-((3',5'-bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxy-2-methylpropanoic Acid

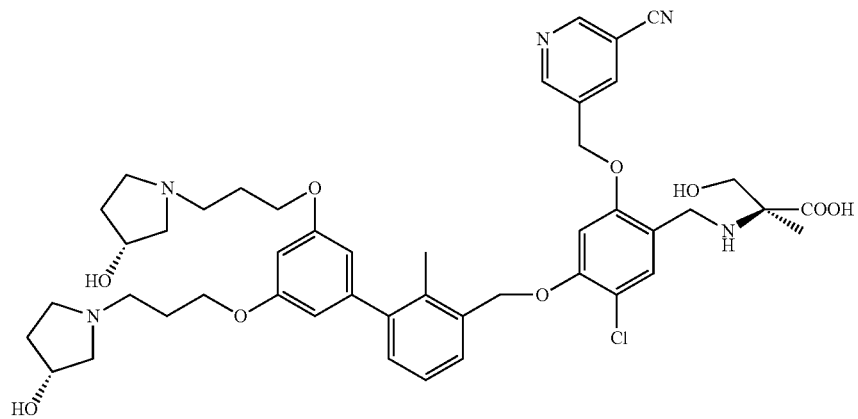 [SMILES: Cc1c(COc2cc(OCc3cncc(C#N)c3)c(CN[C@@](C)(CO)C(=O)O)cc2Cl)cccc1-c1cc(OCCCN2CC[C@@H](O)C2)cc(OCCCN2CC[C@@H](O)C2)c1]

(S)-2-((4-((3',5'-Bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxy-2-methylpropanoic acid (3.6 mg, 15%) was obtained from 5-((5-((3',5'-bis(3-((R)-3-hydroxypyrrolidin-1-yl)propoxy)-2-methyl-[1,1'-biphenyl]-3-yl)methoxy)-4-chloro-2-formylphenoxy)methyl)nicotinonitrile and (S)-2-amino-3-hydroxy-2-methylpropanoic acid by reduction using sodium triacetoxyborohydride in DMF at room temperature. The crude material was purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (s, 1H), 9.01 (s, 1H), 8.51 (s, 1H), 7.57 (s, 1H), 7.48 (d, J=7.7 Hz, 1H), 7.30-7.23 (m, 1H), 7.20 (d, J=7.3 Hz, 1H), 7.13 (s, 1H), 6.52 (br. s., 1H), 6.43 (s, 2H), 5.37 (s, 2H), 5.29 (s, 2H), 4.39 (d, J=2.2 Hz, 2H), 4.10-3.95 (d, J=0.7 Hz, 6H), 3.70-3.54 (m, 5H), 3.5-4.40 (m, 1H), 3.25-3.00 (m, 7H), 2.68 (br. s., 1H), 2.23 (s, 3H), 2.18-2.00 (m, 6H), 1.83 (d, J=1.5 Hz, 2H), 1.24 (S, 3H).

Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm LCMS (Injection 1 conditions) Rt=1.467 min, ESI m/z 858 (M+1).

LCMS (Injection 2 conditions) Rt=1.143 min, ESI m/z 858 (M+1), 856 (M−1).

Example 3065: (S)-2-((4-((3',5'-bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxypropanoic Acid

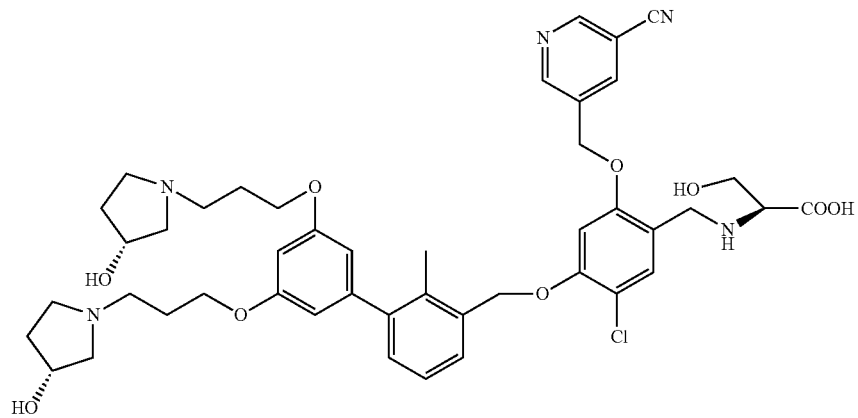 [SMILES: Cc1c(COc2cc(OCc3cncc(C#N)c3)c(CN[C@@H](CO)C(=O)O)cc2Cl)cccc1-c1cc(OCCCN2CC[C@@H](O)C2)cc(OCCCN2CC[C@@H](O)C2)c1]

(S)-2-((4-((3',5'-Bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxypropanoic acid (0.9 mg, 3.6%) was obtained from 5-((5-((3',5'-bis(3-((R)-3-hydroxypyrrolidin-1-yl)propoxy)-2-methyl-[1,1'-biphenyl]-3-yl)methoxy)-4-chloro-2-formylphenoxy)methyl)nicotinonitrile and (S)-2-amino-3-hydroxypropanoic acid using the procedure described for Example 3064. The crude material was purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 20-100% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.03 (s, 2H), 8.55-8.51 (m, 1H), 7.52 (s, 1H), 7.48 (d, J=7.3 Hz, 1H), 7.30-7.24 (m, 1H), 7.23-7.19 (m, 1H), 7.14 (s, 1H), 6.49 (t, J=2.1 Hz, 1H), 6.40 (d, J=2.2 Hz, 2H), 5.40-5.31 (m, 2H), 5.28 (s, 2H), 4.23-4.16 (m, 2H), 4.03 (t, J=6.3 Hz, 4H), 3.96 (d, J=1.9 Hz, 2H), 3.72-3.66 (m, 1H), 3.64-3.58 (m, 1H), 3.16-3.12 (m, 1H), 2.73 (dd, J=9.3, 6.3 Hz, 2H), 2.67-2.41 (m, 8H), 2.37 (d, J=1.9 Hz, 2H), 2.25 (s, 3H), 2.02-1.93 (m, 2H), 1.90-1.83 (m, 4H), 1.55 (dd, J=8.0, 4.7 Hz, 2H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.446 min, ESI m/z 844 (M+1), 842 (M−1).

LCMS (Injection 2 conditions) Rt=1.143 min, ESI m/z 844 (M+1).

Example 3066: (S)-ethyl 2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoate

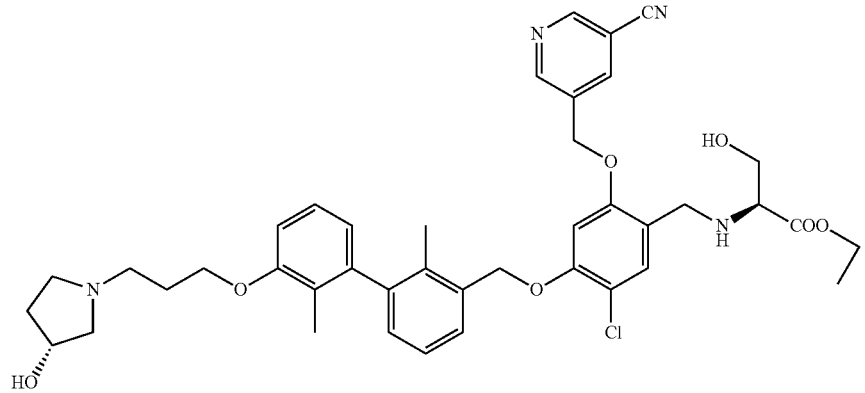

(S)-Ethyl 2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoate (6.0 mg, 20%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and (S)-ethyl 2-amino-3-hydroxypropanoate, HCl using using the procedure described for (S)-2-(((3'-((4-((((S)-1-carboxy-4-guanidinobutyl)amino)methyl)-2-chloro-5-((5-cyanopyridin-3-yl)methoxy)phenoxy)methyl)-2'-methyl-[1,1'-biphenyl]-3-yl)methyl)amino)-5-guanidinopentanoic acid Example 3061. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. $^1$H NMR (500 MHz, METHANOL-$d_4$) δ 8.98 (s, 1H), 8.96 (s, 1H), 8.51 (s, 1H), 7.55 (s, 1H), 7.49 (d, J=7.3 Hz, 1H), 7.30-7.21 (m, 2H), 7.12-7.07 (m, 2H), 6.98 (d, J=8.4 Hz, 1H), 6.75 (d, J=7.3 Hz, 1H), 5.39 (s, 2H), 5.34 (s, 2H), 4.85 (br. s., 1H), 4.60 (br. s., 1H), 4.33 (d, J=5.1 Hz, 2H), 4.27 (dd, J=11.0, 7.3 Hz, 2H), 4.19 (br. s., 2H), 4.11 (br. s., 1H), 4.02 (d, J=3.3 Hz, 2H), 3.87 (br, s, 1H), 3.68-3.42 (m, 2H), 3.20 (m, 1H), 3.07 (m, 1H), 2.40 (br, s, 1H), 2.32 (br. s., 2H), 2.22-2.01 (m, 1H), 2.11 (s, 3H), 1.94 (s, 3H), 1.30 (t, J=7.3 Hz, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.358 min, ESI m/z 743 (M+1).

LCMS (Injection 2 conditions) Rt=1.560 min, ESI m/z 743 (M+1).

Example 3067: methyl (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylate

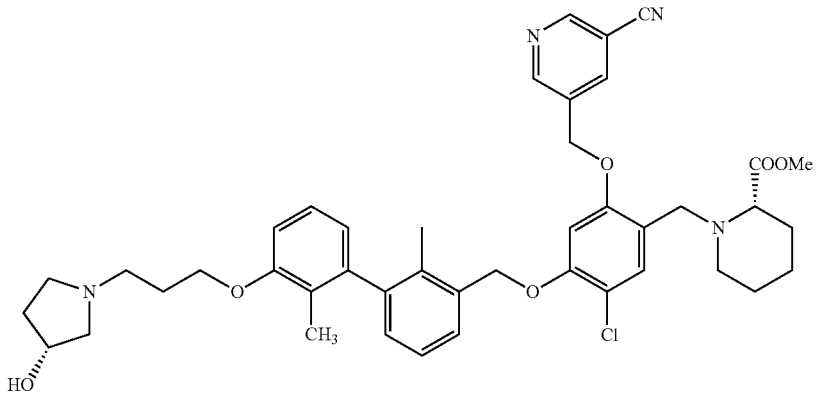 [SMILES: COC(=O)[C@@H]1CCCCN1Cc1cc(Cl)c(OCc2cccc(-c3cccc(OCCCN4CC[C@@H](O)C4)c3C)c2C)cc1OCc1cncc(C#N)c1]

Methyl (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylate was prepared in a similar manner. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.02 (d, J=2.0 Hz, 1H), 8.99 (d, J=2.0 Hz, 1H), 8.46-8.43 (m, 1H), 7.49 (d, J=7.4 Hz, 1H), 7.32 (s, 1H), 7.27 (t, J=7.5 Hz, 1H), 7.21 (t, J=7.9 Hz, 1H), 7.12-7.05 (m, 2H), 6.96 (d, J=8.2 Hz, 1H), 6.68 (d, J=7.4 Hz, 1H), 5.33 (s, 2H), 5.26 (s, 2H), 4.18 (br. s., 1H), 4.12-3.99 (m, 2H), 3.62-3.55 (m, 4H), 3.47 (d, J=13.7 Hz, 1H), 3.24 (t, J=5.5 Hz, 1H), 2.86-2.79 (m, 1H), 2.70 (dd, J=9.3, 6.3 Hz, 1H), 2.61-2.53 (m, 3H), 2.43 (dt, J=5.4, 2.6 Hz, 1H), 2.32 (dd, J=9.6, 3.8 Hz, 1H), 2.25-2.17 (m, 1H), 2.04 (s, 3H), 1.99 (dt, J=13.2, 6.9 Hz, 1H), 1.94-1.87 (m, 2H), 1.82 (s, 3H), 1.77-1.69 (m, 2H), 1.58-1.50 (m, 1H), 1.50-1.35 (m, 4H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.224 min, ESI m/z 753 (M+1), 775 (M+Na).

LCMS (Injection 2 conditions) Rt=1.545 min, ESI m/z 753 (M+1), 775 (M+Na).

Example 3068: 1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylic Acid

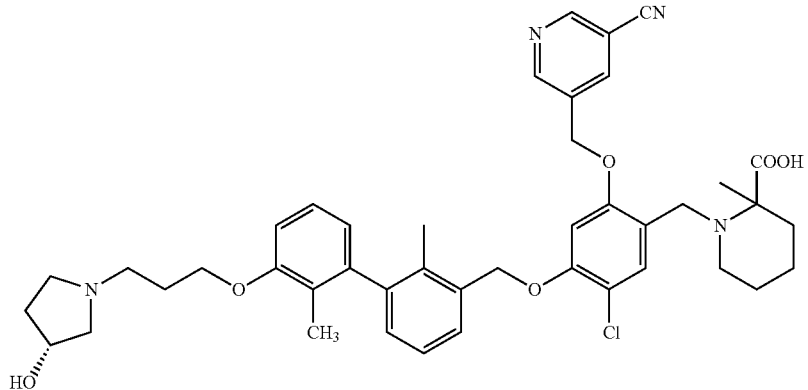 [SMILES: Cc1c(COc2cc(OCc3cncc(C#N)c3)c(CN3CCCCC3(C)C(=O)O)cc2Cl)cccc1-c1cccc(OCCCN2CC[C@@H](O)C2)c1C]

1-(5-Chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylic acid (2.1 mg, 3.4%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and 2-methylpiperidine-2-carboxylic acid, HCl using the procedure described for Example 3064. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation.

$^1$H NMR (500 MHz, DMSO-$d_6$) δ 9.03-8.97 (m, 2H), 8.46 (s, 0.28H), 8.41 (s, 0.72H), 7.52-7.41 (m, 2H), 7.27 (s, 1H), 7.21 (t, J=7.9 Hz, 1H), 7.12-7.05 (m, 2H), 6.96 (d, J=8.1 Hz, 1H), 6.68 (d, J=7.7 Hz, 1H), 5.33 (br. s., 2H), 5.28-5.20 (m, 2H), 4.23-4.15 (m, 1H), 4.11-3.99 (m, 2H), 3.87-3.74 (m, 1H), 3.64-3.56 (m, 1H), 2.74-2.62 (m, 1H), 2.61-2.54 (m, 2H), 2.49-2.36 (m, 2H), 2.35-2.29 (m, 1H), 2.16 (s, 2H), 2.03 (s, 3H), 2.20-1.93 (m, 2H), 1.93-1.88 (m, 2H), 1.82 (s, 3H), 1.50 (d, J=5.5 Hz, 6H), 1.27 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1× 50 mm, 1.7-μm particles; Mobile Phase A: 5:95 water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.494 min, ESI m/z 753 (M+1), 751 (M−1).

LCMS (Injection 2 conditions) Rt=1.476 min, ESI m/z 753 (M+1).

Example 3069: methyl 1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylate

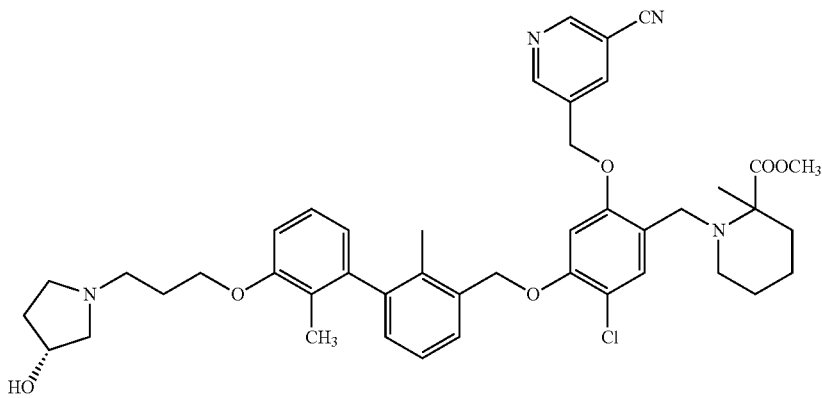 [SMILES: COC(=O)C1(C)CCCCN1Cc1cc(Cl)c(OCc2cccc(-c3cccc(OCCCN4CC[C@@H](O)C4)c3C)c2C)cc1OCc1cncc(C#N)c1]

Methyl 1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylate (2.2 mg, 3.37%) was obtained from (R)-5-((4-chloro-2-formyl-5-((3'-(3-(3-hydroxypyrrolidin-1-yl)propoxy)-2,2'-dimethyl-[1,1'-biphenyl]-3-yl)methoxy)phenoxy)methyl)nicotinonitrile and methyl 2-methylpiperidine-2-carboxylate using the procedure described Example 3064. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (d, J=1.8 Hz, 1H), 8.97 (d, J=1.8 Hz, 1H), 8.38 (s, 1H), 7.47 (d, J=7.3 Hz, 1H), 7.39 (s, 1H), 7.26 (t, J=7.5 Hz, 1H), 7.20 (t, J=7.9 Hz, 1H), 7.09-7.03 (m, 2H), 6.95 (d, J=8.1 Hz, 1H), 6.67 (d, J=7.7 Hz, 1H), 5.38-5.28 (m, 2H), 5.23 (s, 2H), 4.22-4.15 (m, 1H), 4.10-3.99 (m, 2H), 3.82 (d, J=15.8 Hz, 1H), 3.64 (s, 3H), 2.74-2.66 (m, 1H), 2.60-2.55 (3H), 2.42 (d, J=10.6 Hz, 2H), 2.34-2.28 (m, 1H), 2.06-1.93 (m, 2H), 2.02 (s, 3H), 1.93-1.86 (m, 2H), 1.85-1.74 (m, 2H), 1.81 (s, 3H), 1.59-1.33 (m, 5H), 1.23 (br. s., 4H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.520 min, ESI m/z 767 (M+1).

LCMS (Injection 2 conditions) Rt=1.614 min, ESI m/z 767 (M+1).

Example 3070: methyl 1-(5-chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)-2-methylpiperidine-2-carboxylate methyl 1-(5-chloro-4-((2'-chloro-3'-(3-((R)-3-hydroxypyrrolidin-1-yl)propoxy)-2-methyl-[1,1'-biphenyl]-yl)methoxy)-2-((5-cyanopyridin-3-yl)methoxy)benzyl)-2-methylpiperidine-2-carboxylate (7.6 mg, 18.3%) was obtained from methyl 1-(5-chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)-2-methylpiperidine-2-carboxylate, and methyl 2-methylpiperidine-2-carboxylate using the procedure described Example 3064. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (d, J=1.5 Hz, 1H), 8.97 (s, 1H), 8.39 (s, 1H), 7.51 (d, J=7.0 Hz, 1H), 7.40 (s, 1H), 7.36 (t, J=8.1 Hz, 1H), 7.29 (s, 1H), 7.17 (d, J=8.4 Hz, 1H), 7.11 (d, J=7.3 Hz, 1H), 7.07 (s, 1H), 6.85 (d, J=7.7 Hz, 1H), 5.38-5.28 (m, 2H), 5.28-5.19 (m, 2H), 4.22-4.09 (m, 3H), 3.82 (d, J=15.8 Hz, 1H), 3.64 (s, 3H), 2.72-2.67 (m, 1H), 2.62-2.53 (m, 3H), 2.46-2.38 (m, 2H), 2.32 (br. s., 1H), 2.07 (s, 3H), 2.03-1.83 (m, 5H), 1.59-1.35 (m, 6H), 1.28 (s, 4H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=2.496 min, ESI m/z 787 (M+1).

LCMS (Injection 2 conditions) Rt=1.599 min, ESI m/z 787 (M+1).

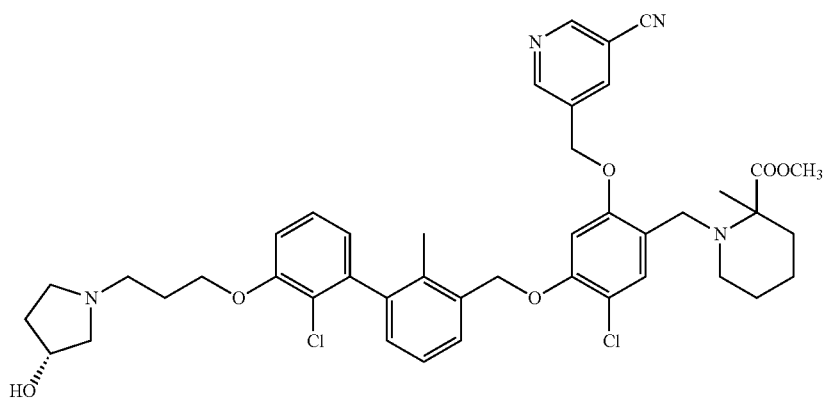 [SMILES: COC(=O)C1(C)CCCCN1Cc1cc(Cl)c(OCc2cccc(-c3cccc(OCCCN4CC[C@@H](O)C4)c3Cl)c2C)cc1OCc1cncc(C#N)c1]

Intermediate: 3-chloro-4-((2-methyl-3-(4,4,5,5-tetramethyl-1,3,2-dioxaborolan-2-yl)benzyl)oxy)benzaldehyde

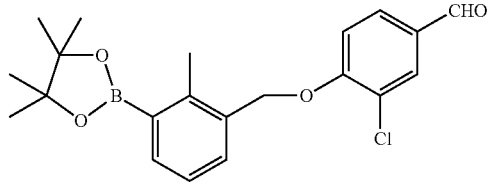 [SMILES: Cc1c(COc2ccc(C=O)cc2Cl)cccc1B1OC(C)(C)C(C)(C)O1]

3-chloro-4-((2-methyl-3-(4,4,5,5-tetramethyl-1,3,2-dioxaborolan-2-yl)benzyl)oxy)benzaldehyde (1.95 g, 623%) was obtained from (2-methyl-3-(4,4,5,5-tetramethyl-1,3,2-dioxaborolan-2-yl)phenyl)methanol and 3-chloro-4-hydroxybenzaldehyde by using diisopropyl azodicarboxylate and triphenylphosphine in tetrahydrofuran at room temperature. $^1$H NMR (500 MHz, CHLOROFORM-d) δ 9.87 (s, 1H), 7.95 (d, J=2.0 Hz, 1H), 7.85-7.73 (m, 2H), 7.55 (d, J=7.1 Hz, 1H), 7.25 (s, 1H), 7.13 (d, J=8.5 Hz, 1H), 5.25 (s, 2H), 2.61 (s, 3H), 1.39 (s, 12H).

Intermediate: 3-chloro-4-((3'-(3-chloropropoxy)-2,2'-dimethyl-[1,1'-biphenyl]-3-yl)methoxy)benzaldehyde

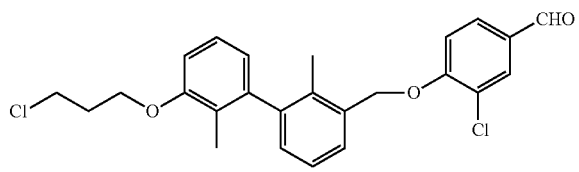 [SMILES: Cc1c(COc2ccc(C=O)cc2Cl)cccc1-c1cccc(OCCCCl)c1C]

3-Chloro-4-((3'-(3-chloropropoxy)-2,2'-dimethyl-[1,1'-biphenyl]-3-yl)methoxy)benzaldehyde (382 mg, 56%) was obtained from 3-chloro-4-((2-methyl-3-(4,4,5,5-tetramethyl-1,3,2-dioxaborolan-2-yl)benzyl)oxy)benzaldehyde and 1-bromo-3-(3-chloropropoxy)-2-methylbenzene under the conditions using 2nd generation XPhos precatalyst and potassium phosphate tribasic in THF at room temperature. $^1$H NMR (500 MHz, CHLOROFORM-d) δ 9.89 (s, 1H), 7.97 (d, J=1.9 Hz, 1H), 7.81 (dd, J=8.4, 2.0 Hz, 1H), 7.55-7.47 (m, 1H), 7.35-7.27 (m, 1H), 7.26-7.16 (m, 3H), 6.91 (d, J=7.9 Hz, 1H), 6.84-6.77 (m, 1H), 5.30 (s, 2H), 4.27-4.14 (m, 2H), 3.83 (t, J=6.4 Hz, 2H), 2.38-2.27 (m, 2H), 2.12 (s, 3H), 1.96 (s, 3H).

Intermediate: (R)-3-chloro-4-((3'-(3-(3-hydroxypyrrolidin-1-yl)propoxy)-2,2'-dimethyl-[1,1'-biphenyl]-3-1)methoxy)benzaldehyde

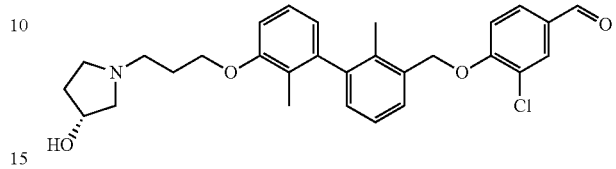

(R)-3-chloro-4-((3'-(3-(3-hydroxypyrrolidin-1-yl)propoxy)-2,2'-dimethyl-[1,1'-biphenyl]-3-yl)methoxy)benzaldehyde (273 mg, 64%) was obtained from 3-chloro-4-((3'-(3-chloropropoxy)-2,2'-dimethyl-[1,1'-biphenyl]-3-yl)methoxy)benzaldehyde and (R)-pyrrolidin-3-ol, HCl under the conditions using K$_2$CO$_3$, sodium iodide in DMF with heating at 60° C. $^1$H NMR (500 MHz, CHLOROFORM-d) δ 9.89 (s, 1H), 7.96 (d, J=1.9 Hz, 1H), 7.80 (dd, J=8.5, 1.9 Hz, 1H), 7.51 (d, J=7.6 Hz, 1H), 7.33-7.27 (m, 1H), 7.25-7.13 (m, 3H), 6.86 (d, J=8.2 Hz, 1H), 6.81 (d, J=7.6 Hz, 1H), 5.29 (d, J=2.4 Hz, 2H), 4.74 (br. s., 1H), 4.23-4.11 (m, 2H), 3.69-3.31 (m, 6H), 2.55-2.47 (m, 2H), 2.46-2.36 (m, 1H), 2.29-2.20 (m, 1H), 2.10 (s, 3H), 1.92 (s, 3H).

Example 3071: 2-((3-chloro-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic Acid

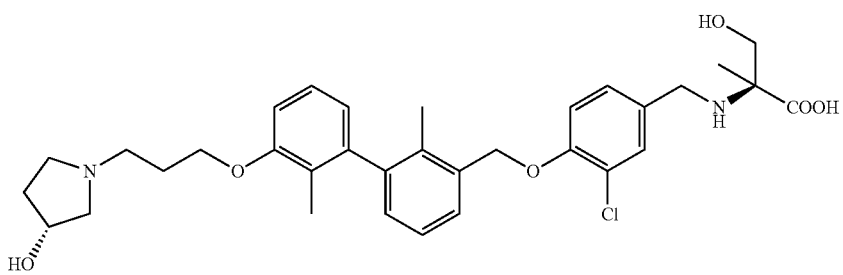 [SMILES: Cc1c(COc2ccc(CN[C@@](C)(CO)C(=O)O)cc2Cl)cccc1-c1cccc(OCCCN2CC[C@@H](O)C2)c1C]

2-((3-Chloro-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid (30.5 mg, 46%) was obtained from (R)-3-chloro-4-((3'-(3-(3-hydroxypyrrolidin-1-yl)propoxy)-2,2'-dimethyl-[1,1'-biphenyl]-3-yl)methoxy)benzaldehyde and 2-amino-3-hydroxy-2-methylpropanoic acid using the procedure described for Example 3061. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. ¹H NMR (500 MHz, DMSO-$d_6$) δ 7.57 (d, J=1.8 Hz, 1H), 7.50 (d, J=7.3 Hz, 1H), 7.40-7.35 (m, 1H), 7.34-7.30 (m, 1H), 7.28 (t, J=7.7 Hz, 1H), 7.21 (t, J=7.9 Hz, 1H), 7.07 (d, J=7.0 Hz, 1H), 6.96 (d, J=8.1 Hz, 1H), 6.68 (d, J=7.3 Hz, 1H), 5.26 (s, 2H), 4.22 (br. s., 1H), 4.11-4.00 (m, 2H), 3.93-3.82 (m, 2H), 3.67-3.60 (m, 1H), 3.58-3.53 (m, 1H), 2.84-2.76 (m, 1H), 2.74-2.61 (m, 3H), 2.60-2.50 (M, 1H), 2.47 (br. s., 1H), 2.06-1.90 (m, 6H), 1.83 (s, 3H), 1.64-1.54 (m, 1H), 1.28 (s, 3H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.305 min, ESI m/z 597 (M+1), 595 (M−1).

LCMS (Injection 2 conditions) Rt=1.296 min, ESI m/z 597 (M+1), 595 (M−1).

Example 3072: (S)-1-(3-chloro-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

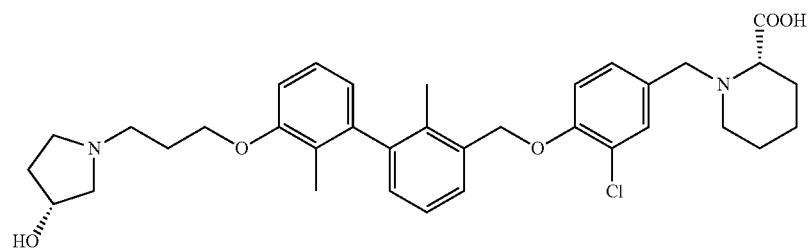 [SMILES: Cc1c(COc2ccc(CN3CCCC[C@H]3C(=O)O)cc2Cl)cccc1-c1cccc(OCCCN2CC[C@@H](O)C2)c1C]

(S)-1-(3-Chloro-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid (28.9 mg, 43%) was obtained from (R)-3-chloro-4-((3'-(3-(3-hydroxypyrrolidin-1-yl)propoxy)-2,2'-dimethyl-[1,1'-biphenyl]-3-yl)methoxy)benzaldehyde and (S)-piperidine-2-carboxylic acid using the procedure described for Example 3061. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. ¹H NMR (500 MHz, DMSO-$d_6$) δ 7.50 (d, J=7.7 Hz, 1H), 7.44 (s, 1H), 7.32-7.25 (m, 3H), 7.23-7.17 (m, 1H), 7.07 (d, J=7.0 Hz, 1H), 6.95 (d, J=8.1 Hz, 1H), 6.67 (d, J=7.7 Hz, 1H), 5.23 (s, 2H), 4.24-4.16 (m, 1H), 4.10-4.00 (m, 2H), 3.85 (d, J=13.6 Hz, 1H), 3.06 (dd, J=8.3, 3.9 Hz, 1H), 2.88 (br. s., 1H), 2.74 (dd, J=9.7, 6.4 Hz, 1H), 2.66-2.57 (m, 3H), 2.54-2.44 (m, 1H), 2.37 (dd, J=9.7, 3.5 Hz, 1H), 2.25 (br. s., 1H), 2.04-1.96 (m, 1H), 2.02 (s, 3H), 1.95-1.88 (m, 3H), 1.82 (m, 1H), 1.82 (s, 3H), 1.69 (m, 1H), 1.61-1.41 (m, 4H), 1.31-1.30 (m, 1H).

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.371 min, ESI m/z 607 (M+1), 605 (M−1).

LCMS (Injection 2 conditions) Rt=1.296 min, ESI m/z 607 (M+1), 605 (M−1).

Example 4001 to Example 4157 and Example 4501 to Example 4516 were prepared in a manner analogous to those described above.

Preparation of Example 4001

(S)-1-(4-((3'-(aziridine-1-carbonyl)-2,2'-dimethyl-[1,1'-biphenyl]-3-yl)methoxy)-5-chloro-2-((5-cyanopyridin-3-yl)methoxy)benzyl)piperidine-2-carboxylic Acid

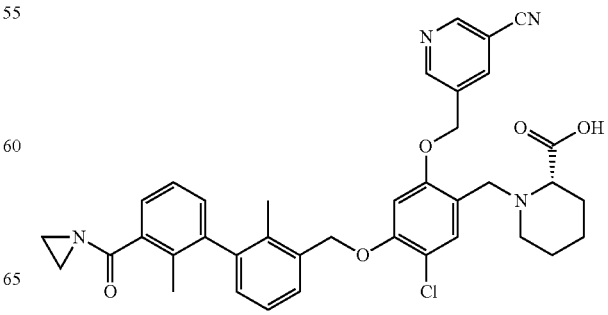

Example 4001

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.84 min, ESI m/z 665.0 (M+H).

LC/MS (Injection 2 conditions) Rt=1.55 min, ESI m/z 665.0 (M+H).

Preparation of Example 4002

(S)-1-(5-chloro-2-((5-cyanopyridin-3-yl)methoxy)-4-((2,2'-dimethyl-3'-((2-(pyrrolidin-1-yl)ethyl)carbamoyl)-[1,1'-biphenyl]-3-yl)methoxy)benzyl)piperidine-2-carboxylic Acid

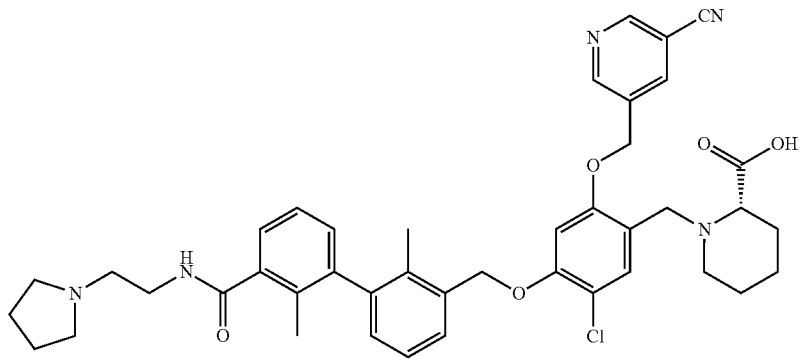 [SMILES: Cc1c(COc2cc(OCc3cncc(C#N)c3)c(CN3CCCC[C@H]3C(=O)O)cc2Cl)cccc1-c1cccc(C(=O)NCCN2CCCC2)c1C]

Example 4002

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 0-minute hold at 100% B; Flow: 20 mL/min. Fractions containing the desired product were combined and dried via centrifugal evaporation.

Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.37 min, ESI m/z 736.1 (M+H).

Preparation of Example 4003

3'-((2-chloro-5-((5-cyanopyridin-3-yl)methoxy)-4-(((1,3-dihydroxypropan-2-yl)amino)methyl)phenoxy)methyl)-2,2'-dimethyl-N-(2-(pyrrolidin-1-yl)ethyl)-[1,1'-biphenyl]-3-carboxamide

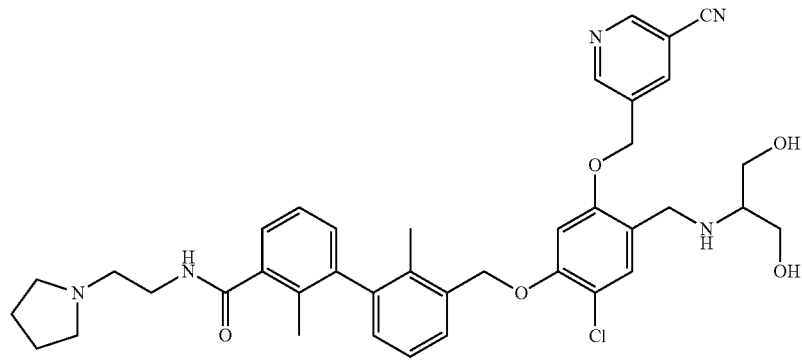 [SMILES: Cc1c(COc2cc(OCc3cncc(C#N)c3)c(CNC(CO)CO)cc2Cl)cccc1-c1cccc(C(=O)NCCN2CCCC2)c1C]

Example 4003

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.42 min, ESI m/z 698.1 (M+H).

LCMS (Injection 2 conditions) Rt=1.38 min, ESI m/z 698.0 (M+H).

Preparation of Example 4004

(S)-1-(5-chloro-2-((5-cyanopyridin-3-yl)methoxy)-4-((3'-((2-(1,1-dioxidothiomorpholino)ethyl)carbamoyl)-2,2'-dimethyl-[1,1'-biphenyl]-3-yl)methoxy)benzyl)piperidine-2-carboxylic Acid

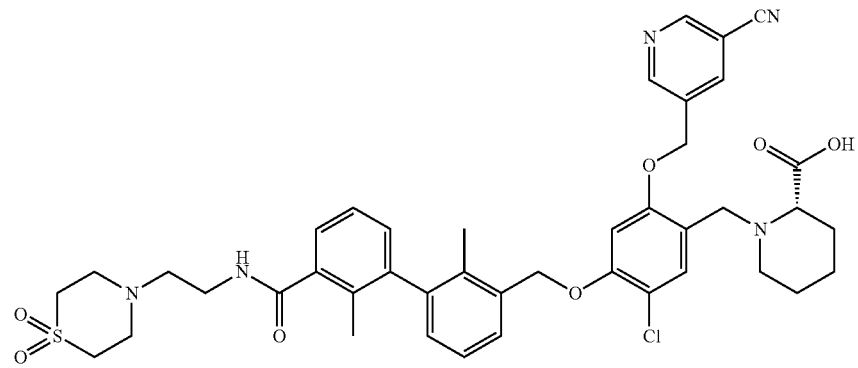 [SMILES: Cc1c(COc2cc(OCc3cncc(C#N)c3)c(CN3CCCC[C@H]3C(=O)O)cc2Cl)cccc1-c1cccc(C(=O)NCCN2CCS(=O)(=O)CC2)c1C]

Example 4004

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.51 min, ESI m/z 800.0 (M+H).

LCMS (Injection 2 conditions) Rt=1.47 min, ESI m/z 800.0 (M+H).

Preparation of Example 4005

3'-((2-chloro-5-((5-cyanopyridin-3-yl)methoxy)-4-(((1,3-dihydroxypropan-2-yl)amino)methyl)phenoxy)methyl)-N-(2-(1,1-dioxidothiomorpholino)ethyl)-2,2'-dimethyl-[1,1'-biphenyl]-3-carboxamide

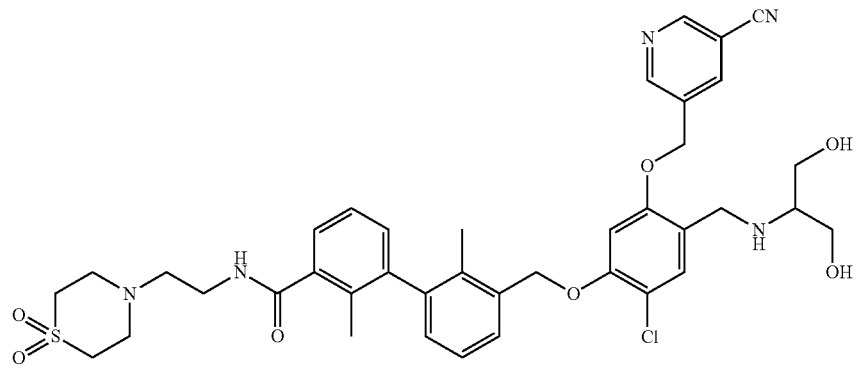 [SMILES: Cc1c(COc2cc(OCc3cncc(C#N)c3)c(CNC(CO)CO)cc2Cl)cccc1-c1cccc(C(=O)NCCN2CCS(=O)(=O)CC2)c1C]

Example 4005

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 23 minutes, then a 3-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.50 min, ESI m/z 762.1 (M+H).

LCMS (Injection 2 conditions) Rt=1.40 min, ESI m/z 762.0 (M+H).

Preparation of Example 4006

(S)-1-(5-chloro-2-((5-cyanopyridin-3-yl)methoxy)-4-((3'-(ethylcarbamoyl)-2,2'-dimethyl-[1,1'-biphenyl]-3-yl)methoxy)benzyl)piperidine-2-carboxylic Acid

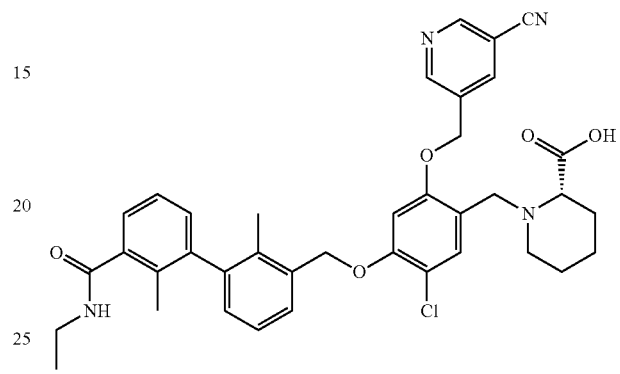

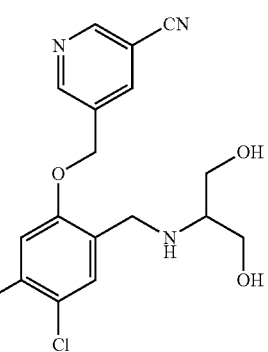

Example 4006

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.58 min, ESI m/z 667.0 (M+H).

LCMS (Injection 2 conditions) Rt=1.72 min, ESI m/z 667.0 (M+H).

Preparation of Example 4007

(5-chloro-2-((5-cyanopyridin-3-yl)methoxy)-4-((3'-(ethylcarbamoyl)-2,2'-dimethyl-[1,1'-biphenyl]-3-yl)methoxy)benzyl)-L-proline

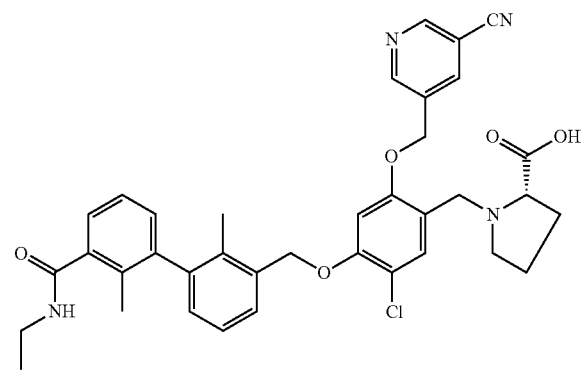 [SMILES: CCNC(=O)c1cccc(-c2cccc(COc3cc(OCc4cncc(C#N)c4)c(CN4CCC[C@H]4C(=O)O)cc3Cl)c2C)c1C]

Example 4007

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.59 min, ESI m/z 653.1 (M+H).

LC/MS (Injection 2 conditions) Rt=1.63 min, ESI m/z 653.0 (M+H).

Preparation of Example 4008

(2S,4R)-1-(5-chloro-2-((5-cyanopyridin-3-yl)methoxy)-4-((3'-(ethylcarbamoyl)-2,2'-dimethyl-[1,1'-biphenyl]-3-yl)methoxy)benzyl)-4-hydroxypyrrolidine-2-carboxylic Acid

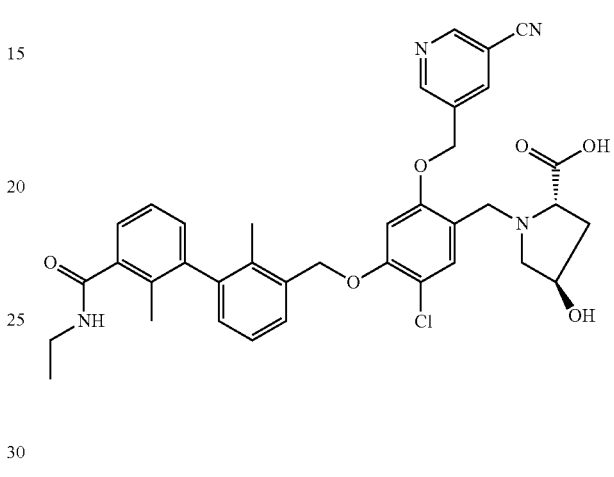

Example 4008

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 conditions) Rt=1.45 min, ESI m/z 669.0 (M+H).

LCMS (Injection 2 conditions) Rt=1.55 min, ESI m/z 669.0 (M+H).

Preparation of Example 4009

3'-((2-chloro-5-((5-cyanopyridin-3-yl)methoxy)-4-(((1,3-dihydroxypropan-2-yl)amino)methyl)phenoxy)methyl)-N-ethyl-2,2'-dimethyl-[1,1'-biphenyl]-3-carboxamide

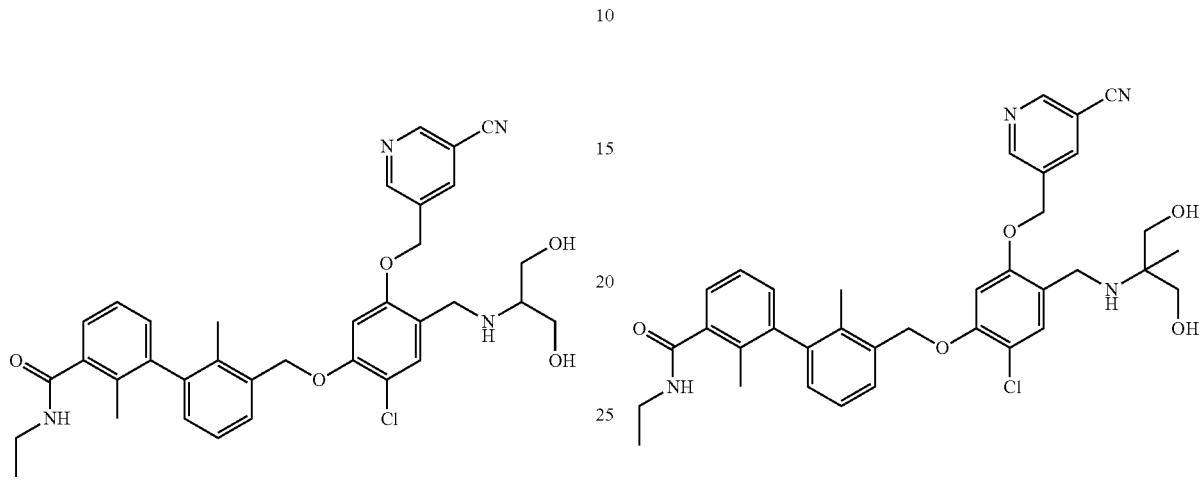

Example 4009

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Injection 2 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.54 min, ESI m/z 629.1 (M+H).

LCMS (Injection 2 conditions) Rt=1.52 min, ESI m/z 629.1 (M+H).

Preparation of Example 4010

3'-((2-chloro-5-((5-cyanopyridin-3-yl)methoxy)-4-(((1,3-dihydroxy-2-methylpropan-2-yl)amino)methyl)phenoxy)methyl)-N-ethyl-2,2'-dimethyl-[1,1'-biphenyl]-3-carboxamide

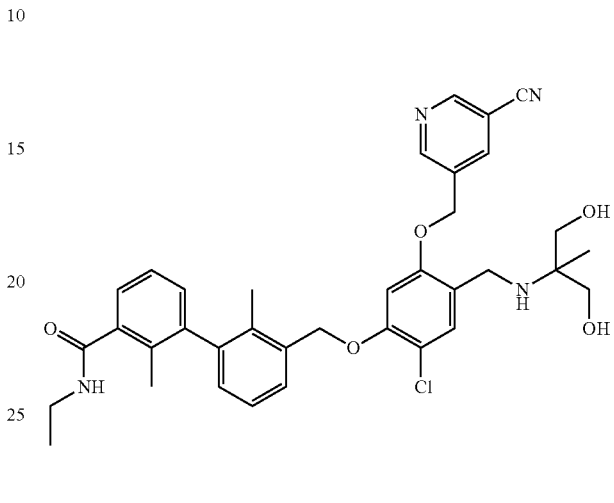

Example 4010

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.53 min, ESI m/z 643.1 (M+H).

LCMS (Injection 2 conditions) Rt=1.54 min, ESI m/z 643.1 (M+H).

Preparation of Example 4011

(S)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)piperidine-2-carboxylic Acid

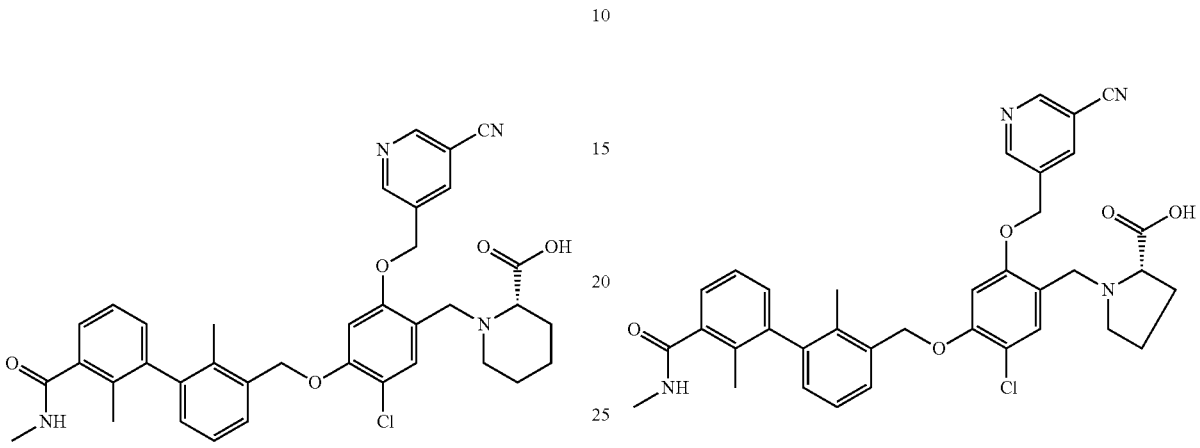

Example 4011

The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.44 min, ESI m/z 652.1 (M+H).

LCMS (Injection 2 conditions) Rt=1.48 min, ESI m/z 652.3 (M+H).

Preparation of Example 4012

(5-chloro-2-((5-cyanopyridin-3-yl)methoxy)-4-((2,2'-dimethyl-3'-(methylcarbamoyl)-[1,1'-biphenyl]-3-yl)methoxy)benzyl)-L-proline

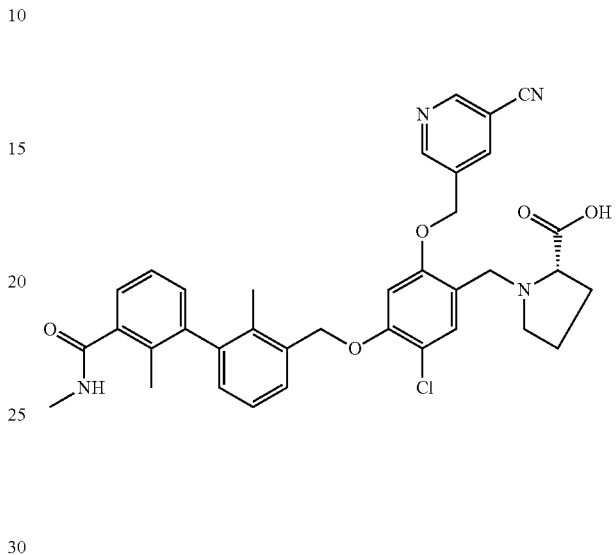

Example 4012

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.42 min, ESI m/z 639.1 (M+H).

LCMS (Injection 2 conditions) Rt=1.45 min, ESI m/z 639.1 (M+H).

Preparation of Example 4013

(2S,4R)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)-4-hydroxypyrrolidine-2-carboxylic Acid

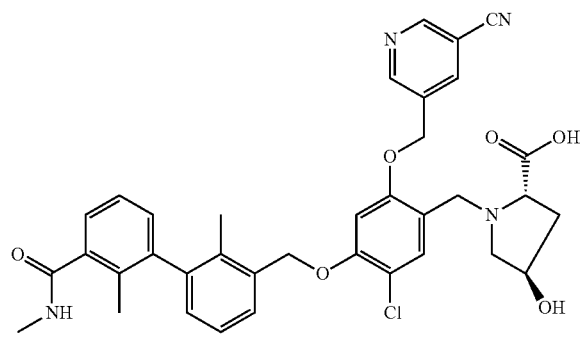 [SMILES: CNC(=O)c1cccc(-c2cccc(COc3cc(OCc4cncc(C#N)c4)c(CN4C[C@H](O)C[C@H]4C(=O)O)cc3Cl)c2C)c1C]

Example 4013

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 3-minute hold at 100% B; Flow: 20 mL/min. Fractions containing the desired product were combined and dried via centrifugal evaporation. The yield of the product was 1.2 mg, and its estimated purity by LCMS analysis was 95%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.42 min, ESI m/z 655.1 (M+H).

LCMS (Injection 2 conditions) Rt=1.59 min, ESI m/z 655.0 (M+H).

Preparation of Example 4014

(2S,4S)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)-4-hydroxypyrrolidine-2-carboxylic Acid

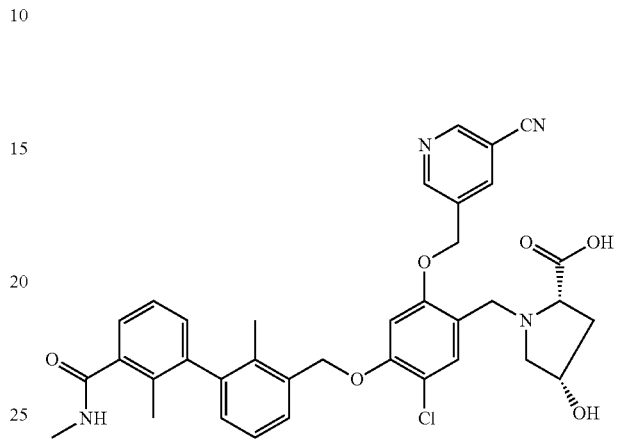

Example 4014

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.81 min, ESI m/z 542.1 (M+H).

LCMS (Injection 2 conditions) Rt=1.93 min, ESI m/z 542.0 (M+H).

Preparation of Example 4015

3'-((2-chloro-5-((5-cyanopyridin-3-yl)methoxy)-4-(((1,3-dihydroxypropan-2-yl)amino)methyl)phenoxy)methyl)-N,2,2'-trimethyl-[1,1'-biphenyl]-3-carboxamide

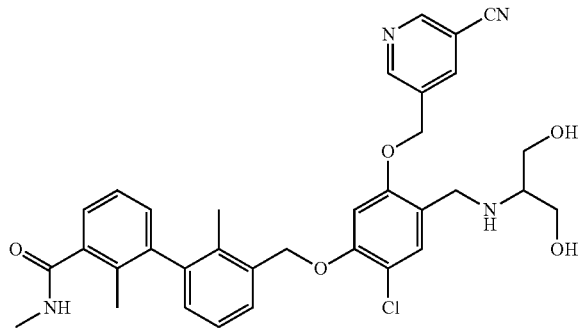

Example 4015

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.48 min, ESI m/z 615.1 (M+H).

LCMS (Injection 2 conditions) Rt=1.57 min, ESI m/z 615.0 (M+H).

Preparation of Example 4016

3'-((2-chloro-5-((5-cyanopyridin-3-yl)methoxy)-4-(((1,3-dihydroxy-2-methylpropan-2-yl)amino)methyl)phenoxy)methyl)-N,2,2'-trimethyl-[1,1'-biphenyl]-3-carboxamide

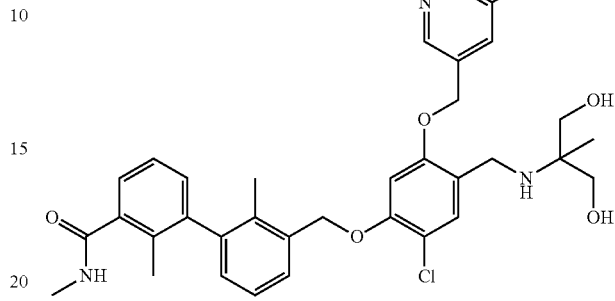

Example 4016

LCMS (Injection 1 conditions) Rt=1.49 min, ESI m/z 629.1 (M+H).

LCMS (Injection 2 conditions) Rt=1.60 min, ESI m/z 629.0 (M+H).

Preparation of Example 4017

(S)-1-(5-chloro-2-((3,5-difluorobenzyl)oxy)-4-((3'-(ethylcarbamoyl)-2,2'-dimethyl-[1,1'-biphenyl]-3-yl)methoxy)benzyl)piperidine-2-carboxylic Acid

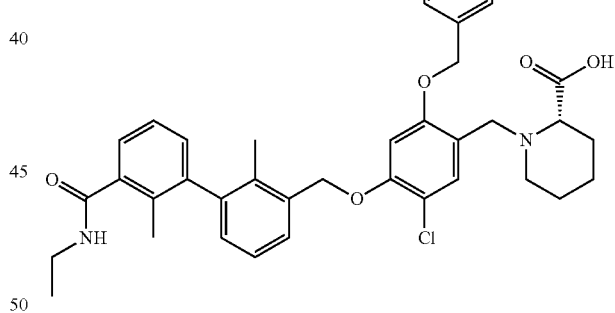

Example 4017

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100%

B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.80 min, ESI m/z 677.1 (M+H).

LCMS (Injection 2 conditions) Rt=1.97 min, ESI m/z 677.1 (M+H).

Preparation of Example 4018

(5-chloro-2-((3,5-difluorobenzyl)oxy)-4-((3'-(ethyl-carbamoyl)-2,2'-dimethyl-[1,1'-biphenyl]-3-yl) methoxy)benzyl)-L-proline

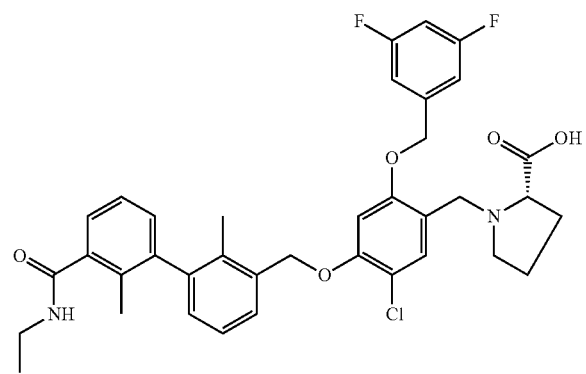 [SMILES: CCNC(=O)c1cccc(-c2cccc(COc3cc(OCc4cc(F)cc(F)c4)c(CN4CCC[C@H]4C(=O)O)cc3Cl)c2C)c1C]

Example 4018

LCMS (Injection 1 conditions) Rt=1.80 min, ESI m/z 663.0 (M+H).

LCMS (Injection 2 conditions) Rt=1.93 min, ESI m/z 663.0 (M+H).

Preparation of Example 4019

(2S,4R)-1-(5-chloro-2-((3,5-difluorobenzyl)oxy)-4-((3'-(ethylcarbamoyl)-2,2'-dimethyl-[1,1'-biphenyl]-3-yl)methoxy)benzyl)-4-hydroxypyrrolidine-2-carboxylic Acid

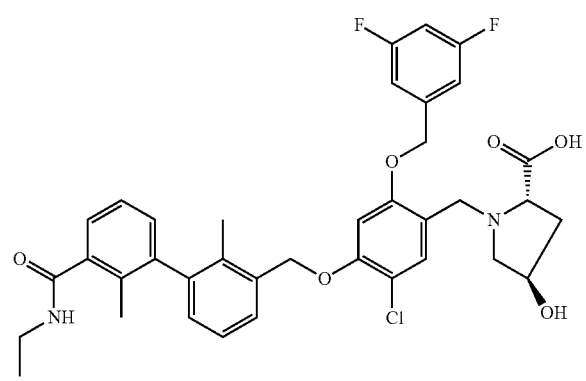

Example 4019

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.72 min, ESI m/z 679.0 (M+H).

LCMS (Injection 2 conditions) Rt=1.88 min, ESI m/z 679.0 (M+H).

Preparation of Example 4020

(S)-4-(5-chloro-2-((3,5-difluorobenzyl)oxy)-4-((3'-(ethylcarbamoyl)-2,2'-dimethyl-[1,1'-biphenyl]-3-yl) methoxy)benzyl)morpholine-3-carboxylic Acid

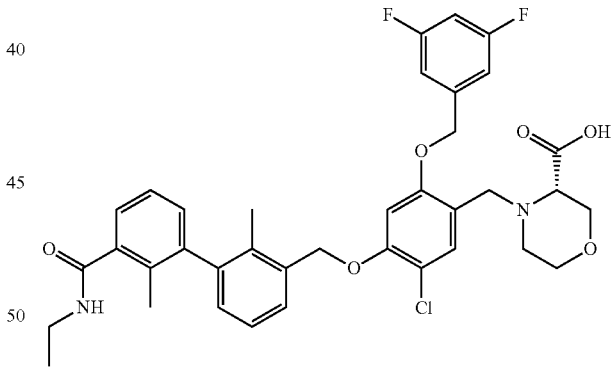

Example 4020

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A:

5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 679.01; Retention Time: 1.92 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.77 min, ESI m/z 679.0 (M+H).

LCMS (Injection 2 conditions) Rt=1.90 min, ESI m/z 679.0 (M+H).

Preparation of Example 4021

3'-((2-chloro-5-((3,5-difluorobenzyl)oxy)-4-(((1,3-dihydroxypropan-2-yl)amino)methyl)phenoxy)methyl)-N-ethyl-2,2'-dimethyl-[1,1'-biphenyl]-3-carboxamide

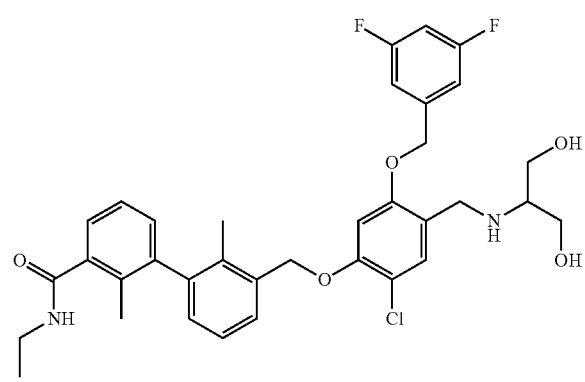 [SMILES: CCNC(=O)c1cccc(-c2cccc(COc3cc(OCc4cc(F)cc(F)c4)c(CNC(CO)CO)cc3Cl)c2C)c1C]

Example 4021

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 639.07; Retention Time: 1.87 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.83 min, ESI m/z 639.1 (M+H).

LCMS (Injection 2 conditions) Rt=1.86 min, ESI m/z 639.1 (M+H).

Preparation of Example 4022

3'-((2-chloro-5-((3,5-difluorobenzyl)oxy)-4-(((1,3-dihydroxy-2-methylpropan-2-yl)amino)methyl)phenoxy)methyl)-N-ethyl-2,2'-dimethyl-[1,1'-biphenyl]-3-carboxamide

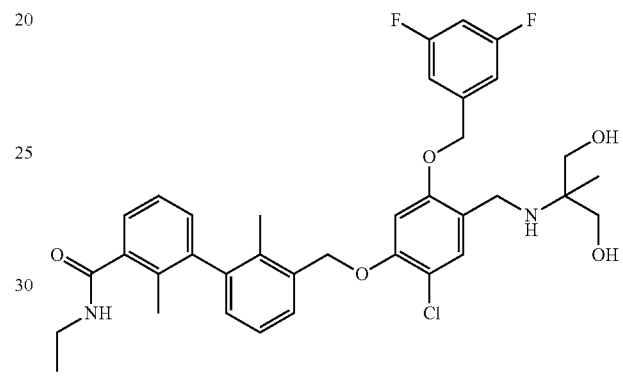

Example 4022

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.83 min, ESI m/z 653.1 (M+H).

LCMS (Injection 2 conditions) Rt=1.90 min, ESI m/z 653.1 (M+H).

701
Preparation of Example 4023

(S)-1-(5-chloro-2-((3,5-difluorobenzyl)oxy)-4-((2,2'-dimethyl-3'-(methylcarbamoyl)-[1,1'-biphenyl]-3-yl)methoxy)benzyl)piperidine-2-carboxylic Acid

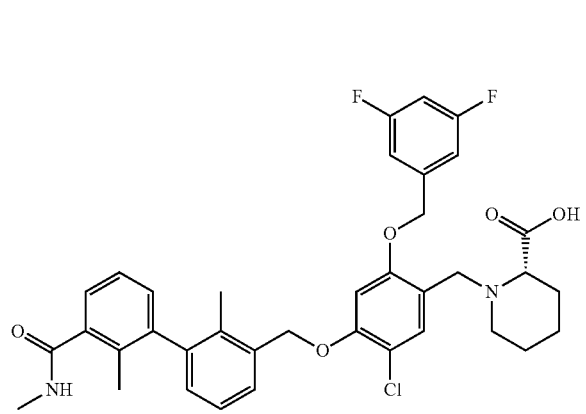

Example 4023

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.72 min, ESI m/z 663.1 (M+H).

LCMS (Injection 2 conditions) Rt=1.89 min, ESI m/z 663.1 (M+H).

702
Preparation of Example 4024

(5-chloro-2-((3,5-difluorobenzyl)oxy)-4-((2,2'-dimethyl-3'-(methylcarbamoyl)-[1,1'-biphenyl]-3-yl)methoxy)benzyl)-L-proline

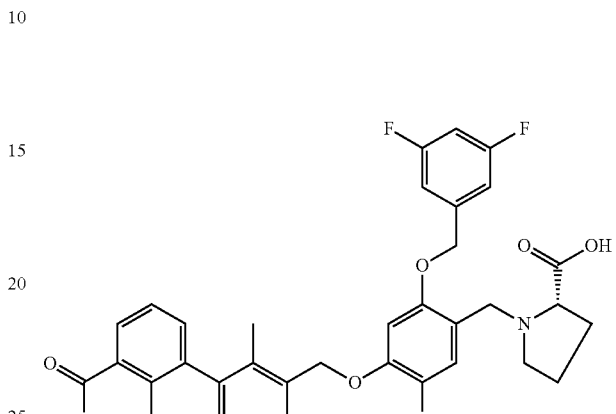

Example 4024

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.71 min, ESI m/z 649.0 (M+H).

LCMS (Injection 2 conditions) Rt=1.65 min, ESI m/z 649.0 (M+H).

Preparation of Example 4025

(2S,4R)-1-(5-chloro-2-((3,5-difluorobenzyl)oxy)-4-((2,2'-dimethyl-3'-(methylcarbamoyl)-[1,1'-biphenyl]-3-yl)methoxy)benzyl)-4-hydroxypyrrolidine-2-carboxylic Acid

Preparation of Example 4026

(2S,4S)-1-(5-chloro-2-((3,5-difluorobenzyl)oxy)-4-((2,2'-dimethyl-3'-(methylcarbamoyl)-[1,1'-biphenyl]-3-yl)methoxy)benzyl)-4-hydroxypyrrolidine-2-carboxylic Acid

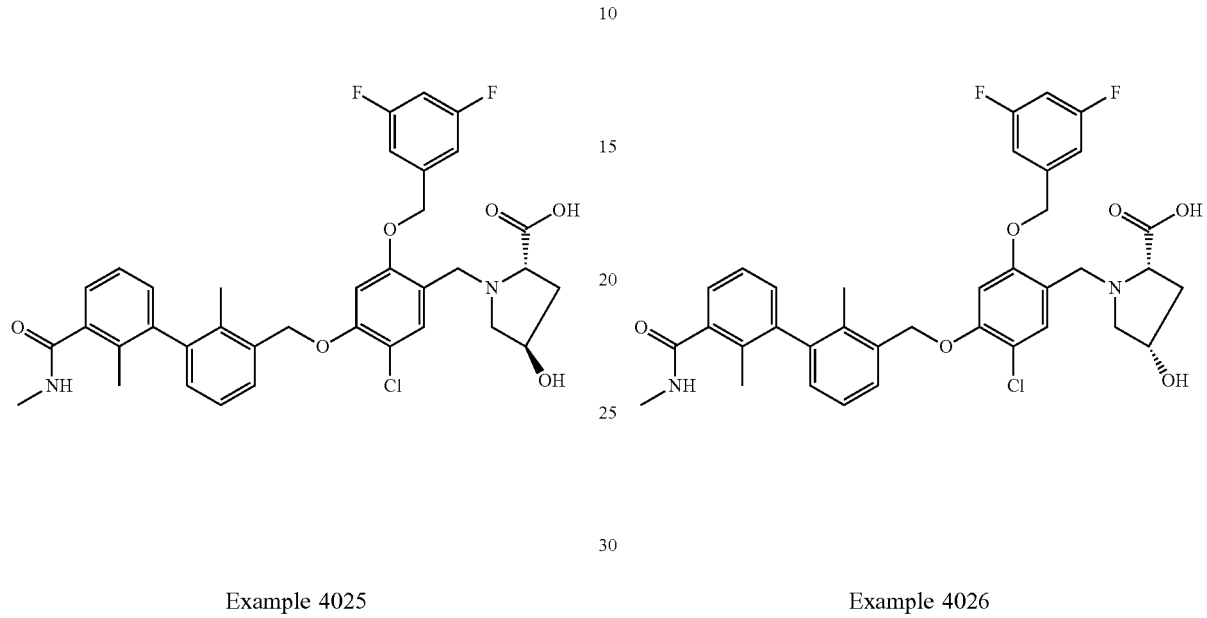

Example 4025

Example 4026

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 664.94; Retention Time: 1.6 min.

LCMS (Injection 1 conditions) Rt=1.64 min, ESI m/z 665.1 (M+H).

LCMS (Injection 2 conditions) Rt=1.60 min, ESI m/z 664.9 (M+H).

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.63 min, ESI m/z 665.0 (M+H).

LCMS (Injection 2 conditions) Rt=1.81 min, ESI m/z 665.0 (M+H).

705
Preparation of Example 4027

(S)-4-(5-chloro-2-((3,5-difluorobenzyl)oxy)-4-((2,2'-dimethyl-3'-(methylcarbamoyl)-[1,1'-biphenyl]-3-yl)methoxy)benzyl)morpholine-3-carboxylic Acid

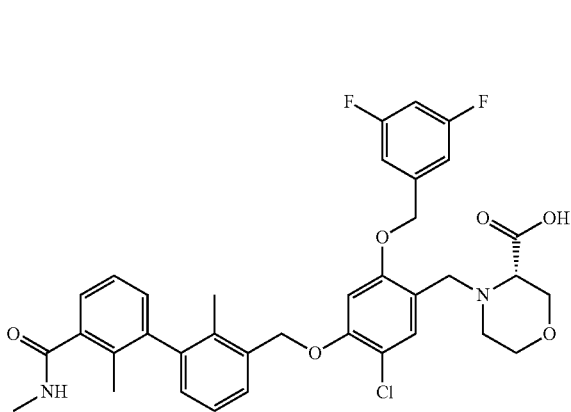 [SMILES: CNC(=O)c1cccc(-c2cccc(COc3cc(OCc4cc(F)cc(F)c4)c(CN4CCCC[C@H]4C(=O)O)cc3Cl)c2C)c1C]

Example 4027

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.81 min, ESI m/z 665.0 (M+H).

LCMS (Injection 2 conditions) Rt=1.69 min, ESI m/z 665.0 (M+H).

706
Preparation of Example 4028

3'-((2-chloro-5-((3,5-difluorobenzyl)oxy)-4-formylphenoxy)methyl)-N,2,2'-trimethyl-[1,1'-biphenyl]-3-carboxamide

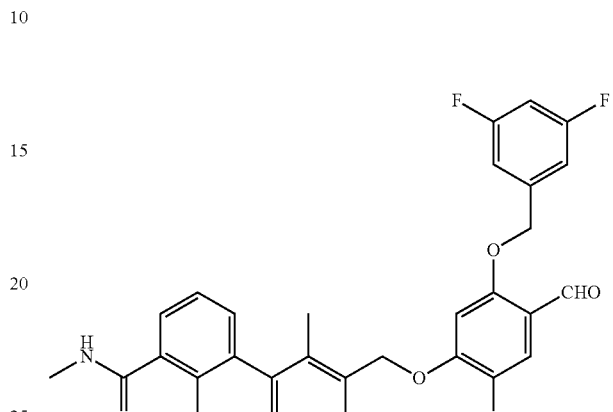

Example 4028

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 28-68% B over 18 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.66 min, ESI m/z 625.0 (M+H).

LCMS (Injection 2 conditions) Rt=1.75 min, ESI m/z 625.1 (M+H).

Preparation of Example 4029

3'-((2-chloro-5-((3,5-difluorobenzyl)oxy)-4-(((1,3-dihydroxy-2-methylpropan-2-yl)amino)methyl)phenoxy)methyl)-N,2,2'-trimethyl-[1,1'-biphenyl]-3-carboxamide

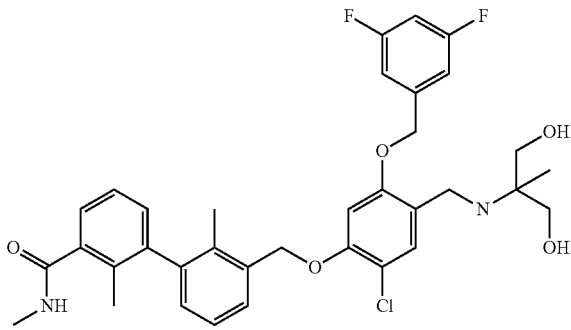 [SMILES: CNC(=O)c1cccc(-c2cccc(COc3cc(OCc4cc(F)cc(F)c4)c(CNC(C)(CO)CO)cc3Cl)c2C)c1C]

Example 4029

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.62 min, ESI m/z 639.1 (M+H).

LCMS (Injection 2 conditions) Rt=1.68 min, ESI m/z 639.1 (M+H).

Preparation of Example 4030

(S)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)piperidine-2-carboxylic Acid

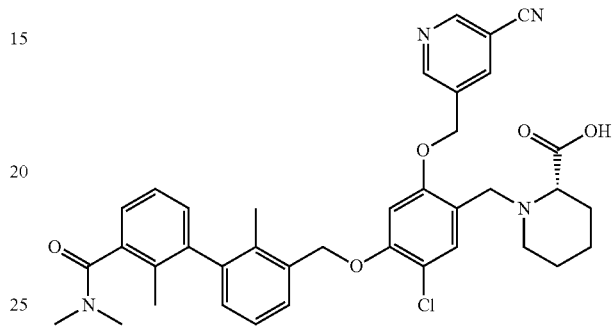

Example 4030

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.86 min, ESI m/z 667.0 (M+H).

LCMS (Injection 2 conditions) Rt=1.64 min, ESI m/z 667.1 (M+H).

Preparation of Example 4031

(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)-L-proline

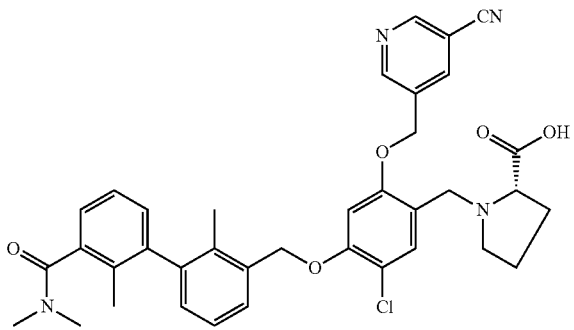 [SMILES: Cc1c(COc2cc(OCc3cncc(C#N)c3)c(CN3CCC[C@H]3C(=O)O)cc2Cl)cccc1-c1cccc(C(=O)N(C)C)c1C]

Example 4031

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.73 min, ESI m/z 635.0 (M+H).

LCMS (Injection 2 conditions) Rt=1.61 min, ESI m/z 635.1 (M+H).

Preparation of Example 4032

(2S,4R)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)-4-hydroxypyrrolidine-2-carboxylic Acid

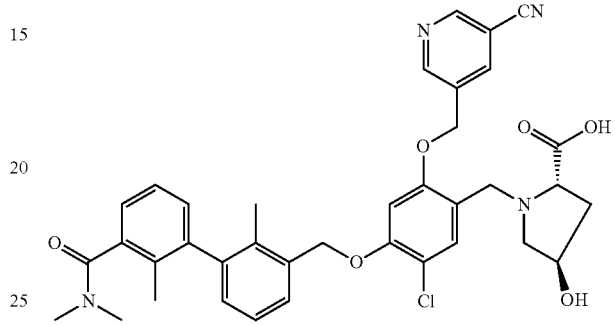

Example 4032

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.65 min, ESI m/z 669.0 (M+H).

LCMS (Injection 2 conditions) Rt=1.56 min, ESI m/z 669.0 (M+H).

Preparation of Example 4033

(2S,4S)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)-4-hydroxypyrrolidine-2-carboxylic Acid

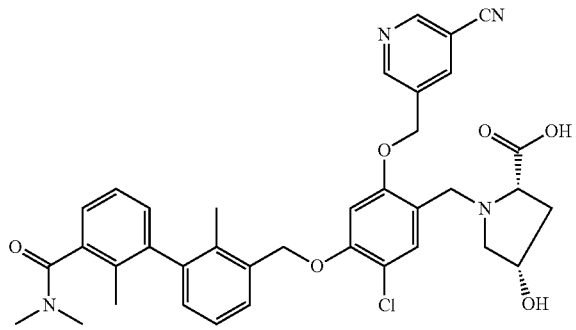 [SMILES: Cc1c(COc2cc(OCc3cncc(C#N)c3)c(CN3C[C@@H](O)C[C@H]3C(=O)O)cc2Cl)cccc1-c1cccc(C(=O)N(C)C)c1C]

Example 4033

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-58% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.55 min, ESI m/z 669.0 (M+H).

LCMS (Injection 2 conditions) Rt=1.67 min, ESI m/z 669.0 (M+H).

Preparation of Example 4034

3'-((2-chloro-5-((5-cyanopyridin-3-yl)methoxy)-4-(((1,3-dihydroxypropan-2-yl)amino)methyl)phenoxy)methyl)-N,N,2,2'-tetramethyl-[1,1'-biphenyl]-3-carboxamide

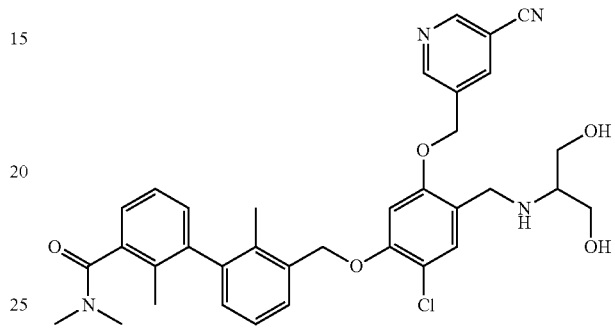

Example 4034

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 18 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

LCMS (Injection 1 conditions) Rt=1.60 min, ESI m/z 629.0 (M+H).

LCMS (Injection 2 conditions) Rt=1.63 min, ESI m/z 629.0 (M+H).

713
Preparation of Example 4035

3'-((2-chloro-5-((5-cyanopyridin-3-yl)methoxy)-4-
(((1,3-dihydroxy-2-methylpropan-2-yl)amino)
methyl)phenoxy)methyl)-N,N,2,2'-tetramethyl-[1,1'-
biphenyl]-3-carboxamide

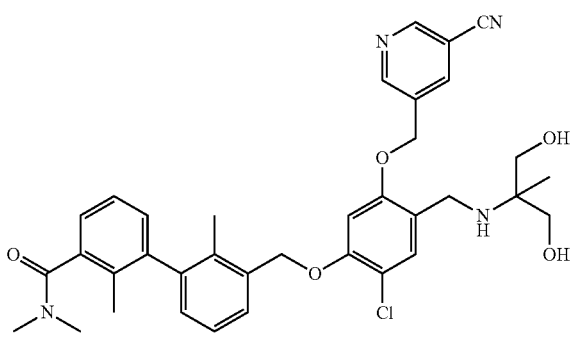 [SMILES: Cc1c(COc2cc(OCc3cncc(C#N)c3)c(CNC(C)(CO)CO)cc2Cl)cccc1-c1cccc(C(=O)N(C)C)c1C]

Example 4035

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 23 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 643.05; Retention Time: 1.67 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 643.07; Retention Time: 1.66 min.

714
Preparation of Example 4036

(S)-4-(5-chloro-2-((5-cyanopyridin-3-yl)methoxy)-4-
((3'-(dimethylcarbamoyl)-2,2'-dimethyl-[1,1'-biphe-
nyl]-3-yl)methoxy)benzyl)morpholine-3-carboxylic
Acid

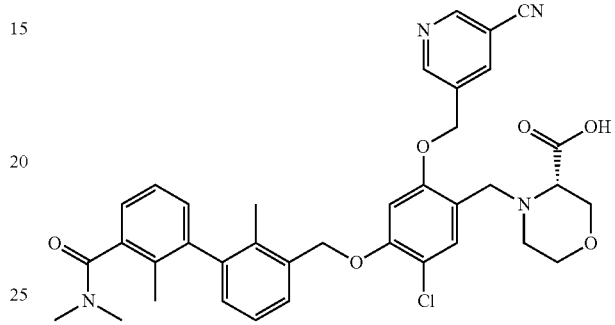

Example 4036

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.0%; Observed Mass: 669.05; Retention Time: 1.59 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Injection 2 results: Purity: 95.7%; Observed Mass: 669.02; Retention Time: 1.7 μmin.

715
Preparation of Example 4037

(S)-1-(5-chloro-2-((5-cyanopyridin-3-yl)methoxy)-4-((2,2'-dimethyl-3'-(pyrrolidine-1-carbonyl)-[1,1'-biphenyl]-3-yl)methoxy)benzyl)piperidine-2-carboxylic Acid

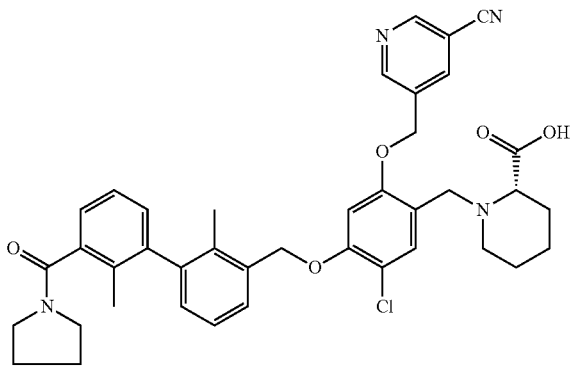 [SMILES: Cc1c(COc2cc(OCc3cncc(C#N)c3)c(CN3CCCC[C@H]3C(=O)O)cc2Cl)cccc1-c1cccc(C(=O)N2CCCC2)c1C]

Example 4037

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 693.07; Retention Time: 1.7 μmin. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 693.06; Retention Time: 1.88 min.

716
Preparation of Example 4038

5-((4-chloro-2-(((1,3-dihydroxypropan-2-yl)amino)methyl)-5-((2,2'-dimethyl-3'-(pyrrolidine-1-carbonyl)-[1,1'-biphenyl]-3-yl)methoxy)phenoxy)methyl)nicotinonitrile

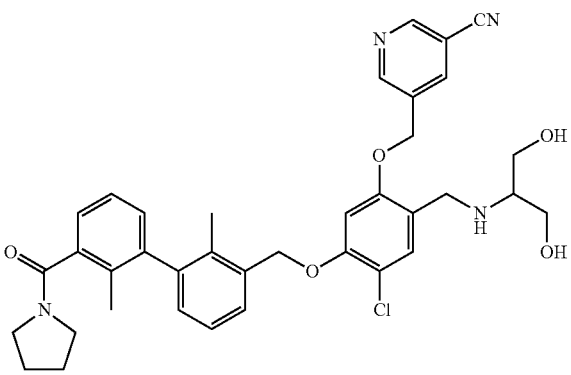 [SMILES: Cc1c(COc2cc(OCc3cncc(C#N)c3)c(CNC(CO)CO)cc2Cl)cccc1-c1cccc(C(=O)N2CCCC2)c1C]

Example 4038

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 655.07; Retention Time: 1.68 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 655.32; Retention Time: 1.59 min.

Preparation of Example 4039

5-((4-chloro-2-(((1,3-dihydroxy-2-methylpropan-2-yl)amino)methyl)-5-((2,2'-dimethyl-3'-(pyrrolidine-1-carbonyl)-[1,1'-biphenyl]-3-yl)methoxy)phenoxy)methyl)nicotinonitrile

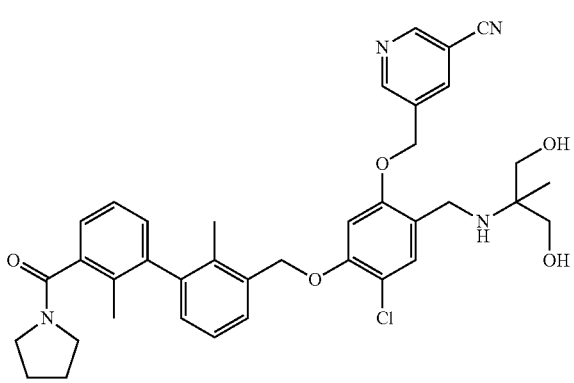 [SMILES: Cc1c(COc2cc(OCc3cncc(C#N)c3)c(CNC(C)(CO)CO)cc2Cl)cccc1-c1cccc(C(=O)N2CCCC2)c1C]

Example 4039

The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 669.07, 669.07; Retention Time: 1.74, 1.78 min. Injection 2 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.0%; Observed Mass: 669.11; Retention Time: 1.75 min.

Preparation of Example 4040

(S)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)piperidine-2-carboxylic Acid

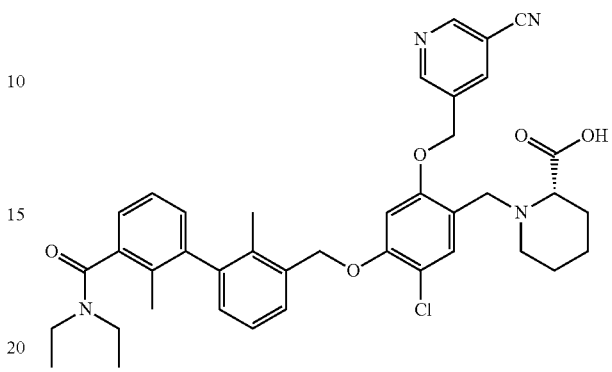

Example 4040

Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 695.1; Retention Time: 1.79 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 695.14; Retention Time: 1.89 min.

Preparation of Example 4041

(5-chloro-2-((5-cyanopyridin-3-yl)methoxy)-4-((3'-(diethylcarbamoyl)-2,2'-dimethyl-[1,1'-biphenyl]-3-yl)methoxy)benzyl)-L-proline

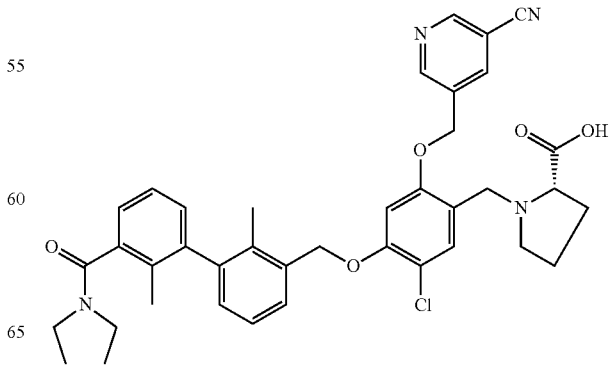

Example 4041

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 681.08; Retention Time: 1.79 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 681.1; Retention Time: 1.88 min.

Preparation of Example 4042

(2S,4R)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)-4-hydroxypyrrolidine-2-carboxylic Acid

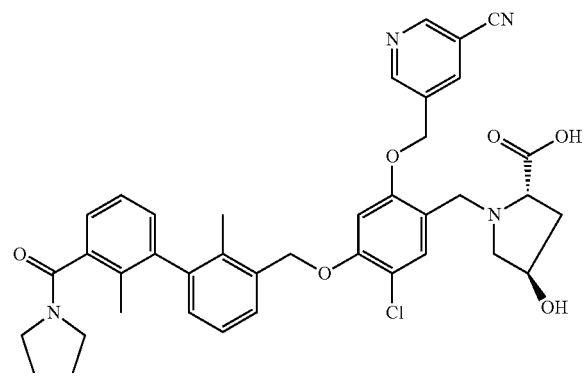

Example 4042

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 697.04; Retention Time: 1.68 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 697.06; Retention Time: 1.67 min.

Preparation of Example 4043

(2S,4S)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)-4-hydroxypyrrolidine-2-carboxylic Acid

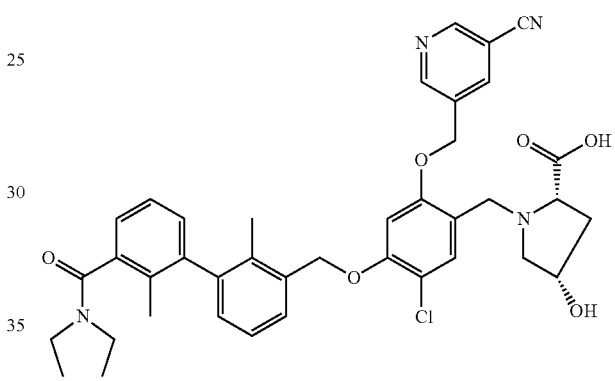

Example 4043

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 697.05; Retention Time: 1.85 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 697.06; Retention Time: 1.73 min.

721
Preparation of Example 4044

3'-((2-chloro-5-((5-cyanopyridin-3-yl)methoxy)-4-(((1,3-dihydroxypropan-2-yl)amino)methyl)phenoxy)methyl)-N,N-diethyl-2,2'-dimethyl-[1,1'-biphenyl]-3-carboxamide

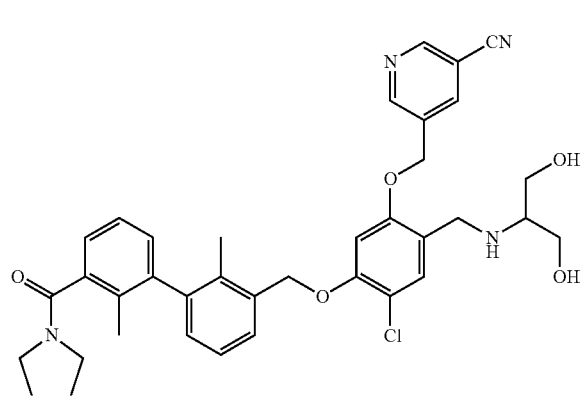

Example 4044

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 22 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 657.09; Retention Time: 1.85 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 657.06; Retention Time: 1.85 min.

722
Preparation of Example 4045

3'-((2-chloro-5-((5-cyanopyridin-3-yl)methoxy)-4-(((1,3-dihydroxy-2-methylpropan-2-yl)amino)methyl)phenoxy)methyl)-N,N-diethyl-2,2'-dimethyl-[1,1'-biphenyl]-3-carboxamide

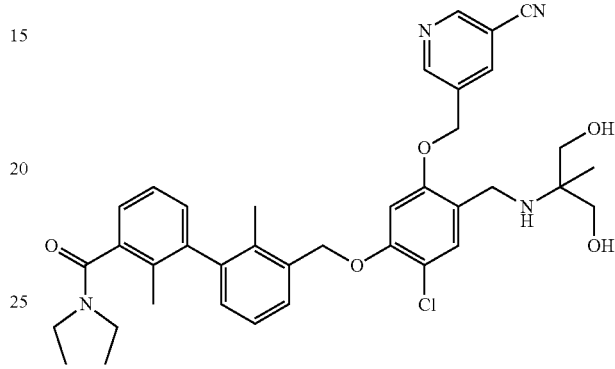

Example 4045

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 18 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 671.09; Retention Time: 1.87 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 671.09; Retention Time: 1.86 min.

723
Preparation of Example 4046

(S)-4-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)morpholine-3-carboxylic Acid

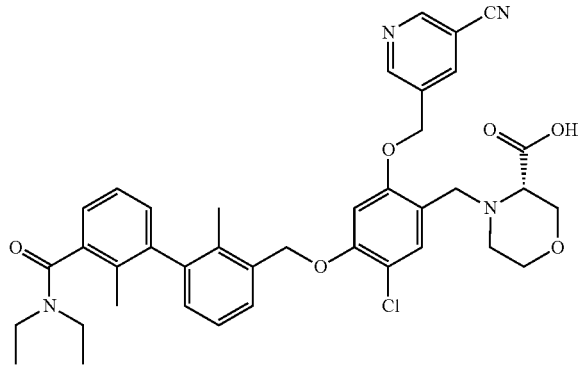 [SMILES: CCN(CC)C(=O)c1cccc(-c2cccc(COc3cc(OCc4cncc(C#N)c4)c(CN4CCCC[C@H]4C(=O)O)cc3Cl)c2C)c1C]

Example 4046

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 697.04; Retention Time: 1.86 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 697.03; Retention Time: 1.75 min.

724
Preparation of Example 4047

(S)-4-(tert-butoxycarbonyl)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)piperazine-2-carboxylic Acid

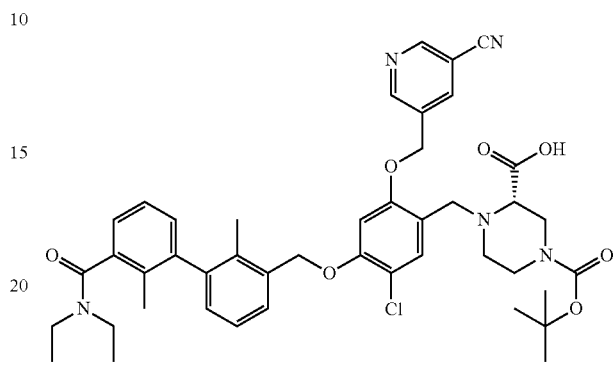

Example 4047

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.8%; Observed Mass: 796.15; Retention Time: 1.9 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.5%; Observed Mass: 796.13; Retention Time: 1.96 min.

Preparation of Example 4048

(S)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperidine-2-carboxylic Acid

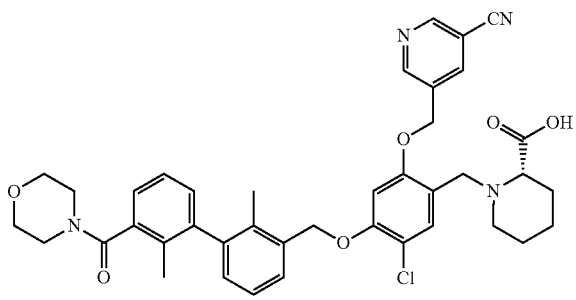 [SMILES: Cc1c(COc2cc(OCc3cncc(C#N)c3)c(CN3CCCC[C@H]3C(=O)O)cc2Cl)cccc1-c1cccc(C(=O)N2CCOCC2)c1C]

Example 4048

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 709.04; Retention Time: 1.58 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 709.05; Retention Time: 1.83 min.

Preparation of Example 4049

(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-L-proline

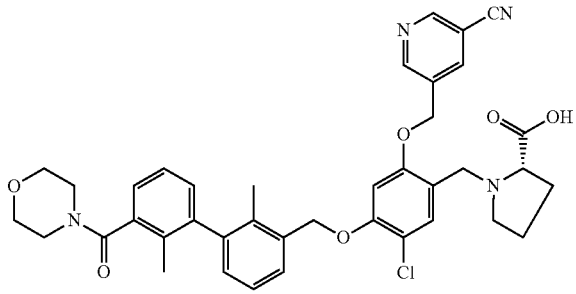 [SMILES: Cc1c(COc2cc(OCc3cncc(C#N)c3)c(CN3CCC[C@H]3C(=O)O)cc2Cl)cccc1-c1cccc(C(=O)N2CCOCC2)c1C]

Example 4049

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 695.04; Retention Time: 1.69 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 695.07; Retention Time: 1.53 min.

Preparation of Example 4050

(2S,4R)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-4-hydroxypyrrolidine-2-carboxylic Acid

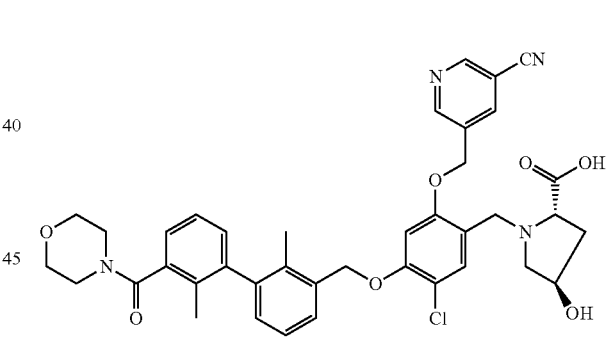

Example 4050

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 711.05; Retention Time: 1.71 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM mL/min; Detection: MS and UV (220 nm). Injection 2 results: Purity: 100.0%; Observed Mass: 711.03; Retention Time: 1.51 min.

Preparation of Example 4051

(2S,4S)-1-(5-chloro-2-((5-cyanopyridin-3-yl) methoxy)-4-((2,2'-dimethyl-3'-(morpholine-4-carbonyl)-[1,1'-biphenyl]-3-yl)methoxy)benzyl)-4-hydroxypyrrolidine-2-carboxylic Acid

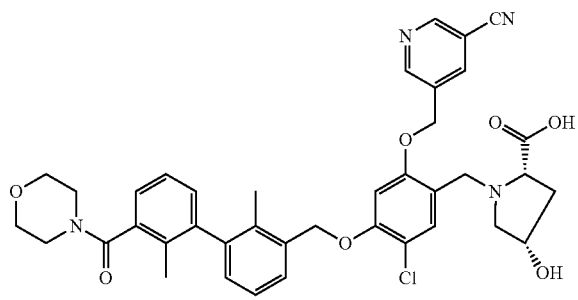 [SMILES: Cc1c(COc2cc(OCc3cncc(C#N)c3)c(CN3C[C@@H](O)C[C@H]3C(=O)O)cc2Cl)cccc1-c1cccc(C(=O)N2CCOCC2)c1C]

Example 4051

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 711.03; Retention Time: 1.48 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 711.04; Retention Time: 1.64 min.

Preparation of Example 4052

5-((4-chloro-2-(((1,3-dihydroxypropan-2-yl)amino) methyl)-5-((2,2'-dimethyl-3'-(morpholine-4-carbonyl)-[1,1'-biphenyl]-3-yl)methoxy)phenoxy)methyl) nicotinonitrile

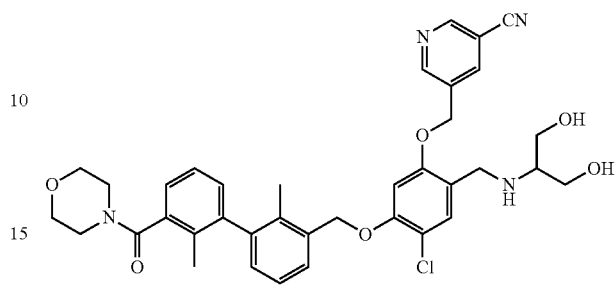

Example 4052

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 671.04; Retention Time: 1.52 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 671.09; Retention Time: 1.62 min.

Preparation of Example 4053

5-((4-chloro-2-(((1,3-dihydroxy-2-methylpropan-2-yl)amino)methyl)-5-((2,2'-dimethyl-3'-(morpholine-4-carbonyl)-[1,1'-biphenyl]-3-yl)methoxy)phenoxy) methyl)nicotinonitrile

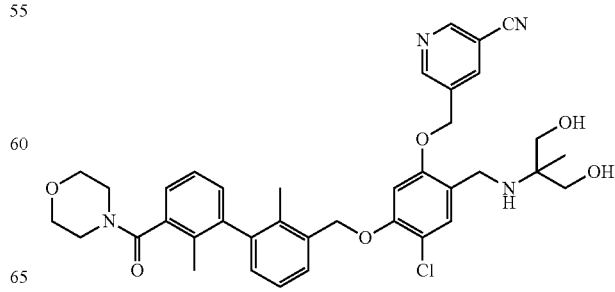

Example 4053

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 685.06; Retention Time: 1.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 685.05; Retention Time: 1.79 min.

Preparation of Example 4054

(S)-4-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)morpholine-3-carboxylic Acid

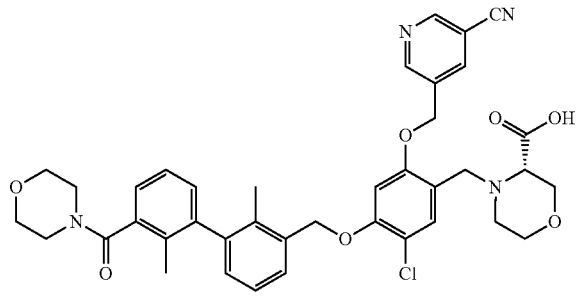 [SMILES: Cc1c(COc2cc(OCc3cncc(C#N)c3)c(CN3CCOC[C@H]3C(=O)O)cc2Cl)cccc1-c1cccc(C(=O)N2CCOCC2)c1C]

Example 4054

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.3%; Observed Mass: 711.05; Retention Time: 1.55 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 711.02; Retention Time: 1.81 min.

Preparation of Example 4055

(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-L-serine

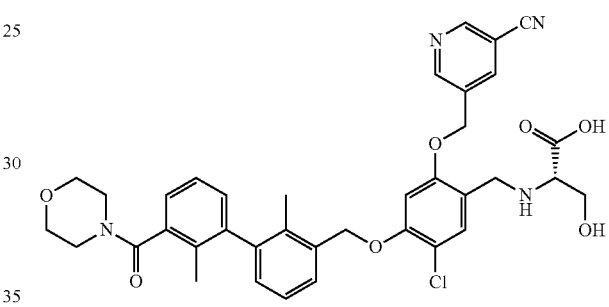

Example 4055

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.6%; Observed Mass: 684.98; Retention Time: 1.51 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 685.04; Retention Time: 1.76 min.

731

Preparation of Example 4056

(S)-3-((tert-butoxycarbonyl)amino)-2-((5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)amino)propanoic Acid

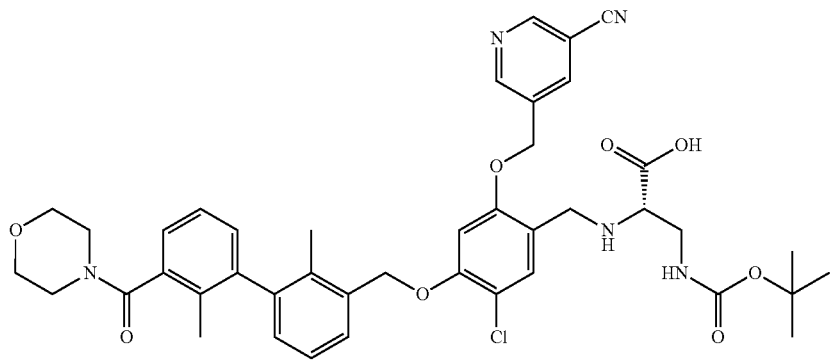 [SMILES: Cc1c(COc2cc(OCc3cncc(C#N)c3)c(CN[C@@H](CNC(=O)OC(C)(C)C)C(=O)O)cc2Cl)cccc1-c1cccc(C(=O)N2CCOCC2)c1C]

Example 4056

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 784; Retention Time: 1.78 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 784.03; Retention Time: 1.99 min.

Preparation of Example 4057

(S)-4-(tert-butoxycarbonyl)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperazine-2-carboxylic Acid

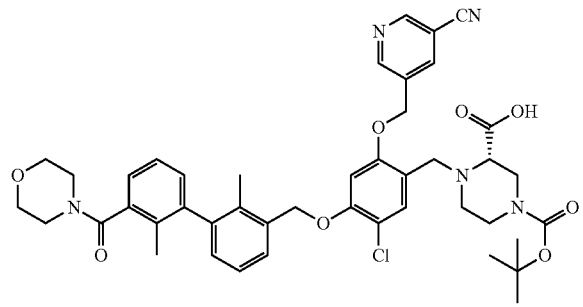 [SMILES: Cc1c(COc2cc(OCc3cncc(C#N)c3)c(CN3CCN(C(=O)OC(C)(C)C)C[C@H]3C(=O)O)cc2Cl)cccc1-c1cccc(C(=O)N2CCOCC2)c1C]

732

Example 4057

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 810.05; Retention Time: 1.8 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 810.03; Retention Time: 2 min.

Preparation of Example 4058

5-((4-chloro-2-(((1,3-dihydroxy-2-(hydroxymethyl)propan-2-yl)amino)methyl)-5-((2,2'-dimethyl-3'-(morpholine-4-carbonyl)-[1,1'-biphenyl]-3-yl)methoxy)phenoxy)methyl)nicotinonitrile

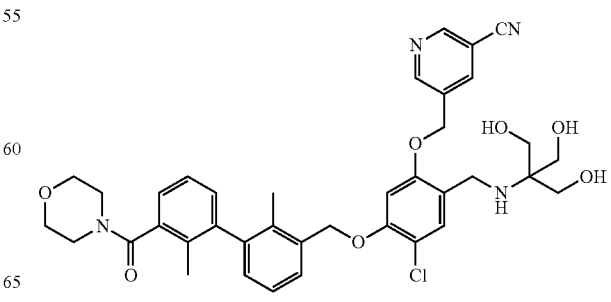

Example 4058

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 701.03; Retention Time: 1.62 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 701.04; Retention Time: 1.74 min.

Preparation of Example 4059

(S)-3-amino-2-((5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)amino)propanoic Acid

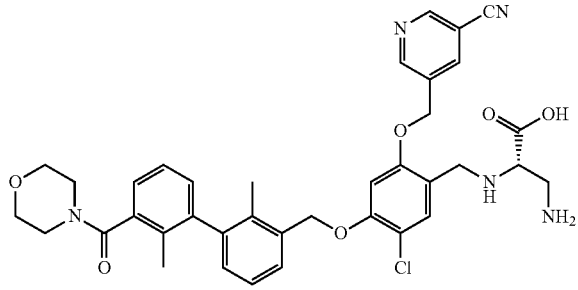 [SMILES: Cc1c(COc2cc(OCc3cncc(C#N)c3)c(CN[C@@H](CN)C(=O)O)cc2Cl)cccc1-c1cccc(C(=O)N2CCOCC2)c1C]

Example 4059

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 684.04; Retention Time: 1.45 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 684.01; Retention Time: 1.42 min.

Preparation of Example 4060

(S)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperazine-2-carboxylic Acid

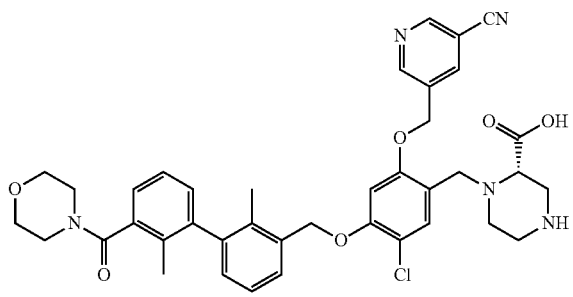 [SMILES: Cc1c(COc2cc(OCc3cncc(C#N)c3)c(CN3CCNC[C@H]3C(=O)O)cc2Cl)cccc1-c1cccc(C(=O)N2CCOCC2)c1C]

Example 4060

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 conditions) Rt=1.50 min, ESI m/z 710.1 (M+H).

Preparation of Example 4061

(S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperidine-2-carboxylic Acid

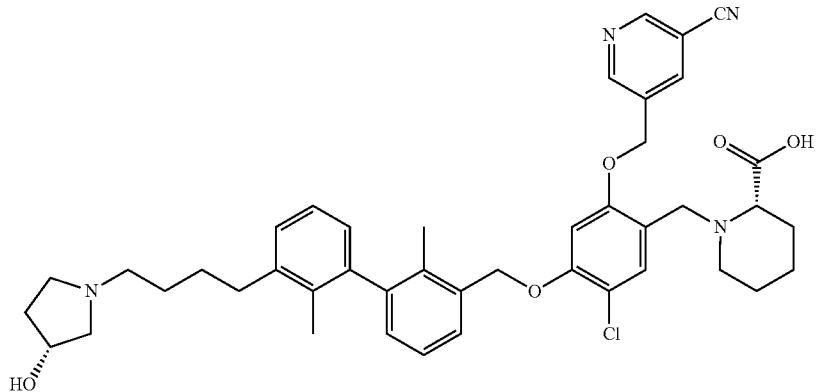 [SMILES: Cc1c(CCCCN2CC[C@@H](O)C2)cccc1-c1cccc(COc2cc(OCc3cncc(C#N)c3)c(CN3CCCC[C@H]3C(=O)O)cc2Cl)c1C]

Example 4061

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 18 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 737.1; Retention Time: 1.55 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 737.07; Retention Time: 1.7 μmin. $^1$H NMR (500 MHz, DMSO-$d_6$) δ 8.99 (s, 2H), 8.41 (s, 1H), 7.48 (d, J=8.1 Hz, 1H), 7.41 (s, 1H), 7.27 (t, J=7.5 Hz, 1H), 7.17 (d, J=4.4 Hz, 2H), 7.11-7.03 (m, 2H), 6.91 (t, J=4.4 Hz, 1H), 5.32 (br. s., 2H), 5.26 (s, 2H), 4.19 (br. s., 1H), 3.75 (d, J=13.6 Hz, 1H), 3.58 (d, J=15.4 Hz, 1H), 3.14 (br. s., 1H), 2.89 (d, J=11.7 Hz, 1H), 2.77-2.22 (m, 7H), 2.06-1.88 (m, 10H), 1.77 (br. s., 2H), 1.66-1.31 (m, 10H).

Preparation of Example 4062

(2S,4R)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)-4-hydroxypyrrolidine-2-carboxylic Acid

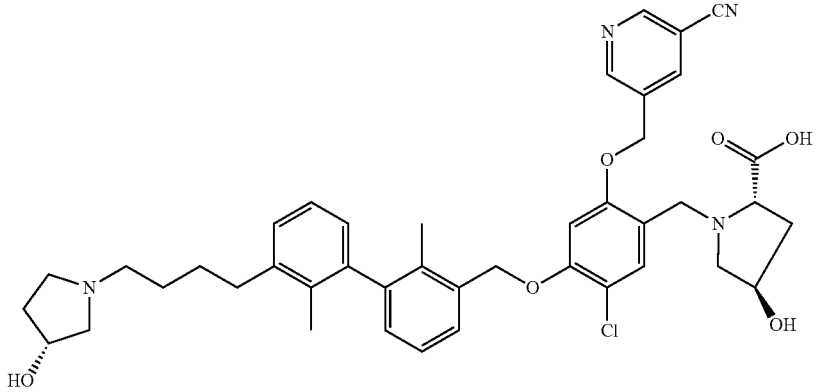 [SMILES: Cc1c(CCCCN2CC[C@@H](O)C2)cccc1-c1cccc(COc2cc(OCc3cncc(C#N)c3)c(CN3C[C@H](O)C[C@H]3C(=O)O)cc2Cl)c1C]

Example 4062

Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.4%; Observed Mass: 739.07; Retention Time: 1.64 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 739.09; Retention Time: 1.48 min. $^1$H NMR (500 MHz, DMSO-$d_6$) δ 8.99 (br. s., 2H), 8.46 (s, 1H), 7.49 (d, J=8.1 Hz, 1H), 7.43 (s, 1H), 7.28 (t, J=7.7 Hz, 1H), 7.18 (d, J=4.8 Hz, 2H), 7.13-7.03 (m, 2H), 6.91 (t, J=4.4 Hz, 1H), 5.41-5.22 (m, 4H), 4.29-4.11 (m, 2H), 3.95 (d, J=13.2 Hz, 1H), 3.81 (d, J=13.6 Hz, 1H), 3.51 (t, J=7.7 Hz, 1H), 2.73-2.26 (m, 11H), 2.07-1.87 (m, 12H), 1.66-1.48 (m, 4H).

Preparation of Example 4063

(2S,4S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)-4-hydroxypyrrolidine-2-carboxylic Acid desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.9%; Observed Mass: 739.06; Retention Time: 1.67 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.0%; Observed Mass: 739.06; Retention Time: 1.48 min. $^1$H NMR (500 MHz, DMSO-$d_6$) δ 8.99 (s, 2H), 8.43 (s, 1H), 7.52-7.40 (m, 2H), 7.27 (t, J=7.5 Hz, 1H), 7.22-7.13 (m, 2H), 7.13-7.05 (m, 2H), 6.91 (t, J=4.4 Hz, 1H), 5.49 (s, 2H), 5.27 (s, 2H), 4.19 (d, J=2.6 Hz, 2H), 3.99-3.87 (m, 1H), 3.77 (d, J=13.2 Hz, 1H), 2.90 (d, J=10.6 Hz, 1H), 2.76-2.26 (m, 10H), 2.06-1.79 (m, 11H), 1.66-1.44 (m, 6H).

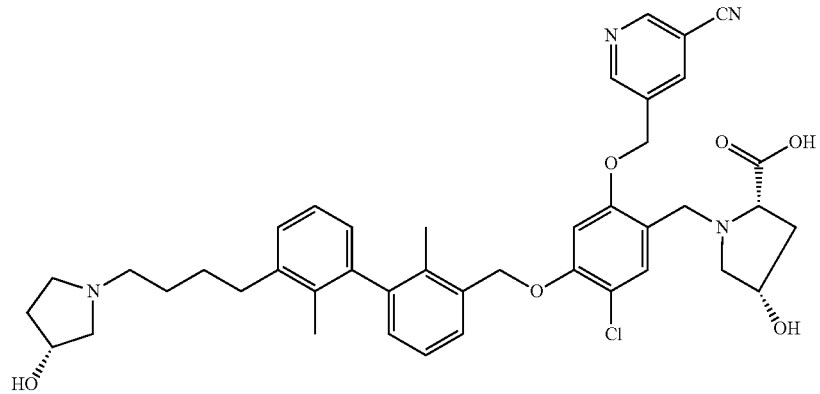 [SMILES: Cc1c(CCCCN2CC[C@@H](O)C2)cccc1-c1cccc(COc2cc(OCc3cncc(C#N)c3)c(CN3C[C@@H](O)C[C@H]3C(=O)O)cc2Cl)c1C]

Example 4063

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 18 minutes, then a 4-minute hold at 100% B; Flow: 20 mL/min. Fractions containing the Preparation of Example 4064

(R)-5-((4-chloro-2-(((1,3-dihydroxypropan-2-yl)amino)methyl)-5-((3'-(4-(3-hydroxypyrrolidin-1-yl)butyl)-2,2'-dimethyl-[1,1'-biphenyl]-3-yl)methoxy)phenoxy)methyl)nicotinonitrile

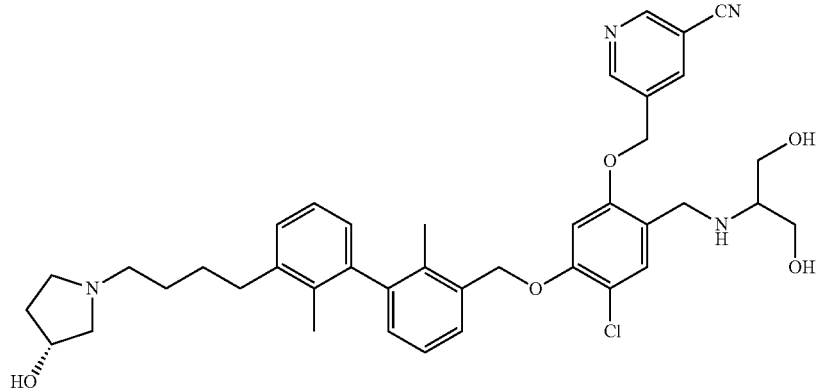

Example 4064

Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 699.07; Retention Time: 1.64 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 699.08; Retention Time: 1.56 min.

Preparation of Example 4065

(R)-5-((4-chloro-2-(((1,3-dihydroxy-2-methylpropan-2-yl)amino)methyl)-5-((3'-(4-(3-hydroxypyrrolidin-1-yl)butyl)-2,2'-dimethyl-[1,1'-biphenyl]-3-yl) methoxy)phenoxy)methyl)nicotinonitrile

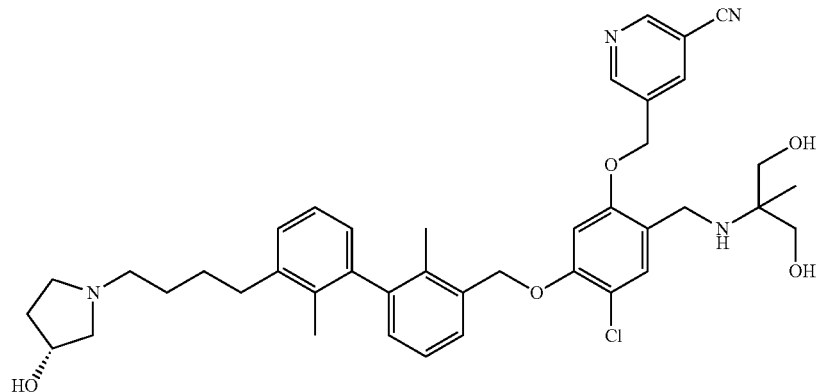

Example 4065

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 120 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.9%; Observed Mass: 713.1; Retention Time: 1.67 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.7%; Observed Mass: 713.1; Retention Time: 1.56 min. $^1$H NMR (500 MHz, DMSO-$d_6$) δ 8.98 (d, J=1.8 Hz, 2H), 8.40 (s, 1H), 7.47 (d, J=7.3 Hz, 1H), 7.41 (s, 1H), 7.26 (t, J=7.7 Hz, 1H), 7.17 (d, J=4.4 Hz, 2H), 7.07 (t, J=3.3 Hz, 2H), 6.90 (t, J=4.4 Hz, 1H), 5.32 (s, 2H), 5.25 (s, 2H), 4.18 (br. s., 1H), 3.65 (s, 2H), 2.76-2.26 (m, 10H), 2.06-1.84 (m, 13H), 1.65-1.43 (m, 5H), 0.93 (s, 3H).

Preparation of Example 4066

(R)-5-((4-chloro-2-(((1,3-dihydroxy-2-(hydroxymethyl)propan-2-yl)amino)methyl)-5-((3'-(4-(3-hydroxypyrrolidin-1-yl)butyl)-2,2'-dimethyl-[1,1'-biphenyl]-3-yl)methoxy)phenoxy)methyl)nicotinonitrile

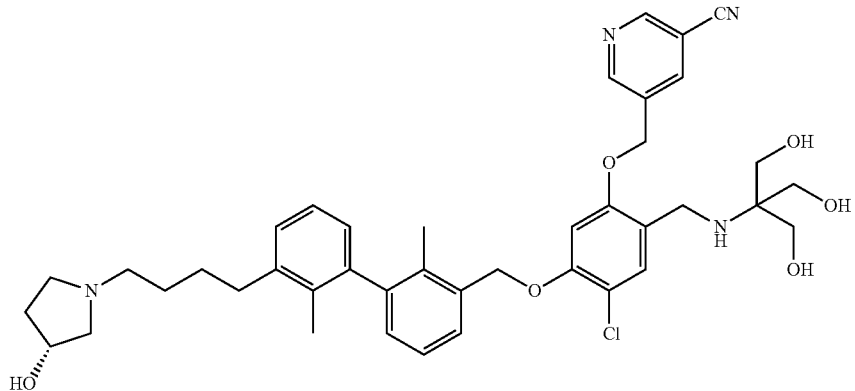 [SMILES: Cc1c(CCCCN2CC[C@@H](O)C2)cccc1-c1cccc(COc2cc(OCc3cncc(C#N)c3)c(CNC(CO)(CO)CO)cc2Cl)c1C]

Example 4066

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.4%; Observed Mass: 729.12; Retention Time: 1.47 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 m L/min; Detection: MS and UV (220 nm). Injection 2 results: Purity: 98.2%; Observed Mass: 729.12; Retention Time: 1.55 min. $^1$H NMR (500 MHz, DMSO-$d_6$) δ 8.98 (s, 2H), 8.40 (s, 1H), 7.47 (d, J=7.3 Hz, 1H), 7.42 (s, 1H), 7.26 (t, J=7.7 Hz, 1H), 7.17 (d, J=4.4 Hz, 2H), 7.11-7.03 (m, 2H), 6.91 (t, J=4.6 Hz, 1H), 5.32 (s, 2H), 5.25 (s, 2H), 4.19 (br. s., 1H), 3.74 (s, 2H), 3.42 (s, 2H), 2.75-2.33 (m, 12H), 2.06-1.88 (m, 12H), 1.65-1.49 (m, 5H).

Preparation of Example 4067

(S)-3-((tert-butoxycarbonyl)amino)-2-((5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)amino)propanoic Acid

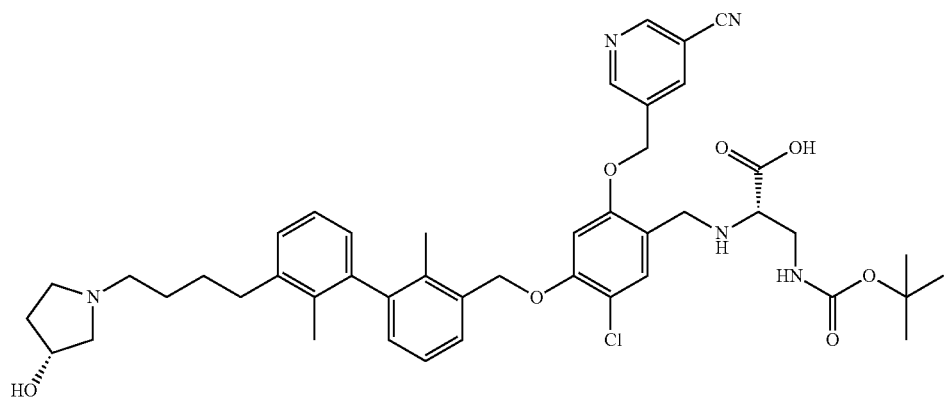 [SMILES: Cc1c(CCCCN2CC[C@@H](O)C2)cccc1-c1cccc(COc2cc(OCc3cncc(C#N)c3)c(CN[C@@H](CNC(=O)OC(C)(C)C)C(=O)O)cc2Cl)c1C]

Example 4067

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 812.12; Retention Time: 1.72 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 812.1; Retention Time: 1.72 min. $^1$H NMR (500 MHz, DMSO-$d_6$) δ 8.99 (s, 2H), 8.42 (s, 1H), 7.50-7.40 (m, 2H), 7.26 (t, J=7.2 Hz, 1H), 7.20-7.13 (m, 2H), 7.10-7.01 (m, 2H), 6.91 (t, J=4.4 Hz, 1H), 5.31 (s, 2H), 5.27 (s, 2H), 4.21 (br. s., 1H), 3.86-3.70 (m, 2H), 3.18 (d, J=13.6 Hz, 1H), 2.82-2.76 (m, 1H), 2.72-2.41 (m, 11H), 2.06-1.88 (m, 9H), 1.65-1.51 (m, 5H), 1.36 (s, 9H).

Preparation of Example 4068

(S)-4-(tert-butoxycarbonyl)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperazine-2-carboxylic Acid

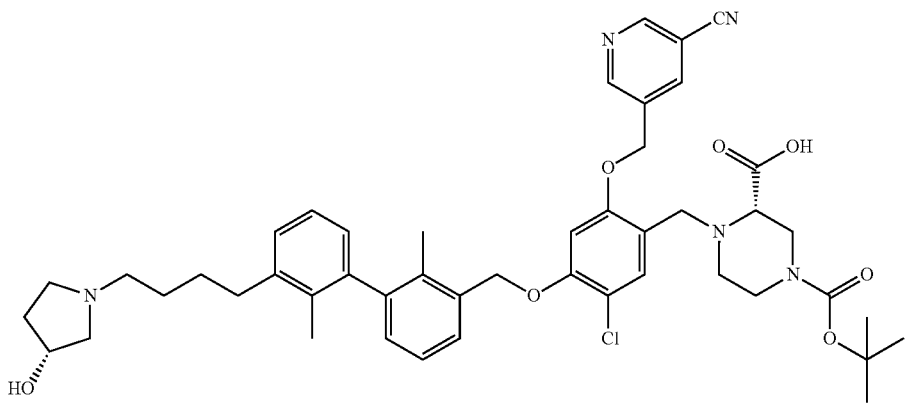 [SMILES: Cc1c(CCCCN2CC[C@@H](O)C2)cccc1-c1cccc(COc2cc(OCc3cncc(C#N)c3)c(CN3CCN(C(=O)OC(C)(C)C)C[C@H]3C(=O)O)cc2Cl)c1C]

Example 4068

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 23 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.5%; Observed Mass: 838.2; Retention Time: 1.64 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.1%; Observed Mass: 838.19; Retention Time: 1.7 μmin.

Preparation of Example 4069

(S)-3-amino-2-((5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)amino)propanoic Acid

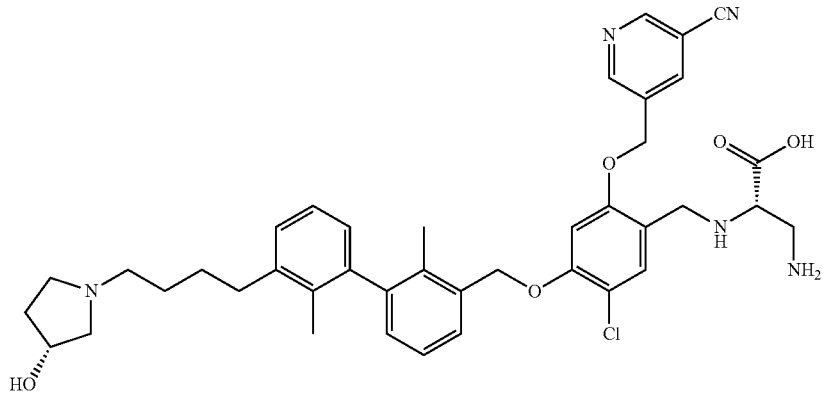 [SMILES: Cc1c(CCCCN2CC[C@@H](O)C2)cccc1-c1cccc(COc2cc(OCc3cncc(C#N)c3)c(CN[C@@H](CN)C(=O)O)cc2Cl)c1C]

Example 4069

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 712.15; Retention Time: 1.45 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 712.15; Retention Time: 1.24 min. $^1$H NMR (500 MHz, DMSO-$d_6$) δ 9.01 (d, J=13.9 Hz, 2H), 8.46 (s, 1H), 7.47 (d, J=7.3 Hz, 1H), 7.40 (s, 1H), 7.27 (t, J=7.5 Hz, 1H), 7.17 (d, J=4.4 Hz, 2H), 7.10-7.01 (m, 2H), 6.91 (t, J=4.6 Hz, 1H), 5.32 (br. s., 2H), 5.26 (s, 2H), 4.18 (br. s., 1H), 3.79-3.61 (m, 2H), 2.98-2.79 (m, 2H), 2.73-2.27 (m, 8H), 2.06-1.87 (m, 13H), 1.64-1.46 (m, 5H)

Preparation of Example 4070

(S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperazine-2-carboxylic Acid

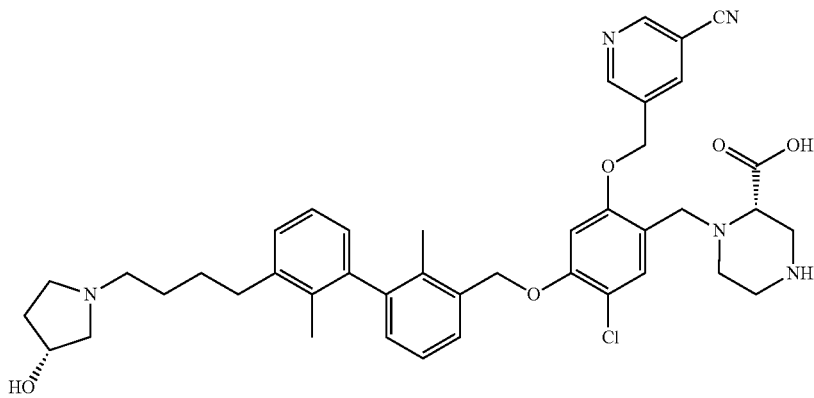 [SMILES: Cc1c(CCCCN2CC[C@@H](O)C2)cccc1-c1cccc(COc2cc(OCc3cncc(C#N)c3)c(CN3CCNC[C@H]3C(=O)O)cc2Cl)c1C]

Example 4070

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.7%; Observed Mass: 738.21; Retention Time: 1.32 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 738.14; Retention Time: 1.45 min. $^1$H NMR (500 MHz, DMSO-$d_6$) δ 9.07-8.92 (m, 2H), 8.39 (s, 1H), 7.52-7.41 (m, 2H), 7.27 (t, J=7.5 Hz, 1H), 7.17 (d, J=4.4 Hz, 2H), 7.07 (d, J=3.3 Hz, 2H), 6.91 (t, J=4.4 Hz, 1H), 5.32 (s, 2H), 5.25 (s, 2H), 4.19 (br. s., 1H), 3.67 (d, J=6.2 Hz, 2H), 3.07 (d, J=4.8 Hz, 2H), 2.96-2.28 (m, 11H), 2.05-1.88 (m, 12H), 1.67-1.47 (m, 5H).

Preparation of Example 4079

(S)-1-(5-chloro-2-((5-cyanopyridin-3-yl)methoxy)-4-((3'-(((2-(1,1-dioxidothiomorpholino)ethyl)(methyl)amino)methyl)-2,2'-dimethyl-[1,1'-biphenyl]-3-yl)methoxy)benzyl)piperidine-2-carboxylic Acid

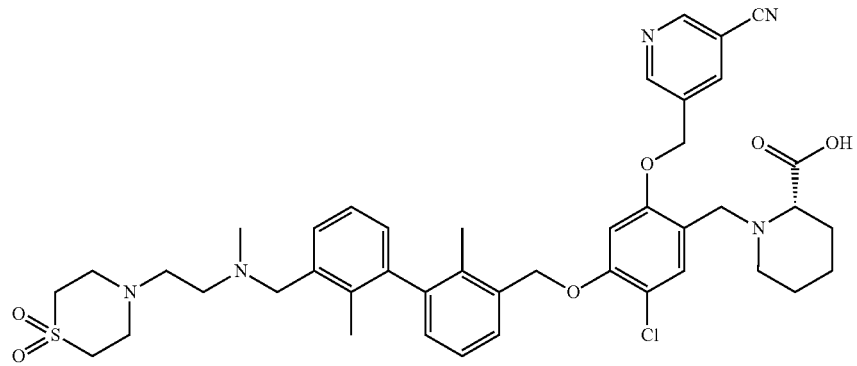 [SMILES: Cc1c(COc2cc(OCc3cncc(C#N)c3)c(CN3CCCC[C@H]3C(=O)O)cc2Cl)cccc1-c1cccc(CN(C)CCN2CCS(=O)(=O)CC2)c1C]

Example 4079

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.1%; Observed Mass: 800.07; Retention Time: 1.6 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.9%; Observed Mass: 800.09; Retention Time: 1.43 min.

Preparation of Example 4080

5-((4-chloro-2-(((1,3-dihydroxypropan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile

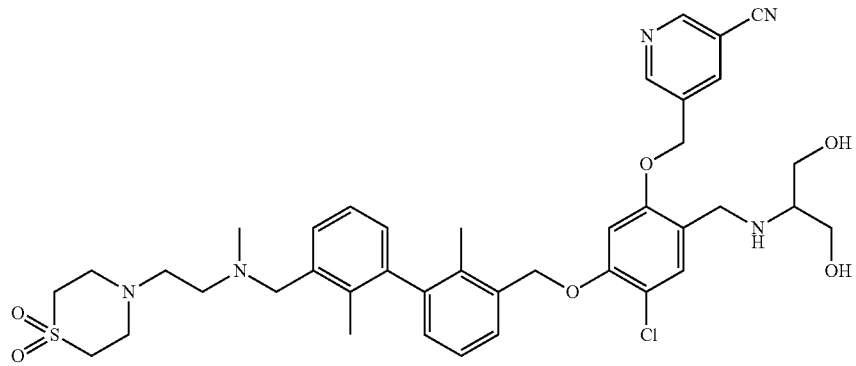 [SMILES: Cc1c(COc2cc(OCc3cncc(C#N)c3)c(CNC(CO)CO)cc2Cl)cccc1-c1cccc(CN(C)CCN2CCS(=O)(=O)CC2)c1C]

Example 4080

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.55 min, ESI m/z 762.1 (M+H).

LC/MS (Injection 2 conditions) Rt=1.34 min, ESI m/z 762.1 (M+H).

Preparation of Example 4081

(S)-2-((5-chloro-2-((5-cyanopyridin-3-yl)methoxy)-4-((3'-(((2-(1,1-dioxidothiomorpholino)ethyl)(methyl)amino)methyl)-2,2'-dimethyl-[1,1'-biphenyl]-3-yl)methoxy)benzyl)amino)-3-hydroxy-2-methylpropanoic Acid

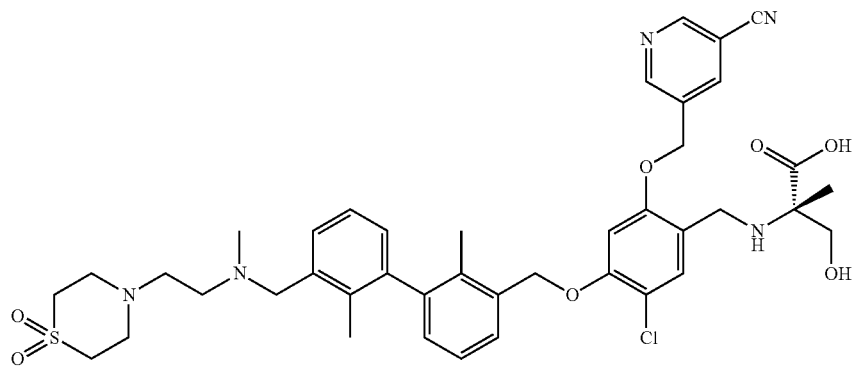 [SMILES: Cc1c(COc2cc(OCc3cncc(C#N)c3)c(CN[C@@](C)(CO)C(=O)O)cc2Cl)cccc1-c1cccc(CN(C)CCN2CCS(=O)(=O)CC2)c1C]

Example 4081

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 790.05; Retention Time: 1.56 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 790.01; Retention Time: 1.37 min.

Preparation of Example 4082

5-((4-chloro-2-(((1,3-dihydroxy-2-methylpropan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 776.14; Retention Time: 1.35 min.

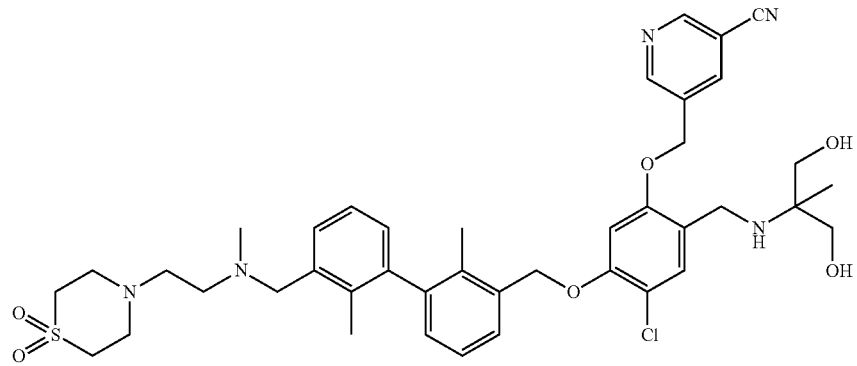 [SMILES: Cc1c(COc2cc(OCc3cncc(C#N)c3)c(CNC(C)(CO)CO)cc2Cl)cccc1-c1cccc(CN(C)CCN2CCS(=O)(=O)CC2)c1C]

Example 4082

Preparation of Example 4083

5-((4-chloro-2-(((1,3-dihydroxy-2-(hydroxymethyl)propan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile

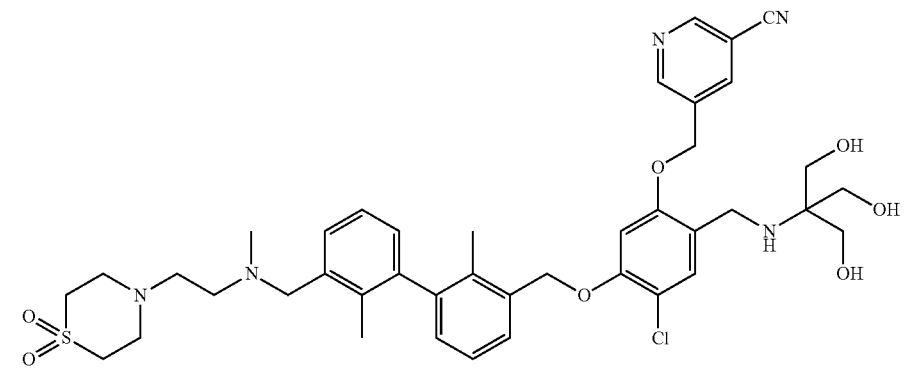 [SMILES: Cc1c(COc2cc(OCc3cncc(C#N)c3)c(CNC(CO)(CO)CO)cc2Cl)cccc1-c1cccc(CN(C)CCN2CCS(=O)(=O)CC2)c1C]

Example 4083

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min.

LC/MS (Injection 1 conditions) Rt=1.56 min, ESI m/z 792.1 (M+H).

LC/MS (Injection 2 conditions) Rt=1.31 min, ESI m/z 792.1 (M+H).

Preparation of Example 4084

5-((2-((bis(2-hydroxyethyl)amino)methyl)-4-chloro-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile

Example 4084

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.64 min, ESI m/z 776.2 (M+H).

LC/MS (Injection 2 conditions) Rt=1.33 min, ESI m/z 776.2 (M+H).

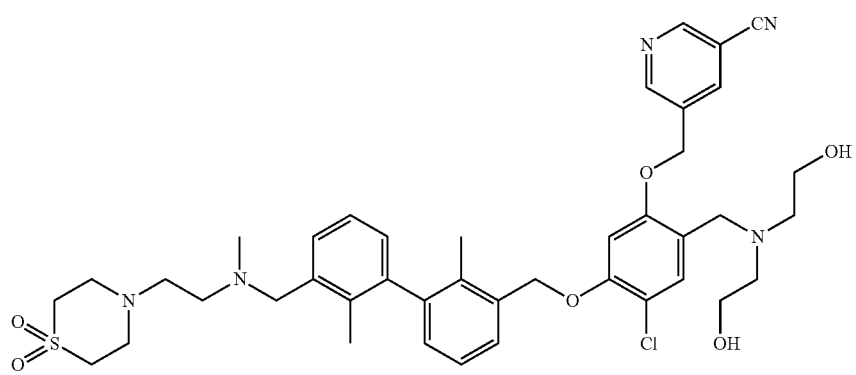 [SMILES: Cc1c(COc2cc(OCc3cncc(C#N)c3)c(CN(CCO)CCO)cc2Cl)cccc1-c1cccc(CN(C)CCN2CCS(=O)(=O)CC2)c1C]

Preparation of Example 4085

5-((4-chloro-5-(((3'-(((2-(1,1-dioxidothiomorpholino)ethyl)(methyl)amino)methyl)-2,2'-dimethyl-[1,1'-biphenyl]-3-yl)methoxy)-2-(((2-hydroxyethyl)(3-hydroxypropyl)amino)methyl)phenoxy)methyl)nicotinonitrile

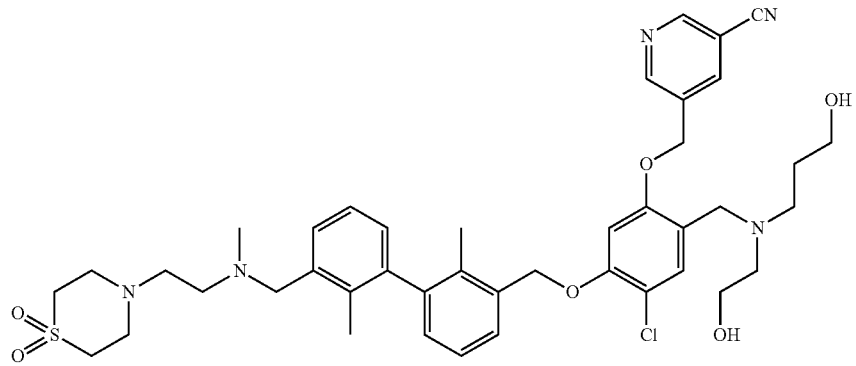 [SMILES: Cc1c(COc2cc(OCc3cncc(C#N)c3)c(CN(CCO)CCCO)cc2Cl)cccc1-c1cccc(CN(C)CCN2CCS(=O)(=O)CC2)c1C]

Example 4085

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 37-53% B over 25 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.7%; Observed Mass: 790.13; Retention Time: 1.56 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 790.13; Retention Time: 1.4 min.

Preparation of Example 4086

(S)-1-(2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-6-methylbenzyl)piperidine-2-carboxylic Acid

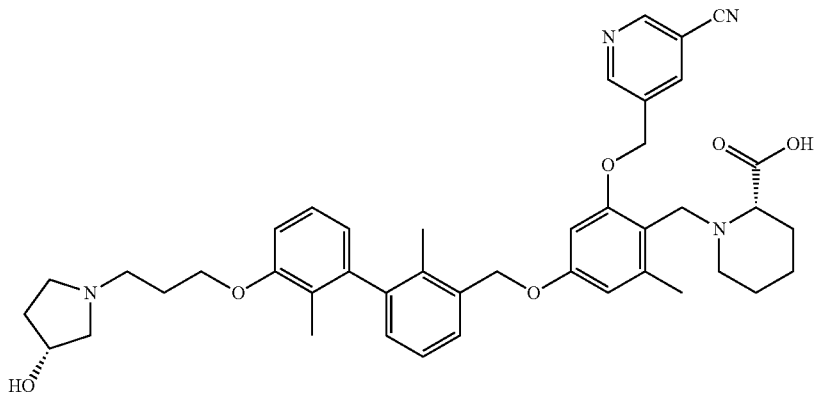 [SMILES: Cc1cc(OCc2cccc(-c3cccc(OCCCN4CC[C@@H](O)C4)c3C)c2C)cc(OCc2cncc(C#N)c2)c1CN1CCCC[C@H]1C(=O)O]

Example 4086

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.2%; Observed Mass: 719.19; Retention Time: 1.36 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.0%; Observed Mass: 719.16; Retention Time: 1.55 min.

Preparation of Example 4087

(R)-5-((2-(((1,3-dihydroxypropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

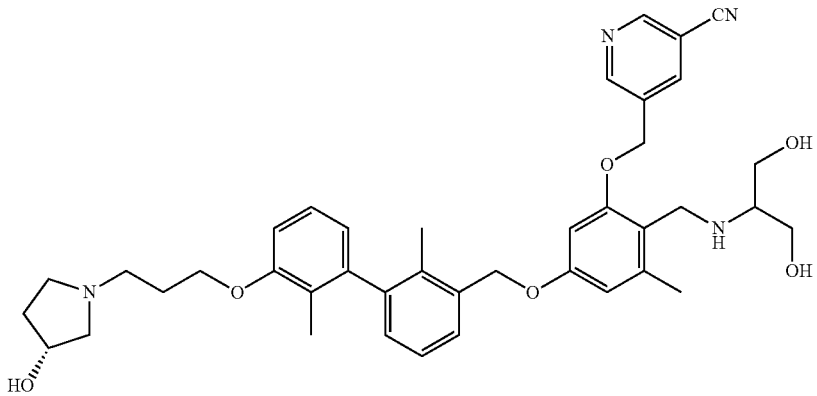 [SMILES: Cc1cc(OCc2cccc(-c3cccc(OCCCN4CC[C@@H](O)C4)c3C)c2C)cc(OCc2cncc(C#N)c2)c1CNC(CO)CO]

Example 4087

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 681.2, 341.21; Retention Time: 1.26, 1.33 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.5%; Observed Mass: 681.23; Retention Time: 1.48 min.

Preparation of Example 4088

(R)-5-((2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

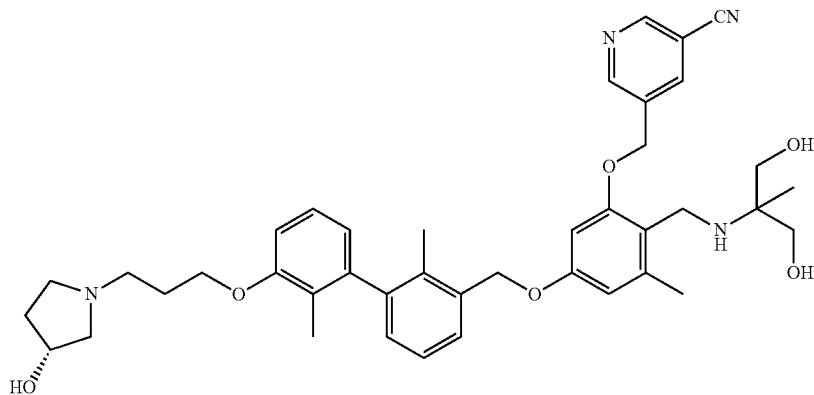 [SMILES: Cc1cc(OCc2cccc(-c3cccc(OCCCN4CC[C@@H](O)C4)c3C)c2C)cc(OCc2cncc(C#N)c2)c1CNC(C)(CO)CO]

Example 4088

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 695.17; Retention Time: 1.52 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.5%; Observed Mass: 695.19; Retention Time: 1.27 min.

Preparation of Example 4089

(R)-5-((2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

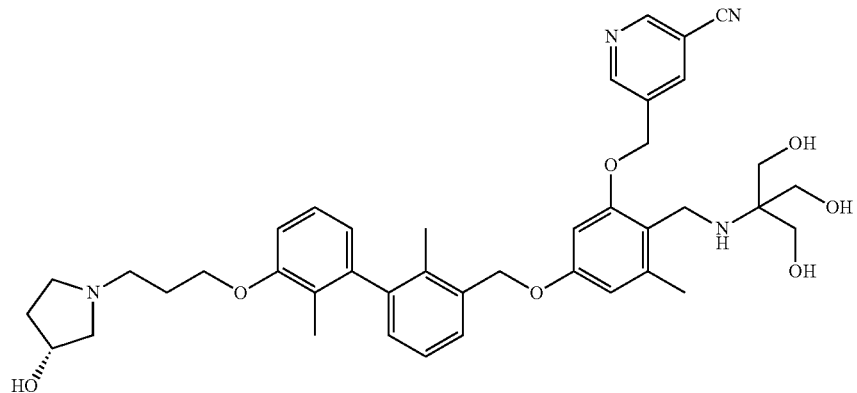 [SMILES: Cc1cc(OCc2cccc(-c3cccc(OCCCN4CC[C@@H](O)C4)c3C)c2C)cc(OCc2cncc(C#N)c2)c1CNC(CO)(CO)CO]

Example 4089

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.9%; Observed Mass: 711.14; Retention Time: 1.41 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 711.13; Retention Time: 1.37 min.

Preparation of Example 4090

(R)-5-((2-(((bis(2-hydroxyethyl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

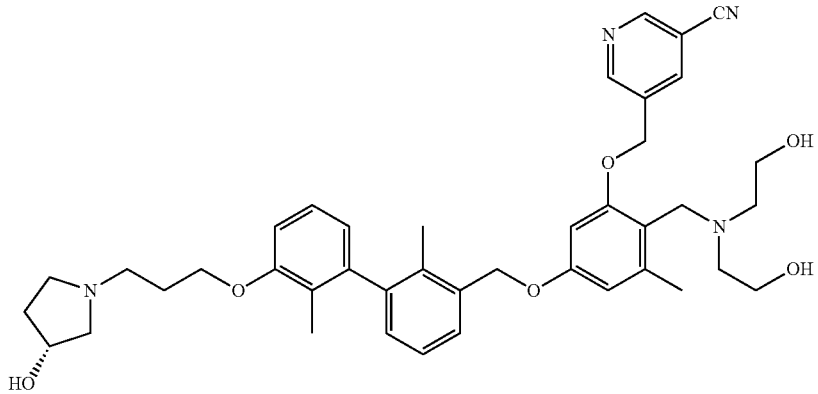 [SMILES: Cc1cc(OCc2cccc(-c3cccc(OCCCN4CC[C@@H](O)C4)c3C)c2C)cc(OCc2cncc(C#N)c2)c1CN(CCO)CCO]

Example 4090

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 22 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.2%; Observed Mass: 695.17; Retention Time: 1.42 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 695.11; Retention Time: 1.32 min.

Preparation of Example 4091

(S)-2-((2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-6-methylbenzyl)amino)-3-hydroxy-2-methylpropanoic Acid

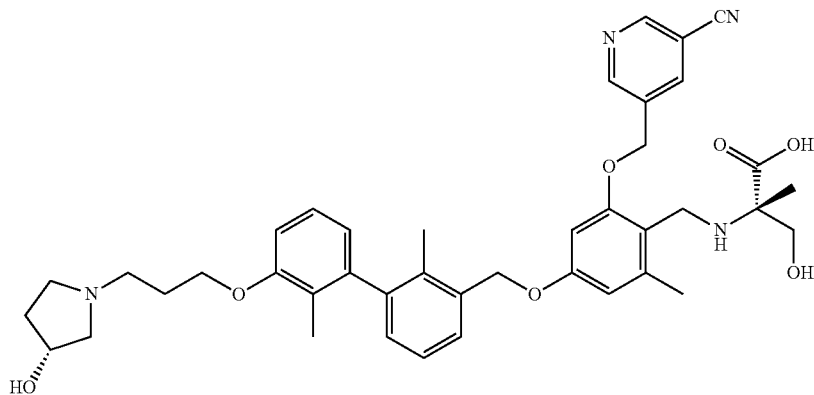 [SMILES: Cc1cc(OCc2cccc(-c3cccc(OCCCN4CC[C@@H](O)C4)c3C)c2C)cc(OCc2cncc(C#N)c2)c1CN[C@@](C)(CO)C(=O)O]

Example 4091

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 709.15; Retention Time: 1.34 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 709.13; Retention Time: 1.37 min.

Preparation of Example 4100

(S)-2-((3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)(methyl)amino)-3-hydroxy-2-methylpropanoic Acid

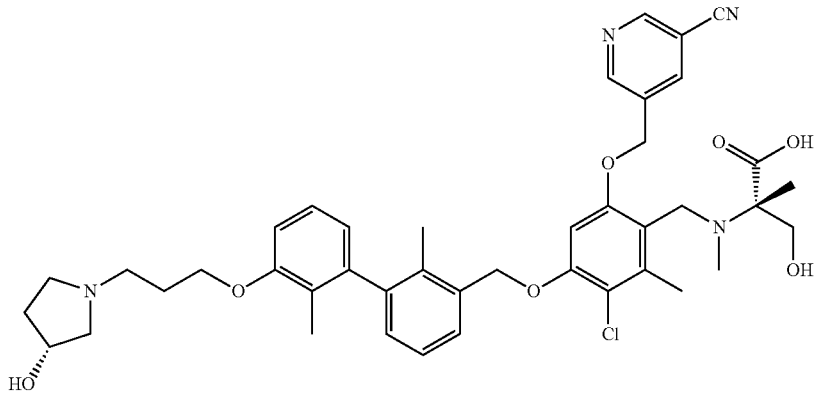 [SMILES: Cc1c(COc2cc(OCc3cncc(C#N)c3)c(CN(C)[C@@](C)(CO)C(=O)O)c(C)c2Cl)cccc1-c1cccc(OCCCN2CC[C@@H](O)C2)c1C]

Example 4100

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.2%; Observed Mass: 757.12; Retention Time: 1.5 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 757.1; Retention Time: 1.43 min.

Preparation of Example 4101

(S)-1-(3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)piperidine-2-carboxylic Acid at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.42 min, ESI m/z 753.1 (M+H).

LC/MS (Injection 2 conditions) Rt=1.45 min, ESI m/z 753.2 (M+H).

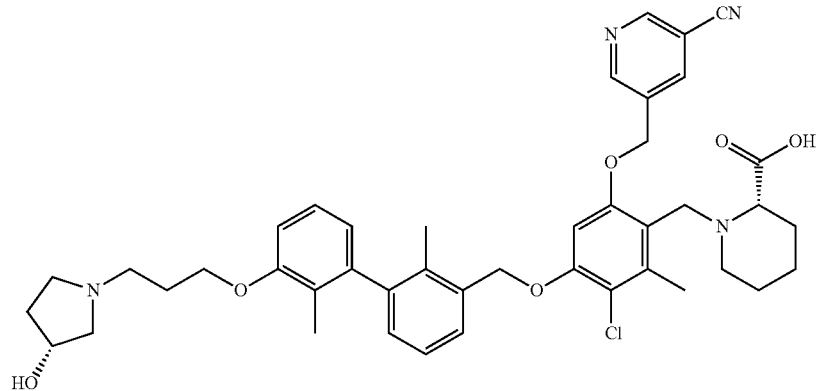 [SMILES: Cc1c(COc2cc(OCc3cncc(C#N)c3)c(CN3CCCC[C@H]3C(=O)O)c(C)c2Cl)cccc1-c1cccc(OCCCN2CC[C@@H](O)C2)c1C]

Example 4101

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 22-62% B over 15 minutes, then a 5-minute hold Preparation of Example 4102

(R)-5-((4-chloro-2-(((1,3-dihydroxypropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

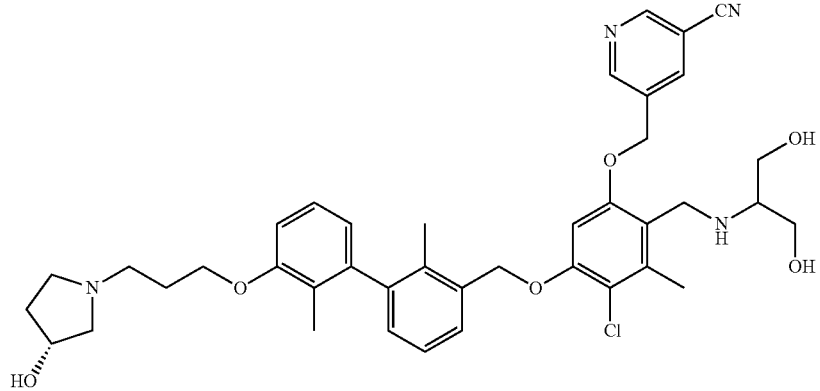 [SMILES: Cc1c(COc2cc(OCc3cncc(C#N)c3)c(CNC(CO)CO)c(C)c2Cl)cccc1-c1cccc(OCCCN2CC[C@@H](O)C2)c1C]

Example 4102

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Preparation of Example 4103

(R)-5-((4-chloro-2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl) nicotinonitrile

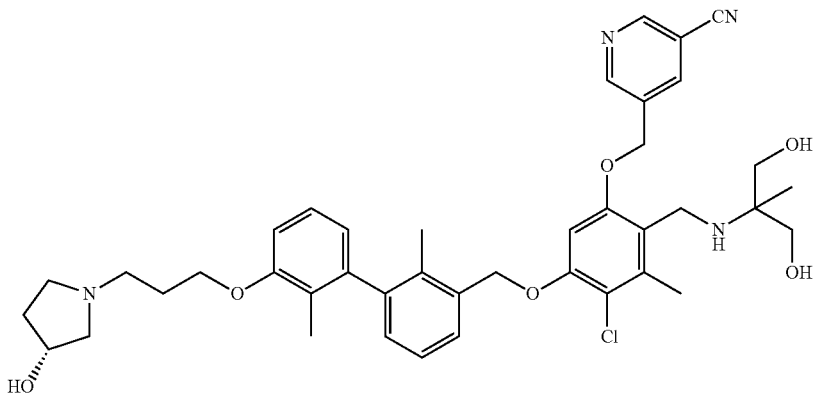 [SMILES: Cc1c(COc2cc(OCc3cncc(C#N)c3)c(CNC(C)(CO)CO)c(C)c2Cl)cccc1-c1cccc(OCCCN2CC[C@@H](O)C2)c1C]

Example 4103

Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. 729.1

LC/MS (Injection 1 conditions) Rt=1.51 min, ESI m/z 729.1 (M+H).

LC/MS (Injection 2 conditions) Rt=1.38 min, ESI m/z 729.1 (M+H).

Preparation of Example 4104

(R)-5-((4-chloro-2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

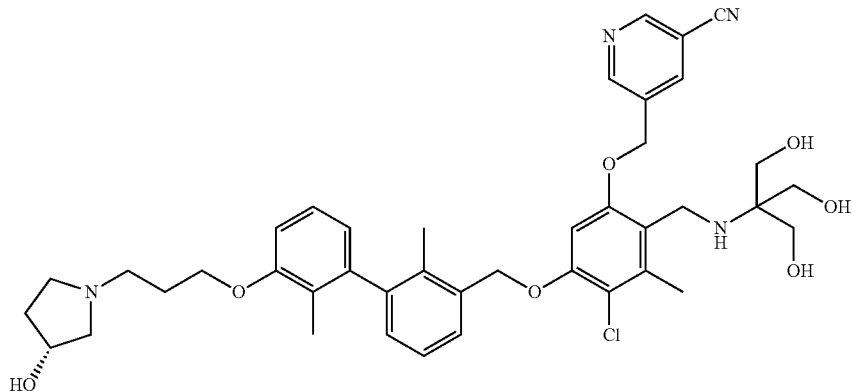 [SMILES: Cc1c(COc2cc(OCc3cncc(C#N)c3)c(CNC(CO)(CO)CO)c(C)c2Cl)cccc1-c1cccc(OCCCN2CC[C@@H](O)C2)c1C]

Example 4104

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LC/MS (Injection 1 conditions) Rt=1.51 min, ESI m/z 745.1 (M+H).

LC/MS (Injection 2 conditions) Rt=1.35 min, ESI m/z 745.1 (M+H).

Preparation of Example 4105

(R)-5-((2-((bis(2-hydroxyethyl)amino)methyl)-4-chloro-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

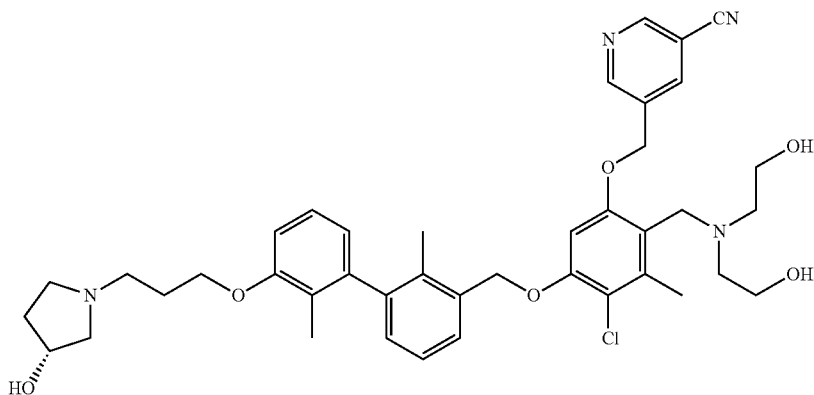 [SMILES: Cc1c(COc2cc(OCc3cncc(C#N)c3)c(CN(CCO)CCO)c(C)c2Cl)cccc1-c1cccc(OCCCN2CC[C@@H](O)C2)c1C]

Example 4105

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.3%; Observed Mass: 729.11; Retention Time: 1.59 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 729.13; Retention Time: 1.38 min.

Preparation of Example 4106

(S)-2-((3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)amino)-3-hydroxy-2-methylpropanoic Acid Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.4%; Observed Mass: 743.07; Retention Time: 1.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 743.13; Retention Time: 1.39 min.

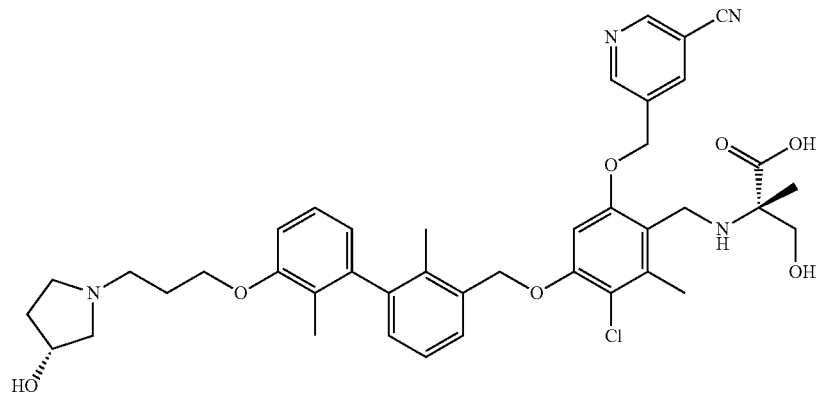 [SMILES: Cc1c(COc2cc(OCc3cncc(C#N)c3)c(CN[C@@](C)(CO)C(=O)O)c(C)c2Cl)cccc1-c1cccc(OCCCN2CC[C@@H](O)C2)c1C]

Example 4106

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate;

Preparation of Example 4107

(R)-5-((4-chloro-2-(((1,3-dihydroxy-2-methylpropan-2-yl)(methyl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile

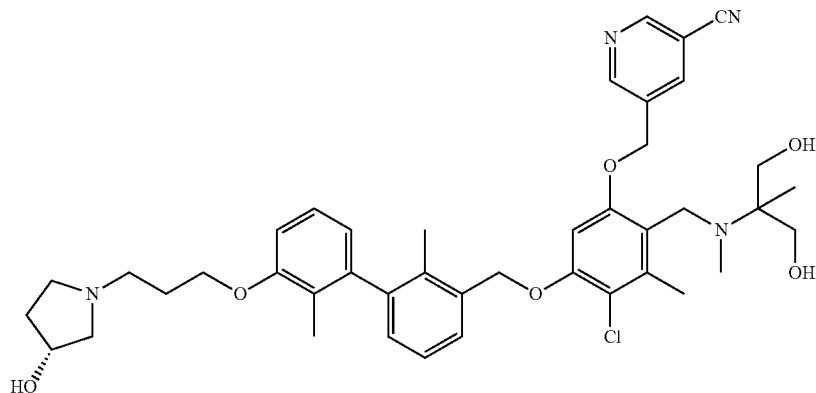 [SMILES: Cc1c(COc2cc(OCc3cncc(C#N)c3)c(CN(C)C(C)(CO)CO)c(C)c2Cl)cccc1-c1cccc(OCCCN2CC[C@@H](O)C2)c1C]

Example 4107

Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.7%; Observed Mass: 743.12; Retention Time: 1.53 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.2%; Observed Mass: 743.12; Retention Time: 1.42 min.

Preparation of Example 4108

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(methyl)amino)-3-hydroxy-2-methylpropanoic Acid

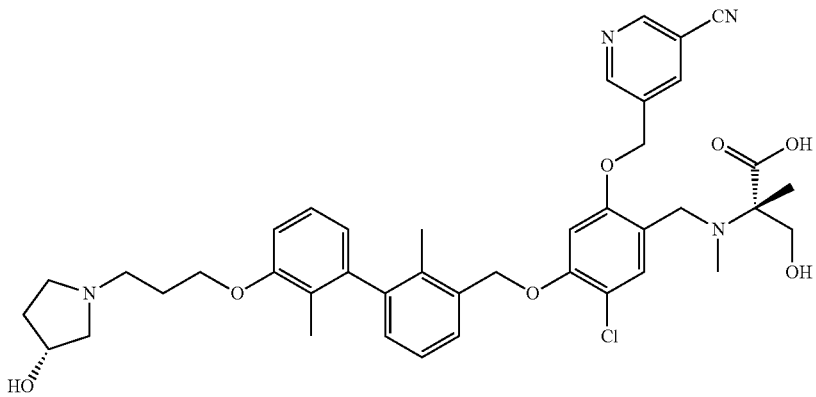 [SMILES: Cc1c(COc2cc(OCc3cncc(C#N)c3)c(CN(C)[C@@](C)(CO)C(=O)O)cc2Cl)cccc1-c1cccc(OCCCN2CC[C@@H](O)C2)c1C]

Example 4108

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.5%; Observed Mass: 743.14; Retention Time: 1.47 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.9%; Observed Mass: 743.1; Retention Time: 1.38 min.

Preparation of Example 4109

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(ethyl)amino)-3-hydroxy-2-methylpropanoic Acid

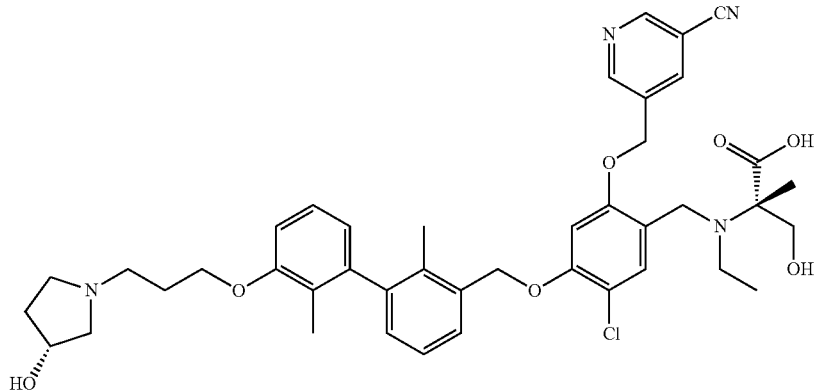 [SMILES: CCN(Cc1cc(Cl)c(OCc2cccc(-c3cccc(OCCCN4CC[C@@H](O)C4)c3C)c2C)cc1OCc1cncc(C#N)c1)[C@@](C)(CO)C(=O)O]

Example 4109

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 757.12, 757.12; Retention Time: 1.4, 1.43 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.6%; Observed Mass: 757.14; Retention Time: 1.5 min.

Preparation of Example 4110

(R)-1-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)cyclopropane-1-carboxylic Acid

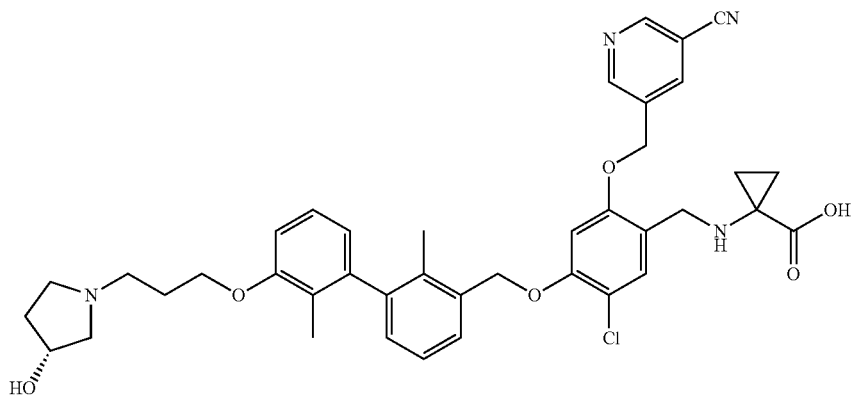 [SMILES: Cc1c(COc2cc(OCc3cncc(C#N)c3)c(CNC3(C(=O)O)CC3)cc2Cl)cccc1-c1cccc(OCCCN2CC[C@@H](O)C2)c1C]

Example 4110

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid;

Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 711.09; Retention Time: 1.37 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 711.09, 711.09, 711.09; Retention Time: 1.41 min.

Preparation of Example 4111

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(2-hydroxyethyl)amino)-3-hydroxy-2-methylpropanoic Acid

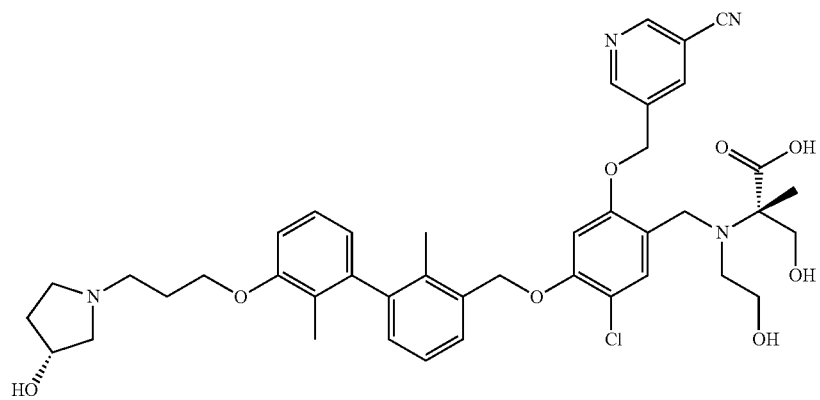 [SMILES: Cc1c(COc2cc(OCc3cncc(C#N)c3)c(CN(CCO)[C@@](C)(CO)C(=O)O)cc2Cl)cccc1-c1cccc(OCCCN2CC[C@@H](O)C2)c1C]

Example 4111

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 773.11; Retention Time: 1.38 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 773.13; Retention Time: 1.34 min.

Preparation of Example 4112

(S)-1-(5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)piperidine-2-carboxylic Acid

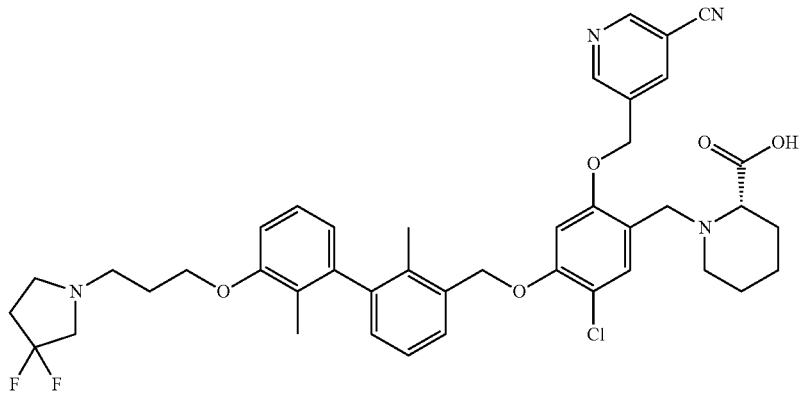 [SMILES: Cc1c(COc2cc(OCc3cncc(C#N)c3)c(CN3CCCC[C@H]3C(=O)O)cc2Cl)cccc1-c1cccc(OCCCN2CCC(F)(F)C2)c1C]

Example 4112

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.5%; Observed Mass: 759.09; Retention Time: 2.16 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.0%; Observed Mass: 759.09; Retention Time: 1.54 min.

Preparation of Example 4113

5-((4-chloro-5-((3'-(3-(3,3-difluoropyrrolidin-1-yl)propoxy)-2,2'-dimethyl-[1,1'-biphenyl]-3-yl)methoxy)-2-((2-hydroxyethyl)(3-hydroxypropyl)amino)methyl)phenoxy)methyl)nicotinonitrile

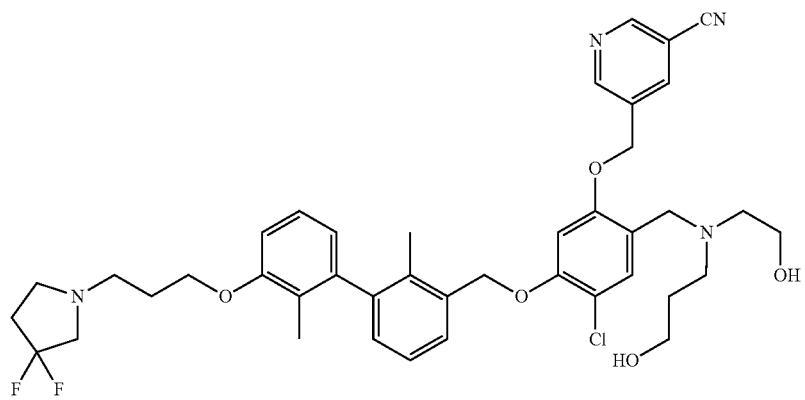 [SMILES: Cc1c(COc2cc(OCc3cncc(C#N)c3)c(CN(CCO)CCCO)cc2Cl)cccc1-c1cccc(OCCCN2CCC(F)(F)C2)c1C]

Example 4113

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. Fractions containing the desired product were combined and dried via centrifugal evaporation.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 749.05; Retention Time: 2.33 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 749.06; Retention Time: 1.46 min.

Preparation of Example 4114

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-methylpropan-2-yl)(methyl)amino)methyl)phenoxy)methyl)nicotinonitrile

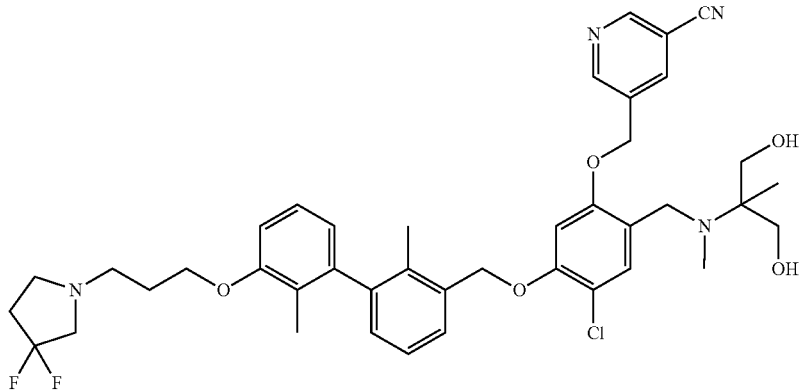 [SMILES: Cc1c(COc2cc(OCc3cncc(C#N)c3)c(CN(C)C(C)(CO)CO)cc2Cl)cccc1-c1cccc(OCCCN2CCC(F)(F)C2)c1C]

Example 4114

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 91.0%; Observed Mass: 749.06; Retention Time: 2.31 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.9%; Observed Mass: 749.06; Retention Time: 1.49 min.

Preparation of Example 4115

(S)-2-((5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)(methyl)amino)-3-hydroxy-2-methylpropanoic Acid

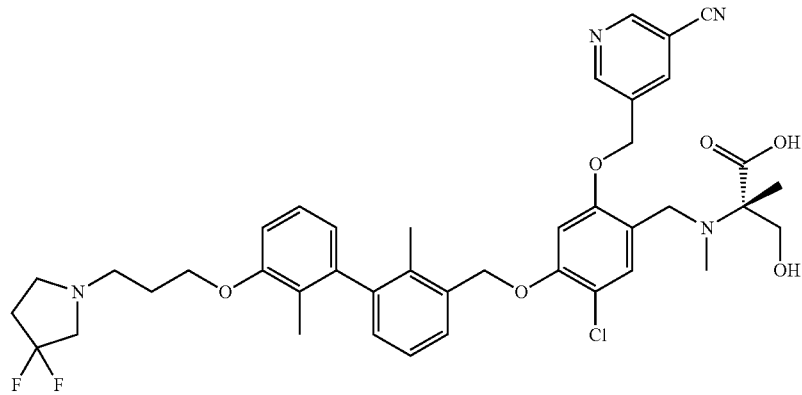 [SMILES: Cc1c(COc2cc(OCc3cncc(C#N)c3)c(CN(C)[C@@](C)(CO)C(=O)O)cc2Cl)cccc1-c1cccc(OCCCN2CCC(F)(F)C2)c1C]

Example 4115

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.3%; Observed Mass: 763.04; Retention Time: 2.14 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.3%; Observed Mass: 763.04; Retention Time: 1.49 min.

Preparation of Example 4116

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxypropan-2-yl)amino)methyl)phenoxy)methyl)nicotinonitrile

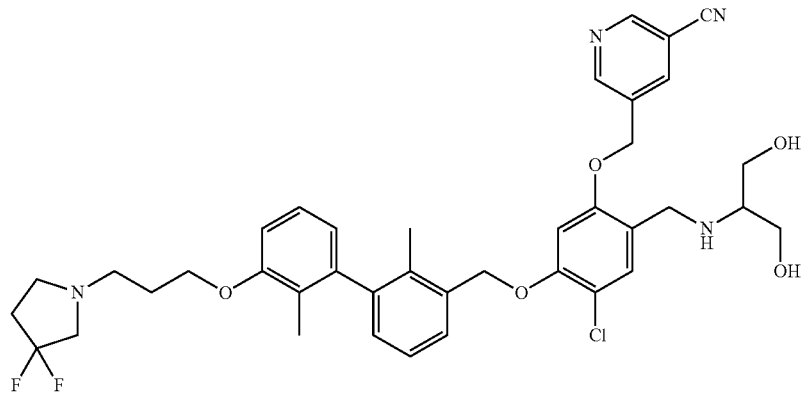 [SMILES: Cc1c(COc2cc(OCc3cncc(C#N)c3)c(CNC(CO)CO)cc2Cl)cccc1-c1cccc(OCCCN2CCC(F)(F)C2)c1C]

Example 4116

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.8%; Observed Mass: 721.07; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 721.09; Retention Time: 2.19 min.

Preparation of Example 4117

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-methylpropan-2-yl)amino)methyl)phenoxy)methyl)nicotinonitrile product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.5%; Observed Mass: 735.07; Retention Time: 1.47 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.0%; Observed Mass: 735.06; Retention Time: 2.2 min.

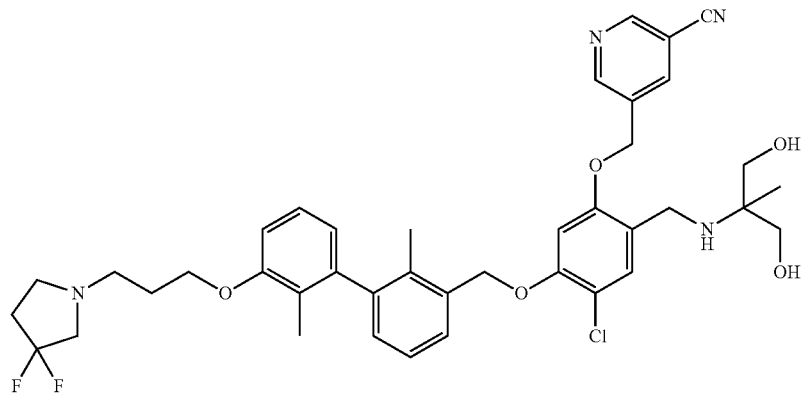 [SMILES: Cc1c(COc2cc(OCc3cncc(C#N)c3)c(CNC(C)(CO)CO)cc2Cl)cccc1-c1cccc(OCCCN2CCC(F)(F)C2)c1C]

Example 4117

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min. Fractions containing the desired Preparation of Example 4118

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-(hydroxymethyl)propan-2-yl)amino)methyl)phenoxy)methyl)nicotinonitrile

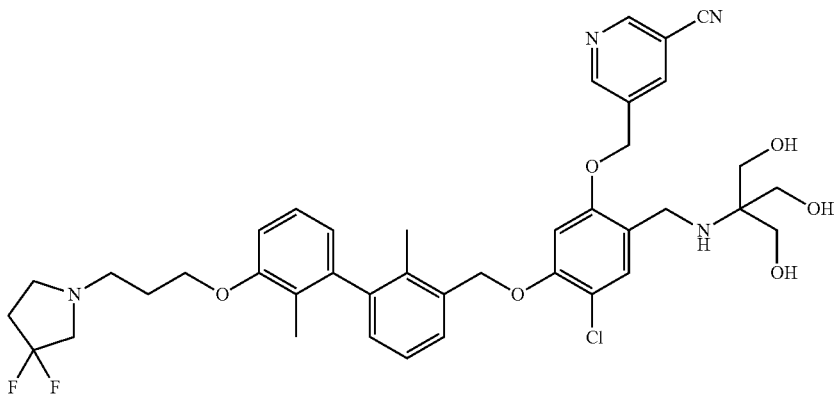 [SMILES: Cc1c(COc2cc(OCc3cncc(C#N)c3)c(CNC(CO)(CO)CO)cc2Cl)cccc1-c1cccc(OCCCN2CCC(F)(F)C2)c1C]

Example 4118

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 94%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 751.04; Retention Time: 1.44 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.6%; Observed Mass: 751.1; Retention Time: 2.19 min.

Preparation of Example 4119

(S)-2-((5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)amino)-3-hydroxy-2-methylpropanoic Acid

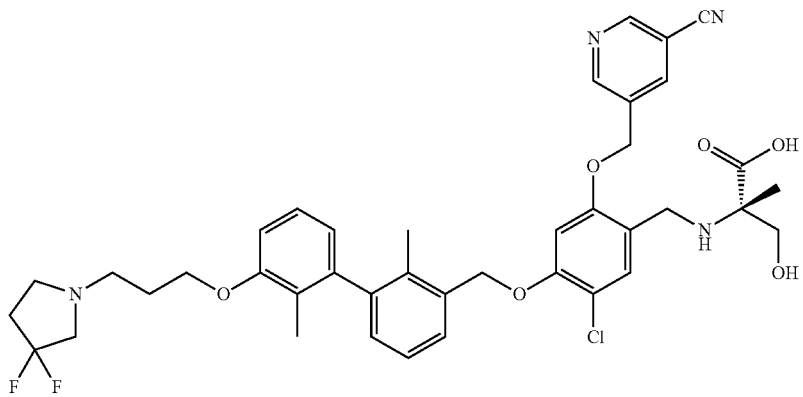 [SMILES: Cc1c(COc2cc(OCc3cncc(C#N)c3)c(CN[C@@](C)(CO)C(=O)O)cc2Cl)cccc1-c1cccc(OCCCN2CCC(F)(F)C2)c1C]

Example 4119

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.3%; Observed Mass: 749; Retention Time: 1.48 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.6%; Observed Mass: 749.04; Retention Time: 2.07 min.

Preparation of Example 4120

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxypropan-2-yl)(methyl)amino)methyl)phenoxy)methyl)nicotinonitrile

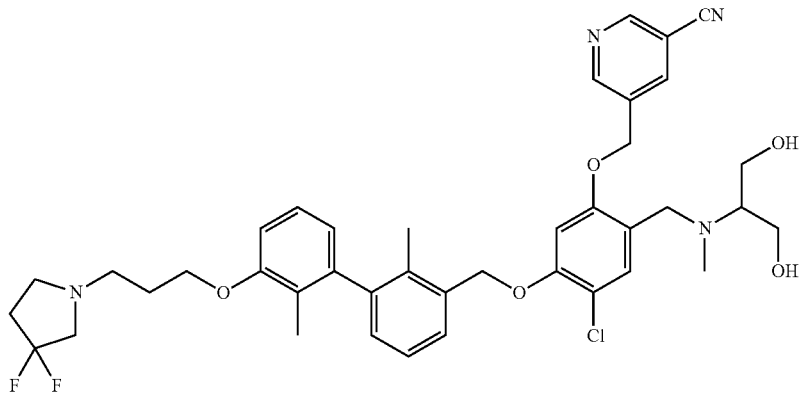 [SMILES: Cc1c(COc2cc(OCc3cncc(C#N)c3)c(CN(C)C(CO)CO)cc2Cl)cccc1-c1cccc(OCCCN2CCC(F)(F)C2)c1C]

Example 4120

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 19 minutes, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 47-87% B over 24 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 86.1%; Observed Mass: 735.08; Retention Time: 1.47 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 735.04; Retention Time: 2.31 min.

Preparation of Example 4121

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-(hydroxymethyl)propan-2-yl)(methyl)amino)methyl)phenoxy)methyl)nicotinonitrile

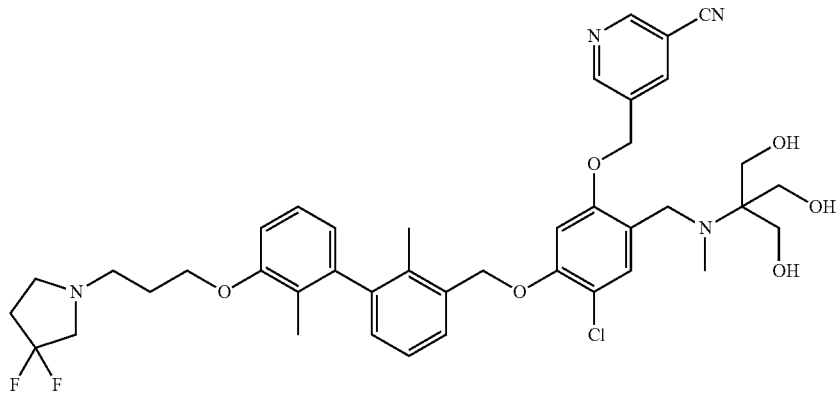 [SMILES: Cc1c(COc2cc(OCc3cncc(C#N)c3)c(CN(C)C(CO)(CO)CO)cc2Cl)cccc1-c1cccc(OCCCN2CCC(F)(F)C2)c1C]

Example 4121

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 19 minutes, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 23 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.7%; Observed Mass: 765.04; Retention Time: 1.46 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.1%; Observed Mass: 765.06; Retention Time: 2.25 min.

Preparation of Example 4122

(R)-5-((4-chloro-2-(((1,3-dihydroxypropan-2-yl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile

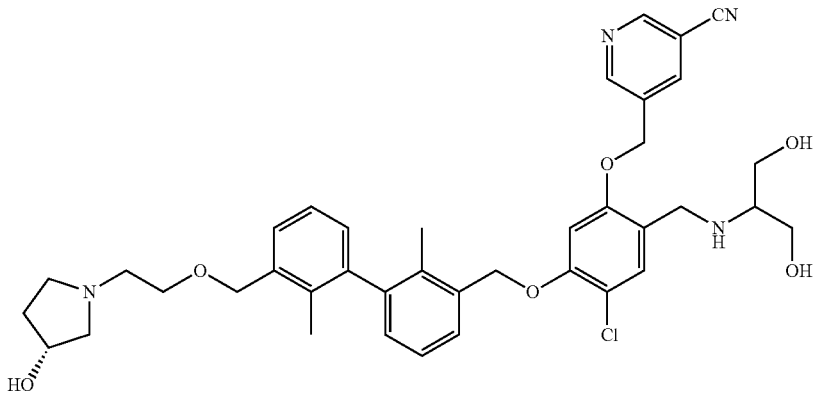 [SMILES: Cc1c(COCCN2CC[C@@H](O)C2)cccc1-c1cccc(COc2cc(OCc3cncc(C#N)c3)c(CNC(CO)CO)cc2Cl)c1C]

Example 4122

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.0%; Observed Mass: 701.12; Retention Time: 1.36 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.6%; Observed Mass: 701.13; Retention Time: 1.3 min.

Preparation of Example 4123

(S)-2-((5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)amino)-3-hydroxy-2-methylpropanoic Acid

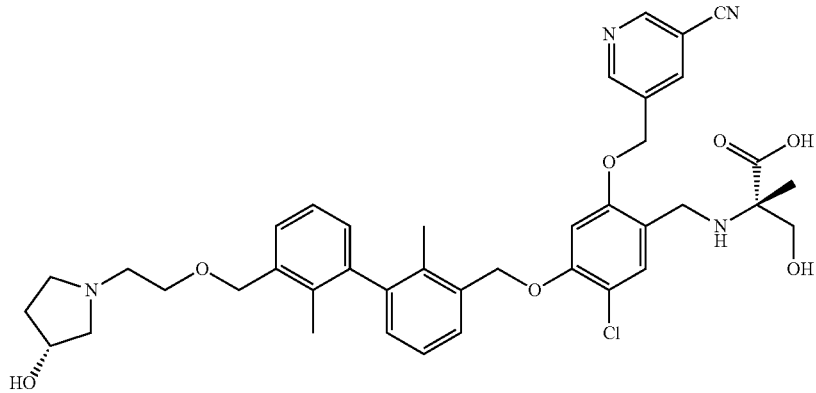 [SMILES: Cc1c(COCCN2CC[C@@H](O)C2)cccc1-c1cccc(COc2cc(OCc3cncc(C#N)c3)c(CN[C@@](C)(CO)C(=O)O)cc2Cl)c1C]

Example 4123

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.0%; Observed Mass: 729.08; Retention Time: 1.36 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.1%; Observed Mass: 729.09; Retention Time: 1.33 min.

Preparation of Example 4124

(R)-1-((5-chloro-2-((5-cyanopyridin-3-yl)methoxy)-4-((3'-((2-(3-hydroxypyrrolidin-1-yl)ethoxy)methyl)-2,2'-dimethyl-[1,1'-biphenyl]-3-yl)methoxy)benzyl)amino)cyclopropane-1-carboxylic Acid

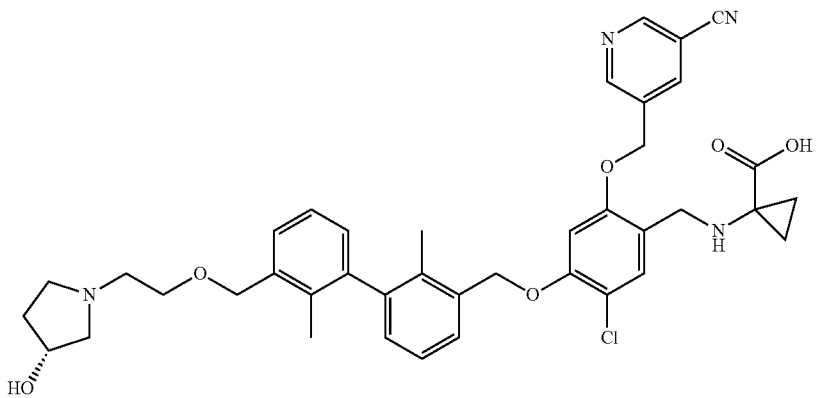 [SMILES: Cc1c(COCCN2CC[C@@H](O)C2)cccc1-c1cccc(COc2cc(OCc3cncc(C#N)c3)c(CNC3(C(=O)O)CC3)cc2Cl)c1C]

Example 4124

Mobile Phase A: 5:95 acetonitrile:water with 10-mM ammonium acetate; Mobile Phase B: 95:5 acetonitrile:water with 10-mM ammonium acetate; Gradient: 10-55% B over 25 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.4%; Observed Mass: 711.07; Retention Time: 1.36 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.7%; Observed Mass: 711.07; Retention Time: 1.37 min.

Preparation of Example 4125

(R)-5-((4-chloro-2-(((1,3-dihydroxy-2-(hydroxymethyl)propan-2-yl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile

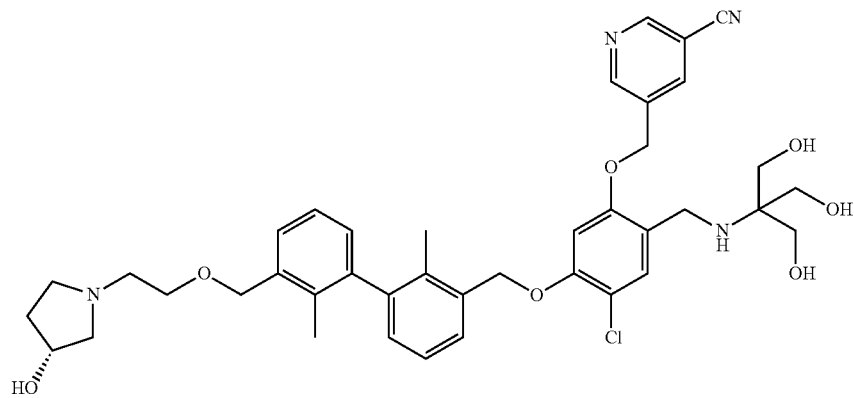 [SMILES: Cc1c(COCCN2CC[C@@H](O)C2)cccc1-c1cccc(COc2cc(OCc3cncc(C#N)c3)c(CNC(CO)(CO)CO)cc2Cl)c1C]

Example 4125

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-58% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.7%; Observed Mass: 731.14; Retention Time: 1.42 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.8%; Observed Mass: 731.13; Retention Time: 1.44 min.

Preparation of Example 4126

(S)-1-(5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)piperidine-2-carboxylic Acid

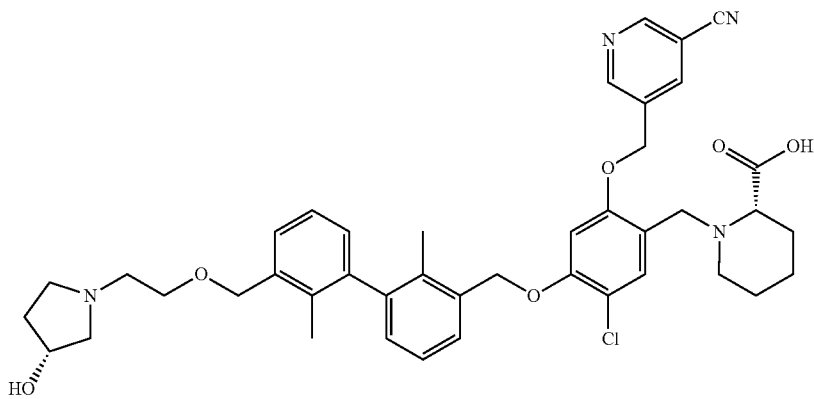 [SMILES: Cc1c(COCCN2CC[C@@H](O)C2)cccc1-c1cccc(COc2cc(OCc3cncc(C#N)c3)c(CN3CCCC[C@H]3C(=O)O)cc2Cl)c1C]

Example 4126

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.8%; Observed Mass: 739.09; Retention Time: 1.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 89.0%; Observed Mass: 739.09; Retention Time: 1.38 min.

Preparation of Example 4127

(R)-5-((4-chloro-2-(((1,3-dihydroxypropan-2-yl)(methyl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile

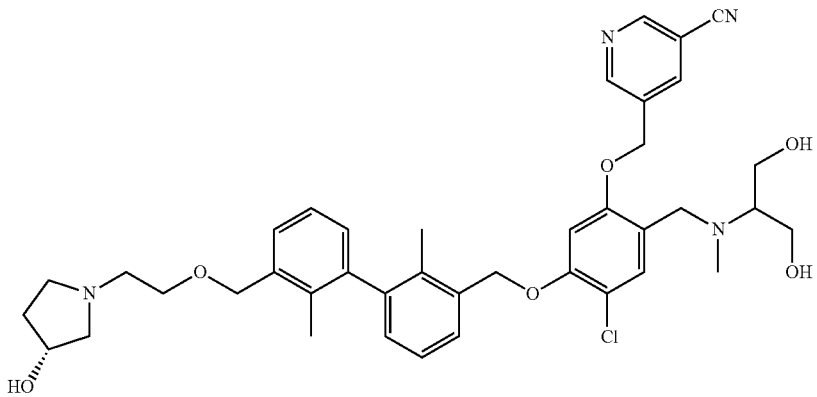 [SMILES: Cc1c(COCCN2CC[C@@H](O)C2)cccc1-c1cccc(COc2cc(OCc3cncc(C#N)c3)c(CN(C)C(CO)CO)cc2Cl)c1C]

Example 4127

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 88.5%; Observed Mass: 715.08; Retention Time: 1.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 715.14; Retention Time: 1.3 min. Injection 3 conditions: Column: Waters XBridge C18, 2.1 mm×50 mm, 1.7 μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B to 100% B over 3.5 min, then a 0.5 min hold at 100% B; Flow: 0.5 mL/min; Detection: MS and UV (220 nm). Injection 3 results: Purity: 91.7%; Observed Mass: 715.11; Retention Time: 2.98 min.

Preparation of Example 4128

(R)-5-((4-chloro-2-(((1,3-dihydroxy-2-methylpropan-2-yl)(methyl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile

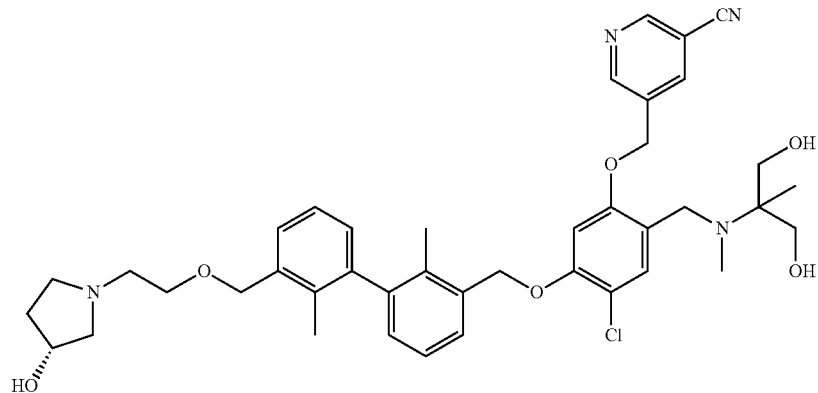 [SMILES: Cc1c(COCCN2CC[C@@H](O)C2)cccc1-c1cccc(COc2cc(OCc3cncc(C#N)c3)c(CN(C)C(C)(CO)CO)cc2Cl)c1C]

Example 4128

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 729.09, 729.09, 729.09; Retention Time: 1.34, 1.4, 1.43 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.0%; Observed Mass: 729.13; Retention Time: 1.33 min.

Preparation of Example 4129

(R)-1-((5-chloro-2-((5-cyanopyridin-3-yl)methoxy)-4-((3'-((2-(3-hydroxypyrrolidin-1-yl)ethoxy)methyl)-2,2'-dimethyl-[1,1'-biphenyl]-3-yl)methoxy)benzyl)(methyl)amino)cyclopropane-1-carboxylic Acid

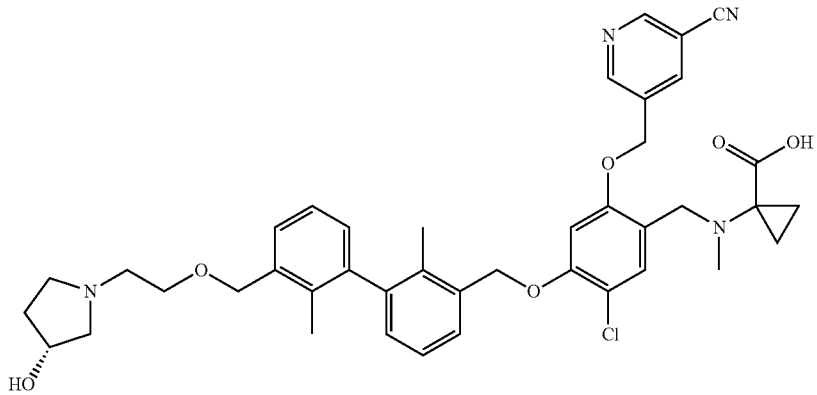 [SMILES: Cc1c(COCCN2CC[C@@H](O)C2)cccc1-c1cccc(COc2cc(OCc3cncc(C#N)c3)c(CN(C)C3(C(=O)O)CC3)cc2Cl)c1C]

Example 4129

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.4%; Observed Mass: 725.09; Retention Time: 1.54 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 90.8%; Observed Mass: 725.12; Retention Time: 1.37 min.

Preparation of Example 4130

N-(5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)-N-methyl-L-serine

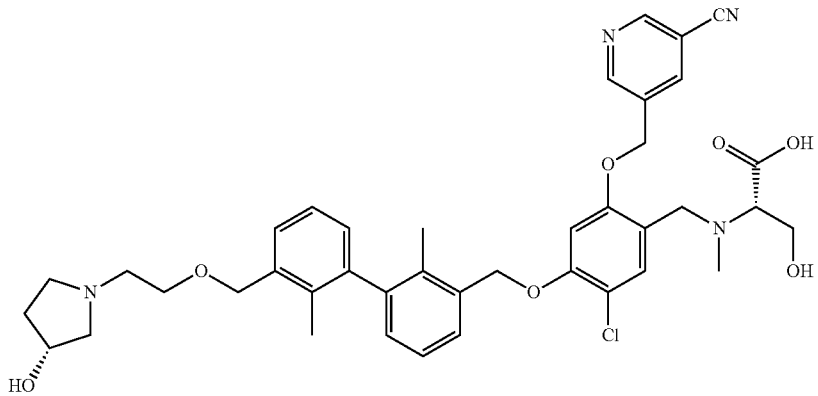 [SMILES: Cc1c(COCCN2CC[C@@H](O)C2)cccc1-c1cccc(COc2cc(OCc3cncc(C#N)c3)c(CN(C)[C@@H](CO)C(=O)O)cc2Cl)c1C]

Example 4130

Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.2%; Observed Mass: 729.08, 729.08; Retention Time: 1.36, 1.39 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 729.09; Retention Time: 1.31 min.

Preparation of Example 4131

(R)-5-((4-chloro-2-(((1,3-dihydroxy-2-methylpropan-2-yl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile

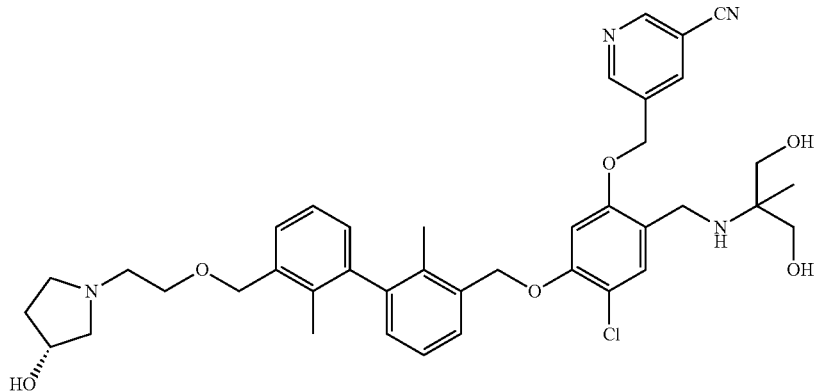

Example 4131

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Two LCMS were used to determine purity. Injection1: Column: Waters BEH C18, 2.0×50 mm, 1.7 μm; Mobile Phase A: 5:95 ACN:H2O with 10 mM NH4OAc; Mobile Phase B: 95:5 ACN:H2O with 10 mM NH4OAc; Temperature: 50° C.; Gradient: 0-100% B over 3 min, then a 0.75 min hold at 100% B; Flow: 1 mL/min. Injection2: Column: Waters BEH C18, 2.0×50 mm, 1.7-μm; Mobile Phase A: 5:95 MeOH:H2O with 10 mM NH4OAc; Mobile Phase B: 95:5 MeOH:H2O with 10 mM NH4OAc; Temperature: 50° C.; Gradient: 0-100% B over 3.5 min, then a 0.5-min hold at 100% B; Flow: 0.5 mL/min.

LCMS (Injection 1 conditions) Rt=1.46 min, ESI m/z 715.1 (M+H).

LCMS (Injection 2 conditions) Rt=1.39 min, ESI m/z 715.1 (M+H).

Preparation of Example 4132

N-(5-chloro-2-((5-cyanopyridin-3-yl)methoxy)-4-((3'-(3 ((R)-3-hydroxypyrrolidin-1-yl)propoxy)-2,2'-dimethyl-[1,1'-biphenyl]-3-yl)methoxy)benzyl)-N-methyl-L-alanine

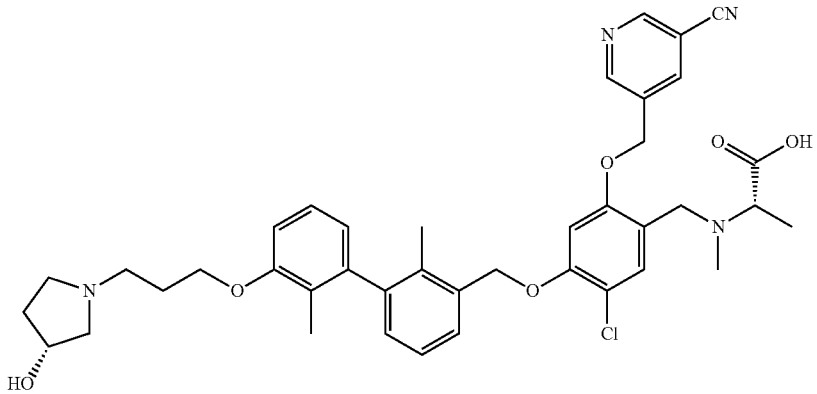 [SMILES: Cc1c(COc2cc(OCc3cncc(C#N)c3)c(CN(C)[C@@H](C)C(=O)O)cc2Cl)cccc1-c1cccc(OCCCN2CC[C@@H](O)C2)c1C]

Example 4132

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 20 minutes, then a 4-minute hold at 100% B; Flow: 20 mL/min. Fractions containing the desired product were combined and dried via centrifugal evaporation. The yield of the product was 3.5 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 713.1; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 713.07; Retention Time: 1.43 min.

Preparation of Example 4133

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(methyl)amino)butanoic Acid

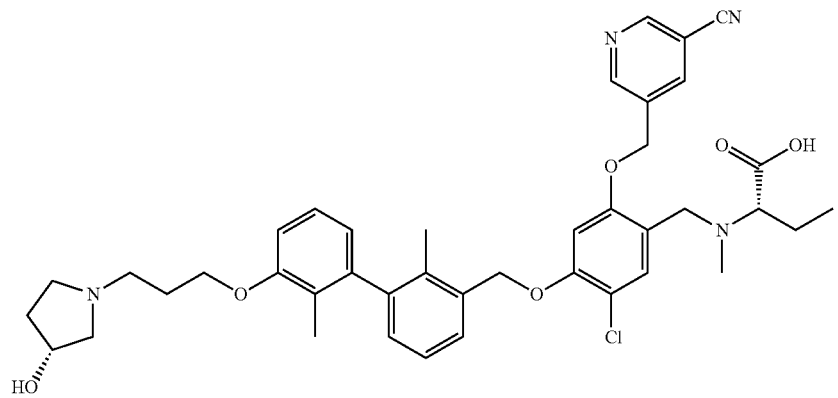 [SMILES: CC[C@@H](C(=O)O)N(C)Cc1cc(Cl)c(OCc2cccc(-c3cccc(OCCCN4CC[C@@H](O)C4)c3C)c2C)cc1OCc1cncc(C#N)c1]

Example 4133

Mobile Phase A: 5:95 acetonitrile:water with 10-mM ammonium acetate; Mobile Phase B: 95:5 acetonitrile:water with 10-mM ammonium acetate; Gradient: 10-50% B over 28 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.8%; Observed Mass: 727.1; Retention Time: 1.53 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: 727.11; Retention Time: 1.44 min.

Preparation of Example 4134

(R)-1-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)(methyl)amino)cyclopropane-1-carboxylic Acid

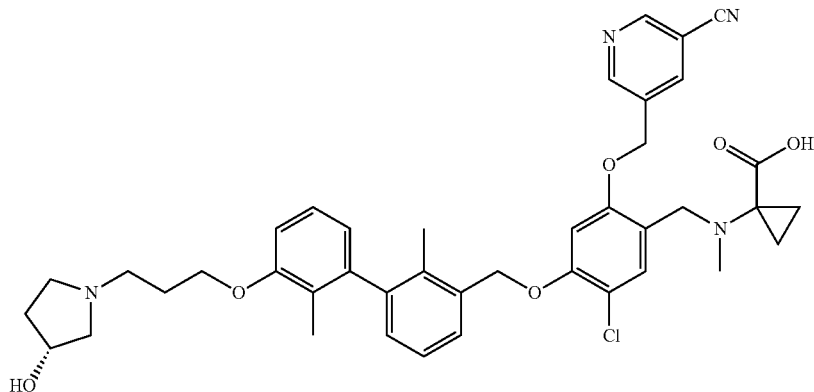

Example 4134

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-58% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.0%; Observed Mass: 725.11; Retention Time: 1.61 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 89.8%; Observed Mass: 725.08; Retention Time: 1.47 min.

Preparation of Example 4135

N-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-N-methyl-L-homoserine

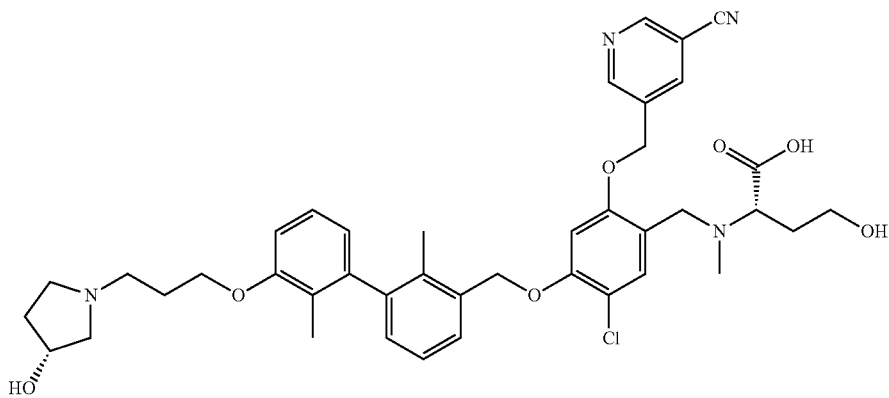 [SMILES: Cc1c(COc2cc(OCc3cncc(C#N)c3)c(CN(C)[C@@H](CCO)C(=O)O)cc2Cl)cccc1-c1cccc(OCCCN2CC[C@@H](O)C2)c1C]

Example 4135

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A:

5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.2%; Observed Mass: 743.11; Retention Time: 1.4 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 743.09; Retention Time: 1.42 min.

Preparation of Example 4136

N-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-N-methyl-L-serine at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 729.05; Retention Time: 1.44 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 729.04; Retention Time: 1.41 min.

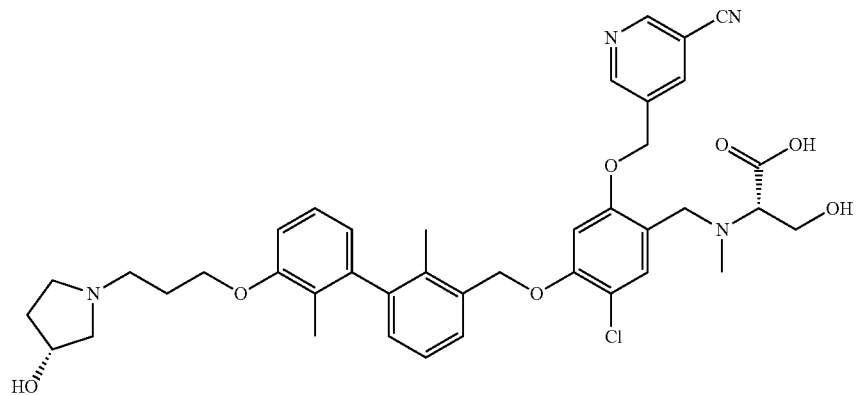 [SMILES: Cc1c(COc2cc(OCc3cncc(C#N)c3)c(CN(C)[C@@H](CO)C(=O)O)cc2Cl)cccc1-c1cccc(OCCCN2CC[C@@H](O)C2)c1C]

Example 4136

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 22 minutes, then a 4-minute hold Preparation of Example 4137

5-((4-chloro-2-(1-((1,3-dihydroxypropan-2-yl)amino)ethyl)-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile

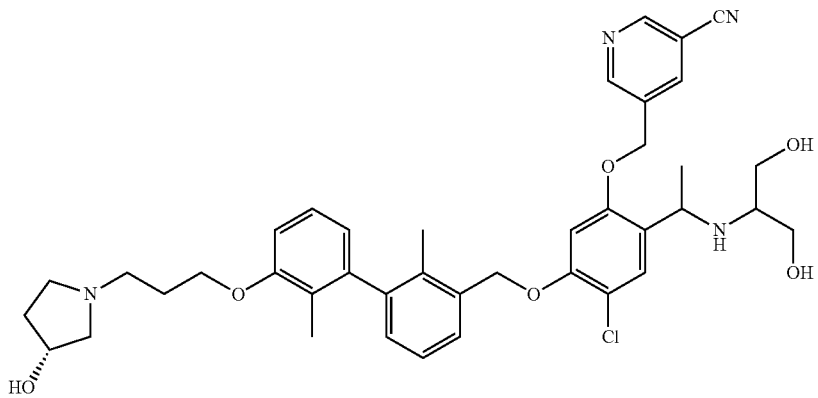 [SMILES: Cc1c(COc2cc(OCc3cncc(C#N)c3)c(C(C)NC(CO)CO)cc2Cl)cccc1-c1cccc(OCCCN2CC[C@@H](O)C2)c1C]

Example 4137

A mixture of (R)-5-((2-acetyl-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile (25.6 mg, 0.04 mmol), 2-aminopropane-1,3-diol (14.58 mg, 0.160 mmol), acetic acid (0.016 mL, 0.280 mmol) in MeOH (4 mL) and sodium cyanoborohydride (1M in THF) (0.160 mL, 0.160 mmol) was stirred for 3 days at 60° C. After the solvent were removed, the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 22 minutes, then a 5-minute hold at 100% B; Flow: 20 mL/min. Fractions containing the desired product were combined and dried via centrifugal evaporation. The yield of the product was 18.5 mg. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 715.09; Retention Time: 1.6 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 715.07; Retention Time: 1.42 min.

Preparation of Example 4138

(2S,4R)-1-(1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)phenyl)ethyl)-4-hydroxypyrrolidine-2-carboxylic Acid

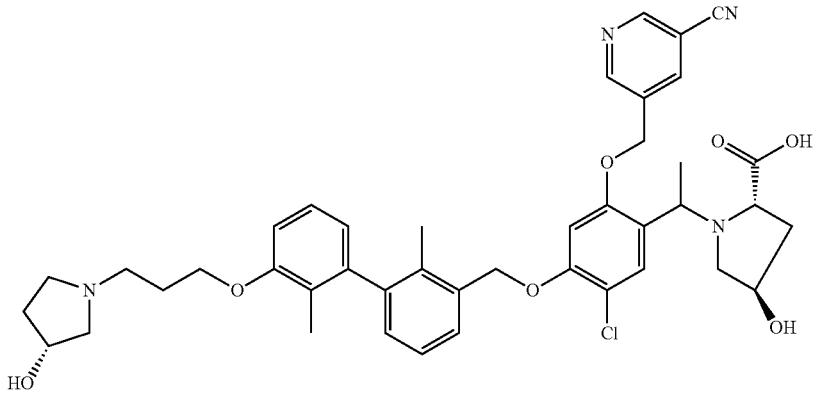 [SMILES: Cc1c(COc2cc(OCc3cncc(C#N)c3)c(C(C)N3C[C@H](O)C[C@H]3C(=O)O)cc2Cl)cccc1-c1cccc(OCCCN2CC[C@@H](O)C2)c1C]

Example 4138

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 12-52% B over 23 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 755.11; Retention Time: 1.47 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.8%; Observed Mass: 755.08; Retention Time: 1.43 min.

Preparation of Example 4139

N-(1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)phenyl)ethyl)-N-methyl-L-serine

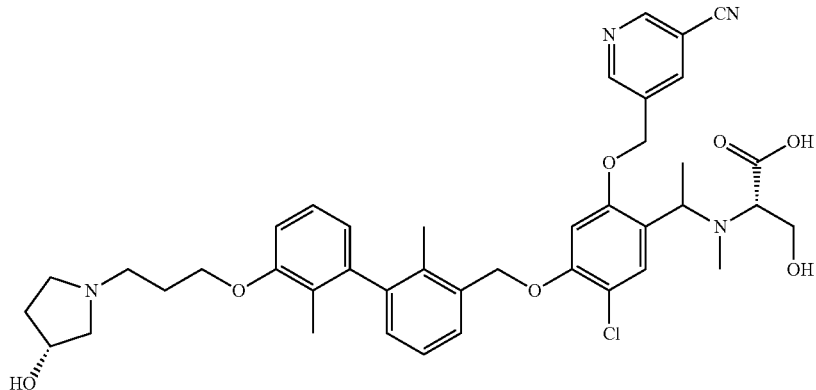 [SMILES: Cc1c(COc2cc(OCc3cncc(C#N)c3)c(C(C)N(C)[C@@H](CO)C(=O)O)cc2Cl)cccc1-c1cccc(OCCCN2CC[C@@H](O)C2)c1C]

Example 4139

A mixture of (R)-5-((2-acetyl-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile (25.6 mg, 0.04 mmol), (S)-2-amino-3-hydroxypropanoic acid (16.81 mg, 0.160 mmol), acetic acid (0.016 mL, 0.280 mmol) and sodium cyanoborohydride (1M in THF) (0.160 mL, 0.160 mmol) in MeOH (4 mL) was stirred for 3 days at 60° C. After cooling to rt, to the reaction mixture was added 0.02 mL of formaldehyde solution in water, then stirred for 16 h. After concentration, the crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 743.09; Retention Time: 1.51 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 743.09; Retention Time: 1.46 min.

Preparation of Example 4140

5-((4-chloro-2-(1-(((1,3-dihydroxypropan-2-yl)(methyl)amino)ethyl)-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile

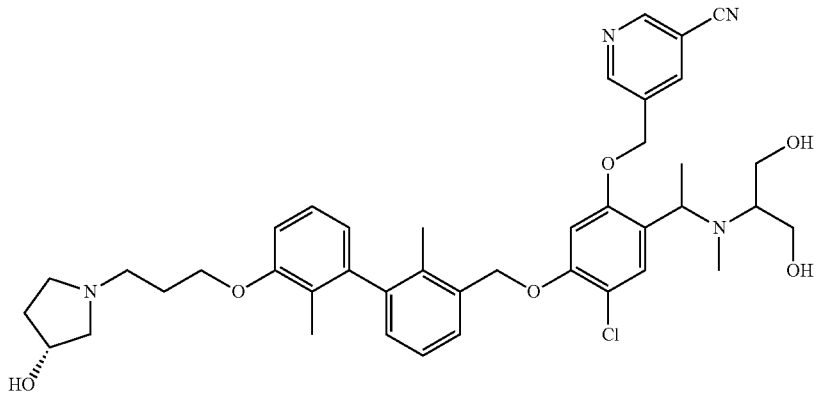 [SMILES: Cc1c(COc2cc(OCc3cncc(C#N)c3)c(C(C)N(C)C(CO)CO)cc2Cl)cccc1-c1cccc(OCCCN2CC[C@@H](O)C2)c1C]

Example 4140

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 23 minutes, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 14-54% B over 20 minutes, then a 3-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 729.13; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 729.13; Retention Time: 1.66 min.

Preparation of Example 4141

(1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)phenyl)ethyl)-L-serine

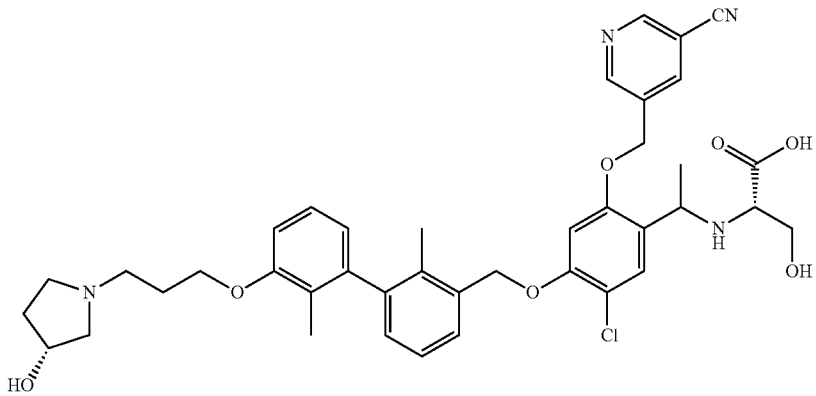 [SMILES: Cc1c(COc2cc(OCc3cncc(C#N)c3)c(C(C)N[C@@H](CO)C(=O)O)cc2Cl)cccc1-c1cccc(OCCCN2CC[C@@H](O)C2)c1C]

Example 4141

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 12-52% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.5%; Observed Mass: 729.08; Retention Time: 1.45 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.0%; Observed Mass: 729.08, 729.08; Retention Time: 1.42 min.

Preparation of Example 4147

(R)-(5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)glycine

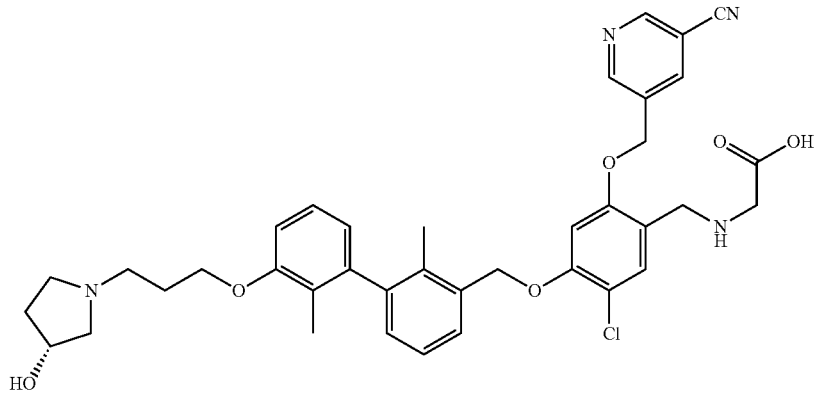 [SMILES: Cc1c(COc2cc(OCc3cncc(C#N)c3)c(CNCC(=O)O)cc2Cl)cccc1-c1cccc(OCCCN2CC[C@@H](O)C2)c1C]

Example 4147

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 13-53% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.3%; Observed Mass: 685.07; Retention Time: 1.45 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.1%; Observed Mass: 685.08; Retention Time: 1.43 min.

Preparation of Example 4148

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-threonine

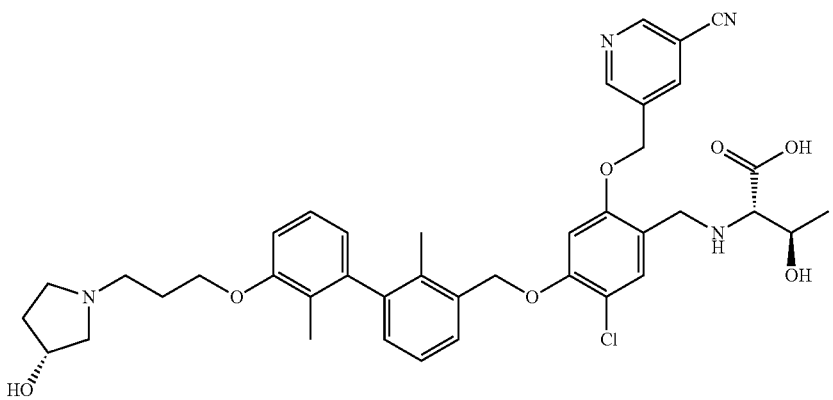 [SMILES: Cc1c(COc2cc(OCc3cncc(C#N)c3)c(CN[C@H](C(=O)O)[C@@H](C)O)cc2Cl)cccc1-c1cccc(OCCCN2CC[C@@H](O)C2)c1C]

Example 4148

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 13-53% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A:

5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.0%; Observed Mass: 729.06; Retention Time: 1.45 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.7%; Observed Mass: 729.08; Retention Time: 1.43 min.

Preparation of Example 4149

(R)-3-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)propanoic Acid The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 14-54% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 699.07; Retention Time: 1.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 699.08; Retention Time: 1.44 min.

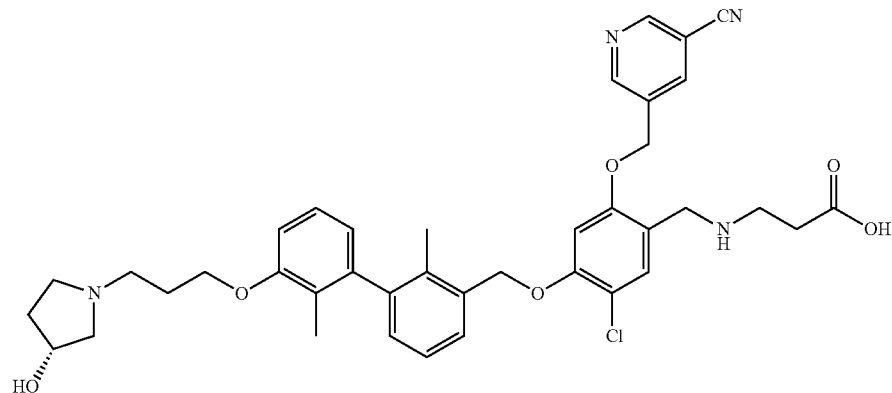 [SMILES: Cc1c(COc2cc(OCc3cncc(C#N)c3)c(CNCCC(=O)O)cc2Cl)cccc1-c1cccc(OCCCN2CC[C@@H](O)C2)c1C]

Example 4149

Preparation of Example 4150

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-valine

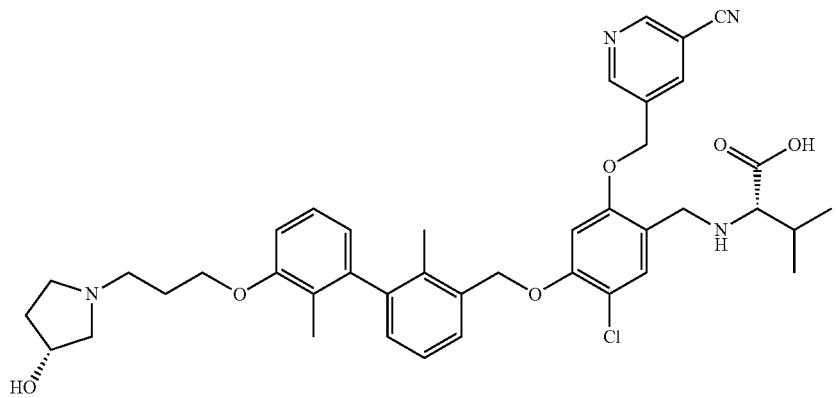 [SMILES: Cc1c(COc2cc(OCc3cncc(C#N)c3)c(CN[C@H](C(=O)O)C(C)C)cc2Cl)cccc1-c1cccc(OCCCN2CC[C@@H](O)C2)c1C]

Example 4150

Mobile Phase A: 5:95 acetonitrile:water with 10-mM ammonium acetate; Mobile Phase B: 95:5 acetonitrile:water with 10-mM ammonium acetate; Gradient: 14-54% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.6%; Observed Mass: 727.11; Retention Time: 1.49 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.0%; Observed Mass: 727.1; Retention Time: 1.5 min.

Preparation of Example 4151

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)hexanoic Acid

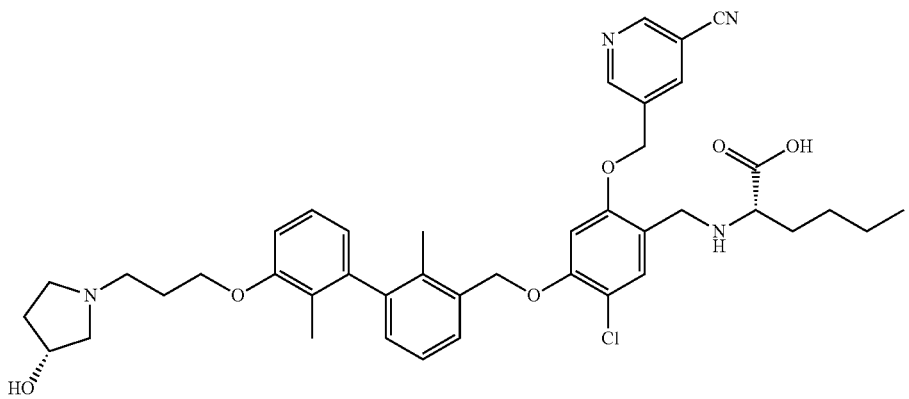 [SMILES: CCCC[C@H](NCc1cc(Cl)c(OCc2cccc(-c3cccc(OCCCN4CC[C@@H](O)C4)c3C)c2C)cc1OCc1cncc(C#N)c1)C(=O)O]

Example 4151

Mobile Phase A: 5:95 acetonitrile:water with 10-mM ammonium acetate; Mobile Phase B: 95:5 acetonitrile:water with 10-mM ammonium acetate; Gradient: 14-54% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 741.15; Retention Time: 1.56 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 741.12; Retention Time: 1.58 min.

Preparation of Example 4152

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-phenylalanin

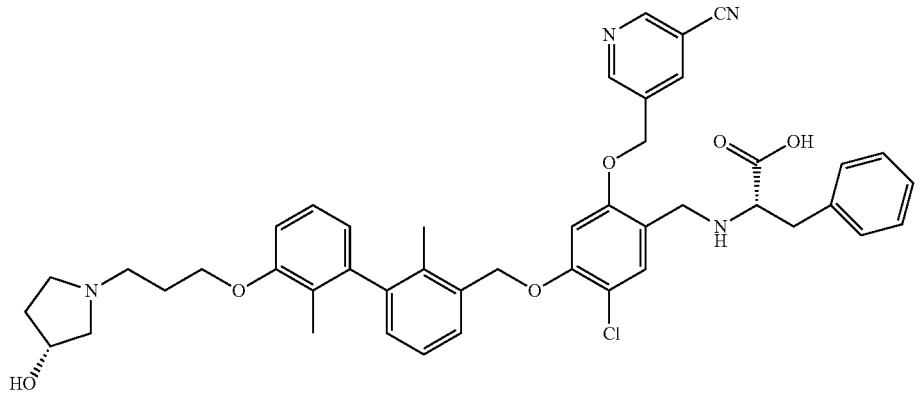 [SMILES: Cc1c(COc2cc(OCc3cncc(C#N)c3)c(CN[C@@H](Cc3ccccc3)C(=O)O)cc2Cl)cccc1-c1cccc(OCCCN2CC[C@@H](O)C2)c1C]

Example 4152

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.1%; Observed Mass: 775.06; Retention Time: 1.58 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 775.06; Retention Time: 1.6 min.

Preparation of Example 4153

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-leucine

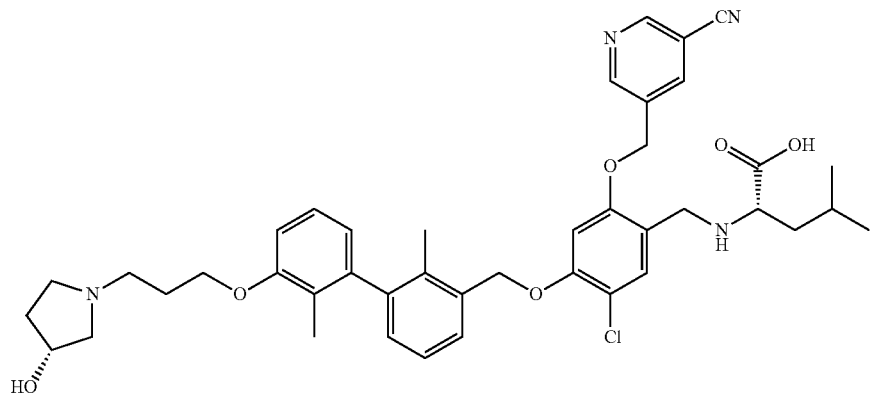 [SMILES: Cc1c(COc2cc(OCc3cncc(C#N)c3)c(CN[C@@H](CC(C)C)C(=O)O)cc2Cl)cccc1-c1cccc(OCCCN2CC[C@@H](O)C2)c1C]

Example 4153

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid;

Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.0%; Observed Mass: 741.11; Retention Time: 1.55 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.7%; Observed Mass: 741.12; Retention Time: 1.56 min.

Preparation of Example 4154

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)pentanoic Acid

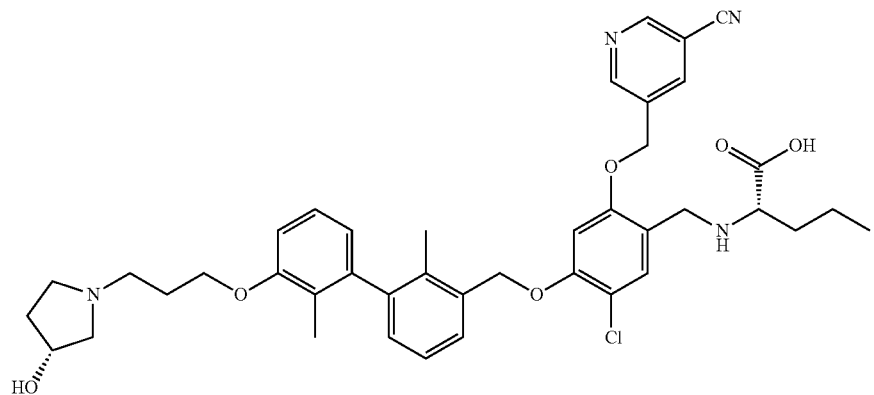 [SMILES: CCC[C@H](NCc1cc(Cl)c(OCc2cccc(-c3cccc(OCCCN4CC[C@@H](O)C4)c3C)c2C)cc1OCc1cncc(C#N)c1)C(=O)O]

Example 4154

Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 727.16; Retention Time: 1.52 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 727.11; Retention Time: 1.52 min.

Preparation of Example 4155

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)pent-4-enoic Acid

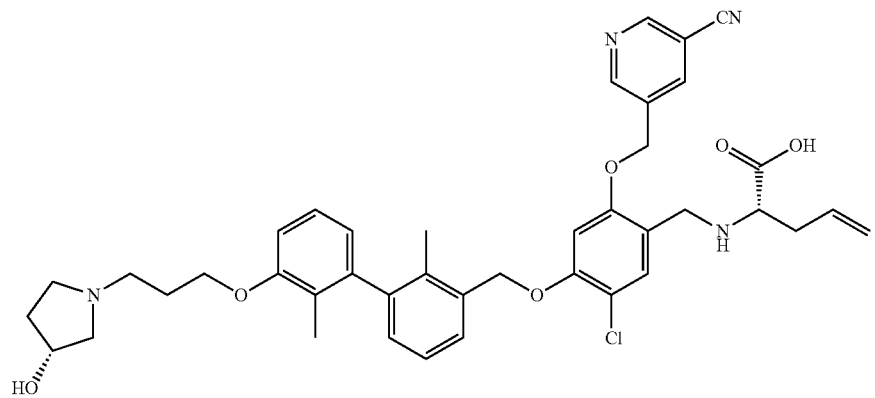 [SMILES: C=CC[C@H](NCc1cc(Cl)c(OCc2cccc(-c3cccc(OCCCN4CC[C@@H](O)C4)c3C)c2C)cc1OCc1cncc(C#N)c1)C(=O)O]

Example 4155

Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 725.09, 725.09; Retention Time: 1.45, 1.49 min. Injection 2 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 725.12; Retention Time: 1.47 min.

Preparation of Example 4156

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-2-phenylacetic Acid

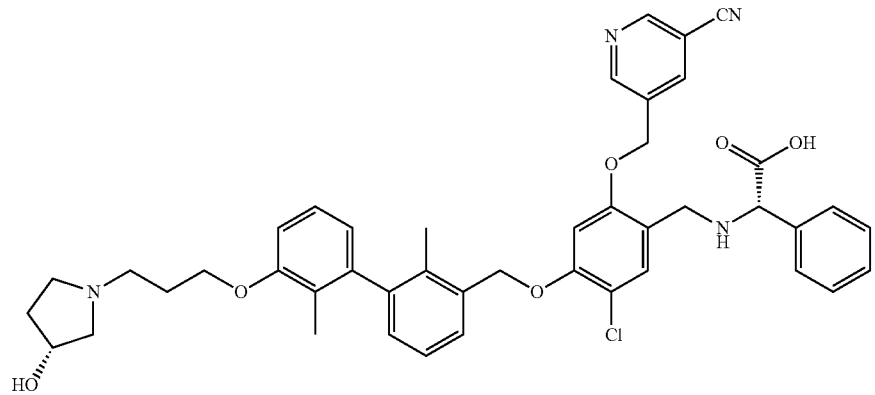 [SMILES: Cc1c(COc2cc(OCc3cncc(C#N)c3)c(CN[C@H](C(=O)O)c3ccccc3)cc2Cl)cccc1-c1cccc(OCCCN2CC[C@@H](O)C2)c1C]

Example 4156

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 761.12; Retention Time: 1.56 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 761.11; Retention Time: 1.59 min.

Preparation of Example 4157

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-tyrosine

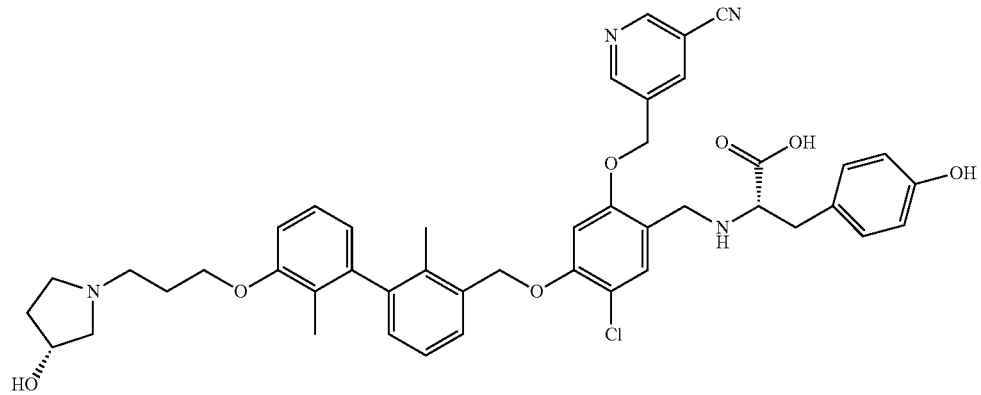 [SMILES: Cc1c(COc2cc(OCc3cncc(C#N)c3)c(CN[C@@H](Cc3ccc(O)cc3)C(=O)O)cc2Cl)cccc1-c1cccc(OCCCN2CC[C@@H](O)C2)c1C]

Example 4157

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 12-52% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 92.3%; Observed Mass: 791.25; Retention Time: 1.49 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.2%; Observed Mass: 791.14; Retention Time: 1.48 min.

Example 4501: (R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol

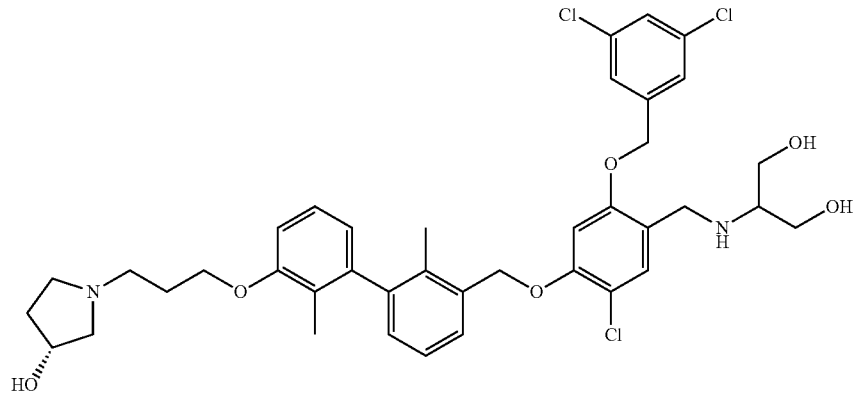 [SMILES: Cc1c(COc2cc(OCc3cc(Cl)cc(Cl)c3)c(CNC(CO)CO)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 14.2 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 742.99; Retention Time: 1.79 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 742.99; Retention Time: 1.94 min.

Example 4502: (R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol

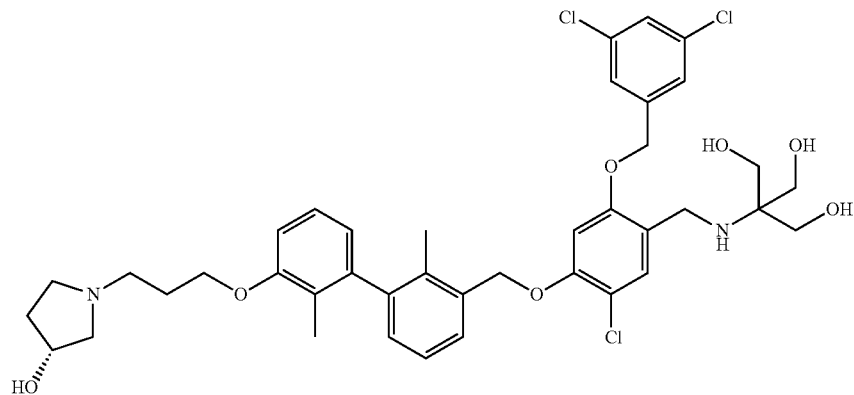 [SMILES: Cc1c(COc2cc(OCc3cc(Cl)cc(Cl)c3)c(CNC(CO)(CO)CO)cc2Cl)cccc1-c1cccc(OCCCN2CC[C@@H](O)C2)c1C]

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 99%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 773; Retention Time: 1.93 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 772.98; Retention Time: 1.75 min.

Example 4503: (S)-1-(5-chloro-2-((3,5-dichlorobenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

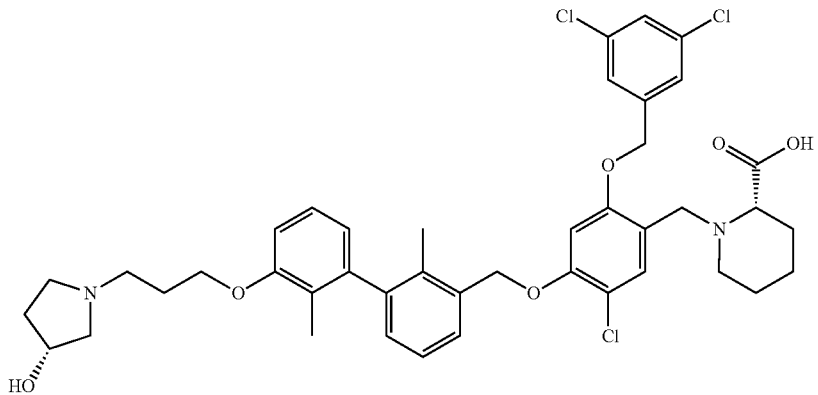 [SMILES: Cc1c(COc2cc(OCc3cc(Cl)cc(Cl)c3)c(CN3CCCC[C@H]3C(=O)O)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 780.98; Retention Time: 1.87 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 780.95; Retention Time: 1.87 min.

Example 4504: (R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol

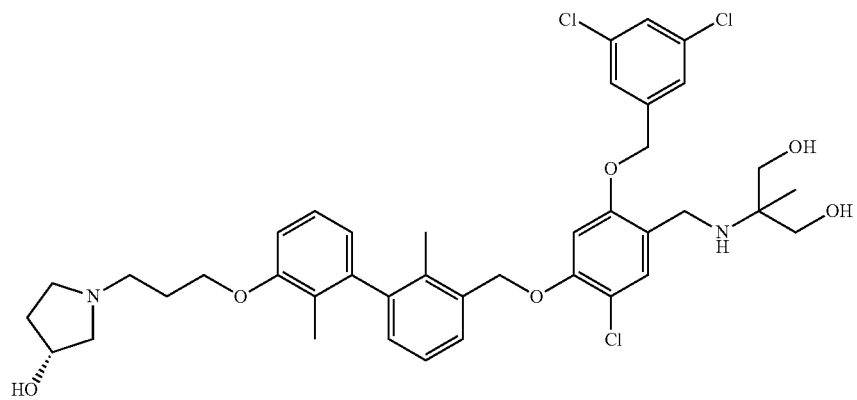 [SMILES: Cc1c(COc2cc(OCc3cc(Cl)cc(Cl)c3)c(CNC(C)(CO)CO)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 12.5 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 756.99; Retention Time: 1.8 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.0%; Observed Mass: 756.99; Retention Time: 1.96 min.

Example 4505: (R)-2-((5-chloro-2-((3,4-dimethyl-benzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol

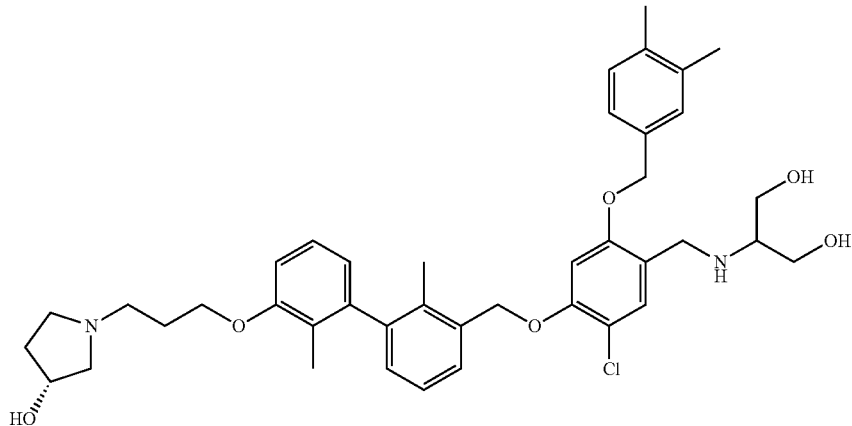 [SMILES: Cc1ccc(COc2cc(OCc3cccc(-c4cccc(OCCCN5CC[C@@H](O)C5)c4C)c3C)c(Cl)cc2CNC(CO)CO)cc1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 18 minutes, then a 3-minute hold at 100% B; Flow: 20 mL/min. Fractions containing the desired product were combined and dried via centrifugal evaporation. The yield of the product was 16.7 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 703.12; Retention Time: 1.88 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: 703.13; Retention Time: 1.73 min.

Example 4506: (R)-2-((5-chloro-2-((3,4-dimethyl-benzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol

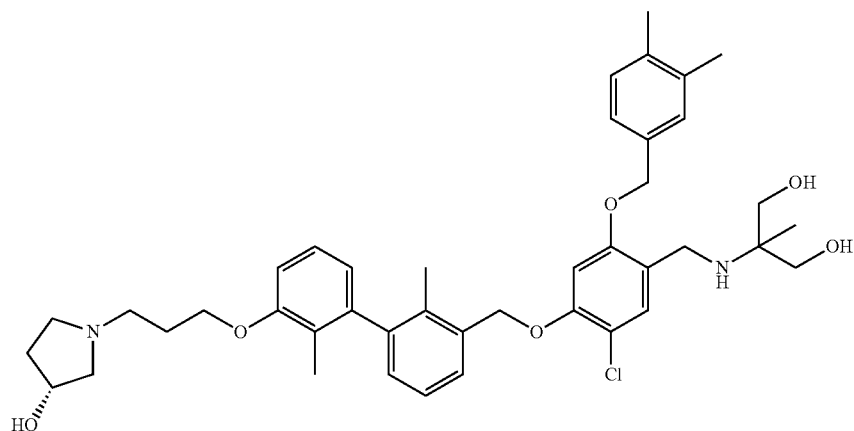 [SMILES: Cc1ccc(COc2cc(OCc3cccc(-c4cccc(OCCCN5CC[C@@H](O)C5)c4C)c3C)c(Cl)cc2CNC(C)(CO)CO)cc1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 20 minutes, then a 3-minute hold at 100% B; Flow: 20 mL/min. Fractions containing the desired product were combined and dried via centrifugal evaporation. The yield of the product was 17.3 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 717.16; Retention Time: 1.72 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 717.24; Retention Time: 1.62 min.

Example 4507: (R)-2-((5-chloro-2-((3,4-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol

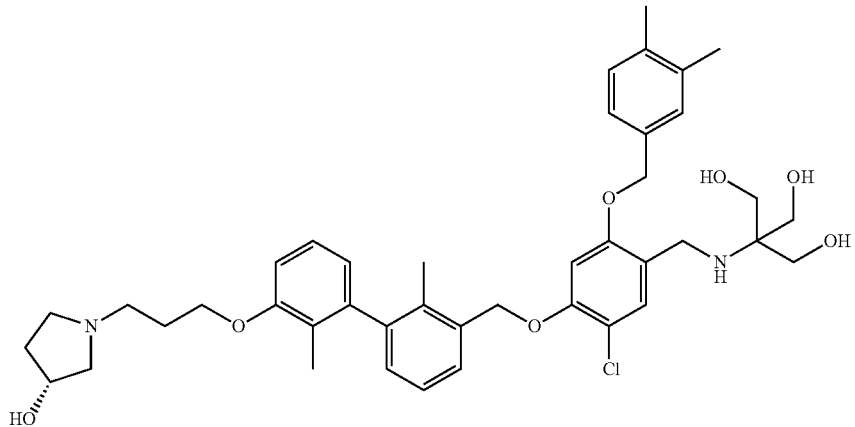 [SMILES: Cc1ccc(COc2cc(OCc3cccc(-c4cccc(OCCCN5CC[C@@H](O)C5)c4C)c3C)c(Cl)cc2CNC(CO)(CO)CO)cc1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 19 minutes, then a 3-minute hold at 100% B; Flow: 20 mL/min. Fractions containing the desired product were combined and dried via centrifugal evaporation. The yield of the product was 16.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 733.1; Retention Time: 1.72 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 733.12; Retention Time: 1.85 min.

Example 4508: (S)-1-(5-chloro-2-((3,4-dimethyl-benzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

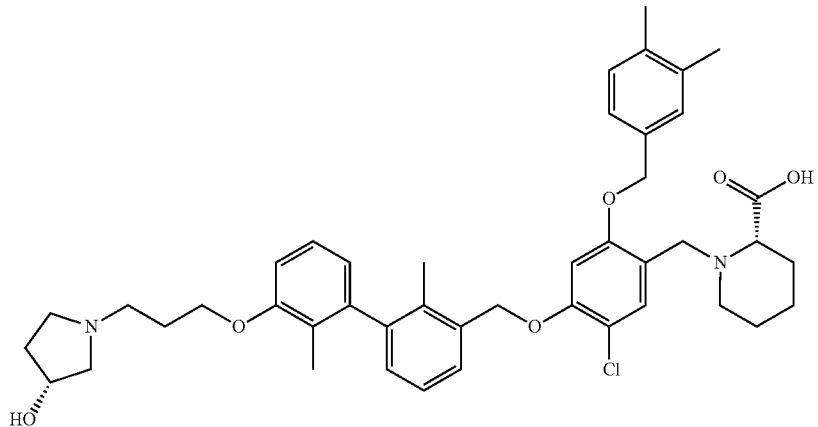 [SMILES: Cc1ccc(COc2cc(OCc3cccc(-c4cccc(OCCCN5CC[C@@H](O)C5)c4C)c3C)c(Cl)cc2CN2CCCC[C@H]2C(=O)O)cc1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 19 minutes, then a 3-minute hold at 100% B; Flow: 20 mL/min. Fractions containing the desired product were combined and dried via centrifugal evaporation. The yield of the product was 15.9 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 741.12; Retention Time: 1.68 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.5%; Observed Mass: 741.16; Retention Time: 1.74 min.

Example 4509: (R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol

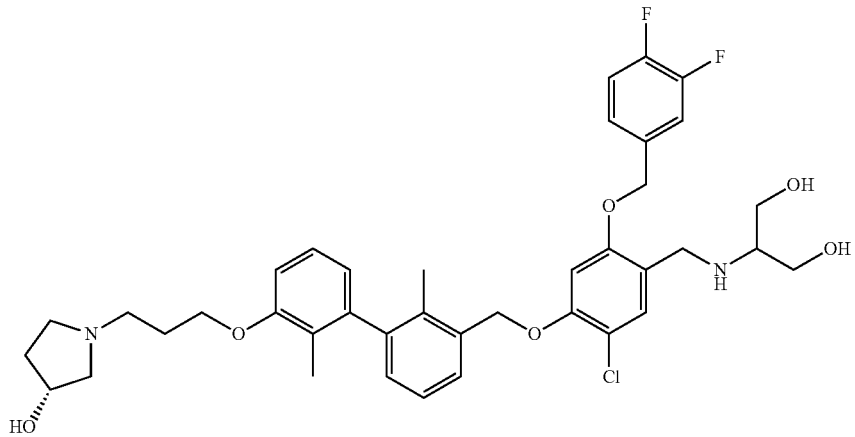 [SMILES: Cc1c(COc2cc(OCc3ccc(F)c(F)c3)c(CNC(CO)CO)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 18 minutes, then a 4-minute hold at 100% B; Flow: 20 mL/min. Fractions containing the desired product were combined and dried via centrifugal evaporation. The yield of the product was 12.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 711.12; Retention Time: 1.53 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 711.08; Retention Time: 1.62 min.

Example 4510: (R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol

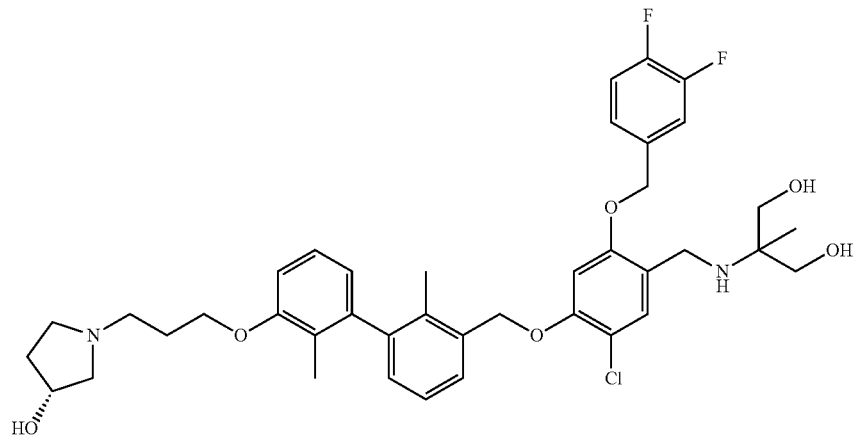 [SMILES: Cc1c(COc2cc(OCc3ccc(F)c(F)c3)c(CNC(C)(CO)CO)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 18 minutes, then a 4-minute hold at 100% B; Flow: 20 mL/min. Fractions containing the desired product were combined and dried via centrifugal evaporation. The yield of the product was 20.8 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 725.11; Retention Time: 1.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 725.3; Retention Time: 1.56 min.

Example 4511: (R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol

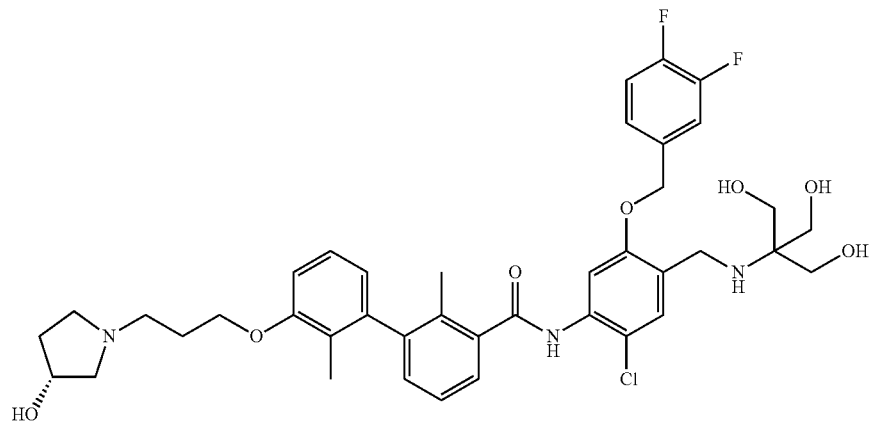 [SMILES: Cc1c(OCCCN2CC[C@@H](O)C2)cccc1-c1cccc(C(=O)Nc2cc(OCc3ccc(F)c(F)c3)c(CNC(CO)(CO)CO)cc2Cl)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 18 minutes, then a 4-minute hold at 100% B; Flow: 20 mL/min. Fractions containing the desired product were combined and dried via centrifugal evaporation. The yield of the product was 10.8 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 741.07; Retention Time: 1.76 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.7%; Observed Mass: 741.09; Retention Time: 1.64 min.

Example 4512: (S)-1-(5-chloro-2-((3,4-difluorobenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

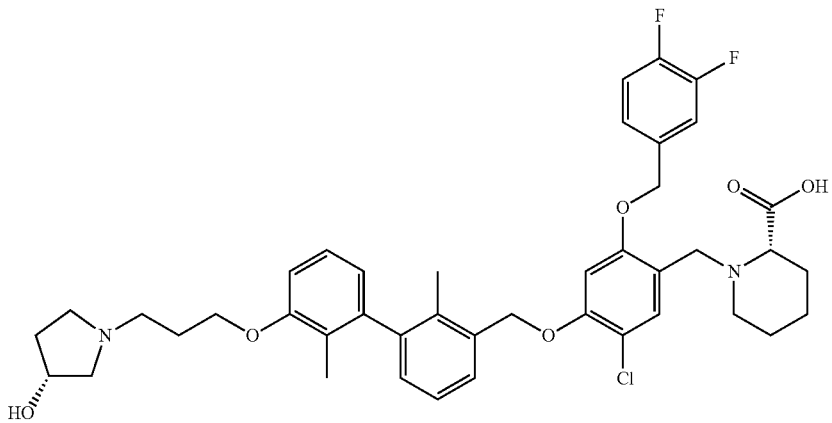 [SMILES: Cc1c(COc2cc(OCc3ccc(F)c(F)c3)c(CN3CCCC[C@H]3C(=O)O)cc2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 19 minutes, then a 4-minute hold at 100% B; Flow: 20 mL/min. Fractions containing the desired product were combined and dried via centrifugal evaporation. The yield of the product was 13.2 mg, and its estimated purity by LCMS analysis was 92%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.0%; Observed Mass: 749.1; Retention Time: 1.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.5%; Observed Mass: 749.34; Retention Time: 1.62 min.

Example 4513: (R)-2-((5-chloro-2-((2,6-dimethyl-benzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol

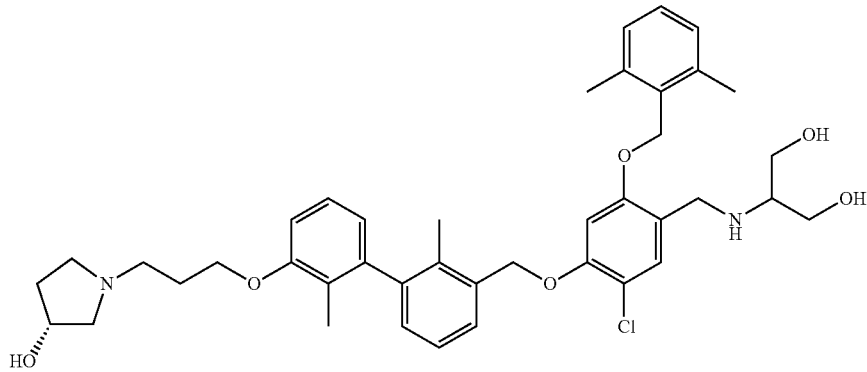 [SMILES: Cc1cccc(C)c1COc1cc(OCc2cccc(-c3cccc(OCCCN4CC[C@@H](O)C4)c3C)c2C)c(Cl)cc1CNC(CO)CO]

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 703.14; Retention Time: 1.86 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 703.1; Retention Time: 1.73 min.

Example 4514: (R)-2-((5-chloro-2-((2,6-dimethyl-benzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol

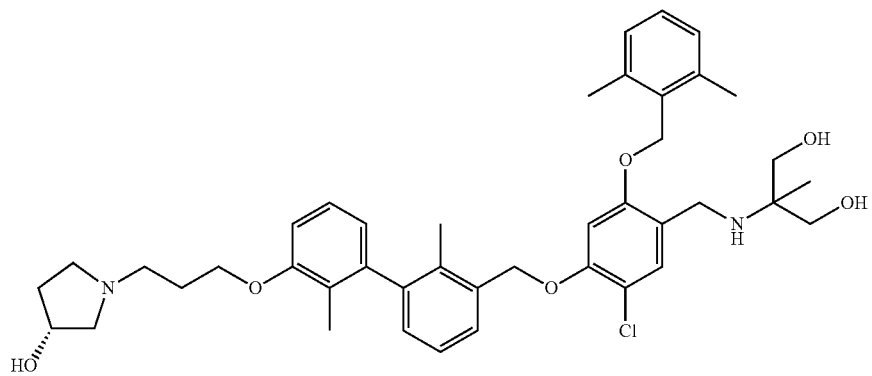 [SMILES: Cc1cccc(C)c1COc1cc(OCc2cccc(-c3cccc(OCCCN4CC[C@@H](O)C4)c3C)c2C)c(Cl)cc1CNC(C)(CO)CO]

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 15 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 717.13; Retention Time: 1.87 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 717.13; Retention Time: 1.77 min.

Example 4515: (R)-2-((5-chloro-2-((2,6-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol tion. The yield of the product was 19.1 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.3%; Observed Mass: 733.11; Retention Time: 1.83 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

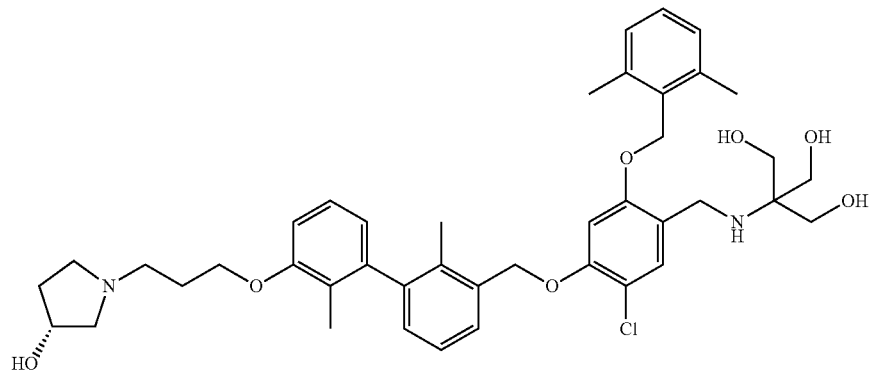 [SMILES: Cc1cccc(C)c1COc1cc(OCc2cccc(-c3cccc(OCCCN4CC[C@@H](O)C4)c3C)c2C)c(Cl)cc1CNC(CO)(CO)CO]

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min. Fractions containing the desired product were combined and dried via centrifugal evapora- Injection 2 results: Purity: 100.0%; Observed Mass: 733.1; Retention Time: 1.71 min.

Example 4516: (S)-1-(5-chloro-2-((2,6-dimethylbenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

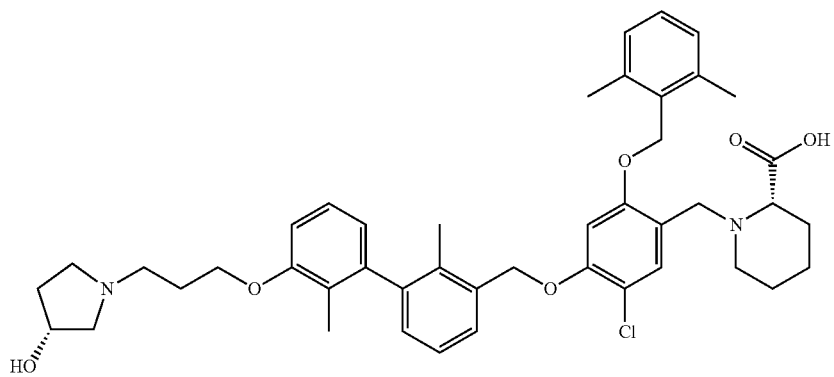 [SMILES: Cc1cccc(C)c1COc1cc(OCc2cccc(-c3cccc(OCCCN4CC[C@@H](O)C4)c3C)c2C)c(Cl)cc1CN1CCCC[C@H]1C(=O)O]

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 15 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 741.12; Retention Time: 1.82 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 741.09; Retention Time: 1.85 min.

Example 4517: (S)-1-(5-chloro-4-((E)-2-(3'-(3-((R)-3-hydroxypyrrolidin-1-yl)propoxy)-2,2'-dimethyl-[1,1'-biphenyl]-3-yl)vinyl)-2-methoxybenzyl)piperidine-2-carboxylic Acid

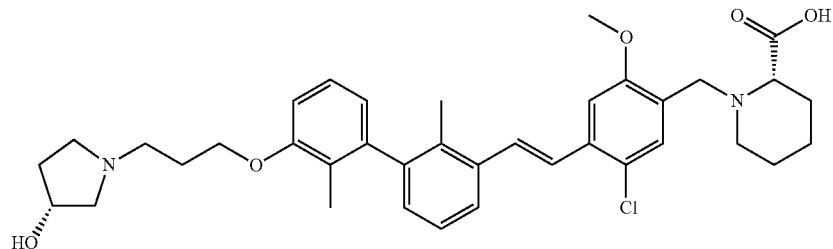 [SMILES: COc1cc(/C=C/c2cccc(-c3cccc(OCCCN4CC[C@@H](O)C4)c3C)c2C)c(Cl)cc1CN1CCCC[C@H]1C(=O)O]

For the following intermediates prepared in step 1 to step 6, LC data was recorded on a Nexera X2 LC-30AD liquid chromatograph equipped with a Waters Aquity BEH C18 2.1×50 mm 1.7 um column using a SPD-20AV prominence UV-Vis detector at a detector wave length of 220 nm. The elution conditions employed a flow rate of 0.8 mL/min, a gradient of 100% solvent A/0% solvent B to 0% solvent A/100% solvent B, a gradient time of 1.5 min, a hold time of 0.5 min, and an analysis time of 2 min where solvent A was $H_2O$/0.05% trifluoroacetic acid and solvent B was acetonitrile/0.05% trifluoroacetic acid. MS data was determined using a Shimadzu LCMS 2020 ESI ionization method.

Step 1: Preparation of Methyl 4-bromo-5-chloro-2-methoxybenzoate

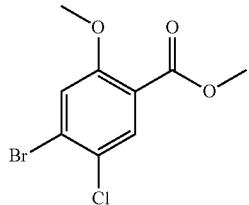

To a mixture of tert-Butyl nitrite (555 μl, 4.20 mmol) and cupric bromide (1.12 g, 5.04 mmol) in acetonitrile (28 ml) at rt was added a solution of methyl 4-amino-5-chloro-2-methoxybenzoate (923 mg, 4.28 mmol) in acetonitrile (28 mL) dropwise. The reaction was then stirred at 65° C. for 1 hr. The reaction was then concentrated, adsorbed onto diatomaceous earth (Celite®) and was purified on silica gel (Biotage, EtOAc/hexanes gradient) to give isolated methyl 4-bromo-5-chloro-2-methoxybenzoate (1.00 g, 3.58 mmol, 85% yield) consistent by LCMS (M+H)=278.80, 280.80, Retention time=1.229 min, and NMR: $^1$H NMR (400 MHz, CHLOROFORM-d) δ 7.90 (s, 1H), 7.24 (s, 1H), 3.91 (s, 3H), 3.90 (s, 3H).

Step 2: Preparation of Methyl 5-chloro-2-methoxy-4-vinylbenzoate

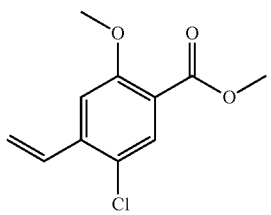

Methyl 4-bromo-5-chloro-2-methoxybenzoate (950 mg, 3.40 mmol), potassium trifluoro(vinyl)borate (683 mg, 5.10 mmol), $PdCl_2$(dppf) (124 mg, 0.170 mmol), and Hunig's Base (594 µl, 3.40 mmol) were combined in dioxane (34 ml) under N₂ and stirred at 90° C. overnight. The reaction was concentrated, adsorbed onto diatomaceous earth (Celite®) and was purified on silica gel (Biotage, 0-30% EtOAc/hexanes gradient over 10 CVs) to give methyl 5-chloro-2-methoxy-4-vinylbenzoate (480 mg, 2.118 mmol, 62.3% yield) as an of white solid consistent by LCMS: M+H=226.95, Retention time=1.225 min, and NMR: $^1$H NMR (500 MHz, CHLOROFORM-d) δ 7.83 (s, 1H), 7.13 (s, 1H), 5.83 (dd, J=17.5, 0.8 Hz, 1H), 5.51 (dd, J=11.0, 0.8 Hz, 1H), 3.94 (s, 3H), 3.90 (s, 3H).

Step 3: Preparation of (E)-methyl 4-(3-bromo-2-methylstyryl)-5-chloro-2-methoxybenzoate

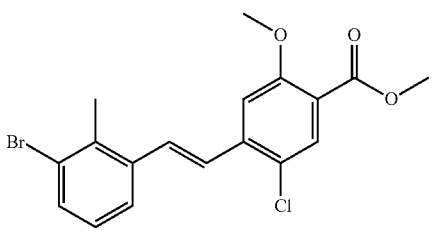 [SMILES: COC(=O)c1cc(Cl)c(/C=C/c2cccc(Br)c2C)cc1OC]

1-Bromo-3-iodo-2-methylbenzene (616 mg, 2.07 mmol), methyl 5-chloro-2-methoxy-4-vinylbenzoate (470 mg, 2.07 mmol), Pd(Oac)₂ (47 mg, 0.21 mmol), tri-o-tolylphosphine (126 mg, 0.415 mmol), Hunig's Base (724 µl, 4.15 mmol), tetrabutylammonium chloride (576 mg, 2.07 mmol) were combined under N₂ in acetonitrile (21 ml) at rt and warmed to 70° C. The reaction was stirred for 6 hr and then was concentrated, adsorbed onto diatomaceous earth (Celite®) and was purified on silica gel (Biotage, 0-50% EtOAc/hexanes gradient over 10 CVs) to afford (E)-methyl 4-(3-bromo-2-methylstyryl)-5-chloro-2-methoxybenzoate (550 mg, 67% yield) as a yellow solid consistent by LCMS: M+H=396.80, Retention time=1.625 min, and NMR: $^1$H NMR (500 MHz, CHLOROFORM-d) δ 7.88 (s, 1H), 7.55 (t, J=8.1 Hz, 2H), 7.37-7.35 (m, 1H), 7.29 (s, 1H), 7.21 (s, 1H), 7.11 (t, J=7.9 Hz, 1H), 3.99 (s, 3H), 3.91 (s, 3H), 2.54 (s, 3H).

Step 4: Preparation of (E)-(4-(3-bromo-2-methylstyryl)-5-chloro-2-methoxyphenyl)methanol

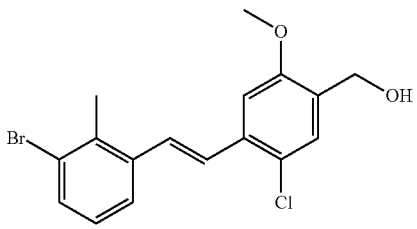 [SMILES: COc1cc(/C=C/c2cccc(Br)c2C)c(Cl)cc1CO]

LAH, 1M in THF (1.26 ml, 1.26 mmol) was added to a stirring solution of (E)-methyl 4-(3-bromo-2-methylstyryl)-5-chloro-2-methoxybenzoate (500 mg, 1.26 mmol) in THF (12 mL) at −78° C. The reaction was warmed to rt and stir for 30 min. The mixture was then diluted with EtOAc and washed with a saturated solution of Rochelle's salt. The organic phase was concentrated, adsorbed onto diatomaceous earth (Celite®) and was purified on silica gel (Biotage, EtOAc/hexanes gradient) to give (E)-(4-(3-bromo-2-methylstyryl)-5-chloro-2-methoxyphenyl)methanol (398 mg, 1.083 mmol, 86% yield) consistent by NMR: $^1$H NMR (500 MHz, CHLOROFORM-d) δ 7.53 (d, J=8.0 Hz, 1H), 7.35 (d, J=5.0 Hz, 1H), 7.30-7.28 (m, 2H), 7.25-7.20 (m, 1H), 7.16-7.06 (m, 2H), 4.71-4.65 (m, 2H), 3.95 (s, 3H), 2.53 (s, 2H), 2.46 (s, 1H). LCMS Retention time=1.489 min.

Step 5: Preparation of (E)-4-(3-bromo-2-methylstyryl)-5-chloro-2-methoxybenzaldehyde

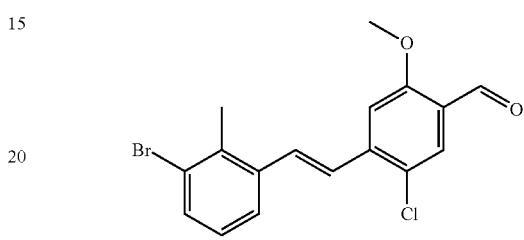

Dess-Martin periodinane (505 mg, 1.19 mmol) was added to a stirring solution of (E)-(4-(3-bromo-2-methylstyryl)-5-chloro-2-methoxyphenyl)methanol (398 mg, 1.08 mmol) in DCM (11 mL) at rt. The reaction was stirred for 1 hr. The reaction was then concentrated, adsorbed onto diatomaceous earth (Celite®) and was purified on silica gel (Biotage, EtOAc/hexanes gradient) to give (E)-4-(3-bromo-2-methylstyryl)-5-chloro-2-methoxybenzaldehyde (298 mg, 0.815 mmol, 75% yield) consistent by LCMS: M+H=364.85, 366.80, Retention time=1.145 min, and NMR: $^1$H NMR (500 MHz, CHLOROFORM-d) δ 10.40 (d, J=3.0 Hz, 1H), 7.86 (d, J=2.0 Hz, 1H), 7.67-7.63 (m, 0.5H), 7.56 (dd, J=10.3, 7.8 Hz, 1.5H), 7.44-7.38 (m, 1H), 7.26-7.22 (m, 2H), 7.12 (t, J=7.8 Hz, 1H), 4.02 (d, J=1.6 Hz, 3H), 2.55 (s, 2H), 2.48 (s, 1H).

Step 6: Preparation of (S,E)-methyl 1-(4-(3-bromo-2-methylstyryl)-5-chloro-2-methoxybenzyl)piperidine-2-carboxylate

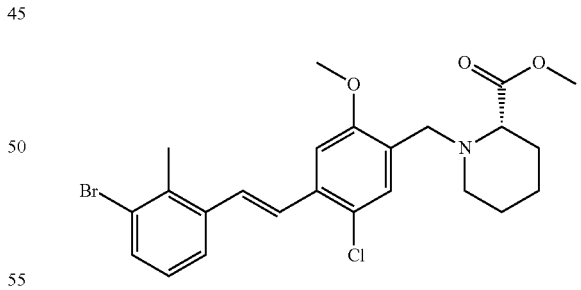

(S)-Methyl piperidine-2-carboxylate hydrochloride (161 mg, 0.896 mmol) was added to a stirring solution of (E)-4-(3-bromo-2-methylstyryl)-5-chloro-2-methoxybenzaldehyde (298 mg, 0.815 mmol) in DCM (16 ml) and acetic acid (49 µl, 0.86 mmol) at rt. The reaction was allowed to stir overnight. Then, sodium triacetoxyborohydride (432 mg, 2.037 mmol) was added. The reaction was stirred for 3 hrs. The mixture was then diluted with EtOAc and washed with sat. NaHCO₃, and sat. aq. NaCl. The organic phase was concentrated, adsorbed onto diatomaceous earth (Celite®) and was purified on silica gel (Biotage, EtOAc/hexanes gradient) to afford (S,E)-methyl 1-(4-(3-bromo-2-methylstyryl)-5-chloro-2-methoxybenzyl)piperidine-2-carboxylate (190 mg, 0.386 mmol, 47.3% yield) consistent by LCMS: M+H=492.00, 494.00, Retention time=1.260 min.

Step 7: Preparation of Example 4517: (S)-1-(5-chloro-4-((E)-2-(3'-(3-((R)-3-hydroxypyrrolidin-1-yl)propoxy)-2,2'-dimethyl-[1,1'-biphenyl]-3-yl)vinyl)-2-methoxybenzyl)piperidine-2-carboxylic Acid

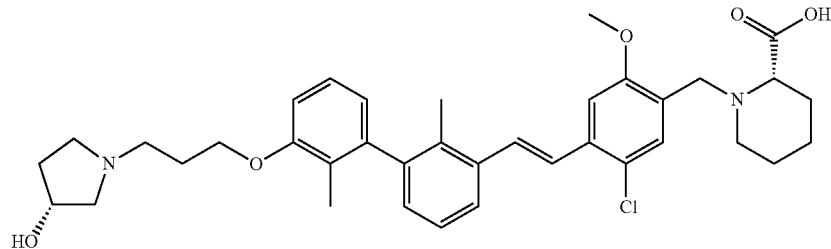 [SMILES: COc1cc(/C=C/c2cccc(-c3cccc(OCCCN4CC[C@@H](O)C4)c3C)c2C)c(Cl)cc1CN1CCCC[C@H]1C(=O)O]

(R)-1-(3-(2-Methyl-3-(4,4,5,5-tetramethyl-1,3,2-dioxaborolan-2-yl)phenoxy)propyl)pyrrolidin-3-ol (33 mg, 0.091 mmol), (S,E)-methyl 1-(4-(3-bromo-2-methylstyryl)-5-chloro-2-methoxybenzyl)piperidine-2-carboxylate (45 mg, 0.091 mmol), tBuXPhos Pd G3 precatalyst (7.3 mg, 0.0091 mmol), potassium phosphate tribasic (39 mg, 0.18 mmol) were combined in THF (1 ml) and water (0.2 mL) and stirred at 60° C. The reaction was allowed to stir overnight. The reaction was concentrated and taken up in MeOH (1.5 mL), and NaOH 1M aq (0.5 mL) was added and the reaction was stirred at 60° C. until hydrolysis was complete as monitored by LCMS. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 3.7 mg (6.4% yield), and its estimated purity by LCMS analysis was 93%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Retention time: 1.594 min, M+H=633.1. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Retention time 1.591 min, M+H=633.2. Proton NMR was acquired in deuterated DMSO. $^1$H NMR (500 MHz, DMSO-$d_6$) δ 7.62 (d, J=7.7 Hz, 1H), 7.58-7.53 (m, 1H), 7.48 (s, 1H), 7.38 (s, 1H), 7.31-7.24 (m, 2H), 7.20 (t, J=8.1 Hz, 1H), 7.03 (d, J=7.3 Hz, 1H), 6.96 (d, J=8.4 Hz, 1H), 6.68 (d, J=7.7 Hz, 1H), 4.19 (br s, 1H), 4.07 (q, J=6.8 Hz, 2H), 3.87 (s, 3H) 3.72 (br d, J=16.1 Hz, 1H), 3.58 (d, J=14.7 Hz, 1H), 2.71 (dd, J=9.5, 6.2 Hz, 1H), 2.60-2.56 (m, 3H), 2.48-2.40 (m, 1H), 2.34 (dd, J=9.5, 3.7 Hz, 1H), 2.23 (br s, 1H), 2.10 (s, 3H), 2.0-1.91 (m, 3H), 1.89 (s, 3H), 1.87 (s, 3H), 1.76 (br s, 2H), 1.58-1.47 (m, 4H).

Example 4518: (S)-1-(5-chloro-4-(2-(3'-(3-((R)-3-hydroxypyrrolidin-1-yl)propoxy)-2,2'-dimethyl-[1, 1'-biphenyl]-3-yl)ethyl)-2-methoxybenzyl)piperidine-2-carboxylic Acid

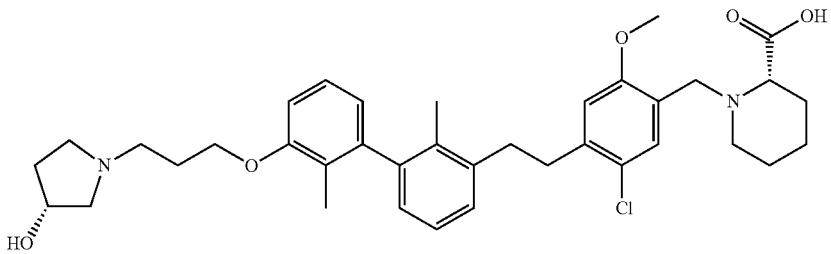 [SMILES: COc1cc(CCc2cccc(-c3cccc(OCCCN4CC[C@@H](O)C4)c3C)c2C)c(Cl)cc1CN1CCCC[C@H]1C(=O)O]

(S)-Methyl 1-(5-chloro-4-((E)-2-(3'-(3-((R)-3-hydroxypyrrolidin-1-yl)propoxy)-2,2'-dimethyl-[1,1'-biphenyl]-3-yl)vinyl)-2-methoxybenzyl)piperidine-2-carboxylate (40 mg, 0.062 mmol) was dissolved in ethyl acetate (2 mL) and MeOH (2 mL) under a blanket of $N_2$. Pd—C (6.58 mg, 6.18 μmol) was added and the flask was flushed with $N_2$ then placed under a blanket of $H_2$ via a balloon. The reaction was stirred for 2 h. LCMS indicated completion of the reaction. $N_2$ was bubbled through the reaction mixture followed by filtration through diatomaceous earth (Celite®) and concentrated under vacuum. The crude material was carried to the next step without further purification. A solution of LiOH (2.434 mg, 0.102 mmol) in water (0.5 mL) was added to a solution of the above crude material in MeOH (0.5 mL). The reaction was stirred at 50° C. for 6 h. After concentration, the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 635.13; Retention Time: 1.54 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 635.15, 635.15; Retention Time: 1.5, 1.56 min.

Example 4519: (S)-1-(5-chloro-4-(3'-(3-((R)-3-hydroxypyrrolidin-1-yl)propoxy)-2,2'-dimethyl-[1,1'-biphenyl]-3-ylcarboxamido)-2-methoxybenzoyl)piperidine-2-carboxylic Acid Final Step: Diisopropylethylamine (24 μl, 0.14 mmol) was added to a stirring solution of (R)-5-chloro-4-(3'-(3-(3-hydroxypyrrolidin-1-yl)propoxy)-2,2'-dimethyl-[1,1'-biphenyl]-3-ylcarboxamido)-2-methoxybenzoic acid (25 mg, 0.045 mmol), (S)-methyl piperidine-2-carboxylate hydrochloride (16 mg, 0.090 mmol) and HATU (26 mg, 0.068 mmol) in DMF (0.5 ml) at rt. The reaction was stirred for 2 hrs and then was concentrated. The residue was taken up in 2 mL of MeOH and 0.5 mL of 1N NaOH was added. The mixture was stirred at 70° C. for 1 hr. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 7-47% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. The yield of the product was 3.7 mg (12% yield), and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Retention time=1.278, M+H=664.0.

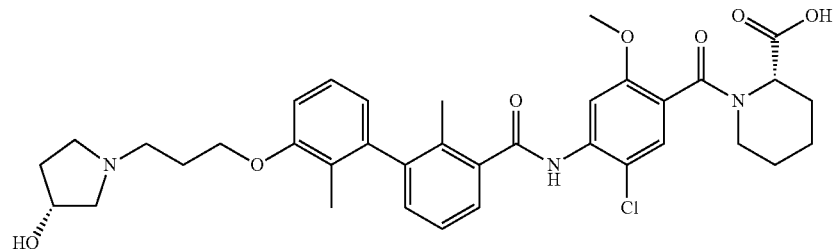 [SMILES: COc1cc(NC(=O)c2cccc(-c3cccc(OCCCN4CC[C@@H](O)C4)c3C)c2C)c(Cl)cc1C(=O)N1CCCC[C@H]1C(=O)O]

Intermediate preparation: Starting with a standard HATU amide coupling between methyl 4-amino-2-methoxybenzoate and 3-bromo-2-methylbenzoic acid, methyl 4-(3-bromo-2-methylbenzamido)-2-methoxybenzoate was realized. A subsequent chlorination with NCS afforded methyl 4-(3-bromo-2-methylbenzamido)-5-chloro-2-methoxybenzoate. Then a standard Miyura borylation gave methyl 5-chloro-2-methoxy-4-(2-methyl-3-(4,4,5,5-tetramethyl-1,3,2-dioxaborolan-2-yl)benzamido)benzoate which was coupled with (R)-1-(3-(3-bromo-2-methylphenoxy)propyl)pyrrolidin-3-ol by means of a Suzuki cross-coupling to give (R)-methyl 5-chloro-4-(3'-(3-(3-hydroxypyrrolidin-1-yl)propoxy)-2,2'-dimethyl-[1,1'-biphenyl]-3-ylcarboxamido)-2-methoxybenzoate. This was then hydrolyzed to afford (R)-5-chloro-4-(3'-(3-(3-hydroxypyrrolidin-1-yl)propoxy)-2,2'-dimethyl-[1,1'-biphenyl]-3-ylcarboxamido)-2-methoxybenzoic acid.

Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Retention time=1.527, M+H=664.0. $^1$H NMR (500 MHz, DMSO-$d_6$) δ 9.92 (br d, J=10.6 Hz, 0.5H), 7.56 (br d, J=7.7 Hz, 1H), 7.48 (br s, 1H), 7.37 (br t, J=7.5 Hz, 1H), 7.30-7.13 (m, 3H), 6.99 (d, J=8.1 Hz, 1H), 6.73-6.68 (m, 1H), 5.19 (br s, 0.5H), 4.44 (br s, 1H), 4.16-4.06 (m, 2H), 3.82 (br s, 2H), 3.32 (br s, 1H), 2.54 (s, 10H), 2.22-2.14 (m, 3H), 2.11 (br s, 3H), 1.90 (s, 4H), 1.71-1.56 (m, 3H), 1.38 (br s, 1H), 1.35-1.21 (m, 2H).

Example 4520 to Example 4522 were prepared according to the following scheme.

857 858
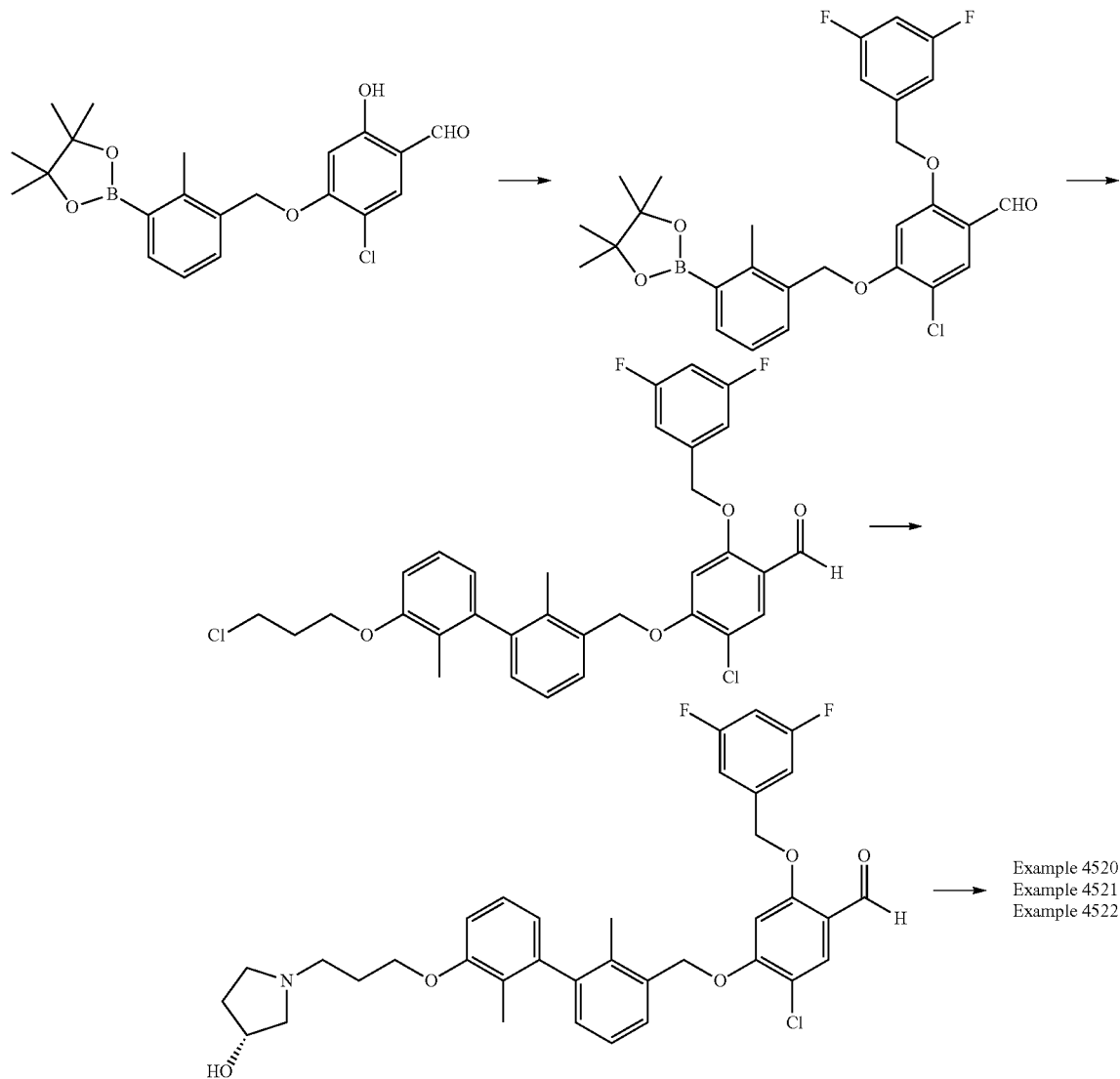
Example 4520
Example 4521
Example 4522
Example 4520: (R)-2-((5-chloro-2-((3,5-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol
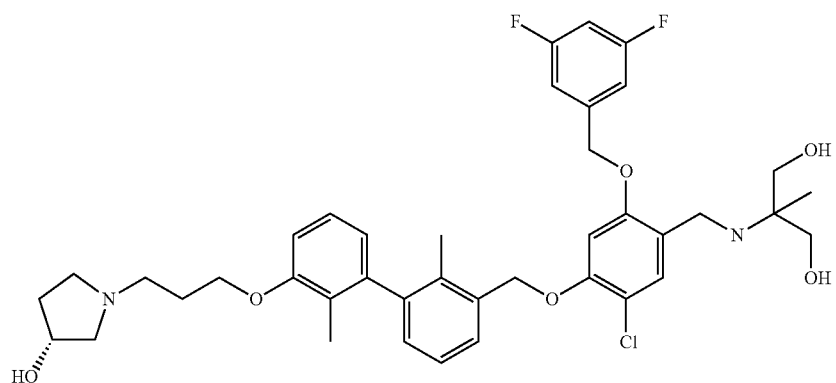 [SMILES: Cc1c(COc2cc(OCc3cc(F)cc(F)c3)c(CNC(C)(CO)CO)cc2Cl)cccc1-c1cccc(OCCCN2CC[C@@H](O)C2)c1C]

Step 1. A vessel containing a mixture of 5-chloro-2-hydroxy-4-((2-methyl-3-(4,4,5,5-tetramethyl-1,3,2-dioxaborolan-2-yl)benzyl)oxy)benzaldehyde (2.500 g, 6.21 mmol), cesium carbonate (2.427 g, 7.45 mmol), and 1-(bromomethyl)-3,5-difluorobenzene (1.414 g, 6.83 mmol) in DMF (40 mL) was sealed and was stirred at rt. overnight. An aliquot was taken for LCMS analysis, which suggested reaction was completed with the desired M+1 seen. The mixture was diluted with water (450 mL) and extracted with EtOAc (100 mL). The separated organic layer was washed with water and brine, dried over $MgSO_4$, filtered, and evaporated in vacuo. The residual solid was triturated with hexanes, filtered, and dried in vacuo to afford the desired product 5-chloro-2-((3,5-difluorobenzyl)oxy)-4-((2-methyl-3-(4,4,5,5-tetramethyl-1,3,2-dioxaborolan-2-yl)benzyl)oxy)benzaldehyde (2.76 g, 5.22 mmol, 84% yield) as a white solid and was used for the next coupling reaction without further purification. LC/MS: 529.10 (M+H), Retention time: 1.70 min (LC/MS condition A-1: Injection Vol: =3 µL, Start % B=2, Final % B=98, Gradient Time=1.5 min, Flow Rate 0.8 ml/min, Wavelength=220, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm 1.7 U, MW1=200+, Oven Temp=40); $^1H$ NMR (500 MHz, CHLOROFORM-d) δ 10.35 (s, 1H), 7.92 (s, 1H), 7.80 (d, J=7.4 Hz, 1H), 7.44 (d, J=7.4 Hz, 1H), 7.23 (t, J=7.6 Hz, 1H), 7.00-6.90 (m, 2H), 6.86-6.77 (m, 1H), 6.50 (s, 1H), 5.18 (s, 2H), 5.11 (s, 2H), 2.58 (s, 3H), 1.39 (s, 12H).

Step 2. A mixture of 5-chloro-2-((3,5-difluorobenzyl)oxy)-4-((2-methyl-3-(4,4,5,5-tetramethyl-1,3,2-dioxaborolan-2-yl)benzyl)oxy)benzaldehyde (212 mg, 0.401 mmol), 1-bromo-3-(3-chloropropoxy)-2-methylbenzene (127 mg, 0.481 mmol), 2nd Generation XPhos precatalyst (31.5 mg, 0.040 mmol), and potassium phosphate tribasic (170 mg, 0.802 mmol) in THF (3 mL) and water (0.750 mL) was sealed and heated in an oil bath at 80° C. for 6 h. The mixture was cooled to rt, and filtered through a bed of diatomaceous earth (Celite®). The filtrate was partitioned between water (10 mL) and EtOAc (10 ml). The separated organic layer was washed with brine, dried over $MgSO_4$, filtered, and evaporated in vacuo. The residue (300 mg) was taken up into DCM and purified by flash column chromatography (40 g silica gel cartridge), eluted with gradient 10%~40% EtOAc-Hexanes to afford the desired product 5-chloro-4-((3'-(3-chloropropoxy)-2,2'-dimethyl-[1,1'-biphenyl]-3-yl)methoxy)-2-((3,5-difluorobenzyl)oxy)benzaldehyde (181 mg, 0.309 mmol, 77% yield) as a colorless glass. LC/MS: 585.10 (M+H), Retention time: 1.73 min (LC/MS condition A-1); $^1H$ NMR (400 MHz, CHLOROFORM-d) δ 10.37 (s, 1H), 7.93 (s, 1H), 7.44 (d, J=6.8 Hz, 1H), 7.33-7.14 (m, 3H), 6.98 (dd, J=7.8, 2.3 Hz, 2H), 6.90 (d, J=8.0 Hz, 1H), 6.87-6.80 (m, 1H), 6.80-6.74 (m, 1H), 6.60 (s, 1H), 5.22 (s, 2H), 5.17 (s, 2H), 4.25-4.12 (m, 2H), 3.82 (t, J=6.4 Hz, 2H), 2.38-2.26 (m, 2H), 2.10 (s, 3H), 1.93 (s, 3H).

Step 3. A mixture of 5-chloro-4-((3'-(3-chloropropoxy)-2,2'-dimethyl-[1,1'-biphenyl]-3-yl)methoxy)-2-((3,5-difluorobenzyl)oxy)benzaldehyde (175 mg, 0.299 mmol), (R)-pyrrolidin-3-ol HCl (48.0 mg, 0.389 mmol), potassium carbonate (62.0 mg, 0.448 mmol) and sodium iodide (44.8 mg, 0.299 mmol) in DMF (4 mL) was heated at 80° C. for 8 h. The reaction mixture was cooled to rt, poured into 1.5 M $K_3PO_4$, and extracted with EtOAc. The separated organic layer was washed with brine, dried over $MgSO_4$, filtered, and evaporated in vacuo. The residue was purified by preparative HPLC to afford the desired product (103 mg, 54% yield) as an off-white glass. LC/MS: 636.10 (M+H), Retention time: 1.30 min (LC/MS condition A-1); $^1H$ NMR (400 MHz, CHLOROFORM-d) δ 10.37 (s, 1H), 7.93 (s, 1H), 7.43 (d, J=7.0 Hz, 1H), 7.34-7.25 (m, 1H), 7.24-7.13 (m, 2H), 6.98 (dd, J=7.7, 2.1 Hz, 2H), 6.91-6.80 (m, 2H), 6.76 (d, J=7.5 Hz, 1H), 6.60 (s, 1H), 5.22 (s, 2H), 5.16 (s, 2H), 4.44 (br. s., 1H), 4.19-4.06 (m, 3H), 3.17-3.08 (m, 1H), 2.95-2.92 (m, 1H), 2.85-2.82 (m, 2H), 2.75-2.45 (b, 2H), 2.33-2.21 (m, 2H), 2.18-2.11 (m, 2H), 2.09 (s, 3H), 1.92 (s, 3H).

Step 4. To a solution of 2-amino-2-methylpropane-1,3-diol (16.53 mg, 0.157 mmol) and (R)-5-chloro-2-((3,5-difluorobenzyl)oxy)-4-((3'-(3-(3-hydroxypyrrolidin-1-yl)propoxy)-2,2'-dimethyl-[1,1'-biphenyl]-3-yl)methoxy)benzaldehyde (50 mg, 0.079 mmol) in DCE (0.5 mL) and ethanol (0.500 mL) was added acetic acid (9.00 µl, 0.157 mmol). After the mixture was stirred for 30 minutes at rt, sodium cyanoborohydride (7.41 mg, 0.118 mmol) was added. The reaction mixture was stirred overnight. LC/MS suggested the desired product was formed. The reaction was evaporated in vacuo, the residue was taken up into DMF, and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation to afford the desired product as a white solid. The yield of the product was 40.1 mg, and its estimated purity by LCMS analysis was 98%. LC/MS: 725.0 (M+H), Retention time: 1.795 min in ammonium acetate and 1.536 min in TFA (Two analytical LC/MS injections were used to determine the final purity. Injection 1 conditions: Column: Waters Acquity UPLC BEH C18, 2.1×50 mm, 1.7-µm particles; Mobile PhaseA: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm); $^1H$ NMR (500 MHz, DMSO-$d_6$) δ 7.45 (d, J=7.7 Hz, 1H), 7.41 (s, 1H), 7.29-7.12 (m, 5H), 7.07 (d, J=7.7 Hz, 1H), 7.01 (s, 1H), 6.96 (d, J=8.1 Hz, 1H), 6.68 (d, J=7.3 Hz, 1H), 5.24 (s, 4H), 4.20 (br. s., 1H), 4.13-4.02 (m, 2H), 3.68 (s, 2H), 2.75-2.71 (m, 1H), 2.62-2.57 (m, 3H), 2.47-2.45 (m, 1H), 2.36 (dd, J=9.5, 3.7 Hz, 1H), 2.04 (s, 3H), 2.02-1.94 (m, 1H), 1.94-1.88 (m, 5H), 1.87-1.86 (m, 1H), 1.84 (s, 3H), 1.60-1.50 (m, 1H), 0.95 (s, 3H). $^{19}F$ NMR (471 MHz, DMSO-$d_6$) δ-109.58 (s, 2F).

Example 4521: (S)-1-(5-chloro-2-((3,5-difluorobenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic Acid

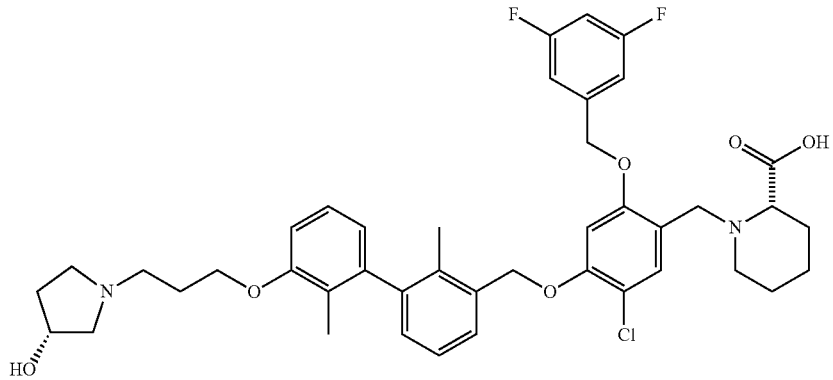 [SMILES: Cc1c(COc2cc(OCc3cc(F)cc(F)c3)c(CN3CCCC[C@H]3C(=O)O)cc2Cl)cccc1-c1cccc(OCCCN2CC[C@@H](O)C2)c1C]

To a milky mixture of (S)-piperidine-2-carboxylic acid (10.15 mg, 0.079 mmol) and (R)-5-chloro-2-((3,5-difluorobenzyl)oxy)-4-((3'-(3-(3-hydroxypyrrolidin-1-yl)propoxy)-2,2'-dimethyl-[1,1'-biphenyl]-3-yl)methoxy)benzaldehyde (50 mg, 0.079 mmol) in DCE (0.5 mL) and ethanol (0.500 mL) was added acetic acid (9.00 µl, 0.157 mmol). After the mixture was stirred for 30 minutes at rt, sodium cyanoborohydride (7.41 mg, 0.118 mmol) was added. The reaction mixture was stirred overnight. LC/MS suggested the desired product was formed. The reaction was evaporated in vacuo, the residue was taken up into DMF and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation to afford the desired product as a white solid. The yield of the product was 20.3 mg, and its estimated purity by LCMS analysis was 99%. LC/MS: 749.0 (M+H), Retention time: 1.639 min in TFA (Two analytical LC/MS injections were used to determine the final purity. Injection 1 conditions: Column: Waters Acquity UPLC BEH C18, 2.1×50 mm, 1.7-µm particles; Mobile PhaseA: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm); $^1$H NMR (500 MHz, DMSO-$d_6$) δ 7.47 (d, J=7.3 Hz, 1H), 7.41 (s, 1H), 7.26 (t, J=7.5 Hz, 1H), 7.23-7.12 (m, 4H), 7.07 (d, J=7.3 Hz, 1H), 7.02 (s, 1H), 6.96 (d, J=8.1 Hz, 1H), 6.68 (d, J=7.7 Hz, 1H), 5.24 (s 2H), 5.23 (s, 2H), 4.20 (br. s., 1H), 4.13-3.99 (m, 3H), 3.75 (d, J=13.6 Hz, 1H), 3.61 (d, J=13.9 Hz, 1H), 2.96-2.86 (m, 1H), 2.77-2.70 (m, 1H), 2.66-2.57 (m, 3H), 2.47 (d, J=7.3 Hz, 1H), 2.37 (dd, J=9.7, 3.5 Hz, 1H), 2.33-2.24 (m, 1H), 2.04 (s, 3H), 2.02-1.88 (m, 4H), 1.83 (s, 3H), 1.78 (br. s., 2H), 1.61-1.35 (m, 4H). $^{19}$F NMR (471 MHz, DMSO-$d_6$) δ-109.54 (s, 2F).

Example 4522: (R)-1-(3-((3'-((2-chloro-5-((3,5-difluorobenzyl)oxy)-4-(hydroxymethyl)phenoxy)methyl)-2,2'-dimethyl-[1,1'-biphenyl]-3-yl)oxy)propyl)pyrrolidin-3-ol

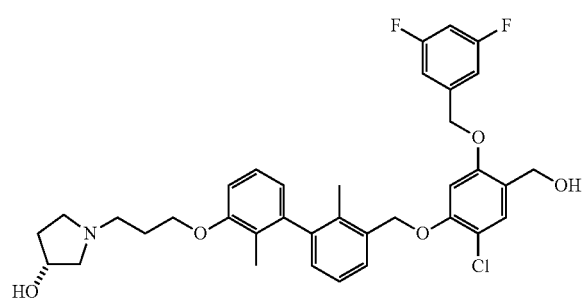 [SMILES: Cc1c(COc2cc(OCc3cc(F)cc(F)c3)c(CO)cc2Cl)cccc1-c1cccc(OCCCN2CC[C@@H](O)C2)c1C]

Example 4522 was isolated from the reaction mixture for Example 4521. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 7.6 mg, and its estimated purity by LCMS analysis was 94%. LC/MS: 638.0 (M+H), Retention time: 2.111 min in ammonium acetate and 1.950 min in TFA (Two analytical LC/MS injections were used to determine the final purity. Injection 1 conditions: Column: Waters Acquity UPLC BEH C18, 2.1×50 mm, 1.7-µm particles; Mobile PhaseA: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm).

Intermediate: 5-chloro-4-hydroxy-2-methylbenzaldehyde (A) and 3-chloro-4-hydroxy-2-methylbenzaldehyde (B)

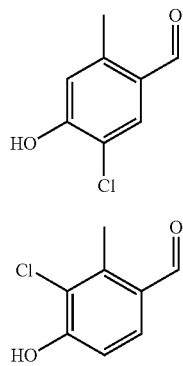

NCS (1.177 g, 8.81 mmol) was added to a stirring solution of 4-hydroxy-2-methylbenzaldehyde (1 g, 7.34 mmol) in DCM (24.48 ml) and acetonitrile (12.24 ml) at rt for 16 h. The solvent was removed under vacuum and the crude residue was purified by flash silica gel chromatography using DCM. The product fractions were collected and the solvent removed under vacuum to give a mixture of regioisomers 5-chloro-4-hydroxy-2-methylbenzaldehyde (A) and 3-chloro-4-hydroxy-2-methylbenzaldehyde (B) (923 mg, 74% yield) which were not separated. LCMS (M+H)=171.03, 172.94.

Intermediate: 5-chloro-2-methyl-4-((2-methyl-3-(4,4,5,5-tetramethyl-1,3,2-dioxaborolan-2-yl)benzyl)oxy)benzaldehyde (A) and 3-chloro-2-methyl-4-((2-methyl-3-(4,4,5,5-tetramethyl-1,3,2-dioxaborolan-2-yl)benzyl)oxy)benzaldehyde (B)

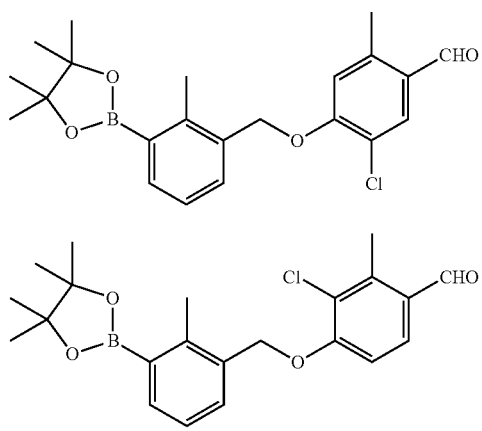

A solution of diisopropyl azodicarboxylate (334 µl, 1.612 mmol) in THF (3053 µl) was added dropwise to the solution of (2-methyl-3-(4,4,5,5-tetramethyl-1,3,2-dioxaborolan-2-yl)phenyl)methanol (364 mg, 1.465 mmol), a mixture of regioisomers 5-chloro-4-hydroxy-2-methylbenzaldehyde and 3-chloro-4-hydroxy-2-methylbenzaldehyde (250 mg, 1.465 mmol), and triphenylphosphine (423 mg, 1.612 mmol) in THF (6106 µl) at 0° C. The resulting yellow solution was allowed to warm to rt and stirred for 16 h. The solvent was removed under vacuum. The crude material was purified by silica gel chromatography using 5-50% EtOAc/Hex. The product fractions were collected and the solvent removed under vacuum to give: 5-chloro-2-methyl-4-((2-methyl-3-(4,4,5,5-tetramethyl-1,3,2-dioxaborolan-2-yl)benzyl)oxy)benzaldehyde (A) and 3-chloro-2-methyl-4-((2-methyl-3-(4,4,5,5-tetramethyl-1,3,2-dioxaborolan-2-yl)benzyl)oxy)benzaldehyde (B). The regio isomers were then separated by SFC chromatography.

Experimental Details for SFC Chromatography:

| Column: | ChiralCel OD-H, 30 × 250 mm, 5 µm |
|---|---|
| Mobile Phase: | 15% MeOH/85% $CO_2$ |
| Pressure: | 150 bar |
| Temperature: | 35° C. |
| Flow Rate: | 80 mL/min |
| UV: | 220 nm |
| Injection: | 0.5 mL (~30 mg/mL in MeOH:$CHCl_3$, 1:1) |
| Fraction Collection: | Slope and Level - |
| | Peak 1 Window: 6.00'-8.00' |
| | Peak 2 Window: 7.50'-9.50' |

Peak 1 and Peak 2 were concentrated under vacuum. Peak 1 corresponded to the acetal of 5-chloro-2-methyl-4-((2-methyl-3-(4,4,5,5-tetramethyl-1,3,2-dioxaborolan-2-yl)benzyl)oxy)benzaldehyde (A) by NMR formed under SFC conditions. The aldehyde was reformed by dissolving Peak 1 in 2 mL DCM and adding 1 mL water and 1 mL TFA. The mixture was stirred for 30 min. The organic layer was collected and washed with bicarbonate and brine, dried over sodium sulfate and concentrated to give 5-chloro-2-methyl-4-((2-methyl-3-(4,4,5,5-tetramethyl-1,3,2-dioxaborolan-2-yl)benzyl)oxy)benzaldehyde (70 mg, 12% yield). LCMS (M+H)=400.97. $^{1}$H NMR (400 MHz, DMSO-$d_6$) δ 10.07 (s, 1H), 8.31 (s, 1H), 7.86 (s, 1H), 7.64 (dd, J=7.5, 1.5 Hz, 1H), 7.60-7.55 (m, 1H), 7.32 (s, 1H), 7.23 (t, J=7.4 Hz, 1H), 5.30 (s, 2H), 2.63 (s, 3H), 1.31 (s, 11H). The same procedure was followed for Peak 2 to give 3-chloro-2-methyl-4-((2-methyl-3-(4,4,5,5-tetramethyl-1,3,2-dioxaborolan-2-yl)benzyl)oxy)benzaldehyde (B) (100 mg, 17% yield). LCMS (M+H)=400.97.

Example 4523 and Example 4524 were prepared in a manner analogous to those described above.

Example 4523: (S)-1-(5-chloro-4-((3'-(3-((R)-3-hydroxypyrrolidin-1-yl)propoxy)-2,2'-dimethyl-[1,1'-biphenyl]-3-yl)methoxy)-2-methylbenzyl)piperidine-2-carboxylic Acid

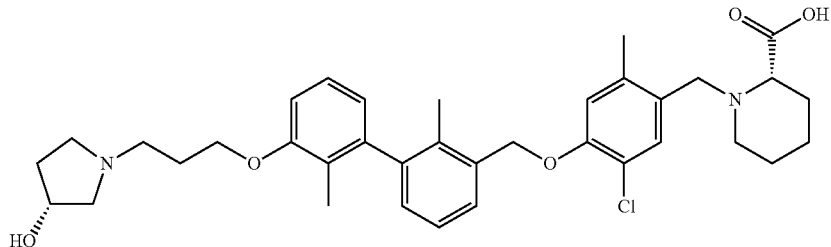 [SMILES: Cc1cc(OCc2cccc(-c3cccc(OCCCN4CC[C@@H](O)C4)c3C)c2C)c(Cl)cc1CN1CCCC[C@H]1C(=O)O]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. The yield of the product was 40.8 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 621.1; Retention Time: 1.49 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 621.09; Retention Time: 1.39 min.

Example 4524: (S)-1-(3-chloro-4-((3'-(3-((R)-3-hydroxypyrrolidin-1-yl)propoxy)-2,2'-dimethyl-[1,1'-biphenyl]-3-yl)methoxy)-2-methylbenzyl)piperidine-2-carboxylic Acid

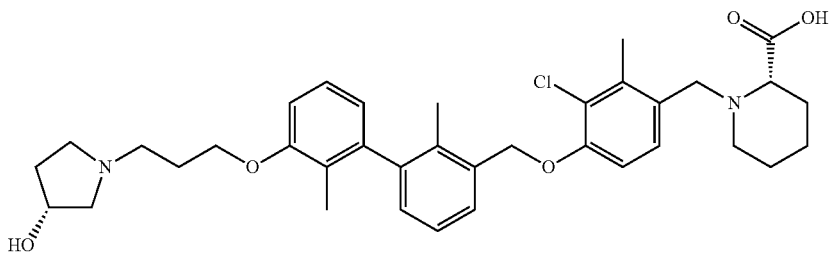 [SMILES: Cc1c(COc2ccc(CN3CCCC[C@H]3C(=O)O)c(C)c2Cl)cccc1-c1cccc(OCCCN2CC[C@@H](O)C2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 621.16; Retention Time: 1.48 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 621.16; Retention Time: 1.55 min.

Biological Assay

The ability of the compounds of formula (I) to bind to PD-L1 was investigated using a PD-1/PD-L1 Homogenous Time-Resolved Fluorescence (HTRF) binding assay.

HTRF detection buffer and 5 μl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD80-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and CD80-His was obtained through commercial sources.

```
Sequences of recombinant human PD-1-Ig
hPD1 (25-167)-3S-IG
                                                       (SEQ ID NO: 1)
  1  LDSPDRPWNP PTFSPALLVV TEGDNATFTC SFSNTSESFV LNWYRMSPSN

51  QTDKLAAFPE DRSQPGQDCR FRVTQLPNGR DFHMSVVRAR RNDSGTYLCG

101  AISLAPKAQI KESLRAELRV TERRAEVPTA HPSPSPRPAG QFQGSPGGGG

151  GREPKSSDKT HTSPPSPAPE LLGGSSVFLF PPKPKDTLMI SRTPEVTCVV

201  VDVSHEDPEV KFNWYVDGVE VHNAKTKPRE EQYNSTYRVV SVLTVLHQDW

251  LKGKEYKCKV SNKALPAPIE KTISKAKGQP REPQVYTLPP SRDELTKNQV

301  SLTCLVKGFY PSDIAVEWES NGQPENNYKT TPPVLDSDGS FFLYSKLTVD

351  KSRWQQONVF SCSVMHEALH NHYTQKSLSL SPGK

Sequence of recombinant human PD-L1-His
hPDL1 (18-239)-TVMV-HIs
                                                       (SEQ ID NO: 2)
  1  AFTVTVPKDL YVVEYGSNMT IECKFPVEKQ LDLAALIVYW EMEDKNIIQF

51  VHGEEDLKVQ HSSYRQRARL LKDQLSLGNA ALQITDVKLQ DAGVYRCMIS

101  YGGADYKRIT VKVNAPYNKI NQRILVVDPV TSEHELTCQA EGYPKAEVIW

151  TSSDHQVLSG KTTTTNSKRE EKLFNVTSTL RINTTTNEIF YCTFRRLDPE

201  ENHTAELVIP ELPLAHPPNE RTGSSETVRF QGHHHHHH
```

Homogenous Time-Resolved Fluorescence (HTRF) Binding Assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. HTRF detection was achieved using europium crypate-labeled anti-Ig (1 nM final) and allophycocyanin (APC) labeled anti-His (20 nM final). Antibodies were diluted in The table below lists the $IC_{50}$ values for representative examples of this disclosure measured in the PD-1/PD-L1 Homogenous Time-Resolved Fluorescence (HTRF) binding assay. Ranges are as follows: A=0.21 nM-10 nM; B=10.01 nM-100 nM; C=100.01 nM-2.0 μM; and D=2.01 μM-10 μM.

| Example Number | Range or IC50 (nM) |
| --- | --- |
| Example 1001 | B |
| Example 1002 | B |
| Example 1003 | B |
| Example 1004 | B |
| Example 1005 | 37 nM |
| Example 1006 | B |
| Example 1007 | 26 nM |
| Example 1008 | B |
| Example 1009 | A |
| Example 1010 | A |
| Example 1011 | C |
| Example 1012 | A |
| Example 1013 | A |

-continued

| Example Number | Range or IC50 (nM) |
|---|---|
| Example 1014 | A |
| Example 1015 | A |
| Example 1016 | A |
| Example 1017 | A |
| Example 1018 | A |
| Example 1019 | A |
| Example 1020 | B |
| Example 1021 | A |
| Example 1022 | A |
| Example 1023 | A |
| Example 1024 | A |
| Example 1025 | A |
| Example 1026 | A |
| Example 1027 | A |
| Example 1028 | A |
| Example 1029 | A |
| Example 1030 | A |
| Example 1031 | B |
| Example 1032 | A |
| Example 1033 | A |
| Example 1034 | B |
| Example 1035 | A |
| Example 1036 | A |
| Example 1037 | A |
| Example 1038 | A |
| Example 1039 | A |
| Example 1040 | A |
| Example 1041 | A |
| Example 1042 | A |
| Example 1043 | A |
| Example 1044 | A |
| Example 1045 | A |
| Example 1046 | A |
| Example 1047 | A |
| Example 1048 | A |
| Example 1049 | A |
| Example 1050 | A |
| Example 1051 | A |
| Example 1052 | A |
| Example 1053 | A |
| Example 1054 | A |
| Example 1055 | A |
| Example 1056 | A |
| Example 1057 | A |
| Example 1058 | 0.48 nM |
| Example 1059 | A |
| Example 1060 | A |
| Example 1061 | A |
| Example 1062 | A |
| Example 1063 | A |
| Example 1064 | A |
| Example 1065 | A |
| Example 1066 | A |
| Example 1067 | A |
| Example 1068 | A |
| Example 1069 | A |
| Example 1070 | A |
| Example 1071 | A |
| Example 1072 | A |
| Example 1073 | A |
| Example 1074 | A |
| Example 1075 | A |
| Example 1076 | A |
| Example 1077 | A |
| Example 1078 | A |
| Example 1079 | A |
| Example 1080 | A |
| Example 1081 | A |
| Example 1082 | A |
| Example 1083 | A |
| Example 1084 | A |
| Example 1085 | A |
| Example 1086 | A |
| Example 1087 | B |
| Example 1501 | A |
| Example 1502 | B |

-continued

| Example Number | Range or IC50 (nM) |
|---|---|
| Example 1503 | B |
| Example 1504 | A |
| Example 1505 | A |
| Example 1506 | A |
| Example 1507 | A |
| Example 1508 | A |
| Example 1509 | 12 nM |
| Example 1510 | A |
| Example 1511 | A |
| Example 1512 | A |
| Example 1513 | B |
| Example 1514 | A |
| Example 1515 | B |
| Example 1516 | A |
| Example 1517 | A |
| Example 1518 | B |
| Example 1519 | A |
| Example 1520 | A |
| Example 1521 | A |
| Example 1522 | A |
| Example 1523 | A |
| Example 1524 | A |
| Example 1525 | A |
| Example 1526 | A |
| Example 1527 | B |
| Example 1528 | A |
| Example 2001 | A |
| Example 2002 | A |
| Example 2003 | A |
| Example 2004 | A |
| Example 2005 | A |
| Example 2006 | A |
| Example 2007 | 0.88 nM |
| Example 2008 | A |
| Example 2009 | B |
| Example 2010 | A |
| Example 2011 | A |
| Example 2013 | A |
| Example 2014 | B |
| Example 2015 | A |
| Example 2016 | A |
| Example 2017 | B |
| Example 2018 | A |
| Example 2019 | A |
| Example 2020 | 63 nM |
| Example 2021 | A |
| Example 2022 | A |
| Example 2023 | A |
| Example 2024 | A |
| Example 2025 | A |
| Example 2027 | A |
| Example 2028 | A |
| Example 2029 | A |
| Example 2030 | A |
| Example 2031 | A |
| Example 2032 | A |
| Example 2033 | A |
| Example 2034 | A |
| Example 2201 | A |
| Example 2202 | A |
| Example 2203 | A |
| Example 2204 | A |
| Example 2205 | A |
| Example 2206 | A |
| Example 2207 | A |
| Example 2208 | A |
| Example 2209 | B |
| Example 2210 | A |
| Example 2211 | A |
| Example 2212 | A |
| Example 2213 | A |
| Example 2214 | A |
| Example 2215 | A |
| Example 2216 | 30 nM |
| Example 2217 | A |
| Example 2218 | A |

871
-continued

| Example Number | Range or IC50 (nM) |
|---|---|
| Example 2219 | A |
| Example 2220 | A |
| Example 2221 | A |
| Example 2222 | A |
| Example 2223 | A |
| Example 2224 | A |
| Example 2225 | A |
| Example 2226 | A |
| Example 2227 | A |
| Example 2228 | B |
| Example 2229 | A |
| Example 2230 | A |
| Example 2231 | 12 nM |
| Example 2232 | A |
| Example 2233 | A |
| Example 2234 | A |
| Example 2235 | A |
| Example 2236 | A |
| Example 2237 | A |
| Example 2238 | A |
| Example 2239 | A |
| Example 2240 | A |
| Example 2241 | A |
| Example 2242 | A |
| Example 2243 | A |
| Example 2244 | A |
| Example 2245 | A |
| Example 2246 | A |
| Example 2247 | A |
| Example 2248 | A |
| Example 2249 | A |
| Example 2250 | A |
| Example 2251 | A |
| Example 2252 | A |
| Example 2253 | 5.3 nM |
| Example 2254 | A |
| Example 2255 | A |
| Example 2256 | A |
| Example 2257 | A |
| Example 2258 | A |
| Example 2259 | A |
| Example 2260 | A |
| Example 2261 | A |
| Example 2262 | A |
| Example 2263 | A |
| Example 2264 | A |
| Example 2265 | A |
| Example 2266 | A |
| Example 2267 | A |
| Example 2268 | A |
| Example 2269 | A |
| Example 2270 | A |
| Example 2271 | A |
| Example 2272 | A |
| Example 2273 | A |
| Example 2274 | A |
| Example 2275 | A |
| Example 2276 | A |
| Example 2277 | A |
| Example 3001 | A |
| Example 3002 | A |
| Example 3003 | A |
| Example 3004 | A |
| Example 3005 | A |
| Example 3006 | A |
| Example 3007 | A |
| Example 3008 | A |
| Example 3009 | A |
| Example 3010 | A |
| Example 3011 | 9 nM |
| Example 3012 | A |
| Example 3013 | A |
| Example 3014 | B |
| Example 3015 | A |
| Example 3016 | A |
| Example 3017 | A |

872
-continued

| Example Number | Range or IC50 (nM) |
|---|---|
| Example 3018 | A |
| Example 3019 | A |
| Example 3020 | A |
| Example 3021 | A |
| Example 3022 | A |
| Example 3023 | A |
| Example 3024 | 1.91 |
| Example 3025 | A |
| Example 3026 | A |
| Example 3027 | B |
| Example 3028 | A |
| Example 3029 | A |
| Example 3030 | A |
| Example 3031 | A |
| Example 3032 | C |
| Example 3033 | A |
| Example 3034 | A |
| Example 3035 | A |
| Example 3036 | A |
| Example 3037 | A |
| Example 3038 | A |
| Example 3039 | A |
| Example 3040 | A |
| Example 3041 | A |
| Example 3042 | A |
| Example 3043 | 3 nM |
| Example 3044 | A |
| Example 1121 | A |
| Example 3061 | >10 |
| Example 3062 | C |
| Example 3063 | D |
| Example 3065 | B |
| Example 3064 | D |
| Example 3066 | A |
| Example 3045 | D |
| Example 1120 | >10 |
| Example 1088 | A |
| Example 1089 | A |
| Example 2123 | 2.00 uM |
| Example 1090 | A |
| Example 1091 | A |
| Example 1092 | A |
| Example 1093 | A |
| Example 2035 | A |
| Example 2036 | A |
| Example 2037 | A |
| Example 1529 | 2 nM |
| Example 1530 | A |
| Example 2097 | A |
| Example 2098 | A |
| Example 2099 | A |
| Example 2038 | A |
| Example 2039 | A |
| Example 2040 | A |
| Example 2041 | B |
| Example 2042 | A |
| Example 2100 | A |
| Example 2101 | A |
| Example 2102 | A |
| Example 1531 | A |
| Example 2278 | A |
| Example 2279 | A |
| Example 2280 | A |
| Example 2281 | 3 nM |
| Example 2282 | A |
| Example 2103 | A |
| Example 2104 | A |
| Example 2283 | A |
| Example 2105 | A |
| Example 2284 | A |
| Example 2285 | A |
| Example 2044 | A |
| Example 2043 | A |
| Example 2286 | A |
| Example 2045 | A |
| Example 2046 | A |

| Example Number | Range or IC50 (nM) |
|---|---|
| Example 2047 | A |
| Example 2048 | A |
| Example 2049 | A |
| Example 2106 | A |
| Example 2050 | A |
| Example 2051 | A |
| Example 2052 | A |
| Example 2287 | A |
| Example 2288 | A |
| Example 2289 | A |
| Example 2290 | A |
| Example 2291 | 1.9 nM |
| Example 2292 | A |
| Example 2293 | A |
| Example 2294 | A |
| Example 2295 | A |
| Example 2296 | A |
| Example 2053 | A |
| Example 2054 | A |
| Example 2107 | A |
| Example 2055 | A |
| Example 2297 | A |
| Example 2056 | A |
| Example 2057 | A |
| Example 2058 | A |
| Example 2059 | A |
| Example 2060 | A |
| Example 2108 | A |
| Example 2061 | A |
| Example 2062 | A |
| Example 2063 | C |
| Example 2064 | A |
| Example 2065 | A |
| Example 2109 | A |
| Example 1094 | A |
| Example 2298 | A |
| Example 2110 | A |
| Example 1532 | A |
| Example 2066 | A |
| Example 2067 | A |
| Example 2299 | A |
| Example 2111 | A |
| Example 2300 | 1.7 nM |
| Example 1533 | A |
| Example 2301 | A |
| Example 2112 | A |
| Example 2068 | A |
| Example 2302 | A |
| Example 2069 | A |
| Example 2303 | A |
| Example 2304 | A |
| Example 2070 | A |
| Example 2305 | A |
| Example 2306 | A |
| Example 2071 | A |
| Example 2307 | A |
| Example 2113 | A |
| Example 2308 | A |
| Example 2309 | 3 nM |
| Example 2310 | A |
| Example 2072 | A |
| Example 2313 | A |
| Example 2314 | A |
| Example 2073 | A |
| Example 2311 | A |
| Example 2312 | A |
| Example 2315 | A |
| Example 1095 | A |
| Example 2074 | A |
| Example 2114 | A |
| Example 1097 | A |
| Example 2316 | A |
| Example 2317 | A |
| Example 2075 | 5 nM |
| Example 1098 | A |
| Example 1534 | A |

| Example Number | Range or IC50 (nM) |
|---|---|
| Example 1099 | A |
| Example 2318 | A |
| Example 2319 | A |
| Example 2320 | A |
| Example 2321 | A |
| Example 1100 | A |
| Example 3046 | A |
| Example 3047 | A |
| Example 3048 | A |
| Example 2322 | B |
| Example 2323 | A |
| Example 2115 | A |
| Example 2324 | A |
| Example 2325 | A |
| Example 3067 | A |
| Example 2076 | A |
| Example 2077 | A |
| Example 1101 | A |
| Example 1102 | 2.8 nM |
| Example 1104 | B |
| Example 1103 | A |
| Example 2326 | A |
| Example 3049 | A |
| Example 3050 | A |
| Example 3051 | A |
| Example 1105 | A |
| Example 1119 | A |
| Example 1106 | 1 nM |
| Example 1107 | A |
| Example 1108 | A |
| Example 1109 | — |
| Example 2116 | A |
| Example 2117 | A |
| Example 3052 | A |
| Example 3054 | A |
| Example 3053 | C |
| Example 1110 | B |
| Example 1111 | A |
| Example 1112 | A |
| Example 1113 | A |
| Example 1114 | A |
| Example 1115 | A |
| Example 1116 | A |
| Example 3068 | A |
| Example 3055 | A |
| Example 1535 | A |
| Example 3069 | A |
| Example 3070 | A |
| Example 2078 | A |
| Example 2079 | A |
| Example 2327 | A |
| Example 2080 | A |
| Example 2328 | A |
| Example 2329 | A |
| Example 2330 | A |
| Example 2081 | A |
| Example 2331 | A |
| Example 2082 | A |
| Example 2083 | 4 nM |
| Example 3056 | A |
| Example 3057 | A |
| Example 2118 | A |
| Example 2084 | C |
| Example 1117 | A |
| Example 2085 | A |
| Example 3058 | A |
| Example 3059 | C |
| Example 2086 | A |
| Example 1118 | B |
| Example 2332 | A |
| Example 2119 | A |
| Example 2120 | A |
| Example 2333 | 0.9 nM |
| Example 2334 | A |
| Example 2088 | A |
| Example 3060 | B |

TABLE-continued

| Example Number | Range or IC50 (nM) |
|---|---|
| Example 2089 | A |
| Example 2335 | — |
| Example 2336 | — |
| Example 3071 | — |
| Example 3072 | A |
| Example 2340 | B |
| Example 2341 | A |
| Example 2342 | A |
| Example 2343 | >10 |
| Example 4519 | C |
| Example 2346 | A |
| Example 2347 | A |
| Example 2348 | A |
| Example 2349 | B |
| Example 2092 | A |
| Example 2350 | A |
| Example 4520 | A |
| Example 4521 | A |
| Example 4522 | B |
| Example 2093 | A |
| Example 2094 | 6 nM |
| Example 4001 | A |
| Example 2351 | >10 |
| Example 2352 | >10 |
| Example 2122 | A |
| Example 4002 | B |
| Example 4003 | A |
| Example 2354 | B |
| Example 4004 | B |
| Example 4005 | A |
| Example 4517 | A |
| Example 4006 | B |
| Example 4007 | C |
| Example 4008 | B |
| Example 4009 | B |
| Example 4010 | 11 nM |
| Example 4011 | B |
| Example 4012 | B |
| Example 4013 | B |
| Example 4014 | D |
| Example 4015 | A |
| Example 4016 | A |
| Example 4017 | C |
| Example 4018 | C |
| Example 4019 | C |
| Example 4020 | D |
| Example 4021 | C |
| Example 4022 | C |
| Example 4024 | 87 nM |
| Example 4025 | C |
| Example 4026 | C |
| Example 4023 | C |
| Example 4027 | D |
| Example 4028 | C |
| Example 4029 | B |
| Example 4033 | C |
| Example 4034 | B |
| Example 4035 | B |
| Example 4030 | C |
| Example 4031 | D |
| Example 4036 | D |
| Example 4032 | C |
| Example 2364 | A |
| Example 4040 | 92 nM |
| Example 4041 | C |
| Example 4042 | C |
| Example 4043 | B |
| Example 4037 | C |
| Example 4038 | B |
| Example 4039 | B |
| Example 4044 | C |
| Example 4045 | C |
| Example 4046 | C |
| Example 4047 | >10 |
| Example 2370 | B |
| Example 4501 | A |

TABLE-continued

| Example Number | Range or IC50 (nM) |
|---|---|
| Example 4502 | A |
| Example 4503 | A |
| Example 4504 | A |
| Example 4505 | A |
| Example 4506 | 3 nM |
| Example 4507 | A |
| Example 4508 | A |
| Example 4509 | A |
| Example 4510 | B |
| Example 4511 | A |
| Example 4512 | A |
| Example 4513 | >10 |
| Example 4514 | C |
| Example 4515 | >10 |
| Example 4516 | D |
| Example 4048 | C |
| Example 4049 | C |
| Example 4050 | C |
| Example 4052 | B |
| Example 4051 | B |
| Example 4053 | B |
| Example 4054 | C |
| Example 4055 | B |
| Example 4057 | >10 |
| Example 4061 | A |
| Example 4062 | A |
| Example 4056 | C |
| Example 4058 | B |
| Example 4065 | A |
| Example 4066 | A |
| Example 4068 | A |
| Example 4063 | A |
| Example 4064 | A |
| Example 4067 | A |
| Example 2378 | A |
| Example 2379 | A |
| Example 2380 | B |
| Example 2385 | A |
| Example 4059 | C |
| Example 4060 | C |
| Example 4069 | A |
| Example 4070 | A |
| Example 4079 | 73 nM |
| Example 4080 | A |
| Example 4081 | B |
| Example 4082 | A |
| Example 4083 | A |
| Example 4084 | B |
| Example 4085 | B |
| Example 4518 | A |
| Example 4086 | A |
| Example 4087 | A |
| Example 4088 | A |
| Example 4089 | A |
| Example 4090 | A |
| Example 4091 | A |
| Example 4100 | A |
| Example 4101 | A |
| Example 4102 | A |
| Example 4103 | A |
| Example 4104 | A |
| Example 4105 | A |
| Example 4106 | A |
| Example 4107 | A |
| Example 4108 | A |
| Example 4109 | A |
| Example 4110 | A |
| Example 4111 | A |
| Example 4112 | A |
| Example 4113 | A |
| Example 4114 | A |
| Example 4115 | A |
| Example 4116 | A |
| Example 4117 | A |
| Example 4118 | A |
| Example 4119 | A |

| Example Number | Range or IC50 (nM) |
|---|---|
| Example 4120 | A |
| Example 4121 | 0.5 nM |
| Example 4122 | A |
| Example 4123 | A |
| Example 4124 | A |
| Example 4125 | A |
| Example 4126 | A |
| Example 4127 | A |
| Example 4128 | A |
| Example 4129 | A |
| Example 4130 | A |
| Example 4131 | A |
| Example 4132 | A |
| Example 4133 | A |
| Example 4134 | A |
| Example 4135 | A |
| Example 4136 | A |
| Example 4137 | 3 nM |
| Example 4138 | A |
| Example 4139 | A |
| Example 4140 | A |
| Example 4141 | A |
| Example 4147 | A |
| Example 4148 | A |
| Example 4149 | A |
| Example 4150 | A |
| Example 4151 | A |
| Example 4152 | A |
| Example 4153 | A |
| Example 4154 | A |
| Example 4155 | A |
| Example 4156 | A |
| Example 4157 | 3 nM |
| Example 1121 | A |
| Example 3061 | >10 |
| Example 3062 | C |
| Example 3063 | D |
| Example 3065 | B |
| Example 3064 | D |
| Example 3066 | A |
| Example 3045 | D |
| Example 1120 | >10 |
| Example 1088 | A |
| Example 1089 | A |
| Example 2123 | 2.00 uM |
| Example 1090 | A |
| Example 1091 | A |
| Example 1092 | A |
| Example 1093 | A |
| Example 2035 | A |
| Example 2036 | A |
| Example 2037 | A |
| Example 1529 | 2 nM |
| Example 1530 | A |
| Example 2097 | A |
| Example 2098 | A |
| Example 2099 | A |
| Example 2038 | A |
| Example 2039 | A |
| Example 2040 | A |
| Example 2041 | B |
| Example 2042 | A |
| Example 2100 | A |
| Example 2101 | A |
| Example 2102 | A |
| Example 1531 | A |
| Example 2278 | A |
| Example 2386 | A |
| Example 4523 | A |
| Example 4524 | B |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, septic shock, Hepatitis A, B, C, or D and cancer.

What is claimed is:

1. A compound of formula (I):

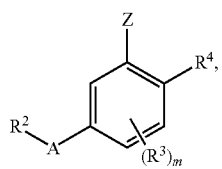

or a pharmaceutically acceptable salt thereof, wherein:

m is 0, 1, or 2;

Z is —$OR^1$; wherein $R^1$ is selected from hydrogen, $C_3$-$C_6$alkenyl, halo$C_1$-$C_4$alkyl, hydroxy$C_1$-$C_4$alkyl, —$(CH_2)_nX$, and —$(CH_2)_nAr$;

n is 1, 2, 3, or 4;

X is selected from —$CH_3$, —$CF_3$, $C_1$-$C_4$alkoxy, —$N(CH_3)_2$, $C_3$-$C_6$cycloalkyl optionally substituted with one or two halo groups, —CN, —$CO_2R^g$, —$C(O)NH_2$, —$C(O)N(CH_3)_2$,

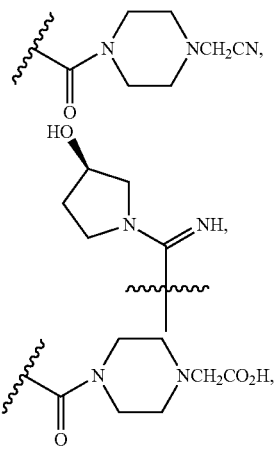

morpholinyl, tetrahydropyranyl, pyrrolidonyl optionally substituted with a hydroxy group, and piperidinyl optionally substituted with one or two groups independently selected from $C_1$-$C_4$alkyl, carboxy, hydroxy, and $C_1$-$C_4$alkoxycarbonyl;

$R^g$ is selected from hydrogen and $C_1$-$C_4$alkyl; and

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, $C_1$-$C_4$alkylcarbonyl, $C_1$-$C_4$alkylsulfonyl, amido, amido$C_1$-$C_4$alkyl, —$(CH_2)_qCO_2C_1$-$C_4$alkyl, —$(CH_2)_qOH$, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4;

A is selected from —$CH_2O$—, —$OCH_2$—, —$(CH_2)_2$—, —CH=CH—, —C(O)NH—, and —NHC(O)—, wherein each group is drawn with its left side attached to $R^2$ and its right side attached to the phenyl ring;

$R^2$ is selected from

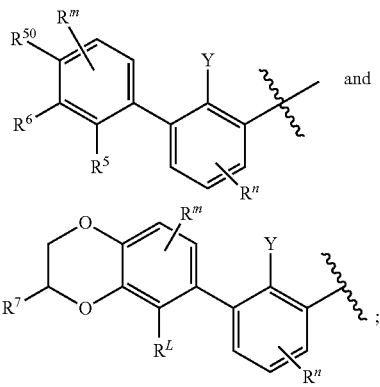

wherein
R$^m$ is selected from hydrogen, C$_1$-C$_3$alkyl, —C≡C-Ph, halo, haloC$_1$-C$_3$alkyl, and

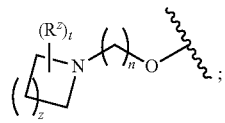

R$^n$ is selected from hydrogen, C$_1$-C$_3$alkyl, halo, haloC$_1$-C$_3$alkyl, and

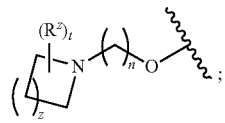

Y is selected from hydrogen, C$_1$-C$_3$alkoxy, C$_1$-C$_3$alkyl, cyano, and halo;
R$^5$ is selected from hydrogen, C$_1$-C$_3$alkyl, cyano, halo, haloC$_1$-C$_3$alkyl, and

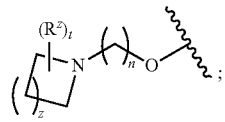

R$^L$ is selected from hydrogen, C$_1$-C$_3$alkyl, cyano, halo, and haloC$_1$-C$_3$alkyl;
R$^6$ and R$^{50}$ are selected from hydrogen, —(CH$_2$)NR$^c$R$^d$, —C(O)NR$^c$R$^d$, —NHC(O)(CH$_2$)$_n$NR$^c$R$^d$, —O—(CH$_2$)$_n$C(O)NR$^c$R$^d$, —O—(CH$_2$)$_n$NR$^c$R$^d$, hydroxyC$_1$-C$_6$alkoxy wherein the C$_1$-C$_6$alkoxy is optionally substituted with one or two additional hydroxy groups,

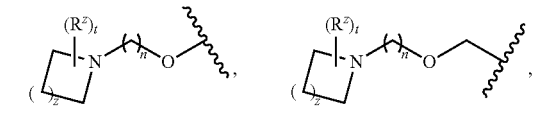

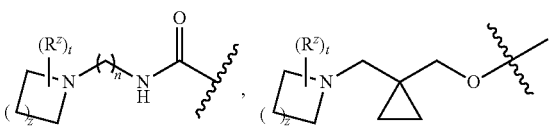

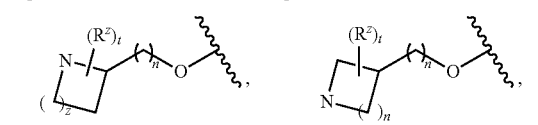

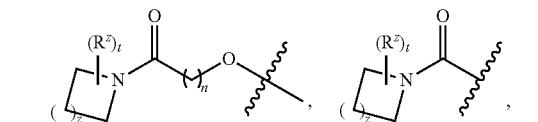

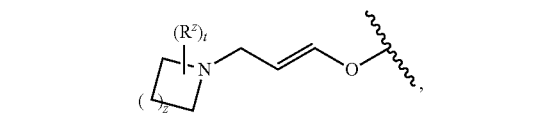

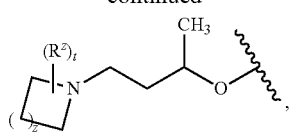

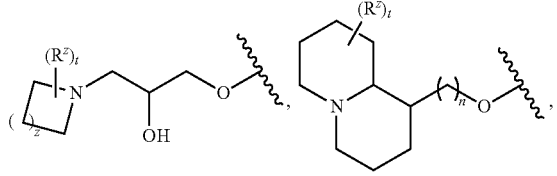

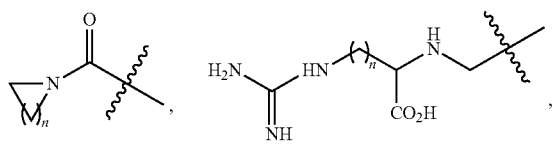

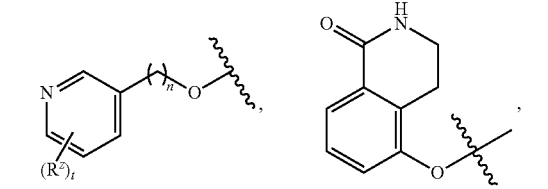

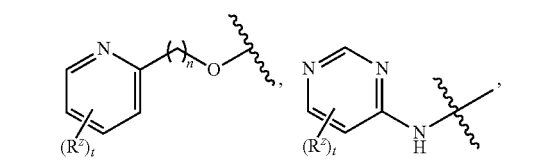

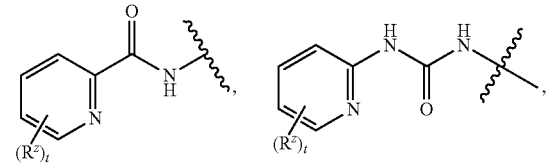

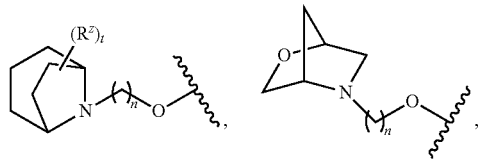

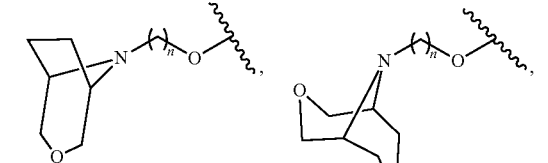

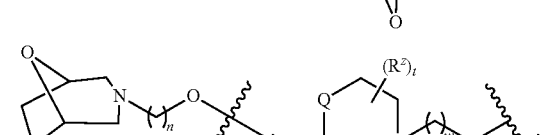

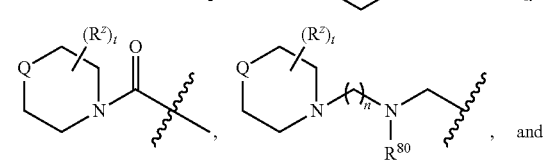

and

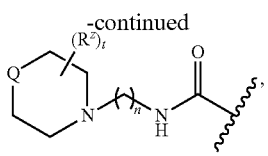

n is 1, 2, 3, or 4;
t is 0, 1, 2, 3, or 4;
w is 1, 2, 3, 4;
z is 1, 2, or 3;
$R^{80}$ is hydrogen or $C_1$-$C_3$alkyl;
each $R^z$ is independently selected from $C_1$-$C_4$alkoxy, $C_1$-$C_4$alkoxycarbonyl, $C_1$-$C_4$alkoxycarbonyl$C_1$-$C_4$alkyl, $C_1$-$C_4$alkyl, $C_1$-$C_4$alkylamido, $C_1$-$C_4$alkylamino, $C_1$-$C_4$alkylcarbonyl, amido, carboxy, carboxy$C_1$-$C_4$alkyl, di($C_1$-$C_4$alkyl)amido, di($C_1$-$C_4$alkyl)amino, halo, halo$C_1$-$C_4$alkoxy, halo$C_1$-$C_4$alkyl, hydroxy, hydroxy$C_1$-$C_4$alkyl, morpholinyl, —$NR^cR^d$, ($NR^cR^d$)$C_1$-$C_4$alkyl, —$NR^eR^f$ ($NR^eR^f$)$C_1$-$C_4$alkyl, oxo, phenyl, and phenyl$C_1$-$C_4$alkyl, wherein the phenyl and the phenyl part of the phenyl$C_1$-$C_4$alkyl are optionally substituted with one, two, or three groups independently selected from $C_1$-$C_3$alkyl and halo;
$R^c$ and $R^d$ are independently selected from hydrogen, $C_2$-$C_4$alkenylcarbonyl, $C_1$-$C_4$alkoxycarbonyl, $C_1$-$C_6$alkyl, $C_1$-$C_4$alkylcarbonyl, amido$C_1$-$C_4$alkyl, amino$C_1$-$C_4$alkyl, aryl$C_1$-$C_4$alkyl, $C_3$-$C_{10}$cycloalkyl, ($C_3$-$C_{10}$cycloalkyl)$C_1$-$C_4$alkyl, halo$C_1$-$C_4$alkylcarbonyl, heterocyclyl$C_1$-$C_4$alkyl, heterocyclyl$C_1$-$C_4$alkylcarbonyl, hydroxy$C_1$-$C_6$alkyl, and hydroxy$C_1$-$C_4$alkylcarbonyl, wherein the alkyl part of the amido$C_1$-$C_4$alkyl, the amino$C_1$-$C_4$alkyl, the aryl$C_1$-$C_4$alkyl, the ($C_3$-$C_{10}$cycloalkyl)$C_1$-$C_4$alkyl, the heterocyclyl$C_1$-$C_4$alkyl and the heterocyclyl$C_1$-$C_4$alkylcarbonyl is optionally substituted with one or two groups independently selected from carboxy and hydroxy; wherein the alkyl part of the hydroxy$C_1$-$C_4$alkyl and the hydroxy$C_1$-$C_4$alkylcarbonyl is optionally substituted with one or two groups independently selected from carboxy and hydroxy; and wherein the aryl part of the aryl$C_1$-$C_4$alkyl, the $C_3$-$C_{10}$cycloalkyl, the cycloalkyl part of the ($C_3$-$C_{10}$cycloalkyl)$C_1$-$C_4$alkyl and the heterocyclyl part of the heterocyclyl$C_1$-$C_4$alkyl and the heterocyclyl$C_1$-$C_4$alkylcarbonyl are each optionally substituted with one, two, or three groups independently selected from $C_1$-$C_4$alkoxycarbonyl, $C_1$-$C_4$alkyl, and halo;
$R^e$ and $R^f$, together with the atom to which they are attached, form a ring selected from morpholine and

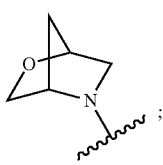 [SMILES: *N1CC2CC1CO2]

Q is selected from S, S(O)$_2$, O, and $NR^p$; wherein $R^p$ is selected from hydrogen, $C_1$-$C_4$alkyl, $C_1$-$C_4$alkylamido$C_1$-$C_4$alkyl, $C_1$-$C_4$alkylamino$C_1$-$C_4$alkyl, amido$C_1$-$C_4$alkyl, amino$C_1$-$C_4$alkyl, di($C_1$-$C_4$alkyl)amido$C_1$-$C_4$alkyl, di($C_1$-$C_4$alkyl)amino$C_1$-$C_3$alkyl, hydroxy$C_1$-$C_4$alkyl, pyridinyl, and phenyl optionally substituted with methoxy;
provided that one of $R^5$, $R^6$, and $R^{50}$ is other than hydrogen; and
$R^7$ is hydrogen or

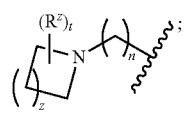

wherein n, z, t, and $R^z$ are as defined above in $R^6$;
provided that one of $R^L$ and $R^7$ is other than hydrogen;
each $R^3$ is independently selected from $C_2$-$C_4$alkenyl, $C_1$-$C_4$alkoxy, $C_1$-$C_4$alkyl, cyano, halo, and halo$C_1$-$C_4$alkyl; and
$R^4$ is selected from —(CH$_2$)$_p$CHO, —(CH$_2$)$_p$CO$_2$H, —(CH$_2$)$_n$OH, —C(O)NR$^{100}$R$^{101}$, —CH(CH$_3$)NR$^q$R$^8$, and —(CH$_2$)$_n$NR$^q$R$^8$; wherein
$R^{100}$ and $R^{101}$ are selected from hydrogen, $C_1$-$C_6$alkyl, and hydroxy($C_1$-$C_6$alkyl) optionally substituted with an additional hydroxy group; or, $R^{100}$ and $R^{101}$, together with the nitrogen atom to which they are attached, form a six-membered ring optionally substituted with a carboxy group;
p is 0, 1, 2, or 3;
n is 1, 2, 3, or 4;
$R^q$ is selected from hydrogen, $C_1$-$C_4$alkyl, benzyl, ($C_3$-$C_6$cycloalkyl)$C_1$-$C_3$alkyl, halo$C_1$-$C_4$alkyl, hydroxy$C_1$-$C_6$alkyl optionally substituted with a second hydroxy group, and pyridinyl($C_1$-$C_3$alkyl) optionally substituted with a cyano group; and
$R^8$ is selected from hydrogen, $C_1$-$C_4$alkyl, —(CH$_2$)$_n$N(CH$_3$)$_2$, carboxy$C_2$-$C_6$alkenyl, carboxy$C_1$-$C_6$alkyl, and hydroxy$C_1$-$C_6$alkyl, wherein the alkyl part of the carboxy$C_1$-$C_6$alkyl and the hydroxy$C_1$-$C_6$alkyl is optionally substituted with one hydroxy or phenyl group wherein the phenyl group is further optionally substituted with a hydroxy group;

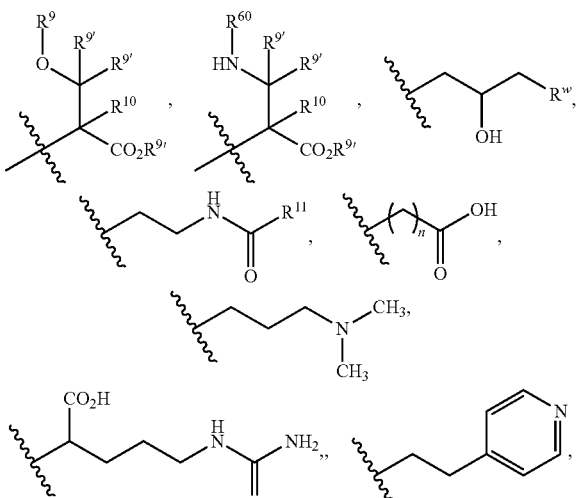

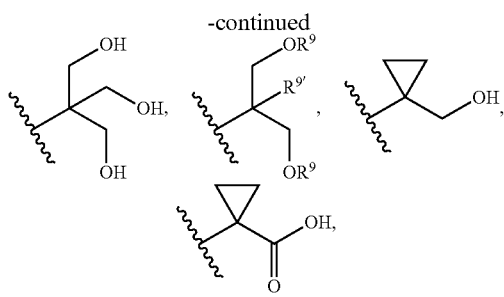

and $R^w$ is —CONH$_2$, $R^9$ is selected from hydrogen, benzyl, and methyl;

each $R^{9'}$ is independently selected from hydrogen and C$_1$-C$_3$alkyl;

$R^{10}$ is selected from hydrogen, C$_1$-C$_3$alkyl, and benzyl;

$R^{11}$ is selected from C$_2$-C$_4$alkenyl and C$_1$-C$_4$alkyl; and $R^{60}$ is selected from hydrogen, C$_1$-C$_6$alkyl, and C$_1$-C$_6$alkoxycarbonyl, or $R^8$ and $R^d$, together with the nitrogen atom to which they are attached, form a ring selected from

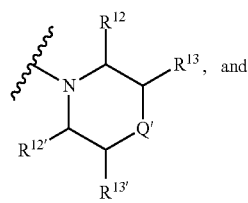

wherein s is 0, 1, or 2;

z is 1, 2, or 3;

Q' is selected from CHR$^{13''}$, S, O, NH, NC(O)OC$_1$-C$_6$alkyl, N(CH$_2$)$_2$OH, and NCH$_3$;

$R^{12}$ and $R^{12'}$ are independently selected from hydrogen, —CO$_2$H, hydroxyC$_1$-C$_4$alkyl, oxo, and —C(O)NHSO$_2$R$^{16}$;

$R^{13}$ and $R^{13'}$ are independently selected from hydrogen, hydroxyC$_1$-C$_4$alkyl, oxo, and —CO$_2$H;

$R^{13''}$ is selected from hydroxyC$_1$-C$_3$alkyl, and —CO$_2$H;

each $R^{14}$ is independently selected from C$_1$-C$_4$alkoxycarbonyl, C$_1$-C$_6$alkyl, carboxy, halo, hydroxy, hydroxyC$_1$-C$_4$alkyl, —NR$^c$R$^{d'}$, and phenyloxycarbonyl wherein the phenyl is optionally substituted with a nitro group, wherein R$^{c1}$ and R$^{d1}$ are independently selected from hydrogen, C$_1$-C$_4$alkoxycarbonyl, and C$_1$-C$_4$alkylcarbonyl; and $R^{16}$ is selected from trifluoromethyl, cyclopropyl, C$_1$-C$_4$alkyl, dimethylamino, and imidazolyl substituted with a methyl group.

2. A compound of claim 1, or a pharmaceutically acceptable salt thereof, wherein m is 1 and R$^3$ is halo.

3. A compound of claim 2, or a pharmaceutically acceptable salt thereof, wherein A is —CH$_2$O—.

4. A compound of claim 3, or a pharmaceutically acceptable salt thereof, wherein R$^2$ is

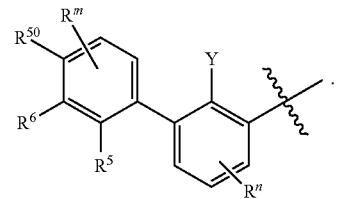

5. A compound of claim 4, or a pharmaceutically acceptable salt thereof, wherein R$^1$ is —(CH$_2$)$_n$Ar, wherein n is 1 and Ar is pyridinyl optionally substituted with one or two groups independently selected from C$_1$-C$_4$alkyl, C$_1$-C$_4$alkylsulfonyl, amido, cyano, and halo.

6. A compound of claim 5, or a pharmaceutically acceptable salt thereof, wherein Y and R$^5$ are independently selected from —CH$_3$ and halo.

7. A compound of claim 6, or a pharmaceutically acceptable salt thereof, wherein one of R$^6$ and R$^{50}$ is hydrogen and the other is selected from —O—(CH$_2$)$_n$NR$^c$R$^d$ and

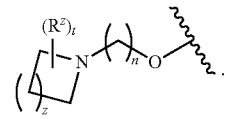

8. A compound of claim 3, or a pharmaceutically acceptable salt thereof, wherein R$^2$ is

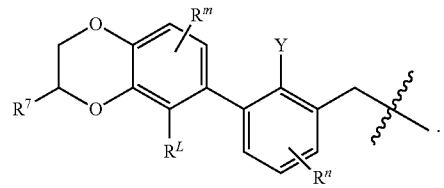

9. A compound selected from (R)-2-((5-chloro-2-((5-cyanopyridin-3-yl)methoxy)-4-((2-methyl-3'-(2-morpholinoethoxy)-[1,1'-biphenyl]-3-yl)methoxy)benzyl)amino)-3-hydroxypropanoic acid;

(S)-2-((5-chloro-2-((5-cyanopyridin-3-yl)methoxy)-4-((2-methyl-3'-(2-morpholinoethoxy)-[1,1'-biphenyl]-3-yl)methoxy)benzyl)amino)-3-hydroxy-2-methylpropanoic acid;

(R)-2-((5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)amino)-3-hydroxypropanoic acid;

(S)-2-((5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((3'-(2-((S)-3-hydroxypyrrolidin-1-yl)-2-oxoethoxy)-2-methyl-[1,1'-biphenyl]-3-yl)methoxy)benzyl)piperidine-2-carboxylic acid;

(R)-2-((5-chloro-2-((5-cyanopyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)amino)-3-hydroxypropanoic acid;

(S)-1-(5-chloro-2-((5-cyanopyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)piperidine-2-carboxylic acid;

(2S,4S)-1-(5-chloro-2-((5-cyanopyridin-3-yl)methoxy)-4-((3'-(2-((R)-3-hydroxypyrrolidin-1-yl)-2-oxoethoxy)-2-methyl-[1,1'-biphenyl]-3-yl)methoxy)benzyl)-4-hydroxypyrrolidine-2-carboxylic acid;

(R)-2-((5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)amino)-3-hydroxypropanoic acid;

(S)-2-((5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((3'-(3-((R)-3-hydroxypyrrolidin-1l-yl)-3-oxopropoxy)-2-methyl-[1,1'-biphenyl]-3-yl)methoxy)benzyl)piperidine-2-carboxylic acid;

(S)-1-(5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)piperidine-2-carboxylic acid;

(S)-A-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxybutanoic acid;

(R)—N-(2-((5-chloro-2-((5-cyanopyridin-3-yl)methoxy)-4-((3'-(3-(3-hydroxypyrrolidin-1-yl)propoxy)-2-methyl-[1,1'-biphenyl]-3-yl)methoxy)benzyl)amino)ethyl)acetamide;

(S)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((3'-(3-((R)-3-hydroxypiperidin-1-yl)propoxy)-2-methyl-[1,1'-biphenyl]-3-yl)methoxy)benzyl)piperidine-2-carboxylic acid;

(S)-1-(5-chloro-2-((5-cyanopyridin-3-yl)methoxy)-4-((3'-(3-((S)-3-hydroxypiperidin-1-yl)propoxy)-2-methyl-[1,1'-biphenyl]-3-yl)methoxy)benzyl)piperidine-2-carboxylic acid;

(S)-1-(4-((3'-(3-acrylamidopropoxy)-2-methyl-[1,1'-biphenyl]-3-yl)methoxy)-5-chloro-2-((5-cyanopyridin-3-yl)methoxy)benzyl)piperidine-2-carboxylic acid;

(R)-2-((4-((3'-(3-acrylamidopropoxy)-2-methyl-[1,1'-biphenyl]-3-yl)methoxy)-5-chloro-2-((5-cyanopyridin-3-yl)methoxy)benzyl)amino)-3-hydroxypropanoic acid;

(S)-1-(5-chloro-4-((3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)piperidine-2-carboxylic acid;

(R)-2-((5-chloro-4-((3'-(3-((R)-3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)amino)-3-hydroxypropanoic acid;

(S)-2-((5-chloro-4-((3'-(3-((R)-3-hydroxypyrrolidin-1-yl)propoxy)-2-methyl-[1,1'-biphenyl]-3-yl)methoxy)-2-((5-(methyl sulfonyl)pyridin-3-yl)methoxy)benzyl)amino)-3-hydroxy-2-methylpropanoic acid;

(R)-2-((5-chloro-4-(3'-(3-((R)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic acid;

(R)-2-((5-chloro-4-(3'-(3-((R)-3-hydroxypyrrolidin-1-yl)propoxy)-2,2'-dimethyl-[1,1'-biphenyl]-3-yl)methoxy)-2-((5-(methyl sulfonyl)pyridin-3-yl)methoxy)benzyl)amino)-3-hydroxy-2-methylpropanoic acid;

(S)-1-(5-chloro-4-((3'-(3-((R)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic acid;

(R)-2-((5-chloro-2-((5-cyanopyridin-3-yl)methoxy)-4-((3'-(3-(4-hydroxy-4-(methoxycarbonyl)piperidin-1-yl)propoxy)-2-methyl-[1,1'-biphenyl]-3-yl)methoxy)benzyl)amino)-3-hydroxypropanoic acid;

(R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxy-2-methylpropanoic acid;

(R)-1-(3-((3'-((5-((5-carbamoylpyridin-3-yl)methoxy)-4-(((1-carboxy-2-hydroxyethyl)amino)methyl)-2-chlorophenoxy)methyl)-2'-methyl-[1,1'-biphenyl]-3-yl)oxy)propyl)-4-hydroxypiperidine-4-carboxylic acid (R)—N-(2-((5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)ethyl)acrylamide;

(R)-1-(3-((3'-((4-(((1-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-hydroxypiperidine-4-carboxylic acid;

(R)-2-((5-chloro-4-((3'-(3-(4-hydroxy-4-(methoxycarbonyl)piperidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic acid;

(S)-2-((5-chloro-4-((3'-(3-(4-hydroxy-4-(methoxycarbonyl)piperidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid;

(R)-1-(3-((3'-((4-(((1-carboxy-2-hydroxyethyl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypiperidine-4-carboxylic acid;

(S)-1-(3-((3'-((4-(((2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypiperidine-4-carboxylic acid;

(R)-2-((5-chloro-2-((5-cyanopyridin-3-yl)methoxy)-4-((2,2'-dimethyl-3'-(((1R,9aR)-octahydro-1H-quinolizin-1-yl)methoxy)-[1,1'-biphenyl]-3-yl)methoxy)benzyl)amino)-3-hydroxypropanoic acid;

(S)-1-(5-chloro-2-((5-cyanopyridin-3-yl)methoxy)-4-((2,2'-dimethyl-3'-(((1R,9aR)-octahydro-1H-quinolizin-1-yl)methoxy)-[1,1'-biphenyl]-3-yl)methoxy)benzyl)piperidine-2-carboxylic acid;

(2R)-2-((5-chloro-2-((5-cyanopyridin-3-yl)methoxy)-4-((3'-(3-(3-hydroxy-3-(methoxycarbonyl)pyrrolidin-1-yl)propoxy)-2,2'-dimethyl-[1,1'-biphenyl]-3-yl)methoxy)benzyl)amino)-3-hydroxy-2-methylpropanoic acid;

(2R)-2-((5-chloro-2-((5-cyanopyridin-3-yl)methoxy)-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)benzyl)amino)-3-hydroxypropanoic acid;

(2R)-2-((5-chloro-2-((5-cyanopyridin-3-yl)methoxy)-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)benzyl)amino)-3-hydroxy-2-methylpropanoic acid;

1-(3-((3'-((4-((((R)-1-carboxy-2-hydroxyethyl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic acid;

1-(3-((3'-((4-((((R)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic acid;

1-(3-((3'-((5-((5-carbamoylpyridin-3-yl)methoxy)-4-((((R)-1-carboxy-2-hydroxyethyl)amino)methyl)-2-chlorophenoxy)methyl)-2,2'-dimethyl-[1,1'-biphenyl]-3-yl)oxy)propyl)-3-(hydroxymethyl)pyrrolidine-3-carboxylic acid;

1-(3-((3'-((4-((((R)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-hydroxypyrrolidine-3-carboxylic acid;

1-(3-((3'-((5-((5-carbamoylpyridin-3-yl)methoxy)-4-((((R)-2-carboxy-1-hydroxypropan-2-yl)amino)methyl)-2-chlorophenoxy)methyl)-2,2'-dimethyl-[1,1'-biphenyl]-3-yl)oxy)propyl)-3-hydroxypyrrolidine-3-carboxylic acid;

(2R)-2-((5-chloro-4-((3'-(3-(3-hydroxy-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid;

(2R)-2-((5-chloro-4-((3'-(3-(3-hydroxy-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic acid;

(S)-1-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)piperidine-2-carboxylic acid;

(R)-2-((5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)amino)-3-hydroxy-2-methylpropanoic acid;

(2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic acid (diastereomer 1);

1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2-chloro-2'-methyl-[1,1'-biphenyl]-3-yl)oxy)propyl)-3-(hydroxymethyl)pyrrolidine-3-carboxylic acid (diastereomer 1);

1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2-chloro-2'-methyl-[1,1'-biphenyl]-3-yl)oxy)propyl)-3-(hydroxymethyl)pyrrolidine-3-carboxylic acid (diastereomer 2);

(2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic acid (diastereomer 2);

(2S)-1-(4-((3'-(3-(3-carboxy-3-(hydroxymethyl)pyrrolidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid (diastereomer 1);

(2S)-1-(4-((3'-(3-(3-carboxy-3-(hydroxymethyl)pyrrolidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid (diastereomer 1);

(S)-1-(5-chloro-4-((2'-chloro-3'-(3-((2S,4R)-4-hydroxy-2-(methoxycarbonyl)pyrrolidin-1-yl)propoxy)-2-methyl-[1,1'-biphenyl]-3-yl)methoxy)-2-((5-(methylsulfonyl)pyridin-3-yl)methoxy)benzyl)piperidine-2-carboxylic acid;

(R)-2-((5-chloro-2-((5-cyanopyridin-3-yl)methoxy)-4-((4'-(3-((R)-3-hydroxypyrrolidin-1-yl)propoxy)-2,2'-dimethyl-[1,1'-biphenyl]-3-yl)methoxy)benzyl)amino)-3-hydroxypropanoic acid;

(S)-1-(5-chloro-2-((5-cyanopyridin-3-yl)methoxy)-4-((4'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(2S)-1-(5-chloro-4-((3'-(3-(3-hydroxy-4-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic acid;

(2R)-2-((5-chloro-4-((3'-(3-(3-hydroxy-4-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid;

(2S)-1-(4-((3'-(3-(3-carboxy-4-hydroxypyrrolidin-1-yl)propoxy)-2,2'-dimethyl-[1,1'-biphenyl]-3-yl)methoxy)-5-chloro-2-((5-(methylsulfonyl)pyridin-3-yl)methoxy)benzyl)piperidine-2-carboxylic acid;

1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-4-hydroxypyrrolidine-3-carboxylic acid;

(R)-2-((5-chloro-4-((2'-chloro-2-methyl-3'-(3-(4-(methylcarbamoyl)piperidin-1-yl)propoxy)-[1,1'-biphenyl]-3-yl)methoxy)-2-((5-cyanopyridin-3-yl)methoxy)benzyl)amino)-3-hydroxy-2-methylpropanoic acid;

(S)-1-(5-chloro-4-((2'-chloro-2-methyl-3'-(3-(4-(methylcarbamoyl)piperidin-1-yl)propoxy)-[1,1'-biphenyl]-3-yl)methoxy)-2-((5-cyanopyridin-3-yl)methoxy)benzyl)piperidine-2-carboxylic acid;

(S)-1-(4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic acid;

(R)-2-((5-chloro-2-((5-cyanopyridin-3-yl)methoxy)-4-((3'-(3-(3-hydroxyazetidin-1-yl)propoxy)-2,2'-dimethyl-[1,1'-biphenyl]-3-yl)methoxy)benzyl)amino)-3-hydroxypropanoic acid;

(S)-1-(4-((3'-(3-((2S,4R)-2-carboxy-4-hydroxypyrrolidin-1-yl)propoxy)-2'-chloro-2-methyl-[1,1'-biphenyl]-3-yl)methoxy)-5-chloro-2-((5-(methylsulfonyl)pyridin-3-yl)methoxy)benzyl)piperidine-2-carboxylic acid;

(R)-2-((5-chloro-4-((3'-(3-((R)-3-(methoxycarbonyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid;

(R)-1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)pyrrolidine-3-carboxylic acid;

(S)-1-(4-((3'-(3-((R)-3-carboxypyrrolidin-1-yl)propoxy)-2,2'-dimethyl-[1,1'-biphenyl]-3-yl)methoxy)-5-chloro-2-((5-(methylsulfonyl)pyridin-3-yl)methoxy)benzyl)piperidine-2-carboxylic acid;

(S)-1-(4-((3'-(3-((2S,4R)-2-carbamoyl-4-hydroxypyrrolidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic acid;

(R)-2-((4-((3'-(3-((2S,4R)-2-carbamoyl-4-hydroxypyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

(S)-1-(5-chloro-2-((5-cyanopyridin-3-yl)methoxy)-4-((3'-(((E)-4-((R)-3-hydroxypyrrolidin-1-yl)but-2-en-1-yl)oxy)-2-methyl-[1,1'-biphenyl]-3-yl)methoxy)benzyl)piperidine-2-carboxylic acid;

5-((4-chloro-5-((2'-chloro-3'-(3-((R)-3-hydroxypyrrolidin-1-yl)propoxy)-2-methyl-[1,1'-biphenyl]-3-yl)methoxy)-2-(((R)-3-hydroxypyrrolidin-1-yl)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(hydroxymethyl)phenoxy)methyl)nicotinonitrile;

5-((4-chloro-5-((2'-chloro-3'-(3-(((S)-2,3-dihydroxypropyl)amino)propoxy)-2-methyl-[1,1'-biphenyl]-3-yl)methoxy)-2-((((S)-2,3-dihydroxypropyl)amino)methyl)phenoxy)methyl)nicotinonitrile;

(S)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxypropanoic acid;

(S)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-1-(3-((3'-((4-((((R)-2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)piperidine-3-carboxylic acid;

(S)-1-(3-((2-chloro-3'-((2-chloro-5-((5-cyanopyridin-3-yl)methoxy)-4-(hydroxymethyl)phenoxy)methyl)-2'-methyl-[1,1'-biphenyl]-3-yl)oxy)propyl)piperidine-3-carboxylic acid;

5-((4-chloro-5-((2'-chloro-2-methyl-3'-(3-((2-(pyridin-4-yl)ethyl)amino)propoxy)-[1,1'-biphenyl]-3-yl)methoxy)-2-(((2-(pyridin-4-yl)ethyl)amino)methyl)phenoxy)methyl)nicotinonitrile;

5-((4-chloro-5-((2'-chloro-3'-(3-(4-(2-hydroxyethyl)piperazin-1-yl)propoxy)-2-methyl-[1,1'-biphenyl]-3-yl)methoxy)-2-((4-(2-hydroxyethyl)piperazin-1-yl)methyl)phenoxy)methyl)nicotinonitrile;

(R)-2-((5-chloro-4-((2'-chloro-3'-(3-(3-(dimethylamino)azetidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

4-chloro-5-((2'-chloro-3'-(3-(3-(dimethylamino)azetidin-1-yl)propoxy)-2-methyl-[1,1'-biphenyl]-3-yl)methoxy)-2-(hydroxymethyl)phenol;

5-((4-chloro-5-((2'-chloro-3'-(3-(3-(dimethylamino)azetidin-1-yl)propoxy)-2-methyl-[1,1'-biphenyl]-3-yl)methoxy)-2-(hydroxymethyl)phenoxy)methyl)nicotinonitrile;

4-chloro-5-((2'-chloro-2-methyl-3'-(3-(piperidin-1-yl)propoxy)-[1,1'-biphenyl]-3-yl)methoxy)-2-(hydroxymethyl)phenol;

5-((4-chloro-5-((2'-chloro-2-methyl-3'-(3-(piperidin-1-yl)propoxy)-[1,1'-biphenyl]-3-yl)methoxy)-2-(hydroxymethyl)phenoxy)methyl)nicotinonitrile;

(2R)-2-((4-((3'-(3-(3-acetamidopyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

N-(1-(3-((2-chloro-3'-((2-chloro-5-hydroxy-4-(hydroxymethyl)phenoxy)methyl)-2'-methyl-[1,1'-biphenyl]-3-yl)oxy)propyl)pyrrolidin-3-yl)acetamide;

N-(1 (3-(2-chloro-3'-((2-chloro-5-((5-cyanopyridin-3-yl)methoxy)-(hydroxymethyl)phenoxy)methyl)-2'-methyl-[1,1'-biphenyl]-3-yl)oxy)propyl)pyrrolidin-3-yl)acetamide;

(R)-2-((4-((3'-(3-((R)-3-acetamidopyrrolidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

(R)-2-((3-((3'-((4-((((R)-2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)amino)-3-hydroxy-2-methylpropanoic acid;

(R)-2-((5-chloro-4-((2'-chloro-3'-(3-(((S)-2,3-dihydroxypropyl)(methyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-5-((4-chloro-5-((2'-chloro-3'-(3-((2,3-dihydroxypropyl)(methyl)amino)propoxy)-2-methyl-[1,1'-biphenyl]-3-yl)methoxy)-2-(hydroxymethyl)phenoxy)methyl)nicotinonitrile;

(S)-methyl 1-(3-((2-chloro-3'-((2-chloro-5-((5-cyanopyridin-3-yl)methoxy)-4-(((2,3-dihydroxypropyl)amino)methyl)phenoxy)methyl)-2'-methyl-[1,1'-biphenyl]-3-yl)oxy)propyl)piperidine-4-carboxylate;

(S)-5-((4-chloro-5-((2'-chloro-3'-(3-(3-(dimethylamino)azetidin-1-yl)propoxy)-2-methyl-[1,1'-biphenyl]-3-yl)methoxy)-2-(((2,3-dihydroxypropyl)amino)methyl)phenoxy)methyl)nicotinonitrile;

5-((4-chloro-5-((2'-chloro-3'-(3-(((S)-2,3-dihydroxypropyl)(methyl)amino)propoxy)-2-methyl-[1,1'-biphenyl]-3-yl)methoxy)-2-((((S)-2,3-dihydroxypropyl)amino)methyl)phenoxy)methyl)nicotinonitrile;

5-((4-chloro-5-((2'-chloro-3'-(3-((3 S,4S)-3,4-dihydroxypiperidin-1-yl)propoxy)-2-methyl-[1,1'-biphenyl]-3-yl)methoxy)-2-((((S)-2,3-dihydroxypropyl)amino)methyl)phenoxy)methyl)nicotinonitrile;

5-((4-chloro-5-((2'-chloro-3'-(3-((3 S,4R)-3-hydroxy-4-(hydroxymethyl)piperidin-1-yl)propoxy)-2-methyl-[1,1'-biphenyl]-3-yl)methoxy)-2-((((S)-2,3-dihydroxypropyl)amino)methyl)phenoxy)methyl)nicotinonitrile;

5-((4-chloro-5-((2,2'-dichloro-3'-(3-((R)-3-hydroxypyrrolidin-1-yl)propoxy)-[1,1'-biphenyl]-3-yl)methoxy)-2-((((S)-2,3-dihydroxypropyl)amino)methyl)phenoxy)methyl)nicotinonitrile;

5-((4-chloro-2-(((R)-3-hydroxypyrrolidin-1-yl)methyl)-5-((3'-(3-((R)-3-hydroxypyrrolidin-1-yl)propoxy)-2,2'-dimethylbiphenyl-3-yl)methoxy)phenoxy)methyl)nicotinonitrile;

(2S)-1-(5-chloro-2-((5-cyanopyridin-3-yl)methoxy)-4-((3'-(3-(2-(hydroxymethyl)piperidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((3 S,4R)-3-hydroxy-4-(hydroxymethyl)piperidin-1-yl)propoxy)-2,2'-dimethylbiphenyl-3-yl)methoxy)benzyl)piperidine-2-carboxylic acid;

(2S)-1-(4-((3'-(3-((S)-3-carboxypiperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-((R)-3-carboxypiperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-(3-(hydroxymethyl)piperidin-1-yl)propoxy)-2,2'-dimethylbiphenyl-3-yl)methoxy)benzyl)piperidine-2-carboxylic acid;

(2S)-1-(4-((3'-(3-(3-carbamoylpiperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-((S)-1-carboxy-2-(pyridin-4-yl)ethylamino)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(2-(pyridin-4-yl)ethylamino)propoxy)biphenyl-3-yl)methoxy)benzyl)piperidine-2-carboxylic acid;

(2S)-1-(5-chloro-2-((5-cyanopyridin-3-yl)methoxy)-4-((3'-(3-(4-(2-hydroxyethyl)piperazin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-morpholinopropoxy)biphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(piperidin-1-yl)propoxy)biphenyl-3-yl)methoxy)benzyl)piperidine-2-carboxylic acid;

(2S)-1-(5-chloro-2-((5-cyanopyridin-3-yl)methoxy)-4-((3'-(3-(4-(hydroxymethyl)piperidin-1-yl)propoxy)-2,2'-dimethylbiphenyl-3-yl)methoxy)benzyl)piperidine-2-carboxylic acid;

(2S)-1-(4-((3'-(3-(3-acetamidopyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-(4-(2-(isopropylamino)-2-oxoethyl)piperazin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-(4-(2-methoxyphenyl)piperazin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((R)-2-hydroxy-2-phenylethylamino)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((S)-2-hydroxy-2-phenylethylamino)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-(2-hydroxy-2-(pyridin-2-yl)ethylamino)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((R)-3-hydroxypiperidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((S)-3-hydroxypiperidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(2-(pyridin-2-yl)ethylamino)propoxy)biphenyl-3-yl)methoxy)benzyl)piperidine-2-carboxylic acid;

(S)-1-(4-((3'-(3-((3 s,5s,7s)-adamantan-1-ylamino)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(methyl(pyridin-2-ylmethyl)amino)propoxy)biphenyl-3-yl)methoxy)benzyl)piperidine-2-carboxylic acid;

(2S)-1-(5-chloro-2-((5-cyanopyridin-3-yl)methoxy)-4-((3'-(3-((1 r,4r)-4-(methoxycarbonyl)cyclohexylamino)propoxy)-2,2'-dimethylbiphenyl-3-yl)methoxy)benzyl)piperidine-2-carboxylic acid;

(2S)-1-(5-chloro-4-((3'-(3-(2-(5-chloro-1-methyl-1H-imidazol-4-yl)ethylamino)propoxy)-2,2'-dimethylbiphenyl-3-yl)methoxy)-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-(3-(dimethylamino)azetidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((2-hydroxyethyl)(methyl)amino)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-(3-hydroxy-2,2-dimethylpropylamino)propoxy)-2,2'-dimethylbiphenyl-3-yl)methoxy)benzyl)piperidine-2-carboxylic acid;

(2S)-1-(4-((3'-(3-(benzyl(2-hydroxyethyl)amino)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-((R)-1-hydroxy-3-methylbutan-2-ylamino)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-((S)-1-hydroxy-3-methylbutan-2-ylamino)propoxy)-2,2'-dimethylbiphenyl-3-yl)methoxy)benzyl)piperidine-2-carboxylic acid;

(3R)-1-(3-(3'-((4-(((S)-2-carboxy-1-hydroxypropan-2-ylamino)methyl)-2-chloro-5-((5-cyanopyridin-3-yl)methoxy)phenoxy)methyl)-2,2'-dimethylbiphenyl-3-yloxy)propyl)piperidine-3-carboxylic acid;

(2S)-1-(4-((3'-(3-((2S,4S)-2-carboxy-4-hydroxypyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-((2S,4R)-2-carboxy-4-hydroxypyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-((S)-2-carboxy-2-hydroxyethylamino)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-((S)-2-(methoxycarbonyl)piperidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(2-methylpiperidin-1-yl)propoxy)biphenyl-3-yl)methoxy)benzyl)piperidine-2-carboxylic acid;

(2S)-1-(5-chloro-2-((5-cyanopyridin-3-yl)methoxy)-4-((3'-(3-((S)-3-fluoropyrrolidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(4-morpholinopiperidin-1-yl)propoxy)biphenyl-3-yl)methoxy)benzyl)piperidine-2-carboxylic acid;

(2S)-1-(4-((3'-(3-(2-oxa-5-azabicyclo[2.2.1]heptan-5-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-((R)-3-acetamidopyrrolidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(4-((3'-(3-(2-(carboxymethyl)piperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(2S)-1-(5-chloro-2-((5-cyanopyridin-3-yl)methoxy)-4-((3'-(3-((R)-3-methoxypyrrolidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((3'-(3-(dimethylamino)propoxy)-2,2'-dimethylbiphenyl-3-yl)methoxy)benzyl)piperidine-2-carboxylic acid;

5-((4-chloro-2-(((2,3-dihydroxypropyl)(methyl)amino)methyl)-5-((3'-(3-((2,3-dihydroxypropyl)(methyl)amino)propoxy)-2,2'-dimethylbiphenyl-3-yl)methoxy)phenoxy)methyl)nicotinonitrile;

5-((4-chloro-2-((3-(hydroxymethyl)piperidin-1-yl)methyl)-5-((3'-(3-(3-(hydroxymethyl)piperidin-1-yl)propoxy)-2,2'-dimethylbiphenyl-3-yl)methoxy)phenoxy)methyl)nicotinonitrile;

5-((4-chloro-2-((2-(hydroxymethyl)piperidin-1-yl)methyl)-5-((3'-(3-(2-(hydroxymethyl)piperidin-1-yl)propoxy)-2,2'-dimethylbiphenyl-3-yl)methoxy)phenoxy)methyl)nicotinonitrile;

5-((4-chloro-2-(((3 S,4R)-3-hydroxy-4-(hydroxymethyl)piperidin-1-yl)methyl)-5-((3'-(3-((3 S,4R)-3-hydroxy-4-(hydroxymethyl)piperidin-1-yl)propoxy)-2,2'-dimethylbiphenyl-3-yl)methoxy)phenoxy)methyl)nicotinonitrile;

5-((4-chloro-2-((4-(2-hydroxyethyl)piperazin-1-yl)methyl)-5-((3'-(3-(4-(2-hydroxyethyl)piperazin-1-yl)propoxy)-2,2'-dimethylbiphenyl-3-yl)methoxy)phenoxy)methyl)nicotinonitrile;

(2S)-2-(5-chloro-2-((5-cyanopyridin-3-yl)methoxy)-4-((3'-(3-(3-(hydroxymethyl)piperidin-1-yl)propoxy)-2,2'-dimethylbiphenyl-3-yl)methoxy)benzylamino)-3-hydroxy-2-methylpropanoic acid;

(2S)-2-(5-chloro-2-((5-cyanopyridin-3-yl)methoxy)-4-((3'-(3-((3 S,4R)-3-hydroxy-4-(hydroxymethyl)piperidin-1-yl)propoxy)-2,2'-dimethylbiphenyl-3-yl)methoxy)benzylamino)-3-hydroxy-2-methylpropanoic acid;

(2S)-2-(5-chloro-2-((5-cyanopyridin-3-yl)methoxy)-4-((3'-(3-((S)-3-hydroxypiperidin-1-yl)propoxy)-2,2'-dimethylbiphenyl-3-yl)methoxy)benzylamino)-3-hydroxy-2-methylpropanoic acid;

(2S)-2-(5-chloro-2-((5-cyanopyridin-3-yl)methoxy)-4-((3'-(3-(4-(2-hydroxyethyl)piperazin-1-yl)propoxy)-2,2'-dimethylbiphenyl-3-yl)methoxy)benzylamino)-3-hydroxy-2-methylpropanoic acid;

(3 S)-1-(3-(3'-((4-(((S)-2-carboxy-1-hydroxypropan-2-ylamino)methyl)-2-chloro-5-((5-cyanopyridin-3-yl)methoxy)phenoxy)methyl)-2,2'-dimethylbiphenyl-3-yloxy)propyl)piperidine-3-carboxylic acid;

5-((4-chloro-2-(((S)-2,3-dihydroxypropylamino)methyl)-5-((3'-(3-((S)-2,3-dihydroxypropylamino)propoxy)-2,2'-dimethylbiphenyl-3-yl)methoxy)phenoxy)methyl)nicotinonitrile;

3-((3-(3'-((4-(((3-amino-3-oxopropyl)(methyl)amino)methyl)-2-chloro-5-((5-cyanopyridin-3-yl)methoxy)phenoxy)methyl)-2,2'-dimethylbiphenyl-3-yloxy)propyl)(methyl)amino)propanamide;

N-((3R)-1-(3-(3'-((4-(((R)-3-acetamidopyrrolidin-1-yl)methyl)-2-chloro-5-((5-cyanopyridin-3-yl)methoxy)phenoxy)methyl)-2,2'-dimethylbiphenyl-3-yloxy)propyl)pyrrolidin-3-yl)acetamide;

(2S)-1-(3-(3'-((4-(((S)-2-carboxypiperidin-1-yl)methyl)-2-chloro-5-((5-cyanopyridin-3-yl)methoxy)phenoxy)methyl)-2,2'-dimethylbiphenyl-3-yloxy)propyl)piperidine-2-carboxylic acid;

(2S)-1-(5-chloro-2-((5-cyanopyridin-3-yl)methoxy)-4-((2,2'-dimethyl-3'-(3-(4-(methylamino)piperidin-1-yl)propoxy)biphenyl-3-yl)methoxy)benzyl)piperidine-2-carboxylic acid;

5-((4-chloro-2-((((S)-2,3-dihydroxypropyl)(methyl)amino)methyl)-5-((3'-(3-(((S)-2,3-dihydroxypropyl)(methyl)amino)propoxy)-2,2'-dimethylbiphenyl-3-yl)methoxy)phenoxy)methyl)nicotinonitrile;

(S)-2-((5-chloro-2-((5-cyanopyridin-3-yl)methoxy)-A-((2,2'-dimethyl-3'-(3-(piperidin-1-yl)propoxy)-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((2,2'-dimethyl-3'-(3-morpholinopropoxy)-[1,1'-biphenyl]-3-yl)methoxy)benzyl)amino)-3-hydroxy-2-methylpropanoic acid;

(2S)-2-((5-chloro-2-((5-cyanopyridin-3-yl)methoxy)-4-((2,2'-dimethyl-3'-(3-(3-(2,2,2-trifluoroacetamido)pyrrolidin-1-yl)propoxy)-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((3'-(3-(4-(hydroxymethyl)piperidin-1-yl)propoxy)-2,2'-dimethyl-[1,1'-biphenyl]-3-yl)methoxy)benzyl)amino)-3-hydroxy-2-methylpropanoic acid;

N-((3R)-1-(3-(3'-((2-chloro-5-((5-cyanopyridin-3-yl)methoxy)-4-(hydroxymethyl)phenoxy)methyl)-2,2'-dimethylbiphenyl-3-yloxy)propyl)pyrrolidin-3-yl)acetamide;

(R)-5-((4-chloro-2-(((3-(dimethylamino)propyl)amino)methyl)-5-((3'-(3-3-hydroxypyrrolidin-1-yl)propoxy)-2-methyl-[1,1'-biphenyl]-3-yl)methoxy)phenoxy)methyl)nicotinonitrile;

(S)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-5-guanidinopentanoic acid;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoic acid;

(R)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid;

(R)-5-((4-chloro-2-(((3-(dimethylamino)propyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxypropanoic acid;

(R)-2-((5-chloro-4-((2'-cyano-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxypropanoic acid;

(R)-2-((5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((3'-(3-((R)-3-hydroxypyrrolidin-1-yl)propoxy)-2-methyl-2'-(trifluoromethyl)-[1,1'-biphenyl]-3-yl)methoxy)benzyl)piperidine-2-carboxylic acid;

(R)-2-((5-chloro-2-((5-cyanopyridin-3-yl)methoxy)-4-((3'-(3-((R)-3-hydroxypyrrolidin-1-yl)propoxy)-2'-methyl-[1,1'-biphenyl]-3-yl)methoxy)benzyl)amino)-3-hydroxypropanoic acid;

(R)-2-((5-chloro-2-((5-cyanopyridin-3-yl)methoxy)-4-((3'-(3-((R)-3-hydroxypyrrolidin-1-yl)propoxy)-2'-methyl-[1,1'-biphenyl]-3-yl)methoxy)benzyl)amino)-3-hydroxypropanoic acid;

(R)-2-((5-chloro-4-((2-chloro-3'-(3-((R)-3-hydroxypyrrolidin-1-yl)propoxy)-2'-methyl-[1,1'-biphenyl]-3-yl)methoxy)-2-((5-cyanopyridin-3-yl)methoxy)benzyl)amino)-3-hydroxy-2-methylpropanoic acid;

2-((5-chloro-2-((5-cyanopyridin-3-yl)methoxy)-4-((3'-((5-cyanopyridin-3-yl)methoxy)-2-methyl-[1,1'-biphenyl]-3-yl)methoxy)benzyl)amino)-3-hydroxy-2-methylpropanoic acid;

(R)-2-((5-chloro-2-((5-cyanopyridin-3-yl)methoxy)-4-((3'-(3-((1R,3R,5 S)-3-hydroxy-8-azabicyclo[3.2.1]octan-8-yl)propoxy)-2-methyl-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((2,2'-dimethyl-[1,1'-biphenyl]-3-yl)methoxy)benzyl)amino)-3-hydroxypropanoic acid;

(R)-2-((5-chloro-2-((5-cyanopyridin-3-yl)methoxy)-4-((2,2'-dimethyl-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((2,2'-dimethyl-[1,1'-biphenyl]-3-yl)methoxy)benzyl)piperidine-2-carboxylic acid;

(R)-5-((4-chloro-2-formyl-5-((3'-(3-(3-hydroxypyrrolidin-1-yl)propoxy)-2-methoxy-2'-methyl-[1,1'-biphenyl]-3-yl)methoxy)phenoxy)methyl)nicotinonitrile (R)-2-((5-chloro-2-((5-cyanopyridin-3-yl)methoxy)-4-((3'-(3-((R)-3-hydroxypyrrolidin-1-yl)propoxy)-2-methoxy-2'-methyl-[1,1'-biphenyl]-3-yl)methoxy)benzyl)amino)-3-hydroxy-2-methylpropanoic acid;

(R)-2-((5-chloro-2-((5-cyanopyridin-3-yl)methoxy)-4-((3'-(3-((R)-3-hydroxypyrrolidin-1-yl)propoxy)-2,2',5-trimethyl-[1,1'-biphenyl]-3-yl)methoxy)benzyl)amino)-3-hydroxy-2-methylpropanoic acid, 2TFA;

5-((4-chloro-2-formyl-5-((3'-(3-((R)-3-hydroxypyrrolidin-1-yl)propoxy)-2,2',6'-trimethyl-[1,1'-biphenyl]-3-yl)methoxy)phenoxy)methyl)nicotinonitrile;

(2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid;

(2R)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxy-2-methylpropanoic acid;

(2S)-1-(5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)piperidine-2-carboxylic acid;

(2S)-2-((5-chloro-2-((5-cyanopyridin-3-yl)methoxy)-4-((3'-(3-((R)-3-hydroxypyrrolidin-1-yl)propoxy)-2,2',6'-trimethyl-[1,1'-biphenyl]-3-yl)methoxy)benzyl)amino)-3-hydroxypropanoic acid;

(2S)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic acid;

(2R)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxy-2-methylpropanoic acid;

(2S)-2-((5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)amino)-3-hydroxypropanoic acid;

(2S)-1-(5-chloro-2-((5-cyanopyridin-3-yl)methoxy)-4-((3'-(3-(3-hydroxy-3-phenylpyrrolidin-1-yl)propoxy)-2,2'-dimethyl-[1,1'-biphenyl]-3-yl)methoxy)benzyl)piperidine-2-carboxylic acid;

(2S)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic acid;

(2R)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxy-2-methylpropanoic acid;

(2S)-2-((5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)amino)-3-hydroxypropanoic acid;

(2S)-1-(5-chloro-2-((5-cyanopyridin-3-yl)methoxy)-4-((2-methyl-3-(5-methyl-2,3-dihydrobenzo[b][1,4]dioxin-6-yl)benzyl)oxy)benzyl)piperidine-2-carboxylic acid;

(S)-1-(5-chloro-4-((2'-chloro-3'-(3-((3R,4R)-4-(4-chlorophenyl)-3,4-dihydroxy-3-methylpiperidin-1-yl)propoxy)-2-methyl-[1,1'-biphenyl]-3-yl)methoxy)-2-((5-cyanopyridin-3-yl)methoxy)benzyl)piperidine-2-carboxylic acid;

(5-chloro-4-((2'-chloro-3'-(3-((3R,4R)-4-(4-chlorophenyl)-3,4-dihydroxy-3-methylpiperidin-1-yl)propoxy)-2-methyl-[1,1'-biphenyl]-3-yl)methoxy)-2-((5-cyanopyridin-3-yl)methoxy)benzyl)-D-serine;

(S)-1-(5-chloro-4-((3'-(3-((S)-3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)piperidine-2-carboxylic acid;

methyl 1-(5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)-4-hydroxypiperidine-4-carboxylate;

(5-chloro-2-((5-cyanopyridin-3-yl)methoxy)-4-((4'-(4-((R)-3-hydroxypyrrolidin-1-yl)butoxy)-2,2'-dimethyl-[1,1'-biphenyl]-3-yl)methoxy)benzyl)-D-serine;

(S)-1-(5-chloro-2-((5-cyanopyridin-3-yl)methoxy)-4-((4'-(4-((R)-3-hydroxypyrrolidin-1-yl)butoxy)-2,2'-dimethyl-[1,1'-biphenyl]-3-yl)methoxy)benzyl)piperidine-2-carboxylic acid;

(5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)-L-serine;

(S)-1-(4-((3'-(3-(4-carboxy-4-hydroxypiperidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic acid;

(R)-2-((5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(R)-1-(3-((3'-((4-(((2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)-4-hydroxypiperidine-4-carboxylic acid;

(S)-1-(5-chloro-4-((2'-chloro-3'-(3-(4-(ethoxycarbonyl)-4-hydroxypiperidin-1-yl)propoxy)-2-methyl-[1,1'-biphenyl]-3-yl)methoxy)-2-((5-cyanopyridin-3-yl)methoxy)benzyl)piperidine-2-carboxylic acid;

(2S)-1-(5-chloro-4-((2'-chloro-3'-(3-(3-(ethoxycarbonyl)-3-(hydroxymethyl)pyrrolidin-1-yl)propoxy)-2-methyl-[1,1'-biphenyl]-3-yl)methoxy)-2-((5-cyanopyridin-3-yl)methoxy)benzyl)piperidine-2-carboxylic acid;

ethyl 1-(3-((2-chloro-3'-((2-chloro-5-((5-cyanopyridin-3-yl)methoxy)-4-((3-(ethoxycarbonyl)-3-(hydroxymethyl)pyrrolidin-1-yl)methyl)phenoxy)methyl)-2'-methyl-[1,1'-biphenyl]-3-yl)oxy)propyl)-3-(hydroxymethyl)pyrrolidine-3-carboxylate;

(2R)-2-((5-chloro-4-((2'-chloro-3'-(3-(3-(ethoxycarbonyl)-3-(hydroxymethyl)pyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

ethyl 1-(3-((2-chloro-3'-((2-chloro-5-((5-cyanopyridin-3-yl)methoxy)-4-((3-(ethoxycarbonyl)-3-(hydroxymethyl)pyrrolidin-1-yl)methyl)phenoxy)methyl)-2'-methyl-[1,1'-biphenyl]-3-yl)oxy)propyl)-3-(hydroxymethyl)pyrrolidine-3-carboxylate;

(S)-1-(4-((3'-(3-(4-acetamidopiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(2S)-1-(4-((3'-(3-(3-carboxy-3-(hydroxymethyl)pyrrolidin-1-yl)propoxy)-2'-chloro-2-methyl-[1,1'-biphenyl]-3-yl)methoxy)-5-chloro-2-((5-cyanopyridin-3-yl)methoxy)benzyl)piperidine-2-carboxylic acid;

(2S)-1-(2-((5-carbamoylpyridin-3-yl)methoxy)-4-((3'-(3-(3-carboxy-3-(hydroxymethyl)pyrrolidin-1-yl)propoxy)-2'-chloro-2-methyl-[1,1'-biphenyl]-3-yl)methoxy)-5-chlorobenzyl)piperidine-2-carboxylic acid;

1-(3-((3'-((4-((((R)-2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)-3-(hydroxymethyl)pyrrolidine-3-carboxylic acid;

1-(3-((3'-((5-((5-carbamoylpyridin-3-yl)methoxy)-4-((((R)-2-carboxy-1-hydroxypropan-2-yl)amino)methyl)-2-chlorophenoxy)methyl)-2-chloro-2'-methyl-[1,1'-biphenyl]-3-yl)oxy)propyl)-3-(hydroxymethyl)pyrrolidine-3-carboxylic acid;

(S)-1-(4-((3'-(3-(4-carboxy-4-(hydroxymethyl)piperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(S)-1-(2-((5-carbamoylpyridin-3-yl)methoxy)-4-((3'-(3-(4-carboxy-4-(hydroxymethyl)piperidin-1-yl)propoxy)-2,2'-dimethyl-[1,1'-biphenyl]-3-yl)methoxy)-5-chlorobenzyl)piperidine-2-carboxylic acid;

(R)-1-(3-((3'-((4-(((2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-(hydroxymethyl)piperidine-4-carboxylic acid;

(R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2,2'-dimethyl-[1,1'-biphenyl]-3-yl)oxy)propyl)-4-(hydroxymethyl)piperidine-4-carboxylic acid;

(S)-1-(2-((5-carbamoylpyridin-3-yl)methoxy)-4-((3'-(3-(4-carboxy-4-(hydroxymethyl)piperidin-1-yl)propoxy)-2'-chloro-2-methyl-[1,1'-biphenyl]-3-yl)methoxy)-5-chlorobenzyl)piperidine-2-carboxylic acid;

(R)-1-(3-((3'-((4-(((2-carboxy-1-hydroxypropan-2-yl)amino)methyl)-2-chloro-5-((5-cyanopyridin-3-yl)methoxy)phenoxy)methyl)-2-chloro-2'-methyl-[1,1'-biphenyl]-3-yl)oxy)propyl)-4-(hydroxymethyl)piperidine-4-carboxylic acid;

(R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2-chloro-2'-methyl-[1,1'-biphenyl]-3-yl)oxy)propyl)-4-(hydroxymethyl)piperidine-4-carboxylic acid;

ethyl 1-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-3-(hydroxymethyl)pyrrolidine-3-carboxylate;

1-(3-((2-chloro-3'-((2-chloro-5-((5-cyanopyridin-3-yl)methoxy)-4-(((1,3-dihydroxy-2-methylpropan-2-yl)

amino)methyl)phenoxy)methyl)-2'-methyl-[1,1'-biphenyl]-3-yl)oxy)propyl)-3-(hydroxymethyl)pyrrolidine-3-carboxylic acid;

(R)-2-((4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

(S)-1-(5-Chloro-2-((5-cyanopyridin-3-yl)methoxy)-4-((2'-(3-((R)-3-hydroxypyrrolidin-1-yl)propoxy)-2-methyl-[1,1'-biphenyl]-3-yl)methoxy)benzyl)piperidine-2-carboxylic acid;

(R)-2-((5-Chloro-4-((2'-chloro-3'-(3-((R)-3-hydroxypyrrolidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(5-chloro-2-(3-((R)-3-hydroxypyrrolidin-1-yl)propoxy)-4-((3'-(3-((R)-3-hydroxypyrrolidin-1-yl)propoxy)-2,2'-dimethyl-[1,1'-biphenyl]-3-yl)methoxy)benzyl)-L-serine;

(R)-2-((5-chloro-2-(3-((R)-3-hydroxypyrrolidin-1-yl)propoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid;

(R)-2-((5-chloro-4-((2'-chloro-3'-(3-(3-hydroxypyrrolidin-1-yl)propoxy)-2-methyl-[1,1'-biphenyl]-3-yl)methoxy)-2-((5-(methylsulfonyl)pyridin-3-yl)methoxy)benzyl)amino)-2-methylpropane-1,3-diol;

(R)-2-((5-chloro-4-((3'-(3-(3-hydroxypyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-2-methylpropane-1,3-diol;

5-((4-chloro-5-((2'-fluoro-3'-(3-((R)-2-(hydroxymethyl)pyrrolidin-1-yl)propoxy)-2-methyl-[1,1'-biphenyl]-3-yl)methoxy)-2-(((R)-2-(hydroxymethyl)pyrrolidin-1-yl)methyl)phenoxy)methyl)nicotinonitrile;

(S)-1-(5-chloro-4-(((2'-chloro-3'-(3-((R)-3-hydroxypyrrolidin-1-yl)propoxy)-2-methyl-[1,1'-biphenyl]-3-yl)oxy)methyl)-2-((5-cyanopyridin-3-yl)methoxy)benzyl)piperidine-2-carboxylic acid;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxypropan-2-yl)amino)methyl)phenoxy)methyl)nicotinonitrile;

(S)-5-((4-chloro-5-((2'-chloro-3'-(3-((2,3-dihydroxypropyl)amino)propoxy)-2-methyl-[1,1'-biphenyl]-3-yl)methoxy)-2-(((1,3-dihydroxypropan-2-yl)amino)methyl)phenoxy)methyl)nicotinonitrile;

5-((4-chloro-5-((2'-chloro-2-methyl-3'-(3-((2-(pyridin-3-yl)ethyl)amino)propoxy)-[1,1'-biphenyl]-3-yl)methoxy)-2-(((1,3-dihydroxypropan-2-yl)amino)methyl)phenoxy)methyl)nicotinonitrile;

(R)-2-((5-chloro-4-((2'-chloro-3'-(3-((1,3-dihydroxypropan-2-yl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

5-((4-chloro-5-((2'-chloro-3'-(3-((1,3-dihydroxypropan-2-yl)amino)propoxy)-2-methyl-[1,1'-biphenyl]-3-yl)methoxy)-2-(hydroxymethyl)phenoxy)methyl)nicotinonitrile;

(R)-2-((5-chloro-4-((2'-chloro-3'-(3-((1,3-dihydroxy-2-(hydroxymethyl)propan-2-yl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

5-((4-chloro-5-((2'-chloro-3'-(3-((1,3-dihydroxy-2-(hydroxymethyl)propan-2-yl)amino)propoxy)-2-methyl-[1,1'-biphenyl]-3-yl)methoxy)-2-(hydroxymethyl)phenoxy)methyl)nicotinonitrile;

5-((4-chloro-5-((2'-chloro-3'-(3-((1,3-dihydroxypropan-2-yl)amino)propoxy)-2-methyl-[1,1'-biphenyl]-3-yl)methoxy)-2-(((1,3-dihydroxypropan-2-yl)amino)methyl)phenoxy)methyl)nicotinonitrile;

(2R)-2-((5-chloro-4-((2'-chloro-3'-(3-(3-(hydroxymethyl)piperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

5-((4-chloro-5-((2'-chloro-3'-(3-(3-(hydroxymethyl)piperidin-1-yl)propoxy)-2-methyl-[1,1'-biphenyl]-3-yl)methoxy)-2-(hydroxymethyl)phenoxy)methyl)nicotinonitrile;

(S)-1-(5-chloro-2-((5-cyanopyridin-3-yl)methoxy)-4-((2,2'-dichloro-3'-(3-(piperidin-1-yl)propoxy)-[1,1'-biphenyl]-3-yl)methoxy)benzyl)piperidine-2-carboxylic acid;

5-((4-chloro-5-((2,2'-dichloro-3'-(3-(piperidin-1-yl)propoxy)-[1,1'-biphenyl]-3-yl)methoxy)-2-(hydroxymethyl)phenoxy)methyl)nicotinonitrile;

(2S)-1-(4-((3'-(3-(3-acetamidopyrrolidin-1-yl)propoxy)-2,2'-dichloro-[1,1'-biphenyl]-3-yl)methoxy)-5-chloro-2-((5-cyanopyridin-3-yl)methoxy)benzyl)piperidine-2-carboxylic acid;

(R)-2-((5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-1-(5-chloro-2-((5-cyanopyridin-3-yl)methoxy)-4-((2,2'-dichloro-3'-(3-(((S)-2,3-dihydroxypropyl)amino)propoxy)-[1,1'-biphenyl]-3-yl)methoxy)benzyl)piperidine-2-carboxylic acid;

(S)-5-((4-chloro-5-((2'-chloro-3'-(3-((2,3-dihydroxypropyl)(methyl)amino)propoxy)-2-methyl-[1,1'-biphenyl]-3-yl)methoxy)-2-(((1,3-dihydroxypropan-2-yl)amino)methyl)phenoxy)methyl)nicotinonitrile;

5-((4-chloro-5-((2'-chloro-2-methyl-3'-(3-(piperidin-1-yl)propoxy)-[1,1'-biphenyl]-3-yl)methoxy)-2-(((1,3-dihydroxypropan-2-yl)amino)methyl)phenoxy)methyl)nicotinonitrile;

N-(1 3-(2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)pyrrolidin-3-yl)acetamide;

(R)-5-((4-chloro-5-((2,2'-dichloro-3'-(3-(3-hydroxypyrrolidin-1-yl)propoxy)-[1,1'-biphenyl]-3-yl)methoxy)-2-(((1,3-dihydroxy-2-methylpropan-2-yl)amino)methyl)phenoxy)methyl)nicotinonitrile;

(R)-3-((4-chloro-5-((2,2'-dichloro-3'-(3-(3-hydroxypyrrolidin-1-yl)propoxy)-[1,1'-biphenyl]-3-yl)methoxy)-2-(((1,3-dihydroxy-2-methylpropan-2-yl)amino)methyl)phenoxy)methyl)-4-fluorobenzonitrile;

1-(3-((2-chloro-3'-((2-chloro-5-((5-cyanopyridin-3-yl)methoxy)-4-(((1,3-dihydroxypropan-2-yl)amino)methyl)phenoxy)methyl)-2'-methyl-[1,1'-biphenyl]-3-yl)oxy)propyl)-4-hydroxypiperidine-4-carboxylic acid;

(S)-5-((4-chloro-5-((2'-chloro-3'-(3-((2,3-dihydroxypropyl)amino)propoxy)-2-methyl-[1,1'-biphenyl]-3-yl)methoxy)-2-(((1,3-dihydroxypropan-2-yl)(methyl)amino)methyl)phenoxy)methyl)nicotinonitrile;

(R)-2-((5-chloro-2-((5-cyanopyridin-3-yl)methoxy)-A-((2,2'-dichloro-3'-(3-(piperidin-1-yl)propoxy)-[1,1'-biphenyl]-3-yl)methoxy)benzyl)amino)-3-hydroxy-2-methylpropanoic acid;

(R)-3-((4-chloro-5-((2,2'-dichloro-3'-(3-(3-hydroxypyrrolidin-1-yl)propoxy)-[1,1'-biphenyl]-3-yl)methoxy)-2-

(((1,3-dihydroxy-2-methylpropan-2-yl)amino)methyl) phenoxy)methyl)benzonitrile;

(S)-3-((4-chloro-5-((2,2'-dichloro-3'-(3-((2,3-dihydroxypropyl)amino)propoxy)-[1,1'-biphenyl]-3-yl) methoxy)-2-(((1,3-dihydroxy-2-methylpropan-2-yl) amino)methyl)phenoxy)methyl)benzonitrile;

N-(1 (3-(2-chloro-3'-((2-chloro-5-((5-cyanopyridin-3-yl) methoxy)-4-(((1,3-dihydroxypropan-2-yl)amino) methyl)phenoxy)methyl)-2'-methyl-[1,1'-biphenyl]-3-yl)oxy)propyl)piperidin-4-yl)acetamide;

5-((4-chloro-5-((2'-chloro-3'-(3-(4-hydroxy-4-(hydroxymethyl)piperidin-1-yl)propoxy)-2-methyl-[1,1'-biphenyl]-3-yl)methoxy)-2-(((1,3-dihydroxypropan-2-yl)amino)methyl)phenoxy)methyl)nicotinonitrile;

(R)-2-((5-chloro-2-((5-cyanopyridin-3-yl)methoxy)-4-((2,2'-dichloro-3'-(3-(((S)-2,3-dihydroxypropyl) (methyl)amino)propoxy)-[1,1'-biphenyl]-3-yl) methoxy)benzyl)amino)-3-hydroxy-2-methylpropanoic acid;

(R)-2-((5-chloro-2-((3-chlorobenzyl)oxy)-4-((2,2'-dichloro-3'-(3-(3-hydroxypyrrolidin-1-yl)propoxy)-[1,1'-biphenyl]-3-yl)methoxy)benzyl)amino)-2-methylpropane-1,3-diol;

(R)-5-((4-chloro-5-((2'-chloro-3'-(3-(3-hydroxypyrrolidin-1-yl)propoxy)-2-methyl-[1,1'-biphenyl]-3-yl) methoxy)-2-(((1-hydroxy-2-methylpropan-2-yl)amino) methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl) methoxy)-2-(((2-hydroxy-2-methylpropyl)(methyl) amino)methyl)phenoxy)methyl)nicotinonitrile;

(S)—N-(1-(3-((2-chloro-3'-((2-chloro-5-((5-cyanopyridin-3-yl)methoxy)-4-(((1,3-dihydroxypropan-2-yl) amino)methyl)phenoxy)methyl)-2'-methyl-[1,1'-biphenyl]-3-yl)oxy)propyl)pyrrolidin-3-yl)acetamide;

(R)-2-((4-((3'-(3-((S)-3-acetamidopyrrolidin-1-yl) propoxy)-2,2'-dichloro-[1,1'-biphenyl]-3-yl)methoxy)-5-chloro-2-((5-cyanopyridin-3-yl)methoxy)benzyl) amino)-3-hydroxy-2-methylpropanoic acid;

(R)-2-((4-((3'-(3-((S)-3-acetamidopyrrolidin-1-yl) propoxy)-2'-chloro-2-methyl-[1,1'-biphenyl]-3-yl) methoxy)-5-chloro-2-((5-cyanopyridin-3-yl)methoxy) benzyl)amino)-3-hydroxy-2-methylpropanoic acid;

(R)-2-((5-chloro-4-((2'-chloro-3'-(3-((R)-3-hydroxypyrrolidin-1-yl)propoxy)-2-methyl-[1,1'-biphenyl]-3-yl) methoxy)-2-((5-cyanopyridin-3-yl)methoxy)benzyl) (ethyl)amino)-3-hydroxy-2-methylpropanoic acid;

N-(1-(3-((2-chloro-3'-((2-chloro-5-((5-cyanopyridin-3-yl) methoxy)-4-(((1,3-dihydroxypropan-2-yl)(3,3,3-trifluoropropyl)amino)methyl)phenoxy)methyl)-2'-methyl-[1,1'-biphenyl]-3-yl)oxy)propyl)piperidin-4-yl) acetamide;

5-((4-chloro-5-((2'-chloro-3'-(3-(4-hydroxy-4-(hydroxymethyl)piperidin-1-yl)propoxy)-2-methyl-[1,1'-biphenyl]-3-yl)methoxy)-2-(((1,3-dihydroxypropan-2-yl)(3,3,3-trifluoropropyl)amino)methyl)phenoxy) methyl)nicotinonitrile;

5-((4-chloro-5-((2'-chloro-3'-(3-(((S)-2,3-dihydroxypropyl)(ethyl)amino)propoxy)-2-methyl-[1,1'-biphenyl]-3-yl)methoxy)-2-((((S)-2,3-dihydroxypropyl)(ethyl) amino)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl) methoxy)-2-(((1,3-dihydroxy-2-methylpropan-2-yl) (methyl)amino)methyl)phenoxy)methyl) nicotinonitrile;

(R)-5-((4-chloro-5-((2'-chloro-3'-(3-(3-hydroxypyrrolidin-1-yl)propoxy)-2-methyl-[1,1'-biphenyl]-3-yl) methoxy)-2-(((1-(hydroxymethyl)cyclopropyl)amino) methyl)phenoxy)methyl)nicotinonitrile;

(R)-2-((5-chloro-2-((5-cyanopyridin-3-yl)methoxy)-4-((2,2'-dichloro-3'-(3-((3R,4R)-3,4-dihydroxypyrrolidin-1-yl)propoxy)-[1,1'-biphenyl]-3-yl)methoxy)benzyl)amino)-3-hydroxy-2-methylpropanoic acid;

5-((4-chloro-5-((2'-chloro-3'-(3-hydroxy-2-(hydroxymethyl)propoxy)-2-methyl-[1,1'-biphenyl]-3-yl) methoxy)-2-(((1,3-dihydroxy-2-methylpropan-2-yl) amino)methyl)phenoxy)methyl)nicotinonitrile;

5-((4-chloro-5-((2'-chloro-3'-(3-hydroxy-3-methylbutoxy)-2-methyl-[1,1'-biphenyl]-3-yl)methoxy)-2-(((1, 3-dihydroxy-2-methylpropan-2-yl)amino)methyl)phenoxy)methyl)nicotinonitrile;

5-((4-chloro-5-((2'-chloro-2-methyl-3'-(2-(pyridin-2-yl) ethoxy)-[1,1'-biphenyl]-3-yl)methoxy)-2-(((1,3-dihydroxy-2-methylpropan-2-yl)amino)methyl)phenoxy) methyl)nicotinonitrile;

5-((4-chloro-5-((2'-chloro-3'-(2,3-dihydroxypropoxy)-2-methyl-[1,1'-biphenyl]-3-yl)methoxy)-2-(((1,3-dihydroxy-2-methylpropan-2-yl)amino)methyl)phenoxy) methyl)nicotinonitrile;

(2S)-1-(5-chloro-4-((2'-chloro-3'-(2,3-dihydroxypropoxy)-2-methyl-[1,1'-biphenyl]-3-yl)methoxy)-2-((5-cyanopyridin-3-yl)methoxy)benzyl)piperidine-2-carboxylic acid;

(S)-1-(5-chloro-4-((2'-chloro-3'-(3-hydroxy-2,2-bis(hydroxymethyl)propoxy)-2-methyl-[1,1'-biphenyl]-3-yl) methoxy)-2-((5-cyanopyridin-3-yl)methoxy)benzyl)piperidine-2-carboxylic acid;

5-((4-chloro-5-((2'-chloro-3'-(3-hydroxy-2,2-bis(hydroxymethyl)propoxy)-2-methyl-[1,1'-biphenyl]-3-yl) methoxy)-2-(((1,3-dihydroxy-2-methylpropan-2-yl) amino)methyl)phenoxy)methyl)nicotinonitrile;

5-((4-chloro-5-((2'-chloro-3'-(2-hydroxy-3-((R)-3-hydroxypyrrolidin-1-yl)propoxy)-2-methyl-[1,1'-biphenyl]-3-yl)methoxy)-2-(((1,3-dihydroxy-2-methylpropan-2-yl)amino)methyl)phenoxy)methyl) nicotinonitrile;

2088: N-(3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)propyl)-2,3-dihydroxypropanamide;

N-(3-((2-chloro-3'-((2-chloro-5-((5-cyanopyridin-3-yl) methoxy)-4-(((1,3-dihydroxy-2-methylpropan-2-yl) amino)methyl)phenoxy)methyl)-2'-methyl-[1,1'-biphenyl]-3-yl)oxy)propyl)-2-(pyridin-2-yl)acetamide;

5-((4-chloro-5-((2'-chloro-2-methyl-3'-(((2-morpholinoethyl)amino)methyl)-[1,1'-biphenyl]-3-yl)methoxy)-2-(((1,3-dihydroxy-2-methylpropan-2-yl)amino)methyl) phenoxy)methyl)nicotinonitrile;

5-((4-chloro-5-((2,6-dichloro-3'-(3-((R)-3-hydroxypyrrolidin-1-yl)propoxy)-2'-methyl-[1,1'-biphenyl]-3-yl) methoxy)-2-(((1,3-dihydroxy-2-methylpropan-2-yl) amino)methyl)phenoxy)methyl)nicotinonitrile;

N-((3 S)-1-(3-((2',6'-dichloro-3'-((2-chloro-5-((5-cyanopyridin-3-yl)methoxy)-4-(((1,3-dihydroxy-2-methylpropan-2-yl)amino)methyl)phenoxy)methyl)-2-methyl-[1,1'-biphenyl]-3-yl)oxy)propyl)pyrrolidin-3-yl)acetamide;

(S)-5-((4-chloro-5-((2'-chloro-3'-(3-((2,3-dihydroxypropyl)amino)propoxy)-2-methyl-[1,1'-biphenyl]-3-yl) methoxy)-2-(((1,3-dihydroxy-2-methylpropan-2-yl) amino)methyl)phenoxy)methyl)nicotinonitrile;

5-((4-chloro-5-((2'-chloro-3'-(3-(3-(hydroxymethyl)piperidin-1-yl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile;

2-((5-chloro-4-((2'-chloro-3'-(3-(3-(hydroxymethyl)piperidin-1-yl)propoxy)-2-methyl-[1,1'-biphenyl]-3-yl)methoxy)-2-((5-((3-(hydroxymethyl)piperidin-1-yl)(imino)methyl)pyridin-3-yl)methoxy)benzyl)amino)-2-methylpropane-1,3-diol;

5-((4-chloro-5-((2,2'-dichloro-3'-(3-((R)-3-hydroxypyrrolidin-1-yl)propoxy)-[1,1'-biphenyl]-3-yl)methoxy)-2-((((S)-2,3-dihydroxypropyl)amino)methyl)phenoxy)methyl)nicotinonitrile;

(S)-3-((5-chloro-4-((2,2'-dichloro-3'-(3-((R)-3-hydroxypyrrolidin-1-yl)propoxy)-[1,1'-biphenyl]-3-yl)methoxy)-2-((5-(((R)-3-hydroxypyrrolidin-1-yl)(imino)methyl)pyridin-3-yl)methoxy)benzyl)amino)propane-1,2-diol;

5-((4-chloro-5-((2'-chloro-3'-(3-((1,3-dihydroxy-2-methylpropan-2-yl)amino)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile;

5-((4-chloro-5-((2,2'-dichloro-3'-(3-(((S)-2,3-dihydroxypropyl)amino)propoxy)-[1,1'-biphenyl]-3-yl)methoxy)-2-((((S)-2,3-dihydroxypropyl)amino)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxy-2-methylpropan-2-yl)amino)methyl)phenoxy)methyl)nicotinonitrile;

2-((5-chloro-4-((2'-chloro-3'-(3-((R)-3-hydroxypyrrolidin-1-yl)propoxy)-2-methyl-[1,1'-biphenyl]-3-yl)methoxy)-2-((5-(((R)-3-hydroxypyrrolidin-1-yl)(imino)methyl)pyridin-3-yl)methoxy)benzyl)amino)-2-methylpropane-1,3-diol;

(S)-1-(5-chloro-2-((5-cyanopyridin-3-yl)methoxy)-4-((2,2'-dichloro-3'-(3-((R)-3-hydroxypyrrolidin-1-yl)propoxy)-[1,1'-biphenyl]-3-yl)methoxy)benzyl)piperidine-2-carboxylic acid;

(R)-2-((5-chloro-4-((2,2'-dichloro-3'-(3-(3-hydroxypyrrolidin-1-yl)propoxy)-[1,1'-biphenyl]-3-yl)methoxy)-2-(3,3,3-trifluoropropoxy)benzyl)amino)-2-methylpropane-1,3-diol;

(R)-2-((5-chloro-4-((2,2'-dichloro-3'-(3-(3-hydroxypyrrolidin-1-yl)propoxy)-[1,1'-biphenyl]-3-yl)methoxy)-2-(2-(dimethylamino)ethoxy)benzyl)amino)-2-methylpropane-1,3-diol;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dimethoxy propan-2-yl)amino)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((3-(hydroxymethyl)oxetan-3-yl)amino)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((1,3-dihydroxypropan-2-yl)(ethyl)amino)methyl)phenoxy)methyl)nicotinonitrile;

(R)-2-((5-chloro-4-((2,2'-dichloro-3'-(3-(3-hydroxypyrrolidin-1-yl)propoxy)-[1,1'-biphenyl]-3-yl)methoxy)-2-((2,5-dichlorobenzyl)oxy)benzyl)amino)-2-methylpropane-1,3-diol;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((cyclopropylmethyl)(1,3-dihydroxypropan-2-yl)amino)methyl)phenoxy)methyl)nicotinonitrile;

(R)-5-((4-chloro-5-((2'-chloro-3'-(3-(3-hydroxypyrrolidin-1-yl)propoxy)-2-methyl-[1,1'-biphenyl]-3-yl)methoxy)-2-(((cyclopropylmethyl)(1,3-dihydroxy-2-methylpropan-2-yl)amino)methyl)phenoxy)methyl)nicotinonitrile;

5-((4-chloro-5-((2'-chloro-3'-(3-((R)-3-hydroxypyrrolidin-1-yl)propoxy)-2-methyl-[1,1'-biphenyl]-3-yl)methoxy)-2-(((R)-3-(hydroxymethyl)morpholino)methyl)phenoxy)methyl)nicotinonitrile;

(S)-5-((4-chloro-5-((2'-chloro-3'-(3-hydroxypropoxy)-2-methyl-[1,1'-biphenyl]-3-yl)methoxy)-2-(((2,3-dihydroxypropyl)amino)methyl)phenoxy)methyl)nicotinonitrile;

(S)-5-((4-chloro-5-((2'-chloro-3'-(3-hydroxypropoxy)-2-methyl-[1,1'-biphenyl]-3-yl)methoxy)-2-(((2,3-dihydroxypropyl)amino)methyl)phenoxy)methyl)nicotinamide;

(S)-3-((2-chloro-3'-((2-chloro-5-((5-cyanopyridin-3-yl)methoxy)-4-(((1,3-dihydroxy-2-methylpropan-2-yl)amino)methyl)phenoxy)methyl)-2'-methyl-[1,1'-biphenyl]-3-yl)oxy)-N-(2,3-dihydroxypropyl)propanamide;

5-((4-chloro-5-((2'-chloro-3'-(((3 S)-1-(2,3-dihydroxypropyl)pyrrolidin-3-yl)methoxy)-2-methyl-[1,1'-biphenyl]-3-yl)methoxy)-2-(((1,3-dihydroxy-2-methylpropan-2-yl)amino)methyl)phenoxy)methyl)nicotinonitrile;

(2S)-1-(5-chloro-4-((2'-chloro-3'-(((3 S)-1-(2,3-dihydroxypropyl)pyrrolidin-3-yl)methoxy)-2-methyl-[1,1'-biphenyl]-3-yl)methoxy)-2-((5-cyanopyridin-3-yl)methoxy)benzyl)piperidine-2-carboxylic acid;

(R)-5-((4-chloro-5-((3'-(3-(3-hydroxypyrrolidin-1-yl)propoxy)-2,2'-dimethyl-[1,1'-biphenyl]-3-yl)methoxy)-2-(((2-morpholinoethyl)amino)methyl)phenoxy)methyl)nicotinonitrile;

(R)-1-(3-((3'-((2-chloro-4-((dimethylamino)methyl)-5-hydroxybenzyl)oxy)-2,2'-dimethyl-[1,1'-biphenyl]-3-yl)oxy)propyl)pyrrolidin-3-ol;

5-((4-chloro-2-(((1-hydroxy-2-(hydroxymethyl)butan-2-yl)amino)methyl)-5-((3'-(3-((1-hydroxy-2-(hydroxymethyl)butan-2-yl)amino)propoxy)-2,2'-dimethyl-[1,1'-biphenyl]-3-yl)methoxy)phenoxy)methyl)nicotinonitrile;

(S)-5-((4-chloro-5-((3'-(3-((2,3-dihydroxypropyl)amino)propoxy)-2,2'-dimethyl-[1,1'-biphenyl]-3-yl)methoxy)-2-(((1-hydroxy-2-(hydroxymethyl)butan-2-yl)amino)methyl)phenoxy)methyl)nicotinonitrile;

(R)-5-((4-chloro-2-(((1-hydroxy-2-(hydroxymethyl)butan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

5-((4-chloro-2-(((1,3-dihydroxy-2-(hydroxymethyl)propan-2-yl)amino)methyl)-5-((3'-(3-((1,3-dihydroxy-2-(hydroxymethyl)propan-2-yl)amino)propoxy)-2,2'-dimethyl-[1,1'-biphenyl]-3-yl)methoxy)phenoxy)methyl)nicotinonitrile;

(S)-5-((4-chloro-2-(((1,3-dihydroxy-2-(hydroxymethyl)propan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile;

5-((4-chloro-2-(((1-hydroxy-2-(hydroxymethyl)butan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

5-((4-chloro-2-(((1,3-dihydroxy-2-(hydroxymethyl)propan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

(R)-5-((4-chloro-2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(S)-2-((5-chloro-2-((5-cyanopyridin-3-yl)methoxy)-4-((3'-(3-(((S)-2,3-dihydroxypropyl)amino)propoxy)-2,2'-dimethyl-[1,1'-biphenyl]-3-yl)methoxy)benzyl)amino)-3-hydroxy-2-methylpropanoic acid;

5-((4-chloro-2-(((1,3-dihydroxy-2-methylpropan-2-yl)amino)methyl)-5-((2,2'-dimethyl-3'-(3-(piperidin-1-yl)propoxy)-[1,1'-biphenyl]-3-yl)methoxy)phenoxy)methyl)nicotinonitrile;

5-((4-chloro-2-(((1,3-dihydroxy-2-methylpropan-2-yl)amino)methyl)-5-((3'-(3-(4-(hydroxymethyl)piperidin-1-yl)propoxy)-2,2'-dimethyl-[1,1'-biphenyl]-3-yl)methoxy)phenoxy)methyl)nicotinonitrile;

(R)-5-((4-chloro-2-(((1,3-dihydroxy-2-methylpropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

(R)—N-(1-(3-((3'-((2-chloro-5-((5-cyanopyridin-3-yl)methoxy)-4-(((1,3-dihydroxy-2-methylpropan-2-yl)amino)methyl)phenoxy)methyl)-2,2'-dimethyl-[1,1'-biphenyl]-3-yl)oxy)propyl)pyrrolidin-3-yl)acetamide;

5-((4-chloro-2-(((1,3-dihydroxypropan-2-yl)amino)methyl)-5-((2,2'-dimethyl-3'-(3-(piperidin-1-yl)propoxy)-[1,1'-biphenyl]-3-yl)methoxy)phenoxy)methyl)nicotinonitrile;

(R)-5-((4-chloro-2-(((1,3-dihydroxypropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

(S)-5-((4-chloro-2-(((1,3-dihydroxypropan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile;

5-((4-chloro-2-(((1,3-dihydroxypropan-2-yl)amino)methyl)-5-((3'-(3-(4-(hydroxymethyl)piperidin-1-yl)propoxy)-2,2'-dimethyl-[1,1'-biphenyl]-3-yl)methoxy)phenoxy)methyl)nicotinonitrile;

(S)-5-((4-chloro-2-(((1,3-dihydroxy-2-methylpropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

(S)-5-((4-chloro-2-(((1,3-dihydroxypropan-2-yl)amino)methyl)-5-((3'-(3-(3-(hydroxymethyl)piperidin-1-yl)propoxy)-2,2'-dimethyl-[1,1'-biphenyl]-3-yl)methoxy)phenoxy)methyl)nicotinonitrile;

(S)-5-((4-chloro-2-(((1,3-dihydroxy-2-methylpropan-2-yl)amino)methyl)-5-((3'-(3-((2,3-dihydroxypropyl)amino)propoxy)-2,2'-dimethyl-[1,1'-biphenyl]-3-yl)methoxy)phenoxy)methyl)nicotinonitrile;

5-((4-chloro-5-((2-chloro-3'-(3-((3 S,4R)-3-hydroxy-4-(hydroxymethyl)piperidin-1-yl)propoxy)-2'-methyl-[1,1'-biphenyl]-3-yl)methoxy)-2-(((1,3-dihydroxypropan-2-yl)amino)methyl)phenoxy)methyl)nicotinonitrile;

(S)-5-((4-chloro-5-((2-chloro-3'-(3-((2,3-dihydroxypropyl)amino)propoxy)-2'-methyl-[1,1'-biphenyl]-3-yl)methoxy)-2-(((1,3-dihydroxypropan-2-yl)amino)methyl)phenoxy)methyl)nicotinonitrile;

(R)-5-((4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)methyl)nicotinonitrile;

5-((4-chloro-5-((2-chloro-2'-methyl-3'-(3-(piperidin-1-yl)propoxy)-[1,1'-biphenyl]-3-yl)methoxy)-2-(((1,3-dihydroxypropan-2-yl)amino)methyl)phenoxy)methyl)nicotinonitrile;

(S)-1-(5-chloro-4-((2-chloro-3'-(3-((S)-3-hydroxypyrrolidin-1-yl)propoxy)-2'-methyl-[1,1'-biphenyl]-3-yl)methoxy)-2-((5-cyanopyridin-3-yl)methoxy)benzyl)piperidine-2-carboxylic acid;

(R)-5-((4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxy-2-methylpropan-2-yl)amino)methyl)phenoxy)methyl)nicotinonitrile;

(S)-1-(5-chloro-4-((2-chloro-2'-methyl-3'-(3-(piperidin-1-yl)propoxy)-[1,1'-biphenyl]-3-yl)methoxy)-2-((5-cyanopyridin-3-yl)methoxy)benzyl)piperidine-2-carboxylic acid;

(S)-5-((4-chloro-5-((2-chloro-3'-(3-((2,3-dihydroxypropyl)amino)propoxy)-2'-methyl-[1,1'-biphenyl]-3-yl)methoxy)-2-(((1,3-dihydroxy-2-methylpropan-2-yl)amino)methyl)phenoxy)methyl)nicotinonitrile;

5-((4-chloro-5-((2-chloro-2'-methyl-3'-(3-(piperidin-1-yl)propoxy)-[1,1'-biphenyl]-3-yl)methoxy)-2-(((1,3-dihydroxy-2-methylpropan-2-yl)amino)methyl)phenoxy)methyl)nicotinonitrile;

(S)-1-(5-chloro-4-((2-chloro-2'-methyl-3'-(3-morpholinopropoxy)-[1,1'-biphenyl]-3-yl)methoxy)-2-((5-cyanopyridin-3-yl)methoxy)benzyl)piperidine-2-carboxylic acid;

(S)-1-(5-chloro-4-((2-chloro-3'-(3-(1,1-dioxidothiomorpholino)propoxy)-2'-methyl-[1,1'-biphenyl]-3-yl)methoxy)-2-((5-cyanopyridin-3-yl)methoxy)benzyl)piperidine-2-carboxylic acid;

(S)—N-(1-(3-((2'-chloro-3'-((2-chloro-5-((5-cyanopyridin-3-yl)methoxy)-4-(((1,3-dihydroxypropan-2-yl)amino)methyl)phenoxy)methyl)-2-methyl-[1,1'-biphenyl]-3-yl)oxy)propyl)pyrrolidin-3-yl)acetamide;

(R)-5-(2-((5-chloro-4-((2-chloro-3'-(3-(3-hydroxypyrrolidin-1-yl)propoxy)-2'-methyl-[1,1'-biphenyl]-3-yl)methoxy)-2-((5-cyanopyridin-3-yl)methoxy)benzyl)(1,3-dihydroxypropan-2-yl)amino)ethyl)nicotinonitrile;

(R)-2-((2-(allyloxy)-5-chloro-4-((2-chloro-3'-(3-(3-hydroxypyrrolidin-1-yl)propoxy)-2'-methyl-[1,1'-biphenyl]-3-yl)methoxy)benzyl)amino)propane-1,3-diol;

2-((5-chloro-4-((2-chloro-3'-(3-((R)-3-hydroxypyrrolidin-1-yl)propoxy)-2'-methyl-[1,1'-biphenyl]-3-yl)methoxy)-2-(2-((R)-3-hydroxypyrrolidin-1l-yl)-2-iminoethoxy)benzyl)amino)propane-1,3-diol;

(R)-2-(4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)acetamide;

(R)-2-(4-chloro-5-((2-chloro-3'-(3-(3-hydroxypyrrolidin-1-yl)propoxy)-2'-methyl-[1,1'-biphenyl]-3-yl)methoxy)-2-(((1,3-dihydroxypropan-2-yl)amino)methyl)phenoxy)-N,N-dimethylacetamide;

(R)-2-((5-chloro-4-((2-chloro-3'-(3-(3-hydroxypyrrolidin-1-yl)propoxy)-2'-methyl-[1,1'-biphenyl]-3-yl)methoxy)-2-(2,2-difluoroethoxy)benzyl)amino)propane-1,3-diol;

(R)-2-((5-chloro-4-((2-chloro-3'-(3-(3-hydroxypyrrolidin-1-yl)propoxy)-2'-methyl-[1,1'-biphenyl]-3-yl)methoxy)-2-(cyclopropylmethoxy)benzyl)amino)propane-1,3-diol;

2-((5-chloro-4-((2-chloro-3'-(3-((R)-3-hydroxypyrrolidin-1-yl)propoxy)-2'-methyl-[1,1'-biphenyl]-3-yl)

methoxy)-2-((2,2-difluorocyclopropyl)methoxy)benzyl)amino)propane-1,3-diol;

(R)-2-((5-chloro-4-((2-chloro-3'-(3-(3-hydroxypyrrolidin-1-yl)propoxy)-2'-methyl-[1,1'-biphenyl]-3-yl)methoxy)-2-((3-methylbut-2-en-1-yl)oxy)benzyl)amino)propane-1,3-diol;

tert-butyl (S)-3-(((3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)oxy)methyl)pyrrolidine-1-carboxylate;

(S)-5-((4-chloro-2-(((1,3-dihydroxypropan-2-yl)amino)methyl)-5-((2,2'-dimethyl-3'-(pyrrolidin-3-ylmethoxy)-[1,1'-biphenyl]-3-yl)methoxy)phenoxy)methyl)nicotinonitrile;

(R)-5-((4-chloro-2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(R)-5-((4-chloro-2-(((1,3-dihydroxypropan-2-yl)(methyl)amino)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(R)-5-((2-((tert-butylamino)methyl)-4-chloro-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(S)-2-((5-chloro-2-((5-cyanopyridin-3-yl)methoxy)-4-((3'-(3-(3,5-dioxopiperazin-1-yl)propoxy)-2,2'-dimethyl-[1,1'-biphenyl]-3-yl)methoxy)benzyl)amino)-3-hydroxy-2-methylpropanoic acid;

(S)-2-((5-chloro-2-((5-cyanopyridin-3-yl)methoxy)-4-((2,2'-dimethyl-3'-(3-(4-methyl-3-oxopiperazin-1-yl)propoxy)-[1,1'-biphenyl]-3-yl)methoxy)benzyl)amino)-3-hydroxy-2-methylpropanoic acid;

(R)-5-((4-chloro-2-((3,5-dioxopiperazin-11-yl)methyl)-5-((3'-(3-(3-hydroxypyrrolidin-1-yl)propoxy)-2,2'-dimethyl-[1,1'-biphenyl]-3-yl)methoxy)phenoxy)methyl)nicotinonitrile;

(R)-5-((4-chloro-5-((3'-(3-(3-hydroxypyrrolidin-1-yl)propoxy)-2,2'-dimethyl-[1,1'-biphenyl]-3-yl)methoxy)-2-((4-methyl-3-oxopiperazin-1-yl)methyl)phenoxy)methyl)nicotinonitrile;

(R)-5-((4-chloro-5-((3'-(3-(3-hydroxypyrrolidin-1-yl)propoxy)-2,2'-dimethyl-[1,1'-biphenyl]-3-yl)methoxy)-2-((3-oxopiperazin-1-yl)methyl)phenoxy)methyl)nicotinonitrile;

(S)-1-(5-chloro-2-((5-cyanopyridin-3-yl)methoxy)-4-((3'-(3-(((S)-2,3-dihydroxypropyl)(methyl)amino)propoxy)-2,2'-dimethyl-[1,1'-biphenyl]-3-yl)methoxy)benzyl)piperidine-2-carboxylic acid;

(S)-1-(5-chloro-2-((5-cyanopyridin-3-yl)methoxy)-4-((3'-(3-(((S)-2,3-dihydroxypropyl)amino)propoxy)-2,2'-dimethyl-[1,1'-biphenyl]-3-yl)methoxy)benzyl)piperidine-2-carboxylic acid;

5-((4-chloro-2-((2-(hydroxymethyl)piperidin-1-yl)methyl)-5-((3'-(3-((R)-3-hydroxypyrrolidin-1-yl)propoxy)-2,2'-dimethyl-[1,1'-biphenyl]-3-yl)methoxy)phenoxy)methyl)nicotinonitrile;

(2S)-1-(5-chloro-2-((5-cyanopyridin-3-yl)methoxy)-4-((3'-(((3R)-1-(2,3-dihydroxypropyl)piperidin-3-yl)methoxy)-2,2'-dimethyl-[1,1'-biphenyl]-3-yl)methoxy)benzyl)piperidine-2-carboxylic acid;

(R)-4-(3-((3'-((4-(((4-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-methylmorpholin-4-ium;

N-(3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)-3-(hydroxymethyl)picolinamide;

(R)-2-((5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)amino)-3-hydroxy-2-methylpropanoic acid;

(R)-5-((4-chloro-2-(((1,3-dihydroxypropan-2-yl)amino)methyl)-5-((3'-((1-((3-hydroxypyrrolidin-1-yl)methyl)cyclopropyl)methoxy)-2,2'-dimethyl-[1,1'-biphenyl]-3-yl)methoxy)phenoxy)methyl)nicotinonitrile;

1-(3'-((2-chloro-5-((5-cyanopyridin-3-yl)methoxy)-4-formylphenoxy)methyl)-2,2'-dimethyl-[1,1'-biphenyl]-3-yl)-3-(cyclopropylmethyl)urea;

(S)-1-(5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)piperidine-2-carboxylic acid;

N-(3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)-2-(cyclopropylamino)acetamide;

(S)-2-((5-chloro-2-((5-cyanopyridin-3-yl)methoxy)-4-((3'-((1-(((R)-3-hydroxypyrrolidin-1-yl)methyl)cyclopropyl)methoxy)-2,2'-dimethyl-[1,1'-biphenyl]-3-yl)methoxy)benzyl)amino)-3-hydroxy-2-methylpropanoic acid;

5-((4-chloro-2-(((1,3-dihydroxypropan-2-yl)amino)methyl)-5-((2,2'-dimethyl-4'-(morpholine-4-carbonyl)-[1,1'-biphenyl]-3-yl)methoxy)phenoxy)methyl)nicotinonitrile;

5-((4-chloro-2-(((1,3-dihydroxypropan-2-yl)amino)methyl)-5-((2,2'-dimethyl-3'-((6-morpholinopyrimidin-4-yl)amino)-[1,1'-biphenyl]-3-yl)methoxy)phenoxy)methyl)nicotinonitrile;

1-(3'-((2-chloro-5-((5-cyanopyridin-3-yl)methoxy)-4-formylphenoxy)methyl)-2,2'-dimethyl-[1,1'-biphenyl]-3-yl)-3-(pyridin-2-yl)urea;

5-((4-chloro-5-((2,2'-dimethyl-3'-((1-oxo-1,2,3,4-tetrahydroisoquinolin-5-yl)oxy)-[1,1'-biphenyl]-3-yl)methoxy)-2-formylphenoxy)methyl)nicotinonitrile;

5-((4-chloro-2-(((1,3-dihydroxypropan-2-yl)amino)methyl)-5-((2,2'-dimethyl-3'-((1-oxo-1,2,3,4-tetrahydroisoquinolin-5-yl)oxy)-[1,1'-biphenyl]-3-yl)methoxy)phenoxy)methyl)nicotinonitrile;

(S)-1-(4-((3'-(3-(4-carboxypiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

4-nitrophenyl (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylate;

(R)-5-chloro-2-((5-cyanopyridin-3-yl)methoxy)-N-(1,3-dihydroxy-2-methylpropan-2-yl)-4-((3'-(3-(3-hydroxypyrrolidin-11-yl)propoxy)-2,2'-dimethyl-[1,1'-biphenyl]-3-yl)methoxy)benzamide;

(R)-5-chloro-2-((5-cyanopyridin-3-yl)methoxy)-N-(2-hydroxyethyl)-4-((3'-(3-(3-hydroxypyrrolidin-1-yl)propoxy)-2,2'-dimethyl-[1,1'-biphenyl]-3-yl)methoxy)benzamide;

(S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzoyl)piperidine-2-carboxylic acid;

1-(3-((3'-((2-chloro-5-((5-cyanopyridin-3-yl)methoxy)-4-formylphenoxy)methyl)-2,2'-dimethyl-[1,1'-biphenyl]-3-yl)oxy)propyl)-4-hydroxypiperidine-4-carboxylic acid;

(R)-2-((5-chloro-2-((5-cyanopyridin-3-yl)methoxy)-4-((3'-3-((R)-3-hydroxypyrrolidin-1-yl)propoxy)-2-methyl-5'-(phenylethynyl)-[1,1'-biphenyl]-3-yl)methoxy)benzyl)amino)-3-hydroxy-2-methylpropanoic acid;

(S)-1-(4-((3'-(3-((1R,5 S)-8-oxa-3-azabicyclo[3.2.1]octan-3-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(S)-1-(5-chloro-2-((5-cyanopyridin-3-yl)methoxy)-4-((3'-(3-((R)-2-(hydroxymethyl)morpholino) propoxy)-2,2'-dimethyl-[1,1'-biphenyl]-3-yl)methoxy)benzyl)piperidine-2-carboxylic acid;

(2S)-1-(5-chloro-2-((5-cyanopyridin-3-yl)methoxy)-4-((3'-(3-((1R, 5 S)-3-hydroxy-8-azabicyclo[3.2.1]octan-8-yl)propoxy)-2,2'-dimethyl-[1,1'-biphenyl]-3-yl)methoxy)benzyl)piperidine-2-carboxylic acid;

(S)-1-(5-chloro-2-((5-cyanopyridin-3-yl)methoxy)-4-((3'-(3-((2S,6R)-2,6-dimethylmorpholino)propoxy)-2,2'-dimethyl-[1,1'-biphenyl]-3-yl)methoxy)benzyl)piperidine-2-carboxylic acid;

(2S)-1-(5-chloro-2-((5-cyanopyridin-3-yl)methoxy)-4-((3'-(3-(3-(hydroxymethyl)morpholino)propoxy)-2,2'-dimethyl-[1,1'-biphenyl]-3-yl)methoxy)benzyl)piperidine-2-carboxylic acid;

(S)-1-(4-((3'-(3-((1R,5 S)-3-oxa-8-azabicyclo[3.2.1]octan-8-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(S)-1-(4-((3'-(3-((1 s,5s)-3,7-dioxa-9-azabicyclo[3.3.1]nonan-9-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(S)-methyl 1-(5-chloro-2-((3-cyanobenzyl)oxy)-A-((2,2'-dimethyl-3'-(3-morpholinopropoxy)-[1,1'-biphenyl]-3-yl)methoxy)benzyl)piperidine-2-carboxylate, 2 TFA;

(S)-1-(5-chloro-2-((3-cyanobenzyl)oxy)-4-((2,2'-dimethyl-3'-(3-morpholinopropoxy)-[1,1'-biphenyl]-3-yl)methoxy)benzyl)piperidine-2-carboxylic acid;

(S)-1-(4-((3'-(3-((1R,5 S)-3-oxa-8-azabicyclo[3.2.1]octan-8-yl)propoxy)-2,2'-dimethyl-[1,1'-biphenyl]-3-yl)methoxy)-5-chloro-2-((3-cyanobenzyl)oxy)benzyl)piperidine-2-carboxylic acid;

(2S)-1-(5-chloro-2-((5-cyanopyridin-3-yl)methoxy)-4-((2,2'-dimethyl-3'-(3-(2-phenylmorpholino) propoxy)-[1,1'-biphenyl]-3-yl)methoxy)benzyl)piperidine-2-carboxylic acid;

(S)-1-(5-chloro-2-((5-cyanopyridin-3-yl)methoxy)-4-((3'-(3-((R)-3-fluoropyrrolidin-1-yl)propoxy)-2,2'-dimethyl-[1,1'-biphenyl]-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(2-(trifluoromethyl)morpholino)propoxy)-[1,1'-biphenyl]-3-yl)methoxy)benzyl)piperidine-2-carboxylic acid;

(S)-1-(5-chloro-2-((5-cyanopyridin-3-yl)methoxy)-4-((2,2'-dimethyl-3'-(4-methylpiperazine-1-carbonyl)-[1,1'-biphenyl]-3-yl)methoxy)benzyl)piperidine-2-carboxylic acid;

(S)-1-(5-chloro-2-((5-cyanopyridin-3-yl)methoxy)-4-((3'-((2-((R)-3-hydroxypyrrolidin-1-yl)ethyl)carbamoyl)-2,2'-dimethyl-[1,1'-biphenyl]-3-yl)methoxy)benzyl)piperidine-2-carboxylic acid;

(S)-2-(((3'-((4-(((((S)-1-carboxy-4-guanidinobutyl)amino)methyl)-2-chloro-5-((5-cyanopyridin-3-yl)methoxy)phenoxy)methyl)-2'-methyl-[1,1'-biphenyl]-3-yl)methyl)amino)-5-guanidinopentanoic acid;

5-((4-chloro-2-(((3-(dimethylamino)propyl)amino)methyl)-5-((3'-(((3-(dimethylamino)propyl)amino)methyl)-2-methyl-[1,1'-biphenyl]-3-yl)methoxy)phenoxy)methyl)nicotinonitrile;

5-((5-((3',5'-bis(3-((R)-3-hydroxypyrrolidin-1-yl)propoxy)-2-methyl-[1,1'-biphenyl]-3-yl)methoxy)-4-chloro-2-(hydroxymethyl)phenoxy)methyl)nicotinonitrile;

(S)-2-((4-((3',5'-bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

(S)-2-((4-((3',5'-bis(3-((R)-3-hydroxypyrrolidin-1-yl)propoxy)-2-methyl-[1,1'-biphenyl]-3-yl)methoxy)-5-chloro-2-((5-cyanopyridin-3-yl)methoxy)benzyl)amino)-3-hydroxypropanoic acid;

(S)-ethyl 2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxypropanoate;

methyl (S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylate;

methyl 1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylate;

(S)-1-(4-((3'-(aziridine-1-carbonyl)-2,2'-dimethyl-[1,1'-biphenyl]-3-yl)methoxy)-5-chloro-2-((5-cyanopyridin-3-yl)methoxy)benzyl)piperidine-2-carboxylic acid;

(S)-1-(5-chloro-2-((5-cyanopyridin-3-yl)methoxy)-4-((2,2'-dimethyl-3'-((2-(pyrrolidin-1-yl)ethyl)carbamoyl)-[1,1'-biphenyl]-3-yl)methoxy)benzyl)piperidine-2-carboxylic acid;

3'-((2-chloro-5-((5-cyanopyridin-3-yl)methoxy)-4-(((1,3-dihydroxypropan-2-yl)amino)methyl)phenoxy)methyl)-2,2'-dimethyl-N-(2-(pyrrolidin-1-yl)ethyl)-[1,1'-biphenyl]-3-carboxamide;

(S)-1-(5-chloro-2-((5-cyanopyridin-3-yl)methoxy)-4-((3'-((2-(1,1-dioxidothiomorpholino)ethyl)carbamoyl)-2,2'-dimethyl-[1,1'-biphenyl]-3-yl)methoxy)benzyl)piperidine-2-carboxylic acid;

3'-((2-chloro-5-((5-cyanopyridin-3-yl)methoxy)-4-(((1,3-dihydroxypropan-2-yl)amino)methyl)phenoxy)methyl)-N-(2-(1,1-dioxidothiomorpholino)ethyl)-2,2'-dimethyl-[1,1'-biphenyl]-3-carboxamide;

(S)-1-(5-chloro-2-((5-cyanopyridin-3-yl)methoxy)-4-((3'-(ethylcarbamoyl)-2,2'-dimethyl-[1,1'-biphenyl]-3-yl)methoxy)benzyl)piperidine-2-carboxylic acid;

(5-chloro-2-((5-cyanopyridin-3-yl)methoxy)-4-((3'-(ethylcarbamoyl)-2,2'-dimethyl-[1,1'-biphenyl]-3-yl)methoxy)benzyl)-L-proline;

(2S,4R)-1-(5-chloro-2-((5-cyanopyridin-3-yl)methoxy)-4-((3'-(ethylcarbamoyl)-2,2'-dimethyl-[1,1'-biphenyl]-3-yl)methoxy)benzyl)-4-hydroxypyrrolidine-2-carboxylic acid;

3'-((2-chloro-5-((5-cyanopyridin-3-yl)methoxy)-4-(((1,3-dihydroxypropan-2-yl)amino)methyl)phenoxy)methyl)-N-ethyl-2,2'-dimethyl-[1,1'-biphenyl]-3-carboxamide;

3'-((2-chloro-5-((5-cyanopyridin-3-yl)methoxy)-4-(((1,3-dihydroxy-2-methylpropan-2-yl)amino)methyl)phenoxy)methyl)-N-ethyl-2,2'-dimethyl-[1,1'-biphenyl]-3-carboxamide;

(S)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)piperidine-2-carboxylic acid;

(5-chloro-2-((5-cyanopyridin-3-yl)methoxy)-4-((2,2'-dimethyl-3'-(methylcarbamoyl)-[1,1'-biphenyl]-3-yl)methoxy)benzyl)-L-proline;

(2S,4R)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)-4-hydroxypyrrolidine-2-carboxylic acid;

(2S,4S)-1-(5-chloro-2-((5-cyanopyridin-3-yl)methoxy)-4-((2,2'-dimethyl-3'-(methylcarbamoyl)-[1,1'-biphenyl]-3-yl)methoxy)benzyl)-4-hydroxypyrrolidine-2-carboxylic acid;

3'-((2-chloro-5-((5-cyanopyridin-3-yl)methoxy)-4-(((1,3-dihydroxypropan-2-yl)amino)methyl)phenoxy)methyl)-N,2,2'-trimethyl-[1,1'-biphenyl]-3-carboxamide;

3'-((2-chloro-5-((5-cyanopyridin-3-yl)methoxy)-4-(((1,3-dihydroxy-2-methylpropan-2-yl)amino)methyl)phenoxy)methyl)-N,2,2'-trimethyl-[1,1'-biphenyl]-3-carboxamide;

(S)-1-(5-chloro-2-((3,5-difluorobenzyl)oxy)-4-((3'-(ethylcarbamoyl)-2,2'-dimethyl-[1,1'-biphenyl]-3-yl)methoxy)benzyl)piperidine-2-carboxylic acid;

(5-chloro-2-((3,5-difluorobenzyl)oxy)-4-((3'-(ethylcarbamoyl)-2,2'-dimethyl-[1,1'-biphenyl]-3-yl)methoxy)benzyl)-L-proline;

(2S,4R)-1 (5-chloro-2-((3,5-difluorobenzyl)oxy)-4-((3'-(ethylcarbamoyl)-2,2'-dimethyl-[1,1'-biphenyl]-3-yl)methoxy)benzyl)-4-hydroxypyrrolidine-2-carboxylic acid;

(S)-4-(5-chloro-2-((3,5-difluorobenzyl)oxy)-4-((3'-(ethylcarbamoyl)-2,2'-dimethyl-[1,1'-biphenyl]-3-yl)methoxy)benzyl)morpholine-3-carboxylic acid;

3'-((2-chloro-5-((3,5-difluorobenzyl)oxy)-4-(((1,3-dihydroxypropan-2-yl)amino)methyl)phenoxy)methyl)-N-ethyl-2,2'-dimethyl-[1,1'-biphenyl]-3-carboxamide;

3'-((2-chloro-5-((3,5-difluorobenzyl)oxy)-4-(((1,3-dihydroxy-2-methylpropan-2-yl)amino)methyl)phenoxy)methyl)-N-ethyl-2,2'-dimethyl-[1,1'-biphenyl]-3-carboxamide;

(S)-1-(5-chloro-2-((3,5-difluorobenzyl)oxy)-4-((2,2'-dimethyl-3'-(methylcarbamoyl)-[1,1'-biphenyl]-3-yl)methoxy)benzyl)piperidine-2-carboxylic acid;

(5-chloro-2-((3,5-difluorobenzyl)oxy)-4-((2,2'-dimethyl-3'-(methylcarbamoyl)-[1,1'-biphenyl]-3-yl)methoxy)benzyl)-L-proline;

(2S,4R)-1-(5-chloro-2-((3,5-difluorobenzyl)oxy)-4-((2,2'-dimethyl-3'-(methylcarbamoyl)-[1,1'-biphenyl]-3-yl)methoxy)benzyl)-4-hydroxypyrrolidine-2-carboxylic acid;

(2S,4S)-1-(5-chloro-2-((3,5-difluorobenzyl)oxy)-4-((2,2'-dimethyl-3'-(methylcarbamoyl)-[1,1'-biphenyl]-3-yl)methoxy)benzyl)-4-hydroxypyrrolidine-2-carboxylic acid;

(S)-4-(5-chloro-2-((3,5-difluorobenzyl)oxy)-4-((2,2'-dimethyl-3'-(methylcarbamoyl)-[1,1'-biphenyl]-3-yl)methoxy)benzyl)morpholine-3-carboxylic acid;

3'-((2-chloro-5-((3,5-difluorobenzyl)oxy)-4-formylphenoxy)methyl)-N,2,2'-trimethyl-[1,1'-biphenyl]-3-carboxamide;

3'-((2-chloro-5-((3,5-difluorobenzyl)oxy)-4-(((1,3-dihydroxy-2-methylpropan-2-yl)amino)methyl)phenoxy)methyl)-N,2,2'-trimethyl-[1,1'-biphenyl]-3-carboxamide;

(S)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)piperidine-2-carboxylic acid;

(5-chloro-2-((5-cyanopyridin-3-yl)methoxy)-A-((3'-(dimethylcarbamoyl)-2,2'-dimethyl-[1,1'-biphenyl]-3-yl)methoxy)benzyl)-L-proline;

(2S,4R)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)-4-hydroxypyrrolidine-2-carboxylic acid;

(2S,4S)-1-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)-4-hydroxypyrrolidine-2-carboxylic acid;

3'-((2-chloro-5-((5-cyanopyridin-3-yl)methoxy)-4-(((1,3-dihydroxypropan-2-yl)amino)methyl)phenoxy)methyl)-N,N,2,2'-tetramethyl-[1,1'-biphenyl]-3-carboxamide;

3'-((2-chloro-5-((5-cyanopyridin-3-yl)methoxy)-4-(((1,3-dihydroxy-2-methylpropan-2-yl)amino)methyl)phenoxy)methyl)-N,N,2,2'-tetramethyl-[1,1'-biphenyl]-3-carboxamide;

(S)-4-(5-chloro-2-((5-cyanopyridin-3-yl)methoxy)-4-((3'-(dimethylcarbamoyl)-2,2'-dimethyl-[1,1'-biphenyl]-3-yl)methoxy)benzyl)morpholine-3-carboxylic acid;

(S)-1-(5-chloro-2-((5-cyanopyridin-3-yl)methoxy)-4-((2,2'-dimethyl-3'-(pyrrolidine-1-carbonyl)-[1,1'-biphenyl]-3-yl)methoxy)benzyl)piperidine-2-carboxylic acid;

5-((4-chloro-2-(((1,3-dihydroxypropan-2-yl)amino)methyl)-5-((2,2'-dimethyl-3'-(pyrrolidine-1-carbonyl)-[1,1'-biphenyl]-3-yl)methoxy)phenoxy)methyl)nicotinonitrile;

5-((4-chloro-2-(((1,3-dihydroxy-2-methylpropan-2-yl)amino)methyl)-5-((2,2'-dimethyl-3'-(pyrrolidine-1-carbonyl)-[1,1'-biphenyl]-3-yl)methoxy)phenoxy)methyl)nicotinonitrile;

(S)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)piperidine-2-carboxylic acid;

(5-chloro-2-((5-cyanopyridin-3-yl)methoxy)-A-((3'-(diethylcarbamoyl)-2,2'-dimethyl-[1,1'-biphenyl]-3-yl)methoxy)benzyl)-L-proline;

(2S,4R)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)-4-hydroxypyrrolidine-2-carboxylic acid;

(2S,4S)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)-4-hydroxypyrrolidine-2-carboxylic acid;

3'-((2-chloro-5-((5-cyanopyridin-3-yl)methoxy)-4-(((1,3-dihydroxypropan-2-yl)amino)methyl)phenoxy)methyl)-N,N-diethyl-2,2'-dimethyl-[1,1'-biphenyl]-3-carboxamide;

3'-((2-chloro-5-((5-cyanopyridin-3-yl)methoxy)-4-(((1,3-dihydroxy-2-methylpropan-2-yl)amino)methyl)phenoxy)methyl)-N,N-diethyl-2,2'-dimethyl-[1,1'-biphenyl]-3-carboxamide;

(S)-4-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)morpholine-3-carboxylic acid;

(S)-4-(tert-butoxycarbonyl)-1-(5-chloro-2-((5-cyanopyridin-3-yl)methoxy)-4-((3'-(diethylcarbamoyl)-2,2'-dimethyl-[1,1'-biphenyl]-3-yl)methoxy)benzyl)piperazine-2-carboxylic acid;

(S)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperidine-2-carboxylic acid;

(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-L-proline;

(2S,4R)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-4-hydroxypyrrolidine-2-carboxylic acid;

(2S,4S)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-4-hydroxypyrrolidine-2-carboxylic acid;

5-((4-chloro-2-(((1,3-dihydroxypropan-2-yl)amino)methyl)-5-((2,2'-dimethyl-3'-(morpholine-4-carbonyl)-[1,1'-biphenyl]-3-yl)methoxy)phenoxy)methyl)nicotinonitrile;

5-((4-chloro-2-(((1,3-dihydroxy-2-methylpropan-2-yl)amino)methyl)-5-((2,2'-dimethyl-3'-(morpholine-4-carbonyl)-[1,1'-biphenyl]-3-yl)methoxy)phenoxy)methyl)nicotinonitrile;

(S)-4-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)morpholine-3-carboxylic acid;

(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)-L-serine;

(S)-3-((tert-butoxycarbonyl)amino)-2-((5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)amino)propanoic acid;

(S)-4-(tert-butoxycarbonyl)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperazine-2-carboxylic acid;

5-((4-chloro-2-(((1,3-dihydroxy-2-(hydroxymethyl)propan-2-yl)amino)methyl)-5-((2,2'-dimethyl-3'-(morpholine-4-carbonyl)-[1,1'-biphenyl]-3-yl)methoxy)phenoxy)methyl)nicotinonitrile;

(S)-3-amino-2-((5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)amino)propanoic acid;

(S)-1-(5-chloro-2-((5-cyanopyridin-3-yl)methoxy)-4-((2,2'-dimethyl-3'-(morpholine-4-carbonyl)-[1,1'-biphenyl]-3-yl)methoxy)benzyl)piperazine-2-carboxylic acid;

(S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperidine-2-carboxylic acid;

(2S,4R)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)-4-hydroxypyrrolidine-2-carboxylic acid;

(2S,4S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)-4-hydroxypyrrolidine-2-carboxylic acid;

(R)-5-((4-chloro-2-(((1,3-dihydroxypropan-2-yl)amino)methyl)-5-((3'-(4-(3-hydroxypyrrolidin-1-yl)butyl)-2,2'-dimethyl-[1,1'-biphenyl]-3-yl)methoxy)phenoxy)methyl)nicotinonitrile;

(R)-5-((4-chloro-2-(((1,3-dihydroxy-2-methylpropan-2-yl)amino)methyl)-5-((3'-(4-(3-hydroxypyrrolidin-1-yl)butyl)-2,2'-dimethyl-[1,1'-biphenyl]-3-yl)methoxy)phenoxy)methyl)nicotinonitrile;

(R)-5-((4-chloro-2-(((1,3-dihydroxy-2-(hydroxymethyl)propan-2-yl)amino)methyl)-5-((3'-(4-(3-hydroxypyrrolidin-1-yl)butyl)-2,2'-dimethyl-[1,1'-biphenyl]-3-yl)methoxy)phenoxy)methyl)nicotinonitrile;

(S)-3-((tert-butoxycarbonyl)amino)-2-((5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)amino)propanoic acid;

(S)-4-(tert-butoxycarbonyl)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperazine-2-carboxylic acid;

(S)-3-amino-2-((5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)amino)propanoic acid;

(S)-1-(5-chloro-2-((5-cyanopyridin-3-yl)methoxy)-4-((3'-(4-((R)-3-hydroxypyrrolidin-1-yl)butyl)-2,2'-dimethyl-[1,1'-biphenyl]-3-yl)methoxy)benzyl)piperazine-2-carboxylic acid;

(S)-1-(5-chloro-2-((5-cyanopyridin-3-yl)methoxy)-4-((3'-(((2-(1,1-dioxidothiomorpholino)ethyl)(methyl)amino)methyl)-2,2'-dimethyl-[1,1'-biphenyl]-3-yl)methoxy)benzyl)piperidine-2-carboxylic acid;

5-((4-chloro-2-(((1,3-dihydroxypropan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile;

(S)-2-((5-chloro-2-((5-cyanopyridin-3-yl)methoxy)-4-((3'-(((2-(1,1-dioxidothiomorpholino)ethyl)(methyl)amino)methyl)-2,2'-dimethyl-[1,1'-biphenyl]-3-yl)methoxy)benzyl)amino)-3-hydroxy-2-methylpropanoic acid;

5-((4-chloro-2-(((1,3-dihydroxy-2-methylpropan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile;

5-((4-chloro-2-(((1,3-dihydroxy-2-(hydroxymethyl)propan-2-yl)amino)methyl)-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile;

5-((2-((bis(2-hydroxyethyl)amino)methyl)-4-chloro-5-((3'-(((2-(1,1-dioxidothiomorpholino)ethyl)(methyl)amino)methyl)-2,2'-dimethyl-[1,1'-biphenyl]-3-yl)methoxy)phenoxy)methyl)nicotinonitrile;

5-((4-chloro-5-((3'-(((2-(1,1-dioxidothiomorpholino)ethyl)(methyl)amino)methyl)-2,2'-dimethyl-[1,1'-biphenyl]-3-yl)methoxy)-2-(((2-hydroxyethyl)(3-hydroxypropyl)amino)methyl)phenoxy)methyl)nicotinonitrile;

(S)-1-(2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-6-methylbenzyl)piperidine-2-carboxylic acid;

(R)-5-((2-(((1,3-dihydroxypropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((2-((bis(2-hydroxyethyl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(S)-2-((2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-6-methylbenzyl)amino)-3-hydroxy-2-methylpropanoic acid;

(S)-2-((3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)(methyl)amino)-3-hydroxy-2-methylpropanoic acid;

(S)-1-(3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)piperidine-2-carboxylic acid;

(R)-5-((4-chloro-2-(((1,3-dihydroxypropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((4-chloro-2-(((1,3-dihydroxy-2-methylpropan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((4-chloro-2-(((1,3-dihydroxy-2-(hydroxymethyl)propan-2-yl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(R)-5-((2-((bis(2-hydroxyethyl)amino)methyl)-4-chloro-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(S)-2-((3-chloro-6-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)-2-methylbenzyl)amino)-3-hydroxy-2-methylpropanoic acid;

(R)-5-((4-chloro-2-(((1,3-dihydroxy-2-methylpropan-2-yl)(methyl)amino)methyl)-5-((3'-(3-(3-hydroxypyrrolidin-1-yl)propoxy)-2,2'-dimethyl-[1,1'-biphenyl]-3-yl)methoxy)-3-methylphenoxy)methyl)nicotinonitrile;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(methyl)amino)-3-hydroxy-2-methylpropanoic acid;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(ethyl)amino)-3-hydroxy-2-methylpropanoic acid;

(R)-1-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)cyclopropane-1-carboxylic acid;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)(2-hydroxyethyl)amino)-3-hydroxy-2-methylpropanoic acid;

(S)-1-(5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)piperidine-2-carboxylic acid;

5-((4-chloro-5-((3'-(3-(3,3-difluoropyrrolidin-1-yl)propoxy)-2,2'-dimethyl-[1,1'-biphenyl]-3-yl)methoxy)-2-(((2-hydroxyethyl)(3-hydroxypropyl)amino)methyl)phenoxy)methyl)nicotinonitrile;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-methylpropan-2-yl)(methyl)amino)methyl)phenoxy)methyl)nicotinonitrile;

(S)-2-((5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)(methyl)amino)-3-hydroxy-2-methylpropanoic acid;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxypropan-2-yl)amino)methyl)phenoxy)methyl)nicotinonitrile;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-methylpropan-2-yl)amino)methyl)phenoxy)methyl)nicotinonitrile;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-(hydroxymethyl)propan-2-yl)amino)methyl)phenoxy)methyl)nicotinonitrile;

(S)-2-((5-chloro-2-((5-cyanopyridin-3-yl)methoxy)-4-((3'-(3-(3,3-difluoropyrrolidin-1-yl)propoxy)-2,2'-dimethyl-[1,1'-biphenyl]-3-yl)methoxy)benzyl)amino)-3-hydroxy-2-methylpropanoic acid;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxypropan-2-yl)(methyl)amino)methyl)phenoxy)methyl)nicotinonitrile;

5-((4-chloro-5-((3'-(3-(3,3-difluoropyrrolidin-1-yl)propoxy)-2,2'-dimethyl-[1,1'-biphenyl]-3-yl)methoxy)-2-(((1,3-dihydroxy-2-(hydroxymethyl)propan-2-yl)(methyl)amino)methyl)phenoxy)methyl)nicotinonitrile;

(R)-5-((4-chloro-2-(((1,3-dihydroxypropan-2-yl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile;

(S)-2-((5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)amino)-3-hydroxy-2-methylpropanoic acid;

(R)-1-((5-chloro-2-((5-cyanopyridin-3-yl)methoxy)-4-((3'-((2-(3-hydroxypyrrolidin-1-yl)ethoxy)methyl)-2,2'-dimethyl-[1,1'-biphenyl]-3-yl)methoxy)benzyl)amino)cyclopropane-1-carboxylic acid;

(R)-5-((4-chloro-2-(((1,3-dihydroxy-2-(hydroxymethyl)propan-2-yl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile;

(S)-1-(5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)piperidine-2-carboxylic acid;

(R)-5-((4-chloro-2-(((1,3-dihydroxypropan-2-yl)(methyl) amino)methyl)-5-((3'-((2-(3-hydroxypyrrolidin-1-yl) ethoxy)methyl)-2,2'-dimethyl-[1,1'-biphenyl]-3-yl) methoxy)phenoxy)methyl)nicotinonitrile;

(R)-5-((4-chloro-2-(((1,3-dihydroxy-2-methylpropan-2-yl)(methyl)amino)methyl)-5-((3'-((2-(3-hydroxypyrrolidin-1-yl)ethoxy)methyl)-2,2'-dimethyl-[1,1'-biphenyl]-3-yl)methoxy)phenoxy)methyl)nicotinonitrile;

(R)-1-((5-chloro-2-((5-cyanopyridin-3-yl)methoxy)-4-((3'-((2-(3-hydroxypyrrolidin-1-yl)ethoxy)methyl)-2,2'-dimethyl-[1,1'-biphenyl]-3-yl)methoxy)benzyl) (methyl)amino)cyclopropane-1-carboxylic acid;

N-(5-chloro-2-((5-cyanopyridin-3-yl)methoxy)-4-((3'-((2-((R)-3-hydroxypyrrolidin-1-yl)ethoxy)methyl)-2,2'-dimethyl-[1,1'-biphenyl]-3-yl)methoxy)benzyl)-N-methyl-L-serine;

(R)-5-((4-chloro-2-(((1,3-dihydroxy-2-methylpropan-2-yl)amino)methyl)-5-((3'-((2-(3-hydroxypyrrolidin-1-yl)ethoxy)methyl)-2,2'-dimethyl-[1,1'-biphenyl]-3-yl) methoxy)phenoxy)methyl)nicotinonitrile;

N-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-N-methyl-L-alanine;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl) (methyl)amino)butanoic acid;

(R)-1-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)(methyl) amino)cyclopropane-1-carboxylic acid;

N-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-N-methyl-L-homoserine;

N-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-N-methyl-L-serine;

5-((4-chloro-2-(1-((1,3-dihydroxypropan-2-yl)amino) ethyl)-5-((3'-(3-((R)-3-hydroxypyrrolidin-1-yl) propoxy)-2,2'-dimethyl-[1,1'-biphenyl]-3-yl)methoxy) phenoxy)methyl)nicotinonitrile;

(2S,4R)-1-(1-(5-chloro-2-((5-cyanopyridin-3-yl) methoxy)-4-((3'-(3-((R)-3-hydroxypyrrolidin-1-yl) propoxy)-2,2'-dimethyl-[1,1'-biphenyl]-3-yl)methoxy) phenyl)ethyl)-4-hydroxypyrrolidine-2-carboxylic acid;

N-(1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)phenyl)ethyl)-N-methyl-L-serine;

5-((4-chloro-2-(1-((1,3-dihydroxypropan-2-yl)(methyl) amino)ethyl)-5-((3'-(3-((R)-3-hydroxypyrrolidin-1-yl) propoxy)-2,2'-dimethyl-[1,1'-biphenyl]-3-yl)methoxy) phenoxy)methyl)nicotinonitrile;

(1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)phenyl)ethyl)-L-serine;

(R)-(5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)glycine;

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-threonine;

(R)-3-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)propanoic acid;

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-valine;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino) hexanoic acid;

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-phenylalanine;

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-leucine;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino) pentanoic acid;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino) pent-4-enoic acid;

(S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl) amino)-2-phenylacetic acid;

(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-L-tyrosine;

(R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol;

(R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol;

(S)-1-(5-chloro-2-((3,5-dichlorobenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(R)-2-((5-chloro-2-((3,5-dichlorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol;

(R)-2-((5-chloro-2-((3,4-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol;

(R)-2-((5-chloro-2-((3,4-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol;

(R)-2-((5-chloro-2-((3,4-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol;

(S)-1-(5-chloro-2-((3,4-dimethylbenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol;

(R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol;

(R)-2-((5-chloro-2-((3,4-difluorobenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol;

(S)-1-(5-chloro-2-((3,4-difluorobenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(R)-2-((5-chloro-2-((2,6-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)propane-1,3-diol;

(R)-2-((5-chloro-2-((2,6-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-methylpropane-1,3-diol;

(R)-2-((5-chloro-2-((2,6-dimethylbenzyl)oxy)-4-((3'-(3-(3-hydroxypyrrolidin-1-yl)propoxy)-2,2'-dimethyl-[1,1'-biphenyl]-3-yl)methoxy)benzyl)amino)-2-(hydroxymethyl)propane-1,3-diol;

(S)-1-(5-chloro-2-((2,6-dimethylbenzyl)oxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(R)-2-((5-chloro-2-((3,5-difluorobenzyl)oxy)-4-((3'(3-(3-hydroxypyrrolidin-1-yl)propoxy)-2,2'-dimethyl-[1,1') biphenyl]-3-yl)methoxy)benzyl)amino)-2-methylpropane-1,3-diol;

(S)-1-(5-chloro-2-((3,5-difluorobenzyl)oxy)-4-((3'-(3-((3-hydroxypyrrolidin-1-yl)propoxy)-2,2'-dimethyl-[1,1'-biphenyl]-3-yl)methoxy)benzyl)piperidine-2-carboxylic acid;

(R)-1-(3-((3'-((2-chloro-5-((3,5-difluorobenzyl)oxy)-4-(hydroxymethyl)phenoxy)methyl)-2,2'-dimethyl-[1,1'-biphenyl]-3-yl)oxy)propyl)pyrrolidin-3-ol; and (S)-2-((5-chloro-2-((5-cyanopyridin-3-yl)methoxy)-4-((2,2'-dimethyl-3'-(3-(piperidin-1-yl)propoxy)-[1,1'-biphenyl]-3-yl)methoxy)benzyl)amino)-3-hydroxy-2-methylpropanoic acid;

or a pharmaceutically acceptable salt thereof.

10. A compound selected from (R)-2-((5-chloro-2-((5-cyanopyridin-3-yl)methoxy)-4-((3'-(3-(4-hydroxy-4-(methoxycarbonyl)piperidin-1-yl)propoxy)-2,2'-dimethyl-[1,1'-biphenyl]-3-yl)methoxy)benzyl)amino)-3-hydroxypropanoic acid;

(R)-1-(3-((3'-((4-(((1-carboxy-2-hydroxyethyl)amino)methyl)-2-chloro-5-((5-cyanopyridin-3-yl)methoxy)phenoxy)methyl)-2'-methyl-[1,1'-biphenyl]-3-yl)oxy)propyl)-4-hydroxypiperidine-4-carboxylic acid;

(S)-5-((4-chloro-5-((2'-chloro-3'-(3-((2,3-dihydroxypropyl)amino)propoxy)-2-methyl-[1,1'-biphenyl]-3-yl)methoxy)-2-(hydroxymethyl)phenoxy)methyl)nicotinonitrile;

(S)-3-((2-chloro-3'-((2-chloro-5-((5-cyanopyridin-3-yl)methoxy)-4-(((2,3-dihydroxypropyl)amino)methyl)phenoxy)methyl)-2'-methyl-[1,1'-biphenyl]-3-yl)oxy)propyl)(methyl)amino)propanamide;

(2S)-1-(5-chloro-2-((5-cyanopyridin-3-yl)methoxy)-4-((2,2'-dimethyl-3'-(3-(4-(pyridin-2-yl)piperazin-1-yl)propoxy)biphenyl-3-yl)methoxy)benzyl)piperidine-2-carboxylic acid;

(2S)-1-(5-chloro-2-((5-cyanopyridin-3-yl)methoxy)-4-((3'-(3-((R)-2-hydroxy-1-phenylethylamino)propoxy)-2,2'-dimethylbiphenyl-3-yl)methoxy)benzyl)piperidine-2-carboxylic acid;

(2S)-1-(4-((3'-(3-(4-(tert-butoxycarbonyl(methyl)amino)piperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid;

(3 S)-1-(3-(3'-((4-(((S)-3-carboxypiperidin-1-yl)methyl)-2-chloro-5-((5-cyanopyridin-3-yl)methoxy)phenoxy)methyl)-2,2'-dimethylbiphenyl-3-yloxy)propyl)piperidine-3-carboxylic acid;

(2S)-2-(4-((3'-(3-((R)-3-acetamidopyrrolidin-1-yl)propoxy)-2,2'-dimethylbiphenyl-3-yl)methoxy)-5-chloro-2-((5-cyanopyridin-3-yl)methoxy)benzylamino)-3-hydroxy-2-methylpropanoic acid; and 5-((4-chloro-2-(hydroxymethyl)-5-((3'-(3-((R)-3-methoxypyrrolidin-1-yl)propoxy)-2,2'-dimethylbiphenyl-3-yl)methoxy)phenoxy)methyl)nicotinonitrile;

or a pharmaceutically acceptable salt thereof.

11. A compound selected from (S)-2-((5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)amino)-3-hydroxy-2-methylpropanoic acid;

(S)-1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)piperidine-2-carboxylic acid;

(R)-1-(3-((3'-((4-(((2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)oxy)propyl)-4-hydroxypiperidine-4-carboxylic acid;

methyl 1-(5-chloro-4-((2'-chloro-3'-((R)-3-hydroxypyrrolidin-1-yl)propoxy)-2-methyl-[1,1'-biphenyl]-3-yl)methoxy)-2-((5-cyanopyridin-3-yl)methoxy)benzyl)-2-methylpiperidine-2-carboxylate;

1-(5-chloro-2-((5-cyanopyridin-3-yl)methoxy)-4-((3'-(3-((R)-3-hydroxypyrrolidin-1-yl)propoxy)-2,2'-dimethyl-[1,1'-biphenyl]-3-yl)methoxy)benzyl)-2-methylpiperidine-2-carboxylic acid;

(R)-1-(3-((3'-((5-((5-carbamoylpyridin-3-yl)methoxy)-4-(((2-carboxy-1-hydroxypropan-2-yl)amino)methyl)-2-chlorophenoxy)methyl)-2,2'-dimethyl-[1,1'-biphenyl]-3-yl)oxy)propyl)-4-hydroxypiperidine-4-carboxylic acid;

(R)-2-((5-chloro-4-((2'-chloro-3'-(3-(4-hydroxy-4-(hydroxymethyl)piperidin-1-yl)propoxy)-2-methyl-[1,1'-biphenyl]-3-yl)methoxy)-2-((5-cyanopyridin-3-yl)methoxy)benzyl)amino)-3-hydroxy-2-methylpropanoic acid;

(S)-1-(5-chloro-4-((2-chloro-3'-(3-(((S)-2,3-dihydroxypropyl)amino)propoxy)-2'-methyl-[1,1'-biphenyl]-3-yl)methoxy)-2-((5-cyanopyridin-3-yl)methoxy)benzyl)piperidine-2-carboxylic acid;

(S)-5-((4-chloro-5-((2,2'-dichloro-3'-(3-((2,3-dihydroxypropyl)amino)propoxy)-[1,1'-biphenyl]-3-yl)methoxy)-2-(((1,3-dihydroxy-2-methylpropan-2-yl)amino)methyl)phenoxy)methyl)nicotinonitrile;

(R)-2-((5-chloro-2-((5-cyanopyridin-3-yl)methoxy)-4-((2,2'-dichloro-3'-(3-(4-hydroxy-4-(hydroxymethyl)piperidin-1-yl)propoxy)-[1,1'-biphenyl]-3-yl)methoxy)benzyl)amino)-3-hydroxy-2-methylpropanoic acid;

(S)-1-(5-chloro-4-((2'-chloro-3'-(3-(((S)-2,3-dihydroxypropyl)amino)propoxy)-2-methyl-[1,1'-biphenyl]-3-yl)methoxy)-2-((5-cyanopyridin-3-yl)methoxy)benzyl)piperidine-2-carboxylic acid; and (S)-1-(5-chloro-4-((2-chloro-3'-(3-((R)-3-hydroxypyrrolidin-1-yl)propoxy)-2'-methyl-[1,1'-biphenyl]-3-yl)methoxy)-2-((5-cyanopyridin-3-yl)methoxy)benzyl)piperidine-2-carboxylic acid;

or a pharmaceutically acceptable salt thereof.

12. A compound selected from (R)-2-((5-chloro-2-((5-cyanopyridin-3-yl)methoxy)-4-((3'-(3-((R)-3-hydroxypyrrolidin-1-yl)propoxy)-2-methyl-[1,1'-biphenyl]-3-yl)methoxy)benzyl)amino)-3-hydroxypropanoic acid;

(2R)-2-((5-chloro-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxypropanoic acid;

(R)-2-((4-((3'-(3-(4-acetamidopiperidin-1-yl)propoxy)-2'-chloro-2-methyl-[1,1'-biphenyl]-3-yl)methoxy)-5-chloro-2-((5-cyanopyridin-3-yl)methoxy)benzyl)amino)-3-hydroxy-2-methylpropanoic acid;

(R)-2-((5-chloro-4-((2'-chloro-2-methyl-3'-(3-(piperidin-1-yl)propoxy)-[1,1'-biphenyl]-3-yl)methoxy)-2-((5-cyanopyridin-3-yl)methoxy)benzyl)amino)-3-hydroxy-2-methylpropanoic acid;

5-((4-chloro-5-((2,2'-dichloro-3'-(3-(((S)-2,3-dihydroxypropyl)amino)propoxy)-[1,1'-biphenyl]-3-yl)methoxy)-2-((((S)-2,3-dihydroxypropyl)amino)methyl)phenoxy)methyl)nicotinonitrile;

(2S)-1-(5-chloro-2-((5-cyanopyridin-3-yl)methoxy)-4-((3'-(3-(diethylcarbamoyl)piperidin-1-yl)propoxy)-2,2'-dimethylbiphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(methyl(phenethyl)amino)propoxy)biphenyl-3-yl)methoxy)benzyl)piperidine-2-carboxylic acid;

(2S)-1-(5-chloro-2-((5-cyanopyridin-3-yl)methoxy)-4-((2,2'-dimethyl-3'-(3-(methyl(pyridin-3-ylmethyl)amino)propoxy)biphenyl-3-yl)methoxy)benzyl)piperidine-2-carboxylic acid;

(2S)-1-(5-chloro-2-((5-cyanopyridin-3-yl)methoxy)-4-((3'-3-(2,3-dihydroxypropylamino)propoxy)-2,2'-dimethylbiphenyl-3-yl)methoxy)benzyl)piperidine-2-carboxylic acid;

(2S)-1-(4-((3'-(3-(2-carbamoylpiperidin-1-yl)propoxy)-2,2'-dimethylbiphenyl-3-yl)methoxy)-5-chloro-2-((5-cyanopyridin-3-yl)methoxy)benzyl)piperidine-2-carboxylic acid; and (R)-2-((5-chloro-4-((2'-chloro-3'-(3-((2S,4R)-4-hydroxy-2-(methoxycarbonyl)pyrrolidin-1-yl)propoxy)-2-methyl-[1,1'-biphenyl]-3-yl)methoxy)-2-((5-(methylsulfonyl)pyridin-3-yl)methoxy)benzyl)amino)-3-hydroxy-2-methylpropanoic acid;

or a pharmaceutically acceptable salt thereof.

13. A compound selected from (S)-1-(5-chloro-2-((5-cyanopyridin-3-yl)methoxy)-4-((3'-(3-((R)-3-hydroxypyrrolidin-1-yl)-3-oxopropoxy)-2-methyl-[1,1'-biphenyl]-3-yl)methoxy)benzyl)azetidine-2-carboxylic acid;

1-(3-((3'-((4-((((R)-2-carboxy-1-hydroxypropan-2-yl)amino)methyl)-2-chloro-5-((5-(methylsulfonyl)pyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic acid;

(S)-1-(4-((3'-(3-(4-carboxy-4-hydroxypiperidin-1-yl)propoxy)-2,2'-dimethyl-[1,1'-biphenyl]-3-yl)methoxy)-5-chloro-2-((5-cyanopyridin-3-yl)methoxy)benzyl)piperidine-2-carboxylic acid;

(R)—N-(2-((5-chloro-2-((5-cyanopyridin-3-yl)methoxy)-4-((3'-(3-(3-hydroxypyrrolidin-1-yl)propoxy)-2,2'-dimethyl-[1,1'-biphenyl]-3-yl)methoxy)benzyl)amino)ethyl)acrylamide;

(R)-1-(3-((3'-((5-((5-carbamoylpyridin-3-yl)methoxy)-4-(((1-carboxy-2-hydroxyethyl)amino)methyl)-2-chlorophenoxy)methyl)-2,2'-dimethyl-[1,1'-biphenyl]-3-yl)oxy)propyl)-4-hydroxypiperidine-4-carboxylic acid;

(2R)-2-((5-chloro-4-((3'-(3-(3-(ethoxycarbonyl)-3-(hydroxymethyl)pyrrolidin-1-yl)propoxy)-2,2'-dimethyl-[1,1'-biphenyl]-3-yl)methoxy)-2-((5-(methylsulfonyl)pyridin-3-yl)methoxy)benzyl)amino)-3-hydroxy-2-methylpropanoic acid;

1-(3-((3'-((4-(((((R)-1-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)oxy)propyl)-3-(hydroxymethyl)pyrrolidine-3-carboxylic acid;

(R)-2-((5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)benzyl)amino)-3-hydroxypropanoic acid;

or a pharmaceutically acceptable salt thereof.

14. A compound selected from

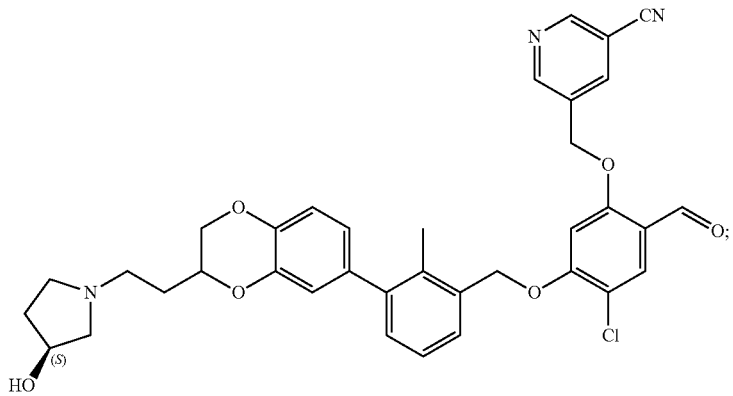

-continued
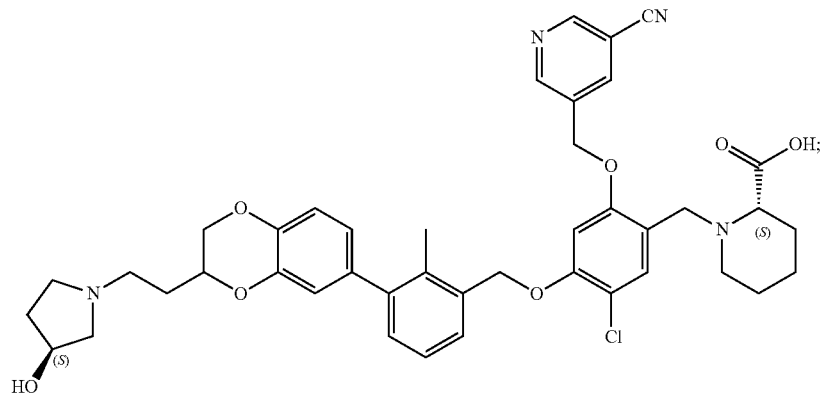
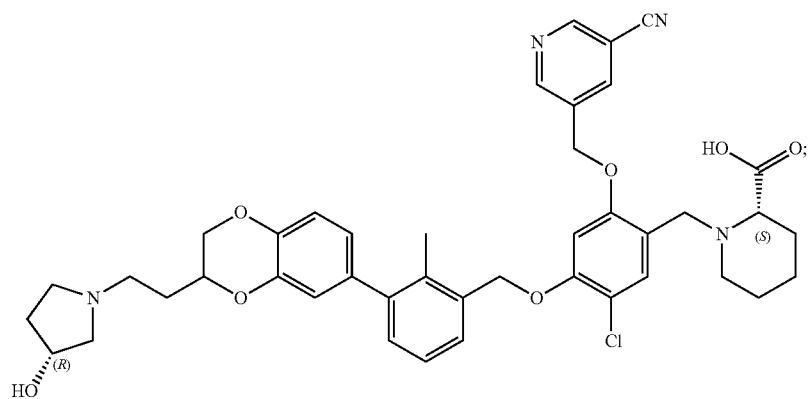
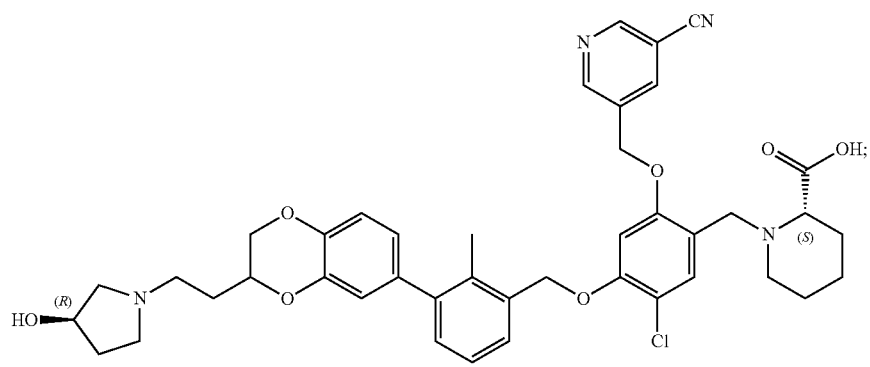
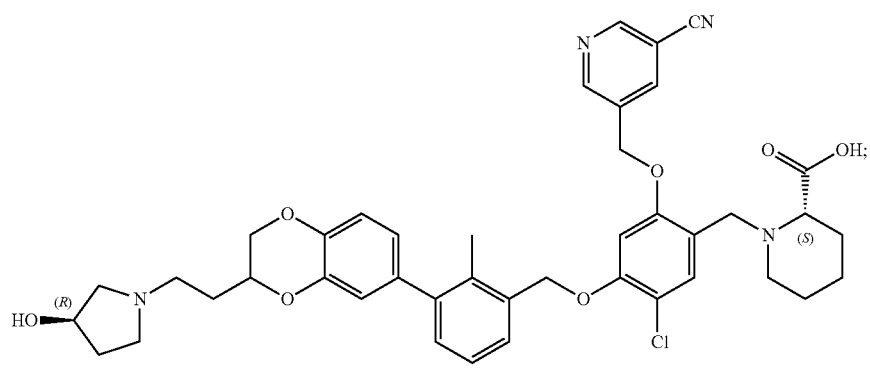

-continued
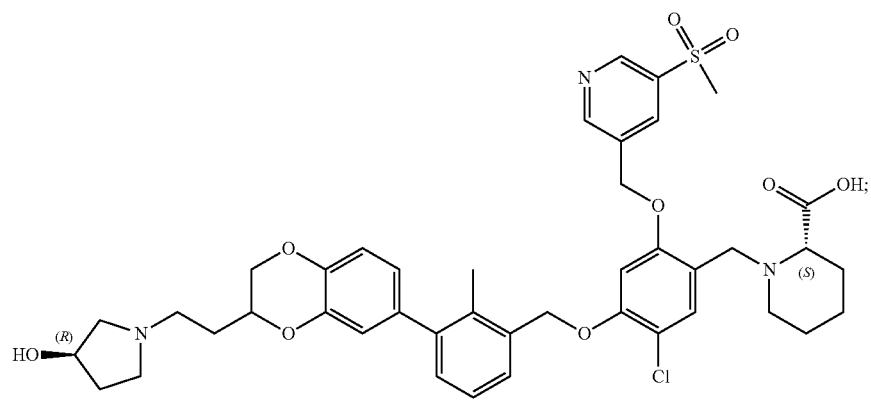
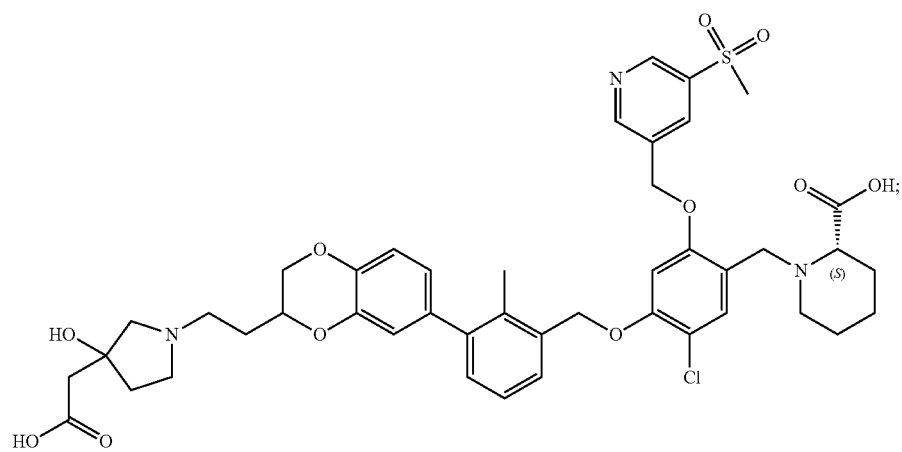
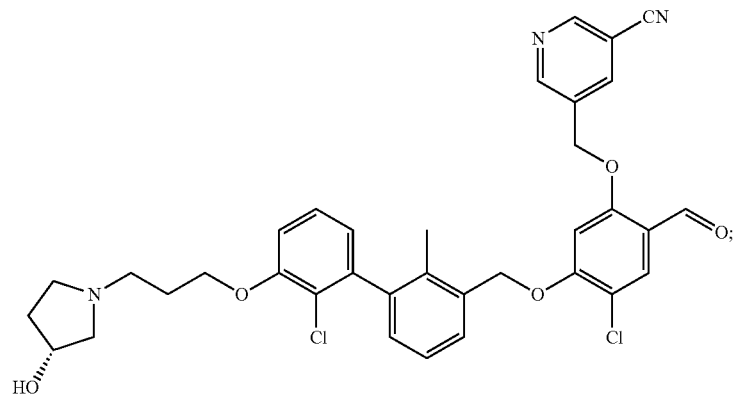
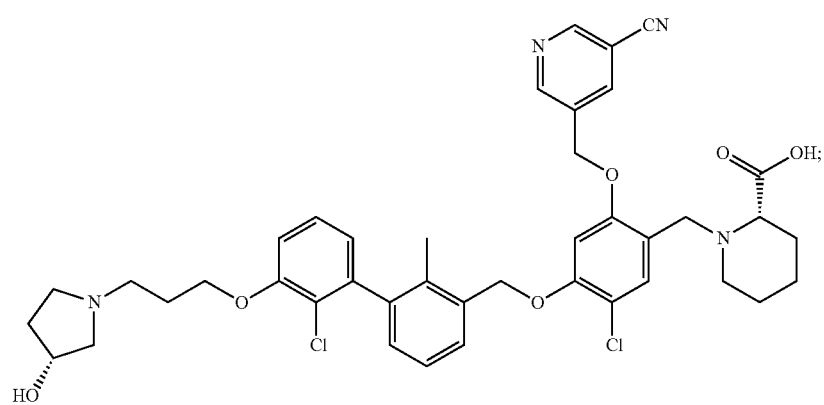

-continued
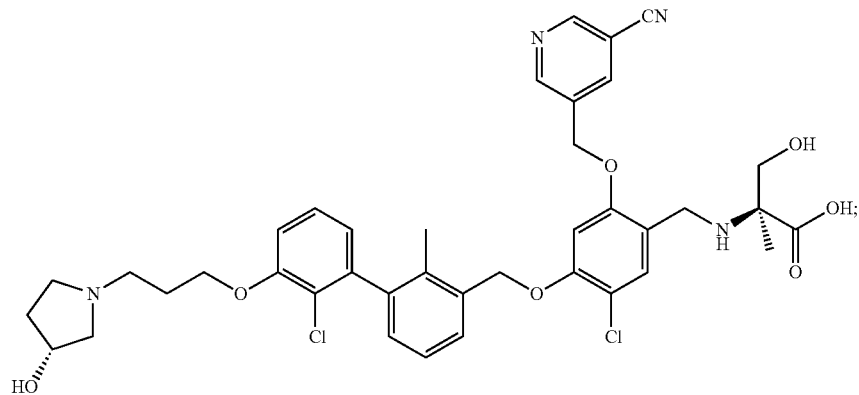
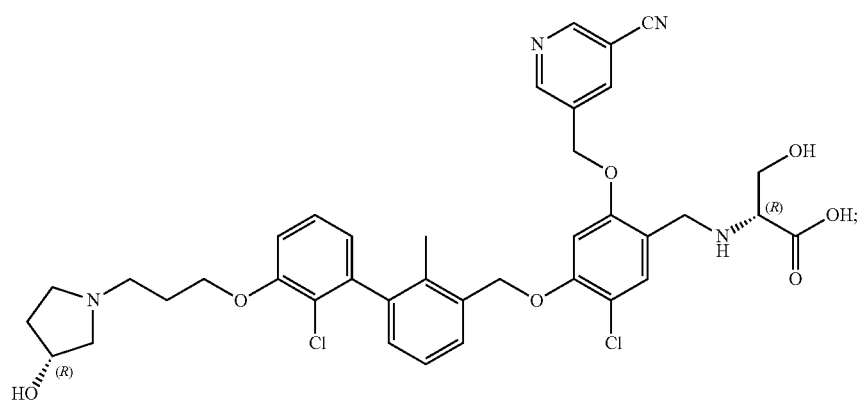
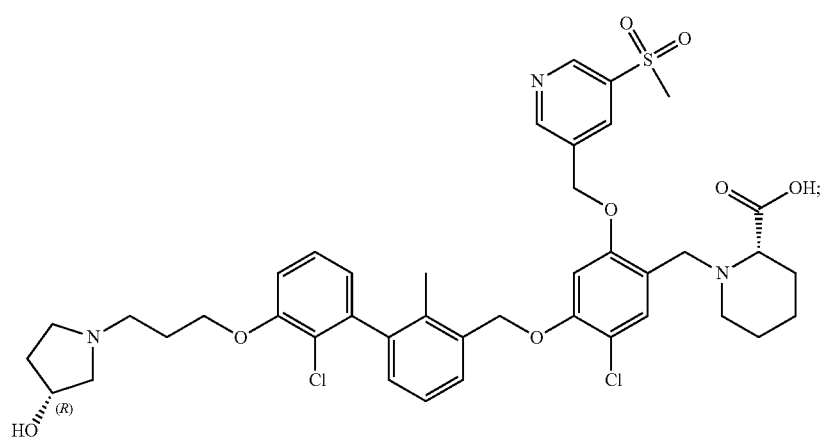
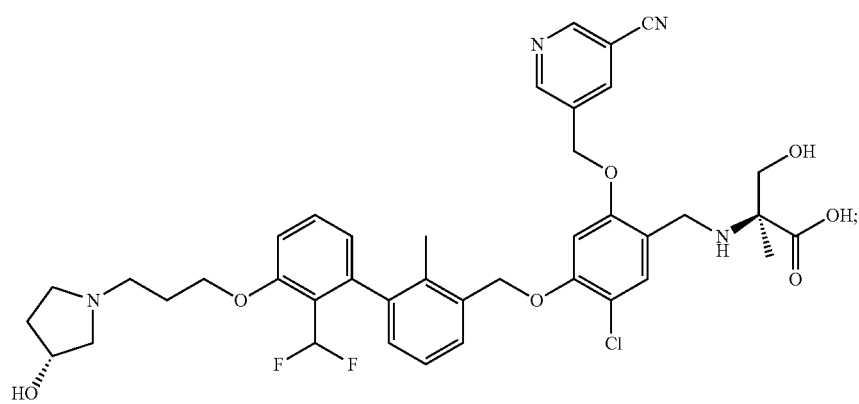

-continued
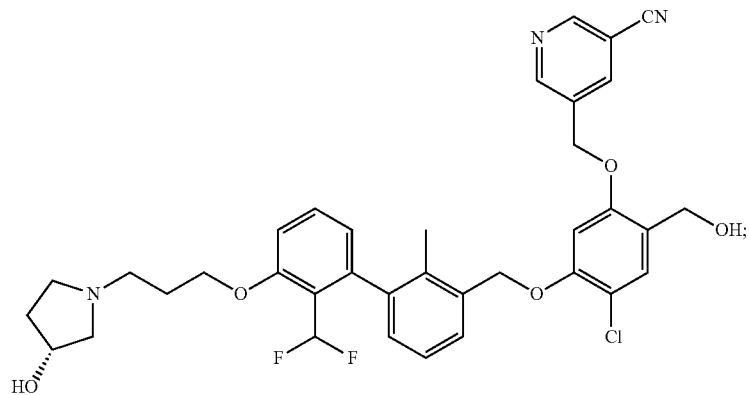
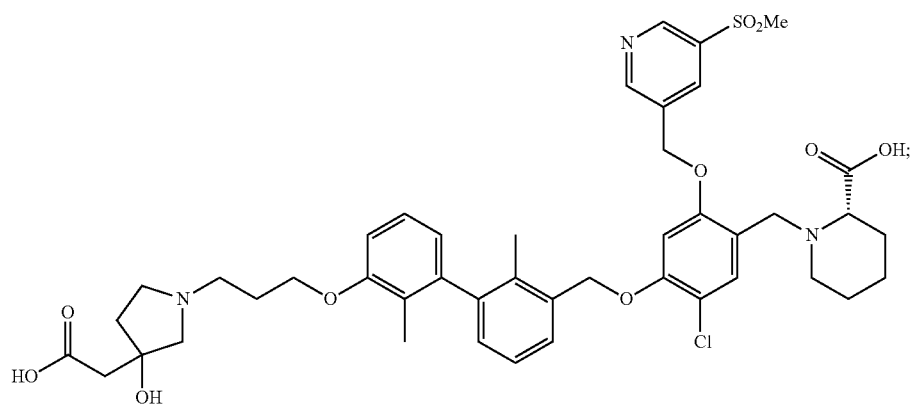
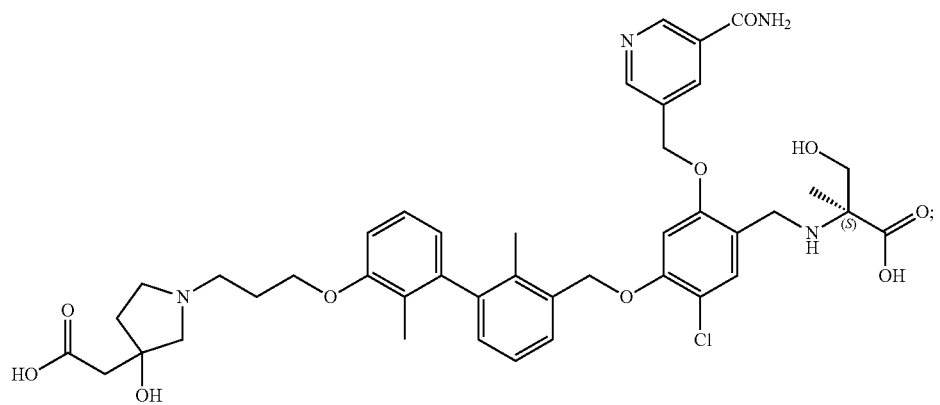
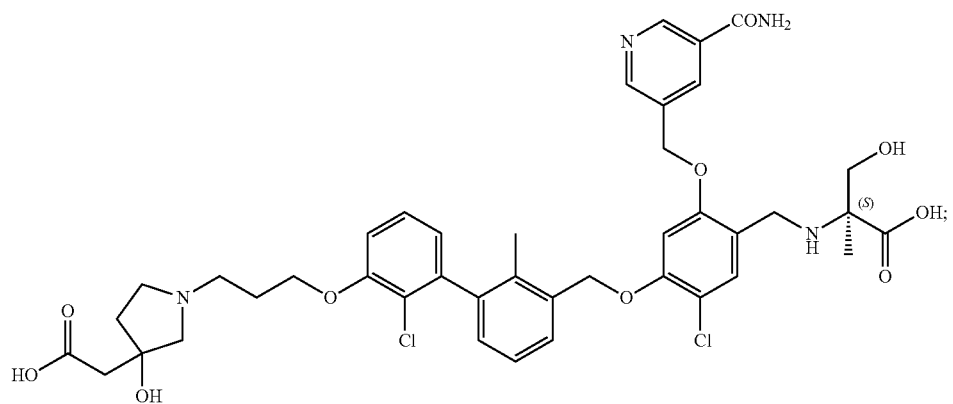

-continued
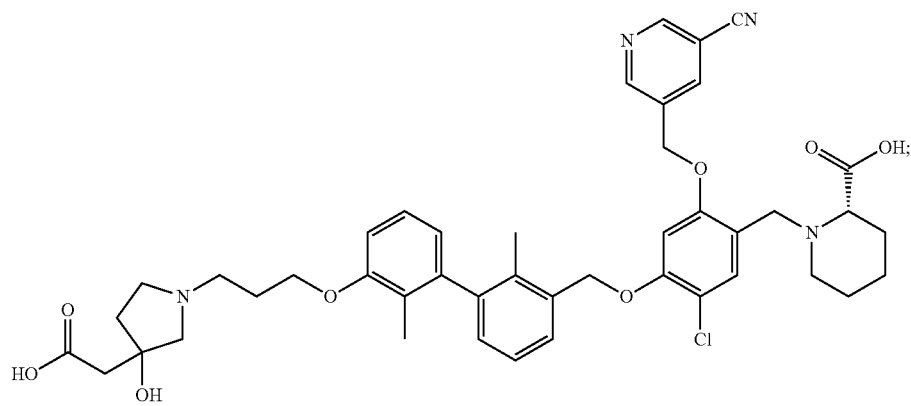
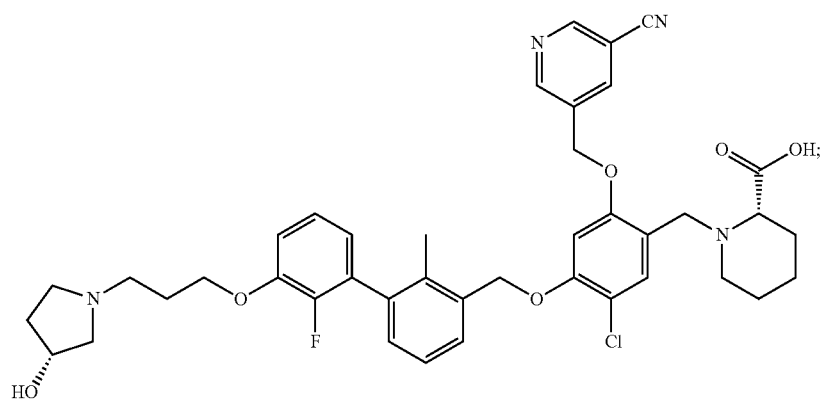
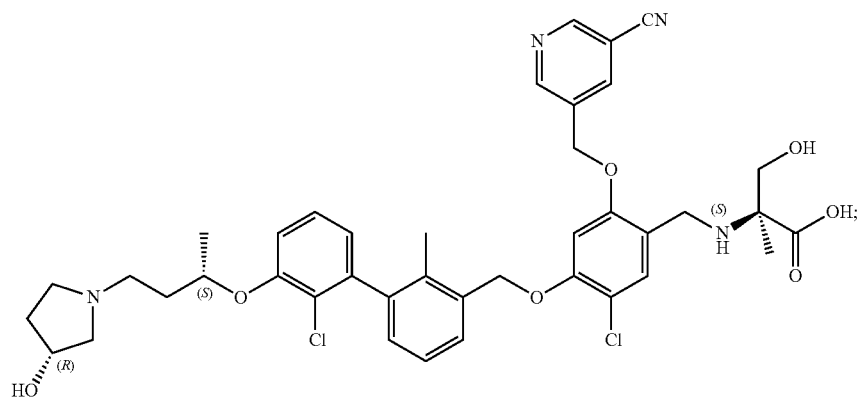
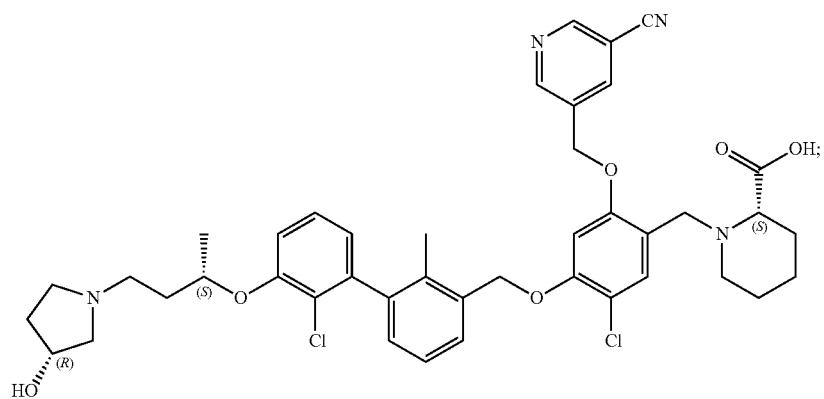

-continued
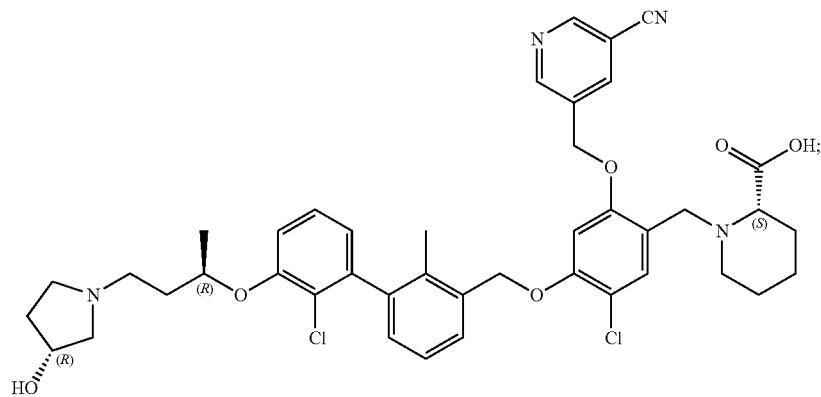
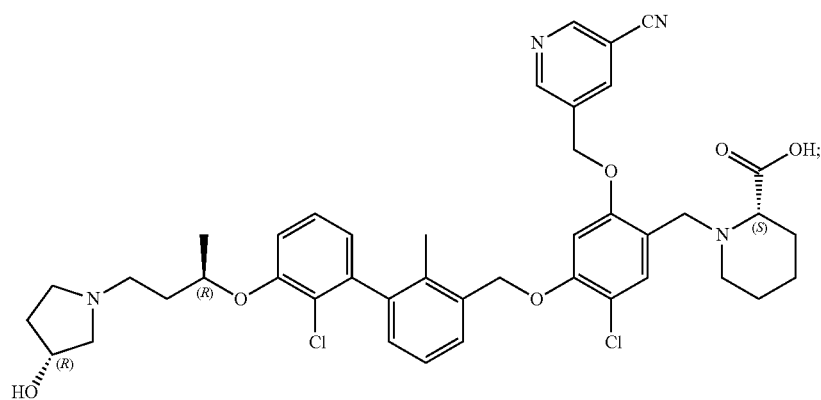
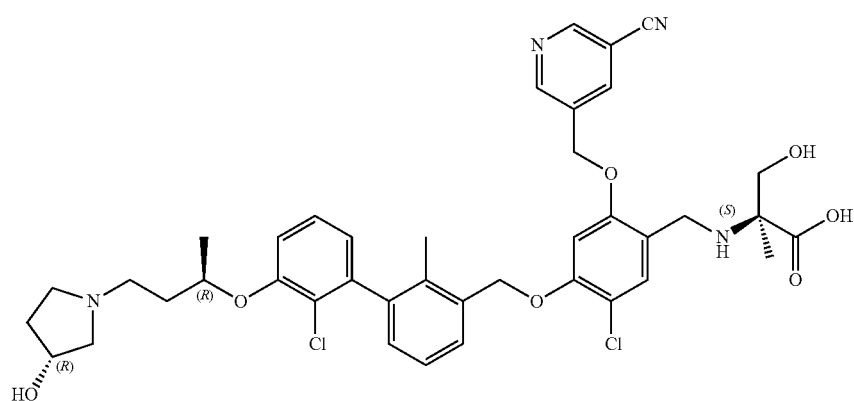
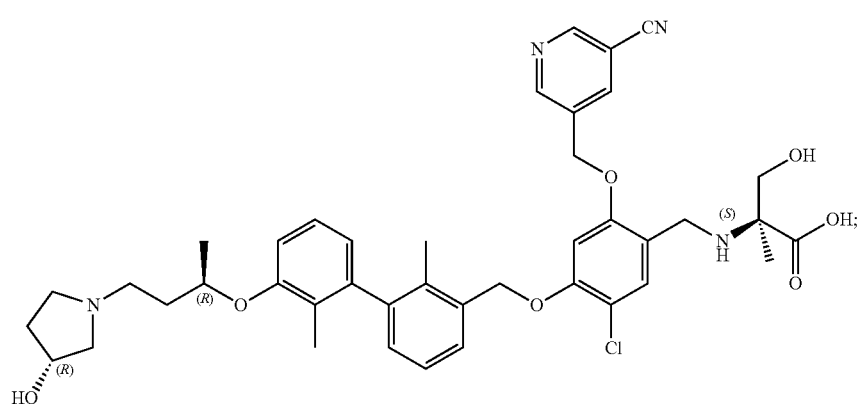

-continued

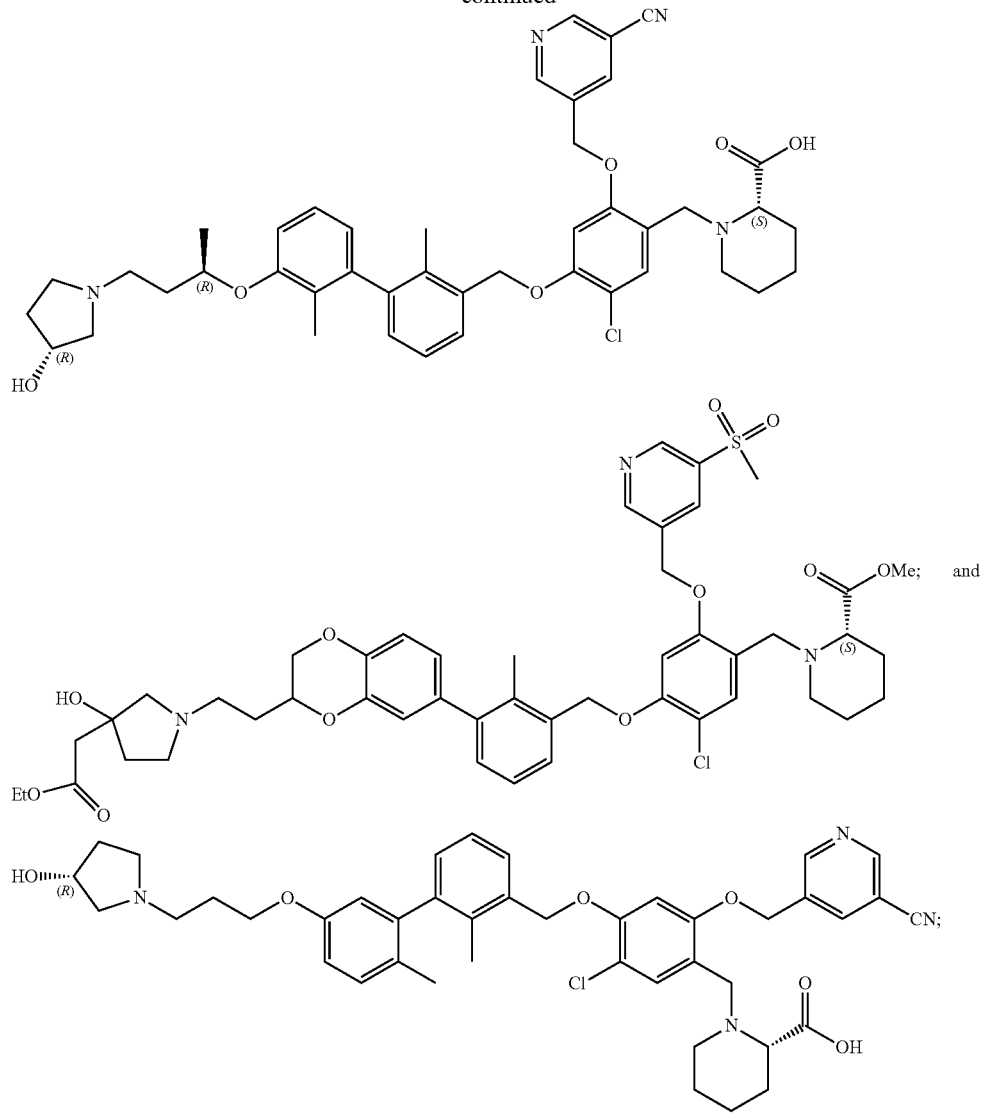

15. A pharmaceutical composition comprising a compound of claim 1, or a pharmaceutically acceptable salt thereof, and a pharmaceutically acceptable carrier.

16. A method of enhancing, stimulating, modulating and/or increasing the immune response in a subject in need thereof, said method comprising administering to the subject a therapeutically effective amount of a compound of claim 1, or a pharmaceutically acceptable salt thereof.

17. The method of claim 16 further comprising administering an additional agent prior to or after the compound, or the pharmaceutically acceptable salt thereof.

18. The method of claim 17 wherein the additional agent is an antimicrobial agent, an antiviral agent, a cytotoxic agent, a gene expression modulatory agent, and/or an immune response modifier.

19. A method of inhibiting growth, proliferation, or metastasis of cancer cells in a subject in need thereof, said method comprising administering to the subject a therapeutically effective amount of a compound of claim 1, or a pharmaceutically acceptable salt.

20. The method of claim 19 wherein the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

21. A method of treating an infectious disease in a subject in need thereof, the method comprising administering to the subject a therapeutically effective amount of a compound of claim 1, or a pharmaceutically acceptable salt thereof.

22. The method of claim 21 wherein the infectious disease is caused by a virus.

23. The method of claim 22 wherein the virus is selected from HIV, Hepatitis A, Hepatitis B, Hepatitis C, Hepatitis D, herpes viruses, papillomaviruses, and influenza.

24. A method of treating septic shock in a subject in need thereof, the method comprising administering to the subject a therapeutically effective amount of a compound of claim 1, or a pharmaceutically acceptable salt thereof.

25. The method of claim 16 further comprising administering an additional agent simultaneously with the compound, or the pharmaceutically acceptable salt thereof.

* * * * *

UNITED STATES PATENT AND TRADEMARK OFFICE
CERTIFICATE OF CORRECTION

PATENT NO. : 10,745,382 B2  
APPLICATION NO. : 15/290167  
DATED : August 18, 2020  
INVENTOR(S) : Kap-Sun Yeung et al.

Page 1 of 2

It is certified that error appears in the above-identified patent and that said Letters Patent is hereby corrected as shown below:

In the Claims

<u>Column 885</u>  
Line 10, Claim 1, after "3," insert -- or --;  
Line 21, Claim 1, "—NR$^e$R$^{f''}$" should read -- —NR$^e$R$^f$, --.

<u>Column 889</u>  
Line 14, Claim 9, "-1l-yl)-" should read -- -1-yl)- --;  
Line 21, Claim 9, delete "-A-" and insert -- -4- --.

<u>Column 890</u>  
Line 18, Claim 9, "acid" should read -- acid; --.

<u>Column 894</u>  
Line 14, Claim 9, "N-(1 3-(2-chloro-3'-" should read -- N-(1-(3-((2-chloro-3'- --.

<u>Column 898</u>  
Line 40, Claim 9, "-A-" should read -- -4- --.

<u>Column 900</u>  
Line 12, Claim 9, "nicotinonitrile" should read -- nicotinonitrile; --.

<u>Column 904</u>  
Line 42, Claim 9, "N-(1 3-(2-chloro-3'-" should read -- N-(1-(3-((2-chloro-3'- --;  
Line 62, Claim 9, "-A-" should read -- -4- --.

<u>Column 905</u>  
Line 7, Claim 9, "N-(1 3-(2-chloro-3'-" should read -- N-(1-(3-((2-chloro-3'- --.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*

Column 910
Line 48, Claim 9, "1l-yl)" should read -- 1-yl) --.

Column 911
Line 36, Claim 9, "1l-yl)" should read -- 1-yl) --.

Column 912
Line 58, Claim 9, "1l-yl)" should read -- 1-yl) --.

Column 913
Line 38, Claim 9, "-A-" should read -- -4- --.

Column 915
Line 34, Claim 9, "-1 (5-" should read -- -1-(5- --.

Column 916
Line 8, Claim 9, "-A-" should read -- -4- --;
Line 46, Claim 9, "-A-" should read -- -4- --.

Column 923
Line 34, Claim 9, after "chloro-" insert -- 2- --;
Line 34, Claim 9, "-4-((3'(3-" should read -- -4-((3'-(3- --; and
Line 39-40, Claim 9, "-4-((3'-(3-((3-hydroxypyrrolidin-1-yl)" should read -- -4-((3'-(3-((R)-3-hydroxypyrrolidin-1-yl) --.

Column 926
Line 47, Claim 13, after "acid;" insert -- and --.

Column 939-940

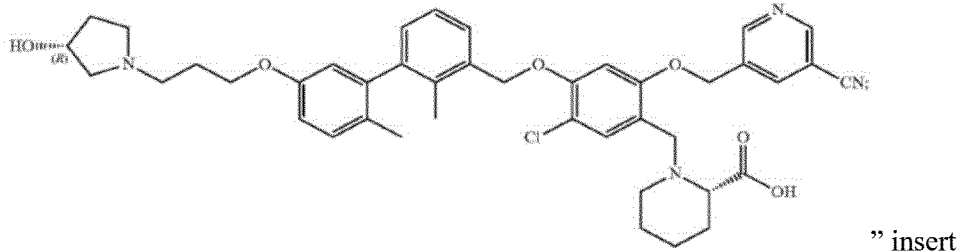

Claim 14, after "                                                                              " insert
-- or a pharmaceutically acceptable salt thereof. --.